US007148046B2

(12) United States Patent
Williams

(10) Patent No.: US 7,148,046 B2
(45) Date of Patent: Dec. 12, 2006

(54) CRYSTAL STRUCTURE OF CYTOCHROME P450

(75) Inventor: Pamela A. Williams, Cambridge (GB)

(73) Assignee: Astex Therapeutics Limited, Cambridge (GB)

( * ) Notice: Subject to any disclaimer, the term of this patent is extended or adjusted under 35 U.S.C. 154(b) by 109 days.

(21) Appl. No.: 10/690,991

(22) Filed: Oct. 23, 2003

(65) Prior Publication Data

US 2004/0243319 A1    Dec. 2, 2004

Related U.S. Application Data

(63) Continuation-in-part of application No. PCT/GB02/02668, filed on May 30, 2002, and a continuation-in-part of application No. 10/221,036, filed on Apr. 2, 2002.

(60) Provisional application No. 60/479,448, filed on Jun. 19, 2003, provisional application No. 60/421,063, filed on Oct. 25, 2002, provisional application No. 60/306,873, filed on Jul. 23, 2001, provisional application No. 60/306,874, filed on Jul. 23, 2001.

(30) Foreign Application Priority Data

Apr. 2, 2001    (GB) ................................ 0108212.2
Apr. 2, 2001    (GB) ................................ 0108214.8

(51) Int. Cl.
*C12N 9/02* (2006.01)
(52) U.S. Cl. .................................................. 435/189
(58) Field of Classification Search ..................... None
See application file for complete search history.

(56) References Cited

U.S. PATENT DOCUMENTS

| | | | |
|---|---|---|---|
| 5,786,191 A | 7/1998 | Goldstein et al. | 435/189 |
| 5,834,250 A | 11/1998 | Wells et al. | 435/7.1 |
| 5,886,157 A | 3/1999 | Guengerich et al. | 530/412 |
| 5,912,120 A | 6/1999 | Goldstein et al. | 435/16 |
| 6,080,568 A | 6/2000 | Day et al. | 435/202 |
| 6,136,553 A | 10/2000 | Christianson et al. | 435/23 |
| 6,162,613 A | 12/2000 | Su et al. | 435/15 |
| 6,312,917 B1 | 11/2001 | Thakker et al. | 435/25 |
| 6,432,639 B1 | 8/2002 | Lichter et al. | 435/6 |
| 2003/0170842 A1 | 9/2003 | Williams et al. | |

FOREIGN PATENT DOCUMENTS

| | | |
|---|---|---|
| DE | 195 49 267 A1 | 7/1997 |
| WO | WO 98/02554 | 1/1998 |
| WO | WO 99/08812 | 2/1999 |
| WO | WO 01/11035 | 2/2001 |
| WO | WO 01/14565 | 3/2001 |
| WO | WO 03/035693 A | 5/2003 |
| WO | WO 03/040994 A | 5/2003 |
| WO | WO 03/102192 | 12/2003 |
| WO | WO 2004/038015 | 5/2004 |
| WO | WO 2004/038655 | 5/2004 |

OTHER PUBLICATIONS

Abstract 4, Abstracts from 8th European ISSX Meeting (Monday 28th Apr. 2003), Structural Characterisation of Substrate and Inhibitor Binding to 2C P450s, Eric Johnson, Scripps Research Institute, La Jolla, CA, USA.
Wester et al, Structure of a Substrate Complex of Mammalian Cytochrome P450 2C5 at 2.3 Å Resolution: Evidence of Multiple Substrate Binding Modes, Biochemistry 2003, 42, 6370-6379.
Wester et al, Structure of Mammalian Cytochrome P450 2C5 Complexed with Diclofenac at 2.1 Å Resolution: Evidence for an Induced Fit Model of Substrate Binding, Biochemistry 2003, 42, 9335-9345.
Crystal Structure of human cytochrome P450 2C9 with bound warfarin; Williams, P.A.; Cosme, J.; Ward, A.; Angrove, H.C.; Matak-Vinkovic, D.; Jhoti, H.; *Nature*, Jul. 24, 2003; 424(6947); 464-8. (Published online Jul. 13, 2003).
IF Sevrioukova, H Li, H Zhang, JA Peterson, TL Poulos, Structure of a cytochrome P450-redox partner electron-transfer complex, *Proceedings of the National Academy of Sciences of the United States of America* (1999) 96, pp. 1863-1869.
Szklarz GD, Halpert JR.; Molecular modeling of cytochrome P450 3A4; *J. Comput. Aided Mol. Des.;* 1997;11(3); 265-72.
Lewis DF, Eddershaw PJ, Goldfarb PS, Tarbit MH.; Molecular modelling of CYP3A4 from an alignment with CYP102: identification of key interactions between putative active site residues and CYP3A-specific chemicals; *Xenobiotica;* 1996; 26(10);1067-86.
Guengerich FP; Cytochrome P-450 3A4: regulation and role in drug metabolism; Annu. Rev. Pharmacol. Toxicol.; 1999; 39;1-17.
Ekins S, Bravi G, Wikel JH, Wrighton SA.; Three-dimensional-quantitative structure activity relationship analysis of cytochrome P-450 3A4 substrates; J Pharmacol Exp Ther.; 1999; 291(1); 424-33.
Ekins S, Bravi G, Binkley S, Gillespie JS, Ring BJ, Wikel JH, Wrighton SA.; Three- and four-dimensional quantitative structure activity relationship analyses of cytochrome P-450 3A4 inhibitors; J Pharmacol Exp Ther.; 1999; 290(1); 429-38.
Gonzalez,F.J., Schmid,B.J., Umeno,M., Mcbride,O.W., Hardwick,J. P., Meyer,U.A., Gelboin,H.V. and Idle,J.R., Human P450PCN1: sequence, chromosome localization, and direct evidence through cDNA expression that P450PCN1 is nifedipine oxidase, DNA 7(2), 79-86 (1988).
Beaune,P.H., Umbenhauer,D.R., Bork,R.W., Lloyd,R.S. and Guengerich,F.P., Isolation and sequence determination of a cDNA clone related to human cytochrome P-450 nifedipine oxidase, Proc. Natl. Acad. Sci. U.S.A.; 83 (21), 8064-8068 (1986).

(Continued)

*Primary Examiner*—Nashaat T. Nashed
(74) *Attorney, Agent, or Firm*—Nixon & Vanderhye, P.C.

(57) ABSTRACT

The invention provides the crystal structure of the cytochrome P450 3A4 protein molecule. The structure is set out in Table 5. The structure may be used in to model the interaction of compounds such as pharmaceuticals with this protein, and to determine the structure of related cytochrome P450 molecules.

2 Claims, 213 Drawing Sheets

OTHER PUBLICATIONS

Korzekwa, K.R.; Krishnamachary, N.; Shou, M.; Ogai, A.; Parise, R.A.; Rettie, A.E.; Gonzalez, F.J.; Tracey, T.S.; Evaluation Of Atypical Cytochrome P450 Kinetics With Two-Substrate Models: Evidence That Multiple Substrate Can Bind Simultaneously Bind To Cytochrome P450 Active Sites; *Biochemistry;* 1998, vol. 37, 4137-4147.

Hosea NA, Miller GP, Guengerich FP.; Elucidation of distinct ligand binding sites for cytochrome P450 3A4; *Biochemistry;* 2000; 39(20), 5929-39.

Williams, P.; Cosme, J.; Sridhar, V.; Johnson, E. and McRee, D.; Microsomal cytochrome P450 2C5: comparison of microbial P450s and unique features, *Journal of Inorganic Biochemistry,* 2000, vol. 81, pp. 183-190.

T. H. Richardson, F. Jung, K. J. Griffin, M. Wester, J. L. Raucy, B. Kemper, L. M. Bornheim, C. Hassett, C. J. Omiecinski and E. F. Johnson; A Universal Approach to the Expression of Human and Rabbit Cytochrome P450s of the 2C Subfamily in *Escherichia coli; Archives of Biochemistry and Biophysics,* 1995, vol. 323, 87-96.

JP10033166A2; Mass Expression System Of Modified Substance Of Ctochrome P450 2c19 in *Escherichia Coli;* Inventor: Baba Takahiko; Kirita Shiro; Aoyama Junko; Assignee: Shionogi & Co Ltd; Filed: Jul. 23, 1996. (with English abstract.).

Barnes HJ, Arlotto MP, Waterman MR; Expression and enzymatic activity of recombinant cytochrome P450 17 alpha-hydroxylase in *Escherichia coli; Proc. Natl. acad. Sci. USA;* 1991, 88, 5597-5601.

Kempf AC, Zanger UM, Meyer UA; Truncated human P450 2D6: expression in *Escherichia coli,* Ni(2+)-chelate affinity purification, and characterization of solubility and aggregation; *Arch. Biochem. Biophys.,* 1995, 321, 277-288.

Gillam EM, Guo Z, Martin MV, Jenkins CM, Guengerich FP; Expression of cytochrome P450 2D6 in *Escherichia coli,* purification, and spectral and catalytic characterization; *Arch. Biochem. Biophys.,* 1995, 319, 540-550.

Pernecky SJ, Larson JR, Philpot RM, Coon MJ; Expression of truncated forms of liver microsomal P450 cytochromes 2B4 and 2E1 in *Escherichia coli;* influence of NH2-terminal region on localization in cytosol and membranes; *Proc. Natl. Acad. Sci. USA,* 1993, 90, 2651-2655.

JR Larson, MJ Coon, and TD Porter; Alcohol-inducible cytochrome P-450IIE1 lacking the hydrophobic NH2-terminal segment retains catalytic activity and is membrane-bound when expressed in *Escherichia coli; J. Biol. Chem,* 1991, 266, 7321-7324.

Sagara Y., Barnes H. J. and Waterman M. R.; Expression in *Escherichia coli* of Functional Cytochrome P450$_{c17}$ Lacking Its Hydrophobic Amino-Terminal Signal Anchor, *Arch. Biochem. Biophys.,* 1993, 304, 272-278.

Emily E. Scott, Margit Spatzenegger and James R. Halpert ; A Truncation of 2B Subfamily Cytochromes P450 Yields Increased Expression Levels, Increased Solubility, and Decreased Aggregation While Retaining Function, *Arch. Biochem. Biophys.,* 2001, vol. 395, Issue 1, 57-68.

Gillam EM, Baba T, Kim BR, Ohmori S, Guengerich FP; Expression of modified human cytochrome P450 3A4 in *Escherichia coli;* and purification and reconstitution of the enzyme; *Arch Biochem Biophys.,* 1993; 305(1): 123-31.

Meehan,R.R., Gosden,J.R., Rout,D., Hastie,N.D., Friedberg,T., Adesnik,M., Buckland,R., van Heyninen,V., Fletcher,J.M., Spurr,N. K., Sweeney,J. and Wolf,C.R.; Human cytochrome P-450 PB1: a multigene family involved in mephenytoin and steroid oxidations that maps to chromosome 10; *Am. J. Hum. Genet.;* 1988, 42 (1), 26-37.

Kimura,S., Pastewka,J., Gelboin,H.V. and Gonzalez,F.J.; cDNA and amino acid sequences of two members of the human P450IIC gene subfamily; *Nucleic Acids Res.;* 1987, 15 (23), 10053-10054.

Romkes,M., Faletto,M.B., Blaisdell,J.A., Raucy,J.L. and Goldstein,J.A.; Cloning and expression of complementary DNAs for multiple members of the human cytochrome P450IIC subfamily; *Biochemistry;* 1991, 30 (13), 3247-3255.

Gonzalez,F.J., Vilbois,F., Hardwick,J.P., McBride,O.W., Nebert,D. W., Gelboin,H.V. and Meyer,U.A.; Human debrisoquine 4-hydroxylase (P450IID1): cDNA and deduced amino acid sequence and assignment of the CYP2D locus to chromosome 22; *Genomics,* 1988, vol. 2 (2), 174-179.

David R. Nelson et al., P450 Superfamily: update on new sequences, gene mapping, accession numbers and nomenclature, *Pharmacogenetics* 6 1-42 (1996).

Nienaber et al., Re-engineering of Human Urokinase Provides a System for Structure-based Drug Design at High Resolution and Reveals a Novel Structural Subsite, *J. Biol. Chem.* 275(10) 7239-7248 (2000).

Dale et al., Crystal Engineering: deletion mutagenesis of the 24 kDa fragment of the DNA gyrase B subunit from *Staphylococcus aureus, Acta Crystallographica* D55, 1626-1629 (1999).

Wolfram Schiweck and Arne Skerra, The Rational Construction of an Antibody against Cystatin: Lessons from the crystal structure of an artificial Fab fragment, *J. Mol. Biol.* 268 934-951 (1997).

Stephen R. Price and Kiyoshi Nagai, Protein Engineering as a Tool for Crystallography, *Current Opinion in Biotechnology* 6 425-430 (1995).

Lawson et al., Solving the Structure of Human H Ferritin by Genetically Engineering Intermolecular Crystal Contacts, *Nature* 349 541-544 (1991).

Park Sam-Yong et al, Crystallization and Preliminary X-ray Diffraction Analysis of a Cytochrome P450 (CYP119) from *Sulfobus solfataricus,* Acta Crystallographica Section D Biological Crystallography 56: 1173-1175, 2000.

Ridderstrom et al, Arginines 97 and 108 in CYP2C9 Are Important Determinants of the Catalytic Function, Biochemical and Biophysical Research Communications 270: 983-987, 2000.

Payne et al, Homology Modeling and Substrate Binding Study of Human CYP2C9 Enzyme, Proteins, 37: 176-190, 1999.

Ekins et al, Pharmacophore and Three-Dimensional Quantitative Structure Activity Relationship Methods For Modeling Cytochrome P450 Active Sites, Drug Metabolism and Disposition, 29: 936-944, 2001.

Stubbins et al, Genetic Analysis of the Human Cytochrome P450 CYP2C9 Locus, Pharmacogenetics, 6: 429-439, 1996.

Sueyoshi et al, Molecular Engineering of Microsomal P450 2a-4 to a Stable, Water-Soluble Enzyme, Archives of Biochemistry and Biophysics, vol. 322, No. 1, Sep. 10, 1995, pp. 265-271.

Williams et al., "Mammalian Microsomal Cytochrome P450 Monooxygenase: Structural Adaptations for Membrane Binding and Functional Diversity," Molecular Cell, vol. 5 (Jan. 2000), pp. 121-131.

Wachenfeldt et al., "Microsomal P450 2C3 Is Expressed as a Soluble Dimer in *Escherichia coli* Following Modifications of Its N-terminus," Archives of Biochemistry and Biophysics, vol. 339, No. 1 (Mar. 1997), pp. 107-114.

Cosme et al., "Engineering Microsomal Cytochrome P450 2C5 to Be a Soluble, Monomeric Enzyme," The Journal of Biological Chemistry, vol. 275, No. 4 (Jan. 2000), pp. 2545-2553.

Hasemann et al., "Crystal Structure and Refinement of Cytochrome P450$_{terp}$ at 2·3 Å Resolution," J. Mol. Biol. 236 (1994), pp. 1169-1185.

Lewis, David, "Homology modeling of human cytochromes P450 involved in xenobiotic metabolism and rationalization of substrate selectivity," Exp Toxic Pathol. 51 (1999), pp. 369-374.

Ibeanu et al., "Identification of Residues 99, 220, and 221 of Human Cytochrome P450 2C19 ad Key Determinants of Omeprazole Hydroxylase Activity," The Journal of Biological Chemistry, vol. 271, No. 21 (May 1988), pp. 12496-12501.

Williams et al, Science Jul. 30, 2004; 305: 683-686; published online Jul. 15, 2004.

Yano et al, JBC, Sep. 2004; 279: 38091-38094.

Afzelius Lovisa et al., Molecular Pharmacology, Apr. 2001; vol. 59, No. 4: 909-919.

Armelle Melet et al.; *Archives of Biochemistry and Biophysics,* vol. 409, Issue 1, Jan. 1, 2003, pp. 80-91.

Blundell, T. L. et al., Nature Reviews. Drug Discovery, Nature Publishing Group, Basingstoke, GB; vol. 1, No. 1, Jan. 2002, 45-54.

Cheng-Chung Tsao et al; *Biochemistry;* 2001; 40(7), 1937-1944.

Dansette, Patrick M.; Universite Rene Descartes, Paris, France. Abstract/Poster 81. Sulphenazole Derivatives as Tools for Comparing CYP 2C5 and Human 2C's: Identification of a New High Affinity Substrate (DMZ) Common to Those CYP 2C Enzymes.
de Groot, M. J. et al., *J. Med. Chem.;* 2002; 45(10); 1983-1993.
He M et al.; *Arch Biochem Biophys.* Dec. 1, 1999;372(1):16-28.
Hutzler, J.M. et al.; *Archives of Biochemistry and Biophysics;* 2003, 410, 16-24.
Hutzler, J.M. et al.; *Drug Metabolism and Disposition,* 2002, vol. 30, pp. 1194-1200.
Hutzler, J.M.et al.; *Drug Metabolism and Disposition,* 2001, vol. 29, 1029-1034.
Kaminsky LS, Zhang ZY.; *Pharmacol Ther.* 1997;73(1):67-74.
Kunze KL et al.; *Drug Metab Dispos. 1996 Apr.;* 24(4):414-21.
Lewis, D. F. V., Archives of Biochemistry and Biophysics; 2003, vol. 409, No. 1: 32-44.
Longenecker KL et al.; *Acta Crystallogr D Biol Crystallogr,* 2001, 57(Pt 5), 679-88.
Mansuy, Daniel: Universite Rene Descartes, Paris, France. Abstract 5. Origin of Substrate Specificity of Cytochromes P450 2C: Chemical and Biochemical Approaches.
Marques-Soares, C. et al; *Biochemistry ;* 2003; 42(21); 6363-6369.
Ravichandran K G et al., *Science,* vol. 261, pp. 731-736, Aug. 6, 1993.
Schoch GA et al; *J Biol. Chem.* Mar. 5, 2004; 279(10): 9497-9503.
Wester et al., JBC, Aug. 2004; 279: 35630-35637.
Zamora, I.; Afzelius, L.; Cruciani, G.; *J. Med. Chem.,* 2003; 46(12); 2313-2324.
Zamora, Isobel; Lead Molecular Design, S.L. Sant Cugat del Valles, Spain. Abstract/Poster 77. Metabolism Prediction for Cytochrome P450.
Caffre, Journal of Structural Biolo 2003, 142 (1), 108-132.
Mestres, Proteins: Structure, Function, and Bioinformatics (2005), 58(3), 596-609.
Tickle et al, Chem. Soc. Rev. (2004), 33 (8), 558-565.
Partial International Search Report dated Nov. 2, 2005 issued in connection with PCT/GB2005/001642.
Boddupalli et al, Proc. Natl. Acad. Sci., 1992, vol. 89, pp. 5567-5571.
Shimizu et al, Journal of Inorganic Biochemistry 81 (2000) 191-205.
Obayashi et al, Journal of Inorganic Biochemistry 82 (2000) 103-111.
Ost et al, Biochemistry 2001, 40, 13430-13438.
Ost et al, J. Am. Chem. Soc. 2003, 125, 15010-15020.
Li et al, Acta Cryst. (1995), D51, 21-32.
Ravichandran et al, Science, 1993, vol. 261, pp. 731-736.
Poulos, The Journal of Biological Chemistry, 1982, vol. 257, No. 17, 10427-10429.
Raag et al, Biochemistry 1991, 30, 11420-11429.
Hishiki et al, J. Biochem. 2000, 128, 965-974.
Vidakovic et al, Biochemistry, 1998, vol. 37, No. 26, pp. 9211-9219.
Caffrey, Journal of Structural Biology (2003), 142(1), 108-132.
Mestres, Proteins: Structurem Function, and Bioinformatics (2005), 58(3):596-609.
Tickle et al, Chem. Soc. Rev. (2004), 33(8), 558-565.
Partial International Search Report dated Nov. 2, 2005 issued in connection with PCT/GB2005/001642.

Figure 1 (162 pages)

Table 3

Copyright © 2002-2003 Astex Technology Ltd. All rights reserved.

| | | | | | | | |
|---|---|---|---|---|---|---|---|
| 0 | 0 | 2 | 7.678 | 5.328 | 0.000 | 0.00 | 0.000 |
| 0 | 0 | 4 | 596.002 | 13.637 | 830.981 | 0.00 | 1.000 |
| 0 | 0 | 8 | 503.049 | 10.762 | 147.045 | 0.00 | 0.210 |
| 0 | 0 | 10 | 916.070 | 19.109 | 1270.218 | 180.00 | 1.000 |
| 0 | 0 | 12 | 1667.431 | 37.857 | 2301.430 | 0.00 | 1.000 |
| 0 | 0 | 14 | 616.081 | 13.226 | 849.169 | 180.00 | 1.000 |
| 0 | 0 | 16 | 295.837 | 5.555 | 406.223 | 0.00 | 1.000 |
| 0 | 0 | 18 | 478.528 | 7.881 | 653.782 | 180.00 | 1.000 |
| 0 | 0 | 20 | 42.184 | 12.801 | 39.119 | 180.00 | 0.707 |
| 0 | 0 | 22 | 245.609 | 5.074 | 332.299 | 180.00 | 1.000 |
| 0 | 0 | 24 | 516.627 | 8.288 | 694.534 | 180.00 | 1.000 |
| 0 | 0 | 26 | 173.434 | 7.253 | 153.749 | 0.00 | 0.664 |
| 0 | 0 | 28 | 558.227 | 11.628 | 740.466 | 180.00 | 1.000 |
| 0 | 0 | 30 | 218.609 | 7.254 | 287.593 | 180.00 | 1.000 |
| 0 | 0 | 32 | 649.374 | 10.457 | 848.003 | 180.00 | 1.000 |
| 0 | 0 | 34 | 338.306 | 8.815 | 438.050 | 180.00 | 1.000 |
| 0 | 0 | 36 | 493.791 | 12.528 | 632.769 | 180.00 | 1.000 |
| 0 | 0 | 38 | 408.290 | 10.917 | 517.902 | 180.00 | 1.000 |
| 0 | 0 | 40 | 41.633 | 18.048 | 47.023 | 180.00 | 0.906 |
| 0 | 0 | 42 | 59.069 | 23.691 | 66.989 | 180.00 | 0.939 |
| 0 | 1 | 3 | 41.208 | 2.888 | 28.295 | 180.00 | 0.492 |
| 0 | 1 | 5 | 231.950 | 3.847 | 323.319 | 0.00 | 1.000 |
| 0 | 1 | 7 | 280.814 | 4.914 | 390.902 | 0.00 | 1.000 |
| 0 | 1 | 9 | 268.971 | 4.644 | 370.105 | 180.00 | 0.990 |
| 0 | 1 | 11 | 720.470 | 11.467 | 997.930 | 0.00 | 1.000 |
| 0 | 1 | 13 | 654.992 | 10.734 | 904.492 | 0.00 | 1.000 |
| 0 | 1 | 15 | 289.882 | 5.360 | 398.960 | 0.00 | 1.000 |
| 0 | 1 | 17 | 151.011 | 3.380 | 206.821 | 180.00 | 0.999 |
| 0 | 1 | 19 | 413.113 | 6.356 | 563.356 | 0.00 | 1.000 |
| 0 | 1 | 21 | 63.302 | 6.270 | 83.903 | 180.00 | 0.977 |
| 0 | 1 | 23 | 41.428 | 13.475 | 41.569 | 180.00 | 0.746 |
| 0 | 1 | 25 | 205.171 | 3.970 | 275.053 | 0.00 | 1.000 |
| 0 | 1 | 27 | 490.380 | 5.933 | 653.005 | 180.00 | 1.000 |
| 0 | 1 | 29 | 56.986 | 12.351 | 49.666 | 180.00 | 0.660 |
| 0 | 1 | 31 | 497.590 | 6.479 | 652.621 | 180.00 | 1.000 |
| 0 | 1 | 33 | 50.154 | 17.623 | 33.915 | 180.00 | 0.522 |
| 0 | 1 | 35 | 231.352 | 6.226 | 298.200 | 180.00 | 1.000 |
| 0 | 1 | 37 | 180.542 | 10.622 | 229.834 | 180.00 | 1.000 |
| 0 | 1 | 39 | 135.559 | 14.749 | 169.434 | 180.00 | 0.998 |
| 0 | 1 | 41 | 37.164 | 16.228 | 23.833 | 0.00 | 0.523 |
| 0 | 1 | 43 | 152.116 | 19.701 | 179.259 | 0.00 | 1.000 |
| 0 | 2 | 2 | 140.539 | 6.938 | 190.335 | 180.00 | 0.974 |
| 0 | 2 | 4 | 1211.783 | 21.028 | 1686.511 | 180.00 | 1.000 |
| 0 | 2 | 6 | 1398.622 | 35.122 | 1936.348 | 0.00 | 1.000 |
| 0 | 2 | 8 | 78.700 | 3.148 | 25.835 | 180.00 | 0.239 |
| 0 | 2 | 10 | 59.943 | 7.012 | 5.014 | 180.00 | 0.061 |
| 0 | 2 | 12 | 472.409 | 7.508 | 652.878 | 180.00 | 1.000 |
| 0 | 2 | 14 | 82.791 | 6.536 | 73.908 | 0.00 | 0.655 |
| 0 | 2 | 16 | 389.267 | 5.605 | 534.532 | 180.00 | 1.000 |
| 0 | 2 | 18 | 284.901 | 4.870 | 388.783 | 0.00 | 1.000 |
| 0 | 2 | 20 | 575.406 | 7.975 | 782.239 | 0.00 | 1.000 |
| 0 | 2 | 22 | 330.070 | 4.307 | 446.576 | 180.00 | 1.000 |
| 0 | 2 | 24 | 308.920 | 4.068 | 415.120 | 0.00 | 1.000 |
| 0 | 2 | 26 | 28.229 | 11.562 | 16.518 | 0.00 | 0.461 |
| 0 | 2 | 28 | 69.409 | 11.141 | 62.494 | 0.00 | 0.680 |
| 0 | 2 | 30 | 205.586 | 5.143 | 270.430 | 180.00 | 1.000 |
| 0 | 2 | 32 | 203.158 | 6.796 | 265.194 | 180.00 | 1.000 |
| 0 | 2 | 34 | 123.294 | 8.814 | 159.347 | 0.00 | 0.999 |
| 0 | 2 | 36 | 51.215 | 21.651 | 64.223 | 0.00 | 0.997 |
| 0 | 2 | 38 | 62.877 | 21.263 | 18.630 | 0.00 | 0.238 |
| 0 | 2 | 40 | 41.608 | 15.958 | 12.290 | 0.00 | 0.238 |
| 0 | 2 | 42 | 160.997 | 8.970 | 170.566 | 0.00 | 0.858 |
| 0 | 3 | 1 | 38.765 | 3.616 | 30.472 | 0.00 | 0.575 |
| 0 | 3 | 3 | 325.122 | 5.394 | 453.725 | 180.00 | 1.000 |
| 0 | 3 | 5 | 89.991 | 2.103 | 101.024 | 180.00 | 0.808 |
| 0 | 3 | 7 | 104.357 | 3.034 | 48.943 | 180.00 | 0.338 |
| 0 | 3 | 9 | 478.549 | 8.676 | 664.641 | 180.00 | 1.000 |
| 0 | 3 | 11 | 638.075 | 9.069 | 883.873 | 180.00 | 1.000 |

| | | | | | | | |
|---|---|---|---|---|---|---|---|
| 0 | 3 | 13 | 271.203 | 4.637 | 374.479 | 180.00 | 1.000 |
| 0 | 3 | 15 | 622.079 | 10.378 | 855.789 | 180.00 | 1.000 |
| 0 | 3 | 17 | 126.171 | 5.440 | 172.666 | 0.00 | 1.000 |
| 0 | 3 | 19 | 208.942 | 5.388 | 284.721 | 180.00 | 1.000 |
| 0 | 3 | 21 | 597.539 | 9.479 | 809.981 | 180.00 | 1.000 |
| 0 | 3 | 23 | 160.201 | 4.588 | 207.254 | 0.00 | 0.959 |
| 0 | 3 | 25 | 175.917 | 5.689 | 235.725 | 0.00 | 1.000 |
| 0 | 3 | 27 | 52.856 | 12.920 | 30.866 | 0.00 | 0.439 |
| 0 | 3 | 29 | 328.860 | 5.916 | 434.714 | 0.00 | 1.000 |
| 0 | 3 | 31 | 268.842 | 4.903 | 352.627 | 0.00 | 1.000 |
| 0 | 3 | 33 | 237.369 | 5.989 | 308.713 | 180.00 | 1.000 |
| 0 | 3 | 35 | 525.110 | 6.901 | 676.655 | 0.00 | 1.000 |
| 0 | 3 | 37 | 119.482 | 9.578 | 152.145 | 180.00 | 1.000 |
| 0 | 3 | 39 | 40.968 | 16.493 | 46.383 | 180.00 | 0.907 |
| 0 | 3 | 41 | 31.111 | 14.412 | 33.412 | 0.00 | 0.873 |
| 0 | 4 | 2 | 978.619 | 27.264 | 1360.805 | 180.00 | 1.000 |
| 0 | 4 | 4 | 1051.887 | 15.095 | 1479.632 | 180.00 | 1.000 |
| 0 | 4 | 6 | 416.927 | 5.476 | 580.079 | 180.00 | 1.000 |
| 0 | 4 | 8 | 925.546 | 13.955 | 1286.069 | 180.00 | 1.000 |
| 0 | 4 | 10 | 263.453 | 4.822 | 365.112 | 180.00 | 0.999 |
| 0 | 4 | 12 | 453.626 | 12.596 | 626.735 | 0.00 | 1.000 |
| 0 | 4 | 14 | 500.311 | 8.026 | 689.530 | 0.00 | 1.000 |
| 0 | 4 | 16 | 159.513 | 3.745 | 218.892 | 180.00 | 1.000 |
| 0 | 4 | 18 | 85.165 | 9.157 | 84.170 | 0.00 | 0.736 |
| 0 | 4 | 20 | 135.946 | 4.123 | 166.668 | 0.00 | 0.903 |
| 0 | 4 | 22 | 169.260 | 4.735 | 97.439 | 0.00 | 0.426 |
| 0 | 4 | 24 | 54.517 | 11.344 | 49.018 | 0.00 | 0.687 |
| 0 | 4 | 26 | 207.613 | 4.385 | 277.237 | 180.00 | 1.000 |
| 0 | 4 | 28 | 100.500 | 7.343 | 131.702 | 0.00 | 0.988 |
| 0 | 4 | 30 | 308.269 | 4.873 | 405.796 | 0.00 | 1.000 |
| 0 | 4 | 32 | 33.806 | 13.924 | 17.845 | 0.00 | 0.411 |
| 0 | 4 | 34 | 364.047 | 6.026 | 471.329 | 0.00 | 1.000 |
| 0 | 4 | 36 | 175.087 | 9.746 | 224.069 | 0.00 | 1.000 |
| 0 | 4 | 38 | 89.461 | 13.381 | 59.360 | 180.00 | 0.527 |
| 0 | 4 | 40 | 115.520 | 11.887 | 144.045 | 180.00 | 1.000 |
| 0 | 4 | 42 | 63.106 | 29.569 | 64.788 | 180.00 | 0.906 |
| 0 | 5 | 1 | 144.213 | 2.467 | 163.347 | 180.00 | 0.814 |
| 0 | 5 | 3 | 558.858 | 9.218 | 779.627 | 180.00 | 1.000 |
| 0 | 5 | 5 | 385.159 | 9.401 | 534.980 | 180.00 | 0.997 |
| 0 | 5 | 7 | 180.764 | 3.272 | 222.577 | 0.00 | 0.887 |
| 0 | 5 | 9 | 260.038 | 4.614 | 356.295 | 0.00 | 0.986 |
| 0 | 5 | 11 | 785.753 | 11.827 | 1088.069 | 180.00 | 1.000 |
| 0 | 5 | 13 | 418.919 | 7.585 | 578.286 | 0.00 | 1.000 |
| 0 | 5 | 15 | 478.832 | 8.651 | 658.683 | 0.00 | 1.000 |
| 0 | 5 | 17 | 242.688 | 4.766 | 300.896 | 0.00 | 0.905 |
| 0 | 5 | 19 | 182.440 | 4.866 | 248.456 | 0.00 | 1.000 |
| 0 | 5 | 21 | 127.149 | 4.510 | 172.473 | 180.00 | 1.000 |
| 0 | 5 | 23 | 294.604 | 4.941 | 397.293 | 0.00 | 1.000 |
| 0 | 5 | 25 | 163.905 | 4.775 | 219.498 | 180.00 | 1.000 |
| 0 | 5 | 27 | 139.479 | 7.469 | 185.342 | 180.00 | 0.998 |
| 0 | 5 | 29 | 65.088 | 15.952 | 22.539 | 0.00 | 0.263 |
| 0 | 5 | 31 | 279.675 | 5.038 | 366.740 | 180.00 | 1.000 |
| 0 | 5 | 33 | 338.795 | 5.894 | 440.558 | 0.00 | 1.000 |
| 0 | 5 | 35 | 296.743 | 6.196 | 382.366 | 0.00 | 1.000 |
| 0 | 5 | 37 | 102.516 | 13.388 | 128.027 | 180.00 | 0.985 |
| 0 | 5 | 39 | 82.249 | 18.647 | 100.895 | 180.00 | 0.988 |
| 0 | 5 | 41 | 47.128 | 17.733 | 27.510 | 180.00 | 0.480 |
| 0 | 6 | 0 | 131.484 | 3.204 | 155.401 | 180.00 | 0.854 |
| 0 | 6 | 2 | 266.773 | 3.849 | 372.123 | 180.00 | 1.000 |
| 0 | 6 | 4 | 659.148 | 7.361 | 919.135 | 180.00 | 1.000 |
| 0 | 6 | 6 | 832.037 | 11.819 | 1158.183 | 0.00 | 1.000 |
| 0 | 6 | 8 | 443.086 | 6.872 | 615.887 | 0.00 | 1.000 |
| 0 | 6 | 10 | 579.444 | 7.980 | 803.627 | 0.00 | 1.000 |
| 0 | 6 | 12 | 188.239 | 3.220 | 259.531 | 0.00 | 1.000 |
| 0 | 6 | 14 | 105.413 | 3.958 | 144.420 | 180.00 | 0.997 |
| 0 | 6 | 16 | 76.266 | 11.501 | 93.408 | 180.00 | 0.895 |
| 0 | 6 | 18 | 258.171 | 7.370 | 352.301 | 180.00 | 1.000 |
| 0 | 6 | 20 | 326.879 | 5.406 | 444.429 | 180.00 | 1.000 |
| 0 | 6 | 22 | 180.218 | 4.457 | 243.745 | 180.00 | 1.000 |
| 0 | 6 | 24 | 25.229 | 12.174 | 8.372 | 180.00 | 0.269 |
| 0 | 6 | 26 | 210.852 | 5.858 | 281.547 | 0.00 | 1.000 |
| 0 | 6 | 28 | 284.863 | 5.554 | 377.890 | 0.00 | 1.000 |
| 0 | 6 | 30 | 64.369 | 15.941 | 5.797 | 180.00 | 0.069 |
| 0 | 6 | 32 | 126.177 | 8.985 | 155.357 | 0.00 | 0.944 |
| 0 | 6 | 34 | 330.130 | 6.415 | 427.293 | 180.00 | 1.000 |
| 0 | 6 | 36 | 76.579 | 19.838 | 95.749 | 0.00 | 0.988 |
| 0 | 6 | 38 | 158.078 | 7.718 | 200.364 | 0.00 | 1.000 |

| | | | | | | | |
|---|---|---|---|---|---|---|---|
| 0 | 6 | 40 | 183.184 | 8.414 | 229.335 | 0.00 | 1.000 |
| 0 | 6 | 42 | 40.690 | 24.786 | 42.088 | 0.00 | 0.909 |
| 0 | 7 | 1 | 511.656 | 5.560 | 713.895 | 180.00 | 1.000 |
| 0 | 7 | 3 | 634.838 | 7.094 | 885.644 | 0.00 | 1.000 |
| 0 | 7 | 5 | 358.989 | 5.063 | 499.923 | 0.00 | 1.000 |
| 0 | 7 | 7 | 838.119 | 10.296 | 1165.817 | 180.00 | 1.000 |
| 0 | 7 | 9 | 204.783 | 3.787 | 267.667 | 0.00 | 0.941 |
| 0 | 7 | 11 | 389.025 | 5.478 | 538.539 | 180.00 | 1.000 |
| 0 | 7 | 13 | 471.789 | 6.622 | 651.090 | 180.00 | 1.000 |
| 0 | 7 | 15 | 299.977 | 4.651 | 412.669 | 180.00 | 1.000 |
| 0 | 7 | 17 | 131.263 | 3.811 | 179.124 | 180.00 | 0.999 |
| 0 | 7 | 19 | 135.592 | 4.588 | 184.126 | 180.00 | 1.000 |
| 0 | 7 | 21 | 249.754 | 5.467 | 338.719 | 180.00 | 1.000 |
| 0 | 7 | 23 | 38.269 | 15.123 | 2.735 | 0.00 | 0.054 |
| 0 | 7 | 25 | 353.793 | 5.697 | 473.977 | 180.00 | 1.000 |
| 0 | 7 | 27 | 29.355 | 13.212 | 30.859 | 180.00 | 0.793 |
| 0 | 7 | 29 | 809.198 | 14.281 | 1067.235 | 0.00 | 1.000 |
| 0 | 7 | 31 | 134.739 | 9.680 | 169.772 | 0.00 | 0.963 |
| 0 | 7 | 33 | 246.259 | 6.805 | 320.078 | 180.00 | 1.000 |
| 0 | 7 | 35 | 39.071 | 16.801 | 32.712 | 180.00 | 0.657 |
| 0 | 7 | 37 | 48.982 | 19.220 | 4.479 | 180.00 | 0.073 |
| 0 | 7 | 39 | 46.106 | 16.980 | 37.108 | 180.00 | 0.648 |
| 0 | 7 | 41 | 29.200 | 14.274 | 5.302 | 180.00 | 0.149 |
| 0 | 8 | 0 | 249.840 | 4.125 | 319.012 | 0.00 | 0.916 |
| 0 | 8 | 2 | 328.168 | 4.581 | 457.881 | 0.00 | 1.000 |
| 0 | 8 | 4 | 275.883 | 3.971 | 384.624 | 180.00 | 1.000 |
| 0 | 8 | 6 | 404.904 | 5.623 | 563.622 | 0.00 | 1.000 |
| 0 | 8 | 8 | 140.368 | 3.017 | 155.736 | 180.00 | 0.799 |
| 0 | 8 | 10 | 22.273 | 7.666 | 17.948 | 0.00 | 0.595 |
| 0 | 8 | 12 | 797.021 | 10.961 | 1101.536 | 180.00 | 1.000 |
| 0 | 8 | 14 | 419.659 | 7.637 | 578.115 | 180.00 | 1.000 |
| 0 | 8 | 16 | 260.371 | 4.342 | 357.375 | 180.00 | 1.000 |
| 0 | 8 | 18 | 30.433 | 13.020 | 10.247 | 0.00 | 0.259 |
| 0 | 8 | 20 | 79.294 | 11.834 | 107.325 | 180.00 | 0.999 |
| 0 | 8 | 22 | 307.264 | 5.319 | 415.517 | 180.00 | 1.000 |
| 0 | 8 | 24 | 79.379 | 10.564 | 92.621 | 180.00 | 0.872 |
| 0 | 8 | 26 | 187.632 | 6.087 | 250.525 | 0.00 | 1.000 |
| 0 | 8 | 28 | 61.326 | 18.304 | 79.297 | 0.00 | 0.979 |
| 0 | 8 | 30 | 189.165 | 6.710 | 245.456 | 180.00 | 0.986 |
| 0 | 8 | 32 | 291.532 | 8.069 | 380.368 | 0.00 | 1.000 |
| 0 | 8 | 34 | 191.807 | 10.890 | 247.761 | 180.00 | 1.000 |
| 0 | 8 | 36 | 84.142 | 15.770 | 44.969 | 0.00 | 0.421 |
| 0 | 8 | 38 | 110.779 | 14.955 | 137.659 | 180.00 | 0.990 |
| 0 | 8 | 40 | 24.407 | 12.246 | 3.534 | 180.00 | 0.117 |
| 0 | 9 | 1 | 291.852 | 4.584 | 360.158 | 180.00 | 0.886 |
| 0 | 9 | 3 | 102.028 | 4.251 | 58.098 | 180.00 | 0.408 |
| 0 | 9 | 5 | 180.528 | 3.656 | 217.953 | 0.00 | 0.870 |
| 0 | 9 | 7 | 28.344 | 8.396 | 0.640 | 180.00 | 0.020 |
| 0 | 9 | 9 | 35.790 | 8.698 | 30.606 | 180.00 | 0.617 |
| 0 | 9 | 11 | 218.741 | 3.170 | 302.257 | 0.00 | 1.000 |
| 0 | 9 | 13 | 97.544 | 4.405 | 124.169 | 0.00 | 0.934 |
| 0 | 9 | 15 | 94.555 | 4.731 | 39.179 | 0.00 | 0.301 |
| 0 | 9 | 17 | 82.642 | 4.831 | 110.695 | 180.00 | 0.988 |
| 0 | 9 | 19 | 381.728 | 5.567 | 519.963 | 0.00 | 1.000 |
| 0 | 9 | 21 | 24.744 | 10.621 | 0.249 | 0.00 | 0.007 |
| 0 | 9 | 23 | 132.437 | 7.109 | 178.037 | 0.00 | 1.000 |
| 0 | 9 | 25 | 188.504 | 4.949 | 252.197 | 0.00 | 1.000 |
| 0 | 9 | 27 | 240.752 | 6.756 | 320.348 | 0.00 | 1.000 |
| 0 | 9 | 29 | 114.550 | 10.576 | 150.919 | 0.00 | 1.000 |
| 0 | 9 | 31 | 179.288 | 6.643 | 234.739 | 0.00 | 1.000 |
| 0 | 9 | 33 | 142.439 | 18.531 | 183.930 | 180.00 | 1.000 |
| 0 | 9 | 35 | 78.450 | 21.756 | 99.416 | 0.00 | 1.000 |
| 0 | 9 | 37 | 24.646 | 12.407 | 3.826 | 180.00 | 0.126 |
| 0 | 9 | 39 | 110.005 | 13.491 | 137.040 | 0.00 | 0.999 |
| 0 | 9 | 41 | 33.832 | 22.701 | 15.562 | 180.00 | 0.406 |
| 0 | 10 | 0 | 315.322 | 5.000 | 376.211 | 0.00 | 0.855 |
| 0 | 10 | 2 | 580.132 | 7.468 | 809.265 | 180.00 | 1.000 |
| 0 | 10 | 4 | 650.875 | 7.322 | 907.253 | 0.00 | 1.000 |
| 0 | 10 | 6 | 695.424 | 10.587 | 967.835 | 180.00 | 1.000 |
| 0 | 10 | 8 | 636.723 | 7.580 | 884.704 | 0.00 | 1.000 |
| 0 | 10 | 10 | 929.065 | 11.343 | 1287.264 | 180.00 | 1.000 |
| 0 | 10 | 12 | 327.623 | 4.201 | 452.838 | 0.00 | 1.000 |
| 0 | 10 | 14 | 68.228 | 5.228 | 64.259 | 180.00 | 0.685 |
| 0 | 10 | 16 | 40.073 | 14.611 | 42.246 | 0.00 | 0.771 |
| 0 | 10 | 18 | 233.874 | 4.214 | 319.440 | 0.00 | 1.000 |
| 0 | 10 | 20 | 170.819 | 4.272 | 232.198 | 0.00 | 1.000 |
| 0 | 10 | 22 | 440.273 | 6.707 | 595.122 | 0.00 | 1.000 |

| | | | | | | | |
|---|---|---|---|---|---|---|---|
| 0 | 10 | 24 | 38.843 | 14.693 | 46.118 | 0.00 | 0.890 |
| 0 | 10 | 26 | 826.902 | 12.260 | 1102.773 | 0.00 | 1.000 |
| 0 | 10 | 28 | 326.306 | 6.027 | 432.611 | 180.00 | 1.000 |
| 0 | 10 | 30 | 546.454 | 9.583 | 718.396 | 0.00 | 1.000 |
| 0 | 10 | 32 | 90.546 | 15.549 | 91.526 | 0.00 | 0.778 |
| 0 | 10 | 34 | 47.989 | 17.938 | 10.864 | 180.00 | 0.176 |
| 0 | 10 | 36 | 67.721 | 21.093 | 83.249 | 0.00 | 0.978 |
| 0 | 10 | 38 | 61.683 | 16.952 | 70.271 | 0.00 | 0.913 |
| 0 | 10 | 40 | 35.266 | 15.994 | 13.851 | 180.00 | 0.321 |
| 0 | 11 | 1 | 44.370 | 4.950 | 31.766 | 0.00 | 0.559 |
| 0 | 11 | 3 | 357.236 | 5.728 | 498.129 | 180.00 | 1.000 |
| 0 | 11 | 5 | 105.777 | 4.706 | 145.467 | 0.00 | 1.000 |
| 0 | 11 | 7 | 600.867 | 7.864 | 835.175 | 180.00 | 1.000 |
| 0 | 11 | 9 | 19.076 | 8.695 | 8.309 | 0.00 | 0.315 |
| 0 | 11 | 11 | 246.013 | 3.452 | 339.950 | 180.00 | 1.000 |
| 0 | 11 | 13 | 223.640 | 3.514 | 307.480 | 0.00 | 0.999 |
| 0 | 11 | 15 | 223.763 | 3.525 | 307.608 | 180.00 | 1.000 |
| 0 | 11 | 17 | 145.477 | 4.235 | 198.486 | 0.00 | 1.000 |
| 0 | 11 | 19 | 54.827 | 12.327 | 44.217 | 180.00 | 0.611 |
| 0 | 11 | 21 | 260.857 | 4.815 | 353.612 | 0.00 | 1.000 |
| 0 | 11 | 23 | 180.531 | 4.532 | 243.033 | 180.00 | 1.000 |
| 0 | 11 | 25 | 179.359 | 7.464 | 238.953 | 180.00 | 0.997 |
| 0 | 11 | 27 | 84.307 | 12.610 | 91.327 | 0.00 | 0.816 |
| 0 | 11 | 29 | 103.367 | 9.891 | 135.330 | 0.00 | 0.994 |
| 0 | 11 | 31 | 118.973 | 15.604 | 152.637 | 180.00 | 0.985 |
| 0 | 11 | 33 | 392.598 | 7.783 | 509.676 | 0.00 | 1.000 |
| 0 | 11 | 35 | 128.963 | 12.078 | 165.096 | 180.00 | 1.000 |
| 0 | 11 | 37 | 33.745 | 15.323 | 20.376 | 0.00 | 0.486 |
| 0 | 11 | 39 | 45.263 | 17.689 | 30.207 | 0.00 | 0.544 |
| 0 | 12 | 0 | 665.409 | 9.968 | 928.120 | 180.00 | 1.000 |
| 0 | 12 | 2 | 208.336 | 3.069 | 290.567 | 0.00 | 1.000 |
| 0 | 12 | 4 | 402.687 | 5.728 | 561.122 | 0.00 | 1.000 |
| 0 | 12 | 6 | 598.082 | 7.760 | 832.138 | 0.00 | 1.000 |
| 0 | 12 | 8 | 190.630 | 5.200 | 264.792 | 180.00 | 1.000 |
| 0 | 12 | 10 | 101.762 | 5.973 | 136.586 | 180.00 | 0.969 |
| 0 | 12 | 12 | 555.043 | 6.676 | 766.700 | 180.00 | 1.000 |
| 0 | 12 | 14 | 444.244 | 5.179 | 611.713 | 180.00 | 1.000 |
| 0 | 12 | 16 | 125.750 | 3.748 | 172.068 | 0.00 | 0.997 |
| 0 | 12 | 18 | 594.822 | 8.910 | 811.771 | 0.00 | 1.000 |
| 0 | 12 | 20 | 353.446 | 4.595 | 480.343 | 0.00 | 1.000 |
| 0 | 12 | 22 | 289.939 | 4.315 | 391.912 | 180.00 | 1.000 |
| 0 | 12 | 24 | 607.672 | 8.393 | 816.078 | 180.00 | 1.000 |
| 0 | 12 | 26 | 273.178 | 6.384 | 364.586 | 180.00 | 1.000 |
| 0 | 12 | 28 | 425.746 | 6.683 | 564.162 | 180.00 | 1.000 |
| 0 | 12 | 30 | 44.288 | 11.834 | 11.834 | 0.00 | 0.204 |
| 0 | 12 | 32 | 373.314 | 7.020 | 486.794 | 0.00 | 1.000 |
| 0 | 12 | 34 | 186.052 | 9.371 | 239.984 | 180.00 | 1.000 |
| 0 | 12 | 36 | 200.012 | 9.592 | 255.286 | 180.00 | 1.000 |
| 0 | 12 | 38 | 61.323 | 16.781 | 66.286 | 180.00 | 0.871 |
| 0 | 12 | 40 | 114.644 | 21.289 | 136.055 | 180.00 | 1.000 |
| 0 | 13 | 1 | 271.161 | 3.501 | 377.473 | 0.00 | 1.000 |
| 0 | 13 | 3 | 321.787 | 3.989 | 448.537 | 180.00 | 1.000 |
| 0 | 13 | 5 | 438.653 | 5.224 | 610.341 | 180.00 | 1.000 |
| 0 | 13 | 7 | 225.914 | 3.470 | 313.269 | 0.00 | 1.000 |
| 0 | 13 | 9 | 372.857 | 4.531 | 517.225 | 180.00 | 1.000 |
| 0 | 13 | 11 | 33.640 | 11.162 | 23.689 | 0.00 | 0.559 |
| 0 | 13 | 13 | 443.047 | 5.470 | 610.648 | 180.00 | 1.000 |
| 0 | 13 | 15 | 112.474 | 5.171 | 145.898 | 180.00 | 0.944 |
| 0 | 13 | 17 | 35.425 | 10.668 | 27.531 | 180.00 | 0.600 |
| 0 | 13 | 19 | 136.071 | 4.717 | 184.515 | 0.00 | 1.000 |
| 0 | 13 | 21 | 157.836 | 4.419 | 213.749 | 180.00 | 0.999 |
| 0 | 13 | 23 | 350.130 | 4.829 | 471.639 | 0.00 | 1.000 |
| 0 | 13 | 25 | 32.680 | 13.303 | 15.359 | 180.00 | 0.369 |
| 0 | 13 | 27 | 152.866 | 5.744 | 203.263 | 0.00 | 1.000 |
| 0 | 13 | 29 | 129.913 | 8.042 | 171.117 | 180.00 | 1.000 |
| 0 | 13 | 31 | 293.322 | 6.126 | 383.973 | 180.00 | 1.000 |
| 0 | 13 | 33 | 97.284 | 12.273 | 124.228 | 0.00 | 0.988 |
| 0 | 13 | 35 | 62.614 | 20.680 | 71.265 | 180.00 | 0.904 |
| 0 | 13 | 37 | 32.334 | 14.570 | 38.642 | 0.00 | 0.963 |
| 0 | 13 | 39 | 29.043 | 20.484 | 0.828 | 180.00 | 0.025 |
| 0 | 14 | 0 | 111.333 | 6.979 | 154.258 | 0.00 | 0.994 |
| 0 | 14 | 2 | 36.262 | 10.320 | 2.569 | 0.00 | 0.051 |
| 0 | 14 | 4 | 71.645 | 5.647 | 91.423 | 0.00 | 0.916 |
| 0 | 14 | 6 | 317.291 | 4.774 | 441.310 | 180.00 | 1.000 |
| 0 | 14 | 8 | 501.628 | 6.079 | 696.300 | 180.00 | 1.000 |
| 0 | 14 | 10 | 33.377 | 11.969 | 33.434 | 180.00 | 0.725 |
| 0 | 14 | 12 | 508.081 | 7.426 | 701.419 | 180.00 | 1.000 |

| | | | | | | | |
|---|---|---|---|---|---|---|---|
| 0 | 14 | 14 | 331.040 | 4.333 | 455.708 | 0.00 | 1.000 |
| 0 | 14 | 16 | 212.061 | 3.700 | 290.550 | 0.00 | 0.999 |
| 0 | 14 | 18 | 482.146 | 6.085 | 658.088 | 0.00 | 1.000 |
| 0 | 14 | 20 | 464.118 | 7.367 | 630.264 | 180.00 | 1.000 |
| 0 | 14 | 22 | 418.760 | 5.432 | 565.754 | 0.00 | 1.000 |
| 0 | 14 | 24 | 221.621 | 4.758 | 290.193 | 0.00 | 0.975 |
| 0 | 14 | 26 | 40.446 | 14.184 | 51.048 | 0.00 | 0.948 |
| 0 | 14 | 28 | 440.401 | 6.218 | 583.325 | 0.00 | 1.000 |
| 0 | 14 | 30 | 166.007 | 8.819 | 218.013 | 0.00 | 1.000 |
| 0 | 14 | 32 | 158.378 | 12.195 | 205.656 | 0.00 | 1.000 |
| 0 | 14 | 34 | 41.151 | 18.555 | 22.898 | 0.00 | 0.437 |
| 0 | 14 | 36 | 28.225 | 13.520 | 20.447 | 0.00 | 0.573 |
| 0 | 14 | 38 | 33.165 | 16.099 | 16.705 | 0.00 | 0.408 |
| 0 | 15 | 1 | 170.240 | 2.941 | 236.456 | 0.00 | 1.000 |
| 0 | 15 | 3 | 43.330 | 10.337 | 34.621 | 180.00 | 0.574 |
| 0 | 15 | 5 | 75.846 | 4.779 | 43.756 | 180.00 | 0.422 |
| 0 | 15 | 7 | 42.407 | 14.071 | 49.572 | 0.00 | 0.895 |
| 0 | 15 | 9 | 18.377 | 8.607 | 8.932 | 0.00 | 0.352 |
| 0 | 15 | 11 | 28.066 | 10.490 | 30.000 | 0.00 | 0.858 |
| 0 | 15 | 13 | 269.392 | 4.792 | 370.964 | 0.00 | 1.000 |
| 0 | 15 | 15 | 76.916 | 8.108 | 105.374 | 180.00 | 0.998 |
| 0 | 15 | 17 | 20.049 | 9.768 | 7.051 | 0.00 | 0.297 |
| 0 | 15 | 19 | 244.139 | 4.242 | 305.830 | 0.00 | 0.921 |
| 0 | 15 | 21 | 41.288 | 12.474 | 42.162 | 180.00 | 0.756 |
| 0 | 15 | 23 | 150.407 | 6.294 | 202.189 | 0.00 | 1.000 |
| 0 | 15 | 25 | 298.750 | 4.929 | 399.673 | 180.00 | 1.000 |
| 0 | 15 | 27 | 91.532 | 15.825 | 120.750 | 180.00 | 0.996 |
| 0 | 15 | 29 | 113.748 | 8.298 | 149.747 | 0.00 | 1.000 |
| 0 | 15 | 31 | 97.829 | 10.418 | 93.950 | 0.00 | 0.737 |
| 0 | 15 | 33 | 31.799 | 14.147 | 36.912 | 0.00 | 0.903 |
| 0 | 15 | 35 | 52.935 | 17.176 | 41.146 | 0.00 | 0.617 |
| 0 | 15 | 37 | 35.468 | 16.547 | 10.583 | 0.00 | 0.242 |
| 0 | 16 | 0 | 144.198 | 6.230 | 4.573 | 180.00 | 0.023 |
| 0 | 16 | 2 | 258.653 | 3.815 | 360.341 | 0.00 | 1.000 |
| 0 | 16 | 4 | 162.090 | 4.022 | 225.594 | 180.00 | 1.000 |
| 0 | 16 | 6 | 180.076 | 3.758 | 250.220 | 0.00 | 1.000 |
| 0 | 16 | 8 | 139.587 | 4.232 | 179.169 | 0.00 | 0.925 |
| 0 | 16 | 10 | 32.342 | 12.602 | 10.256 | 180.00 | 0.230 |
| 0 | 16 | 12 | 286.324 | 4.029 | 395.239 | 180.00 | 1.000 |
| 0 | 16 | 14 | 273.895 | 4.047 | 376.857 | 0.00 | 1.000 |
| 0 | 16 | 16 | 313.239 | 5.356 | 429.277 | 0.00 | 1.000 |
| 0 | 16 | 18 | 29.797 | 12.089 | 25.631 | 0.00 | 0.640 |
| 0 | 16 | 20 | 270.965 | 4.516 | 367.924 | 180.00 | 1.000 |
| 0 | 16 | 22 | 216.677 | 6.252 | 292.548 | 180.00 | 1.000 |
| 0 | 16 | 24 | 24.855 | 11.744 | 28.578 | 0.00 | 0.868 |
| 0 | 16 | 26 | 37.905 | 14.813 | 26.333 | 0.00 | 0.524 |
| 0 | 16 | 28 | 53.199 | 17.367 | 39.094 | 180.00 | 0.558 |
| 0 | 16 | 30 | 57.708 | 18.453 | 65.447 | 180.00 | 0.872 |
| 0 | 16 | 32 | 121.840 | 18.707 | 156.417 | 180.00 | 1.000 |
| 0 | 16 | 34 | 49.746 | 18.761 | 16.818 | 180.00 | 0.267 |
| 0 | 16 | 36 | 44.543 | 16.008 | 38.251 | 0.00 | 0.687 |
| 0 | 16 | 38 | 51.291 | 29.102 | 38.625 | 180.00 | 0.674 |
| 0 | 17 | 1 | 223.718 | 3.725 | 311.016 | 0.00 | 0.999 |
| 0 | 17 | 3 | 283.779 | 4.370 | 395.129 | 180.00 | 1.000 |
| 0 | 17 | 5 | 20.741 | 9.720 | 2.086 | 0.00 | 0.086 |
| 0 | 17 | 7 | 504.040 | 5.740 | 699.697 | 180.00 | 1.000 |
| 0 | 17 | 9 | 271.535 | 3.861 | 376.342 | 180.00 | 1.000 |
| 0 | 17 | 11 | 115.937 | 4.083 | 142.930 | 0.00 | 0.895 |
| 0 | 17 | 13 | 30.314 | 12.798 | 20.882 | 0.00 | 0.533 |
| 0 | 17 | 15 | 343.486 | 4.623 | 471.606 | 0.00 | 1.000 |
| 0 | 17 | 17 | 93.461 | 8.998 | 124.954 | 180.00 | 0.982 |
| 0 | 17 | 19 | 30.062 | 13.326 | 16.198 | 180.00 | 0.415 |
| 0 | 17 | 21 | 171.367 | 5.014 | 231.991 | 0.00 | 1.000 |
| 0 | 17 | 23 | 390.022 | 6.119 | 524.840 | 0.00 | 1.000 |
| 0 | 17 | 25 | 33.929 | 14.781 | 23.048 | 0.00 | 0.521 |
| 0 | 17 | 27 | 134.476 | 10.036 | 178.358 | 0.00 | 1.000 |
| 0 | 17 | 29 | 376.366 | 5.583 | 496.134 | 180.00 | 1.000 |
| 0 | 17 | 31 | 46.737 | 16.439 | 37.221 | 180.00 | 0.619 |
| 0 | 17 | 33 | 68.951 | 21.087 | 87.164 | 180.00 | 1.000 |
| 0 | 17 | 35 | 37.027 | 15.322 | 14.793 | 180.00 | 0.318 |
| 0 | 17 | 37 | 36.226 | 24.768 | 26.257 | 180.00 | 0.652 |
| 0 | 18 | 0 | 928.352 | 14.512 | 1291.494 | 180.00 | 1.000 |
| 0 | 18 | 2 | 465.399 | 5.292 | 647.946 | 180.00 | 1.000 |
| 0 | 18 | 4 | 91.722 | 7.594 | 108.013 | 180.00 | 0.848 |
| 0 | 18 | 6 | 534.152 | 6.094 | 741.977 | 0.00 | 1.000 |
| 0 | 18 | 8 | 42.266 | 11.983 | 17.685 | 180.00 | 0.304 |
| 0 | 18 | 10 | 202.974 | 3.471 | 280.866 | 0.00 | 1.000 |

| | | | | | | | |
|---|---|---|---|---|---|---|---|
| 0 | 18 | 12 | 34.031 | 12.066 | 40.175 | 180.00 | 0.880 |
| 0 | 18 | 14 | 31.096 | 12.710 | 10.206 | 0.00 | 0.242 |
| 0 | 18 | 16 | 622.365 | 7.323 | 852.277 | 180.00 | 1.000 |
| 0 | 18 | 18 | 65.136 | 12.992 | 4.175 | 180.00 | 0.047 |
| 0 | 18 | 20 | 74.174 | 10.702 | 88.916 | 180.00 | 0.886 |
| 0 | 18 | 22 | 117.903 | 7.060 | 159.046 | 180.00 | 1.000 |
| 0 | 18 | 24 | 260.738 | 8.921 | 337.628 | 0.00 | 0.966 |
| 0 | 18 | 26 | 238.514 | 5.978 | 317.761 | 180.00 | 1.000 |
| 0 | 18 | 28 | 76.955 | 16.093 | 4.708 | 180.00 | 0.047 |
| 0 | 18 | 30 | 37.662 | 16.301 | 29.235 | 180.00 | 0.601 |
| 0 | 18 | 32 | 99.128 | 10.616 | 128.316 | 180.00 | 1.000 |
| 0 | 18 | 34 | 35.054 | 15.864 | 8.149 | 0.00 | 0.184 |
| 0 | 18 | 36 | 39.405 | 24.050 | 13.718 | 180.00 | 0.298 |
| 0 | 19 | 1 | 181.972 | 4.328 | 253.095 | 180.00 | 1.000 |
| 0 | 19 | 3 | 257.121 | 4.274 | 357.818 | 180.00 | 1.000 |
| 0 | 19 | 5 | 28.593 | 11.101 | 4.532 | 0.00 | 0.119 |
| 0 | 19 | 7 | 405.517 | 6.001 | 562.628 | 0.00 | 1.000 |
| 0 | 19 | 9 | 126.117 | 5.230 | 174.670 | 0.00 | 1.000 |
| 0 | 19 | 11 | 286.054 | 4.196 | 395.090 | 180.00 | 1.000 |
| 0 | 19 | 13 | 54.747 | 11.034 | 38.545 | 180.00 | 0.517 |
| 0 | 19 | 15 | 710.585 | 8.382 | 974.595 | 180.00 | 1.000 |
| 0 | 19 | 17 | 76.386 | 12.192 | 14.881 | 180.00 | 0.143 |
| 0 | 19 | 19 | 100.764 | 13.741 | 129.907 | 180.00 | 0.952 |
| 0 | 19 | 21 | 479.776 | 7.930 | 648.762 | 180.00 | 1.000 |
| 0 | 19 | 23 | 337.396 | 6.167 | 453.502 | 0.00 | 1.000 |
| 0 | 19 | 25 | 54.361 | 22.056 | 51.837 | 180.00 | 0.724 |
| 0 | 19 | 27 | 343.773 | 5.865 | 456.175 | 0.00 | 1.000 |
| 0 | 19 | 29 | 247.841 | 5.797 | 326.320 | 0.00 | 1.000 |
| 0 | 19 | 31 | 33.597 | 15.662 | 41.202 | 180.00 | 0.957 |
| 0 | 19 | 33 | 53.681 | 17.730 | 66.647 | 0.00 | 0.984 |
| 0 | 19 | 35 | 60.941 | 35.130 | 38.850 | 0.00 | 0.585 |
| 0 | 20 | 0 | 562.451 | 9.167 | 782.589 | 180.00 | 1.000 |
| 0 | 20 | 2 | 152.422 | 4.133 | 212.001 | 180.00 | 1.000 |
| 0 | 20 | 4 | 89.387 | 11.132 | 19.445 | 0.00 | 0.157 |
| 0 | 20 | 6 | 629.355 | 7.331 | 873.561 | 180.00 | 1.000 |
| 0 | 20 | 8 | 502.437 | 6.824 | 696.251 | 0.00 | 1.000 |
| 0 | 20 | 10 | 262.494 | 4.197 | 363.009 | 0.00 | 1.000 |
| 0 | 20 | 12 | 97.972 | 7.914 | 132.115 | 180.00 | 0.982 |
| 0 | 20 | 14 | 223.240 | 4.719 | 306.745 | 180.00 | 1.000 |
| 0 | 20 | 16 | 67.210 | 15.708 | 91.087 | 180.00 | 0.994 |
| 0 | 20 | 18 | 218.394 | 5.311 | 297.468 | 180.00 | 1.000 |
| 0 | 20 | 20 | 263.386 | 6.147 | 353.859 | 0.00 | 0.991 |
| 0 | 20 | 22 | 54.579 | 14.489 | 48.189 | 180.00 | 0.657 |
| 0 | 20 | 24 | 66.261 | 16.295 | 86.323 | 0.00 | 0.981 |
| 0 | 20 | 26 | 164.768 | 7.214 | 218.649 | 180.00 | 0.998 |
| 0 | 20 | 28 | 126.155 | 13.495 | 165.515 | 0.00 | 1.000 |
| 0 | 20 | 30 | 91.670 | 12.387 | 115.195 | 0.00 | 0.967 |
| 0 | 20 | 32 | 114.794 | 13.053 | 147.243 | 180.00 | 1.000 |
| 0 | 20 | 34 | 120.374 | 15.750 | 150.507 | 0.00 | 1.000 |
| 0 | 21 | 1 | 73.168 | 8.263 | 100.079 | 180.00 | 0.986 |
| 0 | 21 | 3 | 348.712 | 4.559 | 484.976 | 180.00 | 1.000 |
| 0 | 21 | 5 | 124.540 | 6.752 | 172.834 | 180.00 | 1.000 |
| 0 | 21 | 7 | 44.757 | 14.574 | 38.326 | 0.00 | 0.623 |
| 0 | 21 | 9 | 43.476 | 13.700 | 14.104 | 0.00 | 0.235 |
| 0 | 21 | 11 | 44.891 | 16.019 | 28.221 | 180.00 | 0.459 |
| 0 | 21 | 13 | 266.426 | 4.906 | 366.629 | 0.00 | 1.000 |
| 0 | 21 | 15 | 20.494 | 10.200 | 12.401 | 180.00 | 0.442 |
| 0 | 21 | 17 | 246.998 | 6.270 | 335.490 | 0.00 | 0.995 |
| 0 | 21 | 19 | 197.199 | 5.316 | 127.259 | 180.00 | 0.475 |
| 0 | 21 | 21 | 198.623 | 6.609 | 268.425 | 180.00 | 1.000 |
| 0 | 21 | 23 | 115.319 | 15.518 | 154.151 | 180.00 | 1.000 |
| 0 | 21 | 25 | 177.252 | 12.627 | 235.487 | 180.00 | 1.000 |
| 0 | 21 | 27 | 27.728 | 13.047 | 3.903 | 0.00 | 0.107 |
| 0 | 21 | 29 | 190.006 | 7.661 | 247.855 | 180.00 | 0.994 |
| 0 | 21 | 31 | 251.644 | 5.633 | 328.102 | 180.00 | 1.000 |
| 0 | 21 | 33 | 131.598 | 16.551 | 135.820 | 180.00 | 0.825 |
| 0 | 22 | 0 | 39.752 | 20.759 | 4.715 | 180.00 | 0.089 |
| 0 | 22 | 2 | 180.614 | 5.152 | 251.069 | 0.00 | 1.000 |
| 0 | 22 | 4 | 125.350 | 7.608 | 12.800 | 0.00 | 0.074 |
| 0 | 22 | 6 | 216.324 | 5.477 | 299.887 | 180.00 | 1.000 |
| 0 | 22 | 8 | 252.182 | 4.572 | 349.279 | 0.00 | 1.000 |
| 0 | 22 | 10 | 133.932 | 6.057 | 184.474 | 180.00 | 0.997 |
| 0 | 22 | 12 | 298.023 | 4.730 | 402.673 | 180.00 | 0.981 |
| 0 | 22 | 14 | 364.663 | 4.933 | 500.772 | 0.00 | 1.000 |
| 0 | 22 | 16 | 63.540 | 17.164 | 67.107 | 0.00 | 0.776 |
| 0 | 22 | 18 | 330.165 | 6.155 | 449.414 | 0.00 | 1.000 |
| 0 | 22 | 20 | 425.496 | 6.191 | 576.375 | 180.00 | 1.000 |

| | | | | | | | |
|---|---|---|---|---|---|---|---|
| 0 | 22 | 22 | 116.192 | 10.375 | 156.190 | 180.00 | 1.000 |
| 0 | 22 | 24 | 245.986 | 7.433 | 328.883 | 0.00 | 1.000 |
| 0 | 22 | 26 | 208.610 | 7.005 | 277.075 | 0.00 | 1.000 |
| 0 | 22 | 28 | 289.936 | 6.519 | 382.309 | 0.00 | 1.000 |
| 0 | 22 | 30 | 114.748 | 10.366 | 148.950 | 180.00 | 1.000 |
| 0 | 22 | 32 | 46.803 | 26.120 | 29.245 | 0.00 | 0.530 |
| 0 | 23 | 1 | 346.761 | 4.875 | 482.148 | 0.00 | 1.000 |
| 0 | 23 | 3 | 487.026 | 5.973 | 676.743 | 0.00 | 1.000 |
| 0 | 23 | 5 | 36.367 | 14.121 | 42.589 | 0.00 | 0.847 |
| 0 | 23 | 7 | 660.148 | 9.275 | 914.293 | 0.00 | 1.000 |
| 0 | 23 | 9 | 53.934 | 13.927 | 29.344 | 180.00 | 0.394 |
| 0 | 23 | 11 | 39.094 | 15.907 | 26.111 | 0.00 | 0.486 |
| 0 | 23 | 13 | 260.227 | 4.808 | 357.873 | 0.00 | 1.000 |
| 0 | 23 | 15 | 53.752 | 18.544 | 35.646 | 0.00 | 0.487 |
| 0 | 23 | 17 | 230.220 | 4.897 | 314.112 | 180.00 | 1.000 |
| 0 | 23 | 19 | 314.184 | 7.556 | 426.320 | 180.00 | 1.000 |
| 0 | 23 | 21 | 103.817 | 11.626 | 139.517 | 0.00 | 0.998 |
| 0 | 23 | 23 | 40.647 | 14.890 | 49.699 | 180.00 | 0.919 |
| 0 | 23 | 25 | 59.286 | 23.365 | 67.456 | 180.00 | 0.877 |
| 0 | 23 | 27 | 54.074 | 19.093 | 69.633 | 0.00 | 0.996 |
| 0 | 23 | 29 | 43.516 | 17.159 | 26.581 | 0.00 | 0.478 |
| 0 | 23 | 31 | 33.071 | 22.023 | 17.189 | 180.00 | 0.441 |
| 0 | 24 | 0 | 33.853 | 20.656 | 3.931 | 180.00 | 0.089 |
| 0 | 24 | 2 | 153.383 | 6.374 | 212.991 | 0.00 | 1.000 |
| 0 | 24 | 4 | 357.864 | 6.277 | 496.764 | 0.00 | 1.000 |
| 0 | 24 | 6 | 44.202 | 11.369 | 56.654 | 0.00 | 0.946 |
| 0 | 24 | 8 | 293.189 | 4.756 | 405.778 | 0.00 | 1.000 |
| 0 | 24 | 10 | 79.497 | 16.276 | 62.586 | 180.00 | 0.573 |
| 0 | 24 | 12 | 86.779 | 9.629 | 78.258 | 0.00 | 0.659 |
| 0 | 24 | 14 | 138.814 | 8.465 | 190.180 | 0.00 | 1.000 |
| 0 | 24 | 16 | 114.587 | 12.560 | 119.465 | 180.00 | 0.765 |
| 0 | 24 | 18 | 46.093 | 14.951 | 60.949 | 180.00 | 0.988 |
| 0 | 24 | 20 | 29.678 | 14.342 | 30.905 | 180.00 | 0.783 |
| 0 | 24 | 22 | 95.518 | 13.853 | 127.183 | 180.00 | 0.998 |
| 0 | 24 | 24 | 39.285 | 17.208 | 14.099 | 180.00 | 0.275 |
| 0 | 24 | 26 | 143.541 | 7.385 | 190.137 | 0.00 | 1.000 |
| 0 | 24 | 28 | 104.471 | 20.102 | 124.996 | 0.00 | 0.946 |
| 0 | 24 | 30 | 106.112 | 36.587 | 94.548 | 0.00 | 0.822 |
| 0 | 25 | 1 | 335.792 | 5.019 | 466.508 | 180.00 | 1.000 |
| 0 | 25 | 3 | 295.900 | 6.211 | 410.783 | 0.00 | 1.000 |
| 0 | 25 | 5 | 394.643 | 5.464 | 547.361 | 0.00 | 1.000 |
| 0 | 25 | 7 | 64.198 | 18.734 | 53.982 | 180.00 | 0.611 |
| 0 | 25 | 9 | 323.012 | 6.511 | 446.247 | 0.00 | 1.000 |
| 0 | 25 | 11 | 102.189 | 8.638 | 22.682 | 0.00 | 0.161 |
| 0 | 25 | 13 | 341.361 | 5.514 | 468.968 | 180.00 | 1.000 |
| 0 | 25 | 15 | 148.884 | 8.930 | 203.139 | 180.00 | 0.998 |
| 0 | 25 | 17 | 231.192 | 5.689 | 315.019 | 0.00 | 1.000 |
| 0 | 25 | 19 | 43.663 | 17.926 | 58.420 | 0.00 | 1.000 |
| 0 | 25 | 21 | 48.873 | 20.309 | 63.535 | 0.00 | 0.983 |
| 0 | 25 | 23 | 36.872 | 15.664 | 43.471 | 0.00 | 0.892 |
| 0 | 25 | 25 | 165.209 | 7.492 | 179.816 | 0.00 | 0.820 |
| 0 | 25 | 27 | 128.042 | 10.689 | 167.423 | 0.00 | 1.000 |
| 0 | 26 | 0 | 57.251 | 26.710 | 60.834 | 0.00 | 0.778 |
| 0 | 26 | 2 | 395.489 | 5.990 | 548.921 | 0.00 | 1.000 |
| 0 | 26 | 4 | 464.283 | 6.373 | 643.842 | 0.00 | 1.000 |
| 0 | 26 | 6 | 513.038 | 6.289 | 710.466 | 180.00 | 1.000 |
| 0 | 26 | 8 | 308.646 | 7.871 | 426.427 | 180.00 | 1.000 |
| 0 | 26 | 10 | 241.259 | 6.425 | 332.680 | 180.00 | 1.000 |
| 0 | 26 | 12 | 153.742 | 10.059 | 16.900 | 0.00 | 0.080 |
| 0 | 26 | 14 | 28.769 | 13.157 | 19.701 | 180.00 | 0.507 |
| 0 | 26 | 16 | 233.314 | 6.408 | 318.239 | 0.00 | 1.000 |
| 0 | 26 | 18 | 47.118 | 15.789 | 30.831 | 180.00 | 0.491 |
| 0 | 26 | 20 | 255.821 | 5.414 | 345.687 | 180.00 | 1.000 |
| 0 | 26 | 22 | 170.174 | 6.543 | 228.370 | 0.00 | 1.000 |
| 0 | 26 | 24 | 46.412 | 16.657 | 17.896 | 0.00 | 0.298 |
| 0 | 26 | 26 | 23.462 | 11.911 | 22.087 | 180.00 | 0.728 |
| 0 | 27 | 1 | 230.844 | 6.085 | 320.293 | 0.00 | 1.000 |
| 0 | 27 | 3 | 84.265 | 19.849 | 78.020 | 180.00 | 0.673 |
| 0 | 27 | 5 | 329.156 | 6.435 | 455.924 | 180.00 | 1.000 |
| 0 | 27 | 7 | 61.975 | 18.636 | 73.669 | 180.00 | 0.867 |
| 0 | 27 | 9 | 59.886 | 22.283 | 81.414 | 180.00 | 0.999 |
| 0 | 27 | 11 | 131.607 | 11.951 | 180.359 | 0.00 | 1.000 |
| 0 | 27 | 13 | 145.310 | 10.029 | 198.724 | 180.00 | 1.000 |
| 0 | 27 | 15 | 125.475 | 7.774 | 171.213 | 0.00 | 1.000 |
| 0 | 27 | 17 | 140.494 | 8.490 | 189.862 | 180.00 | 0.996 |
| 0 | 27 | 19 | 270.097 | 5.430 | 365.674 | 180.00 | 1.000 |
| 0 | 27 | 21 | 33.974 | 14.251 | 20.142 | 0.00 | 0.447 |

| | | | | | | | |
|---|---|---|---|---|---|---|---|
| 0 | 27 | 23 | 110.400 | 9.688 | 51.446 | 180.00 | 0.351 |
| 0 | 27 | 25 | 39.447 | 25.710 | 13.961 | 0.00 | 0.302 |
| 0 | 28 | 0 | 253.018 | 10.367 | 350.529 | 180.00 | 1.000 |
| 0 | 28 | 2 | 130.367 | 10.174 | 180.269 | 0.00 | 1.000 |
| 0 | 28 | 4 | 298.723 | 6.170 | 413.696 | 180.00 | 1.000 |
| 0 | 28 | 6 | 39.782 | 18.019 | 52.762 | 180.00 | 0.981 |
| 0 | 28 | 8 | 53.643 | 19.133 | 71.889 | 0.00 | 0.986 |
| 0 | 28 | 10 | 138.946 | 9.988 | 190.710 | 0.00 | 1.000 |
| 0 | 28 | 12 | 183.857 | .6.239 | 252.230 | 180.00 | 1.000 |
| 0 | 28 | 14 | 213.914 | 6.629 | 292.433 | 180.00 | 1.000 |
| 0 | 28 | 16 | 31.243 | 14.254 | 18.594 | 0.00 | 0.443 |
| 0 | 28 | 18 | 32.346 | 14.874 | 36.160 | 0.00 | 0.846 |
| 0 | 28 | 20 | 81.090 | 15.715 | 97.828 | 0.00 | 0.916 |
| 0 | 28 | 22 | 34.588 | 15.397 | 29.964 | 180.00 | 0.665 |
| 0 | 28 | 24 | 119.447 | 16.073 | 137.646 | 0.00 | 0.902 |
| 0 | 29 | 1 | 155.624 | 9.587 | 214.967 | 0.00 | 1.000 |
| 0 | 29 | 3 | 72.106 | 19.781 | 98.141 | 180.00 | 1.000 |
| 0 | 29 | 5 | 133.294 | 9.879 | 183.736 | 180.00 | 1.000 |
| 0 | 29 | 7 | 206.889 | 8.964 | 284.955 | 180.00 | 1.000 |
| 0 | 29 | 9 | 41.434 | 18.033 | 15.021 | 180.00 | 0.267 |
| 0 | 29 | 11 | 175.263 | 11.715 | 239.273 | 180.00 | 1.000 |
| 0 | 29 | 13 | 163.745 | 8.618 | 223.552 | 180.00 | 1.000 |
| 0 | 29 | 15 | 95.889 | 15.738 | 128.450 | 180.00 | 1.000 |
| 0 | 29 | 17 | 34.807 | 15.048 | 46.056 | 0.00 | 0.995 |
| 0 | 29 | 19 | 128.583 | 8.589 | 150.356 | 180.00 | 0.871 |
| 0 | 29 | 21 | 33.212 | 21.120 | 37.997 | 180.00 | 0.929 |
| 0 | 30 | 0 | 105.750 | 20.228 | 113.112 | 0.00 | 0.781 |
| 0 | 30 | 2 | 50.215 | 19.305 | 54.477 | 0.00 | 0.800 |
| 0 | 30 | 4 | 24.028 | 11.587 | 0.851 | 0.00 | 0.026 |
| 0 | 30 | 6 | 126.368 | 7.334 | 174.146 | 180.00 | 1.000 |
| 0 | 30 | 8 | 158.457 | 6.409 | 218.210 | 180.00 | 1.000 |
| 0 | 30 | 10 | 118.729 | 13.533 | 147.710 | 0.00 | 0.916 |
| 0 | 30 | 12 | 31.365 | 13.624 | 3.087 | 180.00 | 0.073 |
| 0 | 30 | 14 | 131.203 | 8.106 | 176.268 | 180.00 | 0.988 |
| 0 | 30 | 16 | 70.631 | 17.498 | 91.899 | 0.00 | 0.990 |
| 0 | 30 | 18 | 26.932 | 18.802 | 21.482 | 180.00 | 0.658 |
| 0 | 31 | 1 | 54.339 | 17.708 | 52.467 | 180.00 | 0.715 |
| 0 | 31 | 3 | 220.083 | 6.143 | 303.983 | 0.00 | 1.000 |
| 0 | 31 | 5 | 36.381 | 15.328 | 5.457 | 0.00 | 0.111 |
| 0 | 31 | 7 | 35.142 | 17.180 | 33.856 | 0.00 | 0.719 |
| 0 | 31 | 9 | 121.437 | 17.923 | 162.145 | 0.00 | 1.000 |
| 0 | 31 | 11 | 168.061 | 12.144 | 227.278 | 0.00 | 1.000 |
| 0 | 31 | 13 | 31.422 | 14.407 | 18.847 | 0.00 | 0.451 |
| 0 | 31 | 15 | 84.329 | 21.089 | 107.641 | 180.00 | 0.999 |
| 0 | 31 | 17 | 28.984 | 19.864 | 29.231 | 0.00 | 0.837 |
| 0 | 32 | 0 | 46.384 | 25.747 | 4.336 | 180.00 | 0.070 |
| 0 | 32 | 2 | 43.319 | 16.615 | 27.793 | 0.00 | 0.478 |
| 0 | 32 | 4 | 73.513 | 17.751 | 97.785 | 0.00 | 0.997 |
| 0 | 32 | 6 | 33.469 | 15.238 | 23.193 | 180.00 | 0.518 |
| 0 | 32 | 8 | 165.546 | 7.282 | 226.803 | 0.00 | 1.000 |
| 0 | 32 | 10 | 42.364 | 16.558 | 6.479 | 180.00 | 0.116 |
| 0 | 32 | 12 | 52.727 | 24.095 | 30.139 | 180.00 | 0.458 |
| 0 | 33 | 1 | 43.900 | 23.482 | 35.528 | 180.00 | 0.638 |
| 0 | 33 | 3 | 31.458 | 15.041 | 7.273 | 0.00 | 0.173 |
| 0 | 33 | 5 | 31.845 | 15.240 | 27.281 | 180.00 | 0.646 |
| 0 | 33 | 7 | 63.161 | 15.860 | 79.198 | 0.00 | 0.951 |
| 1 | 0 | 1 | 5.152 | 2.523 | 0.000 | 0.00 | 0.000 |
| 1 | 0 | 3 | 6.538 | 3.417 | 0.078 | 0.00 | 0.009 |
| 1 | 0 | 5 | 600.970 | 6.634 | 837.942 | 0.00 | 1.000 |
| 1 | 0 | 7 | 332.264 | 4.669 | 462.490 | 0.00 | 1.000 |
| 1 | 0 | 9 | 31.028 | 5.369 | 6.958 | 180.00 | 0.161 |
| 1 | 0 | 11 | 397.721 | 8.583 | 548.223 | 180.00 | 0.995 |
| 1 | 0 | 13 | 26.134 | 10.574 | 2.894 | 180.00 | 0.082 |
| 1 | 0 | 15 | 370.115 | 6.028 | 509.472 | 180.00 | 1.000 |
| 1 | 0 | 17 | 55.368 | 6.763 | 11.243 | 0.00 | 0.149 |
| 1 | 0 | 19 | 134.375 | 3.968 | 153.960 | 0.00 | 0.840 |
| 1 | 0 | 21 | 55.972 | 13.056 | 34.851 | 0.00 | 0.460 |
| 1 | 0 | 23 | 45.982 | 10.790 | 30.791 | 180.00 | 0.498 |
| 1 | 0 | 25 | 245.086 | 4.927 | 328.629 | 180.00 | 1.000 |
| 1 | 0 | 27 | 198.003 | 5.930 | 263.719 | 0.00 | 1.000 |
| 1 | 0 | 29 | 74.946 | 13.713 | 87.100 | 180.00 | 0.881 |
| 1 | 0 | 31 | 125.615 | 9.699 | 164.638 | 180.00 | 1.000 |
| 1 | 0 | 33 | 119.851 | 10.158 | 72.933 | 180.00 | 0.468 |
| 1 | 0 | 35 | 80.315 | 22.096 | 102.458 | 0.00 | 0.999 |
| 1 | 0 | 37 | 56.912 | 16.653 | 44.204 | 180.00 | 0.614 |
| 1 | 0 | 39 | 25.473 | 12.566 | 2.831 | 180.00 | 0.089 |
| 1 | 0 | 41 | 45.726 | 14.135 | 28.415 | 180.00 | 0.504 |

| | | | | | | | |
|---|---|---|---|---|---|---|---|
| 1 | 0 | 43 | 93.295 | 42.981 | 23.683 | 0.00 | 0.255 |
| 1 | 1 | 0 | 11.761 | 2.899 | 5.103 | 0.00 | 0.312 |
| 1 | 1 | 2 | 45.528 | 13.716 | 573.931 | 81.86 | 0.803 |
| 1 | 1 | 4 | 657.703 | 5.246 | 794.201 | 115.75 | 0.992 |
| 1 | 1 | 6 | 452.118 | 3.990 | 589.090 | 4.79 | 0.974 |
| 1 | 1 | 8 | 310.576 | 4.381 | 490.151 | 107.00 | 0.970 |
| 1 | 1 | 10 | 650.403 | 5.961 | 922.948 | 96.05 | 0.989 |
| 1 | 1 | 12 | 389.017 | 3.644 | 493.490 | 180.50 | 0.963 |
| 1 | 1 | 14 | 330.113 | 3.246 | 477.627 | 214.00 | 0.987 |
| 1 | 1 | 16 | 378.790 | 3.918 | 499.442 | 244.91 | 0.993 |
| 1 | 1 | 18 | 287.665 | 3.370 | 414.461 | 250.24 | 0.980 |
| 1 | 1 | 20 | 421.159 | 4.519 | 529.327 | 54.51 | 0.994 |
| 1 | 1 | 22 | 125.557 | 3.535 | 152.681 | 111.42 | 0.976 |
| 1 | 1 | 24 | 191.563 | 3.323 | 234.831 | 271.63 | 0.966 |
| 1 | 1 | 26 | 114.453 | 4.524 | 163.340 | 209.06 | 0.902 |
| 1 | 1 | 28 | 198.787 | 3.939 | 227.158 | 282.29 | 0.983 |
| 1 | 1 | 30 | 176.630 | 3.975 | 265.877 | 157.71 | 0.952 |
| 1 | 1 | 32 | 169.148 | 4.177 | 240.307 | 259.52 | 0.955 |
| 1 | 1 | 34 | 238.386 | 4.676 | 368.582 | 257.93 | 0.973 |
| 1 | 1 | 36 | 123.320 | 6.754 | 93.412 | 265.31 | 0.956 |
| 1 | 1 | 38 | 185.742 | 5.853 | 283.864 | 290.14 | 0.975 |
| 1 | 1 | 40 | 165.085 | 6.637 | 279.316 | 227.47 | 0.947 |
| 1 | 1 | 42 | 69.563 | 13.475 | 68.738 | 319.05 | 0.827 |
| 1 | 2 | 1 | 34.294 | 10.447 | 16.459 | 280.86 | 0.075 |
| 1 | 2 | 3 | 213.956 | 2.379 | 335.867 | 226.17 | 0.900 |
| 1 | 2 | 5 | 576.752 | 5.088 | 883.047 | 103.41 | 0.980 |
| 1 | 2 | 7 | 216.289 | 2.140 | 263.988 | 161.09 | 0.961 |
| 1 | 2 | 9 | 615.332 | 5.642 | 848.675 | 37.59 | 0.985 |
| 1 | 2 | 11 | 498.147 | 4.922 | 720.333 | 349.06 | 0.976 |
| 1 | 2 | 13 | 442.797 | 5.018 | 627.623 | 80.69 | 0.992 |
| 1 | 2 | 15 | 254.345 | 3.058 | 294.399 | 277.66 | 0.982 |
| 1 | 2 | 17 | 193.740 | 2.975 | 291.425 | 116.43 | 0.951 |
| 1 | 2 | 19 | 140.332 | 3.326 | 141.446 | 215.40 | 0.961 |
| 1 | 2 | 21 | 256.042 | 3.201 | 389.487 | 105.18 | 0.979 |
| 1 | 2 | 23 | 125.288 | 4.271 | 160.089 | 320.59 | 0.919 |
| 1 | 2 | 25 | 271.044 | 3.564 | 426.547 | 66.98 | 0.975 |
| 1 | 2 | 27 | 59.992 | 7.944 | 14.611 | 159.50 | 0.262 |
| 1 | 2 | 29 | 262.641 | 3.617 | 317.399 | 151.20 | 0.986 |
| 1 | 2 | 31 | 138.923 | 5.026 | 155.271 | 162.49 | 0.946 |
| 1 | 2 | 33 | 63.448 | 14.277 | 20.450 | 104.42 | 0.400 |
| 1 | 2 | 35 | 172.865 | 8.732 | 263.963 | 248.40 | 0.960 |
| 1 | 2 | 37 | 295.408 | 6.552 | 368.973 | 95.47 | 0.993 |
| 1 | 2 | 39 | 133.619 | 9.374 | 133.091 | 217.12 | 0.947 |
| 1 | 2 | 41 | 91.116 | 10.783 | 116.841 | 32.58 | 0.900 |
| 1 | 2 | 43 | 85.548 | 17.667 | 118.268 | 8.48 | 0.795 |
| 1 | 3 | 0 | 5.647 | 4.049 | 0.278 | 0.00 | 0.047 |
| 1 | 3 | 2 | 280.485 | 3.437 | 287.663 | 206.27 | 0.976 |
| 1 | 3 | 4 | 459.688 | 4.214 | 649.061 | 249.80 | 0.985 |
| 1 | 3 | 6 | 661.389 | 6.688 | 891.919 | 261.03 | 0.987 |
| 1 | 3 | 8 | 614.865 | 5.598 | 859.586 | 357.89 | 0.984 |
| 1 | 3 | 10 | 466.002 | 4.655 | 663.842 | 286.90 | 0.985 |
| 1 | 3 | 12 | 623.169 | 5.478 | 889.882 | 53.23 | 0.984 |
| 1 | 3 | 14 | 462.448 | 4.493 | 618.576 | 46.79 | 0.994 |
| 1 | 3 | 16 | 352.776 | 4.931 | 497.977 | 104.82 | 0.990 |
| 1 | 3 | 18 | 429.548 | 5.906 | 649.254 | 350.07 | 0.993 |
| 1 | 3 | 20 | 149.225 | 4.180 | 155.609 | 189.79 | 0.968 |
| 1 | 3 | 22 | 269.053 | 4.938 | 387.040 | 216.84 | 0.982 |
| 1 | 3 | 24 | 146.841 | 4.005 | 169.763 | 208.33 | 0.946 |
| 1 | 3 | 26 | 365.738 | 4.244 | 530.272 | 280.76 | 0.992 |
| 1 | 3 | 28 | 110.574 | 5.157 | 122.084 | 36.38 | 0.946 |
| 1 | 3 | 30 | 177.691 | 4.489 | 264.762 | 318.20 | 0.955 |
| 1 | 3 | 32 | 56.288 | 11.722 | 29.139 | 311.99 | 0.449 |
| 1 | 3 | 34 | 199.471 | 4.548 | 230.224 | 332.61 | 0.973 |
| 1 | 3 | 36 | 37.041 | 11.120 | 2.782 | 71.30 | 0.159 |
| 1 | 3 | 38 | 112.515 | 7.429 | 164.240 | 94.66 | 0.928 |
| 1 | 3 | 40 | 119.244 | 6.618 | 128.316 | 221.89 | 0.958 |
| 1 | 3 | 42 | 65.498 | 16.093 | 59.752 | 115.89 | 0.717 |
| 1 | 4 | 1 | 368.645 | 3.286 | 488.387 | 100.12 | 0.970 |
| 1 | 4 | 3 | 138.031 | 1.745 | 143.521 | 156.78 | 0.945 |
| 1 | 4 | 5 | 165.776 | 1.850 | 220.011 | 303.68 | 0.892 |
| 1 | 4 | 7 | 452.333 | 4.677 | 581.745 | 12.55 | 0.973 |
| 1 | 4 | 9 | 533.791 | 5.015 | 758.910 | 202.47 | 0.977 |
| 1 | 4 | 11 | 548.121 | 5.569 | 774.866 | 150.16 | 0.980 |
| 1 | 4 | 13 | 857.925 | 7.806 | 1213.503 | 238.65 | 0.998 |
| 1 | 4 | 15 | 278.523 | 2.848 | 323.809 | 102.16 | 0.988 |
| 1 | 4 | 17 | 538.115 | 5.046 | 767.946 | 260.40 | 0.995 |
| 1 | 4 | 19 | 291.786 | 3.476 | 470.581 | 276.97 | 0.981 |

| | | | | | | | |
|---|---|---|---|---|---|---|---|
| 1 | 4 | 21 | 314.132 | 3.207 | 428.627 | 232.57 | 0.989 |
| 1 | 4 | 23 | 117.046 | 3.667 | 125.972 | 142.57 | 0.749 |
| 1 | 4 | 25 | 173.129 | 3.295 | 254.039 | 287.39 | 0.943 |
| 1 | 4 | 27 | 369.899 | 3.747 | 523.216 | 187.70 | 0.992 |
| 1 | 4 | 29 | 275.759 | 3.787 | 361.862 | 49.86 | 0.986 |
| 1 | 4 | 31 | 105.783 | 6.837 | 124.262 | 313.44 | 0.878 |
| 1 | 4 | 33 | 158.266 | 5.027 | 225.003 | 348.32 | 0.938 |
| 1 | 4 | 35 | 372.557 | 4.592 | 474.496 | 52.69 | 0.994 |
| 1 | 4 | 37 | 108.840 | 11.083 | 112.574 | 225.91 | 0.947 |
| 1 | 4 | 39 | 61.238 | 12.176 | 48.261 | 121.58 | 0.750 |
| 1 | 4 | 41 | 38.990 | 11.440 | 4.965 | 331.10 | 0.396 |
| 1 | 5 | 0 | 389.213 | 5.797 | 244.891 | 180.00 | 0.451 |
| 1 | 5 | 2 | 61.045 | 1.764 | 49.136 | 248.21 | 0.688 |
| 1 | 5 | 4 | 672.604 | 6.286 | 982.711 | 261.93 | 0.988 |
| 1 | 5 | 6 | 781.436 | 7.960 | 1180.268 | 319.89 | 0.990 |
| 1 | 5 | 8 | 170.982 | 2.395 | 218.810 | 354.87 | 0.935 |
| 1 | 5 | 10 | 193.099 | 2.292 | 268.826 | 184.22 | 0.959 |
| 1 | 5 | 12 | 243.075 | 2.592 | 369.208 | 114.52 | 0.972 |
| 1 | 5 | 14 | 265.972 | 2.953 | 369.710 | 254.58 | 0.988 |
| 1 | 5 | 16 | 189.260 | 2.543 | 268.044 | 252.41 | 0.986 |
| 1 | 5 | 18 | 211.334 | 2.529 | 288.141 | 216.00 | 0.972 |
| 1 | 5 | 20 | 336.484 | 3.118 | 439.677 | 91.52 | 0.992 |
| 1 | 5 | 22 | 263.480 | 2.793 | 322.466 | 131.63 | 0.988 |
| 1 | 5 | 24 | 162.786 | 3.563 | 204.335 | 144.46 | 0.950 |
| 1 | 5 | 26 | 123.497 | 4.489 | 125.962 | 266.55 | 0.955 |
| 1 | 5 | 28 | 405.186 | 4.076 | 502.914 | 69.56 | 0.994 |
| 1 | 5 | 30 | 177.224 | 3.970 | 188.270 | 114.07 | 0.972 |
| 1 | 5 | 32 | 155.793 | 5.011 | 192.175 | 99.26 | 0.954 |
| 1 | 5 | 34 | 369.000 | 4.659 | 472.048 | 105.11 | 0.994 |
| 1 | 5 | 36 | 48.264 | 12.758 | 11.400 | 123.32 | 0.683 |
| 1 | 5 | 38 | 108.771 | 9.998 | 121.430 | 185.95 | 0.946 |
| 1 | 5 | 40 | 79.093 | 12.870 | 39.697 | 329.95 | 0.317 |
| 1 | 5 | 42 | 81.506 | 20.223 | 63.423 | 167.96 | 0.891 |
| 1 | 6 | 1 | 334.943 | 4.310 | 459.314 | 31.16 | 0.946 |
| 1 | 6 | 3 | 370.960 | 5.527 | 496.024 | 220.33 | 0.965 |
| 1 | 6 | 5 | 507.039 | 5.409 | 613.594 | 214.31 | 0.982 |
| 1 | 6 | 7 | 453.690 | 4.366 | 751.961 | 242.72 | 0.952 |
| 1 | 6 | 9 | 652.374 | 6.489 | 947.025 | 306.14 | 0.986 |
| 1 | 6 | 11 | 443.931 | 4.742 | 549.158 | 87.72 | 0.994 |
| 1 | 6 | 13 | 603.599 | 5.434 | 878.599 | 59.41 | 0.996 |
| 1 | 6 | 15 | 282.484 | 2.832 | 404.449 | 43.11 | 0.984 |
| 1 | 6 | 17 | 184.553 | 2.766 | 257.968 | 276.30 | 0.971 |
| 1 | 6 | 19 | 264.390 | 2.921 | 357.132 | 340.24 | 0.985 |
| 1 | 6 | 21 | 273.849 | 2.760 | 344.321 | 84.84 | 0.990 |
| 1 | 6 | 23 | 79.837 | 4.669 | 91.989 | 335.26 | 0.893 |
| 1 | 6 | 25 | 252.078 | 3.010 | 347.841 | 238.10 | 0.983 |
| 1 | 6 | 27 | 452.621 | 4.429 | 586.710 | 271.56 | 0.995 |
| 1 | 6 | 29 | 282.855 | 3.760 | 366.293 | 306.95 | 0.987 |
| 1 | 6 | 31 | 97.532 | 7.519 | 96.467 | 52.96 | 0.884 |
| 1 | 6 | 33 | 75.367 | 10.469 | 51.318 | 265.84 | 0.740 |
| 1 | 6 | 35 | 240.427 | 5.379 | 326.398 | 324.15 | 0.983 |
| 1 | 6 | 37 | 143.393 | 6.530 | 239.619 | 233.24 | 0.945 |
| 1 | 6 | 39 | 69.795 | 13.501 | 32.492 | 148.78 | 0.289 |
| 1 | 6 | 41 | 91.450 | 10.210 | 125.066 | 278.69 | 0.892 |
| 1 | 7 | 0 | 162.352 | 3.531 | 225.896 | 0.00 | 0.997 |
| 1 | 7 | 2 | 479.140 | 4.321 | 692.717 | 158.75 | 0.976 |
| 1 | 7 | 4 | 507.056 | 6.300 | 774.008 | 162.64 | 0.976 |
| 1 | 7 | 6 | 378.316 | 4.142 | 570.226 | 39.73 | 0.953 |
| 1 | 7 | 8 | 85.925 | 2.672 | 52.539 | 165.75 | 0.657 |
| 1 | 7 | 10 | 358.671 | 3.548 | 464.973 | 54.23 | 0.991 |
| 1 | 7 | 12 | 435.029 | 4.602 | 578.951 | 199.96 | 0.993 |
| 1 | 7 | 14 | 25.189 | 6.780 | 22.299 | 320.20 | 0.232 |
| 1 | 7 | 16 | 58.874 | 4.820 | 44.708 | 325.02 | 0.831 |
| 1 | 7 | 18 | 182.657 | 2.762 | 251.743 | 306.86 | 0.967 |
| 1 | 7 | 20 | 120.144 | 2.716 | 128.338 | 267.82 | 0.969 |
| 1 | 7 | 22 | 186.056 | 3.397 | 285.163 | 320.96 | 0.949 |
| 1 | 7 | 24 | 280.568 | 3.263 | 351.026 | 242.72 | 0.984 |
| 1 | 7 | 26 | 199.220 | 3.091 | 247.742 | 150.51 | 0.979 |
| 1 | 7 | 28 | 267.618 | 3.383 | 365.796 | 226.59 | 0.983 |
| 1 | 7 | 30 | 135.203 | 4.907 | 202.380 | 38.60 | 0.911 |
| 1 | 7 | 32 | 258.446 | 4.135 | 296.193 | 232.40 | 0.984 |
| 1 | 7 | 34 | 138.282 | 7.268 | 193.574 | 45.12 | 0.943 |
| 1 | 7 | 36 | 54.645 | 13.855 | 34.285 | 288.14 | 0.699 |
| 1 | 7 | 38 | 69.326 | 11.250 | 59.473 | 288.95 | 0.850 |
| 1 | 7 | 40 | 57.889 | 13.824 | 43.369 | 348.80 | 0.788 |
| 1 | 7 | 42 | 80.642 | 20.685 | 78.491 | 129.79 | 0.839 |
| 1 | 8 | 1 | 411.544 | 4.165 | 586.266 | 24.55 | 0.965 |

| | | | | | | | |
|---|---|---|---|---|---|---|---|
| 1 | 8 | 3 | 672.640 | 6.272 | 1003.677 | 138.87 | 0.988 |
| 1 | 8 | 5 | 465.398 | 4.634 | 616.731 | 270.70 | 0.978 |
| 1 | 8 | 7 | 649.602 | 7.101 | 904.681 | 117.74 | 0.987 |
| 1 | 8 | 9 | 652.695 | 6.564 | 846.804 | 275.94 | 0.997 |
| 1 | 8 | 11 | 475.811 | 4.064 | 686.290 | 244.15 | 0.994 |
| 1 | 8 | 13 | 518.579 | 5.715 | 673.098 | 236.04 | 0.995 |
| 1 | 8 | 15 | 376.635 | 4.537 | 513.974 | 92.93 | 0.992 |
| 1 | 8 | 17 | 254.298 | 2.864 | 345.035 | 272.43 | 0.986 |
| 1 | 8 | 19 | 215.831 | 2.472 | 299.150 | 121.79 | 0.978 |
| 1 | 8 | 21 | 365.883 | 3.432 | 481.553 | 83.53 | 0.992 |
| 1 | 8 | 23 | 48.647 | 8.250 | 31.542 | 344.09 | 0.521 |
| 1 | 8 | 25 | 197.542 | 2.837 | 330.219 | 115.92 | 0.957 |
| 1 | 8 | 27 | 423.010 | 4.180 | 567.297 | 91.37 | 0.994 |
| 1 | 8 | 29 | 226.673 | 3.987 | 279.555 | 22.85 | 0.982 |
| 1 | 8 | 31 | 136.175 | 6.473 | 191.439 | 250.39 | 0.914 |
| 1 | 8 | 33 | 328.154 | 4.414 | 462.975 | 241.18 | 0.991 |
| 1 | 8 | 35 | 115.613 | 7.791 | 143.294 | 124.25 | 0.925 |
| 1 | 8 | 37 | 53.046 | 13.852 | 23.631 | 238.88 | 0.399 |
| 1 | 8 | 39 | 142.533 | 6.206 | 190.182 | 83.53 | 0.964 |
| 1 | 8 | 41 | 54.187 | 14.206 | 28.157 | 243.32 | 0.538 |
| 1 | 9 | 0 | 735.200 | 11.415 | 34.296 | 0.00 | 0.033 |
| 1 | 9 | 2 | 345.980 | 3.247 | 447.496 | 258.12 | 0.971 |
| 1 | 9 | 4 | 110.393 | 2.194 | 130.436 | 199.47 | 0.976 |
| 1 | 9 | 6 | 342.955 | 3.635 | 447.590 | 127.35 | 0.989 |
| 1 | 9 | 8 | 364.831 | 3.324 | 518.700 | 168.18 | 0.989 |
| 1 | 9 | 10 | 663.474 | 5.829 | 879.762 | 118.42 | 0.997 |
| 1 | 9 | 12 | 719.950 | 6.961 | 1109.191 | 266.27 | 0.997 |
| 1 | 9 | 14 | 107.915 | 2.914 | 137.773 | 124.07 | 0.892 |
| 1 | 9 | 16 | 250.871 | 2.756 | 264.992 | 311.50 | 0.988 |
| 1 | 9 | 18 | 203.008 | 2.931 | 280.650 | 199.44 | 0.972 |
| 1 | 9 | 20 | 133.067 | 2.744 | 177.360 | 98.21 | 0.944 |
| 1 | 9 | 22 | 316.256 | 3.318 | 381.815 | 84.59 | 0.989 |
| 1 | 9 | 24 | 530.368 | 4.567 | 730.013 | 64.08 | 0.996 |
| 1 | 9 | 26 | 346.037 | 3.455 | 478.701 | 336.15 | 0.991 |
| 1 | 9 | 28 | 244.186 | 3.452 | 321.983 | 263.03 | 0.983 |
| 1 | 9 | 30 | 375.730 | 3.766 | 483.246 | 305.94 | 0.992 |
| 1 | 9 | 32 | 236.115 | 4.737 | 337.209 | 14.19 | 0.975 |
| 1 | 9 | 34 | 203.881 | 4.718 | 414.397 | 65.32 | 0.885 |
| 1 | 9 | 36 | 136.574 | 5.918 | 85.501 | 78.54 | 0.977 |
| 1 | 9 | 38 | 115.290 | 7.811 | 191.747 | 338.90 | 0.816 |
| 1 | 9 | 40 | 87.509 | 10.519 | 107.685 | 312.50 | 0.903 |
| 1 | 10 | 1 | 293.038 | 4.706 | 317.388 | 165.29 | 0.988 |
| 1 | 10 | 3 | 311.232 | 3.971 | 411.742 | 85.45 | 0.992 |
| 1 | 10 | 5 | 339.124 | 3.167 | 445.088 | 104.59 | 0.990 |
| 1 | 10 | 7 | 317.687 | 3.001 | 429.380 | 141.89 | 0.987 |
| 1 | 10 | 9 | 342.379 | 3.359 | 446.832 | 284.17 | 0.993 |
| 1 | 10 | 11 | 497.855 | 5.198 | 699.373 | 94.10 | 0.994 |
| 1 | 10 | 13 | 427.495 | 4.824 | 621.118 | 105.75 | 0.993 |
| 1 | 10 | 15 | 247.616 | 2.747 | 323.063 | 48.19 | 0.990 |
| 1 | 10 | 17 | 133.905 | 2.797 | 179.152 | 176.34 | 0.925 |
| 1 | 10 | 19 | 224.748 | 2.772 | 272.864 | 235.37 | 0.977 |
| 1 | 10 | 21 | 283.579 | 3.017 | 338.036 | 269.07 | 0.991 |
| 1 | 10 | 23 | 224.428 | 2.987 | 294.373 | 2.77 | 0.981 |
| 1 | 10 | 25 | 224.060 | 3.161 | 289.817 | 27.59 | 0.979 |
| 1 | 10 | 27 | 125.908 | 5.116 | 142.063 | 256.41 | 0.957 |
| 1 | 10 | 29 | 115.178 | 5.825 | 65.520 | 9.27 | 0.951 |
| 1 | 10 | 31 | 186.089 | 4.729 | 271.645 | 319.01 | 0.955 |
| 1 | 10 | 33 | 446.101 | 4.657 | 574.420 | 80.09 | 0.996 |
| 1 | 10 | 35 | 118.781 | 7.172 | 161.184 | 90.12 | 0.947 |
| 1 | 10 | 37 | 128.969 | 6.232 | 149.466 | 295.24 | 0.962 |
| 1 | 10 | 39 | 34.707 | 11.056 | 11.875 | 298.95 | 0.489 |
| 1 | 10 | 41 | 77.025 | 17.794 | 82.383 | 178.26 | 0.704 |
| 1 | 11 | 0 | 65.837 | 5.406 | 36.756 | 180.00 | 0.402 |
| 1 | 11 | 2 | 314.645 | 2.807 | 442.002 | 296.46 | 0.985 |
| 1 | 11 | 4 | 334.173 | 3.121 | 552.754 | 114.60 | 0.984 |
| 1 | 11 | 6 | 1257.311 | 11.298 | 1760.297 | 112.75 | 0.999 |
| 1 | 11 | 8 | 191.320 | 2.301 | 299.629 | 131.91 | 0.938 |
| 1 | 11 | 10 | 243.199 | 3.236 | 286.268 | 165.10 | 0.978 |
| 1 | 11 | 12 | 395.645 | 4.197 | 560.711 | 238.27 | 0.992 |
| 1 | 11 | 14 | 444.284 | 4.453 | 660.356 | 298.58 | 0.994 |
| 1 | 11 | 16 | 204.196 | 2.696 | 348.603 | 259.71 | 0.958 |
| 1 | 11 | 18 | 97.454 | 4.125 | 93.834 | 84.43 | 0.761 |
| 1 | 11 | 20 | 273.315 | 3.008 | 505.261 | 38.57 | 0.865 |
| 1 | 11 | 22 | 368.954 | 3.643 | 513.031 | 304.17 | 0.992 |
| 1 | 11 | 24 | 102.130 | 4.913 | 83.646 | 134.39 | 0.515 |
| 1 | 11 | 26 | 325.026 | 3.291 | 436.060 | 234.93 | 0.990 |
| 1 | 11 | 28 | 199.603 | 3.513 | 231.603 | 237.90 | 0.975 |

| | | | | | | | |
|---|---|---|---|---|---|---|---|
| 1 | 11 | 30 | 251.779 | 3.760 | 320.378 | 143.43 | 0.981 |
| 1 | 11 | 32 | 64.955 | 10.465 | 30.631 | 310.87 | 0.843 |
| 1 | 11 | 34 | 90.004 | 9.273 | 98.392 | 141.60 | 0.916 |
| 1 | 11 | 36 | 89.611 | 8.233 | 93.096 | 100.12 | 0.920 |
| 1 | 11 | 38 | 50.727 | 13.161 | 9.917 | 326.41 | 0.769 |
| 1 | 11 | 40 | 40.445 | 13.143 | 4.810 | 64.73 | 0.481 |
| 1 | 12 | 1 | 205.404 | 2.294 | 255.206 | 189.43 | 0.744 |
| 1 | 12 | 3 | 228.088 | 2.286 | 304.397 | 298.49 | 0.993 |
| 1 | 12 | 5 | 202.771 | 2.365 | 220.178 | 325.43 | 0.974 |
| 1 | 12 | 7 | 680.549 | 7.863 | 990.956 | 270.85 | 0.997 |
| 1 | 12 | 9 | 523.050 | 4.662 | 782.404 | 222.64 | 0.995 |
| 1 | 12 | 11 | 590.816 | 6.305 | 826.376 | 232.61 | 0.997 |
| 1 | 12 | 13 | 44.593 | 7.453 | 19.277 | 22.80 | 0.364 |
| 1 | 12 | 15 | 490.282 | 5.184 | 617.879 | 247.74 | 0.996 |
| 1 | 12 | 17 | 48.009 | 7.258 | 44.888 | 270.36 | 0.800 |
| 1 | 12 | 19 | 377.937 | 3.626 | 504.362 | 71.89 | 0.991 |
| 1 | 12 | 21 | 289.408 | 3.228 | 431.926 | 299.62 | 0.989 |
| 1 | 12 | 23 | 200.226 | 3.336 | 318.447 | 300.31 | 0.968 |
| 1 | 12 | 25 | 285.196 | 3.544 | 378.598 | 108.70 | 0.987 |
| 1 | 12 | 27 | 95.022 | 6.970 | 122.439 | 291.61 | 0.852 |
| 1 | 12 | 29 | 41.131 | 10.497 | 20.558 | 164.90 | 0.322 |
| 1 | 12 | 31 | 124.361 | 6.623 | 170.010 | 289.28 | 0.933 |
| 1 | 12 | 33 | 143.490 | 6.196 | 162.006 | 312.04 | 0.966 |
| 1 | 12 | 35 | 133.057 | 6.174 | 177.005 | 248.67 | 0.960 |
| 1 | 12 | 37 | 81.481 | 10.170 | 96.267 | 120.35 | 0.631 |
| 1 | 12 | 39 | 48.857 | 12.641 | 23.120 | 4.53 | 0.426 |
| 1 | 13 | 0 | 298.513 | 3.643 | 416.355 | 180.00 | 1.000 |
| 1 | 13 | 2 | 342.287 | 3.176 | 489.146 | 335.70 | 0.988 |
| 1 | 13 | 4 | 286.237 | 2.896 | 465.831 | 128.31 | 0.976 |
| 1 | 13 | 6 | 411.116 | 3.408 | 597.549 | 236.14 | 0.991 |
| 1 | 13 | 8 | 338.314 | 5.475 | 451.052 | 308.31 | 0.990 |
| 1 | 13 | 10 | 219.026 | 2.606 | 300.397 | 293.00 | 0.975 |
| 1 | 13 | 12 | 238.829 | 3.305 | 343.550 | 202.78 | 0.980 |
| 1 | 13 | 14 | 228.896 | 2.835 | 362.374 | 191.55 | 0.972 |
| 1 | 13 | 16 | 498.218 | 4.384 | 644.362 | 84.11 | 0.995 |
| 1 | 13 | 18 | 277.748 | 3.166 | 324.741 | 109.04 | 0.986 |
| 1 | 13 | 20 | 347.572 | 3.595 | 519.340 | 282.57 | 0.990 |
| 1 | 13 | 22 | 444.522 | 4.250 | 546.223 | 278.90 | 0.995 |
| 1 | 13 | 24 | 738.259 | 6.806 | 979.403 | 80.68 | 0.998 |
| 1 | 13 | 26 | 354.347 | 3.759 | 440.027 | 17.62 | 0.992 |
| 1 | 13 | 28 | 217.377 | 4.357 | 261.873 | 317.65 | 0.976 |
| 1 | 13 | 30 | 252.810 | 3.871 | 291.439 | 54.20 | 0.988 |
| 1 | 13 | 32 | 185.239 | 4.548 | 209.974 | 10.89 | 0.977 |
| 1 | 13 | 34 | 41.470 | 11.835 | 7.939 | 170.28 | 0.682 |
| 1 | 13 | 36 | 75.822 | 9.794 | 84.137 | 150.28 | 0.602 |
| 1 | 13 | 38 | 90.822 | 9.527 | 89.181 | 329.47 | 0.934 |
| 1 | 13 | 40 | 59.279 | 24.302 | 32.882 | 128.24 | 0.502 |
| 1 | 14 | 1 | 542.067 | 4.773 | 787.371 | 287.48 | 0.995 |
| 1 | 14 | 3 | 306.125 | 2.782 | 442.029 | 219.15 | 0.990 |
| 1 | 14 | 5 | 255.181 | 2.517 | 364.190 | 117.89 | 0.987 |
| 1 | 14 | 7 | 483.506 | 4.494 | 743.646 | 93.93 | 0.995 |
| 1 | 14 | 9 | 357.229 | 4.004 | 495.327 | 48.32 | 0.992 |
| 1 | 14 | 11 | 440.674 | 4.137 | 627.750 | 74.71 | 0.994 |
| 1 | 14 | 13 | 462.465 | 4.939 | 652.158 | 78.80 | 0.995 |
| 1 | 14 | 15 | 220.193 | 2.937 | 326.063 | 253.75 | 0.984 |
| 1 | 14 | 17 | 213.585 | 2.962 | 264.171 | 275.73 | 0.981 |
| 1 | 14 | 19 | 191.546 | 3.129 | 233.411 | 0.50 | 0.975 |
| 1 | 14 | 21 | 417.386 | 4.179 | 579.424 | 278.78 | 0.994 |
| 1 | 14 | 23 | 143.682 | 4.447 | 207.671 | 346.59 | 0.934 |
| 1 | 14 | 25 | 156.373 | 4.095 | 139.574 | 168.14 | 0.972 |
| 1 | 14 | 27 | 212.980 | 4.294 | 275.030 | 21.57 | 0.980 |
| 1 | 14 | 29 | 234.955 | 4.849 | 352.250 | 106.62 | 0.974 |
| 1 | 14 | 31 | 156.386 | 6.346 | 174.366 | 115.09 | 0.969 |
| 1 | 14 | 33 | 37.390 | 10.967 | 17.744 | 158.29 | 0.454 |
| 1 | 14 | 35 | 78.463 | 9.549 | 63.910 | 324.42 | 0.906 |
| 1 | 14 | 37 | 142.768 | 6.071 | 178.105 | 62.79 | 0.972 |
| 1 | 14 | 39 | 70.190 | 15.380 | 90.293 | 323.43 | 0.862 |
| 1 | 15 | 0 | 120.355 | 4.410 | 167.653 | 0.00 | 1.000 |
| 1 | 15 | 2 | 140.505 | 2.342 | 137.821 | 324.46 | 0.968 |
| 1 | 15 | 4 | 45.064 | 5.294 | 36.160 | 318.84 | 0.715 |
| 1 | 15 | 6 | 280.139 | 3.062 | 444.506 | 270.18 | 0.981 |
| 1 | 15 | 8 | 129.963 | 2.935 | 194.615 | 272.35 | 0.924 |
| 1 | 15 | 10 | 349.296 | 4.323 | 485.341 | 26.56 | 0.991 |
| 1 | 15 | 12 | 136.709 | 2.925 | 124.842 | 161.23 | 0.958 |
| 1 | 15 | 14 | 101.779 | 4.399 | 93.528 | 190.43 | 0.913 |
| 1 | 15 | 16 | 278.468 | 3.061 | 356.395 | 60.12 | 0.985 |
| 1 | 15 | 18 | 260.541 | 3.131 | 364.318 | 88.54 | 0.984 |

| | | | | | | | |
|---|---|---|---|---|---|---|---|
| 1 | 15 | 20 | 285.924 | 3.230 | 398.615 | 101.48 | 0.987 |
| 1 | 15 | 22 | 277.217 | 3.495 | 311.579 | 270.98 | 0.988 |
| 1 | 15 | 24 | 218.973 | 3.503 | 265.758 | 51.96 | 0.980 |
| 1 | 15 | 26 | 459.541 | 4.995 | 618.279 | 55.21 | 0.994 |
| 1 | 15 | 28 | 174.739 | 5.916 | 195.034 | 299.01 | 0.965 |
| 1 | 15 | 30 | 202.191 | 6.203 | 272.870 | 170.93 | 0.978 |
| 1 | 15 | 32 | 40.530 | 11.434 | 2.772 | 165.77 | 0.438 |
| 1 | 15 | 34 | 154.695 | 5.472 | 201.345 | 95.45 | 0.972 |
| 1 | 15 | 36 | 65.317 | 11.811 | 57.938 | 69.79 | 0.567 |
| 1 | 15 | 38 | 55.430 | 14.082 | 22.929 | 249.11 | 0.283 |
| 1 | 16 | 1 | 237.705 | 2.559 | 308.812 | 47.03 | 0.986 |
| 1 | 16 | 3 | 220.480 | 2.434 | 310.709 | 217.45 | 0.981 |
| 1 | 16 | 5 | 228.693 | 2.520 | 305.797 | 143.74 | 0.985 |
| 1 | 16 | 7 | 162.710 | 2.625 | 232.205 | 117.73 | 0.968 |
| 1 | 16 | 9 | 267.579 | 2.623 | 387.625 | 215.10 | 0.987 |
| 1 | 16 | 11 | 154.281 | 3.205 | 173.780 | 94.86 | 0.969 |
| 1 | 16 | 13 | 241.503 | 2.727 | 290.448 | 102.32 | 0.983 |
| 1 | 16 | 15 | 395.998 | 3.549 | 523.594 | 352.10 | 0.993 |
| 1 | 16 | 17 | 214.188 | 2.983 | 292.029 | 122.16 | 0.981 |
| 1 | 16 | 19 | 75.053 | 6.776 | 59.759 | 113.07 | 0.769 |
| 1 | 16 | 21 | 194.985 | 3.498 | 230.232 | 122.31 | 0.981 |
| 1 | 16 | 23 | 320.988 | 3.637 | 426.540 | 138.13 | 0.990 |
| 1 | 16 | 25 | 207.493 | 3.638 | 258.595 | 147.60 | 0.977 |
| 1 | 16 | 27 | 313.867 | 4.608 | 414.656 | 13.04 | 0.989 |
| 1 | 16 | 29 | 209.837 | 5.442 | 281.173 | 66.50 | 0.981 |
| 1 | 16 | 31 | 111.956 | 8.188 | 158.977 | 190.46 | 0.937 |
| 1 | 16 | 33 | 111.108 | 6.887 | 96.545 | 73.37 | 0.962 |
| 1 | 16 | 35 | 54.558 | 11.359 | 14.247 | 232.94 | 0.854 |
| 1 | 16 | 37 | 32.822 | 11.013 | 2.057 | 180.55 | 0.210 |
| 1 | 17 | 0 | 176.977 | 3.385 | 246.576 | 0.00 | 1.000 |
| 1 | 17 | 2 | 349.548 | 3.102 | 533.691 | 228.75 | 0.989 |
| 1 | 17 | 4 | 221.706 | 2.869 | 310.927 | 320.08 | 0.981 |
| 1 | 17 | 6 | 348.108 | 3.100 | 460.557 | 241.15 | 0.990 |
| 1 | 17 | 8 | 237.832 | 2.611 | 366.347 | 264.08 | 0.976 |
| 1 | 17 | 10 | 317.373 | 2.927 | 464.870 | 232.24 | 0.987 |
| 1 | 17 | 12 | 328.487 | 3.651 | 563.005 | 80.24 | 0.982 |
| 1 | 17 | 14 | 264.506 | 2.872 | 343.091 | 45.02 | 0.988 |
| 1 | 17 | 16 | 64.767 | 8.296 | 38.000 | 52.32 | 0.809 |
| 1 | 17 | 18 | 162.603 | 4.366 | 168.496 | 269.33 | 0.970 |
| 1 | 17 | 20 | 151.620 | 4.251 | 208.755 | 233.25 | 0.950 |
| 1 | 17 | 22 | 476.459 | 4.927 | 562.636 | 248.90 | 0.996 |
| 1 | 17 | 24 | 415.305 | 4.430 | 562.615 | 240.01 | 0.993 |
| 1 | 17 | 26 | 56.268 | 12.210 | 5.468 | 148.90 | 0.581 |
| 1 | 17 | 28 | 190.865 | 5.103 | 197.567 | 92.87 | 0.981 |
| 1 | 17 | 30 | 131.386 | 6.876 | 87.622 | 102.77 | 0.976 |
| 1 | 17 | 32 | 138.752 | 8.768 | 177.121 | 233.32 | 0.966 |
| 1 | 17 | 34 | 68.097 | 11.092 | 53.503 | 302.73 | 0.873 |
| 1 | 17 | 36 | 43.509 | 12.754 | 14.145 | 303.37 | 0.594 |
| 1 | 18 | 1 | 263.142 | 2.703 | 409.724 | 107.11 | 0.979 |
| 1 | 18 | 3 | 95.544 | 3.536 | 97.422 | 202.80 | 0.919 |
| 1 | 18 | 5 | 155.648 | 2.701 | 139.559 | 290.17 | 0.973 |
| 1 | 18 | 7 | 252.160 | 2.772 | 352.278 | 262.39 | 0.981 |
| 1 | 18 | 9 | 38.942 | 7.963 | 6.562 | 206.94 | 0.591 |
| 1 | 18 | 11 | 320.954 | 3.023 | 423.333 | 272.82 | 0.989 |
| 1 | 18 | 13 | 101.222 | 5.594 | 72.220 | 306.49 | 0.943 |
| 1 | 18 | 15 | 148.412 | 3.241 | 164.428 | 297.59 | 0.972 |
| 1 | 18 | 17 | 533.327 | 5.234 | 879.194 | 260.71 | 0.996 |
| 1 | 18 | 19 | 311.897 | 3.905 | 424.378 | 116.40 | 0.990 |
| 1 | 18 | 21 | 53.545 | 9.196 | 29.574 | 283.57 | 0.822 |
| 1 | 18 | 23 | 344.167 | 3.999 | 461.766 | 290.59 | 0.990 |
| 1 | 18 | 25 | 325.155 | 4.464 | 493.135 | 236.22 | 0.987 |
| 1 | 18 | 27 | 335.686 | 5.370 | 434.718 | 246.97 | 0.993 |
| 1 | 18 | 29 | 133.712 | 5.876 | 164.457 | 90.68 | 0.966 |
| 1 | 18 | 31 | 97.764 | 7.883 | 94.900 | 195.54 | 0.942 |
| 1 | 18 | 33 | 84.674 | 10.021 | 80.757 | 123.36 | 0.919 |
| 1 | 18 | 35 | 99.578 | 9.370 | 159.794 | 134.91 | 0.873 |
| 1 | 19 | 0 | 214.491 | 3.561 | 298.722 | 180.00 | 1.000 |
| 1 | 19 | 2 | 214.561 | 2.747 | 301.574 | 105.21 | 0.980 |
| 1 | 19 | 4 | 389.498 | 4.340 | 569.395 | 113.80 | 0.991 |
| 1 | 19 | 6 | 273.568 | 2.809 | 343.611 | 337.02 | 0.985 |
| 1 | 19 | 8 | 255.523 | 3.232 | 328.081 | 234.02 | 0.982 |
| 1 | 19 | 10 | 448.529 | 3.775 | 542.995 | 48.45 | 0.996 |
| 1 | 19 | 12 | 73.209 | 5.123 | 69.408 | 326.76 | 0.817 |
| 1 | 19 | 14 | 382.899 | 4.681 | 498.719 | 311.65 | 0.994 |
| 1 | 19 | 16 | 75.073 | 7.760 | 61.963 | 171.03 | 0.851 |
| 1 | 19 | 18 | 248.378 | 3.239 | 319.555 | 276.27 | 0.984 |
| 1 | 19 | 20 | 379.945 | 3.609 | 523.482 | 111.79 | 0.993 |

| | | | | | | | |
|---|---|---|---|---|---|---|---|
| 1 | 19 | 22 | 99.395  | 6.380  | 99.370  | 84.16  | 0.573 |
| 1 | 19 | 24 | 183.168 | 5.064  | 219.237 | 97.90  | 0.978 |
| 1 | 19 | 26 | 258.743 | 5.567  | 339.250 | 247.75 | 0.988 |
| 1 | 19 | 28 | 162.671 | 6.119  | 228.681 | 290.74 | 0.974 |
| 1 | 19 | 30 | 52.558  | 13.635 | 27.114  | 326.88 | 0.710 |
| 1 | 19 | 32 | 109.506 | 6.815  | 180.888 | 240.69 | 0.861 |
| 1 | 19 | 34 | 157.852 | 5.589  | 225.931 | 59.95  | 0.975 |
| 1 | 19 | 36 | 58.221  | 25.180 | 33.905  | 35.24  | 0.681 |
| 1 | 20 | 1  | 126.778 | 3.706  | 220.573 | 86.83  | 0.881 |
| 1 | 20 | 3  | 345.872 | 3.242  | 447.337 | 308.42 | 0.993 |
| 1 | 20 | 5  | 520.567 | 4.649  | 642.841 | 311.20 | 0.997 |
| 1 | 20 | 7  | 392.193 | 4.015  | 548.759 | 12.43  | 0.994 |
| 1 | 20 | 9  | 195.819 | 2.953  | 256.601 | 345.70 | 0.980 |
| 1 | 20 | 11 | 180.380 | 3.218  | 254.957 | 197.89 | 0.965 |
| 1 | 20 | 13 | 239.077 | 3.082  | 330.088 | 279.86 | 0.982 |
| 1 | 20 | 15 | 257.023 | 4.301  | 453.278 | 120.45 | 0.973 |
| 1 | 20 | 17 | 30.216  | 9.052  | 35.873  | 50.70  | 0.238 |
| 1 | 20 | 19 | 32.877  | 9.987  | 55.374  | 241.74 | 0.437 |
| 1 | 20 | 21 | 207.603 | 3.650  | 280.310 | 91.14  | 0.975 |
| 1 | 20 | 23 | 107.973 | 8.493  | 145.973 | 239.67 | 0.904 |
| 1 | 20 | 25 | 227.771 | 4.490  | 246.297 | 295.79 | 0.987 |
| 1 | 20 | 27 | 64.807  | 12.934 | 36.460  | 124.93 | 0.311 |
| 1 | 20 | 29 | 129.856 | 6.532  | 137.700 | 351.63 | 0.968 |
| 1 | 20 | 31 | 73.859  | 13.659 | 78.224  | 301.14 | 0.841 |
| 1 | 20 | 33 | 111.703 | 8.235  | 141.552 | 281.09 | 0.954 |
| 1 | 21 | 0  | 77.002  | 6.798  | 101.411 | 180.00 | 0.947 |
| 1 | 21 | 2  | 88.727  | 5.046  | 123.993 | 138.09 | 0.917 |
| 1 | 21 | 4  | 337.863 | 3.702  | 450.222 | 102.14 | 0.993 |
| 1 | 21 | 6  | 427.312 | 3.753  | 510.780 | 156.67 | 0.995 |
| 1 | 21 | 8  | 330.272 | 3.195  | 429.904 | 24.85  | 0.992 |
| 1 | 21 | 10 | 249.831 | 3.152  | 389.459 | 342.40 | 0.976 |
| 1 | 21 | 12 | 398.617 | 3.649  | 527.844 | 280.55 | 0.994 |
| 1 | 21 | 14 | 168.082 | 3.657  | 192.073 | 113.92 | 0.976 |
| 1 | 21 | 16 | 189.155 | 4.661  | 276.130 | 121.19 | 0.970 |
| 1 | 21 | 18 | 64.812  | 10.235 | 15.818  | 63.03  | 0.772 |
| 1 | 21 | 20 | 132.414 | 5.881  | 136.158 | 353.16 | 0.949 |
| 1 | 21 | 22 | 355.230 | 5.003  | 483.422 | 232.59 | 0.994 |
| 1 | 21 | 24 | 192.291 | 6.878  | 274.566 | 254.45 | 0.976 |
| 1 | 21 | 26 | 149.902 | 5.776  | 172.076 | 142.57 | 0.977 |
| 1 | 21 | 28 | 153.929 | 5.266  | 198.752 | 77.07  | 0.976 |
| 1 | 21 | 30 | 191.699 | 4.386  | 292.276 | 252.44 | 0.979 |
| 1 | 21 | 32 | 146.730 | 6.738  | 237.898 | 252.57 | 0.964 |
| 1 | 21 | 34 | 67.657  | 25.598 | 48.395  | 100.51 | 0.832 |
| 1 | 22 | 1  | 290.870 | 3.125  | 403.294 | 111.04 | 0.988 |
| 1 | 22 | 3  | 303.232 | 3.213  | 419.901 | 140.94 | 0.990 |
| 1 | 22 | 5  | 288.523 | 3.565  | 471.642 | 106.60 | 0.985 |
| 1 | 22 | 7  | 238.136 | 3.979  | 400.227 | 88.91  | 0.976 |
| 1 | 22 | 9  | 358.550 | 3.536  | 427.138 | 90.65  | 0.994 |
| 1 | 22 | 11 | 289.842 | 3.241  | 370.645 | 205.28 | 0.989 |
| 1 | 22 | 13 | 155.184 | 3.794  | 267.980 | 280.72 | 0.927 |
| 1 | 22 | 15 | 399.436 | 3.726  | 517.714 | 167.05 | 0.994 |
| 1 | 22 | 17 | 64.963  | 10.908 | 9.372   | 356.83 | 0.265 |
| 1 | 22 | 19 | 411.943 | 4.197  | 550.083 | 260.20 | 0.994 |
| 1 | 22 | 21 | 288.807 | 3.978  | 364.104 | 62.54  | 0.991 |
| 1 | 22 | 23 | 107.581 | 8.381  | 98.427  | 52.45  | 0.943 |
| 1 | 22 | 25 | 77.626  | 11.221 | 87.377  | 173.90 | 0.882 |
| 1 | 22 | 27 | 186.582 | 7.569  | 226.469 | 281.91 | 0.984 |
| 1 | 22 | 29 | 109.024 | 7.806  | 115.926 | 45.73  | 0.953 |
| 1 | 22 | 31 | 40.936  | 11.646 | 4.886   | 246.86 | 0.210 |
| 1 | 22 | 33 | 43.714  | 20.224 | 9.340   | 104.61 | 0.269 |
| 1 | 23 | 0  | 275.990 | 4.492  | 383.870 | 0.00   | 1.000 |
| 1 | 23 | 2  | 473.938 | 4.215  | 699.260 | 315.96 | 0.995 |
| 1 | 23 | 4  | 111.084 | 5.622  | 170.056 | 304.73 | 0.779 |
| 1 | 23 | 6  | 257.601 | 3.516  | 272.591 | 89.18  | 0.988 |
| 1 | 23 | 8  | 35.733  | 9.993  | 38.009  | 123.54 | 0.474 |
| 1 | 23 | 10 | 105.505 | 5.479  | 87.637  | 342.96 | 0.907 |
| 1 | 23 | 12 | 290.984 | 3.370  | 385.471 | 190.78 | 0.987 |
| 1 | 23 | 14 | 440.500 | 4.131  | 548.044 | 246.64 | 0.995 |
| 1 | 23 | 16 | 60.009  | 12.253 | 11.399  | 210.55 | 0.753 |
| 1 | 23 | 18 | 196.289 | 4.878  | 263.481 | 262.32 | 0.979 |
| 1 | 23 | 20 | 279.723 | 3.907  | 361.674 | 93.70  | 0.991 |
| 1 | 23 | 22 | 102.039 | 6.666  | 94.400  | 107.71 | 0.957 |
| 1 | 23 | 24 | 46.825  | 10.676 | 10.589  | 98.80  | 0.734 |
| 1 | 23 | 26 | 188.140 | 4.764  | 332.296 | 266.29 | 0.970 |
| 1 | 23 | 28 | 135.368 | 7.796  | 141.195 | 44.87  | 0.971 |
| 1 | 23 | 30 | 80.171  | 9.662  | 93.304  | 99.55  | 0.899 |
| 1 | 23 | 32 | 51.089  | 22.088 | 22.804  | 236.27 | 0.635 |

| | | | | | | | |
|---|---|---|---|---|---|---|---|
| 1 | 24 | 1 | 248.089 | 3.564 | 358.565 | 284.77 | 0.983 |
| 1 | 24 | 3 | 330.813 | 3.355 | 379.480 | 316.00 | 0.992 |
| 1 | 24 | 5 | 268.021 | 3.288 | 331.645 | 157.18 | 0.988 |
| 1 | 24 | 7 | 390.467 | 4.393 | 573.444 | 87.12 | 0.992 |
| 1 | 24 | 9 | 204.966 | 4.414 | 272.679 | 164.97 | 0.974 |
| 1 | 24 | 11 | 414.867 | 3.916 | 598.957 | 75.06 | 0.993 |
| 1 | 24 | 13 | 69.437 | 9.940 | 21.801 | 350.72 | 0.809 |
| 1 | 24 | 15 | 98.952 | 7.156 | 114.809 | 47.14 | 0.919 |
| 1 | 24 | 17 | 187.965 | 5.047 | 244.202 | 179.86 | 0.978 |
| 1 | 24 | 19 | 75.549 | 9.454 | 54.789 | 4.06 | 0.876 |
| 1 | 24 | 21 | 129.146 | 6.283 | 202.193 | 80.66 | 0.953 |
| 1 | 24 | 23 | 83.834 | 11.395 | 87.566 | 67.94 | 0.912 |
| 1 | 24 | 25 | 139.297 | 6.012 | 184.994 | 130.11 | 0.967 |
| 1 | 24 | 27 | 47.006 | 12.105 | 26.785 | 2.65 | 0.648 |
| 1 | 24 | 29 | 108.545 | 14.130 | 123.299 | 44.89 | 0.950 |
| 1 | 25 | 0 | 416.694 | 6.045 | 578.950 | 180.00 | 1.000 |
| 1 | 25 | 2 | 371.715 | 3.712 | 529.019 | 317.35 | 0.992 |
| 1 | 25 | 4 | 524.297 | 4.960 | 653.036 | 52.88 | 0.997 |
| 1 | 25 | 6 | 265.553 | 3.553 | 386.014 | 227.32 | 0.983 |
| 1 | 25 | 8 | 463.320 | 4.840 | 619.740 | 312.12 | 0.995 |
| 1 | 25 | 10 | 299.374 | 4.216 | 441.315 | 196.01 | 0.986 |
| 1 | 25 | 12 | 388.936 | 4.195 | 511.257 | 79.77 | 0.995 |
| 1 | 25 | 14 | 144.913 | 6.719 | 169.278 | 110.59 | 0.967 |
| 1 | 25 | 16 | 219.185 | 4.349 | 251.763 | 135.95 | 0.987 |
| 1 | 25 | 18 | 117.359 | 7.100 | 111.284 | 39.59 | 0.967 |
| 1 | 25 | 20 | 136.449 | 6.868 | 261.302 | 290.91 | 0.930 |
| 1 | 25 | 22 | 223.499 | 4.304 | 338.321 | 23.40 | 0.986 |
| 1 | 25 | 24 | 208.171 | 4.663 | 275.102 | 55.27 | 0.987 |
| 1 | 25 | 26 | 78.810 | 11.132 | 33.159 | 119.20 | 0.275 |
| 1 | 25 | 28 | 49.365 | 13.753 | 26.602 | 351.93 | 0.534 |
| 1 | 26 | 1 | 210.067 | 3.961 | 296.967 | 87.53 | 0.975 |
| 1 | 26 | 3 | 194.090 | 7.074 | 281.334 | 320.40 | 0.968 |
| 1 | 26 | 5 | 286.484 | 3.898 | 294.611 | 359.29 | 0.990 |
| 1 | 26 | 7 | 333.664 | 4.825 | 514.822 | 295.87 | 0.992 |
| 1 | 26 | 9 | 265.472 | 5.129 | 374.168 | 66.87 | 0.989 |
| 1 | 26 | 11 | 302.211 | 4.240 | 427.673 | 272.61 | 0.991 |
| 1 | 26 | 13 | 196.551 | 4.900 | 233.085 | 257.34 | 0.982 |
| 1 | 26 | 15 | 54.561 | 13.078 | 35.990 | 108.19 | 0.457 |
| 1 | 26 | 17 | 108.279 | 7.367 | 105.744 | 86.60 | 0.959 |
| 1 | 26 | 19 | 123.184 | 5.437 | 140.189 | 197.25 | 0.965 |
| 1 | 26 | 21 | 85.493 | 8.933 | 108.309 | 86.77 | 0.902 |
| 1 | 26 | 23 | 63.210 | 14.249 | 58.012 | 331.72 | 0.652 |
| 1 | 26 | 25 | 42.109 | 10.602 | 17.468 | 234.96 | 0.632 |
| 1 | 26 | 27 | 67.242 | 18.269 | 65.933 | 283.59 | 0.896 |
| 1 | 27 | 0 | 464.376 | 6.230 | 644.466 | 180.00 | 1.000 |
| 1 | 27 | 2 | 104.606 | 8.701 | 88.226 | 158.20 | 0.945 |
| 1 | 27 | 4 | 226.856 | 4.347 | 274.179 | 77.54 | 0.988 |
| 1 | 27 | 6 | 119.351 | 7.773 | 116.769 | 68.30 | 0.955 |
| 1 | 27 | 8 | 81.025 | 13.524 | 79.002 | 347.07 | 0.506 |
| 1 | 27 | 10 | 215.789 | 4.318 | 274.439 | 104.89 | 0.985 |
| 1 | 27 | 12 | 166.304 | 4.679 | 228.985 | 211.52 | 0.979 |
| 1 | 27 | 14 | 204.227 | 4.713 | 283.455 | 264.91 | 0.987 |
| 1 | 27 | 16 | 184.507 | 4.670 | 229.776 | 268.26 | 0.985 |
| 1 | 27 | 18 | 120.603 | 6.978 | 228.034 | 307.60 | 0.899 |
| 1 | 27 | 20 | 32.764 | 10.552 | 15.019 | 352.04 | 0.487 |
| 1 | 27 | 22 | 55.662 | 11.195 | 53.066 | 107.89 | 0.712 |
| 1 | 27 | 24 | 134.817 | 8.906 | 140.635 | 260.92 | 0.975 |
| 1 | 27 | 26 | 54.767 | 24.576 | 24.720 | 38.96 | 0.713 |
| 1 | 28 | 1 | 272.361 | 4.037 | 407.107 | 255.35 | 0.989 |
| 1 | 28 | 3 | 175.671 | 5.879 | 355.781 | 260.96 | 0.832 |
| 1 | 28 | 5 | 176.403 | 5.148 | 184.821 | 274.05 | 0.986 |
| 1 | 28 | 7 | 63.550 | 13.666 | 52.981 | 252.16 | 0.849 |
| 1 | 28 | 9 | 52.564 | 14.229 | 15.212 | 217.13 | 0.829 |
| 1 | 28 | 11 | 213.067 | 4.826 | 386.675 | 293.72 | 0.979 |
| 1 | 28 | 13 | 61.842 | 11.536 | 44.717 | 212.95 | 0.859 |
| 1 | 28 | 15 | 109.255 | 7.549 | 166.633 | 353.23 | 0.933 |
| 1 | 28 | 17 | 114.064 | 5.666 | 157.766 | 301.67 | 0.953 |
| 1 | 28 | 19 | 29.623 | 9.608 | 8.459 | 130.17 | 0.305 |
| 1 | 28 | 21 | 105.097 | 7.903 | 126.091 | 212.91 | 0.956 |
| 1 | 28 | 23 | 51.091 | 12.902 | 47.156 | 87.55 | 0.842 |
| 1 | 29 | 0 | 118.603 | 7.794 | 164.125 | 180.00 | 1.000 |
| 1 | 29 | 2 | 319.997 | 4.181 | 431.557 | 241.59 | 0.995 |
| 1 | 29 | 4 | 63.471 | 11.153 | 49.728 | 325.60 | 0.844 |
| 1 | 29 | 6 | 105.110 | 8.777 | 144.318 | 322.40 | 0.942 |
| 1 | 29 | 8 | 65.605 | 10.726 | 73.099 | 13.27 | 0.852 |
| 1 | 29 | 10 | 64.840 | 12.140 | 73.552 | 41.60 | 0.676 |
| 1 | 29 | 12 | 85.363 | 8.799 | 112.971 | 146.07 | 0.903 |

| | | | | | | | |
|---|---|---|---|---|---|---|---|
| 1 | 29 | 14 | 82.854 | 9.104 | 122.145 | 202.01 | 0.843 |
| 1 | 29 | 16 | 47.565 | 11.945 | 22.541 | 103.17 | 0.361 |
| 1 | 29 | 18 | 96.381 | 6.513 | 147.135 | 346.63 | 0.924 |
| 1 | 29 | 20 | 43.813 | 12.590 | 13.819 | 228.70 | 0.701 |
| 1 | 29 | 22 | 60.187 | 21.526 | 34.422 | 292.26 | 0.888 |
| 1 | 30 | 1 | 99.250 | 7.234 | 103.553 | 209.98 | 0.951 |
| 1 | 30 | 3 | 101.064 | 7.847 | 149.317 | 102.52 | 0.624 |
| 1 | 30 | 5 | 80.338 | 10.574 | 61.956 | 80.18 | 0.934 |
| 1 | 30 | 7 | 108.450 | 8.855 | 99.723 | 87.68 | 0.962 |
| 1 | 30 | 9 | 201.919 | 5.051 | 330.581 | 72.38 | 0.982 |
| 1 | 30 | 11 | 38.182 | 12.083 | 4.740 | 231.68 | 0.228 |
| 1 | 30 | 13 | 92.782 | 6.791 | 131.255 | 168.77 | 0.933 |
| 1 | 30 | 15 | 80.049 | 9.837 | 122.275 | 223.98 | 0.797 |
| 1 | 30 | 17 | 96.082 | 8.183 | 79.947 | 319.68 | 0.959 |
| 1 | 30 | 19 | 57.002 | 14.613 | 62.020 | 159.88 | 0.832 |
| 1 | 31 | 0 | 39.097 | 16.332 | 23.106 | 180.00 | 0.435 |
| 1 | 31 | 2 | 77.441 | 12.368 | 81.630 | 303.83 | 0.899 |
| 1 | 31 | 4 | 235.396 | 4.492 | 329.275 | 340.49 | 0.990 |
| 1 | 31 | 6 | 100.147 | 7.250 | 139.351 | 297.92 | 0.936 |
| 1 | 31 | 8 | 48.108 | 10.774 | 31.441 | 15.60 | 0.773 |
| 1 | 31 | 10 | 140.039 | 5.974 | 185.390 | 11.70 | 0.976 |
| 1 | 31 | 12 | 44.742 | 12.740 | 20.723 | 204.91 | 0.654 |
| 1 | 31 | 14 | 62.783 | 12.628 | 63.530 | 89.60 | 0.649 |
| 1 | 31 | 16 | 72.241 | 15.474 | 101.935 | 263.79 | 0.886 |
| 1 | 32 | 1 | 86.932 | 8.487 | 142.597 | 184.90 | 0.853 |
| 1 | 32 | 3 | 64.093 | 11.533 | 43.529 | 69.65 | 0.896 |
| 1 | 32 | 5 | 39.055 | 11.007 | 12.787 | 129.00 | 0.782 |
| 1 | 32 | 7 | 92.037 | 7.942 | 101.888 | 100.82 | 0.948 |
| 1 | 32 | 9 | 83.008 | 12.115 | 99.782 | 31.07 | 0.921 |
| 1 | 32 | 11 | 102.939 | 9.726 | 121.313 | 303.17 | 0.952 |
| 1 | 32 | 13 | 77.288 | 25.125 | 72.705 | 299.77 | 0.899 |
| 1 | 33 | 0 | 49.257 | 18.958 | 8.233 | 180.00 | 0.128 |
| 1 | 33 | 2 | 103.197 | 9.237 | 109.829 | 23.46 | 0.961 |
| 1 | 33 | 4 | 61.597 | 10.788 | 74.795 | 4.93 | 0.897 |
| 1 | 33 | 6 | 71.433 | 18.974 | 94.909 | 20.61 | 0.841 |
| 1 | 33 | 8 | 39.978 | 18.906 | 10.613 | 246.54 | 0.370 |
| 1 | 33 | 10 | 43.875 | 19.420 | 14.470 | 205.43 | 0.704 |
| 2 | 0 | 2 | 14.468 | 6.738 | 0.534 | 180.00 | 0.040 |
| 2 | 0 | 4 | 122.973 | 1.700 | 161.359 | 0.00 | 0.943 |
| 2 | 0 | 6 | 866.460 | 15.566 | 1206.531 | 0.00 | 1.000 |
| 2 | 0 | 8 | 109.485 | 2.481 | 19.629 | 180.00 | 0.129 |
| 2 | 0 | 10 | 283.669 | 3.487 | 372.019 | 0.00 | 0.945 |
| 2 | 0 | 12 | 44.527 | 8.570 | 4.516 | 180.00 | 0.080 |
| 2 | 0 | 14 | 193.862 | 3.013 | 267.175 | 180.00 | 1.000 |
| 2 | 0 | 16 | 265.737 | 3.599 | 365.204 | 180.00 | 1.000 |
| 2 | 0 | 18 | 407.908 | 6.256 | 557.717 | 0.00 | 1.000 |
| 2 | 0 | 20 | 40.749 | 10.529 | 24.810 | 180.00 | 0.459 |
| 2 | 0 | 22 | 386.701 | 4.816 | 523.625 | 0.00 | 1.000 |
| 2 | 0 | 24 | 518.284 | 5.888 | 697.401 | 0.00 | 1.000 |
| 2 | 0 | 26 | 284.524 | 4.335 | 380.427 | 0.00 | 1.000 |
| 2 | 0 | 28 | 328.795 | 6.293 | 436.596 | 0.00 | 1.000 |
| 2 | 0 | 30 | 39.661 | 15.975 | 29.914 | 0.00 | 0.587 |
| 2 | 0 | 32 | 69.141 | 17.041 | 43.241 | 0.00 | 0.482 |
| 2 | 0 | 34 | 186.921 | 8.446 | 232.295 | 180.00 | 0.960 |
| 2 | 0 | 36 | 150.398 | 13.786 | 192.194 | 0.00 | 1.000 |
| 2 | 0 | 38 | 352.062 | 8.385 | 446.700 | 180.00 | 1.000 |
| 2 | 0 | 40 | 112.407 | 20.721 | 137.833 | 0.00 | 1.000 |
| 2 | 0 | 42 | 150.167 | 11.073 | 184.756 | 0.00 | 1.000 |
| 2 | 1 | 1 | 51.511 | 15.528 | 125.363 | 234.17 | 0.249 |
| 2 | 1 | 3 | 431.448 | 3.554 | 573.670 | 4.93 | 0.983 |
| 2 | 1 | 5 | 876.548 | 14.523 | 1186.227 | 113.31 | 0.993 |
| 2 | 1 | 7 | 178.261 | 1.792 | 230.847 | 201.23 | 0.949 |
| 2 | 1 | 9 | 128.947 | 1.597 | 82.631 | 214.63 | 0.463 |
| 2 | 1 | 11 | 317.023 | 3.027 | 436.703 | 35.76 | 0.961 |
| 2 | 1 | 13 | 322.860 | 3.404 | 535.284 | 72.20 | 0.982 |
| 2 | 1 | 15 | 334.295 | 3.345 | 489.116 | 303.94 | 0.989 |
| 2 | 1 | 17 | 57.875 | 4.687 | 28.500 | 163.36 | 0.832 |
| 2 | 1 | 19 | 357.245 | 3.175 | 508.688 | 280.42 | 0.990 |
| 2 | 1 | 21 | 43.483 | 6.585 | 56.799 | 173.20 | 0.694 |
| 2 | 1 | 23 | 362.886 | 3.286 | 523.735 | 309.13 | 0.989 |
| 2 | 1 | 25 | 330.901 | 3.365 | 433.486 | 91.41 | 0.988 |
| 2 | 1 | 27 | 235.536 | 3.352 | 322.039 | 27.79 | 0.981 |
| 2 | 1 | 29 | 250.344 | 3.628 | 324.935 | 311.63 | 0.984 |
| 2 | 1 | 31 | 234.874 | 4.107 | 296.261 | 273.11 | 0.981 |
| 2 | 1 | 33 | 186.127 | 5.373 | 216.407 | 177.91 | 0.969 |
| 2 | 1 | 35 | 215.139 | 5.852 | 274.793 | 340.23 | 0.981 |
| 2 | 1 | 37 | 54.047 | 13.741 | 23.825 | 343.44 | 0.756 |

| | | | | | | | |
|---|---|---|---|---|---|---|---|
| 2 | 1 | 39 | 174.975 | 7.013 | 220.390 | 231.73 | 0.978 |
| 2 | 1 | 41 | 120.689 | 9.799 | 157.809 | 285.61 | 0.952 |
| 2 | 1 | 43 | 55.087 | 17.913 | 34.826 | 247.20 | 0.841 |
| 2 | 2 | 0 | 43.795 | 28.571 | 21.760 | 0.00 | 0.425 |
| 2 | 2 | 2 | 458.876 | 3.353 | 551.296 | 9.58 | 0.985 |
| 2 | 2 | 4 | 1043.019 | 9.524 | 1575.153 | 116.58 | 0.994 |
| 2 | 2 | 6 | 108.502 | 1.444 | 55.450 | 71.70 | 0.351 |
| 2 | 2 | 8 | 602.643 | 5.830 | 847.572 | 167.53 | 0.985 |
| 2 | 2 | 10 | 195.880 | 1.951 | 263.391 | 94.53 | 0.879 |
| 2 | 2 | 12 | 272.207 | 2.523 | 342.236 | 336.80 | 0.989 |
| 2 | 2 | 14 | 266.996 | 2.605 | 410.495 | 314.17 | 0.979 |
| 2 | 2 | 16 | 297.099 | 2.643 | 383.488 | 273.32 | 0.985 |
| 2 | 2 | 18 | 255.691 | 2.576 | 371.302 | 165.92 | 0.991 |
| 2 | 2 | 20 | 351.217 | 3.094 | 474.079 | 147.22 | 0.991 |
| 2 | 2 | 22 | 195.201 | 2.861 | 206.243 | 303.21 | 0.975 |
| 2 | 2 | 24 | 425.472 | 3.853 | 568.664 | 197.00 | 0.993 |
| 2 | 2 | 26 | 370.204 | 3.475 | 467.504 | 198.73 | 0.993 |
| 2 | 2 | 28 | 340.373 | 3.789 | 458.096 | 96.05 | 0.991 |
| 2 | 2 | 30 | 297.906 | 3.638 | 419.697 | 100.06 | 0.986 |
| 2 | 2 | 32 | 197.493 | 4.719 | 258.120 | 164.44 | 0.970 |
| 2 | 2 | 34 | 229.947 | 6.310 | 298.636 | 237.70 | 0.975 |
| 2 | 2 | 36 | 62.497 | 16.720 | 31.790 | 54.05 | 0.540 |
| 2 | 2 | 38 | 51.466 | 14.162 | 20.955 | 276.26 | 0.692 |
| 2 | 2 | 40 | 52.800 | 16.521 | 23.103 | 209.66 | 0.596 |
| 2 | 2 | 42 | 35.451 | 11.846 | 1.451 | 139.77 | 0.443 |
| 2 | 3 | 1 | 138.614 | 1.755 | 164.397 | 324.99 | 0.830 |
| 2 | 3 | 3 | 305.636 | 2.507 | 333.318 | 184.50 | 0.700 |
| 2 | 3 | 5 | 797.161 | 6.919 | 1137.484 | 294.95 | 0.991 |
| 2 | 3 | 7 | 269.305 | 2.459 | 364.035 | 46.80 | 0.951 |
| 2 | 3 | 9 | 682.041 | 5.883 | 979.599 | 127.50 | 0.988 |
| 2 | 3 | 11 | 445.530 | 3.856 | 668.060 | 223.96 | 0.973 |
| 2 | 3 | 13 | 403.320 | 3.795 | 516.880 | 355.78 | 0.992 |
| 2 | 3 | 15 | 57.707 | 3.950 | 79.052 | 30.27 | 0.812 |
| 2 | 3 | 17 | 377.035 | 3.471 | 566.146 | 251.01 | 0.989 |
| 2 | 3 | 19 | 300.885 | 2.998 | 404.067 | 168.25 | 0.988 |
| 2 | 3 | 21 | 212.035 | 2.712 | 293.568 | 60.13 | 0.978 |
| 2 | 3 | 23 | 97.477 | 4.508 | 118.607 | 220.47 | 0.741 |
| 2 | 3 | 25 | 267.015 | 3.134 | 381.080 | 169.82 | 0.980 |
| 2 | 3 | 27 | 257.985 | 3.219 | 336.550 | 187.10 | 0.986 |
| 2 | 3 | 29 | 183.019 | 4.213 | 214.021 | 249.51 | 0.972 |
| 2 | 3 | 31 | 374.589 | 5.065 | 541.519 | 110.49 | 0.991 |
| 2 | 3 | 33 | 249.962 | 4.174 | 385.480 | 252.27 | 0.975 |
| 2 | 3 | 35 | 177.013 | 5.282 | 214.843 | 55.46 | 0.973 |
| 2 | 3 | 37 | 46.014 | 12.093 | 13.849 | 242.95 | 0.292 |
| 2 | 3 | 39 | 118.157 | 8.112 | 155.246 | 248.29 | 0.945 |
| 2 | 3 | 41 | 68.035 | 13.330 | 9.032 | 66.34 | 0.100 |
| 2 | 3 | 43 | 61.589 | 25.297 | 28.449 | 117.01 | 0.847 |
| 2 | 4 | 0 | 220.477 | 4.320 | 295.228 | 180.00 | 0.961 |
| 2 | 4 | 2 | 200.116 | 2.071 | 264.844 | 190.32 | 0.889 |
| 2 | 4 | 4 | 540.392 | 4.645 | 676.668 | 342.37 | 0.985 |
| 2 | 4 | 6 | 442.331 | 3.790 | 692.595 | 345.46 | 0.983 |
| 2 | 4 | 8 | 847.557 | 7.681 | 1220.821 | 346.50 | 0.992 |
| 2 | 4 | 10 | 676.427 | 5.887 | 961.392 | 224.39 | 0.987 |
| 2 | 4 | 12 | 231.383 | 2.330 | 293.820 | 117.73 | 0.983 |
| 2 | 4 | 14 | 121.146 | 2.278 | 139.269 | 123.49 | 0.963 |
| 2 | 4 | 16 | 242.041 | 2.745 | 282.060 | 61.24 | 0.980 |
| 2 | 4 | 18 | 95.972 | 3.548 | 100.333 | 69.70 | 0.952 |
| 2 | 4 | 20 | 319.335 | 3.621 | 385.053 | 174.88 | 0.990 |
| 2 | 4 | 22 | 320.008 | 3.305 | 410.972 | 71.25 | 0.988 |
| 2 | 4 | 24 | 118.287 | 4.033 | 124.206 | 243.90 | 0.922 |
| 2 | 4 | 26 | 259.153 | 3.266 | 340.352 | 173.03 | 0.986 |
| 2 | 4 | 28 | 428.188 | 4.394 | 546.113 | 43.00 | 0.995 |
| 2 | 4 | 30 | 174.016 | 3.966 | 207.234 | 124.93 | 0.968 |
| 2 | 4 | 32 | 222.405 | 4.413 | 253.086 | 328.73 | 0.978 |
| 2 | 4 | 34 | 287.337 | 4.670 | 365.260 | 318.62 | 0.990 |
| 2 | 4 | 36 | 73.645 | 14.118 | 73.484 | 233.68 | 0.742 |
| 2 | 4 | 38 | 62.207 | 11.808 | 7.433 | 280.12 | 0.084 |
| 2 | 4 | 40 | 118.395 | 6.985 | 184.334 | 33.90 | 0.919 |
| 2 | 4 | 42 | 43.367 | 13.600 | 7.999 | 66.69 | 0.511 |
| 2 | 5 | 1 | 379.434 | 3.252 | 558.393 | 101.96 | 0.967 |
| 2 | 5 | 3 | 295.341 | 2.639 | 369.691 | 103.59 | 0.978 |
| 2 | 5 | 5 | 135.476 | 1.566 | 172.274 | 29.48 | 0.920 |
| 2 | 5 | 7 | 313.875 | 2.840 | 393.013 | 358.77 | 0.975 |
| 2 | 5 | 9 | 148.410 | 1.934 | 187.015 | 273.96 | 0.969 |
| 2 | 5 | 11 | 247.950 | 2.380 | 366.586 | 312.17 | 0.985 |
| 2 | 5 | 13 | 526.046 | 5.583 | 723.828 | 288.23 | 0.995 |
| 2 | 5 | 15 | 29.173 | 7.080 | 2.797 | 117.50 | 0.241 |

| | | | | | | | |
|---|---|---|---|---|---|---|---|
| 2 | 5 | 17 | 220.249 | 2.572 | 318.009 | 213.59 | 0.982 |
| 2 | 5 | 19 | 260.654 | 2.884 | 357.862 | 160.52 | 0.986 |
| 2 | 5 | 21 | 314.276 | 3.157 | 434.785 | 129.82 | 0.989 |
| 2 | 5 | 23 | 386.703 | 3.696 | 538.159 | 199.75 | 0.991 |
| 2 | 5 | 25 | 334.139 | 3.408 | 435.196 | 191.88 | 0.991 |
| 2 | 5 | 27 | 267.176 | 3.285 | 325.231 | 220.55 | 0.987 |
| 2 | 5 | 29 | 610.185 | 6.418 | 804.911 | 57.68 | 0.997 |
| 2 | 5 | 31 | 229.588 | 3.735 | 367.615 | 15.25 | 0.969 |
| 2 | 5 | 33 | 155.436 | 6.329 | 215.822 | 272.64 | 0.938 |
| 2 | 5 | 35 | 117.114 | 7.576 | 178.830 | 100.13 | 0.887 |
| 2 | 5 | 37 | 53.455 | 13.177 | 34.001 | 78.68 | 0.510 |
| 2 | 5 | 39 | 93.690 | 9.093 | 88.598 | 115.87 | 0.933 |
| 2 | 5 | 41 | 53.705 | 12.824 | 37.810 | 31.40 | 0.688 |
| 2 | 6 | 0 | 153.425 | 2.809 | 202.932 | 180.00 | 0.951 |
| 2 | 6 | 2 | 139.461 | 1.621 | 167.221 | 271.83 | 0.840 |
| 2 | 6 | 4 | 569.040 | 4.857 | 805.586 | 315.76 | 0.984 |
| 2 | 6 | 6 | 144.967 | 1.701 | 158.943 | 187.44 | 0.772 |
| 2 | 6 | 8 | 287.894 | 2.622 | 413.850 | 204.40 | 0.975 |
| 2 | 6 | 10 | 756.575 | 6.861 | 1080.360 | 171.02 | 0.997 |
| 2 | 6 | 12 | 333.853 | 3.359 | 491.404 | 4.11 | 0.989 |
| 2 | 6 | 14 | 224.410 | 2.599 | 298.695 | 324.73 | 0.972 |
| 2 | 6 | 16 | 360.825 | 3.688 | 502.716 | 352.45 | 0.988 |
| 2 | 6 | 18 | 169.796 | 2.899 | 255.961 | 23.94 | 0.966 |
| 2 | 6 | 20 | 110.381 | 4.088 | 126.481 | 184.70 | 0.724 |
| 2 | 6 | 22 | 128.829 | 3.449 | 166.766 | 325.43 | 0.942 |
| 2 | 6 | 24 | 137.826 | 3.933 | 122.495 | 164.65 | 0.962 |
| 2 | 6 | 26 | 246.395 | 3.243 | 302.247 | 211.23 | 0.986 |
| 2 | 6 | 28 | 79.102 | 8.642 | 66.105 | 276.42 | 0.755 |
| 2 | 6 | 30 | 188.155 | 4.013 | 249.819 | 315.62 | 0.968 |
| 2 | 6 | 32 | 252.094 | 3.737 | 351.178 | 234.81 | 0.979 |
| 2 | 6 | 34 | 331.135 | 4.384 | 371.761 | 334.16 | 0.993 |
| 2 | 6 | 36 | 173.917 | 4.952 | 220.551 | 137.32 | 0.979 |
| 2 | 6 | 38 | 104.470 | 8.900 | 80.691 | 230.14 | 0.953 |
| 2 | 6 | 40 | 148.365 | 5.978 | 228.365 | 169.08 | 0.954 |
| 2 | 6 | 42 | 65.390 | 15.845 | 48.157 | 80.01 | 0.496 |
| 2 | 7 | 1 | 515.525 | 5.216 | 759.333 | 28.02 | 0.976 |
| 2 | 7 | 3 | 641.556 | 5.552 | 884.328 | 233.88 | 0.987 |
| 2 | 7 | 5 | 372.527 | 3.383 | 543.038 | 189.95 | 0.979 |
| 2 | 7 | 7 | 55.150 | 4.786 | 66.790 | 73.33 | 0.886 |
| 2 | 7 | 9 | 788.403 | 7.151 | 1121.873 | 224.02 | 0.998 |
| 2 | 7 | 11 | 86.763 | 2.829 | 119.190 | 108.14 | 0.920 |
| 2 | 7 | 13 | 58.874 | 5.358 | 62.260 | 61.96 | 0.762 |
| 2 | 7 | 15 | 230.454 | 2.712 | 300.830 | 133.10 | 0.975 |
| 2 | 7 | 17 | 334.195 | 3.854 | 482.513 | 349.57 | 0.989 |
| 2 | 7 | 19 | 239.635 | 2.741 | 358.470 | 332.23 | 0.984 |
| 2 | 7 | 21 | 161.804 | 3.468 | 172.945 | 21.36 | 0.948 |
| 2 | 7 | 23 | 35.973 | 8.291 | 14.626 | 101.39 | 0.362 |
| 2 | 7 | 25 | 287.801 | 3.436 | 399.367 | 317.45 | 0.988 |
| 2 | 7 | 27 | 180.345 | 3.601 | 246.268 | 203.61 | 0.964 |
| 2 | 7 | 29 | 271.891 | 3.616 | 420.485 | 134.00 | 0.980 |
| 2 | 7 | 31 | 272.038 | 3.578 | 362.884 | 70.30 | 0.983 |
| 2 | 7 | 33 | 141.818 | 6.401 | 226.793 | 134.07 | 0.931 |
| 2 | 7 | 35 | 148.550 | 5.920 | 184.536 | 311.80 | 0.957 |
| 2 | 7 | 37 | 141.117 | 6.079 | 134.621 | 190.59 | 0.973 |
| 2 | 7 | 39 | 96.597 | 8.770 | 142.734 | 348.93 | 0.785 |
| 2 | 7 | 41 | 42.124 | 12.327 | 7.928 | 207.79 | 0.243 |
| 2 | 8 | 0 | 35.583 | 5.187 | 9.148 | 0.00 | 0.192 |
| 2 | 8 | 2 | 613.852 | 4.901 | 897.232 | 215.23 | 0.985 |
| 2 | 8 | 4 | 452.161 | 5.405 | 627.090 | 101.28 | 0.977 |
| 2 | 8 | 6 | 462.141 | 4.449 | 645.327 | 118.52 | 0.977 |
| 2 | 8 | 8 | 125.661 | 2.245 | 131.023 | 152.56 | 0.967 |
| 2 | 8 | 10 | 351.614 | 3.374 | 465.887 | 158.38 | 0.991 |
| 2 | 8 | 12 | 199.837 | 2.503 | 259.286 | 291.70 | 0.979 |
| 2 | 8 | 14 | 409.347 | 4.552 | 568.987 | 58.96 | 0.992 |
| 2 | 8 | 16 | 294.508 | 3.058 | 410.510 | 83.95 | 0.988 |
| 2 | 8 | 18 | 175.008 | 2.880 | 207.496 | 176.70 | 0.976 |
| 2 | 8 | 20 | 196.645 | 2.691 | 280.916 | 357.11 | 0.942 |
| 2 | 8 | 22 | 113.663 | 3.527 | 89.196 | 31.09 | 0.939 |
| 2 | 8 | 24 | 174.595 | 3.149 | 253.414 | 196.14 | 0.962 |
| 2 | 8 | 26 | 316.111 | 4.019 | 393.635 | 100.85 | 0.991 |
| 2 | 8 | 28 | 327.383 | 3.782 | 398.982 | 61.13 | 0.991 |
| 2 | 8 | 30 | 367.363 | 3.693 | 576.427 | 76.68 | 0.988 |
| 2 | 8 | 32 | 122.526 | 5.863 | 156.069 | 152.79 | 0.682 |
| 2 | 8 | 34 | 188.030 | 7.000 | 242.478 | 38.16 | 0.975 |
| 2 | 8 | 36 | 153.459 | 6.761 | 216.148 | 266.22 | 0.968 |
| 2 | 8 | 38 | 42.713 | 12.445 | 9.591 | 267.06 | 0.511 |
| 2 | 8 | 40 | 53.553 | 14.402 | 24.403 | 141.00 | 0.780 |

| | | | | | | | |
|---|---|---|---|---|---|---|---|
| 2 | 8 | 42 | 47.483 | 23.151 | 12.975 | 290.33 | 0.499 |
| 2 | 9 | 1 | 1133.262 | 10.235 | 1591.973 | 243.78 | 0.996 |
| 2 | 9 | 3 | 511.513 | 4.780 | 716.720 | 250.70 | 0.979 |
| 2 | 9 | 5 | 624.067 | 7.166 | 889.344 | 53.55 | 0.996 |
| 2 | 9 | 7 | 666.682 | 7.060 | 911.701 | 101.14 | 0.997 |
| 2 | 9 | 9 | 49.042 | 3.506 | 37.811 | 206.29 | 0.890 |
| 2 | 9 | 11 | 247.527 | 2.550 | 332.606 | 69.77 | 0.984 |
| 2 | 9 | 13 | 605.550 | 5.754 | 860.745 | 174.29 | 0.996 |
| 2 | 9 | 15 | 472.152 | 5.345 | 677.679 | 76.18 | 0.995 |
| 2 | 9 | 17 | 318.995 | 3.136 | 431.953 | 52.03 | 0.989 |
| 2 | 9 | 19 | 373.934 | 3.724 | 465.038 | 108.16 | 0.992 |
| 2 | 9 | 21 | 121.096 | 3.206 | 125.452 | 67.23 | 0.631 |
| 2 | 9 | 23 | 174.153 | 3.255 | 198.855 | 351.39 | 0.978 |
| 2 | 9 | 25 | 200.265 | 3.145 | 238.351 | 299.33 | 0.983 |
| 2 | 9 | 27 | 114.714 | 4.782 | 116.949 | 0.74 | 0.931 |
| 2 | 9 | 29 | 45.988 | 10.184 | 15.601 | 88.90 | 0.362 |
| 2 | 9 | 31 | 205.795 | 4.184 | 296.022 | 15.50 | 0.969 |
| 2 | 9 | 33 | 104.718 | 7.026 | 124.084 | 62.17 | 0.899 |
| 2 | 9 | 35 | 109.993 | 7.463 | 180.167 | 347.30 | 0.882 |
| 2 | 9 | 37 | 184.369 | 5.749 | 253.232 | 16.79 | 0.979 |
| 2 | 9 | 39 | 104.301 | 8.794 | 131.199 | 103.50 | 0.927 |
| 2 | 9 | 41 | 53.602 | 16.068 | 28.179 | 110.64 | 0.444 |
| 2 | 10 | 0 | 672.082 | 7.109 | 938.514 | 0.00 | 1.000 |
| 2 | 10 | 2 | 442.909 | 4.834 | 637.439 | 351.49 | 0.992 |
| 2 | 10 | 4 | 641.497 | 5.695 | 950.458 | 91.76 | 0.996 |
| 2 | 10 | 6 | 627.035 | 7.235 | 820.345 | 358.26 | 0.997 |
| 2 | 10 | 8 | 349.659 | 3.676 | 468.185 | 246.60 | 0.990 |
| 2 | 10 | 10 | 190.781 | 2.413 | 270.268 | 288.84 | 0.981 |
| 2 | 10 | 12 | 457.745 | 4.108 | 620.052 | 203.11 | 0.993 |
| 2 | 10 | 14 | 185.702 | 2.639 | 313.200 | 221.48 | 0.954 |
| 2 | 10 | 16 | 62.611 | 5.173 | 44.765 | 77.26 | 0.469 |
| 2 | 10 | 18 | 258.578 | 2.876 | 357.409 | 222.92 | 0.981 |
| 2 | 10 | 20 | 184.965 | 2.951 | 163.574 | 260.04 | 0.978 |
| 2 | 10 | 22 | 247.253 | 2.871 | 428.856 | 258.28 | 0.966 |
| 2 | 10 | 24 | 497.353 | 4.749 | 674.940 | 346.02 | 0.996 |
| 2 | 10 | 26 | 411.098 | 3.677 | 539.818 | 252.39 | 0.994 |
| 2 | 10 | 28 | 96.177 | 5.369 | 79.949 | 1.33 | 0.921 |
| 2 | 10 | 30 | 120.442 | 5.335 | 110.621 | 128.16 | 0.928 |
| 2 | 10 | 32 | 139.491 | 6.434 | 237.658 | 194.54 | 0.905 |
| 2 | 10 | 34 | 167.375 | 4.561 | 253.158 | 79.40 | 0.958 |
| 2 | 10 | 36 | 97.535 | 8.951 | 148.742 | 28.09 | 0.823 |
| 2 | 10 | 38 | 114.508 | 7.971 | 117.689 | 93.86 | 0.954 |
| 2 | 10 | 40 | 98.615 | 11.232 | 150.665 | 11.34 | 0.847 |
| 2 | 11 | 1 | 439.861 | 3.963 | 818.973 | 330.39 | 0.985 |
| 2 | 11 | 3 | 726.372 | 9.088 | 1039.366 | 256.89 | 0.997 |
| 2 | 11 | 5 | 112.149 | 3.460 | 123.674 | 260.84 | 0.842 |
| 2 | 11 | 7 | 375.737 | 4.002 | 520.815 | 341.31 | 0.992 |
| 2 | 11 | 9 | 397.301 | 4.808 | 512.797 | 219.33 | 0.991 |
| 2 | 11 | 11 | 245.790 | 2.744 | 343.629 | 308.72 | 0.973 |
| 2 | 11 | 13 | 400.392 | 3.726 | 532.396 | 144.41 | 0.994 |
| 2 | 11 | 15 | 112.085 | 2.668 | 160.804 | 67.18 | 0.783 |
| 2 | 11 | 17 | 251.536 | 2.864 | 374.021 | 223.49 | 0.984 |
| 2 | 11 | 19 | 294.778 | 2.926 | 431.095 | 204.23 | 0.986 |
| 2 | 11 | 21 | 65.980 | 5.666 | 9.337 | 329.45 | 0.356 |
| 2 | 11 | 23 | 478.767 | 4.051 | 703.970 | 22.85 | 0.995 |
| 2 | 11 | 25 | 124.681 | 3.817 | 178.280 | 277.22 | 0.917 |
| 2 | 11 | 27 | 110.576 | 5.138 | 151.492 | 140.92 | 0.869 |
| 2 | 11 | 29 | 211.866 | 3.205 | 321.560 | 311.97 | 0.963 |
| 2 | 11 | 31 | 245.271 | 3.686 | 320.993 | 244.70 | 0.979 |
| 2 | 11 | 33 | 316.070 | 4.142 | 406.128 | 192.59 | 0.991 |
| 2 | 11 | 35 | 116.966 | 6.544 | 65.463 | 357.90 | 0.970 |
| 2 | 11 | 37 | 71.750 | 13.119 | 82.141 | 280.54 | 0.754 |
| 2 | 11 | 39 | 45.301 | 12.067 | 12.940 | 148.14 | 0.631 |
| 2 | 11 | 41 | 83.134 | 29.808 | 63.596 | 41.23 | 0.878 |
| 2 | 12 | 0 | 310.926 | 3.761 | 434.092 | 0.00 | 1.000 |
| 2 | 12 | 2 | 525.186 | 5.232 | 725.714 | 261.10 | 0.995 |
| 2 | 12 | 4 | 832.991 | 8.834 | 1181.548 | 223.88 | 0.998 |
| 2 | 12 | 6 | 471.438 | 4.716 | 669.150 | 173.34 | 0.993 |
| 2 | 12 | 8 | 344.923 | 3.821 | 478.574 | 284.93 | 0.989 |
| 2 | 12 | 10 | 66.903 | 4.947 | 55.955 | 61.96 | 0.749 |
| 2 | 12 | 12 | 167.418 | 2.499 | 227.779 | 12.50 | 0.952 |
| 2 | 12 | 14 | 147.246 | 2.692 | 156.342 | 285.95 | 0.973 |
| 2 | 12 | 16 | 76.284 | 4.042 | 59.823 | 9.02 | 0.732 |
| 2 | 12 | 18 | 516.786 | 4.371 | 836.562 | 189.14 | 0.994 |
| 2 | 12 | 20 | 116.747 | 3.196 | 128.770 | 216.68 | 0.930 |
| 2 | 12 | 22 | 233.062 | 2.764 | 368.224 | 30.12 | 0.972 |
| 2 | 12 | 24 | 461.613 | 4.141 | 620.833 | 357.68 | 0.995 |

| | | | | | | | |
|---|---|---|---|---|---|---|---|
| 2 | 12 | 26 | 162.847 | 3.950 | 245.319 | 123.67 | 0.948 |
| 2 | 12 | 28 | 54.910 | 10.615 | 7.154 | 111.03 | 0.717 |
| 2 | 12 | 30 | 96.561 | 7.566 | 79.053 | 331.79 | 0.878 |
| 2 | 12 | 32 | 68.285 | 11.137 | 41.831 | 195.99 | 0.825 |
| 2 | 12 | 34 | 34.792 | 10.718 | 7.392 | 320.78 | 0.395 |
| 2 | 12 | 36 | 113.275 | 7.253 | 80.519 | 3.14 | 0.964 |
| 2 | 12 | 38 | 57.342 | 12.102 | 44.307 | 212.86 | 0.519 |
| 2 | 12 | 40 | 47.477 | 15.110 | 33.915 | 10.23 | 0.666 |
| 2 | 13 | 1 | 275.137 | 3.908 | 358.214 | 260.40 | 0.984 |
| 2 | 13 | 3 | 49.958 | 6.487 | 1.736 | 158.36 | 0.487 |
| 2 | 13 | 5 | 308.073 | 3.360 | 407.002 | 327.50 | 0.989 |
| 2 | 13 | 7 | 24.444 | 7.743 | 14.506 | 89.91 | 0.232 |
| 2 | 13 | 9 | 500.923 | 5.431 | 659.277 | 283.18 | 0.996 |
| 2 | 13 | 11 | 217.458 | 3.908 | 331.677 | 138.74 | 0.970 |
| 2 | 13 | 13 | 139.921 | 3.042 | 179.366 | 292.20 | 0.966 |
| 2 | 13 | 15 | 186.019 | 2.467 | 247.151 | 253.34 | 0.958 |
| 2 | 13 | 17 | 183.682 | 2.697 | 245.505 | 84.55 | 0.934 |
| 2 | 13 | 19 | 139.059 | 3.054 | 169.684 | 51.42 | 0.933 |
| 2 | 13 | 21 | 372.769 | 3.462 | 525.937 | 63.26 | 0.992 |
| 2 | 13 | 23 | 111.542 | 5.020 | 122.772 | 224.46 | 0.910 |
| 2 | 13 | 25 | 103.652 | 5.539 | 124.139 | 259.93 | 0.934 |
| 2 | 13 | 27 | 155.565 | 4.576 | 222.645 | 94.48 | 0.941 |
| 2 | 13 | 29 | 394.079 | 4.253 | 517.793 | 61.30 | 0.992 |
| 2 | 13 | 31 | 250.424 | 3.884 | 326.227 | 32.14 | 0.987 |
| 2 | 13 | 33 | 87.392 | 10.527 | 127.931 | 77.02 | 0.779 |
| 2 | 13 | 35 | 149.270 | 5.367 | 180.408 | 273.37 | 0.973 |
| 2 | 13 | 37 | 53.391 | 12.819 | 27.698 | 124.53 | 0.750 |
| 2 | 13 | 39 | 75.904 | 13.733 | 79.137 | 271.61 | 0.865 |
| 2 | 14 | 0 | 74.321 | 5.909 | 100.715 | 180.00 | 0.972 |
| 2 | 14 | 2 | 187.350 | 3.726 | 251.002 | 169.09 | 0.970 |
| 2 | 14 | 4 | 164.777 | 2.718 | 200.416 | 248.50 | 0.977 |
| 2 | 14 | 6 | 263.398 | 3.018 | 304.253 | 160.76 | 0.988 |
| 2 | 14 | 8 | 448.822 | 4.580 | 661.880 | 295.32 | 0.994 |
| 2 | 14 | 10 | 318.529 | 3.178 | 449.556 | 311.48 | 0.990 |
| 2 | 14 | 12 | 115.006 | 4.858 | 159.075 | 17.89 | 0.860 |
| 2 | 14 | 14 | 304.197 | 3.319 | 434.684 | 177.30 | 0.984 |
| 2 | 14 | 16 | 165.683 | 2.641 | 201.581 | 41.48 | 0.972 |
| 2 | 14 | 18 | 80.102 | 5.095 | 22.706 | 129.27 | 0.856 |
| 2 | 14 | 20 | 184.111 | 3.013 | 220.624 | 295.03 | 0.978 |
| 2 | 14 | 22 | 360.904 | 3.586 | 468.786 | 240.17 | 0.993 |
| 2 | 14 | 24 | 87.526 | 6.237 | 77.077 | 306.45 | 0.848 |
| 2 | 14 | 26 | 238.029 | 3.404 | 263.851 | 66.92 | 0.984 |
| 2 | 14 | 28 | 208.989 | 4.263 | 327.745 | 118.03 | 0.965 |
| 2 | 14 | 30 | 119.833 | 6.588 | 133.041 | 351.23 | 0.944 |
| 2 | 14 | 32 | 75.933 | 9.506 | 64.403 | 73.64 | 0.903 |
| 2 | 14 | 34 | 68.977 | 10.422 | 67.313 | 37.29 | 0.684 |
| 2 | 14 | 36 | 159.621 | 5.065 | 154.206 | 102.29 | 0.980 |
| 2 | 14 | 38 | 66.818 | 14.716 | 53.396 | 341.27 | 0.511 |
| 2 | 15 | 1 | 174.867 | 3.725 | 215.863 | 3.89 | 0.980 |
| 2 | 15 | 3 | 81.650 | 3.972 | 64.391 | 224.18 | 0.451 |
| 2 | 15 | 5 | 196.233 | 2.804 | 234.101 | 79.63 | 0.984 |
| 2 | 15 | 7 | 238.297 | 3.176 | 330.047 | 110.70 | 0.971 |
| 2 | 15 | 9 | 303.913 | 3.025 | 437.711 | 171.93 | 0.987 |
| 2 | 15 | 11 | 98.618 | 3.580 | 66.690 | 80.82 | 0.796 |
| 2 | 15 | 13 | 356.747 | 4.182 | 558.186 | 255.52 | 0.985 |
| 2 | 15 | 15 | 428.945 | 4.931 | 651.754 | 307.37 | 0.992 |
| 2 | 15 | 17 | 170.217 | 3.267 | 251.827 | 359.20 | 0.971 |
| 2 | 15 | 19 | 488.682 | 4.341 | 603.634 | 289.51 | 0.996 |
| 2 | 15 | 21 | 226.844 | 3.181 | 308.126 | 9.82 | 0.980 |
| 2 | 15 | 23 | 170.829 | 3.890 | 192.790 | 216.51 | 0.968 |
| 2 | 15 | 25 | 202.472 | 3.534 | 265.239 | 325.14 | 0.975 |
| 2 | 15 | 27 | 116.257 | 5.393 | 118.375 | 45.80 | 0.918 |
| 2 | 15 | 29 | 181.795 | 4.522 | 257.286 | 44.81 | 0.971 |
| 2 | 15 | 31 | 92.294 | 11.288 | 123.132 | 232.83 | 0.730 |
| 2 | 15 | 33 | 195.982 | 4.772 | 325.193 | 228.52 | 0.976 |
| 2 | 15 | 35 | 81.725 | 9.990 | 85.363 | 166.23 | 0.556 |
| 2 | 15 | 37 | 54.415 | 11.773 | 17.458 | 26.03 | 0.852 |
| 2 | 15 | 39 | 43.301 | 20.217 | 7.939 | 206.38 | 0.515 |
| 2 | 16 | 0 | 46.389 | 10.984 | 55.398 | 0.00 | 0.863 |
| 2 | 16 | 2 | 127.453 | 3.977 | 171.359 | 176.20 | 0.939 |
| 2 | 16 | 4 | 144.466 | 2.897 | 208.368 | 273.16 | 0.965 |
| 2 | 16 | 6 | 173.270 | 3.484 | 208.028 | 129.04 | 0.967 |
| 2 | 16 | 8 | 196.602 | 2.722 | 297.194 | 154.98 | 0.973 |
| 2 | 16 | 10 | 267.526 | 2.830 | 388.660 | 108.85 | 0.983 |
| 2 | 16 | 12 | 45.282 | 8.235 | 20.591 | 102.03 | 0.524 |
| 2 | 16 | 14 | 71.804 | 5.233 | 44.455 | 135.70 | 0.469 |
| 2 | 16 | 16 | 323.849 | 3.773 | 438.129 | 158.84 | 0.990 |

| | | | | | | | |
|---|---|---|---|---|---|---|---|
| 2 | 16 | 18 | 239.465 | 3.189 | 325.312 | 170.70 | 0.983 |
| 2 | 16 | 20 | 575.626 | 5.520 | 813.681 | 64.20 | 0.997 |
| 2 | 16 | 22 | 142.684 | 4.384 | 189.126 | 24.85 | 0.926 |
| 2 | 16 | 24 | 220.395 | 3.598 | 311.860 | 235.20 | 0.974 |
| 2 | 16 | 26 | 243.915 | 3.653 | 328.543 | 60.45 | 0.980 |
| 2 | 16 | 28 | 131.952 | 6.127 | 109.137 | 242.57 | 0.964 |
| 2 | 16 | 30 | 120.178 | 7.166 | 156.563 | 146.21 | 0.931 |
| 2 | 16 | 32 | 68.226 | 10.946 | 57.903 | 302.73 | 0.856 |
| 2 | 16 | 34 | 72.144 | 9.971 | 75.886 | 42.40 | 0.859 |
| 2 | 16 | 36 | 37.935 | 11.307 | 6.722 | 68.81 | 0.602 |
| 2 | 16 | 38 | 58.426 | 23.175 | 25.321 | 321.30 | 0.858 |
| 2 | 17 | 1 | 226.146 | 3.106 | 291.590 | 206.15 | 0.986 |
| 2 | 17 | 3 | 193.055 | 3.214 | 234.728 | 256.45 | 0.976 |
| 2 | 17 | 5 | 71.422 | 4.993 | 84.371 | 112.36 | 0.896 |
| 2 | 17 | 7 | 310.087 | 3.119 | 497.293 | 9.80 | 0.986 |
| 2 | 17 | 9 | 240.032 | 2.887 | 325.147 | 119.31 | 0.980 |
| 2 | 17 | 11 | 370.971 | 3.475 | 502.228 | 196.08 | 0.992 |
| 2 | 17 | 13 | 305.253 | 3.282 | 422.048 | 80.10 | 0.985 |
| 2 | 17 | 15 | 360.066 | 3.634 | 557.667 | 234.36 | 0.991 |
| 2 | 17 | 17 | 289.852 | 3.236 | 396.733 | 186.99 | 0.988 |
| 2 | 17 | 19 | 155.034 | 4.195 | 150.522 | 178.16 | 0.971 |
| 2 | 17 | 21 | 119.814 | 5.495 | 125.315 | 227.91 | 0.938 |
| 2 | 17 | 23 | 447.974 | 5.105 | 607.012 | 215.28 | 0.994 |
| 2 | 17 | 25 | 65.126 | 10.611 | 46.085 | 251.72 | 0.493 |
| 2 | 17 | 27 | 159.947 | 5.110 | 217.443 | 218.27 | 0.965 |
| 2 | 17 | 29 | 254.026 | 4.151 | 298.005 | 292.20 | 0.988 |
| 2 | 17 | 31 | 33.127 | 10.551 | 10.997 | 253.58 | 0.419 |
| 2 | 17 | 33 | 48.533 | 12.258 | 7.891 | 73.83 | 0.767 |
| 2 | 17 | 35 | 64.230 | 10.589 | 63.601 | 83.58 | 0.812 |
| 2 | 17 | 37 | 68.460 | 26.727 | 41.809 | 19.49 | 0.864 |
| 2 | 18 | 0 | 118.677 | 3.768 | 165.114 | 0.00 | 1.000 |
| 2 | 18 | 2 | 283.009 | 3.111 | 393.453 | 43.13 | 0.985 |
| 2 | 18 | 4 | 396.458 | 4.528 | 510.501 | 38.63 | 0.993 |
| 2 | 18 | 6 | 133.814 | 3.025 | 200.804 | 323.71 | 0.867 |
| 2 | 18 | 8 | 277.285 | 3.138 | 409.676 | 15.55 | 0.983 |
| 2 | 18 | 10 | 398.505 | 3.687 | 537.424 | 140.60 | 0.992 |
| 2 | 18 | 12 | 573.651 | 5.414 | 739.260 | 74.35 | 0.997 |
| 2 | 18 | 14 | 143.073 | 3.583 | 171.070 | 64.26 | 0.949 |
| 2 | 18 | 16 | 369.392 | 3.774 | 487.990 | 9.04 | 0.993 |
| 2 | 18 | 18 | 145.062 | 3.730 | 175.085 | 231.25 | 0.961 |
| 2 | 18 | 20 | 382.937 | 4.091 | 517.156 | 53.95 | 0.993 |
| 2 | 18 | 22 | 194.423 | 4.035 | 265.295 | 241.50 | 0.970 |
| 2 | 18 | 24 | 274.906 | 5.096 | 301.656 | 123.62 | 0.987 |
| 2 | 18 | 26 | 48.905 | 12.848 | 5.710 | 30.80 | 0.588 |
| 2 | 18 | 28 | 185.760 | 5.101 | 238.233 | 302.41 | 0.976 |
| 2 | 18 | 30 | 329.351 | 3.855 | 382.217 | 250.03 | 0.995 |
| 2 | 18 | 32 | 80.618 | 10.010 | 54.928 | 261.06 | 0.925 |
| 2 | 18 | 34 | 124.024 | 5.973 | 188.335 | 228.03 | 0.952 |
| 2 | 18 | 36 | 82.396 | 13.173 | 111.628 | 89.57 | 0.920 |
| 2 | 19 | 1 | 365.774 | 3.356 | 599.017 | 86.18 | 0.986 |
| 2 | 19 | 3 | 160.826 | 3.196 | 154.731 | 170.91 | 0.971 |
| 2 | 19 | 5 | 218.128 | 3.075 | 303.003 | 51.59 | 0.977 |
| 2 | 19 | 7 | 94.890 | 3.709 | 123.942 | 147.71 | 0.819 |
| 2 | 19 | 9 | 143.368 | 3.419 | 143.511 | 156.93 | 0.966 |
| 2 | 19 | 11 | 91.351 | 4.982 | 120.650 | 115.52 | 0.775 |
| 2 | 19 | 13 | 382.976 | 3.613 | 532.657 | 38.94 | 0.994 |
| 2 | 19 | 15 | 588.531 | 5.624 | 802.438 | 11.43 | 0.997 |
| 2 | 19 | 17 | 386.455 | 3.930 | 558.627 | 255.83 | 0.993 |
| 2 | 19 | 19 | 70.170 | 10.142 | 57.470 | 237.09 | 0.557 |
| 2 | 19 | 21 | 299.371 | 4.506 | 363.187 | 31.87 | 0.988 |
| 2 | 19 | 23 | 248.649 | 4.124 | 423.047 | 229.97 | 0.968 |
| 2 | 19 | 25 | 104.511 | 10.108 | 153.884 | 197.60 | 0.728 |
| 2 | 19 | 27 | 397.186 | 5.185 | 559.578 | 112.29 | 0.996 |
| 2 | 19 | 29 | 93.398 | 7.831 | 92.219 | 157.90 | 0.938 |
| 2 | 19 | 31 | 115.047 | 7.478 | 197.522 | 295.74 | 0.799 |
| 2 | 19 | 33 | 39.136 | 11.545 | 5.920 | 48.79 | 0.704 |
| 2 | 19 | 35 | 48.526 | 14.379 | 10.639 | 143.66 | 0.735 |
| 2 | 20 | 0 | 118.028 | 5.005 | 163.844 | 180.00 | 0.999 |
| 2 | 20 | 2 | 328.973 | 3.090 | 566.524 | 270.43 | 0.987 |
| 2 | 20 | 4 | 121.073 | 3.994 | 108.002 | 26.04 | 0.960 |
| 2 | 20 | 6 | 682.191 | 5.450 | 964.397 | 296.46 | 0.998 |
| 2 | 20 | 8 | 254.639 | 3.369 | 329.701 | 283.41 | 0.987 |
| 2 | 20 | 10 | 103.253 | 4.478 | 129.685 | 132.34 | 0.924 |
| 2 | 20 | 12 | 201.588 | 3.453 | 260.112 | 314.14 | 0.979 |
| 2 | 20 | 14 | 204.754 | 3.708 | 286.921 | 284.00 | 0.977 |
| 2 | 20 | 16 | 469.135 | 4.747 | 629.469 | 214.62 | 0.996 |
| 2 | 20 | 18 | 368.959 | 4.027 | 560.229 | 295.74 | 0.991 |

| | | | | | | | |
|---|---|---|---|---|---|---|---|
| 2 | 20 | 20 | 371.773 | 4.811 | 519.473 | 64.58 | 0.992 |
| 2 | 20 | 22 | 276.665 | 4.028 | 361.497 | 266.14 | 0.985 |
| 2 | 20 | 24 | 191.290 | 5.459 | 290.986 | 203.05 | 0.974 |
| 2 | 20 | 26 | 168.626 | 6.089 | 242.395 | 24.63 | 0.976 |
| 2 | 20 | 28 | 233.355 | 5.025 | 299.958 | 93.77 | 0.989 |
| 2 | 20 | 30 | 82.502 | 9.557 | 85.466 | 129.68 | 0.913 |
| 2 | 20 | 32 | 58.057 | 12.771 | 26.239 | 47.11 | 0.861 |
| 2 | 20 | 34 | 75.736 | 14.714 | 81.651 | 189.40 | 0.848 |
| 2 | 21 | 1 | 186.319 | 3.279 | 255.387 | 107.54 | 0.974 |
| 2 | 21 | 3 | 342.668 | 3.165 | 520.186 | 109.30 | 0.991 |
| 2 | 21 | 5 | 355.444 | 3.623 | 462.920 | 306.47 | 0.993 |
| 2 | 21 | 7 | 637.856 | 5.857 | 845.023 | 353.09 | 0.998 |
| 2 | 21 | 9 | 149.051 | 3.615 | 189.281 | 271.93 | 0.962 |
| 2 | 21 | 11 | 135.280 | 4.275 | 149.796 | 163.29 | 0.954 |
| 2 | 21 | 13 | 373.520 | 3.918 | 531.477 | 76.88 | 0.993 |
| 2 | 21 | 15 | 216.216 | 3.788 | 316.600 | 108.28 | 0.977 |
| 2 | 21 | 17 | 363.863 | 3.930 | 405.243 | 162.91 | 0.993 |
| 2 | 21 | 19 | 291.352 | 3.658 | 527.028 | 73.04 | 0.977 |
| 2 | 21 | 21 | 130.618 | 4.907 | 186.597 | 46.07 | 0.947 |
| 2 | 21 | 23 | 169.100 | 5.259 | 180.302 | 92.89 | 0.976 |
| 2 | 21 | 25 | 132.693 | 9.937 | 143.343 | 243.59 | 0.970 |
| 2 | 21 | 27 | 99.898 | 8.815 | 85.765 | 323.14 | 0.950 |
| 2 | 21 | 29 | 221.746 | 4.419 | 387.903 | 111.32 | 0.980 |
| 2 | 21 | 31 | 72.813 | 10.764 | 65.401 | 288.06 | 0.903 |
| 2 | 21 | 33 | 101.781 | 10.941 | 147.350 | 275.68 | 0.911 |
| 2 | 22 | 0 | 218.525 | 4.399 | 197.421 | 0.00 | 0.649 |
| 2 | 22 | 2 | 219.469 | 3.100 | 252.894 | 198.39 | 0.985 |
| 2 | 22 | 4 | 92.319 | 4.827 | 111.827 | 261.07 | 0.860 |
| 2 | 22 | 6 | 311.403 | 3.577 | 461.595 | 0.78 | 0.990 |
| 2 | 22 | 8 | 117.961 | 4.376 | 170.285 | 42.96 | 0.910 |
| 2 | 22 | 10 | 67.812 | 8.762 | 58.895 | 130.26 | 0.724 |
| 2 | 22 | 12 | 260.851 | 3.252 | 453.518 | 245.44 | 0.936 |
| 2 | 22 | 14 | 276.414 | 3.341 | 331.188 | 231.08 | 0.988 |
| 2 | 22 | 16 | 454.705 | 4.405 | 627.286 | 244.98 | 0.995 |
| 2 | 22 | 18 | 209.212 | 3.982 | 378.075 | 231.87 | 0.948 |
| 2 | 22 | 20 | 256.675 | 4.886 | 324.752 | 349.78 | 0.989 |
| 2 | 22 | 22 | 48.323 | 13.691 | 1.536 | 139.00 | 0.600 |
| 2 | 22 | 24 | 83.252 | 15.675 | 75.848 | 159.06 | 0.923 |
| 2 | 22 | 26 | 186.114 | 7.754 | 280.485 | 125.01 | 0.979 |
| 2 | 22 | 28 | 49.949 | 12.215 | 3.162 | 6.00 | 0.813 |
| 2 | 22 | 30 | 84.545 | 10.433 | 120.292 | 34.84 | 0.884 |
| 2 | 22 | 32 | 76.531 | 13.225 | 82.704 | 292.55 | 0.878 |
| 2 | 23 | 1 | 89.265 | 6.919 | 99.615 | 208.25 | 0.862 |
| 2 | 23 | 3 | 110.776 | 4.596 | 110.145 | 149.59 | 0.925 |
| 2 | 23 | 5 | 388.219 | 3.666 | 522.548 | 2.45 | 0.994 |
| 2 | 23 | 7 | 173.768 | 4.666 | 243.397 | 337.68 | 0.967 |
| 2 | 23 | 9 | 375.941 | 3.561 | 530.918 | 271.59 | 0.993 |
| 2 | 23 | 11 | 367.546 | 3.567 | 492.607 | 262.73 | 0.992 |
| 2 | 23 | 13 | 425.123 | 3.832 | 589.049 | 243.98 | 0.994 |
| 2 | 23 | 15 | 252.594 | 3.868 | 397.022 | 143.89 | 0.977 |
| 2 | 23 | 17 | 185.439 | 3.769 | 357.211 | 140.44 | 0.953 |
| 2 | 23 | 19 | 314.883 | 6.339 | 455.936 | 298.83 | 0.992 |
| 2 | 23 | 21 | 55.989 | 12.247 | 12.377 | 195.70 | 0.848 |
| 2 | 23 | 23 | 75.988 | 10.492 | 90.429 | 308.67 | 0.621 |
| 2 | 23 | 25 | 119.346 | 9.733 | 161.626 | 91.36 | 0.952 |
| 2 | 23 | 27 | 131.258 | 8.794 | 223.579 | 257.77 | 0.936 |
| 2 | 23 | 29 | 93.408 | 16.052 | 98.200 | 110.34 | 0.934 |
| 2 | 23 | 31 | 49.733 | 14.422 | 39.449 | 255.30 | 0.527 |
| 2 | 24 | 0 | 67.323 | 13.953 | 73.775 | 0.00 | 0.795 |
| 2 | 24 | 2 | 536.340 | 4.377 | 743.180 | 259.12 | 0.997 |
| 2 | 24 | 4 | 150.703 | 4.280 | 180.553 | 82.95 | 0.956 |
| 2 | 24 | 6 | 88.766 | 6.712 | 109.497 | 277.65 | 0.862 |
| 2 | 24 | 8 | 90.423 | 5.372 | 33.813 | 4.29 | 0.920 |
| 2 | 24 | 10 | 367.481 | 3.623 | 550.737 | 139.70 | 0.991 |
| 2 | 24 | 12 | 352.985 | 3.722 | 486.894 | 188.55 | 0.992 |
| 2 | 24 | 14 | 346.904 | 3.906 | 473.139 | 97.51 | 0.991 |
| 2 | 24 | 16 | 376.353 | 4.069 | 628.246 | 169.98 | 0.993 |
| 2 | 24 | 18 | 195.134 | 4.401 | 271.473 | 43.62 | 0.978 |
| 2 | 24 | 20 | 244.056 | 4.714 | 360.227 | 133.09 | 0.989 |
| 2 | 24 | 22 | 211.890 | 4.705 | 265.542 | 319.19 | 0.988 |
| 2 | 24 | 24 | 62.181 | 10.597 | 68.611 | 334.53 | 0.755 |
| 2 | 24 | 26 | 85.352 | 8.883 | 112.882 | 19.16 | 0.891 |
| 2 | 24 | 28 | 79.129 | 14.056 | 106.080 | 214.54 | 0.837 |
| 2 | 24 | 30 | 58.740 | 15.226 | 63.012 | 147.88 | 0.643 |
| 2 | 25 | 1 | 134.050 | 4.865 | 157.327 | 34.46 | 0.945 |
| 2 | 25 | 3 | 127.549 | 6.932 | 113.412 | 281.88 | 0.950 |
| 2 | 25 | 5 | 383.530 | 3.815 | 545.565 | 267.88 | 0.993 |

| | | | | | | | |
|---|---|---|---|---|---|---|---|
| 2 | 25 | 7 | 164.604 | 6.521 | 206.260 | 68.82 | 0.961 |
| 2 | 25 | 9 | 220.733 | 5.248 | 272.434 | 229.59 | 0.980 |
| 2 | 25 | 11 | 277.473 | 4.089 | 368.175 | 127.11 | 0.991 |
| 2 | 25 | 13 | 144.002 | 6.779 | 164.656 | 317.71 | 0.966 |
| 2 | 25 | 15 | 126.341 | 6.040 | 196.565 | 176.39 | 0.926 |
| 2 | 25 | 17 | 282.760 | 3.696 | 343.815 | 155.50 | 0.994 |
| 2 | 25 | 19 | 202.380 | 4.395 | 340.498 | 173.48 | 0.981 |
| 2 | 25 | 21 | 71.215 | 11.089 | 58.818 | 14.66 | 0.909 |
| 2 | 25 | 23 | 87.182 | 8.939 | 79.997 | 358.61 | 0.930 |
| 2 | 25 | 25 | 110.499 | 9.453 | 145.019 | 340.13 | 0.953 |
| 2 | 25 | 27 | 58.593 | 14.020 | 53.551 | 301.82 | 0.638 |
| 2 | 25 | 29 | 192.422 | 14.753 | 273.751 | 25.46 | 0.988 |
| 2 | 26 | 0 | 411.050 | 5.505 | 571.131 | 180.00 | 1.000 |
| 2 | 26 | 2 | 120.458 | 6.311 | 179.348 | 88.71 | 0.896 |
| 2 | 26 | 4 | 275.256 | 4.105 | 434.978 | 234.41 | 0.983 |
| 2 | 26 | 6 | 393.335 | 4.176 | 489.587 | 31.39 | 0.996 |
| 2 | 26 | 8 | 212.233 | 4.664 | 322.605 | 50.01 | 0.981 |
| 2 | 26 | 10 | 148.876 | 5.645 | 235.521 | 49.16 | 0.955 |
| 2 | 26 | 12 | 176.390 | 5.514 | 242.253 | 216.06 | 0.587 |
| 2 | 26 | 14 | 218.500 | 5.053 | 289.780 | 277.30 | 0.984 |
| 2 | 26 | 16 | 172.656 | 4.724 | 252.418 | 136.75 | 0.979 |
| 2 | 26 | 18 | 79.315 | 8.993 | 83.037 | 30.02 | 0.910 |
| 2 | 26 | 20 | 37.391 | 10.697 | 8.326 | 90.05 | 0.574 |
| 2 | 26 | 22 | 140.439 | 5.480 | 174.875 | 230.53 | 0.971 |
| 2 | 26 | 24 | 51.868 | 11.727 | 36.223 | 263.32 | 0.678 |
| 2 | 26 | 26 | 103.222 | 14.130 | 133.297 | 192.39 | 0.938 |
| 2 | 26 | 28 | 113.537 | 22.056 | 114.697 | 320.64 | 0.964 |
| 2 | 27 | 1 | 272.409 | 4.281 | 326.188 | 122.96 | 0.991 |
| 2 | 27 | 3 | 152.986 | 8.276 | 216.832 | 242.45 | 0.964 |
| 2 | 27 | 5 | 323.731 | 4.237 | 398.477 | 15.15 | 0.994 |
| 2 | 27 | 7 | 263.662 | 4.854 | 262.385 | 169.16 | 0.992 |
| 2 | 27 | 9 | 203.317 | 7.431 | 269.906 | 89.45 | 0.982 |
| 2 | 27 | 11 | 117.499 | 6.212 | 160.800 | 55.99 | 0.956 |
| 2 | 27 | 13 | 137.311 | 5.417 | 173.623 | 117.52 | 0.971 |
| 2 | 27 | 15 | 131.589 | 5.782 | 172.244 | 59.52 | 0.967 |
| 2 | 27 | 17 | 69.759 | 10.313 | 71.133 | 3.75 | 0.877 |
| 2 | 27 | 19 | 115.086 | 6.359 | 149.767 | 295.61 | 0.955 |
| 2 | 27 | 21 | 40.749 | 11.218 | 1.014 | 13.32 | 0.127 |
| 2 | 27 | 23 | 124.206 | 6.767 | 168.804 | 302.45 | 0.965 |
| 2 | 27 | 25 | 51.407 | 15.672 | 48.103 | 85.86 | 0.768 |
| 2 | 27 | 27 | 67.601 | 24.878 | 54.738 | 167.95 | 0.711 |
| 2 | 28 | 0 | 29.738 | 14.135 | 15.895 | 0.00 | 0.393 |
| 2 | 28 | 2 | 203.036 | 4.481 | 265.566 | 87.25 | 0.982 |
| 2 | 28 | 4 | 197.805 | 4.568 | 285.935 | 1.11 | 0.979 |
| 2 | 28 | 6 | 50.375 | 12.128 | 30.081 | 322.82 | 0.638 |
| 2 | 28 | 8 | 46.397 | 11.063 | 24.057 | 183.08 | 0.507 |
| 2 | 28 | 10 | 136.486 | 6.369 | 135.092 | 199.60 | 0.976 |
| 2 | 28 | 12 | 72.231 | 10.460 | 42.048 | 27.02 | 0.922 |
| 2 | 28 | 14 | 106.521 | 6.032 | 96.426 | 315.79 | 0.961 |
| 2 | 28 | 16 | 87.953 | 8.196 | 142.679 | 209.66 | 0.835 |
| 2 | 28 | 18 | 146.195 | 5.507 | 225.788 | 318.42 | 0.966 |
| 2 | 28 | 20 | 63.633 | 10.757 | 59.812 | 188.38 | 0.869 |
| 2 | 28 | 22 | 104.838 | 10.524 | 100.621 | 271.91 | 0.960 |
| 2 | 28 | 24 | 70.427 | 25.464 | 57.857 | 32.68 | 0.868 |
| 2 | 29 | 1 | 217.917 | 4.849 | 295.901 | 31.37 | 0.989 |
| 2 | 29 | 3 | 163.147 | 5.242 | 194.862 | 43.72 | 0.981 |
| 2 | 29 | 5 | 43.915 | 11.927 | 16.404 | 357.54 | 0.472 |
| 2 | 29 | 7 | 116.461 | 8.988 | 136.711 | 179.46 | 0.962 |
| 2 | 29 | 9 | 54.627 | 13.726 | 9.381 | 35.56 | 0.875 |
| 2 | 29 | 11 | 165.003 | 6.279 | 215.425 | 326.22 | 0.980 |
| 2 | 29 | 13 | 158.604 | 6.521 | 204.186 | 293.95 | 0.978 |
| 2 | 29 | 15 | 40.791 | 10.970 | 5.219 | 314.13 | 0.697 |
| 2 | 29 | 17 | 28.259 | 9.671 | 16.697 | 188.25 | 0.469 |
| 2 | 29 | 19 | 70.070 | 11.154 | 88.668 | 0.71 | 0.742 |
| 2 | 29 | 21 | 82.871 | 14.076 | 104.739 | 202.29 | 0.938 |
| 2 | 29 | 23 | 51.458 | 22.667 | 19.977 | 54.73 | 0.382 |
| 2 | 30 | 0 | 35.797 | 16.125 | 46.244 | 0.00 | 0.951 |
| 2 | 30 | 2 | 70.127 | 14.917 | 49.381 | 244.71 | 0.903 |
| 2 | 30 | 4 | 111.440 | 6.288 | 202.786 | 37.96 | 0.865 |
| 2 | 30 | 6 | 128.128 | 5.961 | 127.290 | 22.30 | 0.974 |
| 2 | 30 | 8 | 50.175 | 11.535 | 28.159 | 225.00 | 0.469 |
| 2 | 30 | 10 | 92.208 | 9.391 | 105.720 | 19.55 | 0.935 |
| 2 | 30 | 12 | 43.451 | 11.623 | 10.353 | 115.20 | 0.629 |
| 2 | 30 | 14 | 86.652 | 8.734 | 55.399 | 164.62 | 0.324 |
| 2 | 30 | 16 | 130.630 | 5.440 | 123.959 | 94.47 | 0.978 |
| 2 | 30 | 18 | 77.235 | 13.768 | 69.829 | 7.25 | 0.918 |
| 2 | 30 | 20 | 41.384 | 18.996 | 5.986 | 313.24 | 0.784 |

| | | | | | | | |
|---|---|---|---|---|---|---|---|
| 2 | 31 | 1 | 50.422 | 12.187 | 28.608 | 111.17 | 0.700 |
| 2 | 31 | 3 | 79.751 | 9.523 | 5.675 | 157.16 | 0.954 |
| 2 | 31 | 5 | 102.294 | 8.000 | 177.806 | 280.62 | 0.871 |
| 2 | 31 | 7 | 49.157 | 10.610 | 23.246 | 12.12 | 0.803 |
| 2 | 31 | 9 | 44.045 | 12.764 | 16.860 | 241.89 | 0.364 |
| 2 | 31 | 11 | 66.237 | 12.737 | 67.529 | 271.09 | 0.529 |
| 2 | 31 | 13 | 76.421 | 15.173 | 96.588 | 210.60 | 0.866 |
| 2 | 31 | 15 | 51.308 | 13.503 | 38.318 | 65.28 | 0.879 |
| 2 | 31 | 17 | 40.510 | 18.564 | 9.943 | 290.47 | 0.406 |
| 2 | 32 | 0 | 215.118 | 6.607 | 296.783 | 180.00 | 1.000 |
| 2 | 32 | 2 | 144.217 | 5.706 | 231.041 | 53.53 | 0.971 |
| 2 | 32 | 4 | 81.855 | 10.280 | 62.973 | 124.31 | 0.945 |
| 2 | 32 | 6 | 105.588 | 9.750 | 149.273 | 244.72 | 0.949 |
| 2 | 32 | 8 | 75.472 | 13.301 | 78.429 | 95.12 | 0.902 |
| 2 | 32 | 10 | 89.640 | 8.211 | 107.234 | 219.14 | 0.940 |
| 2 | 32 | 12 | 117.007 | 12.607 | 168.489 | 276.93 | 0.971 |
| 2 | 32 | 14 | 49.614 | 20.504 | 25.995 | 148.89 | 0.731 |
| 2 | 33 | 1 | 78.110 | 12.301 | 100.503 | 134.97 | 0.880 |
| 2 | 33 | 3 | 76.775 | 12.008 | 108.900 | 63.72 | 0.925 |
| 2 | 33 | 5 | 36.415 | 12.282 | 14.940 | 104.78 | 0.671 |
| 2 | 33 | 7 | 41.425 | 12.365 | 30.803 | 174.01 | 0.730 |
| 2 | 33 | 9 | 40.147 | 12.958 | 7.175 | 5.45 | 0.830 |
| 2 | 33 | 11 | 53.672 | 21.031 | 39.327 | 11.36 | 0.685 |
| 3 | 0 | 1 | 203.954 | 2.986 | 284.136 | 0.00 | 0.999 |
| 3 | 0 | 3 | 843.769 | 9.767 | 1179.302 | 0.00 | 1.000 |
| 3 | 0 | 5 | 32.821 | 6.064 | 12.569 | 180.00 | 0.315 |
| 3 | 0 | 7 | 91.774 | 2.223 | 23.691 | 180.00 | 0.188 |
| 3 | 0 | 9 | 66.610 | 3.688 | 2.015 | 180.00 | 0.022 |
| 3 | 0 | 11 | 1011.136 | 11.144 | 1402.964 | 0.00 | 1.000 |
| 3 | 0 | 13 | 348.830 | 4.155 | 482.263 | 180.00 | 1.000 |
| 3 | 0 | 15 | 327.792 | 4.122 | 451.945 | 0.00 | 1.000 |
| 3 | 0 | 17 | 138.171 | 3.320 | 150.790 | 0.00 | 0.798 |
| 3 | 0 | 19 | 354.193 | 4.270 | 483.664 | 180.00 | 1.000 |
| 3 | 0 | 21 | 37.732 | 11.818 | 11.943 | 0.00 | 0.234 |
| 3 | 0 | 23 | 272.264 | 3.893 | 287.145 | 180.00 | 0.781 |
| 3 | 0 | 25 | 25.410 | 11.418 | 2.617 | 0.00 | 0.084 |
| 3 | 0 | 27 | 608.879 | 7.108 | 812.112 | 180.00 | 1.000 |
| 3 | 0 | 29 | 112.910 | 7.400 | 149.246 | 0.00 | 1.000 |
| 3 | 0 | 31 | 95.238 | 11.416 | 115.176 | 180.00 | 0.924 |
| 3 | 0 | 33 | 242.477 | 6.067 | 315.919 | 180.00 | 1.000 |
| 3 | 0 | 35 | 57.497 | 18.586 | 65.265 | 0.00 | 0.887 |
| 3 | 0 | 37 | 203.009 | 8.193 | 259.155 | 180.00 | 1.000 |
| 3 | 0 | 39 | 29.229 | 14.203 | 35.121 | 180.00 | 0.960 |
| 3 | 0 | 41 | 33.238 | 15.299 | 24.640 | 0.00 | 0.605 |
| 3 | 0 | 43 | 69.626 | 30.413 | 76.114 | 180.00 | 0.998 |
| 3 | 1 | 0 | 295.731 | 4.397 | 402.658 | 180.00 | 0.973 |
| 3 | 1 | 2 | 918.228 | 13.634 | 1225.153 | 346.54 | 0.994 |
| 3 | 1 | 4 | 977.220 | 8.937 | 1491.759 | 68.16 | 0.994 |
| 3 | 1 | 6 | 517.451 | 4.191 | 750.435 | 184.58 | 0.977 |
| 3 | 1 | 8 | 592.014 | 4.710 | 743.778 | 101.28 | 0.987 |
| 3 | 1 | 10 | 461.723 | 3.558 | 607.860 | 6.59 | 0.974 |
| 3 | 1 | 12 | 718.625 | 5.790 | 943.816 | 353.33 | 0.989 |
| 3 | 1 | 14 | 323.528 | 3.013 | 462.812 | 266.86 | 0.989 |
| 3 | 1 | 16 | 618.457 | 5.830 | 883.426 | 94.68 | 0.996 |
| 3 | 1 | 18 | 252.151 | 2.467 | 353.998 | 234.02 | 0.981 |
| 3 | 1 | 20 | 450.388 | 4.437 | 600.437 | 149.61 | 0.995 |
| 3 | 1 | 22 | 312.908 | 2.891 | 420.490 | 20.80 | 0.988 |
| 3 | 1 | 24 | 311.910 | 3.009 | 451.450 | 85.21 | 0.985 |
| 3 | 1 | 26 | 172.124 | 3.016 | 251.059 | 196.58 | 0.952 |
| 3 | 1 | 28 | 48.574 | 9.516 | 22.993 | 306.86 | 0.831 |
| 3 | 1 | 30 | 124.858 | 4.805 | 158.965 | 16.56 | 0.919 |
| 3 | 1 | 32 | 211.544 | 3.888 | 250.638 | 149.23 | 0.971 |
| 3 | 1 | 34 | 251.340 | 5.103 | 302.196 | 207.91 | 0.987 |
| 3 | 1 | 36 | 165.407 | 5.705 | 269.617 | 232.22 | 0.948 |
| 3 | 1 | 38 | 244.488 | 5.271 | 320.159 | 176.46 | 0.989 |
| 3 | 1 | 40 | 100.039 | 8.513 | 103.003 | 10.57 | 0.933 |
| 3 | 1 | 42 | 99.668 | 10.966 | 126.313 | 217.43 | 0.923 |
| 3 | 2 | 1 | 344.553 | 3.648 | 410.076 | 25.70 | 0.978 |
| 3 | 2 | 3 | 220.287 | 1.859 | 276.201 | 349.32 | 0.931 |
| 3 | 2 | 5 | 44.708 | 2.673 | 20.191 | 312.09 | 0.490 |
| 3 | 2 | 7 | 205.919 | 2.087 | 278.315 | 8.58 | 0.984 |
| 3 | 2 | 9 | 992.993 | 8.254 | 1375.111 | 126.46 | 0.994 |
| 3 | 2 | 11 | 978.057 | 7.901 | 1331.257 | 141.55 | 0.994 |
| 3 | 2 | 13 | 549.307 | 4.525 | 751.935 | 30.92 | 0.995 |
| 3 | 2 | 15 | 190.533 | 2.351 | 268.389 | 203.74 | 0.958 |
| 3 | 2 | 17 | 270.002 | 2.715 | 392.107 | 257.09 | 0.982 |
| 3 | 2 | 19 | 61.630 | 5.144 | 40.508 | 34.00 | 0.623 |

| | | | | | | | |
|---|---|---|---|---|---|---|---|
| 3 | 2 | 21 | 151.399 | 2.876 | 204.774 | 355.47 | 0.952 |
| 3 | 2 | 23 | 297.645 | 3.208 | 413.620 | 62.78 | 0.985 |
| 3 | 2 | 25 | 187.199 | 3.189 | 247.820 | 225.11 | 0.969 |
| 3 | 2 | 27 | 40.143 | 9.191 | 26.655 | 14.09 | 0.539 |
| 3 | 2 | 29 | 513.272 | 5.363 | 704.662 | 326.30 | 0.996 |
| 3 | 2 | 31 | 134.782 | 5.468 | 168.771 | 121.64 | 0.918 |
| 3 | 2 | 33 | 222.826 | 4.759 | 270.041 | 222.87 | 0.977 |
| 3 | 2 | 35 | 128.048 | 6.882 | 179.110 | 348.14 | 0.932 |
| 3 | 2 | 37 | 250.301 | 4.818 | 337.857 | 217.01 | 0.989 |
| 3 | 2 | 39 | 65.225 | 12.875 | 44.551 | 230.18 | 0.839 |
| 3 | 2 | 41 | 51.073 | 14.294 | 25.227 | 210.56 | 0.581 |
| 3 | 2 | 43 | 61.945 | 19.007 | 58.203 | 269.83 | 0.794 |
| 3 | 3 | 0 | 995.906 | 14.911 | 1391.716 | 180.00 | 1.000 |
| 3 | 3 | 2 | 512.982 | 4.271 | 663.716 | 271.81 | 0.985 |
| 3 | 3 | 4 | 410.113 | 3.575 | 650.712 | 10.89 | 0.967 |
| 3 | 3 | 6 | 421.295 | 3.788 | 607.053 | 305.79 | 0.968 |
| 3 | 3 | 8 | 363.793 | 3.176 | 476.810 | 160.07 | 0.964 |
| 3 | 3 | 10 | 887.261 | 7.399 | 1312.117 | 99.57 | 0.992 |
| 3 | 3 | 12 | 573.176 | 4.658 | 725.858 | 261.47 | 0.996 |
| 3 | 3 | 14 | 482.259 | 4.588 | 712.396 | 152.09 | 0.993 |
| 3 | 3 | 16 | 324.531 | 3.246 | 459.529 | 317.89 | 0.988 |
| 3 | 3 | 18 | 308.892 | 2.916 | 424.871 | 145.05 | 0.988 |
| 3 | 3 | 20 | 254.526 | 2.620 | 383.655 | 64.08 | 0.984 |
| 3 | 3 | 22 | 161.672 | 2.838 | 167.642 | 62.80 | 0.975 |
| 3 | 3 | 24 | 341.225 | 3.193 | 415.323 | 43.66 | 0.990 |
| 3 | 3 | 26 | 79.895 | 6.013 | 83.345 | 173.38 | 0.645 |
| 3 | 3 | 28 | 155.386 | 3.600 | 217.004 | 160.02 | 0.949 |
| 3 | 3 | 30 | 172.971 | 4.358 | 252.152 | 113.05 | 0.952 |
| 3 | 3 | 32 | 311.326 | 3.958 | 429.122 | 303.78 | 0.987 |
| 3 | 3 | 34 | 71.375 | 11.124 | 62.345 | 113.02 | 0.558 |
| 3 | 3 | 36 | 77.713 | 10.659 | 60.840 | 40.11 | 0.583 |
| 3 | 3 | 38 | 120.736 | 8.919 | 164.358 | 248.95 | 0.944 |
| 3 | 3 | 40 | 112.583 | 8.189 | 140.848 | 55.85 | 0.939 |
| 3 | 3 | 42 | 79.707 | 14.919 | 38.584 | 310.00 | 0.929 |
| 3 | 4 | 1 | 259.580 | 2.172 | 356.909 | 164.75 | 0.845 |
| 3 | 4 | 3 | 174.840 | 1.936 | 155.692 | 181.86 | 0.928 |
| 3 | 4 | 5 | 237.640 | 2.381 | 337.718 | 270.25 | 0.920 |
| 3 | 4 | 7 | 388.652 | 3.319 | 606.802 | 152.80 | 0.980 |
| 3 | 4 | 9 | 480.147 | 4.499 | 740.469 | 88.38 | 0.973 |
| 3 | 4 | 11 | 545.323 | 4.627 | 744.481 | 64.59 | 0.996 |
| 3 | 4 | 13 | 292.536 | 2.884 | 355.706 | 341.20 | 0.991 |
| 3 | 4 | 15 | 694.404 | 5.714 | 989.682 | 352.21 | 0.997 |
| 3 | 4 | 17 | 103.184 | 2.769 | 110.170 | 189.85 | 0.975 |
| 3 | 4 | 19 | 202.915 | 2.606 | 247.879 | 188.91 | 0.986 |
| 3 | 4 | 21 | 216.252 | 2.507 | 306.728 | 78.90 | 0.975 |
| 3 | 4 | 23 | 165.289 | 2.944 | 204.721 | 132.91 | 0.964 |
| 3 | 4 | 25 | 71.905 | 6.915 | 74.562 | 226.30 | 0.857 |
| 3 | 4 | 27 | 446.172 | 3.932 | 609.754 | 325.17 | 0.995 |
| 3 | 4 | 29 | 251.008 | 3.195 | 334.242 | 78.98 | 0.983 |
| 3 | 4 | 31 | 230.286 | 3.467 | 365.208 | 10.45 | 0.971 |
| 3 | 4 | 33 | 49.178 | 11.991 | 12.200 | 46.86 | 0.275 |
| 3 | 4 | 35 | 79.459 | 11.618 | 61.456 | 309.65 | 0.611 |
| 3 | 4 | 37 | 46.170 | 12.547 | 15.385 | 98.10 | 0.788 |
| 3 | 4 | 39 | 76.774 | 11.079 | 28.139 | 282.77 | 0.926 |
| 3 | 4 | 41 | 40.763 | 12.054 | 6.663 | 126.61 | 0.660 |
| 3 | 4 | 43 | 84.257 | 25.835 | 81.664 | 258.75 | 0.884 |
| 3 | 5 | 0 | 356.970 | 5.354 | 499.060 | 0.00 | 1.000 |
| 3 | 5 | 2 | 476.632 | 4.231 | 616.146 | 72.99 | 0.983 |
| 3 | 5 | 4 | 251.877 | 2.586 | 316.358 | 126.11 | 0.981 |
| 3 | 5 | 6 | 959.061 | 7.916 | 1291.869 | 225.55 | 0.994 |
| 3 | 5 | 8 | 339.093 | 3.185 | 502.482 | 306.52 | 0.959 |
| 3 | 5 | 10 | 424.073 | 3.732 | 580.122 | 217.45 | 0.976 |
| 3 | 5 | 12 | 319.085 | 3.325 | 449.766 | 130.76 | 0.987 |
| 3 | 5 | 14 | 394.607 | 3.828 | 636.267 | 25.62 | 0.989 |
| 3 | 5 | 16 | 148.706 | 3.034 | 176.104 | 148.90 | 0.972 |
| 3 | 5 | 18 | 212.488 | 2.379 | 282.948 | 315.24 | 0.982 |
| 3 | 5 | 20 | 396.792 | 3.406 | 572.486 | 194.18 | 0.992 |
| 3 | 5 | 22 | 123.831 | 3.200 | 130.723 | 347.76 | 0.938 |
| 3 | 5 | 24 | 484.228 | 4.084 | 663.619 | 261.10 | 0.994 |
| 3 | 5 | 26 | 316.409 | 3.211 | 431.838 | 232.87 | 0.990 |
| 3 | 5 | 28 | 181.107 | 3.558 | 226.357 | 274.41 | 0.973 |
| 3 | 5 | 30 | 149.956 | 4.513 | 176.025 | 9.55 | 0.955 |
| 3 | 5 | 32 | 220.715 | 3.869 | 305.680 | 7.25 | 0.973 |
| 3 | 5 | 34 | 389.032 | 4.744 | 513.072 | 326.18 | 0.994 |
| 3 | 5 | 36 | 223.480 | 5.455 | 286.907 | 131.69 | 0.987 |
| 3 | 5 | 38 | 100.339 | 10.319 | 92.993 | 354.63 | 0.942 |
| 3 | 5 | 40 | 57.895 | 12.576 | 8.125 | 78.84 | 0.108 |

| | | | | | | | |
|---|---|---|---|---|---|---|---|
| 3 | 5 | 42 | 42.480 | 13.182 | 9.439 | 53.29 | 0.462 |
| 3 | 6 | 1 | 220.395 | 2.368 | 223.941 | 101.97 | 0.981 |
| 3 | 6 | 3 | 896.997 | 8.098 | 1265.497 | 241.52 | 0.993 |
| 3 | 6 | 5 | 91.562 | 1.991 | 52.670 | 238.48 | 0.409 |
| 3 | 6 | 7 | 439.885 | 4.128 | 618.926 | 343.41 | 0.980 |
| 3 | 6 | 9 | 170.854 | 1.895 | 189.397 | 37.73 | 0.854 |
| 3 | 6 | 11 | 531.250 | 4.720 | 735.074 | 243.17 | 0.995 |
| 3 | 6 | 13 | 481.062 | 4.746 | 663.439 | 115.62 | 0.994 |
| 3 | 6 | 15 | 193.991 | 2.319 | 182.210 | 262.95 | 0.981 |
| 3 | 6 | 17 | 134.530 | 2.617 | 181.068 | 151.36 | 0.934 |
| 3 | 6 | 19 | 99.307 | 3.269 | 133.233 | 226.57 | 0.934 |
| 3 | 6 | 21 | 53.404 | 6.853 | 30.481 | 192.20 | 0.826 |
| 3 | 6 | 23 | 176.396 | 3.021 | 244.702 | 200.08 | 0.967 |
| 3 | 6 | 25 | 146.910 | 3.556 | 192.760 | 30.73 | 0.963 |
| 3 | 6 | 27 | 218.726 | 3.134 | 293.431 | 138.07 | 0.979 |
| 3 | 6 | 29 | 97.134 | 5.527 | 85.517 | 94.54 | 0.900 |
| 3 | 6 | 31 | 359.239 | 3.972 | 484.867 | 13.00 | 0.991 |
| 3 | 6 | 33 | 192.296 | 5.039 | 249.335 | 218.54 | 0.964 |
| 3 | 6 | 35 | 248.833 | 4.541 | 379.526 | 164.06 | 0.982 |
| 3 | 6 | 37 | 170.904 | 6.294 | 214.212 | 30.76 | 0.978 |
| 3 | 6 | 39 | 49.760 | 14.799 | 14.600 | 218.98 | 0.372 |
| 3 | 6 | 41 | 164.836 | 6.303 | 199.270 | 67.45 | 0.979 |
| 3 | 7 | 0 | 103.105 | 2.127 | 118.943 | 180.00 | 0.832 |
| 3 | 7 | 2 | 119.450 | 2.520 | 140.622 | 142.62 | 0.827 |
| 3 | 7 | 4 | 997.690 | 9.815 | 1397.260 | 275.59 | 0.994 |
| 3 | 7 | 6 | 566.860 | 4.842 | 736.994 | 262.75 | 0.987 |
| 3 | 7 | 8 | 89.965 | 2.199 | 113.917 | 47.11 | 0.975 |
| 3 | 7 | 10 | 683.431 | 5.743 | 921.341 | 135.50 | 0.997 |
| 3 | 7 | 12 | 437.920 | 3.783 | 639.307 | 312.30 | 0.992 |
| 3 | 7 | 14 | 82.192 | 2.785 | 95.312 | 173.66 | 0.871 |
| 3 | 7 | 16 | 186.054 | 2.382 | 212.460 | 316.10 | 0.983 |
| 3 | 7 | 18 | 397.443 | 3.509 | 538.980 | 203.38 | 0.993 |
| 3 | 7 | 20 | 55.188 | 6.814 | 33.312 | 313.88 | 0.829 |
| 3 | 7 | 22 | 197.455 | 2.703 | 210.686 | 167.80 | 0.971 |
| 3 | 7 | 24 | 460.427 | 4.166 | 560.712 | 270.68 | 0.996 |
| 3 | 7 | 26 | 28.455 | 8.961 | 39.685 | 174.58 | 0.399 |
| 3 | 7 | 28 | 312.117 | 3.639 | 473.399 | 28.51 | 0.986 |
| 3 | 7 | 30 | 320.099 | 3.726 | 401.378 | 96.71 | 0.990 |
| 3 | 7 | 32 | 196.667 | 4.687 | 247.120 | 20.45 | 0.970 |
| 3 | 7 | 34 | 262.427 | 4.491 | 363.442 | 220.94 | 0.986 |
| 3 | 7 | 36 | 126.670 | 7.719 | 189.731 | 198.95 | 0.932 |
| 3 | 7 | 38 | 65.827 | 12.998 | 65.015 | 126.50 | 0.797 |
| 3 | 7 | 40 | 53.944 | 14.556 | 12.027 | 238.46 | 0.839 |
| 3 | 7 | 42 | 71.655 | 20.092 | 82.464 | 11.41 | 0.829 |
| 3 | 8 | 1 | 497.806 | 7.470 | 613.328 | 142.06 | 0.981 |
| 3 | 8 | 3 | 418.227 | 3.342 | 588.170 | 354.59 | 0.964 |
| 3 | 8 | 5 | 739.070 | 5.934 | 996.934 | 230.10 | 0.991 |
| 3 | 8 | 7 | 354.979 | 3.101 | 542.992 | 318.16 | 0.989 |
| 3 | 8 | 9 | 396.714 | 3.596 | 629.988 | 296.84 | 0.990 |
| 3 | 8 | 11 | 38.585 | 5.367 | 32.057 | 148.13 | 0.627 |
| 3 | 8 | 13 | 207.810 | 2.330 | 314.512 | 190.92 | 0.974 |
| 3 | 8 | 15 | 591.999 | 5.516 | 820.273 | 286.28 | 0.997 |
| 3 | 8 | 17 | 315.960 | 2.917 | 441.241 | 74.32 | 0.990 |
| 3 | 8 | 19 | 162.543 | 2.796 | 183.950 | 207.87 | 0.969 |
| 3 | 8 | 21 | 91.182 | 4.041 | 97.803 | 210.84 | 0.732 |
| 3 | 8 | 23 | 348.282 | 3.513 | 547.052 | 121.29 | 0.984 |
| 3 | 8 | 25 | 150.059 | 3.978 | 170.222 | 290.91 | 0.964 |
| 3 | 8 | 27 | 84.565 | 8.427 | 101.941 | 216.71 | 0.824 |
| 3 | 8 | 29 | 392.027 | 4.123 | 547.213 | 138.25 | 0.992 |
| 3 | 8 | 31 | 199.277 | 4.215 | 268.966 | 7.12 | 0.966 |
| 3 | 8 | 33 | 80.297 | 11.596 | 28.412 | 44.69 | 0.906 |
| 3 | 8 | 35 | 48.916 | 14.009 | 2.932 | 262.18 | 0.769 |
| 3 | 8 | 37 | 91.739 | 10.595 | 130.373 | 1.47 | 0.864 |
| 3 | 8 | 39 | 69.116 | 13.811 | 52.031 | 356.45 | 0.851 |
| 3 | 8 | 41 | 52.346 | 16.289 | 2.361 | 319.76 | 0.062 |
| 3 | 9 | 0 | 224.567 | 4.736 | 313.069 | 0.00 | 0.999 |
| 3 | 9 | 2 | 690.545 | 6.092 | 928.716 | 70.58 | 0.989 |
| 3 | 9 | 4 | 458.973 | 4.178 | 672.286 | 160.25 | 0.993 |
| 3 | 9 | 6 | 327.962 | 3.307 | 510.747 | 160.30 | 0.988 |
| 3 | 9 | 8 | 355.652 | 3.203 | 512.349 | 116.25 | 0.987 |
| 3 | 9 | 10 | 252.584 | 2.524 | 381.181 | 240.40 | 0.969 |
| 3 | 9 | 12 | 346.047 | 3.242 | 509.061 | 82.39 | 0.986 |
| 3 | 9 | 14 | 292.655 | 2.866 | 378.207 | 117.72 | 0.988 |
| 3 | 9 | 16 | 230.843 | 2.562 | 259.969 | 73.53 | 0.983 |
| 3 | 9 | 18 | 110.514 | 3.050 | 160.146 | 110.80 | 0.927 |
| 3 | 9 | 20 | 179.487 | 3.446 | 271.465 | 58.83 | 0.960 |
| 3 | 9 | 22 | 376.352 | 3.756 | 535.941 | 333.47 | 0.990 |

| | | | | | | | |
|---|---|---|---|---|---|---|---|
| 3 | 9 | 24 | 104.162 | 4.417 | 87.643 | 180.42 | 0.948 |
| 3 | 9 | 26 | 543.051 | 5.089 | 684.265 | 96.83 | 0.997 |
| 3 | 9 | 28 | 271.772 | 3.685 | 331.025 | 25.78 | 0.987 |
| 3 | 9 | 30 | 57.312 | 11.401 | 25.169 | 257.53 | 0.679 |
| 3 | 9 | 32 | 277.389 | 4.854 | 389.473 | 82.83 | 0.988 |
| 3 | 9 | 34 | 259.909 | 4.969 | 345.935 | 278.48 | 0.987 |
| 3 | 9 | 36 | 82.437 | 14.311 | 85.025 | 95.48 | 0.593 |
| 3 | 9 | 38 | 51.588 | 12.379 | 32.371 | 82.25 | 0.483 |
| 3 | 9 | 40 | 70.885 | 13.538 | 54.775 | 97.29 | 0.886 |
| 3 | 9 | 42 | 61.546 | 27.545 | 27.437 | 106.03 | 0.770 |
| 3 | 10 | 1 | 718.413 | 6.100 | 952.047 | 18.66 | 0.997 |
| 3 | 10 | 3 | 441.823 | 4.306 | 609.276 | 347.52 | 0.993 |
| 3 | 10 | 5 | 1250.288 | 11.389 | 1708.816 | 285.49 | 0.999 |
| 3 | 10 | 7 | 155.775 | 2.127 | 181.905 | 133.05 | 0.976 |
| 3 | 10 | 9 | 501.001 | 6.099 | 676.809 | 146.73 | 0.995 |
| 3 | 10 | 11 | 33.131 | 6.330 | 24.271 | 321.45 | 0.537 |
| 3 | 10 | 13 | 172.952 | 2.263 | 236.291 | 97.25 | 0.966 |
| 3 | 10 | 15 | 194.038 | 2.697 | 272.736 | 52.43 | 0.980 |
| 3 | 10 | 17 | 234.842 | 2.770 | 311.068 | 120.51 | 0.981 |
| 3 | 10 | 19 | 81.012 | 5.573 | 73.748 | 108.54 | 0.610 |
| 3 | 10 | 21 | 424.908 | 4.045 | 581.441 | 294.20 | 0.993 |
| 3 | 10 | 23 | 298.850 | 3.325 | 459.714 | 318.00 | 0.985 |
| 3 | 10 | 25 | 142.953 | 3.909 | 130.497 | 275.46 | 0.960 |
| 3 | 10 | 27 | 230.268 | 3.428 | 330.212 | 294.41 | 0.979 |
| 3 | 10 | 29 | 333.108 | 4.003 | 404.011 | 129.02 | 0.990 |
| 3 | 10 | 31 | 217.709 | 5.177 | 329.234 | 82.31 | 0.967 |
| 3 | 10 | 33 | 138.640 | 6.074 | 134.159 | 275.31 | 0.964 |
| 3 | 10 | 35 | 100.303 | 10.651 | 100.850 | 211.62 | 0.940 |
| 3 | 10 | 37 | 173.878 | 5.651 | 189.042 | 114.97 | 0.981 |
| 3 | 10 | 39 | 117.573 | 6.281 | 173.207 | 112.36 | 0.945 |
| 3 | 10 | 41 | 62.693 | 27.899 | 6.877 | 51.45 | 0.882 |
| 3 | 11 | 0 | 715.086 | 8.465 | 999.047 | 180.00 | 1.000 |
| 3 | 11 | 2 | 232.725 | 2.333 | 306.452 | 133.39 | 0.978 |
| 3 | 11 | 4 | 512.416 | 5.677 | 704.638 | 285.85 | 0.995 |
| 3 | 11 | 6 | 655.047 | 5.864 | 863.119 | 326.99 | 0.997 |
| 3 | 11 | 8 | 75.629 | 3.220 | 88.957 | 52.58 | 0.831 |
| 3 | 11 | 10 | 202.097 | 2.687 | 307.777 | 301.11 | 0.961 |
| 3 | 11 | 12 | 264.462 | 2.591 | 389.229 | 131.93 | 0.985 |
| 3 | 11 | 14 | 233.684 | 2.763 | 297.555 | 324.65 | 0.984 |
| 3 | 11 | 16 | 282.267 | 3.445 | 469.001 | 278.66 | 0.979 |
| 3 | 11 | 18 | 104.066 | 4.023 | 115.534 | 31.89 | 0.950 |
| 3 | 11 | 20 | 50.970 | 7.995 | 42.049 | 278.85 | 0.674 |
| 3 | 11 | 22 | 347.332 | 3.597 | 559.555 | 50.60 | 0.989 |
| 3 | 11 | 24 | 84.952 | 6.588 | 103.243 | 356.66 | 0.796 |
| 3 | 11 | 26 | 191.986 | 3.601 | 227.451 | 89.90 | 0.975 |
| 3 | 11 | 28 | 172.322 | 3.896 | 232.313 | 303.21 | 0.957 |
| 3 | 11 | 30 | 157.916 | 4.616 | 221.653 | 15.58 | 0.951 |
| 3 | 11 | 32 | 382.555 | 4.506 | 495.344 | 99.91 | 0.994 |
| 3 | 11 | 34 | 165.802 | 5.251 | 166.982 | 13.89 | 0.981 |
| 3 | 11 | 36 | 80.676 | 10.856 | 106.054 | 210.75 | 0.796 |
| 3 | 11 | 38 | 157.307 | 5.198 | 265.051 | 213.34 | 0.956 |
| 3 | 11 | 40 | 48.639 | 13.302 | 18.078 | 303.42 | 0.694 |
| 3 | 12 | 1 | 210.518 | 2.401 | 292.809 | 115.20 | 0.975 |
| 3 | 12 | 3 | 404.916 | 3.960 | 578.505 | 24.99 | 0.991 |
| 3 | 12 | 5 | 120.397 | 3.027 | 148.555 | 100.37 | 0.944 |
| 3 | 12 | 7 | 193.024 | 2.339 | 249.754 | 156.04 | 0.972 |
| 3 | 12 | 9 | 155.734 | 2.524 | 232.877 | 209.05 | 0.969 |
| 3 | 12 | 11 | 157.508 | 2.628 | 169.647 | 289.71 | 0.976 |
| 3 | 12 | 13 | 95.541 | 2.816 | 110.850 | 56.44 | 0.919 |
| 3 | 12 | 15 | 346.607 | 3.420 | 500.149 | 296.07 | 0.990 |
| 3 | 12 | 17 | 212.252 | 3.254 | 282.996 | 188.08 | 0.971 |
| 3 | 12 | 19 | 116.561 | 4.633 | 138.124 | 347.35 | 0.593 |
| 3 | 12 | 21 | 403.870 | 4.116 | 574.810 | 85.66 | 0.994 |
| 3 | 12 | 23 | 185.544 | 3.537 | 322.525 | 67.11 | 0.956 |
| 3 | 12 | 25 | 219.277 | 3.563 | 299.532 | 278.24 | 0.977 |
| 3 | 12 | 27 | 159.083 | 4.132 | 216.358 | 237.95 | 0.955 |
| 3 | 12 | 29 | 202.928 | 3.979 | 255.804 | 341.29 | 0.968 |
| 3 | 12 | 31 | 119.629 | 6.014 | 146.652 | 294.85 | 0.936 |
| 3 | 12 | 33 | 234.266 | 4.365 | 292.571 | 134.23 | 0.989 |
| 3 | 12 | 35 | 268.370 | 4.136 | 360.590 | 336.30 | 0.991 |
| 3 | 12 | 37 | 157.366 | 5.441 | 202.126 | 268.29 | 0.973 |
| 3 | 12 | 39 | 44.638 | 13.210 | 17.397 | 238.70 | 0.552 |
| 3 | 12 | 41 | 54.630 | 24.989 | 18.644 | 218.18 | 0.720 |
| 3 | 13 | 0 | 235.249 | 3.454 | 322.734 | 180.00 | 0.984 |
| 3 | 13 | 2 | 200.424 | 2.603 | 330.701 | 23.72 | 0.967 |
| 3 | 13 | 4 | 810.435 | 6.962 | 1137.382 | 338.47 | 0.998 |
| 3 | 13 | 6 | 88.820 | 2.867 | 61.729 | 104.70 | 0.492 |

| | | | | | | | |
|---|---|---|---|---|---|---|---|
| 3 | 13 | 8 | 399.504 | 3.753 | 577.556 | 306.40 | 0.993 |
| 3 | 13 | 10 | 331.760 | 3.383 | 491.175 | 235.00 | 0.989 |
| 3 | 13 | 12 | 96.371 | 3.318 | 143.459 | 324.16 | 0.938 |
| 3 | 13 | 14 | 174.140 | 2.780 | 246.191 | 339.73 | 0.965 |
| 3 | 13 | 16 | 272.554 | 2.935 | 423.425 | 282.08 | 0.977 |
| 3 | 13 | 18 | 80.550 | 5.482 | 100.666 | 286.99 | 0.811 |
| 3 | 13 | 20 | 210.803 | 3.356 | 223.974 | 341.29 | 0.984 |
| 3 | 13 | 22 | 347.440 | 3.514 | 411.883 | 276.72 | 0.992 |
| 3 | 13 | 24 | 394.187 | 3.921 | 490.914 | 251.29 | 0.994 |
| 3 | 13 | 26 | 446.765 | 4.700 | 547.104 | 185.73 | 0.995 |
| 3 | 13 | 28 | 161.098 | 4.230 | 193.408 | 258.38 | 0.950 |
| 3 | 13 | 30 | 54.007 | 12.782 | 26.386 | 162.77 | 0.587 |
| 3 | 13 | 32 | 147.133 | 5.837 | 227.939 | 186.97 | 0.942 |
| 3 | 13 | 34 | 118.473 | 7.020 | 104.354 | 19.02 | 0.964 |
| 3 | 13 | 36 | 120.681 | 5.735 | 205.443 | 85.03 | 0.827 |
| 3 | 13 | 38 | 114.518 | 7.305 | 161.208 | 168.05 | 0.943 |
| 3 | 13 | 40 | 69.102 | 24.779 | 35.303 | 101.89 | 0.364 |
| 3 | 14 | 1 | 426.013 | 3.446 | 583.489 | 162.24 | 0.994 |
| 3 | 14 | 3 | 274.841 | 3.209 | 377.212 | 300.57 | 0.988 |
| 3 | 14 | 5 | 129.247 | 2.690 | 141.454 | 124.50 | 0.957 |
| 3 | 14 | 7 | 114.085 | 3.064 | 64.522 | 146.80 | 0.944 |
| 3 | 14 | 9 | 419.224 | 4.307 | 632.433 | 183.04 | 0.992 |
| 3 | 14 | 11 | 200.692 | 2.657 | 300.931 | 230.90 | 0.969 |
| 3 | 14 | 13 | 115.585 | 2.943 | 113.635 | 186.83 | 0.902 |
| 3 | 14 | 15 | 219.048 | 2.809 | 273.524 | 325.24 | 0.979 |
| 3 | 14 | 17 | 65.503 | 6.208 | 8.221 | 170.68 | 0.784 |
| 3 | 14 | 19 | 130.167 | 4.664 | 177.384 | 202.30 | 0.932 |
| 3 | 14 | 21 | 376.039 | 3.916 | 440.953 | 336.61 | 0.994 |
| 3 | 14 | 23 | 100.695 | 6.016 | 139.602 | 102.41 | 0.771 |
| 3 | 14 | 25 | 143.895 | 5.053 | 198.784 | 29.46 | 0.940 |
| 3 | 14 | 27 | 171.829 | 4.044 | 253.049 | 116.32 | 0.954 |
| 3 | 14 | 29 | 276.541 | 3.996 | 407.229 | 21.25 | 0.987 |
| 3 | 14 | 31 | 335.954 | 3.751 | 441.982 | 90.60 | 0.992 |
| 3 | 14 | 33 | 164.590 | 4.930 | 200.617 | 83.20 | 0.978 |
| 3 | 14 | 35 | 135.449 | 5.179 | 187.179 | 13.01 | 0.955 |
| 3 | 14 | 37 | 45.849 | 13.237 | 15.638 | 173.10 | 0.628 |
| 3 | 14 | 39 | 51.020 | 15.194 | 26.383 | 141.04 | 0.858 |
| 3 | 15 | 0 | 221.140 | 3.342 | 308.308 | 180.00 | 1.000 |
| 3 | 15 | 2 | 141.462 | 2.519 | 188.273 | 287.64 | 0.961 |
| 3 | 15 | 4 | 83.727 | 4.414 | 91.685 | 319.33 | 0.876 |
| 3 | 15 | 6 | 131.648 | 3.325 | 203.908 | 349.65 | 0.942 |
| 3 | 15 | 8 | 349.878 | 3.346 | 496.690 | 126.61 | 0.991 |
| 3 | 15 | 10 | 383.436 | 4.245 | 557.234 | 159.56 | 0.992 |
| 3 | 15 | 12 | 99.340 | 3.502 | 127.430 | 140.90 | 0.847 |
| 3 | 15 | 14 | 87.890 | 4.857 | 101.318 | 54.15 | 0.767 |
| 3 | 15 | 16 | 185.436 | 2.914 | 244.876 | 85.01 | 0.962 |
| 3 | 15 | 18 | 169.246 | 3.276 | 204.281 | 149.89 | 0.976 |
| 3 | 15 | 20 | 310.061 | 3.691 | 381.764 | 91.86 | 0.991 |
| 3 | 15 | 22 | 47.745 | 10.518 | 15.018 | 317.41 | 0.228 |
| 3 | 15 | 24 | 123.608 | 5.512 | 146.868 | 196.28 | 0.945 |
| 3 | 15 | 26 | 63.537 | 9.861 | 29.787 | 162.66 | 0.597 |
| 3 | 15 | 28 | 202.497 | 4.341 | 301.367 | 59.49 | 0.976 |
| 3 | 15 | 30 | 247.145 | 4.114 | 327.450 | 18.70 | 0.987 |
| 3 | 15 | 32 | 168.449 | 4.838 | 204.707 | 139.89 | 0.980 |
| 3 | 15 | 34 | 126.807 | 6.537 | 120.196 | 228.13 | 0.968 |
| 3 | 15 | 36 | 76.253 | 12.435 | 94.656 | 273.76 | 0.714 |
| 3 | 15 | 38 | 44.724 | 13.242 | 1.078 | 109.07 | 0.036 |
| 3 | 16 | 1 | 228.600 | 2.511 | 291.397 | 263.35 | 0.983 |
| 3 | 16 | 3 | 175.638 | 2.954 | 201.350 | 76.26 | 0.980 |
| 3 | 16 | 5 | 210.559 | 2.643 | 330.183 | 105.07 | 0.968 |
| 3 | 16 | 7 | 185.578 | 2.930 | 232.399 | 182.97 | 0.975 |
| 3 | 16 | 9 | 337.159 | 3.284 | 513.855 | 174.02 | 0.986 |
| 3 | 16 | 11 | 157.669 | 3.943 | 241.221 | 82.40 | 0.930 |
| 3 | 16 | 13 | 142.142 | 2.807 | 110.163 | 201.18 | 0.967 |
| 3 | 16 | 15 | 526.123 | 5.067 | 744.832 | 177.30 | 0.996 |
| 3 | 16 | 17 | 150.264 | 3.869 | 174.102 | 82.94 | 0.961 |
| 3 | 16 | 19 | 382.635 | 3.879 | 554.293 | 111.69 | 0.993 |
| 3 | 16 | 21 | 62.854 | 10.285 | 33.019 | 270.74 | 0.602 |
| 3 | 16 | 23 | 193.167 | 4.139 | 221.618 | 102.45 | 0.976 |
| 3 | 16 | 25 | 171.717 | 4.266 | 257.391 | 304.04 | 0.949 |
| 3 | 16 | 27 | 323.824 | 3.660 | 430.668 | 145.30 | 0.992 |
| 3 | 16 | 29 | 180.234 | 4.562 | 223.332 | 335.02 | 0.975 |
| 3 | 16 | 31 | 142.283 | 5.452 | 207.431 | 99.34 | 0.962 |
| 3 | 16 | 33 | 73.000 | 11.360 | 55.817 | 217.73 | 0.887 |
| 3 | 16 | 35 | 28.203 | 9.155 | 29.190 | 332.72 | 0.454 |
| 3 | 16 | 37 | 73.658 | 12.316 | 86.566 | 303.29 | 0.710 |
| 3 | 17 | 0 | 375.032 | 4.501 | 523.216 | 180.00 | 1.000 |

| | | | | | | | |
|---|---|---|---|---|---|---|---|
| 3 | 17 | 2 | 232.895 | 2.497 | 288.503 | 264.77 | 0.982 |
| 3 | 17 | 4 | 112.041 | 3.576 | 68.329 | 43.86 | 0.943 |
| 3 | 17 | 6 | 376.753 | 3.928 | 537.993 | 93.81 | 0.990 |
| 3 | 17 | 8 | 72.351 | 6.022 | 65.507 | 108.78 | 0.739 |
| 3 | 17 | 10 | 438.481 | 4.137 | 600.926 | 141.79 | 0.994 |
| 3 | 17 | 12 | 392.339 | 4.344 | 546.322 | 82.17 | 0.992 |
| 3 | 17 | 14 | 202.727 | 2.991 | 283.544 | 185.70 | 0.980 |
| 3 | 17 | 16 | 380.849 | 4.525 | 511.581 | 265.80 | 0.993 |
| 3 | 17 | 18 | 358.224 | 4.466 | 576.229 | 154.41 | 0.990 |
| 3 | 17 | 20 | 115.344 | 5.084 | 137.276 | 251.81 | 0.932 |
| 3 | 17 | 22 | 134.365 | 4.574 | 119.041 | 351.44 | 0.955 |
| 3 | 17 | 24 | 246.026 | 3.929 | 341.215 | 89.80 | 0.982 |
| 3 | 17 | 26 | 111.222 | 6.264 | 146.538 | 125.07 | 0.923 |
| 3 | 17 | 28 | 209.841 | 4.965 | 273.879 | 273.30 | 0.981 |
| 3 | 17 | 30 | 65.871 | 10.055 | 54.201 | 84.86 | 0.526 |
| 3 | 17 | 32 | 92.199 | 7.700 | 76.119 | 118.40 | 0.944 |
| 3 | 17 | 34 | 96.093 | 7.473 | 129.733 | 160.87 | 0.907 |
| 3 | 17 | 36 | 76.060 | 13.151 | 89.260 | 314.66 | 0.734 |
| 3 | 17 | 38 | 92.289 | 24.193 | 94.531 | 226.59 | 0.913 |
| 3 | 18 | 1 | 131.536 | 2.933 | 133.730 | 6.51 | 0.960 |
| 3 | 18 | 3 | 374.172 | 4.064 | 516.577 | 291.43 | 0.992 |
| 3 | 18 | 5 | 200.434 | 3.479 | 273.694 | 323.54 | 0.973 |
| 3 | 18 | 7 | 327.255 | 3.535 | 463.076 | 286.63 | 0.988 |
| 3 | 18 | 9 | 240.306 | 2.935 | 376.792 | 247.46 | 0.975 |
| 3 | 18 | 11 | 403.983 | 3.986 | 585.216 | 75.18 | 0.994 |
| 3 | 18 | 13 | 423.732 | 4.746 | 587.195 | 67.70 | 0.995 |
| 3 | 18 | 15 | 141.327 | 4.136 | 223.533 | 276.13 | 0.940 |
| 3 | 18 | 17 | 398.810 | 4.677 | 605.010 | 100.74 | 0.993 |
| 3 | 18 | 19 | 172.613 | 3.998 | 185.458 | 192.26 | 0.974 |
| 3 | 18 | 21 | 146.913 | 3.943 | 131.181 | 320.75 | 0.957 |
| 3 | 18 | 23 | 75.038 | 9.455 | 18.105 | 258.41 | 0.209 |
| 3 | 18 | 25 | 322.548 | 3.819 | 403.585 | 338.48 | 0.993 |
| 3 | 18 | 27 | 119.555 | 7.124 | 174.640 | 296.53 | 0.921 |
| 3 | 18 | 29 | 159.922 | 5.971 | 193.544 | 154.93 | 0.978 |
| 3 | 18 | 31 | 99.532 | 8.477 | 153.125 | 300.42 | 0.824 |
| 3 | 18 | 33 | 175.107 | 6.441 | 218.218 | 244.89 | 0.980 |
| 3 | 18 | 35 | 129.039 | 8.812 | 225.364 | 56.45 | 0.920 |
| 3 | 18 | 37 | 53.124 | 22.474 | 26.731 | 270.61 | 0.596 |
| 3 | 19 | 0 | 66.536 | 7.403 | 37.101 | 180.00 | 0.402 |
| 3 | 19 | 2 | 213.940 | 3.273 | 259.973 | 281.61 | 0.978 |
| 3 | 19 | 4 | 190.271 | 3.920 | 267.725 | 152.89 | 0.968 |
| 3 | 19 | 6 | 156.881 | 3.576 | 213.689 | 261.40 | 0.960 |
| 3 | 19 | 8 | 216.403 | 3.523 | 351.461 | 281.01 | 0.975 |
| 3 | 19 | 10 | 681.645 | 6.555 | 963.392 | 202.55 | 0.998 |
| 3 | 19 | 12 | 310.557 | 3.240 | 424.767 | 345.55 | 0.991 |
| 3 | 19 | 14 | 88.354 | 7.882 | 110.701 | 267.82 | 0.695 |
| 3 | 19 | 16 | 596.857 | 5.535 | 795.870 | 246.02 | 0.997 |
| 3 | 19 | 18 | 189.895 | 3.300 | 294.404 | 16.47 | 0.970 |
| 3 | 19 | 20 | 61.564 | 9.992 | 32.598 | 2.23 | 0.570 |
| 3 | 19 | 22 | 109.125 | 7.375 | 141.222 | 247.67 | 0.873 |
| 3 | 19 | 24 | 224.075 | 4.918 | 270.511 | 203.42 | 0.986 |
| 3 | 19 | 26 | 207.668 | 4.742 | 271.875 | 105.69 | 0.981 |
| 3 | 19 | 28 | 159.209 | 5.323 | 264.764 | 29.08 | 0.965 |
| 3 | 19 | 30 | 90.383 | 9.691 | 107.453 | 97.76 | 0.922 |
| 3 | 19 | 32 | 92.893 | 8.016 | 110.591 | 314.82 | 0.922 |
| 3 | 19 | 34 | 53.297 | 16.278 | 32.807 | 134.32 | 0.626 |
| 3 | 19 | 36 | 47.979 | 22.342 | 13.216 | 195.68 | 0.312 |
| 3 | 20 | 1 | 138.661 | 5.246 | 153.131 | 270.93 | 0.960 |
| 3 | 20 | 3 | 522.099 | 6.642 | 701.056 | 124.22 | 0.997 |
| 3 | 20 | 5 | 427.465 | 5.605 | 599.774 | 159.09 | 0.995 |
| 3 | 20 | 7 | 227.342 | 3.298 | 327.697 | 87.84 | 0.982 |
| 3 | 20 | 9 | 326.225 | 3.812 | 459.089 | 290.50 | 0.991 |
| 3 | 20 | 11 | 348.449 | 4.004 | 458.282 | 23.02 | 0.993 |
| 3 | 20 | 13 | 222.167 | 3.353 | 315.209 | 154.74 | 0.980 |
| 3 | 20 | 15 | 508.398 | 5.758 | 741.926 | 1.41 | 0.996 |
| 3 | 20 | 17 | 228.791 | 3.442 | 335.064 | 299.87 | 0.979 |
| 3 | 20 | 19 | 114.619 | 5.782 | 150.610 | 266.90 | 0.911 |
| 3 | 20 | 21 | 234.483 | 3.733 | 339.858 | 244.91 | 0.977 |
| 3 | 20 | 23 | 331.100 | 4.806 | 471.265 | 95.39 | 0.992 |
| 3 | 20 | 25 | 273.634 | 4.091 | 359.252 | 195.04 | 0.990 |
| 3 | 20 | 27 | 95.423 | 8.743 | 119.617 | 351.73 | 0.587 |
| 3 | 20 | 29 | 64.587 | 13.041 | 63.545 | 284.75 | 0.756 |
| 3 | 20 | 31 | 116.909 | 7.150 | 111.032 | 277.85 | 0.961 |
| 3 | 20 | 33 | 39.625 | 11.747 | 4.076 | 48.91 | 0.594 |
| 3 | 21 | 0 | 583.914 | 10.671 | 813.104 | 180.00 | 1.000 |
| 3 | 21 | 2 | 361.983 | 4.548 | 420.673 | 167.20 | 0.994 |
| 3 | 21 | 4 | 200.525 | 4.234 | 184.101 | 242.87 | 0.984 |

| | | | | | | | |
|---|---|---|---|---|---|---|---|
| 3 | 21 | 6 | 195.619 | 4.547 | 241.630 | 340.53 | 0.977 |
| 3 | 21 | 8 | 89.661 | 5.668 | 35.474 | 351.60 | 0.937 |
| 3 | 21 | 10 | 173.603 | 3.745 | 237.952 | 147.48 | 0.966 |
| 3 | 21 | 12 | 171.803 | 3.519 | 238.746 | 92.32 | 0.964 |
| 3 | 21 | 14 | 46.414 | 9.214 | 29.374 | 218.81 | 0.634 |
| 3 | 21 | 16 | 170.295 | 5.673 | 292.852 | 340.39 | 0.930 |
| 3 | 21 | 18 | 354.099 | 4.115 | 687.463 | 117.55 | 0.983 |
| 3 | 21 | 20 | 106.716 | 5.787 | 127.392 | 129.75 | 0.896 |
| 3 | 21 | 22 | 300.449 | 4.677 | 459.924 | 334.85 | 0.990 |
| 3 | 21 | 24 | 165.436 | 4.555 | 265.084 | 46.77 | 0.959 |
| 3 | 21 | 26 | 234.331 | 4.025 | 313.347 | 328.08 | 0.989 |
| 3 | 21 | 28 | 83.899 | 10.661 | 92.504 | 332.64 | 0.903 |
| 3 | 21 | 30 | 133.390 | 6.839 | 146.584 | 318.58 | 0.968 |
| 3 | 21 | 32 | 77.557 | 12.800 | 99.430 | 266.56 | 0.832 |
| 3 | 21 | 34 | 64.350 | 24.273 | 50.612 | 331.71 | 0.687 |
| 3 | 22 | 1 | 235.433 | 4.730 | 322.775 | 270.80 | 0.982 |
| 3 | 22 | 3 | 189.089 | 5.147 | 244.434 | 260.98 | 0.974 |
| 3 | 22 | 5 | 276.476 | 5.170 | 362.954 | 154.45 | 0.988 |
| 3 | 22 | 7 | 56.018 | 11.993 | 23.604 | 104.52 | 0.288 |
| 3 | 22 | 9 | 507.878 | 4.677 | 622.326 | 317.19 | 0.997 |
| 3 | 22 | 11 | 254.958 | 3.277 | 350.070 | 12.14 | 0.985 |
| 3 | 22 | 13 | 147.592 | 4.534 | 275.003 | 28.10 | 0.841 |
| 3 | 22 | 15 | 503.959 | 4.773 | 773.570 | 273.48 | 0.995 |
| 3 | 22 | 17 | 86.941 | 9.676 | 101.958 | 296.10 | 0.703 |
| 3 | 22 | 19 | 315.017 | 3.853 | 419.940 | 285.77 | 0.992 |
| 3 | 22 | 21 | 198.442 | 5.266 | 280.894 | 199.36 | 0.978 |
| 3 | 22 | 23 | 203.272 | 5.182 | 280.413 | 244.08 | 0.986 |
| 3 | 22 | 25 | 178.748 | 5.132 | 299.944 | 203.98 | 0.973 |
| 3 | 22 | 27 | 137.430 | 8.781 | 264.473 | 32.07 | 0.908 |
| 3 | 22 | 29 | 46.810 | 12.269 | 23.636 | 188.20 | 0.512 |
| 3 | 22 | 31 | 53.848 | 13.811 | 26.411 | 207.06 | 0.324 |
| 3 | 22 | 33 | 51.927 | 22.259 | 20.118 | 257.13 | 0.777 |
| 3 | 23 | 0 | 412.875 | 7.839 | 574.855 | 0.00 | 1.000 |
| 3 | 23 | 2 | 652.764 | 6.989 | 922.537 | 11.44 | 0.998 |
| 3 | 23 | 4 | 221.208 | 4.117 | 272.899 | 24.82 | 0.982 |
| 3 | 23 | 6 | 94.424 | 6.620 | 109.661 | 277.47 | 0.878 |
| 3 | 23 | 8 | 240.447 | 3.375 | 313.675 | 330.56 | 0.986 |
| 3 | 23 | 10 | 218.125 | 3.523 | 289.351 | 31.22 | 0.978 |
| 3 | 23 | 12 | 181.247 | 3.741 | 199.248 | 290.91 | 0.971 |
| 3 | 23 | 14 | 119.009 | 5.447 | 170.088 | 66.41 | 0.793 |
| 3 | 23 | 16 | 183.535 | 4.324 | 303.619 | 249.05 | 0.955 |
| 3 | 23 | 18 | 190.616 | 4.531 | 226.915 | 84.90 | 0.981 |
| 3 | 23 | 20 | 107.516 | 9.227 | 134.223 | 169.57 | 0.920 |
| 3 | 23 | 22 | 139.458 | 6.974 | 199.126 | 325.03 | 0.965 |
| 3 | 23 | 24 | 48.231 | 12.369 | 19.355 | 337.40 | 0.482 |
| 3 | 23 | 26 | 56.260 | 14.169 | 37.411 | 191.66 | 0.597 |
| 3 | 23 | 28 | 108.423 | 7.031 | 167.975 | 190.58 | 0.936 |
| 3 | 23 | 30 | 93.572 | 13.695 | 104.943 | 255.48 | 0.929 |
| 3 | 23 | 32 | 59.816 | 23.495 | 31.572 | 141.72 | 0.826 |
| 3 | 24 | 1 | 375.327 | 3.634 | 500.512 | 349.25 | 0.994 |
| 3 | 24 | 3 | 137.911 | 10.777 | 194.175 | 28.95 | 0.939 |
| 3 | 24 | 5 | 365.820 | 4.439 | 412.542 | 32.48 | 0.993 |
| 3 | 24 | 7 | 65.105 | 13.773 | 26.382 | 193.88 | 0.365 |
| 3 | 24 | 9 | 369.848 | 4.000 | 579.663 | 311.82 | 0.991 |
| 3 | 24 | 11 | 129.745 | 5.534 | 152.829 | 200.11 | 0.945 |
| 3 | 24 | 13 | 346.275 | 4.579 | 465.865 | 184.58 | 0.991 |
| 3 | 24 | 15 | 257.264 | 3.986 | 402.673 | 152.94 | 0.986 |
| 3 | 24 | 17 | 70.781 | 11.771 | 30.202 | 128.05 | 0.259 |
| 3 | 24 | 19 | 73.341 | 10.568 | 63.698 | 4.23 | 0.912 |
| 3 | 24 | 21 | 107.517 | 6.437 | 152.830 | 334.27 | 0.938 |
| 3 | 24 | 23 | 87.584 | 7.685 | 62.570 | 60.95 | 0.943 |
| 3 | 24 | 25 | 136.747 | 5.410 | 213.915 | 2.42 | 0.957 |
| 3 | 24 | 27 | 133.499 | 8.634 | 194.159 | 25.78 | 0.964 |
| 3 | 24 | 29 | 93.266 | 12.789 | 137.164 | 64.51 | 0.781 |
| 3 | 24 | 31 | 66.690 | 28.272 | 33.690 | 126.58 | 0.782 |
| 3 | 25 | 0 | 591.180 | 7.532 | 822.367 | 0.00 | 1.000 |
| 3 | 25 | 2 | 184.439 | 3.849 | 240.492 | 43.35 | 0.972 |
| 3 | 25 | 4 | 354.129 | 3.930 | 556.817 | 165.55 | 0.989 |
| 3 | 25 | 6 | 226.301 | 4.605 | 406.939 | 345.51 | 0.967 |
| 3 | 25 | 8 | 210.183 | 4.264 | 259.446 | 160.51 | 0.980 |
| 3 | 25 | 10 | 296.056 | 4.107 | 392.302 | 232.43 | 0.988 |
| 3 | 25 | 12 | 73.346 | 15.342 | 51.729 | 311.46 | 0.395 |
| 3 | 25 | 14 | 124.198 | 6.957 | 220.377 | 138.20 | 0.873 |
| 3 | 25 | 16 | 138.933 | 5.924 | 179.427 | 16.82 | 0.960 |
| 3 | 25 | 18 | 92.809 | 8.253 | 134.015 | 132.70 | 0.905 |
| 3 | 25 | 20 | 135.750 | 6.210 | 206.211 | 121.39 | 0.961 |
| 3 | 25 | 22 | 63.106 | 13.189 | 57.234 | 264.88 | 0.592 |

| | | | | | | | |
|---|---|---|---|---|---|---|---|
| 3 | 25 | 24 | 61.078 | 13.503 | 54.772 | 258.58 | 0.655 |
| 3 | 25 | 26 | 117.209 | 7.221 | 199.559 | 191.29 | 0.913 |
| 3 | 25 | 28 | 100.640 | 15.149 | 121.067 | 276.91 | 0.962 |
| 3 | 25 | 30 | 44.946 | 21.963 | 6.360 | 167.67 | 0.423 |
| 3 | 26 | 1 | 358.876 | 4.345 | 490.001 | 50.46 | 0.992 |
| 3 | 26 | 3 | 271.751 | 4.223 | 345.575 | 25.03 | 0.986 |
| 3 | 26 | 5 | 194.085 | 4.342 | 186.388 | 122.84 | 0.988 |
| 3 | 26 | 7 | 278.841 | 6.076 | 325.897 | 159.89 | 0.992 |
| 3 | 26 | 9 | 402.714 | 5.109 | 490.844 | 238.79 | 0.996 |
| 3 | 26 | 11 | 157.285 | 5.391 | 248.303 | 57.57 | 0.958 |
| 3 | 26 | 13 | 120.909 | 6.081 | 170.847 | 64.96 | 0.933 |
| 3 | 26 | 15 | 99.142 | 8.324 | 52.739 | 186.45 | 0.962 |
| 3 | 26 | 17 | 65.040 | 11.559 | 43.949 | 121.11 | 0.884 |
| 3 | 26 | 19 | 130.899 | 6.695 | 202.291 | 161.54 | 0.955 |
| 3 | 26 | 21 | 69.341 | 9.034 | 62.064 | 64.96 | 0.883 |
| 3 | 26 | 23 | 34.399 | 11.702 | 4.115 | 329.76 | 0.220 |
| 3 | 26 | 25 | 58.746 | 14.703 | 56.012 | 337.83 | 0.648 |
| 3 | 26 | 27 | 39.917 | 13.505 | 17.799 | 331.39 | 0.411 |
| 3 | 27 | 0 | 257.998 | 6.512 | 358.562 | 0.00 | 1.000 |
| 3 | 27 | 2 | 333.573 | 4.236 | 521.511 | 89.67 | 0.992 |
| 3 | 27 | 4 | 207.156 | 4.930 | 317.174 | 120.40 | 0.980 |
| 3 | 27 | 6 | 112.273 | 9.108 | 154.624 | 37.71 | 0.928 |
| 3 | 27 | 8 | 69.469 | 11.789 | 57.723 | 112.33 | 0.832 |
| 3 | 27 | 10 | 127.008 | 7.381 | 146.704 | 292.79 | 0.969 |
| 3 | 27 | 12 | 109.551 | 7.391 | 177.262 | 319.73 | 0.930 |
| 3 | 27 | 14 | 109.231 | 6.420 | 138.307 | 6.38 | 0.955 |
| 3 | 27 | 16 | 155.543 | 5.941 | 224.262 | 152.21 | 0.974 |
| 3 | 27 | 18 | 78.961 | 10.858 | 88.452 | 341.91 | 0.897 |
| 3 | 27 | 20 | 166.592 | 5.431 | 288.951 | 88.76 | 0.967 |
| 3 | 27 | 22 | 42.161 | 11.554 | 5.786 | 346.65 | 0.785 |
| 3 | 27 | 24 | 79.220 | 17.683 | 72.654 | 320.72 | 0.903 |
| 3 | 27 | 26 | 150.481 | 16.274 | 219.185 | 87.79 | 0.977 |
| 3 | 28 | 1 | 202.460 | 5.610 | 268.129 | 194.06 | 0.983 |
| 3 | 28 | 3 | 67.724 | 12.676 | 81.705 | 73.49 | 0.796 |
| 3 | 28 | 5 | 50.352 | 12.696 | 33.059 | 6.20 | 0.512 |
| 3 | 28 | 7 | 44.103 | 13.042 | 15.262 | 341.06 | 0.537 |
| 3 | 28 | 9 | 99.875 | 10.081 | 92.213 | 63.48 | 0.954 |
| 3 | 28 | 11 | 180.871 | 4.536 | 269.256 | 203.21 | 0.981 |
| 3 | 28 | 13 | 98.285 | 10.123 | 110.191 | 247.16 | 0.942 |
| 3 | 28 | 15 | 157.103 | 4.810 | 290.104 | 84.08 | 0.961 |
| 3 | 28 | 17 | 104.563 | 7.371 | 93.662 | 303.64 | 0.959 |
| 3 | 28 | 19 | 177.861 | 5.257 | 242.709 | 75.71 | 0.985 |
| 3 | 28 | 21 | 65.362 | 14.014 | 71.190 | 81.51 | 0.774 |
| 3 | 28 | 23 | 60.833 | 14.574 | 75.794 | 132.28 | 0.804 |
| 3 | 28 | 25 | 54.797 | 21.684 | 33.882 | 117.67 | 0.775 |
| 3 | 29 | 0 | 241.832 | 6.587 | 335.412 | 180.00 | 1.000 |
| 3 | 29 | 2 | 260.582 | 6.202 | 389.172 | 43.41 | 0.991 |
| 3 | 29 | 4 | 141.472 | 5.585 | 198.633 | 279.49 | 0.971 |
| 3 | 29 | 6 | 44.875 | 11.286 | 8.505 | 323.21 | 0.809 |
| 3 | 29 | 8 | 100.653 | 6.300 | 92.684 | 224.22 | 0.956 |
| 3 | 29 | 10 | 254.345 | 4.856 | 441.422 | 132.71 | 0.988 |
| 3 | 29 | 12 | 53.683 | 9.835 | 44.759 | 65.86 | 0.783 |
| 3 | 29 | 14 | 145.715 | 6.104 | 232.049 | 292.48 | 0.966 |
| 3 | 29 | 16 | 44.356 | 10.746 | 17.966 | 333.88 | 0.435 |
| 3 | 29 | 18 | 71.678 | 10.990 | 1.543 | 70.16 | 0.946 |
| 3 | 29 | 20 | 38.907 | 12.751 | 9.146 | 47.27 | 0.337 |
| 3 | 29 | 22 | 49.262 | 15.366 | 42.794 | 164.33 | 0.674 |
| 3 | 30 | 1 | 52.825 | 11.743 | 31.821 | 357.22 | 0.423 |
| 3 | 30 | 3 | 135.493 | 5.698 | 173.988 | 31.50 | 0.971 |
| 3 | 30 | 5 | 143.585 | 5.440 | 230.856 | 8.05 | 0.966 |
| 3 | 30 | 7 | 112.062 | 8.693 | 98.954 | 267.38 | 0.965 |
| 3 | 30 | 9 | 48.359 | 13.243 | 29.592 | 260.39 | 0.875 |
| 3 | 30 | 11 | 123.558 | 7.277 | 187.670 | 62.19 | 0.955 |
| 3 | 30 | 13 | 67.304 | 11.112 | 63.425 | 261.05 | 0.897 |
| 3 | 30 | 15 | 128.656 | 6.101 | 209.538 | 228.66 | 0.960 |
| 3 | 30 | 17 | 47.244 | 12.693 | 25.046 | 81.52 | 0.580 |
| 3 | 30 | 19 | 59.408 | 12.812 | 48.408 | 250.05 | 0.914 |
| 3 | 30 | 21 | 58.927 | 25.792 | 9.130 | 48.46 | 0.848 |
| 3 | 31 | 0 | 32.704 | 14.836 | 29.690 | 0.00 | 0.668 |
| 3 | 31 | 2 | 141.403 | 7.008 | 208.909 | 296.28 | 0.968 |
| 3 | 31 | 4 | 123.844 | 6.954 | 132.411 | 122.12 | 0.970 |
| 3 | 31 | 6 | 86.929 | 9.291 | 105.310 | 260.87 | 0.918 |
| 3 | 31 | 8 | 36.342 | 10.771 | 9.534 | 167.32 | 0.377 |
| 3 | 31 | 10 | 181.815 | 4.736 | 263.698 | 123.11 | 0.985 |
| 3 | 31 | 12 | 118.858 | 9.035 | 140.918 | 301.17 | 0.967 |
| 3 | 31 | 14 | 74.005 | 13.715 | 57.934 | 259.65 | 0.913 |
| 3 | 31 | 16 | 66.547 | 14.216 | 31.843 | 224.50 | 0.263 |

| | | | | | | | |
|---|---|---|---|---|---|---|---|
| 3 | 31 | 18 | 41.672 | 18.778 | 2.756 | 204.59 | 0.738 |
| 3 | 32 | 1 | 82.401 | 12.163 | 93.575 | 231.02 | 0.924 |
| 3 | 32 | 3 | 61.711 | 12.135 | 68.423 | 311.99 | 0.776 |
| 3 | 32 | 5 | 34.258 | 10.483 | 8.642 | 101.19 | 0.515 |
| 3 | 32 | 7 | 70.018 | 9.476 | 44.118 | 267.13 | 0.924 |
| 3 | 32 | 9 | 100.429 | 8.482 | 143.419 | 132.53 | 0.940 |
| 3 | 32 | 11 | 103.640 | 9.189 | 149.351 | 67.79 | 0.965 |
| 3 | 32 | 13 | 74.962 | 17.931 | 86.562 | 262.68 | 0.911 |
| 3 | 32 | 15 | 50.024 | 22.562 | 10.307 | 303.22 | 0.280 |
| 3 | 33 | 0 | 24.216 | 17.069 | 12.752 | 180.00 | 0.423 |
| 3 | 33 | 2 | 63.917 | 14.778 | 63.665 | 154.73 | 0.915 |
| 3 | 33 | 4 | 75.551 | 12.250 | 98.431 | 176.63 | 0.931 |
| 3 | 33 | 6 | 98.791 | 15.971 | 140.085 | 144.09 | 0.950 |
| 3 | 33 | 8 | 66.937 | 17.765 | 67.657 | 0.41 | 0.903 |
| 3 | 33 | 10 | 104.233 | 11.643 | 145.669 | 74.64 | 0.964 |
| 3 | 33 | 12 | 52.617 | 22.346 | 24.785 | 77.14 | 0.714 |
| 3 | 34 | 1 | 48.525 | 20.961 | 16.461 | 211.10 | 0.748 |
| 3 | 34 | 3 | 52.057 | 13.639 | 42.223 | 130.09 | 0.523 |
| 3 | 34 | 5 | 53.870 | 19.223 | 36.055 | 93.07 | 0.539 |
| 4 | 0 | 0 | 458.906 | 9.618 | 642.718 | 180.00 | 1.000 |
| 4 | 0 | 2 | 803.740 | 18.704 | 1123.837 | 0.00 | 1.000 |
| 4 | 0 | 4 | 631.373 | 10.793 | 883.196 | 180.00 | 1.000 |
| 4 | 0 | 6 | 52.907 | 3.988 | 10.030 | 180.00 | 0.137 |
| 4 | 0 | 8 | 311.897 | 4.362 | 420.185 | 0.00 | 0.966 |
| 4 | 0 | 10 | 188.423 | 2.823 | 144.172 | 0.00 | 0.550 |
| 4 | 0 | 12 | 206.019 | 2.985 | 248.672 | 0.00 | 0.870 |
| 4 | 0 | 14 | 290.947 | 3.882 | 402.425 | 180.00 | 1.000 |
| 4 | 0 | 16 | 493.602 | 5.927 | 680.001 | 180.00 | 1.000 |
| 4 | 0 | 18 | 200.095 | 3.619 | 274.348 | 180.00 | 1.000 |
| 4 | 0 | 20 | 122.266 | 4.594 | 166.766 | 180.00 | 1.000 |
| 4 | 0 | 22 | 56.504 | 10.324 | 72.647 | 180.00 | 0.949 |
| 4 | 0 | 24 | 364.119 | 4.638 | 491.277 | 180.00 | 1.000 |
| 4 | 0 | 26 | 184.107 | 4.361 | 246.794 | 180.00 | 1.000 |
| 4 | 0 | 28 | 190.371 | 4.983 | 253.427 | 180.00 | 1.000 |
| 4 | 0 | 30 | 28.795 | 12.936 | 31.935 | 0.00 | 0.847 |
| 4 | 0 | 32 | 83.529 | 15.052 | 108.842 | 180.00 | 0.998 |
| 4 | 0 | 34 | 159.150 | 10.304 | 206.444 | 180.00 | 1.000 |
| 4 | 0 | 36 | 142.612 | 9.058 | 182.702 | 0.00 | 0.997 |
| 4 | 0 | 38 | 56.016 | 18.114 | 66.708 | 180.00 | 0.948 |
| 4 | 0 | 40 | 58.917 | 17.946 | 62.764 | 0.00 | 0.863 |
| 4 | 0 | 42 | 37.335 | 16.883 | 25.696 | 180.00 | 0.570 |
| 4 | 1 | 1 | 422.785 | 4.087 | 543.101 | 294.33 | 0.980 |
| 4 | 1 | 3 | 506.872 | 4.270 | 821.360 | 220.76 | 0.977 |
| 4 | 1 | 5 | 267.016 | 2.436 | 343.157 | 269.65 | 0.982 |
| 4 | 1 | 7 | 612.815 | 5.407 | 788.850 | 147.75 | 0.988 |
| 4 | 1 | 9 | 857.371 | 7.230 | 1221.874 | 93.01 | 0.993 |
| 4 | 1 | 11 | 719.211 | 5.998 | 999.413 | 151.41 | 0.989 |
| 4 | 1 | 13 | 792.202 | 6.318 | 1135.488 | 191.11 | 0.998 |
| 4 | 1 | 15 | 439.812 | 3.723 | 553.321 | 181.26 | 0.994 |
| 4 | 1 | 17 | 450.803 | 4.026 | 615.526 | 278.39 | 0.994 |
| 4 | 1 | 19 | 237.773 | 2.504 | 262.625 | 238.68 | 0.983 |
| 4 | 1 | 21 | 194.939 | 2.650 | 254.073 | 330.12 | 0.977 |
| 4 | 1 | 23 | 293.646 | 2.838 | 415.471 | 223.50 | 0.985 |
| 4 | 1 | 25 | 181.437 | 2.952 | 312.310 | 254.13 | 0.933 |
| 4 | 1 | 27 | 100.634 | 4.623 | 125.539 | 235.29 | 0.938 |
| 4 | 1 | 29 | 147.033 | 4.130 | 182.528 | 37.82 | 0.958 |
| 4 | 1 | 31 | 109.141 | 5.945 | 124.919 | 326.44 | 0.897 |
| 4 | 1 | 33 | 299.682 | 3.940 | 425.657 | 151.38 | 0.984 |
| 4 | 1 | 35 | 313.804 | 5.173 | 411.212 | 257.05 | 0.991 |
| 4 | 1 | 37 | 112.086 | 9.596 | 189.344 | 261.06 | 0.841 |
| 4 | 1 | 39 | 142.814 | 6.416 | 234.501 | 298.04 | 0.940 |
| 4 | 1 | 41 | 58.171 | 12.729 | 44.740 | 126.76 | 0.558 |
| 4 | 1 | 43 | 41.398 | 13.988 | 2.435 | 201.50 | 0.803 |
| 4 | 2 | 0 | 610.146 | 6.463 | 854.603 | 0.00 | 1.000 |
| 4 | 2 | 2 | 351.399 | 2.990 | 480.508 | 186.84 | 0.967 |
| 4 | 2 | 4 | 281.937 | 2.638 | 264.960 | 319.61 | 0.967 |
| 4 | 2 | 6 | 394.476 | 3.654 | 621.245 | 276.32 | 0.940 |
| 4 | 2 | 8 | 593.028 | 4.853 | 862.627 | 296.16 | 0.983 |
| 4 | 2 | 10 | 398.913 | 3.646 | 550.509 | 169.11 | 0.961 |
| 4 | 2 | 12 | 785.278 | 6.529 | 1040.761 | 303.77 | 0.998 |
| 4 | 2 | 14 | 214.276 | 2.294 | 286.394 | 236.57 | 0.976 |
| 4 | 2 | 16 | 280.418 | 2.623 | 375.911 | 354.29 | 0.982 |
| 4 | 2 | 18 | 49.089 | 5.003 | 18.502 | 38.58 | 0.321 |
| 4 | 2 | 20 | 160.910 | 2.740 | 206.826 | 77.36 | 0.960 |
| 4 | 2 | 22 | 261.994 | 2.962 | 342.949 | 89.27 | 0.981 |
| 4 | 2 | 24 | 592.485 | 5.292 | 811.271 | 340.41 | 0.996 |
| 4 | 2 | 26 | 175.580 | 3.440 | 199.411 | 57.11 | 0.974 |

| | | | | | | | |
|---|---|---|---|---|---|---|---|
| 4 | 2 | 28 | 135.121 | 4.389 | 153.473 | 329.36 | 0.950 |
| 4 | 2 | 30 | 345.127 | 3.538 | 519.866 | 300.05 | 0.989 |
| 4 | 2 | 32 | 371.408 | 3.791 | 472.274 | 332.01 | 0.992 |
| 4 | 2 | 34 | 253.228 | 4.312 | 387.748 | 4.88 | 0.983 |
| 4 | 2 | 36 | 75.016 | 10.633 | 62.475 | 95.26 | 0.481 |
| 4 | 2 | 38 | 131.433 | 6.335 | 217.081 | 139.89 | 0.932 |
| 4 | 2 | 40 | 98.508 | 9.011 | 139.558 | 334.31 | 0.892 |
| 4 | 2 | 42 | 82.575 | 16.911 | 83.424 | 289.89 | 0.884 |
| 4 | 3 | 1 | 394.809 | 3.405 | 600.279 | 104.03 | 0.975 |
| 4 | 3 | 3 | 65.214 | 1.356 | 39.649 | 47.94 | 0.446 |
| 4 | 3 | 5 | 225.047 | 2.397 | 317.634 | 77.18 | 0.979 |
| 4 | 3 | 7 | 453.309 | 3.909 | 567.477 | 341.87 | 0.980 |
| 4 | 3 | 9 | 1029.566 | 10.765 | 1430.222 | 305.80 | 0.995 |
| 4 | 3 | 11 | 510.624 | 4.477 | 709.116 | 58.54 | 0.995 |
| 4 | 3 | 13 | 91.446 | 2.818 | 88.276 | 255.21 | 0.951 |
| 4 | 3 | 15 | 506.191 | 4.659 | 703.790 | 358.42 | 0.994 |
| 4 | 3 | 17 | 231.077 | 2.495 | 301.154 | 96.71 | 0.987 |
| 4 | 3 | 19 | 157.206 | 2.751 | 206.846 | 333.39 | 0.956 |
| 4 | 3 | 21 | 84.936 | 4.001 | 81.464 | 341.62 | 0.852 |
| 4 | 3 | 23 | 313.004 | 3.050 | 453.799 | 347.74 | 0.983 |
| 4 | 3 | 25 | 204.948 | 2.774 | 249.982 | 263.34 | 0.977 |
| 4 | 3 | 27 | 418.992 | 3.615 | 556.482 | 62.14 | 0.995 |
| 4 | 3 | 29 | 107.760 | 5.575 | 121.507 | 41.64 | 0.934 |
| 4 | 3 | 31 | 144.441 | 4.496 | 183.910 | 101.73 | 0.939 |
| 4 | 3 | 33 | 146.774 | 6.305 | 103.370 | 7.09 | 0.969 |
| 4 | 3 | 35 | 91.622 | 14.138 | 87.433 | 295.94 | 0.892 |
| 4 | 3 | 37 | 194.318 | 5.086 | 230.835 | 285.96 | 0.984 |
| 4 | 3 | 39 | 51.093 | 13.536 | 23.313 | 62.91 | 0.704 |
| 4 | 3 | 41 | 39.577 | 11.592 | 2.112 | 149.11 | 0.028 |
| 4 | 3 | 43 | 52.501 | 17.827 | 35.846 | 356.62 | 0.578 |
| 4 | 4 | 0 | 335.447 | 4.505 | 5.610 | 0.00 | 0.012 |
| 4 | 4 | 2 | 529.806 | 4.711 | 791.348 | 148.37 | 0.976 |
| 4 | 4 | 4 | 571.229 | 4.620 | 758.357 | 86.98 | 0.985 |
| 4 | 4 | 6 | 269.126 | 2.498 | 320.311 | 98.18 | 0.896 |
| 4 | 4 | 8 | 914.468 | 7.464 | 1320.887 | 104.43 | 0.993 |
| 4 | 4 | 10 | 1409.606 | 14.217 | 1968.095 | 71.49 | 0.999 |
| 4 | 4 | 12 | 235.127 | 2.403 | 337.735 | 312.23 | 0.975 |
| 4 | 4 | 14 | 290.485 | 2.943 | 395.633 | 275.76 | 0.985 |
| 4 | 4 | 16 | 188.250 | 2.343 | 287.270 | 215.36 | 0.922 |
| 4 | 4 | 18 | 117.081 | 3.166 | 148.295 | 262.93 | 0.937 |
| 4 | 4 | 20 | 281.193 | 2.805 | 394.132 | 301.57 | 0.984 |
| 4 | 4 | 22 | 106.771 | 3.991 | 39.415 | 339.58 | 0.228 |
| 4 | 4 | 24 | 274.285 | 2.872 | 424.581 | 51.07 | 0.976 |
| 4 | 4 | 26 | 88.631 | 5.177 | 61.743 | 108.08 | 0.917 |
| 4 | 4 | 28 | 380.331 | 3.614 | 536.809 | 177.76 | 0.992 |
| 4 | 4 | 30 | 268.805 | 3.352 | 372.296 | 46.03 | 0.984 |
| 4 | 4 | 32 | 254.317 | 3.550 | 284.533 | 195.09 | 0.984 |
| 4 | 4 | 34 | 50.557 | 12.695 | 11.234 | 212.51 | 0.561 |
| 4 | 4 | 36 | 48.169 | 11.086 | 28.309 | 225.93 | 0.482 |
| 4 | 4 | 38 | 88.930 | 8.377 | 61.141 | 182.29 | 0.936 |
| 4 | 4 | 40 | 41.768 | 12.307 | 2.357 | 112.75 | 0.550 |
| 4 | 4 | 42 | 56.141 | 14.582 | 35.398 | 3.95 | 0.627 |
| 4 | 5 | 1 | 615.016 | 5.322 | 941.169 | 301.86 | 0.984 |
| 4 | 5 | 3 | 448.632 | 4.041 | 600.814 | 280.36 | 0.986 |
| 4 | 5 | 5 | 244.216 | 2.287 | 261.749 | 322.46 | 0.884 |
| 4 | 5 | 7 | 698.756 | 5.718 | 962.606 | 293.38 | 0.989 |
| 4 | 5 | 9 | 588.366 | 4.894 | 794.979 | 80.02 | 0.988 |
| 4 | 5 | 11 | 588.951 | 4.883 | 875.992 | 78.89 | 0.996 |
| 4 | 5 | 13 | 565.533 | 5.328 | 811.247 | 102.32 | 0.995 |
| 4 | 5 | 15 | 378.106 | 3.556 | 521.556 | 296.14 | 0.992 |
| 4 | 5 | 17 | 345.492 | 3.259 | 493.851 | 249.71 | 0.991 |
| 4 | 5 | 19 | 78.997 | 4.255 | 79.528 | 239.86 | 0.667 |
| 4 | 5 | 21 | 221.323 | 2.817 | 338.014 | 158.65 | 0.970 |
| 4 | 5 | 23 | 302.836 | 3.057 | 396.522 | 38.50 | 0.987 |
| 4 | 5 | 25 | 143.430 | 3.217 | 184.523 | 98.54 | 0.950 |
| 4 | 5 | 27 | 285.986 | 3.193 | 472.433 | 212.62 | 0.976 |
| 4 | 5 | 29 | 290.473 | 3.215 | 387.843 | 257.12 | 0.988 |
| 4 | 5 | 31 | 133.109 | 4.577 | 162.385 | 253.63 | 0.927 |
| 4 | 5 | 33 | 345.314 | 3.857 | 417.860 | 50.44 | 0.991 |
| 4 | 5 | 35 | 119.875 | 7.683 | 128.435 | 260.99 | 0.942 |
| 4 | 5 | 37 | 58.570 | 12.489 | 43.761 | 288.79 | 0.732 |
| 4 | 5 | 39 | 132.673 | 5.552 | 177.248 | 237.80 | 0.958 |
| 4 | 5 | 41 | 88.098 | 11.238 | 117.802 | 106.86 | 0.865 |
| 4 | 5 | 43 | 96.849 | 25.529 | 98.547 | 126.91 | 0.919 |
| 4 | 6 | 0 | 350.737 | 4.744 | 478.060 | 180.00 | 0.973 |
| 4 | 6 | 2 | 382.219 | 3.818 | 523.125 | 19.87 | 0.965 |
| 4 | 6 | 4 | 199.585 | 2.041 | 285.937 | 121.08 | 0.975 |

| | | | | | | | |
|---|---|---|---|---|---|---|---|
| 4 | 6 | 6 | 323.881 | 3.040 | 440.343 | 310.26 | 0.957 |
| 4 | 6 | 8 | 382.115 | 3.798 | 554.515 | 213.24 | 0.962 |
| 4 | 6 | 10 | 254.490 | 2.501 | 353.163 | 234.74 | 0.986 |
| 4 | 6 | 12 | 727.073 | 6.574 | 1051.938 | 160.28 | 0.997 |
| 4 | 6 | 14 | 360.044 | 3.136 | 550.656 | 279.30 | 0.989 |
| 4 | 6 | 16 | 477.360 | 4.529 | 682.367 | 158.74 | 0.995 |
| 4 | 6 | 18 | 156.046 | 2.617 | 245.048 | 341.38 | 0.792 |
| 4 | 6 | 20 | 148.104 | 2.836 | 179.083 | 95.95 | 0.972 |
| 4 | 6 | 22 | 383.698 | 3.716 | 567.389 | 150.25 | 0.990 |
| 4 | 6 | 24 | 320.830 | 3.168 | 469.147 | 295.61 | 0.989 |
| 4 | 6 | 26 | 206.762 | 2.987 | 284.666 | 276.12 | 0.978 |
| 4 | 6 | 28 | 75.898 | 7.636 | 57.846 | 197.00 | 0.899 |
| 4 | 6 | 30 | 92.378 | 6.549 | 82.755 | 248.63 | 0.645 |
| 4 | 6 | 32 | 395.703 | 3.919 | 546.647 | 55.45 | 0.992 |
| 4 | 6 | 34 | 44.943 | 12.277 | 6.021 | 155.54 | 0.261 |
| 4 | 6 | 36 | 194.440 | 4.899 | 257.398 | 349.39 | 0.982 |
| 4 | 6 | 38 | 97.611 | 9.286 | 97.921 | 179.25 | 0.937 |
| 4 | 6 | 40 | 50.103 | 11.811 | 25.671 | 347.92 | 0.553 |
| 4 | 6 | 42 | 51.576 | 15.363 | 35.403 | 298.25 | 0.490 |
| 4 | 7 | 1 | 200.734 | 2.312 | 219.140 | 193.12 | 0.914 |
| 4 | 7 | 3 | 581.358 | 5.127 | 766.595 | 119.53 | 0.986 |
| 4 | 7 | 5 | 742.353 | 6.023 | 1069.989 | 162.20 | 0.989 |
| 4 | 7 | 7 | 758.953 | 6.301 | 965.927 | 344.98 | 0.998 |
| 4 | 7 | 9 | 407.522 | 3.435 | 554.239 | 320.31 | 0.992 |
| 4 | 7 | 11 | 262.173 | 2.515 | 343.077 | 339.68 | 0.984 |
| 4 | 7 | 13 | 182.990 | 2.495 | 249.903 | 225.28 | 0.947 |
| 4 | 7 | 15 | 324.906 | 3.032 | 442.619 | 332.44 | 0.991 |
| 4 | 7 | 17 | 280.945 | 2.721 | 388.972 | 85.89 | 0.987 |
| 4 | 7 | 19 | 303.159 | 2.953 | 403.032 | 154.68 | 0.988 |
| 4 | 7 | 21 | 269.339 | 2.770 | 361.526 | 273.23 | 0.987 |
| 4 | 7 | 23 | 192.670 | 2.801 | 204.656 | 89.89 | 0.971 |
| 4 | 7 | 25 | 169.497 | 3.038 | 229.924 | 218.89 | 0.966 |
| 4 | 7 | 27 | 184.716 | 3.380 | 227.825 | 5.29 | 0.972 |
| 4 | 7 | 29 | 364.954 | 3.880 | 517.253 | 147.80 | 0.991 |
| 4 | 7 | 31 | 289.473 | 3.653 | 375.691 | 281.91 | 0.986 |
| 4 | 7 | 33 | 59.487 | 12.877 | 26.241 | 211.75 | 0.645 |
| 4 | 7 | 35 | 195.227 | 5.025 | 265.087 | 116.68 | 0.982 |
| 4 | 7 | 37 | 145.557 | 4.934 | 153.371 | 292.12 | 0.974 |
| 4 | 7 | 39 | 95.539 | 8.691 | 122.542 | 356.05 | 0.907 |
| 4 | 7 | 41 | 65.439 | 12.498 | 58.727 | 47.88 | 0.837 |
| 4 | 8 | 0 | 522.078 | 5.926 | 731.013 | 0.00 | 1.000 |
| 4 | 8 | 2 | 560.574 | 4.581 | 821.450 | 261.58 | 0.986 |
| 4 | 8 | 4 | 634.841 | 5.360 | 891.749 | 347.09 | 0.986 |
| 4 | 8 | 6 | 907.920 | 8.296 | 1191.759 | 266.29 | 0.998 |
| 4 | 8 | 8 | 277.276 | 2.775 | 334.989 | 289.88 | 0.989 |
| 4 | 8 | 10 | 499.485 | 4.931 | 728.833 | 296.26 | 0.994 |
| 4 | 8 | 12 | 306.149 | 3.216 | 441.962 | 341.70 | 0.984 |
| 4 | 8 | 14 | 191.809 | 2.433 | 281.133 | 254.48 | 0.985 |
| 4 | 8 | 16 | 131.164 | 2.768 | 197.352 | 257.28 | 0.974 |
| 4 | 8 | 18 | 354.571 | 3.564 | 525.648 | 151.03 | 0.990 |
| 4 | 8 | 20 | 127.624 | 2.926 | 198.644 | 217.18 | 0.940 |
| 4 | 8 | 22 | 201.373 | 2.840 | 230.508 | 46.76 | 0.974 |
| 4 | 8 | 24 | 264.311 | 2.968 | 356.038 | 41.52 | 0.985 |
| 4 | 8 | 26 | 221.485 | 3.326 | 284.278 | 18.59 | 0.979 |
| 4 | 8 | 28 | 286.015 | 3.275 | 428.970 | 115.20 | 0.986 |
| 4 | 8 | 30 | 258.757 | 3.355 | 407.956 | 244.11 | 0.976 |
| 4 | 8 | 32 | 118.809 | 6.025 | 162.025 | 191.95 | 0.876 |
| 4 | 8 | 34 | 85.062 | 11.483 | 50.198 | 187.89 | 0.899 |
| 4 | 8 | 36 | 152.035 | 5.601 | 219.723 | 125.95 | 0.966 |
| 4 | 8 | 38 | 58.726 | 11.152 | 15.910 | 106.26 | 0.197 |
| 4 | 8 | 40 | 68.928 | 11.115 | 76.604 | 59.79 | 0.840 |
| 4 | 8 | 42 | 51.046 | 22.977 | 8.772 | 35.39 | 0.787 |
| 4 | 9 | 1 | 906.938 | 8.218 | 1233.006 | 49.84 | 0.998 |
| 4 | 9 | 3 | 251.312 | 2.233 | 360.167 | 264.81 | 0.986 |
| 4 | 9 | 5 | 652.268 | 5.290 | 862.902 | 172.22 | 0.997 |
| 4 | 9 | 7 | 355.475 | 3.963 | 431.975 | 166.34 | 0.991 |
| 4 | 9 | 9 | 317.867 | 3.440 | 413.555 | 170.21 | 0.988 |
| 4 | 9 | 11 | 474.627 | 3.877 | 603.492 | 223.38 | 0.994 |
| 4 | 9 | 13 | 304.897 | 3.422 | 401.476 | 53.61 | 0.988 |
| 4 | 9 | 15 | 238.476 | 2.552 | 276.343 | 226.47 | 0.987 |
| 4 | 9 | 17 | 278.688 | 2.835 | 351.092 | 37.13 | 0.988 |
| 4 | 9 | 19 | 341.502 | 3.189 | 493.583 | 256.02 | 0.988 |
| 4 | 9 | 21 | 54.488 | 6.798 | 35.115 | 176.28 | 0.608 |
| 4 | 9 | 23 | 327.791 | 3.488 | 444.682 | 38.81 | 0.991 |
| 4 | 9 | 25 | 178.314 | 3.365 | 257.331 | 209.25 | 0.963 |
| 4 | 9 | 27 | 300.289 | 3.297 | 380.101 | 226.29 | 0.989 |
| 4 | 9 | 29 | 288.273 | 3.388 | 402.428 | 114.21 | 0.984 |

| | | | | | | | |
|---|---|---|---|---|---|---|---|
| 4 | 9 | 31 | 233.878 | 3.848 | 277.169 | 213.62 | 0.980 |
| 4 | 9 | 33 | 159.939 | 5.629 | 253.008 | 39.10 | 0.949 |
| 4 | 9 | 35 | 367.606 | 4.487 | 508.668 | 141.13 | 0.995 |
| 4 | 9 | 37 | 54.680 | 11.890 | 33.226 | 180.34 | 0.645 |
| 4 | 9 | 39 | 132.253 | 7.186 | 176.198 | 214.98 | 0.963 |
| 4 | 9 | 41 | 46.980 | 14.595 | 23.489 | 346.17 | 0.804 |
| 4 | 10 | 0 | 483.059 | 5.420 | 676.205 | 180.00 | 1.000 |
| 4 | 10 | 2 | 527.749 | 5.133 | 804.640 | 256.41 | 0.995 |
| 4 | 10 | 4 | 656.682 | 5.484 | 928.375 | 214.67 | 0.997 |
| 4 | 10 | 6 | 352.189 | 3.574 | 477.023 | 264.04 | 0.989 |
| 4 | 10 | 8 | 189.367 | 2.545 | 234.284 | 168.80 | 0.979 |
| 4 | 10 | 10 | 364.530 | 3.184 | 486.095 | 82.97 | 0.993 |
| 4 | 10 | 12 | 316.172 | 3.145 | 424.659 | 255.22 | 0.989 |
| 4 | 10 | 14 | 175.933 | 2.550 | 288.658 | 250.73 | 0.981 |
| 4 | 10 | 16 | 162.017 | 2.266 | 243.077 | 219.90 | 0.961 |
| 4 | 10 | 18 | 228.967 | 2.532 | 218.794 | 330.97 | 0.982 |
| 4 | 10 | 20 | 399.293 | 3.618 | 579.195 | 83.62 | 0.992 |
| 4 | 10 | 22 | 165.955 | 2.850 | 238.886 | 357.01 | 0.941 |
| 4 | 10 | 24 | 507.135 | 4.367 | 722.096 | 169.39 | 0.996 |
| 4 | 10 | 26 | 133.734 | 4.058 | 178.953 | 182.45 | 0.922 |
| 4 | 10 | 28 | 338.541 | 3.456 | 524.713 | 283.65 | 0.989 |
| 4 | 10 | 30 | 207.417 | 4.005 | 272.424 | 264.19 | 0.972 |
| 4 | 10 | 32 | 125.463 | 7.502 | 179.358 | 260.27 | 0.930 |
| 4 | 10 | 34 | 113.696 | 7.872 | 84.592 | 69.32 | 0.968 |
| 4 | 10 | 36 | 55.189 | 12.338 | 22.603 | 15.79 | 0.315 |
| 4 | 10 | 38 | 207.100 | 4.703 | 288.769 | 229.62 | 0.983 |
| 4 | 10 | 40 | 46.955 | 14.584 | 21.589 | 224.01 | 0.592 |
| 4 | 11 | 1 | 389.084 | 3.549 | 594.121 | 121.30 | 0.989 |
| 4 | 11 | 3 | 450.037 | 6.246 | 612.904 | 24.24 | 0.993 |
| 4 | 11 | 5 | 181.376 | 2.272 | 234.602 | 267.05 | 0.966 |
| 4 | 11 | 7 | 360.638 | 3.408 | 560.150 | 197.01 | 0.988 |
| 4 | 11 | 9 | 302.436 | 3.177 | 436.496 | 194.84 | 0.984 |
| 4 | 11 | 11 | 187.571 | 2.323 | 237.489 | 198.07 | 0.977 |
| 4 | 11 | 13 | 141.974 | 2.472 | 156.262 | 9.48 | 0.965 |
| 4 | 11 | 15 | 263.052 | 2.586 | 380.128 | 154.41 | 0.982 |
| 4 | 11 | 17 | 355.095 | 3.332 | 463.148 | 329.41 | 0.990 |
| 4 | 11 | 19 | 246.913 | 2.759 | 365.235 | 124.71 | 0.977 |
| 4 | 11 | 21 | 160.047 | 2.933 | 164.605 | 323.81 | 0.970 |
| 4 | 11 | 23 | 134.396 | 4.395 | 181.290 | 103.98 | 0.940 |
| 4 | 11 | 25 | 342.344 | 3.351 | 478.482 | 15.14 | 0.991 |
| 4 | 11 | 27 | 271.389 | 3.209 | 299.268 | 321.39 | 0.988 |
| 4 | 11 | 29 | 213.453 | 3.949 | 330.208 | 100.12 | 0.966 |
| 4 | 11 | 31 | 424.955 | 4.231 | 531.967 | 20.41 | 0.996 |
| 4 | 11 | 33 | 336.545 | 3.986 | 438.714 | 343.53 | 0.993 |
| 4 | 11 | 35 | 52.072 | 13.015 | 13.534 | 157.84 | 0.798 |
| 4 | 11 | 37 | 106.545 | 10.768 | 101.967 | 125.77 | 0.949 |
| 4 | 11 | 39 | 51.271 | 13.453 | 19.927 | 240.53 | 0.348 |
| 4 | 11 | 41 | 75.493 | 29.669 | 32.251 | 156.26 | 0.885 |
| 4 | 12 | 0 | 12.202 | 5.954 | 2.620 | 0.00 | 0.154 |
| 4 | 12 | 2 | 300.244 | 3.554 | 383.877 | 27.61 | 0.988 |
| 4 | 12 | 4 | 329.079 | 2.969 | 462.457 | 56.62 | 0.991 |
| 4 | 12 | 6 | 152.097 | 2.595 | 163.130 | 269.04 | 0.948 |
| 4 | 12 | 8 | 234.936 | 2.434 | 312.075 | 46.92 | 0.988 |
| 4 | 12 | 10 | 201.906 | 2.775 | 281.085 | 79.99 | 0.988 |
| 4 | 12 | 12 | 334.026 | 3.068 | 484.457 | 71.93 | 0.989 |
| 4 | 12 | 14 | 207.638 | 2.642 | 219.104 | 55.56 | 0.621 |
| 4 | 12 | 16 | 306.209 | 2.891 | 446.999 | 149.09 | 0.985 |
| 4 | 12 | 18 | 152.547 | 2.733 | 223.395 | 341.64 | 0.928 |
| 4 | 12 | 20 | 332.079 | 3.195 | 464.518 | 209.98 | 0.991 |
| 4 | 12 | 22 | 501.213 | 4.456 | 596.193 | 312.15 | 0.997 |
| 4 | 12 | 24 | 236.397 | 3.243 | 236.963 | 312.07 | 0.985 |
| 4 | 12 | 26 | 152.912 | 3.898 | 193.563 | 86.43 | 0.964 |
| 4 | 12 | 28 | 454.612 | 4.410 | 624.156 | 89.57 | 0.994 |
| 4 | 12 | 30 | 38.663 | 11.326 | 12.782 | 288.45 | 0.432 |
| 4 | 12 | 32 | 68.073 | 12.148 | 15.787 | 85.20 | 0.869 |
| 4 | 12 | 34 | 109.838 | 7.193 | 91.138 | 10.55 | 0.964 |
| 4 | 12 | 36 | 79.080 | 11.155 | 65.049 | 189.84 | 0.908 |
| 4 | 12 | 38 | 60.840 | 13.140 | 8.875 | 354.03 | 0.098 |
| 4 | 12 | 40 | 49.705 | 15.894 | 35.126 | 130.30 | 0.590 |
| 4 | 13 | 1 | 362.205 | 3.289 | 502.590 | 7.04 | 0.990 |
| 4 | 13 | 3 | 216.315 | 2.855 | 308.160 | 311.44 | 0.968 |
| 4 | 13 | 5 | 609.526 | 5.308 | 812.421 | 288.33 | 0.997 |
| 4 | 13 | 7 | 259.651 | 2.463 | 452.273 | 37.55 | 0.974 |
| 4 | 13 | 9 | 181.941 | 2.407 | 249.440 | 44.16 | 0.964 |
| 4 | 13 | 11 | 36.099 | 7.709 | 18.980 | 268.65 | 0.048 |
| 4 | 13 | 13 | 377.561 | 3.457 | 575.534 | 347.83 | 0.991 |
| 4 | 13 | 15 | 483.813 | 4.127 | 674.600 | 248.68 | 0.994 |

| | | | | | | | |
|---|---|---|---|---|---|---|---|
| 4 | 13 | 17 | 92.804 | 3.858 | 112.188 | 233.49 | 0.860 |
| 4 | 13 | 19 | 165.615 | 3.154 | 182.689 | 115.84 | 0.964 |
| 4 | 13 | 21 | 418.218 | 3.832 | 583.851 | 244.01 | 0.994 |
| 4 | 13 | 23 | 354.280 | 3.417 | 445.103 | 54.15 | 0.992 |
| 4 | 13 | 25 | 185.684 | 3.279 | 270.518 | 202.98 | 0.965 |
| 4 | 13 | 27 | 303.562 | 3.566 | 389.007 | 165.15 | 0.988 |
| 4 | 13 | 29 | 73.897 | 9.698 | 55.795 | 84.48 | 0.560 |
| 4 | 13 | 31 | 50.808 | 12.704 | 10.156 | 192.23 | 0.616 |
| 4 | 13 | 33 | 131.980 | 7.738 | 194.285 | 213.54 | 0.953 |
| 4 | 13 | 35 | 135.248 | 7.085 | 159.340 | 64.82 | 0.967 |
| 4 | 13 | 37 | 81.528 | 12.078 | 90.978 | 266.25 | 0.893 |
| 4 | 13 | 39 | 57.446 | 14.030 | 37.678 | 147.95 | 0.536 |
| 4 | 14 | 0 | 220.493 | 3.527 | 308.410 | 180.00 | 1.000 |
| 4 | 14 | 2 | 374.198 | 3.415 | 451.907 | 51.09 | 0.994 |
| 4 | 14 | 4 | 160.858 | 2.277 | 218.861 | 274.90 | 0.990 |
| 4 | 14 | 6 | 41.339 | 7.020 | 52.208 | 273.67 | 0.597 |
| 4 | 14 | 8 | 189.915 | 2.407 | 266.832 | 87.76 | 0.988 |
| 4 | 14 | 10 | 338.391 | 3.100 | 458.618 | 160.96 | 0.991 |
| 4 | 14 | 12 | 55.876 | 5.042 | 9.344 | 104.97 | 0.480 |
| 4 | 14 | 14 | 73.489 | 5.257 | 72.296 | 167.01 | 0.727 |
| 4 | 14 | 16 | 370.270 | 3.331 | 506.634 | 279.11 | 0.992 |
| 4 | 14 | 18 | 644.894 | 5.598 | 929.211 | 96.87 | 0.998 |
| 4 | 14 | 20 | 333.263 | 3.223 | 490.765 | 74.23 | 0.991 |
| 4 | 14 | 22 | 176.713 | 3.345 | 216.036 | 208.75 | 0.974 |
| 4 | 14 | 24 | 138.234 | 3.850 | 193.407 | 298.72 | 0.925 |
| 4 | 14 | 26 | 162.510 | 4.799 | 164.110 | 175.55 | 0.965 |
| 4 | 14 | 28 | 52.107 | 10.984 | 17.131 | 323.39 | 0.439 |
| 4 | 14 | 30 | 167.301 | 7.093 | 199.832 | 58.64 | 0.971 |
| 4 | 14 | 32 | 142.148 | 5.853 | 153.995 | 52.13 | 0.973 |
| 4 | 14 | 34 | 138.723 | 5.580 | 211.527 | 103.61 | 0.957 |
| 4 | 14 | 36 | 41.331 | 12.709 | 2.120 | 312.05 | 0.186 |
| 4 | 14 | 38 | 77.462 | 13.703 | 62.992 | 39.01 | 0.902 |
| 4 | 14 | 40 | 58.257 | 25.847 | 26.022 | 223.77 | 0.742 |
| 4 | 15 | 1 | 141.012 | 2.381 | 163.005 | 31.70 | 0.962 |
| 4 | 15 | 3 | 80.954 | 4.124 | 84.612 | 63.32 | 0.804 |
| 4 | 15 | 5 | 291.006 | 2.718 | 430.213 | 219.50 | 0.985 |
| 4 | 15 | 7 | 160.123 | 2.798 | 208.781 | 343.33 | 0.963 |
| 4 | 15 | 9 | 96.693 | 2.965 | 89.113 | 331.23 | 0.939 |
| 4 | 15 | 11 | 407.400 | 3.509 | 589.623 | 310.39 | 0.992 |
| 4 | 15 | 13 | 436.506 | 3.750 | 541.322 | 78.98 | 0.994 |
| 4 | 15 | 15 | 305.289 | 3.136 | 409.073 | 160.58 | 0.986 |
| 4 | 15 | 17 | 295.067 | 3.052 | 420.132 | 121.45 | 0.988 |
| 4 | 15 | 19 | 351.166 | 3.269 | 461.483 | 137.64 | 0.992 |
| 4 | 15 | 21 | 445.499 | 4.086 | 524.220 | 205.21 | 0.996 |
| 4 | 15 | 23 | 107.696 | 7.406 | 93.195 | 298.23 | 0.937 |
| 4 | 15 | 25 | 227.212 | 3.969 | 253.264 | 55.56 | 0.980 |
| 4 | 15 | 27 | 253.939 | 4.508 | 305.654 | 186.62 | 0.984 |
| 4 | 15 | 29 | 268.687 | 4.610 | 332.194 | 136.18 | 0.989 |
| 4 | 15 | 31 | 111.986 | 8.509 | 128.377 | 46.95 | 0.952 |
| 4 | 15 | 33 | 157.579 | 5.771 | 145.945 | 112.41 | 0.980 |
| 4 | 15 | 35 | 34.041 | 10.660 | 7.279 | 210.70 | 0.261 |
| 4 | 15 | 37 | 50.308 | 11.982 | 1.166 | 38.61 | 0.852 |
| 4 | 15 | 39 | 54.009 | 22.695 | 27.313 | 325.16 | 0.630 |
| 4 | 16 | 0 | 69.996 | 5.397 | 78.718 | 0.00 | 0.805 |
| 4 | 16 | 2 | 211.588 | 2.413 | 303.841 | 244.99 | 0.986 |
| 4 | 16 | 4 | 161.387 | 2.706 | 249.781 | 352.45 | 0.926 |
| 4 | 16 | 6 | 29.558 | 7.906 | 45.599 | 125.22 | 0.203 |
| 4 | 16 | 8 | 425.881 | 3.538 | 589.332 | 189.92 | 0.993 |
| 4 | 16 | 10 | 218.370 | 2.609 | 289.134 | 315.83 | 0.984 |
| 4 | 16 | 12 | 55.491 | 6.806 | 21.889 | 286.67 | 0.326 |
| 4 | 16 | 14 | 474.646 | 4.272 | 612.230 | 103.43 | 0.995 |
| 4 | 16 | 16 | 147.314 | 2.947 | 189.431 | 13.20 | 0.867 |
| 4 | 16 | 18 | 196.209 | 2.848 | 238.115 | 17.77 | 0.976 |
| 4 | 16 | 20 | 263.641 | 3.429 | 316.876 | 237.22 | 0.987 |
| 4 | 16 | 22 | 366.224 | 3.999 | 460.188 | 297.06 | 0.993 |
| 4 | 16 | 24 | 304.717 | 3.613 | 368.510 | 79.94 | 0.989 |
| 4 | 16 | 26 | 217.697 | 4.603 | 316.139 | 176.03 | 0.970 |
| 4 | 16 | 28 | 86.830 | 11.048 | 115.780 | 92.41 | 0.769 |
| 4 | 16 | 30 | 138.813 | 7.098 | 216.920 | 254.97 | 0.956 |
| 4 | 16 | 32 | 79.415 | 11.941 | 99.241 | 231.57 | 0.754 |
| 4 | 16 | 34 | 120.465 | 6.568 | 128.604 | 213.22 | 0.962 |
| 4 | 16 | 36 | 71.716 | 12.489 | 59.936 | 356.40 | 0.891 |
| 4 | 16 | 38 | 44.053 | 14.357 | 25.222 | 116.34 | 0.473 |
| 4 | 17 | 1 | 46.047 | 6.688 | 18.993 | 327.88 | 0.820 |
| 4 | 17 | 3 | 156.577 | 3.291 | 170.783 | 144.82 | 0.962 |
| 4 | 17 | 5 | 223.029 | 2.646 | 301.824 | 9.83 | 0.976 |
| 4 | 17 | 7 | 283.463 | 2.942 | 405.277 | 176.86 | 0.984 |

| | | | | | | | |
|---|---|---|---|---|---|---|---|
| 4 | 17 | 9 | 206.201 | 2.585 | 314.110 | 206.64 | 0.970 |
| 4 | 17 | 11 | 281.243 | 3.065 | 385.749 | 73.78 | 0.984 |
| 4 | 17 | 13 | 419.063 | 3.608 | 647.706 | 190.32 | 0.994 |
| 4 | 17 | 15 | 172.188 | 2.931 | 233.864 | 288.54 | 0.972 |
| 4 | 17 | 17 | 491.919 | 5.052 | 706.616 | 329.64 | 0.996 |
| 4 | 17 | 19 | 109.104 | 5.921 | 132.887 | 20.38 | 0.908 |
| 4 | 17 | 21 | 248.061 | 3.374 | 299.028 | 222.43 | 0.987 |
| 4 | 17 | 23 | 120.000 | 4.946 | 123.389 | 21.90 | 0.946 |
| 4 | 17 | 25 | 252.476 | 3.825 | 371.591 | 331.38 | 0.979 |
| 4 | 17 | 27 | 228.355 | 4.671 | 307.023 | 218.49 | 0.984 |
| 4 | 17 | 29 | 153.088 | 5.391 | 218.792 | 1.24 | 0.967 |
| 4 | 17 | 31 | 51.270 | 12.248 | 12.962 | 182.07 | 0.180 |
| 4 | 17 | 33 | 61.478 | 12.254 | 36.954 | 208.62 | 0.835 |
| 4 | 17 | 35 | 67.154 | 12.733 | 72.059 | 40.81 | 0.807 |
| 4 | 17 | 37 | 54.811 | 15.363 | 50.814 | 229.05 | 0.726 |
| 4 | 18 | 0 | 171.939 | 4.031 | 240.210 | 0.00 | 1.000 |
| 4 | 18 | 2 | 120.264 | 3.654 | 115.123 | 332.58 | 0.943 |
| 4 | 18 | 4 | 268.092 | 3.268 | 379.497 | 130.40 | 0.982 |
| 4 | 18 | 6 | 81.951 | 4.050 | 71.672 | 305.25 | 0.847 |
| 4 | 18 | 8 | 255.213 | 2.765 | 397.865 | 144.04 | 0.980 |
| 4 | 18 | 10 | 419.420 | 3.597 | 599.566 | 234.53 | 0.995 |
| 4 | 18 | 12 | 499.403 | 4.989 | 688.267 | 329.64 | 0.996 |
| 4 | 18 | 14 | 189.837 | 3.415 | 285.713 | 164.98 | 0.965 |
| 4 | 18 | 16 | 331.833 | 3.452 | 465.484 | 260.09 | 0.991 |
| 4 | 18 | 18 | 230.977 | 3.502 | 299.065 | 205.48 | 0.982 |
| 4 | 18 | 20 | 127.915 | 5.322 | 134.972 | 162.50 | 0.940 |
| 4 | 18 | 22 | 91.469 | 6.632 | 113.806 | 313.08 | 0.876 |
| 4 | 18 | 24 | 165.465 | 5.209 | 274.462 | 60.56 | 0.934 |
| 4 | 18 | 26 | 163.642 | 6.264 | 215.983 | 200.91 | 0.967 |
| 4 | 18 | 28 | 42.301 | 11.801 | 3.790 | 176.68 | 0.708 |
| 4 | 18 | 30 | 114.065 | 9.101 | 131.191 | 39.49 | 0.953 |
| 4 | 18 | 32 | 39.483 | 11.055 | 12.897 | 189.98 | 0.283 |
| 4 | 18 | 34 | 194.681 | 4.437 | 285.036 | 76.67 | 0.984 |
| 4 | 18 | 36 | 41.972 | 13.181 | 23.479 | 28.39 | 0.488 |
| 4 | 19 | 1 | 282.528 | 2.838 | 347.162 | 250.34 | 0.987 |
| 4 | 19 | 3 | 148.532 | 3.292 | 150.801 | 241.27 | 0.968 |
| 4 | 19 | 5 | 50.940 | 9.057 | 37.294 | 50.77 | 0.496 |
| 4 | 19 | 7 | 257.605 | 2.763 | 378.491 | 279.70 | 0.984 |
| 4 | 19 | 9 | 43.533 | 8.746 | 94.817 | 305.09 | 0.845 |
| 4 | 19 | 11 | 489.830 | 4.476 | 713.624 | 56.29 | 0.996 |
| 4 | 19 | 13 | 570.680 | 5.281 | 775.454 | 150.99 | 0.997 |
| 4 | 19 | 15 | 194.092 | 3.724 | 272.366 | 184.72 | 0.974 |
| 4 | 19 | 17 | 384.248 | 3.891 | 548.240 | 51.11 | 0.993 |
| 4 | 19 | 19 | 190.806 | 4.246 | 259.371 | 72.82 | 0.969 |
| 4 | 19 | 21 | 71.146 | 11.593 | 61.384 | 23.93 | 0.581 |
| 4 | 19 | 23 | 391.043 | 4.899 | 542.815 | 45.32 | 0.995 |
| 4 | 19 | 25 | 118.802 | 7.077 | 157.108 | 45.97 | 0.934 |
| 4 | 19 | 27 | 230.316 | 5.363 | 342.004 | 264.66 | 0.987 |
| 4 | 19 | 29 | 49.588 | 11.359 | 27.602 | 246.32 | 0.583 |
| 4 | 19 | 31 | 123.739 | 8.473 | 143.959 | 5.44 | 0.962 |
| 4 | 19 | 33 | 44.889 | 12.154 | 19.430 | 89.82 | 0.496 |
| 4 | 19 | 35 | 128.166 | 11.004 | 150.563 | 36.64 | 0.978 |
| 4 | 20 | 0 | 176.785 | 4.446 | 244.064 | 0.00 | 0.989 |
| 4 | 20 | 2 | 162.771 | 2.940 | 169.669 | 186.82 | 0.981 |
| 4 | 20 | 4 | 89.913 | 5.033 | 71.934 | 159.81 | 0.891 |
| 4 | 20 | 6 | 175.968 | 3.544 | 251.768 | 27.53 | 0.968 |
| 4 | 20 | 8 | 410.040 | 4.582 | 665.655 | 250.39 | 0.993 |
| 4 | 20 | 10 | 335.206 | 3.556 | 401.045 | 89.31 | 0.993 |
| 4 | 20 | 12 | 273.489 | 3.347 | 351.809 | 169.94 | 0.988 |
| 4 | 20 | 14 | 321.676 | 3.561 | 372.231 | 314.89 | 0.992 |
| 4 | 20 | 16 | 367.090 | 3.755 | 490.361 | 326.45 | 0.993 |
| 4 | 20 | 18 | 257.219 | 3.611 | 358.612 | 35.36 | 0.983 |
| 4 | 20 | 20 | 174.338 | 4.941 | 179.289 | 244.86 | 0.972 |
| 4 | 20 | 22 | 433.541 | 4.587 | 608.959 | 37.54 | 0.996 |
| 4 | 20 | 24 | 221.976 | 5.042 | 366.507 | 190.92 | 0.978 |
| 4 | 20 | 26 | 233.520 | 4.125 | 284.351 | 78.26 | 0.990 |
| 4 | 20 | 28 | 218.707 | 5.616 | 268.328 | 229.46 | 0.988 |
| 4 | 20 | 30 | 233.684 | 4.088 | 313.133 | 356.46 | 0.989 |
| 4 | 20 | 32 | 178.779 | 5.483 | 220.028 | 223.80 | 0.984 |
| 4 | 20 | 34 | 54.870 | 16.412 | 53.613 | 265.38 | 0.769 |
| 4 | 20 | 36 | 38.823 | 18.448 | 0.362 | 117.13 | 0.400 |
| 4 | 21 | 1 | 215.394 | 2.931 | 252.276 | 274.60 | 0.984 |
| 4 | 21 | 3 | 171.371 | 3.880 | 269.834 | 319.25 | 0.941 |
| 4 | 21 | 5 | 260.670 | 3.208 | 375.201 | 130.57 | 0.986 |
| 4 | 21 | 7 | 82.347 | 7.247 | 79.432 | 221.28 | 0.748 |
| 4 | 21 | 9 | 144.409 | 4.311 | 176.790 | 311.02 | 0.960 |
| 4 | 21 | 11 | 158.027 | 4.290 | 210.657 | 282.30 | 0.963 |

| | | | | | | | |
|---|---|---|---|---|---|---|---|
| 4 | 21 | 13 | 377.189 | 3.801 | 512.409 | 221.44 | 0.993 |
| 4 | 21 | 15 | 188.003 | 4.298 | 289.355 | 355.41 | 0.954 |
| 4 | 21 | 17 | 555.877 | 6.084 | 763.680 | 306.94 | 0.996 |
| 4 | 21 | 19 | 228.243 | 5.061 | 307.573 | 35.46 | 0.978 |
| 4 | 21 | 21 | 222.378 | 4.374 | 375.578 | 208.40 | 0.974 |
| 4 | 21 | 23 | 243.110 | 4.005 | 355.954 | 100.18 | 0.985 |
| 4 | 21 | 25 | 54.906 | 16.256 | 36.405 | 57.26 | 0.703 |
| 4 | 21 | 27 | 106.203 | 8.039 | 148.290 | 220.21 | 0.933 |
| 4 | 21 | 29 | 208.389 | 4.620 | 211.007 | 348.57 | 0.989 |
| 4 | 21 | 31 | 177.420 | 5.200 | 314.986 | 235.30 | 0.972 |
| 4 | 21 | 33 | 44.222 | 13.240 | 34.139 | 274.52 | 0.650 |
| 4 | 22 | 0 | 174.679 | 5.296 | 243.694 | 180.00 | 1.000 |
| 4 | 22 | 2 | 189.539 | 3.320 | 256.035 | 75.90 | 0.973 |
| 4 | 22 | 4 | 140.294 | 3.950 | 134.528 | 167.98 | 0.965 |
| 4 | 22 | 6 | 99.225 | 7.127 | 76.154 | 264.95 | 0.914 |
| 4 | 22 | 8 | 218.378 | 4.673 | 325.343 | 32.93 | 0.976 |
| 4 | 22 | 10 | 143.594 | 4.270 | 228.570 | 44.93 | 0.937 |
| 4 | 22 | 12 | 321.921 | 3.706 | 642.389 | 187.34 | 0.926 |
| 4 | 22 | 14 | 117.242 | 6.293 | 79.113 | 167.57 | 0.946 |
| 4 | 22 | 16 | 265.205 | 3.716 | 393.000 | 14.40 | 0.982 |
| 4 | 22 | 18 | 205.961 | 5.661 | 240.261 | 102.87 | 0.983 |
| 4 | 22 | 20 | 62.466 | 12.672 | 28.863 | 149.75 | 0.819 |
| 4 | 22 | 22 | 210.838 | 4.414 | 300.275 | 239.74 | 0.981 |
| 4 | 22 | 24 | 142.194 | 8.811 | 195.827 | 61.21 | 0.968 |
| 4 | 22 | 26 | 55.557 | 10.798 | 33.739 | 278.72 | 0.457 |
| 4 | 22 | 28 | 91.106 | 10.227 | 123.358 | 22.73 | 0.897 |
| 4 | 22 | 30 | 45.781 | 11.643 | 8.001 | 346.55 | 0.760 |
| 4 | 22 | 32 | 51.983 | 16.243 | 38.048 | 217.45 | 0.825 |
| 4 | 22 | 34 | 49.016 | 23.463 | 9.619 | 123.47 | 0.505 |
| 4 | 23 | 1 | 130.998 | 4.431 | 167.483 | 254.89 | 0.947 |
| 4 | 23 | 3 | 259.907 | 3.376 | 463.351 | 215.74 | 0.969 |
| 4 | 23 | 5 | 208.363 | 3.185 | 282.975 | 166.60 | 0.979 |
| 4 | 23 | 7 | 188.970 | 5.654 | 243.612 | 123.70 | 0.975 |
| 4 | 23 | 9 | 187.683 | 4.374 | 229.173 | 166.37 | 0.979 |
| 4 | 23 | 11 | 231.791 | 3.715 | 478.717 | 260.74 | 0.949 |
| 4 | 23 | 13 | 223.483 | 4.312 | 336.216 | 66.70 | 0.975 |
| 4 | 23 | 15 | 144.252 | 6.833 | 125.668 | 221.82 | 0.957 |
| 4 | 23 | 17 | 347.470 | 4.109 | 463.540 | 331.77 | 0.994 |
| 4 | 23 | 19 | 266.302 | 5.455 | 378.823 | 221.30 | 0.988 |
| 4 | 23 | 21 | 129.289 | 8.292 | 214.775 | 282.13 | 0.941 |
| 4 | 23 | 23 | 54.146 | 12.379 | 47.201 | 34.59 | 0.613 |
| 4 | 23 | 25 | 136.193 | 7.505 | 139.345 | 217.20 | 0.974 |
| 4 | 23 | 27 | 93.127 | 7.743 | 120.899 | 70.79 | 0.911 |
| 4 | 23 | 29 | 66.637 | 15.076 | 70.056 | 194.08 | 0.732 |
| 4 | 23 | 31 | 63.144 | 16.366 | 20.784 | 208.92 | 0.932 |
| 4 | 23 | 33 | 55.970 | 25.585 | 12.523 | 149.20 | 0.789 |
| 4 | 24 | 0 | 321.503 | 4.954 | 448.257 | 0.00 | 1.000 |
| 4 | 24 | 2 | 533.436 | 4.435 | 702.037 | 48.70 | 0.997 |
| 4 | 24 | 4 | 335.780 | 3.339 | 474.568 | 242.27 | 0.990 |
| 4 | 24 | 6 | 383.986 | 5.944 | 562.951 | 293.88 | 0.992 |
| 4 | 24 | 8 | 438.085 | 4.995 | 652.304 | 110.61 | 0.994 |
| 4 | 24 | 10 | 89.225 | 7.857 | 110.549 | 113.36 | 0.711 |
| 4 | 24 | 12 | 297.306 | 3.793 | 433.110 | 294.25 | 0.987 |
| 4 | 24 | 14 | 186.933 | 5.633 | 221.779 | 162.90 | 0.980 |
| 4 | 24 | 16 | 201.962 | 5.675 | 274.988 | 277.01 | 0.980 |
| 4 | 24 | 18 | 157.358 | 5.328 | 200.623 | 199.05 | 0.969 |
| 4 | 24 | 20 | 138.515 | 6.559 | 156.408 | 315.85 | 0.974 |
| 4 | 24 | 22 | 33.385 | 10.085 | 12.024 | 149.80 | 0.483 |
| 4 | 24 | 24 | 63.556 | 9.771 | 59.134 | 283.72 | 0.512 |
| 4 | 24 | 26 | 106.232 | 9.054 | 162.914 | 185.03 | 0.935 |
| 4 | 24 | 28 | 57.276 | 16.375 | 41.595 | 331.79 | 0.563 |
| 4 | 24 | 30 | 120.753 | 9.386 | 171.826 | 10.30 | 0.972 |
| 4 | 25 | 1 | 478.257 | 4.352 | 642.159 | 352.73 | 0.996 |
| 4 | 25 | 3 | 388.779 | 4.814 | 547.270 | 312.19 | 0.993 |
| 4 | 25 | 5 | 129.200 | 6.051 | 126.900 | 28.34 | 0.958 |
| 4 | 25 | 7 | 80.734 | 16.076 | 67.249 | 47.29 | 0.803 |
| 4 | 25 | 9 | 338.191 | 5.223 | 475.710 | 128.53 | 0.991 |
| 4 | 25 | 11 | 256.078 | 4.528 | 390.581 | 289.00 | 0.987 |
| 4 | 25 | 13 | 153.842 | 6.600 | 193.673 | 113.45 | 0.969 |
| 4 | 25 | 15 | 64.336 | 12.519 | 49.710 | 203.92 | 0.821 |
| 4 | 25 | 17 | 53.785 | 12.318 | 31.148 | 333.27 | 0.751 |
| 4 | 25 | 19 | 101.948 | 7.951 | 95.571 | 140.84 | 0.955 |
| 4 | 25 | 21 | 165.594 | 6.092 | 194.335 | 227.02 | 0.982 |
| 4 | 25 | 23 | 54.225 | 12.500 | 34.283 | 41.83 | 0.652 |
| 4 | 25 | 25 | 69.185 | 10.175 | 49.062 | 210.07 | 0.916 |
| 4 | 25 | 27 | 111.969 | 10.242 | 185.266 | 17.63 | 0.881 |
| 4 | 25 | 29 | 39.377 | 19.066 | 2.143 | 291.63 | 0.692 |

| | | | | | | | |
|---|---|---|---|---|---|---|---|
| 4 | 26 | 0 | 107.691 | 14.392 | 103.503 | 0.00 | 0.693 |
| 4 | 26 | 2 | 92.825 | 9.616 | 66.477 | 146.93 | 0.932 |
| 4 | 26 | 4 | 90.348 | 9.619 | 106.708 | 259.09 | 0.894 |
| 4 | 26 | 6 | 63.885 | 11.881 | 9.387 | 265.27 | 0.888 |
| 4 | 26 | 8 | 168.287 | 8.490 | 226.081 | 122.23 | 0.973 |
| 4 | 26 | 10 | 263.525 | 4.657 | 384.856 | 149.34 | 0.988 |
| 4 | 26 | 12 | 159.405 | 5.226 | 268.711 | 149.50 | 0.955 |
| 4 | 26 | 14 | 140.191 | 4.926 | 140.019 | 158.49 | 0.977 |
| 4 | 26 | 16 | 127.855 | 6.152 | 251.335 | 219.06 | 0.899 |
| 4 | 26 | 18 | 109.833 | 5.771 | 104.122 | 220.71 | 0.962 |
| 4 | 26 | 20 | 75.843 | 9.370 | 104.273 | 127.13 | 0.755 |
| 4 | 26 | 22 | 96.559 | 8.181 | 159.523 | 321.68 | 0.787 |
| 4 | 26 | 24 | 90.485 | 11.073 | 110.086 | 311.23 | 0.930 |
| 4 | 26 | 26 | 61.072 | 15.241 | 61.970 | 287.44 | 0.882 |
| 4 | 26 | 28 | 96.367 | 13.531 | 116.834 | 119.73 | 0.956 |
| 4 | 27 | 1 | 261.210 | 5.788 | 388.110 | 247.24 | 0.988 |
| 4 | 27 | 3 | 82.011 | 20.149 | 102.025 | 157.67 | 0.795 |
| 4 | 27 | 5 | 296.972 | 4.910 | 400.899 | 248.05 | 0.992 |
| 4 | 27 | 7 | 214.722 | 5.946 | 236.277 | 5.78 | 0.986 |
| 4 | 27 | 9 | 222.992 | 5.496 | 281.636 | 73.61 | 0.990 |
| 4 | 27 | 11 | 75.323 | 10.064 | 84.178 | 194.22 | 0.887 |
| 4 | 27 | 13 | 207.819 | 4.171 | 353.588 | 295.00 | 0.982 |
| 4 | 27 | 15 | 282.843 | 3.791 | 415.894 | 232.00 | 0.993 |
| 4 | 27 | 17 | 111.251 | 7.974 | 156.347 | 3.27 | 0.939 |
| 4 | 27 | 19 | 39.380 | 11.026 | 7.968 | 141.69 | 0.396 |
| 4 | 27 | 21 | 57.850 | 11.650 | 61.772 | 33.80 | 0.764 |
| 4 | 27 | 23 | 112.065 | 13.124 | 190.105 | 155.49 | 0.910 |
| 4 | 27 | 25 | 38.928 | 18.069 | 7.517 | 203.75 | 0.538 |
| 4 | 27 | 27 | 42.436 | 19.968 | 22.620 | 160.44 | 0.828 |
| 4 | 28 | 0 | 284.037 | 8.794 | 394.318 | 0.00 | 1.000 |
| 4 | 28 | 2 | 51.863 | 15.532 | 21.177 | 22.04 | 0.303 |
| 4 | 28 | 4 | 100.017 | 11.871 | 41.438 | 316.55 | 0.966 |
| 4 | 28 | 6 | 64.355 | 11.712 | 55.196 | 309.00 | 0.861 |
| 4 | 28 | 8 | 39.013 | 12.185 | 8.532 | 351.17 | 0.191 |
| 4 | 28 | 10 | 179.760 | 6.210 | 284.352 | 47.09 | 0.979 |
| 4 | 28 | 12 | 80.878 | 9.805 | 115.561 | 26.93 | 0.863 |
| 4 | 28 | 14 | 156.391 | 5.849 | 273.575 | 184.73 | 0.965 |
| 4 | 28 | 16 | 163.948 | 4.750 | 235.262 | 5.79 | 0.977 |
| 4 | 28 | 18 | 139.080 | 6.323 | 162.277 | 135.17 | 0.977 |
| 4 | 28 | 20 | 45.001 | 12.772 | 4.070 | 18.56 | 0.799 |
| 4 | 28 | 22 | 54.993 | 14.406 | 6.325 | 143.26 | 0.878 |
| 4 | 28 | 24 | 43.552 | 14.037 | 22.777 | 241.25 | 0.787 |
| 4 | 28 | 26 | 40.796 | 19.181 | 7.347 | 230.88 | 0.540 |
| 4 | 29 | 1 | 193.801 | 5.945 | 222.147 | 173.33 | 0.987 |
| 4 | 29 | 3 | 259.876 | 5.044 | 366.533 | 203.89 | 0.992 |
| 4 | 29 | 5 | 103.800 | 11.505 | 136.412 | 138.66 | 0.944 |
| 4 | 29 | 7 | 244.830 | 5.561 | 338.498 | 13.03 | 0.991 |
| 4 | 29 | 9 | 53.004 | 14.675 | 37.956 | 291.79 | 0.696 |
| 4 | 29 | 11 | 52.939 | 13.078 | 33.826 | 355.56 | 0.485 |
| 4 | 29 | 13 | 238.635 | 4.568 | 366.337 | 140.62 | 0.989 |
| 4 | 29 | 15 | 119.501 | 6.979 | 157.343 | 359.66 | 0.965 |
| 4 | 29 | 17 | 64.703 | 10.046 | 77.319 | 191.72 | 0.674 |
| 4 | 29 | 19 | 61.433 | 13.934 | 60.196 | 21.16 | 0.761 |
| 4 | 29 | 21 | 109.393 | 14.433 | 124.113 | 330.55 | 0.971 |
| 4 | 29 | 23 | 42.757 | 20.858 | 14.883 | 236.08 | 0.764 |
| 4 | 30 | 0 | 26.456 | 13.026 | 28.632 | 0.00 | 0.788 |
| 4 | 30 | 2 | 85.233 | 15.546 | 104.350 | 72.90 | 0.908 |
| 4 | 30 | 4 | 78.270 | 10.409 | 81.684 | 288.89 | 0.909 |
| 4 | 30 | 6 | 44.814 | 12.065 | 4.337 | 156.11 | 0.767 |
| 4 | 30 | 8 | 105.517 | 12.894 | 135.190 | 350.09 | 0.941 |
| 4 | 30 | 10 | 54.659 | 13.398 | 19.959 | 347.34 | 0.844 |
| 4 | 30 | 12 | 45.301 | 12.145 | 23.373 | 221.45 | 0.519 |
| 4 | 30 | 14 | 76.571 | 9.332 | 72.906 | 275.70 | 0.923 |
| 4 | 30 | 16 | 65.792 | 13.445 | 41.861 | 277.10 | 0.896 |
| 4 | 30 | 18 | 49.278 | 13.238 | 4.163 | 28.71 | 0.911 |
| 4 | 30 | 20 | 63.784 | 14.456 | 46.958 | 342.76 | 0.921 |
| 4 | 30 | 22 | 56.414 | 25.081 | 15.091 | 1.43 | 0.784 |
| 4 | 31 | 1 | 137.901 | 5.578 | 168.482 | 347.18 | 0.973 |
| 4 | 31 | 3 | 81.203 | 8.092 | 99.256 | 344.95 | 0.909 |
| 4 | 31 | 5 | 33.316 | 10.307 | 9.643 | 177.85 | 0.506 |
| 4 | 31 | 7 | 67.945 | 11.266 | 69.720 | 103.33 | 0.893 |
| 4 | 31 | 9 | 47.976 | 13.102 | 26.493 | 178.96 | 0.464 |
| 4 | 31 | 11 | 46.803 | 14.072 | 25.461 | 134.11 | 0.508 |
| 4 | 31 | 13 | 50.695 | 14.599 | 33.682 | 27.55 | 0.614 |
| 4 | 31 | 15 | 46.797 | 12.988 | 33.261 | 98.01 | 0.821 |
| 4 | 31 | 17 | 37.895 | 12.374 | 20.496 | 222.01 | 0.561 |
| 4 | 31 | 19 | 55.029 | 21.766 | 36.042 | 94.57 | 0.739 |

| | | | | | | | |
|---|---|---|---|---|---|---|---|
| 4 | 32 | 0 | 178.669 | 7.393 | 120.035 | 0.00 | 0.487 |
| 4 | 32 | 2 | 120.278 | 6.059 | 136.492 | 143.67 | 0.972 |
| 4 | 32 | 4 | 64.363 | 10.006 | 52.107 | 179.68 | 0.903 |
| 4 | 32 | 6 | 42.286 | 13.652 | 11.432 | 295.23 | 0.646 |
| 4 | 32 | 8 | 66.933 | 18.044 | 58.544 | 228.30 | 0.835 |
| 4 | 32 | 10 | 98.551 | 10.288 | 132.994 | 27.53 | 0.963 |
| 4 | 32 | 12 | 55.374 | 15.889 | 49.146 | 84.73 | 0.859 |
| 4 | 32 | 14 | 36.179 | 16.997 | 6.450 | 217.21 | 0.361 |
| 4 | 32 | 16 | 44.862 | 21.023 | 3.369 | 264.56 | 0.772 |
| 4 | 33 | 1 | 59.313 | 15.812 | 50.433 | 48.07 | 0.903 |
| 4 | 33 | 3 | 74.300 | 12.155 | 95.945 | 17.12 | 0.932 |
| 4 | 33 | 5 | 53.951 | 14.820 | 40.067 | 4.31 | 0.886 |
| 4 | 33 | 7 | 39.542 | 11.735 | 15.989 | 214.54 | 0.337 |
| 4 | 33 | 9 | 49.103 | 14.756 | 29.136 | 58.19 | 0.427 |
| 4 | 33 | 11 | 49.424 | 21.544 | 13.909 | 91.70 | 0.870 |
| 4 | 33 | 13 | 86.310 | 19.747 | 116.878 | 274.91 | 0.855 |
| 4 | 34 | 0 | 45.765 | 23.185 | 2.241 | 180.00 | 0.040 |
| 4 | 34 | 2 | 43.857 | 12.677 | 12.576 | 2.98 | 0.189 |
| 4 | 34 | 4 | 43.307 | 13.761 | 11.811 | 147.21 | 0.188 |
| 5 | 0 | 1 | 777.216 | 10.128 | 1089.932 | 180.00 | 1.000 |
| 5 | 0 | 3 | 428.548 | 6.305 | 341.653 | 0.00 | 0.568 |
| 5 | 0 | 5 | 315.695 | 3.786 | 410.178 | 0.00 | 0.929 |
| 5 | 0 | 7 | 481.586 | 9.282 | 673.003 | 180.00 | 1.000 |
| 5 | 0 | 9 | 337.579 | 3.816 | 466.592 | 180.00 | 0.990 |
| 5 | 0 | 11 | 131.033 | 2.955 | 180.902 | 0.00 | 1.000 |
| 5 | 0 | 13 | 169.518 | 2.935 | 233.947 | 0.00 | 1.000 |
| 5 | 0 | 15 | 135.277 | 3.059 | 187.012 | 180.00 | 1.000 |
| 5 | 0 | 17 | 208.857 | 3.498 | 287.008 | 180.00 | 1.000 |
| 5 | 0 | 19 | 91.387 | 4.923 | 75.545 | 180.00 | 0.612 |
| 5 | 0 | 21 | 182.467 | 3.603 | 248.801 | 180.00 | 1.000 |
| 5 | 0 | 23 | 305.074 | 4.329 | 413.392 | 0.00 | 1.000 |
| 5 | 0 | 25 | 223.045 | 4.269 | 300.091 | 0.00 | 1.000 |
| 5 | 0 | 27 | 428.903 | 5.356 | 573.999 | 0.00 | 1.000 |
| 5 | 0 | 29 | 260.533 | 5.065 | 346.004 | 0.00 | 1.000 |
| 5 | 0 | 31 | 123.172 | 7.693 | 161.461 | 0.00 | 0.998 |
| 5 | 0 | 33 | 363.926 | 6.832 | 475.532 | 180.00 | 1.000 |
| 5 | 0 | 35 | 245.303 | 7.932 | 317.427 | 180.00 | 1.000 |
| 5 | 0 | 37 | 51.353 | 19.555 | 63.054 | 0.00 | 0.979 |
| 5 | 0 | 39 | 29.890 | 14.357 | 16.660 | 0.00 | 0.445 |
| 5 | 0 | 41 | 35.640 | 16.997 | 6.860 | 180.00 | 0.158 |
| 5 | 0 | 43 | 34.954 | 23.653 | 30.416 | 0.00 | 0.806 |
| 5 | 1 | 0 | 355.831 | 5.687 | 497.173 | 0.00 | 0.996 |
| 5 | 1 | 2 | 484.266 | 4.226 | 581.887 | 152.43 | 0.978 |
| 5 | 1 | 4 | 285.519 | 2.347 | 354.141 | 339.68 | 0.939 |
| 5 | 1 | 6 | 427.348 | 3.806 | 587.147 | 263.89 | 0.971 |
| 5 | 1 | 8 | 703.021 | 5.651 | 927.639 | 327.11 | 0.989 |
| 5 | 1 | 10 | 933.409 | 7.264 | 1227.264 | 187.78 | 0.998 |
| 5 | 1 | 12 | 489.876 | 4.367 | 722.921 | 161.24 | 0.994 |
| 5 | 1 | 14 | 354.792 | 3.487 | 529.727 | 9.96 | 0.987 |
| 5 | 1 | 16 | 230.699 | 2.522 | 308.219 | 80.11 | 0.971 |
| 5 | 1 | 18 | 175.940 | 2.575 | 295.785 | 172.98 | 0.944 |
| 5 | 1 | 20 | 71.442 | 4.338 | 52.325 | 15.80 | 0.708 |
| 5 | 1 | 22 | 225.573 | 2.723 | 336.180 | 123.31 | 0.969 |
| 5 | 1 | 24 | 217.222 | 2.943 | 340.833 | 22.87 | 0.963 |
| 5 | 1 | 26 | 604.813 | 5.501 | 783.199 | 53.87 | 0.997 |
| 5 | 1 | 28 | 258.795 | 3.109 | 361.669 | 203.74 | 0.983 |
| 5 | 1 | 30 | 130.468 | 4.802 | 151.320 | 355.66 | 0.936 |
| 5 | 1 | 32 | 369.654 | 3.914 | 377.428 | 277.57 | 0.993 |
| 5 | 1 | 34 | 344.356 | 4.502 | 473.087 | 46.94 | 0.992 |
| 5 | 1 | 36 | 140.189 | 6.329 | 117.970 | 313.00 | 0.976 |
| 5 | 1 | 38 | 133.057 | 6.197 | 159.134 | 111.23 | 0.963 |
| 5 | 1 | 40 | 99.238 | 9.046 | 95.084 | 177.91 | 0.938 |
| 5 | 1 | 42 | 36.874 | 11.913 | 4.794 | 217.09 | 0.479 |
| 5 | 2 | 1 | 271.440 | 2.950 | 420.978 | 47.86 | 0.983 |
| 5 | 2 | 3 | 405.120 | 3.180 | 608.460 | 262.57 | 0.961 |
| 5 | 2 | 5 | 848.613 | 7.885 | 1269.894 | 1.67 | 0.992 |
| 5 | 2 | 7 | 773.850 | 6.176 | 1075.945 | 99.10 | 0.990 |
| 5 | 2 | 9 | 509.930 | 4.496 | 652.000 | 68.50 | 0.979 |
| 5 | 2 | 11 | 384.448 | 3.165 | 529.089 | 218.41 | 0.993 |
| 5 | 2 | 13 | 493.021 | 4.540 | 784.559 | 211.67 | 0.993 |
| 5 | 2 | 15 | 214.961 | 2.304 | 330.579 | 88.59 | 0.960 |
| 5 | 2 | 17 | 162.219 | 2.460 | 255.704 | 238.82 | 0.954 |
| 5 | 2 | 19 | 169.700 | 2.701 | 223.758 | 27.66 | 0.986 |
| 5 | 2 | 21 | 384.821 | 3.313 | 514.139 | 254.59 | 0.991 |
| 5 | 2 | 23 | 126.030 | 3.366 | 173.697 | 47.05 | 0.941 |
| 5 | 2 | 25 | 481.948 | 4.266 | 704.131 | 115.39 | 0.995 |
| 5 | 2 | 27 | 326.799 | 3.396 | 405.291 | 355.18 | 0.991 |

| | | | | | | | |
|---|---|---|---|---|---|---|---|
| 5 | 2 | 29 | 175.637 | 3.656 | 232.522 | 85.41 | 0.963 |
| 5 | 2 | 31 | 350.259 | 3.696 | 446.083 | 283.06 | 0.991 |
| 5 | 2 | 33 | 78.866 | 9.587 | 58.252 | 326.55 | 0.597 |
| 5 | 2 | 35 | 125.765 | 6.679 | 176.174 | 302.22 | 0.932 |
| 5 | 2 | 37 | 103.210 | 8.711 | 103.739 | 347.06 | 0.947 |
| 5 | 2 | 39 | 148.005 | 5.329 | 211.645 | 321.19 | 0.964 |
| 5 | 2 | 41 | 56.419 | 13.843 | 39.150 | 198.79 | 0.507 |
| 5 | 2 | 43 | 66.087 | 19.177 | 66.814 | 208.89 | 0.832 |
| 5 | 3 | 0 | 144.147 | 1.744 | 142.277 | 0.00 | 0.704 |
| 5 | 3 | 2 | 1064.038 | 14.435 | 1501.690 | 282.20 | 0.995 |
| 5 | 3 | 4 | 259.058 | 2.256 | 337.543 | 238.41 | 0.941 |
| 5 | 3 | 6 | 926.599 | 9.893 | 1286.990 | 86.69 | 0.994 |
| 5 | 3 | 8 | 510.594 | 4.336 | 704.929 | 176.79 | 0.979 |
| 5 | 3 | 10 | 764.217 | 6.208 | 1020.253 | 107.23 | 0.998 |
| 5 | 3 | 12 | 248.617 | 2.789 | 351.307 | 114.36 | 0.974 |
| 5 | 3 | 14 | 746.990 | 7.155 | 1042.434 | 324.52 | 0.997 |
| 5 | 3 | 16 | 329.672 | 3.124 | 423.200 | 249.45 | 0.990 |
| 5 | 3 | 18 | 357.963 | 3.345 | 516.072 | 254.91 | 0.990 |
| 5 | 3 | 20 | 165.628 | 2.657 | 233.693 | 225.58 | 0.957 |
| 5 | 3 | 22 | 266.650 | 2.846 | 357.110 | 322.11 | 0.981 |
| 5 | 3 | 24 | 189.801 | 2.628 | 278.849 | 16.26 | 0.963 |
| 5 | 3 | 26 | 406.232 | 3.733 | 552.195 | 180.37 | 0.994 |
| 5 | 3 | 28 | 405.709 | 3.726 | 569.792 | 342.23 | 0.993 |
| 5 | 3 | 30 | 177.756 | 3.611 | 210.144 | 70.64 | 0.969 |
| 5 | 3 | 32 | 139.885 | 4.777 | 189.893 | 140.29 | 0.924 |
| 5 | 3 | 34 | 46.856 | 12.933 | 10.673 | 348.39 | 0.664 |
| 5 | 3 | 36 | 47.606 | 12.381 | 15.287 | 176.23 | 0.408 |
| 5 | 3 | 38 | 40.689 | 11.561 | 4.637 | 5.21 | 0.611 |
| 5 | 3 | 40 | 50.391 | 13.221 | 24.987 | 312.70 | 0.702 |
| 5 | 3 | 42 | 96.703 | 11.714 | 137.730 | 211.23 | 0.884 |
| 5 | 4 | 1 | 469.926 | 4.356 | 631.576 | 229.12 | 0.979 |
| 5 | 4 | 3 | 175.694 | 1.836 | 126.777 | 228.16 | 0.795 |
| 5 | 4 | 5 | 809.243 | 7.135 | 1147.308 | 209.12 | 0.992 |
| 5 | 4 | 7 | 1002.518 | 8.766 | 1469.502 | 335.77 | 0.994 |
| 5 | 4 | 9 | 645.241 | 5.297 | 899.145 | 308.06 | 0.997 |
| 5 | 4 | 11 | 222.374 | 2.168 | 300.083 | 155.37 | 0.992 |
| 5 | 4 | 13 | 472.157 | 4.057 | 643.855 | 62.84 | 0.994 |
| 5 | 4 | 15 | 251.232 | 2.838 | 378.040 | 240.98 | 0.973 |
| 5 | 4 | 17 | 378.657 | 3.697 | 494.644 | 359.18 | 0.994 |
| 5 | 4 | 19 | 131.742 | 2.621 | 176.384 | 50.43 | 0.974 |
| 5 | 4 | 21 | 129.586 | 2.867 | 172.176 | 168.04 | 0.616 |
| 5 | 4 | 23 | 205.242 | 2.862 | 221.254 | 302.31 | 0.978 |
| 5 | 4 | 25 | 406.052 | 3.611 | 586.396 | 154.85 | 0.994 |
| 5 | 4 | 27 | 68.942 | 6.519 | 30.543 | 179.80 | 0.340 |
| 5 | 4 | 29 | 398.928 | 3.757 | 513.933 | 329.96 | 0.994 |
| 5 | 4 | 31 | 203.105 | 3.720 | 237.802 | 209.17 | 0.979 |
| 5 | 4 | 33 | 133.945 | 6.492 | 166.620 | 15.80 | 0.950 |
| 5 | 4 | 35 | 188.678 | 5.287 | 194.817 | 178.46 | 0.980 |
| 5 | 4 | 37 | 194.175 | 5.861 | 280.314 | 254.26 | 0.979 |
| 5 | 4 | 39 | 77.362 | 11.060 | 95.910 | 129.95 | 0.741 |
| 5 | 4 | 41 | 54.235 | 13.736 | 35.337 | 19.10 | 0.495 |
| 5 | 4 | 43 | 42.471 | 21.409 | 6.239 | 310.40 | 0.372 |
| 5 | 5 | 0 | 1101.789 | 14.614 | 1544.784 | 180.00 | 1.000 |
| 5 | 5 | 2 | 442.476 | 3.629 | 602.718 | 258.79 | 0.976 |
| 5 | 5 | 4 | 891.826 | 9.660 | 1306.597 | 17.12 | 0.993 |
| 5 | 5 | 6 | 918.307 | 7.555 | 1312.329 | 51.53 | 0.993 |
| 5 | 5 | 8 | 314.179 | 2.950 | 441.538 | 62.50 | 0.986 |
| 5 | 5 | 10 | 572.634 | 6.049 | 804.482 | 93.20 | 0.996 |
| 5 | 5 | 12 | 111.034 | 2.846 | 162.351 | 337.00 | 0.971 |
| 5 | 5 | 14 | 287.869 | 2.751 | 361.269 | 159.62 | 0.987 |
| 5 | 5 | 16 | 216.436 | 2.519 | 302.694 | 322.00 | 0.976 |
| 5 | 5 | 18 | 259.800 | 2.831 | 358.978 | 22.47 | 0.987 |
| 5 | 5 | 20 | 105.619 | 3.307 | 123.009 | 273.62 | 0.879 |
| 5 | 5 | 22 | 266.620 | 2.776 | 434.389 | 247.33 | 0.973 |
| 5 | 5 | 24 | 303.957 | 3.124 | 440.542 | 177.24 | 0.989 |
| 5 | 5 | 26 | 207.815 | 3.141 | 250.644 | 141.98 | 0.980 |
| 5 | 5 | 28 | 454.702 | 4.162 | 597.473 | 127.89 | 0.995 |
| 5 | 5 | 30 | 204.395 | 3.590 | 300.514 | 306.82 | 0.965 |
| 5 | 5 | 32 | 165.535 | 4.643 | 228.774 | 176.30 | 0.949 |
| 5 | 5 | 34 | 97.862 | 8.306 | 112.575 | 170.61 | 0.896 |
| 5 | 5 | 36 | 211.794 | 4.482 | 255.406 | 236.00 | 0.986 |
| 5 | 5 | 38 | 67.348 | 11.156 | 53.896 | 337.92 | 0.536 |
| 5 | 5 | 40 | 63.590 | 11.928 | 55.891 | 293.73 | 0.815 |
| 5 | 5 | 42 | 49.261 | 16.683 | 32.488 | 318.81 | 0.776 |
| 5 | 6 | 1 | 246.460 | 2.484 | 302.204 | 295.02 | 0.947 |
| 5 | 6 | 3 | 1084.752 | 11.805 | 1493.153 | 110.49 | 0.995 |
| 5 | 6 | 5 | 215.153 | 2.103 | 297.825 | 190.64 | 0.987 |

| | | | | | | | |
|---|---|---|---|---|---|---|---|
| 5 | 6 | 7 | 393.954 | 3.754 | 549.693 | 119.66 | 0.992 |
| 5 | 6 | 9 | 544.864 | 5.183 | 818.313 | 179.86 | 0.995 |
| 5 | 6 | 11 | 359.767 | 3.223 | 486.022 | 179.85 | 0.992 |
| 5 | 6 | 13 | 139.212 | 2.397 | 205.421 | 334.33 | 0.967 |
| 5 | 6 | 15 | 292.930 | 3.158 | 436.292 | 249.09 | 0.985 |
| 5 | 6 | 17 | 222.424 | 2.641 | 303.725 | 248.13 | 0.979 |
| 5 | 6 | 19 | 507.713 | 4.718 | 689.431 | 125.76 | 0.996 |
| 5 | 6 | 21 | 109.547 | 3.482 | 146.256 | 272.51 | 0.792 |
| 5 | 6 | 23 | 298.734 | 3.255 | 388.123 | 179.77 | 0.987 |
| 5 | 6 | 25 | 551.643 | 5.768 | 798.769 | 198.07 | 0.996 |
| 5 | 6 | 27 | 394.193 | 3.592 | 519.155 | 113.48 | 0.993 |
| 5 | 6 | 29 | 74.587 | 7.687 | 66.284 | 129.65 | 0.854 |
| 5 | 6 | 31 | 104.767 | 5.901 | 106.100 | 166.88 | 0.901 |
| 5 | 6 | 33 | 140.428 | 6.793 | 172.143 | 55.77 | 0.955 |
| 5 | 6 | 35 | 93.153 | 9.427 | 94.854 | 288.23 | 0.928 |
| 5 | 6 | 37 | 117.387 | 8.310 | 102.033 | 232.32 | 0.963 |
| 5 | 6 | 39 | 29.763 | 9.802 | 19.011 | 336.13 | 0.335 |
| 5 | 6 | 41 | 61.114 | 13.975 | 53.770 | 198.94 | 0.701 |
| 5 | 6 | 43 | 58.388 | 26.085 | 26.925 | 144.64 | 0.588 |
| 5 | 7 | 0 | 37.666 | 6.274 | 4.070 | 180.00 | 0.086 |
| 5 | 7 | 2 | 726.840 | 6.088 | 1025.134 | 346.66 | 0.990 |
| 5 | 7 | 4 | 652.855 | 5.730 | 876.344 | 175.31 | 0.988 |
| 5 | 7 | 6 | 470.344 | 6.370 | 705.630 | 216.81 | 0.993 |
| 5 | 7 | 8 | 534.865 | 5.017 | 736.537 | 292.00 | 0.996 |
| 5 | 7 | 10 | 739.023 | 5.932 | 1005.443 | 320.12 | 0.997 |
| 5 | 7 | 12 | 489.948 | 4.598 | 633.260 | 50.38 | 0.995 |
| 5 | 7 | 14 | 302.865 | 2.812 | 391.221 | 312.42 | 0.989 |
| 5 | 7 | 16 | 321.124 | 3.112 | 421.516 | 129.59 | 0.989 |
| 5 | 7 | 18 | 291.046 | 2.834 | 409.986 | 82.30 | 0.985 |
| 5 | 7 | 20 | 375.440 | 4.179 | 553.094 | 127.79 | 0.990 |
| 5 | 7 | 22 | 117.959 | 3.669 | 158.481 | 256.66 | 0.756 |
| 5 | 7 | 24 | 190.646 | 3.084 | 220.513 | 95.92 | 0.979 |
| 5 | 7 | 26 | 100.712 | 4.962 | 105.398 | 233.01 | 0.915 |
| 5 | 7 | 28 | 203.734 | 3.447 | 176.293 | 35.73 | 0.981 |
| 5 | 7 | 30 | 170.108 | 4.142 | 206.063 | 305.09 | 0.965 |
| 5 | 7 | 32 | 55.018 | 13.865 | 3.664 | 229.20 | 0.563 |
| 5 | 7 | 34 | 178.067 | 5.882 | 200.773 | 47.18 | 0.975 |
| 5 | 7 | 36 | 80.172 | 12.920 | 94.728 | 329.43 | 0.873 |
| 5 | 7 | 38 | 48.150 | 13.781 | 14.346 | 109.63 | 0.474 |
| 5 | 7 | 40 | 54.228 | 11.018 | 34.125 | 44.82 | 0.742 |
| 5 | 7 | 42 | 38.401 | 12.836 | 9.938 | 163.38 | 0.720 |
| 5 | 8 | 1 | 439.833 | 5.033 | 629.251 | 355.13 | 0.993 |
| 5 | 8 | 3 | 911.068 | 7.048 | 1294.978 | 302.86 | 0.998 |
| 5 | 8 | 5 | 511.674 | 5.181 | 776.381 | 359.40 | 0.994 |
| 5 | 8 | 7 | 87.784 | 2.859 | 133.814 | 116.00 | 0.781 |
| 5 | 8 | 9 | 153.189 | 2.108 | 220.090 | 327.27 | 0.780 |
| 5 | 8 | 11 | 247.595 | 2.628 | 351.825 | 284.05 | 0.974 |
| 5 | 8 | 13 | 313.277 | 2.960 | 416.502 | 68.86 | 0.988 |
| 5 | 8 | 15 | 314.330 | 3.036 | 375.137 | 76.32 | 0.990 |
| 5 | 8 | 17 | 247.192 | 2.803 | 352.839 | 114.45 | 0.979 |
| 5 | 8 | 19 | 614.400 | 5.629 | 937.212 | 67.58 | 0.996 |
| 5 | 8 | 21 | 375.207 | 3.406 | 457.479 | 343.95 | 0.992 |
| 5 | 8 | 23 | 397.870 | 3.532 | 631.814 | 0.56 | 0.992 |
| 5 | 8 | 25 | 189.091 | 3.593 | 263.996 | 146.84 | 0.971 |
| 5 | 8 | 27 | 106.229 | 6.508 | 121.853 | 248.26 | 0.899 |
| 5 | 8 | 29 | 156.749 | 3.810 | 155.697 | 68.50 | 0.961 |
| 5 | 8 | 31 | 118.167 | 5.802 | 163.644 | 152.93 | 0.738 |
| 5 | 8 | 33 | 269.245 | 4.645 | 363.917 | 80.19 | 0.988 |
| 5 | 8 | 35 | 81.416 | 12.016 | 108.922 | 116.71 | 0.782 |
| 5 | 8 | 37 | 135.642 | 5.873 | 176.343 | 78.30 | 0.963 |
| 5 | 8 | 39 | 65.267 | 12.227 | 46.515 | 209.27 | 0.874 |
| 5 | 8 | 41 | 74.209 | 14.187 | 76.007 | 10.39 | 0.924 |
| 5 | 9 | 0 | 272.678 | 3.954 | 381.593 | 180.00 | 1.000 |
| 5 | 9 | 2 | 826.894 | 7.621 | 1192.163 | 192.16 | 0.998 |
| 5 | 9 | 4 | 192.149 | 2.108 | 304.735 | 98.68 | 0.976 |
| 5 | 9 | 6 | 724.872 | 6.757 | 989.625 | 279.44 | 0.997 |
| 5 | 9 | 8 | 591.599 | 5.314 | 860.079 | 335.72 | 0.996 |
| 5 | 9 | 10 | 153.726 | 2.091 | 168.826 | 346.84 | 0.977 |
| 5 | 9 | 12 | 217.734 | 2.490 | 289.070 | 189.29 | 0.992 |
| 5 | 9 | 14 | 102.690 | 2.635 | 130.602 | 315.66 | 0.808 |
| 5 | 9 | 16 | 320.519 | 2.987 | 442.399 | 212.41 | 0.989 |
| 5 | 9 | 18 | 160.628 | 2.686 | 170.248 | 305.32 | 0.982 |
| 5 | 9 | 20 | 31.738 | 8.190 | 32.348 | 246.19 | 0.458 |
| 5 | 9 | 22 | 342.509 | 3.253 | 452.003 | 318.16 | 0.992 |
| 5 | 9 | 24 | 350.620 | 3.331 | 575.666 | 354.51 | 0.989 |
| 5 | 9 | 26 | 196.853 | 3.478 | 256.436 | 358.46 | 0.977 |
| 5 | 9 | 28 | 173.728 | 3.882 | 264.438 | 166.40 | 0.955 |

| | | | | | | | |
|---|---|---|---|---|---|---|---|
| 5 | 9 | 30 | 71.009 | 8.629 | 65.975 | 79.04 | 0.674 |
| 5 | 9 | 32 | 168.924 | 4.209 | 227.830 | 154.27 | 0.970 |
| 5 | 9 | 34 | 53.724 | 12.880 | 34.947 | 154.69 | 0.609 |
| 5 | 9 | 36 | 48.623 | 13.663 | 20.314 | 45.90 | 0.470 |
| 5 | 9 | 38 | 98.595 | 8.670 | 110.205 | 164.95 | 0.932 |
| 5 | 9 | 40 | 51.335 | 14.309 | 26.496 | 236.48 | 0.647 |
| 5 | 9 | 42 | 97.905 | 24.478 | 100.164 | 30.34 | 0.924 |
| 5 | 10 | 1 | 286.819 | 2.561 | 310.769 | 76.80 | 0.988 |
| 5 | 10 | 3 | 231.038 | 2.284 | 345.483 | 214.78 | 0.970 |
| 5 | 10 | 5 | 514.810 | 4.822 | 820.696 | 138.12 | 0.994 |
| 5 | 10 | 7 | 293.532 | 2.901 | 414.108 | 359.82 | 0.985 |
| 5 | 10 | 9 | 275.012 | 2.881 | 379.631 | 25.37 | 0.981 |
| 5 | 10 | 11 | 279.589 | 2.659 | 325.048 | 267.84 | 0.989 |
| 5 | 10 | 13 | 362.632 | 3.279 | 480.411 | 337.01 | 0.992 |
| 5 | 10 | 15 | 123.341 | 2.585 | 145.443 | 88.27 | 0.930 |
| 5 | 10 | 17 | 321.600 | 3.056 | 388.730 | 302.89 | 0.990 |
| 5 | 10 | 19 | 353.160 | 3.261 | 479.451 | 220.45 | 0.990 |
| 5 | 10 | 21 | 388.115 | 3.566 | 510.026 | 160.94 | 0.994 |
| 5 | 10 | 23 | 183.388 | 2.999 | 277.706 | 3.79 | 0.965 |
| 5 | 10 | 25 | 107.300 | 4.787 | 103.776 | 345.50 | 0.926 |
| 5 | 10 | 27 | 216.748 | 3.454 | 279.859 | 146.22 | 0.977 |
| 5 | 10 | 29 | 129.409 | 4.809 | 166.776 | 226.65 | 0.922 |
| 5 | 10 | 31 | 101.452 | 6.981 | 63.406 | 291.73 | 0.943 |
| 5 | 10 | 33 | 240.537 | 3.883 | 298.951 | 185.02 | 0.986 |
| 5 | 10 | 35 | 231.092 | 4.338 | 293.707 | 33.75 | 0.988 |
| 5 | 10 | 37 | 41.292 | 11.332 | 3.797 | 220.87 | 0.455 |
| 5 | 10 | 39 | 44.431 | 12.524 | 14.077 | 19.08 | 0.462 |
| 5 | 10 | 41 | 44.878 | 14.293 | 20.209 | 150.72 | 0.359 |
| 5 | 11 | 0 | 1203.648 | 12.645 | 1685.933 | 0.00 | 1.000 |
| 5 | 11 | 2 | 288.612 | 3.041 | 388.585 | 335.65 | 0.988 |
| 5 | 11 | 4 | 176.482 | 2.062 | 216.337 | 29.16 | 0.973 |
| 5 | 11 | 6 | 404.311 | 3.742 | 530.238 | 226.45 | 0.993 |
| 5 | 11 | 8 | 229.341 | 2.382 | 314.453 | 188.62 | 0.985 |
| 5 | 11 | 10 | 203.956 | 2.402 | 265.461 | 60.80 | 0.975 |
| 5 | 11 | 12 | 223.584 | 2.419 | 351.449 | 166.23 | 0.991 |
| 5 | 11 | 14 | 229.928 | 2.573 | 335.666 | 176.77 | 0.984 |
| 5 | 11 | 16 | 331.997 | 3.035 | 660.166 | 319.31 | 0.948 |
| 5 | 11 | 18 | 456.427 | 4.352 | 619.038 | 140.15 | 0.994 |
| 5 | 11 | 20 | 127.079 | 3.269 | 157.846 | 93.75 | 0.912 |
| 5 | 11 | 22 | 127.681 | 3.724 | 210.217 | 232.64 | 0.858 |
| 5 | 11 | 24 | 358.982 | 3.343 | 512.136 | 6.93 | 0.993 |
| 5 | 11 | 26 | 77.230 | 6.241 | 71.489 | 0.76 | 0.607 |
| 5 | 11 | 28 | 205.641 | 3.315 | 306.065 | 231.05 | 0.966 |
| 5 | 11 | 30 | 192.125 | 3.984 | 255.003 | 279.57 | 0.969 |
| 5 | 11 | 32 | 136.233 | 6.560 | 142.532 | 305.00 | 0.963 |
| 5 | 11 | 34 | 54.992 | 12.565 | 36.812 | 75.48 | 0.709 |
| 5 | 11 | 36 | 76.903 | 10.982 | 31.118 | 325.96 | 0.927 |
| 5 | 11 | 38 | 42.125 | 11.622 | 8.768 | 311.21 | 0.210 |
| 5 | 11 | 40 | 63.328 | 14.928 | 73.472 | 275.88 | 0.759 |
| 5 | 12 | 1 | 211.757 | 2.326 | 327.877 | 115.21 | 0.962 |
| 5 | 12 | 3 | 482.053 | 4.314 | 706.226 | 214.05 | 0.994 |
| 5 | 12 | 5 | 747.706 | 6.674 | 1029.984 | 240.20 | 0.998 |
| 5 | 12 | 7 | 406.107 | 3.838 | 535.849 | 336.84 | 0.994 |
| 5 | 12 | 9 | 209.558 | 2.465 | 261.957 | 121.90 | 0.976 |
| 5 | 12 | 11 | 149.560 | 2.380 | 181.960 | 298.09 | 0.960 |
| 5 | 12 | 13 | 253.595 | 2.581 | 335.128 | 248.52 | 0.983 |
| 5 | 12 | 15 | 562.172 | 4.823 | 848.751 | 82.88 | 0.996 |
| 5 | 12 | 17 | 273.110 | 2.828 | 332.490 | 287.44 | 0.984 |
| 5 | 12 | 19 | 117.587 | 3.782 | 94.350 | 214.93 | 0.926 |
| 5 | 12 | 21 | 360.836 | 3.396 | 450.083 | 274.00 | 0.993 |
| 5 | 12 | 23 | 44.341 | 9.003 | 61.017 | 140.19 | 0.749 |
| 5 | 12 | 25 | 508.793 | 4.439 | 655.697 | 28.12 | 0.996 |
| 5 | 12 | 27 | 52.951 | 9.954 | 2.575 | 217.66 | 0.552 |
| 5 | 12 | 29 | 94.616 | 8.898 | 35.816 | 175.23 | 0.911 |
| 5 | 12 | 31 | 328.759 | 3.935 | 420.666 | 83.95 | 0.992 |
| 5 | 12 | 33 | 297.584 | 3.866 | 356.785 | 326.97 | 0.994 |
| 5 | 12 | 35 | 64.711 | 11.481 | 57.225 | 146.46 | 0.812 |
| 5 | 12 | 37 | 123.821 | 6.611 | 199.164 | 10.68 | 0.928 |
| 5 | 12 | 39 | 99.824 | 10.308 | 124.604 | 266.88 | 0.929 |
| 5 | 12 | 41 | 59.896 | 23.886 | 30.148 | 5.82 | 0.774 |
| 5 | 13 | 0 | 210.711 | 3.029 | 294.296 | 0.00 | 1.000 |
| 5 | 13 | 2 | 67.486 | 9.074 | 24.752 | 131.53 | 0.245 |
| 5 | 13 | 4 | 323.557 | 2.944 | 462.837 | 132.01 | 0.989 |
| 5 | 13 | 6 | 230.483 | 2.806 | 318.246 | 3.03 | 0.992 |
| 5 | 13 | 8 | 200.936 | 2.291 | 295.759 | 238.23 | 0.973 |
| 5 | 13 | 10 | 155.131 | 2.707 | 205.253 | 43.74 | 0.954 |
| 5 | 13 | 12 | 294.587 | 2.891 | 441.388 | 265.42 | 0.978 |

| | | | | | | | |
|---|---|---|---|---|---|---|---|
| 5 | 13 | 14 | 133.782 | 3.011 | 147.640 | 266.45 | 0.954 |
| 5 | 13 | 16 | 303.403 | 2.989 | 531.529 | 240.20 | 0.963 |
| 5 | 13 | 18 | 183.855 | 2.981 | 238.862 | 296.00 | 0.974 |
| 5 | 13 | 20 | 644.671 | 6.214 | 890.945 | 176.59 | 0.998 |
| 5 | 13 | 22 | 257.237 | 3.005 | 359.690 | 160.93 | 0.984 |
| 5 | 13 | 24 | 119.217 | 4.318 | 135.165 | 78.43 | 0.934 |
| 5 | 13 | 26 | 258.758 | 3.330 | 329.559 | 169.04 | 0.985 |
| 5 | 13 | 28 | 315.321 | 3.768 | 422.658 | 106.05 | 0.988 |
| 5 | 13 | 30 | 40.009 | 11.118 | 14.489 | 291.61 | 0.409 |
| 5 | 13 | 32 | 72.193 | 10.107 | 21.686 | 136.02 | 0.927 |
| 5 | 13 | 34 | 106.008 | 7.064 | 76.396 | 142.90 | 0.959 |
| 5 | 13 | 36 | 50.882 | 13.046 | 9.426 | 2.32 | 0.238 |
| 5 | 13 | 38 | 52.253 | 13.077 | 28.319 | 176.38 | 0.777 |
| 5 | 13 | 40 | 41.873 | 20.616 | 1.594 | 236.46 | 0.163 |
| 5 | 14 | 1 | 276.285 | 3.060 | 343.201 | 7.66 | 0.987 |
| 5 | 14 | 3 | 176.322 | 3.557 | 243.398 | 332.05 | 0.959 |
| 5 | 14 | 5 | 250.944 | 2.499 | 372.061 | 314.07 | 0.981 |
| 5 | 14 | 7 | 202.290 | 2.429 | 307.938 | 24.42 | 0.968 |
| 5 | 14 | 9 | 215.025 | 2.716 | 325.366 | 37.33 | 0.971 |
| 5 | 14 | 11 | 104.767 | 3.432 | 56.199 | 230.05 | 0.919 |
| 5 | 14 | 13 | 258.128 | 2.817 | 414.968 | 328.16 | 0.976 |
| 5 | 14 | 15 | 344.173 | 3.111 | 472.802 | 185.55 | 0.989 |
| 5 | 14 | 17 | 74.938 | 5.720 | 71.385 | 173.98 | 0.743 |
| 5 | 14 | 19 | 265.186 | 2.904 | 385.771 | 32.64 | 0.985 |
| 5 | 14 | 21 | 165.735 | 3.489 | 227.562 | 183.47 | 0.960 |
| 5 | 14 | 23 | 465.119 | 4.382 | 663.143 | 264.86 | 0.995 |
| 5 | 14 | 25 | 175.472 | 3.834 | 216.467 | 119.45 | 0.962 |
| 5 | 14 | 27 | 72.529 | 9.368 | 51.687 | 261.12 | 0.689 |
| 5 | 14 | 29 | 107.387 | 7.523 | 168.775 | 19.29 | 0.850 |
| 5 | 14 | 31 | 141.115 | 6.097 | 159.899 | 251.19 | 0.972 |
| 5 | 14 | 33 | 94.468 | 8.226 | 112.057 | 308.45 | 0.922 |
| 5 | 14 | 35 | 84.979 | 8.538 | 45.090 | 189.00 | 0.940 |
| 5 | 14 | 37 | 60.781 | 12.817 | 44.377 | 248.92 | 0.828 |
| 5 | 14 | 39 | 56.688 | 16.360 | 50.591 | 149.80 | 0.632 |
| 5 | 15 | 0 | 176.132 | 3.270 | 245.786 | 0.00 | 1.000 |
| 5 | 15 | 2 | 130.320 | 2.798 | 177.268 | 351.00 | 0.964 |
| 5 | 15 | 4 | 453.412 | 3.943 | 674.708 | 283.79 | 0.994 |
| 5 | 15 | 6 | 136.547 | 2.636 | 185.200 | 140.92 | 0.983 |
| 5 | 15 | 8 | 153.896 | 2.549 | 251.049 | 214.73 | 0.961 |
| 5 | 15 | 10 | 237.172 | 2.800 | 333.936 | 301.49 | 0.981 |
| 5 | 15 | 12 | 144.125 | 2.983 | 188.512 | 177.04 | 0.982 |
| 5 | 15 | 14 | 164.708 | 3.277 | 271.079 | 358.09 | 0.953 |
| 5 | 15 | 16 | 372.139 | 3.671 | 468.387 | 199.22 | 0.994 |
| 5 | 15 | 18 | 418.237 | 3.781 | 607.502 | 328.11 | 0.994 |
| 5 | 15 | 20 | 458.052 | 4.081 | 602.484 | 305.69 | 0.995 |
| 5 | 15 | 22 | 172.716 | 3.900 | 214.481 | 288.33 | 0.969 |
| 5 | 15 | 24 | 205.233 | 3.555 | 286.167 | 196.20 | 0.978 |
| 5 | 15 | 26 | 315.894 | 3.702 | 471.508 | 210.61 | 0.986 |
| 5 | 15 | 28 | 123.039 | 8.979 | 141.591 | 127.46 | 0.947 |
| 5 | 15 | 30 | 184.403 | 4.156 | 255.026 | 105.42 | 0.981 |
| 5 | 15 | 32 | 154.090 | 5.311 | 199.620 | 321.06 | 0.974 |
| 5 | 15 | 34 | 157.423 | 5.385 | 178.097 | 9.83 | 0.977 |
| 5 | 15 | 36 | 52.490 | 12.275 | 43.288 | 301.55 | 0.704 |
| 5 | 15 | 38 | 47.238 | 13.709 | 37.352 | 14.84 | 0.749 |
| 5 | 16 | 1 | 252.560 | 2.548 | 332.038 | 193.70 | 0.985 |
| 5 | 16 | 3 | 195.112 | 2.898 | 232.131 | 248.64 | 0.970 |
| 5 | 16 | 5 | 53.973 | 5.278 | 8.554 | 96.19 | 0.619 |
| 5 | 16 | 7 | 263.070 | 2.786 | 303.596 | 102.33 | 0.985 |
| 5 | 16 | 9 | 246.497 | 2.684 | 295.797 | 44.07 | 0.981 |
| 5 | 16 | 11 | 462.083 | 4.459 | 625.502 | 98.50 | 0.994 |
| 5 | 16 | 13 | 223.422 | 2.880 | 304.824 | 154.94 | 0.974 |
| 5 | 16 | 15 | 271.437 | 3.315 | 401.158 | 161.75 | 0.985 |
| 5 | 16 | 17 | 97.738 | 5.674 | 56.369 | 345.23 | 0.929 |
| 5 | 16 | 19 | 54.635 | 9.168 | 23.723 | 227.25 | 0.798 |
| 5 | 16 | 21 | 121.359 | 4.636 | 193.787 | 221.74 | 0.868 |
| 5 | 16 | 23 | 201.814 | 3.735 | 274.701 | 7.93 | 0.971 |
| 5 | 16 | 25 | 84.711 | 8.371 | 82.670 | 217.54 | 0.795 |
| 5 | 16 | 27 | 50.255 | 11.803 | 10.366 | 295.98 | 0.604 |
| 5 | 16 | 29 | 333.011 | 4.152 | 456.900 | 171.62 | 0.992 |
| 5 | 16 | 31 | 50.615 | 12.770 | 24.302 | 166.30 | 0.396 |
| 5 | 16 | 33 | 53.455 | 12.949 | 29.395 | 192.85 | 0.731 |
| 5 | 16 | 35 | 36.575 | 11.497 | 22.256 | 74.66 | 0.727 |
| 5 | 16 | 37 | 78.171 | 13.752 | 112.749 | 142.08 | 0.832 |
| 5 | 16 | 39 | 47.775 | 22.782 | 9.585 | 5.75 | 0.560 |
| 5 | 17 | 0 | 139.666 | 4.091 | 194.270 | 180.00 | 0.997 |
| 5 | 17 | 2 | 133.720 | 2.708 | 180.306 | 26.57 | 0.951 |
| 5 | 17 | 4 | 242.371 | 2.896 | 248.918 | 153.73 | 0.986 |

| | | | | | | | |
|---|---|---|---|---|---|---|---|
| 5 | 17 | 6 | 208.725 | 2.863 | 300.689 | 346.78 | 0.984 |
| 5 | 17 | 8 | 565.931 | 4.711 | 788.785 | 121.25 | 0.996 |
| 5 | 17 | 10 | 261.206 | 2.730 | 392.577 | 67.76 | 0.979 |
| 5 | 17 | 12 | 185.544 | 3.217 | 269.307 | 91.30 | 0.973 |
| 5 | 17 | 14 | 434.446 | 3.786 | 575.057 | 62.63 | 0.995 |
| 5 | 17 | 16 | 307.833 | 3.340 | 377.945 | 52.91 | 0.991 |
| 5 | 17 | 18 | 202.983 | 3.352 | 313.331 | 36.61 | 0.976 |
| 5 | 17 | 20 | 471.626 | 4.166 | 642.335 | 23.24 | 0.996 |
| 5 | 17 | 22 | 151.574 | 4.462 | 119.633 | 37.10 | 0.968 |
| 5 | 17 | 24 | 180.937 | 4.482 | 187.697 | 79.06 | 0.974 |
| 5 | 17 | 26 | 42.320 | 12.084 | 21.947 | 272.37 | 0.573 |
| 5 | 17 | 28 | 117.401 | 6.574 | 166.631 | 115.96 | 0.915 |
| 5 | 17 | 30 | 53.553 | 12.533 | 31.724 | 117.83 | 0.796 |
| 5 | 17 | 32 | 57.059 | 10.823 | 44.615 | 310.40 | 0.742 |
| 5 | 17 | 34 | 76.775 | 10.242 | 86.760 | 127.64 | 0.891 |
| 5 | 17 | 36 | 61.601 | 15.075 | 65.465 | 149.34 | 0.873 |
| 5 | 17 | 38 | 47.027 | 21.869 | 3.335 | 201.76 | 0.761 |
| 5 | 18 | 1 | 186.099 | 2.610 | 283.471 | 15.27 | 0.972 |
| 5 | 18 | 3 | 284.505 | 3.578 | 471.672 | 45.19 | 0.980 |
| 5 | 18 | 5 | 92.835 | 4.938 | 113.450 | 332.21 | 0.890 |
| 5 | 18 | 7 | 386.319 | 3.628 | 613.306 | 144.17 | 0.990 |
| 5 | 18 | 9 | 80.517 | 4.500 | 95.660 | 296.39 | 0.791 |
| 5 | 18 | 11 | 184.729 | 3.064 | 207.245 | 178.05 | 0.980 |
| 5 | 18 | 13 | 328.321 | 3.386 | 431.598 | 207.85 | 0.992 |
| 5 | 18 | 15 | 173.145 | 3.070 | 261.588 | 255.03 | 0.961 |
| 5 | 18 | 17 | 288.676 | 3.094 | 393.253 | 302.70 | 0.988 |
| 5 | 18 | 19 | 84.600 | 5.739 | 17.959 | 74.99 | 0.926 |
| 5 | 18 | 21 | 237.017 | 3.571 | 288.507 | 163.59 | 0.981 |
| 5 | 18 | 23 | 246.616 | 4.236 | 232.028 | 139.11 | 0.986 |
| 5 | 18 | 25 | 302.452 | 4.636 | 409.888 | 102.69 | 0.991 |
| 5 | 18 | 27 | 41.938 | 12.223 | 1.256 | 237.15 | 0.179 |
| 5 | 18 | 29 | 60.980 | 11.453 | 6.283 | 108.72 | 0.895 |
| 5 | 18 | 31 | 115.080 | 6.321 | 125.094 | 319.09 | 0.963 |
| 5 | 18 | 33 | 254.683 | 3.910 | 318.847 | 54.09 | 0.992 |
| 5 | 18 | 35 | 40.003 | 12.569 | 5.488 | 183.62 | 0.649 |
| 5 | 18 | 37 | 46.787 | 20.974 | 3.496 | 226.68 | 0.080 |
| 5 | 19 | 0 | 311.393 | 4.230 | 435.556 | 180.00 | 1.000 |
| 5 | 19 | 2 | 572.015 | 4.611 | 804.343 | 172.61 | 0.997 |
| 5 | 19 | 4 | 194.511 | 2.896 | 270.916 | 322.59 | 0.976 |
| 5 | 19 | 6 | 33.076 | 8.681 | 56.788 | 296.77 | 0.590 |
| 5 | 19 | 8 | 330.395 | 3.283 | 401.803 | 242.64 | 0.993 |
| 5 | 19 | 10 | 527.551 | 4.449 | 782.456 | 102.16 | 0.996 |
| 5 | 19 | 12 | 562.450 | 4.660 | 821.624 | 195.91 | 0.997 |
| 5 | 19 | 14 | 231.671 | 3.200 | 351.891 | 169.52 | 0.979 |
| 5 | 19 | 16 | 254.749 | 3.133 | 310.040 | 339.76 | 0.987 |
| 5 | 19 | 18 | 412.994 | 3.910 | 616.735 | 206.46 | 0.993 |
| 5 | 19 | 20 | 87.484 | 6.078 | 79.278 | 308.82 | 0.864 |
| 5 | 19 | 22 | 130.781 | 6.409 | 204.360 | 72.71 | 0.885 |
| 5 | 19 | 24 | 359.009 | 4.149 | 514.312 | 337.22 | 0.993 |
| 5 | 19 | 26 | 64.790 | 12.712 | 50.432 | 322.23 | 0.861 |
| 5 | 19 | 28 | 81.097 | 9.694 | 65.816 | 285.12 | 0.920 |
| 5 | 19 | 30 | 242.945 | 4.349 | 340.570 | 273.91 | 0.989 |
| 5 | 19 | 32 | 161.670 | 6.841 | 172.122 | 128.30 | 0.983 |
| 5 | 19 | 34 | 38.515 | 12.171 | 20.487 | 75.00 | 0.745 |
| 5 | 19 | 36 | 61.708 | 13.741 | 67.658 | 342.62 | 0.852 |
| 5 | 20 | 1 | 556.345 | 4.433 | 808.474 | 204.98 | 0.997 |
| 5 | 20 | 3 | 213.682 | 3.171 | 351.013 | 169.73 | 0.973 |
| 5 | 20 | 5 | 82.590 | 5.446 | 90.018 | 278.97 | 0.684 |
| 5 | 20 | 7 | 374.600 | 3.331 | 507.786 | 231.37 | 0.993 |
| 5 | 20 | 9 | 506.724 | 4.185 | 780.852 | 104.41 | 0.996 |
| 5 | 20 | 11 | 130.039 | 3.837 | 145.788 | 238.98 | 0.940 |
| 5 | 20 | 13 | 91.121 | 5.828 | 112.693 | 285.36 | 0.806 |
| 5 | 20 | 15 | 105.446 | 5.230 | 104.520 | 167.11 | 0.915 |
| 5 | 20 | 17 | 131.003 | 4.230 | 213.338 | 213.83 | 0.833 |
| 5 | 20 | 19 | 150.655 | 4.217 | 219.932 | 181.22 | 0.947 |
| 5 | 20 | 21 | 187.092 | 6.166 | 338.348 | 27.16 | 0.962 |
| 5 | 20 | 23 | 274.856 | 5.202 | 399.687 | 326.46 | 0.988 |
| 5 | 20 | 25 | 171.394 | 5.356 | 208.624 | 93.91 | 0.982 |
| 5 | 20 | 27 | 52.905 | 12.816 | 27.494 | 347.16 | 0.392 |
| 5 | 20 | 29 | 154.580 | 7.134 | 226.440 | 191.53 | 0.970 |
| 5 | 20 | 31 | 79.662 | 10.557 | 94.805 | 226.40 | 0.902 |
| 5 | 20 | 33 | 80.808 | 17.779 | 82.454 | 222.88 | 0.884 |
| 5 | 20 | 35 | 84.749 | 18.200 | 103.670 | 329.62 | 0.667 |
| 5 | 21 | 0 | 668.944 | 7.977 | 934.994 | 0.00 | 1.000 |
| 5 | 21 | 2 | 323.135 | 3.148 | 397.442 | 338.25 | 0.992 |
| 5 | 21 | 4 | 216.858 | 2.945 | 327.647 | 1.26 | 0.976 |
| 5 | 21 | 6 | 496.766 | 4.399 | 674.365 | 323.94 | 0.996 |

| | | | | | | | |
|---|---|---|---|---|---|---|---|
| 5 | 21 | 8 | 156.372 | 4.373 | 240.614 | 109.89 | 0.950 |
| 5 | 21 | 10 | 60.314 | 8.163 | 8.446 | 315.90 | 0.781 |
| 5 | 21 | 12 | 157.738 | 3.633 | 200.406 | 81.74 | 0.719 |
| 5 | 21 | 14 | 506.852 | 4.460 | 706.569 | 201.17 | 0.996 |
| 5 | 21 | 16 | 110.057 | 6.358 | 150.786 | 108.80 | 0.679 |
| 5 | 21 | 18 | 211.664 | 3.915 | 382.041 | 224.69 | 0.945 |
| 5 | 21 | 20 | 230.596 | 3.904 | 326.055 | 124.99 | 0.985 |
| 5 | 21 | 22 | 60.219 | 13.297 | 32.444 | 271.90 | 0.469 |
| 5 | 21 | 24 | 73.899 | 11.632 | 90.114 | 130.01 | 0.799 |
| 5 | 21 | 26 | 127.479 | 7.195 | 139.114 | 130.57 | 0.968 |
| 5 | 21 | 28 | 78.348 | 11.905 | 93.495 | 241.68 | 0.864 |
| 5 | 21 | 30 | 125.525 | 6.706 | 169.392 | 348.80 | 0.964 |
| 5 | 21 | 32 | 48.966 | 13.605 | 21.224 | 321.48 | 0.338 |
| 5 | 21 | 34 | 56.752 | 23.851 | 26.251 | 127.43 | 0.757 |
| 5 | 22 | 1 | 197.796 | 3.332 | 228.560 | 60.69 | 0.982 |
| 5 | 22 | 3 | 421.382 | 3.916 | 600.595 | 306.36 | 0.994 |
| 5 | 22 | 5 | 447.178 | 4.264 | 619.980 | 2.04 | 0.995 |
| 5 | 22 | 7 | 281.372 | 3.355 | 312.298 | 307.92 | 0.991 |
| 5 | 22 | 9 | 139.535 | 4.527 | 247.756 | 263.64 | 0.872 |
| 5 | 22 | 11 | 676.733 | 5.675 | 993.071 | 283.21 | 0.998 |
| 5 | 22 | 13 | 158.814 | 4.346 | 170.025 | 140.37 | 0.967 |
| 5 | 22 | 15 | 87.336 | 7.430 | 72.443 | 341.54 | 0.859 |
| 5 | 22 | 17 | 178.221 | 4.690 | 277.155 | 31.79 | 0.955 |
| 5 | 22 | 19 | 279.274 | 4.069 | 370.344 | 50.54 | 0.990 |
| 5 | 22 | 21 | 284.754 | 4.977 | 358.943 | 301.65 | 0.991 |
| 5 | 22 | 23 | 65.362 | 11.912 | 45.722 | 27.73 | 0.884 |
| 5 | 22 | 25 | 119.904 | 11.992 | 149.510 | 303.21 | 0.956 |
| 5 | 22 | 27 | 55.994 | 14.257 | 6.697 | 315.00 | 0.880 |
| 5 | 22 | 29 | 82.896 | 10.927 | 86.127 | 314.08 | 0.932 |
| 5 | 22 | 31 | 42.818 | 12.444 | 21.474 | 53.41 | 0.816 |
| 5 | 22 | 33 | 52.080 | 14.645 | 36.796 | 48.49 | 0.836 |
| 5 | 23 | 0 | 359.393 | 4.896 | 502.184 | 180.00 | 1.000 |
| 5 | 23 | 2 | 429.536 | 4.065 | 646.343 | 151.47 | 0.994 |
| 5 | 23 | 4 | 198.324 | 3.509 | 334.591 | 167.34 | 0.965 |
| 5 | 23 | 6 | 474.740 | 4.250 | 716.417 | 324.72 | 0.995 |
| 5 | 23 | 8 | 166.154 | 5.450 | 277.168 | 286.84 | 0.943 |
| 5 | 23 | 10 | 382.261 | 3.596 | 603.520 | 353.09 | 0.991 |
| 5 | 23 | 12 | 188.044 | 4.106 | 297.065 | 255.22 | 0.960 |
| 5 | 23 | 14 | 107.566 | 6.031 | 123.888 | 90.23 | 0.886 |
| 5 | 23 | 16 | 97.558 | 7.728 | 150.545 | 167.98 | 0.779 |
| 5 | 23 | 18 | 61.583 | 13.807 | 38.541 | 19.79 | 0.743 |
| 5 | 23 | 20 | 209.722 | 4.378 | 302.024 | 304.63 | 0.986 |
| 5 | 23 | 22 | 77.218 | 11.705 | 65.855 | 296.12 | 0.912 |
| 5 | 23 | 24 | 63.121 | 13.007 | 51.712 | 13.14 | 0.839 |
| 5 | 23 | 26 | 46.448 | 13.614 | 17.534 | 251.37 | 0.563 |
| 5 | 23 | 28 | 128.394 | 7.255 | 204.057 | 229.70 | 0.956 |
| 5 | 23 | 30 | 48.939 | 14.756 | 31.764 | 359.68 | 0.457 |
| 5 | 23 | 32 | 52.853 | 14.052 | 49.973 | 170.19 | 0.758 |
| 5 | 24 | 1 | 145.341 | 4.011 | 225.793 | 315.24 | 0.936 |
| 5 | 24 | 3 | 324.771 | 4.093 | 433.993 | 99.00 | 0.990 |
| 5 | 24 | 5 | 272.984 | 3.357 | 374.570 | 135.04 | 0.988 |
| 5 | 24 | 7 | 137.999 | 6.325 | 200.911 | 191.66 | 0.939 |
| 5 | 24 | 9 | 165.970 | 4.504 | 246.611 | 164.23 | 0.953 |
| 5 | 24 | 11 | 97.214 | 8.487 | 103.457 | 31.50 | 0.872 |
| 5 | 24 | 13 | 129.348 | 5.408 | 199.175 | 114.61 | 0.926 |
| 5 | 24 | 15 | 64.229 | 12.741 | 11.157 | 124.59 | 0.870 |
| 5 | 24 | 17 | 114.590 | 7.922 | 193.891 | 284.00 | 0.817 |
| 5 | 24 | 19 | 47.141 | 12.335 | 18.523 | 147.97 | 0.749 |
| 5 | 24 | 21 | 42.858 | 13.151 | 11.603 | 272.05 | 0.481 |
| 5 | 24 | 23 | 131.845 | 7.816 | 175.002 | 340.05 | 0.966 |
| 5 | 24 | 25 | 174.920 | 5.953 | 275.403 | 359.30 | 0.976 |
| 5 | 24 | 27 | 54.057 | 14.508 | 33.400 | 293.25 | 0.434 |
| 5 | 24 | 29 | 94.666 | 14.108 | 87.198 | 260.66 | 0.966 |
| 5 | 24 | 31 | 51.712 | 22.563 | 19.444 | 168.79 | 0.767 |
| 5 | 25 | 0 | 32.333 | 14.886 | 9.423 | 0.00 | 0.210 |
| 5 | 25 | 2 | 163.251 | 4.675 | 128.697 | 162.61 | 0.971 |
| 5 | 25 | 4 | 178.720 | 3.972 | 266.624 | 29.00 | 0.961 |
| 5 | 25 | 6 | 41.875 | 11.297 | 4.764 | 168.93 | 0.159 |
| 5 | 25 | 8 | 65.237 | 11.422 | 47.560 | 193.19 | 0.813 |
| 5 | 25 | 10 | 239.740 | 4.586 | 445.320 | 40.29 | 0.979 |
| 5 | 25 | 12 | 73.215 | 10.656 | 78.600 | 4.63 | 0.792 |
| 5 | 25 | 14 | 232.251 | 4.586 | 294.050 | 195.62 | 0.987 |
| 5 | 25 | 16 | 137.586 | 6.673 | 226.678 | 285.54 | 0.958 |
| 5 | 25 | 18 | 124.992 | 8.056 | 136.543 | 184.68 | 0.968 |
| 5 | 25 | 20 | 99.713 | 11.111 | 132.110 | 269.09 | 0.932 |
| 5 | 25 | 22 | 125.932 | 7.299 | 195.516 | 226.61 | 0.951 |
| 5 | 25 | 24 | 46.125 | 11.390 | 25.225 | 269.19 | 0.619 |

| | | | | | | | |
|---|---|---|---|---|---|---|---|
| 5 | 25 | 26 | 55.963 | 14.170 | 27.164 | 306.32 | 0.841 |
| 5 | 25 | 28 | 59.235 | 16.167 | 59.952 | 170.35 | 0.845 |
| 5 | 25 | 30 | 94.204 | 30.505 | 80.247 | 81.24 | 0.867 |
| 5 | 26 | 1 | 142.481 | 5.964 | 188.832 | 140.82 | 0.966 |
| 5 | 26 | 3 | 238.409 | 4.332 | 281.171 | 168.84 | 0.989 |
| 5 | 26 | 5 | 80.620 | 7.818 | 95.882 | 188.05 | 0.826 |
| 5 | 26 | 7 | 277.666 | 6.384 | 388.110 | 307.84 | 0.991 |
| 5 | 26 | 9 | 79.048 | 12.060 | 65.511 | 99.37 | 0.887 |
| 5 | 26 | 11 | 238.267 | 3.998 | 286.582 | 142.26 | 0.989 |
| 5 | 26 | 13 | 69.357 | 11.870 | 88.175 | 179.88 | 0.820 |
| 5 | 26 | 15 | 53.994 | 12.567 | 41.457 | 245.48 | 0.720 |
| 5 | 26 | 17 | 121.864 | 8.549 | 209.409 | 286.80 | 0.933 |
| 5 | 26 | 19 | 57.564 | 13.382 | 42.306 | 252.02 | 0.815 |
| 5 | 26 | 21 | 35.533 | 10.876 | 0.259 | 204.97 | 0.282 |
| 5 | 26 | 23 | 83.244 | 12.268 | 94.956 | 206.76 | 0.923 |
| 5 | 26 | 25 | 118.789 | 10.519 | 123.383 | 316.36 | 0.966 |
| 5 | 26 | 27 | 99.074 | 10.843 | 121.596 | 158.34 | 0.963 |
| 5 | 26 | 29 | 93.846 | 30.324 | 77.917 | 10.67 | 0.875 |
| 5 | 27 | 0 | 269.326 | 6.575 | 375.404 | 0.00 | 1.000 |
| 5 | 27 | 2 | 236.113 | 4.680 | 367.420 | 93.85 | 0.984 |
| 5 | 27 | 4 | 71.347 | 10.722 | 74.380 | 91.17 | 0.803 |
| 5 | 27 | 6 | 103.252 | 6.120 | 102.188 | 122.52 | 0.939 |
| 5 | 27 | 8 | 338.667 | 4.095 | 369.157 | 195.12 | 0.996 |
| 5 | 27 | 10 | 157.674 | 6.350 | 253.456 | 180.02 | 0.972 |
| 5 | 27 | 12 | 98.342 | 10.778 | 119.524 | 33.01 | 0.939 |
| 5 | 27 | 14 | 41.432 | 12.038 | 4.029 | 319.02 | 0.632 |
| 5 | 27 | 16 | 169.581 | 5.024 | 257.613 | 13.39 | 0.977 |
| 5 | 27 | 18 | 49.724 | 13.968 | 8.389 | 16.73 | 0.127 |
| 5 | 27 | 20 | 49.861 | 13.521 | 21.587 | 284.57 | 0.803 |
| 5 | 27 | 22 | 117.714 | 9.914 | 155.275 | 76.20 | 0.960 |
| 5 | 27 | 24 | 118.728 | 14.905 | 161.662 | 322.20 | 0.970 |
| 5 | 27 | 26 | 91.229 | 20.241 | 122.239 | 277.96 | 0.897 |
| 5 | 28 | 1 | 138.195 | 6.756 | 134.940 | 25.79 | 0.978 |
| 5 | 28 | 3 | 185.382 | 4.902 | 238.700 | 58.97 | 0.985 |
| 5 | 28 | 5 | 228.151 | 4.693 | 305.181 | 339.35 | 0.990 |
| 5 | 28 | 7 | 142.699 | 6.149 | 170.505 | 359.16 | 0.977 |
| 5 | 28 | 9 | 163.306 | 5.624 | 282.245 | 148.70 | 0.970 |
| 5 | 28 | 11 | 78.359 | 11.588 | 58.627 | 332.79 | 0.932 |
| 5 | 28 | 13 | 104.987 | 7.213 | 157.103 | 345.62 | 0.938 |
| 5 | 28 | 15 | 51.584 | 11.041 | 3.793 | 252.45 | 0.869 |
| 5 | 28 | 17 | 136.333 | 6.614 | 144.540 | 148.25 | 0.975 |
| 5 | 28 | 19 | 83.074 | 8.819 | 117.380 | 215.27 | 0.903 |
| 5 | 28 | 21 | 79.801 | 15.474 | 83.155 | 158.09 | 0.904 |
| 5 | 28 | 23 | 54.872 | 15.716 | 43.728 | 326.34 | 0.875 |
| 5 | 28 | 25 | 47.358 | 14.976 | 29.512 | 13.33 | 0.817 |
| 5 | 29 | 0 | 29.876 | 14.652 | 39.025 | 0.00 | 0.952 |
| 5 | 29 | 2 | 36.925 | 11.793 | 0.906 | 132.07 | 0.331 |
| 5 | 29 | 4 | 150.531 | 4.983 | 210.408 | 349.43 | 0.975 |
| 5 | 29 | 6 | 87.240 | 11.419 | 105.775 | 330.14 | 0.919 |
| 5 | 29 | 8 | 40.107 | 11.537 | 6.873 | 17.23 | 0.491 |
| 5 | 29 | 10 | 96.775 | 9.511 | 148.385 | 351.70 | 0.913 |
| 5 | 29 | 12 | 159.612 | 7.427 | 264.121 | 305.61 | 0.971 |
| 5 | 29 | 14 | 65.612 | 13.317 | 59.231 | 182.82 | 0.843 |
| 5 | 29 | 16 | 129.260 | 5.234 | 170.719 | 38.55 | 0.971 |
| 5 | 29 | 18 | 134.640 | 8.793 | 207.700 | 82.87 | 0.964 |
| 5 | 29 | 20 | 40.143 | 12.523 | 21.958 | 142.82 | 0.443 |
| 5 | 29 | 22 | 137.310 | 9.085 | 199.162 | 103.67 | 0.979 |
| 5 | 29 | 24 | 78.518 | 23.519 | 82.867 | 342.52 | 0.774 |
| 5 | 30 | 1 | 172.673 | 5.580 | 273.364 | 301.67 | 0.978 |
| 5 | 30 | 3 | 47.102 | 11.562 | 23.944 | 117.02 | 0.666 |
| 5 | 30 | 5 | 39.776 | 11.024 | 11.967 | 342.41 | 0.449 |
| 5 | 30 | 7 | 52.723 | 11.705 | 33.152 | 342.23 | 0.784 |
| 5 | 30 | 9 | 66.577 | 14.425 | 72.738 | 304.60 | 0.790 |
| 5 | 30 | 11 | 217.599 | 9.486 | 312.920 | 239.99 | 0.989 |
| 5 | 30 | 13 | 76.524 | 16.097 | 90.702 | 338.44 | 0.870 |
| 5 | 30 | 15 | 89.601 | 11.743 | 114.195 | 55.84 | 0.925 |
| 5 | 30 | 17 | 59.123 | 13.762 | 72.386 | 217.26 | 0.738 |
| 5 | 30 | 19 | 37.355 | 12.592 | 18.000 | 0.87 | 0.683 |
| 5 | 30 | 21 | 107.978 | 26.899 | 101.631 | 139.51 | 0.941 |
| 5 | 31 | 0 | 53.827 | 16.679 | 64.093 | 0.00 | 0.880 |
| 5 | 31 | 2 | 83.445 | 11.197 | 121.059 | 189.20 | 0.902 |
| 5 | 31 | 4 | 59.688 | 11.178 | 59.497 | 226.32 | 0.822 |
| 5 | 31 | 6 | 107.438 | 8.560 | 161.008 | 334.29 | 0.947 |
| 5 | 31 | 8 | 59.735 | 13.050 | 53.605 | 52.79 | 0.837 |
| 5 | 31 | 10 | 49.863 | 11.744 | 6.227 | 218.21 | 0.865 |
| 5 | 31 | 12 | 43.542 | 13.660 | 13.846 | 214.32 | 0.718 |
| 5 | 31 | 14 | 72.917 | 17.993 | 63.164 | 159.49 | 0.935 |

| | | | | | | | |
|---|---|---|---|---|---|---|---|
| 5 | 31 | 16 | 38.799 | 11.657 | 18.742 | 73.12 | 0.742 |
| 5 | 31 | 18 | 52.455 | 12.559 | 54.753 | 39.11 | 0.619 |
| 5 | 31 | 20 | 84.312 | 19.492 | 107.027 | 267.81 | 0.877 |
| 5 | 32 | 1 | 51.255 | 13.787 | 42.787 | 48.00 | 0.685 |
| 5 | 32 | 3 | 59.994 | 13.319 | 50.343 | 198.71 | 0.846 |
| 5 | 32 | 5 | 175.677 | 5.635 | 244.198 | 130.00 | 0.985 |
| 5 | 32 | 7 | 89.908 | 11.140 | 133.154 | 110.62 | 0.913 |
| 5 | 32 | 9 | 130.799 | 9.582 | 204.069 | 100.12 | 0.977 |
| 5 | 32 | 11 | 84.602 | 12.859 | 72.560 | 201.96 | 0.962 |
| 5 | 32 | 13 | 58.162 | 14.619 | 47.484 | 26.00 | 0.454 |
| 5 | 32 | 15 | 48.848 | 20.900 | 12.403 | 41.14 | 0.801 |
| 5 | 32 | 17 | 83.663 | 26.042 | 75.578 | 68.14 | 0.710 |
| 5 | 33 | 0 | 24.013 | 17.340 | 3.056 | 0.00 | 0.105 |
| 5 | 33 | 2 | 35.988 | 11.384 | 15.267 | 347.64 | 0.362 |
| 5 | 33 | 4 | 48.796 | 13.060 | 50.759 | 179.22 | 0.745 |
| 5 | 33 | 6 | 51.301 | 15.732 | 11.816 | 21.74 | 0.899 |
| 5 | 33 | 8 | 46.326 | 14.217 | 9.533 | 103.21 | 0.878 |
| 5 | 33 | 10 | 52.367 | 12.924 | 45.852 | 347.21 | 0.862 |
| 5 | 33 | 12 | 76.729 | 20.169 | 82.021 | 210.14 | 0.890 |
| 5 | 33 | 14 | 41.703 | 18.651 | 12.637 | 7.18 | 0.485 |
| 5 | 34 | 1 | 59.185 | 19.902 | 44.845 | 267.98 | 0.838 |
| 5 | 34 | 3 | 46.411 | 13.719 | 41.230 | 114.36 | 0.692 |
| 5 | 34 | 5 | 48.461 | 14.189 | 36.774 | 291.72 | 0.487 |
| 5 | 34 | 7 | 51.507 | 20.526 | 29.384 | 253.75 | 0.704 |
| 5 | 34 | 9 | 43.319 | 19.131 | 10.646 | 104.88 | 0.609 |
| 6 | 0 | 2 | 490.965 | 5.480 | 690.016 | 180.00 | 1.000 |
| 6 | 0 | 4 | 966.662 | 14.501 | 1357.238 | 180.00 | 1.000 |
| 6 | 0 | 8 | 84.597 | 3.448 | 49.876 | 0.00 | 0.421 |
| 6 | 0 | 10 | 251.067 | 4.145 | 350.837 | 180.00 | 1.000 |
| 6 | 0 | 12 | 1140.518 | 13.968 | 1587.842 | 180.00 | 1.000 |
| 6 | 0 | 14 | 301.423 | 3.781 | 418.566 | 0.00 | 1.000 |
| 6 | 0 | 16 | 92.379 | 5.029 | 125.958 | 180.00 | 0.986 |
| 6 | 0 | 18 | 61.167 | 8.135 | 73.459 | 180.00 | 0.875 |
| 6 | 0 | 20 | 404.559 | 4.846 | 554.294 | 0.00 | 1.000 |
| 6 | 0 | 22 | 146.373 | 4.125 | 199.473 | 0.00 | 1.000 |
| 6 | 0 | 24 | 421.056 | 5.155 | 570.333 | 0.00 | 1.000 |
| 6 | 0 | 26 | 22.955 | 10.607 | 2.695 | 0.00 | 0.088 |
| 6 | 0 | 28 | 293.915 | 4.713 | 392.817 | 0.00 | 1.000 |
| 6 | 0 | 30 | 94.879 | 9.374 | 124.783 | 180.00 | 0.993 |
| 6 | 0 | 32 | 149.569 | 6.787 | 196.656 | 0.00 | 1.000 |
| 6 | 0 | 34 | 28.931 | 13.872 | 16.769 | 0.00 | 0.446 |
| 6 | 0 | 36 | 48.472 | 18.149 | 57.451 | 180.00 | 0.929 |
| 6 | 0 | 38 | 220.726 | 9.196 | 281.414 | 0.00 | 1.000 |
| 6 | 0 | 40 | 74.576 | 20.604 | 68.288 | 180.00 | 0.749 |
| 6 | 0 | 42 | 49.785 | 21.361 | 53.175 | 0.00 | 0.906 |
| 6 | 1 | 1 | 518.544 | 5.434 | 719.430 | 94.89 | 0.982 |
| 6 | 1 | 3 | 286.381 | 2.494 | 410.186 | 49.76 | 0.982 |
| 6 | 1 | 5 | 226.562 | 1.931 | 204.553 | 345.53 | 0.618 |
| 6 | 1 | 7 | 69.041 | 2.087 | 67.396 | 10.87 | 0.742 |
| 6 | 1 | 9 | 592.318 | 5.166 | 831.068 | 117.93 | 0.996 |
| 6 | 1 | 11 | 66.865 | 2.389 | 51.910 | 278.96 | 0.977 |
| 6 | 1 | 13 | 285.393 | 2.616 | 388.391 | 250.64 | 0.986 |
| 6 | 1 | 15 | 637.366 | 5.596 | 888.073 | 99.66 | 0.997 |
| 6 | 1 | 17 | 505.753 | 4.901 | 780.744 | 117.30 | 0.995 |
| 6 | 1 | 19 | 324.748 | 3.197 | 488.749 | 76.63 | 0.988 |
| 6 | 1 | 21 | 319.741 | 3.214 | 419.204 | 79.54 | 0.992 |
| 6 | 1 | 23 | 484.853 | 4.552 | 648.567 | 8.97 | 0.995 |
| 6 | 1 | 25 | 65.771 | 8.240 | 43.579 | 68.51 | 0.685 |
| 6 | 1 | 27 | 309.565 | 3.539 | 424.388 | 58.34 | 0.990 |
| 6 | 1 | 29 | 297.547 | 3.542 | 332.765 | 97.28 | 0.991 |
| 6 | 1 | 31 | 114.296 | 5.588 | 124.706 | 76.40 | 0.529 |
| 6 | 1 | 33 | 161.387 | 5.389 | 223.019 | 7.59 | 0.959 |
| 6 | 1 | 35 | 160.523 | 6.227 | 227.221 | 132.34 | 0.960 |
| 6 | 1 | 37 | 64.060 | 13.193 | 43.302 | 245.39 | 0.837 |
| 6 | 1 | 39 | 111.516 | 7.600 | 144.819 | 69.85 | 0.942 |
| 6 | 1 | 41 | 39.250 | 11.590 | 7.001 | 76.45 | 0.450 |
| 6 | 1 | 43 | 50.054 | 17.093 | 16.541 | 169.91 | 0.836 |
| 6 | 2 | 0 | 273.734 | 4.557 | 382.772 | 180.00 | 0.994 |
| 6 | 2 | 2 | 627.878 | 5.703 | 941.809 | 38.94 | 0.984 |
| 6 | 2 | 4 | 1012.782 | 15.066 | 1439.382 | 333.89 | 0.994 |
| 6 | 2 | 6 | 704.505 | 5.545 | 1038.986 | 104.73 | 0.988 |
| 6 | 2 | 8 | 857.440 | 7.040 | 1198.921 | 47.34 | 0.998 |
| 6 | 2 | 10 | 780.020 | 6.462 | 1143.474 | 60.17 | 0.998 |
| 6 | 2 | 12 | 761.893 | 6.180 | 1052.954 | 119.59 | 0.998 |
| 6 | 2 | 14 | 532.908 | 4.736 | 724.560 | 96.78 | 0.995 |
| 6 | 2 | 16 | 160.661 | 2.266 | 228.753 | 246.19 | 0.961 |
| 6 | 2 | 18 | 42.746 | 7.266 | 14.224 | 283.77 | 0.380 |

| | | | | | | | |
|---|---|---|---|---|---|---|---|
| 6 | 2 | 20 | 115.041 | 3.324 | 150.009 | 127.48 | 0.891 |
| 6 | 2 | 22 | 472.990 | 3.992 | 655.929 | 340.86 | 0.994 |
| 6 | 2 | 24 | 568.161 | 4.696 | 809.505 | 107.23 | 0.997 |
| 6 | 2 | 26 | 245.979 | 3.002 | 352.639 | 272.15 | 0.981 |
| 6 | 2 | 28 | 504.197 | 4.516 | 693.991 | 1.76 | 0.996 |
| 6 | 2 | 30 | 455.330 | 4.150 | 614.935 | 58.64 | 0.995 |
| 6 | 2 | 32 | 202.061 | 4.176 | 229.230 | 217.33 | 0.972 |
| 6 | 2 | 34 | 198.244 | 5.069 | 206.058 | 36.27 | 0.982 |
| 6 | 2 | 36 | 226.016 | 4.552 | 245.017 | 212.56 | 0.989 |
| 6 | 2 | 38 | 100.999 | 10.092 | 128.870 | 215.49 | 0.917 |
| 6 | 2 | 40 | 95.431 | 9.830 | 142.360 | 164.61 | 0.768 |
| 6 | 2 | 42 | 56.999 | 14.106 | 56.425 | 261.65 | 0.780 |
| 6 | 3 | 1 | 81.838 | 1.730 | 89.983 | 145.89 | 0.826 |
| 6 | 3 | 3 | 1214.733 | 12.310 | 1712.044 | 72.77 | 0.996 |
| 6 | 3 | 5 | 865.634 | 8.642 | 1237.784 | 222.91 | 0.993 |
| 6 | 3 | 7 | 236.610 | 2.253 | 314.582 | 112.89 | 0.944 |
| 6 | 3 | 9 | 1005.724 | 8.098 | 1396.629 | 78.00 | 0.999 |
| 6 | 3 | 11 | 265.392 | 2.440 | 359.938 | 35.97 | 0.986 |
| 6 | 3 | 13 | 282.765 | 2.841 | 383.242 | 46.12 | 0.985 |
| 6 | 3 | 15 | 189.775 | 2.310 | 218.429 | 346.14 | 0.982 |
| 6 | 3 | 17 | 253.003 | 2.670 | 312.980 | 352.62 | 0.984 |
| 6 | 3 | 19 | 99.391 | 3.577 | 127.651 | 116.91 | 0.846 |
| 6 | 3 | 21 | 361.863 | 3.221 | 485.221 | 158.60 | 0.990 |
| 6 | 3 | 23 | 516.776 | 4.484 | 760.971 | 127.28 | 0.995 |
| 6 | 3 | 25 | 240.653 | 2.969 | 246.633 | 60.64 | 0.987 |
| 6 | 3 | 27 | 116.135 | 4.305 | 137.010 | 172.38 | 0.944 |
| 6 | 3 | 29 | 289.840 | 3.329 | 397.569 | 302.95 | 0.988 |
| 6 | 3 | 31 | 367.752 | 3.720 | 430.485 | 274.89 | 0.992 |
| 6 | 3 | 33 | 115.139 | 6.880 | 158.714 | 270.71 | 0.746 |
| 6 | 3 | 35 | 74.789 | 11.112 | 49.797 | 156.38 | 0.886 |
| 6 | 3 | 37 | 150.109 | 6.490 | 223.019 | 121.68 | 0.962 |
| 6 | 3 | 39 | 86.804 | 9.809 | 104.114 | 56.89 | 0.883 |
| 6 | 3 | 41 | 55.811 | 14.117 | 39.210 | 240.25 | 0.654 |
| 6 | 3 | 43 | 56.385 | 16.837 | 44.630 | 1.96 | 0.601 |
| 6 | 4 | 0 | 229.499 | 2.826 | 321.159 | 180.00 | 0.995 |
| 6 | 4 | 2 | 443.403 | 3.698 | 598.747 | 270.63 | 0.978 |
| 6 | 4 | 4 | 312.153 | 2.798 | 443.773 | 180.10 | 0.959 |
| 6 | 4 | 6 | 428.558 | 3.641 | 643.581 | 232.66 | 0.965 |
| 6 | 4 | 8 | 177.261 | 1.909 | 263.123 | 27.95 | 0.959 |
| 6 | 4 | 10 | 209.691 | 2.124 | 262.463 | 274.87 | 0.985 |
| 6 | 4 | 12 | 260.047 | 2.471 | 327.912 | 64.34 | 0.984 |
| 6 | 4 | 14 | 81.583 | 3.103 | 77.375 | 309.95 | 0.727 |
| 6 | 4 | 16 | 497.100 | 4.445 | 773.534 | 310.36 | 0.994 |
| 6 | 4 | 18 | 136.606 | 2.797 | 127.292 | 244.27 | 0.965 |
| 6 | 4 | 20 | 548.372 | 4.431 | 813.778 | 148.98 | 0.995 |
| 6 | 4 | 22 | 144.482 | 2.806 | 178.037 | 266.20 | 0.956 |
| 6 | 4 | 24 | 153.057 | 3.178 | 219.229 | 224.89 | 0.951 |
| 6 | 4 | 26 | 212.902 | 3.055 | 291.325 | 265.47 | 0.977 |
| 6 | 4 | 28 | 99.300 | 6.208 | 112.298 | 46.81 | 0.879 |
| 6 | 4 | 30 | 348.963 | 3.516 | 487.898 | 239.88 | 0.990 |
| 6 | 4 | 32 | 68.478 | 11.062 | 34.788 | 283.98 | 0.619 |
| 6 | 4 | 34 | 100.463 | 7.538 | 88.135 | 68.66 | 0.928 |
| 6 | 4 | 36 | 121.931 | 6.892 | 176.488 | 266.78 | 0.944 |
| 6 | 4 | 38 | 68.290 | 11.708 | 67.489 | 267.75 | 0.818 |
| 6 | 4 | 40 | 78.176 | 12.454 | 94.323 | 56.32 | 0.834 |
| 6 | 4 | 42 | 38.475 | 12.561 | 11.222 | 278.63 | 0.343 |
| 6 | 5 | 1 | 816.976 | 10.906 | 1165.364 | 111.73 | 0.992 |
| 6 | 5 | 3 | 573.394 | 4.845 | 863.959 | 202.12 | 0.981 |
| 6 | 5 | 5 | 884.836 | 10.923 | 1315.009 | 213.39 | 0.992 |
| 6 | 5 | 7 | 227.156 | 2.052 | 342.628 | 268.71 | 0.982 |
| 6 | 5 | 9 | 151.354 | 1.928 | 222.903 | 131.81 | 0.987 |
| 6 | 5 | 11 | 524.067 | 4.980 | 701.026 | 257.99 | 0.995 |
| 6 | 5 | 13 | 355.381 | 3.094 | 504.145 | 322.90 | 0.989 |
| 6 | 5 | 15 | 221.064 | 2.452 | 311.101 | 173.28 | 0.979 |
| 6 | 5 | 17 | 360.169 | 3.459 | 480.580 | 19.51 | 0.992 |
| 6 | 5 | 19 | 156.255 | 3.084 | 170.832 | 154.87 | 0.959 |
| 6 | 5 | 21 | 166.747 | 3.041 | 229.346 | 112.32 | 0.972 |
| 6 | 5 | 23 | 231.346 | 2.806 | 291.552 | 240.80 | 0.978 |
| 6 | 5 | 25 | 195.099 | 2.867 | 212.071 | 323.98 | 0.979 |
| 6 | 5 | 27 | 563.425 | 4.801 | 703.202 | 67.66 | 0.997 |
| 6 | 5 | 29 | 37.654 | 9.888 | 2.212 | 165.64 | 0.189 |
| 6 | 5 | 31 | 228.909 | 3.696 | 428.605 | 245.15 | 0.953 |
| 6 | 5 | 33 | 180.669 | 4.435 | 233.845 | 175.20 | 0.974 |
| 6 | 5 | 35 | 309.446 | 4.022 | 413.076 | 267.10 | 0.993 |
| 6 | 5 | 37 | 43.194 | 12.356 | 17.371 | 287.41 | 0.766 |
| 6 | 5 | 39 | 49.893 | 12.990 | 15.269 | 354.98 | 0.251 |
| 6 | 5 | 41 | 105.355 | 10.872 | 143.685 | 338.59 | 0.921 |

| | | | | | | | |
|---|---|---|---|---|---|---|---|
| 6 | 5 | 43 | 86.704 | 29.939 | 27.125 | 343.72 | 0.253 |
| 6 | 6 | 0 | 53.533 | 4.048 | 20.933 | 0.00 | 0.279 |
| 6 | 6 | 2 | 436.203 | 3.616 | 617.586 | 72.97 | 0.980 |
| 6 | 6 | 4 | 292.452 | 2.672 | 367.308 | 235.13 | 0.990 |
| 6 | 6 | 6 | 900.431 | 7.878 | 1289.555 | 231.29 | 0.998 |
| 6 | 6 | 8 | 673.489 | 5.675 | 975.171 | 227.75 | 0.997 |
| 6 | 6 | 10 | 262.441 | 2.453 | 329.669 | 286.66 | 0.990 |
| 6 | 6 | 12 | 190.157 | 2.385 | 285.889 | 281.97 | 0.946 |
| 6 | 6 | 14 | 137.163 | 2.377 | 171.165 | 103.72 | 0.980 |
| 6 | 6 | 16 | 165.894 | 2.751 | 197.158 | 339.38 | 0.973 |
| 6 | 6 | 18 | 65.192 | 4.963 | 43.077 | 185.64 | 0.664 |
| 6 | 6 | 20 | 25.768 | 7.059 | 81.576 | 70.82 | 0.723 |
| 6 | 6 | 22 | 273.669 | 2.854 | 409.999 | 232.58 | 0.983 |
| 6 | 6 | 24 | 347.873 | 3.469 | 531.452 | 188.50 | 0.990 |
| 6 | 6 | 26 | 452.072 | 4.345 | 575.965 | 119.90 | 0.995 |
| 6 | 6 | 28 | 119.051 | 4.520 | 144.039 | 196.25 | 0.939 |
| 6 | 6 | 30 | 152.653 | 4.152 | 188.023 | 47.30 | 0.949 |
| 6 | 6 | 32 | 348.454 | 3.957 | 432.241 | 204.63 | 0.994 |
| 6 | 6 | 34 | 228.728 | 3.818 | 331.910 | 208.17 | 0.981 |
| 6 | 6 | 36 | 62.731 | 11.449 | 47.499 | 245.24 | 0.480 |
| 6 | 6 | 38 | 37.363 | 11.216 | 4.576 | 50.55 | 0.188 |
| 6 | 6 | 40 | 86.923 | 8.612 | 118.669 | 274.67 | 0.736 |
| 6 | 6 | 42 | 43.277 | 14.326 | 1.197 | 19.36 | 0.842 |
| 6 | 7 | 1 | 448.383 | 3.800 | 568.133 | 288.84 | 0.994 |
| 6 | 7 | 3 | 244.067 | 2.484 | 328.885 | 41.64 | 0.980 |
| 6 | 7 | 5 | 910.153 | 7.375 | 1344.597 | 357.01 | 0.998 |
| 6 | 7 | 7 | 358.422 | 3.446 | 367.296 | 179.23 | 0.992 |
| 6 | 7 | 9 | 498.692 | 4.798 | 720.895 | 251.39 | 0.994 |
| 6 | 7 | 11 | 94.233 | 2.171 | 91.453 | 231.28 | 0.903 |
| 6 | 7 | 13 | 224.104 | 2.608 | 274.905 | 298.15 | 0.978 |
| 6 | 7 | 15 | 178.939 | 2.324 | 291.322 | 273.83 | 0.980 |
| 6 | 7 | 17 | 205.906 | 2.441 | 236.786 | 248.97 | 0.981 |
| 6 | 7 | 19 | 185.741 | 2.937 | 349.810 | 19.74 | 0.870 |
| 6 | 7 | 21 | 465.771 | 3.987 | 613.494 | 281.64 | 0.994 |
| 6 | 7 | 23 | 299.960 | 2.947 | 410.404 | 318.71 | 0.989 |
| 6 | 7 | 25 | 266.109 | 2.990 | 372.350 | 164.80 | 0.985 |
| 6 | 7 | 27 | 70.291 | 7.710 | 74.890 | 141.06 | 0.804 |
| 6 | 7 | 29 | 176.955 | 3.988 | 237.618 | 305.90 | 0.963 |
| 6 | 7 | 31 | 94.172 | 7.422 | 70.489 | 267.81 | 0.871 |
| 6 | 7 | 33 | 179.023 | 5.187 | 224.280 | 300.21 | 0.975 |
| 6 | 7 | 35 | 191.871 | 4.663 | 240.060 | 2.90 | 0.984 |
| 6 | 7 | 37 | 27.528 | 9.190 | 20.001 | 28.65 | 0.327 |
| 6 | 7 | 39 | 70.685 | 12.429 | 69.494 | 127.90 | 0.854 |
| 6 | 7 | 41 | 40.195 | 12.507 | 16.112 | 258.85 | 0.720 |
| 6 | 7 | 43 | 54.457 | 25.259 | 11.186 | 343.98 | 0.721 |
| 6 | 8 | 0 | 244.557 | 4.809 | 343.775 | 180.00 | 1.000 |
| 6 | 8 | 2 | 523.736 | 4.854 | 792.849 | 94.38 | 0.995 |
| 6 | 8 | 4 | 590.366 | 5.321 | 836.468 | 216.69 | 0.996 |
| 6 | 8 | 6 | 516.686 | 4.634 | 703.005 | 136.60 | 0.995 |
| 6 | 8 | 8 | 180.693 | 2.010 | 245.192 | 291.81 | 0.990 |
| 6 | 8 | 10 | 219.120 | 2.234 | 312.273 | 67.14 | 0.990 |
| 6 | 8 | 12 | 190.906 | 2.290 | 292.215 | 294.88 | 0.960 |
| 6 | 8 | 14 | 153.244 | 2.468 | 196.382 | 10.28 | 0.966 |
| 6 | 8 | 16 | 23.698 | 7.325 | 31.621 | 71.27 | 0.498 |
| 6 | 8 | 18 | 258.623 | 2.715 | 323.159 | 82.59 | 0.983 |
| 6 | 8 | 20 | 480.356 | 4.269 | 664.120 | 44.80 | 0.994 |
| 6 | 8 | 22 | 288.375 | 3.238 | 392.894 | 304.60 | 0.990 |
| 6 | 8 | 24 | 99.423 | 4.353 | 97.419 | 327.78 | 0.884 |
| 6 | 8 | 26 | 72.400 | 7.136 | 16.818 | 316.93 | 0.216 |
| 6 | 8 | 28 | 147.477 | 4.026 | 213.021 | 215.82 | 0.952 |
| 6 | 8 | 30 | 306.677 | 3.676 | 396.884 | 359.54 | 0.987 |
| 6 | 8 | 32 | 199.687 | 4.855 | 258.051 | 128.16 | 0.979 |
| 6 | 8 | 34 | 115.295 | 7.123 | 159.500 | 149.43 | 0.943 |
| 6 | 8 | 36 | 209.359 | 4.023 | 257.294 | 344.20 | 0.986 |
| 6 | 8 | 38 | 94.072 | 7.978 | 104.026 | 86.04 | 0.922 |
| 6 | 8 | 40 | 70.723 | 12.573 | 81.784 | 301.41 | 0.817 |
| 6 | 8 | 42 | 60.736 | 27.299 | 19.676 | 39.35 | 0.733 |
| 6 | 9 | 1 | 299.194 | 3.101 | 394.143 | 301.38 | 0.984 |
| 6 | 9 | 3 | 159.175 | 1.844 | 226.385 | 24.01 | 0.967 |
| 6 | 9 | 5 | 966.987 | 7.809 | 1393.278 | 275.67 | 0.998 |
| 6 | 9 | 7 | 97.728 | 2.428 | 91.502 | 141.16 | 0.820 |
| 6 | 9 | 9 | 232.072 | 2.483 | 364.474 | 19.11 | 0.967 |
| 6 | 9 | 11 | 206.148 | 2.349 | 317.518 | 235.14 | 0.973 |
| 6 | 9 | 13 | 363.518 | 3.190 | 501.567 | 46.02 | 0.992 |
| 6 | 9 | 15 | 233.465 | 2.554 | 243.591 | 70.26 | 0.988 |
| 6 | 9 | 17 | 370.580 | 3.264 | 514.752 | 208.13 | 0.990 |
| 6 | 9 | 19 | 474.852 | 4.179 | 697.769 | 72.16 | 0.994 |

| | | | | | | | |
|---|---|---|---|---|---|---|---|
| 6 | 9 | 21 | 248.298 | 2.783 | 338.005 | 292.16 | 0.985 |
| 6 | 9 | 23 | 534.357 | 4.927 | 687.186 | 246.80 | 0.997 |
| 6 | 9 | 25 | 568.609 | 4.795 | 799.867 | 32.30 | 0.997 |
| 6 | 9 | 27 | 183.578 | 3.385 | 201.040 | 76.29 | 0.975 |
| 6 | 9 | 29 | 238.645 | 3.458 | 336.087 | 336.93 | 0.977 |
| 6 | 9 | 31 | 172.545 | 4.380 | 273.488 | 69.62 | 0.961 |
| 6 | 9 | 33 | 143.137 | 8.637 | 168.477 | 189.66 | 0.960 |
| 6 | 9 | 35 | 92.966 | 12.523 | 115.913 | 261.07 | 0.905 |
| 6 | 9 | 37 | 56.727 | 13.755 | 38.326 | 53.61 | 0.704 |
| 6 | 9 | 39 | 70.174 | 12.227 | 65.603 | 91.18 | 0.872 |
| 6 | 9 | 41 | 46.106 | 15.345 | 28.212 | 117.24 | 0.709 |
| 6 | 10 | 0 | 984.399 | 11.543 | 1382.480 | 0.00 | 1.000 |
| 6 | 10 | 2 | 518.718 | 5.302 | 667.818 | 358.22 | 0.995 |
| 6 | 10 | 4 | 501.866 | 5.571 | 681.661 | 3.91 | 0.995 |
| 6 | 10 | 6 | 131.606 | 1.936 | 196.718 | 17.56 | 0.836 |
| 6 | 10 | 8 | 329.315 | 3.425 | 534.764 | 242.12 | 0.987 |
| 6 | 10 | 10 | 263.704 | 2.768 | 357.442 | 347.57 | 0.987 |
| 6 | 10 | 12 | 79.489 | 3.385 | 76.732 | 102.71 | 0.570 |
| 6 | 10 | 14 | 221.344 | 2.522 | 339.998 | 39.53 | 0.982 |
| 6 | 10 | 16 | 426.612 | 3.668 | 637.792 | 12.70 | 0.992 |
| 6 | 10 | 18 | 211.080 | 2.845 | 269.663 | 169.43 | 0.972 |
| 6 | 10 | 20 | 343.640 | 3.405 | 502.397 | 61.53 | 0.989 |
| 6 | 10 | 22 | 183.293 | 2.837 | 258.878 | 285.89 | 0.982 |
| 6 | 10 | 24 | 271.194 | 3.010 | 450.539 | 145.79 | 0.980 |
| 6 | 10 | 26 | 383.039 | 3.598 | 522.590 | 130.21 | 0.993 |
| 6 | 10 | 28 | 56.600 | 11.275 | 25.018 | 51.44 | 0.453 |
| 6 | 10 | 30 | 140.864 | 5.963 | 187.308 | 29.34 | 0.931 |
| 6 | 10 | 32 | 98.244 | 6.814 | 104.175 | 146.23 | 0.909 |
| 6 | 10 | 34 | 228.154 | 4.462 | 314.017 | 228.77 | 0.987 |
| 6 | 10 | 36 | 95.795 | 7.176 | 107.233 | 80.19 | 0.532 |
| 6 | 10 | 38 | 36.396 | 11.493 | 6.856 | 33.41 | 0.587 |
| 6 | 10 | 40 | 55.154 | 13.592 | 35.315 | 101.34 | 0.892 |
| 6 | 10 | 42 | 47.980 | 23.208 | 5.476 | 77.38 | 0.652 |
| 6 | 11 | 1 | 35.054 | 5.629 | 14.777 | 117.75 | 0.355 |
| 6 | 11 | 3 | 211.685 | 2.327 | 271.223 | 338.96 | 0.973 |
| 6 | 11 | 5 | 250.908 | 2.559 | 359.448 | 305.21 | 0.978 |
| 6 | 11 | 7 | 366.867 | 3.337 | 623.692 | 46.77 | 0.989 |
| 6 | 11 | 9 | 220.883 | 2.466 | 256.033 | 61.09 | 0.982 |
| 6 | 11 | 11 | 117.339 | 2.949 | 161.543 | 21.54 | 0.933 |
| 6 | 11 | 13 | 349.981 | 3.198 | 538.502 | 166.85 | 0.990 |
| 6 | 11 | 15 | 238.045 | 2.619 | 286.462 | 327.05 | 0.979 |
| 6 | 11 | 17 | 268.089 | 2.812 | 371.655 | 182.55 | 0.982 |
| 6 | 11 | 19 | 113.159 | 3.634 | 152.108 | 314.36 | 0.736 |
| 6 | 11 | 21 | 505.319 | 4.619 | 727.191 | 126.93 | 0.996 |
| 6 | 11 | 23 | 327.620 | 3.222 | 477.546 | 287.38 | 0.990 |
| 6 | 11 | 25 | 294.915 | 3.169 | 424.712 | 176.09 | 0.987 |
| 6 | 11 | 27 | 515.666 | 4.491 | 646.859 | 144.98 | 0.996 |
| 6 | 11 | 29 | 54.074 | 11.117 | 10.058 | 193.37 | 0.320 |
| 6 | 11 | 31 | 384.184 | 4.047 | 542.911 | 175.53 | 0.994 |
| 6 | 11 | 33 | 187.628 | 4.727 | 211.688 | 152.39 | 0.984 |
| 6 | 11 | 35 | 94.150 | 7.824 | 114.079 | 79.46 | 0.920 |
| 6 | 11 | 37 | 68.562 | 11.945 | 72.711 | 301.58 | 0.720 |
| 6 | 11 | 39 | 61.532 | 11.880 | 31.284 | 25.37 | 0.352 |
| 6 | 11 | 41 | 43.065 | 20.547 | 3.679 | 97.38 | 0.463 |
| 6 | 12 | 0 | 117.986 | 5.405 | 139.508 | 180.00 | 0.842 |
| 6 | 12 | 2 | 368.730 | 3.369 | 523.380 | 289.70 | 0.994 |
| 6 | 12 | 4 | 476.869 | 3.912 | 656.453 | 336.18 | 0.995 |
| 6 | 12 | 6 | 104.735 | 2.395 | 155.077 | 315.98 | 0.812 |
| 6 | 12 | 8 | 271.954 | 2.977 | 367.802 | 95.66 | 0.991 |
| 6 | 12 | 10 | 214.963 | 2.701 | 298.129 | 55.64 | 0.989 |
| 6 | 12 | 12 | 461.425 | 4.372 | 663.086 | 215.94 | 0.994 |
| 6 | 12 | 14 | 91.083 | 3.332 | 118.804 | 266.05 | 0.867 |
| 6 | 12 | 16 | 553.521 | 4.620 | 739.599 | 274.64 | 0.996 |
| 6 | 12 | 18 | 106.795 | 3.707 | 146.713 | 130.97 | 0.798 |
| 6 | 12 | 20 | 351.473 | 3.279 | 452.950 | 80.20 | 0.993 |
| 6 | 12 | 22 | 192.130 | 3.202 | 258.468 | 106.09 | 0.982 |
| 6 | 12 | 24 | 185.124 | 3.241 | 293.911 | 292.80 | 0.952 |
| 6 | 12 | 26 | 167.087 | 4.042 | 250.281 | 248.19 | 0.955 |
| 6 | 12 | 28 | 507.612 | 4.743 | 704.636 | 313.62 | 0.995 |
| 6 | 12 | 30 | 278.580 | 3.865 | 302.841 | 81.27 | 0.991 |
| 6 | 12 | 32 | 124.087 | 6.791 | 195.356 | 153.96 | 0.940 |
| 6 | 12 | 34 | 68.155 | 10.650 | 72.256 | 141.46 | 0.804 |
| 6 | 12 | 36 | 41.588 | 12.301 | 3.680 | 167.00 | 0.623 |
| 6 | 12 | 38 | 99.597 | 8.895 | 159.872 | 337.82 | 0.860 |
| 6 | 12 | 40 | 40.952 | 12.894 | 9.573 | 248.14 | 0.177 |
| 6 | 13 | 1 | 241.292 | 2.412 | 341.503 | 59.54 | 0.980 |
| 6 | 13 | 3 | 105.525 | 3.117 | 150.859 | 279.54 | 0.714 |

| | | | | | | | |
|---|---|---|---|---|---|---|---|
| 6 | 13 | 5 | 324.258 | 3.231 | 422.708 | 71.18 | 0.990 |
| 6 | 13 | 7 | 197.241 | 2.320 | 268.068 | 188.44 | 0.974 |
| 6 | 13 | 9 | 220.464 | 2.648 | 316.476 | 129.29 | 0.975 |
| 6 | 13 | 11 | 88.437 | 4.025 | 103.486 | 304.81 | 0.806 |
| 6 | 13 | 13 | 120.718 | 2.870 | 173.319 | 84.10 | 0.902 |
| 6 | 13 | 15 | 135.625 | 3.127 | 132.459 | 279.08 | 0.942 |
| 6 | 13 | 17 | 428.940 | 3.876 | 525.996 | 327.81 | 0.994 |
| 6 | 13 | 19 | 215.269 | 2.930 | 286.946 | 144.33 | 0.978 |
| 6 | 13 | 21 | 68.584 | 5.742 | 22.992 | 123.40 | 0.837 |
| 6 | 13 | 23 | 39.065 | 9.283 | 14.779 | 75.04 | 0.342 |
| 6 | 13 | 25 | 97.032 | 5.475 | 121.435 | 356.25 | 0.848 |
| 6 | 13 | 27 | 139.992 | 5.455 | 185.055 | 305.52 | 0.931 |
| 6 | 13 | 29 | 235.995 | 4.755 | 288.900 | 122.55 | 0.986 |
| 6 | 13 | 31 | 91.114 | 8.241 | 115.431 | 48.88 | 0.860 |
| 6 | 13 | 33 | 68.936 | 11.205 | 66.512 | 82.46 | 0.842 |
| 6 | 13 | 35 | 39.852 | 11.054 | 4.396 | 350.78 | 0.252 |
| 6 | 13 | 37 | 81.977 | 9.498 | 115.836 | 265.91 | 0.813 |
| 6 | 13 | 39 | 45.125 | 13.970 | 21.151 | 301.67 | 0.797 |
| 6 | 13 | 41 | 51.799 | 21.694 | 18.763 | 339.55 | 0.487 |
| 6 | 14 | 0 | 303.280 | 4.033 | 425.846 | 0.00 | 1.000 |
| 6 | 14 | 2 | 384.589 | 3.427 | 564.222 | 184.78 | 0.992 |
| 6 | 14 | 4 | 243.505 | 2.582 | 344.603 | 124.94 | 0.989 |
| 6 | 14 | 6 | 303.962 | 2.922 | 518.905 | 89.05 | 0.984 |
| 6 | 14 | 8 | 361.052 | 3.145 | 489.321 | 113.93 | 0.993 |
| 6 | 14 | 10 | 364.457 | 3.509 | 441.383 | 306.43 | 0.993 |
| 6 | 14 | 12 | 279.037 | 2.933 | 531.303 | 8.89 | 0.970 |
| 6 | 14 | 14 | 37.821 | 8.613 | 27.307 | 173.04 | 0.219 |
| 6 | 14 | 16 | 238.509 | 2.767 | 340.366 | 106.99 | 0.988 |
| 6 | 14 | 18 | 578.528 | 5.513 | 827.599 | 260.71 | 0.997 |
| 6 | 14 | 20 | 248.427 | 2.957 | 382.248 | 243.32 | 0.983 |
| 6 | 14 | 22 | 182.031 | 3.517 | 227.832 | 327.40 | 0.978 |
| 6 | 14 | 24 | 312.771 | 3.383 | 461.780 | 309.73 | 0.988 |
| 6 | 14 | 26 | 165.411 | 4.199 | 196.690 | 225.98 | 0.960 |
| 6 | 14 | 28 | 372.136 | 3.838 | 517.982 | 79.38 | 0.994 |
| 6 | 14 | 30 | 138.533 | 5.145 | 124.329 | 162.48 | 0.966 |
| 6 | 14 | 32 | 81.566 | 9.612 | 67.835 | 126.96 | 0.913 |
| 6 | 14 | 34 | 66.725 | 10.602 | 75.596 | 312.09 | 0.830 |
| 6 | 14 | 36 | 39.379 | 11.120 | 3.546 | 156.73 | 0.677 |
| 6 | 14 | 38 | 68.921 | 13.549 | 58.488 | 269.88 | 0.924 |
| 6 | 14 | 40 | 40.322 | 19.359 | 1.619 | 100.77 | 0.049 |
| 6 | 15 | 1 | 289.580 | 2.725 | 448.529 | 58.95 | 0.984 |
| 6 | 15 | 3 | 301.461 | 4.557 | 372.978 | 227.68 | 0.989 |
| 6 | 15 | 5 | 269.723 | 2.790 | 446.933 | 298.19 | 0.979 |
| 6 | 15 | 7 | 69.589 | 3.753 | 51.942 | 178.47 | 0.498 |
| 6 | 15 | 9 | 107.485 | 3.259 | 125.507 | 232.38 | 0.895 |
| 6 | 15 | 11 | 179.505 | 2.793 | 224.328 | 215.89 | 0.966 |
| 6 | 15 | 13 | 375.325 | 3.622 | 512.176 | 203.09 | 0.991 |
| 6 | 15 | 15 | 201.822 | 2.896 | 343.608 | 266.78 | 0.967 |
| 6 | 15 | 17 | 262.949 | 2.959 | 385.098 | 45.10 | 0.985 |
| 6 | 15 | 19 | 458.219 | 4.397 | 676.411 | 34.30 | 0.995 |
| 6 | 15 | 21 | 277.288 | 3.038 | 340.127 | 337.56 | 0.989 |
| 6 | 15 | 23 | 426.157 | 4.032 | 593.662 | 255.20 | 0.994 |
| 6 | 15 | 25 | 203.129 | 3.424 | 280.698 | 240.38 | 0.971 |
| 6 | 15 | 27 | 241.959 | 4.279 | 309.932 | 28.27 | 0.987 |
| 6 | 15 | 29 | 243.255 | 4.492 | 324.468 | 316.85 | 0.986 |
| 6 | 15 | 31 | 63.170 | 10.331 | 42.698 | 207.12 | 0.859 |
| 6 | 15 | 33 | 76.064 | 9.017 | 78.106 | 91.08 | 0.877 |
| 6 | 15 | 35 | 194.501 | 4.530 | 369.506 | 144.35 | 0.970 |
| 6 | 15 | 37 | 40.691 | 13.016 | 3.801 | 348.80 | 0.441 |
| 6 | 15 | 39 | 53.041 | 15.989 | 42.798 | 106.91 | 0.646 |
| 6 | 16 | 0 | 278.037 | 4.012 | 390.223 | 0.00 | 1.000 |
| 6 | 16 | 2 | 135.704 | 3.162 | 159.645 | 154.52 | 0.970 |
| 6 | 16 | 4 | 331.090 | 3.371 | 452.761 | 271.73 | 0.991 |
| 6 | 16 | 6 | 217.078 | 2.401 | 349.211 | 289.61 | 0.965 |
| 6 | 16 | 8 | 345.017 | 3.085 | 460.867 | 84.85 | 0.992 |
| 6 | 16 | 10 | 160.145 | 2.967 | 247.316 | 259.64 | 0.971 |
| 6 | 16 | 12 | 280.589 | 3.121 | 381.831 | 347.17 | 0.988 |
| 6 | 16 | 14 | 306.372 | 3.308 | 465.407 | 114.86 | 0.989 |
| 6 | 16 | 16 | 326.539 | 3.198 | 468.205 | 18.69 | 0.990 |
| 6 | 16 | 18 | 360.793 | 3.699 | 524.019 | 86.70 | 0.992 |
| 6 | 16 | 20 | 291.667 | 3.499 | 429.642 | 160.66 | 0.986 |
| 6 | 16 | 22 | 197.414 | 3.359 | 239.059 | 132.63 | 0.979 |
| 6 | 16 | 24 | 219.815 | 3.269 | 310.617 | 174.51 | 0.974 |
| 6 | 16 | 26 | 105.066 | 8.472 | 144.416 | 181.56 | 0.898 |
| 6 | 16 | 28 | 60.913 | 9.825 | 16.776 | 301.51 | 0.486 |
| 6 | 16 | 30 | 104.833 | 8.465 | 152.259 | 22.16 | 0.925 |
| 6 | 16 | 32 | 74.001 | 10.680 | 89.094 | 135.22 | 0.779 |

| | | | | | | | |
|---|---|---|---|---|---|---|---|
| 6 | 16 | 34 | 46.612 | 12.748 | 7.922 | 112.13 | 0.792 |
| 6 | 16 | 36 | 54.018 | 13.456 | 33.574 | 239.98 | 0.736 |
| 6 | 16 | 38 | 58.683 | 16.620 | 54.893 | 164.37 | 0.723 |
| 6 | 17 | 1 | 487.138 | 3.843 | 612.250 | 354.33 | 0.995 |
| 6 | 17 | 3 | 89.685 | 4.624 | 115.929 | 195.20 | 0.926 |
| 6 | 17 | 5 | 111.883 | 3.830 | 40.984 | 271.80 | 0.951 |
| 6 | 17 | 7 | 284.520 | 3.138 | 381.462 | 99.14 | 0.986 |
| 6 | 17 | 9 | 107.070 | 3.195 | 132.305 | 339.46 | 0.939 |
| 6 | 17 | 11 | 309.309 | 3.249 | 417.527 | 18.32 | 0.990 |
| 6 | 17 | 13 | 146.155 | 3.885 | 236.536 | 223.38 | 0.911 |
| 6 | 17 | 15 | 543.037 | 5.015 | 806.206 | 89.00 | 0.996 |
| 6 | 17 | 17 | 297.276 | 3.582 | 438.482 | 110.21 | 0.988 |
| 6 | 17 | 19 | 149.675 | 4.743 | 199.041 | 73.30 | 0.952 |
| 6 | 17 | 21 | 51.807 | 9.982 | 2.305 | 319.52 | 0.593 |
| 6 | 17 | 23 | 62.969 | 10.167 | 38.965 | 126.93 | 0.507 |
| 6 | 17 | 25 | 393.357 | 4.204 | 569.140 | 127.06 | 0.994 |
| 6 | 17 | 27 | 303.393 | 4.096 | 404.570 | 84.80 | 0.991 |
| 6 | 17 | 29 | 205.443 | 3.892 | 293.301 | 205.06 | 0.985 |
| 6 | 17 | 31 | 49.403 | 11.733 | 13.179 | 44.12 | 0.206 |
| 6 | 17 | 33 | 263.255 | 3.892 | 391.508 | 49.36 | 0.990 |
| 6 | 17 | 35 | 40.501 | 11.252 | 6.268 | 35.05 | 0.264 |
| 6 | 17 | 37 | 58.651 | 14.641 | 49.831 | 220.61 | 0.869 |
| 6 | 18 | 0 | 49.210 | 12.294 | 50.162 | 180.00 | 0.729 |
| 6 | 18 | 2 | 368.863 | 3.444 | 493.241 | 190.32 | 0.991 |
| 6 | 18 | 4 | 345.720 | 3.617 | 484.020 | 251.51 | 0.990 |
| 6 | 18 | 6 | 56.719 | 7.777 | 22.211 | 186.26 | 0.408 |
| 6 | 18 | 8 | 546.078 | 4.564 | 660.616 | 187.00 | 0.997 |
| 6 | 18 | 10 | 268.486 | 2.908 | 407.892 | 228.64 | 0.986 |
| 6 | 18 | 12 | 708.852 | 6.092 | 1062.586 | 170.03 | 0.998 |
| 6 | 18 | 14 | 92.064 | 6.122 | 93.534 | 42.29 | 0.925 |
| 6 | 18 | 16 | 235.987 | 3.165 | 353.556 | 191.55 | 0.978 |
| 6 | 18 | 18 | 240.127 | 3.675 | 390.535 | 78.56 | 0.977 |
| 6 | 18 | 20 | 181.079 | 3.993 | 276.494 | 322.09 | 0.957 |
| 6 | 18 | 22 | 224.787 | 4.187 | 315.473 | 242.01 | 0.976 |
| 6 | 18 | 24 | 96.391 | 7.621 | 96.341 | 149.01 | 0.920 |
| 6 | 18 | 26 | 152.565 | 5.021 | 218.361 | 123.91 | 0.960 |
| 6 | 18 | 28 | 171.505 | 6.276 | 206.800 | 175.02 | 0.981 |
| 6 | 18 | 30 | 151.147 | 4.877 | 215.618 | 46.37 | 0.970 |
| 6 | 18 | 32 | 51.359 | 12.075 | 27.588 | 112.58 | 0.616 |
| 6 | 18 | 34 | 90.981 | 10.212 | 139.403 | 275.64 | 0.869 |
| 6 | 18 | 36 | 61.573 | 16.046 | 65.450 | 81.06 | 0.715 |
| 6 | 18 | 38 | 66.029 | 23.091 | 42.889 | 40.51 | 0.521 |
| 6 | 19 | 1 | 298.508 | 2.968 | 466.742 | 155.62 | 0.988 |
| 6 | 19 | 3 | 223.687 | 3.239 | 307.137 | 205.82 | 0.981 |
| 6 | 19 | 5 | 251.198 | 3.326 | 314.230 | 160.70 | 0.988 |
| 6 | 19 | 7 | 114.873 | 4.518 | 70.017 | 177.67 | 0.961 |
| 6 | 19 | 9 | 410.875 | 3.608 | 585.608 | 185.94 | 0.994 |
| 6 | 19 | 11 | 494.213 | 4.255 | 802.676 | 164.40 | 0.995 |
| 6 | 19 | 13 | 83.630 | 5.798 | 97.176 | 301.71 | 0.674 |
| 6 | 19 | 15 | 284.599 | 3.534 | 470.272 | 280.09 | 0.985 |
| 6 | 19 | 17 | 131.106 | 5.048 | 180.233 | 39.04 | 0.663 |
| 6 | 19 | 19 | 183.690 | 4.078 | 226.827 | 204.43 | 0.967 |
| 6 | 19 | 21 | 287.815 | 3.572 | 338.644 | 229.50 | 0.988 |
| 6 | 19 | 23 | 51.229 | 13.244 | 10.159 | 104.35 | 0.411 |
| 6 | 19 | 25 | 242.106 | 5.242 | 243.927 | 98.77 | 0.989 |
| 6 | 19 | 27 | 235.333 | 3.565 | 359.011 | 269.43 | 0.987 |
| 6 | 19 | 29 | 134.434 | 7.260 | 159.338 | 278.53 | 0.969 |
| 6 | 19 | 31 | 174.776 | 4.809 | 272.079 | 262.44 | 0.975 |
| 6 | 19 | 33 | 58.045 | 14.358 | 25.034 | 241.77 | 0.268 |
| 6 | 19 | 35 | 51.657 | 15.529 | 40.292 | 274.17 | 0.810 |
| 6 | 19 | 37 | 69.719 | 26.305 | 37.748 | 175.86 | 0.832 |
| 6 | 20 | 0 | 145.846 | 4.742 | 204.284 | 0.00 | 0.999 |
| 6 | 20 | 2 | 62.793 | 6.281 | 32.302 | 264.73 | 0.802 |
| 6 | 20 | 4 | 266.082 | 3.160 | 403.996 | 0.38 | 0.984 |
| 6 | 20 | 6 | 73.301 | 8.982 | 54.462 | 191.80 | 0.811 |
| 6 | 20 | 8 | 450.202 | 4.179 | 690.511 | 164.88 | 0.995 |
| 6 | 20 | 10 | 222.992 | 3.155 | 346.921 | 258.39 | 0.978 |
| 6 | 20 | 12 | 293.616 | 3.105 | 485.300 | 92.98 | 0.985 |
| 6 | 20 | 14 | 94.769 | 5.243 | 104.707 | 174.26 | 0.921 |
| 6 | 20 | 16 | 376.685 | 3.818 | 569.489 | 355.03 | 0.991 |
| 6 | 20 | 18 | 139.753 | 4.429 | 219.406 | 277.95 | 0.889 |
| 6 | 20 | 20 | 200.049 | 4.132 | 292.892 | 229.22 | 0.969 |
| 6 | 20 | 22 | 229.738 | 3.765 | 349.130 | 227.92 | 0.982 |
| 6 | 20 | 24 | 296.974 | 5.224 | 440.604 | 32.72 | 0.993 |
| 6 | 20 | 26 | 75.143 | 13.792 | 54.462 | 257.76 | 0.911 |
| 6 | 20 | 28 | 198.350 | 4.183 | 265.083 | 338.99 | 0.985 |
| 6 | 20 | 30 | 138.198 | 6.170 | 191.593 | 247.17 | 0.964 |

| | | | | | | | |
|---|---|---|---|---|---|---|---|
| 6 | 20 | 32 | 54.091 | 11.998 | 43.723 | 28.80 | 0.752 |
| 6 | 20 | 34 | 34.471 | 11.507 | 11.892 | 54.03 | 0.513 |
| 6 | 20 | 36 | 53.234 | 23.640 | 10.891 | 158.33 | 0.245 |
| 6 | 21 | 1 | 329.298 | 3.219 | 466.355 | 128.56 | 0.991 |
| 6 | 21 | 3 | 207.639 | 3.785 | 243.927 | 180.42 | 0.981 |
| 6 | 21 | 5 | 391.880 | 3.748 | 600.017 | 20.61 | 0.993 |
| 6 | 21 | 7 | 218.529 | 3.337 | 344.100 | 195.12 | 0.974 |
| 6 | 21 | 9 | 110.547 | 4.802 | 135.259 | 179.08 | 0.946 |
| 6 | 21 | 11 | 248.196 | 3.075 | 406.266 | 46.79 | 0.980 |
| 6 | 21 | 13 | 251.603 | 3.281 | 366.597 | 58.88 | 0.982 |
| 6 | 21 | 15 | 306.317 | 3.361 | 479.589 | 272.33 | 0.987 |
| 6 | 21 | 17 | 218.015 | 5.844 | 259.418 | 324.09 | 0.980 |
| 6 | 21 | 19 | 59.106 | 11.112 | 43.385 | 159.94 | 0.720 |
| 6 | 21 | 21 | 154.488 | 4.657 | 204.462 | 8.01 | 0.967 |
| 6 | 21 | 23 | 155.743 | 7.975 | 133.879 | 276.46 | 0.982 |
| 6 | 21 | 25 | 119.002 | 7.409 | 100.127 | 37.28 | 0.969 |
| 6 | 21 | 27 | 51.566 | 12.834 | 27.887 | 207.23 | 0.801 |
| 6 | 21 | 29 | 38.516 | 11.038 | 4.076 | 13.20 | 0.408 |
| 6 | 21 | 31 | 85.729 | 10.476 | 125.136 | 132.04 | 0.869 |
| 6 | 21 | 33 | 41.925 | 13.567 | 21.592 | 332.13 | 0.649 |
| 6 | 21 | 35 | 59.645 | 23.155 | 38.548 | 54.64 | 0.620 |
| 6 | 22 | 0 | 202.671 | 4.423 | 283.919 | 0.00 | 1.000 |
| 6 | 22 | 2 | 129.209 | 4.903 | 183.886 | 108.25 | 0.937 |
| 6 | 22 | 4 | 297.952 | 3.212 | 350.771 | 37.43 | 0.991 |
| 6 | 22 | 6 | 269.591 | 3.823 | 311.393 | 81.48 | 0.989 |
| 6 | 22 | 8 | 232.600 | 3.257 | 325.234 | 252.31 | 0.982 |
| 6 | 22 | 10 | 191.765 | 3.346 | 212.903 | 330.23 | 0.976 |
| 6 | 22 | 12 | 118.878 | 4.542 | 92.574 | 25.96 | 0.941 |
| 6 | 22 | 14 | 64.340 | 9.388 | 5.204 | 258.98 | 0.805 |
| 6 | 22 | 16 | 111.042 | 6.092 | 121.338 | 4.07 | 0.912 |
| 6 | 22 | 18 | 240.892 | 4.626 | 370.108 | 322.13 | 0.984 |
| 6 | 22 | 20 | 206.019 | 3.965 | 275.022 | 239.01 | 0.982 |
| 6 | 22 | 22 | 89.086 | 8.847 | 123.208 | 40.89 | 0.647 |
| 6 | 22 | 24 | 110.703 | 8.302 | 120.922 | 9.11 | 0.956 |
| 6 | 22 | 26 | 110.792 | 7.354 | 122.946 | 215.23 | 0.955 |
| 6 | 22 | 28 | 70.422 | 15.555 | 81.201 | 248.44 | 0.793 |
| 6 | 22 | 30 | 65.895 | 13.194 | 52.917 | 163.38 | 0.873 |
| 6 | 22 | 32 | 38.814 | 12.388 | 10.154 | 229.70 | 0.769 |
| 6 | 22 | 34 | 53.122 | 22.972 | 18.572 | 12.31 | 0.692 |
| 6 | 23 | 1 | 475.294 | 4.074 | 716.552 | 2.70 | 0.995 |
| 6 | 23 | 3 | 252.340 | 3.894 | 350.080 | 357.24 | 0.985 |
| 6 | 23 | 5 | 129.958 | 4.936 | 170.049 | 285.10 | 0.937 |
| 6 | 23 | 7 | 280.493 | 3.934 | 358.266 | 209.69 | 0.988 |
| 6 | 23 | 9 | 230.058 | 3.350 | 305.435 | 322.16 | 0.982 |
| 6 | 23 | 11 | 291.626 | 3.669 | 438.755 | 247.99 | 0.986 |
| 6 | 23 | 13 | 63.935 | 10.416 | 18.937 | 351.41 | 0.288 |
| 6 | 23 | 15 | 84.064 | 7.753 | 92.130 | 336.98 | 0.898 |
| 6 | 23 | 17 | 274.724 | 4.076 | 385.606 | 72.04 | 0.990 |
| 6 | 23 | 19 | 228.151 | 4.403 | 311.716 | 345.99 | 0.989 |
| 6 | 23 | 21 | 35.793 | 10.850 | 64.658 | 20.51 | 0.802 |
| 6 | 23 | 23 | 109.815 | 6.578 | 107.732 | 318.66 | 0.964 |
| 6 | 23 | 25 | 55.441 | 11.160 | 35.260 | 114.84 | 0.799 |
| 6 | 23 | 27 | 115.002 | 8.492 | 209.843 | 24.05 | 0.870 |
| 6 | 23 | 29 | 35.901 | 11.845 | 16.399 | 139.83 | 0.680 |
| 6 | 23 | 31 | 108.303 | 12.594 | 148.119 | 25.27 | 0.961 |
| 6 | 23 | 33 | 64.783 | 23.956 | 41.311 | 241.80 | 0.836 |
| 6 | 24 | 0 | 108.765 | 8.244 | 60.870 | 0.00 | 0.400 |
| 6 | 24 | 2 | 81.967 | 6.183 | 82.657 | 206.21 | 0.822 |
| 6 | 24 | 4 | 192.001 | 3.546 | 259.150 | 3.39 | 0.971 |
| 6 | 24 | 6 | 40.089 | 11.743 | 54.230 | 310.60 | 0.626 |
| 6 | 24 | 8 | 230.749 | 5.084 | 332.094 | 191.93 | 0.978 |
| 6 | 24 | 10 | 358.093 | 3.861 | 485.119 | 291.55 | 0.992 |
| 6 | 24 | 12 | 238.147 | 3.844 | 358.544 | 19.54 | 0.985 |
| 6 | 24 | 14 | 80.101 | 8.725 | 94.924 | 117.43 | 0.846 |
| 6 | 24 | 16 | 310.053 | 3.731 | 412.869 | 7.03 | 0.992 |
| 6 | 24 | 18 | 188.929 | 4.047 | 237.462 | 42.43 | 0.986 |
| 6 | 24 | 20 | 49.357 | 12.917 | 0.743 | 341.45 | 0.831 |
| 6 | 24 | 22 | 78.206 | 9.525 | 111.670 | 134.75 | 0.773 |
| 6 | 24 | 24 | 121.715 | 6.677 | 105.592 | 48.40 | 0.970 |
| 6 | 24 | 26 | 228.726 | 4.478 | 347.047 | 277.09 | 0.989 |
| 6 | 24 | 28 | 88.893 | 14.576 | 138.737 | 159.54 | 0.915 |
| 6 | 24 | 30 | 46.961 | 14.833 | 15.514 | 322.41 | 0.228 |
| 6 | 24 | 32 | 42.720 | 21.009 | 9.990 | 116.24 | 0.699 |
| 6 | 25 | 1 | 364.677 | 3.787 | 520.741 | 43.09 | 0.992 |
| 6 | 25 | 3 | 246.629 | 3.993 | 405.103 | 139.45 | 0.975 |
| 6 | 25 | 5 | 247.680 | 3.945 | 447.733 | 356.88 | 0.972 |
| 6 | 25 | 7 | 234.352 | 4.222 | 305.976 | 105.54 | 0.987 |

| | | | | | | | |
|---|---|---|---|---|---|---|---|
| 6 | 25 | 9 | 195.729 | 4.500 | 321.570 | 330.47 | 0.972 |
| 6 | 25 | 11 | 147.431 | 5.754 | 206.716 | 300.16 | 0.960 |
| 6 | 25 | 13 | 56.006 | 12.947 | 7.010 | 230.39 | 0.809 |
| 6 | 25 | 15 | 58.108 | 12.146 | 36.612 | 262.76 | 0.856 |
| 6 | 25 | 17 | 173.014 | 5.219 | 293.585 | 180.88 | 0.973 |
| 6 | 25 | 19 | 35.540 | 10.589 | 3.278 | 31.61 | 0.306 |
| 6 | 25 | 21 | 102.536 | 7.153 | 128.965 | 249.02 | 0.943 |
| 6 | 25 | 23 | 36.626 | 11.702 | 4.563 | 149.47 | 0.220 |
| 6 | 25 | 25 | 176.424 | 5.938 | 366.246 | 351.48 | 0.947 |
| 6 | 25 | 27 | 159.322 | 11.763 | 251.224 | 216.59 | 0.980 |
| 6 | 25 | 29 | 73.190 | 14.197 | 73.632 | 273.75 | 0.928 |
| 6 | 25 | 31 | 64.631 | 27.445 | 25.653 | 129.86 | 0.583 |
| 6 | 26 | 0 | 254.772 | 5.634 | 356.202 | 0.00 | 1.000 |
| 6 | 26 | 2 | 104.612 | 7.831 | 110.337 | 234.77 | 0.938 |
| 6 | 26 | 4 | 391.249 | 4.436 | 581.551 | 297.62 | 0.995 |
| 6 | 26 | 6 | 92.321 | 9.653 | 83.363 | 49.40 | 0.923 |
| 6 | 26 | 8 | 340.753 | 5.024 | 417.142 | 167.36 | 0.994 |
| 6 | 26 | 10 | 248.882 | 4.643 | 368.488 | 273.89 | 0.987 |
| 6 | 26 | 12 | 198.149 | 4.216 | 365.971 | 248.68 | 0.976 |
| 6 | 26 | 14 | 96.124 | 6.144 | 164.012 | 272.18 | 0.878 |
| 6 | 26 | 16 | 45.114 | 10.942 | 14.656 | 111.51 | 0.644 |
| 6 | 26 | 18 | 131.317 | 5.557 | 176.475 | 180.54 | 0.966 |
| 6 | 26 | 20 | 180.914 | 5.155 | 245.650 | 258.48 | 0.983 |
| 6 | 26 | 22 | 74.788 | 11.609 | 90.842 | 61.76 | 0.884 |
| 6 | 26 | 24 | 174.963 | 8.047 | 256.103 | 13.90 | 0.981 |
| 6 | 26 | 26 | 151.079 | 7.878 | 211.328 | 347.63 | 0.984 |
| 6 | 26 | 28 | 42.697 | 14.084 | 17.570 | 207.95 | 0.803 |
| 6 | 26 | 30 | 92.954 | 30.292 | 66.504 | 38.87 | 0.768 |
| 6 | 27 | 1 | 52.115 | 11.794 | 29.705 | 121.66 | 0.602 |
| 6 | 27 | 3 | 137.132 | 6.180 | 180.629 | 217.12 | 0.963 |
| 6 | 27 | 5 | 102.650 | 7.358 | 157.044 | 262.63 | 0.931 |
| 6 | 27 | 7 | 263.908 | 3.955 | 355.128 | 44.78 | 0.993 |
| 6 | 27 | 9 | 159.072 | 5.313 | 268.644 | 214.59 | 0.969 |
| 6 | 27 | 11 | 190.987 | 5.607 | 276.270 | 179.42 | 0.984 |
| 6 | 27 | 13 | 122.139 | 5.547 | 232.779 | 16.84 | 0.907 |
| 6 | 27 | 15 | 109.227 | 5.415 | 112.439 | 52.67 | 0.966 |
| 6 | 27 | 17 | 34.541 | 10.548 | 6.804 | 207.64 | 0.454 |
| 6 | 27 | 19 | 140.771 | 5.186 | 230.005 | 81.79 | 0.967 |
| 6 | 27 | 21 | 86.510 | 11.905 | 95.459 | 210.20 | 0.932 |
| 6 | 27 | 23 | 39.781 | 12.900 | 24.897 | 299.68 | 0.542 |
| 6 | 27 | 25 | 71.968 | 22.729 | 66.930 | 346.25 | -0.871 |
| 6 | 27 | 27 | 53.850 | 14.236 | 21.199 | 267.53 | 0.298 |
| 6 | 28 | 0 | 110.450 | 8.175 | 153.900 | 180.00 | 1.000 |
| 6 | 28 | 2 | 87.451 | 8.758 | 91.162 | 230.81 | 0.934 |
| 6 | 28 | 4 | 31.907 | 9.999 | 13.425 | 330.27 | 0.424 |
| 6 | 28 | 6 | 225.133 | 5.458 | 341.144 | 60.44 | 0.988 |
| 6 | 28 | 8 | 132.331 | 7.128 | 132.187 | 122.68 | 0.975 |
| 6 | 28 | 10 | 61.429 | 13.340 | 57.061 | 255.80 | 0.819 |
| 6 | 28 | 12 | 164.879 | 6.081 | 251.181 | 154.05 | 0.977 |
| 6 | 28 | 14 | 43.195 | 11.638 | 7.773 | 166.13 | 0.126 |
| 6 | 28 | 16 | 163.548 | 4.508 | 242.157 | 134.05 | 0.977 |
| 6 | 28 | 18 | 132.547 | 5.517 | 191.964 | 38.86 | 0.969 |
| 6 | 28 | 20 | 105.879 | 11.970 | 156.297 | 230.64 | 0.935 |
| 6 | 28 | 22 | 64.255 | 13.144 | 35.727 | 61.15 | 0.938 |
| 6 | 28 | 24 | 131.507 | 9.878 | 204.512 | 148.89 | 0.974 |
| 6 | 28 | 26 | 63.365 | 24.857 | 35.530 | 22.64 | 0.605 |
| 6 | 29 | 1 | 104.273 | 6.392 | 90.095 | 172.08 | 0.963 |
| 6 | 29 | 3 | 58.697 | 11.435 | 62.955 | 14.38 | 0.724 |
| 6 | 29 | 5 | 131.426 | 5.492 | 203.580 | 272.70 | 0.962 |
| 6 | 29 | 7 | 58.986 | 11.405 | 46.052 | 162.57 | 0.849 |
| 6 | 29 | 9 | 30.676 | 9.724 | 3.498 | 257.08 | 0.304 |
| 6 | 29 | 11 | 115.529 | 7.668 | 155.112 | 134.88 | 0.956 |
| 6 | 29 | 13 | 102.013 | 6.607 | 166.724 | 308.70 | 0.933 |
| 6 | 29 | 15 | 73.887 | 11.515 | 105.308 | 306.29 | 0.852 |
| 6 | 29 | 17 | 68.787 | 12.460 | 90.036 | 261.62 | 0.775 |
| 6 | 29 | 19 | 53.810 | 13.744 | 58.709 | 310.09 | 0.769 |
| 6 | 29 | 21 | 133.588 | 10.377 | 247.468 | 260.95 | 0.945 |
| 6 | 29 | 23 | 44.321 | 14.863 | 20.911 | 163.38 | 0.809 |
| 6 | 29 | 25 | 65.585 | 23.686 | 10.339 | 353.85 | 0.150 |
| 6 | 30 | 0 | 26.162 | 12.599 | 7.322 | 0.00 | 0.203 |
| 6 | 30 | 2 | 56.376 | 12.489 | 28.562 | 173.61 | 0.307 |
| 6 | 30 | 4 | 91.028 | 7.813 | 99.263 | 239.54 | 0.940 |
| 6 | 30 | 6 | 61.817 | 12.082 | 62.935 | 331.99 | 0.784 |
| 6 | 30 | 8 | 125.616 | 6.711 | 216.129 | 66.12 | 0.947 |
| 6 | 30 | 10 | 41.070 | 12.859 | 11.003 | 268.40 | 0.533 |
| 6 | 30 | 12 | 51.330 | 13.790 | 31.687 | 34.90 | 0.789 |
| 6 | 30 | 14 | 50.912 | 12.056 | 34.171 | 163.96 | 0.601 |

| | | | | | | |
|---|---|---|---|---|---|---|
| 6 | 30 | 16 | 70.429 | 15.008 | 90.717 | 244.07 | 0.905 |
| 6 | 30 | 18 | 47.521 | 13.861 | 35.157 | 226.62 | 0.817 |
| 6 | 30 | 20 | 95.006 | 13.158 | 81.281 | 243.88 | 0.967 |
| 6 | 30 | 22 | 52.990 | 24.129 | 17.801 | 64.52 | 0.587 |
| 6 | 31 | 1 | 59.524 | 12.850 | 60.106 | 49.66 | 0.823 |
| 6 | 31 | 3 | 73.065 | 11.793 | 80.138 | 74.25 | 0.546 |
| 6 | 31 | 5 | 48.826 | 12.907 | 11.092 | 228.95 | 0.838 |
| 6 | 31 | 7 | 104.579 | 7.462 | 112.527 | 258.66 | 0.963 |
| 6 | 31 | 9 | 48.908 | 12.114 | 32.443 | 356.62 | 0.659 |
| 6 | 31 | 11 | 43.204 | 12.495 | 9.460 | 272.10 | 0.742 |
| 6 | 31 | 13 | 83.109 | 12.469 | 120.038 | 113.24 | 0.933 |
| 6 | 31 | 15 | 51.502 | 12.469 | 39.085 | 181.41 | 0.878 |
| 6 | 31 | 17 | 62.141 | 16.250 | 58.866 | 106.43 | 0.885 |
| 6 | 31 | 19 | 54.721 | 13.905 | 55.011 | 7.61 | 0.655 |
| 6 | 32 | 0 | 119.558 | 12.158 | 163.113 | 0.00 | 1.000 |
| 6 | 32 | 2 | 36.976 | 11.452 | 0.985 | 9.66 | 0.448 |
| 6 | 32 | 4 | 49.599 | 13.730 | 30.503 | 325.27 | 0.616 |
| 6 | 32 | 6 | 42.764 | 14.015 | 22.792 | 57.66 | 0.810 |
| 6 | 32 | 8 | 55.276 | 13.504 | 62.615 | 293.70 | 0.854 |
| 6 | 32 | 10 | 64.267 | 14.980 | 82.775 | 27.02 | 0.848 |
| 6 | 32 | 12 | 58.312 | 17.241 | 59.547 | 5.66 | 0.693 |
| 6 | 32 | 14 | 65.969 | 21.459 | 35.291 | 244.41 | 0.381 |
| 6 | 32 | 16 | 55.008 | 22.036 | 33.827 | 64.29 | 0.583 |
| 6 | 32 | 18 | 53.562 | 20.834 | 28.113 | 322.18 | 0.644 |
| 6 | 33 | 1 | 62.732 | 16.420 | 73.415 | 212.57 | 0.864 |
| 6 | 33 | 3 | 52.146 | 13.337 | 39.763 | 329.00 | 0.879 |
| 6 | 33 | 5 | 58.927 | 11.796 | 81.350 | 251.25 | 0.803 |
| 6 | 33 | 7 | 107.016 | 8.011 | 169.465 | 83.91 | 0.965 |
| 6 | 33 | 9 | 44.742 | 13.393 | 35.121 | 74.39 | 0.559 |
| 6 | 33 | 11 | 86.293 | 11.460 | 136.258 | 71.39 | 0.931 |
| 6 | 33 | 13 | 38.433 | 17.330 | 6.886 | 179.62 | 0.532 |
| 6 | 34 | 0 | 44.421 | 27.133 | 22.987 | 180.00 | 0.467 |
| 6 | 34 | 2 | 38.229 | 11.863 | 6.503 | 276.12 | 0.840 |
| 6 | 34 | 4 | 64.418 | 11.704 | 93.978 | 284.53 | 0.858 |
| 6 | 34 | 6 | 42.254 | 13.027 | 30.052 | 114.36 | 0.632 |
| 6 | 34 | 8 | 38.213 | 17.492 | 5.152 | 146.36 | 0.235 |
| 6 | 34 | 10 | 35.927 | 17.367 | 5.861 | 62.93 | 0.216 |
| 7 | 0 | 1 | 614.697 | 9.554 | 866.225 | 0.00 | 1.000 |
| 7 | 0 | 3 | 75.884 | 1.911 | 87.308 | 180.00 | 0.816 |
| 7 | 0 | 5 | 649.362 | 8.712 | 913.768 | 180.00 | 1.000 |
| 7 | 0 | 7 | 545.728 | 6.071 | 766.732 | 0.00 | 1.000 |
| 7 | 0 | 9 | 299.944 | 3.576 | 420.744 | 180.00 | 1.000 |
| 7 | 0 | 11 | 372.645 | 5.110 | 520.838 | 180.00 | 1.000 |
| 7 | 0 | 13 | 62.977 | 8.114 | 53.565 | 180.00 | 0.627 |
| 7 | 0 | 15 | 340.971 | 5.087 | 473.717 | 0.00 | 1.000 |
| 7 | 0 | 17 | 197.015 | 3.423 | 272.193 | 180.00 | 1.000 |
| 7 | 0 | 19 | 405.954 | 4.800 | 558.796 | 0.00 | 1.000 |
| 7 | 0 | 21 | 27.327 | 10.972 | 0.712 | 180.00 | 0.019 |
| 7 | 0 | 23 | 72.877 | 7.422 | 37.943 | 180.00 | 0.385 |
| 7 | 0 | 25 | 544.569 | 6.444 | 736.978 | 0.00 | 1.000 |
| 7 | 0 | 27 | 121.453 | 6.601 | 163.230 | 0.00 | 1.000 |
| 7 | 0 | 29 | 256.104 | 4.847 | 341.779 | 180.00 | 1.000 |
| 7 | 0 | 31 | 33.130 | 13.882 | 24.629 | 180.00 | 0.577 |
| 7 | 0 | 33 | 68.645 | 19.442 | 39.796 | 180.00 | 0.445 |
| 7 | 0 | 35 | 35.058 | 16.801 | 15.051 | 0.00 | 0.335 |
| 7 | 0 | 37 | 48.008 | 15.741 | 58.704 | 0.00 | 0.964 |
| 7 | 0 | 39 | 92.878 | 14.610 | 41.072 | 180.00 | 0.352 |
| 7 | 0 | 41 | 62.231 | 19.493 | 44.256 | 0.00 | 0.589 |
| 7 | 0 | 43 | 70.403 | 30.055 | 74.106 | 180.00 | 1.000 |
| 7 | 1 | 0 | 79.775 | 3.420 | 71.161 | 0.00 | 0.633 |
| 7 | 1 | 2 | 529.090 | 4.994 | 783.213 | 264.79 | 0.981 |
| 7 | 1 | 4 | 438.885 | 3.472 | 543.257 | 230.25 | 0.979 |
| 7 | 1 | 6 | 110.177 | 1.825 | 133.356 | 243.88 | 0.889 |
| 7 | 1 | 8 | 524.483 | 4.194 | 851.836 | 217.83 | 0.993 |
| 7 | 1 | 10 | 552.174 | 4.492 | 724.847 | 318.26 | 0.996 |
| 7 | 1 | 12 | 128.391 | 1.974 | 121.617 | 169.62 | 0.945 |
| 7 | 1 | 14 | 193.652 | 2.209 | 282.238 | 219.57 | 0.840 |
| 7 | 1 | 16 | 323.922 | 3.213 | 511.428 | 146.72 | 0.986 |
| 7 | 1 | 18 | 66.286 | 4.669 | 56.560 | 327.30 | 0.627 |
| 7 | 1 | 20 | 117.880 | 3.689 | 152.862 | 27.06 | 0.895 |
| 7 | 1 | 22 | 260.813 | 2.751 | 388.744 | 253.49 | 0.981 |
| 7 | 1 | 24 | 185.204 | 2.831 | 236.041 | 22.74 | 0.972 |
| 7 | 1 | 26 | 578.414 | 5.037 | 792.831 | 254.37 | 0.997 |
| 7 | 1 | 28 | 600.569 | 5.131 | 766.878 | 343.59 | 0.997 |
| 7 | 1 | 30 | 30.487 | 9.631 | 34.689 | 218.99 | 0.247 |
| 7 | 1 | 32 | 269.982 | 3.879 | 361.902 | 200.15 | 0.982 |
| 7 | 1 | 34 | 54.848 | 13.611 | 19.508 | 224.23 | 0.360 |

| | | | | | | | |
|---|---|---|---|---|---|---|---|
| 7 | 1 | 36 | 233.389 | 4.107 | 253.169 | 115.71 | 0.990 |
| 7 | 1 | 38 | 184.155 | 5.917 | 259.429 | 340.20 | 0.979 |
| 7 | 1 | 40 | 41.781 | 11.631 | 14.229 | 152.95 | 0.550 |
| 7 | 1 | 42 | 64.057 | 14.924 | 54.219 | 197.48 | 0.897 |
| 7 | 2 | 1 | 237.380 | 2.405 | 334.426 | 167.56 | 0.989 |
| 7 | 2 | 3 | 1065.595 | 9.334 | 1507.585 | 140.85 | 0.995 |
| 7 | 2 | 5 | 496.200 | 4.145 | 727.298 | 183.46 | 0.984 |
| 7 | 2 | 7 | 529.550 | 4.160 | 814.048 | 278.68 | 0.994 |
| 7 | 2 | 9 | 277.958 | 2.613 | 378.311 | 86.48 | 0.982 |
| 7 | 2 | 11 | 275.874 | 2.502 | 371.180 | 1.08 | 0.991 |
| 7 | 2 | 13 | 377.139 | 3.354 | 571.242 | 196.61 | 0.991 |
| 7 | 2 | 15 | 159.489 | 2.254 | 187.474 | 144.36 | 0.953 |
| 7 | 2 | 17 | 303.689 | 3.122 | 449.168 | 31.51 | 0.988 |
| 7 | 2 | 19 | 442.631 | 3.926 | 626.618 | 137.35 | 0.994 |
| 7 | 2 | 21 | 388.212 | 3.584 | 563.780 | 30.56 | 0.991 |
| 7 | 2 | 23 | 186.442 | 3.010 | 208.582 | 259.48 | 0.977 |
| 7 | 2 | 25 | 408.257 | 3.768 | 526.139 | 338.36 | 0.995 |
| 7 | 2 | 27 | 365.298 | 3.530 | 468.443 | 100.21 | 0.992 |
| 7 | 2 | 29 | 137.086 | 4.544 | 179.080 | 225.32 | 0.942 |
| 7 | 2 | 31 | 144.801 | 5.435 | 181.512 | 27.00 | 0.949 |
| 7 | 2 | 33 | 153.393 | 5.199 | 220.058 | 317.64 | 0.956 |
| 7 | 2 | 35 | 223.473 | 4.377 | 279.411 | 26.17 | 0.988 |
| 7 | 2 | 37 | 113.028 | 7.707 | 171.542 | 179.59 | 0.928 |
| 7 | 2 | 39 | 58.229 | 11.390 | 47.361 | 82.81 | 0.654 |
| 7 | 2 | 41 | 65.188 | 16.152 | 41.521 | 252.16 | 0.460 |
| 7 | 2 | 43 | 51.686 | 16.951 | 37.404 | 300.73 | 0.689 |
| 7 | 3 | 0 | 1294.617 | 27.009 | 1820.908 | 180.00 | 1.000 |
| 7 | 3 | 2 | 136.029 | 1.718 | 145.066 | 318.64 | 0.760 |
| 7 | 3 | 4 | 108.147 | 1.425 | 126.068 | 72.47 | 0.942 |
| 7 | 3 | 6 | 71.972 | 2.591 | 79.450 | 192.28 | 0.783 |
| 7 | 3 | 8 | 565.527 | 4.770 | 783.949 | 24.64 | 0.996 |
| 7 | 3 | 10 | 87.822 | 2.540 | 119.275 | 344.25 | 0.918 |
| 7 | 3 | 12 | 540.720 | 4.821 | 742.459 | 185.88 | 0.995 |
| 7 | 3 | 14 | 214.132 | 2.571 | 283.809 | 212.23 | 0.976 |
| 7 | 3 | 16 | 152.477 | 2.348 | 183.659 | 50.43 | 0.974 |
| 7 | 3 | 18 | 220.641 | 2.548 | 305.775 | 35.98 | 0.979 |
| 7 | 3 | 20 | 285.946 | 2.829 | 408.475 | 20.91 | 0.981 |
| 7 | 3 | 22 | 210.111 | 2.876 | 261.633 | 112.18 | 0.975 |
| 7 | 3 | 24 | 157.238 | 3.457 | 216.262 | 164.35 | 0.953 |
| 7 | 3 | 26 | 363.963 | 3.309 | 455.964 | 64.20 | 0.993 |
| 7 | 3 | 28 | 439.328 | 3.960 | 553.253 | 102.52 | 0.995 |
| 7 | 3 | 30 | 185.498 | 3.797 | 207.086 | 310.64 | 0.969 |
| 7 | 3 | 32 | 81.110 | 8.330 | 51.567 | 143.72 | 0.835 |
| 7 | 3 | 34 | 159.146 | 5.920 | 193.659 | 295.89 | 0.968 |
| 7 | 3 | 36 | 84.593 | 10.346 | 79.124 | 331.07 | 0.918 |
| 7 | 3 | 38 | 46.585 | 12.842 | 9.341 | 295.38 | 0.613 |
| 7 | 3 | 40 | 44.594 | 12.242 | 10.502 | 22.23 | 0.208 |
| 7 | 3 | 42 | 53.658 | 13.882 | 40.193 | 229.52 | 0.834 |
| 7 | 4 | 1 | 280.056 | 2.680 | 383.172 | 70.98 | 0.951 |
| 7 | 4 | 3 | 381.267 | 3.095 | 490.021 | 296.83 | 0.992 |
| 7 | 4 | 5 | 425.797 | 3.723 | 575.464 | 338.20 | 0.994 |
| 7 | 4 | 7 | 444.934 | 3.545 | 669.730 | 204.87 | 0.993 |
| 7 | 4 | 9 | 785.386 | 7.295 | 1116.625 | 112.86 | 0.998 |
| 7 | 4 | 11 | 31.531 | 6.280 | 6.067 | 215.59 | 0.170 |
| 7 | 4 | 13 | 174.135 | 2.266 | 243.067 | 253.42 | 0.956 |
| 7 | 4 | 15 | 115.106 | 2.620 | 135.719 | 166.11 | 0.855 |
| 7 | 4 | 17 | 125.894 | 3.103 | 172.445 | 123.43 | 0.954 |
| 7 | 4 | 19 | 198.185 | 2.740 | 253.234 | 17.67 | 0.984 |
| 7 | 4 | 21 | 160.642 | 2.968 | 179.255 | 84.04 | 0.957 |
| 7 | 4 | 23 | 276.045 | 2.888 | 369.779 | 191.89 | 0.988 |
| 7 | 4 | 25 | 325.696 | 3.136 | 489.968 | 298.96 | 0.988 |
| 7 | 4 | 27 | 215.892 | 3.252 | 325.527 | 218.29 | 0.972 |
| 7 | 4 | 29 | 275.090 | 3.150 | 392.236 | 176.53 | 0.986 |
| 7 | 4 | 31 | 231.057 | 3.693 | 294.885 | 295.36 | 0.977 |
| 7 | 4 | 33 | 90.909 | 7.727 | 116.955 | 138.12 | 0.778 |
| 7 | 4 | 35 | 55.468 | 11.660 | 8.944 | 81.98 | 0.837 |
| 7 | 4 | 37 | 51.465 | 11.942 | 28.787 | 6.48 | 0.694 |
| 7 | 4 | 39 | 41.465 | 11.487 | 15.803 | 283.46 | 0.796 |
| 7 | 4 | 41 | 59.161 | 14.233 | 25.305 | 307.52 | 0.843 |
| 7 | 4 | 43 | 66.519 | 24.852 | 41.810 | 199.48 | 0.537 |
| 7 | 5 | 0 | 353.005 | 4.613 | 497.469 | 0.00 | 1.000 |
| 7 | 5 | 2 | 101.245 | 1.930 | 153.911 | 172.61 | 0.956 |
| 7 | 5 | 4 | 342.396 | 3.042 | 471.913 | 175.42 | 0.989 |
| 7 | 5 | 6 | 602.211 | 5.505 | 812.291 | 177.25 | 0.996 |
| 7 | 5 | 8 | 313.766 | 2.915 | 447.527 | 227.00 | 0.987 |
| 7 | 5 | 10 | 427.921 | 4.094 | 586.987 | 353.65 | 0.992 |
| 7 | 5 | 12 | 236.914 | 2.637 | 341.689 | 316.29 | 0.978 |

| | | | | | | | |
|---|---|---|---|---|---|---|---|
| 7 | 5 | 14 | 238.957 | 2.467 | 355.434 | 279.45 | 0.984 |
| 7 | 5 | 16 | 157.185 | 2.773 | 195.447 | 71.55 | 0.972 |
| 7 | 5 | 18 | 464.186 | 4.062 | 677.851 | 235.66 | 0.994 |
| 7 | 5 | 20 | 235.835 | 2.725 | 292.397 | 0.87 | 0.978 |
| 7 | 5 | 22 | 226.132 | 3.110 | 309.135 | 104.21 | 0.977 |
| 7 | 5 | 24 | 388.653 | 3.554 | 490.710 | 262.35 | 0.994 |
| 7 | 5 | 26 | 231.844 | 2.925 | 297.484 | 127.48 | 0.983 |
| 7 | 5 | 28 | 128.419 | 4.159 | 126.997 | 305.36 | 0.951 |
| 7 | 5 | 30 | 159.566 | 4.439 | 186.030 | 302.75 | 0.943 |
| 7 | 5 | 32 | 240.184 | 3.984 | 282.070 | 182.72 | 0.987 |
| 7 | 5 | 34 | 58.580 | 12.497 | 28.839 | 19.96 | 0.526 |
| 7 | 5 | 36 | 220.348 | 4.445 | 300.038 | 337.18 | 0.986 |
| 7 | 5 | 38 | 37.437 | 11.205 | 3.635 | 267.80 | 0.142 |
| 7 | 5 | 40 | 129.481 | 7.143 | 176.126 | 281.59 | 0.961 |
| 7 | 5 | 42 | 51.492 | 15.348 | 41.558 | 234.75 | 0.661 |
| 7 | 6 | 1 | 309.262 | 3.733 | 447.548 | 174.11 | 0.988 |
| 7 | 6 | 3 | 650.653 | 5.854 | 939.075 | 321.08 | 0.997 |
| 7 | 6 | 5 | 845.146 | 7.066 | 1213.709 | 338.16 | 0.998 |
| 7 | 6 | 7 | 204.785 | 2.077 | 305.995 | 183.02 | 0.988 |
| 7 | 6 | 9 | 326.090 | 2.784 | 456.684 | 328.80 | 0.988 |
| 7 | 6 | 11 | 209.298 | 2.183 | 286.255 | 8.48 | 0.985 |
| 7 | 6 | 13 | 260.075 | 2.627 | 345.218 | 214.41 | 0.989 |
| 7 | 6 | 15 | 209.682 | 2.586 | 284.172 | 209.64 | 0.979 |
| 7 | 6 | 17 | 132.221 | 2.603 | 181.401 | 332.97 | 0.970 |
| 7 | 6 | 19 | 229.276 | 2.592 | 312.082 | 313.63 | 0.978 |
| 7 | 6 | 21 | 250.025 | 2.735 | 366.905 | 97.98 | 0.977 |
| 7 | 6 | 23 | 512.771 | 4.396 | 678.799 | 37.09 | 0.996 |
| 7 | 6 | 25 | 304.047 | 3.143 | 420.407 | 151.25 | 0.989 |
| 7 | 6 | 27 | 254.078 | 3.437 | 326.063 | 53.58 | 0.985 |
| 7 | 6 | 29 | 168.330 | 4.684 | 185.924 | 78.82 | 0.963 |
| 7 | 6 | 31 | 330.229 | 3.939 | 469.043 | 158.53 | 0.988 |
| 7 | 6 | 33 | 112.101 | 7.068 | 95.699 | 25.42 | 0.945 |
| 7 | 6 | 35 | 38.435 | 10.779 | 11.808 | 90.54 | 0.348 |
| 7 | 6 | 37 | 87.645 | 8.814 | 90.147 | 168.65 | 0.921 |
| 7 | 6 | 39 | 39.253 | 11.357 | 12.294 | 118.43 | 0.747 |
| 7 | 6 | 41 | 36.500 | 11.856 | 23.671 | 38.62 | 0.845 |
| 7 | 6 | 43 | 78.595 | 25.143 | 21.638 | 328.68 | 0.934 |
| 7 | 7 | 0 | 160.323 | 2.247 | 225.050 | 0.00 | 0.999 |
| 7 | 7 | 2 | 729.824 | 7.162 | 1060.898 | 134.00 | 0.997 |
| 7 | 7 | 4 | 630.189 | 5.147 | 855.500 | 23.34 | 0.997 |
| 7 | 7 | 6 | 118.215 | 2.147 | 167.036 | 303.61 | 0.960 |
| 7 | 7 | 8 | 136.594 | 1.894 | 158.840 | 235.69 | 0.975 |
| 7 | 7 | 10 | 315.614 | 2.750 | 394.164 | 112.21 | 0.987 |
| 7 | 7 | 12 | 345.960 | 3.133 | 483.684 | 227.92 | 0.991 |
| 7 | 7 | 14 | 198.353 | 2.358 | 317.326 | 359.15 | 0.966 |
| 7 | 7 | 16 | 71.937 | 4.336 | 33.375 | 13.63 | 0.876 |
| 7 | 7 | 18 | 283.456 | 2.807 | 355.538 | 32.48 | 0.988 |
| 7 | 7 | 20 | 349.204 | 3.840 | 427.503 | 296.68 | 0.991 |
| 7 | 7 | 22 | 462.258 | 4.070 | 597.190 | 41.53 | 0.996 |
| 7 | 7 | 24 | 68.906 | 6.245 | 41.916 | 156.30 | 0.368 |
| 7 | 7 | 26 | 68.717 | 6.554 | 36.625 | 91.84 | 0.849 |
| 7 | 7 | 28 | 334.042 | 3.360 | 454.646 | 22.02 | 0.991 |
| 7 | 7 | 30 | 150.003 | 4.425 | 207.252 | 154.86 | 0.942 |
| 7 | 7 | 32 | 149.224 | 6.081 | 232.816 | 31.44 | 0.946 |
| 7 | 7 | 34 | 185.801 | 4.024 | 280.674 | 183.16 | 0.978 |
| 7 | 7 | 36 | 112.614 | 6.247 | 141.328 | 8.13 | 0.947 |
| 7 | 7 | 38 | 44.827 | 11.438 | 8.268 | 328.91 | 0.363 |
| 7 | 7 | 40 | 45.532 | 13.047 | 15.448 | 118.68 | 0.516 |
| 7 | 7 | 42 | 37.147 | 12.635 | 11.617 | 13.79 | 0.615 |
| 7 | 8 | 1 | 432.987 | 4.011 | 570.501 | 3.34 | 0.993 |
| 7 | 8 | 3 | 643.832 | 6.012 | 875.463 | 137.41 | 0.997 |
| 7 | 8 | 5 | 383.300 | 3.413 | 540.247 | 136.71 | 0.991 |
| 7 | 8 | 7 | 110.035 | 2.478 | 102.227 | 268.73 | 0.931 |
| 7 | 8 | 9 | 335.682 | 2.909 | 466.243 | 110.63 | 0.989 |
| 7 | 8 | 11 | 664.445 | 5.669 | 977.158 | 33.58 | 0.997 |
| 7 | 8 | 13 | 247.235 | 2.506 | 330.779 | 351.48 | 0.986 |
| 7 | 8 | 15 | 102.808 | 3.432 | 146.325 | 40.36 | 0.804 |
| 7 | 8 | 17 | 326.469 | 2.981 | 439.077 | 235.46 | 0.989 |
| 7 | 8 | 19 | 647.594 | 5.469 | 917.245 | 311.29 | 0.997 |
| 7 | 8 | 21 | 173.422 | 2.746 | 221.153 | 128.45 | 0.973 |
| 7 | 8 | 23 | 523.934 | 4.429 | 757.620 | 233.01 | 0.996 |
| 7 | 8 | 25 | 407.797 | 4.020 | 518.541 | 7.17 | 0.994 |
| 7 | 8 | 27 | 142.735 | 4.283 | 167.401 | 42.31 | 0.957 |
| 7 | 8 | 29 | 208.358 | 3.702 | 267.902 | 296.48 | 0.974 |
| 7 | 8 | 31 | 314.173 | 3.724 | 420.377 | 229.66 | 0.992 |
| 7 | 8 | 33 | 374.034 | 4.292 | 537.343 | 219.82 | 0.993 |
| 7 | 8 | 35 | 137.767 | 5.405 | 208.951 | 263.74 | 0.956 |

| | | | | | | | |
|---|---|---|---|---|---|---|---|
| 7 | 8 | 37 | 173.182 | 4.655 | 261.172 | 304.91 | 0.973 |
| 7 | 8 | 39 | 211.871 | 4.858 | 326.113 | 88.17 | 0.984 |
| 7 | 8 | 41 | 40.882 | 13.723 | 18.998 | 32.19 | 0.567 |
| 7 | 9 | 0 | 26.130 | 8.247 | 19.121 | 0.00 | 0.625 |
| 7 | 9 | 2 | 650.198 | 6.259 | 897.240 | 24.09 | 0.997 |
| 7 | 9 | 4 | 214.092 | 2.337 | 308.418 | 300.97 | 0.964 |
| 7 | 9 | 6 | 216.409 | 2.097 | 353.174 | 51.38 | 0.978 |
| 7 | 9 | 8 | 36.938 | 7.487 | 11.650 | 88.89 | 0.364 |
| 7 | 9 | 10 | 166.593 | 2.188 | 248.813 | 96.84 | 0.964 |
| 7 | 9 | 12 | 414.083 | 3.504 | 610.042 | 37.33 | 0.994 |
| 7 | 9 | 14 | 219.799 | 2.506 | 282.804 | 309.47 | 0.984 |
| 7 | 9 | 16 | 238.348 | 2.628 | 283.659 | 203.16 | 0.983 |
| 7 | 9 | 18 | 434.499 | 3.801 | 666.759 | 135.79 | 0.992 |
| 7 | 9 | 20 | 190.466 | 2.637 | 236.304 | 349.47 | 0.976 |
| 7 | 9 | 22 | 303.406 | 3.146 | 424.951 | 214.55 | 0.989 |
| 7 | 9 | 24 | 352.753 | 3.408 | 517.460 | 144.82 | 0.991 |
| 7 | 9 | 26 | 511.387 | 4.500 | 705.424 | 226.90 | 0.996 |
| 7 | 9 | 28 | 215.737 | 3.256 | 329.603 | 239.62 | 0.970 |
| 7 | 9 | 30 | 230.690 | 3.854 | 286.533 | 97.84 | 0.979 |
| 7 | 9 | 32 | 338.019 | 4.102 | 428.158 | 210.64 | 0.993 |
| 7 | 9 | 34 | 156.091 | 6.169 | 206.828 | 99.18 | 0.973 |
| 7 | 9 | 36 | 44.472 | 12.454 | 8.907 | 64.96 | 0.754 |
| 7 | 9 | 38 | 108.128 | 7.749 | 149.676 | 39.00 | 0.941 |
| 7 | 9 | 40 | 114.173 | 12.418 | 155.151 | 116.95 | 0.964 |
| 7 | 9 | 42 | 49.085 | 23.616 | 12.421 | 186.86 | 0.595 |
| 7 | 10 | 1 | 445.163 | 3.648 | 636.679 | 243.02 | 0.993 |
| 7 | 10 | 3 | 105.822 | 2.254 | 66.432 | 49.95 | 0.435 |
| 7 | 10 | 5 | 468.271 | 4.569 | 679.823 | 347.70 | 0.993 |
| 7 | 10 | 7 | 109.233 | 2.993 | 148.692 | 248.41 | 0.942 |
| 7 | 10 | 9 | 251.676 | 3.193 | 345.535 | 23.72 | 0.983 |
| 7 | 10 | 11 | 235.481 | 2.427 | 350.908 | 145.13 | 0.982 |
| 7 | 10 | 13 | 328.465 | 2.938 | 489.426 | 175.17 | 0.989 |
| 7 | 10 | 15 | 303.043 | 2.906 | 387.867 | 277.32 | 0.989 |
| 7 | 10 | 17 | 498.315 | 4.306 | 715.748 | 114.34 | 0.995 |
| 7 | 10 | 19 | 556.518 | 4.947 | 737.722 | 20.00 | 0.996 |
| 7 | 10 | 21 | 290.190 | 3.066 | 415.955 | 310.56 | 0.988 |
| 7 | 10 | 23 | 532.048 | 4.469 | 743.312 | 154.32 | 0.996 |
| 7 | 10 | 25 | 93.949 | 5.613 | 104.272 | 47.45 | 0.601 |
| 7 | 10 | 27 | 147.166 | 4.070 | 187.960 | 245.68 | 0.951 |
| 7 | 10 | 29 | 190.882 | 4.062 | 264.358 | 187.25 | 0.962 |
| 7 | 10 | 31 | 188.292 | 4.357 | 304.551 | 80.87 | 0.966 |
| 7 | 10 | 33 | 112.465 | 7.961 | 145.010 | 355.26 | 0.949 |
| 7 | 10 | 35 | 147.043 | 5.043 | 220.445 | 50.41 | 0.964 |
| 7 | 10 | 37 | 161.457 | 6.206 | 236.978 | 229.12 | 0.970 |
| 7 | 10 | 39 | 134.695 | 6.332 | 175.394 | 207.00 | 0.967 |
| 7 | 10 | 41 | 53.155 | 16.470 | 27.168 | 234.53 | 0.851 |
| 7 | 11 | 0 | 157.692 | 2.780 | 221.168 | 0.00 | 1.000 |
| 7 | 11 | 2 | 628.445 | 6.943 | 974.062 | 294.54 | 0.997 |
| 7 | 11 | 4 | 210.183 | 2.469 | 306.442 | 56.70 | 0.980 |
| 7 | 11 | 6 | 559.306 | 4.827 | 801.344 | 316.81 | 0.996 |
| 7 | 11 | 8 | 195.130 | 2.268 | 262.666 | 342.02 | 0.983 |
| 7 | 11 | 10 | 216.335 | 3.114 | 299.609 | 104.05 | 0.978 |
| 7 | 11 | 12 | 168.340 | 2.493 | 251.620 | 146.20 | 0.973 |
| 7 | 11 | 14 | 214.714 | 2.671 | 248.019 | 125.04 | 0.981 |
| 7 | 11 | 16 | 191.721 | 2.648 | 183.691 | 64.46 | 0.585 |
| 7 | 11 | 18 | 212.563 | 2.793 | 309.540 | 71.42 | 0.965 |
| 7 | 11 | 20 | 128.748 | 3.450 | 208.128 | 343.60 | 0.879 |
| 7 | 11 | 22 | 229.920 | 2.847 | 307.533 | 273.48 | 0.982 |
| 7 | 11 | 24 | 415.277 | 3.733 | 571.278 | 99.25 | 0.994 |
| 7 | 11 | 26 | 291.580 | 3.574 | 377.706 | 70.11 | 0.987 |
| 7 | 11 | 28 | 257.545 | 3.512 | 285.773 | 22.24 | 0.985 |
| 7 | 11 | 30 | 244.922 | 4.296 | 335.551 | 168.09 | 0.986 |
| 7 | 11 | 32 | 327.615 | 3.779 | 475.262 | 247.08 | 0.994 |
| 7 | 11 | 34 | 81.452 | 7.993 | 88.830 | 157.78 | 0.897 |
| 7 | 11 | 36 | 82.569 | 10.206 | 80.939 | 336.03 | 0.904 |
| 7 | 11 | 38 | 153.869 | 5.240 | 201.493 | 167.74 | 0.976 |
| 7 | 11 | 40 | 41.740 | 12.851 | 0.874 | 17.86 | 0.839 |
| 7 | 11 | 42 | 60.832 | 27.121 | 20.019 | 278.89 | 0.656 |
| 7 | 12 | 1 | 111.904 | 2.829 | 157.056 | 8.67 | 0.943 |
| 7 | 12 | 3 | 529.129 | 4.802 | 695.442 | 67.77 | 0.996 |
| 7 | 12 | 5 | 182.974 | 2.330 | 211.527 | 282.25 | 0.977 |
| 7 | 12 | 7 | 108.258 | 2.936 | 142.618 | 117.14 | 0.891 |
| 7 | 12 | 9 | 378.919 | 3.396 | 591.863 | 341.57 | 0.990 |
| 7 | 12 | 11 | 47.282 | 7.632 | 4.327 | 219.03 | 0.392 |
| 7 | 12 | 13 | 292.670 | 2.836 | 436.059 | 326.30 | 0.983 |
| 7 | 12 | 15 | 261.606 | 2.906 | 373.834 | 233.12 | 0.983 |
| 7 | 12 | 17 | 264.617 | 2.796 | 390.476 | 278.52 | 0.981 |

| | | | | | | | |
|---|---|---|---|---|---|---|---|
| 7 | 12 | 19 | 323.728 | 3.274 | 424.696 | 160.53 | 0.991 |
| 7 | 12 | 21 | 179.241 | 3.266 | 294.151 | 270.58 | 0.964 |
| 7 | 12 | 23 | 198.691 | 3.176 | 296.731 | 192.66 | 0.968 |
| 7 | 12 | 25 | 211.912 | 3.378 | 246.594 | 136.46 | 0.979 |
| 7 | 12 | 27 | 315.530 | 3.477 | 418.612 | 68.23 | 0.989 |
| 7 | 12 | 29 | 60.479 | 10.541 | 10.472 | 353.70 | 0.804 |
| 7 | 12 | 31 | 204.763 | 4.266 | 275.868 | 226.64 | 0.979 |
| 7 | 12 | 33 | 196.573 | 5.224 | 263.083 | 119.57 | 0.983 |
| 7 | 12 | 35 | 100.123 | 8.338 | 147.935 | 199.09 | 0.891 |
| 7 | 12 | 37 | 63.074 | 12.322 | 45.100 | 154.46 | 0.860 |
| 7 | 12 | 39 | 71.254 | 14.295 | 92.399 | 175.94 | 0.857 |
| 7 | 12 | 41 | 56.365 | 25.851 | 13.010 | 123.88 | 0.310 |
| 7 | 13 | 0 | 31.760 | 8.847 | 15.888 | 180.00 | 0.396 |
| 7 | 13 | 2 | 575.870 | 4.949 | 851.671 | 169.49 | 0.997 |
| 7 | 13 | 4 | 387.208 | 3.523 | 553.842 | 216.07 | 0.993 |
| 7 | 13 | 6 | 282.815 | 2.838 | 426.596 | 175.78 | 0.990 |
| 7 | 13 | 8 | 389.615 | 3.244 | 542.866 | 129.89 | 0.993 |
| 7 | 13 | 10 | 200.926 | 2.463 | 271.212 | 236.82 | 0.971 |
| 7 | 13 | 12 | 307.153 | 3.795 | 418.824 | 315.60 | 0.990 |
| 7 | 13 | 14 | 401.611 | 3.774 | 575.855 | 217.72 | 0.992 |
| 7 | 13 | 16 | 241.973 | 3.096 | 302.875 | 179.39 | 0.986 |
| 7 | 13 | 18 | 344.816 | 3.323 | 467.924 | 163.98 | 0.993 |
| 7 | 13 | 20 | 309.603 | 3.333 | 436.634 | 227.08 | 0.989 |
| 7 | 13 | 22 | 447.717 | 4.021 | 634.356 | 296.60 | 0.995 |
| 7 | 13 | 24 | 222.785 | 3.497 | 326.835 | 241.64 | 0.975 |
| 7 | 13 | 26 | 221.812 | 3.475 | 291.661 | 12.79 | 0.978 |
| 7 | 13 | 28 | 209.672 | 3.855 | 290.692 | 169.89 | 0.980 |
| 7 | 13 | 30 | 67.113 | 9.962 | 43.498 | 161.93 | 0.809 |
| 7 | 13 | 32 | 151.894 | 4.769 | 292.443 | 221.32 | 0.930 |
| 7 | 13 | 34 | 72.154 | 11.074 | 66.647 | 345.75 | 0.874 |
| 7 | 13 | 36 | 95.784 | 8.132 | 138.754 | 269.79 | 0.910 |
| 7 | 13 | 38 | 40.191 | 12.165 | 5.752 | 336.04 | 0.820 |
| 7 | 13 | 40 | 35.365 | 11.997 | 10.177 | 182.87 | 0.554 |
| 7 | 14 | 1 | 194.567 | 2.459 | 298.857 | 182.82 | 0.956 |
| 7 | 14 | 3 | 411.848 | 4.003 | 587.584 | 171.47 | 0.993 |
| 7 | 14 | 5 | 369.230 | 4.070 | 489.604 | 240.88 | 0.992 |
| 7 | 14 | 7 | 111.529 | 3.190 | 77.541 | 304.77 | 0.939 |
| 7 | 14 | 9 | 308.396 | 2.833 | 464.915 | 136.87 | 0.986 |
| 7 | 14 | 11 | 114.044 | 3.466 | 150.186 | 291.40 | 0.913 |
| 7 | 14 | 13 | 164.677 | 3.124 | 207.454 | 232.60 | 0.950 |
| 7 | 14 | 15 | 131.285 | 3.185 | 169.410 | 243.93 | 0.962 |
| 7 | 14 | 17 | 675.324 | 6.123 | 952.818 | 162.18 | 0.998 |
| 7 | 14 | 19 | 184.722 | 3.217 | 270.382 | 336.04 | 0.967 |
| 7 | 14 | 21 | 436.934 | 4.192 | 619.010 | 123.18 | 0.995 |
| 7 | 14 | 23 | 175.435 | 3.684 | 229.659 | 358.25 | 0.968 |
| 7 | 14 | 25 | 165.804 | 3.757 | 269.952 | 273.55 | 0.939 |
| 7 | 14 | 27 | 64.868 | 10.209 | 38.883 | 157.62 | 0.835 |
| 7 | 14 | 29 | 165.486 | 4.645 | 239.213 | 231.51 | 0.965 |
| 7 | 14 | 31 | 228.333 | 4.146 | 328.073 | 359.88 | 0.987 |
| 7 | 14 | 33 | 61.170 | 10.629 | 19.650 | 112.21 | 0.882 |
| 7 | 14 | 35 | 88.054 | 8.203 | 115.873 | 68.00 | 0.913 |
| 7 | 14 | 37 | 69.993 | 12.581 | 72.696 | 29.36 | 0.842 |
| 7 | 14 | 39 | 58.651 | 14.952 | 61.513 | 300.30 | 0.766 |
| 7 | 15 | 0 | 38.427 | 11.003 | 21.974 | 0.00 | 0.429 |
| 7 | 15 | 2 | 66.699 | 5.162 | 75.196 | 304.46 | 0.748 |
| 7 | 15 | 4 | 446.371 | 4.304 | 618.583 | 240.60 | 0.994 |
| 7 | 15 | 6 | 192.910 | 2.513 | 266.518 | 350.77 | 0.986 |
| 7 | 15 | 8 | 519.922 | 4.261 | 774.390 | 51.07 | 0.995 |
| 7 | 15 | 10 | 102.409 | 3.170 | 101.831 | 355.17 | 0.927 |
| 7 | 15 | 12 | 579.349 | 4.958 | 814.285 | 348.23 | 0.996 |
| 7 | 15 | 14 | 32.567 | 8.794 | 70.917 | 128.64 | 0.554 |
| 7 | 15 | 16 | 273.341 | 3.249 | 300.577 | 304.54 | 0.989 |
| 7 | 15 | 18 | 354.367 | 3.707 | 518.419 | 79.89 | 0.991 |
| 7 | 15 | 20 | 176.338 | 3.568 | 251.136 | 173.84 | 0.968 |
| 7 | 15 | 22 | 308.248 | 3.591 | 424.968 | 36.17 | 0.989 |
| 7 | 15 | 24 | 69.814 | 8.832 | 42.666 | 66.10 | 0.886 |
| 7 | 15 | 26 | 208.340 | 4.266 | 234.994 | 200.09 | 0.985 |
| 7 | 15 | 28 | 202.528 | 4.112 | 385.178 | 340.21 | 0.959 |
| 7 | 15 | 30 | 139.784 | 6.096 | 189.751 | 54.38 | 0.967 |
| 7 | 15 | 32 | 100.391 | 8.144 | 146.623 | 48.09 | 0.907 |
| 7 | 15 | 34 | 80.261 | 11.934 | 51.657 | 175.83 | 0.923 |
| 7 | 15 | 36 | 50.559 | 12.214 | 17.739 | 40.68 | 0.420 |
| 7 | 15 | 38 | 49.710 | 14.718 | 31.750 | 255.04 | 0.506 |
| 7 | 15 | 40 | 59.318 | 26.015 | 12.864 | 189.09 | 0.738 |
| 7 | 16 | 1 | 31.629 | 7.161 | 18.241 | 277.61 | 0.297 |
| 7 | 16 | 3 | 268.927 | 2.838 | 456.817 | 313.05 | 0.975 |
| 7 | 16 | 5 | 72.841 | 4.913 | 62.253 | 236.12 | 0.637 |

| | | | | | | | |
|---|---|---|---|---|---|---|---|
| 7 | 16 | 7 | 99.655 | 3.660 | 136.747 | 21.09 | 0.884 |
| 7 | 16 | 9 | 217.907 | 2.614 | 297.651 | 28.57 | 0.974 |
| 7 | 16 | 11 | 253.552 | 2.728 | 385.567 | 358.96 | 0.983 |
| 7 | 16 | 13 | 333.379 | 3.142 | 476.673 | 343.52 | 0.991 |
| 7 | 16 | 15 | 252.862 | 3.028 | 277.377 | 20.58 | 0.987 |
| 7 | 16 | 17 | 235.296 | 3.245 | 331.699 | 67.56 | 0.981 |
| 7 | 16 | 19 | 383.436 | 3.887 | 533.078 | 325.52 | 0.993 |
| 7 | 16 | 21 | 463.239 | 4.214 | 618.168 | 303.07 | 0.995 |
| 7 | 16 | 23 | 48.585 | 11.015 | 17.306 | 129.35 | 0.554 |
| 7 | 16 | 25 | 44.035 | 12.388 | 1.755 | 52.92 | 0.416 |
| 7 | 16 | 27 | 252.808 | 3.615 | 302.681 | 176.41 | 0.988 |
| 7 | 16 | 29 | 110.974 | 6.396 | 82.665 | 22.37 | 0.966 |
| 7 | 16 | 31 | 28.301 | 9.558 | 12.209 | 161.01 | 0.281 |
| 7 | 16 | 33 | 30.859 | 10.200 | 43.613 | 283.77 | 0.628 |
| 7 | 16 | 35 | 127.689 | 6.357 | 222.905 | 117.02 | 0.929 |
| 7 | 16 | 37 | 50.229 | 14.933 | 37.426 | 81.82 | 0.565 |
| 7 | 16 | 39 | 42.090 | 19.401 | 3.073 | 97.06 | 0.680 |
| 7 | 17 | 0 | 240.415 | 3.705 | 337.929 | 0.00 | 1.000 |
| 7 | 17 | 2 | 38.852 | 7.850 | 46.303 | 74.10 | 0.501 |
| 7 | 17 | 4 | 411.205 | 4.077 | 641.148 | 1.50 | 0.992 |
| 7 | 17 | 6 | 148.085 | 2.915 | 200.372 | 127.95 | 0.955 |
| 7 | 17 | 8 | 191.038 | 2.896 | 278.722 | 57.07 | 0.975 |
| 7 | 17 | 10 | 180.011 | 2.956 | 249.207 | 293.00 | 0.973 |
| 7 | 17 | 12 | 233.314 | 2.781 | 335.196 | 263.82 | 0.985 |
| 7 | 17 | 14 | 367.668 | 3.482 | 590.499 | 180.19 | 0.991 |
| 7 | 17 | 16 | 179.719 | 3.788 | 234.368 | 54.00 | 0.971 |
| 7 | 17 | 18 | 286.019 | 3.210 | 439.250 | 307.64 | 0.985 |
| 7 | 17 | 20 | 175.364 | 5.210 | 276.166 | 197.85 | 0.927 |
| 7 | 17 | 22 | 123.799 | 5.370 | 113.852 | 97.80 | 0.939 |
| 7 | 17 | 24 | 256.607 | 4.235 | 348.344 | 332.99 | 0.988 |
| 7 | 17 | 26 | 48.365 | 11.399 | 1.444 | 316.85 | 0.174 |
| 7 | 17 | 28 | 101.781 | 8.016 | 142.912 | 247.25 | 0.922 |
| 7 | 17 | 30 | 120.173 | 5.478 | 121.608 | 283.47 | 0.963 |
| 7 | 17 | 32 | 53.599 | 11.471 | 23.521 | 356.95 | 0.338 |
| 7 | 17 | 34 | 45.958 | 12.857 | 14.401 | 313.94 | 0.720 |
| 7 | 17 | 36 | 119.799 | 10.203 | 143.877 | 49.70 | 0.975 |
| 7 | 17 | 38 | 44.044 | 13.776 | 27.992 | 31.98 | 0.722 |
| 7 | 18 | 1 | 95.704 | 4.005 | 127.084 | 59.84 | 0.803 |
| 7 | 18 | 3 | 185.561 | 2.930 | 198.066 | 287.73 | 0.980 |
| 7 | 18 | 5 | 75.314 | 8.690 | 71.493 | 49.35 | 0.859 |
| 7 | 18 | 7 | 48.716 | 8.911 | 12.546 | 244.43 | 0.665 |
| 7 | 18 | 9 | 597.648 | 5.001 | 892.891 | 75.45 | 0.997 |
| 7 | 18 | 11 | 183.495 | 3.072 | 306.372 | 154.26 | 0.950 |
| 7 | 18 | 13 | 247.243 | 2.951 | 335.412 | 161.73 | 0.986 |
| 7 | 18 | 15 | 297.194 | 3.170 | 406.606 | 295.32 | 0.989 |
| 7 | 18 | 17 | 432.554 | 4.090 | 605.100 | 71.82 | 0.995 |
| 7 | 18 | 19 | 101.623 | 6.104 | 129.885 | 134.13 | 0.884 |
| 7 | 18 | 21 | 168.570 | 5.236 | 202.416 | 162.96 | 0.964 |
| 7 | 18 | 23 | 333.188 | 3.689 | 443.347 | 75.67 | 0.993 |
| 7 | 18 | 25 | 320.836 | 4.126 | 448.664 | 164.82 | 0.992 |
| 7 | 18 | 27 | 195.674 | 3.982 | 272.127 | 197.07 | 0.984 |
| 7 | 18 | 29 | 71.397 | 13.868 | 80.766 | 311.64 | 0.707 |
| 7 | 18 | 31 | 129.913 | 5.605 | 207.991 | 148.02 | 0.944 |
| 7 | 18 | 33 | 77.804 | 9.540 | 101.166 | 242.39 | 0.860 |
| 7 | 18 | 35 | 62.973 | 14.679 | 77.137 | 46.21 | 0.741 |
| 7 | 18 | 37 | 57.065 | 15.801 | 47.232 | 212.73 | 0.590 |
| 7 | 19 | 0 | 62.866 | 10.734 | 63.232 | 180.00 | 0.721 |
| 7 | 19 | 2 | 510.245 | 4.189 | 683.867 | 265.44 | 0.997 |
| 7 | 19 | 4 | 45.675 | 8.662 | 25.157 | 57.24 | 0.223 |
| 7 | 19 | 6 | 292.362 | 3.788 | 397.851 | 110.87 | 0.989 |
| 7 | 19 | 8 | 153.898 | 3.126 | 186.150 | 98.78 | 0.961 |
| 7 | 19 | 10 | 354.339 | 3.296 | 751.187 | 123.46 | 0.980 |
| 7 | 19 | 12 | 495.825 | 4.310 | 711.226 | 149.89 | 0.996 |
| 7 | 19 | 14 | 153.067 | 3.558 | 178.193 | 228.96 | 0.967 |
| 7 | 19 | 16 | 205.663 | 3.407 | 314.327 | 71.27 | 0.972 |
| 7 | 19 | 18 | 328.324 | 3.684 | 471.780 | 54.39 | 0.989 |
| 7 | 19 | 20 | 126.952 | 6.873 | 161.955 | 346.61 | 0.908 |
| 7 | 19 | 22 | 56.894 | 13.755 | 21.148 | 178.83 | 0.736 |
| 7 | 19 | 24 | 222.825 | 4.075 | 307.015 | 115.11 | 0.983 |
| 7 | 19 | 26 | 62.562 | 12.795 | 64.587 | 195.06 | 0.727 |
| 7 | 19 | 28 | 227.904 | 4.068 | 312.202 | 180.49 | 0.988 |
| 7 | 19 | 30 | 125.205 | 6.945 | 190.521 | 17.14 | 0.948 |
| 7 | 19 | 32 | 81.480 | 10.132 | 114.325 | 315.81 | 0.874 |
| 7 | 19 | 34 | 44.009 | 13.030 | 27.621 | 324.11 | 0.722 |
| 7 | 19 | 36 | 68.753 | 16.725 | 62.524 | 148.02 | 0.908 |
| 7 | 20 | 1 | 328.585 | 3.168 | 479.633 | 304.16 | 0.991 |
| 7 | 20 | 3 | 226.540 | 3.229 | 307.844 | 289.92 | 0.982 |

| | | | | | | | |
|---|---|---|---|---|---|---|---|
| 7 | 20 | 5 | 167.666 | 3.664 | 300.208 | 250.12 | 0.922 |
| 7 | 20 | 7 | 200.846 | 3.114 | 290.236 | 99.51 | 0.975 |
| 7 | 20 | 9 | 267.388 | 3.151 | 290.398 | 201.98 | 0.989 |
| 7 | 20 | 11 | 422.589 | 3.827 | 538.611 | 146.32 | 0.995 |
| 7 | 20 | 13 | 324.357 | 3.257 | 484.954 | 230.89 | 0.990 |
| 7 | 20 | 15 | 210.393 | 3.107 | 263.620 | 199.21 | 0.977 |
| 7 | 20 | 17 | 42.300 | 10.958 | 58.399 | 50.70 | 0.660 |
| 7 | 20 | 19 | 70.706 | 9.092 | 60.140 | 315.71 | 0.721 |
| 7 | 20 | 21 | 221.025 | 4.338 | 371.831 | 171.37 | 0.978 |
| 7 | 20 | 23 | 39.511 | 11.539 | 3.916 | 98.77 | 0.562 |
| 7 | 20 | 25 | 254.107 | 4.379 | 372.433 | 335.37 | 0.990 |
| 7 | 20 | 27 | 152.164 | 5.343 | 181.129 | 265.33 | 0.976 |
| 7 | 20 | 29 | 139.023 | 6.117 | 198.081 | 358.16 | 0.965 |
| 7 | 20 | 31 | 48.937 | 11.474 | 16.893 | 200.03 | 0.772 |
| 7 | 20 | 33 | 67.824 | 12.825 | 45.311 | 348.68 | 0.939 |
| 7 | 20 | 35 | 47.285 | 14.888 | 3.046 | 270.59 | 0.048 |
| 7 | 21 | 0 | 224.857 | 3.974 | 315.584 | 0.00 | 0.999 |
| 7 | 21 | 2 | 61.677 | 7.561 | 26.262 | 304.17 | 0.386 |
| 7 | 21 | 4 | 128.073 | 4.102 | 168.289 | 73.07 | 0.946 |
| 7 | 21 | 6 | 388.404 | 5.606 | 884.072 | 186.37 | 0.981 |
| 7 | 21 | 8 | 310.653 | 3.424 | 413.900 | 146.23 | 0.990 |
| 7 | 21 | 10 | 62.613 | 7.304 | 14.059 | 231.63 | 0.841 |
| 7 | 21 | 12 | 290.352 | 3.199 | 419.974 | 130.71 | 0.987 |
| 7 | 21 | 14 | 146.711 | 4.416 | 165.410 | 333.86 | 0.948 |
| 7 | 21 | 16 | 271.672 | 3.647 | 347.514 | 267.63 | 0.987 |
| 7 | 21 | 18 | 282.919 | 3.887 | 309.394 | 331.96 | 0.992 |
| 7 | 21 | 20 | 211.898 | 4.989 | 298.098 | 235.49 | 0.982 |
| 7 | 21 | 22 | 151.002 | 5.162 | 193.492 | 240.09 | 0.975 |
| 7 | 21 | 24 | 175.730 | 5.209 | 249.790 | 80.66 | 0.980 |
| 7 | 21 | 26 | 77.222 | 14.357 | 87.495 | 47.14 | 0.581 |
| 7 | 21 | 28 | 87.042 | 7.920 | 125.929 | 56.48 | 0.850 |
| 7 | 21 | 30 | 102.611 | 9.586 | 112.107 | 176.38 | 0.954 |
| 7 | 21 | 32 | 47.917 | 14.673 | 33.207 | 233.02 | 0.807 |
| 7 | 21 | 34 | 42.493 | 13.413 | 21.758 | 121.27 | 0.506 |
| 7 | 22 | 1 | 304.255 | 3.446 | 452.098 | 329.09 | 0.989 |
| 7 | 22 | 3 | 69.513 | 8.097 | 60.042 | 272.70 | 0.630 |
| 7 | 22 | 5 | 287.311 | 3.708 | 398.014 | 144.84 | 0.988 |
| 7 | 22 | 7 | 107.625 | 6.017 | 114.657 | 194.30 | 0.612 |
| 7 | 22 | 9 | 209.567 | 3.228 | 274.956 | 195.27 | 0.976 |
| 7 | 22 | 11 | 303.832 | 3.561 | 400.010 | 132.77 | 0.989 |
| 7 | 22 | 13 | 367.122 | 3.613 | 512.212 | 344.75 | 0.992 |
| 7 | 22 | 15 | 328.447 | 3.656 | 482.126 | 327.81 | 0.989 |
| 7 | 22 | 17 | 212.919 | 4.484 | 288.838 | 303.35 | 0.983 |
| 7 | 22 | 19 | 222.340 | 4.604 | 364.037 | 190.16 | 0.980 |
| 7 | 22 | 21 | 158.260 | 4.202 | 204.951 | 312.52 | 0.978 |
| 7 | 22 | 23 | 307.773 | 3.832 | 458.538 | 62.65 | 0.993 |
| 7 | 22 | 25 | 172.112 | 6.013 | 220.170 | 43.97 | 0.982 |
| 7 | 22 | 27 | 202.840 | 4.823 | 302.055 | 324.03 | 0.984 |
| 7 | 22 | 29 | 48.204 | 12.807 | 18.214 | 24.70 | 0.739 |
| 7 | 22 | 31 | 86.507 | 13.830 | 101.386 | 51.49 | 0.945 |
| 7 | 22 | 33 | 109.167 | 17.833 | 115.706 | 177.35 | 0.964 |
| 7 | 23 | 0 | 78.250 | 13.053 | 108.662 | 0.00 | 0.992 |
| 7 | 23 | 2 | 248.376 | 3.343 | 292.705 | 261.86 | 0.986 |
| 7 | 23 | 4 | 176.994 | 3.944 | 271.727 | 8.99 | 0.959 |
| 7 | 23 | 6 | 210.066 | 4.476 | 266.177 | 140.91 | 0.977 |
| 7 | 23 | 8 | 228.041 | 4.605 | 386.184 | 91.41 | 0.973 |
| 7 | 23 | 10 | 340.044 | 3.619 | 436.193 | 206.11 | 0.992 |
| 7 | 23 | 12 | 366.376 | 3.799 | 549.361 | 31.75 | 0.991 |
| 7 | 23 | 14 | 142.776 | 5.615 | 182.990 | 181.26 | 0.962 |
| 7 | 23 | 16 | 201.194 | 4.916 | 289.313 | 26.73 | 0.980 |
| 7 | 23 | 18 | 140.989 | 5.955 | 243.357 | 79.54 | 0.957 |
| 7 | 23 | 20 | 128.332 | 6.935 | 166.009 | 169.46 | 0.965 |
| 7 | 23 | 22 | 132.529 | 6.029 | 164.626 | 114.96 | 0.969 |
| 7 | 23 | 24 | 54.183 | 12.921 | 37.063 | 221.30 | 0.556 |
| 7 | 23 | 26 | 58.256 | 12.673 | 28.014 | 63.36 | 0.307 |
| 7 | 23 | 28 | 70.138 | 13.677 | 76.756 | 276.70 | 0.857 |
| 7 | 23 | 30 | 42.126 | 13.516 | 18.842 | 51.59 | 0.363 |
| 7 | 23 | 32 | 42.679 | 13.934 | 25.642 | 12.57 | 0.541 |
| 7 | 24 | 1 | 228.648 | 3.893 | 330.599 | 163.26 | 0.980 |
| 7 | 24 | 3 | 258.078 | 3.713 | 402.108 | 156.19 | 0.981 |
| 7 | 24 | 5 | 150.899 | 5.476 | 195.685 | 2.07 | 0.957 |
| 7 | 24 | 7 | 136.689 | 5.883 | 170.308 | 98.50 | 0.953 |
| 7 | 24 | 9 | 246.527 | 3.870 | 307.660 | 257.21 | 0.989 |
| 7 | 24 | 11 | 194.352 | 3.741 | 272.886 | 112.73 | 0.980 |
| 7 | 24 | 13 | 100.311 | 9.447 | 132.625 | 333.38 | 0.905 |
| 7 | 24 | 15 | 98.467 | 7.991 | 155.856 | 149.61 | 0.830 |
| 7 | 24 | 17 | 130.572 | 5.837 | 197.913 | 51.67 | 0.961 |

| | | | | | | | |
|---|---|---|---|---|---|---|---|
| 7 | 24 | 19 | 90.094 | 6.498 | 94.822 | 209.98 | 0.935 |
| 7 | 24 | 21 | 127.792 | 8.134 | 125.889 | 250.69 | 0.972 |
| 7 | 24 | 23 | 166.634 | 5.183 | 213.539 | 291.15 | 0.980 |
| 7 | 24 | 25 | 155.475 | 5.479 | 244.710 | 208.08 | 0.972 |
| 7 | 24 | 27 | 134.417 | 8.141 | 178.208 | 252.43 | 0.969 |
| 7 | 24 | 29 | 80.785 | 16.776 | 116.261 | 352.66 | 0.780 |
| 7 | 24 | 31 | 55.742 | 15.089 | 52.921 | 22.28 | 0.644 |
| 7 | 25 | 0 | 162.969 | 8.182 | 228.368 | 0.00 | 1.000 |
| 7 | 25 | 2 | 85.347 | 7.358 | 115.728 | 243.30 | 0.845 |
| 7 | 25 | 4 | 328.112 | 3.670 | 416.696 | 248.63 | 0.994 |
| 7 | 25 | 6 | 196.136 | 6.089 | 264.455 | 335.16 | 0.981 |
| 7 | 25 | 8 | 220.781 | 6.742 | 310.500 | 182.33 | 0.985 |
| 7 | 25 | 10 | 269.051 | 4.183 | 298.433 | 310.35 | 0.992 |
| 7 | 25 | 12 | 143.122 | 5.356 | 208.344 | 181.62 | 0.958 |
| 7 | 25 | 14 | 374.404 | 4.040 | 561.653 | 338.03 | 0.996 |
| 7 | 25 | 16 | 142.791 | 5.606 | 196.455 | 225.12 | 0.972 |
| 7 | 25 | 18 | 160.837 | 4.945 | 176.492 | 259.57 | 0.982 |
| 7 | 25 | 20 | 202.670 | 4.555 | 312.211 | 253.54 | 0.984 |
| 7 | 25 | 22 | 88.862 | 8.339 | 121.462 | 317.99 | 0.907 |
| 7 | 25 | 24 | 101.538 | 7.299 | 178.484 | 8.83 | 0.787 |
| 7 | 25 | 26 | 100.082 | 15.394 | 73.759 | 339.21 | 0.973 |
| 7 | 25 | 28 | 37.897 | 12.440 | 8.769 | 220.20 | 0.348 |
| 7 | 25 | 30 | 41.882 | 19.664 | 9.165 | 156.71 | 0.743 |
| 7 | 26 | 1 | 147.040 | 6.318 | 188.562 | 258.36 | 0.965 |
| 7 | 26 | 3 | 140.023 | 5.695 | 189.455 | 328.37 | 0.960 |
| 7 | 26 | 5 | 267.767 | 3.715 | 372.022 | 244.60 | 0.990 |
| 7 | 26 | 7 | 35.891 | 10.371 | 31.944 | 358.89 | 0.622 |
| 7 | 26 | 9 | 90.328 | 12.718 | 144.113 | 27.70 | 0.872 |
| 7 | 26 | 11 | 68.820 | 12.692 | 86.841 | 28.15 | 0.733 |
| 7 | 26 | 13 | 60.528 | 12.995 | 62.193 | 16.42 | 0.717 |
| 7 | 26 | 15 | 211.792 | 3.927 | 329.823 | 332.16 | 0.986 |
| 7 | 26 | 17 | 121.452 | 5.860 | 139.999 | 113.20 | 0.965 |
| 7 | 26 | 19 | 107.058 | 6.868 | 177.388 | 57.19 | 0.910 |
| 7 | 26 | 21 | 55.665 | 11.928 | 41.190 | 169.10 | 0.830 |
| 7 | 26 | 23 | 64.863 | 13.159 | 47.902 | 226.83 | 0.437 |
| 7 | 26 | 25 | 73.428 | 18.436 | 67.058 | 194.54 | 0.528 |
| 7 | 26 | 27 | 58.411 | 16.844 | 40.025 | 23.22 | 0.881 |
| 7 | 26 | 29 | 51.912 | 15.277 | 35.353 | 60.62 | 0.503 |
| 7 | 27 | 0 | 112.031 | 8.440 | 156.626 | 180.00 | 1.000 |
| 7 | 27 | 2 | 165.002 | 6.045 | 255.328 | 190.47 | 0.977 |
| 7 | 27 | 4 | 191.510 | 4.324 | 285.999 | 317.30 | 0.984 |
| 7 | 27 | 6 | 70.699 | 13.091 | 67.449 | 92.07 | 0.490 |
| 7 | 27 | 8 | 68.083 | 16.480 | 46.360 | 1.34 | 0.887 |
| 7 | 27 | 10 | 182.374 | 5.191 | 244.248 | 86.34 | 0.984 |
| 7 | 27 | 12 | 55.028 | 10.508 | 33.960 | 335.36 | 0.821 |
| 7 | 27 | 14 | 94.872 | 7.694 | 129.575 | 95.30 | 0.927 |
| 7 | 27 | 16 | 54.758 | 11.228 | 33.882 | 239.31 | 0.821 |
| 7 | 27 | 18 | 126.804 | 6.015 | 184.702 | 198.59 | 0.966 |
| 7 | 27 | 20 | 41.427 | 11.775 | 12.986 | 21.72 | 0.527 |
| 7 | 27 | 22 | 47.471 | 13.641 | 15.364 | 211.41 | 0.398 |
| 7 | 27 | 24 | 128.719 | 13.350 | 197.459 | 24.80 | 0.970 |
| 7 | 27 | 26 | 81.176 | 24.841 | 83.241 | 319.46 | 0.832 |
| 7 | 27 | 28 | 68.399 | 25.910 | 35.725 | 38.04 | 0.688 |
| 7 | 28 | 1 | 130.520 | 5.703 | 235.297 | 286.17 | 0.940 |
| 7 | 28 | 3 | 78.045 | 10.139 | 114.648 | 186.99 | 0.747 |
| 7 | 28 | 5 | 166.072 | 4.923 | 283.139 | 169.64 | 0.972 |
| 7 | 28 | 7 | 93.524 | 8.189 | 64.795 | 164.05 | 0.960 |
| 7 | 28 | 9 | 282.520 | 4.563 | 448.189 | 344.82 | 0.992 |
| 7 | 28 | 11 | 86.669 | 12.431 | 135.899 | 102.56 | 0.856 |
| 7 | 28 | 13 | 101.274 | 7.596 | 172.290 | 194.19 | 0.853 |
| 7 | 28 | 15 | 118.877 | 6.941 | 102.670 | 247.82 | 0.970 |
| 7 | 28 | 17 | 90.406 | 9.897 | 91.977 | 174.37 | 0.945 |
| 7 | 28 | 19 | 39.864 | 12.598 | 9.908 | 288.92 | 0.594 |
| 7 | 28 | 21 | 50.177 | 14.505 | 39.481 | 243.18 | 0.832 |
| 7 | 28 | 23 | 50.050 | 15.089 | 35.796 | 334.22 | 0.798 |
| 7 | 28 | 25 | 46.346 | 15.417 | 33.098 | 169.54 | 0.762 |
| 7 | 28 | 27 | 48.017 | 21.817 | 4.970 | 299.29 | 0.276 |
| 7 | 29 | 0 | 226.114 | 6.497 | 315.890 | 0.00 | 1.000 |
| 7 | 29 | 2 | 99.761 | 7.906 | 122.030 | 68.45 | 0.948 |
| 7 | 29 | 4 | 118.080 | 6.728 | 171.055 | 146.57 | 0.953 |
| 7 | 29 | 6 | 152.104 | 7.045 | 252.213 | 186.97 | 0.969 |
| 7 | 29 | 8 | 72.950 | 12.722 | 91.823 | 126.82 | 0.686 |
| 7 | 29 | 10 | 103.541 | 8.541 | 104.521 | 327.31 | 0.956 |
| 7 | 29 | 12 | 152.088 | 6.565 | 301.781 | 83.66 | 0.955 |
| 7 | 29 | 14 | 89.034 | 8.771 | 115.037 | 59.90 | 0.931 |
| 7 | 29 | 16 | 165.090 | 6.761 | 254.464 | 160.89 | 0.978 |
| 7 | 29 | 18 | 66.334 | 14.596 | 73.400 | 34.82 | 0.911 |

| | | | | | | | |
|---|---|---|---|---|---|---|---|
| 7 | 29 | 20 | 49.602 | 13.609 | 44.342 | 38.86 | 0.624 |
| 7 | 29 | 22 | 59.589 | 13.990 | 74.788 | 264.99 | 0.790 |
| 7 | 29 | 24 | 79.945 | 15.001 | 76.794 | 157.20 | 0.942 |
| 7 | 30 | 1 | 46.759 | 11.697 | 20.564 | 51.91 | 0.704 |
| 7 | 30 | 3 | 84.011 | 8.546 | 75.792 | 319.78 | 0.936 |
| 7 | 30 | 5 | 80.742 | 9.749 | 84.827 | 216.23 | 0.923 |
| 7 | 30 | 7 | 60.564 | 10.410 | 51.308 | 322.69 | 0.861 |
| 7 | 30 | 9 | 116.819 | 6.529 | 233.312 | 195.18 | 0.848 |
| 7 | 30 | 11 | 83.840 | 9.478 | 80.342 | 34.40 | 0.941 |
| 7 | 30 | 13 | 63.772 | 13.453 | 31.105 | 65.67 | 0.906 |
| 7 | 30 | 15 | 35.177 | 11.770 | 12.398 | 48.62 | 0.687 |
| 7 | 30 | 17 | 92.191 | 11.119 | 148.736 | 69.58 | 0.934 |
| 7 | 30 | 19 | 35.752 | 11.716 | 10.547 | 283.19 | 0.595 |
| 7 | 30 | 21 | 61.078 | 15.997 | 57.967 | 329.68 | 0.871 |
| 7 | 30 | 23 | 36.935 | 18.435 | 14.710 | 350.31 | 0.578 |
| 7 | 31 | 0 | 27.913 | 13.111 | 10.578 | 0.00 | 0.278 |
| 7 | 31 | 2 | 148.115 | 4.741 | 249.346 | 342.93 | 0.972 |
| 7 | 31 | 4 | 83.899 | 9.564 | 96.896 | 225.20 | 0.933 |
| 7 | 31 | 6 | 73.178 | 11.566 | 94.462 | 166.27 | 0.880 |
| 7 | 31 | 8 | 36.285 | 11.830 | 1.017 | 122.96 | 0.078 |
| 7 | 31 | 10 | 36.081 | 11.892 | 12.012 | 332.18 | 0.710 |
| 7 | 31 | 12 | 47.316 | 15.866 | 25.970 | 110.11 | 0.368 |
| 7 | 31 | 14 | 40.532 | 13.086 | 25.951 | 6.68 | 0.669 |
| 7 | 31 | 16 | 46.905 | 11.408 | 22.573 | 102.91 | 0.866 |
| 7 | 31 | 18 | 53.353 | 13.384 | 54.852 | 36.77 | 0.761 |
| 7 | 31 | 20 | 38.410 | 17.812 | 1.746 | 99.36 | 0.517 |
| 7 | 32 | 1 | 83.154 | 14.915 | 97.497 | 309.30 | 0.949 |
| 7 | 32 | 3 | 42.337 | 11.957 | 15.805 | 308.97 | 0.858 |
| 7 | 32 | 5 | 60.857 | 13.905 | 40.897 | 355.69 | 0.930 |
| 7 | 32 | 7 | 78.487 | 15.203 | 122.514 | 251.84 | 0.853 |
| 7 | 32 | 9 | 92.725 | 10.475 | 146.761 | 320.00 | 0.945 |
| 7 | 32 | 11 | 92.756 | 10.778 | 136.681 | 88.30 | 0.952 |
| 7 | 32 | 13 | 67.166 | 16.001 | 75.992 | 141.65 | 0.610 |
| 7 | 32 | 15 | 37.653 | 17.660 | 4.273 | 171.11 | 0.391 |
| 7 | 32 | 17 | 47.587 | 21.703 | 3.256 | 30.64 | 0.698 |
| 7 | 33 | 0 | 29.589 | 18.603 | 19.285 | 180.00 | 0.519 |
| 7 | 33 | 2 | 49.177 | 13.240 | 35.787 | 229.95 | 0.856 |
| 7 | 33 | 4 | 43.881 | 12.706 | 36.208 | 355.91 | 0.692 |
| 7 | 33 | 6 | 42.570 | 12.701 | 21.170 | 269.52 | 0.373 |
| 7 | 33 | 8 | 48.818 | 12.627 | 46.998 | 267.22 | 0.580 |
| 7 | 33 | 10 | 39.029 | 12.408 | 10.510 | 223.44 | 0.823 |
| 7 | 33 | 12 | 67.839 | 12.774 | 99.383 | 192.05 | 0.825 |
| 7 | 33 | 14 | 42.130 | 18.857 | 6.840 | 186.52 | 0.598 |
| 7 | 34 | 1 | 43.999 | 13.176 | 35.435 | 82.31 | 0.724 |
| 7 | 34 | 3 | 38.234 | 11.915 | 23.307 | 70.62 | 0.686 |
| 7 | 34 | 5 | 66.658 | 14.431 | 59.222 | 154.04 | 0.927 |
| 7 | 34 | 7 | 53.541 | 15.348 | 39.368 | 102.44 | 0.856 |
| 7 | 34 | 9 | 56.932 | 22.412 | 30.322 | 217.34 | 0.650 |
| 8 | 0 | 0 | 555.973 | 8.132 | 785.951 | 180.00 | 1.000 |
| 8 | 0 | 2 | 195.860 | 2.703 | 276.705 | 180.00 | 1.000 |
| 8 | 0 | 4 | 624.492 | 6.896 | 882.140 | 0.00 | 1.000 |
| 8 | 0 | 6 | 334.403 | 4.614 | 471.337 | 180.00 | 1.000 |
| 8 | 0 | 8 | 110.608 | 2.601 | 148.873 | 180.00 | 0.958 |
| 8 | 0 | 10 | 65.101 | 5.291 | 70.906 | 180.00 | 0.779 |
| 8 | 0 | 12 | 72.288 | 5.667 | 9.888 | 180.00 | 0.099 |
| 8 | 0 | 14 | 24.868 | 8.045 | 22.328 | 180.00 | 0.678 |
| 8 | 0 | 16 | 114.010 | 6.057 | 158.283 | 0.00 | 0.999 |
| 8 | 0 | 18 | 434.166 | 6.263 | 600.768 | 180.00 | 1.000 |
| 8 | 0 | 20 | 84.723 | 6.265 | 60.376 | 0.00 | 0.519 |
| 8 | 0 | 22 | 207.777 | 4.009 | 48.003 | 0.00 | 0.169 |
| 8 | 0 | 24 | 76.237 | 8.683 | 77.599 | 180.00 | 0.753 |
| 8 | 0 | 26 | 21.761 | 10.447 | 5.942 | 180.00 | 0.209 |
| 8 | 0 | 28 | 538.643 | 8.668 | 723.350 | 0.00 | 1.000 |
| 8 | 0 | 30 | 193.013 | 5.703 | 257.226 | 0.00 | 1.000 |
| 8 | 0 | 32 | 31.043 | 14.311 | 28.270 | 180.00 | 0.698 |
| 8 | 0 | 34 | 335.089 | 8.322 | 438.751 | 0.00 | 1.000 |
| 8 | 0 | 36 | 185.083 | 6.938 | 240.046 | 0.00 | 1.000 |
| 8 | 0 | 38 | 41.031 | 18.657 | 41.414 | 0.00 | 0.805 |
| 8 | 0 | 40 | 62.656 | 15.336 | 32.933 | 0.00 | 0.423 |
| 8 | 0 | 42 | 47.200 | 21.492 | 9.871 | 180.00 | 0.180 |
| 8 | 1 | 1 | 734.262 | 9.636 | 1040.860 | 136.34 | 0.997 |
| 8 | 1 | 3 | 124.121 | 1.489 | 137.554 | 159.73 | 0.929 |
| 8 | 1 | 5 | 263.771 | 2.145 | 368.496 | 87.03 | 0.985 |
| 8 | 1 | 7 | 253.145 | 2.165 | 338.038 | 327.77 | 0.980 |
| 8 | 1 | 9 | 432.609 | 3.509 | 622.709 | 38.44 | 0.992 |
| 8 | 1 | 11 | 199.193 | 2.090 | 310.343 | 83.04 | 0.970 |
| 8 | 1 | 13 | 180.993 | 2.218 | 205.259 | 307.29 | 0.970 |

| | | | | | | | |
|---|---|---|---|---|---|---|---|
| 8 | 1 | 15 | 414.882 | 3.587 | 561.895 | 289.18 | 0.994 |
| 8 | 1 | 17 | 280.899 | 2.692 | 363.498 | 314.33 | 0.988 |
| 8 | 1 | 19 | 240.877 | 2.574 | 359.556 | 137.60 | 0.973 |
| 8 | 1 | 21 | 144.498 | 3.336 | 206.200 | 143.46 | 0.928 |
| 8 | 1 | 23 | 423.846 | 3.731 | 593.750 | 129.12 | 0.994 |
| 8 | 1 | 25 | 313.472 | 3.162 | 449.506 | 322.05 | 0.989 |
| 8 | 1 | 27 | 122.801 | 4.242 | 174.935 | 293.34 | 0.923 |
| 8 | 1 | 29 | 305.776 | 3.518 | 407.760 | 332.32 | 0.988 |
| 8 | 1 | 31 | 117.197 | 6.710 | 127.761 | 78.31 | 0.520 |
| 8 | 1 | 33 | 123.677 | 6.702 | 153.544 | 16.77 | 0.935 |
| 8 | 1 | 35 | 120.932 | 6.501 | 146.108 | 110.36 | 0.958 |
| 8 | 1 | 37 | 45.228 | 11.968 | 12.749 | 24.84 | 0.391 |
| 8 | 1 | 39 | 111.829 | 7.815 | 138.983 | 267.78 | 0.954 |
| 8 | 1 | 41 | 65.243 | 22.874 | 58.867 | 133.64 | 0.762 |
| 8 | 1 | 43 | 55.002 | 17.749 | 41.673 | 313.17 | 0.757 |
| 8 | 2 | 0 | 1226.899 | 25.767 | 1730.962 | 180.00 | 1.000 |
| 8 | 2 | 2 | 1145.273 | 14.836 | 1631.296 | 254.50 | 0.999 |
| 8 | 2 | 4 | 424.681 | 3.443 | 636.989 | 107.70 | 0.991 |
| 8 | 2 | 6 | 60.839 | 2.364 | 40.657 | 201.13 | 0.935 |
| 8 | 2 | 8 | 244.629 | 2.140 | 333.490 | 88.42 | 0.983 |
| 8 | 2 | 10 | 472.946 | 3.979 | 615.613 | 345.98 | 0.995 |
| 8 | 2 | 12 | 302.744 | 2.769 | 436.400 | 176.39 | 0.990 |
| 8 | 2 | 14 | 97.394 | 3.099 | 70.172 | 258.37 | 0.874 |
| 8 | 2 | 16 | 293.012 | 2.765 | 428.465 | 8.01 | 0.987 |
| 8 | 2 | 18 | 183.664 | 2.513 | 201.321 | 238.75 | 0.981 |
| 8 | 2 | 20 | 284.445 | 2.859 | 429.357 | 326.09 | 0.983 |
| 8 | 2 | 22 | 302.339 | 2.951 | 407.261 | 122.92 | 0.985 |
| 8 | 2 | 24 | 141.694 | 3.643 | 176.317 | 17.79 | 0.968 |
| 8 | 2 | 26 | 289.528 | 3.056 | 357.356 | 22.27 | 0.990 |
| 8 | 2 | 28 | 150.506 | 4.310 | 205.543 | 338.50 | 0.942 |
| 8 | 2 | 30 | 329.939 | 3.534 | 439.325 | 264.11 | 0.989 |
| 8 | 2 | 32 | 139.116 | 5.804 | 156.230 | 175.87 | 0.962 |
| 8 | 2 | 34 | 362.867 | 4.329 | 420.160 | 198.54 | 0.994 |
| 8 | 2 | 36 | 179.716 | 4.778 | 316.193 | 72.57 | 0.964 |
| 8 | 2 | 38 | 71.875 | 12.206 | 68.652 | 286.66 | 0.855 |
| 8 | 2 | 40 | 49.660 | 13.907 | 11.004 | 145.88 | 0.773 |
| 8 | 2 | 42 | 52.913 | 15.044 | 26.667 | 202.24 | 0.875 |
| 8 | 3 | 1 | 831.520 | 7.792 | 1159.858 | 223.91 | 0.998 |
| 8 | 3 | 3 | 470.713 | 3.880 | 682.677 | 247.78 | 0.994 |
| 8 | 3 | 5 | 411.160 | 4.037 | 546.243 | 48.97 | 0.993 |
| 8 | 3 | 7 | 194.022 | 1.817 | 257.462 | 86.72 | 0.979 |
| 8 | 3 | 9 | 155.983 | 1.947 | 178.292 | 59.03 | 0.988 |
| 8 | 3 | 11 | 132.192 | 2.029 | 201.893 | 333.30 | 0.965 |
| 8 | 3 | 13 | 503.692 | 4.415 | 707.772 | 208.92 | 0.996 |
| 8 | 3 | 15 | 227.393 | 2.582 | 279.426 | 237.93 | 0.987 |
| 8 | 3 | 17 | 390.036 | 3.429 | 553.786 | 256.46 | 0.992 |
| 8 | 3 | 19 | 375.405 | 3.284 | 538.284 | 333.00 | 0.990 |
| 8 | 3 | 21 | 430.450 | 3.663 | 610.777 | 48.36 | 0.993 |
| 8 | 3 | 23 | 364.081 | 3.351 | 500.025 | 290.64 | 0.993 |
| 8 | 3 | 25 | 193.257 | 3.189 | 209.862 | 141.59 | 0.976 |
| 8 | 3 | 27 | 309.026 | 3.157 | 450.174 | 335.03 | 0.987 |
| 8 | 3 | 29 | 104.012 | 6.140 | 127.827 | 199.77 | 0.848 |
| 8 | 3 | 31 | 75.094 | 9.083 | 49.688 | 143.71 | 0.405 |
| 8 | 3 | 33 | 185.578 | 5.053 | 322.479 | 132.86 | 0.958 |
| 8 | 3 | 35 | 102.574 | 7.991 | 148.891 | 189.96 | 0.918 |
| 8 | 3 | 37 | 219.580 | 4.986 | 308.244 | 257.17 | 0.985 |
| 8 | 3 | 39 | 68.091 | 11.607 | 76.871 | 150.82 | 0.836 |
| 8 | 3 | 41 | 58.459 | 14.940 | 47.262 | 208.12 | 0.873 |
| 8 | 3 | 43 | 46.656 | 15.182 | 23.698 | 284.71 | 0.441 |
| 8 | 4 | 0 | 589.255 | 7.782 | 832.914 | 0.00 | 1.000 |
| 8 | 4 | 2 | 248.921 | 2.449 | 351.995 | 103.13 | 0.984 |
| 8 | 4 | 4 | 236.673 | 2.275 | 362.801 | 224.64 | 0.982 |
| 8 | 4 | 6 | 649.598 | 5.113 | 967.003 | 62.16 | 0.996 |
| 8 | 4 | 8 | 234.750 | 2.271 | 293.522 | 183.48 | 0.983 |
| 8 | 4 | 10 | 252.639 | 2.335 | 392.048 | 54.08 | 0.981 |
| 8 | 4 | 12 | 622.335 | 5.523 | 819.232 | 166.02 | 0.997 |
| 8 | 4 | 14 | 75.559 | 4.068 | 95.127 | 191.74 | 0.862 |
| 8 | 4 | 16 | 97.731 | 3.212 | 118.730 | 315.71 | 0.918 |
| 8 | 4 | 18 | 219.828 | 2.463 | 308.027 | 14.61 | 0.985 |
| 8 | 4 | 20 | 219.510 | 2.601 | 345.781 | 354.92 | 0.974 |
| 8 | 4 | 22 | 186.997 | 2.656 | 199.636 | 75.81 | 0.978 |
| 8 | 4 | 24 | 267.777 | 2.933 | 379.058 | 119.65 | 0.985 |
| 8 | 4 | 26 | 175.167 | 3.425 | 245.010 | 325.89 | 0.968 |
| 8 | 4 | 28 | 147.695 | 3.956 | 221.169 | 122.16 | 0.936 |
| 8 | 4 | 30 | 115.326 | 5.657 | 151.615 | 118.18 | 0.894 |
| 8 | 4 | 32 | 111.512 | 7.088 | 160.246 | 64.14 | 0.827 |
| 8 | 4 | 34 | 79.647 | 9.146 | 87.539 | 183.04 | 0.889 |

| | | | | | | | |
|---|---|---|---|---|---|---|---|
| 8 | 4 | 36 | 122.986 | 6.622 | 157.402 | 44.10 | 0.956 |
| 8 | 4 | 38 | 139.099 | 5.261 | 209.608 | 213.12 | 0.955 |
| 8 | 4 | 40 | 120.286 | 6.838 | 199.622 | 185.93 | 0.924 |
| 8 | 4 | 42 | 58.688 | 15.873 | 52.323 | 244.09 | 0.812 |
| 8 | 5 | 1 | 269.646 | 2.607 | 403.963 | 316.66 | 0.978 |
| 8 | 5 | 3 | 197.840 | 1.723 | 293.252 | 235.50 | 0.987 |
| 8 | 5 | 5 | 531.683 | 4.904 | 756.755 | 66.18 | 0.995 |
| 8 | 5 | 7 | 534.308 | 4.700 | 782.529 | 166.64 | 0.995 |
| 8 | 5 | 9 | 437.845 | 3.553 | 572.844 | 231.51 | 0.994 |
| 8 | 5 | 11 | 274.638 | 2.720 | 371.308 | 90.57 | 0.986 |
| 8 | 5 | 13 | 364.109 | 3.597 | 553.758 | 192.12 | 0.991 |
| 8 | 5 | 15 | 115.872 | 2.733 | 163.998 | 236.37 | 0.857 |
| 8 | 5 | 17 | 161.621 | 2.473 | 205.882 | 244.83 | 0.962 |
| 8 | 5 | 19 | 252.920 | 2.658 | 340.650 | 24.19 | 0.984 |
| 8 | 5 | 21 | 161.175 | 2.721 | 246.677 | 43.56 | 0.879 |
| 8 | 5 | 23 | 57.954 | 8.129 | 24.217 | 131.79 | 0.484 |
| 8 | 5 | 25 | 190.813 | 3.199 | 249.606 | 103.26 | 0.974 |
| 8 | 5 | 27 | 164.070 | 3.125 | 216.295 | 305.25 | 0.962 |
| 8 | 5 | 29 | 145.245 | 4.289 | 212.331 | 200.95 | 0.926 |
| 8 | 5 | 31 | 206.936 | 3.915 | 378.157 | 53.85 | 0.964 |
| 8 | 5 | 33 | 151.720 | 4.912 | 181.643 | 249.07 | 0.965 |
| 8 | 5 | 35 | 144.432 | 7.006 | 161.544 | 62.17 | 0.975 |
| 8 | 5 | 37 | 106.570 | 6.647 | 108.613 | 275.20 | 0.950 |
| 8 | 5 | 39 | 172.447 | 5.221 | 225.584 | 76.07 | 0.980 |
| 8 | 5 | 41 | 56.940 | 13.750 | 37.832 | 16.25 | 0.391 |
| 8 | 5 | 43 | 49.194 | 23.321 | 11.396 | 352.37 | 0.465 |
| 8 | 6 | 0 | 507.755 | 5.540 | 717.687 | 0.00 | 1.000 |
| 8 | 6 | 2 | 566.972 | 6.891 | 814.454 | 114.35 | 0.996 |
| 8 | 6 | 4 | 538.534 | 4.570 | 797.600 | 227.62 | 0.995 |
| 8 | 6 | 6 | 92.837 | 2.023 | 108.382 | 103.06 | 0.919 |
| 8 | 6 | 8 | 471.587 | 3.954 | 666.395 | 25.28 | 0.994 |
| 8 | 6 | 10 | 367.689 | 3.030 | 480.062 | 12.30 | 0.993 |
| 8 | 6 | 12 | 321.926 | 2.877 | 405.066 | 342.66 | 0.992 |
| 8 | 6 | 14 | 177.240 | 2.291 | 255.305 | 224.14 | 0.966 |
| 8 | 6 | 16 | 353.565 | 3.467 | 446.169 | 17.22 | 0.992 |
| 8 | 6 | 18 | 223.948 | 2.795 | 258.775 | 141.69 | 0.980 |
| 8 | 6 | 20 | 176.886 | 2.717 | 261.843 | 236.81 | 0.917 |
| 8 | 6 | 22 | 418.236 | 3.735 | 631.092 | 18.21 | 0.994 |
| 8 | 6 | 24 | 300.515 | 3.114 | 403.763 | 49.47 | 0.990 |
| 8 | 6 | 26 | 123.277 | 3.946 | 160.549 | 176.69 | 0.936 |
| 8 | 6 | 28 | 276.432 | 3.242 | 392.771 | 36.48 | 0.984 |
| 8 | 6 | 30 | 303.088 | 3.832 | 404.707 | 202.24 | 0.988 |
| 8 | 6 | 32 | 172.243 | 5.347 | 258.254 | 257.86 | 0.964 |
| 8 | 6 | 34 | 58.839 | 11.962 | 52.162 | 14.85 | 0.783 |
| 8 | 6 | 36 | 157.391 | 5.664 | 235.108 | 245.19 | 0.968 |
| 8 | 6 | 38 | 110.313 | 7.711 | 108.632 | 26.69 | 0.962 |
| 8 | 6 | 40 | 84.051 | 12.091 | 115.376 | 212.04 | 0.791 |
| 8 | 6 | 42 | 68.310 | 18.053 | 65.444 | 88.90 | 0.859 |
| 8 | 7 | 1 | 335.729 | 3.959 | 474.424 | 45.19 | 0.988 |
| 8 | 7 | 3 | 378.039 | 3.690 | 608.502 | 272.23 | 0.989 |
| 8 | 7 | 5 | 197.033 | 1.846 | 274.208 | 190.64 | 0.985 |
| 8 | 7 | 7 | 459.723 | 4.910 | 650.916 | 202.48 | 0.994 |
| 8 | 7 | 9 | 240.283 | 2.384 | 303.562 | 63.12 | 0.987 |
| 8 | 7 | 11 | 244.631 | 2.444 | 361.996 | 103.36 | 0.981 |
| 8 | 7 | 13 | 313.281 | 2.838 | 401.278 | 139.59 | 0.990 |
| 8 | 7 | 15 | 397.499 | 3.530 | 567.051 | 100.54 | 0.993 |
| 8 | 7 | 17 | 207.551 | 2.586 | 253.887 | 105.42 | 0.979 |
| 8 | 7 | 19 | 300.837 | 2.896 | 391.828 | 301.98 | 0.987 |
| 8 | 7 | 21 | 773.885 | 6.834 | 1055.156 | 87.70 | 0.998 |
| 8 | 7 | 23 | 239.188 | 2.824 | 368.094 | 247.85 | 0.975 |
| 8 | 7 | 25 | 293.744 | 3.168 | 445.831 | 355.63 | 0.986 |
| 8 | 7 | 27 | 357.944 | 3.425 | 486.625 | 86.11 | 0.992 |
| 8 | 7 | 29 | 147.835 | 4.462 | 163.006 | 219.62 | 0.959 |
| 8 | 7 | 31 | 270.681 | 3.621 | 304.751 | 150.88 | 0.990 |
| 8 | 7 | 33 | 111.128 | 6.230 | 134.382 | 285.26 | 0.952 |
| 8 | 7 | 35 | 217.775 | 4.333 | 222.844 | 228.54 | 0.990 |
| 8 | 7 | 37 | 157.589 | 5.347 | 198.828 | 346.25 | 0.975 |
| 8 | 7 | 39 | 72.014 | 10.763 | 84.488 | 16.98 | 0.833 |
| 8 | 7 | 41 | 48.414 | 14.103 | 30.234 | 84.76 | 0.797 |
| 8 | 7 | 43 | 49.274 | 23.244 | 10.432 | 208.68 | 0.462 |
| 8 | 8 | 0 | 315.682 | 3.687 | 446.094 | 0.00 | 1.000 |
| 8 | 8 | 2 | 319.448 | 3.327 | 396.653 | 27.05 | 0.989 |
| 8 | 8 | 4 | 318.257 | 3.128 | 472.204 | 2.65 | 0.986 |
| 8 | 8 | 6 | 618.440 | 6.245 | 892.555 | 326.97 | 0.996 |
| 8 | 8 | 8 | 106.008 | 2.730 | 131.908 | 189.58 | 0.938 |
| 8 | 8 | 10 | 265.591 | 2.553 | 369.159 | 284.24 | 0.989 |
| 8 | 8 | 12 | 114.440 | 2.671 | 111.983 | 143.76 | 0.963 |

| | | | | | | | |
|---|---|---|---|---|---|---|---|
| 8 | 8 | 14 | 171.673 | 2.694 | 229.081 | 145.41 | 0.972 |
| 8 | 8 | 16 | 264.456 | 2.705 | 360.702 | 100.96 | 0.985 |
| 8 | 8 | 18 | 659.845 | 5.529 | 915.211 | 317.48 | 0.997 |
| 8 | 8 | 20 | 248.913 | 2.734 | 338.435 | 227.86 | 0.985 |
| 8 | 8 | 22 | 64.621 | 7.561 | 38.567 | 259.66 | 0.494 |
| 8 | 8 | 24 | 232.542 | 2.863 | 283.729 | 214.69 | 0.984 |
| 8 | 8 | 26 | 674.968 | 6.171 | 883.009 | 156.59 | 0.998 |
| 8 | 8 | 28 | 69.713 | 9.308 | 31.393 | 234.20 | 0.320 |
| 8 | 8 | 30 | 298.851 | 3.590 | 394.313 | 201.36 | 0.991 |
| 8 | 8 | 32 | 199.368 | 4.329 | 343.274 | 347.83 | 0.967 |
| 8 | 8 | 34 | 63.510 | 10.951 | 20.040 | 7.70 | 0.893 |
| 8 | 8 | 36 | 107.172 | 6.980 | 164.506 | 42.30 | 0.911 |
| 8 | 8 | 38 | 69.171 | 11.970 | 35.838 | 30.64 | 0.907 |
| 8 | 8 | 40 | 39.428 | 12.027 | 19.894 | 112.36 | 0.665 |
| 8 | 8 | 42 | 48.476 | 15.377 | 30.656 | 105.35 | 0.554 |
| 8 | 9 | 1 | 326.302 | 2.746 | 433.388 | 329.41 | 0.990 |
| 8 | 9 | 3 | 187.292 | 2.943 | 186.690 | 306.99 | 0.973 |
| 8 | 9 | 5 | 294.754 | 2.468 | 414.875 | 36.04 | 0.987 |
| 8 | 9 | 7 | 308.785 | 2.685 | 463.907 | 313.48 | 0.988 |
| 8 | 9 | 9 | 413.576 | 4.314 | 624.201 | 359.00 | 0.993 |
| 8 | 9 | 11 | 365.477 | 3.234 | 451.518 | 335.59 | 0.994 |
| 8 | 9 | 13 | 272.100 | 2.716 | 427.824 | 225.29 | 0.986 |
| 8 | 9 | 15 | 143.614 | 2.698 | 192.436 | 335.99 | 0.918 |
| 8 | 9 | 17 | 408.202 | 3.575 | 573.763 | 23.68 | 0.993 |
| 8 | 9 | 19 | 102.400 | 3.904 | 123.448 | 186.11 | 0.945 |
| 8 | 9 | 21 | 128.454 | 3.778 | 111.911 | 50.68 | 0.959 |
| 8 | 9 | 23 | 150.196 | 3.672 | 224.182 | 359.30 | 0.952 |
| 8 | 9 | 25 | 474.191 | 4.115 | 674.630 | 194.61 | 0.995 |
| 8 | 9 | 27 | 201.263 | 3.490 | 304.657 | 126.38 | 0.965 |
| 8 | 9 | 29 | 203.051 | 3.851 | 291.819 | 210.76 | 0.968 |
| 8 | 9 | 31 | 291.061 | 4.104 | 402.074 | 172.34 | 0.990 |
| 8 | 9 | 33 | 161.038 | 5.262 | 215.048 | 47.93 | 0.976 |
| 8 | 9 | 35 | 54.268 | 12.235 | 31.398 | 82.06 | 0.794 |
| 8 | 9 | 37 | 129.086 | 6.469 | 145.648 | 125.77 | 0.970 |
| 8 | 9 | 39 | 73.606 | 14.336 | 85.405 | 241.11 | 0.801 |
| 8 | 9 | 41 | 43.172 | 14.259 | 22.326 | 38.10 | 0.558 |
| 8 | 10 | 0 | 630.898 | 8.711 | 890.826 | 180.00 | 1.000 |
| 8 | 10 | 2 | 90.425 | 3.435 | 125.537 | 106.13 | 0.876 |
| 8 | 10 | 4 | 141.910 | 2.638 | 197.969 | 228.16 | 0.976 |
| 8 | 10 | 6 | 481.491 | 4.131 | 622.646 | 161.41 | 0.996 |
| 8 | 10 | 8 | 298.706 | 2.753 | 378.661 | 15.93 | 0.989 |
| 8 | 10 | 10 | 414.658 | 4.342 | 663.287 | 107.46 | 0.992 |
| 8 | 10 | 12 | 276.230 | 2.839 | 400.096 | 50.77 | 0.985 |
| 8 | 10 | 14 | 48.097 | 7.515 | 33.786 | 339.09 | 0.680 |
| 8 | 10 | 16 | 73.009 | 4.310 | 83.143 | 287.49 | 0.711 |
| 8 | 10 | 18 | 242.576 | 2.859 | 288.629 | 110.23 | 0.980 |
| 8 | 10 | 20 | 326.091 | 3.123 | 480.881 | 216.17 | 0.989 |
| 8 | 10 | 22 | 295.524 | 3.111 | 405.408 | 102.91 | 0.990 |
| 8 | 10 | 24 | 432.363 | 3.939 | 622.737 | 355.48 | 0.994 |
| 8 | 10 | 26 | 333.220 | 3.371 | 482.183 | 6.12 | 0.989 |
| 8 | 10 | 28 | 188.522 | 3.681 | 301.379 | 107.07 | 0.955 |
| 8 | 10 | 30 | 234.076 | 3.808 | 400.138 | 160.72 | 0.977 |
| 8 | 10 | 32 | 134.760 | 6.362 | 186.830 | 257.56 | 0.961 |
| 8 | 10 | 34 | 44.970 | 11.990 | 11.012 | 212.61 | 0.362 |
| 8 | 10 | 36 | 48.912 | 12.354 | 17.004 | 278.19 | 0.339 |
| 8 | 10 | 38 | 196.875 | 4.742 | 299.757 | 10.57 | 0.982 |
| 8 | 10 | 40 | 54.559 | 15.014 | 36.973 | 267.05 | 0.867 |
| 8 | 10 | 42 | 50.908 | 22.616 | 10.686 | 276.87 | 0.318 |
| 8 | 11 | 1 | 52.071 | 4.929 | 35.062 | 339.07 | 0.491 |
| 8 | 11 | 3 | 219.420 | 2.749 | 308.988 | 83.17 | 0.977 |
| 8 | 11 | 5 | 294.863 | 2.900 | 420.556 | 217.39 | 0.989 |
| 8 | 11 | 7 | 96.181 | 3.228 | 131.863 | 287.65 | 0.899 |
| 8 | 11 | 9 | 157.151 | 2.416 | 172.837 | 64.85 | 0.963 |
| 8 | 11 | 11 | 110.154 | 3.389 | 134.048 | 323.47 | 0.941 |
| 8 | 11 | 13 | 380.349 | 3.659 | 528.723 | 2.14 | 0.992 |
| 8 | 11 | 15 | 44.022 | 7.271 | 9.084 | 149.71 | 0.052 |
| 8 | 11 | 17 | 159.846 | 2.807 | 224.668 | 271.34 | 0.929 |
| 8 | 11 | 19 | 39.050 | 8.771 | 22.327 | 85.65 | 0.569 |
| 8 | 11 | 21 | 523.528 | 4.443 | 743.902 | 233.85 | 0.996 |
| 8 | 11 | 23 | 236.395 | 3.072 | 331.036 | 57.18 | 0.982 |
| 8 | 11 | 25 | 205.518 | 3.285 | 209.824 | 67.96 | 0.981 |
| 8 | 11 | 27 | 233.812 | 3.558 | 340.895 | 327.36 | 0.976 |
| 8 | 11 | 29 | 155.811 | 5.006 | 201.325 | 119.20 | 0.967 |
| 8 | 11 | 31 | 278.895 | 3.914 | 345.686 | 346.18 | 0.990 |
| 8 | 11 | 33 | 83.146 | 9.632 | 85.089 | 168.82 | 0.911 |
| 8 | 11 | 35 | 148.624 | 5.013 | 214.868 | 25.55 | 0.966 |
| 8 | 11 | 37 | 119.578 | 6.165 | 174.349 | 214.74 | 0.949 |

| | | | | | | | |
|---|---|---|---|---|---|---|---|
| 8 | 11 | 39 | 38.897 | 12.134 | 18.273 | 6.05 | 0.596 |
| 8 | 11 | 41 | 49.953 | 14.744 | 39.370 | 235.17 | 0.708 |
| 8 | 12 | 0 | 24.289 | 8.757 | 11.251 | 0.00 | 0.329 |
| 8 | 12 | 2 | 290.252 | 3.642 | 412.921 | 146.65 | 0.988 |
| 8 | 12 | 4 | 169.489 | 2.785 | 215.110 | 235.71 | 0.979 |
| 8 | 12 | 6 | 145.528 | 2.161 | 171.662 | 295.30 | 0.953 |
| 8 | 12 | 8 | 135.794 | 2.245 | 186.037 | 182.03 | 0.949 |
| 8 | 12 | 10 | 309.054 | 2.821 | 440.660 | 259.70 | 0.989 |
| 8 | 12 | 12 | 283.586 | 2.716 | 392.209 | 166.03 | 0.984 |
| 8 | 12 | 14 | 131.081 | 3.331 | 210.702 | 297.55 | 0.908 |
| 8 | 12 | 16 | 97.563 | 3.674 | 108.859 | 8.89 | 0.932 |
| 8 | 12 | 18 | 243.075 | 2.806 | 364.659 | 273.86 | 0.981 |
| 8 | 12 | 20 | 187.582 | 2.959 | 260.319 | 225.58 | 0.974 |
| 8 | 12 | 22 | 357.113 | 3.411 | 432.367 | 253.27 | 0.993 |
| 8 | 12 | 24 | 168.980 | 3.613 | 183.739 | 111.61 | 0.968 |
| 8 | 12 | 26 | 112.559 | 5.020 | 151.786 | 108.07 | 0.891 |
| 8 | 12 | 28 | 154.316 | 4.486 | 210.914 | 130.31 | 0.965 |
| 8 | 12 | 30 | 119.006 | 5.767 | 145.716 | 321.17 | 0.939 |
| 8 | 12 | 32 | 68.327 | 10.145 | 76.287 | 21.60 | 0.823 |
| 8 | 12 | 34 | 72.248 | 11.978 | 67.808 | 339.50 | 0.880 |
| 8 | 12 | 36 | 127.464 | 6.066 | 179.630 | 188.61 | 0.960 |
| 8 | 12 | 38 | 44.013 | 12.989 | 12.383 | 173.31 | 0.846 |
| 8 | 12 | 40 | 46.154 | 15.391 | 24.496 | 164.72 | 0.507 |
| 8 | 13 | 1 | 221.338 | 2.302 | 274.443 | 194.28 | 0.990 |
| 8 | 13 | 3 | 253.441 | 2.890 | 344.811 | 321.95 | 0.983 |
| 8 | 13 | 5 | 642.051 | 5.636 | 982.016 | 262.54 | 0.997 |
| 8 | 13 | 7 | 363.625 | 3.226 | 583.048 | 6.07 | 0.990 |
| 8 | 13 | 9 | 320.675 | 3.105 | 432.624 | 296.26 | 0.988 |
| 8 | 13 | 11 | 389.920 | 3.562 | 559.226 | 243.72 | 0.991 |
| 8 | 13 | 13 | 209.328 | 2.723 | 238.129 | 195.57 | 0.985 |
| 8 | 13 | 15 | 248.183 | 2.715 | 372.648 | 155.29 | 0.982 |
| 8 | 13 | 17 | 481.972 | 4.251 | 659.804 | 239.86 | 0.996 |
| 8 | 13 | 19 | 338.382 | 3.273 | 475.992 | 340.30 | 0.992 |
| 8 | 13 | 21 | 180.410 | 3.407 | 178.734 | 315.84 | 0.975 |
| 8 | 13 | 23 | 295.580 | 3.621 | 433.653 | 231.06 | 0.987 |
| 8 | 13 | 25 | 294.385 | 3.468 | 375.598 | 126.62 | 0.988 |
| 8 | 13 | 27 | 79.727 | 7.175 | 82.530 | 336.57 | 0.854 |
| 8 | 13 | 29 | 334.765 | 3.967 | 443.449 | 346.60 | 0.993 |
| 8 | 13 | 31 | 284.238 | 4.020 | 423.664 | 163.79 | 0.992 |
| 8 | 13 | 33 | 123.460 | 5.808 | 180.623 | 342.54 | 0.949 |
| 8 | 13 | 35 | 43.807 | 11.229 | 4.963 | 174.88 | 0.767 |
| 8 | 13 | 37 | 80.961 | 10.714 | 87.918 | 325.65 | 0.899 |
| 8 | 13 | 39 | 40.601 | 13.460 | 15.674 | 114.29 | 0.394 |
| 8 | 13 | 41 | 44.942 | 21.036 | 2.932 | 348.62 | 0.635 |
| 8 | 14 | 0 | 468.357 | 7.723 | 660.869 | 180.00 | 1.000 |
| 8 | 14 | 2 | 150.223 | 3.228 | 234.086 | 303.54 | 0.930 |
| 8 | 14 | 4 | 211.592 | 2.697 | 315.896 | 312.09 | 0.980 |
| 8 | 14 | 6 | 458.724 | 4.426 | 627.350 | 295.06 | 0.994 |
| 8 | 14 | 8 | 359.480 | 3.227 | 549.138 | 18.93 | 0.989 |
| 8 | 14 | 10 | 260.904 | 2.865 | 361.003 | 120.12 | 0.986 |
| 8 | 14 | 12 | 290.866 | 2.830 | 421.086 | 5.99 | 0.984 |
| 8 | 14 | 14 | 209.602 | 3.053 | 291.309 | 291.01 | 0.981 |
| 8 | 14 | 16 | 502.053 | 5.728 | 743.861 | 280.89 | 0.996 |
| 8 | 14 | 18 | 238.846 | 3.066 | 325.786 | 344.80 | 0.983 |
| 8 | 14 | 20 | 102.256 | 4.931 | 92.185 | 235.31 | 0.934 |
| 8 | 14 | 22 | 132.958 | 4.031 | 188.288 | 359.34 | 0.935 |
| 8 | 14 | 24 | 396.833 | 4.058 | 558.386 | 141.68 | 0.993 |
| 8 | 14 | 26 | 59.798 | 11.537 | 8.380 | 97.82 | 0.838 |
| 8 | 14 | 28 | 98.996 | 6.626 | 92.496 | 298.62 | 0.932 |
| 8 | 14 | 30 | 49.830 | 12.737 | 26.646 | 32.20 | 0.518 |
| 8 | 14 | 32 | 170.386 | 5.159 | 238.285 | 170.34 | 0.977 |
| 8 | 14 | 34 | 77.568 | 10.271 | 94.907 | 224.92 | 0.822 |
| 8 | 14 | 36 | 53.165 | 12.154 | 33.683 | 259.14 | 0.519 |
| 8 | 14 | 38 | 32.794 | 11.251 | 5.053 | 279.85 | 0.542 |
| 8 | 14 | 40 | 50.322 | 23.460 | 6.216 | 141.20 | 0.323 |
| 8 | 15 | 1 | 377.023 | 3.354 | 558.486 | 178.79 | 0.992 |
| 8 | 15 | 3 | 267.333 | 3.105 | 384.104 | 56.93 | 0.982 |
| 8 | 15 | 5 | 518.733 | 5.152 | 699.553 | 147.09 | 0.996 |
| 8 | 15 | 7 | 326.161 | 3.004 | 448.551 | 125.77 | 0.989 |
| 8 | 15 | 9 | 236.544 | 2.872 | 322.774 | 33.60 | 0.978 |
| 8 | 15 | 11 | 387.512 | 3.628 | 511.132 | 73.91 | 0.994 |
| 8 | 15 | 13 | 367.698 | 3.292 | 516.067 | 59.10 | 0.993 |
| 8 | 15 | 15 | 91.671 | 5.707 | 98.478 | 162.09 | 0.885 |
| 8 | 15 | 17 | 102.408 | 4.950 | 108.558 | 138.61 | 0.931 |
| 8 | 15 | 19 | 490.796 | 4.463 | 708.219 | 134.15 | 0.996 |
| 8 | 15 | 21 | 173.498 | 3.382 | 249.805 | 300.05 | 0.962 |
| 8 | 15 | 23 | 31.238 | 9.655 | 59.082 | 154.29 | 0.415 |

| | | | | | | | |
|---|---|---|---|---|---|---|---|
| 8 | 15 | 25 | 460.360 | 4.356 | 647.564 | 171.83 | 0.996 |
| 8 | 15 | 27 | 168.216 | 4.843 | 205.707 | 313.30 | 0.973 |
| 8 | 15 | 29 | 43.158 | 11.814 | 3.062 | 115.54 | 0.723 |
| 8 | 15 | 31 | 137.951 | 6.529 | 176.041 | 231.17 | 0.968 |
| 8 | 15 | 33 | 175.805 | 4.980 | 247.620 | 255.95 | 0.978 |
| 8 | 15 | 35 | 39.559 | 11.867 | 5.154 | 51.28 | 0.615 |
| 8 | 15 | 37 | 47.041 | 14.608 | 28.013 | 274.30 | 0.794 |
| 8 | 15 | 39 | 43.285 | 13.621 | 11.828 | 182.80 | 0.262 |
| 8 | 16 | 0 | 309.385 | 4.164 | 436.577 | 180.00 | 1.000 |
| 8 | 16 | 2 | 352.073 | 3.046 | 540.889 | 12.96 | 0.989 |
| 8 | 16 | 4 | 191.465 | 3.051 | 247.246 | 59.70 | 0.970 |
| 8 | 16 | 6 | 558.562 | 4.851 | 853.471 | 130.38 | 0.996 |
| 8 | 16 | 8 | 193.492 | 2.691 | 253.814 | 297.14 | 0.976 |
| 8 | 16 | 10 | 230.335 | 2.914 | 353.349 | 264.46 | 0.982 |
| 8 | 16 | 12 | 197.164 | 2.847 | 299.656 | 73.37 | 0.964 |
| 8 | 16 | 14 | 264.355 | 2.927 | 326.710 | 250.40 | 0.989 |
| 8 | 16 | 16 | 556.683 | 5.596 | 750.850 | 203.96 | 0.997 |
| 8 | 16 | 18 | 70.363 | 7.805 | 52.227 | 129.70 | 0.630 |
| 8 | 16 | 20 | 287.542 | 3.208 | 375.699 | 40.65 | 0.989 |
| 8 | 16 | 22 | 192.308 | 3.305 | 267.786 | 338.17 | 0.969 |
| 8 | 16 | 24 | 320.441 | 3.443 | 466.985 | 286.48 | 0.992 |
| 8 | 16 | 26 | 230.796 | 4.046 | 360.490 | 74.01 | 0.981 |
| 8 | 16 | 28 | 285.583 | 3.721 | 416.347 | 190.15 | 0.992 |
| 8 | 16 | 30 | 198.275 | 4.101 | 285.653 | 6.77 | 0.983 |
| 8 | 16 | 32 | 78.488 | 9.779 | 88.869 | 15.15 | 0.883 |
| 8 | 16 | 34 | 60.679 | 10.990 | 53.791 | 339.37 | 0.808 |
| 8 | 16 | 36 | 83.279 | 11.941 | 106.929 | 71.74 | 0.933 |
| 8 | 16 | 38 | 60.317 | 15.524 | 51.648 | 330.06 | 0.569 |
| 8 | 17 | 1 | 396.669 | 3.646 | 549.705 | 115.21 | 0.993 |
| 8 | 17 | 3 | 394.933 | 3.883 | 598.264 | 52.33 | 0.994 |
| 8 | 17 | 5 | 247.217 | 3.280 | 300.940 | 110.31 | 0.987 |
| 8 | 17 | 7 | 75.647 | 4.644 | 83.668 | 322.07 | 0.890 |
| 8 | 17 | 9 | 226.634 | 2.666 | 294.882 | 81.39 | 0.984 |
| 8 | 17 | 11 | 111.111 | 3.983 | 128.219 | 321.26 | 0.952 |
| 8 | 17 | 13 | 132.200 | 3.681 | 187.306 | 294.99 | 0.956 |
| 8 | 17 | 15 | 717.583 | 6.124 | 992.000 | 298.39 | 0.998 |
| 8 | 17 | 17 | 356.333 | 3.780 | 516.291 | 21.41 | 0.992 |
| 8 | 17 | 19 | 243.836 | 3.441 | 303.053 | 87.11 | 0.983 |
| 8 | 17 | 21 | 340.469 | 3.639 | 371.891 | 315.46 | 0.992 |
| 8 | 17 | 23 | 237.119 | 3.503 | 332.299 | 343.57 | 0.986 |
| 8 | 17 | 25 | 193.709 | 3.905 | 232.477 | 183.09 | 0.982 |
| 8 | 17 | 27 | 170.428 | 5.632 | 186.475 | 144.89 | 0.983 |
| 8 | 17 | 29 | 148.589 | 4.905 | 210.914 | 71.39 | 0.970 |
| 8 | 17 | 31 | 49.285 | 12.093 | 10.729 | 310.97 | 0.161 |
| 8 | 17 | 33 | 141.180 | 5.637 | 177.430 | 313.71 | 0.974 |
| 8 | 17 | 35 | 63.546 | 12.093 | 39.073 | 142.87 | 0.929 |
| 8 | 17 | 37 | 60.694 | 16.605 | 50.320 | 0.43 | 0.862 |
| 8 | 17 | 39 | 33.063 | 16.815 | 13.581 | 85.10 | 0.421 |
| 8 | 18 | 0 | 263.775 | 3.881 | 371.984 | 180.00 | 1.000 |
| 8 | 18 | 2 | 142.118 | 3.174 | 162.411 | 1.85 | 0.965 |
| 8 | 18 | 4 | 207.814 | 2.986 | 282.556 | 9.45 | 0.980 |
| 8 | 18 | 6 | 244.616 | 2.927 | 341.361 | 124.12 | 0.985 |
| 8 | 18 | 8 | 69.235 | 4.992 | 66.446 | 126.38 | 0.901 |
| 8 | 18 | 10 | 280.321 | 2.882 | 394.692 | 18.31 | 0.988 |
| 8 | 18 | 12 | 300.450 | 3.222 | 389.675 | 95.62 | 0.991 |
| 8 | 18 | 14 | 171.725 | 3.328 | 260.421 | 125.70 | 0.958 |
| 8 | 18 | 16 | 216.958 | 3.209 | 295.602 | 10.10 | 0.979 |
| 8 | 18 | 18 | 208.748 | 3.336 | 372.759 | 65.57 | 0.948 |
| 8 | 18 | 20 | 265.502 | 6.310 | 384.200 | 123.22 | 0.983 |
| 8 | 18 | 22 | 321.499 | 4.159 | 508.928 | 79.51 | 0.991 |
| 8 | 18 | 24 | 45.708 | 12.506 | 2.246 | 72.08 | 0.550 |
| 8 | 18 | 26 | 178.697 | 4.650 | 264.669 | 130.30 | 0.979 |
| 8 | 18 | 28 | 188.895 | 4.821 | 287.601 | 234.52 | 0.980 |
| 8 | 18 | 30 | 80.128 | 10.144 | 83.815 | 248.55 | 0.899 |
| 8 | 18 | 32 | 39.411 | 11.017 | 3.631 | 303.20 | 0.301 |
| 8 | 18 | 34 | 56.946 | 14.034 | 23.691 | 162.30 | 0.235 |
| 8 | 18 | 36 | 63.747 | 14.820 | 72.113 | 290.63 | 0.721 |
| 8 | 18 | 38 | 95.675 | 27.423 | 46.848 | 210.82 | 0.928 |
| 8 | 19 | 1 | 88.438 | 4.951 | 103.833 | 186.25 | 0.897 |
| 8 | 19 | 3 | 597.114 | 5.342 | 877.459 | 33.30 | 0.997 |
| 8 | 19 | 5 | 344.238 | 3.773 | 499.408 | 330.16 | 0.992 |
| 8 | 19 | 7 | 339.895 | 3.796 | 525.668 | 245.20 | 0.990 |
| 8 | 19 | 9 | 171.972 | 3.222 | 217.061 | 71.10 | 0.976 |
| 8 | 19 | 11 | 174.715 | 3.021 | 187.221 | 157.01 | 0.981 |
| 8 | 19 | 13 | 275.237 | 3.406 | 387.190 | 68.21 | 0.987 |
| 8 | 19 | 15 | 337.617 | 3.633 | 467.387 | 191.28 | 0.990 |
| 8 | 19 | 17 | 195.235 | 3.547 | 275.698 | 207.75 | 0.972 |

| | | | | | | | |
|---|---|---|---|---|---|---|---|
| 8 | 19 | 19 | 111.149 | 5.863 | 127.333 | 186.92 | 0.918 |
| 8 | 19 | 21 | 53.506 | 11.614 | 35.275 | 245.00 | 0.862 |
| 8 | 19 | 23 | 102.589 | 7.982 | 128.385 | 302.48 | 0.925 |
| 8 | 19 | 25 | 162.434 | 6.437 | 263.525 | 347.33 | 0.971 |
| 8 | 19 | 27 | 204.896 | 4.549 | 304.179 | 193.57 | 0.984 |
| 8 | 19 | 29 | 61.890 | 11.188 | 55.296 | 102.86 | 0.843 |
| 8 | 19 | 31 | 71.784 | 13.419 | 89.996 | 176.48 | 0.814 |
| 8 | 19 | 33 | 40.503 | 12.924 | 17.928 | 302.23 | 0.722 |
| 8 | 19 | 35 | 37.830 | 11.879 | 16.622 | 37.59 | 0.614 |
| 8 | 19 | 37 | 36.620 | 17.732 | 2.546 | 315.47 | 0.348 |
| 8 | 20 | 0 | 149.699 | 4.729 | 210.790 | 0.00 | 1.000 |
| 8 | 20 | 2 | 95.554 | 4.352 | 36.005 | 75.82 | 0.943 |
| 8 | 20 | 4 | 323.900 | 3.131 | 469.258 | 127.47 | 0.991 |
| 8 | 20 | 6 | 373.768 | 5.382 | 580.809 | 20.39 | 0.992 |
| 8 | 20 | 8 | 349.992 | 3.282 | 539.752 | 325.58 | 0.991 |
| 8 | 20 | 10 | 211.140 | 3.106 | 344.584 | 210.78 | 0.968 |
| 8 | 20 | 12 | 234.158 | 2.918 | 285.318 | 42.27 | 0.984 |
| 8 | 20 | 14 | 395.598 | 3.602 | 594.040 | 167.75 | 0.992 |
| 8 | 20 | 16 | 94.898 | 8.173 | 89.543 | 256.93 | 0.889 |
| 8 | 20 | 18 | 130.368 | 5.207 | 210.694 | 348.80 | 0.901 |
| 8 | 20 | 20 | 84.409 | 10.378 | 113.697 | 139.24 | 0.847 |
| 8 | 20 | 22 | 169.297 | 7.629 | 234.024 | 252.16 | 0.970 |
| 8 | 20 | 24 | 168.327 | 5.395 | 273.786 | 220.92 | 0.973 |
| 8 | 20 | 26 | 176.787 | 5.699 | 235.429 | 192.89 | 0.982 |
| 8 | 20 | 28 | 60.038 | 12.203 | 3.292 | 186.95 | 0.035 |
| 8 | 20 | 30 | 67.677 | 10.707 | 65.314 | 200.84 | 0.882 |
| 8 | 20 | 32 | 42.852 | 14.139 | 10.621 | 33.12 | 0.822 |
| 8 | 20 | 34 | 42.509 | 13.919 | 15.567 | 263.08 | 0.292 |
| 8 | 20 | 36 | 82.633 | 16.757 | 105.762 | 56.46 | 0.787 |
| 8 | 21 | 1 | 159.922 | 3.928 | 202.603 | 278.47 | 0.964 |
| 8 | 21 | 3 | 152.984 | 4.190 | 166.611 | 334.73 | 0.975 |
| 8 | 21 | 5 | 314.489 | 3.584 | 461.524 | 291.74 | 0.990 |
| 8 | 21 | 7 | 520.511 | 5.511 | 814.677 | 203.96 | 0.996 |
| 8 | 21 | 9 | 363.885 | 3.562 | 503.416 | 182.48 | 0.993 |
| 8 | 21 | 11 | 268.510 | 3.212 | 420.416 | 256.89 | 0.982 |
| 8 | 21 | 13 | 181.421 | 3.442 | 246.222 | 233.47 | 0.972 |
| 8 | 21 | 15 | 155.898 | 4.295 | 182.319 | 183.29 | 0.962 |
| 8 | 21 | 17 | 154.478 | 5.409 | 208.659 | 272.14 | 0.967 |
| 8 | 21 | 19 | 136.604 | 5.870 | 121.926 | 228.94 | 0.968 |
| 8 | 21 | 21 | 262.304 | 3.643 | 311.041 | 270.99 | 0.993 |
| 8 | 21 | 23 | 339.766 | 4.660 | 505.392 | 26.01 | 0.994 |
| 8 | 21 | 25 | 236.843 | 4.354 | 371.323 | 174.55 | 0.988 |
| 8 | 21 | 27 | 72.564 | 16.719 | 59.435 | 149.23 | 0.882 |
| 8 | 21 | 29 | 77.677 | 8.905 | 88.130 | 181.38 | 0.897 |
| 8 | 21 | 31 | 101.680 | 9.911 | 116.616 | 56.14 | 0.968 |
| 8 | 21 | 33 | 74.925 | 16.061 | 97.108 | 177.49 | 0.796 |
| 8 | 21 | 35 | 46.214 | 13.073 | 33.325 | 331.52 | 0.618 |
| 8 | 22 | 0 | 51.661 | 13.037 | 29.918 | 180.00 | 0.415 |
| 8 | 22 | 2 | 152.968 | 4.291 | 221.850 | 324.81 | 0.953 |
| 8 | 22 | 4 | 131.638 | 4.155 | 186.837 | 267.55 | 0.870 |
| 8 | 22 | 6 | 256.652 | 4.304 | 349.518 | 225.85 | 0.985 |
| 8 | 22 | 8 | 471.622 | 4.259 | 720.487 | 172.83 | 0.995 |
| 8 | 22 | 10 | 81.127 | 7.644 | 69.631 | 215.42 | 0.803 |
| 8 | 22 | 12 | 293.793 | 3.676 | 572.814 | 139.94 | 0.976 |
| 8 | 22 | 14 | 190.873 | 4.000 | 251.197 | 357.01 | 0.980 |
| 8 | 22 | 16 | 96.984 | 7.085 | 117.466 | 279.82 | 0.916 |
| 8 | 22 | 18 | 177.646 | 5.090 | 247.883 | 53.68 | 0.975 |
| 8 | 22 | 20 | 161.354 | 4.587 | 221.146 | 318.99 | 0.978 |
| 8 | 22 | 22 | 228.012 | 4.368 | 280.127 | 337.91 | 0.990 |
| 8 | 22 | 24 | 61.883 | 13.087 | 63.545 | 283.83 | 0.650 |
| 8 | 22 | 26 | 99.300 | 10.270 | 114.938 | 10.73 | 0.937 |
| 8 | 22 | 28 | 81.005 | 12.254 | 116.633 | 93.93 | 0.796 |
| 8 | 22 | 30 | 115.871 | 9.456 | 165.144 | 358.48 | 0.971 |
| 8 | 22 | 32 | 52.702 | 15.827 | 32.142 | 349.98 | 0.853 |
| 8 | 22 | 34 | 54.973 | 19.252 | 17.623 | 162.70 | 0.252 |
| 8 | 23 | 1 | 214.575 | 3.610 | 265.496 | 263.22 | 0.980 |
| 8 | 23 | 3 | 180.382 | 3.329 | 229.613 | 97.25 | 0.973 |
| 8 | 23 | 5 | 122.964 | 5.231 | 114.254 | 172.20 | 0.951 |
| 8 | 23 | 7 | 118.090 | 5.890 | 144.532 | 92.67 | 0.915 |
| 8 | 23 | 9 | 316.655 | 3.985 | 443.146 | 291.42 | 0.990 |
| 8 | 23 | 11 | 541.598 | 4.686 | 775.944 | 33.91 | 0.997 |
| 8 | 23 | 13 | 108.333 | 5.880 | 135.888 | 110.98 | 0.932 |
| 8 | 23 | 15 | 108.438 | 6.939 | 164.678 | 73.18 | 0.884 |
| 8 | 23 | 17 | 281.977 | 3.712 | 450.765 | 190.69 | 0.991 |
| 8 | 23 | 19 | 249.694 | 3.802 | 320.383 | 137.84 | 0.992 |
| 8 | 23 | 21 | 54.133 | 12.576 | 39.149 | 49.13 | 0.760 |
| 8 | 23 | 23 | 53.508 | 10.577 | 12.130 | 188.18 | 0.224 |

| | | | | | | | |
|---|---|---|---|---|---|---|---|
| 8 | 23 | 25 | 137.399 | 5.244 | 159.047 | 353.62 | 0.977 |
| 8 | 23 | 27 | 42.355 | 13.428 | 18.219 | 338.12 | 0.410 |
| 8 | 23 | 29 | 89.623 | 14.169 | 85.149 | 46.45 | 0.959 |
| 8 | 23 | 31 | 57.179 | 22.008 | 35.750 | 14.59 | 0.759 |
| 8 | 23 | 33 | 37.518 | 13.162 | 13.535 | 98.09 | 0.345 |
| 8 | 24 | 0 | 174.870 | 5.806 | 245.915 | 0.00 | 1.000 |
| 8 | 24 | 2 | 320.722 | 3.893 | 508.826 | 175.36 | 0.988 |
| 8 | 24 | 4 | 395.281 | 3.942 | 525.506 | 264.64 | 0.994 |
| 8 | 24 | 6 | 145.622 | 6.169 | 163.611 | 170.13 | 0.971 |
| 8 | 24 | 8 | 91.397 | 14.570 | 102.805 | 255.29 | 0.900 |
| 8 | 24 | 10 | 121.033 | 6.711 | 159.158 | 318.31 | 0.947 |
| 8 | 24 | 12 | 196.067 | 4.227 | 284.419 | 262.66 | 0.980 |
| 8 | 24 | 14 | 133.828 | 5.094 | 170.532 | 144.19 | 0.960 |
| 8 | 24 | 16 | 219.955 | 3.938 | 320.376 | 126.61 | 0.988 |
| 8 | 24 | 18 | 134.446 | 6.257 | 157.202 | 228.70 | 0.971 |
| 8 | 24 | 20 | 79.632 | 11.026 | 93.116 | 294.21 | 0.902 |
| 8 | 24 | 22 | 109.223 | 7.226 | 150.770 | 302.83 | 0.945 |
| 8 | 24 | 24 | 47.924 | 12.591 | 29.867 | 310.86 | 0.713 |
| 8 | 24 | 26 | 62.431 | 14.046 | 65.277 | 351.00 | 0.654 |
| 8 | 24 | 28 | 43.556 | 12.790 | 29.042 | 121.93 | 0.766 |
| 8 | 24 | 30 | 39.943 | 19.177 | 8.623 | 184.32 | 0.417 |
| 8 | 24 | 32 | 44.907 | 12.611 | 22.044 | 130.21 | 0.810 |
| 8 | 25 | 1 | 484.299 | 4.388 | 663.250 | 204.65 | 0.997 |
| 8 | 25 | 3 | 166.991 | 4.743 | 238.856 | 168.95 | 0.972 |
| 8 | 25 | 5 | 63.035 | 10.160 | 49.551 | 55.79 | 0.468 |
| 8 | 25 | 7 | 226.251 | 4.646 | 364.610 | 288.62 | 0.982 |
| 8 | 25 | 9 | 112.484 | 7.829 | 181.200 | 204.57 | 0.888 |
| 8 | 25 | 11 | 164.070 | 4.417 | 184.974 | 66.20 | 0.983 |
| 8 | 25 | 13 | 49.646 | 11.380 | 23.310 | 172.88 | 0.299 |
| 8 | 25 | 15 | 234.605 | 4.114 | 295.996 | 20.18 | 0.992 |
| 8 | 25 | 17 | 238.153 | 3.586 | 318.970 | 58.02 | 0.991 |
| 8 | 25 | 19 | 101.840 | 7.168 | 169.033 | 344.82 | 0.910 |
| 8 | 25 | 21 | 97.246 | 9.420 | 160.332 | 18.30 | 0.866 |
| 8 | 25 | 23 | 150.544 | 6.667 | 212.198 | 308.76 | 0.977 |
| 8 | 25 | 25 | 105.052 | 11.325 | 183.419 | 310.30 | 0.942 |
| 8 | 25 | 27 | 62.125 | 15.457 | 40.038 | 124.93 | 0.363 |
| 8 | 25 | 29 | 152.836 | 8.321 | 270.650 | 174.19 | 0.975 |
| 8 | 26 | 0 | 92.247 | 14.570 | 115.980 | 180.00 | 0.901 |
| 8 | 26 | 2 | 98.770 | 7.669 | 114.782 | 229.47 | 0.926 |
| 8 | 26 | 4 | 53.943 | 12.218 | 24.694 | 133.78 | 0.697 |
| 8 | 26 | 6 | 224.356 | 4.796 | 278.698 | 203.46 | 0.991 |
| 8 | 26 | 8 | 183.603 | 5.630 | 247.336 | 326.51 | 0.984 |
| 8 | 26 | 10 | 159.246 | 7.957 | 182.446 | 323.91 | 0.981 |
| 8 | 26 | 12 | 129.627 | 7.247 | 195.393 | 195.47 | 0.962 |
| 8 | 26 | 14 | 132.820 | 5.359 | 183.940 | 44.41 | 0.966 |
| 8 | 26 | 16 | 105.532 | 8.427 | 117.257 | 176.14 | 0.954 |
| 8 | 26 | 18 | 132.648 | 5.011 | 235.815 | 127.42 | 0.933 |
| 8 | 26 | 20 | 44.282 | 11.685 | 10.586 | 249.32 | 0.843 |
| 8 | 26 | 22 | 56.599 | 10.220 | 18.678 | 234.19 | 0.894 |
| 8 | 26 | 24 | 96.633 | 10.497 | 131.835 | 244.44 | 0.959 |
| 8 | 26 | 26 | 42.522 | 13.420 | 21.244 | 155.14 | 0.366 |
| 8 | 26 | 28 | 37.616 | 12.639 | 16.180 | 303.80 | 0.511 |
| 8 | 27 | 1 | 56.188 | 12.083 | 50.211 | 18.32 | 0.587 |
| 8 | 27 | 3 | 335.386 | 3.846 | 525.616 | 312.70 | 0.995 |
| 8 | 27 | 5 | 74.619 | 11.032 | 82.283 | 152.70 | 0.894 |
| 8 | 27 | 7 | 134.120 | 8.752 | 176.016 | 257.02 | 0.970 |
| 8 | 27 | 9 | 148.318 | 5.825 | 273.788 | 27.52 | 0.958 |
| 8 | 27 | 11 | 98.100 | 9.520 | 73.112 | 17.34 | 0.960 |
| 8 | 27 | 13 | 34.792 | 10.135 | 13.188 | 66.86 | 0.619 |
| 8 | 27 | 15 | 81.563 | 9.574 | 78.414 | 220.39 | 0.926 |
| 8 | 27 | 17 | 31.738 | 10.439 | 3.194 | 317.79 | 0.162 |
| 8 | 27 | 19 | 72.095 | 8.995 | 76.711 | 230.73 | 0.900 |
| 8 | 27 | 21 | 67.827 | 12.794 | 70.172 | 305.11 | 0.845 |
| 8 | 27 | 23 | 91.618 | 11.580 | 111.207 | 340.80 | 0.958 |
| 8 | 27 | 25 | 45.455 | 14.846 | 15.636 | 31.01 | 0.846 |
| 8 | 28 | 0 | 167.322 | 6.655 | 234.547 | 180.00 | 1.000 |
| 8 | 28 | 2 | 93.622 | 8.205 | 93.439 | 277.89 | 0.947 |
| 8 | 28 | 4 | 105.540 | 6.841 | 121.353 | 128.07 | 0.955 |
| 8 | 28 | 6 | 97.282 | 8.436 | 120.443 | 357.45 | 0.942 |
| 8 | 28 | 8 | 71.076 | 11.988 | 55.149 | 24.62 | 0.902 |
| 8 | 28 | 10 | 190.927 | 4.886 | 324.765 | 15.07 | 0.979 |
| 8 | 28 | 12 | 108.278 | 7.788 | 162.179 | 5.70 | 0.943 |
| 8 | 28 | 14 | 31.658 | 9.803 | 3.982 | 116.31 | 0.468 |
| 8 | 28 | 16 | 56.001 | 11.745 | 39.287 | 196.52 | 0.396 |
| 8 | 28 | 18 | 117.111 | 7.642 | 224.157 | 192.09 | 0.906 |
| 8 | 28 | 20 | 78.291 | 13.394 | 122.463 | 183.37 | 0.897 |
| 8 | 28 | 22 | 40.296 | 12.486 | 25.403 | 16.29 | 0.578 |

| | | | | | | |
|---|---|---|---|---|---|---|
| 8 | 28 | 24 | 62.338 | 14.097 | 76.756 | 326.79 | 0.858 |
| 8 | 28 | 26 | 57.794 | 14.371 | 58.519 | 71.96 | 0.813 |
| 8 | 29 | 1 | 76.741 | 8.629 | 105.758 | 85.73 | 0.878 |
| 8 | 29 | 3 | 39.102 | 11.603 | 3.819 | 170.86 | 0.702 |
| 8 | 29 | 5 | 42.410 | 11.640 | 16.432 | 157.32 | 0.799 |
| 8 | 29 | 7 | 46.799 | 11.615 | 18.520 | 233.21 | 0.304 |
| 8 | 29 | 9 | 126.550 | 5.166 | 205.253 | 333.95 | 0.955 |
| 8 | 29 | 11 | 104.219 | 10.237 | 153.892 | 239.07 | 0.947 |
| 8 | 29 | 13 | 64.713 | 11.678 | 45.447 | 223.54 | 0.900 |
| 8 | 29 | 15 | 125.951 | 8.104 | 173.058 | 215.72 | 0.967 |
| 8 | 29 | 17 | 84.514 | 9.744 | 151.944 | 170.95 | 0.815 |
| 8 | 29 | 19 | 39.649 | 11.833 | 24.144 | 297.15 | 0.663 |
| 8 | 29 | 21 | 50.320 | 13.804 | 27.067 | 310.38 | 0.320 |
| 8 | 29 | 23 | 45.698 | 14.359 | 24.872 | 187.53 | 0.476 |
| 8 | 30 | 0 | 35.783 | 14.595 | 14.684 | 180.00 | 0.300 |
| 8 | 30 | 2 | 78.728 | 7.803 | 77.686 | 51.07 | 0.935 |
| 8 | 30 | 4 | 78.205 | 11.499 | 97.300 | 51.17 | 0.912 |
| 8 | 30 | 6 | 74.990 | 11.065 | 94.270 | 25.68 | 0.899 |
| 8 | 30 | 8 | 87.367 | 10.852 | 105.996 | 42.92 | 0.929 |
| 8 | 30 | 10 | 50.215 | 11.410 | 36.706 | 53.88 | 0.607 |
| 8 | 30 | 12 | 35.036 | 11.522 | 7.168 | 217.15 | 0.241 |
| 8 | 30 | 14 | 80.042 | 14.134 | 129.058 | 117.17 | 0.894 |
| 8 | 30 | 16 | 38.685 | 12.061 | 21.641 | 150.45 | 0.519 |
| 8 | 30 | 18 | 61.012 | 13.316 | 39.791 | 313.39 | 0.376 |
| 8 | 30 | 20 | 55.084 | 13.765 | 44.039 | 18.71 | 0.886 |
| 8 | 30 | 22 | 53.651 | 14.654 | 49.672 | 242.00 | 0.792 |
| 8 | 31 | 1 | 39.343 | 11.195 | 8.459 | 86.47 | 0.490 |
| 8 | 31 | 3 | 81.934 | 9.793 | 131.928 | 317.81 | 0.850 |
| 8 | 31 | 5 | 47.314 | 11.581 | 32.205 | 74.57 | 0.643 |
| 8 | 31 | 7 | 102.141 | 7.591 | 164.939 | 91.86 | 0.936 |
| 8 | 31 | 9 | 61.440 | 12.268 | 46.842 | 52.64 | 0.931 |
| 8 | 31 | 11 | 50.168 | 13.043 | 46.335 | 75.38 | 0.849 |
| 8 | 31 | 13 | 52.815 | 16.605 | 33.865 | 169.70 | 0.868 |
| 8 | 31 | 15 | 40.896 | 14.062 | 23.989 | 193.54 | 0.559 |
| 8 | 31 | 17 | 37.954 | 12.098 | 16.778 | 182.00 | 0.466 |
| 8 | 31 | 19 | 42.655 | 13.136 | 25.005 | 125.95 | 0.735 |
| 8 | 32 | 0 | 125.717 | 10.672 | 163.065 | 180.00 | 0.946 |
| 8 | 32 | 2 | 46.487 | 11.787 | 34.934 | 338.75 | 0.848 |
| 8 | 32 | 4 | 74.802 | 11.263 | 106.106 | 208.17 | 0.638 |
| 8 | 32 | 6 | 36.217 | 11.194 | 16.708 | 339.78 | 0.555 |
| 8 | 32 | 8 | 53.219 | 14.598 | 54.866 | 84.00 | 0.819 |
| 8 | 32 | 10 | 31.526 | 10.944 | 15.459 | 60.26 | 0.770 |
| 8 | 32 | 12 | 46.419 | 13.340 | 38.435 | 325.43 | 0.809 |
| 8 | 32 | 14 | 41.557 | 13.139 | 28.372 | 250.84 | 0.598 |
| 8 | 32 | 16 | 44.493 | 19.148 | 11.509 | 328.18 | 0.484 |
| 8 | 33 | 1 | 35.313 | 11.186 | 13.533 | 94.39 | 0.662 |
| 8 | 33 | 3 | 63.300 | 12.230 | 33.944 | 136.14 | 0.946 |
| 8 | 33 | 5 | 92.314 | 14.434 | 154.697 | 248.82 | 0.821 |
| 8 | 33 | 7 | 52.739 | 16.366 | 42.441 | 172.96 | 0.850 |
| 8 | 33 | 9 | 84.304 | 10.128 | 151.517 | 204.96 | 0.856 |
| 8 | 33 | 11 | 48.963 | 14.001 | 22.782 | 245.93 | 0.315 |
| 8 | 33 | 13 | 82.061 | 17.246 | 85.325 | 51.66 | 0.927 |
| 8 | 34 | 0 | 38.012 | 25.807 | 13.731 | 0.00 | 0.349 |
| 8 | 34 | 2 | 39.510 | 12.111 | 20.646 | 153.04 | 0.393 |
| 8 | 34 | 4 | 48.493 | 12.897 | 41.992 | 125.50 | 0.572 |
| 8 | 34 | 6 | 36.909 | 11.362 | 20.052 | 289.95 | 0.562 |
| 9 | 0 | 1 | 99.630 | 1.890 | 124.973 | 180.00 | 0.886 |
| 9 | 0 | 3 | 20.090 | 5.993 | 15.768 | 180.00 | 0.554 |
| 9 | 0 | 5 | 158.671 | 2.092 | 163.887 | 0.00 | 0.730 |
| 9 | 0 | 7 | 263.832 | 3.660 | 373.067 | 0.00 | 1.000 |
| 9 | 0 | 9 | 101.471 | 2.999 | 101.369 | 0.00 | 0.708 |
| 9 | 0 | 11 | 432.529 | 5.210 | 608.763 | 180.00 | 1.000 |
| 9 | 0 | 13 | 91.672 | 3.501 | 124.160 | 180.00 | 0.967 |
| 9 | 0 | 15 | 109.459 | 3.726 | 151.399 | 180.00 | 0.989 |
| 9 | 0 | 17 | 354.384 | 4.525 | 493.387 | 180.00 | 1.000 |
| 9 | 0 | 19 | 109.949 | 4.620 | 1.104 | 0.00 | 0.007 |
| 9 | 0 | 21 | 454.518 | 5.702 | 626.557 | 0.00 | 1.000 |
| 9 | 0 | 23 | 23.293 | 11.054 | 18.425 | 0.00 | 0.585 |
| 9 | 0 | 25 | 445.923 | 6.572 | 607.346 | 180.00 | 1.000 |
| 9 | 0 | 27 | 182.396 | 6.500 | 246.742 | 0.00 | 1.000 |
| 9 | 0 | 29 | 33.517 | 13.608 | 13.625 | 0.00 | 0.304 |
| 9 | 0 | 31 | 61.909 | 15.083 | 81.952 | 0.00 | 0.999 |
| 9 | 0 | 33 | 243.811 | 6.618 | 321.981 | 0.00 | 1.000 |
| 9 | 0 | 35 | 186.059 | 6.030 | 243.431 | 0.00 | 1.000 |
| 9 | 0 | 37 | 44.394 | 16.811 | 12.391 | 0.00 | 0.219 |
| 9 | 0 | 39 | 59.806 | 16.764 | 38.268 | 0.00 | 0.512 |
| 9 | 0 | 41 | 26.621 | 13.317 | 9.735 | 0.00 | 0.296 |

| | | | | | | | |
|---|---|---|---|---|---|---|---|
| 9 | 0 | 43 | 30.623 | 22.436 | 6.892 | 180.00 | 0.225 |
| 9 | 1 | 0 | 1090.523 | 16.166 | 1545.755 | 180.00 | 1.000 |
| 9 | 1 | 2 | 491.908 | 4.564 | 692.563 | 214.66 | 0.995 |
| 9 | 1 | 4 | 228.636 | 1.851 | 326.059 | 275.34 | 0.994 |
| 9 | 1 | 6 | 314.975 | 2.711 | 382.245 | 131.13 | 0.988 |
| 9 | 1 | 8 | 73.301 | 2.344 | 73.252 | 87.20 | 0.986 |
| 9 | 1 | 10 | 150.014 | 2.013 | 189.029 | 151.63 | 0.981 |
| 9 | 1 | 12 | 85.057 | 2.934 | 38.999 | 338.06 | 0.919 |
| 9 | 1 | 14 | 125.925 | 2.600 | 149.419 | 289.76 | 0.984 |
| 9 | 1 | 16 | 330.997 | 3.084 | 498.529 | 249.80 | 0.991 |
| 9 | 1 | 18 | 160.882 | 2.677 | 194.902 | 2.25 | 0.958 |
| 9 | 1 | 20 | 233.098 | 2.754 | 343.018 | 275.77 | 0.983 |
| 9 | 1 | 22 | 389.116 | 3.446 | 501.950 | 31.51 | 0.994 |
| 9 | 1 | 24 | 90.424 | 5.164 | 95.626 | 208.59 | 0.841 |
| 9 | 1 | 26 | 427.976 | 3.783 | 602.040 | 80.02 | 0.994 |
| 9 | 1 | 28 | 73.591 | 7.158 | 18.510 | 92.43 | 0.887 |
| 9 | 1 | 30 | 171.286 | 4.377 | 238.221 | 235.83 | 0.954 |
| 9 | 1 | 32 | 217.481 | 4.451 | 329.865 | 357.48 | 0.978 |
| 9 | 1 | 34 | 148.308 | 6.182 | 201.278 | 82.10 | 0.970 |
| 9 | 1 | 36 | 168.017 | 5.450 | 199.662 | 13.22 | 0.980 |
| 9 | 1 | 38 | 108.501 | 11.498 | 157.730 | 141.77 | 0.919 |
| 9 | 1 | 40 | 37.301 | 11.453 | 7.130 | 112.45 | 0.168 |
| 9 | 1 | 42 | 55.392 | 15.324 | 34.323 | 194.47 | 0.858 |
| 9 | 2 | 1 | 720.855 | 9.080 | 985.756 | 187.00 | 0.997 |
| 9 | 2 | 3 | 294.468 | 2.690 | 482.880 | 46.80 | 0.980 |
| 9 | 2 | 5 | 164.361 | 1.614 | 223.994 | 313.39 | 0.978 |
| 9 | 2 | 7 | 401.792 | 3.245 | 540.801 | 159.35 | 0.992 |
| 9 | 2 | 9 | 283.598 | 2.606 | 438.782 | 193.43 | 0.979 |
| 9 | 2 | 11 | 171.877 | 2.043 | 239.762 | 341.53 | 0.976 |
| 9 | 2 | 13 | 63.626 | 4.560 | 47.189 | 16.15 | 0.637 |
| 9 | 2 | 15 | 127.507 | 2.480 | 194.637 | 74.52 | 0.910 |
| 9 | 2 | 17 | 275.605 | 2.718 | 385.741 | 326.10 | 0.984 |
| 9 | 2 | 19 | 62.664 | 5.279 | 6.900 | 148.27 | 0.178 |
| 9 | 2 | 21 | 73.472 | 5.980 | 40.042 | 78.33 | 0.853 |
| 9 | 2 | 23 | 242.389 | 2.962 | 311.785 | 57.14 | 0.984 |
| 9 | 2 | 25 | 186.589 | 2.941 | 303.383 | 90.77 | 0.952 |
| 9 | 2 | 27 | 156.020 | 4.034 | 208.222 | 222.68 | 0.954 |
| 9 | 2 | 29 | 97.381 | 6.181 | 80.506 | 26.00 | 0.869 |
| 9 | 2 | 31 | 95.391 | 8.154 | 106.525 | 102.03 | 0.898 |
| 9 | 2 | 33 | 54.897 | 12.451 | 19.680 | 102.29 | 0.636 |
| 9 | 2 | 35 | 231.557 | 4.101 | 318.590 | 204.19 | 0.988 |
| 9 | 2 | 37 | 132.489 | 6.826 | 202.969 | 30.81 | 0.950 |
| 9 | 2 | 39 | 61.246 | 11.793 | 56.628 | 265.76 | 0.678 |
| 9 | 2 | 41 | 83.268 | 15.673 | 93.527 | 219.32 | 0.931 |
| 9 | 2 | 43 | 51.239 | 17.020 | 24.855 | 49.34 | 0.420 |
| 9 | 3 | 0 | 1256.613 | 20.374 | 1779.493 | 0.00 | 1.000 |
| 9 | 3 | 2 | 876.704 | 8.672 | 1276.200 | 80.13 | 0.998 |
| 9 | 3 | 4 | 284.647 | 2.348 | 372.597 | 340.84 | 0.983 |
| 9 | 3 | 6 | 199.005 | 1.838 | 266.405 | 31.45 | 0.971 |
| 9 | 3 | 8 | 309.600 | 2.586 | 407.028 | 97.16 | 0.992 |
| 9 | 3 | 10 | 125.433 | 1.946 | 186.356 | 303.84 | 0.987 |
| 9 | 3 | 12 | 186.180 | 2.301 | 254.402 | 255.30 | 0.968 |
| 9 | 3 | 14 | 540.825 | 4.432 | 772.431 | 155.57 | 0.996 |
| 9 | 3 | 16 | 393.448 | 3.801 | 553.707 | 39.76 | 0.993 |
| 9 | 3 | 18 | 345.209 | 3.079 | 541.102 | 93.46 | 0.986 |
| 9 | 3 | 20 | 316.797 | 3.048 | 496.294 | 158.63 | 0.984 |
| 9 | 3 | 22 | 343.269 | 3.217 | 502.306 | 66.93 | 0.992 |
| 9 | 3 | 24 | 324.255 | 3.180 | 472.652 | 47.16 | 0.990 |
| 9 | 3 | 26 | 72.435 | 6.589 | 62.172 | 274.92 | 0.699 |
| 9 | 3 | 28 | 157.577 | 4.131 | 183.246 | 279.84 | 0.966 |
| 9 | 3 | 30 | 162.465 | 4.610 | 190.740 | 252.35 | 0.959 |
| 9 | 3 | 32 | 101.601 | 8.671 | 128.436 | 252.53 | 0.905 |
| 9 | 3 | 34 | 45.334 | 12.033 | 4.114 | 316.52 | 0.675 |
| 9 | 3 | 36 | 157.506 | 5.975 | 270.384 | 124.14 | 0.958 |
| 9 | 3 | 38 | 117.112 | 6.628 | 196.954 | 119.24 | 0.920 |
| 9 | 3 | 40 | 76.366 | 11.182 | 90.784 | 202.53 | 0.871 |
| 9 | 3 | 42 | 50.847 | 14.200 | 5.774 | 77.64 | 0.889 |
| 9 | 4 | 1 | 451.596 | 4.572 | 615.648 | 68.94 | 0.994 |
| 9 | 4 | 3 | 222.188 | 1.842 | 338.956 | 24.16 | 0.976 |
| 9 | 4 | 5 | 459.369 | 3.808 | 688.333 | 51.00 | 0.993 |
| 9 | 4 | 7 | 535.562 | 4.310 | 754.911 | 101.52 | 0.995 |
| 9 | 4 | 9 | 143.234 | 2.091 | 195.613 | 105.94 | 0.973 |
| 9 | 4 | 11 | 294.384 | 2.849 | 474.059 | 281.62 | 0.985 |
| 9 | 4 | 13 | 74.358 | 3.630 | 80.346 | 215.57 | 0.759 |
| 9 | 4 | 15 | 277.857 | 2.585 | 397.377 | 10.06 | 0.984 |
| 9 | 4 | 17 | 274.904 | 2.759 | 354.158 | 324.57 | 0.986 |
| 9 | 4 | 19 | 67.275 | 5.064 | 25.462 | 168.23 | 0.801 |

| | | | | | | | |
|---|---|---|---|---|---|---|---|
| 9 | 4 | 21 | 273.667 | 2.994 | 364.828 | 282.98 | 0.988 |
| 9 | 4 | 23 | 435.137 | 3.712 | 622.040 | 358.81 | 0.995 |
| 9 | 4 | 25 | 343.857 | 3.284 | 495.753 | 88.37 | 0.991 |
| 9 | 4 | 27 | 440.528 | 4.025 | 613.202 | 73.36 | 0.995 |
| 9 | 4 | 29 | 133.472 | 4.339 | 185.241 | 320.01 | 0.925 |
| 9 | 4 | 31 | 200.415 | 4.588 | 231.666 | 184.10 | 0.982 |
| 9 | 4 | 33 | 251.713 | 3.942 | 401.907 | 206.32 | 0.982 |
| 9 | 4 | 35 | 101.075 | 9.462 | 141.343 | 349.54 | 0.913 |
| 9 | 4 | 37 | 65.440 | 11.103 | 22.480 | 139.95 | 0.244 |
| 9 | 4 | 39 | 50.876 | 12.483 | 29.391 | 190.09 | 0.431 |
| 9 | 4 | 41 | 38.159 | 12.428 | 12.372 | 95.63 | 0.512 |
| 9 | 4 | 43 | 41.602 | 19.519 | 5.430 | 321.93 | 0.362 |
| 9 | 5 | 0 | 240.319 | 3.312 | 340.896 | 0.00 | 1.000 |
| 9 | 5 | 2 | 589.165 | 5.517 | 861.910 | 168.25 | 0.996 |
| 9 | 5 | 4 | 443.848 | 3.797 | 618.348 | 161.30 | 0.993 |
| 9 | 5 | 6 | 177.354 | 2.016 | 247.080 | 1.07 | 0.964 |
| 9 | 5 | 8 | 194.244 | 2.008 | 245.703 | 99.91 | 0.990 |
| 9 | 5 | 10 | 127.443 | 1.962 | 132.699 | 304.14 | 0.987 |
| 9 | 5 | 12 | 315.253 | 3.276 | 484.458 | 253.54 | 0.987 |
| 9 | 5 | 14 | 314.956 | 2.998 | 421.129 | 329.10 | 0.990 |
| 9 | 5 | 16 | 479.750 | 5.456 | 636.838 | 18.84 | 0.995 |
| 9 | 5 | 18 | 310.004 | 2.886 | 405.814 | 275.91 | 0.987 |
| 9 | 5 | 20 | 412.736 | 3.627 | 593.195 | 184.39 | 0.991 |
| 9 | 5 | 22 | 86.212 | 4.282 | 10.292 | 76.69 | 0.954 |
| 9 | 5 | 24 | 505.785 | 4.369 | 668.785 | 45.04 | 0.996 |
| 9 | 5 | 26 | 261.207 | 3.488 | 379.279 | 124.48 | 0.984 |
| 9 | 5 | 28 | 321.889 | 3.607 | 507.863 | 193.05 | 0.984 |
| 9 | 5 | 30 | 83.260 | 7.800 | 85.587 | 94.57 | 0.726 |
| 9 | 5 | 32 | 97.811 | 8.561 | 116.054 | 329.23 | 0.904 |
| 9 | 5 | 34 | 76.837 | 11.868 | 66.443 | 275.35 | 0.907 |
| 9 | 5 | 36 | 196.367 | 5.068 | 265.269 | 283.54 | 0.983 |
| 9 | 5 | 38 | 118.213 | 6.687 | 214.267 | 46.32 | 0.861 |
| 9 | 5 | 40 | 67.911 | 24.078 | 61.968 | 357.53 | 0.807 |
| 9 | 5 | 42 | 90.868 | 14.516 | 116.778 | 349.52 | 0.934 |
| 9 | 6 | 1 | 96.351 | 2.260 | 119.304 | 1.38 | 0.868 |
| 9 | 6 | 3 | 221.178 | 2.336 | 338.930 | 206.92 | 0.967 |
| 9 | 6 | 5 | 495.101 | 5.448 | 693.350 | 153.20 | 0.995 |
| 9 | 6 | 7 | 203.900 | 2.165 | 276.901 | 56.55 | 0.978 |
| 9 | 6 | 9 | 295.675 | 2.608 | 422.736 | 251.93 | 0.991 |
| 9 | 6 | 11 | 267.522 | 2.613 | 385.571 | 351.95 | 0.983 |
| 9 | 6 | 13 | 244.745 | 2.408 | 345.102 | 337.91 | 0.978 |
| 9 | 6 | 15 | 293.456 | 2.809 | 363.931 | 25.18 | 0.987 |
| 9 | 6 | 17 | 99.439 | 3.599 | 49.365 | 319.50 | 0.286 |
| 9 | 6 | 19 | 294.547 | 2.891 | 392.870 | 228.48 | 0.986 |
| 9 | 6 | 21 | 85.803 | 3.864 | 65.485 | 223.59 | 0.931 |
| 9 | 6 | 23 | 379.069 | 3.390 | 535.313 | 247.63 | 0.993 |
| 9 | 6 | 25 | 68.790 | 7.368 | 11.456 | 112.91 | 0.853 |
| 9 | 6 | 27 | 196.705 | 3.409 | 319.053 | 263.08 | 0.963 |
| 9 | 6 | 29 | 88.356 | 7.556 | 92.472 | 321.23 | 0.766 |
| 9 | 6 | 31 | 326.473 | 3.615 | 488.925 | 256.44 | 0.991 |
| 9 | 6 | 33 | 116.337 | 6.127 | 153.462 | 161.11 | 0.952 |
| 9 | 6 | 35 | 150.888 | 6.997 | 239.907 | 329.99 | 0.962 |
| 9 | 6 | 37 | 81.456 | 10.497 | 79.240 | 304.81 | 0.900 |
| 9 | 6 | 39 | 129.822 | 6.633 | 172.733 | 44.89 | 0.964 |
| 9 | 6 | 41 | 50.385 | 14.110 | 36.671 | 89.38 | 0.812 |
| 9 | 6 | 43 | 56.284 | 23.547 | 19.161 | 171.19 | 0.723 |
| 9 | 7 | 0 | 355.503 | 3.861 | 504.182 | 180.00 | 1.000 |
| 9 | 7 | 2 | 373.588 | 5.093 | 527.054 | 329.19 | 0.990 |
| 9 | 7 | 4 | 233.160 | 2.052 | 345.999 | 190.30 | 0.976 |
| 9 | 7 | 6 | 300.216 | 2.592 | 389.706 | 199.01 | 0.990 |
| 9 | 7 | 8 | 124.801 | 2.405 | 126.762 | 173.67 | 0.943 |
| 9 | 7 | 10 | 234.735 | 2.320 | 326.944 | 331.07 | 0.980 |
| 9 | 7 | 12 | 151.751 | 2.371 | 193.306 | 312.79 | 0.959 |
| 9 | 7 | 14 | 221.577 | 2.419 | 325.349 | 167.35 | 0.973 |
| 9 | 7 | 16 | 315.430 | 2.964 | 397.648 | 129.80 | 0.990 |
| 9 | 7 | 18 | 503.534 | 4.265 | 663.444 | 292.15 | 0.995 |
| 9 | 7 | 20 | 397.684 | 4.345 | 621.139 | 47.50 | 0.993 |
| 9 | 7 | 22 | 264.461 | 2.895 | 368.777 | 258.79 | 0.987 |
| 9 | 7 | 24 | 241.375 | 3.146 | 314.723 | 263.06 | 0.983 |
| 9 | 7 | 26 | 111.187 | 4.545 | 142.397 | 249.62 | 0.907 |
| 9 | 7 | 28 | 311.881 | 3.362 | 401.406 | 185.18 | 0.989 |
| 9 | 7 | 30 | 372.738 | 3.930 | 565.733 | 292.16 | 0.993 |
| 9 | 7 | 32 | 71.553 | 9.862 | 53.562 | 108.63 | 0.847 |
| 9 | 7 | 34 | 115.712 | 6.321 | 155.261 | 179.78 | 0.949 |
| 9 | 7 | 36 | 133.793 | 6.233 | 179.685 | 251.14 | 0.962 |
| 9 | 7 | 38 | 124.255 | 6.202 | 155.551 | 47.82 | 0.963 |
| 9 | 7 | 40 | 65.949 | 12.966 | 81.992 | 59.82 | 0.811 |

| | | | | | | | |
|---|---|---|---|---|---|---|---|
| 9 | 7 | 42 | 45.161 | 15.176 | 23.435 | 339.08 | 0.643 |
| 9 | 8 | 1 | 158.686 | 1.843 | 145.804 | 196.78 | 0.977 |
| 9 | 8 | 3 | 50.788 | 4.768 | 61.802 | 182.88 | 0.921 |
| 9 | 8 | 5 | 185.848 | 1.992 | 248.909 | 292.45 | 0.984 |
| 9 | 8 | 7 | 233.313 | 2.239 | 318.555 | 278.05 | 0.981 |
| 9 | 8 | 9 | 301.111 | 3.264 | 432.995 | 211.58 | 0.991 |
| 9 | 8 | 11 | 300.612 | 2.790 | 401.957 | 264.16 | 0.990 |
| 9 | 8 | 13 | 124.079 | 2.564 | 197.322 | 239.29 | 0.938 |
| 9 | 8 | 15 | 274.656 | 2.705 | 373.065 | 160.47 | 0.977 |
| 9 | 8 | 17 | 442.414 | 3.734 | 637.737 | 17.72 | 0.993 |
| 9 | 8 | 19 | 500.255 | 4.345 | 680.150 | 140.16 | 0.996 |
| 9 | 8 | 21 | 31.192 | 8.828 | 83.295 | 309.07 | 0.650 |
| 9 | 8 | 23 | 232.688 | 2.909 | 315.236 | 30.77 | 0.982 |
| 9 | 8 | 25 | 308.621 | 3.268 | 437.514 | 202.90 | 0.989 |
| 9 | 8 | 27 | 73.687 | 9.655 | 11.013 | 187.34 | 0.885 |
| 9 | 8 | 29 | 248.959 | 3.810 | 305.243 | 234.30 | 0.983 |
| 9 | 8 | 31 | 262.014 | 3.716 | 381.288 | 64.61 | 0.987 |
| 9 | 8 | 33 | 92.881 | 8.128 | 138.480 | 7.46 | 0.876 |
| 9 | 8 | 35 | 94.723 | 7.700 | 95.595 | 75.90 | 0.941 |
| 9 | 8 | 37 | 132.378 | 5.620 | 196.011 | 185.71 | 0.961 |
| 9 | 8 | 39 | 64.727 | 11.776 | 76.540 | 197.84 | 0.858 |
| 9 | 8 | 41 | 55.099 | 16.245 | 42.813 | 303.90 | 0.541 |
| 9 | 8 | 43 | 37.440 | 18.720 | 13.343 | 119.54 | 0.553 |
| 9 | 9 | 0 | 93.551 | 3.097 | 124.354 | 0.00 | 0.939 |
| 9 | 9 | 2 | 268.891 | 2.861 | 392.712 | 278.41 | 0.986 |
| 9 | 9 | 4 | 361.439 | 3.791 | 570.662 | 32.74 | 0.990 |
| 9 | 9 | 6 | 153.282 | 2.081 | 205.782 | 63.39 | 0.949 |
| 9 | 9 | 8 | 155.487 | 2.230 | 142.538 | 301.37 | 0.980 |
| 9 | 9 | 10 | 229.778 | 2.613 | 343.298 | 71.65 | 0.980 |
| 9 | 9 | 12 | 189.593 | 2.377 | 271.109 | 219.84 | 0.971 |
| 9 | 9 | 14 | 143.152 | 2.533 | 226.264 | 343.47 | 0.888 |
| 9 | 9 | 16 | 433.649 | 4.097 | 616.557 | 31.27 | 0.993 |
| 9 | 9 | 18 | 227.102 | 2.678 | 413.892 | 238.62 | 0.964 |
| 9 | 9 | 20 | 118.950 | 4.073 | 107.087 | 180.29 | 0.953 |
| 9 | 9 | 22 | 152.753 | 3.406 | 217.439 | 110.62 | 0.954 |
| 9 | 9 | 24 | 410.154 | 3.852 | 618.940 | 271.46 | 0.993 |
| 9 | 9 | 26 | 538.823 | 4.677 | 728.284 | 61.01 | 0.996 |
| 9 | 9 | 28 | 114.320 | 5.246 | 144.406 | 70.37 | 0.897 |
| 9 | 9 | 30 | 461.476 | 4.474 | 705.308 | 228.32 | 0.996 |
| 9 | 9 | 32 | 352.236 | 3.752 | 481.128 | 123.97 | 0.995 |
| 9 | 9 | 34 | 98.045 | 8.145 | 101.784 | 108.33 | 0.941 |
| 9 | 9 | 36 | 94.990 | 8.551 | 146.770 | 157.68 | 0.847 |
| 9 | 9 | 38 | 48.959 | 12.888 | 23.965 | 226.62 | 0.551 |
| 9 | 9 | 40 | 46.572 | 14.103 | 32.518 | 116.84 | 0.633 |
| 9 | 9 | 42 | 62.768 | 27.643 | 7.116 | 265.90 | 0.784 |
| 9 | 10 | 1 | 263.823 | 2.289 | 385.091 | 19.25 | 0.985 |
| 9 | 10 | 3 | 310.759 | 3.285 | 486.123 | 186.23 | 0.982 |
| 9 | 10 | 5 | 95.428 | 3.169 | 144.955 | 123.07 | 0.902 |
| 9 | 10 | 7 | 196.040 | 2.320 | 287.286 | 303.25 | 0.969 |
| 9 | 10 | 9 | 175.813 | 2.199 | 279.848 | 97.76 | 0.989 |
| 9 | 10 | 11 | 168.178 | 2.812 | 219.334 | 329.13 | 0.960 |
| 9 | 10 | 13 | 40.116 | 6.687 | 10.893 | 142.27 | 0.211 |
| 9 | 10 | 15 | 213.311 | 2.605 | 276.844 | 98.17 | 0.988 |
| 9 | 10 | 17 | 137.402 | 3.212 | 189.344 | 235.38 | 0.962 |
| 9 | 10 | 19 | 237.304 | 2.872 | 288.559 | 144.90 | 0.985 |
| 9 | 10 | 21 | 196.796 | 2.920 | 255.219 | 112.07 | 0.984 |
| 9 | 10 | 23 | 464.208 | 4.087 | 661.699 | 312.48 | 0.995 |
| 9 | 10 | 25 | 333.127 | 3.648 | 470.397 | 118.23 | 0.989 |
| 9 | 10 | 27 | 340.597 | 3.511 | 416.887 | 55.55 | 0.992 |
| 9 | 10 | 29 | 85.142 | 7.812 | 100.458 | 299.26 | 0.864 |
| 9 | 10 | 31 | 271.912 | 4.034 | 400.506 | 193.64 | 0.991 |
| 9 | 10 | 33 | 84.321 | 9.609 | 114.660 | 36.23 | 0.859 |
| 9 | 10 | 35 | 176.802 | 4.383 | 197.482 | 210.85 | 0.983 |
| 9 | 10 | 37 | 139.698 | 6.451 | 189.103 | 357.45 | 0.969 |
| 9 | 10 | 39 | 36.357 | 11.283 | 12.498 | 259.89 | 0.839 |
| 9 | 10 | 41 | 53.515 | 16.521 | 42.278 | 63.96 | 0.604 |
| 9 | 11 | 0 | 18.657 | 8.425 | 7.782 | 0.00 | 0.313 |
| 9 | 11 | 2 | 117.700 | 2.907 | 179.467 | 190.79 | 0.898 |
| 9 | 11 | 4 | 202.351 | 2.822 | 301.437 | 249.52 | 0.970 |
| 9 | 11 | 6 | 354.832 | 3.315 | 449.522 | 47.42 | 0.992 |
| 9 | 11 | 8 | 169.492 | 2.472 | 288.814 | 149.65 | 0.954 |
| 9 | 11 | 10 | 38.452 | 7.262 | 27.519 | 290.80 | 0.499 |
| 9 | 11 | 12 | 120.498 | 3.898 | 161.273 | 345.19 | 0.924 |
| 9 | 11 | 14 | 327.045 | 3.069 | 463.116 | 264.89 | 0.987 |
| 9 | 11 | 16 | 288.948 | 2.919 | 503.987 | 62.87 | 0.984 |
| 9 | 11 | 18 | 210.838 | 2.730 | 320.094 | 287.89 | 0.971 |
| 9 | 11 | 20 | 311.142 | 3.141 | 376.906 | 137.20 | 0.991 |

| | | | | | | | |
|---|---|---|---|---|---|---|---|
| 9 | 11 | 22 | 256.344 | 2.914 | 395.840 | 217.84 | 0.982 |
| 9 | 11 | 24 | 265.259 | 3.080 | 324.229 | 281.41 | 0.987 |
| 9 | 11 | 26 | 171.675 | 3.870 | 245.549 | 326.06 | 0.957 |
| 9 | 11 | 28 | 61.715 | 9.437 | 32.892 | 226.28 | 0.355 |
| 9 | 11 | 30 | 209.333 | 4.006 | 315.459 | 15.42 | 0.978 |
| 9 | 11 | 32 | 217.926 | 3.876 | 318.943 | 72.57 | 0.986 |
| 9 | 11 | 34 | 57.909 | 11.558 | 42.418 | 128.90 | 0.783 |
| 9 | 11 | 36 | 129.160 | 5.668 | 154.611 | 212.69 | 0.969 |
| 9 | 11 | 38 | 48.209 | 12.152 | 13.370 | 290.77 | 0.885 |
| 9 | 11 | 40 | 46.974 | 14.666 | 4.947 | 99.50 | 0.875 |
| 9 | 12 | 1 | 422.262 | 3.376 | 652.175 | 11.43 | 0.993 |
| 9 | 12 | 3 | 269.442 | 2.823 | 389.787 | 271.29 | 0.991 |
| 9 | 12 | 5 | 299.766 | 2.923 | 452.226 | 45.44 | 0.987 |
| 9 | 12 | 7 | 386.881 | 3.295 | 609.528 | 96.83 | 0.991 |
| 9 | 12 | 9 | 596.370 | 5.252 | 912.675 | 150.89 | 0.996 |
| 9 | 12 | 11 | 115.907 | 2.765 | 155.265 | 0.46 | 0.822 |
| 9 | 12 | 13 | 229.418 | 2.777 | 333.978 | 64.50 | 0.977 |
| 9 | 12 | 15 | 259.633 | 2.742 | 389.995 | 114.00 | 0.988 |
| 9 | 12 | 17 | 124.636 | 3.140 | 163.749 | 236.18 | 0.962 |
| 9 | 12 | 19 | 169.433 | 2.794 | 224.122 | 37.27 | 0.966 |
| 9 | 12 | 21 | 490.376 | 4.313 | 731.497 | 116.57 | 0.996 |
| 9 | 12 | 23 | 248.516 | 2.981 | 391.838 | 353.86 | 0.977 |
| 9 | 12 | 25 | 119.547 | 4.749 | 181.782 | 352.99 | 0.865 |
| 9 | 12 | 27 | 171.059 | 3.950 | 298.924 | 296.09 | 0.943 |
| 9 | 12 | 29 | 179.638 | 4.882 | 347.217 | 70.72 | 0.943 |
| 9 | 12 | 31 | 91.001 | 7.953 | 121.583 | 250.07 | 0.905 |
| 9 | 12 | 33 | 100.878 | 8.338 | 149.380 | 61.70 | 0.795 |
| 9 | 12 | 35 | 107.248 | 7.518 | 178.291 | 31.33 | 0.910 |
| 9 | 12 | 37 | 45.950 | 12.287 | 7.091 | 315.23 | 0.761 |
| 9 | 12 | 39 | 53.129 | 15.748 | 27.030 | 8.52 | 0.372 |
| 9 | 12 | 41 | 53.602 | 17.171 | 37.635 | 195.35 | 0.628 |
| 9 | 13 | 0 | 206.438 | 3.696 | 292.399 | 180.00 | 1.000 |
| 9 | 13 | 2 | 312.904 | 2.795 | 506.547 | 355.40 | 0.985 |
| 9 | 13 | 4 | 323.293 | 4.846 | 504.817 | 227.25 | 0.987 |
| 9 | 13 | 6 | 165.129 | 2.489 | 183.505 | 271.98 | 0.970 |
| 9 | 13 | 8 | 403.603 | 3.360 | 567.159 | 190.20 | 0.993 |
| 9 | 13 | 10 | 182.789 | 2.649 | 264.639 | 114.41 | 0.959 |
| 9 | 13 | 12 | 196.746 | 2.614 | 302.457 | 5.30 | 0.968 |
| 9 | 13 | 14 | 361.413 | 3.567 | 491.589 | 97.36 | 0.993 |
| 9 | 13 | 16 | 148.816 | 2.704 | 223.829 | 7.03 | 0.948 |
| 9 | 13 | 18 | 86.012 | 5.187 | 100.285 | 65.79 | 0.822 |
| 9 | 13 | 20 | 232.308 | 3.257 | 331.779 | 90.57 | 0.979 |
| 9 | 13 | 22 | 236.548 | 3.306 | 368.721 | 129.64 | 0.979 |
| 9 | 13 | 24 | 127.293 | 4.009 | 174.134 | 310.05 | 0.916 |
| 9 | 13 | 26 | 35.802 | 10.370 | 22.025 | 339.57 | 0.520 |
| 9 | 13 | 28 | 172.584 | 4.949 | 326.160 | 75.36 | 0.944 |
| 9 | 13 | 30 | 57.270 | 11.402 | 47.209 | 56.64 | 0.568 |
| 9 | 13 | 32 | 70.571 | 9.731 | 54.839 | 62.32 | 0.895 |
| 9 | 13 | 34 | 39.110 | 10.930 | 2.294 | 200.67 | 0.403 |
| 9 | 13 | 36 | 83.434 | 8.373 | 100.742 | 171.45 | 0.910 |
| 9 | 13 | 38 | 62.985 | 15.812 | 45.605 | 330.41 | 0.900 |
| 9 | 13 | 40 | 43.953 | 14.404 | 23.843 | 48.45 | 0.634 |
| 9 | 14 | 1 | 195.252 | 2.376 | 296.679 | 95.34 | 0.975 |
| 9 | 14 | 3 | 87.088 | 5.508 | 97.761 | 18.43 | 0.859 |
| 9 | 14 | 5 | 328.442 | 3.268 | 498.390 | 100.16 | 0.988 |
| 9 | 14 | 7 | 312.539 | 2.925 | 415.959 | 234.01 | 0.988 |
| 9 | 14 | 9 | 218.418 | 2.576 | 275.670 | 312.16 | 0.986 |
| 9 | 14 | 11 | 244.333 | 2.924 | 326.811 | 103.53 | 0.987 |
| 9 | 14 | 13 | 291.847 | 2.940 | 495.441 | 29.17 | 0.983 |
| 9 | 14 | 15 | 404.443 | 3.979 | 652.466 | 97.98 | 0.993 |
| 9 | 14 | 17 | 362.076 | 3.503 | 546.853 | 342.82 | 0.991 |
| 9 | 14 | 19 | 117.827 | 4.773 | 145.650 | 137.40 | 0.930 |
| 9 | 14 | 21 | 395.223 | 4.011 | 579.175 | 246.26 | 0.993 |
| 9 | 14 | 23 | 411.059 | 4.040 | 576.238 | 236.56 | 0.993 |
| 9 | 14 | 25 | 221.332 | 3.785 | 311.447 | 280.92 | 0.983 |
| 9 | 14 | 27 | 176.370 | 4.265 | 234.892 | 17.25 | 0.974 |
| 9 | 14 | 29 | 46.536 | 12.598 | 18.106 | 74.28 | 0.434 |
| 9 | 14 | 31 | 57.488 | 11.103 | 50.124 | 160.71 | 0.584 |
| 9 | 14 | 33 | 154.051 | 5.394 | 247.007 | 198.47 | 0.959 |
| 9 | 14 | 35 | 44.185 | 11.829 | 1.820 | 276.50 | 0.815 |
| 9 | 14 | 37 | 72.781 | 12.712 | 83.602 | 229.42 | 0.915 |
| 9 | 14 | 39 | 47.380 | 15.635 | 27.283 | 37.61 | 0.795 |
| 9 | 15 | 0 | 84.741 | 7.216 | 119.029 | 0.00 | 0.994 |
| 9 | 15 | 2 | 348.096 | 3.235 | 489.565 | 98.09 | 0.990 |
| 9 | 15 | 4 | 534.714 | 5.239 | 847.919 | 65.77 | 0.995 |
| 9 | 15 | 6 | 549.068 | 4.997 | 812.691 | 101.24 | 0.996 |
| 9 | 15 | 8 | 386.131 | 3.330 | 524.320 | 196.93 | 0.992 |

| | | | | | | | |
|---|---|---|---|---|---|---|---|
| 9 | 15 | 10 | 259.086 | 2.710 | 408.946 | 281.35 | 0.983 |
| 9 | 15 | 12 | 326.222 | 3.379 | 422.516 | 357.04 | 0.992 |
| 9 | 15 | 14 | 261.643 | 2.953 | 417.576 | 180.29 | 0.983 |
| 9 | 15 | 16 | 171.767 | 3.116 | 185.103 | 189.05 | 0.972 |
| 9 | 15 | 18 | 230.868 | 3.151 | 272.116 | 335.56 | 0.985 |
| 9 | 15 | 20 | 171.982 | 3.176 | 274.686 | 104.71 | 0.951 |
| 9 | 15 | 22 | 194.567 | 3.685 | 272.339 | 176.43 | 0.966 |
| 9 | 15 | 24 | 260.633 | 3.529 | 348.562 | 332.99 | 0.989 |
| 9 | 15 | 26 | 268.879 | 3.702 | 341.926 | 83.57 | 0.990 |
| 9 | 15 | 28 | 159.903 | 4.453 | 188.749 | 208.10 | 0.979 |
| 9 | 15 | 30 | 266.709 | 4.115 | 372.466 | 246.00 | 0.991 |
| 9 | 15 | 32 | 113.083 | 6.787 | 198.238 | 31.42 | 0.880 |
| 9 | 15 | 34 | 57.619 | 12.083 | 10.321 | 287.43 | 0.892 |
| 9 | 15 | 36 | 41.778 | 12.577 | 13.863 | 318.78 | 0.815 |
| 9 | 15 | 38 | 55.699 | 17.117 | 49.741 | 25.08 | 0.731 |
| 9 | 16 | 1 | 138.843 | 2.858 | 185.280 | 8.09 | 0.927 |
| 9 | 16 | 3 | 206.415 | 2.765 | 303.833 | 50.76 | 0.979 |
| 9 | 16 | 5 | 171.625 | 5.031 | 245.569 | 194.38 | 0.966 |
| 9 | 16 | 7 | 89.075 | 3.836 | 37.180 | 307.91 | 0.245 |
| 9 | 16 | 9 | 128.421 | 3.015 | 172.715 | 241.81 | 0.969 |
| 9 | 16 | 11 | 201.402 | 2.798 | 352.867 | 343.11 | 0.933 |
| 9 | 16 | 13 | 400.183 | 4.090 | 577.237 | 282.99 | 0.994 |
| 9 | 16 | 15 | 734.717 | 6.224 | 1069.473 | 255.01 | 0.998 |
| 9 | 16 | 17 | 27.521 | 8.212 | 67.901 | 94.67 | 0.534 |
| 9 | 16 | 19 | 103.833 | 5.486 | 99.067 | 92.00 | 0.918 |
| 9 | 16 | 21 | 177.793 | 3.458 | 215.125 | 90.71 | 0.975 |
| 9 | 16 | 23 | 269.792 | 3.857 | 419.568 | 268.35 | 0.988 |
| 9 | 16 | 25 | 147.790 | 5.150 | 182.104 | 124.09 | 0.965 |
| 9 | 16 | 27 | 96.199 | 8.242 | 97.613 | 172.83 | 0.942 |
| 9 | 16 | 29 | 251.454 | 3.929 | 358.617 | 242.95 | 0.990 |
| 9 | 16 | 31 | 136.131 | 5.283 | 204.889 | 314.34 | 0.959 |
| 9 | 16 | 33 | 76.965 | 12.063 | 54.932 | 33.63 | 0.930 |
| 9 | 16 | 35 | 42.342 | 11.220 | 32.121 | 57.82 | 0.743 |
| 9 | 16 | 37 | 40.428 | 12.880 | 21.301 | 41.66 | 0.598 |
| 9 | 16 | 39 | 40.909 | 13.621 | 18.701 | 218.62 | 0.596 |
| 9 | 17 | 0 | 95.753 | 12.227 | 134.216 | 0.00 | 0.993 |
| 9 | 17 | 2 | 201.687 | 2.850 | 305.655 | 278.00 | 0.974 |
| 9 | 17 | 4 | 247.690 | 3.154 | 292.334 | 264.69 | 0.988 |
| 9 | 17 | 6 | 288.936 | 3.004 | 438.560 | 293.35 | 0.987 |
| 9 | 17 | 8 | 388.841 | 3.375 | 570.759 | 252.24 | 0.994 |
| 9 | 17 | 10 | 314.153 | 3.092 | 499.545 | 290.88 | 0.989 |
| 9 | 17 | 12 | 359.016 | 3.251 | 474.360 | 69.96 | 0.993 |
| 9 | 17 | 14 | 348.898 | 3.555 | 477.885 | 277.27 | 0.993 |
| 9 | 17 | 16 | 247.796 | 3.014 | 392.875 | 164.91 | 0.980 |
| 9 | 17 | 18 | 188.184 | 4.227 | 225.799 | 336.92 | 0.973 |
| 9 | 17 | 20 | 308.972 | 3.679 | 380.896 | 75.32 | 0.990 |
| 9 | 17 | 22 | 98.227 | 7.366 | 72.607 | 194.66 | 0.945 |
| 9 | 17 | 24 | 327.179 | 6.523 | 427.382 | 203.15 | 0.993 |
| 9 | 17 | 26 | 214.529 | 4.443 | 343.632 | 270.18 | 0.984 |
| 9 | 17 | 28 | 250.700 | 3.655 | 328.085 | 268.82 | 0.991 |
| 9 | 17 | 30 | 181.662 | 4.633 | 277.010 | 53.72 | 0.978 |
| 9 | 17 | 32 | 84.397 | 7.959 | 111.801 | 41.42 | 0.907 |
| 9 | 17 | 34 | 72.360 | 11.908 | 12.658 | 21.45 | 0.101 |
| 9 | 17 | 36 | 72.381 | 16.153 | 75.774 | 172.47 | 0.903 |
| 9 | 17 | 38 | 64.429 | 18.021 | 50.611 | 239.59 | 0.533 |
| 9 | 18 | 1 | 286.980 | 2.874 | 404.309 | 167.96 | 0.989 |
| 9 | 18 | 3 | 65.641 | 5.413 | 66.757 | 10.54 | 0.680 |
| 9 | 18 | 5 | 255.959 | 4.608 | 379.278 | 199.52 | 0.985 |
| 9 | 18 | 7 | 233.294 | 3.052 | 341.281 | 138.79 | 0.983 |
| 9 | 18 | 9 | 145.857 | 2.948 | 161.165 | 115.70 | 0.974 |
| 9 | 18 | 11 | 241.962 | 2.983 | 306.428 | 184.69 | 0.984 |
| 9 | 18 | 13 | 122.746 | 3.764 | 159.252 | 348.39 | 0.938 |
| 9 | 18 | 15 | 570.223 | 5.409 | 811.182 | 120.18 | 0.997 |
| 9 | 18 | 17 | 341.748 | 3.454 | 460.967 | 255.10 | 0.991 |
| 9 | 18 | 19 | 179.233 | 4.234 | 233.791 | 46.17 | 0.966 |
| 9 | 18 | 21 | 142.336 | 6.369 | 168.537 | 22.09 | 0.965 |
| 9 | 18 | 23 | 217.194 | 4.376 | 246.878 | 272.35 | 0.986 |
| 9 | 18 | 25 | 162.663 | 4.932 | 212.335 | 51.45 | 0.978 |
| 9 | 18 | 27 | 204.269 | 4.179 | 241.831 | 148.15 | 0.988 |
| 9 | 18 | 29 | 50.199 | 13.508 | 16.829 | 253.84 | 0.334 |
| 9 | 18 | 31 | 103.463 | 6.656 | 142.592 | 50.77 | 0.941 |
| 9 | 18 | 33 | 134.550 | 8.132 | 139.168 | 260.41 | 0.985 |
| 9 | 18 | 35 | 46.027 | 14.632 | 32.489 | 263.34 | 0.696 |
| 9 | 18 | 37 | 74.157 | 13.727 | 92.322 | 114.65 | 0.888 |
| 9 | 19 | 0 | 286.516 | 4.953 | 405.319 | 0.00 | 1.000 |
| 9 | 19 | 2 | 621.688 | 5.292 | 925.089 | 70.68 | 0.997 |
| 9 | 19 | 4 | 134.513 | 3.968 | 176.271 | 121.14 | 0.957 |

| | | | | | | | |
|---|---|---|---|---|---|---|---|
| 9 | 19 | 6 | 218.036 | 3.854 | 307.493 | 70.02 | 0.979 |
| 9 | 19 | 8 | 315.406 | 3.139 | 456.972 | 73.77 | 0.991 |
| 9 | 19 | 10 | 401.380 | 3.592 | 605.029 | 80.59 | 0.994 |
| 9 | 19 | 12 | 209.943 | 3.038 | 291.494 | 77.93 | 0.977 |
| 9 | 19 | 14 | 478.436 | 4.083 | 633.851 | 56.82 | 0.996 |
| 9 | 19 | 16 | 305.114 | 3.668 | 401.165 | 259.94 | 0.989 |
| 9 | 19 | 18 | 76.568 | 7.839 | 73.703 | 201.83 | 0.586 |
| 9 | 19 | 20 | 313.990 | 3.647 | 600.080 | 165.68 | 0.985 |
| 9 | 19 | 22 | 89.153 | 9.141 | 107.716 | 195.12 | 0.860 |
| 9 | 19 | 24 | 71.818 | 12.660 | 88.127 | 159.23 | 0.695 |
| 9 | 19 | 26 | 70.925 | 10.309 | 88.861 | 289.19 | 0.767 |
| 9 | 19 | 28 | 104.118 | 6.199 | 117.621 | 72.56 | 0.518 |
| 9 | 19 | 30 | 40.201 | 12.320 | 9.485 | 122.70 | 0.495 |
| 9 | 19 | 32 | 72.479 | 11.710 | 85.302 | 4.95 | 0.925 |
| 9 | 19 | 34 | 58.340 | 13.226 | 50.128 | 15.89 | 0.870 |
| 9 | 19 | 36 | 70.666 | 13.070 | 79.794 | 355.95 | 0.603 |
| 9 | 20 | 1 | 165.227 | 2.890 | 190.410 | 44.84 | 0.975 |
| 9 | 20 | 3 | 293.931 | 3.038 | 381.598 | 13.07 | 0.990 |
| 9 | 20 | 5 | 564.698 | 5.422 | 840.356 | 324.15 | 0.997 |
| 9 | 20 | 7 | 352.171 | 5.870 | 552.269 | 17.79 | 0.991 |
| 9 | 20 | 9 | 85.435 | 5.588 | 105.503 | 108.45 | 0.646 |
| 9 | 20 | 11 | 341.151 | 3.312 | 446.380 | 334.23 | 0.991 |
| 9 | 20 | 13 | 431.221 | 3.776 | 592.273 | 42.42 | 0.994 |
| 9 | 20 | 15 | 169.897 | 4.406 | 165.699 | 334.31 | 0.970 |
| 9 | 20 | 17 | 45.318 | 11.454 | 8.667 | 316.00 | 0.607 |
| 9 | 20 | 19 | 209.320 | 3.905 | 301.279 | 41.35 | 0.982 |
| 9 | 20 | 21 | 86.309 | 9.365 | 64.949 | 109.09 | 0.918 |
| 9 | 20 | 23 | 105.803 | 7.563 | 124.750 | 78.12 | 0.952 |
| 9 | 20 | 25 | 119.073 | 6.900 | 187.748 | 195.95 | 0.939 |
| 9 | 20 | 27 | 73.469 | 9.586 | 75.935 | 209.47 | 0.897 |
| 9 | 20 | 29 | 82.855 | 9.853 | 73.180 | 213.97 | 0.936 |
| 9 | 20 | 31 | 144.661 | 8.898 | 179.024 | 76.24 | 0.985 |
| 9 | 20 | 33 | 71.792 | 14.970 | 84.863 | 151.33 | 0.892 |
| 9 | 20 | 35 | 48.293 | 15.017 | 28.706 | 103.97 | 0.451 |
| 9 | 21 | 0 | 234.205 | 4.985 | 331.094 | 0.00 | 1.000 |
| 9 | 21 | 2 | 305.566 | 3.437 | 417.286 | 151.86 | 0.990 |
| 9 | 21 | 4 | 252.305 | 3.080 | 378.790 | 231.77 | 0.984 |
| 9 | 21 | 6 | 125.122 | 4.740 | 160.959 | 335.40 | 0.936 |
| 9 | 21 | 8 | 179.591 | 3.869 | 252.487 | 301.32 | 0.966 |
| 9 | 21 | 10 | 251.618 | 3.131 | 334.874 | 210.16 | 0.985 |
| 9 | 21 | 12 | 288.231 | 3.320 | 380.731 | 306.44 | 0.988 |
| 9 | 21 | 14 | 192.513 | 3.834 | 265.794 | 288.29 | 0.974 |
| 9 | 21 | 16 | 108.452 | 6.598 | 82.339 | 350.51 | 0.967 |
| 9 | 21 | 18 | 93.890 | 8.356 | 136.734 | 31.61 | 0.720 |
| 9 | 21 | 20 | 217.208 | 4.153 | 379.481 | 187.65 | 0.982 |
| 9 | 21 | 22 | 177.288 | 4.855 | 238.625 | 318.57 | 0.982 |
| 9 | 21 | 24 | 241.430 | 5.419 | 381.201 | 279.87 | 0.988 |
| 9 | 21 | 26 | 100.139 | 7.941 | 113.641 | 142.87 | 0.943 |
| 9 | 21 | 28 | 59.481 | 10.977 | 61.600 | 332.45 | 0.827 |
| 9 | 21 | 30 | 119.341 | 8.329 | 146.185 | 129.91 | 0.977 |
| 9 | 21 | 32 | 41.715 | 12.717 | 24.589 | 142.53 | 0.712 |
| 9 | 21 | 34 | 72.276 | 16.026 | 71.269 | 163.91 | 0.905 |
| 9 | 22 | 1 | 597.719 | 4.928 | 872.130 | 164.39 | 0.997 |
| 9 | 22 | 3 | 284.091 | 3.236 | 380.620 | 102.30 | 0.988 |
| 9 | 22 | 5 | 141.462 | 4.417 | 223.922 | 338.51 | 0.686 |
| 9 | 22 | 7 | 307.558 | 5.404 | 443.120 | 167.70 | 0.989 |
| 9 | 22 | 9 | 248.600 | 3.803 | 411.662 | 186.79 | 0.978 |
| 9 | 22 | 11 | 250.081 | 3.637 | 357.850 | 10.77 | 0.983 |
| 9 | 22 | 13 | 94.064 | 6.916 | 130.207 | 135.30 | 0.892 |
| 9 | 22 | 15 | 152.524 | 5.026 | 183.277 | 80.65 | 0.971 |
| 9 | 22 | 17 | 40.614 | 11.546 | 6.910 | 308.46 | 0.373 |
| 9 | 22 | 19 | 181.903 | 4.477 | 297.299 | 339.76 | 0.979 |
| 9 | 22 | 21 | 37.247 | 10.621 | 2.743 | 219.21 | 0.487 |
| 9 | 22 | 23 | 226.729 | 4.013 | 262.333 | 244.89 | 0.991 |
| 9 | 22 | 25 | 137.602 | 4.856 | 152.151 | 293.63 | 0.974 |
| 9 | 22 | 27 | 35.040 | 11.201 | 15.744 | 82.88 | 0.654 |
| 9 | 22 | 29 | 80.155 | 14.331 | 110.748 | 31.56 | 0.920 |
| 9 | 22 | 31 | 51.675 | 13.807 | 49.973 | 2.20 | 0.697 |
| 9 | 22 | 33 | 68.218 | 19.750 | 49.797 | 19.60 | 0.888 |
| 9 | 23 | 0 | 499.480 | 8.026 | 694.598 | 180.00 | 0.985 |
| 9 | 23 | 2 | 370.364 | 4.172 | 491.216 | 135.30 | 0.993 |
| 9 | 23 | 4 | 618.617 | 5.151 | 891.119 | 221.88 | 0.997 |
| 9 | 23 | 6 | 77.486 | 13.142 | 65.058 | 272.19 | 0.800 |
| 9 | 23 | 8 | 157.013 | 5.299 | 168.892 | 211.04 | 0.978 |
| 9 | 23 | 10 | 287.183 | 4.671 | 450.341 | 157.13 | 0.989 |
| 9 | 23 | 12 | 84.300 | 7.745 | 107.937 | 264.38 | 0.632 |
| 9 | 23 | 14 | 137.082 | 5.362 | 199.541 | 28.77 | 0.955 |

| | | | | | | | |
|---|---|---|---|---|---|---|---|
| 9 | 23 | 16 | 162.694 | 4.200 | 219.968 | 217.57 | 0.980 |
| 9 | 23 | 18 | 88.418 | 8.062 | 93.211 | 331.95 | 0.933 |
| 9 | 23 | 20 | 115.928 | 7.280 | 117.959 | 294.21 | 0.966 |
| 9 | 23 | 22 | 42.000 | 10.733 | 8.316 | 26.16 | 0.776 |
| 9 | 23 | 24 | 183.135 | 4.867 | 316.626 | 85.84 | 0.979 |
| 9 | 23 | 26 | 48.024 | 13.456 | 14.498 | 87.81 | 0.802 |
| 9 | 23 | 28 | 103.681 | 14.257 | 104.000 | 24.62 | 0.972 |
| 9 | 23 | 30 | 68.213 | 13.198 | 81.676 | 257.88 | 0.886 |
| 9 | 23 | 32 | 47.736 | 21.122 | 5.562 | 329.60 | 0.179 |
| 9 | 24 | 1 | 81.455 | 8.053 | 79.114 | 158.57 | 0.895 |
| 9 | 24 | 3 | 332.453 | 3.812 | 506.856 | 260.07 | 0.993 |
| 9 | 24 | 5 | 400.757 | 3.850 | 555.890 | 255.10 | 0.996 |
| 9 | 24 | 7 | 290.640 | 4.202 | 427.461 | 238.75 | 0.991 |
| 9 | 24 | 9 | 155.821 | 7.091 | 219.498 | 133.35 | 0.967 |
| 9 | 24 | 11 | 128.761 | 5.301 | 227.710 | 222.13 | 0.921 |
| 9 | 24 | 13 | 145.962 | 4.503 | 225.072 | 174.04 | 0.970 |
| 9 | 24 | 15 | 172.205 | 4.368 | 234.752 | 299.26 | 0.982 |
| 9 | 24 | 17 | 154.674 | 4.229 | 241.522 | 160.20 | 0.972 |
| 9 | 24 | 19 | 47.105 | 11.049 | 26.031 | 105.63 | 0.476 |
| 9 | 24 | 21 | 42.713 | 11.893 | 12.114 | 203.88 | 0.557 |
| 9 | 24 | 23 | 127.774 | 7.393 | 193.804 | 330.30 | 0.963 |
| 9 | 24 | 25 | 51.011 | 13.576 | 3.184 | 82.72 | 0.070 |
| 9 | 24 | 27 | 46.469 | 14.335 | 21.376 | 98.98 | 0.842 |
| 9 | 24 | 29 | 102.803 | 14.895 | 160.846 | 24.01 | 0.932 |
| 9 | 24 | 31 | 57.384 | 15.228 | 51.991 | 21.06 | 0.669 |
| 9 | 25 | 0 | 144.061 | 9.769 | 202.232 | 0.00 | 0.997 |
| 9 | 25 | 2 | 324.039 | 4.354 | 397.380 | 11.41 | 0.994 |
| 9 | 25 | 4 | 56.508 | 10.317 | 41.228 | 11.46 | 0.551 |
| 9 | 25 | 6 | 136.883 | 5.659 | 168.652 | 262.98 | 0.963 |
| 9 | 25 | 8 | 56.440 | 11.759 | 31.797 | 256.85 | 0.723 |
| 9 | 25 | 10 | 180.410 | 4.736 | 290.115 | 84.03 | 0.979 |
| 9 | 25 | 12 | 75.591 | 10.197 | 39.324 | 77.65 | 0.933 |
| 9 | 25 | 14 | 43.186 | 10.854 | 5.447 | 145.68 | 0.713 |
| 9 | 25 | 16 | 157.206 | 4.407 | 221.284 | 92.68 | 0.977 |
| 9 | 25 | 18 | 85.946 | 7.500 | 101.656 | 91.47 | 0.921 |
| 9 | 25 | 20 | 98.085 | 7.486 | 142.019 | 358.41 | 0.925 |
| 9 | 25 | 22 | 42.430 | 10.982 | 25.465 | 37.62 | 0.567 |
| 9 | 25 | 24 | 38.956 | 12.326 | 20.620 | 350.67 | 0.492 |
| 9 | 25 | 26 | 51.720 | 14.343 | 39.037 | 255.02 | 0.862 |
| 9 | 25 | 28 | 47.584 | 12.861 | 29.797 | 295.13 | 0.417 |
| 9 | 25 | 30 | 36.419 | 12.752 | 6.869 | 4.31 | 0.671 |
| 9 | 26 | 1 | 177.485 | 5.741 | 250.669 | 7.64 | 0.983 |
| 9 | 26 | 3 | 150.493 | 5.465 | 152.753 | 11.99 | 0.981 |
| 9 | 26 | 5 | 207.785 | 3.850 | 320.488 | 46.11 | 0.986 |
| 9 | 26 | 7 | 95.556 | 9.770 | 78.440 | 276.91 | 0.955 |
| 9 | 26 | 9 | 213.045 | 5.939 | 307.065 | 58.19 | 0.988 |
| 9 | 26 | 11 | 48.608 | 12.854 | 29.772 | 181.22 | 0.649 |
| 9 | 26 | 13 | 129.188 | 5.453 | 222.031 | 239.00 | 0.946 |
| 9 | 26 | 15 | 88.716 | 6.926 | 70.215 | 189.27 | 0.947 |
| 9 | 26 | 17 | 143.643 | 5.020 | 277.174 | 124.36 | 0.943 |
| 9 | 26 | 19 | 53.302 | 12.383 | 39.793 | 159.98 | 0.783 |
| 9 | 26 | 21 | 36.058 | 11.326 | 2.455 | 243.22 | 0.281 |
| 9 | 26 | 23 | 70.101 | 16.775 | 95.968 | 59.61 | 0.824 |
| 9 | 26 | 25 | 81.416 | 17.430 | 103.374 | 116.56 | 0.906 |
| 9 | 26 | 27 | 72.520 | 15.448 | 73.460 | 232.72 | 0.920 |
| 9 | 27 | 0 | 109.675 | 13.197 | 148.949 | 180.00 | 0.971 |
| 9 | 27 | 2 | 139.772 | 7.880 | 157.030 | 18.97 | 0.976 |
| 9 | 27 | 4 | 124.052 | 7.237 | 144.960 | 337.65 | 0.968 |
| 9 | 27 | 6 | 145.310 | 6.764 | 171.338 | 254.23 | 0.977 |
| 9 | 27 | 8 | 117.722 | 5.532 | 146.267 | 0.21 | 0.963 |
| 9 | 27 | 10 | 137.521 | 8.750 | 213.547 | 265.16 | 0.966 |
| 9 | 27 | 12 | 125.642 | 9.497 | 192.425 | 119.06 | 0.957 |
| 9 | 27 | 14 | 104.805 | 7.397 | 103.406 | 13.24 | 0.556 |
| 9 | 27 | 16 | 50.665 | 11.395 | 32.383 | 26.39 | 0.602 |
| 9 | 27 | 18 | 140.996 | 4.999 | 163.172 | 145.39 | 0.979 |
| 9 | 27 | 20 | 73.400 | 14.173 | 93.973 | 316.05 | 0.920 |
| 9 | 27 | 22 | 131.773 | 8.740 | 203.554 | 301.69 | 0.977 |
| 9 | 27 | 24 | 48.414 | 13.706 | 28.561 | 311.42 | 0.864 |
| 9 | 27 | 26 | 60.128 | 15.910 | 55.039 | 315.37 | 0.843 |
| 9 | 28 | 1 | 83.704 | 9.927 | 122.586 | 41.35 | 0.891 |
| 9 | 28 | 3 | 41.907 | 11.388 | 10.200 | 210.15 | 0.597 |
| 9 | 28 | 5 | 69.408 | 11.281 | 71.723 | 163.68 | 0.882 |
| 9 | 28 | 7 | 114.137 | 7.371 | 72.454 | 234.09 | 0.973 |
| 9 | 28 | 9 | 102.095 | 8.646 | 147.911 | 188.29 | 0.935 |
| 9 | 28 | 11 | 114.405 | 7.974 | 155.632 | 96.94 | 0.955 |
| 9 | 28 | 13 | 51.823 | 13.487 | 39.252 | 221.40 | 0.582 |
| 9 | 28 | 15 | 54.001 | 11.271 | 33.344 | 14.25 | 0.851 |

| | | | | | | | |
|---|---|---|---|---|---|---|---|
| 9 | 28 | 17 | 102.017 | 9.720 | 113.222 | 325.89 | 0.956 |
| 9 | 28 | 19 | 81.321 | 10.419 | 84.281 | 290.03 | 0.956 |
| 9 | 28 | 21 | 42.722 | 12.191 | 24.621 | 83.49 | 0.779 |
| 9 | 28 | 23 | 36.658 | 12.036 | 3.447 | 159.72 | 0.783 |
| 9 | 28 | 25 | 35.369 | 12.274 | 8.391 | 169.37 | 0.468 |
| 9 | 29 | 0 | 46.484 | 16.155 | 37.889 | 180.00 | 0.592 |
| 9 | 29 | 2 | 102.268 | 7.799 | 159.003 | 11.92 | 0.682 |
| 9 | 29 | 4 | 136.039 | 5.758 | 200.676 | 201.71 | 0.967 |
| 9 | 29 | 6 | 37.549 | 10.495 | 3.882 | 306.84 | 0.307 |
| 9 | 29 | 8 | 39.000 | 10.617 | 13.256 | 58.74 | 0.568 |
| 9 | 29 | 10 | 93.606 | 11.310 | 92.053 | 106.26 | 0.954 |
| 9 | 29 | 12 | 62.072 | 11.964 | 57.052 | 173.16 | 0.517 |
| 9 | 29 | 14 | 48.042 | 12.902 | 20.406 | 196.01 | 0.275 |
| 9 | 29 | 16 | 75.463 | 11.773 | 123.442 | 334.05 | 0.801 |
| 9 | 29 | 18 | 43.573 | 12.832 | 32.383 | 298.41 | 0.741 |
| 9 | 29 | 20 | 42.914 | 12.745 | 31.247 | 225.97 | 0.698 |
| 9 | 29 | 22 | 72.127 | 12.464 | 105.424 | 87.22 | 0.874 |
| 9 | 30 | 1 | 52.004 | 12.549 | 43.386 | 138.88 | 0.631 |
| 9 | 30 | 3 | 46.388 | 12.491 | 25.620 | 63.62 | 0.494 |
| 9 | 30 | 5 | 51.915 | 13.074 | 0.886 | 286.50 | 0.884 |
| 9 | 30 | 7 | 67.622 | 11.846 | 83.293 | 206.17 | 0.677 |
| 9 | 30 | 9 | 111.257 | 6.743 | 142.703 | 346.73 | 0.963 |
| 9 | 30 | 11 | 57.521 | 11.312 | 37.944 | 33.79 | 0.927 |
| 9 | 30 | 13 | 44.608 | 12.702 | 21.041 | 326.12 | 0.851 |
| 9 | 30 | 15 | 32.731 | 11.337 | 2.580 | 152.62 | 0.623 |
| 9 | 30 | 17 | 61.715 | 12.297 | 48.088 | 235.19 | 0.402 |
| 9 | 30 | 19 | 42.813 | 13.012 | 29.466 | 57.57 | 0.525 |
| 9 | 30 | 21 | 31.300 | 10.757 | 0.287 | 336.46 | 0.568 |
| 9 | 31 | 0 | 30.160 | 19.270 | 23.907 | 180.00 | 0.612 |
| 9 | 31 | 2 | 149.710 | 5.223 | 218.223 | 148.57 | 0.978 |
| 9 | 31 | 4 | 55.779 | 13.306 | 73.351 | 83.10 | 0.797 |
| 9 | 31 | 6 | 148.051 | 6.888 | 231.911 | 232.26 | 0.984 |
| 9 | 31 | 8 | 44.757 | 11.722 | 0.561 | 319.53 | 0.907 |
| 9 | 31 | 10 | 51.152 | 12.973 | 27.603 | 221.97 | 0.902 |
| 9 | 31 | 12 | 55.890 | 16.832 | 56.422 | 171.41 | 0.778 |
| 9 | 31 | 14 | 39.905 | 12.669 | 26.910 | 58.56 | 0.627 |
| 9 | 31 | 16 | 48.454 | 14.482 | 11.321 | 262.30 | 0.202 |
| 9 | 31 | 18 | 33.529 | 11.455 | 11.023 | 346.01 | 0.425 |
| 9 | 32 | 1 | 73.007 | 11.654 | 119.077 | 57.17 | 0.778 |
| 9 | 32 | 3 | 45.847 | 12.244 | 33.744 | 108.11 | 0.843 |
| 9 | 32 | 5 | 57.631 | 13.080 | 71.222 | 277.75 | 0.747 |
| 9 | 32 | 7 | 43.726 | 14.531 | 29.135 | 85.35 | 0.672 |
| 9 | 32 | 9 | 52.312 | 13.353 | 60.101 | 263.89 | 0.806 |
| 9 | 32 | 11 | 53.603 | 13.562 | 50.143 | 27.64 | 0.868 |
| 9 | 32 | 13 | 49.019 | 15.914 | 10.831 | 269.42 | 0.183 |
| 9 | 32 | 15 | 33.972 | 16.313 | 21.227 | 187.39 | 0.727 |
| 9 | 33 | 0 | 30.329 | 21.213 | 28.172 | 0.00 | 0.812 |
| 9 | 33 | 2 | 29.560 | 9.882 | 12.565 | 197.87 | 0.767 |
| 9 | 33 | 4 | 69.323 | 11.306 | 110.634 | 209.43 | 0.806 |
| 9 | 33 | 6 | 33.973 | 11.173 | 13.508 | 116.70 | 0.459 |
| 9 | 33 | 8 | 47.934 | 13.005 | 42.383 | 63.55 | 0.790 |
| 9 | 33 | 10 | 52.457 | 12.838 | 55.854 | 40.50 | 0.817 |
| 9 | 34 | 1 | 65.312 | 11.959 | 66.449 | 184.54 | 0.921 |
| 9 | 34 | 3 | 44.962 | 12.973 | 39.551 | 274.21 | 0.657 |
| 10 | 0 | 0 | 242.750 | 3.786 | 344.746 | 180.00 | 1.000 |
| 10 | 0 | 2 | 376.874 | 5.610 | 536.396 | 180.00 | 1.000 |
| 10 | 0 | 4 | 63.456 | 2.431 | 77.523 | 0.00 | 0.867 |
| 10 | 0 | 6 | 111.992 | 2.331 | 157.075 | 180.00 | 1.000 |
| 10 | 0 | 8 | 74.822 | 3.727 | 94.851 | 180.00 | 0.902 |
| 10 | 0 | 10 | 315.329 | 3.801 | 446.051 | 0.00 | 1.000 |
| 10 | 0 | 12 | 437.833 | 5.008 | 617.207 | 0.00 | 1.000 |
| 10 | 0 | 14 | 174.908 | 3.249 | 245.515 | 0.00 | 1.000 |
| 10 | 0 | 16 | 139.336 | 3.633 | 195.013 | 0.00 | 1.000 |
| 10 | 0 | 18 | 735.424 | 8.442 | 1024.626 | 0.00 | 1.000 |
| 10 | 0 | 20 | 329.796 | 4.439 | 457.478 | 0.00 | 1.000 |
| 10 | 0 | 22 | 19.386 | 9.390 | 3.056 | 0.00 | 0.117 |
| 10 | 0 | 24 | 28.315 | 10.908 | 14.018 | 0.00 | 0.389 |
| 10 | 0 | 26 | 283.383 | 4.316 | 386.129 | 0.00 | 1.000 |
| 10 | 0 | 28 | 20.969 | 10.185 | 5.804 | 180.00 | 0.206 |
| 10 | 0 | 30 | 36.149 | 13.674 | 37.743 | 0.00 | 0.798 |
| 10 | 0 | 32 | 160.404 | 6.973 | 213.400 | 0.00 | 1.000 |
| 10 | 0 | 34 | 44.350 | 16.846 | 39.370 | 180.00 | 0.681 |
| 10 | 0 | 36 | 169.990 | 7.631 | 221.694 | 180.00 | 1.000 |
| 10 | 0 | 38 | 40.939 | 17.883 | 31.735 | 0.00 | 0.619 |
| 10 | 0 | 40 | 88.708 | 14.208 | 110.361 | 180.00 | 1.000 |
| 10 | 0 | 42 | 38.086 | 18.606 | 12.685 | 180.00 | 0.286 |
| 10 | 1 | 1 | 342.738 | 3.381 | 485.387 | 193.31 | 0.988 |

| | | | | | | | |
|---|---|---|---|---|---|---|---|
| 10 | 1 | 3 | 520.013 | 5.307 | 708.081 | 294.39 | 0.995 |
| 10 | 1 | 5 | 219.406 | 1.854 | 356.263 | 157.00 | 0.965 |
| 10 | 1 | 7 | 154.083 | 1.652 | 241.825 | 239.29 | 0.927 |
| 10 | 1 | 9 | 372.398 | 3.086 | 564.465 | 237.44 | 0.991 |
| 10 | 1 | 11 | 129.009 | 2.207 | 152.322 | 327.36 | 0.941 |
| 10 | 1 | 13 | 331.494 | 2.847 | 397.668 | 82.21 | 0.991 |
| 10 | 1 | 15 | 610.026 | 5.350 | 832.464 | 207.52 | 0.997 |
| 10 | 1 | 17 | 172.219 | 2.707 | 251.001 | 114.69 | 0.952 |
| 10 | 1 | 19 | 263.479 | 2.987 | 371.910 | 56.43 | 0.981 |
| 10 | 1 | 21 | 250.953 | 2.865 | 264.542 | 241.90 | 0.987 |
| 10 | 1 | 23 | 415.201 | 3.723 | 574.531 | 334.71 | 0.994 |
| 10 | 1 | 25 | 122.112 | 4.218 | 111.435 | 31.15 | 0.944 |
| 10 | 1 | 27 | 186.220 | 3.964 | 228.104 | 56.16 | 0.969 |
| 10 | 1 | 29 | 114.994 | 6.059 | 90.371 | 227.13 | 0.929 |
| 10 | 1 | 31 | 241.701 | 3.994 | 313.542 | 5.17 | 0.986 |
| 10 | 1 | 33 | 193.972 | 4.291 | 245.681 | 175.07 | 0.985 |
| 10 | 1 | 35 | 70.917 | 10.701 | 47.710 | 105.73 | 0.366 |
| 10 | 1 | 37 | 65.335 | 12.462 | 62.334 | 304.93 | 0.774 |
| 10 | 1 | 39 | 106.183 | 6.705 | 109.512 | 111.46 | 0.956 |
| 10 | 1 | 41 | 35.750 | 11.585 | 9.514 | 210.07 | 0.541 |
| 10 | 1 | 43 | 36.652 | 13.133 | 9.449 | 217.83 | 0.493 |
| 10 | 2 | 0 | 310.058 | 5.105 | 440.819 | 0.00 | 1.000 |
| 10 | 2 | 2 | 271.361 | 2.652 | 339.300 | 130.58 | 0.986 |
| 10 | 2 | 4 | 408.858 | 4.201 | 599.496 | 241.51 | 0.991 |
| 10 | 2 | 6 | 51.648 | 3.435 | 44.367 | 208.93 | 0.623 |
| 10 | 2 | 8 | 201.606 | 2.077 | 266.272 | 172.75 | 0.988 |
| 10 | 2 | 10 | 303.450 | 2.676 | 355.227 | 158.77 | 0.992 |
| 10 | 2 | 12 | 258.998 | 2.506 | 400.397 | 90.05 | 0.977 |
| 10 | 2 | 14 | 435.206 | 3.782 | 606.325 | 254.51 | 0.994 |
| 10 | 2 | 16 | 322.817 | 3.050 | 483.715 | 237.20 | 0.987 |
| 10 | 2 | 18 | 293.554 | 2.894 | 449.360 | 30.36 | 0.989 |
| 10 | 2 | 20 | 209.951 | 2.709 | 292.121 | 166.79 | 0.983 |
| 10 | 2 | 22 | 211.362 | 2.758 | 322.100 | 309.88 | 0.974 |
| 10 | 2 | 24 | 212.054 | 3.147 | 311.446 | 273.55 | 0.975 |
| 10 | 2 | 26 | 280.735 | 3.258 | 372.082 | 288.62 | 0.987 |
| 10 | 2 | 28 | 326.826 | 3.488 | 390.865 | 216.38 | 0.990 |
| 10 | 2 | 30 | 152.245 | 4.818 | 197.046 | 130.60 | 0.970 |
| 10 | 2 | 32 | 177.129 | 4.642 | 249.140 | 108.66 | 0.970 |
| 10 | 2 | 34 | 191.444 | 5.209 | 222.025 | 127.16 | 0.985 |
| 10 | 2 | 36 | 119.033 | 6.903 | 129.573 | 356.39 | 0.961 |
| 10 | 2 | 38 | 41.846 | 12.096 | 6.903 | 159.64 | 0.680 |
| 10 | 2 | 40 | 121.220 | 8.853 | 167.025 | 304.73 | 0.971 |
| 10 | 2 | 42 | 62.079 | 13.757 | 73.251 | 356.55 | 0.820 |
| 10 | 3 | 1 | 394.022 | 5.506 | 614.464 | 163.32 | 0.990 |
| 10 | 3 | 3 | 362.873 | 3.768 | 523.833 | 152.07 | 0.989 |
| 10 | 3 | 5 | 339.918 | 3.329 | 521.198 | 260.83 | 0.986 |
| 10 | 3 | 7 | 241.783 | 2.132 | 367.655 | 173.96 | 0.983 |
| 10 | 3 | 9 | 468.805 | 4.124 | 645.702 | 144.02 | 0.995 |
| 10 | 3 | 11 | 132.060 | 2.298 | 200.598 | 216.60 | 0.880 |
| 10 | 3 | 13 | 149.053 | 2.308 | 214.226 | 337.19 | 0.946 |
| 10 | 3 | 15 | 270.042 | 2.644 | 358.704 | 90.91 | 0.983 |
| 10 | 3 | 17 | 143.570 | 2.899 | 210.072 | 5.07 | 0.938 |
| 10 | 3 | 19 | 434.672 | 4.250 | 649.822 | 95.20 | 0.993 |
| 10 | 3 | 21 | 160.515 | 3.215 | 254.293 | 158.07 | 0.950 |
| 10 | 3 | 23 | 259.447 | 3.057 | 308.804 | 47.47 | 0.987 |
| 10 | 3 | 25 | 262.044 | 3.037 | 350.256 | 46.24 | 0.986 |
| 10 | 3 | 27 | 121.604 | 5.118 | 155.179 | 218.45 | 0.911 |
| 10 | 3 | 29 | 136.121 | 4.795 | 110.613 | 46.26 | 0.951 |
| 10 | 3 | 31 | 77.688 | 8.439 | 74.691 | 164.03 | 0.859 |
| 10 | 3 | 33 | 39.867 | 11.907 | 2.551 | 244.78 | 0.173 |
| 10 | 3 | 35 | 143.454 | 5.679 | 200.478 | 166.64 | 0.967 |
| 10 | 3 | 37 | 76.111 | 11.719 | 72.281 | 59.07 | 0.887 |
| 10 | 3 | 39 | 42.248 | 12.650 | 9.398 | 326.17 | 0.333 |
| 10 | 3 | 41 | 67.111 | 13.469 | 79.584 | 292.30 | 0.865 |
| 10 | 3 | 43 | 55.251 | 16.278 | 45.770 | 320.03 | 0.690 |
| 10 | 4 | 0 | 82.139 | 4.577 | 112.826 | 180.00 | 0.983 |
| 10 | 4 | 2 | 499.755 | 4.762 | 734.724 | 75.39 | 0.994 |
| 10 | 4 | 4 | 317.970 | 2.514 | 452.058 | 53.87 | 0.988 |
| 10 | 4 | 6 | 290.117 | 2.404 | 430.801 | 208.97 | 0.993 |
| 10 | 4 | 8 | 213.949 | 2.129 | 335.021 | 193.74 | 0.981 |
| 10 | 4 | 10 | 186.363 | 2.055 | 224.191 | 313.14 | 0.977 |
| 10 | 4 | 12 | 345.043 | 3.238 | 493.391 | 327.00 | 0.992 |
| 10 | 4 | 14 | 105.993 | 3.349 | 120.656 | 157.86 | 0.954 |
| 10 | 4 | 16 | 287.054 | 2.830 | 374.597 | 153.99 | 0.987 |
| 10 | 4 | 18 | 103.379 | 3.513 | 150.031 | 317.21 | 0.948 |
| 10 | 4 | 20 | 176.643 | 2.726 | 228.987 | 277.20 | 0.970 |
| 10 | 4 | 22 | 411.417 | 3.622 | 588.492 | 143.79 | 0.994 |

| | | | | | | | |
|---|---|---|---|---|---|---|---|
| 10 | 4 | 24 | 278.536 | 3.235 | 387.710 | 23.92 | 0.989 |
| 10 | 4 | 26 | 324.580 | 3.459 | 499.673 | 92.15 | 0.988 |
| 10 | 4 | 28 | 100.400 | 6.121 | 125.945 | 275.15 | 0.824 |
| 10 | 4 | 30 | 162.422 | 4.391 | 194.028 | 19.63 | 0.974 |
| 10 | 4 | 32 | 84.933 | 7.473 | 107.128 | 333.58 | 0.712 |
| 10 | 4 | 34 | 125.595 | 7.660 | 188.589 | 209.34 | 0.948 |
| 10 | 4 | 36 | 114.693 | 8.746 | 142.554 | 274.05 | 0.949 |
| 10 | 4 | 38 | 80.093 | 9.413 | 95.342 | 326.01 | 0.905 |
| 10 | 4 | 40 | 59.732 | 12.062 | 49.440 | 221.11 | 0.898 |
| 10 | 4 | 42 | 60.629 | 16.657 | 52.322 | 350.14 | 0.818 |
| 10 | 5 | 1 | 257.004 | 2.560 | 357.454 | 345.91 | 0.986 |
| 10 | 5 | 3 | 632.602 | 6.061 | 900.850 | 45.36 | 0.997 |
| 10 | 5 | 5 | 229.022 | 2.422 | 339.329 | 319.15 | 0.984 |
| 10 | 5 | 7 | 159.238 | 1.872 | 215.986 | 28.11 | 0.983 |
| 10 | 5 | 9 | 93.762 | 2.380 | 32.303 | 265.99 | 0.256 |
| 10 | 5 | 11 | 120.958 | 2.245 | 134.554 | 13.15 | 0.972 |
| 10 | 5 | 13 | 255.329 | 2.741 | 435.322 | 53.83 | 0.974 |
| 10 | 5 | 15 | 271.568 | 2.607 | 432.119 | 31.30 | 0.980 |
| 10 | 5 | 17 | 393.906 | 3.566 | 566.273 | 318.31 | 0.992 |
| 10 | 5 | 19 | 68.073 | 4.893 | 36.542 | 83.01 | 0.919 |
| 10 | 5 | 21 | 360.767 | 3.260 | 485.034 | 335.34 | 0.993 |
| 10 | 5 | 23 | 231.209 | 2.795 | 335.217 | 168.83 | 0.981 |
| 10 | 5 | 25 | 328.854 | 3.297 | 399.424 | 175.34 | 0.992 |
| 10 | 5 | 27 | 351.232 | 3.497 | 474.174 | 193.27 | 0.991 |
| 10 | 5 | 29 | 124.670 | 5.990 | 156.465 | 97.53 | 0.929 |
| 10 | 5 | 31 | 173.723 | 5.498 | 231.821 | 202.98 | 0.973 |
| 10 | 5 | 33 | 184.107 | 4.538 | 209.263 | 88.80 | 0.984 |
| 10 | 5 | 35 | 127.650 | 7.282 | 235.460 | 16.81 | 0.832 |
| 10 | 5 | 37 | 108.831 | 7.048 | 140.664 | 322.45 | 0.952 |
| 10 | 5 | 39 | 111.169 | 9.324 | 163.876 | 299.50 | 0.933 |
| 10 | 5 | 41 | 48.288 | 13.094 | 31.384 | 5.64 | 0.781 |
| 10 | 5 | 43 | 61.213 | 26.718 | 4.851 | 3.62 | 0.746 |
| 10 | 6 | 0 | 39.417 | 8.479 | 33.146 | 0.00 | 0.625 |
| 10 | 6 | 2 | 314.613 | 4.023 | 473.713 | 288.35 | 0.988 |
| 10 | 6 | 4 | 226.692 | 2.103 | 356.848 | 35.32 | 0.981 |
| 10 | 6 | 6 | 236.790 | 2.187 | 357.473 | 301.84 | 0.987 |
| 10 | 6 | 8 | 187.272 | 2.086 | 263.672 | 357.02 | 0.980 |
| 10 | 6 | 10 | 327.660 | 2.976 | 471.812 | 238.39 | 0.990 |
| 10 | 6 | 12 | 201.540 | 2.328 | 316.021 | 39.09 | 0.983 |
| 10 | 6 | 14 | 558.157 | 4.557 | 730.269 | 136.25 | 0.996 |
| 10 | 6 | 16 | 89.343 | 4.085 | 104.976 | 266.84 | 0.799 |
| 10 | 6 | 18 | 403.289 | 3.870 | 548.830 | 309.11 | 0.993 |
| 10 | 6 | 20 | 164.420 | 2.627 | 230.954 | 72.19 | 0.957 |
| 10 | 6 | 22 | 315.304 | 3.031 | 515.347 | 60.82 | 0.987 |
| 10 | 6 | 24 | 212.976 | 2.895 | 291.077 | 309.95 | 0.977 |
| 10 | 6 | 26 | 150.343 | 3.869 | 187.712 | 324.56 | 0.957 |
| 10 | 6 | 28 | 200.255 | 3.711 | 299.146 | 121.11 | 0.966 |
| 10 | 6 | 30 | 123.242 | 6.154 | 170.476 | 10.55 | 0.942 |
| 10 | 6 | 32 | 169.473 | 4.240 | 217.257 | 56.68 | 0.980 |
| 10 | 6 | 34 | 51.774 | 11.169 | 16.771 | 358.20 | 0.243 |
| 10 | 6 | 36 | 39.387 | 11.619 | 10.774 | 111.38 | 0.530 |
| 10 | 6 | 38 | 33.493 | 10.478 | 4.897 | 205.04 | 0.249 |
| 10 | 6 | 40 | 71.414 | 13.512 | 87.663 | 88.39 | 0.889 |
| 10 | 6 | 42 | 69.783 | 15.323 | 85.222 | 346.90 | 0.812 |
| 10 | 7 | 1 | 108.711 | 1.875 | 160.734 | 3.18 | 0.987 |
| 10 | 7 | 3 | 99.614 | 2.451 | 131.927 | 21.00 | 0.887 |
| 10 | 7 | 5 | 117.085 | 2.028 | 152.197 | 239.34 | 0.973 |
| 10 | 7 | 7 | 235.446 | 2.318 | 285.630 | 353.48 | 0.991 |
| 10 | 7 | 9 | 69.736 | 4.464 | 3.209 | 320.84 | 0.866 |
| 10 | 7 | 11 | 34.894 | 5.772 | 37.302 | 89.25 | 0.767 |
| 10 | 7 | 13 | 235.363 | 2.497 | 272.453 | 47.29 | 0.987 |
| 10 | 7 | 15 | 68.209 | 4.218 | 53.197 | 335.84 | 0.722 |
| 10 | 7 | 17 | 283.514 | 2.854 | 436.690 | 328.90 | 0.984 |
| 10 | 7 | 19 | 146.790 | 2.855 | 224.747 | 120.11 | 0.934 |
| 10 | 7 | 21 | 212.876 | 3.113 | 262.409 | 319.59 | 0.980 |
| 10 | 7 | 23 | 164.335 | 3.151 | 197.461 | 273.45 | 0.971 |
| 10 | 7 | 25 | 146.628 | 3.823 | 217.087 | 46.56 | 0.946 |
| 10 | 7 | 27 | 102.918 | 5.073 | 132.418 | 104.87 | 0.827 |
| 10 | 7 | 29 | 193.963 | 3.541 | 246.067 | 336.58 | 0.980 |
| 10 | 7 | 31 | 253.310 | 4.118 | 360.674 | 299.38 | 0.984 |
| 10 | 7 | 33 | 174.433 | 4.859 | 225.293 | 127.15 | 0.980 |
| 10 | 7 | 35 | 100.447 | 7.755 | 107.726 | 15.82 | 0.942 |
| 10 | 7 | 37 | 151.782 | 5.471 | 168.158 | 85.34 | 0.979 |
| 10 | 7 | 39 | 42.528 | 11.300 | 27.854 | 223.05 | 0.745 |
| 10 | 7 | 41 | 68.195 | 11.508 | 88.105 | 309.70 | 0.885 |
| 10 | 8 | 0 | 165.383 | 2.643 | 235.033 | 180.00 | 1.000 |
| 10 | 8 | 2 | 330.483 | 4.453 | 426.305 | 120.23 | 0.991 |

| | | | | | | | |
|---|---|---|---|---|---|---|---|
| 10 | 8 | 4 | 235.125 | 2.167 | 313.094 | 217.53 | 0.984 |
| 10 | 8 | 6 | 223.168 | 2.211 | 267.950 | 264.76 | 0.984 |
| 10 | 8 | 8 | 292.830 | 2.879 | 418.946 | 95.09 | 0.987 |
| 10 | 8 | 10 | 56.537 | 5.062 | 10.985 | 345.73 | 0.700 |
| 10 | 8 | 12 | 79.338 | 3.611 | 40.249 | 91.59 | 0.836 |
| 10 | 8 | 14 | 258.246 | 2.659 | 387.280 | 345.55 | 0.981 |
| 10 | 8 | 16 | 535.995 | 4.895 | 778.965 | 80.88 | 0.995 |
| 10 | 8 | 18 | 250.477 | 2.679 | 321.794 | 46.36 | 0.988 |
| 10 | 8 | 20 | 269.738 | 2.885 | 316.016 | 162.56 | 0.989 |
| 10 | 8 | 22 | 93.189 | 4.386 | 54.513 | 212.15 | 0.920 |
| 10 | 8 | 24 | 155.348 | 3.543 | 217.491 | 247.09 | 0.955 |
| 10 | 8 | 26 | 199.697 | 3.752 | 301.879 | 316.35 | 0.967 |
| 10 | 8 | 28 | 305.462 | 3.909 | 425.850 | 131.10 | 0.987 |
| 10 | 8 | 30 | 161.096 | 5.572 | 222.059 | 69.22 | 0.965 |
| 10 | 8 | 32 | 92.390 | 7.421 | 93.441 | 139.09 | 0.938 |
| 10 | 8 | 34 | 207.167 | 4.138 | 318.668 | 204.16 | 0.983 |
| 10 | 8 | 36 | 166.543 | 5.132 | 232.404 | 116.19 | 0.979 |
| 10 | 8 | 38 | 34.599 | 11.119 | 8.929 | 343.97 | 0.520 |
| 10 | 8 | 40 | 80.403 | 13.298 | 85.047 | 43.99 | 0.934 |
| 10 | 8 | 42 | 55.127 | 14.796 | 49.528 | 194.12 | 0.782 |
| 10 | 9 | 1 | 490.579 | 3.973 | 700.234 | 133.18 | 0.996 |
| 10 | 9 | 3 | 183.848 | 2.297 | 219.852 | 157.36 | 0.971 |
| 10 | 9 | 5 | 215.927 | 2.087 | 330.952 | 158.30 | 0.989 |
| 10 | 9 | 7 | 57.600 | 5.491 | 72.028 | 275.43 | 0.861 |
| 10 | 9 | 9 | 182.318 | 2.512 | 206.586 | 207.32 | 0.972 |
| 10 | 9 | 11 | 265.010 | 2.609 | 418.730 | 42.14 | 0.982 |
| 10 | 9 | 13 | 64.806 | 4.706 | 75.634 | 276.35 | 0.887 |
| 10 | 9 | 15 | 339.951 | 3.251 | 531.924 | 48.25 | 0.988 |
| 10 | 9 | 17 | 126.541 | 3.005 | 190.076 | 181.35 | 0.964 |
| 10 | 9 | 19 | 119.910 | 3.310 | 164.642 | 14.64 | 0.960 |
| 10 | 9 | 21 | 94.416 | 5.000 | 80.235 | 33.62 | 0.908 |
| 10 | 9 | 23 | 164.017 | 3.920 | 252.261 | 346.78 | 0.961 |
| 10 | 9 | 25 | 100.650 | 5.294 | 126.571 | 305.21 | 0.846 |
| 10 | 9 | 27 | 121.834 | 4.642 | 176.176 | 59.59 | 0.885 |
| 10 | 9 | 29 | 89.317 | 8.090 | 77.172 | 127.59 | 0.931 |
| 10 | 9 | 31 | 306.594 | 3.891 | 467.562 | 343.64 | 0.992 |
| 10 | 9 | 33 | 205.726 | 4.767 | 292.787 | 215.88 | 0.984 |
| 10 | 9 | 35 | 60.406 | 11.542 | 11.003 | 299.41 | 0.883 |
| 10 | 9 | 37 | 111.616 | 6.959 | 165.121 | 355.52 | 0.945 |
| 10 | 9 | 39 | 39.704 | 11.260 | 4.403 | 253.16 | 0.852 |
| 10 | 9 | 41 | 48.934 | 14.448 | 24.572 | 116.21 | 0.851 |
| 10 | 10 | 0 | 292.271 | 3.652 | 415.846 | 180.00 | 1.000 |
| 10 | 10 | 2 | 230.278 | 2.644 | 289.256 | 117.13 | 0.981 |
| 10 | 10 | 4 | 80.686 | 3.869 | 101.386 | 267.58 | 0.837 |
| 10 | 10 | 6 | 509.378 | 4.190 | 733.463 | 27.84 | 0.996 |
| 10 | 10 | 8 | 383.297 | 3.201 | 517.602 | 57.08 | 0.992 |
| 10 | 10 | 10 | 345.064 | 3.606 | 504.516 | 181.39 | 0.989 |
| 10 | 10 | 12 | 87.561 | 4.212 | 76.832 | 74.57 | 0.876 |
| 10 | 10 | 14 | 94.177 | 3.324 | 105.669 | 46.37 | 0.821 |
| 10 | 10 | 16 | 256.398 | 2.894 | 405.252 | 352.69 | 0.982 |
| 10 | 10 | 18 | 207.497 | 2.771 | 339.674 | 113.64 | 0.967 |
| 10 | 10 | 20 | 118.221 | 3.543 | 104.671 | 32.38 | 0.943 |
| 10 | 10 | 22 | 274.829 | 3.072 | 331.606 | 240.00 | 0.988 |
| 10 | 10 | 24 | 180.700 | 3.338 | 258.303 | 111.02 | 0.962 |
| 10 | 10 | 26 | 331.276 | 3.534 | 424.538 | 101.51 | 0.990 |
| 10 | 10 | 28 | 216.511 | 3.905 | 290.177 | 180.82 | 0.983 |
| 10 | 10 | 30 | 201.287 | 4.163 | 295.587 | 261.76 | 0.984 |
| 10 | 10 | 32 | 141.673 | 5.614 | 198.997 | 300.48 | 0.967 |
| 10 | 10 | 34 | 193.752 | 4.944 | 325.797 | 343.15 | 0.977 |
| 10 | 10 | 36 | 46.865 | 11.678 | 23.887 | 187.02 | 0.475 |
| 10 | 10 | 38 | 78.488 | 11.851 | 99.117 | 286.18 | 0.923 |
| 10 | 10 | 40 | 55.945 | 14.575 | 50.555 | 15.88 | 0.602 |
| 10 | 11 | 1 | 318.168 | 3.116 | 488.856 | 346.32 | 0.990 |
| 10 | 11 | 3 | 95.859 | 4.316 | 112.402 | 174.64 | 0.854 |
| 10 | 11 | 5 | 396.389 | 3.764 | 539.078 | 3.78 | 0.994 |
| 10 | 11 | 7 | 226.003 | 2.286 | 328.781 | 35.13 | 0.987 |
| 10 | 11 | 9 | 149.188 | 2.970 | 228.879 | 330.99 | 0.912 |
| 10 | 11 | 11 | 310.413 | 3.056 | 424.302 | 204.54 | 0.990 |
| 10 | 11 | 13 | 81.959 | 4.332 | 104.377 | 105.51 | 0.927 |
| 10 | 11 | 15 | 204.713 | 2.775 | 256.917 | 184.77 | 0.979 |
| 10 | 11 | 17 | 410.416 | 4.105 | 562.838 | 224.56 | 0.995 |
| 10 | 11 | 19 | 146.239 | 3.388 | 182.650 | 17.26 | 0.971 |
| 10 | 11 | 21 | 40.976 | 8.874 | 34.342 | 332.21 | 0.621 |
| 10 | 11 | 23 | 399.474 | 3.618 | 549.278 | 181.35 | 0.993 |
| 10 | 11 | 25 | 159.873 | 3.888 | 243.661 | 129.62 | 0.945 |
| 10 | 11 | 27 | 319.054 | 3.629 | 489.222 | 172.88 | 0.991 |
| 10 | 11 | 29 | 213.474 | 4.212 | 289.246 | 228.48 | 0.982 |

| | | | | | | | |
|---|---|---|---|---|---|---|---|
| 10 | 11 | 31 | 170.662 | 5.182 | 212.392 | 143.69 | 0.981 |
| 10 | 11 | 33 | 115.770 | 6.191 | 107.893 | 271.50 | 0.965 |
| 10 | 11 | 35 | 103.682 | 7.216 | 138.108 | 200.14 | 0.945 |
| 10 | 11 | 37 | 54.459 | 10.776 | 11.770 | 140.85 | 0.164 |
| 10 | 11 | 39 | 37.625 | 11.762 | 15.565 | 179.24 | 0.561 |
| 10 | 11 | 41 | 46.564 | 14.985 | 16.298 | 158.27 | 0.389 |
| 10 | 12 | 0 | 18.530 | 8.561 | 9.132 | 0.00 | 0.348 |
| 10 | 12 | 2 | 162.214 | 2.366 | 195.947 | 91.75 | 0.956 |
| 10 | 12 | 4 | 190.999 | 2.875 | 229.102 | 119.74 | 0.970 |
| 10 | 12 | 6 | 229.216 | 2.334 | 272.130 | 338.80 | 0.979 |
| 10 | 12 | 8 | 154.476 | 2.531 | 160.606 | 247.87 | 0.966 |
| 10 | 12 | 10 | 227.022 | 2.885 | 333.782 | 268.32 | 0.974 |
| 10 | 12 | 12 | 213.248 | 2.707 | 331.364 | 16.19 | 0.967 |
| 10 | 12 | 14 | 277.200 | 3.063 | 360.843 | 38.37 | 0.988 |
| 10 | 12 | 16 | 297.602 | 2.980 | 387.449 | 256.29 | 0.990 |
| 10 | 12 | 18 | 198.210 | 3.092 | 335.330 | 306.89 | 0.965 |
| 10 | 12 | 20 | 202.004 | 3.169 | 366.825 | 288.25 | 0.959 |
| 10 | 12 | 22 | 260.257 | 3.120 | 377.470 | 188.54 | 0.984 |
| 10 | 12 | 24 | 156.527 | 3.869 | 291.789 | 189.59 | 0.872 |
| 10 | 12 | 26 | 234.123 | 3.437 | 325.157 | 348.83 | 0.985 |
| 10 | 12 | 28 | 198.261 | 4.827 | 236.272 | 265.95 | 0.981 |
| 10 | 12 | 30 | 172.089 | 4.742 | 215.872 | 192.55 | 0.981 |
| 10 | 12 | 32 | 65.549 | 10.928 | 66.258 | 256.29 | 0.806 |
| 10 | 12 | 34 | 86.554 | 8.054 | 112.750 | 208.96 | 0.888 |
| 10 | 12 | 36 | 44.721 | 12.489 | 13.656 | 13.41 | 0.664 |
| 10 | 12 | 38 | 37.290 | 11.052 | 5.585 | 216.91 | 0.754 |
| 10 | 12 | 40 | 67.987 | 19.176 | 60.076 | 81.77 | 0.847 |
| 10 | 13 | 1 | 135.808 | 2.472 | 156.915 | 180.70 | 0.985 |
| 10 | 13 | 3 | 287.203 | 3.050 | 473.699 | 312.43 | 0.982 |
| 10 | 13 | 5 | 494.251 | 7.235 | 744.035 | 95.07 | 0.994 |
| 10 | 13 | 7 | 317.425 | 2.808 | 437.678 | 265.16 | 0.989 |
| 10 | 13 | 9 | 254.446 | 2.528 | 374.778 | 38.07 | 0.979 |
| 10 | 13 | 11 | 506.034 | 4.455 | 688.812 | 147.68 | 0.997 |
| 10 | 13 | 13 | 306.578 | 3.223 | 412.454 | 162.87 | 0.992 |
| 10 | 13 | 15 | 185.279 | 3.013 | 271.449 | 297.98 | 0.967 |
| 10 | 13 | 17 | 217.176 | 2.819 | 271.351 | 212.22 | 0.986 |
| 10 | 13 | 19 | 432.075 | 3.987 | 579.777 | 213.53 | 0.995 |
| 10 | 13 | 21 | 200.932 | 3.508 | 276.431 | 168.24 | 0.975 |
| 10 | 13 | 23 | 224.825 | 3.524 | 326.045 | 230.43 | 0.978 |
| 10 | 13 | 25 | 261.661 | 3.385 | 400.832 | 349.86 | 0.988 |
| 10 | 13 | 27 | 73.859 | 10.137 | 69.633 | 320.35 | 0.526 |
| 10 | 13 | 29 | 47.615 | 12.114 | 10.379 | 209.46 | 0.772 |
| 10 | 13 | 31 | 67.366 | 11.534 | 67.627 | 36.36 | 0.838 |
| 10 | 13 | 33 | 65.055 | 11.711 | 64.959 | 174.89 | 0.793 |
| 10 | 13 | 35 | 85.619 | 8.743 | 84.927 | 212.39 | 0.931 |
| 10 | 13 | 37 | 41.055 | 12.154 | 16.921 | 61.47 | 0.294 |
| 10 | 13 | 39 | 72.135 | 15.232 | 52.990 | 160.05 | 0.419 |
| 10 | 14 | 0 | 28.598 | 11.394 | 8.034 | 0.00 | 0.198 |
| 10 | 14 | 2 | 118.122 | 3.171 | 152.114 | 77.39 | 0.903 |
| 10 | 14 | 4 | 184.261 | 4.240 | 314.907 | 57.74 | 0.947 |
| 10 | 14 | 6 | 362.989 | 3.375 | 503.473 | 104.09 | 0.991 |
| 10 | 14 | 8 | 215.975 | 2.518 | 331.441 | 168.14 | 0.977 |
| 10 | 14 | 10 | 246.075 | 2.662 | 317.601 | 336.77 | 0.986 |
| 10 | 14 | 12 | 224.555 | 2.797 | 363.572 | 219.93 | 0.977 |
| 10 | 14 | 14 | 679.594 | 5.595 | 942.383 | 172.78 | 0.998 |
| 10 | 14 | 16 | 279.029 | 3.442 | 414.896 | 216.11 | 0.987 |
| 10 | 14 | 18 | 209.515 | 2.935 | 263.853 | 216.93 | 0.979 |
| 10 | 14 | 20 | 253.653 | 2.997 | 312.360 | 25.90 | 0.985 |
| 10 | 14 | 22 | 65.847 | 9.668 | 32.439 | 184.10 | 0.747 |
| 10 | 14 | 24 | 246.525 | 3.409 | 365.339 | 347.24 | 0.986 |
| 10 | 14 | 26 | 192.105 | 3.974 | 268.414 | 341.49 | 0.977 |
| 10 | 14 | 28 | 212.156 | 4.055 | 234.809 | 208.34 | 0.989 |
| 10 | 14 | 30 | 55.477 | 12.834 | 9.580 | 53.76 | 0.123 |
| 10 | 14 | 32 | 107.562 | 7.981 | 144.997 | 335.33 | 0.937 |
| 10 | 14 | 34 | 38.230 | 11.867 | 2.082 | 248.92 | 0.551 |
| 10 | 14 | 36 | 101.931 | 8.825 | 183.881 | 251.72 | 0.915 |
| 10 | 14 | 38 | 45.571 | 13.475 | 13.091 | 290.00 | 0.902 |
| 10 | 15 | 1 | 390.232 | 3.263 | 485.621 | 206.62 | 0.994 |
| 10 | 15 | 3 | 315.970 | 2.966 | 497.214 | 155.43 | 0.986 |
| 10 | 15 | 5 | 77.957 | 4.135 | 92.298 | 85.05 | 0.924 |
| 10 | 15 | 7 | 174.314 | 2.777 | 276.522 | 103.23 | 0.970 |
| 10 | 15 | 9 | 314.724 | 2.907 | 486.938 | 306.62 | 0.990 |
| 10 | 15 | 11 | 197.345 | 2.921 | 272.517 | 63.25 | 0.978 |
| 10 | 15 | 13 | 215.191 | 2.965 | 328.360 | 186.84 | 0.984 |
| 10 | 15 | 15 | 453.945 | 3.934 | 706.014 | 284.95 | 0.995 |
| 10 | 15 | 17 | 186.979 | 3.710 | 190.505 | 12.66 | 0.982 |
| 10 | 15 | 19 | 336.880 | 3.390 | 502.638 | 1.36 | 0.991 |

| | | | | | | | |
|---|---|---|---|---|---|---|---|
| 10 | 15 | 21 | 191.687 | 3.644 | 168.550 | 55.10 | 0.978 |
| 10 | 15 | 23 | 149.148 | 5.388 | 218.549 | 30.45 | 0.961 |
| 10 | 15 | 25 | 307.636 | 3.671 | 520.563 | 71.73 | 0.987 |
| 10 | 15 | 27 | 54.561 | 11.372 | 39.803 | 247.77 | 0.484 |
| 10 | 15 | 29 | 79.673 | 8.483 | 94.157 | 236.26 | 0.885 |
| 10 | 15 | 31 | 129.450 | 6.154 | 147.579 | 29.88 | 0.971 |
| 10 | 15 | 33 | 55.413 | 11.461 | 40.468 | 119.68 | 0.506 |
| 10 | 15 | 35 | 35.455 | 10.832 | 6.885 | 222.57 | 0.142 |
| 10 | 15 | 37 | 40.004 | 13.138 | 10.931 | 211.48 | 0.207 |
| 10 | 15 | 39 | 43.493 | 14.623 | 13.645 | 299.52 | 0.751 |
| 10 | 16 | 0 | 486.882 | 5.431 | 691.849 | 180.00 | 1.000 |
| 10 | 16 | 2 | 71.768 | 4.852 | 70.848 | 14.33 | 0.704 |
| 10 | 16 | 4 | 200.428 | 2.981 | 256.136 | 243.88 | 0.980 |
| 10 | 16 | 6 | 108.427 | 6.498 | 130.248 | 118.81 | 0.920 |
| 10 | 16 | 8 | 102.426 | 3.110 | 148.372 | 287.31 | 0.883 |
| 10 | 16 | 10 | 459.991 | 3.895 | 631.537 | 39.41 | 0.996 |
| 10 | 16 | 12 | 277.228 | 2.876 | 307.412 | 203.90 | 0.991 |
| 10 | 16 | 14 | 171.027 | 3.194 | 236.508 | 295.88 | 0.964 |
| 10 | 16 | 16 | 306.505 | 3.056 | 397.436 | 116.06 | 0.990 |
| 10 | 16 | 18 | 218.856 | 2.837 | 307.501 | 326.48 | 0.978 |
| 10 | 16 | 20 | 301.679 | 3.624 | 461.568 | 33.70 | 0.987 |
| 10 | 16 | 22 | 280.587 | 3.990 | 346.865 | 137.30 | 0.991 |
| 10 | 16 | 24 | 143.160 | 5.164 | 247.804 | 131.24 | 0.938 |
| 10 | 16 | 26 | 181.478 | 4.380 | 246.658 | 215.56 | 0.983 |
| 10 | 16 | 28 | 51.701 | 12.280 | 25.689 | 26.17 | 0.758 |
| 10 | 16 | 30 | 117.945 | 5.634 | 147.839 | 171.54 | 0.957 |
| 10 | 16 | 32 | 105.975 | 6.857 | 140.449 | 47.54 | 0.949 |
| 10 | 16 | 34 | 58.813 | 13.680 | 69.588 | 340.71 | 0.739 |
| 10 | 16 | 36 | 78.579 | 14.719 | 111.195 | 263.96 | 0.839 |
| 10 | 16 | 38 | 47.069 | 14.330 | 27.522 | 212.66 | 0.784 |
| 10 | 17 | 1 | 78.787 | 4.718 | 16.497 | 339.95 | 0.934 |
| 10 | 17 | 3 | 172.392 | 2.942 | 258.885 | 249.09 | 0.965 |
| 10 | 17 | 5 | 76.561 | 6.166 | 49.574 | 29.66 | 0.911 |
| 10 | 17 | 7 | 81.107 | 5.286 | 84.058 | 256.55 | 0.873 |
| 10 | 17 | 9 | 185.407 | 2.935 | 211.662 | 338.94 | 0.976 |
| 10 | 17 | 11 | 408.800 | 3.564 | 576.969 | 77.34 | 0.994 |
| 10 | 17 | 13 | 568.920 | 4.914 | 839.675 | 2.86 | 0.997 |
| 10 | 17 | 15 | 339.550 | 3.255 | 492.707 | 110.12 | 0.991 |
| 10 | 17 | 17 | 137.352 | 3.803 | 228.882 | 153.22 | 0.878 |
| 10 | 17 | 19 | 240.989 | 3.660 | 367.051 | 36.02 | 0.979 |
| 10 | 17 | 21 | 186.255 | 4.343 | 154.837 | 98.70 | 0.985 |
| 10 | 17 | 23 | 95.964 | 7.642 | 101.417 | 133.32 | 0.920 |
| 10 | 17 | 25 | 235.643 | 4.173 | 281.391 | 5.95 | 0.991 |
| 10 | 17 | 27 | 199.750 | 3.836 | 334.643 | 293.91 | 0.980 |
| 10 | 17 | 29 | 237.572 | 4.431 | 343.139 | 305.80 | 0.989 |
| 10 | 17 | 31 | 82.279 | 9.088 | 99.176 | 117.56 | 0.904 |
| 10 | 17 | 33 | 67.509 | 11.384 | 72.804 | 309.50 | 0.918 |
| 10 | 17 | 35 | 103.828 | 9.103 | 117.220 | 341.12 | 0.970 |
| 10 | 17 | 37 | 59.344 | 17.323 | 56.407 | 353.16 | 0.780 |
| 10 | 18 | 0 | 41.794 | 14.136 | 55.242 | 0.00 | 0.944 |
| 10 | 18 | 2 | 227.190 | 3.197 | 345.296 | 149.05 | 0.980 |
| 10 | 18 | 4 | 243.620 | 2.915 | 332.356 | 310.62 | 0.984 |
| 10 | 18 | 6 | 355.000 | 4.556 | 479.213 | 273.71 | 0.993 |
| 10 | 18 | 8 | 502.357 | 4.377 | 653.014 | 355.93 | 0.997 |
| 10 | 18 | 10 | 298.474 | 3.038 | 473.870 | 65.80 | 0.987 |
| 10 | 18 | 12 | 107.827 | 4.031 | 97.987 | 321.06 | 0.945 |
| 10 | 18 | 14 | 166.527 | 3.289 | 262.138 | 310.08 | 0.949 |
| 10 | 18 | 16 | 166.241 | 3.356 | 264.259 | 156.21 | 0.950 |
| 10 | 18 | 18 | 139.968 | 4.965 | 233.618 | 195.92 | 0.919 |
| 10 | 18 | 20 | 106.452 | 7.188 | 85.616 | 180.32 | 0.949 |
| 10 | 18 | 22 | 212.229 | 4.383 | 303.566 | 285.00 | 0.982 |
| 10 | 18 | 24 | 116.675 | 6.466 | 164.751 | 345.84 | 0.954 |
| 10 | 18 | 26 | 195.158 | 4.855 | 241.821 | 357.28 | 0.986 |
| 10 | 18 | 28 | 99.279 | 7.969 | 137.252 | 313.99 | 0.925 |
| 10 | 18 | 30 | 102.165 | 7.295 | 118.533 | 224.63 | 0.953 |
| 10 | 18 | 32 | 122.629 | 6.800 | 180.000 | 15.11 | 0.956 |
| 10 | 18 | 34 | 44.287 | 13.023 | 26.176 | 184.66 | 0.502 |
| 10 | 18 | 36 | 66.719 | 16.289 | 74.810 | 27.58 | 0.846 |
| 10 | 19 | 1 | 161.881 | 3.193 | 139.562 | 21.78 | 0.981 |
| 10 | 19 | 3 | 289.587 | 3.042 | 387.741 | 337.46 | 0.989 |
| 10 | 19 | 5 | 308.584 | 3.912 | 428.468 | 295.73 | 0.990 |
| 10 | 19 | 7 | 417.790 | 4.308 | 565.513 | 74.05 | 0.995 |
| 10 | 19 | 9 | 210.135 | 2.918 | 303.250 | 270.25 | 0.977 |
| 10 | 19 | 11 | 366.102 | 3.391 | 533.665 | 310.45 | 0.993 |
| 10 | 19 | 13 | 252.563 | 3.099 | 381.473 | 225.04 | 0.982 |
| 10 | 19 | 15 | 47.994 | 9.499 | 12.349 | 156.84 | 0.581 |
| 10 | 19 | 17 | 60.881 | 11.957 | 29.450 | 157.95 | 0.464 |

| | | | | | | | |
|---|---|---|---|---|---|---|---|
| 10 | 19 | 19 | 78.606 | 7.296 | 77.245 | 310.43 | 0.900 |
| 10 | 19 | 21 | 264.481 | 4.992 | 429.661 | 199.80 | 0.986 |
| 10 | 19 | 23 | 48.700 | 11.753 | 32.747 | 254.29 | 0.683 |
| 10 | 19 | 25 | 60.648 | 11.583 | 46.118 | 172.83 | 0.853 |
| 10 | 19 | 27 | 47.129 | 11.034 | 22.811 | 144.89 | 0.460 |
| 10 | 19 | 29 | 61.044 | 11.237 | 58.898 | 171.57 | 0.798 |
| 10 | 19 | 31 | 138.365 | 7.954 | 199.765 | 4.70 | 0.968 |
| 10 | 19 | 33 | 43.630 | 12.818 | 24.494 | 134.57 | 0.756 |
| 10 | 19 | 35 | 56.270 | 14.028 | 58.139 | 186.64 | 0.809 |
| 10 | 20 | 0 | 282.173 | 4.286 | 400.440 | 0.00 | 1.000 |
| 10 | 20 | 2 | 217.763 | 3.108 | 294.109 | 11.04 | 0.982 |
| 10 | 20 | 4 | 397.018 | 3.967 | 598.887 | 267.22 | 0.994 |
| 10 | 20 | 6 | 175.177 | 3.979 | 316.044 | 38.58 | 0.940 |
| 10 | 20 | 8 | 245.678 | 3.407 | 350.335 | 85.08 | 0.981 |
| 10 | 20 | 10 | 165.948 | 3.650 | 192.846 | 166.59 | 0.968 |
| 10 | 20 | 12 | 130.926 | 4.382 | 132.662 | 151.12 | 0.954 |
| 10 | 20 | 14 | 260.868 | 3.327 | 420.475 | 42.23 | 0.981 |
| 10 | 20 | 16 | 324.735 | 3.464 | 419.133 | 313.49 | 0.994 |
| 10 | 20 | 18 | 233.498 | 4.203 | 341.268 | 87.37 | 0.985 |
| 10 | 20 | 20 | 68.149 | 9.705 | 79.564 | 43.52 | 0.634 |
| 10 | 20 | 22 | 207.365 | 4.388 | 303.852 | 249.00 | 0.986 |
| 10 | 20 | 24 | 121.211 | 6.714 | 131.380 | 21.30 | 0.966 |
| 10 | 20 | 26 | 37.174 | 11.640 | 3.040 | 116.86 | 0.316 |
| 10 | 20 | 28 | 48.700 | 11.839 | 30.633 | 158.33 | 0.610 |
| 10 | 20 | 30 | 105.141 | 9.595 | 132.016 | 72.72 | 0.969 |
| 10 | 20 | 32 | 46.488 | 13.934 | 7.252 | 143.40 | 0.134 |
| 10 | 20 | 34 | 40.131 | 13.243 | 17.367 | 30.97 | 0.483 |
| 10 | 21 | 1 | 49.545 | 10.370 | 32.067 | 344.54 | 0.738 |
| 10 | 21 | 3 | 314.054 | 3.213 | 727.515 | 200.25 | 0.959 |
| 10 | 21 | 5 | 135.498 | 5.186 | 168.170 | 104.69 | 0.951 |
| 10 | 21 | 7 | 259.892 | 5.187 | 348.244 | 123.59 | 0.986 |
| 10 | 21 | 9 | 139.941 | 4.372 | 187.154 | 350.84 | 0.944 |
| 10 | 21 | 11 | 149.139 | 4.092 | 251.989 | 340.12 | 0.903 |
| 10 | 21 | 13 | 291.970 | 3.409 | 412.720 | 32.39 | 0.991 |
| 10 | 21 | 15 | 165.333 | 4.280 | 273.097 | 3.78 | 0.964 |
| 10 | 21 | 17 | 122.247 | 6.288 | 168.023 | 253.38 | 0.944 |
| 10 | 21 | 19 | 93.923 | 9.240 | 113.037 | 206.71 | 0.938 |
| 10 | 21 | 21 | 253.598 | 4.019 | 374.352 | 175.31 | 0.991 |
| 10 | 21 | 23 | 155.680 | 5.276 | 233.420 | 213.41 | 0.973 |
| 10 | 21 | 25 | 67.674 | 14.323 | 61.528 | 280.44 | 0.853 |
| 10 | 21 | 27 | 39.452 | 12.011 | 6.949 | 283.81 | 0.576 |
| 10 | 21 | 29 | 34.870 | 11.226 | 11.487 | 330.45 | 0.492 |
| 10 | 21 | 31 | 89.640 | 14.829 | 128.943 | 140.79 | 0.923 |
| 10 | 21 | 33 | 42.441 | 12.841 | 22.608 | 142.88 | 0.765 |
| 10 | 22 | 0 | 35.827 | 15.108 | 14.477 | 180.00 | 0.292 |
| 10 | 22 | 2 | 219.566 | 3.747 | 294.286 | 146.16 | 0.979 |
| 10 | 22 | 4 | 415.624 | 3.907 | 552.535 | 185.06 | 0.994 |
| 10 | 22 | 6 | 168.374 | 4.392 | 180.172 | 188.51 | 0.974 |
| 10 | 22 | 8 | 165.219 | 4.842 | 175.072 | 29.91 | 0.968 |
| 10 | 22 | 10 | 95.827 | 7.150 | 81.362 | 331.77 | 0.936 |
| 10 | 22 | 12 | 194.278 | 3.996 | 341.848 | 298.70 | 0.957 |
| 10 | 22 | 14 | 57.046 | 11.611 | 35.487 | 40.92 | 0.496 |
| 10 | 22 | 16 | 45.700 | 12.815 | 8.793 | 340.57 | 0.750 |
| 10 | 22 | 18 | 158.921 | 4.836 | 284.065 | 282.75 | 0.959 |
| 10 | 22 | 20 | 54.984 | 12.429 | 43.558 | 175.41 | 0.743 |
| 10 | 22 | 22 | 101.274 | 8.908 | 173.299 | 59.51 | 0.895 |
| 10 | 22 | 24 | 44.225 | 12.132 | 19.804 | 3.22 | 0.540 |
| 10 | 22 | 26 | 73.246 | 13.419 | 95.624 | 126.77 | 0.817 |
| 10 | 22 | 28 | 92.066 | 9.211 | 152.340 | 14.86 | 0.934 |
| 10 | 22 | 30 | 68.675 | 16.185 | 71.538 | 182.02 | 0.904 |
| 10 | 22 | 32 | 54.598 | 16.321 | 8.428 | 213.49 | 0.131 |
| 10 | 23 | 1 | 385.122 | 4.082 | 553.759 | 111.15 | 0.993 |
| 10 | 23 | 3 | 307.609 | 3.519 | 420.529 | 228.69 | 0.993 |
| 10 | 23 | 5 | 141.567 | 5.299 | 161.873 | 162.56 | 0.968 |
| 10 | 23 | 7 | 157.573 | 6.273 | 252.596 | 271.97 | 0.963 |
| 10 | 23 | 9 | 326.227 | 4.751 | 480.848 | 150.59 | 0.993 |
| 10 | 23 | 11 | 248.736 | 3.767 | 315.125 | 220.86 | 0.989 |
| 10 | 23 | 13 | 116.690 | 4.806 | 196.912 | 111.61 | 0.901 |
| 10 | 23 | 15 | 144.110 | 4.738 | 179.283 | 256.97 | 0.976 |
| 10 | 23 | 17 | 40.551 | 11.069 | 1.250 | 99.66 | 0.702 |
| 10 | 23 | 19 | 188.576 | 4.407 | 279.070 | 320.77 | 0.983 |
| 10 | 23 | 21 | 69.427 | 10.594 | 49.495 | 261.14 | 0.903 |
| 10 | 23 | 23 | 167.324 | 4.848 | 202.376 | 297.10 | 0.985 |
| 10 | 23 | 25 | 50.023 | 10.526 | 34.788 | 28.91 | 0.608 |
| 10 | 23 | 27 | 66.539 | 13.783 | 52.724 | 209.79 | 0.931 |
| 10 | 23 | 29 | 45.711 | 14.316 | 7.182 | 342.43 | 0.106 |
| 10 | 23 | 31 | 45.541 | 12.993 | 33.047 | 99.30 | 0.730 |

| | | | | | | | |
|---|---|---|---|---|---|---|---|
| 10 | 24 | 0 | 151.648 | 6.447 | 212.573 | 180.00 | 0.991 |
| 10 | 24 | 2 | 164.448 | 5.632 | 211.123 | 29.48 | 0.974 |
| 10 | 24 | 4 | 371.517 | 3.982 | 512.501 | 155.07 | 0.995 |
| 10 | 24 | 6 | 257.170 | 4.014 | 345.973 | 128.62 | 0.991 |
| 10 | 24 | 8 | 48.217 | 12.277 | 23.819 | 106.15 | 0.503 |
| 10 | 24 | 10 | 90.967 | 9.112 | 154.245 | 80.82 | 0.860 |
| 10 | 24 | 12 | 127.810 | 4.802 | 145.295 | 309.46 | 0.973 |
| 10 | 24 | 14 | 234.991 | 4.886 | 360.109 | 304.60 | 0.989 |
| 10 | 24 | 16 | 72.946 | 9.948 | 96.316 | 307.52 | 0.847 |
| 10 | 24 | 18 | 102.998 | 7.484 | 146.751 | 154.22 | 0.934 |
| 10 | 24 | 20 | 172.467 | 5.242 | 259.290 | 224.11 | 0.979 |
| 10 | 24 | 22 | 56.233 | 14.122 | 37.029 | 9.17 | 0.433 |
| 10 | 24 | 24 | 191.213 | 5.734 | 249.184 | 220.68 | 0.988 |
| 10 | 24 | 26 | 79.542 | 13.407 | 64.002 | 119.58 | 0.956 |
| 10 | 24 | 28 | 77.269 | 12.874 | 100.380 | 289.80 | 0.926 |
| 10 | 24 | 30 | 33.067 | 16.288 | 3.619 | 260.55 | 0.489 |
| 10 | 25 | 1 | 180.178 | 5.864 | 237.053 | 14.27 | 0.978 |
| 10 | 25 | 3 | 62.559 | 11.530 | 25.028 | 275.01 | 0.235 |
| 10 | 25 | 5 | 133.454 | 6.810 | 137.193 | 205.88 | 0.976 |
| 10 | 25 | 7 | 40.537 | 11.257 | 5.360 | 87.50 | 0.734 |
| 10 | 25 | 9 | 80.664 | 9.963 | 92.058 | 16.66 | 0.914 |
| 10 | 25 | 11 | 65.784 | 10.792 | 41.007 | 259.68 | 0.311 |
| 10 | 25 | 13 | 64.784 | 11.239 | 77.284 | 320.88 | 0.725 |
| 10 | 25 | 15 | 196.579 | 4.149 | 307.001 | 142.86 | 0.984 |
| 10 | 25 | 17 | 65.057 | 11.704 | 67.312 | 163.38 | 0.831 |
| 10 | 25 | 19 | 120.325 | 6.824 | 131.170 | 142.65 | 0.972 |
| 10 | 25 | 21 | 112.498 | 6.361 | 139.732 | 141.15 | 0.963 |
| 10 | 25 | 23 | 65.647 | 12.376 | 78.973 | 148.11 | 0.907 |
| 10 | 25 | 25 | 69.385 | 15.792 | 82.250 | 333.78 | 0.891 |
| 10 | 25 | 27 | 59.658 | 15.344 | 66.511 | 16.75 | 0.807 |
| 10 | 25 | 29 | 77.703 | 14.654 | 97.535 | 341.05 | 0.898 |
| 10 | 26 | 0 | 158.216 | 8.795 | 219.260 | 0.00 | 0.982 |
| 10 | 26 | 2 | 229.701 | 3.877 | 374.385 | 283.68 | 0.988 |
| 10 | 26 | 4 | 51.267 | 11.850 | 18.937 | 35.14 | 0.818 |
| 10 | 26 | 6 | 117.242 | 5.225 | 126.752 | 25.10 | 0.971 |
| 10 | 26 | 8 | 61.921 | 12.589 | 69.570 | 88.77 | 0.775 |
| 10 | 26 | 10 | 153.036 | 6.865 | 182.698 | 134.51 | 0.980 |
| 10 | 26 | 12 | 33.206 | 10.423 | 8.385 | 255.18 | 0.487 |
| 10 | 26 | 14 | 78.475 | 9.477 | 117.715 | 66.74 | 0.843 |
| 10 | 26 | 16 | 97.262 | 7.363 | 101.638 | 105.85 | 0.950 |
| 10 | 26 | 18 | 60.876 | 11.471 | 56.114 | 196.01 | 0.875 |
| 10 | 26 | 20 | 43.876 | 11.586 | 8.566 | 201.18 | 0.784 |
| 10 | 26 | 22 | 56.121 | 14.455 | 42.808 | 232.64 | 0.893 |
| 10 | 26 | 24 | 73.446 | 14.394 | 78.630 | 57.13 | 0.932 |
| 10 | 26 | 26 | 49.413 | 15.857 | 40.832 | 339.11 | 0.647 |
| 10 | 27 | 1 | 59.979 | 15.671 | 24.032 | 68.63 | 0.879 |
| 10 | 27 | 3 | 79.739 | 9.226 | 94.410 | 128.04 | 0.910 |
| 10 | 27 | 5 | 106.244 | 10.247 | 184.594 | 250.17 | 0.916 |
| 10 | 27 | 7 | 121.645 | 5.745 | 195.175 | 168.71 | 0.953 |
| 10 | 27 | 9 | 34.698 | 10.575 | 10.974 | 326.24 | 0.582 |
| 10 | 27 | 11 | 63.647 | 11.069 | 69.749 | 333.43 | 0.814 |
| 10 | 27 | 13 | 59.787 | 12.411 | 27.524 | 332.96 | 0.879 |
| 10 | 27 | 15 | 42.888 | 11.262 | 19.499 | 50.64 | 0.442 |
| 10 | 27 | 17 | 31.607 | 9.672 | 0.816 | 209.28 | 0.176 |
| 10 | 27 | 19 | 77.781 | 12.427 | 54.082 | 9.71 | 0.960 |
| 10 | 27 | 21 | 46.700 | 13.850 | 31.721 | 315.46 | 0.817 |
| 10 | 27 | 23 | 75.225 | 14.579 | 111.815 | 195.69 | 0.835 |
| 10 | 27 | 25 | 40.775 | 18.542 | 5.714 | 305.54 | 0.338 |
| 10 | 28 | 0 | 63.547 | 19.700 | 53.555 | 180.00 | 0.615 |
| 10 | 28 | 2 | 45.718 | 12.210 | 22.661 | 212.79 | 0.508 |
| 10 | 28 | 4 | 82.670 | 9.956 | 87.434 | 325.91 | 0.926 |
| 10 | 28 | 6 | 157.992 | 4.721 | 224.121 | 234.29 | 0.979 |
| 10 | 28 | 8 | 137.443 | 5.292 | 240.839 | 334.86 | 0.958 |
| 10 | 28 | 10 | 92.687 | 8.954 | 132.983 | 110.56 | 0.937 |
| 10 | 28 | 12 | 101.057 | 8.391 | 104.500 | 262.50 | 0.568 |
| 10 | 28 | 14 | 57.682 | 12.835 | 51.860 | 359.98 | 0.792 |
| 10 | 28 | 16 | 68.356 | 11.792 | 74.432 | 315.86 | 0.932 |
| 10 | 28 | 18 | 62.281 | 14.330 | 63.761 | 157.48 | 0.891 |
| 10 | 28 | 20 | 69.032 | 15.046 | 69.145 | 83.25 | 0.917 |
| 10 | 28 | 22 | 39.200 | 12.683 | 18.237 | 254.37 | 0.751 |
| 10 | 28 | 24 | 63.295 | 15.971 | 35.854 | 152.97 | 0.921 |
| 10 | 29 | 1 | 193.288 | 5.248 | 318.355 | 301.94 | 0.985 |
| 10 | 29 | 3 | 54.572 | 11.856 | 55.126 | 12.54 | 0.691 |
| 10 | 29 | 5 | 45.613 | 11.023 | 26.655 | 290.56 | 0.648 |
| 10 | 29 | 7 | 56.036 | 10.103 | 27.384 | 325.04 | 0.294 |
| 10 | 29 | 9 | 114.674 | 6.063 | 150.716 | 69.23 | 0.965 |
| 10 | 29 | 11 | 47.674 | 12.139 | 27.472 | 21.74 | 0.725 |

| | | | | | | | |
|---|---|---|---|---|---|---|---|
| 10 | 29 | 13 | 76.098  | 12.626 | 75.681  | 73.15  | 0.951 |
| 10 | 29 | 15 | 54.325  | 16.142 | 26.577  | 81.83  | 0.900 |
| 10 | 29 | 17 | 57.827  | 14.764 | 65.520  | 119.49 | 0.740 |
| 10 | 29 | 19 | 55.690  | 13.636 | 62.800  | 124.54 | 0.804 |
| 10 | 29 | 21 | 37.566  | 12.294 | 17.068  | 53.15  | 0.472 |
| 10 | 30 | 0  | 82.565  | 18.743 | 111.019 | 180.00 | 1.000 |
| 10 | 30 | 2  | 75.939  | 11.333 | 112.060 | 139.69 | 0.765 |
| 10 | 30 | 4  | 50.235  | 12.506 | 9.175   | 353.86 | 0.143 |
| 10 | 30 | 6  | 213.403 | 4.410  | 312.082 | 254.82 | 0.990 |
| 10 | 30 | 8  | 124.631 | 7.249  | 194.737 | 280.64 | 0.977 |
| 10 | 30 | 10 | 56.086  | 13.562 | 41.944  | 99.65  | 0.908 |
| 10 | 30 | 12 | 73.846  | 16.121 | 98.856  | 219.08 | 0.890 |
| 10 | 30 | 14 | 58.267  | 17.339 | 46.848  | 324.62 | 0.877 |
| 10 | 30 | 16 | 38.702  | 12.411 | 20.262  | 329.99 | 0.666 |
| 10 | 30 | 18 | 37.633  | 12.324 | 6.020   | 128.77 | 0.120 |
| 10 | 31 | 1  | 56.266  | 11.423 | 67.549  | 119.59 | 0.873 |
| 10 | 31 | 3  | 42.134  | 12.752 | 22.125  | 139.09 | 0.821 |
| 10 | 31 | 5  | 79.632  | 14.675 | 109.611 | 264.73 | 0.929 |
| 10 | 31 | 7  | 45.309  | 12.491 | 9.298   | 191.21 | 0.893 |
| 10 | 31 | 9  | 50.418  | 11.997 | 45.593  | 270.82 | 0.853 |
| 10 | 31 | 11 | 44.331  | 12.060 | 39.903  | 331.81 | 0.584 |
| 10 | 31 | 13 | 34.971  | 11.641 | 12.268  | 293.18 | 0.689 |
| 10 | 31 | 15 | 74.633  | 16.015 | 88.537  | 336.75 | 0.907 |
| 10 | 32 | 0  | 36.977  | 25.031 | 22.492  | 0.00   | 0.539 |
| 10 | 32 | 2  | 35.812  | 11.165 | 14.031  | 26.93  | 0.426 |
| 10 | 32 | 4  | 42.424  | 12.014 | 23.400  | 299.07 | 0.374 |
| 10 | 32 | 6  | 37.758  | 12.492 | 23.935  | 278.10 | 0.633 |
| 10 | 32 | 8  | 35.162  | 11.133 | 14.293  | 153.91 | 0.520 |
| 10 | 32 | 10 | 48.585  | 14.029 | 21.880  | 88.68  | 0.879 |
| 10 | 32 | 12 | 44.130  | 12.604 | 36.497  | 166.78 | 0.762 |
| 10 | 33 | 1  | 48.606  | 12.741 | 48.660  | 196.25 | 0.812 |
| 10 | 33 | 3  | 40.339  | 11.840 | 20.843  | 254.81 | 0.381 |
| 10 | 33 | 5  | 32.830  | 10.742 | 14.185  | 330.32 | 0.533 |
| 10 | 33 | 7  | 44.173  | 12.807 | 22.234  | 314.20 | 0.846 |
| 11 | 0  | 1  | 39.688  | 6.254  | 41.449  | 180.00 | 0.733 |
| 11 | 0  | 3  | 64.287  | 3.023  | 68.515  | 0.00   | 0.746 |
| 11 | 0  | 5  | 45.301  | 4.257  | 21.495  | 0.00   | 0.333 |
| 11 | 0  | 7  | 99.332  | 2.565  | 141.488 | 180.00 | 1.000 |
| 11 | 0  | 9  | 15.596  | 7.206  | 11.781  | 0.00   | 0.531 |
| 11 | 0  | 11 | 483.911 | 5.584  | 686.403 | 0.00   | 1.000 |
| 11 | 0  | 13 | 208.941 | 3.187  | 295.517 | 180.00 | 1.000 |
| 11 | 0  | 15 | 336.903 | 4.392  | 474.767 | 180.00 | 1.000 |
| 11 | 0  | 17 | 409.986 | 5.316  | 575.290 | 0.00   | 1.000 |
| 11 | 0  | 19 | 192.996 | 3.919  | 269.580 | 0.00   | 1.000 |
| 11 | 0  | 21 | 112.921 | 6.222  | 156.419 | 180.00 | 0.997 |
| 11 | 0  | 23 | 231.889 | 4.538  | 320.395 | 0.00   | 1.000 |
| 11 | 0  | 25 | 507.738 | 6.069  | 697.006 | 0.00   | 1.000 |
| 11 | 0  | 27 | 44.920  | 16.272 | 42.912  | 180.00 | 0.703 |
| 11 | 0  | 29 | 50.661  | 17.171 | 37.181  | 180.00 | 0.545 |
| 11 | 0  | 31 | 92.727  | 16.342 | 123.476 | 0.00   | 0.998 |
| 11 | 0  | 33 | 77.388  | 16.680 | 94.147  | 180.00 | 0.924 |
| 11 | 0  | 35 | 224.938 | 6.402  | 296.396 | 180.00 | 1.000 |
| 11 | 0  | 37 | 90.436  | 12.809 | 116.519 | 0.00   | 1.000 |
| 11 | 0  | 39 | 40.556  | 16.092 | 48.913  | 0.00   | 0.967 |
| 11 | 0  | 41 | 31.258  | 15.323 | 33.770  | 180.00 | 0.891 |
| 11 | 1  | 0  | 123.690 | 2.723  | 16.558  | 0.00   | 0.094 |
| 11 | 1  | 2  | 179.306 | 2.628  | 242.264 | 189.88 | 0.943 |
| 11 | 1  | 4  | 154.429 | 1.681  | 223.757 | 283.06 | 0.994 |
| 11 | 1  | 6  | 158.948 | 1.714  | 286.855 | 181.57 | 0.923 |
| 11 | 1  | 8  | 268.966 | 2.255  | 406.375 | 93.59  | 0.992 |
| 11 | 1  | 10 | 244.418 | 2.218  | 351.184 | 357.44 | 0.980 |
| 11 | 1  | 12 | 187.456 | 2.196  | 297.212 | 83.10  | 0.962 |
| 11 | 1  | 14 | 324.666 | 2.827  | 480.808 | 219.57 | 0.988 |
| 11 | 1  | 16 | 142.922 | 2.683  | 182.027 | 279.65 | 0.984 |
| 11 | 1  | 18 | 202.582 | 2.435  | 332.482 | 45.18  | 0.958 |
| 11 | 1  | 20 | 173.898 | 2.952  | 238.020 | 332.01 | 0.968 |
| 11 | 1  | 22 | 91.307  | 4.814  | 101.209 | 111.88 | 0.943 |
| 11 | 1  | 24 | 261.935 | 2.986  | 348.193 | 226.82 | 0.986 |
| 11 | 1  | 26 | 277.663 | 3.273  | 378.997 | 359.46 | 0.985 |
| 11 | 1  | 28 | 223.563 | 3.579  | 282.659 | 336.97 | 0.979 |
| 11 | 1  | 30 | 207.230 | 4.205  | 261.228 | 57.20  | 0.983 |
| 11 | 1  | 32 | 120.025 | 7.435  | 130.234 | 95.01  | 0.965 |
| 11 | 1  | 34 | 48.295  | 13.581 | 8.227   | 121.67 | 0.131 |
| 11 | 1  | 36 | 130.486 | 5.986  | 178.855 | 233.64 | 0.959 |
| 11 | 1  | 38 | 38.914  | 10.871 | 5.039   | 144.69 | 0.234 |
| 11 | 1  | 40 | 76.905  | 11.105 | 60.688  | 230.66 | 0.951 |
| 11 | 1  | 42 | 39.094  | 12.775 | 15.261  | 329.18 | 0.682 |

| | | | | | | | |
|---|---|---|---|---|---|---|---|
| 11 | 2 | 1 | 234.734 | 3.040 | 328.448 | 94.86 | 0.980 |
| 11 | 2 | 3 | 181.329 | 2.020 | 197.161 | 267.48 | 0.979 |
| 11 | 2 | 5 | 262.401 | 2.335 | 313.269 | 219.83 | 0.988 |
| 11 | 2 | 7 | 398.970 | 3.550 | 609.539 | 26.35 | 0.993 |
| 11 | 2 | 9 | 147.878 | 1.945 | 183.075 | 318.74 | 0.959 |
| 11 | 2 | 11 | 308.028 | 2.689 | 439.396 | 186.51 | 0.988 |
| 11 | 2 | 13 | 407.307 | 3.792 | 555.383 | 311.62 | 0.993 |
| 11 | 2 | 15 | 280.487 | 2.715 | 387.860 | 241.70 | 0.984 |
| 11 | 2 | 17 | 229.848 | 2.821 | 273.588 | 154.71 | 0.979 |
| 11 | 2 | 19 | 247.368 | 2.737 | 267.386 | 339.14 | 0.987 |
| 11 | 2 | 21 | 144.779 | 2.841 | 249.260 | 161.02 | 0.879 |
| 11 | 2 | 23 | 48.924 | 8.843 | 14.599 | 164.33 | 0.305 |
| 11 | 2 | 25 | 89.715 | 5.280 | 112.012 | 260.86 | 0.754 |
| 11 | 2 | 27 | 333.136 | 3.506 | 447.636 | 309.81 | 0.990 |
| 11 | 2 | 29 | 243.804 | 3.777 | 347.894 | 304.88 | 0.986 |
| 11 | 2 | 31 | 236.989 | 3.912 | 281.218 | 262.71 | 0.987 |
| 11 | 2 | 33 | 124.272 | 6.178 | 234.107 | 162.82 | 0.887 |
| 11 | 2 | 35 | 120.658 | 7.144 | 161.750 | 79.26 | 0.954 |
| 11 | 2 | 37 | 66.032 | 13.154 | 67.670 | 2.39 | 0.828 |
| 11 | 2 | 39 | 75.430 | 11.706 | 78.667 | 174.09 | 0.935 |
| 11 | 2 | 41 | 38.040 | 12.358 | 12.562 | 237.52 | 0.719 |
| 11 | 3 | 0 | 113.900 | 3.189 | 162.851 | 180.00 | 1.000 |
| 11 | 3 | 2 | 171.187 | 1.972 | 276.478 | 19.49 | 0.950 |
| 11 | 3 | 4 | 255.058 | 2.866 | 337.352 | 136.59 | 0.988 |
| 11 | 3 | 6 | 372.229 | 3.693 | 501.620 | 82.87 | 0.993 |
| 11 | 3 | 8 | 226.534 | 2.091 | 307.521 | 220.79 | 0.989 |
| 11 | 3 | 10 | 176.474 | 2.020 | 237.894 | 295.27 | 0.990 |
| 11 | 3 | 12 | 350.731 | 3.079 | 503.664 | 57.70 | 0.991 |
| 11 | 3 | 14 | 229.790 | 2.731 | 303.236 | 69.75 | 0.987 |
| 11 | 3 | 16 | 380.963 | 3.433 | 556.535 | 192.10 | 0.990 |
| 11 | 3 | 18 | 247.867 | 2.688 | 334.590 | 227.43 | 0.985 |
| 11 | 3 | 20 | 375.387 | 3.629 | 595.455 | 64.19 | 0.992 |
| 11 | 3 | 22 | 48.464 | 9.627 | 31.490 | 207.64 | 0.620 |
| 11 | 3 | 24 | 106.807 | 4.637 | 152.687 | 2.31 | 0.729 |
| 11 | 3 | 26 | 33.514 | 9.431 | 24.323 | 174.43 | 0.129 |
| 11 | 3 | 28 | 152.586 | 4.018 | 213.999 | 184.76 | 0.919 |
| 11 | 3 | 30 | 241.158 | 3.787 | 333.016 | 178.50 | 0.986 |
| 11 | 3 | 32 | 90.112 | 7.800 | 81.828 | 110.02 | 0.938 |
| 11 | 3 | 34 | 107.168 | 8.317 | 122.258 | 166.08 | 0.947 |
| 11 | 3 | 36 | 99.804 | 10.674 | 138.642 | 202.92 | 0.915 |
| 11 | 3 | 38 | 66.427 | 11.709 | 75.035 | 113.88 | 0.782 |
| 11 | 3 | 40 | 47.676 | 12.768 | 30.609 | 5.55 | 0.494 |
| 11 | 3 | 42 | 50.785 | 13.851 | 39.012 | 300.29 | 0.741 |
| 11 | 4 | 1 | 315.578 | 4.580 | 490.514 | 192.41 | 0.988 |
| 11 | 4 | 3 | 101.505 | 2.121 | 107.597 | 44.69 | 0.973 |
| 11 | 4 | 5 | 325.352 | 2.750 | 520.377 | 115.60 | 0.988 |
| 11 | 4 | 7 | 292.921 | 2.468 | 376.680 | 144.09 | 0.990 |
| 11 | 4 | 9 | 382.205 | 3.087 | 562.913 | 281.14 | 0.993 |
| 11 | 4 | 11 | 284.831 | 2.534 | 403.298 | 12.76 | 0.987 |
| 11 | 4 | 13 | 200.832 | 2.471 | 286.053 | 294.43 | 0.970 |
| 11 | 4 | 15 | 394.663 | 3.464 | 593.831 | 268.47 | 0.992 |
| 11 | 4 | 17 | 170.840 | 2.859 | 307.427 | 251.51 | 0.914 |
| 11 | 4 | 19 | 303.253 | 2.942 | 429.469 | 308.01 | 0.990 |
| 11 | 4 | 21 | 388.031 | 3.490 | 535.194 | 79.16 | 0.994 |
| 11 | 4 | 23 | 290.212 | 3.201 | 358.899 | 97.93 | 0.989 |
| 11 | 4 | 25 | 145.933 | 3.530 | 148.542 | 186.09 | 0.960 |
| 11 | 4 | 27 | 102.997 | 6.507 | 104.808 | 126.69 | 0.893 |
| 11 | 4 | 29 | 241.375 | 3.819 | 294.773 | 140.20 | 0.987 |
| 11 | 4 | 31 | 135.684 | 5.081 | 183.260 | 119.27 | 0.951 |
| 11 | 4 | 33 | 109.439 | 6.679 | 109.383 | 117.38 | 0.957 |
| 11 | 4 | 35 | 175.645 | 4.958 | 266.150 | 251.66 | 0.976 |
| 11 | 4 | 37 | 51.571 | 12.266 | 35.654 | 181.05 | 0.585 |
| 11 | 4 | 39 | 65.821 | 13.121 | 71.026 | 211.64 | 0.898 |
| 11 | 4 | 41 | 49.275 | 13.621 | 24.347 | 15.59 | 0.334 |
| 11 | 5 | 0 | 54.843 | 5.142 | 10.514 | 0.00 | 0.134 |
| 11 | 5 | 2 | 112.837 | 2.053 | 163.603 | 188.59 | 0.958 |
| 11 | 5 | 4 | 237.601 | 2.247 | 379.956 | 325.63 | 0.987 |
| 11 | 5 | 6 | 208.029 | 2.191 | 294.858 | 336.12 | 0.975 |
| 11 | 5 | 8 | 335.407 | 2.839 | 448.955 | 102.91 | 0.993 |
| 11 | 5 | 10 | 172.667 | 2.097 | 282.566 | 35.23 | 0.953 |
| 11 | 5 | 12 | 500.689 | 4.049 | 692.376 | 14.53 | 0.995 |
| 11 | 5 | 14 | 157.321 | 2.420 | 230.560 | 234.71 | 0.968 |
| 11 | 5 | 16 | 350.114 | 3.122 | 464.784 | 252.11 | 0.992 |
| 11 | 5 | 18 | 571.375 | 4.694 | 829.551 | 35.94 | 0.997 |
| 11 | 5 | 20 | 293.026 | 2.961 | 434.116 | 32.95 | 0.988 |
| 11 | 5 | 22 | 121.319 | 3.466 | 149.856 | 134.86 | 0.959 |
| 11 | 5 | 24 | 197.033 | 3.084 | 311.493 | 111.74 | 0.967 |

| | | | | | | | |
|---|---|---|---|---|---|---|---|
| 11 | 5 | 26 | 300.643 | 3.264 | 410.450 | 338.32 | 0.987 |
| 11 | 5 | 28 | 125.647 | 4.758 | 136.132 | 259.67 | 0.940 |
| 11 | 5 | 30 | 337.202 | 4.011 | 472.448 | 250.95 | 0.993 |
| 11 | 5 | 32 | 32.644 | 10.326 | 39.232 | 112.88 | 0.664 |
| 11 | 5 | 34 | 68.133 | 9.374 | 44.902 | 136.29 | 0.928 |
| 11 | 5 | 36 | 44.657 | 12.642 | 11.101 | 45.37 | 0.572 |
| 11 | 5 | 38 | 58.013 | 13.151 | 33.271 | 12.30 | 0.823 |
| 11 | 5 | 40 | 53.402 | 13.142 | 44.861 | 37.91 | 0.831 |
| 11 | 5 | 42 | 84.225 | 16.662 | 100.327 | 315.62 | 0.680 |
| 11 | 6 | 1 | 249.895 | 2.650 | 362.601 | 57.61 | 0.985 |
| 11 | 6 | 3 | 213.686 | 2.195 | 264.304 | 342.07 | 0.982 |
| 11 | 6 | 5 | 312.423 | 2.816 | 431.147 | 20.96 | 0.989 |
| 11 | 6 | 7 | 56.413 | 4.217 | 19.852 | 179.15 | 0.888 |
| 11 | 6 | 9 | 272.163 | 2.685 | 460.818 | 55.88 | 0.985 |
| 11 | 6 | 11 | 307.742 | 2.719 | 476.053 | 92.85 | 0.987 |
| 11 | 6 | 13 | 456.999 | 3.825 | 719.109 | 92.54 | 0.993 |
| 11 | 6 | 15 | 155.226 | 2.355 | 191.136 | 255.25 | 0.977 |
| 11 | 6 | 17 | 134.930 | 3.349 | 203.037 | 173.30 | 0.914 |
| 11 | 6 | 19 | 315.832 | 2.945 | 478.564 | 86.64 | 0.989 |
| 11 | 6 | 21 | 436.567 | 3.778 | 606.970 | 38.58 | 0.995 |
| 11 | 6 | 23 | 238.648 | 2.819 | 311.228 | 155.03 | 0.983 |
| 11 | 6 | 25 | 209.298 | 3.428 | 282.157 | 335.29 | 0.975 |
| 11 | 6 | 27 | 129.122 | 6.054 | 191.209 | 154.14 | 0.903 |
| 11 | 6 | 29 | 132.004 | 5.541 | 97.907 | 263.23 | 0.969 |
| 11 | 6 | 31 | 142.003 | 5.757 | 210.092 | 90.52 | 0.965 |
| 11 | 6 | 33 | 179.511 | 4.879 | 211.935 | 175.03 | 0.983 |
| 11 | 6 | 35 | 47.096 | 12.933 | 9.413 | 164.13 | 0.144 |
| 11 | 6 | 37 | 99.719 | 8.868 | 166.190 | 11.91 | 0.825 |
| 11 | 6 | 39 | 64.266 | 12.487 | 57.712 | 89.31 | 0.907 |
| 11 | 6 | 41 | 89.203 | 12.734 | 59.822 | 6.56 | 0.966 |
| 11 | 7 | 0 | 76.784 | 3.918 | 106.980 | 0.00 | 0.975 |
| 11 | 7 | 2 | 178.001 | 2.569 | 207.697 | 200.14 | 0.701 |
| 11 | 7 | 4 | 128.423 | 2.108 | 132.862 | 176.99 | 0.967 |
| 11 | 7 | 6 | 227.902 | 2.333 | 305.523 | 27.43 | 0.980 |
| 11 | 7 | 8 | 83.252 | 3.325 | 84.730 | 228.47 | 0.925 |
| 11 | 7 | 10 | 162.892 | 2.469 | 202.247 | 131.81 | 0.973 |
| 11 | 7 | 12 | 146.308 | 2.508 | 215.116 | 327.62 | 0.922 |
| 11 | 7 | 14 | 196.429 | 2.437 | 249.365 | 53.61 | 0.981 |
| 11 | 7 | 16 | 320.443 | 2.927 | 439.982 | 316.91 | 0.992 |
| 11 | 7 | 18 | 68.414 | 5.684 | 7.614 | 239.43 | 0.881 |
| 11 | 7 | 20 | 189.883 | 2.777 | 366.908 | 96.75 | 0.944 |
| 11 | 7 | 22 | 347.344 | 3.629 | 465.155 | 91.68 | 0.992 |
| 11 | 7 | 24 | 65.042 | 7.639 | 25.458 | 357.37 | 0.796 |
| 11 | 7 | 26 | 88.431 | 5.324 | 93.204 | 101.95 | 0.861 |
| 11 | 7 | 28 | 53.573 | 10.780 | 31.666 | 142.41 | 0.607 |
| 11 | 7 | 30 | 282.129 | 3.594 | 418.301 | 168.09 | 0.989 |
| 11 | 7 | 32 | 215.553 | 4.234 | 282.232 | 84.93 | 0.988 |
| 11 | 7 | 34 | 62.433 | 10.129 | 58.727 | 301.36 | 0.844 |
| 11 | 7 | 36 | 32.739 | 10.279 | 2.491 | 15.90 | 0.255 |
| 11 | 7 | 38 | 55.474 | 10.834 | 59.571 | 176.11 | 0.847 |
| 11 | 7 | 40 | 47.234 | 12.514 | 37.389 | 35.16 | 0.739 |
| 11 | 7 | 42 | 33.508 | 11.505 | 5.152 | 142.43 | 0.197 |
| 11 | 8 | 1 | 41.179 | 4.992 | 68.575 | 71.28 | 0.850 |
| 11 | 8 | 3 | 349.018 | 3.424 | 513.848 | 135.23 | 0.992 |
| 11 | 8 | 5 | 107.437 | 1.945 | 145.421 | 168.37 | 0.961 |
| 11 | 8 | 7 | 249.626 | 2.313 | 344.415 | 127.79 | 0.986 |
| 11 | 8 | 9 | 341.807 | 3.400 | 476.629 | 267.19 | 0.992 |
| 11 | 8 | 11 | 349.884 | 3.122 | 478.970 | 51.69 | 0.991 |
| 11 | 8 | 13 | 61.276 | 5.795 | 31.154 | 188.30 | 0.444 |
| 11 | 8 | 15 | 138.666 | 3.070 | 182.425 | 84.64 | 0.974 |
| 11 | 8 | 17 | 113.505 | 3.229 | 145.232 | 149.14 | 0.948 |
| 11 | 8 | 19 | 120.399 | 4.046 | 168.546 | 160.96 | 0.924 |
| 11 | 8 | 21 | 104.159 | 4.557 | 117.949 | 299.44 | 0.942 |
| 11 | 8 | 23 | 161.798 | 3.420 | 203.224 | 181.82 | 0.964 |
| 11 | 8 | 25 | 272.324 | 3.215 | 377.567 | 164.14 | 0.984 |
| 11 | 8 | 27 | 63.683 | 9.596 | 35.016 | 14.03 | 0.406 |
| 11 | 8 | 29 | 74.797 | 9.598 | 33.334 | 46.64 | 0.894 |
| 11 | 8 | 31 | 146.366 | 5.887 | 175.519 | 336.23 | 0.975 |
| 11 | 8 | 33 | 82.924 | 9.198 | 89.607 | 52.57 | 0.913 |
| 11 | 8 | 35 | 216.266 | 3.923 | 346.398 | 320.74 | 0.981 |
| 11 | 8 | 37 | 60.219 | 10.034 | 39.719 | 72.62 | 0.859 |
| 11 | 8 | 39 | 103.592 | 8.819 | 165.037 | 18.01 | 0.944 |
| 11 | 8 | 41 | 72.621 | 17.606 | 64.586 | 133.34 | 0.904 |
| 11 | 9 | 0 | 35.736 | 11.996 | 31.033 | 180.00 | 0.611 |
| 11 | 9 | 2 | 216.759 | 3.385 | 345.408 | 220.40 | 0.974 |
| 11 | 9 | 4 | 265.970 | 2.841 | 370.025 | 348.31 | 0.987 |
| 11 | 9 | 6 | 298.197 | 2.589 | 406.809 | 256.65 | 0.987 |

| | | | | | | | |
|---|---|---|---|---|---|---|---|
| 11 | 9 | 8 | 208.001 | 2.536 | 324.038 | 23.29 | 0.971 |
| 11 | 9 | 10 | 202.446 | 2.664 | 248.265 | 100.56 | 0.978 |
| 11 | 9 | 12 | 221.067 | 2.777 | 318.490 | 67.91 | 0.973 |
| 11 | 9 | 14 | 277.743 | 2.774 | 382.020 | 173.90 | 0.984 |
| 11 | 9 | 16 | 120.163 | 2.937 | 192.986 | 69.64 | 0.906 |
| 11 | 9 | 18 | 395.789 | 3.392 | 448.918 | 12.39 | 0.995 |
| 11 | 9 | 20 | 292.124 | 2.998 | 517.070 | 178.77 | 0.983 |
| 11 | 9 | 22 | 134.803 | 3.460 | 145.559 | 109.10 | 0.957 |
| 11 | 9 | 24 | 50.501 | 10.447 | 13.022 | 39.76 | 0.659 |
| 11 | 9 | 26 | 173.603 | 3.937 | 179.085 | 147.62 | 0.972 |
| 11 | 9 | 28 | 149.627 | 4.497 | 223.345 | 218.90 | 0.958 |
| 11 | 9 | 30 | 144.894 | 5.198 | 204.373 | 325.90 | 0.969 |
| 11 | 9 | 32 | 371.188 | 4.142 | 565.527 | 315.70 | 0.995 |
| 11 | 9 | 34 | 202.250 | 4.585 | 256.827 | 314.74 | 0.986 |
| 11 | 9 | 36 | 63.636 | 11.534 | 61.276 | 113.57 | 0.833 |
| 11 | 9 | 38 | 38.290 | 11.276 | 17.888 | 124.04 | 0.553 |
| 11 | 9 | 40 | 32.223 | 10.639 | 4.292 | 203.95 | 0.708 |
| 11 | 10 | 1 | 278.900 | 2.618 | 395.934 | 194.10 | 0.985 |
| 11 | 10 | 3 | 129.435 | 2.624 | 187.050 | 136.46 | 0.973 |
| 11 | 10 | 5 | 250.181 | 2.498 | 382.462 | 241.04 | 0.983 |
| 11 | 10 | 7 | 218.052 | 2.215 | 328.054 | 240.99 | 0.976 |
| 11 | 10 | 9 | 203.426 | 2.632 | 273.249 | 177.06 | 0.843 |
| 11 | 10 | 11 | 268.729 | 2.853 | 364.948 | 100.41 | 0.987 |
| 11 | 10 | 13 | 222.840 | 2.510 | 319.370 | 107.54 | 0.982 |
| 11 | 10 | 15 | 339.604 | 3.197 | 390.383 | 110.39 | 0.994 |
| 11 | 10 | 17 | 263.217 | 2.719 | 323.563 | 319.53 | 0.989 |
| 11 | 10 | 19 | 44.366 | 9.098 | 5.438 | 256.64 | 0.451 |
| 11 | 10 | 21 | 383.489 | 3.491 | 571.445 | 88.87 | 0.993 |
| 11 | 10 | 23 | 248.364 | 3.114 | 354.192 | 18.00 | 0.982 |
| 11 | 10 | 25 | 176.116 | 4.332 | 229.496 | 77.86 | 0.964 |
| 11 | 10 | 27 | 220.575 | 3.609 | 275.234 | 253.62 | 0.987 |
| 11 | 10 | 29 | 159.127 | 4.663 | 224.909 | 2.97 | 0.974 |
| 11 | 10 | 31 | 41.113 | 11.413 | 0.588 | 63.93 | 0.633 |
| 11 | 10 | 33 | 59.616 | 11.333 | 54.462 | 216.02 | 0.745 |
| 11 | 10 | 35 | 91.655 | 9.399 | 132.001 | 171.71 | 0.745 |
| 11 | 10 | 37 | 71.127 | 12.451 | 85.519 | 147.18 | 0.909 |
| 11 | 10 | 39 | 44.775 | 12.252 | 33.877 | 296.69 | 0.750 |
| 11 | 11 | 0 | 130.666 | 4.016 | 186.627 | 180.00 | 1.000 |
| 11 | 11 | 2 | 189.434 | 2.509 | 282.578 | 80.36 | 0.965 |
| 11 | 11 | 4 | 253.428 | 3.864 | 395.106 | 128.18 | 0.978 |
| 11 | 11 | 6 | 156.927 | 2.231 | 253.295 | 321.50 | 0.934 |
| 11 | 11 | 8 | 245.101 | 2.403 | 286.668 | 261.29 | 0.983 |
| 11 | 11 | 10 | 313.022 | 2.908 | 430.580 | 228.45 | 0.988 |
| 11 | 11 | 12 | 242.812 | 2.928 | 385.066 | 163.08 | 0.982 |
| 11 | 11 | 14 | 167.396 | 2.661 | 151.143 | 209.31 | 0.975 |
| 11 | 11 | 16 | 449.738 | 4.351 | 624.784 | 220.61 | 0.995 |
| 11 | 11 | 18 | 164.158 | 2.840 | 184.123 | 269.04 | 0.970 |
| 11 | 11 | 20 | 287.680 | 2.964 | 399.490 | 231.55 | 0.988 |
| 11 | 11 | 22 | 161.184 | 4.043 | 216.113 | 245.19 | 0.956 |
| 11 | 11 | 24 | 34.800 | 9.983 | 32.779 | 265.73 | 0.320 |
| 11 | 11 | 26 | 176.351 | 3.644 | 236.405 | 152.85 | 0.975 |
| 11 | 11 | 28 | 123.313 | 5.497 | 127.797 | 85.12 | 0.955 |
| 11 | 11 | 30 | 190.023 | 4.507 | 291.421 | 152.93 | 0.981 |
| 11 | 11 | 32 | 36.335 | 11.174 | 5.964 | 24.28 | 0.520 |
| 11 | 11 | 34 | 36.055 | 10.499 | 10.952 | 185.38 | 0.683 |
| 11 | 11 | 36 | 116.558 | 7.514 | 159.123 | 98.60 | 0.954 |
| 11 | 11 | 38 | 37.837 | 11.167 | 16.591 | 274.42 | 0.564 |
| 11 | 11 | 40 | 40.949 | 13.742 | 9.278 | 61.29 | 0.846 |
| 11 | 12 | 1 | 487.642 | 3.880 | 750.915 | 243.18 | 0.994 |
| 11 | 12 | 3 | 131.310 | 4.007 | 163.624 | 319.64 | 0.933 |
| 11 | 12 | 5 | 359.968 | 3.907 | 497.875 | 54.67 | 0.991 |
| 11 | 12 | 7 | 401.538 | 3.743 | 550.668 | 276.37 | 0.993 |
| 11 | 12 | 9 | 561.334 | 4.407 | 814.634 | 18.14 | 0.996 |
| 11 | 12 | 11 | 179.942 | 2.423 | 235.068 | 164.94 | 0.970 |
| 11 | 12 | 13 | 246.646 | 3.016 | 343.678 | 185.11 | 0.985 |
| 11 | 12 | 15 | 517.187 | 4.839 | 744.999 | 283.46 | 0.997 |
| 11 | 12 | 17 | 173.033 | 3.014 | 263.973 | 312.80 | 0.958 |
| 11 | 12 | 19 | 157.282 | 3.564 | 158.866 | 263.69 | 0.970 |
| 11 | 12 | 21 | 386.901 | 3.563 | 512.453 | 283.46 | 0.994 |
| 11 | 12 | 23 | 168.724 | 3.971 | 263.836 | 173.39 | 0.929 |
| 11 | 12 | 25 | 182.579 | 3.780 | 289.490 | 247.87 | 0.971 |
| 11 | 12 | 27 | 127.518 | 5.240 | 140.884 | 173.87 | 0.961 |
| 11 | 12 | 29 | 36.783 | 11.024 | 3.287 | 173.14 | 0.487 |
| 11 | 12 | 31 | 87.781 | 7.251 | 136.150 | 71.13 | 0.789 |
| 11 | 12 | 33 | 59.299 | 11.269 | 41.552 | 248.69 | 0.856 |
| 11 | 12 | 35 | 54.387 | 11.760 | 45.278 | 230.48 | 0.738 |
| 11 | 12 | 37 | 65.289 | 12.954 | 70.261 | 196.50 | 0.577 |

| | | | | | | | |
|---|---|---|---|---|---|---|---|
| 11 | 12 | 39 | 66.518 | 13.996 | 69.355 | 359.70 | 0.883 |
| 11 | 13 | 0 | 252.859 | 3.406 | 361.114 | 0.00 | 1.000 |
| 11 | 13 | 2 | 122.517 | 2.855 | 153.526 | 289.73 | 0.908 |
| 11 | 13 | 4 | 423.688 | 4.488 | 674.997 | 66.19 | 0.992 |
| 11 | 13 | 6 | 280.983 | 2.743 | 412.601 | 86.88 | 0.983 |
| 11 | 13 | 8 | 299.627 | 2.978 | 417.852 | 5.18 | 0.990 |
| 11 | 13 | 10 | 239.085 | 2.481 | 339.322 | 236.15 | 0.984 |
| 11 | 13 | 12 | 624.237 | 5.351 | 852.147 | 109.45 | 0.998 |
| 11 | 13 | 14 | 289.070 | 3.268 | 463.058 | 130.34 | 0.987 |
| 11 | 13 | 16 | 217.734 | 3.154 | 270.138 | 316.52 | 0.982 |
| 11 | 13 | 18 | 246.903 | 2.817 | 402.256 | 335.98 | 0.980 |
| 11 | 13 | 20 | 261.928 | 3.271 | 375.712 | 275.52 | 0.983 |
| 11 | 13 | 22 | 67.609 | 8.599 | 48.846 | 130.42 | 0.611 |
| 11 | 13 | 24 | 138.955 | 4.502 | 199.924 | 95.28 | 0.953 |
| 11 | 13 | 26 | 255.962 | 3.561 | 301.571 | 15.44 | 0.990 |
| 11 | 13 | 28 | 72.760 | 10.094 | 8.554 | 113.77 | 0.943 |
| 11 | 13 | 30 | 112.633 | 8.361 | 115.898 | 279.09 | 0.961 |
| 11 | 13 | 32 | 156.472 | 5.649 | 224.691 | 332.11 | 0.973 |
| 11 | 13 | 34 | 42.512 | 11.963 | 13.692 | 129.59 | 0.460 |
| 11 | 13 | 36 | 42.839 | 11.522 | 29.278 | 8.93 | 0.630 |
| 11 | 13 | 38 | 51.433 | 15.623 | 16.939 | 146.67 | 0.883 |
| 11 | 14 | 1 | 290.577 | 2.839 | 480.893 | 353.39 | 0.979 |
| 11 | 14 | 3 | 356.541 | 3.268 | 510.605 | 56.73 | 0.994 |
| 11 | 14 | 5 | 176.187 | 4.128 | 199.474 | 86.49 | 0.977 |
| 11 | 14 | 7 | 305.027 | 2.868 | 478.853 | 63.97 | 0.989 |
| 11 | 14 | 9 | 260.137 | 2.832 | 367.579 | 258.08 | 0.990 |
| 11 | 14 | 11 | 223.916 | 2.856 | 319.534 | 54.44 | 0.980 |
| 11 | 14 | 13 | 609.759 | 5.229 | 880.258 | 139.38 | 0.997 |
| 11 | 14 | 15 | 455.102 | 4.493 | 662.153 | 313.39 | 0.995 |
| 11 | 14 | 17 | 181.005 | 3.210 | 250.124 | 7.91 | 0.972 |
| 11 | 14 | 19 | 70.282 | 6.771 | 52.142 | 151.87 | 0.622 |
| 11 | 14 | 21 | 55.635 | 10.646 | 43.278 | 184.36 | 0.643 |
| 11 | 14 | 23 | 210.531 | 3.576 | 277.049 | 0.41 | 0.982 |
| 11 | 14 | 25 | 42.919 | 10.538 | 1.964 | 356.85 | 0.329 |
| 11 | 14 | 27 | 122.285 | 5.229 | 209.093 | 208.20 | 0.918 |
| 11 | 14 | 29 | 49.377 | 10.679 | 14.334 | 111.91 | 0.241 |
| 11 | 14 | 31 | 113.269 | 6.657 | 143.693 | 294.10 | 0.952 |
| 11 | 14 | 33 | 92.051 | 9.333 | 123.143 | 16.36 | 0.923 |
| 11 | 14 | 35 | 68.304 | 12.563 | 95.135 | 140.84 | 0.820 |
| 11 | 14 | 37 | 75.699 | 15.917 | 101.368 | 291.50 | 0.761 |
| 11 | 15 | 0 | 281.670 | 3.810 | 402.083 | 180.00 | 1.000 |
| 11 | 15 | 2 | 315.231 | 2.938 | 401.234 | 176.37 | 0.992 |
| 11 | 15 | 4 | 218.638 | 4.205 | 269.158 | 156.58 | 0.983 |
| 11 | 15 | 6 | 264.815 | 3.102 | 362.959 | 141.80 | 0.987 |
| 11 | 15 | 8 | 229.954 | 2.610 | 279.681 | 349.84 | 0.984 |
| 11 | 15 | 10 | 267.382 | 2.771 | 375.227 | 14.02 | 0.987 |
| 11 | 15 | 12 | 227.194 | 2.978 | 301.426 | 127.81 | 0.983 |
| 11 | 15 | 14 | 508.834 | 4.408 | 674.797 | 46.27 | 0.997 |
| 11 | 15 | 16 | 269.135 | 3.404 | 412.126 | 48.32 | 0.985 |
| 11 | 15 | 18 | 292.743 | 3.644 | 487.246 | 291.07 | 0.984 |
| 11 | 15 | 20 | 52.342 | 10.116 | 7.746 | 106.97 | 0.341 |
| 11 | 15 | 22 | 208.267 | 3.637 | 287.610 | 231.48 | 0.982 |
| 11 | 15 | 24 | 60.572 | 10.874 | 47.294 | 105.68 | 0.597 |
| 11 | 15 | 26 | 222.804 | 3.820 | 317.194 | 304.85 | 0.988 |
| 11 | 15 | 28 | 54.168 | 11.768 | 36.474 | 104.31 | 0.748 |
| 11 | 15 | 30 | 56.733 | 10.317 | 43.679 | 8.22 | 0.548 |
| 11 | 15 | 32 | 41.643 | 10.732 | 18.968 | 245.59 | 0.826 |
| 11 | 15 | 34 | 34.659 | 10.614 | 7.570 | 161.98 | 0.662 |
| 11 | 15 | 36 | 41.677 | 12.390 | 22.085 | 172.16 | 0.677 |
| 11 | 15 | 38 | 47.765 | 15.539 | 30.589 | 319.79 | 0.643 |
| 11 | 16 | 1 | 108.704 | 4.243 | 144.070 | 49.88 | 0.935 |
| 11 | 16 | 3 | 431.355 | 3.661 | 686.700 | 179.42 | 0.994 |
| 11 | 16 | 5 | 409.385 | 3.952 | 557.633 | 161.39 | 0.995 |
| 11 | 16 | 7 | 69.785 | 6.675 | 23.801 | 202.77 | 0.334 |
| 11 | 16 | 9 | 699.673 | 5.457 | 1037.253 | 303.23 | 0.998 |
| 11 | 16 | 11 | 329.742 | 3.095 | 464.208 | 210.09 | 0.991 |
| 11 | 16 | 13 | 240.974 | 3.139 | 344.271 | 74.92 | 0.984 |
| 11 | 16 | 15 | 308.458 | 3.167 | 418.087 | 72.73 | 0.991 |
| 11 | 16 | 17 | 178.250 | 3.214 | 219.830 | 111.74 | 0.972 |
| 11 | 16 | 19 | 389.814 | 3.979 | 533.199 | 188.54 | 0.993 |
| 11 | 16 | 21 | 283.500 | 3.437 | 434.396 | 207.70 | 0.989 |
| 11 | 16 | 23 | 252.924 | 3.812 | 321.561 | 203.72 | 0.989 |
| 11 | 16 | 25 | 152.904 | 5.773 | 189.746 | 333.46 | 0.977 |
| 11 | 16 | 27 | 149.613 | 4.434 | 239.838 | 75.53 | 0.965 |
| 11 | 16 | 29 | 93.986 | 7.787 | 154.912 | 155.38 | 0.848 |
| 11 | 16 | 31 | 44.154 | 11.005 | 16.836 | 199.91 | 0.450 |
| 11 | 16 | 33 | 35.419 | 11.377 | 3.339 | 297.25 | 0.782 |

| | | | | | | | |
|---|---|---|---|---|---|---|---|
| 11 | 16 | 35 | 37.154 | 11.737 | 15.168 | 273.79 | 0.356 |
| 11 | 16 | 37 | 45.797 | 14.558 | 24.056 | 111.50 | 0.780 |
| 11 | 17 | 0 | 313.964 | 4.149 | 447.958 | 180.00 | 1.000 |
| 11 | 17 | 2 | 155.791 | 3.198 | 204.894 | 111.48 | 0.968 |
| 11 | 17 | 4 | 332.263 | 3.888 | 425.696 | 179.37 | 0.993 |
| 11 | 17 | 6 | 364.662 | 3.989 | 552.268 | 55.49 | 0.993 |
| 11 | 17 | 8 | 548.025 | 4.558 | 898.072 | 4.32 | 0.996 |
| 11 | 17 | 10 | 109.597 | 4.088 | 129.189 | 4.68 | 0.930 |
| 11 | 17 | 12 | 286.368 | 3.015 | 412.038 | 321.16 | 0.988 |
| 11 | 17 | 14 | 235.693 | 3.443 | 406.303 | 246.93 | 0.969 |
| 11 | 17 | 16 | 205.023 | 3.144 | 313.640 | 283.32 | 0.971 |
| 11 | 17 | 18 | 482.661 | 4.253 | 691.272 | 143.14 | 0.995 |
| 11 | 17 | 20 | 183.146 | 3.948 | 216.940 | 256.79 | 0.980 |
| 11 | 17 | 22 | 142.244 | 6.696 | 214.139 | 317.06 | 0.953 |
| 11 | 17 | 24 | 178.019 | 4.224 | 214.280 | 342.13 | 0.984 |
| 11 | 17 | 26 | 179.225 | 4.606 | 216.467 | 157.98 | 0.984 |
| 11 | 17 | 28 | 249.364 | 3.851 | 319.104 | 161.61 | 0.991 |
| 11 | 17 | 30 | 146.463 | 5.423 | 187.188 | 247.04 | 0.977 |
| 11 | 17 | 32 | 106.562 | 7.135 | 124.608 | 312.07 | 0.974 |
| 11 | 17 | 34 | 58.738 | 12.482 | 59.989 | 333.68 | 0.874 |
| 11 | 17 | 36 | 109.884 | 10.108 | 177.590 | 314.93 | 0.951 |
| 11 | 18 | 1 | 204.594 | 3.235 | 235.271 | 336.30 | 0.980 |
| 11 | 18 | 3 | 407.532 | 3.494 | 623.246 | 247.58 | 0.994 |
| 11 | 18 | 5 | 212.985 | 3.568 | 267.085 | 95.77 | 0.982 |
| 11 | 18 | 7 | 542.056 | 5.403 | 807.189 | 8.59 | 0.997 |
| 11 | 18 | 9 | 162.452 | 3.216 | 209.801 | 261.70 | 0.975 |
| 11 | 18 | 11 | 641.425 | 5.318 | 985.927 | 1.71 | 0.997 |
| 11 | 18 | 13 | 77.353 | 6.690 | 45.559 | 130.79 | 0.848 |
| 11 | 18 | 15 | 267.928 | 3.482 | 404.533 | 260.58 | 0.985 |
| 11 | 18 | 17 | 216.146 | 3.495 | 326.816 | 145.24 | 0.974 |
| 11 | 18 | 19 | 217.476 | 3.431 | 281.143 | 20.68 | 0.986 |
| 11 | 18 | 21 | 116.339 | 5.771 | 181.660 | 78.81 | 0.886 |
| 11 | 18 | 23 | 152.784 | 4.841 | 216.820 | 8.60 | 0.975 |
| 11 | 18 | 25 | 148.778 | 4.855 | 178.591 | 231.96 | 0.977 |
| 11 | 18 | 27 | 77.506 | 9.202 | 74.907 | 304.93 | 0.915 |
| 11 | 18 | 29 | 188.510 | 4.857 | 236.751 | 232.59 | 0.987 |
| 11 | 18 | 31 | 99.222 | 6.979 | 145.458 | 18.07 | 0.931 |
| 11 | 18 | 33 | 48.117 | 13.514 | 23.711 | 76.60 | 0.866 |
| 11 | 18 | 35 | 41.491 | 13.686 | 21.340 | 354.95 | 0.603 |
| 11 | 19 | 0 | 297.614 | 4.322 | 424.370 | 0.00 | 1.000 |
| 11 | 19 | 2 | 340.022 | 3.570 | 464.490 | 319.82 | 0.992 |
| 11 | 19 | 4 | 426.348 | 3.778 | 582.009 | 310.82 | 0.995 |
| 11 | 19 | 6 | 373.645 | 5.012 | 504.705 | 290.10 | 0.994 |
| 11 | 19 | 8 | 70.028 | 7.596 | 16.079 | 331.54 | 0.864 |
| 11 | 19 | 10 | 337.048 | 3.248 | 423.829 | 287.46 | 0.992 |
| 11 | 19 | 12 | 220.190 | 3.017 | 395.432 | 324.27 | 0.967 |
| 11 | 19 | 14 | 295.573 | 3.568 | 424.147 | 256.56 | 0.987 |
| 11 | 19 | 16 | 195.454 | 4.330 | 262.700 | 9.48 | 0.982 |
| 11 | 19 | 18 | 192.509 | 3.903 | 245.325 | 34.40 | 0.981 |
| 11 | 19 | 20 | 150.690 | 4.715 | 190.085 | 113.17 | 0.978 |
| 11 | 19 | 22 | 133.174 | 9.285 | 244.221 | 260.29 | 0.937 |
| 11 | 19 | 24 | 108.852 | 7.670 | 197.859 | 42.71 | 0.889 |
| 11 | 19 | 26 | 35.308 | 11.217 | 2.556 | 305.88 | 0.152 |
| 11 | 19 | 28 | 86.561 | 9.727 | 102.522 | 25.89 | 0.921 |
| 11 | 19 | 30 | 86.608 | 11.021 | 121.976 | 113.59 | 0.890 |
| 11 | 19 | 32 | 50.104 | 12.929 | 42.943 | 168.71 | 0.819 |
| 11 | 19 | 34 | 74.550 | 12.111 | 104.817 | 138.23 | 0.895 |
| 11 | 20 | 1 | 317.503 | 3.628 | 556.177 | 193.52 | 0.986 |
| 11 | 20 | 3 | 151.453 | 3.764 | 239.403 | 141.30 | 0.943 |
| 11 | 20 | 5 | 148.185 | 4.134 | 266.402 | 74.37 | 0.909 |
| 11 | 20 | 7 | 163.783 | 4.446 | 185.742 | 134.19 | 0.965 |
| 11 | 20 | 9 | 126.983 | 5.057 | 176.933 | 265.18 | 0.934 |
| 11 | 20 | 11 | 274.800 | 3.251 | 380.793 | 153.34 | 0.986 |
| 11 | 20 | 13 | 173.263 | 3.713 | 220.182 | 341.54 | 0.976 |
| 11 | 20 | 15 | 110.130 | 5.919 | 132.104 | 151.53 | 0.943 |
| 11 | 20 | 17 | 218.452 | 3.830 | 443.394 | 279.91 | 0.942 |
| 11 | 20 | 19 | 96.250 | 6.163 | 108.788 | 301.40 | 0.948 |
| 11 | 20 | 21 | 209.590 | 3.428 | 309.854 | 257.90 | 0.987 |
| 11 | 20 | 23 | 58.197 | 14.562 | 51.101 | 346.39 | 0.765 |
| 11 | 20 | 25 | 108.615 | 6.808 | 134.709 | 22.13 | 0.952 |
| 11 | 20 | 27 | 61.218 | 13.046 | 65.835 | 66.96 | 0.794 |
| 11 | 20 | 29 | 93.460 | 9.419 | 96.686 | 49.42 | 0.968 |
| 11 | 20 | 31 | 45.343 | 12.878 | 35.809 | 282.86 | 0.669 |
| 11 | 20 | 33 | 48.479 | 14.088 | 1.375 | 88.22 | 0.050 |
| 11 | 21 | 0 | 248.984 | 4.583 | 354.744 | 0.00 | 1.000 |
| 11 | 21 | 2 | 315.056 | 3.574 | 465.215 | 323.86 | 0.989 |
| 11 | 21 | 4 | 166.109 | 3.819 | 166.740 | 114.98 | 0.974 |

| | | | | | | | |
|---|---|---|---|---|---|---|---|
| 11 | 21 | 6 | 128.885 | 5.172 | 231.649 | 106.45 | 0.848 |
| 11 | 21 | 8 | 171.023 | 4.381 | 271.241 | 287.53 | 0.960 |
| 11 | 21 | 10 | 152.046 | 5.281 | 157.523 | 147.89 | 0.975 |
| 11 | 21 | 12 | 99.738 | 5.586 | 111.001 | 180.37 | 0.931 |
| 11 | 21 | 14 | 248.909 | 3.569 | 333.648 | 138.27 | 0.989 |
| 11 | 21 | 16 | 230.355 | 3.851 | 363.527 | 136.73 | 0.983 |
| 11 | 21 | 18 | 69.331 | 10.584 | 74.648 | 158.53 | 0.868 |
| 11 | 21 | 20 | 101.838 | 7.864 | 151.738 | 319.26 | 0.933 |
| 11 | 21 | 22 | 130.991 | 6.220 | 209.439 | 208.71 | 0.957 |
| 11 | 21 | 24 | 145.626 | 6.194 | 182.824 | 179.25 | 0.975 |
| 11 | 21 | 26 | 85.294 | 10.137 | 120.807 | 288.16 | 0.888 |
| 11 | 21 | 28 | 54.170 | 13.194 | 46.841 | 219.63 | 0.869 |
| 11 | 21 | 30 | 85.833 | 13.999 | 102.863 | 326.42 | 0.942 |
| 11 | 21 | 32 | 40.471 | 12.603 | 23.910 | 258.26 | 0.494 |
| 11 | 22 | 1 | 248.213 | 3.959 | 396.184 | 342.94 | 0.980 |
| 11 | 22 | 3 | 163.594 | 3.820 | 148.549 | 204.61 | 0.974 |
| 11 | 22 | 5 | 219.095 | 3.857 | 377.188 | 210.91 | 0.980 |
| 11 | 22 | 7 | 38.745 | 10.673 | 31.247 | 185.53 | 0.689 |
| 11 | 22 | 9 | 434.643 | 5.514 | 613.351 | 100.65 | 0.996 |
| 11 | 22 | 11 | 139.295 | 5.067 | 245.728 | 85.38 | 0.940 |
| 11 | 22 | 13 | 83.530 | 9.487 | 85.565 | 123.07 | 0.534 |
| 11 | 22 | 15 | 128.232 | 4.757 | 248.301 | 208.42 | 0.930 |
| 11 | 22 | 17 | 101.444 | 7.764 | 162.336 | 39.27 | 0.922 |
| 11 | 22 | 19 | 90.023 | 7.744 | 144.675 | 268.23 | 0.732 |
| 11 | 22 | 21 | 35.894 | 11.392 | 2.067 | 41.31 | 0.346 |
| 11 | 22 | 23 | 181.160 | 4.728 | 298.608 | 261.96 | 0.981 |
| 11 | 22 | 25 | 60.418 | 10.722 | 58.891 | 47.46 | 0.582 |
| 11 | 22 | 27 | 170.736 | 6.201 | 273.249 | 117.80 | 0.986 |
| 11 | 22 | 29 | 60.821 | 14.509 | 69.488 | 156.25 | 0.694 |
| 11 | 22 | 31 | 41.306 | 13.566 | 16.890 | 80.93 | 0.346 |
| 11 | 23 | 0 | 151.845 | 7.498 | 139.058 | 180.00 | 0.644 |
| 11 | 23 | 2 | 240.312 | 3.406 | 294.488 | 192.83 | 0.990 |
| 11 | 23 | 4 | 115.299 | 7.638 | 167.437 | 128.77 | 0.939 |
| 11 | 23 | 6 | 163.622 | 5.081 | 222.517 | 193.89 | 0.973 |
| 11 | 23 | 8 | 145.919 | 6.745 | 190.505 | 144.62 | 0.968 |
| 11 | 23 | 10 | 155.508 | 5.572 | 275.753 | 72.16 | 0.956 |
| 11 | 23 | 12 | 133.139 | 4.673 | 154.624 | 297.04 | 0.974 |
| 11 | 23 | 14 | 151.795 | 4.876 | 185.081 | 3.05 | 0.979 |
| 11 | 23 | 16 | 136.371 | 4.401 | 153.491 | 125.00 | 0.978 |
| 11 | 23 | 18 | 36.400 | 10.417 | 7.290 | 285.91 | 0.597 |
| 11 | 23 | 20 | 38.378 | 10.629 | 8.558 | 336.59 | 0.444 |
| 11 | 23 | 22 | 47.351 | 12.406 | 16.744 | 306.75 | 0.772 |
| 11 | 23 | 24 | 103.095 | 6.961 | 85.829 | 346.02 | 0.965 |
| 11 | 23 | 26 | 96.562 | 10.862 | 174.566 | 74.44 | 0.858 |
| 11 | 23 | 28 | 40.096 | 12.160 | 9.990 | 280.39 | 0.175 |
| 11 | 23 | 30 | 104.319 | 10.928 | 126.347 | 54.24 | 0.968 |
| 11 | 24 | 1 | 193.718 | 4.208 | 309.355 | 342.43 | 0.977 |
| 11 | 24 | 3 | 246.972 | 3.825 | 535.655 | 206.74 | 0.972 |
| 11 | 24 | 5 | 188.290 | 4.598 | 292.457 | 326.40 | 0.976 |
| 11 | 24 | 7 | 208.078 | 6.107 | 269.064 | 340.35 | 0.989 |
| 11 | 24 | 9 | 206.961 | 5.420 | 295.185 | 339.97 | 0.987 |
| 11 | 24 | 11 | 62.531 | 11.815 | 46.098 | 339.18 | 0.876 |
| 11 | 24 | 13 | 186.210 | 3.986 | 319.258 | 354.98 | 0.980 |
| 11 | 24 | 15 | 62.230 | 10.226 | 52.805 | 98.19 | 0.862 |
| 11 | 24 | 17 | 75.431 | 7.311 | 64.788 | 19.83 | 0.919 |
| 11 | 24 | 19 | 92.114 | 6.496 | 130.992 | 205.52 | 0.919 |
| 11 | 24 | 21 | 96.056 | 8.069 | 151.692 | 219.07 | 0.923 |
| 11 | 24 | 23 | 197.056 | 5.381 | 271.226 | 197.90 | 0.987 |
| 11 | 24 | 25 | 45.575 | 13.323 | 31.495 | 82.21 | 0.479 |
| 11 | 24 | 27 | 77.668 | 14.736 | 117.605 | 66.45 | 0.823 |
| 11 | 24 | 29 | 59.091 | 14.783 | 46.900 | 88.15 | 0.475 |
| 11 | 25 | 0 | 388.339 | 5.739 | 551.900 | 180.00 | 1.000 |
| 11 | 25 | 2 | 109.808 | 6.504 | 127.371 | 215.28 | 0.963 |
| 11 | 25 | 4 | 48.996 | 12.473 | 25.986 | 329.95 | 0.820 |
| 11 | 25 | 6 | 43.409 | 12.713 | 16.099 | 181.16 | 0.451 |
| 11 | 25 | 8 | 144.143 | 5.514 | 210.509 | 67.75 | 0.973 |
| 11 | 25 | 10 | 91.583 | 9.373 | 95.511 | 128.59 | 0.948 |
| 11 | 25 | 12 | 205.779 | 4.236 | 321.871 | 297.23 | 0.986 |
| 11 | 25 | 14 | 42.581 | 10.684 | 10.806 | 132.61 | 0.626 |
| 11 | 25 | 16 | 98.335 | 6.124 | 101.061 | 93.41 | 0.957 |
| 11 | 25 | 18 | 106.426 | 5.680 | 138.042 | 264.30 | 0.958 |
| 11 | 25 | 20 | 88.588 | 6.766 | 120.744 | 41.46 | 0.931 |
| 11 | 25 | 22 | 125.210 | 8.398 | 169.087 | 301.70 | 0.980 |
| 11 | 25 | 24 | 93.648 | 16.415 | 113.598 | 266.34 | 0.950 |
| 11 | 25 | 26 | 38.973 | 12.657 | 24.882 | 89.26 | 0.648 |
| 11 | 25 | 28 | 41.330 | 12.819 | 29.304 | 100.76 | 0.605 |
| 11 | 26 | 1 | 43.521 | 11.502 | 1.542 | 61.63 | 0.782 |

| | | | | | | | |
|---|---|---|---|---|---|---|---|
| 11 | 26 | 3 | 230.499 | 3.975 | 309.792 | 202.83 | 0.991 |
| 11 | 26 | 5 | 73.399 | 8.723 | 86.798 | 272.88 | 0.889 |
| 11 | 26 | 7 | 135.319 | 5.577 | 223.307 | 325.79 | 0.963 |
| 11 | 26 | 9 | 111.886 | 10.274 | 108.436 | 133.62 | 0.965 |
| 11 | 26 | 11 | 41.654 | 11.809 | 10.938 | 238.13 | 0.604 |
| 11 | 26 | 13 | 40.246 | 11.493 | 1.994 | 235.89 | 0.677 |
| 11 | 26 | 15 | 154.069 | 5.163 | 258.397 | 136.23 | 0.975 |
| 11 | 26 | 17 | 110.409 | 6.102 | 175.917 | 255.70 | 0.948 |
| 11 | 26 | 19 | 70.928 | 8.530 | 100.744 | 284.22 | 0.734 |
| 11 | 26 | 21 | 49.274 | 13.088 | 49.681 | 47.15 | 0.733 |
| 11 | 26 | 23 | 35.898 | 12.347 | 4.239 | 56.44 | 0.735 |
| 11 | 26 | 25 | 32.928 | 10.743 | 8.041 | 310.45 | 0.596 |
| 11 | 27 | 0 | 33.432 | 15.742 | 34.415 | 0.00 | 0.737 |
| 11 | 27 | 2 | 149.232 | 5.403 | 191.966 | 274.81 | 0.980 |
| 11 | 27 | 4 | 38.912 | 10.675 | 8.813 | 341.65 | 0.227 |
| 11 | 27 | 6 | 157.276 | 5.422 | 244.356 | 353.57 | 0.976 |
| 11 | 27 | 8 | 134.151 | 5.391 | 210.327 | 39.62 | 0.964 |
| 11 | 27 | 10 | 185.065 | 5.767 | 258.772 | 35.03 | 0.985 |
| 11 | 27 | 12 | 117.778 | 7.893 | 215.752 | 173.17 | 0.939 |
| 11 | 27 | 14 | 98.282 | 9.532 | 104.025 | 136.88 | 0.958 |
| 11 | 27 | 16 | 40.006 | 11.721 | 9.693 | 171.45 | 0.174 |
| 11 | 27 | 18 | 77.474 | 10.166 | 105.794 | 4.74 | 0.938 |
| 11 | 27 | 20 | 92.670 | 9.169 | 168.715 | 283.00 | 0.878 |
| 11 | 27 | 22 | 101.544 | 12.081 | 160.520 | 164.11 | 0.950 |
| 11 | 27 | 24 | 55.716 | 15.016 | 36.199 | 121.09 | 0.887 |
| 11 | 28 | 1 | 60.029 | 12.659 | 50.799 | 168.69 | 0.830 |
| 11 | 28 | 3 | 47.238 | 11.625 | 6.476 | 90.17 | 0.803 |
| 11 | 28 | 5 | 59.563 | 10.961 | 56.920 | 209.04 | 0.860 |
| 11 | 28 | 7 | 37.586 | 11.660 | 7.497 | 183.14 | 0.726 |
| 11 | 28 | 9 | 58.235 | 10.490 | 61.646 | 105.16 | 0.821 |
| 11 | 28 | 11 | 62.376 | 10.289 | 62.575 | 38.99 | 0.514 |
| 11 | 28 | 13 | 69.254 | 10.646 | 83.762 | 250.12 | 0.877 |
| 11 | 28 | 15 | 90.941 | 8.432 | 133.743 | 171.41 | 0.957 |
| 11 | 28 | 17 | 65.040 | 13.631 | 89.408 | 203.61 | 0.857 |
| 11 | 28 | 19 | 49.189 | 13.798 | 45.936 | 33.89 | 0.792 |
| 11 | 28 | 21 | 40.920 | 12.565 | 14.397 | 343.02 | 0.817 |
| 11 | 29 | 0 | 37.689 | 15.778 | 29.495 | 180.00 | 0.569 |
| 11 | 29 | 2 | 78.580 | 10.636 | 73.253 | 171.91 | 0.932 |
| 11 | 29 | 4 | 99.760 | 6.990 | 123.404 | 140.70 | 0.959 |
| 11 | 29 | 6 | 59.102 | 10.607 | 67.384 | 300.84 | 0.683 |
| 11 | 29 | 8 | 94.040 | 7.468 | 155.566 | 8.29 | 0.910 |
| 11 | 29 | 10 | 51.303 | 10.042 | 60.413 | 306.32 | 0.803 |
| 11 | 29 | 12 | 64.272 | 11.759 | 39.757 | 206.06 | 0.944 |
| 11 | 29 | 14 | 47.940 | 13.750 | 21.419 | 203.33 | 0.322 |
| 11 | 29 | 16 | 72.288 | 13.157 | 94.786 | 203.71 | 0.904 |
| 11 | 29 | 18 | 62.824 | 13.941 | 81.266 | 254.68 | 0.825 |
| 11 | 29 | 20 | 33.157 | 10.997 | 12.608 | 280.84 | 0.453 |
| 11 | 30 | 1 | 113.585 | 6.106 | 181.438 | 313.80 | 0.973 |
| 11 | 30 | 3 | 56.197 | 12.955 | 62.679 | 153.26 | 0.880 |
| 11 | 30 | 5 | 38.776 | 11.507 | 22.911 | 184.55 | 0.747 |
| 11 | 30 | 7 | 68.958 | 13.456 | 61.296 | 83.25 | 0.940 |
| 11 | 30 | 9 | 40.534 | 11.809 | 28.830 | 285.24 | 0.755 |
| 11 | 30 | 11 | 44.443 | 15.008 | 17.289 | 349.32 | 0.833 |
| 11 | 30 | 13 | 68.735 | 16.301 | 86.471 | 142.23 | 0.672 |
| 11 | 30 | 15 | 57.956 | 15.998 | 53.163 | 56.71 | 0.872 |
| 11 | 30 | 17 | 50.893 | 13.332 | 45.077 | 49.77 | 0.836 |
| 11 | 31 | 0 | 40.704 | 26.562 | 33.105 | 0.00 | 0.702 |
| 11 | 31 | 2 | 46.308 | 12.621 | 39.313 | 38.02 | 0.737 |
| 11 | 31 | 4 | 59.940 | 16.745 | 72.550 | 275.09 | 0.770 |
| 11 | 31 | 6 | 81.090 | 16.366 | 109.000 | 234.97 | 0.917 |
| 11 | 31 | 8 | 52.877 | 14.106 | 52.731 | 330.46 | 0.643 |
| 11 | 31 | 10 | 31.129 | 10.527 | 11.191 | 20.67 | 0.500 |
| 11 | 31 | 12 | 51.168 | 14.976 | 39.631 | 321.91 | 0.521 |
| 11 | 31 | 14 | 44.169 | 14.805 | 28.403 | 357.26 | 0.700 |
| 11 | 32 | 1 | 31.751 | 10.508 | 4.512 | 189.66 | 0.679 |
| 11 | 32 | 3 | 48.059 | 13.144 | 37.414 | 270.64 | 0.862 |
| 11 | 32 | 5 | 46.050 | 12.658 | 39.751 | 101.75 | 0.655 |
| 11 | 32 | 7 | 92.823 | 9.788 | 124.331 | 267.91 | 0.961 |
| 11 | 32 | 9 | 32.694 | 10.564 | 11.431 | 50.15 | 0.296 |
| 11 | 32 | 11 | 34.304 | 10.792 | 3.390 | 333.98 | 0.759 |
| 11 | 33 | 0 | 18.097 | 13.074 | 2.436 | 0.00 | 0.110 |
| 11 | 33 | 2 | 33.796 | 10.821 | 12.137 | 127.64 | 0.357 |
| 12 | 0 | 0 | 745.688 | 11.341 | 1070.157 | 180.00 | 1.000 |
| 12 | 0 | 2 | 14.271 | 6.065 | 3.349 | 180.00 | 0.191 |
| 12 | 0 | 4 | 307.230 | 4.046 | 440.755 | 0.00 | 1.000 |
| 12 | 0 | 6 | 643.604 | 6.777 | 921.704 | 0.00 | 1.000 |
| 12 | 0 | 8 | 220.364 | 2.659 | 315.090 | 180.00 | 1.000 |

| | | | | | | | |
|---|---|---|---|---|---|---|---|
| 12 | 0 | 10 | 176.718 | 2.811 | 252.112 | 0.00 | 1.000 |
| 12 | 0 | 12 | 230.315 | 3.732 | 327.297 | 180.00 | 1.000 |
| 12 | 0 | 14 | 304.877 | 3.875 | 432.303 | 0.00 | 1.000 |
| 12 | 0 | 16 | 370.850 | 4.698 | 523.867 | 0.00 | 1.000 |
| 12 | 0 | 18 | 387.505 | 4.921 | 544.819 | 180.00 | 1.000 |
| 12 | 0 | 20 | 90.307 | 5.694 | 73.800 | 0.00 | 0.585 |
| 12 | 0 | 22 | 120.986 | 5.617 | 168.278 | 180.00 | 1.000 |
| 12 | 0 | 24 | 63.378 | 11.872 | 80.175 | 180.00 | 0.923 |
| 12 | 0 | 26 | 126.754 | 7.108 | 173.988 | 0.00 | 1.000 |
| 12 | 0 | 28 | 41.280 | 15.856 | 16.457 | 180.00 | 0.294 |
| 12 | 0 | 30 | 33.815 | 14.999 | 23.940 | 180.00 | 0.534 |
| 12 | 0 | 32 | 78.232 | 15.437 | 85.451 | 0.00 | 0.822 |
| 12 | 0 | 34 | 84.269 | 12.533 | 110.095 | 0.00 | 0.990 |
| 12 | 0 | 36 | 101.996 | 10.374 | 132.010 | 0.00 | 0.991 |
| 12 | 0 | 38 | 58.038 | 16.820 | 50.556 | 0.00 | 0.694 |
| 12 | 0 | 40 | 39.675 | 17.183 | 12.330 | 180.00 | 0.257 |
| 12 | 0 | 42 | 24.967 | 12.738 | 17.818 | 0.00 | 0.593 |
| 12 | 1 | 1 | 53.602 | 3.763 | 43.865 | 226.02 | 0.777 |
| 12 | 1 | 3 | 355.019 | 3.725 | 438.282 | 152.03 | 0.993 |
| 12 | 1 | 5 | 162.974 | 1.706 | 239.465 | 34.75 | 0.968 |
| 12 | 1 | 7 | 28.034 | 5.820 | 53.654 | 259.50 | 0.515 |
| 12 | 1 | 9 | 284.185 | 2.540 | 440.666 | 130.82 | 0.987 |
| 12 | 1 | 11 | 34.229 | 6.419 | 63.915 | 39.39 | 0.803 |
| 12 | 1 | 13 | 311.221 | 2.812 | 427.327 | 256.70 | 0.988 |
| 12 | 1 | 15 | 329.516 | 3.146 | 493.398 | 52.12 | 0.988 |
| 12 | 1 | 17 | 127.952 | 3.222 | 188.250 | 351.29 | 0.903 |
| 12 | 1 | 19 | 116.186 | 3.969 | 157.717 | 23.55 | 0.916 |
| 12 | 1 | 21 | 343.412 | 3.248 | 513.784 | 28.66 | 0.991 |
| 12 | 1 | 23 | 352.215 | 3.408 | 466.018 | 91.15 | 0.993 |
| 12 | 1 | 25 | 236.400 | 3.153 | 277.483 | 319.68 | 0.983 |
| 12 | 1 | 27 | 256.013 | 3.143 | 313.722 | 287.17 | 0.985 |
| 12 | 1 | 29 | 90.558 | 7.432 | 102.068 | 93.30 | 0.901 |
| 12 | 1 | 31 | 133.192 | 6.307 | 196.162 | 158.11 | 0.960 |
| 12 | 1 | 33 | 44.643 | 11.953 | 11.329 | 276.53 | 0.662 |
| 12 | 1 | 35 | 50.876 | 11.549 | 18.517 | 234.56 | 0.277 |
| 12 | 1 | 37 | 82.959 | 9.615 | 101.298 | 91.14 | 0.907 |
| 12 | 1 | 39 | 75.861 | 11.621 | 88.816 | 287.47 | 0.925 |
| 12 | 1 | 41 | 52.483 | 14.977 | 36.925 | 113.55 | 0.841 |
| 12 | 2 | 0 | 17.220 | 9.830 | 0.013 | 0.00 | 0.002 |
| 12 | 2 | 2 | 41.913 | 5.506 | 29.579 | 124.41 | 0.867 |
| 12 | 2 | 4 | 171.765 | 1.975 | 264.490 | 18.14 | 0.961 |
| 12 | 2 | 6 | 204.986 | 1.883 | 272.262 | 215.68 | 0.992 |
| 12 | 2 | 8 | 372.475 | 3.283 | 529.057 | 164.00 | 0.993 |
| 12 | 2 | 10 | 176.807 | 1.992 | 192.830 | 249.43 | 0.968 |
| 12 | 2 | 12 | 170.790 | 2.221 | 247.350 | 286.78 | 0.956 |
| 12 | 2 | 14 | 207.877 | 2.360 | 286.993 | 277.56 | 0.976 |
| 12 | 2 | 16 | 323.584 | 3.132 | 399.410 | 138.45 | 0.990 |
| 12 | 2 | 18 | 155.909 | 3.233 | 210.703 | 178.45 | 0.977 |
| 12 | 2 | 20 | 530.990 | 5.177 | 730.625 | 10.78 | 0.997 |
| 12 | 2 | 22 | 82.860 | 5.435 | 88.727 | 351.86 | 0.844 |
| 12 | 2 | 24 | 115.512 | 4.454 | 139.242 | 110.98 | 0.940 |
| 12 | 2 | 26 | 437.423 | 4.427 | 598.282 | 92.43 | 0.994 |
| 12 | 2 | 28 | 105.070 | 6.685 | 122.846 | 139.32 | 0.929 |
| 12 | 2 | 30 | 57.802 | 11.629 | 47.890 | 89.55 | 0.687 |
| 12 | 2 | 32 | 104.485 | 9.541 | 104.574 | 349.35 | 0.952 |
| 12 | 2 | 34 | 152.293 | 4.559 | 199.725 | 324.66 | 0.974 |
| 12 | 2 | 36 | 39.917 | 11.149 | 9.833 | 82.21 | 0.489 |
| 12 | 2 | 38 | 35.644 | 10.865 | 9.417 | 239.83 | 0.538 |
| 12 | 2 | 40 | 39.296 | 12.112 | 17.564 | 174.70 | 0.651 |
| 12 | 2 | 42 | 42.864 | 13.498 | 22.912 | 130.88 | 0.676 |
| 12 | 3 | 1 | 43.003 | 6.851 | 44.889 | 243.66 | 0.776 |
| 12 | 3 | 3 | 289.857 | 2.762 | 377.776 | 290.13 | 0.990 |
| 12 | 3 | 5 | 215.611 | 2.271 | 324.552 | 351.87 | 0.976 |
| 12 | 3 | 7 | 314.366 | 2.684 | 445.944 | 202.95 | 0.990 |
| 12 | 3 | 9 | 286.039 | 2.733 | 422.777 | 347.30 | 0.986 |
| 12 | 3 | 11 | 149.427 | 2.145 | 200.849 | 81.28 | 0.953 |
| 12 | 3 | 13 | 170.599 | 2.356 | 195.719 | 298.79 | 0.975 |
| 12 | 3 | 15 | 336.210 | 3.236 | 446.119 | 280.60 | 0.990 |
| 12 | 3 | 17 | 53.510 | 8.035 | 29.693 | 91.21 | 0.623 |
| 12 | 3 | 19 | 417.748 | 3.634 | 618.326 | 281.43 | 0.994 |
| 12 | 3 | 21 | 274.816 | 3.014 | 346.616 | 257.23 | 0.989 |
| 12 | 3 | 23 | 439.049 | 4.298 | 604.521 | 224.38 | 0.995 |
| 12 | 3 | 25 | 341.756 | 3.678 | 520.664 | 300.00 | 0.989 |
| 12 | 3 | 27 | 197.289 | 3.716 | 258.090 | 290.30 | 0.973 |
| 12 | 3 | 29 | 94.321 | 10.100 | 120.899 | 199.64 | 0.891 |
| 12 | 3 | 31 | 221.178 | 3.804 | 381.144 | 53.43 | 0.983 |
| 12 | 3 | 33 | 83.631 | 10.114 | 104.090 | 359.01 | 0.884 |

| | | | | | | |
|---|---|---|---|---|---|---|
| 12 | 3 | 35 | 132.143 | 6.115 | 155.298 | 67.85 | 0.968 |
| 12 | 3 | 37 | 77.058 | 12.198 | 93.359 | 65.76 | 0.869 |
| 12 | 3 | 39 | 101.511 | 9.068 | 126.873 | 279.72 | 0.964 |
| 12 | 3 | 41 | 40.355 | 12.744 | 10.079 | 218.65 | 0.798 |
| 12 | 4 | 0 | 30.278 | 14.669 | 5.613 | 0.00 | 0.142 |
| 12 | 4 | 2 | 108.423 | 2.932 | 139.655 | 253.48 | 0.937 |
| 12 | 4 | 4 | 380.326 | 4.640 | 596.085 | 307.18 | 0.992 |
| 12 | 4 | 6 | 319.570 | 2.964 | 468.910 | 14.27 | 0.992 |
| 12 | 4 | 8 | 467.996 | 3.906 | 745.983 | 340.88 | 0.994 |
| 12 | 4 | 10 | 270.529 | 2.429 | 438.694 | 155.50 | 0.982 |
| 12 | 4 | 12 | 140.464 | 2.188 | 219.841 | 335.01 | 0.980 |
| 12 | 4 | 14 | 467.453 | 4.068 | 696.357 | 338.07 | 0.994 |
| 12 | 4 | 16 | 227.095 | 2.462 | 316.093 | 346.98 | 0.984 |
| 12 | 4 | 18 | 87.528 | 3.989 | 108.845 | 245.97 | 0.905 |
| 12 | 4 | 20 | 143.958 | 3.022 | 226.833 | 270.70 | 0.870 |
| 12 | 4 | 22 | 121.320 | 4.398 | 152.111 | 278.34 | 0.569 |
| 12 | 4 | 24 | 231.001 | 3.018 | 273.095 | 191.74 | 0.986 |
| 12 | 4 | 26 | 306.091 | 3.369 | 443.832 | 315.65 | 0.987 |
| 12 | 4 | 28 | 209.189 | 3.598 | 270.328 | 204.39 | 0.982 |
| 12 | 4 | 30 | 150.788 | 5.618 | 175.432 | 194.14 | 0.969 |
| 12 | 4 | 32 | 141.570 | 5.860 | 203.343 | 108.83 | 0.966 |
| 12 | 4 | 34 | 162.582 | 5.844 | 265.787 | 170.08 | 0.969 |
| 12 | 4 | 36 | 88.691 | 9.276 | 37.338 | 154.86 | 0.961 |
| 12 | 4 | 38 | 49.631 | 13.109 | 41.784 | 156.48 | 0.536 |
| 12 | 4 | 40 | 55.740 | 14.195 | 46.070 | 253.86 | 0.507 |
| 12 | 5 | 1 | 252.832 | 3.109 | 383.436 | 110.88 | 0.982 |
| 12 | 5 | 3 | 73.587 | 2.752 | 91.599 | 133.01 | 0.542 |
| 12 | 5 | 5 | 85.365 | 2.573 | 104.017 | 122.48 | 0.849 |
| 12 | 5 | 7 | 321.703 | 2.907 | 492.526 | 292.34 | 0.989 |
| 12 | 5 | 9 | 40.988 | 5.526 | 31.215 | 197.34 | 0.714 |
| 12 | 5 | 11 | 75.371 | 4.056 | 72.984 | 85.86 | 0.709 |
| 12 | 5 | 13 | 118.437 | 2.569 | 168.646 | 100.96 | 0.945 |
| 12 | 5 | 15 | 157.908 | 2.591 | 186.691 | 212.46 | 0.949 |
| 12 | 5 | 17 | 398.580 | 3.559 | 507.869 | 110.77 | 0.995 |
| 12 | 5 | 19 | 285.006 | 2.866 | 279.876 | 306.71 | 0.992 |
| 12 | 5 | 21 | 215.251 | 2.893 | 292.803 | 125.12 | 0.980 |
| 12 | 5 | 23 | 278.111 | 3.054 | 397.224 | 90.10 | 0.987 |
| 12 | 5 | 25 | 172.718 | 3.499 | 139.066 | 250.76 | 0.973 |
| 12 | 5 | 27 | 151.450 | 4.166 | 224.846 | 325.25 | 0.936 |
| 12 | 5 | 29 | 185.797 | 3.869 | 211.323 | 200.20 | 0.981 |
| 12 | 5 | 31 | 119.682 | 5.330 | 120.168 | 114.49 | 0.971 |
| 12 | 5 | 33 | 125.524 | 6.096 | 139.088 | 210.84 | 0.967 |
| 12 | 5 | 35 | 131.448 | 6.604 | 148.140 | 201.34 | 0.969 |
| 12 | 5 | 37 | 93.498 | 8.610 | 144.312 | 119.46 | 0.895 |
| 12 | 5 | 39 | 65.970 | 12.430 | 65.338 | 307.50 | 0.904 |
| 12 | 5 | 41 | 45.508 | 14.105 | 30.561 | 66.34 | 0.606 |
| 12 | 6 | 0 | 312.457 | 4.351 | 448.457 | 180.00 | 1.000 |
| 12 | 6 | 2 | 136.449 | 2.095 | 165.249 | 43.70 | 0.975 |
| 12 | 6 | 4 | 247.148 | 2.417 | 361.295 | 132.55 | 0.985 |
| 12 | 6 | 6 | 183.105 | 1.928 | 261.938 | 121.80 | 0.967 |
| 12 | 6 | 8 | 181.066 | 2.068 | 288.262 | 188.88 | 0.970 |
| 12 | 6 | 10 | 213.505 | 2.465 | 313.446 | 61.12 | 0.971 |
| 12 | 6 | 12 | 46.348 | 6.302 | 30.005 | 68.67 | 0.892 |
| 12 | 6 | 14 | 195.091 | 2.557 | 244.367 | 23.34 | 0.978 |
| 12 | 6 | 16 | 434.552 | 3.651 | 620.455 | 121.00 | 0.995 |
| 12 | 6 | 18 | 450.577 | 4.215 | 690.762 | 117.68 | 0.995 |
| 12 | 6 | 20 | 542.817 | 4.568 | 777.184 | 326.04 | 0.997 |
| 12 | 6 | 22 | 87.630 | 4.651 | 72.257 | 117.98 | 0.895 |
| 12 | 6 | 24 | 200.396 | 3.195 | 280.789 | 152.49 | 0.975 |
| 12 | 6 | 26 | 153.034 | 4.490 | 187.346 | 307.55 | 0.956 |
| 12 | 6 | 28 | 114.426 | 6.272 | 140.910 | 84.21 | 0.941 |
| 12 | 6 | 30 | 85.122 | 9.335 | 114.987 | 186.03 | 0.898 |
| 12 | 6 | 32 | 116.277 | 7.003 | 154.189 | 6.73 | 0.952 |
| 12 | 6 | 34 | 82.711 | 10.886 | 106.212 | 163.29 | 0.872 |
| 12 | 6 | 36 | 157.409 | 4.953 | 191.937 | 31.77 | 0.981 |
| 12 | 6 | 38 | 124.336 | 6.067 | 175.293 | 161.59 | 0.974 |
| 12 | 6 | 40 | 125.894 | 7.801 | 179.592 | 319.99 | 0.974 |
| 12 | 7 | 1 | 127.465 | 1.684 | 176.384 | 75.53 | 0.967 |
| 12 | 7 | 3 | 229.992 | 2.257 | 355.214 | 22.84 | 0.979 |
| 12 | 7 | 5 | 278.765 | 2.707 | 391.817 | 190.03 | 0.988 |
| 12 | 7 | 7 | 138.138 | 2.088 | 186.109 | 140.91 | 0.969 |
| 12 | 7 | 9 | 216.747 | 2.297 | 263.333 | 322.06 | 0.981 |
| 12 | 7 | 11 | 181.199 | 2.399 | 219.826 | 67.01 | 0.978 |
| 12 | 7 | 13 | 437.623 | 3.702 | 624.442 | 347.11 | 0.994 |
| 12 | 7 | 15 | 218.389 | 2.466 | 283.687 | 49.45 | 0.983 |
| 12 | 7 | 17 | 472.109 | 4.016 | 617.197 | 130.78 | 0.996 |
| 12 | 7 | 19 | 43.575 | 8.797 | 13.162 | 90.56 | 0.523 |

| | | | | | | | |
|---|---|---|---|---|---|---|---|
| 12 | 7 | 21 | 328.827 | 3.236 | 506.388 | 4.05 | 0.990 |
| 12 | 7 | 23 | 582.126 | 5.407 | 821.586 | 118.20 | 0.997 |
| 12 | 7 | 25 | 258.952 | 3.082 | 311.941 | 170.88 | 0.987 |
| 12 | 7 | 27 | 127.328 | 4.904 | 193.592 | 219.97 | 0.938 |
| 12 | 7 | 29 | 87.226 | 7.086 | 71.808 | 98.49 | 0.905 |
| 12 | 7 | 31 | 100.027 | 7.283 | 119.136 | 104.52 | 0.941 |
| 12 | 7 | 33 | 138.231 | 5.789 | 198.210 | 34.15 | 0.963 |
| 12 | 7 | 35 | 96.415 | 7.047 | 136.265 | 36.23 | 0.928 |
| 12 | 7 | 37 | 48.479 | 11.528 | 30.583 | 326.64 | 0.869 |
| 12 | 7 | 39 | 79.882 | 12.082 | 73.253 | 344.17 | 0.947 |
| 12 | 7 | 41 | 42.666 | 14.238 | 14.766 | 32.07 | 0.443 |
| 12 | 8 | 0 | 312.972 | 3.795 | 449.239 | 0.00 | 1.000 |
| 12 | 8 | 2 | 287.947 | 3.912 | 439.050 | 243.98 | 0.985 |
| 12 | 8 | 4 | 153.818 | 2.292 | 223.097 | 236.48 | 0.948 |
| 12 | 8 | 6 | 203.033 | 2.034 | 266.006 | 105.82 | 0.979 |
| 12 | 8 | 8 | 106.159 | 3.092 | 133.930 | 190.64 | 0.932 |
| 12 | 8 | 10 | 429.744 | 3.637 | 603.741 | 86.86 | 0.994 |
| 12 | 8 | 12 | 115.173 | 2.855 | 132.978 | 242.55 | 0.911 |
| 12 | 8 | 14 | 73.117 | 4.178 | 81.049 | 313.93 | 0.831 |
| 12 | 8 | 16 | 94.807 | 3.682 | 48.637 | 195.85 | 0.927 |
| 12 | 8 | 18 | 271.101 | 2.759 | 386.210 | 159.86 | 0.988 |
| 12 | 8 | 20 | 152.830 | 3.278 | 181.243 | 2.02 | 0.966 |
| 12 | 8 | 22 | 87.703 | 6.005 | 79.408 | 71.59 | 0.870 |
| 12 | 8 | 24 | 175.402 | 3.406 | 261.102 | 341.98 | 0.961 |
| 12 | 8 | 26 | 160.429 | 3.656 | 208.697 | 65.56 | 0.972 |
| 12 | 8 | 28 | 164.975 | 4.611 | 230.191 | 285.36 | 0.969 |
| 12 | 8 | 30 | 111.244 | 7.322 | 183.620 | 178.12 | 0.909 |
| 12 | 8 | 32 | 282.119 | 4.097 | 401.100 | 252.07 | 0.992 |
| 12 | 8 | 34 | 241.468 | 4.814 | 379.364 | 340.90 | 0.987 |
| 12 | 8 | 36 | 87.855 | 10.751 | 66.804 | 100.30 | 0.946 |
| 12 | 8 | 38 | 97.243 | 9.743 | 158.653 | 336.42 | 0.930 |
| 12 | 8 | 40 | 34.953 | 12.323 | 9.481 | 341.91 | 0.404 |
| 12 | 9 | 1 | 147.001 | 2.034 | 201.917 | 57.42 | 0.962 |
| 12 | 9 | 3 | 197.842 | 2.696 | 229.664 | 289.64 | 0.976 |
| 12 | 9 | 5 | 87.998 | 3.107 | 93.865 | 3.34 | 0.954 |
| 12 | 9 | 7 | 231.491 | 2.267 | 316.440 | 312.64 | 0.986 |
| 12 | 9 | 9 | 102.956 | 3.137 | 101.420 | 29.75 | 0.840 |
| 12 | 9 | 11 | 208.806 | 2.816 | 230.223 | 163.60 | 0.983 |
| 12 | 9 | 13 | 397.747 | 3.571 | 598.382 | 339.57 | 0.994 |
| 12 | 9 | 15 | 317.388 | 2.990 | 524.511 | 95.12 | 0.989 |
| 12 | 9 | 17 | 487.868 | 4.114 | 716.816 | 133.43 | 0.996 |
| 12 | 9 | 19 | 252.205 | 2.852 | 359.705 | 240.96 | 0.984 |
| 12 | 9 | 21 | 338.192 | 3.278 | 464.816 | 230.62 | 0.992 |
| 12 | 9 | 23 | 44.267 | 9.148 | 28.362 | 93.71 | 0.568 |
| 12 | 9 | 25 | 168.144 | 3.727 | 277.601 | 183.46 | 0.952 |
| 12 | 9 | 27 | 223.862 | 3.679 | 316.781 | 272.21 | 0.983 |
| 12 | 9 | 29 | 134.836 | 5.489 | 232.176 | 150.50 | 0.913 |
| 12 | 9 | 31 | 46.713 | 11.778 | 33.114 | 85.49 | 0.882 |
| 12 | 9 | 33 | 221.254 | 4.151 | 269.111 | 321.33 | 0.989 |
| 12 | 9 | 35 | 117.180 | 7.204 | 173.736 | 147.01 | 0.950 |
| 12 | 9 | 37 | 102.765 | 8.148 | 115.837 | 200.81 | 0.971 |
| 12 | 9 | 39 | 47.098 | 13.271 | 38.338 | 160.81 | 0.720 |
| 12 | 10 | 0 | 155.085 | 4.916 | 222.433 | 0.00 | 1.000 |
| 12 | 10 | 2 | 42.910 | 6.703 | 36.376 | 336.59 | 0.529 |
| 12 | 10 | 4 | 74.493 | 4.496 | 52.076 | 211.14 | 0.754 |
| 12 | 10 | 6 | 85.784 | 3.394 | 61.640 | 298.09 | 0.885 |
| 12 | 10 | 8 | 191.583 | 2.398 | 242.724 | 192.06 | 0.968 |
| 12 | 10 | 10 | 176.742 | 2.518 | 176.121 | 249.60 | 0.974 |
| 12 | 10 | 12 | 387.305 | 3.713 | 557.725 | 337.73 | 0.994 |
| 12 | 10 | 14 | 218.557 | 2.634 | 320.534 | 17.35 | 0.979 |
| 12 | 10 | 16 | 352.941 | 3.281 | 527.313 | 107.79 | 0.992 |
| 12 | 10 | 18 | 244.276 | 2.813 | 372.248 | 167.21 | 0.983 |
| 12 | 10 | 20 | 280.072 | 3.091 | 336.738 | 262.65 | 0.990 |
| 12 | 10 | 22 | 44.791 | 9.306 | 30.162 | 291.07 | 0.726 |
| 12 | 10 | 24 | 145.260 | 4.119 | 129.904 | 187.96 | 0.963 |
| 12 | 10 | 26 | 184.063 | 4.063 | 262.722 | 264.89 | 0.976 |
| 12 | 10 | 28 | 178.642 | 4.263 | 204.653 | 4.64 | 0.985 |
| 12 | 10 | 30 | 152.784 | 5.297 | 228.544 | 122.58 | 0.971 |
| 12 | 10 | 32 | 90.702 | 7.637 | 115.241 | 78.30 | 0.915 |
| 12 | 10 | 34 | 113.936 | 6.270 | 190.957 | 358.05 | 0.918 |
| 12 | 10 | 36 | 93.054 | 9.495 | 117.745 | 115.89 | 0.957 |
| 12 | 10 | 38 | 83.065 | 12.131 | 128.549 | 137.44 | 0.869 |
| 12 | 10 | 40 | 39.773 | 12.904 | 13.720 | 240.45 | 0.648 |
| 12 | 11 | 1 | 425.824 | 3.496 | 572.696 | 199.85 | 0.994 |
| 12 | 11 | 3 | 123.406 | 2.771 | 94.107 | 46.95 | 0.939 |
| 12 | 11 | 5 | 331.032 | 3.645 | 451.130 | 174.54 | 0.991 |
| 12 | 11 | 7 | 135.967 | 2.482 | 169.404 | 205.45 | 0.977 |

| | | | | | | | |
|---|---|---|---|---|---|---|---|
| 12 | 11 | 9  | 248.711 | 2.601  | 328.841 | 183.33 | 0.987 |
| 12 | 11 | 11 | 461.320 | 3.898  | 752.938 | 130.75 | 0.995 |
| 12 | 11 | 13 | 186.130 | 2.840  | 189.586 | 276.17 | 0.980 |
| 12 | 11 | 15 | 83.353  | 4.644  | 84.650  | 21.85  | 0.816 |
| 12 | 11 | 17 | 224.663 | 3.038  | 254.938 | 27.35  | 0.987 |
| 12 | 11 | 19 | 489.885 | 4.339  | 710.948 | 217.26 | 0.996 |
| 12 | 11 | 21 | 194.263 | 3.411  | 209.066 | 11.98  | 0.977 |
| 12 | 11 | 23 | 109.752 | 5.425  | 146.343 | 12.89  | 0.898 |
| 12 | 11 | 25 | 245.214 | 3.452  | 354.144 | 11.73  | 0.987 |
| 12 | 11 | 27 | 402.696 | 3.886  | 648.886 | 347.22 | 0.994 |
| 12 | 11 | 29 | 172.357 | 4.606  | 277.826 | 126.98 | 0.975 |
| 12 | 11 | 31 | 44.621  | 11.639 | 21.911  | 205.17 | 0.408 |
| 12 | 11 | 33 | 30.638  | 9.831  | 19.323  | 137.26 | 0.542 |
| 12 | 11 | 35 | 49.626  | 12.213 | 30.056  | 95.95  | 0.574 |
| 12 | 11 | 37 | 57.675  | 11.615 | 66.366  | 106.39 | 0.838 |
| 12 | 11 | 39 | 54.215  | 14.064 | 52.394  | 1.47   | 0.695 |
| 12 | 12 | 0  | 389.444 | 5.572  | 558.684 | 0.00   | 1.000 |
| 12 | 12 | 2  | 193.569 | 2.334  | 249.728 | 220.59 | 0.973 |
| 12 | 12 | 4  | 228.305 | 2.963  | 321.757 | 122.69 | 0.979 |
| 12 | 12 | 6  | 274.088 | 3.106  | 442.697 | 71.17  | 0.986 |
| 12 | 12 | 8  | 140.726 | 2.495  | 160.765 | 188.67 | 0.965 |
| 12 | 12 | 10 | 153.772 | 2.969  | 172.925 | 168.85 | 0.972 |
| 12 | 12 | 12 | 180.065 | 2.686  | 255.606 | 35.61  | 0.970 |
| 12 | 12 | 14 | 102.752 | 4.063  | 148.948 | 9.70   | 0.861 |
| 12 | 12 | 16 | 416.790 | 3.739  | 522.601 | 127.55 | 0.995 |
| 12 | 12 | 18 | 200.926 | 3.377  | 196.598 | 116.75 | 0.982 |
| 12 | 12 | 20 | 191.460 | 3.216  | 237.761 | 247.68 | 0.974 |
| 12 | 12 | 22 | 214.689 | 3.488  | 299.808 | 333.15 | 0.975 |
| 12 | 12 | 24 | 62.100  | 9.293  | 42.641  | 119.73 | 0.787 |
| 12 | 12 | 26 | 174.924 | 4.348  | 258.495 | 331.09 | 0.971 |
| 12 | 12 | 28 | 161.616 | 5.013  | 311.787 | 244.91 | 0.924 |
| 12 | 12 | 30 | 173.215 | 4.405  | 288.217 | 273.21 | 0.974 |
| 12 | 12 | 32 | 42.823  | 11.984 | 6.377   | 355.18 | 0.326 |
| 12 | 12 | 34 | 34.441  | 11.052 | 4.138   | 55.57  | 0.210 |
| 12 | 12 | 36 | 43.193  | 12.430 | 29.155  | 204.19 | 0.678 |
| 12 | 12 | 38 | 85.617  | 12.913 | 117.317 | 6.48   | 0.690 |
| 12 | 13 | 1  | 283.927 | 2.731  | 409.911 | 11.07  | 0.991 |
| 12 | 13 | 3  | 581.406 | 5.736  | 796.668 | 98.04  | 0.997 |
| 12 | 13 | 5  | 233.928 | 3.162  | 287.033 | 94.43  | 0.985 |
| 12 | 13 | 7  | 318.159 | 2.851  | 436.712 | 128.33 | 0.992 |
| 12 | 13 | 9  | 165.678 | 2.588  | 260.564 | 172.05 | 0.959 |
| 12 | 13 | 11 | 336.915 | 3.356  | 482.061 | 70.97  | 0.991 |
| 12 | 13 | 13 | 89.533  | 4.407  | 55.266  | 114.02 | 0.919 |
| 12 | 13 | 15 | 274.046 | 3.437  | 432.747 | 334.03 | 0.985 |
| 12 | 13 | 17 | 291.645 | 3.474  | 385.396 | 101.51 | 0.989 |
| 12 | 13 | 19 | 315.986 | 3.413  | 426.137 | 55.73  | 0.990 |
| 12 | 13 | 21 | 122.717 | 4.709  | 154.605 | 284.64 | 0.918 |
| 12 | 13 | 23 | 155.303 | 4.126  | 234.541 | 106.24 | 0.963 |
| 12 | 13 | 25 | 56.943  | 10.049 | 41.883  | 129.74 | 0.655 |
| 12 | 13 | 27 | 129.920 | 5.748  | 115.844 | 346.02 | 0.974 |
| 12 | 13 | 29 | 91.834  | 8.059  | 138.983 | 133.21 | 0.894 |
| 12 | 13 | 31 | 105.821 | 6.498  | 167.645 | 24.22  | 0.924 |
| 12 | 13 | 33 | 39.251  | 11.297 | 0.916   | 30.82  | 0.670 |
| 12 | 13 | 35 | 79.571  | 9.458  | 123.039 | 201.00 | 0.912 |
| 12 | 13 | 37 | 60.124  | 11.354 | 74.335  | 209.56 | 0.809 |
| 12 | 14 | 0  | 389.178 | 4.448  | 558.169 | 0.00   | 1.000 |
| 12 | 14 | 2  | 67.490  | 5.674  | 80.504  | 22.93  | 0.750 |
| 12 | 14 | 4  | 126.540 | 3.373  | 156.372 | 70.27  | 0.954 |
| 12 | 14 | 6  | 167.402 | 3.010  | 288.212 | 50.10  | 0.952 |
| 12 | 14 | 8  | 244.563 | 2.612  | 325.352 | 261.90 | 0.987 |
| 12 | 14 | 10 | 322.879 | 2.910  | 437.167 | 182.41 | 0.992 |
| 12 | 14 | 12 | 202.182 | 3.023  | 316.152 | 27.82  | 0.973 |
| 12 | 14 | 14 | 359.447 | 3.259  | 469.338 | 54.42  | 0.993 |
| 12 | 14 | 16 | 295.206 | 3.256  | 385.233 | 109.83 | 0.990 |
| 12 | 14 | 18 | 264.169 | 3.250  | 360.158 | 47.27  | 0.985 |
| 12 | 14 | 20 | 231.241 | 4.122  | 346.207 | 326.49 | 0.977 |
| 12 | 14 | 22 | 115.004 | 5.397  | 110.484 | 210.73 | 0.960 |
| 12 | 14 | 24 | 123.323 | 5.857  | 214.992 | 132.27 | 0.906 |
| 12 | 14 | 26 | 162.614 | 4.964  | 220.981 | 10.82  | 0.978 |
| 12 | 14 | 28 | 40.038  | 11.021 | 1.767   | 243.27 | 0.588 |
| 12 | 14 | 30 | 75.698  | 11.069 | 75.580  | 173.25 | 0.506 |
| 12 | 14 | 32 | 36.270  | 10.866 | 4.273   | 244.48 | 0.447 |
| 12 | 14 | 34 | 69.425  | 10.143 | 78.127  | 224.00 | 0.929 |
| 12 | 14 | 36 | 38.826  | 11.828 | 19.049  | 253.24 | 0.437 |
| 12 | 14 | 38 | 32.097  | 11.181 | 2.286   | 223.52 | 0.435 |
| 12 | 15 | 1  | 298.127 | 2.711  | 426.839 | 15.88  | 0.991 |
| 12 | 15 | 3  | 161.964 | 2.954  | 231.430 | 325.83 | 0.966 |

| | | | | | | | |
|---|---|---|---|---|---|---|---|
| 12 | 15 | 5 | 125.301 | 3.940 | 196.864 | 224.58 | 0.889 |
| 12 | 15 | 7 | 550.047 | 4.902 | 789.479 | 301.70 | 0.997 |
| 12 | 15 | 9 | 112.335 | 3.366 | 170.076 | 311.63 | 0.868 |
| 12 | 15 | 11 | 178.754 | 2.859 | 293.973 | 234.88 | 0.957 |
| 12 | 15 | 13 | 134.557 | 3.896 | 171.464 | 208.62 | 0.951 |
| 12 | 15 | 15 | 82.621 | 5.611 | 93.021 | 322.89 | 0.833 |
| 12 | 15 | 17 | 170.643 | 3.970 | 247.201 | 106.14 | 0.959 |
| 12 | 15 | 19 | 261.089 | 3.375 | 341.391 | 195.42 | 0.987 |
| 12 | 15 | 21 | 278.599 | 3.992 | 378.999 | 289.68 | 0.990 |
| 12 | 15 | 23 | 326.510 | 3.718 | 495.147 | 171.27 | 0.992 |
| 12 | 15 | 25 | 80.321 | 8.026 | 83.667 | 294.18 | 0.931 |
| 12 | 15 | 27 | 111.637 | 5.721 | 190.936 | 150.86 | 0.905 |
| 12 | 15 | 29 | 62.056 | 11.972 | 51.241 | 188.81 | 0.836 |
| 12 | 15 | 31 | 59.811 | 12.471 | 59.346 | 253.39 | 0.796 |
| 12 | 15 | 33 | 84.327 | 7.694 | 143.533 | 184.25 | 0.910 |
| 12 | 15 | 35 | 77.202 | 11.299 | 83.906 | 1.95 | 0.940 |
| 12 | 15 | 37 | 57.998 | 14.819 | 46.455 | 61.23 | 0.873 |
| 12 | 16 | 0 | 101.606 | 6.783 | 129.735 | 180.00 | 0.892 |
| 12 | 16 | 2 | 124.967 | 3.417 | 181.450 | 90.37 | 0.922 |
| 12 | 16 | 4 | 70.394 | 5.632 | 75.095 | 30.98 | 0.734 |
| 12 | 16 | 6 | 130.942 | 4.781 | 222.124 | 219.95 | 0.903 |
| 12 | 16 | 8 | 133.498 | 4.018 | 157.432 | 5.92 | 0.955 |
| 12 | 16 | 10 | 420.380 | 3.588 | 679.552 | 302.28 | 0.994 |
| 12 | 16 | 12 | 261.223 | 2.984 | 367.143 | 27.16 | 0.987 |
| 12 | 16 | 14 | 489.586 | 4.536 | 648.025 | 288.65 | 0.996 |
| 12 | 16 | 16 | 184.755 | 3.236 | 217.335 | 254.60 | 0.975 |
| 12 | 16 | 18 | 301.101 | 3.742 | 419.549 | 216.51 | 0.989 |
| 12 | 16 | 20 | 282.208 | 4.111 | 414.783 | 273.72 | 0.990 |
| 12 | 16 | 22 | 188.296 | 4.048 | 229.528 | 177.10 | 0.980 |
| 12 | 16 | 24 | 239.994 | 3.435 | 305.338 | 160.29 | 0.991 |
| 12 | 16 | 26 | 126.537 | 5.669 | 176.400 | 258.79 | 0.961 |
| 12 | 16 | 28 | 127.060 | 5.878 | 170.303 | 209.40 | 0.963 |
| 12 | 16 | 30 | 34.851 | 10.652 | 4.056 | 145.98 | 0.376 |
| 12 | 16 | 32 | 56.107 | 12.090 | 69.166 | 60.43 | 0.818 |
| 12 | 16 | 34 | 47.832 | 13.238 | 38.687 | 176.81 | 0.746 |
| 12 | 16 | 36 | 63.718 | 14.444 | 68.132 | 68.16 | 0.871 |
| 12 | 17 | 1 | 268.866 | 2.802 | 309.568 | 177.41 | 0.991 |
| 12 | 17 | 3 | 258.215 | 2.836 | 387.416 | 257.07 | 0.985 |
| 12 | 17 | 5 | 307.469 | 4.503 | 486.032 | 182.52 | 0.989 |
| 12 | 17 | 7 | 227.877 | 3.449 | 324.141 | 19.20 | 0.984 |
| 12 | 17 | 9 | 382.715 | 3.520 | 538.371 | 284.30 | 0.994 |
| 12 | 17 | 11 | 332.715 | 3.141 | 435.572 | 309.05 | 0.992 |
| 12 | 17 | 13 | 202.308 | 3.372 | 301.955 | 162.45 | 0.972 |
| 12 | 17 | 15 | 284.191 | 3.493 | 359.375 | 228.46 | 0.988 |
| 12 | 17 | 17 | 257.660 | 3.524 | 425.096 | 156.34 | 0.986 |
| 12 | 17 | 19 | 250.088 | 3.309 | 320.801 | 8.99 | 0.990 |
| 12 | 17 | 21 | 176.777 | 4.491 | 228.851 | 268.63 | 0.977 |
| 12 | 17 | 23 | 72.463 | 10.680 | 59.362 | 358.60 | 0.906 |
| 12 | 17 | 25 | 45.275 | 11.351 | 19.535 | 199.44 | 0.673 |
| 12 | 17 | 27 | 134.663 | 6.333 | 218.102 | 286.36 | 0.956 |
| 12 | 17 | 29 | 64.418 | 9.930 | 76.889 | 314.87 | 0.649 |
| 12 | 17 | 31 | 70.939 | 10.746 | 107.845 | 3.92 | 0.794 |
| 12 | 17 | 33 | 107.294 | 10.019 | 158.083 | 162.04 | 0.646 |
| 12 | 17 | 35 | 38.987 | 10.588 | 21.162 | 100.33 | 0.635 |
| 12 | 18 | 0 | 95.142 | 8.134 | 105.355 | 180.00 | 0.774 |
| 12 | 18 | 2 | 110.074 | 4.667 | 129.749 | 216.89 | 0.940 |
| 12 | 18 | 4 | 280.353 | 3.212 | 429.267 | 199.52 | 0.987 |
| 12 | 18 | 6 | 229.011 | 3.435 | 366.997 | 104.78 | 0.978 |
| 12 | 18 | 8 | 175.481 | 3.434 | 203.229 | 265.00 | 0.972 |
| 12 | 18 | 10 | 349.367 | 3.292 | 521.010 | 178.38 | 0.991 |
| 12 | 18 | 12 | 200.803 | 3.050 | 299.807 | 27.99 | 0.972 |
| 12 | 18 | 14 | 64.063 | 8.047 | 52.999 | 182.02 | 0.650 |
| 12 | 18 | 16 | 95.471 | 7.320 | 141.704 | 277.82 | 0.874 |
| 12 | 18 | 18 | 362.153 | 3.669 | 505.182 | 72.19 | 0.994 |
| 12 | 18 | 20 | 86.047 | 7.863 | 52.753 | 10.62 | 0.949 |
| 12 | 18 | 22 | 64.734 | 11.185 | 75.644 | 135.25 | 0.776 |
| 12 | 18 | 24 | 55.482 | 11.045 | 2.195 | 25.50 | 0.049 |
| 12 | 18 | 26 | 65.906 | 9.712 | 73.866 | 300.35 | 0.817 |
| 12 | 18 | 28 | 44.328 | 11.027 | 7.826 | 36.80 | 0.118 |
| 12 | 18 | 30 | 142.507 | 5.594 | 211.337 | 62.65 | 0.982 |
| 12 | 18 | 32 | 58.305 | 10.244 | 77.189 | 355.93 | 0.817 |
| 12 | 18 | 34 | 39.690 | 12.737 | 17.557 | 10.39 | 0.677 |
| 12 | 19 | 1 | 235.848 | 2.918 | 343.565 | 276.55 | 0.981 |
| 12 | 19 | 3 | 150.315 | 3.853 | 155.563 | 321.68 | 0.964 |
| 12 | 19 | 5 | 259.741 | 3.500 | 360.680 | 134.16 | 0.986 |
| 12 | 19 | 7 | 229.833 | 4.111 | 322.223 | 357.18 | 0.981 |
| 12 | 19 | 9 | 166.244 | 4.256 | 256.999 | 58.31 | 0.956 |

| | | | | | | | |
|---|---|---|---|---|---|---|---|
| 12 | 19 | 11 | 281.120 | 3.194 | 345.855 | 22.68 | 0.989 |
| 12 | 19 | 13 | 251.598 | 3.162 | 319.041 | 12.68 | 0.990 |
| 12 | 19 | 15 | 112.010 | 5.413 | 130.188 | 110.29 | 0.946 |
| 12 | 19 | 17 | 194.059 | 4.397 | 269.333 | 12.48 | 0.980 |
| 12 | 19 | 19 | 175.186 | 3.925 | 351.309 | 72.78 | 0.955 |
| 12 | 19 | 21 | 134.172 | 4.612 | 170.192 | 355.18 | 0.972 |
| 12 | 19 | 23 | 84.915 | 11.574 | 96.898 | 195.95 | 0.917 |
| 12 | 19 | 25 | 115.969 | 7.204 | 189.654 | 288.72 | 0.924 |
| 12 | 19 | 27 | 210.538 | 6.450 | 300.794 | 281.25 | 0.988 |
| 12 | 19 | 29 | 51.584 | 10.996 | 59.159 | 127.66 | 0.807 |
| 12 | 19 | 31 | 53.619 | 13.170 | 44.877 | 153.03 | 0.868 |
| 12 | 19 | 33 | 47.927 | 13.083 | 34.103 | 310.90 | 0.469 |
| 12 | 20 | 0 | 172.989 | 5.073 | 247.527 | 180.00 | 1.000 |
| 12 | 20 | 2 | 88.267 | 5.987 | 120.448 | 61.06 | 0.765 |
| 12 | 20 | 4 | 94.677 | 6.877 | 83.812 | 75.57 | 0.900 |
| 12 | 20 | 6 | 121.493 | 5.385 | 155.125 | 112.65 | 0.872 |
| 12 | 20 | 8 | 202.663 | 3.965 | 225.934 | 108.30 | 0.980 |
| 12 | 20 | 10 | 261.127 | 4.000 | 353.858 | 43.94 | 0.990 |
| 12 | 20 | 12 | 214.586 | 3.490 | 295.038 | 355.04 | 0.985 |
| 12 | 20 | 14 | 245.067 | 3.378 | 376.114 | 10.70 | 0.987 |
| 12 | 20 | 16 | 102.773 | 5.783 | 98.731 | 145.26 | 0.937 |
| 12 | 20 | 18 | 77.740 | 9.392 | 70.228 | 51.39 | 0.923 |
| 12 | 20 | 20 | 28.283 | 9.483 | 21.445 | 150.17 | 0.410 |
| 12 | 20 | 22 | 92.811 | 8.186 | 103.404 | 292.07 | 0.941 |
| 12 | 20 | 24 | 53.371 | 12.997 | 44.909 | 38.43 | 0.730 |
| 12 | 20 | 26 | 132.022 | 5.429 | 175.136 | 302.23 | 0.972 |
| 12 | 20 | 28 | 34.375 | 10.833 | 26.204 | 344.12 | 0.858 |
| 12 | 20 | 30 | 56.066 | 13.389 | 33.409 | 283.87 | 0.345 |
| 12 | 20 | 32 | 40.910 | 12.162 | 6.203 | 251.20 | 0.123 |
| 12 | 21 | 1 | 210.802 | 3.300 | 303.512 | 39.57 | 0.977 |
| 12 | 21 | 3 | 42.658 | 10.667 | 1.412 | 246.05 | 0.076 |
| 12 | 21 | 5 | 195.972 | 3.904 | 366.080 | 120.58 | 0.956 |
| 12 | 21 | 7 | 60.663 | 10.470 | 17.040 | 108.32 | 0.888 |
| 12 | 21 | 9 | 49.464 | 11.894 | 20.584 | 109.39 | 0.563 |
| 12 | 21 | 11 | 121.411 | 4.943 | 114.031 | 196.72 | 0.962 |
| 12 | 21 | 13 | 152.434 | 3.914 | 226.683 | 199.32 | 0.966 |
| 12 | 21 | 15 | 108.826 | 6.261 | 127.924 | 207.81 | 0.958 |
| 12 | 21 | 17 | 228.853 | 3.678 | 353.760 | 81.52 | 0.988 |
| 12 | 21 | 19 | 123.384 | 5.741 | 148.893 | 82.97 | 0.967 |
| 12 | 21 | 21 | 158.483 | 4.029 | 206.395 | 228.93 | 0.980 |
| 12 | 21 | 23 | 52.835 | 10.479 | 34.384 | 284.29 | 0.585 |
| 12 | 21 | 25 | 122.886 | 5.778 | 168.169 | 316.52 | 0.966 |
| 12 | 21 | 27 | 37.765 | 11.387 | 20.726 | 185.36 | 0.706 |
| 12 | 21 | 29 | 52.944 | 15.677 | 32.265 | 178.79 | 0.863 |
| 12 | 21 | 31 | 44.060 | 13.779 | 25.466 | 113.47 | 0.475 |
| 12 | 22 | 0 | 43.499 | 14.261 | 36.443 | 0.00 | 0.593 |
| 12 | 22 | 2 | 115.336 | 5.570 | 212.661 | 182.11 | 0.779 |
| 12 | 22 | 4 | 192.833 | 4.445 | 326.275 | 8.94 | 0.975 |
| 12 | 22 | 6 | 202.756 | 3.999 | 262.113 | 16.61 | 0.985 |
| 12 | 22 | 8 | 98.683 | 8.345 | 165.226 | 332.24 | 0.834 |
| 12 | 22 | 10 | 126.414 | 8.126 | 193.759 | 309.00 | 0.944 |
| 12 | 22 | 12 | 104.843 | 5.812 | 121.310 | 293.89 | 0.962 |
| 12 | 22 | 14 | 67.857 | 8.212 | 87.663 | 142.04 | 0.828 |
| 12 | 22 | 16 | 205.442 | 3.886 | 331.055 | 92.24 | 0.985 |
| 12 | 22 | 18 | 79.357 | 9.359 | 28.993 | 297.99 | 0.949 |
| 12 | 22 | 20 | 70.626 | 9.967 | 87.851 | 59.11 | 0.847 |
| 12 | 22 | 22 | 125.005 | 6.279 | 139.353 | 273.39 | 0.974 |
| 12 | 22 | 24 | 46.057 | 11.119 | 14.620 | 190.08 | 0.797 |
| 12 | 22 | 26 | 68.162 | 10.772 | 95.758 | 281.16 | 0.896 |
| 12 | 22 | 28 | 41.860 | 13.530 | 15.678 | 268.98 | 0.785 |
| 12 | 22 | 30 | 34.549 | 11.664 | 15.402 | 0.03 | 0.574 |
| 12 | 23 | 1 | 158.256 | 5.344 | 281.923 | 337.64 | 0.946 |
| 12 | 23 | 3 | 39.486 | 10.909 | 13.965 | 297.95 | 0.683 |
| 12 | 23 | 5 | 101.381 | 6.004 | 164.899 | 304.61 | 0.866 |
| 12 | 23 | 7 | 67.175 | 10.286 | 50.767 | 133.79 | 0.865 |
| 12 | 23 | 9 | 56.247 | 12.230 | 28.875 | 105.85 | 0.304 |
| 12 | 23 | 11 | 59.958 | 9.924 | 57.445 | 7.20 | 0.597 |
| 12 | 23 | 13 | 119.179 | 5.825 | 196.375 | 259.88 | 0.949 |
| 12 | 23 | 15 | 34.063 | 10.139 | 2.729 | 315.92 | 0.477 |
| 12 | 23 | 17 | 125.468 | 5.763 | 198.792 | 17.76 | 0.957 |
| 12 | 23 | 19 | 52.592 | 10.179 | 28.873 | 138.09 | 0.827 |
| 12 | 23 | 21 | 52.653 | 11.757 | 46.669 | 239.14 | 0.599 |
| 12 | 23 | 23 | 95.205 | 10.419 | 103.414 | 128.46 | 0.948 |
| 12 | 23 | 25 | 125.937 | 8.680 | 181.248 | 112.79 | 0.978 |
| 12 | 23 | 27 | 70.775 | 13.454 | 104.769 | 134.07 | 0.810 |
| 12 | 23 | 29 | 40.011 | 12.474 | 10.425 | 139.23 | 0.816 |
| 12 | 24 | 0 | 217.568 | 6.624 | 310.508 | 0.00 | 1.000 |

| | | | | | | | |
|---|---|---|---|---|---|---|---|
| 12 | 24 | 2 | 205.310 | 4.116 | 307.096 | 292.38 | 0.987 |
| 12 | 24 | 4 | 114.244 | 6.584 | 147.797 | 318.23 | 0.960 |
| 12 | 24 | 6 | 277.027 | 3.699 | 394.111 | 246.38 | 0.993 |
| 12 | 24 | 8 | 39.809 | 11.974 | 23.738 | 77.95 | 0.810 |
| 12 | 24 | 10 | 55.082 | 9.633 | 37.303 | 218.59 | 0.846 |
| 12 | 24 | 12 | 77.146 | 9.032 | 109.626 | 129.92 | 0.877 |
| 12 | 24 | 14 | 137.442 | 4.865 | 165.084 | 184.16 | 0.975 |
| 12 | 24 | 16 | 168.175 | 4.478 | 264.053 | 133.59 | 0.977 |
| 12 | 24 | 18 | 190.886 | 4.351 | 290.343 | 240.64 | 0.986 |
| 12 | 24 | 20 | 56.845 | 11.044 | 43.459 | 298.22 | 0.828 |
| 12 | 24 | 22 | 165.199 | 4.952 | 232.807 | 138.16 | 0.989 |
| 12 | 24 | 24 | 110.669 | 9.282 | 154.960 | 51.94 | 0.972 |
| 12 | 24 | 26 | 133.831 | 8.997 | 223.754 | 34.95 | 0.975 |
| 12 | 24 | 28 | 41.276 | 13.234 | 12.231 | 121.65 | 0.805 |
| 12 | 25 | 1 | 96.152 | 7.540 | 122.908 | 303.38 | 0.943 |
| 12 | 25 | 3 | 109.599 | 5.836 | 153.096 | 245.88 | 0.955 |
| 12 | 25 | 5 | 275.495 | 3.732 | 416.948 | 220.50 | 0.993 |
| 12 | 25 | 7 | 126.432 | 4.573 | 251.273 | 146.60 | 0.928 |
| 12 | 25 | 9 | 111.893 | 6.434 | 148.582 | 326.01 | 0.956 |
| 12 | 25 | 11 | 119.625 | 5.999 | 218.416 | 187.11 | 0.937 |
| 12 | 25 | 13 | 120.559 | 6.173 | 147.941 | 338.59 | 0.966 |
| 12 | 25 | 15 | 132.953 | 5.635 | 199.793 | 77.05 | 0.971 |
| 12 | 25 | 17 | 35.143 | 10.195 | 20.233 | 97.21 | 0.757 |
| 12 | 25 | 19 | 114.349 | 6.968 | 167.952 | 354.16 | 0.958 |
| 12 | 25 | 21 | 165.632 | 6.214 | 271.079 | 351.24 | 0.986 |
| 12 | 25 | 23 | 39.065 | 13.073 | 17.826 | 270.19 | 0.513 |
| 12 | 25 | 25 | 43.739 | 12.637 | 28.794 | 45.86 | 0.507 |
| 12 | 26 | 0 | 31.162 | 15.026 | 25.163 | 180.00 | 0.580 |
| 12 | 26 | 2 | 186.156 | 3.935 | 275.278 | 69.78 | 0.984 |
| 12 | 26 | 4 | 64.750 | 10.803 | 80.077 | 311.31 | 0.760 |
| 12 | 26 | 6 | 52.066 | 11.392 | 33.006 | 234.21 | 0.578 |
| 12 | 26 | 8 | 114.315 | 6.991 | 154.511 | 201.98 | 0.957 |
| 12 | 26 | 10 | 128.727 | 9.326 | 255.572 | 45.70 | 0.919 |
| 12 | 26 | 12 | 95.106 | 9.346 | 152.363 | 200.18 | 0.925 |
| 12 | 26 | 14 | 117.785 | 6.566 | 181.870 | 273.44 | 0.959 |
| 12 | 26 | 16 | 39.323 | 10.393 | 16.292 | 25.41 | 0.530 |
| 12 | 26 | 18 | 78.846 | 8.316 | 94.339 | 19.35 | 0.956 |
| 12 | 26 | 20 | 75.388 | 11.721 | 118.259 | 191.46 | 0.881 |
| 12 | 26 | 22 | 33.510 | 11.085 | 11.763 | 105.43 | 0.641 |
| 12 | 26 | 24 | 90.417 | 14.998 | 115.485 | 212.18 | 0.944 |
| 12 | 27 | 1 | 65.588 | 8.853 | 72.685 | 309.91 | 0.586 |
| 12 | 27 | 3 | 35.601 | 10.444 | 0.365 | 127.85 | 0.575 |
| 12 | 27 | 5 | 78.043 | 8.476 | 109.571 | 5.19 | 0.882 |
| 12 | 27 | 7 | 115.111 | 5.798 | 180.423 | 37.06 | 0.948 |
| 12 | 27 | 9 | 63.564 | 11.041 | 62.012 | 105.12 | 0.518 |
| 12 | 27 | 11 | 51.890 | 11.857 | 48.486 | 196.54 | 0.670 |
| 12 | 27 | 13 | 85.243 | 11.019 | 112.641 | 136.27 | 0.923 |
| 12 | 27 | 15 | 44.428 | 11.255 | 41.947 | 52.09 | 0.781 |
| 12 | 27 | 17 | 31.219 | 9.804 | 2.987 | 57.26 | 0.084 |
| 12 | 27 | 19 | 73.084 | 14.659 | 97.633 | 269.32 | 0.901 |
| 12 | 27 | 21 | 38.127 | 12.363 | 18.148 | 169.43 | 0.697 |
| 12 | 27 | 23 | 32.418 | 11.269 | 4.918 | 130.30 | 0.280 |
| 12 | 28 | 0 | 45.108 | 17.196 | 43.366 | 180.00 | 0.699 |
| 12 | 28 | 2 | 34.577 | 10.306 | 26.245 | 328.26 | 0.766 |
| 12 | 28 | 4 | 31.647 | 10.278 | 2.936 | 217.90 | 0.316 |
| 12 | 28 | 6 | 38.316 | 12.019 | 15.582 | 270.23 | 0.415 |
| 12 | 28 | 8 | 114.154 | 6.511 | 169.360 | 56.81 | 0.960 |
| 12 | 28 | 10 | 67.218 | 10.888 | 26.391 | 128.04 | 0.930 |
| 12 | 28 | 12 | 36.935 | 11.252 | 19.843 | 354.39 | 0.411 |
| 12 | 28 | 14 | 53.610 | 13.652 | 52.402 | 135.98 | 0.569 |
| 12 | 28 | 16 | 38.411 | 11.777 | 11.281 | 90.26 | 0.795 |
| 12 | 28 | 18 | 50.635 | 13.633 | 54.172 | 150.15 | 0.671 |
| 12 | 28 | 20 | 43.576 | 13.653 | 23.487 | 304.67 | 0.788 |
| 12 | 29 | 1 | 155.004 | 5.369 | 244.599 | 99.07 | 0.978 |
| 12 | 29 | 3 | 49.314 | 11.770 | 33.178 | 148.82 | 0.754 |
| 12 | 29 | 5 | 73.694 | 9.392 | 113.443 | 115.86 | 0.812 |
| 12 | 29 | 7 | 60.143 | 10.524 | 80.246 | 102.16 | 0.894 |
| 12 | 29 | 9 | 66.043 | 9.469 | 93.419 | 192.69 | 0.904 |
| 12 | 29 | 11 | 44.630 | 12.431 | 36.398 | 301.35 | 0.789 |
| 12 | 29 | 13 | 52.761 | 14.134 | 58.662 | 342.76 | 0.725 |
| 12 | 29 | 15 | 44.186 | 14.293 | 17.459 | 249.24 | 0.257 |
| 12 | 29 | 17 | 54.004 | 14.593 | 53.646 | 160.57 | 0.816 |
| 12 | 29 | 19 | 28.855 | 9.812 | 5.145 | 178.71 | 0.376 |
| 12 | 30 | 0 | 68.867 | 22.589 | 77.982 | 180.00 | 0.884 |
| 12 | 30 | 2 | 44.162 | 10.673 | 41.454 | 190.69 | 0.596 |
| 12 | 30 | 4 | 114.512 | 8.064 | 174.524 | 136.88 | 0.973 |
| 12 | 30 | 6 | 47.927 | 12.719 | 46.757 | 213.10 | 0.671 |

| | | | | | | | |
|---|---|---|---|---|---|---|---|
| 12 | 30 | 8 | 92.929 | 10.384 | 162.617 | 266.65 | 0.932 |
| 12 | 30 | 10 | 53.981 | 13.475 | 63.545 | 162.35 | 0.671 |
| 12 | 30 | 12 | 35.016 | 11.558 | 18.476 | 224.88 | 0.590 |
| 12 | 30 | 14 | 42.629 | 12.637 | 27.978 | 52.47 | 0.757 |
| 12 | 30 | 16 | 51.712 | 14.910 | 38.684 | 52.34 | 0.826 |
| 12 | 31 | 1 | 41.943 | 12.198 | 36.311 | 135.50 | 0.637 |
| 12 | 31 | 3 | 82.095 | 10.045 | 129.538 | 250.09 | 0.936 |
| 12 | 31 | 5 | 73.816 | 11.308 | 114.074 | 261.21 | 0.763 |
| 12 | 31 | 7 | 54.469 | 13.761 | 65.538 | 324.77 | 0.796 |
| 12 | 31 | 9 | 36.557 | 11.383 | 21.476 | 243.39 | 0.653 |
| 12 | 31 | 11 | 35.839 | 11.100 | 16.521 | 221.55 | 0.724 |
| 12 | 32 | 0 | 24.970 | 17.008 | 3.185 | 0.00 | 0.105 |
| 12 | 32 | 2 | 39.397 | 12.022 | 25.039 | 325.52 | 0.518 |
| 12 | 32 | 4 | 79.568 | 10.746 | 118.231 | 165.55 | 0.671 |
| 12 | 32 | 6 | 45.677 | 12.507 | 36.913 | 173.07 | 0.818 |
| 13 | 0 | 1 | 39.370 | 6.498 | 26.621 | 180.00 | 0.483 |
| 13 | 0 | 3 | 14.632 | 6.539 | 10.555 | 180.00 | 0.500 |
| 13 | 0 | 5 | 239.897 | 3.409 | 345.513 | 180.00 | 1.000 |
| 13 | 0 | 7 | 271.958 | 3.024 | 391.141 | 180.00 | 1.000 |
| 13 | 0 | 9 | 218.716 | 2.713 | 314.106 | 0.00 | 1.000 |
| 13 | 0 | 11 | 116.837 | 3.086 | 166.826 | 180.00 | 0.999 |
| 13 | 0 | 13 | 158.000 | 3.058 | 222.649 | 0.00 | 0.988 |
| 13 | 0 | 15 | 160.416 | 3.759 | 228.214 | 180.00 | 1.000 |
| 13 | 0 | 17 | 266.411 | 3.730 | 377.336 | 0.00 | 1.000 |
| 13 | 0 | 19 | 339.306 | 4.560 | 478.342 | 180.00 | 1.000 |
| 13 | 0 | 21 | 44.278 | 12.248 | 30.407 | 0.00 | 0.491 |
| 13 | 0 | 23 | 169.426 | 4.358 | 236.202 | 180.00 | 1.000 |
| 13 | 0 | 25 | 99.660 | 7.789 | 137.637 | 180.00 | 0.999 |
| 13 | 0 | 27 | 323.745 | 5.039 | 445.592 | 0.00 | 1.000 |
| 13 | 0 | 29 | 78.268 | 12.414 | 105.565 | 0.00 | 0.992 |
| 13 | 0 | 31 | 210.680 | 6.159 | 285.196 | 180.00 | 1.000 |
| 13 | 0 | 33 | 45.809 | 16.564 | 46.972 | 0.00 | 0.776 |
| 13 | 0 | 35 | 28.090 | 13.432 | 27.930 | 0.00 | 0.762 |
| 13 | 0 | 37 | 152.039 | 8.411 | 198.754 | 180.00 | 1.000 |
| 13 | 0 | 39 | 32.134 | 14.900 | 16.209 | 180.00 | 0.406 |
| 13 | 0 | 41 | 35.452 | 15.934 | 3.804 | 180.00 | 0.090 |
| 13 | 1 | 0 | 251.345 | 3.924 | 362.817 | 180.00 | 1.000 |
| 13 | 1 | 2 | 568.891 | 5.426 | 874.981 | 78.55 | 0.997 |
| 13 | 1 | 4 | 220.664 | 2.450 | 316.907 | 89.45 | 0.986 |
| 13 | 1 | 6 | 65.144 | 2.337 | 38.315 | 83.84 | 0.786 |
| 13 | 1 | 8 | 179.931 | 1.745 | 262.716 | 105.85 | 0.983 |
| 13 | 1 | 10 | 105.267 | 2.395 | 115.467 | 313.76 | 0.920 |
| 13 | 1 | 12 | 112.666 | 2.671 | 131.703 | 314.80 | 0.908 |
| 13 | 1 | 14 | 272.019 | 2.552 | 456.109 | 53.78 | 0.979 |
| 13 | 1 | 16 | 114.948 | 3.000 | 156.979 | 20.05 | 0.891 |
| 13 | 1 | 18 | 495.379 | 4.481 | 694.319 | 229.94 | 0.996 |
| 13 | 1 | 20 | 393.108 | 3.569 | 573.728 | 335.09 | 0.993 |
| 13 | 1 | 22 | 418.849 | 3.771 | 551.120 | 259.74 | 0.995 |
| 13 | 1 | 24 | 410.534 | 3.809 | 578.737 | 350.77 | 0.994 |
| 13 | 1 | 26 | 54.225 | 9.764 | 9.231 | 315.26 | 0.570 |
| 13 | 1 | 28 | 163.723 | 4.251 | 228.059 | 133.19 | 0.971 |
| 13 | 1 | 30 | 124.411 | 5.408 | 131.625 | 308.26 | 0.969 |
| 13 | 1 | 32 | 44.972 | 11.072 | 21.539 | 236.49 | 0.620 |
| 13 | 1 | 34 | 34.466 | 10.511 | 5.275 | 191.05 | 0.286 |
| 13 | 1 | 36 | 130.953 | 6.218 | 191.095 | 121.26 | 0.963 |
| 13 | 1 | 38 | 37.630 | 11.328 | 14.950 | 126.48 | 0.389 |
| 13 | 1 | 40 | 35.037 | 11.236 | 8.772 | 55.12 | 0.638 |
| 13 | 2 | 1 | 140.374 | 2.543 | 171.440 | 2.62 | 0.979 |
| 13 | 2 | 3 | 121.890 | 2.286 | 194.121 | 299.94 | 0.878 |
| 13 | 2 | 5 | 254.726 | 2.690 | 353.490 | 128.16 | 0.985 |
| 13 | 2 | 7 | 221.523 | 2.028 | 304.553 | 269.36 | 0.982 |
| 13 | 2 | 9 | 139.396 | 1.909 | 144.246 | 57.14 | 0.959 |
| 13 | 2 | 11 | 225.341 | 2.141 | 303.150 | 8.53 | 0.986 |
| 13 | 2 | 13 | 319.568 | 2.880 | 415.534 | 169.99 | 0.991 |
| 13 | 2 | 15 | 152.588 | 2.540 | 295.560 | 279.16 | 0.901 |
| 13 | 2 | 17 | 185.846 | 2.643 | 290.689 | 350.35 | 0.975 |
| 13 | 2 | 19 | 34.851 | 8.089 | 16.261 | 273.74 | 0.153 |
| 13 | 2 | 21 | 395.171 | 3.820 | 531.012 | 152.95 | 0.994 |
| 13 | 2 | 23 | 79.483 | 6.310 | 65.300 | 128.30 | 0.836 |
| 13 | 2 | 25 | 178.982 | 3.615 | 206.117 | 37.82 | 0.972 |
| 13 | 2 | 27 | 51.360 | 10.040 | 19.316 | 143.98 | 0.446 |
| 13 | 2 | 29 | 137.108 | 4.719 | 256.925 | 44.75 | 0.898 |
| 13 | 2 | 31 | 86.571 | 8.698 | 130.581 | 112.56 | 0.854 |
| 13 | 2 | 33 | 65.772 | 10.143 | 56.905 | 264.06 | 0.858 |
| 13 | 2 | 35 | 49.055 | 12.838 | 26.647 | 139.57 | 0.693 |
| 13 | 2 | 37 | 46.121 | 13.205 | 26.982 | 235.43 | 0.834 |
| 13 | 2 | 39 | 33.081 | 10.642 | 17.129 | 220.26 | 0.789 |

| | | | | | | | |
|---|---|---|---|---|---|---|---|
| 13 | 2 | 41 | 40.942 | 12.783 | 19.581 | 45.37 | 0.404 |
| 13 | 3 | 0 | 178.850 | 3.401 | 258.112 | 180.00 | 1.000 |
| 13 | 3 | 2 | 118.094 | 2.922 | 175.241 | 3.27 | 0.920 |
| 13 | 3 | 4 | 336.871 | 3.251 | 438.149 | 288.62 | 0.992 |
| 13 | 3 | 6 | 549.260 | 5.922 | 789.584 | 232.67 | 0.996 |
| 13 | 3 | 8 | 180.717 | 1.906 | 250.976 | 158.14 | 0.959 |
| 13 | 3 | 10 | 259.020 | 2.491 | 409.404 | 102.44 | 0.984 |
| 13 | 3 | 12 | 234.755 | 2.348 | 354.805 | 257.14 | 0.973 |
| 13 | 3 | 14 | 277.270 | 2.853 | 385.691 | 352.15 | 0.987 |
| 13 | 3 | 16 | 527.703 | 5.572 | 718.435 | 259.92 | 0.997 |
| 13 | 3 | 18 | 125.350 | 3.928 | 133.266 | 169.87 | 0.950 |
| 13 | 3 | 20 | 274.418 | 3.185 | 365.709 | 246.66 | 0.989 |
| 13 | 3 | 22 | 218.045 | 3.030 | 304.737 | 291.78 | 0.981 |
| 13 | 3 | 24 | 329.734 | 3.348 | 461.909 | 212.71 | 0.990 |
| 13 | 3 | 26 | 169.492 | 4.790 | 215.012 | 301.21 | 0.966 |
| 13 | 3 | 28 | 130.885 | 8.036 | 153.462 | 200.14 | 0.957 |
| 13 | 3 | 30 | 88.694 | 12.485 | 131.717 | 181.87 | 0.874 |
| 13 | 3 | 32 | 217.842 | 4.945 | 376.637 | 121.72 | 0.983 |
| 13 | 3 | 34 | 87.382 | 8.692 | 76.168 | 81.75 | 0.939 |
| 13 | 3 | 36 | 32.421 | 10.431 | 13.780 | 246.34 | 0.549 |
| 13 | 3 | 38 | 30.311 | 9.903 | 0.516 | 118.03 | 0.293 |
| 13 | 3 | 40 | 41.048 | 12.887 | 21.973 | 235.54 | 0.487 |
| 13 | 4 | 1 | 165.552 | 3.180 | 216.557 | 286.25 | 0.971 |
| 13 | 4 | 3 | 445.406 | 4.262 | 620.097 | 62.39 | 0.994 |
| 13 | 4 | 5 | 274.916 | 2.939 | 395.220 | 305.25 | 0.986 |
| 13 | 4 | 7 | 148.282 | 1.910 | 248.666 | 194.98 | 0.963 |
| 13 | 4 | 9 | 488.014 | 4.083 | 698.330 | 71.22 | 0.995 |
| 13 | 4 | 11 | 310.584 | 3.006 | 417.009 | 53.98 | 0.989 |
| 13 | 4 | 13 | 144.253 | 2.241 | 228.031 | 196.55 | 0.928 |
| 13 | 4 | 15 | 318.961 | 2.970 | 497.538 | 147.85 | 0.990 |
| 13 | 4 | 17 | 270.346 | 2.799 | 365.336 | 101.35 | 0.988 |
| 13 | 4 | 19 | 177.905 | 2.816 | 237.238 | 100.56 | 0.973 |
| 13 | 4 | 21 | 342.191 | 3.258 | 445.682 | 5.04 | 0.993 |
| 13 | 4 | 23 | 391.445 | 3.541 | 540.194 | 110.28 | 0.993 |
| 13 | 4 | 25 | 127.053 | 4.644 | 150.639 | 288.78 | 0.942 |
| 13 | 4 | 27 | 189.664 | 4.001 | 276.339 | 231.47 | 0.976 |
| 13 | 4 | 29 | 117.767 | 5.522 | 185.052 | 248.16 | 0.919 |
| 13 | 4 | 31 | 74.169 | 10.028 | 82.116 | 290.07 | 0.864 |
| 13 | 4 | 33 | 44.935 | 10.566 | 14.873 | 136.43 | 0.608 |
| 13 | 4 | 35 | 76.203 | 11.999 | 45.263 | 129.06 | 0.934 |
| 13 | 4 | 37 | 120.059 | 7.791 | 205.368 | 151.77 | 0.959 |
| 13 | 4 | 39 | 51.574 | 12.913 | 32.831 | 299.07 | 0.881 |
| 13 | 4 | 41 | 39.657 | 12.478 | 2.907 | 244.32 | 0.819 |
| 13 | 5 | 0 | 26.416 | 15.393 | 12.219 | 180.00 | 0.333 |
| 13 | 5 | 2 | 304.997 | 3.415 | 476.792 | 45.45 | 0.987 |
| 13 | 5 | 4 | 345.522 | 3.451 | 500.993 | 80.14 | 0.990 |
| 13 | 5 | 6 | 83.652 | 1.972 | 22.788 | 260.56 | 0.921 |
| 13 | 5 | 8 | 219.016 | 2.270 | 342.646 | 240.04 | 0.980 |
| 13 | 5 | 10 | 262.679 | 2.649 | 381.742 | 219.06 | 0.981 |
| 13 | 5 | 12 | 382.616 | 3.228 | 541.468 | 36.04 | 0.992 |
| 13 | 5 | 14 | 308.359 | 2.818 | 424.010 | 16.39 | 0.991 |
| 13 | 5 | 16 | 300.070 | 2.870 | 426.333 | 113.31 | 0.991 |
| 13 | 5 | 18 | 233.602 | 2.733 | 348.753 | 150.52 | 0.982 |
| 13 | 5 | 20 | 76.382 | 5.622 | 68.693 | 20.09 | 0.709 |
| 13 | 5 | 22 | 386.612 | 3.618 | 608.236 | 98.09 | 0.992 |
| 13 | 5 | 24 | 234.971 | 3.381 | 320.092 | 82.28 | 0.980 |
| 13 | 5 | 26 | 131.381 | 4.652 | 171.452 | 43.62 | 0.957 |
| 13 | 5 | 28 | 148.154 | 5.068 | 197.390 | 117.13 | 0.965 |
| 13 | 5 | 30 | 223.865 | 3.719 | 347.706 | 63.20 | 0.985 |
| 13 | 5 | 32 | 34.025 | 10.628 | 13.787 | 282.53 | 0.477 |
| 13 | 5 | 34 | 61.306 | 12.008 | 55.973 | 256.29 | 0.774 |
| 13 | 5 | 36 | 55.856 | 11.124 | 43.658 | 161.17 | 0.771 |
| 13 | 5 | 38 | 73.598 | 11.593 | 96.353 | 182.24 | 0.905 |
| 13 | 5 | 40 | 55.601 | 14.471 | 52.072 | 31.93 | 0.705 |
| 13 | 6 | 1 | 166.795 | 2.302 | 249.200 | 95.03 | 0.970 |
| 13 | 6 | 3 | 169.894 | 2.063 | 270.931 | 152.21 | 0.934 |
| 13 | 6 | 5 | 321.513 | 2.894 | 485.514 | 61.57 | 0.989 |
| 13 | 6 | 7 | 550.338 | 4.808 | 746.392 | 213.05 | 0.996 |
| 13 | 6 | 9 | 51.871 | 4.317 | 19.545 | 19.11 | 0.593 |
| 13 | 6 | 11 | 178.916 | 2.466 | 270.886 | 308.14 | 0.968 |
| 13 | 6 | 13 | 464.775 | 3.742 | 653.958 | 305.53 | 0.996 |
| 13 | 6 | 15 | 294.557 | 2.795 | 426.364 | 56.21 | 0.989 |
| 13 | 6 | 17 | 201.581 | 2.880 | 256.362 | 113.59 | 0.982 |
| 13 | 6 | 19 | 497.054 | 4.434 | 714.712 | 320.65 | 0.996 |
| 13 | 6 | 21 | 142.747 | 3.549 | 182.655 | 250.81 | 0.961 |
| 13 | 6 | 23 | 295.366 | 3.258 | 379.323 | 54.52 | 0.989 |
| 13 | 6 | 25 | 121.270 | 4.678 | 131.722 | 220.20 | 0.941 |

| | | | | | | | |
|---|---|---|---|---|---|---|---|
| 13 | 6 | 27 | 76.836 | 7.629 | 58.301 | 16.47 | 0.379 |
| 13 | 6 | 29 | 104.488 | 6.287 | 137.257 | 159.18 | 0.944 |
| 13 | 6 | 31 | 90.792 | 8.194 | 127.117 | 68.09 | 0.910 |
| 13 | 6 | 33 | 102.474 | 6.790 | 128.205 | 329.38 | 0.945 |
| 13 | 6 | 35 | 52.815 | 12.486 | 34.188 | 6.81 | 0.751 |
| 13 | 6 | 37 | 44.019 | 11.865 | 23.065 | 347.05 | 0.414 |
| 13 | 6 | 39 | 67.631 | 13.912 | 26.875 | 358.98 | 0.229 |
| 13 | 7 | 0 | 310.117 | 4.506 | 447.331 | 180.00 | 1.000 |
| 13 | 7 | 2 | 131.740 | 1.692 | 179.594 | 319.32 | 0.947 |
| 13 | 7 | 4 | 382.220 | 3.693 | 548.560 | 330.38 | 0.992 |
| 13 | 7 | 6 | 93.400 | 2.257 | 121.118 | 323.60 | 0.960 |
| 13 | 7 | 8 | 395.243 | 3.298 | 610.699 | 2.40 | 0.992 |
| 13 | 7 | 10 | 280.158 | 2.588 | 369.213 | 116.78 | 0.988 |
| 13 | 7 | 12 | 73.407 | 4.320 | 91.478 | 112.01 | 0.908 |
| 13 | 7 | 14 | 408.648 | 3.498 | 650.184 | 320.23 | 0.993 |
| 13 | 7 | 16 | 428.734 | 3.533 | 613.871 | 133.64 | 0.995 |
| 13 | 7 | 18 | 115.103 | 3.493 | 150.464 | 143.28 | 0.934 |
| 13 | 7 | 20 | 268.517 | 2.983 | 353.325 | 43.26 | 0.988 |
| 13 | 7 | 22 | 481.224 | 4.168 | 619.073 | 220.84 | 0.996 |
| 13 | 7 | 24 | 234.901 | 3.339 | 373.166 | 330.94 | 0.974 |
| 13 | 7 | 26 | 146.611 | 4.497 | 192.703 | 175.69 | 0.966 |
| 13 | 7 | 28 | 134.877 | 5.136 | 198.152 | 176.86 | 0.949 |
| 13 | 7 | 30 | 183.927 | 3.799 | 256.702 | 311.48 | 0.983 |
| 13 | 7 | 32 | 179.355 | 4.583 | 241.592 | 215.77 | 0.982 |
| 13 | 7 | 34 | 204.517 | 4.931 | 286.299 | 12.17 | 0.987 |
| 13 | 7 | 36 | 40.567 | 11.457 | 4.819 | 290.87 | 0.111 |
| 13 | 7 | 38 | 166.543 | 6.149 | 268.117 | 348.98 | 0.983 |
| 13 | 7 | 40 | 47.672 | 13.874 | 30.745 | 53.55 | 0.588 |
| 13 | 8 | 1 | 125.581 | 1.885 | 169.952 | 92.72 | 0.962 |
| 13 | 8 | 3 | 217.048 | 2.323 | 317.524 | 294.27 | 0.981 |
| 13 | 8 | 5 | 221.097 | 2.354 | 321.306 | 323.94 | 0.971 |
| 13 | 8 | 7 | 115.782 | 2.256 | 158.907 | 344.18 | 0.928 |
| 13 | 8 | 9 | 254.479 | 2.504 | 314.553 | 99.18 | 0.988 |
| 13 | 8 | 11 | 92.075 | 3.646 | 122.683 | 114.75 | 0.805 |
| 13 | 8 | 13 | 404.380 | 3.574 | 593.052 | 41.00 | 0.994 |
| 13 | 8 | 15 | 185.212 | 2.570 | 305.374 | 39.43 | 0.960 |
| 13 | 8 | 17 | 304.079 | 2.905 | 421.387 | 131.07 | 0.989 |
| 13 | 8 | 19 | 159.417 | 3.280 | 268.613 | 188.98 | 0.944 |
| 13 | 8 | 21 | 144.464 | 3.503 | 101.156 | 248.62 | 0.969 |
| 13 | 8 | 23 | 61.254 | 7.659 | 11.514 | 151.72 | 0.273 |
| 13 | 8 | 25 | 300.827 | 3.447 | 456.272 | 30.71 | 0.991 |
| 13 | 8 | 27 | 131.804 | 5.057 | 247.731 | 238.50 | 0.888 |
| 13 | 8 | 29 | 57.952 | 11.476 | 50.913 | 80.78 | 0.738 |
| 13 | 8 | 31 | 164.806 | 5.582 | 201.537 | 210.77 | 0.981 |
| 13 | 8 | 33 | 114.070 | 7.883 | 150.310 | 51.64 | 0.952 |
| 13 | 8 | 35 | 64.937 | 14.156 | 69.775 | 51.95 | 0.791 |
| 13 | 8 | 37 | 83.564 | 12.078 | 95.958 | 22.18 | 0.946 |
| 13 | 8 | 39 | 42.688 | 12.780 | 29.672 | 288.29 | 0.620 |
| 13 | 9 | 0 | 92.211 | 3.943 | 129.442 | 180.00 | 0.977 |
| 13 | 9 | 2 | 149.877 | 1.999 | 234.569 | 125.71 | 0.898 |
| 13 | 9 | 4 | 181.784 | 2.668 | 296.694 | 123.01 | 0.962 |
| 13 | 9 | 6 | 348.573 | 3.465 | 488.172 | 89.09 | 0.990 |
| 13 | 9 | 8 | 382.123 | 3.359 | 539.585 | 141.93 | 0.994 |
| 13 | 9 | 10 | 205.396 | 2.379 | 278.087 | 208.73 | 0.982 |
| 13 | 9 | 12 | 172.415 | 2.497 | 236.925 | 20.35 | 0.979 |
| 13 | 9 | 14 | 468.001 | 4.135 | 752.822 | 54.94 | 0.995 |
| 13 | 9 | 16 | 411.093 | 3.586 | 614.110 | 122.73 | 0.994 |
| 13 | 9 | 18 | 355.410 | 3.260 | 557.119 | 128.73 | 0.991 |
| 13 | 9 | 20 | 230.484 | 2.946 | 321.151 | 353.26 | 0.981 |
| 13 | 9 | 22 | 408.683 | 3.800 | 521.609 | 44.10 | 0.994 |
| 13 | 9 | 24 | 177.379 | 3.837 | 215.934 | 197.00 | 0.979 |
| 13 | 9 | 26 | 83.422 | 7.796 | 109.816 | 84.49 | 0.803 |
| 13 | 9 | 28 | 147.644 | 4.992 | 216.726 | 41.04 | 0.971 |
| 13 | 9 | 30 | 93.089 | 7.201 | 119.389 | 286.30 | 0.929 |
| 13 | 9 | 32 | 149.846 | 4.944 | 163.337 | 263.93 | 0.978 |
| 13 | 9 | 34 | 72.933 | 10.729 | 92.809 | 102.27 | 0.834 |
| 13 | 9 | 36 | 144.258 | 5.635 | 212.695 | 316.06 | 0.982 |
| 13 | 9 | 38 | 31.416 | 10.316 | 4.008 | 263.38 | 0.426 |
| 13 | 10 | 1 | 313.525 | 2.987 | 509.386 | 184.36 | 0.985 |
| 13 | 10 | 3 | 373.266 | 3.999 | 538.019 | 306.16 | 0.992 |
| 13 | 10 | 5 | 181.658 | 2.756 | 310.639 | 359.16 | 0.913 |
| 13 | 10 | 7 | 298.013 | 2.778 | 469.037 | 293.36 | 0.989 |
| 13 | 10 | 9 | 242.838 | 2.597 | 301.464 | 157.51 | 0.990 |
| 13 | 10 | 11 | 315.124 | 3.252 | 452.365 | 212.65 | 0.991 |
| 13 | 10 | 13 | 178.462 | 2.479 | 295.446 | 207.83 | 0.956 |
| 13 | 10 | 15 | 287.178 | 3.187 | 576.511 | 253.18 | 0.973 |
| 13 | 10 | 17 | 337.873 | 3.182 | 464.301 | 128.01 | 0.992 |

| | | | | | | | |
|---|---|---|---|---|---|---|---|
| 13 | 10 | 19 | 247.025 | 2.911 | 318.022 | 338.26 | 0.986 |
| 13 | 10 | 21 | 274.609 | 3.087 | 421.643 | 245.02 | 0.985 |
| 13 | 10 | 23 | 163.563 | 4.004 | 278.807 | 279.38 | 0.881 |
| 13 | 10 | 25 | 225.515 | 3.361 | 368.284 | 272.95 | 0.981 |
| 13 | 10 | 27 | 142.785 | 4.670 | 226.986 | 156.27 | 0.964 |
| 13 | 10 | 29 | 113.507 | 6.193 | 151.249 | 241.77 | 0.952 |
| 13 | 10 | 31 | 93.505 | 7.408 | 154.465 | 328.83 | 0.856 |
| 13 | 10 | 33 | 120.482 | 6.238 | 126.773 | 277.68 | 0.972 |
| 13 | 10 | 35 | 86.594 | 9.007 | 84.677 | 36.66 | 0.961 |
| 13 | 10 | 37 | 43.143 | 12.035 | 19.815 | 160.77 | 0.808 |
| 13 | 10 | 39 | 103.669 | 10.031 | 171.983 | 52.19 | 0.933 |
| 13 | 11 | 0 | 77.845 | 4.901 | 111.538 | 180.00 | 1.000 |
| 13 | 11 | 2 | 175.638 | 2.645 | 288.550 | 254.36 | 0.779 |
| 13 | 11 | 4 | 457.587 | 4.717 | 680.993 | 287.04 | 0.996 |
| 13 | 11 | 6 | 197.337 | 2.798 | 264.884 | 38.14 | 0.982 |
| 13 | 11 | 8 | 318.963 | 2.751 | 503.063 | 324.07 | 0.990 |
| 13 | 11 | 10 | 106.315 | 3.754 | 150.041 | 331.96 | 0.884 |
| 13 | 11 | 12 | 126.820 | 3.121 | 117.550 | 135.70 | 0.965 |
| 13 | 11 | 14 | 28.984 | 8.055 | 59.201 | 290.91 | 0.333 |
| 13 | 11 | 16 | 149.755 | 3.346 | 200.052 | 205.60 | 0.958 |
| 13 | 11 | 18 | 130.720 | 3.792 | 191.264 | 203.10 | 0.945 |
| 13 | 11 | 20 | 64.387 | 7.849 | 48.985 | 293.05 | 0.749 |
| 13 | 11 | 22 | 75.269 | 7.282 | 44.947 | 217.74 | 0.820 |
| 13 | 11 | 24 | 238.312 | 3.444 | 348.298 | 180.45 | 0.986 |
| 13 | 11 | 26 | 233.322 | 3.736 | 322.118 | 200.55 | 0.990 |
| 13 | 11 | 28 | 42.213 | 11.738 | 6.823 | 145.58 | 0.263 |
| 13 | 11 | 30 | 197.255 | 4.017 | 301.331 | 278.00 | 0.983 |
| 13 | 11 | 32 | 67.339 | 10.076 | 83.817 | 269.16 | 0.738 |
| 13 | 11 | 34 | 112.633 | 6.934 | 138.350 | 144.50 | 0.960 |
| 13 | 11 | 36 | 47.605 | 13.207 | 27.104 | 190.27 | 0.851 |
| 13 | 11 | 38 | 70.456 | 12.624 | 54.334 | 351.63 | 0.430 |
| 13 | 12 | 1 | 303.004 | 2.739 | 429.234 | 147.28 | 0.990 |
| 13 | 12 | 3 | 166.466 | 3.230 | 244.026 | 67.18 | 0.974 |
| 13 | 12 | 5 | 197.466 | 3.017 | 266.363 | 258.16 | 0.980 |
| 13 | 12 | 7 | 237.075 | 2.650 | 321.581 | 39.46 | 0.985 |
| 13 | 12 | 9 | 257.941 | 2.552 | 368.312 | 190.41 | 0.986 |
| 13 | 12 | 11 | 276.472 | 2.774 | 367.207 | 92.89 | 0.989 |
| 13 | 12 | 13 | 90.534 | 3.601 | 96.857 | 60.54 | 0.883 |
| 13 | 12 | 15 | 345.109 | 3.966 | 508.937 | 35.65 | 0.992 |
| 13 | 12 | 17 | 336.259 | 3.337 | 472.865 | 323.71 | 0.992 |
| 13 | 12 | 19 | 198.644 | 3.298 | 305.559 | 239.04 | 0.967 |
| 13 | 12 | 21 | 102.530 | 6.004 | 114.659 | 354.14 | 0.891 |
| 13 | 12 | 23 | 101.812 | 5.572 | 158.848 | 29.73 | 0.885 |
| 13 | 12 | 25 | 205.338 | 3.889 | 308.290 | 330.74 | 0.980 |
| 13 | 12 | 27 | 151.361 | 5.224 | 212.057 | 243.19 | 0.975 |
| 13 | 12 | 29 | 160.898 | 4.261 | 239.883 | 179.68 | 0.975 |
| 13 | 12 | 31 | 36.117 | 10.817 | 1.349 | 125.59 | 0.326 |
| 13 | 12 | 33 | 35.804 | 10.997 | 2.070 | 90.52 | 0.338 |
| 13 | 12 | 35 | 37.914 | 11.108 | 7.802 | 188.12 | 0.203 |
| 13 | 12 | 37 | 54.892 | 11.423 | 55.731 | 235.96 | 0.856 |
| 13 | 13 | 0 | 186.485 | 5.040 | 268.559 | 0.00 | 1.000 |
| 13 | 13 | 2 | 293.454 | 2.867 | 410.248 | 158.10 | 0.990 |
| 13 | 13 | 4 | 62.602 | 5.469 | 44.095 | 12.60 | 0.533 |
| 13 | 13 | 6 | 227.634 | 2.922 | 292.005 | 39.00 | 0.987 |
| 13 | 13 | 8 | 201.945 | 2.458 | 309.381 | 204.46 | 0.977 |
| 13 | 13 | 10 | 157.307 | 2.899 | 180.713 | 159.19 | 0.972 |
| 13 | 13 | 12 | 129.149 | 3.508 | 137.194 | 178.76 | 0.966 |
| 13 | 13 | 14 | 178.700 | 2.974 | 260.975 | 342.10 | 0.971 |
| 13 | 13 | 16 | 167.772 | 3.921 | 221.923 | 219.61 | 0.963 |
| 13 | 13 | 18 | 190.509 | 3.200 | 273.228 | 271.21 | 0.970 |
| 13 | 13 | 20 | 180.262 | 3.385 | 171.660 | 332.99 | 0.976 |
| 13 | 13 | 22 | 214.877 | 3.747 | 241.206 | 340.47 | 0.986 |
| 13 | 13 | 24 | 270.647 | 3.582 | 410.744 | 327.79 | 0.989 |
| 13 | 13 | 26 | 258.113 | 3.584 | 435.846 | 350.21 | 0.989 |
| 13 | 13 | 28 | 145.742 | 4.798 | 202.042 | 352.16 | 0.972 |
| 13 | 13 | 30 | 43.809 | 11.047 | 20.370 | 276.17 | 0.679 |
| 13 | 13 | 32 | 129.332 | 5.669 | 197.463 | 175.15 | 0.962 |
| 13 | 13 | 34 | 127.781 | 5.917 | 189.728 | 106.37 | 0.977 |
| 13 | 13 | 36 | 43.973 | 13.005 | 34.656 | 328.56 | 0.652 |
| 13 | 14 | 1 | 43.474 | 7.922 | 2.833 | 92.67 | 0.410 |
| 13 | 14 | 3 | 245.461 | 3.281 | 349.945 | 277.38 | 0.987 |
| 13 | 14 | 5 | 133.264 | 4.148 | 168.250 | 340.26 | 0.952 |
| 13 | 14 | 7 | 151.651 | 2.912 | 222.306 | 36.70 | 0.956 |
| 13 | 14 | 9 | 94.183 | 4.584 | 63.525 | 297.29 | 0.332 |
| 13 | 14 | 11 | 305.715 | 2.977 | 435.836 | 227.71 | 0.991 |
| 13 | 14 | 13 | 110.253 | 3.507 | 146.831 | 351.74 | 0.902 |
| 13 | 14 | 15 | 105.850 | 5.047 | 80.248 | 344.23 | 0.943 |

| | | | | | | | |
|---|---|---|---|---|---|---|---|
| 13 | 14 | 17 | 171.406 | 3.823 | 178.759 | 217.72 | 0.975 |
| 13 | 14 | 19 | 273.033 | 3.845 | 433.983 | 206.52 | 0.983 |
| 13 | 14 | 21 | 119.634 | 5.658 | 190.336 | 245.02 | 0.930 |
| 13 | 14 | 23 | 213.877 | 3.735 | 255.160 | 140.99 | 0.986 |
| 13 | 14 | 25 | 119.645 | 6.505 | 141.905 | 71.47 | 0.964 |
| 13 | 14 | 27 | 74.309 | 7.931 | 92.683 | 281.54 | 0.861 |
| 13 | 14 | 29 | 51.175 | 11.243 | 30.853 | 239.34 | 0.557 |
| 13 | 14 | 31 | 94.247 | 8.706 | 156.324 | 34.56 | 0.871 |
| 13 | 14 | 33 | 35.895 | 11.071 | 12.682 | 74.75 | 0.848 |
| 13 | 14 | 35 | 73.006 | 13.219 | 107.168 | 274.36 | 0.863 |
| 13 | 14 | 37 | 40.203 | 12.799 | 16.775 | 71.23 | 0.395 |
| 13 | 15 | 0 | 344.294 | 5.142 | 495.976 | 0.00 | 1.000 |
| 13 | 15 | 2 | 352.753 | 3.165 | 473.774 | 206.13 | 0.993 |
| 13 | 15 | 4 | 196.538 | 3.739 | 302.422 | 18.04 | 0.975 |
| 13 | 15 | 6 | 288.500 | 3.269 | 402.494 | 1.29 | 0.990 |
| 13 | 15 | 8 | 189.047 | 3.357 | 186.512 | 278.24 | 0.980 |
| 13 | 15 | 10 | 125.151 | 4.253 | 148.241 | 106.55 | 0.957 |
| 13 | 15 | 12 | 33.299 | 9.056 | 13.565 | 104.75 | 0.552 |
| 13 | 15 | 14 | 50.837 | 10.582 | 29.431 | 56.80 | 0.812 |
| 13 | 15 | 16 | 346.364 | 3.448 | 520.486 | 59.44 | 0.991 |
| 13 | 15 | 18 | 279.084 | 3.566 | 398.382 | 190.64 | 0.991 |
| 13 | 15 | 20 | 209.033 | 4.313 | 282.040 | 358.89 | 0.984 |
| 13 | 15 | 22 | 110.514 | 5.772 | 192.148 | 128.53 | 0.786 |
| 13 | 15 | 24 | 141.677 | 5.362 | 173.548 | 176.16 | 0.976 |
| 13 | 15 | 26 | 156.904 | 5.030 | 221.517 | 196.56 | 0.977 |
| 13 | 15 | 28 | 144.030 | 4.789 | 180.738 | 149.69 | 0.974 |
| 13 | 15 | 30 | 54.916 | 12.151 | 25.399 | 333.39 | 0.868 |
| 13 | 15 | 32 | 40.251 | 11.246 | 13.980 | 356.70 | 0.829 |
| 13 | 15 | 34 | 108.795 | 9.334 | 172.879 | 30.79 | 0.956 |
| 13 | 15 | 36 | 46.711 | 11.762 | 40.853 | 168.75 | 0.640 |
| 13 | 16 | 1 | 219.913 | 2.979 | 304.845 | 242.46 | 0.983 |
| 13 | 16 | 3 | 117.182 | 4.112 | 118.575 | 71.72 | 0.960 |
| 13 | 16 | 5 | 95.211 | 4.698 | 94.917 | 15.62 | 0.934 |
| 13 | 16 | 7 | 131.228 | 5.003 | 140.472 | 2.27 | 0.957 |
| 13 | 16 | 9 | 89.100 | 4.694 | 98.659 | 11.45 | 0.913 |
| 13 | 16 | 11 | 163.574 | 3.482 | 233.345 | 341.53 | 0.962 |
| 13 | 16 | 13 | 332.382 | 3.224 | 510.401 | 115.93 | 0.989 |
| 13 | 16 | 15 | 559.066 | 5.025 | 837.143 | 103.75 | 0.996 |
| 13 | 16 | 17 | 231.391 | 3.288 | 324.933 | 209.77 | 0.986 |
| 13 | 16 | 19 | 129.206 | 5.412 | 179.884 | 39.03 | 0.952 |
| 13 | 16 | 21 | 118.113 | 6.251 | 214.582 | 73.16 | 0.934 |
| 13 | 16 | 23 | 55.205 | 11.072 | 50.652 | 254.88 | 0.763 |
| 13 | 16 | 25 | 174.600 | 4.269 | 237.509 | 101.24 | 0.982 |
| 13 | 16 | 27 | 185.098 | 4.766 | 351.587 | 119.34 | 0.969 |
| 13 | 16 | 29 | 61.222 | 11.335 | 38.924 | 272.30 | 0.354 |
| 13 | 16 | 31 | 99.879 | 6.887 | 100.882 | 55.45 | 0.974 |
| 13 | 16 | 33 | 97.796 | 7.567 | 143.677 | 207.35 | 0.955 |
| 13 | 16 | 35 | 79.487 | 13.925 | 87.509 | 57.74 | 0.935 |
| 13 | 17 | 0 | 135.225 | 8.000 | 191.292 | 0.00 | 0.984 |
| 13 | 17 | 2 | 118.816 | 3.908 | 201.723 | 175.25 | 0.782 |
| 13 | 17 | 4 | 494.303 | 4.967 | 749.566 | 225.71 | 0.996 |
| 13 | 17 | 6 | 120.324 | 5.308 | 137.787 | 286.68 | 0.942 |
| 13 | 17 | 8 | 165.372 | 4.534 | 192.781 | 129.13 | 0.969 |
| 13 | 17 | 10 | 162.789 | 3.533 | 222.818 | 330.64 | 0.965 |
| 13 | 17 | 12 | 110.774 | 4.663 | 171.571 | 334.52 | 0.885 |
| 13 | 17 | 14 | 174.173 | 3.150 | 194.591 | 69.68 | 0.972 |
| 13 | 17 | 16 | 129.866 | 5.507 | 134.544 | 236.85 | 0.965 |
| 13 | 17 | 18 | 193.472 | 3.893 | 230.638 | 20.84 | 0.983 |
| 13 | 17 | 20 | 237.857 | 4.452 | 346.086 | 164.88 | 0.990 |
| 13 | 17 | 22 | 55.426 | 11.530 | 20.864 | 43.22 | 0.866 |
| 13 | 17 | 24 | 132.767 | 5.431 | 254.890 | 45.45 | 0.928 |
| 13 | 17 | 26 | 197.742 | 3.848 | 282.160 | 30.42 | 0.985 |
| 13 | 17 | 28 | 61.173 | 11.268 | 53.540 | 294.28 | 0.861 |
| 13 | 17 | 30 | 66.292 | 9.586 | 70.214 | 358.78 | 0.926 |
| 13 | 17 | 32 | 102.660 | 10.478 | 162.611 | 159.20 | 0.951 |
| 13 | 17 | 34 | 59.958 | 13.463 | 64.565 | 161.34 | 0.635 |
| 13 | 18 | 1 | 269.112 | 3.110 | 349.976 | 176.31 | 0.988 |
| 13 | 18 | 3 | 48.839 | 9.830 | 9.443 | 163.82 | 0.382 |
| 13 | 18 | 5 | 80.493 | 8.829 | 89.749 | 256.05 | 0.795 |
| 13 | 18 | 7 | 86.224 | 5.700 | 69.473 | 220.29 | 0.505 |
| 13 | 18 | 9 | 28.645 | 8.503 | 8.733 | 193.55 | 0.068 |
| 13 | 18 | 11 | 354.581 | 3.425 | 584.849 | 217.36 | 0.990 |
| 13 | 18 | 13 | 319.787 | 3.443 | 435.340 | 333.88 | 0.993 |
| 13 | 18 | 15 | 142.734 | 4.430 | 196.515 | 31.51 | 0.963 |
| 13 | 18 | 17 | 111.454 | 6.154 | 147.280 | 204.29 | 0.938 |
| 13 | 18 | 19 | 215.678 | 3.735 | 317.404 | 192.59 | 0.988 |
| 13 | 18 | 21 | 34.989 | 9.555 | 8.749 | 338.12 | 0.328 |

| | | | | | | | |
|---|---|---|---|---|---|---|---|
| 13 | 18 | 23 | 90.202 | 9.868 | 100.742 | 276.57 | 0.937 |
| 13 | 18 | 25 | 138.028 | 6.066 | 173.396 | 14.51 | 0.973 |
| 13 | 18 | 27 | 51.465 | 10.344 | 31.534 | 345.25 | 0.733 |
| 13 | 18 | 29 | 87.213 | 8.052 | 69.007 | 348.68 | 0.969 |
| 13 | 18 | 31 | 40.346 | 11.777 | 24.906 | 258.09 | 0.662 |
| 13 | 18 | 33 | 98.913 | 9.942 | 145.159 | 40.22 | 0.954 |
| 13 | 19 | 0 | 84.880 | 15.832 | 67.591 | 0.00 | 0.556 |
| 13 | 19 | 2 | 275.314 | 3.182 | 337.582 | 208.32 | 0.989 |
| 13 | 19 | 4 | 192.399 | 3.754 | 298.220 | 1.33 | 0.969 |
| 13 | 19 | 6 | 88.182 | 8.560 | 50.773 | 333.75 | 0.920 |
| 13 | 19 | 8 | 269.509 | 4.175 | 412.149 | 36.49 | 0.985 |
| 13 | 19 | 10 | 244.693 | 3.275 | 326.117 | 228.61 | 0.989 |
| 13 | 19 | 12 | 107.096 | 5.264 | 122.755 | 41.59 | 0.942 |
| 13 | 19 | 14 | 136.252 | 5.811 | 168.040 | 222.63 | 0.964 |
| 13 | 19 | 16 | 79.457 | 7.361 | 92.832 | 317.54 | 0.871 |
| 13 | 19 | 18 | 161.460 | 4.492 | 265.647 | 132.32 | 0.973 |
| 13 | 19 | 20 | 62.927 | 10.310 | 28.252 | 95.07 | 0.242 |
| 13 | 19 | 22 | 165.437 | 4.502 | 186.365 | 306.74 | 0.984 |
| 13 | 19 | 24 | 169.012 | 5.825 | 256.042 | 291.43 | 0.977 |
| 13 | 19 | 26 | 74.781 | 10.954 | 90.972 | 149.54 | 0.898 |
| 13 | 19 | 28 | 109.211 | 6.703 | 197.766 | 237.05 | 0.952 |
| 13 | 19 | 30 | 48.677 | 12.128 | 39.044 | 231.27 | 0.815 |
| 13 | 19 | 32 | 85.581 | 12.730 | 135.336 | 316.14 | 0.899 |
| 13 | 20 | 1 | 210.677 | 3.583 | 234.668 | 76.58 | 0.983 |
| 13 | 20 | 3 | 273.520 | 3.298 | 417.353 | 264.86 | 0.986 |
| 13 | 20 | 5 | 167.156 | 3.892 | 189.517 | 97.95 | 0.969 |
| 13 | 20 | 7 | 190.913 | 4.141 | 284.528 | 109.80 | 0.980 |
| 13 | 20 | 9 | 220.625 | 4.872 | 373.751 | 55.66 | 0.980 |
| 13 | 20 | 11 | 241.028 | 3.322 | 359.314 | 316.56 | 0.987 |
| 13 | 20 | 13 | 91.455 | 6.459 | 125.537 | 118.55 | 0.903 |
| 13 | 20 | 15 | 145.134 | 4.598 | 212.832 | 81.62 | 0.973 |
| 13 | 20 | 17 | 334.065 | 3.611 | 505.109 | 23.60 | 0.995 |
| 13 | 20 | 19 | 77.082 | 9.571 | 69.838 | 85.11 | 0.928 |
| 13 | 20 | 21 | 79.871 | 8.273 | 119.158 | 28.83 | 0.868 |
| 13 | 20 | 23 | 179.840 | 5.042 | 252.575 | 259.45 | 0.982 |
| 13 | 20 | 25 | 55.015 | 15.586 | 18.358 | 13.89 | 0.253 |
| 13 | 20 | 27 | 166.419 | 4.740 | 288.988 | 266.57 | 0.985 |
| 13 | 20 | 29 | 33.828 | 10.588 | 11.555 | 306.10 | 0.621 |
| 13 | 20 | 31 | 40.967 | 12.253 | 22.911 | 258.83 | 0.494 |
| 13 | 21 | 0 | 185.317 | 8.832 | 266.121 | 180.00 | 1.000 |
| 13 | 21 | 2 | 195.623 | 3.776 | 308.697 | 68.27 | 0.979 |
| 13 | 21 | 4 | 71.940 | 10.027 | 96.389 | 174.73 | 0.764 |
| 13 | 21 | 6 | 182.075 | 4.380 | 222.206 | 39.84 | 0.981 |
| 13 | 21 | 8 | 242.869 | 4.378 | 329.448 | 162.69 | 0.989 |
| 13 | 21 | 10 | 206.480 | 4.245 | 298.182 | 41.28 | 0.983 |
| 13 | 21 | 12 | 130.238 | 4.297 | 209.141 | 79.21 | 0.962 |
| 13 | 21 | 14 | 268.534 | 3.505 | 418.834 | 4.85 | 0.992 |
| 13 | 21 | 16 | 125.027 | 5.686 | 127.489 | 284.17 | 0.973 |
| 13 | 21 | 18 | 57.507 | 10.792 | 54.575 | 161.73 | 0.774 |
| 13 | 21 | 20 | 138.029 | 5.752 | 179.198 | 132.02 | 0.973 |
| 13 | 21 | 22 | 37.954 | 10.700 | 4.528 | 139.07 | 0.609 |
| 13 | 21 | 24 | 78.824 | 7.584 | 107.294 | 47.58 | 0.905 |
| 13 | 21 | 26 | 44.869 | 11.706 | 36.460 | 269.54 | 0.797 |
| 13 | 21 | 28 | 84.881 | 13.960 | 134.895 | 152.61 | 0.852 |
| 13 | 21 | 30 | 65.084 | 14.056 | 74.153 | 165.18 | 0.646 |
| 13 | 22 | 1 | 144.948 | 5.071 | 247.325 | 22.38 | 0.956 |
| 13 | 22 | 3 | 248.261 | 3.734 | 323.112 | 33.47 | 0.989 |
| 13 | 22 | 5 | 74.399 | 9.382 | 80.533 | 28.49 | 0.611 |
| 13 | 22 | 7 | 66.507 | 12.221 | 28.767 | 128.56 | 0.867 |
| 13 | 22 | 9 | 233.987 | 4.903 | 341.015 | 281.75 | 0.990 |
| 13 | 22 | 11 | 103.107 | 6.602 | 128.053 | 296.80 | 0.955 |
| 13 | 22 | 13 | 94.207 | 6.667 | 62.615 | 333.46 | 0.370 |
| 13 | 22 | 15 | 148.956 | 4.695 | 164.346 | 37.58 | 0.981 |
| 13 | 22 | 17 | 63.725 | 10.535 | 62.858 | 293.53 | 0.863 |
| 13 | 22 | 19 | 40.022 | 11.568 | 13.048 | 96.52 | 0.730 |
| 13 | 22 | 21 | 45.884 | 11.046 | 9.957 | 219.02 | 0.819 |
| 13 | 22 | 23 | 117.472 | 5.637 | 181.736 | 57.01 | 0.958 |
| 13 | 22 | 25 | 69.281 | 9.981 | 98.773 | 273.51 | 0.700 |
| 13 | 22 | 27 | 68.926 | 12.724 | 104.176 | 29.18 | 0.834 |
| 13 | 22 | 29 | 45.804 | 15.523 | 29.639 | 217.55 | 0.720 |
| 13 | 23 | 0 | 68.490 | 16.605 | 97.315 | 0.00 | 1.000 |
| 13 | 23 | 2 | 189.834 | 4.001 | 294.038 | 22.73 | 0.984 |
| 13 | 23 | 4 | 106.138 | 7.888 | 152.422 | 28.64 | 0.951 |
| 13 | 23 | 6 | 37.276 | 10.251 | 2.622 | 83.00 | 0.597 |
| 13 | 23 | 8 | 149.031 | 5.126 | 245.211 | 307.67 | 0.970 |
| 13 | 23 | 10 | 214.379 | 4.641 | 298.158 | 293.09 | 0.989 |
| 13 | 23 | 12 | 87.893 | 8.834 | 141.491 | 250.88 | 0.881 |

| | | | | | | | |
|---|---|---|---|---|---|---|---|
| 13 | 23 | 14 | 153.257 | 4.523 | 210.418 | 156.17 | 0.978 |
| 13 | 23 | 16 | 54.780 | 10.711 | 32.030 | 43.16 | 0.831 |
| 13 | 23 | 18 | 87.449 | 7.045 | 113.349 | 233.57 | 0.934 |
| 13 | 23 | 20 | 82.653 | 8.099 | 123.036 | 322.77 | 0.897 |
| 13 | 23 | 22 | 34.837 | 11.165 | 18.138 | 267.55 | 0.560 |
| 13 | 23 | 24 | 198.370 | 5.419 | 325.037 | 242.23 | 0.991 |
| 13 | 23 | 26 | 36.867 | 11.702 | 17.777 | 242.34 | 0.621 |
| 13 | 23 | 28 | 64.756 | 14.185 | 73.434 | 125.83 | 0.886 |
| 13 | 24 | 1 | 96.405 | 6.022 | 181.865 | 212.95 | 0.841 |
| 13 | 24 | 3 | 115.379 | 6.847 | 137.477 | 36.58 | 0.965 |
| 13 | 24 | 5 | 56.131 | 11.493 | 44.431 | 117.45 | 0.784 |
| 13 | 24 | 7 | 196.858 | 4.161 | 425.523 | 218.33 | 0.905 |
| 13 | 24 | 9 | 55.721 | 12.426 | 32.101 | 311.32 | 0.846 |
| 13 | 24 | 11 | 77.554 | 10.722 | 79.324 | 121.52 | 0.921 |
| 13 | 24 | 13 | 132.415 | 5.452 | 211.969 | 230.25 | 0.964 |
| 13 | 24 | 15 | 46.783 | 11.592 | 17.722 | 258.47 | 0.291 |
| 13 | 24 | 17 | 177.543 | 3.824 | 272.386 | 229.94 | 0.984 |
| 13 | 24 | 19 | 33.978 | 10.011 | 3.036 | 293.73 | 0.598 |
| 13 | 24 | 21 | 147.215 | 6.053 | 245.352 | 117.34 | 0.982 |
| 13 | 24 | 23 | 77.184 | 11.803 | 113.037 | 85.38 | 0.915 |
| 13 | 24 | 25 | 47.839 | 13.628 | 41.681 | 208.12 | 0.815 |
| 13 | 24 | 27 | 45.982 | 13.268 | 29.552 | 130.64 | 0.498 |
| 13 | 25 | 0 | 120.656 | 12.977 | 171.488 | 180.00 | 1.000 |
| 13 | 25 | 2 | 60.150 | 10.040 | 53.569 | 210.37 | 0.844 |
| 13 | 25 | 4 | 98.205 | 10.262 | 118.733 | 288.38 | 0.950 |
| 13 | 25 | 6 | 106.199 | 7.115 | 162.501 | 101.52 | 0.943 |
| 13 | 25 | 8 | 81.245 | 7.482 | 72.494 | 141.89 | 0.943 |
| 13 | 25 | 10 | 46.374 | 11.500 | 15.350 | 322.59 | 0.330 |
| 13 | 25 | 12 | 97.601 | 6.965 | 164.244 | 69.19 | 0.910 |
| 13 | 25 | 14 | 38.302 | 11.453 | 7.724 | 296.58 | 0.746 |
| 13 | 25 | 16 | 99.331 | 7.285 | 101.037 | 2.29 | 0.963 |
| 13 | 25 | 18 | 91.392 | 6.754 | 178.705 | 337.56 | 0.909 |
| 13 | 25 | 20 | 165.874 | 5.430 | 252.265 | 163.88 | 0.988 |
| 13 | 25 | 22 | 139.803 | 10.427 | 198.982 | 98.83 | 0.982 |
| 13 | 25 | 24 | 47.041 | 13.147 | 27.477 | 93.13 | 0.856 |
| 13 | 26 | 1 | 74.219 | 10.025 | 28.630 | 222.60 | 0.942 |
| 13 | 26 | 3 | 236.373 | 4.043 | 344.733 | 269.07 | 0.991 |
| 13 | 26 | 5 | 108.552 | 7.640 | 92.476 | 261.03 | 0.969 |
| 13 | 26 | 7 | 90.085 | 7.185 | 124.485 | 112.20 | 0.927 |
| 13 | 26 | 9 | 172.399 | 5.405 | 310.569 | 282.71 | 0.979 |
| 13 | 26 | 11 | 74.554 | 11.519 | 107.915 | 131.32 | 0.849 |
| 13 | 26 | 13 | 72.198 | 11.214 | 97.145 | 118.46 | 0.858 |
| 13 | 26 | 15 | 42.312 | 10.450 | 19.658 | 150.79 | 0.517 |
| 13 | 26 | 17 | 42.981 | 11.345 | 9.514 | 122.47 | 0.163 |
| 13 | 26 | 19 | 126.095 | 7.493 | 193.094 | 183.12 | 0.977 |
| 13 | 26 | 21 | 43.608 | 13.271 | 34.189 | 160.84 | 0.721 |
| 13 | 26 | 23 | 51.361 | 15.048 | 40.204 | 194.33 | 0.617 |
| 13 | 27 | 0 | 46.901 | 17.886 | 63.807 | 180.00 | 0.982 |
| 13 | 27 | 2 | 66.082 | 9.267 | 92.310 | 211.61 | 0.719 |
| 13 | 27 | 4 | 34.452 | 10.421 | 3.016 | 54.14 | 0.553 |
| 13 | 27 | 6 | 117.187 | 6.428 | 229.371 | 205.98 | 0.931 |
| 13 | 27 | 8 | 165.202 | 4.218 | 318.222 | 113.61 | 0.972 |
| 13 | 27 | 10 | 37.069 | 11.050 | 4.648 | 194.30 | 0.568 |
| 13 | 27 | 12 | 89.607 | 10.011 | 133.529 | 24.65 | 0.920 |
| 13 | 27 | 14 | 26.783 | 9.140 | 4.012 | 105.26 | 0.145 |
| 13 | 27 | 16 | 36.006 | 10.868 | 4.279 | 73.17 | 0.812 |
| 13 | 27 | 18 | 72.227 | 12.799 | 106.153 | 328.96 | 0.896 |
| 13 | 27 | 20 | 45.633 | 13.140 | 38.774 | 172.41 | 0.651 |
| 13 | 28 | 1 | 103.349 | 7.752 | 159.488 | 192.37 | 0.949 |
| 13 | 28 | 3 | 103.112 | 6.873 | 152.872 | 190.42 | 0.950 |
| 13 | 28 | 5 | 63.830 | 10.829 | 55.901 | 88.98 | 0.906 |
| 13 | 28 | 7 | 51.406 | 12.053 | 25.185 | 77.23 | 0.833 |
| 13 | 28 | 9 | 61.879 | 10.268 | 75.168 | 120.15 | 0.910 |
| 13 | 28 | 11 | 37.185 | 11.524 | 15.938 | 253.14 | 0.775 |
| 13 | 28 | 13 | 62.527 | 12.213 | 87.543 | 50.77 | 0.835 |
| 13 | 28 | 15 | 40.101 | 13.086 | 21.866 | 41.40 | 0.773 |
| 13 | 28 | 17 | 39.088 | 12.440 | 15.614 | 211.56 | 0.889 |
| 13 | 28 | 19 | 84.074 | 12.433 | 89.484 | 283.93 | 0.954 |
| 13 | 29 | 0 | 29.182 | 12.965 | 1.645 | 180.00 | 0.041 |
| 13 | 29 | 2 | 48.296 | 10.921 | 52.662 | 63.50 | 0.698 |
| 13 | 29 | 4 | 64.371 | 11.999 | 66.710 | 4.93 | 0.928 |
| 13 | 29 | 6 | 53.110 | 13.151 | 62.367 | 201.19 | 0.722 |
| 13 | 29 | 8 | 69.711 | 8.926 | 74.000 | 248.23 | 0.943 |
| 13 | 29 | 10 | 61.201 | 11.279 | 69.618 | 219.75 | 0.905 |
| 13 | 29 | 12 | 41.069 | 13.414 | 15.206 | 325.43 | 0.824 |
| 13 | 29 | 14 | 40.760 | 14.208 | 25.177 | 232.21 | 0.550 |
| 13 | 29 | 16 | 50.774 | 14.618 | 47.472 | 251.04 | 0.796 |

| | | | | | | | |
|---|---|---|---|---|---|---|---|
| 13 | 30 | 1 | 111.756 | 8.555 | 195.983 | 32.31 | 0.964 |
| 13 | 30 | 3 | 39.879 | 11.833 | 5.891 | 159.22 | 0.850 |
| 13 | 30 | 5 | 40.486 | 14.153 | 26.639 | 160.84 | 0.583 |
| 13 | 30 | 7 | 36.361 | 11.399 | 24.006 | 155.01 | 0.608 |
| 13 | 30 | 9 | 50.160 | 12.832 | 51.721 | 103.20 | 0.603 |
| 13 | 30 | 11 | 30.743 | 10.182 | 4.013 | 270.04 | 0.206 |
| 13 | 30 | 13 | 56.432 | 14.823 | 53.350 | 111.16 | 0.643 |
| 13 | 31 | 0 | 25.122 | 16.756 | 7.119 | 180.00 | 0.227 |
| 13 | 31 | 2 | 49.166 | 13.660 | 48.400 | 136.98 | 0.801 |
| 13 | 31 | 4 | 49.701 | 12.499 | 53.775 | 212.79 | 0.748 |
| 13 | 31 | 6 | 36.620 | 11.342 | 10.804 | 98.38 | 0.777 |
| 13 | 31 | 8 | 115.752 | 7.399 | 187.648 | 182.36 | 0.973 |
| 14 | 0 | 0 | 343.092 | 7.156 | 497.751 | 0.00 | 1.000 |
| 14 | 0 | 2 | 261.529 | 3.497 | 379.429 | 180.00 | 1.000 |
| 14 | 0 | 4 | 458.187 | 6.217 | 664.011 | 180.00 | 1.000 |
| 14 | 0 | 6 | 127.933 | 2.263 | 183.434 | 180.00 | 0.991 |
| 14 | 0 | 8 | 150.627 | 3.315 | 50.833 | 0.00 | 0.234 |
| 14 | 0 | 10 | 19.163 | 8.247 | 0.959 | 180.00 | 0.035 |
| 14 | 0 | 12 | 286.137 | 3.580 | 411.336 | 0.00 | 1.000 |
| 14 | 0 | 14 | 117.801 | 4.244 | 168.738 | 0.00 | 1.000 |
| 14 | 0 | 16 | 410.419 | 5.834 | 585.686 | 180.00 | 1.000 |
| 14 | 0 | 18 | 82.835 | 6.787 | 53.606 | 0.00 | 0.456 |
| 14 | 0 | 20 | 565.512 | 6.681 | 799.327 | 0.00 | 1.000 |
| 14 | 0 | 22 | 154.092 | 4.213 | 216.686 | 0.00 | 1.000 |
| 14 | 0 | 24 | 69.236 | 13.150 | 37.965 | 180.00 | 0.394 |
| 14 | 0 | 26 | 146.787 | 6.794 | 203.681 | 0.00 | 1.000 |
| 14 | 0 | 28 | 80.670 | 13.571 | 101.100 | 0.00 | 0.914 |
| 14 | 0 | 30 | 139.442 | 9.424 | 190.049 | 0.00 | 1.000 |
| 14 | 0 | 32 | 223.766 | 5.851 | 303.219 | 0.00 | 1.000 |
| 14 | 0 | 34 | 147.076 | 7.497 | 195.997 | 180.00 | 0.995 |
| 14 | 0 | 36 | 52.375 | 17.298 | 48.442 | 0.00 | 0.725 |
| 14 | 0 | 38 | 30.321 | 13.500 | 29.086 | 0.00 | 0.758 |
| 14 | 0 | 40 | 32.604 | 15.711 | 13.795 | 180.00 | 0.351 |
| 14 | 1 | 1 | 212.625 | 2.095 | 256.607 | 339.09 | 0.983 |
| 14 | 1 | 3 | 311.912 | 4.173 | 495.395 | 283.21 | 0.988 |
| 14 | 1 | 5 | 256.023 | 2.471 | 390.019 | 245.69 | 0.984 |
| 14 | 1 | 7 | 138.004 | 1.660 | 165.020 | 299.97 | 0.974 |
| 14 | 1 | 9 | 186.873 | 1.877 | 279.386 | 136.55 | 0.982 |
| 14 | 1 | 11 | 175.437 | 2.020 | 321.882 | 271.66 | 0.967 |
| 14 | 1 | 13 | 210.699 | 2.448 | 311.201 | 325.84 | 0.980 |
| 14 | 1 | 15 | 378.107 | 3.264 | 562.515 | 324.48 | 0.993 |
| 14 | 1 | 17 | 129.077 | 3.368 | 101.146 | 239.00 | 0.970 |
| 14 | 1 | 19 | 137.881 | 3.506 | 200.422 | 318.73 | 0.939 |
| 14 | 1 | 21 | 151.345 | 3.587 | 204.146 | 180.32 | 0.956 |
| 14 | 1 | 23 | 128.222 | 4.654 | 146.633 | 260.56 | 0.949 |
| 14 | 1 | 25 | 181.548 | 3.708 | 194.638 | 184.96 | 0.981 |
| 14 | 1 | 27 | 115.840 | 5.273 | 130.755 | 142.08 | 0.955 |
| 14 | 1 | 29 | 77.674 | 9.361 | 77.421 | 166.39 | 0.928 |
| 14 | 1 | 31 | 100.013 | 6.819 | 160.627 | 177.95 | 0.705 |
| 14 | 1 | 33 | 66.872 | 10.413 | 76.457 | 64.26 | 0.647 |
| 14 | 1 | 35 | 70.849 | 9.759 | 81.143 | 244.52 | 0.653 |
| 14 | 1 | 37 | 107.068 | 7.815 | 184.809 | 71.83 | 0.948 |
| 14 | 1 | 39 | 66.469 | 12.176 | 78.764 | 244.88 | 0.644 |
| 14 | 2 | 0 | 20.719 | 11.177 | 12.273 | 180.00 | 0.428 |
| 14 | 2 | 2 | 211.681 | 3.008 | 388.922 | 354.45 | 0.956 |
| 14 | 2 | 4 | 99.216 | 2.127 | 134.805 | 50.53 | 0.922 |
| 14 | 2 | 6 | 349.736 | 3.367 | 518.487 | 343.21 | 0.991 |
| 14 | 2 | 8 | 209.955 | 1.986 | 244.199 | 21.15 | 0.980 |
| 14 | 2 | 10 | 328.729 | 3.330 | 448.146 | 152.30 | 0.990 |
| 14 | 2 | 12 | 134.024 | 2.363 | 193.178 | 350.82 | 0.960 |
| 14 | 2 | 14 | 219.335 | 2.393 | 341.907 | 87.23 | 0.978 |
| 14 | 2 | 16 | 387.118 | 3.355 | 569.815 | 257.66 | 0.994 |
| 14 | 2 | 18 | 190.976 | 2.856 | 190.020 | 138.12 | 0.980 |
| 14 | 2 | 20 | 290.654 | 2.955 | 459.505 | 229.85 | 0.987 |
| 14 | 2 | 22 | 231.483 | 2.880 | 350.696 | 122.83 | 0.978 |
| 14 | 2 | 24 | 51.773 | 10.968 | 6.572 | 239.80 | 0.560 |
| 14 | 2 | 26 | 235.450 | 3.897 | 304.280 | 229.17 | 0.987 |
| 14 | 2 | 28 | 93.419 | 6.254 | 77.704 | 143.31 | 0.930 |
| 14 | 2 | 30 | 136.903 | 5.004 | 159.477 | 65.10 | 0.972 |
| 14 | 2 | 32 | 105.584 | 6.411 | 150.298 | 39.29 | 0.938 |
| 14 | 2 | 34 | 82.042 | 9.410 | 76.116 | 110.63 | 0.935 |
| 14 | 2 | 36 | 44.585 | 12.084 | 35.721 | 109.36 | 0.723 |
| 14 | 2 | 38 | 52.775 | 12.260 | 55.946 | 214.53 | 0.732 |
| 14 | 2 | 40 | 33.575 | 11.249 | 7.563 | 265.96 | 0.338 |
| 14 | 3 | 1 | 96.242 | 3.161 | 87.078 | 185.63 | 0.562 |
| 14 | 3 | 3 | 160.462 | 2.127 | 247.723 | 22.25 | 0.975 |
| 14 | 3 | 5 | 166.616 | 2.219 | 269.905 | 126.92 | 0.958 |

| | | | | | | | |
|---|---|---|---|---|---|---|---|
| 14 | 3 | 7 | 354.778 | 3.124 | 528.156 | 42.77 | 0.990 |
| 14 | 3 | 9 | 218.629 | 2.362 | 309.039 | 291.72 | 0.987 |
| 14 | 3 | 11 | 250.899 | 2.334 | 309.649 | 135.02 | 0.989 |
| 14 | 3 | 13 | 129.355 | 2.507 | 205.778 | 197.12 | 0.890 |
| 14 | 3 | 15 | 109.017 | 3.334 | 57.510 | 109.95 | 0.973 |
| 14 | 3 | 17 | 64.096 | 6.770 | 48.570 | 192.18 | 0.824 |
| 14 | 3 | 19 | 192.976 | 3.115 | 280.319 | 255.20 | 0.974 |
| 14 | 3 | 21 | 435.083 | 4.622 | 645.688 | 24.36 | 0.994 |
| 14 | 3 | 23 | 411.308 | 4.457 | 577.608 | 113.82 | 0.994 |
| 14 | 3 | 25 | 91.740 | 8.032 | 76.305 | 235.78 | 0.933 |
| 14 | 3 | 27 | 70.268 | 9.798 | 57.977 | 106.98 | 0.468 |
| 14 | 3 | 29 | 118.472 | 5.781 | 180.203 | 88.09 | 0.952 |
| 14 | 3 | 31 | 49.548 | 12.259 | 18.131 | 122.73 | 0.768 |
| 14 | 3 | 33 | 46.538 | 12.810 | 7.165 | 209.36 | 0.727 |
| 14 | 3 | 35 | 72.437 | 10.110 | 86.564 | 65.05 | 0.679 |
| 14 | 3 | 37 | 35.968 | 11.070 | 3.736 | 21.08 | 0.111 |
| 14 | 3 | 39 | 50.679 | 13.638 | 48.196 | 121.62 | 0.727 |
| 14 | 4 | 0 | 21.246 | 12.427 | 0.143 | 180.00 | 0.005 |
| 14 | 4 | 2 | 417.652 | 5.733 | 566.930 | 28.90 | 0.994 |
| 14 | 4 | 4 | 60.291 | 3.146 | 57.493 | 52.57 | 0.841 |
| 14 | 4 | 6 | 250.706 | 3.918 | 379.792 | 147.27 | 0.981 |
| 14 | 4 | 8 | 368.886 | 3.382 | 523.426 | 60.32 | 0.992 |
| 14 | 4 | 10 | 50.033 | 4.797 | 29.037 | 354.27 | 0.737 |
| 14 | 4 | 12 | 301.683 | 3.869 | 415.762 | 122.84 | 0.991 |
| 14 | 4 | 14 | 308.475 | 2.810 | 416.182 | 87.82 | 0.992 |
| 14 | 4 | 16 | 89.802 | 3.441 | 79.949 | 310.95 | 0.920 |
| 14 | 4 | 18 | 135.995 | 3.549 | 156.565 | 191.51 | 0.957 |
| 14 | 4 | 20 | 512.795 | 4.479 | 670.101 | 51.14 | 0.997 |
| 14 | 4 | 22 | 211.096 | 3.239 | 322.380 | 80.06 | 0.972 |
| 14 | 4 | 24 | 51.383 | 10.482 | 27.505 | 286.19 | 0.481 |
| 14 | 4 | 26 | 229.783 | 3.669 | 371.578 | 240.11 | 0.982 |
| 14 | 4 | 28 | 74.383 | 9.661 | 64.067 | 166.76 | 0.918 |
| 14 | 4 | 30 | 170.980 | 4.481 | 223.256 | 233.62 | 0.981 |
| 14 | 4 | 32 | 123.152 | 6.388 | 166.165 | 212.50 | 0.960 |
| 14 | 4 | 34 | 174.760 | 6.070 | 257.996 | 225.78 | 0.981 |
| 14 | 4 | 36 | 96.783 | 8.820 | 154.350 | 185.07 | 0.944 |
| 14 | 4 | 38 | 49.891 | 13.735 | 28.295 | 337.99 | 0.871 |
| 14 | 4 | 40 | 34.414 | 11.261 | 11.001 | 126.07 | 0.426 |
| 14 | 5 | 1 | 97.681 | 4.246 | 135.030 | 232.97 | 0.895 |
| 14 | 5 | 3 | 238.994 | 2.520 | 317.957 | 272.88 | 0.988 |
| 14 | 5 | 5 | 175.820 | 2.348 | 312.262 | 269.91 | 0.937 |
| 14 | 5 | 7 | 60.661 | 3.680 | 23.989 | 219.39 | 0.207 |
| 14 | 5 | 9 | 108.586 | 2.295 | 138.299 | 78.62 | 0.974 |
| 14 | 5 | 11 | 58.729 | 5.135 | 47.712 | 37.97 | 0.721 |
| 14 | 5 | 13 | 51.919 | 5.348 | 6.450 | 78.21 | 0.089 |
| 14 | 5 | 15 | 282.231 | 2.740 | 414.806 | 147.60 | 0.988 |
| 14 | 5 | 17 | 322.110 | 2.995 | 440.163 | 215.42 | 0.992 |
| 14 | 5 | 19 | 32.618 | 9.218 | 54.795 | 272.13 | 0.496 |
| 14 | 5 | 21 | 143.836 | 3.586 | 191.398 | 149.78 | 0.948 |
| 14 | 5 | 23 | 195.580 | 3.536 | 261.198 | 22.51 | 0.974 |
| 14 | 5 | 25 | 216.141 | 3.839 | 281.923 | 338.59 | 0.985 |
| 14 | 5 | 27 | 127.655 | 4.974 | 167.926 | 322.91 | 0.953 |
| 14 | 5 | 29 | 270.405 | 3.919 | 379.839 | 5.24 | 0.992 |
| 14 | 5 | 31 | 43.892 | 11.333 | 16.585 | 225.46 | 0.361 |
| 14 | 5 | 33 | 42.998 | 11.574 | 15.802 | 16.62 | 0.609 |
| 14 | 5 | 35 | 66.530 | 10.948 | 76.039 | 253.16 | 0.734 |
| 14 | 5 | 37 | 56.829 | 13.503 | 61.945 | 178.17 | 0.746 |
| 14 | 5 | 39 | 34.670 | 10.894 | 8.905 | 66.19 | 0.821 |
| 14 | 6 | 0 | 465.488 | 10.064 | 674.495 | 180.00 | 1.000 |
| 14 | 6 | 2 | 433.716 | 6.452 | 628.000 | 238.89 | 0.994 |
| 14 | 6 | 4 | 405.670 | 3.883 | 653.225 | 21.30 | 0.991 |
| 14 | 6 | 6 | 436.936 | 4.461 | 573.227 | 239.29 | 0.994 |
| 14 | 6 | 8 | 134.526 | 2.046 | 221.187 | 49.42 | 0.961 |
| 14 | 6 | 10 | 264.242 | 2.644 | 381.620 | 112.30 | 0.989 |
| 14 | 6 | 12 | 252.790 | 3.162 | 403.126 | 167.04 | 0.984 |
| 14 | 6 | 14 | 497.100 | 4.081 | 743.783 | 340.64 | 0.996 |
| 14 | 6 | 16 | 189.358 | 2.935 | 273.484 | 257.75 | 0.977 |
| 14 | 6 | 18 | 352.191 | 3.152 | 457.367 | 298.34 | 0.993 |
| 14 | 6 | 20 | 481.910 | 4.564 | 770.461 | 119.52 | 0.995 |
| 14 | 6 | 22 | 432.152 | 3.858 | 646.097 | 159.90 | 0.994 |
| 14 | 6 | 24 | 213.049 | 3.338 | 319.761 | 298.39 | 0.982 |
| 14 | 6 | 26 | 212.993 | 3.653 | 274.519 | 308.62 | 0.985 |
| 14 | 6 | 28 | 166.036 | 4.206 | 185.665 | 253.51 | 0.983 |
| 14 | 6 | 30 | 239.110 | 3.912 | 301.598 | 40.86 | 0.991 |
| 14 | 6 | 32 | 108.258 | 6.166 | 187.169 | 261.23 | 0.861 |
| 14 | 6 | 34 | 68.725 | 11.692 | 58.711 | 87.38 | 0.899 |
| 14 | 6 | 36 | 149.965 | 6.170 | 258.314 | 181.95 | 0.978 |

| | | | | | | | |
|---|---|---|---|---|---|---|---|
| 14 | 6 | 38 | 66.201 | 11.572 | 67.885 | 28.03 | 0.914 |
| 14 | 7 | 1 | 298.743 | 3.383 | 430.775 | 193.68 | 0.987 |
| 14 | 7 | 3 | 251.387 | 2.581 | 350.778 | 136.59 | 0.984 |
| 14 | 7 | 5 | 109.776 | 2.770 | 164.608 | 245.80 | 0.922 |
| 14 | 7 | 7 | 84.082 | 2.548 | 73.019 | 343.37 | 0.939 |
| 14 | 7 | 9 | 121.441 | 2.421 | 104.211 | 0.32 | 0.946 |
| 14 | 7 | 11 | 492.313 | 4.703 | 735.042 | 302.72 | 0.996 |
| 14 | 7 | 13 | 262.018 | 2.594 | 392.050 | 52.36 | 0.985 |
| 14 | 7 | 15 | 256.253 | 2.590 | 364.674 | 256.72 | 0.987 |
| 14 | 7 | 17 | 277.755 | 2.762 | 475.637 | 36.62 | 0.984 |
| 14 | 7 | 19 | 127.996 | 3.309 | 180.764 | 45.12 | 0.933 |
| 14 | 7 | 21 | 415.798 | 3.724 | 623.682 | 154.16 | 0.993 |
| 14 | 7 | 23 | 258.233 | 3.168 | 355.104 | 322.20 | 0.984 |
| 14 | 7 | 25 | 130.341 | 5.754 | 170.046 | 253.33 | 0.952 |
| 14 | 7 | 27 | 54.246 | 11.185 | 38.667 | 117.20 | 0.485 |
| 14 | 7 | 29 | 67.822 | 9.646 | 78.863 | 141.06 | 0.761 |
| 14 | 7 | 31 | 40.814 | 11.700 | 8.274 | 290.23 | 0.521 |
| 14 | 7 | 33 | 170.536 | 4.730 | 262.324 | 274.68 | 0.980 |
| 14 | 7 | 35 | 51.799 | 12.359 | 52.921 | 23.32 | 0.786 |
| 14 | 7 | 37 | 121.768 | 6.213 | 159.176 | 149.06 | 0.977 |
| 14 | 7 | 39 | 37.910 | 11.731 | 8.233 | 92.12 | 0.786 |
| 14 | 8 | 0 | 178.797 | 4.057 | 166.356 | 180.00 | 0.642 |
| 14 | 8 | 2 | 243.834 | 2.133 | 363.127 | 282.72 | 0.986 |
| 14 | 8 | 4 | 169.116 | 2.180 | 205.353 | 74.98 | 0.985 |
| 14 | 8 | 6 | 409.162 | 3.800 | 584.585 | 87.57 | 0.995 |
| 14 | 8 | 8 | 168.739 | 2.257 | 228.397 | 113.62 | 0.982 |
| 14 | 8 | 10 | 69.946 | 3.962 | 65.009 | 294.75 | 0.879 |
| 14 | 8 | 12 | 547.238 | 5.121 | 759.819 | 82.09 | 0.997 |
| 14 | 8 | 14 | 255.188 | 2.581 | 326.970 | 115.17 | 0.989 |
| 14 | 8 | 16 | 283.000 | 2.759 | 390.512 | 252.39 | 0.990 |
| 14 | 8 | 18 | 234.947 | 2.756 | 297.776 | 160.00 | 0.985 |
| 14 | 8 | 20 | 193.910 | 3.234 | 324.213 | 307.53 | 0.958 |
| 14 | 8 | 22 | 159.330 | 3.602 | 234.421 | 91.77 | 0.959 |
| 14 | 8 | 24 | 226.274 | 3.413 | 258.914 | 116.73 | 0.988 |
| 14 | 8 | 26 | 275.781 | 3.583 | 362.549 | 277.29 | 0.991 |
| 14 | 8 | 28 | 183.378 | 4.259 | 258.338 | 72.37 | 0.983 |
| 14 | 8 | 30 | 58.226 | 10.965 | 50.663 | 269.33 | 0.787 |
| 14 | 8 | 32 | 42.797 | 11.383 | 15.380 | 148.69 | 0.397 |
| 14 | 8 | 34 | 132.036 | 6.142 | 232.490 | 354.06 | 0.945 |
| 14 | 8 | 36 | 122.255 | 7.631 | 206.260 | 203.74 | 0.965 |
| 14 | 8 | 38 | 41.711 | 12.743 | 4.807 | 30.86 | 0.099 |
| 14 | 9 | 1 | 570.125 | 4.720 | 792.167 | 241.75 | 0.997 |
| 14 | 9 | 3 | 214.713 | 2.742 | 321.359 | 21.92 | 0.979 |
| 14 | 9 | 5 | 195.317 | 2.384 | 258.039 | 162.02 | 0.981 |
| 14 | 9 | 7 | 104.618 | 3.322 | 169.409 | 310.99 | 0.887 |
| 14 | 9 | 9 | 246.325 | 2.611 | 313.718 | 30.82 | 0.989 |
| 14 | 9 | 11 | 91.349 | 3.741 | 71.842 | 3.78 | 0.933 |
| 14 | 9 | 13 | 30.421 | 8.339 | 19.444 | 153.55 | 0.519 |
| 14 | 9 | 15 | 108.432 | 3.322 | 162.519 | 194.13 | 0.890 |
| 14 | 9 | 17 | 332.300 | 3.187 | 497.229 | 218.61 | 0.991 |
| 14 | 9 | 19 | 98.135 | 4.335 | 107.978 | 95.39 | 0.854 |
| 14 | 9 | 21 | 156.690 | 3.721 | 178.713 | 96.34 | 0.964 |
| 14 | 9 | 23 | 290.588 | 3.419 | 389.090 | 135.29 | 0.992 |
| 14 | 9 | 25 | 191.092 | 3.568 | 290.050 | 11.70 | 0.977 |
| 14 | 9 | 27 | 123.405 | 5.718 | 168.475 | 195.48 | 0.963 |
| 14 | 9 | 29 | 101.537 | 6.460 | 156.606 | 308.57 | 0.918 |
| 14 | 9 | 31 | 157.122 | 4.571 | 235.802 | 195.46 | 0.974 |
| 14 | 9 | 33 | 100.049 | 7.265 | 159.707 | 284.50 | 0.916 |
| 14 | 9 | 35 | 152.944 | 5.079 | 244.035 | 8.64 | 0.982 |
| 14 | 9 | 37 | 53.400 | 12.051 | 48.417 | 326.07 | 0.866 |
| 14 | 10 | 0 | 83.322 | 4.056 | 120.565 | 180.00 | 0.998 |
| 14 | 10 | 2 | 416.504 | 3.684 | 589.483 | 213.37 | 0.995 |
| 14 | 10 | 4 | 87.986 | 2.998 | 124.265 | 353.79 | 0.926 |
| 14 | 10 | 6 | 158.311 | 2.708 | 263.494 | 321.42 | 0.953 |
| 14 | 10 | 8 | 362.485 | 2.966 | 499.077 | 309.91 | 0.994 |
| 14 | 10 | 10 | 382.630 | 3.208 | 547.102 | 338.06 | 0.994 |
| 14 | 10 | 12 | 324.713 | 3.073 | 452.328 | 112.95 | 0.992 |
| 14 | 10 | 14 | 211.131 | 3.087 | 278.765 | 254.28 | 0.984 |
| 14 | 10 | 16 | 308.925 | 3.060 | 425.316 | 275.24 | 0.992 |
| 14 | 10 | 18 | 134.329 | 3.987 | 170.159 | 324.36 | 0.943 |
| 14 | 10 | 20 | 275.508 | 3.199 | 285.850 | 111.70 | 0.991 |
| 14 | 10 | 22 | 35.598 | 8.650 | 26.214 | 139.38 | 0.743 |
| 14 | 10 | 24 | 62.804 | 10.757 | 56.136 | 164.59 | 0.718 |
| 14 | 10 | 26 | 165.921 | 3.946 | 231.857 | 195.69 | 0.978 |
| 14 | 10 | 28 | 170.002 | 3.925 | 226.092 | 12.00 | 0.981 |
| 14 | 10 | 30 | 148.240 | 4.493 | 217.245 | 275.05 | 0.971 |
| 14 | 10 | 32 | 167.108 | 4.298 | 259.893 | 336.91 | 0.978 |

| | | | | | | | |
|---|---|---|---|---|---|---|---|
| 14 | 10 | 34 | 97.138 | 8.716 | 98.838 | 63.03 | 0.972 |
| 14 | 10 | 36 | 39.498 | 11.731 | 4.826 | 328.99 | 0.128 |
| 14 | 10 | 38 | 48.219 | 12.208 | 37.612 | 177.14 | 0.600 |
| 14 | 11 | 1 | 28.130 | 7.052 | 43.941 | 307.04 | 0.499 |
| 14 | 11 | 3 | 200.797 | 2.459 | 329.743 | 250.55 | 0.974 |
| 14 | 11 | 5 | 394.056 | 4.139 | 553.008 | 61.40 | 0.994 |
| 14 | 11 | 7 | 166.574 | 3.148 | 235.100 | 262.52 | 0.962 |
| 14 | 11 | 9 | 524.129 | 4.162 | 716.047 | 129.56 | 0.997 |
| 14 | 11 | 11 | 322.658 | 2.964 | 530.511 | 177.16 | 0.989 |
| 14 | 11 | 13 | 531.160 | 4.716 | 744.746 | 101.72 | 0.997 |
| 14 | 11 | 15 | 301.940 | 3.079 | 489.999 | 95.30 | 0.988 |
| 14 | 11 | 17 | 408.431 | 3.688 | 409.519 | 91.46 | 0.995 |
| 14 | 11 | 19 | 134.429 | 4.097 | 235.206 | 345.25 | 0.896 |
| 14 | 11 | 21 | 81.767 | 5.734 | 85.793 | 286.69 | 0.889 |
| 14 | 11 | 23 | 172.967 | 3.775 | 225.508 | 155.60 | 0.976 |
| 14 | 11 | 25 | 43.399 | 9.953 | 16.470 | 253.23 | 0.302 |
| 14 | 11 | 27 | 52.453 | 11.672 | 38.723 | 119.07 | 0.564 |
| 14 | 11 | 29 | 152.672 | 4.336 | 319.654 | 240.91 | 0.911 |
| 14 | 11 | 31 | 53.528 | 10.381 | 3.082 | 116.86 | 0.900 |
| 14 | 11 | 33 | 126.604 | 5.533 | 149.927 | 69.52 | 0.971 |
| 14 | 11 | 35 | 51.891 | 12.082 | 48.612 | 150.82 | 0.824 |
| 14 | 11 | 37 | 109.702 | 8.726 | 184.910 | 192.50 | 0.953 |
| 14 | 12 | 0 | 206.718 | 3.976 | 299.667 | 180.00 | 1.000 |
| 14 | 12 | 2 | 30.731 | 7.164 | 71.690 | 315.45 | 0.690 |
| 14 | 12 | 4 | 100.145 | 4.515 | 151.449 | 309.87 | 0.918 |
| 14 | 12 | 6 | 204.158 | 2.986 | 272.685 | 12.33 | 0.979 |
| 14 | 12 | 8 | 261.530 | 3.029 | 375.827 | 281.88 | 0.988 |
| 14 | 12 | 10 | 258.956 | 2.650 | 355.611 | 237.75 | 0.988 |
| 14 | 12 | 12 | 153.357 | 3.299 | 194.142 | 176.92 | 0.963 |
| 14 | 12 | 14 | 128.615 | 4.215 | 186.203 | 119.53 | 0.931 |
| 14 | 12 | 16 | 201.537 | 2.949 | 312.107 | 239.26 | 0.975 |
| 14 | 12 | 18 | 45.471 | 10.470 | 1.978 | 41.33 | 0.104 |
| 14 | 12 | 20 | 241.261 | 3.188 | 320.387 | 3.52 | 0.988 |
| 14 | 12 | 22 | 252.802 | 3.442 | 360.893 | 43.58 | 0.989 |
| 14 | 12 | 24 | 115.938 | 5.051 | 109.713 | 302.03 | 0.968 |
| 14 | 12 | 26 | 72.217 | 7.211 | 91.078 | 66.39 | 0.628 |
| 14 | 12 | 28 | 106.482 | 6.396 | 98.018 | 27.54 | 0.960 |
| 14 | 12 | 30 | 101.638 | 7.185 | 154.913 | 307.76 | 0.935 |
| 14 | 12 | 32 | 80.935 | 7.963 | 104.525 | 270.77 | 0.911 |
| 14 | 12 | 34 | 33.307 | 10.373 | 9.506 | 290.11 | 0.774 |
| 14 | 12 | 36 | 38.070 | 11.789 | 17.911 | 272.93 | 0.427 |
| 14 | 13 | 1 | 236.479 | 2.598 | 391.967 | 279.23 | 0.979 |
| 14 | 13 | 3 | 95.962 | 3.551 | 91.395 | 145.89 | 0.916 |
| 14 | 13 | 5 | 279.002 | 3.416 | 359.939 | 1.55 | 0.990 |
| 14 | 13 | 7 | 197.237 | 3.040 | 332.724 | 7.92 | 0.968 |
| 14 | 13 | 9 | 302.886 | 2.854 | 400.915 | 230.12 | 0.991 |
| 14 | 13 | 11 | 220.596 | 2.694 | 337.502 | 330.91 | 0.980 |
| 14 | 13 | 13 | 338.997 | 3.447 | 489.373 | 279.82 | 0.992 |
| 14 | 13 | 15 | 123.907 | 4.033 | 75.827 | 30.27 | 0.955 |
| 14 | 13 | 17 | 125.731 | 4.420 | 100.121 | 242.41 | 0.949 |
| 14 | 13 | 19 | 44.140 | 9.326 | 7.176 | 186.46 | 0.694 |
| 14 | 13 | 21 | 72.271 | 9.693 | 48.994 | 282.96 | 0.882 |
| 14 | 13 | 23 | 80.658 | 8.079 | 31.607 | 291.88 | 0.952 |
| 14 | 13 | 25 | 322.651 | 3.506 | 483.992 | 299.38 | 0.994 |
| 14 | 13 | 27 | 90.978 | 7.184 | 126.469 | 307.81 | 0.915 |
| 14 | 13 | 29 | 97.661 | 6.455 | 156.937 | 274.25 | 0.902 |
| 14 | 13 | 31 | 50.227 | 11.488 | 31.127 | 271.21 | 0.767 |
| 14 | 13 | 33 | 99.563 | 7.718 | 139.965 | 34.00 | 0.962 |
| 14 | 13 | 35 | 63.344 | 12.773 | 44.282 | 33.93 | 0.930 |
| 14 | 14 | 0 | 100.921 | 6.111 | 146.168 | 0.00 | 1.000 |
| 14 | 14 | 2 | 99.925 | 4.472 | 120.838 | 102.63 | 0.934 |
| 14 | 14 | 4 | 138.517 | 3.620 | 219.616 | 157.12 | 0.919 |
| 14 | 14 | 6 | 27.106 | 7.938 | 38.300 | 295.88 | 0.264 |
| 14 | 14 | 8 | 87.690 | 5.804 | 39.003 | 200.66 | 0.950 |
| 14 | 14 | 10 | 226.204 | 2.677 | 339.750 | 155.27 | 0.983 |
| 14 | 14 | 12 | 32.009 | 9.315 | 16.889 | 239.61 | 0.182 |
| 14 | 14 | 14 | 340.896 | 3.594 | 484.274 | 4.55 | 0.991 |
| 14 | 14 | 16 | 92.673 | 5.486 | 89.230 | 113.79 | 0.913 |
| 14 | 14 | 18 | 92.499 | 6.889 | 128.675 | 245.20 | 0.888 |
| 14 | 14 | 20 | 100.454 | 6.036 | 166.172 | 261.89 | 0.838 |
| 14 | 14 | 22 | 139.694 | 4.676 | 242.965 | 262.40 | 0.948 |
| 14 | 14 | 24 | 270.335 | 3.778 | 384.326 | 219.04 | 0.992 |
| 14 | 14 | 26 | 120.770 | 5.112 | 170.958 | 129.87 | 0.958 |
| 14 | 14 | 28 | 34.388 | 10.899 | 4.682 | 67.91 | 0.497 |
| 14 | 14 | 30 | 186.334 | 4.282 | 367.513 | 306.29 | 0.972 |
| 14 | 14 | 32 | 95.070 | 7.756 | 168.308 | 105.07 | 0.934 |
| 14 | 14 | 34 | 65.470 | 10.504 | 63.562 | 101.88 | 0.934 |

| | | | | | | | |
|---|---|---|---|---|---|---|---|
| 14 | 14 | 36 | 59.307 | 13.377 | 56.253 | 136.54 | 0.561 |
| 14 | 15 | 1 | 352.439 | 3.172 | 561.527 | 1.50 | 0.992 |
| 14 | 15 | 3 | 244.807 | 2.885 | 359.414 | 172.67 | 0.984 |
| 14 | 15 | 5 | 135.221 | 3.518 | 162.912 | 73.44 | 0.956 |
| 14 | 15 | 7 | 241.515 | 3.569 | 322.181 | 244.51 | 0.985 |
| 14 | 15 | 9 | 240.390 | 2.837 | 408.330 | 300.35 | 0.978 |
| 14 | 15 | 11 | 63.908 | 5.296 | 41.799 | 238.15 | 0.808 |
| 14 | 15 | 13 | 259.943 | 3.000 | 394.418 | 339.45 | 0.984 |
| 14 | 15 | 15 | 65.434 | 10.119 | 50.947 | 14.54 | 0.707 |
| 14 | 15 | 17 | 377.009 | 3.817 | 521.763 | 231.33 | 0.995 |
| 14 | 15 | 19 | 278.229 | 4.317 | 402.909 | 325.25 | 0.990 |
| 14 | 15 | 21 | 131.025 | 4.916 | 205.914 | 64.48 | 0.962 |
| 14 | 15 | 23 | 121.814 | 5.360 | 142.031 | 246.84 | 0.966 |
| 14 | 15 | 25 | 158.837 | 4.618 | 144.170 | 344.00 | 0.984 |
| 14 | 15 | 27 | 54.034 | 11.162 | 41.616 | 96.43 | 0.645 |
| 14 | 15 | 29 | 66.612 | 11.921 | 67.595 | 356.75 | 0.876 |
| 14 | 15 | 31 | 43.738 | 11.367 | 28.780 | 41.00 | 0.818 |
| 14 | 15 | 33 | 105.246 | 8.845 | 156.324 | 221.29 | 0.634 |
| 14 | 15 | 35 | 74.134 | 12.577 | 106.356 | 188.34 | 0.856 |
| 14 | 16 | 0 | 184.982 | 3.767 | 267.122 | 180.00 | 0.997 |
| 14 | 16 | 2 | 318.334 | 3.100 | 479.047 | 203.33 | 0.990 |
| 14 | 16 | 4 | 319.198 | 3.434 | 456.867 | 156.14 | 0.991 |
| 14 | 16 | 6 | 609.877 | 6.690 | 877.756 | 325.72 | 0.997 |
| 14 | 16 | 8 | 117.035 | 5.522 | 205.568 | 303.00 | 0.819 |
| 14 | 16 | 10 | 204.776 | 2.849 | 268.000 | 226.04 | 0.980 |
| 14 | 16 | 12 | 165.645 | 3.536 | 164.871 | 13.66 | 0.971 |
| 14 | 16 | 14 | 277.153 | 3.288 | 417.147 | 115.31 | 0.990 |
| 14 | 16 | 16 | 177.661 | 3.930 | 218.327 | 24.29 | 0.981 |
| 14 | 16 | 18 | 151.386 | 4.595 | 228.271 | 33.28 | 0.964 |
| 14 | 16 | 20 | 105.691 | 8.143 | 131.540 | 184.96 | 0.954 |
| 14 | 16 | 22 | 133.240 | 4.675 | 201.688 | 213.26 | 0.965 |
| 14 | 16 | 24 | 184.136 | 4.145 | 266.850 | 332.63 | 0.983 |
| 14 | 16 | 26 | 211.428 | 4.234 | 262.884 | 89.23 | 0.989 |
| 14 | 16 | 28 | 52.326 | 11.704 | 38.421 | 111.93 | 0.802 |
| 14 | 16 | 30 | 58.710 | 11.490 | 67.955 | 264.59 | 0.875 |
| 14 | 16 | 32 | 114.366 | 6.967 | 188.465 | 251.97 | 0.965 |
| 14 | 16 | 34 | 55.500 | 12.872 | 44.041 | 276.37 | 0.893 |
| 14 | 17 | 1 | 54.083 | 7.572 | 5.377 | 322.54 | 0.705 |
| 14 | 17 | 3 | 487.323 | 4.462 | 662.397 | 173.87 | 0.996 |
| 14 | 17 | 5 | 168.378 | 4.095 | 233.483 | 342.02 | 0.965 |
| 14 | 17 | 7 | 262.585 | 3.989 | 429.317 | 83.09 | 0.982 |
| 14 | 17 | 9 | 258.678 | 3.714 | 323.465 | 66.29 | 0.987 |
| 14 | 17 | 11 | 347.550 | 3.298 | 500.860 | 142.11 | 0.992 |
| 14 | 17 | 13 | 83.250 | 6.025 | 82.413 | 138.99 | 0.540 |
| 14 | 17 | 15 | 177.844 | 3.867 | 225.140 | 71.90 | 0.980 |
| 14 | 17 | 17 | 127.919 | 5.641 | 161.479 | 354.23 | 0.956 |
| 14 | 17 | 19 | 145.428 | 4.428 | 217.326 | 234.35 | 0.972 |
| 14 | 17 | 21 | 105.320 | 9.844 | 184.869 | 301.76 | 0.768 |
| 14 | 17 | 23 | 216.740 | 4.738 | 327.960 | 182.21 | 0.987 |
| 14 | 17 | 25 | 178.223 | 4.960 | 312.030 | 142.33 | 0.974 |
| 14 | 17 | 27 | 144.553 | 4.991 | 210.832 | 185.65 | 0.975 |
| 14 | 17 | 29 | 125.391 | 6.476 | 199.182 | 142.57 | 0.975 |
| 14 | 17 | 31 | 99.545 | 8.105 | 134.445 | 320.21 | 0.963 |
| 14 | 17 | 33 | 73.736 | 11.403 | 107.585 | 225.11 | 0.893 |
| 14 | 18 | 0 | 117.736 | 6.246 | 170.246 | 0.00 | 1.000 |
| 14 | 18 | 2 | 143.575 | 3.280 | 171.477 | 319.11 | 0.959 |
| 14 | 18 | 4 | 201.815 | 3.416 | 240.571 | 80.11 | 0.981 |
| 14 | 18 | 6 | 450.060 | 5.341 | 714.218 | 86.84 | 0.995 |
| 14 | 18 | 8 | 79.975 | 7.673 | 81.698 | 52.07 | 0.840 |
| 14 | 18 | 10 | 93.289 | 7.876 | 85.072 | 20.08 | 0.938 |
| 14 | 18 | 12 | 111.776 | 4.847 | 192.157 | 274.14 | 0.904 |
| 14 | 18 | 14 | 242.559 | 3.326 | 363.624 | 257.24 | 0.987 |
| 14 | 18 | 16 | 94.779 | 6.282 | 141.208 | 168.71 | 0.927 |
| 14 | 18 | 18 | 123.779 | 6.028 | 153.250 | 358.45 | 0.967 |
| 14 | 18 | 20 | 174.919 | 4.113 | 253.102 | 153.95 | 0.982 |
| 14 | 18 | 22 | 53.856 | 9.866 | 37.525 | 254.35 | 0.804 |
| 14 | 18 | 24 | 93.744 | 6.239 | 92.941 | 250.62 | 0.948 |
| 14 | 18 | 26 | 156.615 | 5.311 | 254.071 | 275.11 | 0.976 |
| 14 | 18 | 28 | 78.850 | 9.271 | 58.291 | 39.49 | 0.374 |
| 14 | 18 | 30 | 61.780 | 10.940 | 82.725 | 43.80 | 0.822 |
| 14 | 18 | 32 | 87.658 | 11.814 | 143.457 | 29.13 | 0.886 |
| 14 | 19 | 1 | 163.803 | 3.423 | 264.745 | 331.24 | 0.949 |
| 14 | 19 | 3 | 205.351 | 3.681 | 244.199 | 237.41 | 0.982 |
| 14 | 19 | 5 | 209.788 | 3.601 | 325.725 | 355.67 | 0.983 |
| 14 | 19 | 7 | 110.280 | 5.526 | 139.350 | 21.90 | 0.945 |
| 14 | 19 | 9 | 183.732 | 4.497 | 243.717 | 288.89 | 0.981 |
| 14 | 19 | 11 | 262.582 | 3.568 | 379.693 | 308.15 | 0.990 |

| | | | | | | | |
|---|---|---|---|---|---|---|---|
| 14 | 19 | 13 | 144.714 | 4.181 | 178.004 | 176.73 | 0.514 |
| 14 | 19 | 15 | 142.799 | 4.991 | 283.910 | 285.63 | 0.946 |
| 14 | 19 | 17 | 178.398 | 4.363 | 255.825 | 89.86 | 0.983 |
| 14 | 19 | 19 | 42.473 | 12.309 | 16.738 | 100.11 | 0.594 |
| 14 | 19 | 21 | 224.172 | 3.938 | 308.756 | 174.48 | 0.990 |
| 14 | 19 | 23 | 37.564 | 10.979 | 8.731 | 98.23 | 0.519 |
| 14 | 19 | 25 | 42.167 | 12.073 | 17.446 | 189.07 | 0.625 |
| 14 | 19 | 27 | 44.893 | 11.197 | 39.153 | 290.68 | 0.582 |
| 14 | 19 | 29 | 38.600 | 11.775 | 15.091 | 252.47 | 0.765 |
| 14 | 19 | 31 | 73.067 | 11.730 | 107.839 | 61.10 | 0.887 |
| 14 | 20 | 0 | 79.684 | 11.719 | 13.363 | 0.00 | 0.116 |
| 14 | 20 | 2 | 128.563 | 4.951 | 248.282 | 170.48 | 0.905 |
| 14 | 20 | 4 | 164.724 | 5.094 | 302.083 | 157.56 | 0.957 |
| 14 | 20 | 6 | 91.577 | 7.455 | 111.625 | 170.55 | 0.911 |
| 14 | 20 | 8 | 191.263 | 5.167 | 290.088 | 349.59 | 0.978 |
| 14 | 20 | 10 | 96.382 | 7.262 | 134.218 | 224.69 | 0.908 |
| 14 | 20 | 12 | 108.348 | 6.301 | 113.924 | 96.71 | 0.967 |
| 14 | 20 | 14 | 42.930 | 10.491 | 10.497 | 22.70 | 0.758 |
| 14 | 20 | 16 | 86.799 | 7.622 | 139.501 | 151.82 | 0.890 |
| 14 | 20 | 18 | 72.009 | 9.518 | 94.233 | 105.42 | 0.864 |
| 14 | 20 | 20 | 41.690 | 10.421 | 16.885 | 4.45 | 0.330 |
| 14 | 20 | 22 | 41.986 | 10.461 | 21.675 | 217.74 | 0.681 |
| 14 | 20 | 24 | 61.910 | 10.621 | 36.510 | 343.88 | 0.332 |
| 14 | 20 | 26 | 149.467 | 8.155 | 271.396 | 129.58 | 0.978 |
| 14 | 20 | 28 | 34.016 | 10.798 | 10.584 | 344.87 | 0.364 |
| 14 | 20 | 30 | 74.297 | 11.702 | 100.078 | 134.36 | 0.911 |
| 14 | 21 | 1 | 96.973 | 6.654 | 160.232 | 268.21 | 0.865 |
| 14 | 21 | 3 | 143.079 | 6.209 | 263.570 | 55.91 | 0.942 |
| 14 | 21 | 5 | 115.171 | 5.796 | 187.626 | 189.06 | 0.894 |
| 14 | 21 | 7 | 60.560 | 11.815 | 55.865 | 304.82 | 0.553 |
| 14 | 21 | 9 | 156.723 | 4.821 | 215.949 | 313.52 | 0.981 |
| 14 | 21 | 11 | 134.353 | 5.429 | 205.008 | 52.63 | 0.967 |
| 14 | 21 | 13 | 94.470 | 7.855 | 135.753 | 112.85 | 0.933 |
| 14 | 21 | 15 | 109.046 | 6.202 | 161.262 | 128.54 | 0.952 |
| 14 | 21 | 17 | 125.255 | 5.851 | 206.012 | 90.34 | 0.954 |
| 14 | 21 | 19 | 101.196 | 7.920 | 98.734 | 310.19 | 0.958 |
| 14 | 21 | 21 | 40.469 | 11.792 | 20.162 | 321.37 | 0.528 |
| 14 | 21 | 23 | 87.854 | 8.340 | 119.683 | 145.53 | 0.921 |
| 14 | 21 | 25 | 57.533 | 12.119 | 40.377 | 11.14 | 0.920 |
| 14 | 21 | 27 | 60.744 | 12.091 | 82.227 | 40.34 | 0.847 |
| 14 | 21 | 29 | 94.634 | 11.309 | 129.505 | 133.39 | 0.956 |
| 14 | 22 | 0 | 40.852 | 15.969 | 57.675 | 0.00 | 0.989 |
| 14 | 22 | 2 | 37.366 | 10.787 | 2.213 | 201.05 | 0.633 |
| 14 | 22 | 4 | 38.093 | 10.804 | 3.041 | 59.91 | 0.686 |
| 14 | 22 | 6 | 50.998 | 10.753 | 43.970 | 279.36 | 0.621 |
| 14 | 22 | 8 | 47.668 | 10.671 | 25.086 | 353.07 | 0.779 |
| 14 | 22 | 10 | 45.127 | 10.412 | 20.791 | 276.95 | 0.356 |
| 14 | 22 | 12 | 55.680 | 11.902 | 47.530 | 320.25 | 0.780 |
| 14 | 22 | 14 | 92.350 | 6.515 | 104.374 | 48.01 | 0.944 |
| 14 | 22 | 16 | 89.359 | 6.885 | 135.263 | 142.57 | 0.762 |
| 14 | 22 | 18 | 58.250 | 11.500 | 33.299 | 155.02 | 0.892 |
| 14 | 22 | 20 | 150.040 | 4.843 | 224.350 | 279.21 | 0.978 |
| 14 | 22 | 22 | 41.786 | 11.693 | 31.033 | 118.07 | 0.780 |
| 14 | 22 | 24 | 40.763 | 10.797 | 24.547 | 35.49 | 0.800 |
| 14 | 22 | 26 | 38.222 | 11.972 | 22.969 | 3.64 | 0.681 |
| 14 | 22 | 28 | 49.097 | 14.070 | 43.906 | 249.32 | 0.687 |
| 14 | 23 | 1 | 111.878 | 5.441 | 139.192 | 139.22 | 0.962 |
| 14 | 23 | 3 | 166.767 | 4.618 | 314.436 | 128.37 | 0.970 |
| 14 | 23 | 5 | 132.132 | 4.853 | 176.182 | 160.20 | 0.971 |
| 14 | 23 | 7 | 137.061 | 4.399 | 208.100 | 216.01 | 0.970 |
| 14 | 23 | 9 | 33.676 | 10.531 | 6.867 | 147.65 | 0.359 |
| 14 | 23 | 11 | 109.413 | 5.705 | 182.587 | 92.09 | 0.937 |
| 14 | 23 | 13 | 116.642 | 6.455 | 185.035 | 191.29 | 0.952 |
| 14 | 23 | 15 | 88.600 | 7.629 | 110.432 | 258.28 | 0.934 |
| 14 | 23 | 17 | 32.703 | 10.325 | 13.945 | 145.14 | 0.655 |
| 14 | 23 | 19 | 52.715 | 11.823 | 46.675 | 353.41 | 0.727 |
| 14 | 23 | 21 | 36.916 | 10.569 | 18.765 | 42.25 | 0.494 |
| 14 | 23 | 23 | 79.196 | 10.193 | 119.859 | 115.71 | 0.929 |
| 14 | 23 | 25 | 39.327 | 12.377 | 24.994 | 302.24 | 0.613 |
| 14 | 23 | 27 | 33.526 | 11.465 | 12.937 | 300.10 | 0.386 |
| 14 | 24 | 0 | 46.101 | 15.318 | 61.113 | 180.00 | 0.932 |
| 14 | 24 | 2 | 65.019 | 10.346 | 29.958 | 267.82 | 0.914 |
| 14 | 24 | 4 | 84.107 | 6.765 | 98.498 | 25.92 | 0.931 |
| 14 | 24 | 6 | 167.736 | 4.213 | 216.479 | 28.59 | 0.984 |
| 14 | 24 | 8 | 39.263 | 10.911 | 4.686 | 225.18 | 0.639 |
| 14 | 24 | 10 | 82.864 | 8.762 | 88.712 | 280.14 | 0.930 |
| 14 | 24 | 12 | 100.298 | 8.058 | 162.158 | 353.90 | 0.923 |

| | | | | | | | |
|---|---|---|---|---|---|---|---|
| 14 | 24 | 14 | 78.275 | 9.707 | 73.050 | 142.49 | 0.398 |
| 14 | 24 | 16 | 102.364 | 5.823 | 166.117 | 155.99 | 0.942 |
| 14 | 24 | 18 | 127.290 | 5.992 | 192.082 | 78.60 | 0.968 |
| 14 | 24 | 20 | 54.415 | 13.215 | 64.885 | 269.70 | 0.703 |
| 14 | 24 | 22 | 41.897 | 11.551 | 24.558 | 338.10 | 0.791 |
| 14 | 24 | 24 | 33.512 | 11.282 | 7.803 | 38.09 | 0.397 |
| 14 | 25 | 1 | 45.562 | 11.055 | 26.123 | 124.80 | 0.576 |
| 14 | 25 | 3 | 122.912 | 5.299 | 215.054 | 292.34 | 0.950 |
| 14 | 25 | 5 | 190.723 | 4.356 | 270.732 | 358.51 | 0.986 |
| 14 | 25 | 7 | 195.987 | 4.109 | 294.150 | 337.90 | 0.986 |
| 14 | 25 | 9 | 113.546 | 6.357 | 151.975 | 118.28 | 0.967 |
| 14 | 25 | 11 | 106.515 | 9.842 | 163.819 | 95.23 | 0.948 |
| 14 | 25 | 13 | 68.685 | 12.283 | 42.569 | 134.20 | 0.925 |
| 14 | 25 | 15 | 83.247 | 7.755 | 105.282 | 309.96 | 0.933 |
| 14 | 25 | 17 | 68.434 | 9.632 | 51.269 | 64.02 | 0.953 |
| 14 | 25 | 19 | 52.827 | 12.286 | 37.844 | 287.37 | 0.898 |
| 14 | 25 | 21 | 44.134 | 12.136 | 28.175 | 261.73 | 0.857 |
| 14 | 25 | 23 | 34.938 | 11.662 | 6.701 | 355.02 | 0.728 |
| 14 | 26 | 0 | 53.701 | 15.059 | 72.672 | 180.00 | 0.961 |
| 14 | 26 | 2 | 126.582 | 5.302 | 213.477 | 286.65 | 0.965 |
| 14 | 26 | 4 | 65.512 | 9.916 | 47.609 | 351.02 | 0.344 |
| 14 | 26 | 6 | 72.513 | 8.094 | 113.279 | 334.29 | 0.815 |
| 14 | 26 | 8 | 77.237 | 7.528 | 105.767 | 207.11 | 0.911 |
| 14 | 26 | 10 | 88.445 | 9.536 | 156.414 | 83.39 | 0.839 |
| 14 | 26 | 12 | 52.746 | 11.559 | 42.487 | 59.84 | 0.831 |
| 14 | 26 | 14 | 74.796 | 11.559 | 126.406 | 188.32 | 0.878 |
| 14 | 26 | 16 | 35.882 | 10.512 | 16.530 | 158.89 | 0.379 |
| 14 | 26 | 18 | 63.991 | 12.140 | 68.722 | 246.20 | 0.916 |
| 14 | 26 | 20 | 52.723 | 14.617 | 55.502 | 220.10 | 0.730 |
| 14 | 26 | 22 | 37.229 | 12.167 | 4.425 | 2.39 | 0.092 |
| 14 | 27 | 1 | 62.810 | 9.944 | 46.050 | 202.75 | 0.910 |
| 14 | 27 | 3 | 103.340 | 9.153 | 147.788 | 88.50 | 0.950 |
| 14 | 27 | 5 | 36.154 | 9.945 | 11.245 | 223.80 | 0.323 |
| 14 | 27 | 7 | 85.097 | 7.441 | 138.851 | 67.31 | 0.900 |
| 14 | 27 | 9 | 65.702 | 22.924 | 51.081 | 158.93 | 0.904 |
| 14 | 27 | 11 | 57.460 | 11.054 | 79.194 | 185.96 | 0.726 |
| 14 | 27 | 13 | 81.614 | 10.162 | 96.269 | 320.60 | 0.957 |
| 14 | 27 | 15 | 27.287 | 9.472 | 15.946 | 130.77 | 0.738 |
| 14 | 27 | 17 | 32.932 | 10.950 | 9.140 | 179.47 | 0.321 |
| 14 | 27 | 19 | 59.194 | 13.423 | 70.303 | 211.59 | 0.844 |
| 14 | 28 | 0 | 67.055 | 15.550 | 89.081 | 0.00 | 0.964 |
| 14 | 28 | 2 | 57.211 | 10.755 | 82.341 | 215.07 | 0.836 |
| 14 | 28 | 4 | 38.564 | 10.142 | 26.615 | 23.28 | 0.561 |
| 14 | 28 | 6 | 39.705 | 11.195 | 1.648 | 169.67 | 0.869 |
| 14 | 28 | 8 | 137.869 | 4.991 | 208.212 | 217.97 | 0.984 |
| 14 | 28 | 10 | 48.718 | 11.522 | 45.866 | 125.93 | 0.516 |
| 14 | 28 | 12 | 32.111 | 10.420 | 8.389 | 235.88 | 0.591 |
| 14 | 28 | 14 | 38.912 | 12.962 | 6.441 | 156.94 | 0.142 |
| 14 | 28 | 16 | 38.615 | 13.253 | 21.582 | 323.54 | 0.525 |
| 14 | 29 | 1 | 37.880 | 10.735 | 12.300 | 343.64 | 0.816 |
| 14 | 29 | 3 | 75.775 | 11.933 | 103.476 | 152.30 | 0.935 |
| 14 | 29 | 5 | 52.853 | 12.202 | 62.211 | 267.39 | 0.757 |
| 14 | 29 | 7 | 48.964 | 11.506 | 51.071 | 259.36 | 0.823 |
| 14 | 29 | 9 | 44.716 | 10.405 | 35.149 | 220.62 | 0.849 |
| 14 | 29 | 11 | 42.204 | 12.143 | 31.950 | 49.37 | 0.655 |
| 14 | 29 | 13 | 42.371 | 13.128 | 3.538 | 180.77 | 0.059 |
| 14 | 30 | 0 | 40.093 | 20.989 | 26.747 | 0.00 | 0.535 |
| 14 | 30 | 2 | 64.141 | 13.442 | 90.729 | 188.97 | 0.773 |
| 14 | 30 | 4 | 41.606 | 12.584 | 23.781 | 114.64 | 0.826 |
| 14 | 30 | 6 | 32.856 | 10.415 | 5.841 | 234.60 | 0.803 |
| 14 | 30 | 8 | 45.598 | 12.148 | 24.642 | 172.00 | 0.868 |
| 14 | 30 | 10 | 32.079 | 10.557 | 9.691 | 343.09 | 0.396 |
| 14 | 31 | 1 | 68.318 | 10.685 | 82.771 | 334.02 | 0.929 |
| 14 | 31 | 3 | 39.158 | 12.955 | 11.765 | 69.93 | 0.344 |
| 15 | 0 | 1 | 645.770 | 8.847 | 941.481 | 180.00 | 1.000 |
| 15 | 0 | 3 | 127.429 | 3.126 | 185.657 | 0.00 | 0.999 |
| 15 | 0 | 5 | 57.583 | 8.154 | 72.896 | 0.00 | 0.884 |
| 15 | 0 | 7 | 112.083 | 2.547 | 162.084 | 0.00 | 0.998 |
| 15 | 0 | 9 | 61.488 | 7.352 | 88.076 | 0.00 | 0.987 |
| 15 | 0 | 11 | 86.035 | 4.324 | 123.811 | 180.00 | 0.999 |
| 15 | 0 | 13 | 313.777 | 3.918 | 452.762 | 180.00 | 1.000 |
| 15 | 0 | 15 | 283.076 | 3.808 | 407.178 | 180.00 | 1.000 |
| 15 | 0 | 17 | 21.355 | 9.982 | 15.460 | 180.00 | 0.541 |
| 15 | 0 | 19 | 166.292 | 5.156 | 236.742 | 180.00 | 1.000 |
| 15 | 0 | 21 | 111.630 | 6.321 | 158.220 | 180.00 | 1.000 |
| 15 | 0 | 23 | 93.583 | 9.254 | 129.336 | 180.00 | 0.983 |
| 15 | 0 | 25 | 268.354 | 5.055 | 375.821 | 0.00 | 1.000 |

| | | | | | | | |
|---|---|---|---|---|---|---|---|
| 15 | 0 | 27 | 164.524 | 6.889 | 228.643 | 0.00 | 1.000 |
| 15 | 0 | 29 | 107.148 | 8.418 | 145.677 | 0.00 | 0.988 |
| 15 | 0 | 31 | 133.945 | 9.329 | 181.393 | 0.00 | 0.994 |
| 15 | 0 | 33 | 48.523 | 16.293 | 7.723 | 0.00 | 0.120 |
| 15 | 0 | 35 | 168.036 | 6.914 | 224.804 | 0.00 | 1.000 |
| 15 | 0 | 37 | 47.199 | 16.975 | 31.634 | 0.00 | 0.539 |
| 15 | 0 | 39 | 37.392 | 16.762 | 21.792 | 0.00 | 0.485 |
| 15 | 1 | 2 | 151.457 | 1.928 | 287.179 | 78.10 | 0.905 |
| 15 | 1 | 4 | 44.122 | 4.501 | 11.514 | 204.41 | 0.271 |
| 15 | 1 | 6 | 147.188 | 1.760 | 211.216 | 223.73 | 0.949 |
| 15 | 1 | 8 | 211.780 | 1.901 | 325.759 | 46.59 | 0.979 |
| 15 | 1 | 10 | 35.504 | 6.422 | 11.669 | 257.10 | 0.273 |
| 15 | 1 | 12 | 132.530 | 2.493 | 143.208 | 156.18 | 0.957 |
| 15 | 1 | 14 | 375.541 | 3.258 | 495.987 | 154.37 | 0.994 |
| 15 | 1 | 16 | 175.047 | 2.650 | 254.493 | 187.91 | 0.966 |
| 15 | 1 | 18 | 297.021 | 2.957 | 406.060 | 24.07 | 0.990 |
| 15 | 1 | 20 | 229.333 | 2.781 | 264.990 | 139.52 | 0.984 |
| 15 | 1 | 22 | 34.048 | 9.768 | 15.019 | 63.05 | 0.225 |
| 15 | 1 | 24 | 243.821 | 3.698 | 315.256 | 119.41 | 0.989 |
| 15 | 1 | 26 | 45.373 | 10.403 | 8.704 | 341.72 | 0.158 |
| 15 | 1 | 28 | 154.737 | 4.792 | 226.432 | 355.52 | 0.975 |
| 15 | 1 | 30 | 71.596 | 9.619 | 57.497 | 64.96 | 0.401 |
| 15 | 1 | 32 | 101.461 | 7.486 | 115.906 | 99.78 | 0.947 |
| 15 | 1 | 34 | 29.145 | 9.498 | 28.281 | 139.11 | 0.583 |
| 15 | 1 | 36 | 28.531 | 9.559 | 36.130 | 239.09 | 0.804 |
| 15 | 1 | 38 | 125.383 | 6.509 | 208.966 | 213.61 | 0.971 |
| 15 | 2 | 1 | 170.045 | 2.372 | 222.172 | 329.04 | 0.973 |
| 15 | 2 | 3 | 108.232 | 1.980 | 138.521 | 10.52 | 0.866 |
| 15 | 2 | 5 | 184.225 | 2.338 | 268.772 | 307.93 | 0.972 |
| 15 | 2 | 7 | 325.149 | 3.433 | 408.445 | 171.86 | 0.994 |
| 15 | 2 | 9 | 165.116 | 1.890 | 262.404 | 352.25 | 0.961 |
| 15 | 2 | 11 | 307.997 | 2.850 | 455.302 | 22.50 | 0.992 |
| 15 | 2 | 13 | 75.831 | 3.773 | 106.891 | 26.02 | 0.895 |
| 15 | 2 | 15 | 284.218 | 2.729 | 379.681 | 15.87 | 0.990 |
| 15 | 2 | 17 | 146.158 | 3.068 | 231.609 | 271.19 | 0.895 |
| 15 | 2 | 19 | 180.535 | 3.114 | 180.578 | 319.92 | 0.983 |
| 15 | 2 | 21 | 122.796 | 4.173 | 200.479 | 205.38 | 0.877 |
| 15 | 2 | 23 | 325.030 | 3.318 | 489.057 | 299.52 | 0.989 |
| 15 | 2 | 25 | 335.382 | 3.564 | 390.407 | 244.82 | 0.994 |
| 15 | 2 | 27 | 37.869 | 10.886 | 6.926 | 91.66 | 0.636 |
| 15 | 2 | 29 | 98.631 | 7.166 | 66.445 | 68.60 | 0.959 |
| 15 | 2 | 31 | 113.200 | 6.401 | 167.875 | 134.20 | 0.946 |
| 15 | 2 | 33 | 43.353 | 12.424 | 25.959 | 239.11 | 0.854 |
| 15 | 2 | 35 | 40.043 | 12.060 | 27.067 | 40.32 | 0.608 |
| 15 | 2 | 37 | 77.488 | 10.189 | 111.052 | 80.32 | 0.897 |
| 15 | 2 | 39 | 33.705 | 10.977 | 5.487 | 242.06 | 0.618 |
| 15 | 3 | 0 | 303.324 | 4.787 | 442.583 | 0.00 | 1.000 |
| 15 | 3 | 2 | 83.851 | 3.430 | 73.933 | 181.59 | 0.548 |
| 15 | 3 | 4 | 195.453 | 3.077 | 227.379 | 39.31 | 0.979 |
| 15 | 3 | 6 | 74.938 | 3.513 | 83.875 | 84.10 | 0.899 |
| 15 | 3 | 8 | 177.671 | 2.049 | 238.727 | 327.93 | 0.978 |
| 15 | 3 | 10 | 397.925 | 3.677 | 626.645 | 2.47 | 0.994 |
| 15 | 3 | 12 | 209.056 | 2.234 | 339.617 | 314.50 | 0.971 |
| 15 | 3 | 14 | 171.548 | 2.474 | 233.497 | 238.51 | 0.971 |
| 15 | 3 | 16 | 206.644 | 2.545 | 332.898 | 141.02 | 0.975 |
| 15 | 3 | 18 | 140.296 | 3.199 | 131.838 | 340.08 | 0.965 |
| 15 | 3 | 20 | 124.612 | 3.266 | 182.596 | 247.26 | 0.919 |
| 15 | 3 | 22 | 341.039 | 3.592 | 457.297 | 187.17 | 0.991 |
| 15 | 3 | 24 | 180.662 | 3.801 | 287.877 | 243.06 | 0.968 |
| 15 | 3 | 26 | 127.782 | 5.786 | 161.736 | 217.05 | 0.954 |
| 15 | 3 | 28 | 188.266 | 4.084 | 264.686 | 158.37 | 0.984 |
| 15 | 3 | 30 | 66.107 | 9.072 | 50.171 | 252.20 | 0.422 |
| 15 | 3 | 32 | 46.436 | 12.461 | 9.517 | 303.47 | 0.235 |
| 15 | 3 | 34 | 75.190 | 9.879 | 57.962 | 134.06 | 0.926 |
| 15 | 3 | 36 | 64.143 | 11.402 | 87.608 | 342.18 | 0.851 |
| 15 | 3 | 38 | 32.857 | 10.504 | 6.757 | 356.37 | 0.258 |
| 15 | 4 | 1 | 206.707 | 3.446 | 303.580 | 149.75 | 0.978 |
| 15 | 4 | 3 | 238.580 | 3.396 | 308.619 | 278.38 | 0.981 |
| 15 | 4 | 5 | 228.499 | 2.598 | 351.535 | 259.89 | 0.983 |
| 15 | 4 | 7 | 333.760 | 3.726 | 449.301 | 319.66 | 0.993 |
| 15 | 4 | 9 | 118.999 | 2.242 | 171.956 | 315.23 | 0.927 |
| 15 | 4 | 11 | 78.153 | 3.227 | 78.775 | 216.02 | 0.907 |
| 15 | 4 | 13 | 431.236 | 3.938 | 631.253 | 100.54 | 0.995 |
| 15 | 4 | 15 | 32.287 | 7.251 | 15.496 | 319.22 | 0.341 |
| 15 | 4 | 17 | 390.505 | 3.670 | 575.449 | 256.01 | 0.994 |
| 15 | 4 | 19 | 33.337 | 9.643 | 37.354 | 68.97 | 0.370 |
| 15 | 4 | 21 | 228.370 | 3.416 | 236.683 | 235.79 | 0.984 |

| | | | | | | | |
|---|---|---|---|---|---|---|---|
| 15 | 4 | 23 | 86.988 | 6.354 | 74.938 | 282.82 | 0.927 |
| 15 | 4 | 25 | 97.676 | 7.042 | 131.315 | 213.38 | 0.926 |
| 15 | 4 | 27 | 205.483 | 3.587 | 313.415 | 278.73 | 0.985 |
| 15 | 4 | 29 | 86.213 | 8.423 | 132.131 | 178.09 | 0.864 |
| 15 | 4 | 31 | 84.501 | 8.005 | 104.346 | 153.05 | 0.642 |
| 15 | 4 | 33 | 133.512 | 6.212 | 160.442 | 230.67 | 0.974 |
| 15 | 4 | 35 | 95.265 | 8.327 | 160.482 | 51.52 | 0.936 |
| 15 | 4 | 37 | 70.123 | 12.423 | 70.397 | 241.88 | 0.935 |
| 15 | 4 | 39 | 68.350 | 12.699 | 84.278 | 179.24 | 0.877 |
| 15 | 5 | 0 | 296.230 | 4.980 | 432.095 | 180.00 | 1.000 |
| 15 | 5 | 2 | 340.812 | 3.888 | 499.743 | 359.74 | 0.992 |
| 15 | 5 | 4 | 201.317 | 2.386 | 309.383 | 260.09 | 0.975 |
| 15 | 5 | 6 | 156.384 | 2.286 | 207.789 | 161.43 | 0.975 |
| 15 | 5 | 8 | 169.073 | 1.998 | 247.486 | 8.27 | 0.972 |
| 15 | 5 | 10 | 232.866 | 2.695 | 305.079 | 189.93 | 0.985 |
| 15 | 5 | 12 | 349.436 | 3.285 | 502.283 | 198.73 | 0.993 |
| 15 | 5 | 14 | 261.530 | 2.757 | 446.450 | 105.96 | 0.982 |
| 15 | 5 | 16 | 301.152 | 2.933 | 448.889 | 289.12 | 0.989 |
| 15 | 5 | 18 | 204.602 | 2.865 | 330.292 | 319.23 | 0.974 |
| 15 | 5 | 20 | 148.612 | 3.319 | 198.977 | 50.89 | 0.957 |
| 15 | 5 | 22 | 396.187 | 3.797 | 614.034 | 249.47 | 0.993 |
| 15 | 5 | 24 | 380.863 | 3.711 | 611.612 | 310.65 | 0.994 |
| 15 | 5 | 26 | 43.063 | 11.238 | 16.270 | 296.65 | 0.576 |
| 15 | 5 | 28 | 119.540 | 5.364 | 161.416 | 5.89 | 0.960 |
| 15 | 5 | 30 | 155.268 | 4.358 | 155.127 | 107.18 | 0.983 |
| 15 | 5 | 32 | 88.479 | 8.713 | 126.139 | 85.74 | 0.917 |
| 15 | 5 | 34 | 93.859 | 7.914 | 135.980 | 80.32 | 0.921 |
| 15 | 5 | 36 | 68.229 | 12.378 | 70.953 | 37.14 | 0.915 |
| 15 | 5 | 38 | 43.143 | 11.725 | 26.003 | 301.21 | 0.793 |
| 15 | 6 | 1 | 277.387 | 3.407 | 379.190 | 320.82 | 0.990 |
| 15 | 6 | 3 | 238.752 | 2.672 | 329.703 | 93.42 | 0.985 |
| 15 | 6 | 5 | 305.856 | 3.948 | 432.714 | 201.16 | 0.991 |
| 15 | 6 | 7 | 157.948 | 2.918 | 219.825 | 110.73 | 0.969 |
| 15 | 6 | 9 | 319.569 | 3.403 | 477.534 | 221.06 | 0.991 |
| 15 | 6 | 11 | 56.603 | 5.244 | 10.049 | 113.43 | 0.909 |
| 15 | 6 | 13 | 210.670 | 2.583 | 315.161 | 115.43 | 0.978 |
| 15 | 6 | 15 | 184.893 | 2.743 | 239.827 | 349.78 | 0.975 |
| 15 | 6 | 17 | 334.157 | 3.182 | 489.367 | 76.70 | 0.991 |
| 15 | 6 | 19 | 219.863 | 2.978 | 323.047 | 175.59 | 0.980 |
| 15 | 6 | 21 | 140.378 | 4.340 | 228.655 | 155.05 | 0.923 |
| 15 | 6 | 23 | 326.804 | 3.432 | 463.071 | 156.39 | 0.993 |
| 15 | 6 | 25 | 203.509 | 3.753 | 276.277 | 86.74 | 0.983 |
| 15 | 6 | 27 | 172.540 | 4.532 | 255.179 | 205.24 | 0.980 |
| 15 | 6 | 29 | 116.280 | 6.202 | 176.598 | 29.81 | 0.631 |
| 15 | 6 | 31 | 152.631 | 5.280 | 199.870 | 221.91 | 0.977 |
| 15 | 6 | 33 | 142.843 | 5.331 | 295.870 | 17.66 | 0.893 |
| 15 | 6 | 35 | 33.294 | 10.904 | 10.120 | 13.00 | 0.327 |
| 15 | 6 | 37 | 38.554 | 11.156 | 23.432 | 47.15 | 0.687 |
| 15 | 7 | 0 | 327.351 | 7.542 | 477.161 | 0.00 | 1.000 |
| 15 | 7 | 2 | 105.955 | 4.457 | 158.630 | 133.96 | 0.902 |
| 15 | 7 | 4 | 154.647 | 2.316 | 212.979 | 258.80 | 0.958 |
| 15 | 7 | 6 | 174.834 | 2.618 | 249.040 | 195.55 | 0.982 |
| 15 | 7 | 8 | 165.038 | 2.169 | 229.344 | 217.07 | 0.975 |
| 15 | 7 | 10 | 673.883 | 6.499 | 921.810 | 334.96 | 0.998 |
| 15 | 7 | 12 | 425.815 | 3.928 | 624.036 | 44.26 | 0.995 |
| 15 | 7 | 14 | 293.776 | 2.746 | 445.813 | 62.86 | 0.989 |
| 15 | 7 | 16 | 152.803 | 2.936 | 176.075 | 37.27 | 0.968 |
| 15 | 7 | 18 | 256.189 | 3.033 | 433.462 | 43.59 | 0.977 |
| 15 | 7 | 20 | 190.953 | 3.380 | 202.674 | 202.73 | 0.978 |
| 15 | 7 | 22 | 189.678 | 3.506 | 257.079 | 0.21 | 0.980 |
| 15 | 7 | 24 | 230.109 | 3.179 | 373.466 | 102.49 | 0.981 |
| 15 | 7 | 26 | 215.036 | 3.798 | 303.423 | 295.74 | 0.988 |
| 15 | 7 | 28 | 153.870 | 5.296 | 202.751 | 290.65 | 0.977 |
| 15 | 7 | 30 | 30.260 | 9.759 | 6.850 | 104.39 | 0.296 |
| 15 | 7 | 32 | 238.839 | 4.352 | 337.316 | 301.85 | 0.991 |
| 15 | 7 | 34 | 90.303 | 8.144 | 149.239 | 295.84 | 0.936 |
| 15 | 7 | 36 | 46.566 | 11.236 | 43.696 | 304.19 | 0.679 |
| 15 | 7 | 38 | 30.887 | 10.334 | 6.945 | 355.51 | 0.671 |
| 15 | 8 | 1 | 53.876 | 6.809 | 28.830 | 247.23 | 0.772 |
| 15 | 8 | 3 | 132.513 | 2.460 | 177.601 | 38.76 | 0.943 |
| 15 | 8 | 5 | 440.258 | 4.420 | 643.003 | 120.34 | 0.995 |
| 15 | 8 | 7 | 155.841 | 2.557 | 246.945 | 12.15 | 0.966 |
| 15 | 8 | 9 | 563.371 | 4.479 | 762.612 | 333.05 | 0.997 |
| 15 | 8 | 11 | 172.774 | 2.778 | 331.994 | 153.70 | 0.855 |
| 15 | 8 | 13 | 206.643 | 2.688 | 311.600 | 315.63 | 0.978 |
| 15 | 8 | 15 | 84.321 | 4.460 | 85.388 | 268.73 | 0.859 |
| 15 | 8 | 17 | 376.729 | 3.334 | 549.290 | 125.40 | 0.993 |

| | | | | | | | |
|---|---|---|---|---|---|---|---|
| 15 | 8 | 19 | 111.713 | 4.429 | 174.270 | 23.64 | 0.754 |
| 15 | 8 | 21 | 226.910 | 3.176 | 302.422 | 12.18 | 0.987 |
| 15 | 8 | 23 | 139.102 | 3.991 | 220.133 | 350.11 | 0.953 |
| 15 | 8 | 25 | 82.794 | 7.806 | 70.247 | 281.91 | 0.932 |
| 15 | 8 | 27 | 197.958 | 3.616 | 337.694 | 79.25 | 0.981 |
| 15 | 8 | 29 | 194.558 | 4.243 | 411.207 | 316.82 | 0.961 |
| 15 | 8 | 31 | 46.893 | 11.413 | 36.485 | 276.32 | 0.622 |
| 15 | 8 | 33 | 105.629 | 6.836 | 166.577 | 286.77 | 0.936 |
| 15 | 8 | 35 | 33.616 | 9.957 | 7.070 | 227.68 | 0.161 |
| 15 | 8 | 37 | 64.579 | 11.665 | 66.292 | 136.31 | 0.915 |
| 15 | 9 | 0 | 234.474 | 4.312 | 341.696 | 0.00 | 1.000 |
| 15 | 9 | 2 | 243.494 | 2.379 | 246.434 | 244.04 | 0.991 |
| 15 | 9 | 4 | 501.991 | 4.369 | 696.103 | 164.61 | 0.997 |
| 15 | 9 | 6 | 387.248 | 3.705 | 620.730 | 216.96 | 0.993 |
| 15 | 9 | 8 | 261.097 | 2.422 | 419.284 | 7.48 | 0.987 |
| 15 | 9 | 10 | 175.160 | 2.479 | 280.458 | 19.12 | 0.967 |
| 15 | 9 | 12 | 408.653 | 3.773 | 607.709 | 111.37 | 0.994 |
| 15 | 9 | 14 | 51.146 | 8.235 | 37.299 | 121.46 | 0.633 |
| 15 | 9 | 16 | 124.177 | 3.830 | 161.253 | 317.30 | 0.700 |
| 15 | 9 | 18 | 176.238 | 3.375 | 231.193 | 96.55 | 0.975 |
| 15 | 9 | 20 | 189.457 | 3.003 | 237.661 | 100.35 | 0.976 |
| 15 | 9 | 22 | 168.967 | 3.849 | 217.668 | 195.51 | 0.977 |
| 15 | 9 | 24 | 212.975 | 3.207 | 284.696 | 74.71 | 0.983 |
| 15 | 9 | 26 | 87.752 | 7.005 | 108.723 | 164.60 | 0.932 |
| 15 | 9 | 28 | 120.164 | 4.524 | 166.728 | 154.33 | 0.959 |
| 15 | 9 | 30 | 69.988 | 8.567 | 69.818 | 18.21 | 0.889 |
| 15 | 9 | 32 | 59.621 | 11.266 | 57.672 | 36.51 | 0.840 |
| 15 | 9 | 34 | 114.412 | 6.626 | 212.739 | 190.07 | 0.953 |
| 15 | 9 | 36 | 100.758 | 8.074 | 163.209 | 227.76 | 0.953 |
| 15 | 10 | 1 | 546.207 | 4.927 | 757.940 | 353.08 | 0.997 |
| 15 | 10 | 3 | 72.654 | 3.247 | 43.163 | 180.95 | 0.379 |
| 15 | 10 | 5 | 171.770 | 2.545 | 199.909 | 153.41 | 0.974 |
| 15 | 10 | 7 | 435.548 | 3.945 | 623.068 | 111.08 | 0.995 |
| 15 | 10 | 9 | 51.720 | 6.499 | 2.049 | 142.21 | 0.731 |
| 15 | 10 | 11 | 180.963 | 2.448 | 248.691 | 4.01 | 0.974 |
| 15 | 10 | 13 | 226.597 | 2.973 | 391.472 | 19.44 | 0.977 |
| 15 | 10 | 15 | 242.046 | 2.988 | 363.894 | 351.05 | 0.981 |
| 15 | 10 | 17 | 193.185 | 3.157 | 283.829 | 44.85 | 0.971 |
| 15 | 10 | 19 | 190.341 | 3.426 | 280.182 | 164.62 | 0.970 |
| 15 | 10 | 21 | 185.906 | 3.631 | 264.185 | 168.90 | 0.978 |
| 15 | 10 | 23 | 101.150 | 5.286 | 89.367 | 95.79 | 0.945 |
| 15 | 10 | 25 | 143.753 | 4.346 | 174.713 | 231.37 | 0.976 |
| 15 | 10 | 27 | 54.457 | 10.376 | 47.210 | 17.12 | 0.752 |
| 15 | 10 | 29 | 124.103 | 6.649 | 228.974 | 289.95 | 0.925 |
| 15 | 10 | 31 | 164.511 | 4.865 | 308.654 | 1.15 | 0.968 |
| 15 | 10 | 33 | 121.191 | 7.343 | 158.520 | 65.82 | 0.978 |
| 15 | 10 | 35 | 38.617 | 11.662 | 17.018 | 256.00 | 0.403 |
| 15 | 10 | 37 | 43.673 | 12.785 | 10.522 | 301.70 | 0.850 |
| 15 | 11 | 0 | 325.701 | 4.286 | 474.690 | 0.00 | 1.000 |
| 15 | 11 | 2 | 172.119 | 2.306 | 234.448 | 187.10 | 0.978 |
| 15 | 11 | 4 | 451.496 | 4.371 | 655.575 | 126.00 | 0.996 |
| 15 | 11 | 6 | 395.166 | 3.854 | 543.009 | 163.78 | 0.995 |
| 15 | 11 | 8 | 132.861 | 2.790 | 216.264 | 230.40 | 0.848 |
| 15 | 11 | 10 | 35.093 | 8.298 | 49.389 | 22.40 | 0.566 |
| 15 | 11 | 12 | 292.554 | 3.236 | 403.860 | 338.62 | 0.991 |
| 15 | 11 | 14 | 339.362 | 3.404 | 464.297 | 37.52 | 0.992 |
| 15 | 11 | 16 | 170.273 | 3.284 | 263.082 | 322.32 | 0.960 |
| 15 | 11 | 18 | 165.292 | 3.237 | 198.116 | 155.42 | 0.976 |
| 15 | 11 | 20 | 148.404 | 4.344 | 261.349 | 56.70 | 0.933 |
| 15 | 11 | 22 | 126.181 | 4.630 | 163.701 | 11.85 | 0.955 |
| 15 | 11 | 24 | 121.063 | 4.482 | 172.037 | 2.59 | 0.964 |
| 15 | 11 | 26 | 114.198 | 5.807 | 158.502 | 318.11 | 0.957 |
| 15 | 11 | 28 | 65.316 | 9.340 | 2.227 | 325.55 | 0.026 |
| 15 | 11 | 30 | 185.855 | 4.522 | 303.256 | 266.75 | 0.981 |
| 15 | 11 | 32 | 57.013 | 11.863 | 49.062 | 147.66 | 0.908 |
| 15 | 11 | 34 | 108.218 | 6.845 | 156.409 | 319.82 | 0.968 |
| 15 | 11 | 36 | 50.676 | 11.799 | 55.155 | 324.52 | 0.717 |
| 15 | 12 | 1 | 219.627 | 2.847 | 341.549 | 18.18 | 0.979 |
| 15 | 12 | 3 | 183.465 | 2.400 | 201.933 | 173.12 | 0.978 |
| 15 | 12 | 5 | 91.524 | 4.681 | 66.270 | 349.46 | 0.321 |
| 15 | 12 | 7 | 282.800 | 3.169 | 342.381 | 124.05 | 0.990 |
| 15 | 12 | 9 | 102.642 | 3.722 | 127.468 | 270.04 | 0.910 |
| 15 | 12 | 11 | 255.056 | 2.723 | 305.589 | 141.45 | 0.988 |
| 15 | 12 | 13 | 269.220 | 3.130 | 407.272 | 188.11 | 0.985 |
| 15 | 12 | 15 | 343.120 | 3.808 | 453.226 | 155.94 | 0.992 |
| 15 | 12 | 17 | 292.631 | 3.425 | 406.174 | 70.81 | 0.988 |
| 15 | 12 | 19 | 116.625 | 4.871 | 103.979 | 355.30 | 0.959 |

| | | | | | | | |
|---|---|---|---|---|---|---|---|
| 15 | 12 | 21 | 52.043 | 10.118 | 6.410 | 225.62 | 0.793 |
| 15 | 12 | 23 | 62.383 | 9.742 | 50.245 | 295.42 | 0.868 |
| 15 | 12 | 25 | 52.159 | 10.067 | 40.316 | 351.67 | 0.687 |
| 15 | 12 | 27 | 124.660 | 5.105 | 174.553 | 348.35 | 0.962 |
| 15 | 12 | 29 | 139.395 | 5.286 | 212.230 | 25.76 | 0.971 |
| 15 | 12 | 31 | 77.737 | 8.020 | 112.739 | 339.62 | 0.866 |
| 15 | 12 | 33 | 54.316 | 10.581 | 61.121 | 97.11 | 0.832 |
| 15 | 12 | 35 | 41.053 | 11.805 | 23.228 | 230.21 | 0.449 |
| 15 | 13 | 0 | 183.791 | 3.990 | 267.531 | 0.00 | 1.000 |
| 15 | 13 | 2 | 529.113 | 4.358 | 790.366 | 332.13 | 0.997 |
| 15 | 13 | 4 | 296.254 | 3.002 | 410.401 | 81.41 | 0.990 |
| 15 | 13 | 6 | 43.617 | 8.502 | 10.320 | 302.68 | 0.531 |
| 15 | 13 | 8 | 47.543 | 8.466 | 3.318 | 293.51 | 0.125 |
| 15 | 13 | 10 | 379.185 | 3.360 | 611.436 | 255.00 | 0.992 |
| 15 | 13 | 12 | 151.553 | 3.103 | 253.565 | 226.04 | 0.956 |
| 15 | 13 | 14 | 59.483 | 10.326 | 13.161 | 120.86 | 0.247 |
| 15 | 13 | 16 | 150.376 | 3.876 | 215.273 | 193.76 | 0.950 |
| 15 | 13 | 18 | 142.469 | 6.960 | 208.266 | 296.86 | 0.963 |
| 15 | 13 | 20 | 111.227 | 5.490 | 138.676 | 213.13 | 0.938 |
| 15 | 13 | 22 | 84.280 | 7.485 | 116.586 | 176.63 | 0.908 |
| 15 | 13 | 24 | 151.103 | 4.329 | 201.361 | 233.47 | 0.980 |
| 15 | 13 | 26 | 268.770 | 3.533 | 407.048 | 188.14 | 0.992 |
| 15 | 13 | 28 | 57.964 | 11.957 | 51.081 | 162.32 | 0.829 |
| 15 | 13 | 30 | 62.291 | 11.976 | 69.661 | 323.20 | 0.817 |
| 15 | 13 | 32 | 44.324 | 11.112 | 28.516 | 122.72 | 0.484 |
| 15 | 13 | 34 | 110.339 | 8.167 | 207.914 | 217.59 | 0.941 |
| 15 | 14 | 1 | 195.743 | 2.600 | 268.920 | 98.42 | 0.978 |
| 15 | 14 | 3 | 200.614 | 2.692 | 275.868 | 164.34 | 0.979 |
| 15 | 14 | 5 | 166.474 | 3.069 | 300.190 | 331.05 | 0.952 |
| 15 | 14 | 7 | 366.834 | 3.763 | 471.302 | 277.11 | 0.993 |
| 15 | 14 | 9 | 145.845 | 3.447 | 216.516 | 296.00 | 0.947 |
| 15 | 14 | 11 | 161.957 | 3.348 | 307.025 | 301.23 | 0.921 |
| 15 | 14 | 13 | 165.658 | 3.309 | 252.556 | 299.87 | 0.959 |
| 15 | 14 | 15 | 291.307 | 3.711 | 406.745 | 244.37 | 0.992 |
| 15 | 14 | 17 | 180.567 | 3.404 | 332.754 | 151.30 | 0.966 |
| 15 | 14 | 19 | 185.296 | 5.352 | 273.693 | 283.10 | 0.977 |
| 15 | 14 | 21 | 83.704 | 7.656 | 137.925 | 190.34 | 0.807 |
| 15 | 14 | 23 | 153.930 | 4.320 | 165.305 | 222.18 | 0.981 |
| 15 | 14 | 25 | 145.208 | 4.758 | 204.032 | 243.91 | 0.974 |
| 15 | 14 | 27 | 68.907 | 10.082 | 95.959 | 224.90 | 0.762 |
| 15 | 14 | 29 | 84.083 | 10.330 | 79.339 | 250.78 | 0.939 |
| 15 | 14 | 31 | 64.410 | 11.199 | 64.032 | 154.86 | 0.921 |
| 15 | 14 | 33 | 41.518 | 11.623 | 30.006 | 111.60 | 0.584 |
| 15 | 15 | 0 | 114.866 | 7.157 | 120.022 | 0.00 | 0.719 |
| 15 | 15 | 2 | 417.041 | 4.071 | 595.299 | 357.65 | 0.995 |
| 15 | 15 | 4 | 185.002 | 2.701 | 326.156 | 184.28 | 0.964 |
| 15 | 15 | 6 | 181.919 | 3.127 | 252.823 | 261.28 | 0.973 |
| 15 | 15 | 8 | 249.915 | 3.310 | 355.557 | 174.67 | 0.985 |
| 15 | 15 | 10 | 78.852 | 5.283 | 101.405 | 297.41 | 0.803 |
| 15 | 15 | 12 | 67.910 | 7.670 | 82.889 | 72.95 | 0.815 |
| 15 | 15 | 14 | 162.805 | 3.290 | 188.709 | 186.90 | 0.979 |
| 15 | 15 | 16 | 130.864 | 5.492 | 135.190 | 207.84 | 0.967 |
| 15 | 15 | 18 | 167.867 | 3.875 | 252.031 | 121.20 | 0.971 |
| 15 | 15 | 20 | 65.693 | 9.792 | 80.031 | 172.25 | 0.834 |
| 15 | 15 | 22 | 65.584 | 9.344 | 49.945 | 265.58 | 0.884 |
| 15 | 15 | 24 | 83.765 | 8.137 | 117.834 | 302.86 | 0.904 |
| 15 | 15 | 26 | 88.484 | 7.786 | 117.536 | 41.36 | 0.929 |
| 15 | 15 | 28 | 156.569 | 4.942 | 212.666 | 341.43 | 0.981 |
| 15 | 15 | 30 | 66.032 | 11.470 | 62.425 | 144.43 | 0.936 |
| 15 | 15 | 32 | 98.745 | 7.837 | 172.892 | 224.18 | 0.944 |
| 15 | 15 | 34 | 57.382 | 12.155 | 42.777 | 173.99 | 0.901 |
| 15 | 16 | 1 | 137.004 | 3.665 | 225.265 | 112.74 | 0.838 |
| 15 | 16 | 3 | 315.457 | 3.107 | 474.776 | 215.23 | 0.990 |
| 15 | 16 | 5 | 208.481 | 3.496 | 336.843 | 244.89 | 0.973 |
| 15 | 16 | 7 | 156.724 | 4.561 | 218.291 | 128.39 | 0.958 |
| 15 | 16 | 9 | 238.781 | 3.662 | 323.813 | 195.68 | 0.984 |
| 15 | 16 | 11 | 127.102 | 4.104 | 197.991 | 354.25 | 0.949 |
| 15 | 16 | 13 | 164.624 | 3.411 | 248.399 | 342.73 | 0.972 |
| 15 | 16 | 15 | 309.225 | 3.339 | 456.291 | 261.41 | 0.992 |
| 15 | 16 | 17 | 53.856 | 9.923 | 43.818 | 311.54 | 0.741 |
| 15 | 16 | 19 | 198.296 | 4.392 | 259.614 | 57.57 | 0.988 |
| 15 | 16 | 21 | 305.761 | 4.143 | 447.271 | 1.29 | 0.994 |
| 15 | 16 | 23 | 176.806 | 3.988 | 229.234 | 52.03 | 0.984 |
| 15 | 16 | 25 | 102.016 | 6.453 | 126.463 | 167.25 | 0.956 |
| 15 | 16 | 27 | 78.155 | 8.478 | 77.198 | 240.49 | 0.447 |
| 15 | 16 | 29 | 39.723 | 11.264 | 24.051 | 88.18 | 0.711 |
| 15 | 16 | 31 | 84.747 | 10.363 | 112.094 | 253.30 | 0.949 |

| | | | | | | | |
|---|---|---|---|---|---|---|---|
| 15 | 16 | 33 | 40.254 | 11.157 | 25.803 | 10.10 | 0.634 |
| 15 | 17 | 0 | 160.771 | 6.279 | 233.784 | 180.00 | 1.000 |
| 15 | 17 | 2 | 164.453 | 3.749 | 261.686 | 95.27 | 0.955 |
| 15 | 17 | 4 | 470.809 | 4.467 | 703.024 | 17.96 | 0.996 |
| 15 | 17 | 6 | 167.401 | 4.692 | 310.433 | 198.78 | 0.908 |
| 15 | 17 | 8 | 196.954 | 4.295 | 244.578 | 278.35 | 0.985 |
| 15 | 17 | 10 | 68.383 | 8.978 | 67.965 | 241.25 | 0.849 |
| 15 | 17 | 12 | 160.082 | 3.505 | 282.804 | 4.20 | 0.965 |
| 15 | 17 | 14 | 67.389 | 9.019 | 69.817 | 315.86 | 0.688 |
| 15 | 17 | 16 | 89.404 | 6.158 | 58.677 | 15.23 | 0.956 |
| 15 | 17 | 18 | 217.050 | 3.906 | 356.385 | 20.42 | 0.987 |
| 15 | 17 | 20 | 110.270 | 6.702 | 124.323 | 273.92 | 0.963 |
| 15 | 17 | 22 | 130.629 | 7.929 | 148.335 | 314.57 | 0.972 |
| 15 | 17 | 24 | 41.070 | 12.021 | 12.455 | 93.47 | 0.377 |
| 15 | 17 | 26 | 48.407 | 12.873 | 30.839 | 258.17 | 0.674 |
| 15 | 17 | 28 | 166.650 | 4.590 | 226.681 | 34.28 | 0.989 |
| 15 | 17 | 30 | 73.996 | 10.858 | 79.187 | 90.45 | 0.946 |
| 15 | 17 | 32 | 113.406 | 7.578 | 193.720 | 336.07 | 0.961 |
| 15 | 18 | 1 | 108.821 | 5.495 | 155.606 | 336.17 | 0.931 |
| 15 | 18 | 3 | 103.275 | 5.469 | 60.608 | 172.69 | 0.238 |
| 15 | 18 | 5 | 148.467 | 3.767 | 296.462 | 284.30 | 0.876 |
| 15 | 18 | 7 | 87.838 | 6.626 | 112.195 | 97.41 | 0.914 |
| 15 | 18 | 9 | 148.442 | 4.914 | 167.368 | 316.13 | 0.973 |
| 15 | 18 | 11 | 242.931 | 3.444 | 310.311 | 339.27 | 0.990 |
| 15 | 18 | 13 | 273.104 | 3.229 | 384.263 | 75.57 | 0.993 |
| 15 | 18 | 15 | 131.434 | 4.589 | 178.846 | 151.25 | 0.970 |
| 15 | 18 | 17 | 188.536 | 3.948 | 312.932 | 71.80 | 0.982 |
| 15 | 18 | 19 | 125.476 | 6.059 | 151.593 | 31.25 | 0.970 |
| 15 | 18 | 21 | 110.778 | 5.887 | 168.277 | 271.95 | 0.945 |
| 15 | 18 | 23 | 54.901 | 12.032 | 53.201 | 177.13 | 0.780 |
| 15 | 18 | 25 | 34.042 | 9.562 | 8.627 | 352.73 | 0.691 |
| 15 | 18 | 27 | 38.438 | 12.192 | 21.619 | 78.49 | 0.548 |
| 15 | 18 | 29 | 66.941 | 9.890 | 77.012 | 71.32 | 0.931 |
| 15 | 18 | 31 | 31.910 | 10.601 | 8.037 | 2.75 | 0.627 |
| 15 | 19 | 0 | 25.181 | 12.245 | 26.048 | 180.00 | 0.727 |
| 15 | 19 | 2 | 63.161 | 9.237 | 38.757 | 80.07 | 0.857 |
| 15 | 19 | 4 | 208.507 | 3.610 | 312.334 | 173.44 | 0.984 |
| 15 | 19 | 6 | 212.815 | 4.501 | 381.414 | 80.08 | 0.976 |
| 15 | 19 | 8 | 93.928 | 7.094 | 151.545 | 229.49 | 0.835 |
| 15 | 19 | 10 | 169.854 | 5.007 | 251.822 | 78.34 | 0.974 |
| 15 | 19 | 12 | 154.587 | 4.247 | 232.772 | 14.68 | 0.978 |
| 15 | 19 | 14 | 34.236 | 9.799 | 3.214 | 287.23 | 0.360 |
| 15 | 19 | 16 | 196.773 | 4.233 | 328.508 | 127.25 | 0.984 |
| 15 | 19 | 18 | 42.473 | 10.485 | 28.937 | 248.93 | 0.481 |
| 15 | 19 | 20 | 133.008 | 6.699 | 161.213 | 165.21 | 0.973 |
| 15 | 19 | 22 | 122.743 | 5.948 | 224.375 | 93.52 | 0.726 |
| 15 | 19 | 24 | 55.576 | 11.991 | 39.671 | 4.78 | 0.854 |
| 15 | 19 | 26 | 110.800 | 7.743 | 161.143 | 206.61 | 0.972 |
| 15 | 19 | 28 | 112.518 | 10.208 | 201.745 | 15.94 | 0.954 |
| 15 | 19 | 30 | 31.534 | 10.349 | 4.486 | 178.80 | 0.691 |
| 15 | 20 | 1 | 127.691 | 4.639 | 202.954 | 329.92 | 0.950 |
| 15 | 20 | 3 | 86.957 | 6.641 | 124.382 | 90.42 | 0.871 |
| 15 | 20 | 5 | 50.813 | 9.959 | 25.234 | 102.02 | 0.865 |
| 15 | 20 | 7 | 80.385 | 7.487 | 104.526 | 105.47 | 0.907 |
| 15 | 20 | 9 | 82.505 | 7.483 | 104.667 | 133.20 | 0.919 |
| 15 | 20 | 11 | 130.123 | 6.820 | 216.644 | 77.72 | 0.957 |
| 15 | 20 | 13 | 38.981 | 10.323 | 11.412 | 280.02 | 0.719 |
| 15 | 20 | 15 | 68.815 | 9.216 | 64.251 | 134.56 | 0.901 |
| 15 | 20 | 17 | 106.841 | 6.888 | 172.028 | 154.43 | 0.941 |
| 15 | 20 | 19 | 122.449 | 4.460 | 220.448 | 309.14 | 0.934 |
| 15 | 20 | 21 | 81.289 | 8.681 | 116.686 | 166.27 | 0.905 |
| 15 | 20 | 23 | 46.211 | 11.179 | 13.163 | 55.36 | 0.190 |
| 15 | 20 | 25 | 150.159 | 4.515 | 192.707 | 298.26 | 0.988 |
| 15 | 20 | 27 | 64.203 | 13.511 | 73.423 | 88.94 | 0.901 |
| 15 | 20 | 29 | 48.322 | 11.763 | 37.740 | 167.03 | 0.857 |
| 15 | 21 | 0 | 37.148 | 14.994 | 45.828 | 180.00 | 0.860 |
| 15 | 21 | 2 | 36.891 | 10.228 | 12.282 | 329.25 | 0.730 |
| 15 | 21 | 4 | 102.721 | 5.939 | 161.410 | 229.26 | 0.939 |
| 15 | 21 | 6 | 55.715 | 10.694 | 49.401 | 164.20 | 0.803 |
| 15 | 21 | 8 | 87.945 | 8.678 | 52.298 | 15.63 | 0.955 |
| 15 | 21 | 10 | 111.782 | 7.425 | 198.498 | 238.12 | 0.935 |
| 15 | 21 | 12 | 133.309 | 5.321 | 267.152 | 65.89 | 0.937 |
| 15 | 21 | 14 | 65.174 | 9.361 | 44.638 | 39.69 | 0.899 |
| 15 | 21 | 16 | 173.421 | 3.711 | 272.953 | 121.47 | 0.980 |
| 15 | 21 | 18 | 128.281 | 5.863 | 187.110 | 31.30 | 0.971 |
| 15 | 21 | 20 | 171.256 | 4.461 | 292.307 | 314.02 | 0.980 |
| 15 | 21 | 22 | 45.723 | 11.564 | 34.272 | 68.69 | 0.846 |

| | | | | | | | |
|---|---|---|---|---|---|---|---|
| 15 | 21 | 24 | 177.141 | 4.654 | 304.762 | 188.27 | 0.988 |
| 15 | 21 | 26 | 35.101 | 10.724 | 15.808 | 172.87 | 0.708 |
| 15 | 21 | 28 | 68.608 | 14.851 | 88.909 | 131.49 | 0.790 |
| 15 | 22 | 1 | 99.057 | 6.725 | 142.648 | 67.15 | 0.942 |
| 15 | 22 | 3 | 127.872 | 5.577 | 185.810 | 137.49 | 0.967 |
| 15 | 22 | 5 | 53.679 | 11.700 | 25.932 | 42.38 | 0.265 |
| 15 | 22 | 7 | 100.351 | 6.284 | 183.541 | 43.38 | 0.902 |
| 15 | 22 | 9 | 46.840 | 11.333 | 25.020 | 284.05 | 0.442 |
| 15 | 22 | 11 | 63.114 | 10.268 | 41.583 | 280.58 | 0.889 |
| 15 | 22 | 13 | 66.889 | 10.977 | 91.345 | 141.24 | 0.826 |
| 15 | 22 | 15 | 192.764 | 4.309 | 324.359 | 230.10 | 0.983 |
| 15 | 22 | 17 | 57.583 | 10.954 | 64.643 | 62.67 | 0.720 |
| 15 | 22 | 19 | 101.609 | 6.907 | 153.425 | 357.19 | 0.949 |
| 15 | 22 | 21 | 68.158 | 10.544 | 54.836 | 131.30 | 0.948 |
| 15 | 22 | 23 | 61.913 | 11.358 | 41.141 | 143.15 | 0.938 |
| 15 | 22 | 25 | 40.757 | 11.066 | 26.719 | 241.62 | 0.763 |
| 15 | 22 | 27 | 38.659 | 12.292 | 19.103 | 202.27 | 0.455 |
| 15 | 23 | 0 | 92.479 | 8.299 | 133.531 | 180.00 | 0.998 |
| 15 | 23 | 2 | 34.836 | 10.239 | 1.403 | 1.35 | 0.468 |
| 15 | 23 | 4 | 36.610 | 10.276 | 7.990 | 296.40 | 0.427 |
| 15 | 23 | 6 | 60.771 | 9.984 | 25.206 | 153.60 | 0.908 |
| 15 | 23 | 8 | 58.269 | 11.535 | 55.895 | 169.03 | 0.815 |
| 15 | 23 | 10 | 70.156 | 12.442 | 60.251 | 299.27 | 0.903 |
| 15 | 23 | 12 | 82.554 | 11.131 | 81.058 | 282.84 | 0.426 |
| 15 | 23 | 14 | 118.532 | 6.482 | 192.266 | 185.25 | 0.960 |
| 15 | 23 | 16 | 68.632 | 9.658 | 63.922 | 317.64 | 0.912 |
| 15 | 23 | 18 | 85.677 | 7.868 | 126.155 | 260.51 | 0.919 |
| 15 | 23 | 20 | 71.778 | 9.077 | 111.936 | 29.00 | 0.910 |
| 15 | 23 | 22 | 80.937 | 11.277 | 106.001 | 102.12 | 0.943 |
| 15 | 23 | 24 | 39.179 | 10.559 | 13.718 | 83.07 | 0.222 |
| 15 | 24 | 1 | 127.496 | 4.874 | 218.973 | 341.31 | 0.956 |
| 15 | 24 | 3 | 41.510 | 11.971 | 5.617 | 169.35 | 0.705 |
| 15 | 24 | 5 | 114.955 | 5.730 | 194.006 | 335.96 | 0.945 |
| 15 | 24 | 7 | 55.290 | 10.568 | 57.487 | 251.02 | 0.707 |
| 15 | 24 | 9 | 51.653 | 12.546 | 45.688 | 182.11 | 0.760 |
| 15 | 24 | 11 | 117.880 | 6.809 | 192.904 | 278.70 | 0.959 |
| 15 | 24 | 13 | 29.197 | 9.615 | 14.979 | 311.02 | 0.579 |
| 15 | 24 | 15 | 66.503 | 8.925 | 91.204 | 8.17 | 0.829 |
| 15 | 24 | 17 | 56.334 | 10.550 | 77.072 | 82.35 | 0.828 |
| 15 | 24 | 19 | 44.327 | 12.147 | 37.051 | 284.33 | 0.619 |
| 15 | 24 | 21 | 41.877 | 12.142 | 26.897 | 135.82 | 0.442 |
| 15 | 24 | 23 | 58.182 | 12.796 | 13.317 | 242.53 | 0.158 |
| 15 | 25 | 0 | 97.568 | 11.217 | 134.232 | 0.00 | 0.960 |
| 15 | 25 | 2 | 68.777 | 10.349 | 102.127 | 270.45 | 0.762 |
| 15 | 25 | 4 | 58.538 | 12.571 | 69.002 | 84.67 | 0.765 |
| 15 | 25 | 6 | 75.669 | 9.654 | 87.610 | 82.71 | 0.922 |
| 15 | 25 | 8 | 65.747 | 10.803 | 73.787 | 290.46 | 0.883 |
| 15 | 25 | 10 | 60.680 | 12.387 | 49.217 | 334.60 | 0.882 |
| 15 | 25 | 12 | 72.000 | 11.337 | 82.473 | 175.14 | 0.901 |
| 15 | 25 | 14 | 32.368 | 10.791 | 11.722 | 172.95 | 0.579 |
| 15 | 25 | 16 | 45.245 | 11.019 | 25.304 | 29.75 | 0.325 |
| 15 | 25 | 18 | 65.554 | 11.049 | 96.473 | 15.26 | 0.871 |
| 15 | 25 | 20 | 29.642 | 10.118 | 3.200 | 271.46 | 0.141 |
| 15 | 25 | 22 | 33.201 | 11.169 | 5.443 | 140.04 | 0.224 |
| 15 | 26 | 1 | 38.956 | 11.373 | 9.297 | 190.30 | 0.160 |
| 15 | 26 | 3 | 92.773 | 8.032 | 169.412 | 113.62 | 0.894 |
| 15 | 26 | 5 | 101.859 | 7.457 | 134.295 | 55.44 | 0.960 |
| 15 | 26 | 7 | 51.391 | 10.207 | 49.075 | 352.46 | 0.805 |
| 15 | 26 | 9 | 141.938 | 5.059 | 256.493 | 182.44 | 0.981 |
| 15 | 26 | 11 | 35.580 | 10.800 | 19.348 | 295.16 | 0.570 |
| 15 | 26 | 13 | 55.657 | 12.820 | 69.984 | 214.18 | 0.668 |
| 15 | 26 | 15 | 40.587 | 11.676 | 24.247 | 349.05 | 0.449 |
| 15 | 26 | 17 | 66.730 | 9.550 | 92.625 | 357.82 | 0.919 |
| 15 | 26 | 19 | 39.906 | 12.671 | 23.115 | 295.91 | 0.446 |
| 15 | 27 | 0 | 30.117 | 13.265 | 33.256 | 0.00 | 0.786 |
| 15 | 27 | 2 | 52.680 | 10.763 | 66.246 | 290.87 | 0.845 |
| 15 | 27 | 4 | 37.700 | 11.200 | 21.370 | 4.34 | 0.419 |
| 15 | 27 | 6 | 44.598 | 11.530 | 20.802 | 32.74 | 0.881 |
| 15 | 27 | 8 | 75.586 | 9.798 | 110.387 | 310.25 | 0.610 |
| 15 | 27 | 10 | 60.426 | 9.746 | 90.144 | 149.56 | 0.861 |
| 15 | 27 | 12 | 58.714 | 12.263 | 79.270 | 205.21 | 0.719 |
| 15 | 27 | 14 | 56.304 | 11.389 | 75.425 | 237.68 | 0.837 |
| 15 | 27 | 16 | 32.317 | 10.842 | 11.880 | 108.26 | 0.815 |
| 15 | 27 | 18 | 51.123 | 12.611 | 53.121 | 41.21 | 0.678 |
| 15 | 28 | 1 | 54.162 | 11.580 | 63.197 | 9.76 | 0.875 |
| 15 | 28 | 3 | 38.432 | 10.927 | 27.250 | 228.50 | 0.646 |
| 15 | 28 | 5 | 43.501 | 11.163 | 23.262 | 45.69 | 0.366 |

| | | | | | | | |
|---|---|---|---|---|---|---|---|
| 15 | 28 | 7  | 80.182  | 8.706  | 144.024 | 111.66 | 0.903 |
| 15 | 28 | 9  | 30.680  | 9.563  | 9.359   | 203.41 | 0.371 |
| 15 | 28 | 11 | 43.548  | 12.656 | 26.971  | 231.16 | 0.475 |
| 15 | 28 | 13 | 55.465  | 12.526 | 61.164  | 146.02 | 0.828 |
| 15 | 28 | 15 | 40.271  | 13.603 | 19.797  | 135.84 | 0.693 |
| 15 | 29 | 0  | 42.454  | 14.710 | 42.560  | 0.00   | 0.741 |
| 15 | 29 | 2  | 39.410  | 13.002 | 27.095  | 359.39 | 0.686 |
| 15 | 29 | 4  | 59.675  | 12.291 | 78.115  | 167.97 | 0.660 |
| 15 | 29 | 6  | 44.820  | 12.310 | 20.783  | 264.14 | 0.876 |
| 15 | 29 | 8  | 37.574  | 11.241 | 11.487  | 250.65 | 0.207 |
| 15 | 29 | 10 | 36.611  | 11.378 | 11.272  | 312.86 | 0.788 |
| 15 | 30 | 1  | 31.212  | 10.202 | 7.963   | 177.81 | 0.699 |
| 15 | 30 | 3  | 38.829  | 11.883 | 15.544  | 270.58 | 0.322 |
| 15 | 30 | 5  | 41.729  | 12.288 | 27.072  | 149.85 | 0.597 |
| 16 | 0  | 0  | 225.194 | 3.558  | 330.719 | 0.00   | 1.000 |
| 16 | 0  | 2  | 28.559  | 10.727 | 20.711  | 180.00 | 0.495 |
| 16 | 0  | 4  | 100.586 | 3.757  | 72.527  | 0.00   | 0.492 |
| 16 | 0  | 6  | 146.221 | 2.897  | 214.224 | 180.00 | 1.000 |
| 16 | 0  | 8  | 253.789 | 3.016  | 371.167 | 180.00 | 1.000 |
| 16 | 0  | 10 | 38.001  | 9.895  | 15.722  | 180.00 | 0.284 |
| 16 | 0  | 12 | 208.188 | 3.041  | 302.887 | 180.00 | 1.000 |
| 16 | 0  | 14 | 452.244 | 5.234  | 655.595 | 180.00 | 1.000 |
| 16 | 0  | 16 | 196.969 | 3.651  | 284.475 | 180.00 | 1.000 |
| 16 | 0  | 18 | 27.124  | 11.837 | 18.416  | 0.00   | 0.474 |
| 16 | 0  | 20 | 58.697  | 9.650  | 39.639  | 180.00 | 0.473 |
| 16 | 0  | 22 | 114.447 | 8.913  | 162.566 | 0.00   | 1.000 |
| 16 | 0  | 24 | 281.495 | 4.727  | 398.009 | 0.00   | 1.000 |
| 16 | 0  | 26 | 299.123 | 4.967  | 420.001 | 0.00   | 1.000 |
| 16 | 0  | 28 | 91.135  | 12.852 | 125.996 | 0.00   | 1.000 |
| 16 | 0  | 30 | 42.008  | 15.979 | 55.829  | 0.00   | 0.979 |
| 16 | 0  | 32 | 146.411 | 7.040  | 200.031 | 180.00 | 1.000 |
| 16 | 0  | 34 | 150.470 | 6.546  | 203.511 | 0.00   | 1.000 |
| 16 | 0  | 36 | 42.070  | 14.798 | 42.508  | 180.00 | 0.792 |
| 16 | 0  | 38 | 50.004  | 16.906 | 54.239  | 180.00 | 0.899 |
| 16 | 1  | 1  | 167.092 | 2.818  | 213.545 | 192.91 | 0.976 |
| 16 | 1  | 3  | 174.174 | 1.934  | 243.377 | 270.00 | 0.991 |
| 16 | 1  | 5  | 153.436 | 2.961  | 302.530 | 278.14 | 0.933 |
| 16 | 1  | 7  | 200.293 | 1.933  | 231.091 | 196.96 | 0.984 |
| 16 | 1  | 9  | 126.135 | 2.373  | 184.846 | 304.39 | 0.962 |
| 16 | 1  | 11 | 197.049 | 2.074  | 290.311 | 74.41  | 0.981 |
| 16 | 1  | 13 | 286.134 | 2.550  | 467.379 | 125.32 | 0.987 |
| 16 | 1  | 15 | 312.042 | 2.820  | 447.718 | 133.92 | 0.992 |
| 16 | 1  | 17 | 135.694 | 3.278  | 114.495 | 207.08 | 0.962 |
| 16 | 1  | 19 | 68.031  | 5.955  | 9.340   | 117.95 | 0.083 |
| 16 | 1  | 21 | 208.524 | 3.271  | 265.382 | 217.91 | 0.982 |
| 16 | 1  | 23 | 279.152 | 3.233  | 316.599 | 191.20 | 0.992 |
| 16 | 1  | 25 | 181.773 | 3.627  | 297.421 | 99.34  | 0.980 |
| 16 | 1  | 27 | 155.953 | 5.118  | 218.136 | 235.47 | 0.979 |
| 16 | 1  | 29 | 39.932  | 11.523 | 4.383   | 223.96 | 0.538 |
| 16 | 1  | 31 | 34.991  | 10.506 | 3.021   | 236.44 | 0.179 |
| 16 | 1  | 33 | 116.067 | 5.616  | 195.573 | 39.86  | 0.935 |
| 16 | 1  | 35 | 31.055  | 9.797  | 5.137   | 303.26 | 0.682 |
| 16 | 1  | 37 | 69.292  | 10.326 | 100.223 | 110.79 | 0.739 |
| 16 | 2  | 0  | 113.855 | 5.581  | 141.522 | 180.00 | 0.847 |
| 16 | 2  | 2  | 57.654  | 4.225  | 32.052  | 160.07 | 0.598 |
| 16 | 2  | 4  | 253.909 | 2.852  | 356.576 | 15.75  | 0.987 |
| 16 | 2  | 6  | 417.800 | 4.220  | 550.199 | 149.79 | 0.996 |
| 16 | 2  | 8  | 334.406 | 3.101  | 457.713 | 342.11 | 0.993 |
| 16 | 2  | 10 | 298.831 | 2.498  | 380.871 | 338.93 | 0.991 |
| 16 | 2  | 12 | 94.733  | 4.470  | 125.432 | 355.52 | 0.871 |
| 16 | 2  | 14 | 134.092 | 3.351  | 174.402 | 188.76 | 0.954 |
| 16 | 2  | 16 | 158.541 | 2.795  | 249.730 | 64.47  | 0.955 |
| 16 | 2  | 18 | 42.155  | 8.214  | 18.913  | 152.91 | 0.663 |
| 16 | 2  | 20 | 203.757 | 3.180  | 340.756 | 85.93  | 0.968 |
| 16 | 2  | 22 | 338.107 | 3.441  | 479.795 | 210.94 | 0.994 |
| 16 | 2  | 24 | 205.188 | 3.477  | 237.163 | 174.95 | 0.985 |
| 16 | 2  | 26 | 143.080 | 4.439  | 174.813 | 61.20  | 0.976 |
| 16 | 2  | 28 | 81.731  | 7.596  | 119.408 | 276.15 | 0.870 |
| 16 | 2  | 30 | 219.734 | 3.432  | 255.426 | 248.76 | 0.990 |
| 16 | 2  | 32 | 83.040  | 8.914  | 101.550 | 339.18 | 0.922 |
| 16 | 2  | 34 | 48.914  | 11.953 | 25.468  | 201.50 | 0.885 |
| 16 | 2  | 36 | 68.962  | 12.708 | 59.213  | 329.61 | 0.938 |
| 16 | 2  | 38 | 48.200  | 12.564 | 30.814  | 122.77 | 0.842 |
| 16 | 3  | 1  | 400.223 | 4.309  | 621.468 | 295.14 | 0.994 |
| 16 | 3  | 3  | 292.809 | 4.914  | 448.033 | 341.87 | 0.989 |
| 16 | 3  | 5  | 245.112 | 2.739  | 389.628 | 87.35  | 0.984 |
| 16 | 3  | 7  | 191.842 | 2.553  | 327.133 | 288.40 | 0.971 |

| | | | | | | | |
|---|---|---|---|---|---|---|---|
| 16 | 3 | 9 | 245.008 | 2.343 | 376.035 | 61.13 | 0.988 |
| 16 | 3 | 11 | 226.406 | 2.902 | 284.005 | 340.22 | 0.986 |
| 16 | 3 | 13 | 133.834 | 2.684 | 162.318 | 127.79 | 0.949 |
| 16 | 3 | 15 | 62.358 | 5.539 | 46.835 | 224.62 | 0.880 |
| 16 | 3 | 17 | 114.393 | 3.593 | 181.886 | 275.50 | 0.911 |
| 16 | 3 | 19 | 52.715 | 9.354 | 19.360 | 332.44 | 0.597 |
| 16 | 3 | 21 | 281.331 | 3.120 | 394.003 | 105.91 | 0.989 |
| 16 | 3 | 23 | 106.603 | 6.017 | 187.334 | 311.00 | 0.842 |
| 16 | 3 | 25 | 201.501 | 3.788 | 312.510 | 163.93 | 0.985 |
| 16 | 3 | 27 | 83.572 | 7.543 | 102.409 | 123.10 | 0.922 |
| 16 | 3 | 29 | 97.865 | 6.330 | 169.357 | 157.27 | 0.813 |
| 16 | 3 | 31 | 53.696 | 10.811 | 8.823 | 119.37 | 0.890 |
| 16 | 3 | 33 | 37.866 | 11.245 | 1.152 | 160.74 | 0.695 |
| 16 | 3 | 35 | 43.639 | 12.628 | 26.258 | 88.45 | 0.403 |
| 16 | 3 | 37 | 107.494 | 6.736 | 166.756 | 194.06 | 0.965 |
| 16 | 4 | 0 | 71.492 | 6.829 | 50.871 | 180.00 | 0.485 |
| 16 | 4 | 2 | 363.932 | 4.120 | 510.644 | 301.51 | 0.994 |
| 16 | 4 | 4 | 229.617 | 2.723 | 359.373 | 228.15 | 0.983 |
| 16 | 4 | 6 | 186.191 | 2.324 | 318.683 | 276.56 | 0.967 |
| 16 | 4 | 8 | 378.269 | 3.835 | 489.777 | 170.93 | 0.995 |
| 16 | 4 | 10 | 181.184 | 2.432 | 259.698 | 339.72 | 0.973 |
| 16 | 4 | 12 | 358.751 | 3.176 | 547.008 | 214.16 | 0.993 |
| 16 | 4 | 14 | 187.243 | 2.819 | 234.325 | 70.07 | 0.977 |
| 16 | 4 | 16 | 210.602 | 2.623 | 314.019 | 128.77 | 0.979 |
| 16 | 4 | 18 | 390.212 | 3.472 | 549.764 | 30.20 | 0.994 |
| 16 | 4 | 20 | 398.891 | 3.680 | 604.753 | 140.01 | 0.993 |
| 16 | 4 | 22 | 162.789 | 3.850 | 169.623 | 200.11 | 0.978 |
| 16 | 4 | 24 | 170.041 | 4.170 | 275.156 | 86.21 | 0.968 |
| 16 | 4 | 26 | 161.419 | 4.565 | 274.568 | 89.70 | 0.972 |
| 16 | 4 | 28 | 52.753 | 11.464 | 8.248 | 300.32 | 0.857 |
| 16 | 4 | 30 | 99.148 | 6.393 | 124.163 | 99.81 | 0.941 |
| 16 | 4 | 32 | 36.758 | 10.847 | 5.691 | 101.88 | 0.229 |
| 16 | 4 | 34 | 135.816 | 5.837 | 206.619 | 76.21 | 0.980 |
| 16 | 4 | 36 | 34.856 | 10.925 | 8.045 | 118.88 | 0.223 |
| 16 | 5 | 1 | 344.744 | 4.870 | 530.114 | 352.48 | 0.992 |
| 16 | 5 | 3 | 177.462 | 3.815 | 298.194 | 23.68 | 0.956 |
| 16 | 5 | 5 | 251.402 | 2.666 | 328.902 | 76.33 | 0.989 |
| 16 | 5 | 7 | 413.270 | 5.845 | 603.627 | 177.95 | 0.995 |
| 16 | 5 | 9 | 459.794 | 4.164 | 731.838 | 284.50 | 0.995 |
| 16 | 5 | 11 | 60.729 | 4.526 | 64.773 | 139.54 | 0.701 |
| 16 | 5 | 13 | 70.521 | 5.654 | 48.212 | 181.07 | 0.835 |
| 16 | 5 | 15 | 424.294 | 3.872 | 632.970 | 6.68 | 0.995 |
| 16 | 5 | 17 | 173.507 | 3.045 | 264.391 | 70.84 | 0.966 |
| 16 | 5 | 19 | 202.665 | 3.464 | 290.010 | 123.28 | 0.975 |
| 16 | 5 | 21 | 364.270 | 3.430 | 513.031 | 23.38 | 0.995 |
| 16 | 5 | 23 | 93.533 | 6.702 | 151.347 | 262.70 | 0.826 |
| 16 | 5 | 25 | 224.881 | 3.561 | 299.329 | 52.83 | 0.990 |
| 16 | 5 | 27 | 173.164 | 4.451 | 235.756 | 40.62 | 0.983 |
| 16 | 5 | 29 | 43.253 | 12.029 | 18.296 | 220.00 | 0.469 |
| 16 | 5 | 31 | 161.786 | 5.305 | 251.078 | 284.91 | 0.979 |
| 16 | 5 | 33 | 49.523 | 12.246 | 36.082 | 275.21 | 0.408 |
| 16 | 5 | 35 | 88.704 | 8.497 | 120.803 | 338.00 | 0.951 |
| 16 | 5 | 37 | 37.059 | 10.806 | 10.992 | 43.95 | 0.764 |
| 16 | 6 | 0 | 32.727 | 14.960 | 18.334 | 0.00 | 0.383 |
| 16 | 6 | 2 | 279.888 | 4.206 | 425.659 | 100.62 | 0.989 |
| 16 | 6 | 4 | 254.687 | 3.565 | 376.976 | 138.43 | 0.986 |
| 16 | 6 | 6 | 203.476 | 2.554 | 156.527 | 123.41 | 0.986 |
| 16 | 6 | 8 | 405.761 | 5.635 | 561.701 | 302.94 | 0.995 |
| 16 | 6 | 10 | 438.410 | 4.120 | 585.599 | 353.99 | 0.996 |
| 16 | 6 | 12 | 215.046 | 2.394 | 349.918 | 52.55 | 0.977 |
| 16 | 6 | 14 | 129.280 | 2.843 | 197.516 | 197.94 | 0.941 |
| 16 | 6 | 16 | 281.293 | 2.881 | 411.761 | 332.02 | 0.987 |
| 16 | 6 | 18 | 255.519 | 2.880 | 321.745 | 167.99 | 0.986 |
| 16 | 6 | 20 | 292.654 | 3.063 | 436.953 | 303.01 | 0.992 |
| 16 | 6 | 22 | 85.358 | 7.037 | 108.936 | 269.46 | 0.889 |
| 16 | 6 | 24 | 40.656 | 10.971 | 3.999 | 57.32 | 0.667 |
| 16 | 6 | 26 | 120.142 | 5.584 | 136.571 | 56.85 | 0.968 |
| 16 | 6 | 28 | 62.924 | 10.661 | 43.820 | 150.78 | 0.877 |
| 16 | 6 | 30 | 192.464 | 4.659 | 221.941 | 182.62 | 0.987 |
| 16 | 6 | 32 | 117.984 | 6.141 | 157.214 | 237.28 | 0.965 |
| 16 | 6 | 34 | 53.588 | 10.421 | 69.135 | 219.16 | 0.781 |
| 16 | 6 | 36 | 66.485 | 11.544 | 86.299 | 348.57 | 0.889 |
| 16 | 7 | 1 | 370.219 | 4.362 | 557.700 | 225.71 | 0.994 |
| 16 | 7 | 3 | 172.490 | 2.424 | 201.468 | 189.07 | 0.983 |
| 16 | 7 | 5 | 223.675 | 2.678 | 321.976 | 128.19 | 0.983 |
| 16 | 7 | 7 | 309.418 | 3.304 | 461.568 | 223.62 | 0.991 |
| 16 | 7 | 9 | 108.208 | 2.331 | 157.306 | 102.80 | 0.960 |

| | | | | | | | |
|---|---|---|---|---|---|---|---|
| 16 | 7 | 11 | 532.323 | 5.095 | 807.218 | 99.21 | 0.997 |
| 16 | 7 | 13 | 216.404 | 2.704 | 348.325 | 140.81 | 0.977 |
| 16 | 7 | 15 | 117.202 | 3.615 | 134.365 | 42.57 | 0.948 |
| 16 | 7 | 17 | 144.178 | 3.898 | 257.819 | 103.99 | 0.922 |
| 16 | 7 | 19 | 80.432 | 5.524 | 44.207 | 280.26 | 0.295 |
| 16 | 7 | 21 | 156.701 | 3.901 | 245.122 | 284.86 | 0.966 |
| 16 | 7 | 23 | 152.801 | 4.417 | 242.401 | 238.69 | 0.961 |
| 16 | 7 | 25 | 217.958 | 3.750 | 347.957 | 347.11 | 0.987 |
| 16 | 7 | 27 | 142.239 | 5.127 | 169.929 | 354.82 | 0.978 |
| 16 | 7 | 29 | 35.155 | 10.973 | 56.975 | 87.36 | 0.808 |
| 16 | 7 | 31 | 77.448 | 8.841 | 62.085 | 349.26 | 0.936 |
| 16 | 7 | 33 | 45.818 | 12.352 | 37.665 | 245.38 | 0.602 |
| 16 | 7 | 35 | 81.420 | 10.520 | 128.117 | 18.34 | 0.917 |
| 16 | 7 | 37 | 29.659 | 9.845 | 1.751 | 164.16 | 0.597 |
| 16 | 8 | 0 | 247.640 | 6.942 | 363.324 | 180.00 | 1.000 |
| 16 | 8 | 2 | 94.555 | 5.155 | 38.479 | 42.69 | 0.265 |
| 16 | 8 | 4 | 361.141 | 3.468 | 492.862 | 270.12 | 0.994 |
| 16 | 8 | 6 | 158.894 | 2.640 | 253.289 | 259.14 | 0.959 |
| 16 | 8 | 8 | 172.727 | 2.741 | 217.545 | 305.20 | 0.978 |
| 16 | 8 | 10 | 473.970 | 3.933 | 819.719 | 69.82 | 0.995 |
| 16 | 8 | 12 | 60.504 | 6.173 | 55.802 | 305.39 | 0.670 |
| 16 | 8 | 14 | 240.610 | 2.877 | 312.872 | 199.10 | 0.988 |
| 16 | 8 | 16 | 197.977 | 2.635 | 320.882 | 127.60 | 0.973 |
| 16 | 8 | 18 | 240.962 | 3.018 | 394.723 | 134.96 | 0.979 |
| 16 | 8 | 20 | 60.950 | 8.679 | 66.432 | 135.57 | 0.674 |
| 16 | 8 | 22 | 164.040 | 4.110 | 235.363 | 211.88 | 0.972 |
| 16 | 8 | 24 | 128.267 | 5.679 | 147.413 | 227.80 | 0.972 |
| 16 | 8 | 26 | 271.991 | 3.369 | 415.027 | 295.88 | 0.992 |
| 16 | 8 | 28 | 185.761 | 3.985 | 272.248 | 271.75 | 0.983 |
| 16 | 8 | 30 | 108.845 | 7.352 | 151.665 | 258.22 | 0.956 |
| 16 | 8 | 32 | 138.117 | 6.272 | 250.026 | 64.60 | 0.974 |
| 16 | 8 | 34 | 144.428 | 5.146 | 253.575 | 261.59 | 0.975 |
| 16 | 8 | 36 | 111.565 | 6.910 | 159.664 | 334.30 | 0.972 |
| 16 | 9 | 1 | 231.907 | 3.109 | 368.557 | 291.75 | 0.982 |
| 16 | 9 | 3 | 35.212 | 6.987 | 12.733 | 46.17 | 0.361 |
| 16 | 9 | 5 | 202.657 | 2.487 | 283.120 | 358.95 | 0.979 |
| 16 | 9 | 7 | 408.549 | 3.717 | 628.722 | 40.16 | 0.994 |
| 16 | 9 | 9 | 32.422 | 7.679 | 26.940 | 106.95 | 0.379 |
| 16 | 9 | 11 | 361.204 | 3.182 | 545.954 | 98.43 | 0.993 |
| 16 | 9 | 13 | 314.137 | 3.191 | 540.103 | 352.18 | 0.987 |
| 16 | 9 | 15 | 369.885 | 3.654 | 534.094 | 264.32 | 0.993 |
| 16 | 9 | 17 | 170.247 | 3.364 | 245.791 | 236.76 | 0.963 |
| 16 | 9 | 19 | 156.464 | 3.447 | 264.152 | 89.29 | 0.957 |
| 16 | 9 | 21 | 191.194 | 3.693 | 264.301 | 232.14 | 0.981 |
| 16 | 9 | 23 | 102.611 | 6.256 | 77.222 | 248.59 | 0.964 |
| 16 | 9 | 25 | 78.158 | 7.628 | 96.565 | 130.32 | 0.895 |
| 16 | 9 | 27 | 157.214 | 4.681 | 310.174 | 32.78 | 0.956 |
| 16 | 9 | 29 | 55.789 | 11.244 | 40.346 | 235.28 | 0.845 |
| 16 | 9 | 31 | 154.830 | 4.986 | 230.856 | 253.98 | 0.978 |
| 16 | 9 | 33 | 36.931 | 11.239 | 17.586 | 16.03 | 0.612 |
| 16 | 9 | 35 | 62.360 | 11.390 | 70.375 | 209.05 | 0.896 |
| 16 | 10 | 0 | 46.947 | 11.107 | 53.237 | 0.00 | 0.774 |
| 16 | 10 | 2 | 248.730 | 2.396 | 401.618 | 300.14 | 0.985 |
| 16 | 10 | 4 | 151.430 | 2.709 | 231.567 | 85.62 | 0.974 |
| 16 | 10 | 6 | 144.428 | 2.813 | 199.670 | 47.21 | 0.956 |
| 16 | 10 | 8 | 202.947 | 2.908 | 274.050 | 137.74 | 0.983 |
| 16 | 10 | 10 | 249.335 | 2.421 | 377.997 | 68.52 | 0.988 |
| 16 | 10 | 12 | 236.676 | 3.059 | 378.709 | 10.50 | 0.979 |
| 16 | 10 | 14 | 231.173 | 3.899 | 342.185 | 318.41 | 0.981 |
| 16 | 10 | 16 | 195.468 | 3.397 | 299.111 | 193.14 | 0.974 |
| 16 | 10 | 18 | 160.611 | 3.872 | 262.963 | 63.01 | 0.966 |
| 16 | 10 | 20 | 228.031 | 3.398 | 323.176 | 266.62 | 0.987 |
| 16 | 10 | 22 | 351.879 | 3.548 | 546.061 | 12.97 | 0.995 |
| 16 | 10 | 24 | 33.480 | 10.091 | 14.497 | 199.93 | 0.539 |
| 16 | 10 | 26 | 49.070 | 11.218 | 37.087 | 108.11 | 0.648 |
| 16 | 10 | 28 | 136.516 | 5.268 | 207.442 | 178.02 | 0.965 |
| 16 | 10 | 30 | 154.270 | 4.974 | 245.051 | 114.91 | 0.976 |
| 16 | 10 | 32 | 40.864 | 10.964 | 27.238 | 297.39 | 0.772 |
| 16 | 10 | 34 | 44.877 | 11.355 | 43.995 | 294.66 | 0.701 |
| 16 | 10 | 36 | 28.805 | 9.715 | 19.904 | 97.11 | 0.763 |
| 16 | 11 | 1 | 272.264 | 2.846 | 391.445 | 260.88 | 0.988 |
| 16 | 11 | 3 | 234.223 | 2.328 | 352.253 | 224.24 | 0.983 |
| 16 | 11 | 5 | 67.388 | 5.346 | 49.002 | 284.30 | 0.799 |
| 16 | 11 | 7 | 141.825 | 3.058 | 206.635 | 308.44 | 0.951 |
| 16 | 11 | 9 | 206.640 | 2.940 | 300.563 | 337.76 | 0.980 |
| 16 | 11 | 11 | 171.187 | 2.853 | 288.847 | 347.30 | 0.956 |
| 16 | 11 | 13 | 308.502 | 3.447 | 404.890 | 284.54 | 0.990 |

| | | | | | | | |
|---|---|---|---|---|---|---|---|
| 16 | 11 | 15 | 325.491 | 3.882 | 476.269 | 272.12 | 0.991 |
| 16 | 11 | 17 | 346.995 | 3.757 | 677.152 | 275.69 | 0.991 |
| 16 | 11 | 19 | 155.551 | 4.240 | 327.575 | 346.29 | 0.902 |
| 16 | 11 | 21 | 193.064 | 3.727 | 255.290 | 104.06 | 0.987 |
| 16 | 11 | 23 | 95.088 | 6.743 | 146.284 | 286.29 | 0.918 |
| 16 | 11 | 25 | 232.963 | 3.694 | 313.045 | 225.65 | 0.991 |
| 16 | 11 | 27 | 54.472 | 10.478 | 17.480 | 297.00 | 0.177 |
| 16 | 11 | 29 | 133.083 | 5.827 | 258.769 | 231.30 | 0.945 |
| 16 | 11 | 31 | 51.576 | 12.264 | 23.596 | 329.60 | 0.941 |
| 16 | 11 | 33 | 45.159 | 12.085 | 20.661 | 219.11 | 0.314 |
| 16 | 11 | 35 | 44.164 | 12.512 | 31.660 | 325.44 | 0.678 |
| 16 | 12 | 0 | 48.218 | 12.752 | 46.235 | 0.00 | 0.655 |
| 16 | 12 | 2 | 302.158 | 2.925 | 467.502 | 302.23 | 0.991 |
| 16 | 12 | 4 | 297.057 | 2.992 | 451.310 | 344.72 | 0.989 |
| 16 | 12 | 6 | 155.364 | 3.108 | 243.336 | 103.17 | 0.957 |
| 16 | 12 | 8 | 144.609 | 3.729 | 185.364 | 130.12 | 0.966 |
| 16 | 12 | 10 | 69.802 | 5.698 | 55.594 | 156.03 | 0.766 |
| 16 | 12 | 12 | 83.168 | 5.030 | 80.895 | 40.90 | 0.855 |
| 16 | 12 | 14 | 150.450 | 3.593 | 233.988 | 306.31 | 0.955 |
| 16 | 12 | 16 | 102.469 | 6.842 | 108.026 | 337.73 | 0.951 |
| 16 | 12 | 18 | 140.965 | 4.368 | 227.174 | 252.31 | 0.955 |
| 16 | 12 | 20 | 182.947 | 3.943 | 281.466 | 113.18 | 0.984 |
| 16 | 12 | 22 | 147.296 | 4.921 | 204.975 | 208.98 | 0.976 |
| 16 | 12 | 24 | 37.575 | 10.327 | 10.646 | 276.15 | 0.705 |
| 16 | 12 | 26 | 74.777 | 11.689 | 107.012 | 264.09 | 0.819 |
| 16 | 12 | 28 | 111.808 | 6.306 | 183.981 | 22.61 | 0.943 |
| 16 | 12 | 30 | 31.715 | 10.220 | 6.034 | 8.27 | 0.339 |
| 16 | 12 | 32 | 104.334 | 7.414 | 115.987 | 85.51 | 0.976 |
| 16 | 12 | 34 | 34.736 | 10.934 | 17.022 | 117.91 | 0.406 |
| 16 | 13 | 1 | 291.770 | 3.694 | 422.539 | 189.38 | 0.990 |
| 16 | 13 | 3 | 317.997 | 3.048 | 539.842 | 298.65 | 0.988 |
| 16 | 13 | 5 | 233.761 | 3.168 | 344.491 | 233.27 | 0.982 |
| 16 | 13 | 7 | 80.516 | 5.248 | 81.121 | 208.54 | 0.811 |
| 16 | 13 | 9 | 110.509 | 4.415 | 137.338 | 112.88 | 0.916 |
| 16 | 13 | 11 | 150.195 | 3.240 | 197.823 | 143.35 | 0.956 |
| 16 | 13 | 13 | 142.796 | 3.689 | 274.403 | 91.98 | 0.887 |
| 16 | 13 | 15 | 348.516 | 3.531 | 569.722 | 98.11 | 0.993 |
| 16 | 13 | 17 | 148.515 | 4.274 | 284.430 | 58.02 | 0.941 |
| 16 | 13 | 19 | 163.156 | 4.109 | 216.910 | 196.38 | 0.982 |
| 16 | 13 | 21 | 52.167 | 10.759 | 43.700 | 117.68 | 0.647 |
| 16 | 13 | 23 | 107.088 | 5.945 | 114.395 | 359.18 | 0.961 |
| 16 | 13 | 25 | 155.367 | 4.154 | 268.867 | 293.99 | 0.970 |
| 16 | 13 | 27 | 55.871 | 10.974 | 46.988 | 147.94 | 0.830 |
| 16 | 13 | 29 | 58.227 | 11.271 | 50.446 | 322.98 | 0.516 |
| 16 | 13 | 31 | 33.401 | 10.554 | 10.040 | 255.33 | 0.430 |
| 16 | 13 | 33 | 31.769 | 10.033 | 8.559 | 173.67 | 0.462 |
| 16 | 14 | 0 | 89.704 | 7.073 | 127.499 | 180.00 | 0.970 |
| 16 | 14 | 2 | 150.726 | 3.377 | 211.368 | 215.65 | 0.964 |
| 16 | 14 | 4 | 111.372 | 3.351 | 153.491 | 119.58 | 0.745 |
| 16 | 14 | 6 | 82.873 | 7.136 | 82.711 | 115.41 | 0.846 |
| 16 | 14 | 8 | 266.078 | 3.269 | 391.047 | 69.91 | 0.987 |
| 16 | 14 | 10 | 258.498 | 3.201 | 394.821 | 253.65 | 0.986 |
| 16 | 14 | 12 | 328.327 | 3.224 | 502.233 | 148.99 | 0.993 |
| 16 | 14 | 14 | 63.453 | 10.872 | 37.146 | 154.89 | 0.866 |
| 16 | 14 | 16 | 138.028 | 4.468 | 263.205 | 274.50 | 0.875 |
| 16 | 14 | 18 | 71.877 | 9.652 | 41.283 | 275.52 | 0.928 |
| 16 | 14 | 20 | 92.831 | 9.168 | 130.982 | 314.41 | 0.917 |
| 16 | 14 | 22 | 139.582 | 5.191 | 214.934 | 76.84 | 0.968 |
| 16 | 14 | 24 | 182.403 | 3.988 | 295.250 | 333.27 | 0.981 |
| 16 | 14 | 26 | 112.813 | 5.913 | 147.532 | 227.57 | 0.965 |
| 16 | 14 | 28 | 100.668 | 8.590 | 150.171 | 76.92 | 0.942 |
| 16 | 14 | 30 | 58.378 | 11.444 | 71.554 | 282.53 | 0.854 |
| 16 | 14 | 32 | 39.895 | 11.882 | 28.028 | 228.25 | 0.715 |
| 16 | 15 | 1 | 254.601 | 3.141 | 571.193 | 48.72 | 0.870 |
| 16 | 15 | 3 | 316.468 | 3.168 | 475.187 | 15.90 | 0.990 |
| 16 | 15 | 5 | 133.452 | 4.064 | 192.387 | 21.17 | 0.940 |
| 16 | 15 | 7 | 220.469 | 3.537 | 388.023 | 329.76 | 0.973 |
| 16 | 15 | 9 | 52.077 | 10.094 | 29.705 | 241.49 | 0.585 |
| 16 | 15 | 11 | 183.227 | 3.641 | 283.346 | 282.85 | 0.978 |
| 16 | 15 | 13 | 203.331 | 3.464 | 251.396 | 72.75 | 0.985 |
| 16 | 15 | 15 | 159.506 | 4.842 | 200.658 | 192.65 | 0.975 |
| 16 | 15 | 17 | 52.029 | 10.145 | 31.769 | 24.94 | 0.814 |
| 16 | 15 | 19 | 39.069 | 10.810 | 12.949 | 92.74 | 0.748 |
| 16 | 15 | 21 | 112.293 | 5.595 | 145.665 | 101.73 | 0.512 |
| 16 | 15 | 23 | 54.883 | 9.998 | 16.029 | 31.37 | 0.868 |
| 16 | 15 | 25 | 83.422 | 8.065 | 58.900 | 123.36 | 0.952 |
| 16 | 15 | 27 | 128.608 | 6.039 | 165.018 | 52.92 | 0.973 |

| | | | | | | | |
|---|---|---|---|---|---|---|---|
| 16 | 15 | 29 | 42.912 | 10.850 | 37.494 | 121.32 | 0.675 |
| 16 | 15 | 31 | 73.650 | 9.354 | 117.030 | 326.92 | 0.901 |
| 16 | 16 | 0 | 24.538 | 10.832 | 2.466 | 0.00 | 0.069 |
| 16 | 16 | 2 | 70.318 | 8.990 | 79.027 | 310.28 | 0.822 |
| 16 | 16 | 4 | 273.052 | 2.886 | 448.824 | 281.14 | 0.986 |
| 16 | 16 | 6 | 51.946 | 11.081 | 15.571 | 281.28 | 0.242 |
| 16 | 16 | 8 | 95.894 | 6.898 | 136.466 | 306.79 | 0.910 |
| 16 | 16 | 10 | 170.496 | 4.475 | 277.625 | 28.87 | 0.970 |
| 16 | 16 | 12 | 141.487 | 4.994 | 175.738 | 254.47 | 0.968 |
| 16 | 16 | 14 | 125.267 | 5.639 | 192.523 | 96.86 | 0.961 |
| 16 | 16 | 16 | 67.900 | 10.237 | 72.623 | 310.93 | 0.902 |
| 16 | 16 | 18 | 104.824 | 5.324 | 161.439 | 146.26 | 0.942 |
| 16 | 16 | 20 | 175.206 | 3.888 | 327.057 | 132.49 | 0.973 |
| 16 | 16 | 22 | 190.533 | 4.869 | 289.707 | 336.32 | 0.984 |
| 16 | 16 | 24 | 43.506 | 10.536 | 5.858 | 202.80 | 0.101 |
| 16 | 16 | 26 | 127.710 | 5.395 | 136.891 | 280.22 | 0.977 |
| 16 | 16 | 28 | 54.086 | 11.229 | 35.338 | 337.17 | 0.919 |
| 16 | 16 | 30 | 100.456 | 7.085 | 198.066 | 37.18 | 0.918 |
| 16 | 16 | 32 | 78.240 | 11.943 | 112.595 | 26.93 | 0.734 |
| 16 | 17 | 1 | 121.660 | 4.973 | 195.961 | 305.13 | 0.942 |
| 16 | 17 | 3 | 138.841 | 4.704 | 170.642 | 273.08 | 0.969 |
| 16 | 17 | 5 | 120.347 | 4.645 | 173.373 | 197.64 | 0.948 |
| 16 | 17 | 7 | 58.875 | 11.575 | 37.939 | 307.65 | 0.421 |
| 16 | 17 | 9 | 138.499 | 5.607 | 185.769 | 256.91 | 0.965 |
| 16 | 17 | 11 | 165.839 | 4.174 | 184.304 | 301.40 | 0.980 |
| 16 | 17 | 13 | 180.313 | 4.241 | 256.081 | 14.19 | 0.984 |
| 16 | 17 | 15 | 101.104 | 5.999 | 181.007 | 352.41 | 0.907 |
| 16 | 17 | 17 | 132.389 | 5.817 | 153.339 | 238.35 | 0.975 |
| 16 | 17 | 19 | 190.979 | 4.178 | 302.484 | 66.64 | 0.984 |
| 16 | 17 | 21 | 66.205 | 10.650 | 73.384 | 65.05 | 0.853 |
| 16 | 17 | 23 | 124.429 | 7.898 | 216.869 | 348.56 | 0.955 |
| 16 | 17 | 25 | 46.667 | 11.987 | 28.452 | 176.07 | 0.517 |
| 16 | 17 | 27 | 56.887 | 11.767 | 66.958 | 76.73 | 0.666 |
| 16 | 17 | 29 | 40.095 | 11.844 | 27.125 | 240.51 | 0.512 |
| 16 | 17 | 31 | 25.443 | 8.811 | 15.088 | 34.02 | 0.628 |
| 16 | 18 | 0 | 351.596 | 5.283 | 514.697 | 180.00 | 1.000 |
| 16 | 18 | 2 | 69.278 | 8.402 | 83.517 | 198.33 | 0.795 |
| 16 | 18 | 4 | 267.341 | 3.297 | 363.693 | 254.22 | 0.991 |
| 16 | 18 | 6 | 341.711 | 3.994 | 500.435 | 279.27 | 0.994 |
| 16 | 18 | 8 | 90.979 | 8.217 | 146.712 | 238.92 | 0.820 |
| 16 | 18 | 10 | 130.262 | 5.190 | 216.595 | 222.28 | 0.960 |
| 16 | 18 | 12 | 182.397 | 3.843 | 251.349 | 202.36 | 0.986 |
| 16 | 18 | 14 | 233.143 | 3.471 | 340.119 | 21.07 | 0.990 |
| 16 | 18 | 16 | 98.859 | 6.401 | 116.135 | 318.79 | 0.951 |
| 16 | 18 | 18 | 95.588 | 8.118 | 147.798 | 128.34 | 0.924 |
| 16 | 18 | 20 | 44.002 | 11.376 | 15.896 | 293.28 | 0.733 |
| 16 | 18 | 22 | 48.861 | 11.334 | 32.381 | 145.08 | 0.747 |
| 16 | 18 | 24 | 135.367 | 6.855 | 156.383 | 66.06 | 0.978 |
| 16 | 18 | 26 | 46.911 | 11.213 | 35.482 | 93.16 | 0.863 |
| 16 | 18 | 28 | 63.495 | 12.438 | 91.396 | 84.51 | 0.834 |
| 16 | 18 | 30 | 35.460 | 11.189 | 9.653 | 228.55 | 0.289 |
| 16 | 19 | 1 | 183.033 | 3.793 | 296.974 | 125.01 | 0.977 |
| 16 | 19 | 3 | 40.158 | 10.739 | 17.971 | 354.86 | 0.647 |
| 16 | 19 | 5 | 92.346 | 5.848 | 164.499 | 73.02 | 0.897 |
| 16 | 19 | 7 | 196.916 | 4.400 | 294.502 | 39.58 | 0.987 |
| 16 | 19 | 9 | 139.902 | 4.839 | 194.972 | 146.27 | 0.973 |
| 16 | 19 | 11 | 175.718 | 4.728 | 240.989 | 192.95 | 0.984 |
| 16 | 19 | 13 | 101.845 | 6.391 | 55.545 | 94.95 | 0.969 |
| 16 | 19 | 15 | 165.333 | 4.224 | 243.719 | 66.65 | 0.981 |
| 16 | 19 | 17 | 97.662 | 6.009 | 102.847 | 230.54 | 0.954 |
| 16 | 19 | 19 | 46.268 | 11.631 | 21.194 | 236.44 | 0.345 |
| 16 | 19 | 21 | 45.753 | 12.133 | 23.630 | 335.98 | 0.732 |
| 16 | 19 | 23 | 112.143 | 6.377 | 173.851 | 234.64 | 0.973 |
| 16 | 19 | 25 | 31.497 | 10.058 | 6.541 | 195.43 | 0.309 |
| 16 | 19 | 27 | 85.221 | 8.242 | 154.836 | 11.55 | 0.903 |
| 16 | 19 | 29 | 96.857 | 11.547 | 161.208 | 56.22 | 0.932 |
| 16 | 20 | 0 | 50.787 | 14.955 | 73.033 | 0.00 | 0.993 |
| 16 | 20 | 2 | 76.471 | 9.421 | 103.812 | 190.25 | 0.911 |
| 16 | 20 | 4 | 144.291 | 5.009 | 152.723 | 111.09 | 0.981 |
| 16 | 20 | 6 | 79.970 | 7.820 | 128.489 | 26.83 | 0.866 |
| 16 | 20 | 8 | 182.071 | 5.200 | 237.696 | 348.21 | 0.986 |
| 16 | 20 | 10 | 63.629 | 10.641 | 21.793 | 175.78 | 0.914 |
| 16 | 20 | 12 | 121.252 | 6.357 | 191.240 | 283.38 | 0.959 |
| 16 | 20 | 14 | 95.015 | 6.804 | 115.934 | 48.96 | 0.946 |
| 16 | 20 | 16 | 134.120 | 5.957 | 160.178 | 79.40 | 0.975 |
| 16 | 20 | 18 | 79.753 | 9.991 | 91.107 | 230.89 | 0.931 |
| 16 | 20 | 20 | 66.930 | 10.595 | 78.344 | 78.95 | 0.880 |

| | | | | | | | |
|---|---|---|---|---|---|---|---|
| 16 | 20 | 22 | 149.560 | 5.505 | 243.049 | 95.60 | 0.985 |
| 16 | 20 | 24 | 111.268 | 6.357 | 125.562 | 243.29 | 0.980 |
| 16 | 20 | 26 | 115.446 | 5.561 | 222.198 | 265.95 | 0.961 |
| 16 | 20 | 28 | 49.698 | 13.823 | 45.928 | 326.75 | 0.753 |
| 16 | 21 | 1 | 100.047 | 6.744 | 127.156 | 353.55 | 0.953 |
| 16 | 21 | 3 | 48.565 | 12.093 | 7.348 | 188.13 | 0.858 |
| 16 | 21 | 5 | 40.360 | 10.069 | 15.826 | 356.77 | 0.781 |
| 16 | 21 | 7 | 99.807 | 6.255 | 162.006 | 154.71 | 0.924 |
| 16 | 21 | 9 | 51.529 | 10.992 | 27.224 | 146.32 | 0.831 |
| 16 | 21 | 11 | 58.431 | 9.891 | 51.833 | 277.22 | 0.848 |
| 16 | 21 | 13 | 40.116 | 10.698 | 7.694 | 17.92 | 0.567 |
| 16 | 21 | 15 | 80.873 | 7.550 | 136.760 | 181.33 | 0.817 |
| 16 | 21 | 17 | 48.580 | 12.058 | 34.873 | 122.84 | 0.643 |
| 16 | 21 | 19 | 71.784 | 11.090 | 33.056 | 119.33 | 0.940 |
| 16 | 21 | 21 | 114.893 | 6.132 | 222.766 | 74.03 | 0.945 |
| 16 | 21 | 23 | 66.911 | 9.220 | 105.370 | 17.22 | 0.850 |
| 16 | 21 | 25 | 47.276 | 11.573 | 23.266 | 243.91 | 0.890 |
| 16 | 22 | 0 | 169.659 | 5.582 | 247.716 | 0.00 | 1.000 |
| 16 | 22 | 2 | 162.474 | 5.807 | 260.082 | 3.38 | 0.979 |
| 16 | 22 | 4 | 141.301 | 5.035 | 240.625 | 108.81 | 0.968 |
| 16 | 22 | 6 | 120.405 | 4.319 | 208.563 | 224.20 | 0.953 |
| 16 | 22 | 8 | 154.890 | 5.013 | 230.712 | 274.21 | 0.978 |
| 16 | 22 | 10 | 50.213 | 12.488 | 17.676 | 22.89 | 0.223 |
| 16 | 22 | 12 | 140.025 | 5.786 | 198.275 | 89.95 | 0.973 |
| 16 | 22 | 14 | 67.223 | 10.400 | 96.365 | 327.27 | 0.720 |
| 16 | 22 | 16 | 118.745 | 5.374 | 214.746 | 167.60 | 0.951 |
| 16 | 22 | 18 | 104.675 | 7.190 | 149.918 | 278.29 | 0.972 |
| 16 | 22 | 20 | 66.338 | 11.238 | 99.757 | 327.19 | 0.884 |
| 16 | 22 | 22 | 114.010 | 6.886 | 175.956 | 134.25 | 0.975 |
| 16 | 22 | 24 | 56.185 | 12.063 | 26.373 | 183.94 | 0.927 |
| 16 | 23 | 1 | 77.687 | 9.484 | 117.479 | 177.36 | 0.862 |
| 16 | 23 | 3 | 82.044 | 9.528 | 126.686 | 47.86 | 0.893 |
| 16 | 23 | 5 | 73.766 | 8.983 | 108.567 | 236.82 | 0.732 |
| 16 | 23 | 7 | 50.477 | 11.148 | 35.317 | 280.34 | 0.777 |
| 16 | 23 | 9 | 160.962 | 5.260 | 229.643 | 300.06 | 0.984 |
| 16 | 23 | 11 | 39.312 | 10.814 | 5.822 | 148.36 | 0.701 |
| 16 | 23 | 13 | 55.719 | 12.728 | 56.444 | 248.78 | 0.717 |
| 16 | 23 | 15 | 125.966 | 6.906 | 202.621 | 92.04 | 0.966 |
| 16 | 23 | 17 | 51.766 | 10.474 | 68.680 | 158.05 | 0.817 |
| 16 | 23 | 19 | 51.401 | 11.471 | 53.537 | 241.13 | 0.858 |
| 16 | 23 | 21 | 82.607 | 9.541 | 114.286 | 198.52 | 0.954 |
| 16 | 23 | 23 | 57.686 | 13.769 | 48.104 | 211.91 | 0.467 |
| 16 | 24 | 0 | 33.432 | 13.689 | 45.409 | 180.00 | 0.949 |
| 16 | 24 | 2 | 43.023 | 12.646 | 24.200 | 170.97 | 0.621 |
| 16 | 24 | 4 | 53.864 | 11.342 | 30.597 | 97.75 | 0.874 |
| 16 | 24 | 6 | 44.493 | 11.410 | 28.324 | 147.68 | 0.549 |
| 16 | 24 | 8 | 60.528 | 9.499 | 79.988 | 339.07 | 0.720 |
| 16 | 24 | 10 | 67.966 | 10.467 | 48.873 | 83.85 | 0.924 |
| 16 | 24 | 12 | 45.582 | 11.905 | 21.195 | 174.38 | 0.772 |
| 16 | 24 | 14 | 70.643 | 11.599 | 74.750 | 199.89 | 0.945 |
| 16 | 24 | 16 | 43.896 | 10.677 | 22.208 | 14.01 | 0.285 |
| 16 | 24 | 18 | 71.143 | 9.528 | 105.272 | 283.00 | 0.915 |
| 16 | 24 | 20 | 34.405 | 10.808 | 16.998 | 7.56 | 0.525 |
| 16 | 24 | 22 | 52.891 | 13.829 | 53.485 | 20.48 | 0.761 |
| 16 | 25 | 1 | 36.650 | 10.066 | 10.360 | 149.58 | 0.344 |
| 16 | 25 | 3 | 28.783 | 9.473 | 6.305 | 234.28 | 0.164 |
| 16 | 25 | 5 | 41.190 | 10.479 | 12.863 | 80.41 | 0.719 |
| 16 | 25 | 7 | 130.175 | 5.249 | 177.076 | 183.02 | 0.975 |
| 16 | 25 | 9 | 35.983 | 9.778 | 28.156 | 91.84 | 0.628 |
| 16 | 25 | 11 | 79.247 | 9.817 | 141.647 | 299.67 | 0.898 |
| 16 | 25 | 13 | 52.162 | 10.593 | 53.164 | 343.94 | 0.886 |
| 16 | 25 | 15 | 72.689 | 11.181 | 58.122 | 283.64 | 0.958 |
| 16 | 25 | 17 | 37.386 | 11.280 | 18.421 | 276.05 | 0.794 |
| 16 | 25 | 19 | 49.173 | 13.345 | 48.184 | 344.62 | 0.725 |
| 16 | 26 | 0 | 75.697 | 13.874 | 39.637 | 0.00 | 0.371 |
| 16 | 26 | 2 | 67.283 | 13.567 | 106.415 | 296.31 | 0.869 |
| 16 | 26 | 4 | 62.782 | 11.076 | 86.057 | 230.02 | 0.904 |
| 16 | 26 | 6 | 38.278 | 10.787 | 2.817 | 302.26 | 0.874 |
| 16 | 26 | 8 | 90.217 | 7.439 | 150.931 | 65.54 | 0.953 |
| 16 | 26 | 10 | 102.203 | 6.401 | 188.282 | 127.71 | 0.957 |
| 16 | 26 | 12 | 34.893 | 10.738 | 17.563 | 348.02 | 0.605 |
| 16 | 26 | 14 | 43.343 | 12.691 | 30.428 | 84.66 | 0.468 |
| 16 | 26 | 16 | 40.966 | 12.006 | 30.366 | 43.19 | 0.625 |
| 16 | 26 | 18 | 37.639 | 11.951 | 11.072 | 352.36 | 0.769 |
| 16 | 27 | 1 | 99.718 | 7.081 | 144.525 | 53.44 | 0.971 |
| 16 | 27 | 3 | 34.657 | 10.609 | 5.839 | 115.84 | 0.818 |
| 16 | 27 | 5 | 37.929 | 10.931 | 17.241 | 98.96 | 0.809 |

| | | | | | | | |
|---|---|---|---|---|---|---|---|
| 16 | 27 | 7 | 36.169 | 10.447 | 18.933 | 344.09 | 0.690 |
| 16 | 27 | 9 | 52.409 | 11.308 | 68.830 | 179.13 | 0.796 |
| 16 | 27 | 11 | 40.299 | 11.718 | 22.492 | 115.08 | 0.793 |
| 16 | 27 | 13 | 63.356 | 12.566 | 67.261 | 83.34 | 0.920 |
| 16 | 27 | 15 | 33.844 | 11.351 | 8.170 | 110.84 | 0.768 |
| 16 | 28 | 0 | 26.688 | 12.670 | 12.584 | 0.00 | 0.340 |
| 16 | 28 | 2 | 42.775 | 12.174 | 31.094 | 73.90 | 0.830 |
| 16 | 28 | 4 | 50.445 | 12.436 | 13.608 | 112.46 | 0.924 |
| 16 | 28 | 6 | 28.211 | 9.419 | 3.921 | 208.51 | 0.325 |
| 16 | 28 | 8 | 111.500 | 5.919 | 229.648 | 274.50 | 0.955 |
| 16 | 28 | 10 | 49.915 | 12.525 | 54.203 | 196.02 | 0.780 |
| 16 | 28 | 12 | 30.785 | 10.458 | 4.773 | 21.92 | 0.568 |
| 16 | 29 | 1 | 31.758 | 9.910 | 14.949 | 294.06 | 0.515 |
| 16 | 29 | 3 | 54.198 | 16.227 | 47.876 | 296.67 | 0.850 |
| 16 | 29 | 5 | 40.160 | 12.373 | 29.300 | 253.62 | 0.609 |
| 17 | 0 | 1 | 224.663 | 3.509 | 331.829 | 0.00 | 1.000 |
| 17 | 0 | 3 | 57.398 | 5.730 | 57.179 | 0.00 | 0.675 |
| 17 | 0 | 5 | 409.867 | 6.106 | 604.539 | 180.00 | 1.000 |
| 17 | 0 | 7 | 114.694 | 3.419 | 168.528 | 180.00 | 1.000 |
| 17 | 0 | 9 | 37.946 | 6.942 | 17.024 | 180.00 | 0.305 |
| 17 | 0 | 11 | 35.299 | 8.978 | 36.252 | 0.00 | 0.715 |
| 17 | 0 | 13 | 229.630 | 3.350 | 335.532 | 0.00 | 1.000 |
| 17 | 0 | 15 | 39.441 | 11.452 | 49.737 | 0.00 | 0.868 |
| 17 | 0 | 17 | 118.680 | 5.961 | 171.870 | 180.00 | 1.000 |
| 17 | 0 | 19 | 22.324 | 10.779 | 5.423 | 0.00 | 0.176 |
| 17 | 0 | 21 | 331.528 | 4.659 | 475.997 | 180.00 | 1.000 |
| 17 | 0 | 23 | 263.849 | 4.680 | 376.524 | 180.00 | 1.000 |
| 17 | 0 | 25 | 289.314 | 5.564 | 409.970 | 180.00 | 1.000 |
| 17 | 0 | 27 | 33.102 | 15.561 | 33.369 | 180.00 | 0.727 |
| 17 | 0 | 29 | 142.053 | 7.719 | 197.718 | 180.00 | 1.000 |
| 17 | 0 | 31 | 83.703 | 16.427 | 112.176 | 0.00 | 1.000 |
| 17 | 0 | 33 | 64.025 | 17.687 | 82.927 | 0.00 | 0.997 |
| 17 | 0 | 35 | 31.234 | 13.788 | 34.328 | 0.00 | 0.851 |
| 17 | 0 | 37 | 20.896 | 10.633 | 3.687 | 0.00 | 0.138 |
| 17 | 1 | 0 | 90.741 | 3.541 | 133.021 | 0.00 | 0.992 |
| 17 | 1 | 2 | 216.641 | 2.380 | 313.352 | 312.77 | 0.984 |
| 17 | 1 | 4 | 109.030 | 2.007 | 188.209 | 66.23 | 0.916 |
| 17 | 1 | 6 | 355.491 | 4.652 | 524.920 | 296.72 | 0.993 |
| 17 | 1 | 8 | 72.436 | 3.017 | 78.367 | 304.49 | 0.887 |
| 17 | 1 | 10 | 158.725 | 2.005 | 221.056 | 32.07 | 0.961 |
| 17 | 1 | 12 | 143.883 | 2.366 | 189.842 | 52.04 | 0.957 |
| 17 | 1 | 14 | 133.364 | 2.819 | 156.801 | 237.25 | 0.962 |
| 17 | 1 | 16 | 96.996 | 4.425 | 100.949 | 221.39 | 0.927 |
| 17 | 1 | 18 | 125.639 | 3.889 | 162.756 | 155.27 | 0.937 |
| 17 | 1 | 20 | 57.697 | 9.654 | 36.197 | 209.72 | 0.482 |
| 17 | 1 | 22 | 227.114 | 3.662 | 327.896 | 218.12 | 0.986 |
| 17 | 1 | 24 | 259.536 | 3.456 | 316.373 | 232.26 | 0.993 |
| 17 | 1 | 26 | 38.846 | 10.682 | 9.019 | 318.04 | 0.728 |
| 17 | 1 | 28 | 134.485 | 5.230 | 165.577 | 202.14 | 0.973 |
| 17 | 1 | 30 | 47.626 | 11.040 | 16.021 | 94.03 | 0.817 |
| 17 | 1 | 32 | 59.752 | 12.215 | 57.842 | 2.15 | 0.815 |
| 17 | 1 | 34 | 42.709 | 12.289 | 14.987 | 103.09 | 0.847 |
| 17 | 1 | 36 | 35.612 | 10.735 | 13.755 | 293.76 | 0.459 |
| 17 | 2 | 1 | 411.623 | 4.484 | 593.467 | 211.15 | 0.995 |
| 17 | 2 | 3 | 119.752 | 2.795 | 209.893 | 353.96 | 0.899 |
| 17 | 2 | 5 | 437.809 | 4.510 | 681.061 | 21.45 | 0.995 |
| 17 | 2 | 7 | 270.625 | 2.977 | 295.989 | 336.12 | 0.992 |
| 17 | 2 | 9 | 330.616 | 3.045 | 474.634 | 47.61 | 0.992 |
| 17 | 2 | 11 | 204.171 | 2.134 | 294.043 | 89.23 | 0.982 |
| 17 | 2 | 13 | 127.128 | 2.658 | 146.799 | 88.47 | 0.960 |
| 17 | 2 | 15 | 161.914 | 2.933 | 218.130 | 195.24 | 0.964 |
| 17 | 2 | 17 | 172.787 | 3.781 | 189.556 | 205.01 | 0.974 |
| 17 | 2 | 19 | 235.518 | 2.956 | 391.132 | 348.18 | 0.986 |
| 17 | 2 | 21 | 339.323 | 3.375 | 439.206 | 327.45 | 0.995 |
| 17 | 2 | 23 | 286.852 | 3.378 | 425.777 | 165.86 | 0.994 |
| 17 | 2 | 25 | 217.498 | 3.537 | 322.351 | 26.01 | 0.988 |
| 17 | 2 | 27 | 90.726 | 6.774 | 104.838 | 216.60 | 0.939 |
| 17 | 2 | 29 | 90.816 | 9.478 | 141.634 | 107.21 | 0.858 |
| 17 | 2 | 31 | 32.885 | 10.399 | 29.413 | 263.07 | 0.712 |
| 17 | 2 | 33 | 63.333 | 12.418 | 85.629 | 36.12 | 0.688 |
| 17 | 2 | 35 | 66.129 | 10.669 | 64.924 | 147.38 | 0.935 |
| 17 | 3 | 0 | 32.089 | 16.637 | 29.342 | 0.00 | 0.625 |
| 17 | 3 | 2 | 220.216 | 2.762 | 363.087 | 96.75 | 0.980 |
| 17 | 3 | 4 | 149.161 | 3.459 | 201.909 | 192.97 | 0.967 |
| 17 | 3 | 6 | 153.569 | 2.502 | 202.015 | 342.44 | 0.967 |
| 17 | 3 | 8 | 64.454 | 4.816 | 41.307 | 224.49 | 0.858 |
| 17 | 3 | 10 | 321.828 | 2.738 | 470.157 | 188.95 | 0.991 |

| | | | | | | | |
|---|---|---|---|---|---|---|---|
| 17 | 3 | 12 | 204.873 | 2.627 | 311.664 | 27.95 | 0.978 |
| 17 | 3 | 14 | 64.227 | 5.931 | 5.211 | 197.10 | 0.886 |
| 17 | 3 | 16 | 182.938 | 2.825 | 297.434 | 0.05 | 0.962 |
| 17 | 3 | 18 | 164.549 | 3.385 | 283.173 | 74.68 | 0.937 |
| 17 | 3 | 20 | 287.448 | 3.172 | 486.636 | 36.75 | 0.989 |
| 17 | 3 | 22 | 203.781 | 3.633 | 292.404 | 253.83 | 0.983 |
| 17 | 3 | 24 | 186.932 | 3.844 | 292.832 | 116.47 | 0.983 |
| 17 | 3 | 26 | 31.110 | 9.794 | 3.644 | 49.24 | 0.113 |
| 17 | 3 | 28 | 202.902 | 4.168 | 251.424 | 325.64 | 0.988 |
| 17 | 3 | 30 | 42.972 | 11.047 | 21.285 | 149.49 | 0.637 |
| 17 | 3 | 32 | 57.243 | 12.679 | 20.460 | 276.88 | 0.935 |
| 17 | 3 | 34 | 51.532 | 12.302 | 55.682 | 338.25 | 0.786 |
| 17 | 3 | 36 | 145.452 | 5.348 | 274.596 | 199.18 | 0.974 |
| 17 | 4 | 1 | 247.448 | 2.997 | 297.290 | 22.17 | 0.990 |
| 17 | 4 | 3 | 256.788 | 3.862 | 428.927 | 128.19 | 0.984 |
| 17 | 4 | 5 | 219.495 | 2.762 | 294.383 | 111.63 | 0.986 |
| 17 | 4 | 7 | 512.868 | 5.163 | 796.683 | 205.26 | 0.997 |
| 17 | 4 | 9 | 459.521 | 4.602 | 701.950 | 218.65 | 0.996 |
| 17 | 4 | 11 | 308.305 | 2.956 | 480.572 | 308.71 | 0.990 |
| 17 | 4 | 13 | 131.817 | 2.672 | 180.774 | 329.03 | 0.958 |
| 17 | 4 | 15 | 109.043 | 3.890 | 159.138 | 280.14 | 0.898 |
| 17 | 4 | 17 | 259.679 | 3.379 | 418.079 | 49.82 | 0.982 |
| 17 | 4 | 19 | 406.395 | 3.666 | 662.686 | 190.01 | 0.995 |
| 17 | 4 | 21 | 90.573 | 6.071 | 72.841 | 146.34 | 0.936 |
| 17 | 4 | 23 | 178.150 | 3.859 | 269.355 | 249.68 | 0.982 |
| 17 | 4 | 25 | 179.308 | 4.206 | 287.287 | 325.96 | 0.981 |
| 17 | 4 | 27 | 60.909 | 10.414 | 68.290 | 28.32 | 0.665 |
| 17 | 4 | 29 | 131.202 | 6.321 | 184.861 | 126.00 | 0.968 |
| 17 | 4 | 31 | 47.433 | 12.534 | 17.147 | 81.20 | 0.767 |
| 17 | 4 | 33 | 58.697 | 11.344 | 77.427 | 156.62 | 0.733 |
| 17 | 4 | 35 | 47.907 | 11.576 | 36.692 | 255.20 | 0.851 |
| 17 | 5 | 0 | 143.358 | 4.532 | 211.689 | 0.00 | 1.000 |
| 17 | 5 | 2 | 307.684 | 3.643 | 452.456 | 141.64 | 0.991 |
| 17 | 5 | 4 | 216.645 | 3.520 | 346.828 | 344.22 | 0.979 |
| 17 | 5 | 6 | 194.587 | 2.812 | 238.237 | 182.00 | 0.983 |
| 17 | 5 | 8 | 190.699 | 4.205 | 310.692 | 287.07 | 0.971 |
| 17 | 5 | 10 | 252.649 | 2.747 | 390.841 | 57.69 | 0.986 |
| 17 | 5 | 12 | 295.820 | 2.955 | 440.272 | 124.89 | 0.990 |
| 17 | 5 | 14 | 174.624 | 2.701 | 280.260 | 133.44 | 0.964 |
| 17 | 5 | 16 | 342.494 | 3.146 | 497.418 | 86.36 | 0.992 |
| 17 | 5 | 18 | 156.567 | 3.337 | 232.559 | 217.87 | 0.970 |
| 17 | 5 | 20 | 101.622 | 6.398 | 142.289 | 201.73 | 0.918 |
| 17 | 5 | 22 | 223.128 | 3.488 | 325.882 | 31.56 | 0.985 |
| 17 | 5 | 24 | 120.846 | 5.120 | 178.019 | 144.57 | 0.957 |
| 17 | 5 | 26 | 170.975 | 4.085 | 249.565 | 36.15 | 0.982 |
| 17 | 5 | 28 | 78.204 | 8.909 | 99.950 | 40.43 | 0.622 |
| 17 | 5 | 30 | 68.182 | 9.930 | 88.722 | 340.18 | 0.813 |
| 17 | 5 | 32 | 43.060 | 11.688 | 36.713 | 102.59 | 0.628 |
| 17 | 5 | 34 | 72.053 | 10.762 | 75.645 | 262.82 | 0.935 |
| 17 | 5 | 36 | 39.548 | 11.476 | 3.987 | 275.21 | 0.119 |
| 17 | 6 | 1 | 438.821 | 6.283 | 633.812 | 219.53 | 0.996 |
| 17 | 6 | 3 | 141.199 | 3.406 | 188.209 | 254.62 | 0.959 |
| 17 | 6 | 5 | 135.014 | 2.506 | 230.348 | 330.54 | 0.955 |
| 17 | 6 | 7 | 373.108 | 4.081 | 550.170 | 302.25 | 0.994 |
| 17 | 6 | 9 | 134.444 | 3.090 | 197.429 | 92.40 | 0.949 |
| 17 | 6 | 11 | 292.277 | 3.212 | 458.065 | 134.93 | 0.989 |
| 17 | 6 | 13 | 322.425 | 3.159 | 438.155 | 170.21 | 0.992 |
| 17 | 6 | 15 | 392.943 | 4.990 | 560.807 | 106.88 | 0.994 |
| 17 | 6 | 17 | 186.603 | 2.980 | 235.981 | 262.17 | 0.975 |
| 17 | 6 | 19 | 188.519 | 3.390 | 262.115 | 105.14 | 0.981 |
| 17 | 6 | 21 | 162.079 | 4.389 | 261.162 | 44.02 | 0.966 |
| 17 | 6 | 23 | 146.442 | 4.913 | 177.382 | 316.66 | 0.980 |
| 17 | 6 | 25 | 39.055 | 10.987 | 13.683 | 266.67 | 0.565 |
| 17 | 6 | 27 | 91.282 | 7.320 | 127.708 | 356.76 | 0.924 |
| 17 | 6 | 29 | 247.920 | 3.821 | 534.267 | 220.47 | 0.977 |
| 17 | 6 | 31 | 55.653 | 12.039 | 47.919 | 222.59 | 0.793 |
| 17 | 6 | 33 | 45.472 | 12.308 | 35.271 | 209.00 | 0.771 |
| 17 | 6 | 35 | 49.170 | 12.640 | 42.887 | 249.37 | 0.565 |
| 17 | 7 | 0 | 600.229 | 9.801 | 885.771 | 180.00 | 1.000 |
| 17 | 7 | 2 | 337.806 | 4.853 | 490.757 | 137.44 | 0.993 |
| 17 | 7 | 4 | 38.104 | 6.804 | 14.923 | 125.48 | 0.166 |
| 17 | 7 | 6 | 528.112 | 5.100 | 787.594 | 18.86 | 0.997 |
| 17 | 7 | 8 | 426.090 | 5.846 | 662.581 | 133.75 | 0.995 |
| 17 | 7 | 10 | 53.837 | 4.696 | 19.810 | 85.16 | 0.257 |
| 17 | 7 | 12 | 227.406 | 3.042 | 332.882 | 213.44 | 0.983 |
| 17 | 7 | 14 | 300.965 | 2.962 | 362.175 | 132.28 | 0.991 |
| 17 | 7 | 16 | 149.324 | 3.903 | 186.474 | 306.34 | 0.962 |

| | | | | | | | |
|---|---|---|---|---|---|---|---|
| 17 | 7 | 18 | 89.067 | 6.380 | 116.842 | 254.66 | 0.740 |
| 17 | 7 | 20 | 172.578 | 3.673 | 219.927 | 217.17 | 0.979 |
| 17 | 7 | 22 | 169.531 | 4.161 | 235.215 | 94.84 | 0.982 |
| 17 | 7 | 24 | 27.576 | 8.624 | 11.331 | 327.99 | 0.520 |
| 17 | 7 | 26 | 146.692 | 4.798 | 193.227 | 314.69 | 0.977 |
| 17 | 7 | 28 | 64.115 | 9.044 | 44.427 | 357.66 | 0.898 |
| 17 | 7 | 30 | 42.670 | 11.779 | 11.630 | 67.63 | 0.291 |
| 17 | 7 | 32 | 43.163 | 11.619 | 15.738 | 270.60 | 0.867 |
| 17 | 7 | 34 | 104.235 | 8.032 | 155.987 | 222.55 | 0.967 |
| 17 | 8 | 1 | 251.400 | 4.737 | 353.066 | 311.51 | 0.986 |
| 17 | 8 | 3 | 127.039 | 3.393 | 156.541 | 7.02 | 0.957 |
| 17 | 8 | 5 | 161.706 | 2.734 | 232.812 | 339.02 | 0.970 |
| 17 | 8 | 7 | 202.085 | 2.830 | 304.198 | 356.16 | 0.978 |
| 17 | 8 | 9 | 215.927 | 2.854 | 350.067 | 129.25 | 0.977 |
| 17 | 8 | 11 | 306.047 | 2.877 | 430.058 | 300.33 | 0.990 |
| 17 | 8 | 13 | 163.772 | 3.608 | 271.078 | 25.05 | 0.952 |
| 17 | 8 | 15 | 282.101 | 3.197 | 401.478 | 89.98 | 0.988 |
| 17 | 8 | 17 | 375.229 | 3.885 | 507.220 | 323.48 | 0.996 |
| 17 | 8 | 19 | 131.098 | 5.471 | 246.468 | 234.80 | 0.923 |
| 17 | 8 | 21 | 151.116 | 4.155 | 172.594 | 129.47 | 0.981 |
| 17 | 8 | 23 | 86.897 | 7.012 | 138.221 | 113.75 | 0.891 |
| 17 | 8 | 25 | 187.211 | 3.761 | 286.250 | 211.88 | 0.984 |
| 17 | 8 | 27 | 64.943 | 10.791 | 71.654 | 268.80 | 0.818 |
| 17 | 8 | 29 | 100.115 | 7.174 | 129.326 | 266.43 | 0.951 |
| 17 | 8 | 31 | 71.786 | 10.043 | 64.541 | 325.12 | 0.948 |
| 17 | 8 | 33 | 175.011 | 4.874 | 259.070 | 318.21 | 0.989 |
| 17 | 8 | 35 | 38.898 | 11.153 | 25.784 | 340.25 | 0.614 |
| 17 | 9 | 0 | 69.554 | 14.182 | 47.075 | 180.00 | 0.462 |
| 17 | 9 | 2 | 334.566 | 3.822 | 427.297 | 40.14 | 0.993 |
| 17 | 9 | 4 | 276.882 | 2.900 | 356.248 | 311.40 | 0.990 |
| 17 | 9 | 6 | 113.758 | 3.465 | 174.734 | 266.22 | 0.856 |
| 17 | 9 | 8 | 235.961 | 2.673 | 344.389 | 247.83 | 0.983 |
| 17 | 9 | 10 | 213.583 | 2.414 | 264.349 | 310.27 | 0.984 |
| 17 | 9 | 12 | 516.314 | 5.303 | 759.977 | 281.53 | 0.996 |
| 17 | 9 | 14 | 180.612 | 3.232 | 274.771 | 206.84 | 0.969 |
| 17 | 9 | 16 | 123.110 | 4.258 | 164.240 | 254.79 | 0.957 |
| 17 | 9 | 18 | 173.173 | 3.892 | 260.756 | 206.62 | 0.975 |
| 17 | 9 | 20 | 95.243 | 7.211 | 145.667 | 172.24 | 0.928 |
| 17 | 9 | 22 | 59.756 | 9.724 | 68.775 | 148.98 | 0.712 |
| 17 | 9 | 24 | 92.020 | 6.278 | 148.477 | 95.98 | 0.901 |
| 17 | 9 | 26 | 218.820 | 3.751 | 346.580 | 270.91 | 0.987 |
| 17 | 9 | 28 | 105.043 | 5.970 | 123.470 | 289.25 | 0.963 |
| 17 | 9 | 30 | 51.751 | 11.905 | 4.566 | 236.84 | 0.934 |
| 17 | 9 | 32 | 36.717 | 10.387 | 19.975 | 241.09 | 0.419 |
| 17 | 9 | 34 | 43.531 | 12.326 | 33.800 | 82.70 | 0.738 |
| 17 | 10 | 1 | 130.924 | 5.615 | 179.452 | 218.37 | 0.949 |
| 17 | 10 | 3 | 156.371 | 4.991 | 225.533 | 281.34 | 0.964 |
| 17 | 10 | 5 | 64.300 | 4.553 | 62.614 | 334.92 | 0.700 |
| 17 | 10 | 7 | 138.622 | 3.446 | 205.629 | 345.18 | 0.945 |
| 17 | 10 | 9 | 159.350 | 3.235 | 192.741 | 317.79 | 0.968 |
| 17 | 10 | 11 | 215.619 | 2.530 | 309.097 | 204.51 | 0.977 |
| 17 | 10 | 13 | 188.245 | 3.802 | 320.098 | 272.75 | 0.958 |
| 17 | 10 | 15 | 182.212 | 3.624 | 227.028 | 207.48 | 0.981 |
| 17 | 10 | 17 | 304.670 | 3.556 | 418.442 | 227.93 | 0.993 |
| 17 | 10 | 19 | 128.834 | 4.789 | 218.900 | 285.32 | 0.940 |
| 17 | 10 | 21 | 83.704 | 7.971 | 28.640 | 28.16 | 0.217 |
| 17 | 10 | 23 | 211.154 | 3.807 | 415.585 | 187.71 | 0.980 |
| 17 | 10 | 25 | 94.823 | 6.989 | 145.455 | 9.27 | 0.919 |
| 17 | 10 | 27 | 138.398 | 4.805 | 221.074 | 0.10 | 0.971 |
| 17 | 10 | 29 | 141.998 | 4.875 | 197.984 | 60.32 | 0.976 |
| 17 | 10 | 31 | 31.932 | 10.309 | 1.686 | 337.15 | 0.702 |
| 17 | 10 | 33 | 46.804 | 11.550 | 41.356 | 202.72 | 0.779 |
| 17 | 11 | 0 | 97.634 | 5.283 | 108.376 | 0.00 | 0.754 |
| 17 | 11 | 2 | 76.116 | 4.045 | 51.707 | 307.36 | 0.894 |
| 17 | 11 | 4 | 79.253 | 3.545 | 108.790 | 108.18 | 0.834 |
| 17 | 11 | 6 | 110.834 | 3.541 | 125.522 | 46.86 | 0.943 |
| 17 | 11 | 8 | 221.469 | 2.957 | 319.119 | 100.11 | 0.981 |
| 17 | 11 | 10 | 66.079 | 6.771 | 49.874 | 70.91 | 0.444 |
| 17 | 11 | 12 | 212.811 | 2.975 | 316.385 | 349.58 | 0.981 |
| 17 | 11 | 14 | 266.147 | 3.385 | 388.859 | 330.29 | 0.990 |
| 17 | 11 | 16 | 100.297 | 7.072 | 118.367 | 60.86 | 0.930 |
| 17 | 11 | 18 | 163.897 | 4.335 | 166.092 | 326.66 | 0.982 |
| 17 | 11 | 20 | 255.853 | 3.344 | 458.752 | 27.89 | 0.989 |
| 17 | 11 | 22 | 61.448 | 9.401 | 58.142 | 117.55 | 0.856 |
| 17 | 11 | 24 | 82.355 | 9.055 | 96.729 | 283.14 | 0.554 |
| 17 | 11 | 26 | 60.501 | 10.883 | 61.153 | 272.72 | 0.865 |
| 17 | 11 | 28 | 84.492 | 9.352 | 108.907 | 301.81 | 0.926 |

| | | | | | | | |
|---|---|---|---|---|---|---|---|
| 17 | 11 | 30 | 32.641 | 10.287 | 10.996 | 59.16 | 0.488 |
| 17 | 11 | 32 | 103.570 | 6.753 | 168.252 | 29.16 | 0.964 |
| 17 | 11 | 34 | 42.821 | 11.690 | 31.322 | 161.40 | 0.584 |
| 17 | 12 | 1 | 166.237 | 2.539 | 255.266 | 259.60 | 0.962 |
| 17 | 12 | 3 | 324.890 | 3.135 | 495.559 | 132.00 | 0.991 |
| 17 | 12 | 5 | 362.935 | 3.177 | 505.753 | 107.91 | 0.993 |
| 17 | 12 | 7 | 123.362 | 4.312 | 118.170 | 200.05 | 0.948 |
| 17 | 12 | 9 | 291.737 | 3.322 | 443.755 | 175.48 | 0.988 |
| 17 | 12 | 11 | 34.161 | 9.539 | 23.899 | 141.63 | 0.282 |
| 17 | 12 | 13 | 224.029 | 3.337 | 330.640 | 45.47 | 0.986 |
| 17 | 12 | 15 | 288.605 | 3.151 | 389.359 | 349.18 | 0.992 |
| 17 | 12 | 17 | 100.496 | 6.658 | 146.631 | 91.89 | 0.914 |
| 17 | 12 | 19 | 158.701 | 3.519 | 241.771 | 67.23 | 0.978 |
| 17 | 12 | 21 | 307.304 | 3.538 | 422.205 | 124.04 | 0.995 |
| 17 | 12 | 23 | 79.278 | 9.241 | 103.054 | 74.45 | 0.899 |
| 17 | 12 | 25 | 38.870 | 11.434 | 5.409 | 101.11 | 0.487 |
| 17 | 12 | 27 | 29.786 | 9.378 | 56.249 | 162.51 | 0.778 |
| 17 | 12 | 29 | 38.898 | 11.037 | 25.961 | 196.89 | 0.678 |
| 17 | 12 | 31 | 30.280 | 9.660 | 8.845 | 280.49 | 0.725 |
| 17 | 12 | 33 | 35.757 | 10.526 | 18.438 | 317.70 | 0.547 |
| 17 | 13 | 0 | 520.080 | 8.821 | 766.577 | 180.00 | 1.000 |
| 17 | 13 | 2 | 159.470 | 2.702 | 241.331 | 131.63 | 0.960 |
| 17 | 13 | 4 | 111.077 | 3.279 | 165.718 | 197.61 | 0.915 |
| 17 | 13 | 6 | 132.397 | 3.644 | 184.847 | 130.65 | 0.944 |
| 17 | 13 | 8 | 142.283 | 3.962 | 222.658 | 255.50 | 0.936 |
| 17 | 13 | 10 | 216.001 | 3.946 | 272.117 | 136.05 | 0.987 |
| 17 | 13 | 12 | 174.362 | 3.521 | 171.431 | 246.74 | 0.983 |
| 17 | 13 | 14 | 33.806 | 9.947 | 6.897 | 320.57 | 0.336 |
| 17 | 13 | 16 | 77.645 | 6.249 | 88.647 | 276.68 | 0.918 |
| 17 | 13 | 18 | 88.176 | 6.831 | 101.254 | 211.39 | 0.940 |
| 17 | 13 | 20 | 181.604 | 3.644 | 305.770 | 339.24 | 0.981 |
| 17 | 13 | 22 | 223.823 | 3.889 | 314.570 | 149.11 | 0.990 |
| 17 | 13 | 24 | 75.704 | 8.307 | 33.298 | 196.21 | 0.944 |
| 17 | 13 | 26 | 115.291 | 6.899 | 145.412 | 4.91 | 0.968 |
| 17 | 13 | 28 | 66.887 | 11.970 | 103.616 | 217.90 | 0.770 |
| 17 | 13 | 30 | 62.231 | 11.446 | 61.229 | 87.01 | 0.909 |
| 17 | 13 | 32 | 38.089 | 10.695 | 3.145 | 56.51 | 0.082 |
| 17 | 14 | 1 | 236.894 | 2.888 | 416.643 | 14.09 | 0.977 |
| 17 | 14 | 3 | 93.428 | 3.809 | 120.693 | 76.21 | 0.631 |
| 17 | 14 | 5 | 214.770 | 2.773 | 259.341 | 111.30 | 0.982 |
| 17 | 14 | 7 | 59.769 | 7.835 | 50.696 | 84.00 | 0.787 |
| 17 | 14 | 9 | 262.456 | 3.428 | 357.656 | 359.38 | 0.991 |
| 17 | 14 | 11 | 114.593 | 5.706 | 174.153 | 348.68 | 0.937 |
| 17 | 14 | 13 | 102.784 | 6.145 | 160.606 | 134.20 | 0.910 |
| 17 | 14 | 15 | 99.498 | 6.473 | 117.511 | 100.83 | 0.954 |
| 17 | 14 | 17 | 259.134 | 3.276 | 393.326 | 283.25 | 0.992 |
| 17 | 14 | 19 | 188.277 | 3.574 | 337.779 | 8.89 | 0.980 |
| 17 | 14 | 21 | 37.227 | 10.943 | 2.239 | 180.51 | 0.063 |
| 17 | 14 | 23 | 58.693 | 11.375 | 52.623 | 329.06 | 0.528 |
| 17 | 14 | 25 | 187.188 | 3.783 | 324.531 | 303.00 | 0.983 |
| 17 | 14 | 27 | 47.237 | 11.151 | 50.342 | 238.39 | 0.638 |
| 17 | 14 | 29 | 67.241 | 12.016 | 44.819 | 282.19 | 0.311 |
| 17 | 14 | 31 | 38.644 | 11.661 | 17.805 | 228.62 | 0.379 |
| 17 | 15 | 0 | 177.290 | 5.827 | 261.256 | 180.00 | 1.000 |
| 17 | 15 | 2 | 380.131 | 3.823 | 579.452 | 221.10 | 0.995 |
| 17 | 15 | 4 | 131.663 | 3.747 | 182.034 | 34.08 | 0.961 |
| 17 | 15 | 6 | 71.887 | 8.385 | 87.041 | 154.18 | 0.829 |
| 17 | 15 | 8 | 250.441 | 3.523 | 331.758 | 21.86 | 0.991 |
| 17 | 15 | 10 | 233.023 | 3.645 | 384.883 | 292.28 | 0.985 |
| 17 | 15 | 12 | 50.520 | 10.746 | 31.251 | 123.54 | 0.393 |
| 17 | 15 | 14 | 127.016 | 4.795 | 147.308 | 263.00 | 0.975 |
| 17 | 15 | 16 | 67.720 | 8.138 | 49.926 | 17.07 | 0.913 |
| 17 | 15 | 18 | 146.919 | 4.564 | 241.180 | 17.48 | 0.972 |
| 17 | 15 | 20 | 160.590 | 4.257 | 295.510 | 286.66 | 0.969 |
| 17 | 15 | 22 | 39.145 | 10.976 | 10.124 | 142.67 | 0.391 |
| 17 | 15 | 24 | 40.556 | 11.480 | 17.950 | 153.00 | 0.334 |
| 17 | 15 | 26 | 81.832 | 8.782 | 78.294 | 270.46 | 0.963 |
| 17 | 15 | 28 | 90.256 | 7.679 | 138.519 | 143.20 | 0.951 |
| 17 | 15 | 30 | 45.200 | 11.673 | 30.991 | 321.62 | 0.852 |
| 17 | 16 | 1 | 142.014 | 4.275 | 176.333 | 149.30 | 0.971 |
| 17 | 16 | 3 | 56.859 | 9.417 | 37.401 | 252.75 | 0.771 |
| 17 | 16 | 5 | 126.126 | 4.750 | 141.210 | 4.38 | 0.964 |
| 17 | 16 | 7 | 133.990 | 5.499 | 199.653 | 315.29 | 0.959 |
| 17 | 16 | 9 | 53.442 | 10.963 | 28.292 | 249.51 | 0.729 |
| 17 | 16 | 11 | 87.152 | 7.321 | 127.754 | 324.21 | 0.916 |
| 17 | 16 | 13 | 68.685 | 8.426 | 95.595 | 202.74 | 0.851 |
| 17 | 16 | 15 | 51.939 | 10.451 | 29.476 | 9.23 | 0.323 |

| | | | | | | | |
|---|---|---|---|---|---|---|---|
| 17 | 16 | 17 | 55.215 | 11.569 | 24.206 | 217.39 | 0.867 |
| 17 | 16 | 19 | 31.987 | 9.345 | 19.774 | 127.08 | 0.676 |
| 17 | 16 | 21 | 136.354 | 4.675 | 253.968 | 185.01 | 0.962 |
| 17 | 16 | 23 | 34.306 | 10.943 | 3.590 | 87.23 | 0.607 |
| 17 | 16 | 25 | 30.331 | 9.259 | 19.718 | 292.90 | 0.826 |
| 17 | 16 | 27 | 30.290 | 9.909 | 2.276 | 105.78 | 0.655 |
| 17 | 16 | 29 | 51.706 | 11.267 | 60.204 | 359.30 | 0.820 |
| 17 | 17 | 0 | 32.108 | 13.161 | 19.063 | 0.00 | 0.410 |
| 17 | 17 | 2 | 155.295 | 3.604 | 168.794 | 293.03 | 0.980 |
| 17 | 17 | 4 | 33.893 | 9.799 | 14.880 | 223.66 | 0.289 |
| 17 | 17 | 6 | 151.999 | 4.233 | 170.499 | 347.55 | 0.977 |
| 17 | 17 | 8 | 138.482 | 5.491 | 140.824 | 328.91 | 0.980 |
| 17 | 17 | 10 | 252.332 | 3.871 | 334.558 | 15.67 | 0.993 |
| 17 | 17 | 12 | 170.025 | 4.403 | 264.168 | 256.55 | 0.980 |
| 17 | 17 | 14 | 133.114 | 5.481 | 235.432 | 70.15 | 0.958 |
| 17 | 17 | 16 | 192.457 | 3.881 | 259.480 | 69.86 | 0.987 |
| 17 | 17 | 18 | 66.298 | 10.091 | 89.079 | 55.05 | 0.817 |
| 17 | 17 | 20 | 56.915 | 12.214 | 37.165 | 158.87 | 0.877 |
| 17 | 17 | 22 | 100.239 | 6.535 | 154.313 | 120.98 | 0.942 |
| 17 | 17 | 24 | 39.612 | 12.310 | 17.783 | 104.73 | 0.810 |
| 17 | 17 | 26 | 38.799 | 11.679 | 14.762 | 62.14 | 0.810 |
| 17 | 17 | 28 | 35.490 | 10.651 | 15.486 | 42.50 | 0.462 |
| 17 | 18 | 1 | 249.257 | 3.758 | 392.842 | 256.41 | 0.992 |
| 17 | 18 | 3 | 144.641 | 4.607 | 206.827 | 304.98 | 0.976 |
| 17 | 18 | 5 | 204.460 | 3.391 | 326.011 | 15.43 | 0.987 |
| 17 | 18 | 7 | 126.170 | 5.568 | 212.483 | 57.14 | 0.959 |
| 17 | 18 | 9 | 209.479 | 3.679 | 300.772 | 162.21 | 0.989 |
| 17 | 18 | 11 | 48.294 | 11.466 | 25.799 | 333.57 | 0.765 |
| 17 | 18 | 13 | 174.764 | 4.557 | 308.814 | 306.96 | 0.977 |
| 17 | 18 | 15 | 96.841 | 8.402 | 123.646 | 29.16 | 0.945 |
| 17 | 18 | 17 | 38.017 | 9.778 | 17.154 | 303.62 | 0.326 |
| 17 | 18 | 19 | 59.680 | 13.799 | 65.289 | 263.89 | 0.778 |
| 17 | 18 | 21 | 56.255 | 11.568 | 20.927 | 244.05 | 0.891 |
| 17 | 18 | 23 | 103.086 | 5.859 | 177.844 | 140.67 | 0.961 |
| 17 | 18 | 25 | 49.475 | 11.904 | 52.864 | 77.54 | 0.739 |
| 17 | 18 | 27 | 94.043 | 9.803 | 174.009 | 95.55 | 0.910 |
| 17 | 19 | 0 | 33.207 | 14.541 | 34.648 | 180.00 | 0.720 |
| 17 | 19 | 2 | 38.201 | 10.781 | 2.912 | 208.25 | 0.151 |
| 17 | 19 | 4 | 169.367 | 3.798 | 299.836 | 112.86 | 0.976 |
| 17 | 19 | 6 | 210.894 | 3.463 | 287.934 | 198.90 | 0.990 |
| 17 | 19 | 8 | 112.973 | 6.606 | 150.725 | 103.62 | 0.961 |
| 17 | 19 | 10 | 116.305 | 7.244 | 111.704 | 133.55 | 0.972 |
| 17 | 19 | 12 | 111.464 | 6.071 | 162.932 | 233.62 | 0.957 |
| 17 | 19 | 14 | 52.707 | 10.509 | 32.223 | 174.17 | 0.364 |
| 17 | 19 | 16 | 171.500 | 4.521 | 228.964 | 163.85 | 0.984 |
| 17 | 19 | 18 | 127.965 | 5.215 | 172.783 | 161.30 | 0.974 |
| 17 | 19 | 20 | 90.280 | 8.773 | 97.064 | 297.47 | 0.951 |
| 17 | 19 | 22 | 51.795 | 11.436 | 30.678 | 175.67 | 0.910 |
| 17 | 19 | 24 | 78.443 | 9.419 | 110.611 | 163.93 | 0.941 |
| 17 | 19 | 26 | 47.870 | 10.978 | 21.636 | 334.99 | 0.901 |
| 17 | 20 | 1 | 84.950 | 8.805 | 148.511 | 294.68 | 0.844 |
| 17 | 20 | 3 | 74.923 | 7.628 | 81.204 | 51.71 | 0.917 |
| 17 | 20 | 5 | 83.105 | 7.353 | 63.750 | 81.89 | 0.946 |
| 17 | 20 | 7 | 100.688 | 5.992 | 133.652 | 277.25 | 0.952 |
| 17 | 20 | 9 | 45.567 | 11.494 | 20.602 | 355.65 | 0.756 |
| 17 | 20 | 11 | 67.098 | 12.373 | 67.650 | 224.72 | 0.886 |
| 17 | 20 | 13 | 113.728 | 7.404 | 182.182 | 217.23 | 0.952 |
| 17 | 20 | 15 | 63.460 | 10.346 | 87.305 | 163.38 | 0.802 |
| 17 | 20 | 17 | 67.619 | 10.585 | 100.109 | 67.45 | 0.764 |
| 17 | 20 | 19 | 90.203 | 7.339 | 93.199 | 143.52 | 0.952 |
| 17 | 20 | 21 | 94.680 | 8.132 | 156.693 | 256.64 | 0.955 |
| 17 | 20 | 23 | 60.395 | 13.930 | 78.634 | 135.78 | 0.746 |
| 17 | 20 | 25 | 30.608 | 9.696 | 6.488 | 294.41 | 0.788 |
| 17 | 21 | 0 | 23.918 | 11.652 | 4.512 | 180.00 | 0.130 |
| 17 | 21 | 2 | 111.560 | 6.227 | 189.660 | 332.35 | 0.947 |
| 17 | 21 | 4 | 164.271 | 4.177 | 252.140 | 99.87 | 0.981 |
| 17 | 21 | 6 | 74.277 | 9.020 | 116.772 | 318.04 | 0.792 |
| 17 | 21 | 8 | 106.748 | 6.237 | 99.355 | 242.20 | 0.968 |
| 17 | 21 | 10 | 87.485 | 7.761 | 139.989 | 249.55 | 0.900 |
| 17 | 21 | 12 | 108.277 | 8.735 | 125.346 | 120.84 | 0.967 |
| 17 | 21 | 14 | 96.808 | 9.153 | 161.248 | 117.73 | 0.927 |
| 17 | 21 | 16 | 104.531 | 6.183 | 174.534 | 58.95 | 0.942 |
| 17 | 21 | 18 | 125.160 | 6.198 | 232.991 | 211.70 | 0.973 |
| 17 | 21 | 20 | 94.164 | 6.610 | 120.268 | 332.40 | 0.969 |
| 17 | 21 | 22 | 48.623 | 9.677 | 59.141 | 261.99 | 0.784 |
| 17 | 21 | 24 | 67.570 | 10.907 | 95.867 | 59.46 | 0.901 |
| 17 | 22 | 1 | 104.036 | 6.882 | 124.847 | 172.00 | 0.959 |

| | | | | | | | |
|---|---|---|---|---|---|---|---|
| 17 | 22 | 3 | 49.523 | 11.273 | 17.328 | 153.76 | 0.835 |
| 17 | 22 | 5 | 109.232 | 5.816 | 150.890 | 163.30 | 0.959 |
| 17 | 22 | 7 | 170.928 | 3.985 | 232.290 | 249.12 | 0.984 |
| 17 | 22 | 9 | 45.004 | 10.583 | 1.706 | 154.49 | 0.864 |
| 17 | 22 | 11 | 156.669 | 5.326 | 240.303 | 137.93 | 0.981 |
| 17 | 22 | 13 | 148.923 | 5.623 | 203.834 | 252.11 | 0.981 |
| 17 | 22 | 15 | 119.041 | 5.921 | 263.185 | 24.97 | 0.943 |
| 17 | 22 | 17 | 32.666 | 10.012 | 14.862 | 154.52 | 0.523 |
| 17 | 22 | 19 | 91.338 | 8.156 | 162.090 | 124.19 | 0.941 |
| 17 | 22 | 21 | 38.564 | 11.265 | 26.508 | 11.06 | 0.578 |
| 17 | 22 | 23 | 72.200 | 11.411 | 84.550 | 290.40 | 0.936 |
| 17 | 23 | 0 | 122.161 | 7.701 | 19.984 | 0.00 | 0.112 |
| 17 | 23 | 2 | 53.292 | 10.360 | 33.065 | 245.66 | 0.320 |
| 17 | 23 | 4 | 157.003 | 4.322 | 227.075 | 19.06 | 0.983 |
| 17 | 23 | 6 | 65.660 | 9.327 | 65.228 | 83.68 | 0.909 |
| 17 | 23 | 8 | 79.912 | 8.283 | 101.900 | 335.71 | 0.931 |
| 17 | 23 | 10 | 49.692 | 11.375 | 41.425 | 254.16 | 0.583 |
| 17 | 23 | 12 | 78.180 | 10.421 | 112.853 | 279.56 | 0.895 |
| 17 | 23 | 14 | 111.397 | 7.061 | 193.281 | 303.84 | 0.970 |
| 17 | 23 | 16 | 82.094 | 9.402 | 135.611 | 230.27 | 0.935 |
| 17 | 23 | 18 | 90.507 | 7.707 | 176.857 | 80.14 | 0.924 |
| 17 | 23 | 20 | 42.600 | 11.804 | 15.925 | 300.14 | 0.248 |
| 17 | 24 | 1 | 110.818 | 6.485 | 173.583 | 150.18 | 0.961 |
| 17 | 24 | 3 | 62.341 | 10.023 | 83.916 | 321.80 | 0.798 |
| 17 | 24 | 5 | 28.096 | 9.119 | 14.703 | 336.00 | 0.425 |
| 17 | 24 | 7 | 38.174 | 10.686 | 7.336 | 307.77 | 0.747 |
| 17 | 24 | 9 | 77.979 | 7.352 | 112.374 | 81.50 | 0.949 |
| 17 | 24 | 11 | 40.759 | 11.263 | 24.533 | 175.54 | 0.838 |
| 17 | 24 | 13 | 43.466 | 11.375 | 27.228 | 286.66 | 0.847 |
| 17 | 24 | 15 | 30.025 | 9.618 | 1.937 | 292.22 | 0.112 |
| 17 | 24 | 17 | 37.736 | 10.453 | 12.290 | 168.92 | 0.285 |
| 17 | 24 | 19 | 40.810 | 11.841 | 33.394 | 300.45 | 0.686 |
| 17 | 25 | 0 | 58.655 | 15.783 | 80.558 | 180.00 | 0.979 |
| 17 | 25 | 2 | 40.052 | 12.194 | 32.498 | 141.03 | 0.735 |
| 17 | 25 | 4 | 34.110 | 10.517 | 19.377 | 73.24 | 0.614 |
| 17 | 25 | 6 | 112.087 | 5.708 | 194.482 | 238.22 | 0.972 |
| 17 | 25 | 8 | 31.422 | 9.864 | 12.322 | 221.64 | 0.425 |
| 17 | 25 | 10 | 98.903 | 5.927 | 170.152 | 138.63 | 0.961 |
| 17 | 25 | 12 | 47.123 | 10.762 | 51.724 | 221.08 | 0.772 |
| 17 | 25 | 14 | 33.489 | 10.678 | 13.161 | 313.56 | 0.612 |
| 17 | 25 | 16 | 36.860 | 11.796 | 18.376 | 154.54 | 0.361 |
| 17 | 26 | 1 | 47.079 | 11.555 | 50.444 | 53.64 | 0.613 |
| 17 | 26 | 3 | 142.325 | 4.752 | 226.128 | 58.36 | 0.985 |
| 17 | 26 | 5 | 37.017 | 10.644 | 23.899 | 234.38 | 0.738 |
| 17 | 26 | 7 | 53.798 | 11.194 | 65.231 | 73.30 | 0.866 |
| 17 | 26 | 9 | 59.606 | 10.108 | 85.822 | 128.79 | 0.882 |
| 17 | 26 | 11 | 43.097 | 11.539 | 27.186 | 9.30 | 0.362 |
| 17 | 26 | 13 | 56.127 | 11.954 | 72.420 | 350.45 | 0.862 |
| 17 | 26 | 15 | 31.202 | 10.030 | 9.460 | 15.66 | 0.553 |
| 17 | 27 | 0 | 32.066 | 13.972 | 34.440 | 180.00 | 0.778 |
| 17 | 27 | 2 | 80.599 | 12.431 | 131.545 | 355.28 | 0.922 |
| 17 | 27 | 4 | 37.349 | 11.135 | 22.985 | 266.45 | 0.772 |
| 17 | 27 | 6 | 83.631 | 7.722 | 148.857 | 143.67 | 0.938 |
| 17 | 27 | 8 | 31.751 | 9.880 | 14.921 | 55.12 | 0.586 |
| 17 | 27 | 10 | 44.021 | 11.449 | 33.087 | 69.88 | 0.842 |
| 17 | 28 | 1 | 47.159 | 11.774 | 54.787 | 114.98 | 0.731 |
| 17 | 28 | 3 | 50.565 | 10.447 | 27.785 | 340.84 | 0.917 |
| 17 | 28 | 5 | 53.128 | 11.037 | 71.776 | 319.89 | 0.764 |
| 17 | 28 | 7 | 31.047 | 10.161 | 3.904 | 168.96 | 0.339 |
| 18 | 0 | 2 | 48.006 | 9.881 | 9.318 | 180.00 | 0.131 |
| 18 | 0 | 4 | 179.786 | 3.438 | 267.252 | 180.00 | 1.000 |
| 18 | 0 | 6 | 298.544 | 6.853 | 442.938 | 0.00 | 1.000 |
| 18 | 0 | 8 | 393.069 | 5.162 | 582.399 | 0.00 | 1.000 |
| 18 | 0 | 10 | 131.991 | 3.114 | 195.133 | 0.00 | 1.000 |
| 18 | 0 | 12 | 21.144 | 9.486 | 8.753 | 180.00 | 0.292 |
| 18 | 0 | 14 | 433.493 | 4.855 | 636.784 | 180.00 | 1.000 |
| 18 | 0 | 16 | 58.473 | 13.382 | 48.205 | 0.00 | 0.566 |
| 18 | 0 | 18 | 72.291 | 11.310 | 101.992 | 0.00 | 0.973 |
| 18 | 0 | 20 | 50.883 | 14.317 | 72.701 | 180.00 | 0.993 |
| 18 | 0 | 22 | 29.181 | 13.082 | 1.391 | 180.00 | 0.033 |
| 18 | 0 | 24 | 61.480 | 15.722 | 65.637 | 180.00 | 0.757 |
| 18 | 0 | 26 | 48.188 | 15.854 | 63.384 | 180.00 | 0.942 |
| 18 | 0 | 28 | 29.961 | 13.556 | 35.707 | 0.00 | 0.859 |
| 18 | 0 | 30 | 36.757 | 14.428 | 49.329 | 0.00 | 0.988 |
| 18 | 0 | 32 | 119.458 | 15.277 | 158.205 | 0.00 | 1.000 |
| 18 | 0 | 34 | 29.170 | 14.304 | 16.712 | 0.00 | 0.442 |
| 18 | 1 | 1 | 131.562 | 2.328 | 113.465 | 212.83 | 0.967 |

| | | | | | | | |
|---|---|---|---|---|---|---|---|
| 18 | 1 | 3 | 242.481 | 2.441 | 362.414 | 51.88 | 0.987 |
| 18 | 1 | 5 | 273.060 | 2.691 | 416.103 | 142.23 | 0.988 |
| 18 | 1 | 7 | 571.794 | 5.840 | 828.794 | 44.14 | 0.997 |
| 18 | 1 | 9 | 133.380 | 2.775 | 200.449 | 280.67 | 0.962 |
| 18 | 1 | 11 | 239.046 | 2.251 | 374.296 | 233.30 | 0.982 |
| 18 | 1 | 13 | 271.532 | 2.753 | 422.129 | 229.43 | 0.986 |
| 18 | 1 | 15 | 254.814 | 2.667 | 387.530 | 233.80 | 0.985 |
| 18 | 1 | 17 | 146.305 | 3.649 | 228.481 | 297.42 | 0.964 |
| 18 | 1 | 19 | 371.665 | 3.592 | 541.860 | 228.76 | 0.995 |
| 18 | 1 | 21 | 53.242 | 9.913 | 37.120 | 291.11 | 0.450 |
| 18 | 1 | 23 | 162.525 | 4.080 | 269.334 | 244.95 | 0.976 |
| 18 | 1 | 25 | 53.038 | 10.581 | 47.022 | 222.54 | 0.749 |
| 18 | 1 | 27 | 117.498 | 5.007 | 155.632 | 272.93 | 0.964 |
| 18 | 1 | 29 | 33.589 | 10.385 | 25.401 | 213.20 | 0.768 |
| 18 | 1 | 31 | 45.253 | 11.526 | 36.539 | 73.06 | 0.827 |
| 18 | 1 | 33 | 44.295 | 11.469 | 19.335 | 34.58 | 0.865 |
| 18 | 1 | 35 | 47.925 | 11.722 | 49.526 | 53.67 | 0.695 |
| 18 | 2 | 0 | 323.758 | 6.998 | 481.474 | 0.00 | 1.000 |
| 18 | 2 | 2 | 161.532 | 2.660 | 198.719 | 31.19 | 0.975 |
| 18 | 2 | 4 | 199.044 | 2.188 | 313.365 | 220.91 | 0.977 |
| 18 | 2 | 6 | 122.760 | 3.315 | 98.658 | 60.06 | 0.963 |
| 18 | 2 | 8 | 317.355 | 3.412 | 496.289 | 135.05 | 0.991 |
| 18 | 2 | 10 | 282.838 | 2.651 | 417.798 | 69.19 | 0.988 |
| 18 | 2 | 12 | 52.274 | 5.857 | 22.665 | 61.61 | 0.758 |
| 18 | 2 | 14 | 233.675 | 2.575 | 331.831 | 40.89 | 0.982 |
| 18 | 2 | 16 | 89.991 | 5.522 | 130.393 | 297.85 | 0.799 |
| 18 | 2 | 18 | 265.005 | 3.045 | 409.553 | 243.79 | 0.989 |
| 18 | 2 | 20 | 322.116 | 4.040 | 422.786 | 239.90 | 0.994 |
| 18 | 2 | 22 | 112.199 | 5.540 | 118.337 | 303.48 | 0.966 |
| 18 | 2 | 24 | 49.697 | 11.636 | 7.144 | 290.00 | 0.853 |
| 18 | 2 | 26 | 212.547 | 4.025 | 311.951 | 242.15 | 0.988 |
| 18 | 2 | 28 | 45.741 | 11.784 | 23.694 | 214.30 | 0.385 |
| 18 | 2 | 30 | 152.876 | 5.629 | 236.962 | 128.79 | 0.977 |
| 18 | 2 | 32 | 31.274 | 9.655 | 11.745 | 203.02 | 0.512 |
| 18 | 2 | 34 | 36.668 | 11.155 | 14.941 | 275.87 | 0.388 |
| 18 | 3 | 1 | 293.102 | 3.362 | 465.379 | 27.93 | 0.989 |
| 18 | 3 | 3 | 283.537 | 3.394 | 431.769 | 117.07 | 0.990 |
| 18 | 3 | 5 | 67.425 | 3.890 | 41.736 | 75.31 | 0.653 |
| 18 | 3 | 7 | 159.661 | 2.530 | 259.600 | 124.56 | 0.957 |
| 18 | 3 | 9 | 139.680 | 2.837 | 202.405 | 240.68 | 0.963 |
| 18 | 3 | 11 | 324.439 | 4.793 | 444.561 | 282.24 | 0.992 |
| 18 | 3 | 13 | 288.705 | 2.949 | 456.750 | 23.32 | 0.987 |
| 18 | 3 | 15 | 250.508 | 2.635 | 363.111 | 288.50 | 0.986 |
| 18 | 3 | 17 | 301.544 | 3.277 | 519.145 | 52.06 | 0.991 |
| 18 | 3 | 19 | 49.240 | 10.003 | 30.891 | 178.82 | 0.619 |
| 18 | 3 | 21 | 353.158 | 3.520 | 521.940 | 289.89 | 0.996 |
| 18 | 3 | 23 | 130.407 | 4.907 | 246.092 | 103.20 | 0.947 |
| 18 | 3 | 25 | 73.510 | 8.182 | 96.486 | 265.88 | 0.869 |
| 18 | 3 | 27 | 75.194 | 9.523 | 74.691 | 349.93 | 0.922 |
| 18 | 3 | 29 | 98.403 | 7.171 | 143.689 | 218.83 | 0.940 |
| 18 | 3 | 31 | 34.420 | 10.784 | 3.546 | 333.19 | 0.768 |
| 18 | 3 | 33 | 101.470 | 7.910 | 164.867 | 254.80 | 0.958 |
| 18 | 3 | 35 | 114.563 | 6.946 | 173.795 | 265.91 | 0.972 |
| 18 | 4 | 0 | 181.748 | 5.494 | 270.252 | 180.00 | 1.000 |
| 18 | 4 | 2 | 324.832 | 3.677 | 457.827 | 196.09 | 0.992 |
| 18 | 4 | 4 | 255.822 | 4.695 | 445.627 | 221.26 | 0.983 |
| 18 | 4 | 6 | 154.900 | 2.497 | 213.803 | 245.75 | 0.971 |
| 18 | 4 | 8 | 327.517 | 3.693 | 426.707 | 271.70 | 0.993 |
| 18 | 4 | 10 | 231.155 | 2.885 | 257.037 | 225.94 | 0.986 |
| 18 | 4 | 12 | 53.989 | 5.925 | 32.813 | 212.98 | 0.612 |
| 18 | 4 | 14 | 179.359 | 2.700 | 238.437 | 233.04 | 0.972 |
| 18 | 4 | 16 | 115.782 | 3.798 | 97.911 | 33.84 | 0.970 |
| 18 | 4 | 18 | 164.726 | 3.371 | 197.381 | 158.14 | 0.979 |
| 18 | 4 | 20 | 171.889 | 3.297 | 220.901 | 305.31 | 0.979 |
| 18 | 4 | 22 | 138.043 | 4.804 | 189.233 | 239.49 | 0.974 |
| 18 | 4 | 24 | 163.697 | 4.034 | 302.803 | 165.76 | 0.969 |
| 18 | 4 | 26 | 102.804 | 5.820 | 97.745 | 120.75 | 0.962 |
| 18 | 4 | 28 | 70.047 | 10.509 | 60.538 | 167.71 | 0.917 |
| 18 | 4 | 30 | 61.201 | 12.299 | 63.364 | 6.28 | 0.841 |
| 18 | 4 | 32 | 101.545 | 8.324 | 187.847 | 134.80 | 0.932 |
| 18 | 4 | 34 | 32.849 | 10.463 | 5.806 | 317.69 | 0.704 |
| 18 | 5 | 1 | 432.671 | 4.714 | 624.136 | 193.46 | 0.996 |
| 18 | 5 | 3 | 182.179 | 3.616 | 277.429 | 256.69 | 0.974 |
| 18 | 5 | 5 | 204.735 | 3.259 | 278.896 | 185.30 | 0.984 |
| 18 | 5 | 7 | 99.145 | 3.213 | 112.824 | 316.32 | 0.938 |
| 18 | 5 | 9 | 205.803 | 3.130 | 339.741 | 348.32 | 0.970 |
| 18 | 5 | 11 | 84.686 | 3.956 | 109.196 | 138.80 | 0.766 |

| | | | | | | | |
|---|---|---|---|---|---|---|---|
| 18 | 5 | 13 | 137.761 | 2.897 | 179.879 | 273.44 | 0.954 |
| 18 | 5 | 15 | 102.974 | 4.693 | 134.789 | 66.28 | 0.937 |
| 18 | 5 | 17 | 184.353 | 3.357 | 285.952 | 241.21 | 0.978 |
| 18 | 5 | 19 | 67.720 | 8.966 | 86.528 | 284.50 | 0.790 |
| 18 | 5 | 21 | 158.347 | 4.280 | 234.723 | 204.08 | 0.978 |
| 18 | 5 | 23 | 136.981 | 4.609 | 270.843 | 103.11 | 0.947 |
| 18 | 5 | 25 | 146.037 | 4.706 | 198.266 | 256.88 | 0.977 |
| 18 | 5 | 27 | 112.004 | 5.664 | 139.277 | 198.86 | 0.965 |
| 18 | 5 | 29 | 45.183 | 11.411 | 22.601 | 158.82 | 0.519 |
| 18 | 5 | 31 | 61.622 | 11.294 | 66.469 | 58.93 | 0.912 |
| 18 | 5 | 33 | 38.608 | 11.656 | 11.506 | 278.38 | 0.300 |
| 18 | 5 | 35 | 29.138 | 9.597 | 5.475 | 110.69 | 0.418 |
| 18 | 6 | 0 | 16.622 | 11.399 | 16.885 | 0.00 | 0.745 |
| 18 | 6 | 2 | 153.941 | 3.273 | 305.508 | 319.57 | 0.863 |
| 18 | 6 | 4 | 302.815 | 3.732 | 363.738 | 314.70 | 0.992 |
| 18 | 6 | 6 | 260.457 | 2.824 | 407.647 | 57.45 | 0.986 |
| 18 | 6 | 8 | 245.512 | 4.112 | 282.671 | 112.33 | 0.987 |
| 18 | 6 | 10 | 275.522 | 3.214 | 362.714 | 217.96 | 0.989 |
| 18 | 6 | 12 | 96.624 | 4.515 | 31.243 | 34.00 | 0.944 |
| 18 | 6 | 14 | 166.845 | 3.084 | 239.436 | 207.63 | 0.969 |
| 18 | 6 | 16 | 92.820 | 5.422 | 120.733 | 289.48 | 0.908 |
| 18 | 6 | 18 | 86.680 | 7.410 | 126.753 | 207.35 | 0.875 |
| 18 | 6 | 20 | 54.986 | 10.323 | 48.865 | 139.14 | 0.807 |
| 18 | 6 | 22 | 248.495 | 3.325 | 388.192 | 344.73 | 0.991 |
| 18 | 6 | 24 | 51.912 | 11.052 | 34.361 | 99.06 | 0.723 |
| 18 | 6 | 26 | 45.031 | 10.665 | 13.396 | 265.51 | 0.793 |
| 18 | 6 | 28 | 99.672 | 7.127 | 134.768 | 341.61 | 0.949 |
| 18 | 6 | 30 | 75.079 | 11.023 | 99.742 | 217.11 | 0.936 |
| 18 | 6 | 32 | 39.676 | 11.036 | 22.652 | 44.00 | 0.446 |
| 18 | 6 | 34 | 54.875 | 11.633 | 48.902 | 298.05 | 0.885 |
| 18 | 7 | 1 | 396.726 | 5.985 | 580.741 | 12.12 | 0.995 |
| 18 | 7 | 3 | 292.497 | 4.390 | 464.369 | 59.79 | 0.989 |
| 18 | 7 | 5 | 310.471 | 3.541 | 478.952 | 63.83 | 0.990 |
| 18 | 7 | 7 | 197.856 | 2.797 | 263.310 | 113.04 | 0.978 |
| 18 | 7 | 9 | 331.311 | 3.795 | 537.509 | 152.47 | 0.990 |
| 18 | 7 | 11 | 205.622 | 2.504 | 262.674 | 281.06 | 0.982 |
| 18 | 7 | 13 | 316.139 | 4.014 | 442.993 | 59.48 | 0.991 |
| 18 | 7 | 15 | 252.216 | 2.952 | 375.994 | 172.29 | 0.989 |
| 18 | 7 | 17 | 174.449 | 3.884 | 270.583 | 268.32 | 0.975 |
| 18 | 7 | 19 | 167.962 | 3.903 | 230.410 | 143.20 | 0.983 |
| 18 | 7 | 21 | 124.697 | 4.835 | 126.558 | 40.77 | 0.975 |
| 18 | 7 | 23 | 33.139 | 10.116 | 23.593 | 23.50 | 0.616 |
| 18 | 7 | 25 | 144.765 | 5.182 | 202.072 | 74.72 | 0.976 |
| 18 | 7 | 27 | 168.784 | 4.311 | 375.911 | 167.80 | 0.922 |
| 18 | 7 | 29 | 67.147 | 10.624 | 91.038 | 171.86 | 0.822 |
| 18 | 7 | 31 | 127.165 | 5.517 | 210.131 | 224.87 | 0.976 |
| 18 | 7 | 33 | 34.151 | 10.912 | 11.636 | 215.96 | 0.688 |
| 18 | 8 | 0 | 115.013 | 7.856 | 170.860 | 180.00 | 1.000 |
| 18 | 8 | 2 | 328.485 | 4.084 | 488.264 | 65.50 | 0.991 |
| 18 | 8 | 4 | 474.024 | 5.034 | 687.701 | 99.80 | 0.996 |
| 18 | 8 | 6 | 348.125 | 3.592 | 502.467 | 225.79 | 0.992 |
| 18 | 8 | 8 | 323.515 | 3.776 | 586.872 | 251.62 | 0.988 |
| 18 | 8 | 10 | 336.349 | 3.763 | 481.503 | 306.85 | 0.992 |
| 18 | 8 | 12 | 279.602 | 3.270 | 405.038 | 274.32 | 0.987 |
| 18 | 8 | 14 | 279.103 | 3.670 | 487.687 | 337.46 | 0.988 |
| 18 | 8 | 16 | 182.578 | 4.010 | 259.874 | 25.73 | 0.980 |
| 18 | 8 | 18 | 212.203 | 4.230 | 317.677 | 329.11 | 0.984 |
| 18 | 8 | 20 | 193.628 | 3.781 | 331.402 | 156.91 | 0.982 |
| 18 | 8 | 22 | 54.074 | 10.725 | 48.722 | 94.86 | 0.612 |
| 18 | 8 | 24 | 90.117 | 7.485 | 83.551 | 104.87 | 0.948 |
| 18 | 8 | 26 | 109.134 | 6.315 | 154.518 | 107.04 | 0.960 |
| 18 | 8 | 28 | 54.618 | 11.355 | 47.907 | 85.67 | 0.499 |
| 18 | 8 | 30 | 66.026 | 9.912 | 90.666 | 31.70 | 0.908 |
| 18 | 8 | 32 | 125.677 | 6.272 | 163.571 | 309.58 | 0.983 |
| 18 | 8 | 34 | 27.433 | 9.102 | 4.484 | 284.85 | 0.407 |
| 18 | 9 | 1 | 245.252 | 4.799 | 347.775 | 80.39 | 0.985 |
| 18 | 9 | 3 | 257.095 | 3.986 | 431.205 | 195.10 | 0.983 |
| 18 | 9 | 5 | 284.657 | 3.391 | 422.221 | 123.28 | 0.988 |
| 18 | 9 | 7 | 140.785 | 3.904 | 199.239 | 246.37 | 0.951 |
| 18 | 9 | 9 | 34.517 | 9.105 | 22.890 | 149.25 | 0.220 |
| 18 | 9 | 11 | 360.270 | 3.452 | 630.630 | 328.68 | 0.991 |
| 18 | 9 | 13 | 225.634 | 3.382 | 294.227 | 220.32 | 0.988 |
| 18 | 9 | 15 | 344.840 | 3.973 | 537.458 | 68.49 | 0.994 |
| 18 | 9 | 17 | 97.116 | 6.638 | 128.974 | 257.55 | 0.934 |
| 18 | 9 | 19 | 73.955 | 8.301 | 48.332 | 342.82 | 0.935 |
| 18 | 9 | 21 | 90.486 | 7.515 | 64.129 | 151.70 | 0.956 |
| 18 | 9 | 23 | 153.454 | 4.358 | 203.508 | 279.37 | 0.979 |

| | | | | | | | |
|---|---|---|---|---|---|---|---|
| 18 | 9 | 25 | 141.456 | 4.596 | 228.211 | 201.94 | 0.969 |
| 18 | 9 | 27 | 157.954 | 4.344 | 359.125 | 254.21 | 0.912 |
| 18 | 9 | 29 | 46.617 | 11.796 | 48.433 | 53.93 | 0.757 |
| 18 | 9 | 31 | 79.141 | 9.816 | 82.998 | 47.30 | 0.955 |
| 18 | 9 | 33 | 123.452 | 5.476 | 251.293 | 46.20 | 0.950 |
| 18 | 10 | 0 | 95.781 | 7.684 | 77.806 | 180.00 | 0.547 |
| 18 | 10 | 2 | 139.926 | 4.289 | 205.288 | 35.22 | 0.949 |
| 18 | 10 | 4 | 51.225 | 10.470 | 3.481 | 114.13 | 0.624 |
| 18 | 10 | 6 | 386.494 | 3.900 | 522.538 | 182.92 | 0.994 |
| 18 | 10 | 8 | 182.850 | 3.226 | 234.986 | 91.04 | 0.976 |
| 18 | 10 | 10 | 76.832 | 6.486 | 88.994 | 87.25 | 0.890 |
| 18 | 10 | 12 | 99.610 | 5.090 | 133.221 | 316.98 | 0.923 |
| 18 | 10 | 14 | 307.521 | 3.522 | 441.804 | 109.17 | 0.993 |
| 18 | 10 | 16 | 61.466 | 10.129 | 40.957 | 61.48 | 0.832 |
| 18 | 10 | 18 | 144.147 | 4.049 | 257.262 | 160.40 | 0.967 |
| 18 | 10 | 20 | 43.752 | 11.447 | 6.701 | 21.53 | 0.741 |
| 18 | 10 | 22 | 45.554 | 12.075 | 15.043 | 150.30 | 0.252 |
| 18 | 10 | 24 | 64.558 | 9.044 | 73.202 | 294.37 | 0.855 |
| 18 | 10 | 26 | 121.014 | 5.976 | 164.813 | 316.98 | 0.970 |
| 18 | 10 | 28 | 39.385 | 11.068 | 17.632 | 245.12 | 0.827 |
| 18 | 10 | 30 | 87.842 | 7.403 | 134.097 | 31.51 | 0.949 |
| 18 | 10 | 32 | 105.676 | 6.286 | 195.679 | 198.94 | 0.951 |
| 18 | 11 | 1 | 138.768 | 2.972 | 173.559 | 36.23 | 0.964 |
| 18 | 11 | 3 | 252.169 | 3.618 | 359.288 | 286.05 | 0.985 |
| 18 | 11 | 5 | 165.876 | 3.664 | 227.317 | 226.16 | 0.966 |
| 18 | 11 | 7 | 222.373 | 3.126 | 370.398 | 110.70 | 0.975 |
| 18 | 11 | 9 | 37.417 | 10.337 | 2.790 | 223.21 | 0.379 |
| 18 | 11 | 11 | 111.905 | 4.966 | 157.842 | 239.27 | 0.943 |
| 18 | 11 | 13 | 59.606 | 9.159 | 20.507 | 250.48 | 0.867 |
| 18 | 11 | 15 | 151.623 | 3.899 | 254.638 | 249.62 | 0.962 |
| 18 | 11 | 17 | 236.740 | 3.824 | 388.651 | 6.91 | 0.990 |
| 18 | 11 | 19 | 150.332 | 4.763 | 182.645 | 97.43 | 0.981 |
| 18 | 11 | 21 | 63.489 | 9.463 | 68.190 | 44.11 | 0.850 |
| 18 | 11 | 23 | 72.293 | 10.001 | 89.787 | 29.25 | 0.884 |
| 18 | 11 | 25 | 133.777 | 4.810 | 215.785 | 356.41 | 0.970 |
| 18 | 11 | 27 | 59.880 | 10.344 | 57.779 | 9.94 | 0.503 |
| 18 | 11 | 29 | 61.731 | 10.796 | 82.376 | 355.68 | 0.871 |
| 18 | 11 | 31 | 106.501 | 7.194 | 187.285 | 294.95 | 0.956 |
| 18 | 12 | 0 | 86.867 | 10.852 | 29.945 | 0.00 | 0.232 |
| 18 | 12 | 2 | 346.460 | 3.463 | 487.997 | 332.83 | 0.993 |
| 18 | 12 | 4 | 181.384 | 2.642 | 317.716 | 202.55 | 0.939 |
| 18 | 12 | 6 | 43.573 | 9.258 | 5.082 | 6.51 | 0.634 |
| 18 | 12 | 8 | 206.568 | 3.553 | 297.041 | 46.59 | 0.986 |
| 18 | 12 | 10 | 170.159 | 4.055 | 240.015 | 89.19 | 0.978 |
| 18 | 12 | 12 | 57.070 | 8.974 | 42.960 | 116.46 | 0.492 |
| 18 | 12 | 14 | 85.394 | 6.854 | 108.888 | 348.98 | 0.935 |
| 18 | 12 | 16 | 61.731 | 8.966 | 75.949 | 39.92 | 0.720 |
| 18 | 12 | 18 | 151.060 | 4.192 | 267.052 | 153.38 | 0.970 |
| 18 | 12 | 20 | 101.259 | 5.665 | 107.919 | 300.09 | 0.960 |
| 18 | 12 | 22 | 65.212 | 10.575 | 45.591 | 89.00 | 0.898 |
| 18 | 12 | 24 | 54.250 | 11.705 | 47.934 | 176.50 | 0.819 |
| 18 | 12 | 26 | 99.086 | 7.006 | 179.256 | 116.86 | 0.912 |
| 18 | 12 | 28 | 38.047 | 11.104 | 22.541 | 313.37 | 0.574 |
| 18 | 12 | 30 | 30.927 | 9.963 | 5.795 | 57.33 | 0.203 |
| 18 | 12 | 32 | 27.441 | 9.406 | 1.960 | 267.59 | 0.102 |
| 18 | 13 | 1 | 312.894 | 3.364 | 391.915 | 346.90 | 0.994 |
| 18 | 13 | 3 | 124.495 | 3.737 | 254.295 | 25.79 | 0.816 |
| 18 | 13 | 5 | 94.543 | 4.588 | 107.564 | 90.94 | 0.926 |
| 18 | 13 | 7 | 216.825 | 3.509 | 335.003 | 281.48 | 0.985 |
| 18 | 13 | 9 | 264.427 | 3.708 | 388.648 | 323.25 | 0.991 |
| 18 | 13 | 11 | 216.214 | 4.013 | 318.211 | 34.62 | 0.986 |
| 18 | 13 | 13 | 86.497 | 6.553 | 151.429 | 187.11 | 0.804 |
| 18 | 13 | 15 | 173.621 | 4.144 | 339.380 | 192.55 | 0.974 |
| 18 | 13 | 17 | 49.921 | 9.739 | 40.025 | 278.47 | 0.575 |
| 18 | 13 | 19 | 163.935 | 4.111 | 267.019 | 324.93 | 0.979 |
| 18 | 13 | 21 | 219.278 | 3.606 | 330.607 | 112.27 | 0.989 |
| 18 | 13 | 23 | 95.698 | 8.255 | 43.425 | 155.67 | 0.971 |
| 18 | 13 | 25 | 81.639 | 9.646 | 134.748 | 170.05 | 0.860 |
| 18 | 13 | 27 | 48.260 | 10.402 | 53.224 | 66.38 | 0.687 |
| 18 | 13 | 29 | 32.761 | 10.107 | 14.979 | 31.14 | 0.519 |
| 18 | 13 | 31 | 29.769 | 9.627 | 4.868 | 350.76 | 0.122 |
| 18 | 14 | 0 | 312.711 | 4.484 | 464.507 | 180.00 | 1.000 |
| 18 | 14 | 2 | 147.233 | 4.625 | 273.691 | 266.19 | 0.957 |
| 18 | 14 | 4 | 93.986 | 4.871 | 71.539 | 268.05 | 0.952 |
| 18 | 14 | 6 | 107.334 | 5.211 | 179.505 | 287.87 | 0.914 |
| 18 | 14 | 8 | 177.398 | 3.779 | 233.744 | 305.32 | 0.980 |
| 18 | 14 | 10 | 118.569 | 4.981 | 193.442 | 4.01 | 0.934 |

| | | | | | | | |
|---|---|---|---|---|---|---|---|
| 18 | 14 | 12 | 108.700 | 6.131 | 114.781 | 182.36 | 0.966 |
| 18 | 14 | 14 | 166.916 | 3.567 | 260.035 | 249.29 | 0.981 |
| 18 | 14 | 16 | 59.449 | 10.187 | 28.427 | 265.97 | 0.899 |
| 18 | 14 | 18 | 123.480 | 4.520 | 171.480 | 157.89 | 0.967 |
| 18 | 14 | 20 | 160.106 | 3.878 | 237.232 | 179.01 | 0.979 |
| 18 | 14 | 22 | 36.211 | 11.103 | 16.347 | 147.61 | 0.538 |
| 18 | 14 | 24 | 99.990 | 6.728 | 88.116 | 127.97 | 0.966 |
| 18 | 14 | 26 | 62.665 | 10.354 | 86.509 | 325.50 | 0.894 |
| 18 | 14 | 28 | 61.174 | 11.044 | 75.170 | 244.34 | 0.907 |
| 18 | 14 | 30 | 34.490 | 10.492 | 1.399 | 339.12 | 0.033 |
| 18 | 15 | 1 | 193.513 | 3.430 | 362.944 | 244.15 | 0.971 |
| 18 | 15 | 3 | 207.335 | 3.690 | 296.904 | 239.52 | 0.985 |
| 18 | 15 | 5 | 135.200 | 3.857 | 222.494 | 218.42 | 0.957 |
| 18 | 15 | 7 | 44.965 | 10.058 | 18.551 | 297.48 | 0.297 |
| 18 | 15 | 9 | 121.299 | 4.789 | 151.804 | 229.09 | 0.970 |
| 18 | 15 | 11 | 41.690 | 11.164 | 12.720 | 292.89 | 0.512 |
| 18 | 15 | 13 | 139.054 | 4.001 | 243.272 | 172.39 | 0.966 |
| 18 | 15 | 15 | 99.130 | 6.280 | 105.756 | 6.40 | 0.958 |
| 18 | 15 | 17 | 52.834 | 11.146 | 50.718 | 226.18 | 0.619 |
| 18 | 15 | 19 | 170.865 | 3.514 | 258.434 | 257.93 | 0.982 |
| 18 | 15 | 21 | 75.897 | 8.219 | 118.536 | 239.75 | 0.734 |
| 18 | 15 | 23 | 87.369 | 8.451 | 94.295 | 22.89 | 0.949 |
| 18 | 15 | 25 | 50.045 | 11.556 | 28.375 | 217.70 | 0.897 |
| 18 | 15 | 27 | 74.584 | 8.468 | 98.572 | 251.80 | 0.945 |
| 18 | 15 | 29 | 40.590 | 11.802 | 27.389 | 303.59 | 0.712 |
| 18 | 16 | 0 | 198.853 | 6.930 | 294.813 | 0.00 | 1.000 |
| 18 | 16 | 2 | 127.811 | 4.610 | 269.629 | 285.62 | 0.926 |
| 18 | 16 | 4 | 73.375 | 7.183 | 50.641 | 330.29 | 0.360 |
| 18 | 16 | 6 | 168.558 | 3.409 | 267.137 | 177.99 | 0.981 |
| 18 | 16 | 8 | 79.790 | 7.853 | 109.774 | 9.17 | 0.912 |
| 18 | 16 | 10 | 105.359 | 6.238 | 130.502 | 60.37 | 0.960 |
| 18 | 16 | 12 | 58.347 | 10.613 | 45.932 | 263.30 | 0.859 |
| 18 | 16 | 14 | 117.495 | 6.434 | 165.886 | 58.73 | 0.964 |
| 18 | 16 | 16 | 65.867 | 10.436 | 53.949 | 52.47 | 0.896 |
| 18 | 16 | 18 | 90.728 | 7.183 | 106.705 | 9.19 | 0.941 |
| 18 | 16 | 20 | 185.555 | 3.962 | 293.236 | 308.18 | 0.986 |
| 18 | 16 | 22 | 118.283 | 5.307 | 195.150 | 216.21 | 0.959 |
| 18 | 16 | 24 | 35.168 | 10.815 | 10.735 | 355.67 | 0.756 |
| 18 | 16 | 26 | 32.718 | 10.770 | 13.280 | 139.14 | 0.666 |
| 18 | 16 | 28 | 67.561 | 11.582 | 100.800 | 33.09 | 0.770 |
| 18 | 17 | 1 | 127.081 | 4.367 | 172.654 | 223.84 | 0.971 |
| 18 | 17 | 3 | 203.363 | 4.190 | 344.206 | 12.37 | 0.986 |
| 18 | 17 | 5 | 76.616 | 8.575 | 127.805 | 309.20 | 0.832 |
| 18 | 17 | 7 | 51.859 | 10.905 | 53.569 | 76.29 | 0.736 |
| 18 | 17 | 9 | 62.849 | 10.015 | 76.690 | 341.73 | 0.830 |
| 18 | 17 | 11 | 117.340 | 5.848 | 178.663 | 197.38 | 0.961 |
| 18 | 17 | 13 | 49.588 | 12.178 | 32.982 | 14.25 | 0.718 |
| 18 | 17 | 15 | 85.952 | 9.233 | 100.953 | 83.07 | 0.935 |
| 18 | 17 | 17 | 45.107 | 11.229 | 32.054 | 69.66 | 0.478 |
| 18 | 17 | 19 | 114.029 | 6.914 | 166.544 | 195.64 | 0.963 |
| 18 | 17 | 21 | 52.749 | 12.099 | 18.673 | 12.45 | 0.878 |
| 18 | 17 | 23 | 44.038 | 11.395 | 42.941 | 180.50 | 0.634 |
| 18 | 17 | 25 | 45.126 | 12.604 | 40.473 | 296.09 | 0.663 |
| 18 | 17 | 27 | 53.991 | 11.186 | 56.859 | 76.32 | 0.880 |
| 18 | 18 | 0 | 150.467 | 8.052 | 222.525 | 180.00 | 1.000 |
| 18 | 18 | 2 | 39.271 | 10.916 | 14.127 | 6.12 | 0.293 |
| 18 | 18 | 4 | 95.261 | 6.248 | 85.393 | 101.52 | 0.960 |
| 18 | 18 | 6 | 110.562 | 5.755 | 197.893 | 263.55 | 0.936 |
| 18 | 18 | 8 | 191.392 | 4.265 | 275.623 | 28.74 | 0.987 |
| 18 | 18 | 10 | 127.896 | 6.089 | 179.084 | 342.01 | 0.971 |
| 18 | 18 | 12 | 218.064 | 3.614 | 385.616 | 292.79 | 0.986 |
| 18 | 18 | 14 | 160.457 | 4.450 | 281.423 | 231.31 | 0.976 |
| 18 | 18 | 16 | 112.480 | 5.740 | 152.845 | 91.30 | 0.966 |
| 18 | 18 | 18 | 204.035 | 4.175 | 280.166 | 252.47 | 0.990 |
| 18 | 18 | 20 | 63.889 | 11.868 | 80.850 | 139.45 | 0.912 |
| 18 | 18 | 22 | 65.557 | 11.802 | 84.951 | 31.73 | 0.906 |
| 18 | 18 | 24 | 29.065 | 9.269 | 6.779 | 213.37 | 0.543 |
| 18 | 18 | 26 | 31.547 | 10.094 | 6.422 | 79.62 | 0.419 |
| 18 | 19 | 1 | 156.572 | 4.764 | 306.848 | 157.52 | 0.966 |
| 18 | 19 | 3 | 74.748 | 7.951 | 105.960 | 105.59 | 0.886 |
| 18 | 19 | 5 | 123.569 | 4.868 | 108.273 | 171.96 | 0.978 |
| 18 | 19 | 7 | 81.422 | 6.872 | 43.405 | 174.38 | 0.953 |
| 18 | 19 | 9 | 111.470 | 6.083 | 134.051 | 86.75 | 0.967 |
| 18 | 19 | 11 | 66.774 | 10.129 | 71.958 | 129.75 | 0.870 |
| 18 | 19 | 13 | 50.788 | 10.924 | 27.769 | 260.57 | 0.866 |
| 18 | 19 | 15 | 87.355 | 6.910 | 157.674 | 26.68 | 0.879 |
| 18 | 19 | 17 | 76.267 | 9.081 | 55.564 | 354.84 | 0.946 |

| | | | | | | | |
|---|---|---|---|---|---|---|---|
| 18 | 19 | 19 | 36.799 | 11.158 | 18.097 | 233.46 | 0.744 |
| 18 | 19 | 21 | 75.013 | 11.025 | 121.728 | 216.39 | 0.906 |
| 18 | 19 | 23 | 31.120 | 10.202 | 12.963 | 114.66 | 0.408 |
| 18 | 19 | 25 | 76.683 | 8.993 | 133.071 | 260.30 | 0.892 |
| 18 | 20 | 0 | 58.977 | 18.572 | 73.789 | 0.00 | 0.868 |
| 18 | 20 | 2 | 142.705 | 4.698 | 208.930 | 61.89 | 0.976 |
| 18 | 20 | 4 | 45.106 | 10.024 | 6.667 | 239.96 | 0.827 |
| 18 | 20 | 6 | 191.930 | 3.691 | 294.277 | 171.62 | 0.986 |
| 18 | 20 | 8 | 214.939 | 4.361 | 292.726 | 173.30 | 0.990 |
| 18 | 20 | 10 | 51.720 | 11.653 | 49.835 | 126.85 | 0.657 |
| 18 | 20 | 12 | 48.079 | 11.249 | 20.774 | 144.61 | 0.838 |
| 18 | 20 | 14 | 64.529 | 10.491 | 81.872 | 182.21 | 0.834 |
| 18 | 20 | 16 | 36.270 | 10.710 | 5.615 | 161.78 | 0.682 |
| 18 | 20 | 18 | 64.561 | 9.011 | 97.757 | 285.66 | 0.694 |
| 18 | 20 | 20 | 38.528 | 11.226 | 27.833 | 290.25 | 0.640 |
| 18 | 20 | 22 | 44.290 | 11.512 | 35.894 | 71.25 | 0.568 |
| 18 | 20 | 24 | 35.095 | 11.122 | 14.095 | 247.44 | 0.425 |
| 18 | 21 | 1 | 115.659 | 5.736 | 182.488 | 137.66 | 0.959 |
| 18 | 21 | 3 | 93.373 | 7.389 | 85.569 | 39.73 | 0.958 |
| 18 | 21 | 5 | 102.436 | 5.904 | 198.530 | 340.35 | 0.885 |
| 18 | 21 | 7 | 42.697 | 11.217 | 27.967 | 263.48 | 0.692 |
| 18 | 21 | 9 | 69.524 | 11.186 | 74.751 | 46.43 | 0.908 |
| 18 | 21 | 11 | 43.298 | 12.516 | 23.972 | 182.63 | 0.562 |
| 18 | 21 | 13 | 161.380 | 5.509 | 209.186 | 224.99 | 0.985 |
| 18 | 21 | 15 | 62.808 | 11.804 | 67.667 | 354.66 | 0.925 |
| 18 | 21 | 17 | 37.124 | 11.069 | 19.163 | 57.01 | 0.355 |
| 18 | 21 | 19 | 41.021 | 11.382 | 34.907 | 302.28 | 0.676 |
| 18 | 21 | 21 | 87.143 | 8.340 | 132.041 | 120.00 | 0.951 |
| 18 | 21 | 23 | 25.444 | 8.575 | 10.533 | 322.02 | 0.615 |
| 18 | 22 | 0 | 28.455 | 12.857 | 20.105 | 180.00 | 0.489 |
| 18 | 22 | 2 | 120.679 | 5.966 | 203.169 | 195.72 | 0.963 |
| 18 | 22 | 4 | 55.480 | 9.583 | 48.035 | 27.18 | 0.879 |
| 18 | 22 | 6 | 93.683 | 7.171 | 145.266 | 81.95 | 0.941 |
| 18 | 22 | 8 | 32.329 | 9.401 | 3.520 | 58.95 | 0.513 |
| 18 | 22 | 10 | 82.936 | 9.629 | 137.616 | 278.12 | 0.743 |
| 18 | 22 | 12 | 41.401 | 11.929 | 17.122 | 235.59 | 0.866 |
| 18 | 22 | 14 | 48.553 | 11.782 | 50.253 | 73.98 | 0.832 |
| 18 | 22 | 16 | 36.914 | 11.371 | 16.675 | 138.32 | 0.420 |
| 18 | 22 | 18 | 73.931 | 9.896 | 89.859 | 78.53 | 0.948 |
| 18 | 22 | 20 | 31.104 | 10.151 | 26.802 | 266.79 | 0.852 |
| 18 | 23 | 1 | 33.013 | 10.418 | 1.624 | 350.89 | 0.447 |
| 18 | 23 | 3 | 45.352 | 11.880 | 37.059 | 327.13 | 0.544 |
| 18 | 23 | 5 | 101.333 | 6.868 | 160.262 | 269.20 | 0.949 |
| 18 | 23 | 7 | 88.965 | 7.902 | 172.146 | 320.95 | 0.795 |
| 18 | 23 | 9 | 34.769 | 10.457 | 19.694 | 40.21 | 0.721 |
| 18 | 23 | 11 | 47.064 | 13.056 | 20.997 | 357.26 | 0.893 |
| 18 | 23 | 13 | 34.086 | 11.128 | 3.615 | 65.61 | 0.777 |
| 18 | 23 | 15 | 50.301 | 12.160 | 54.481 | 63.64 | 0.827 |
| 18 | 23 | 17 | 47.085 | 10.685 | 54.429 | 180.50 | 0.682 |
| 18 | 23 | 19 | 43.841 | 11.851 | 4.762 | 173.51 | 0.070 |
| 18 | 24 | 0 | 53.045 | 16.088 | 70.662 | 180.00 | 0.949 |
| 18 | 24 | 2 | 57.797 | 12.020 | 77.242 | 87.11 | 0.871 |
| 18 | 24 | 4 | 87.181 | 8.168 | 171.178 | 194.40 | 0.924 |
| 18 | 24 | 6 | 73.649 | 9.928 | 104.936 | 241.01 | 0.935 |
| 18 | 24 | 8 | 76.138 | 10.312 | 114.819 | 278.30 | 0.937 |
| 18 | 24 | 10 | 32.693 | 9.998 | 14.750 | 352.19 | 0.617 |
| 18 | 24 | 12 | 63.295 | 11.359 | 67.397 | 219.27 | 0.931 |
| 18 | 24 | 14 | 43.168 | 11.544 | 29.989 | 15.12 | 0.850 |
| 18 | 24 | 16 | 32.823 | 10.511 | 6.551 | 348.79 | 0.707 |
| 18 | 25 | 1 | 39.118 | 11.306 | 28.306 | 295.67 | 0.598 |
| 18 | 25 | 3 | 48.127 | 11.223 | 49.890 | 44.99 | 0.841 |
| 18 | 25 | 5 | 71.500 | 9.002 | 90.535 | 39.67 | 0.943 |
| 18 | 25 | 7 | 41.853 | 10.219 | 36.496 | 59.38 | 0.677 |
| 18 | 25 | 9 | 56.062 | 9.764 | 78.945 | 189.65 | 0.839 |
| 18 | 25 | 11 | 51.123 | 9.888 | 66.486 | 283.63 | 0.836 |
| 18 | 25 | 13 | 35.215 | 11.031 | 14.802 | 85.20 | 0.747 |
| 18 | 26 | 0 | 26.811 | 12.431 | 18.946 | 180.00 | 0.504 |
| 18 | 26 | 2 | 34.130 | 10.784 | 18.893 | 195.91 | 0.688 |
| 18 | 26 | 4 | 40.005 | 11.774 | 34.210 | 40.42 | 0.661 |
| 18 | 26 | 6 | 27.746 | 8.883 | 2.564 | 30.72 | 0.702 |
| 18 | 26 | 8 | 40.087 | 11.001 | 33.897 | 349.27 | 0.570 |
| 18 | 26 | 10 | 43.603 | 11.161 | 22.142 | 341.47 | 0.331 |
| 18 | 27 | 1 | 45.081 | 11.378 | 45.066 | 228.55 | 0.596 |
| 18 | 27 | 3 | 34.016 | 11.417 | 9.051 | 227.95 | 0.210 |
| 18 | 27 | 5 | 69.008 | 10.231 | 109.049 | 325.31 | 0.723 |
| 19 | 0 | 3 | 347.211 | 5.292 | 520.045 | 0.00 | 1.000 |
| 19 | 0 | 5 | 334.893 | 5.297 | 501.041 | 0.00 | 1.000 |

| | | | | | | | |
|---|---|---|---|---|---|---|---|
| 19 | 0 | 7 | 262.614 | 6.224 | 392.189 | 0.00 | 1.000 |
| 19 | 0 | 9 | 30.482 | 11.145 | 26.087 | 0.00 | 0.575 |
| 19 | 0 | 11 | 45.576 | 11.462 | 15.005 | 180.00 | 0.222 |
| 19 | 0 | 13 | 200.075 | 3.822 | 296.572 | 0.00 | 1.000 |
| 19 | 0 | 15 | 130.266 | 5.395 | 192.334 | 180.00 | 1.000 |
| 19 | 0 | 17 | 292.798 | 4.617 | 430.533 | 0.00 | 1.000 |
| 19 | 0 | 19 | 140.317 | 5.927 | 205.041 | 0.00 | 1.000 |
| 19 | 0 | 21 | 254.095 | 4.856 | 369.735 | 0.00 | 1.000 |
| 19 | 0 | 23 | 25.841 | 12.637 | 7.802 | 180.00 | 0.211 |
| 19 | 0 | 25 | 115.472 | 8.804 | 165.031 | 180.00 | 1.000 |
| 19 | 0 | 27 | 92.476 | 10.079 | 125.559 | 180.00 | 0.962 |
| 19 | 0 | 29 | 67.260 | 16.299 | 90.346 | 0.00 | 0.991 |
| 19 | 0 | 31 | 73.330 | 14.940 | 65.230 | 0.00 | 0.668 |
| 19 | 0 | 33 | 27.607 | 12.951 | 2.677 | 0.00 | 0.074 |
| 19 | 1 | 0 | 37.244 | 9.639 | 2.785 | 180.00 | 0.050 |
| 19 | 1 | 2 | 294.168 | 4.571 | 406.618 | 177.33 | 0.990 |
| 19 | 1 | 4 | 316.466 | 3.538 | 437.135 | 105.12 | 0.992 |
| 19 | 1 | 6 | 266.084 | 2.692 | 343.380 | 71.50 | 0.989 |
| 19 | 1 | 8 | 196.981 | 3.187 | 298.510 | 60.35 | 0.978 |
| 19 | 1 | 10 | 247.393 | 3.180 | 430.829 | 61.02 | 0.980 |
| 19 | 1 | 12 | 315.199 | 3.049 | 487.349 | 354.09 | 0.990 |
| 19 | 1 | 14 | 77.036 | 6.149 | 110.103 | 65.69 | 0.758 |
| 19 | 1 | 16 | 169.367 | 3.548 | 238.234 | 122.00 | 0.977 |
| 19 | 1 | 18 | 108.186 | 5.818 | 185.279 | 55.76 | 0.907 |
| 19 | 1 | 20 | 99.391 | 6.342 | 156.706 | 159.50 | 0.933 |
| 19 | 1 | 22 | 55.883 | 11.102 | 51.030 | 49.05 | 0.654 |
| 19 | 1 | 24 | 179.590 | 3.973 | 231.302 | 267.83 | 0.986 |
| 19 | 1 | 26 | 79.047 | 8.014 | 93.690 | 212.67 | 0.927 |
| 19 | 1 | 28 | 98.482 | 6.949 | 121.293 | 245.16 | 0.550 |
| 19 | 1 | 30 | 54.832 | 12.073 | 69.277 | 238.03 | 0.794 |
| 19 | 1 | 32 | 34.503 | 11.215 | 17.696 | 321.87 | 0.443 |
| 19 | 1 | 34 | 32.237 | 10.814 | 13.111 | 281.81 | 0.578 |
| 19 | 2 | 1 | 427.955 | 4.886 | 639.812 | 54.91 | 0.995 |
| 19 | 2 | 3 | 70.069 | 4.572 | 64.649 | 32.20 | 0.809 |
| 19 | 2 | 5 | 423.608 | 4.235 | 664.574 | 148.23 | 0.995 |
| 19 | 2 | 7 | 121.854 | 4.277 | 219.538 | 291.29 | 0.859 |
| 19 | 2 | 9 | 399.820 | 3.985 | 634.031 | 223.30 | 0.994 |
| 19 | 2 | 11 | 47.011 | 5.982 | 20.384 | 256.61 | 0.497 |
| 19 | 2 | 13 | 191.291 | 2.733 | 326.094 | 192.19 | 0.978 |
| 19 | 2 | 15 | 212.154 | 3.194 | 283.898 | 76.80 | 0.986 |
| 19 | 2 | 17 | 100.824 | 5.222 | 163.119 | 337.10 | 0.904 |
| 19 | 2 | 19 | 158.145 | 4.024 | 248.014 | 152.12 | 0.978 |
| 19 | 2 | 21 | 45.124 | 10.701 | 25.265 | 158.78 | 0.476 |
| 19 | 2 | 23 | 81.827 | 8.699 | 57.777 | 125.02 | 0.946 |
| 19 | 2 | 25 | 216.176 | 4.310 | 293.440 | 261.50 | 0.990 |
| 19 | 2 | 27 | 112.916 | 6.241 | 145.470 | 54.33 | 0.967 |
| 19 | 2 | 29 | 48.227 | 12.087 | 50.063 | 233.21 | 0.640 |
| 19 | 2 | 31 | 110.183 | 6.386 | 181.655 | 49.23 | 0.967 |
| 19 | 2 | 33 | 60.057 | 10.348 | 67.744 | 157.56 | 0.905 |
| 19 | 3 | 0 | 11.257 | 8.102 | 2.388 | 0.00 | 0.151 |
| 19 | 3 | 2 | 199.184 | 2.850 | 266.799 | 279.46 | 0.982 |
| 19 | 3 | 4 | 184.125 | 3.059 | 250.935 | 266.20 | 0.979 |
| 19 | 3 | 6 | 279.954 | 3.057 | 388.936 | 273.77 | 0.989 |
| 19 | 3 | 8 | 239.361 | 2.808 | 356.964 | 208.00 | 0.984 |
| 19 | 3 | 10 | 174.113 | 3.187 | 281.514 | 125.70 | 0.964 |
| 19 | 3 | 12 | 228.472 | 2.826 | 358.333 | 146.23 | 0.980 |
| 19 | 3 | 14 | 166.678 | 2.995 | 266.650 | 218.54 | 0.970 |
| 19 | 3 | 16 | 111.142 | 4.379 | 106.354 | 154.61 | 0.965 |
| 19 | 3 | 18 | 215.477 | 3.183 | 344.831 | 307.95 | 0.988 |
| 19 | 3 | 20 | 143.217 | 4.568 | 204.541 | 182.60 | 0.976 |
| 19 | 3 | 22 | 82.457 | 8.206 | 104.469 | 272.89 | 0.920 |
| 19 | 3 | 24 | 193.329 | 4.095 | 323.458 | 312.11 | 0.984 |
| 19 | 3 | 26 | 96.857 | 7.293 | 130.546 | 93.55 | 0.949 |
| 19 | 3 | 28 | 114.393 | 6.799 | 131.870 | 135.61 | 0.969 |
| 19 | 3 | 30 | 67.346 | 10.596 | 95.528 | 345.35 | 0.903 |
| 19 | 3 | 32 | 71.246 | 10.129 | 113.263 | 351.84 | 0.881 |
| 19 | 4 | 1 | 266.197 | 3.222 | 385.760 | 279.66 | 0.988 |
| 19 | 4 | 3 | 80.476 | 4.985 | 104.452 | 195.29 | 0.874 |
| 19 | 4 | 5 | 103.573 | 5.944 | 116.944 | 11.38 | 0.931 |
| 19 | 4 | 7 | 221.446 | 2.756 | 381.008 | 233.05 | 0.975 |
| 19 | 4 | 9 | 227.783 | 3.063 | 360.514 | 335.02 | 0.980 |
| 19 | 4 | 11 | 408.458 | 4.190 | 662.490 | 111.46 | 0.994 |
| 19 | 4 | 13 | 65.249 | 6.424 | 45.155 | 262.28 | 0.505 |
| 19 | 4 | 15 | 72.557 | 6.419 | 71.678 | 102.84 | 0.880 |
| 19 | 4 | 17 | 102.584 | 4.282 | 122.875 | 172.54 | 0.943 |
| 19 | 4 | 19 | 108.884 | 5.765 | 134.984 | 326.56 | 0.960 |
| 19 | 4 | 21 | 117.492 | 5.074 | 197.011 | 309.88 | 0.669 |

| | | | | | | | |
|---|---|---|---|---|---|---|---|
| 19 | 4 | 23 | 99.409 | 6.746 | 101.390 | 239.70 | 0.957 |
| 19 | 4 | 25 | 105.371 | 5.945 | 142.223 | 111.45 | 0.952 |
| 19 | 4 | 27 | 92.591 | 8.322 | 123.748 | 125.60 | 0.943 |
| 19 | 4 | 29 | 105.154 | 7.314 | 145.707 | 196.93 | 0.973 |
| 19 | 4 | 31 | 33.244 | 10.326 | 13.848 | 16.65 | 0.469 |
| 19 | 4 | 33 | 73.778 | 9.088 | 106.741 | 3.52 | 0.924 |
| 19 | 5 | 0 | 220.110 | 4.448 | 329.826 | 0.00 | 1.000 |
| 19 | 5 | 2 | 34.624 | 9.338 | 54.908 | 169.54 | 0.476 |
| 19 | 5 | 4 | 75.931 | 7.386 | 29.430 | 113.57 | 0.905 |
| 19 | 5 | 6 | 423.320 | 4.656 | 806.324 | 345.95 | 0.993 |
| 19 | 5 | 8 | 35.456 | 8.018 | 19.171 | 148.18 | 0.562 |
| 19 | 5 | 10 | 226.681 | 3.057 | 277.304 | 257.70 | 0.986 |
| 19 | 5 | 12 | 103.959 | 4.215 | 108.040 | 6.20 | 0.950 |
| 19 | 5 | 14 | 102.723 | 4.540 | 142.400 | 246.73 | 0.928 |
| 19 | 5 | 16 | 170.703 | 3.116 | 214.976 | 317.72 | 0.982 |
| 19 | 5 | 18 | 178.071 | 3.504 | 275.589 | 64.36 | 0.983 |
| 19 | 5 | 20 | 158.557 | 4.447 | 219.930 | 260.95 | 0.982 |
| 19 | 5 | 22 | 144.931 | 4.051 | 251.269 | 102.22 | 0.969 |
| 19 | 5 | 24 | 87.924 | 7.311 | 81.540 | 274.51 | 0.946 |
| 19 | 5 | 26 | 43.978 | 10.971 | 2.947 | 61.20 | 0.834 |
| 19 | 5 | 28 | 50.539 | 10.868 | 36.120 | 92.86 | 0.818 |
| 19 | 5 | 30 | 40.401 | 11.103 | 25.048 | 318.62 | 0.450 |
| 19 | 5 | 32 | 41.175 | 10.829 | 13.911 | 299.15 | 0.868 |
| 19 | 6 | 1 | 244.889 | 3.223 | 316.261 | 81.28 | 0.986 |
| 19 | 6 | 3 | 221.449 | 3.321 | 339.100 | 209.31 | 0.980 |
| 19 | 6 | 5 | 253.158 | 4.415 | 443.927 | 149.95 | 0.982 |
| 19 | 6 | 7 | 79.048 | 4.591 | 109.682 | 271.28 | 0.796 |
| 19 | 6 | 9 | 387.520 | 4.318 | 583.446 | 246.00 | 0.994 |
| 19 | 6 | 11 | 187.959 | 3.754 | 278.576 | 294.62 | 0.981 |
| 19 | 6 | 13 | 149.060 | 4.711 | 200.031 | 92.18 | 0.971 |
| 19 | 6 | 15 | 127.381 | 3.755 | 181.182 | 237.86 | 0.960 |
| 19 | 6 | 17 | 124.743 | 4.367 | 157.967 | 174.84 | 0.971 |
| 19 | 6 | 19 | 121.322 | 5.063 | 234.197 | 103.61 | 0.933 |
| 19 | 6 | 21 | 175.140 | 3.830 | 252.419 | 150.11 | 0.983 |
| 19 | 6 | 23 | 39.363 | 9.276 | 16.835 | 263.46 | 0.583 |
| 19 | 6 | 25 | 64.297 | 9.287 | 83.340 | 4.48 | 0.856 |
| 19 | 6 | 27 | 93.831 | 7.782 | 95.105 | 80.70 | 0.958 |
| 19 | 6 | 29 | 80.520 | 9.192 | 104.173 | 26.66 | 0.951 |
| 19 | 6 | 31 | 67.177 | 10.767 | 92.792 | 310.48 | 0.907 |
| 19 | 6 | 33 | 56.301 | 12.697 | 66.417 | 298.39 | 0.822 |
| 19 | 7 | 0 | 276.180 | 5.217 | 413.687 | 0.00 | 1.000 |
| 19 | 7 | 2 | 119.727 | 4.344 | 162.472 | 298.04 | 0.938 |
| 19 | 7 | 4 | 290.645 | 3.902 | 503.614 | 125.00 | 0.986 |
| 19 | 7 | 6 | 322.552 | 3.451 | 446.651 | 163.08 | 0.992 |
| 19 | 7 | 8 | 344.569 | 4.221 | 569.347 | 4.31 | 0.991 |
| 19 | 7 | 10 | 70.435 | 7.877 | 51.687 | 152.77 | 0.880 |
| 19 | 7 | 12 | 183.678 | 2.844 | 259.697 | 127.32 | 0.982 |
| 19 | 7 | 14 | 159.218 | 4.031 | 246.558 | 293.14 | 0.971 |
| 19 | 7 | 16 | 70.010 | 8.773 | 63.415 | 251.45 | 0.917 |
| 19 | 7 | 18 | 192.110 | 3.358 | 255.875 | 172.78 | 0.988 |
| 19 | 7 | 20 | 195.095 | 3.462 | 267.859 | 75.50 | 0.988 |
| 19 | 7 | 22 | 85.986 | 7.015 | 124.182 | 6.61 | 0.606 |
| 19 | 7 | 24 | 165.962 | 4.705 | 237.227 | 76.81 | 0.982 |
| 19 | 7 | 26 | 113.368 | 7.063 | 138.634 | 110.52 | 0.968 |
| 19 | 7 | 28 | 102.150 | 8.247 | 203.523 | 171.21 | 0.930 |
| 19 | 7 | 30 | 40.963 | 11.188 | 28.049 | 179.79 | 0.474 |
| 19 | 7 | 32 | 64.036 | 11.242 | 95.694 | 115.90 | 0.806 |
| 19 | 8 | 1 | 79.698 | 7.803 | 81.114 | 210.79 | 0.523 |
| 19 | 8 | 3 | 341.925 | 5.163 | 493.622 | 246.63 | 0.992 |
| 19 | 8 | 5 | 196.479 | 2.865 | 314.935 | 280.80 | 0.974 |
| 19 | 8 | 7 | 221.261 | 3.429 | 355.966 | 201.48 | 0.978 |
| 19 | 8 | 9 | 249.267 | 4.441 | 324.998 | 28.73 | 0.991 |
| 19 | 8 | 11 | 298.979 | 3.686 | 462.619 | 113.77 | 0.992 |
| 19 | 8 | 13 | 118.818 | 5.387 | 193.758 | 15.20 | 0.933 |
| 19 | 8 | 15 | 169.464 | 4.342 | 225.266 | 323.04 | 0.985 |
| 19 | 8 | 17 | 156.431 | 4.605 | 164.588 | 213.79 | 0.984 |
| 19 | 8 | 19 | 56.459 | 11.255 | 59.189 | 43.43 | 0.624 |
| 19 | 8 | 21 | 158.829 | 4.293 | 320.191 | 293.51 | 0.956 |
| 19 | 8 | 23 | 161.716 | 3.877 | 266.621 | 272.56 | 0.977 |
| 19 | 8 | 25 | 86.065 | 7.192 | 150.286 | 318.00 | 0.862 |
| 19 | 8 | 27 | 61.081 | 11.285 | 65.740 | 250.29 | 0.923 |
| 19 | 8 | 29 | 38.803 | 10.970 | 8.221 | 47.71 | 0.146 |
| 19 | 8 | 31 | 52.123 | 11.333 | 63.518 | 344.29 | 0.761 |
| 19 | 9 | 0 | 298.597 | 6.167 | 447.004 | 180.00 | 1.000 |
| 19 | 9 | 2 | 212.025 | 5.138 | 292.844 | 227.70 | 0.981 |
| 19 | 9 | 4 | 29.153 | 9.593 | 24.061 | 185.21 | 0.185 |
| 19 | 9 | 6 | 30.292 | 8.916 | 23.478 | 93.51 | 0.363 |

| | | | | | | | |
|---|---|---|---|---|---|---|---|
| 19 | 9  | 8  | 252.120 | 3.467  | 486.764 | 72.72  | 0.984 |
| 19 | 9  | 10 | 137.804 | 4.035  | 220.799 | 205.71 | 0.960 |
| 19 | 9  | 12 | 234.262 | 2.863  | 405.845 | 17.81  | 0.983 |
| 19 | 9  | 14 | 42.237  | 9.450  | 7.513   | 327.72 | 0.282 |
| 19 | 9  | 16 | 48.389  | 11.090 | 7.272   | 18.92  | 0.853 |
| 19 | 9  | 18 | 109.274 | 5.927  | 193.957 | 175.98 | 0.936 |
| 19 | 9  | 20 | 50.938  | 10.735 | 45.122  | 245.36 | 0.728 |
| 19 | 9  | 22 | 182.445 | 3.861  | 261.484 | 292.23 | 0.985 |
| 19 | 9  | 24 | 151.594 | 4.670  | 221.945 | 224.68 | 0.980 |
| 19 | 9  | 26 | 37.855  | 10.344 | 3.150   | 100.01 | 0.717 |
| 19 | 9  | 28 | 128.270 | 6.246  | 174.039 | 215.84 | 0.983 |
| 19 | 9  | 30 | 44.939  | 11.004 | 28.708  | 232.86 | 0.395 |
| 19 | 9  | 32 | 49.163  | 11.509 | 28.593  | 291.68 | 0.891 |
| 19 | 10 | 1  | 223.953 | 5.696  | 353.369 | 165.25 | 0.986 |
| 19 | 10 | 3  | 183.903 | 4.227  | 294.542 | 135.13 | 0.979 |
| 19 | 10 | 5  | 112.266 | 7.543  | 115.332 | 29.56  | 0.957 |
| 19 | 10 | 7  | 239.062 | 3.326  | 349.832 | 47.31  | 0.989 |
| 19 | 10 | 9  | 52.313  | 9.563  | 13.791  | 358.50 | 0.708 |
| 19 | 10 | 11 | 189.127 | 3.907  | 288.735 | 298.89 | 0.981 |
| 19 | 10 | 13 | 158.258 | 3.435  | 258.793 | 301.32 | 0.977 |
| 19 | 10 | 15 | 318.139 | 3.406  | 462.787 | 299.54 | 0.995 |
| 19 | 10 | 17 | 232.523 | 3.722  | 332.881 | 349.06 | 0.991 |
| 19 | 10 | 19 | 60.894  | 9.851  | 59.915  | 166.46 | 0.847 |
| 19 | 10 | 21 | 83.066  | 7.787  | 62.945  | 343.31 | 0.949 |
| 19 | 10 | 23 | 105.570 | 5.907  | 204.067 | 217.41 | 0.801 |
| 19 | 10 | 25 | 91.815  | 7.855  | 149.158 | 29.41  | 0.672 |
| 19 | 10 | 27 | 74.604  | 8.442  | 116.170 | 201.77 | 0.912 |
| 19 | 10 | 29 | 71.487  | 10.815 | 109.106 | 188.01 | 0.906 |
| 19 | 10 | 31 | 31.320  | 10.076 | 8.080   | 329.60 | 0.550 |
| 19 | 11 | 0  | 23.700  | 16.274 | 27.320  | 0.00   | 0.812 |
| 19 | 11 | 2  | 79.734  | 11.420 | 83.052  | 343.07 | 0.902 |
| 19 | 11 | 4  | 204.523 | 3.360  | 313.433 | 278.92 | 0.984 |
| 19 | 11 | 6  | 142.919 | 4.597  | 184.166 | 220.00 | 0.971 |
| 19 | 11 | 8  | 92.851  | 5.938  | 115.095 | 24.65  | 0.913 |
| 19 | 11 | 10 | 236.936 | 3.415  | 377.925 | 77.83  | 0.987 |
| 19 | 11 | 12 | 81.388  | 6.736  | 68.720  | 201.54 | 0.945 |
| 19 | 11 | 14 | 36.839  | 9.593  | 11.357  | 262.31 | 0.592 |
| 19 | 11 | 16 | 100.646 | 5.805  | 97.137  | 259.54 | 0.962 |
| 19 | 11 | 18 | 116.833 | 6.048  | 128.137 | 224.38 | 0.970 |
| 19 | 11 | 20 | 48.532  | 9.467  | 34.433  | 229.64 | 0.791 |
| 19 | 11 | 22 | 37.463  | 11.125 | 10.081  | 284.23 | 0.409 |
| 19 | 11 | 24 | 52.891  | 11.534 | 22.613  | 317.13 | 0.877 |
| 19 | 11 | 26 | 42.414  | 10.896 | 11.400  | 353.38 | 0.882 |
| 19 | 11 | 28 | 56.696  | 11.486 | 74.926  | 148.33 | 0.745 |
| 19 | 11 | 30 | 120.610 | 6.284  | 181.175 | 55.25  | 0.978 |
| 19 | 12 | 1  | 32.832  | 7.727  | 5.035   | 277.36 | 0.218 |
| 19 | 12 | 3  | 229.130 | 4.113  | 313.104 | 301.82 | 0.989 |
| 19 | 12 | 5  | 174.041 | 3.978  | 234.077 | 169.47 | 0.984 |
| 19 | 12 | 7  | 99.291  | 5.993  | 152.374 | 146.02 | 0.917 |
| 19 | 12 | 9  | 345.099 | 3.833  | 575.810 | 42.05  | 0.994 |
| 19 | 12 | 11 | 257.661 | 3.412  | 395.958 | 21.76  | 0.993 |
| 19 | 12 | 13 | 71.187  | 7.193  | 106.030 | 322.19 | 0.709 |
| 19 | 12 | 15 | 123.618 | 4.702  | 211.801 | 219.72 | 0.957 |
| 19 | 12 | 17 | 196.555 | 3.287  | 265.608 | 186.88 | 0.989 |
| 19 | 12 | 19 | 123.805 | 5.525  | 200.478 | 129.70 | 0.960 |
| 19 | 12 | 21 | 105.127 | 5.648  | 144.752 | 78.02  | 0.962 |
| 19 | 12 | 23 | 63.916  | 9.205  | 78.636  | 154.15 | 0.862 |
| 19 | 12 | 25 | 60.238  | 10.199 | 71.344  | 312.18 | 0.910 |
| 19 | 12 | 27 | 35.922  | 10.940 | 21.964  | 254.61 | 0.487 |
| 19 | 12 | 29 | 38.100  | 11.027 | 26.648  | 258.03 | 0.535 |
| 19 | 13 | 0  | 105.857 | 13.020 | 122.051 | 0.00   | 0.775 |
| 19 | 13 | 2  | 168.332 | 3.083  | 262.312 | 331.52 | 0.975 |
| 19 | 13 | 4  | 45.217  | 8.893  | 5.954   | 150.05 | 0.771 |
| 19 | 13 | 6  | 141.493 | 4.061  | 205.567 | 342.41 | 0.967 |
| 19 | 13 | 8  | 159.484 | 3.739  | 254.251 | 13.78  | 0.979 |
| 19 | 13 | 10 | 63.655  | 9.523  | 29.366  | 45.39  | 0.917 |
| 19 | 13 | 12 | 73.163  | 10.651 | 105.031 | 242.93 | 0.676 |
| 19 | 13 | 14 | 190.800 | 3.261  | 291.452 | 290.55 | 0.986 |
| 19 | 13 | 16 | 40.855  | 10.722 | 14.207  | 82.81  | 0.530 |
| 19 | 13 | 18 | 133.319 | 4.385  | 183.802 | 109.34 | 0.973 |
| 19 | 13 | 20 | 161.891 | 4.600  | 216.773 | 124.93 | 0.985 |
| 19 | 13 | 22 | 77.463  | 8.732  | 115.820 | 59.84  | 0.893 |
| 19 | 13 | 24 | 42.537  | 11.315 | 27.146  | 40.09  | 0.398 |
| 19 | 13 | 26 | 64.603  | 9.934  | 98.519  | 70.23  | 0.862 |
| 19 | 13 | 28 | 30.618  | 9.668  | 7.523   | 300.24 | 0.335 |
| 19 | 14 | 1  | 134.579 | 4.643  | 240.957 | 344.61 | 0.961 |
| 19 | 14 | 3  | 107.646 | 5.498  | 103.106 | 58.44  | 0.970 |

| | | | | | | | |
|---|---|---|---|---|---|---|---|
| 19 | 14 | 5 | 216.598 | 2.791 | 311.765 | 307.69 | 0.990 |
| 19 | 14 | 7 | 126.881 | 4.917 | 220.723 | 351.56 | 0.961 |
| 19 | 14 | 9 | 48.138 | 11.008 | 11.702 | 245.97 | 0.842 |
| 19 | 14 | 11 | 115.063 | 7.029 | 161.740 | 106.81 | 0.962 |
| 19 | 14 | 13 | 41.430 | 10.916 | 16.790 | 276.80 | 0.498 |
| 19 | 14 | 15 | 72.667 | 7.824 | 30.739 | 150.00 | 0.947 |
| 19 | 14 | 17 | 181.867 | 4.326 | 291.576 | 26.22 | 0.983 |
| 19 | 14 | 19 | 216.235 | 3.362 | 442.985 | 166.48 | 0.983 |
| 19 | 14 | 21 | 74.127 | 9.097 | 110.579 | 36.53 | 0.874 |
| 19 | 14 | 23 | 59.064 | 11.603 | 36.544 | 69.44 | 0.937 |
| 19 | 14 | 25 | 34.800 | 10.549 | 9.768 | 258.59 | 0.845 |
| 19 | 14 | 27 | 55.670 | 11.196 | 77.497 | 55.77 | 0.800 |
| 19 | 15 | 0 | 32.107 | 12.333 | 37.511 | 0.00 | 0.789 |
| 19 | 15 | 2 | 185.842 | 3.467 | 298.002 | 44.04 | 0.985 |
| 19 | 15 | 4 | 63.715 | 8.724 | 62.510 | 228.81 | 0.875 |
| 19 | 15 | 6 | 67.005 | 8.177 | 29.556 | 251.41 | 0.929 |
| 19 | 15 | 8 | 152.207 | 4.208 | 265.018 | 327.90 | 0.973 |
| 19 | 15 | 10 | 64.996 | 9.396 | 68.075 | 125.34 | 0.509 |
| 19 | 15 | 12 | 158.781 | 4.737 | 291.388 | 154.30 | 0.973 |
| 19 | 15 | 14 | 181.456 | 3.793 | 236.721 | 23.32 | 0.987 |
| 19 | 15 | 16 | 49.528 | 11.124 | 32.221 | 358.79 | 0.760 |
| 19 | 15 | 18 | 136.971 | 5.244 | 232.880 | 309.61 | 0.971 |
| 19 | 15 | 20 | 155.888 | 4.341 | 247.731 | 99.39 | 0.980 |
| 19 | 15 | 22 | 71.354 | 8.476 | 126.720 | 7.81 | 0.860 |
| 19 | 15 | 24 | 44.543 | 11.529 | 6.799 | 39.15 | 0.898 |
| 19 | 15 | 26 | 29.857 | 9.457 | 8.708 | 90.75 | 0.283 |
| 19 | 15 | 28 | 39.507 | 10.607 | 25.750 | 300.40 | 0.577 |
| 19 | 16 | 1 | 132.228 | 5.358 | 173.008 | 339.41 | 0.975 |
| 19 | 16 | 3 | 94.172 | 6.110 | 147.694 | 334.21 | 0.808 |
| 19 | 16 | 5 | 131.963 | 3.822 | 244.430 | 214.40 | 0.959 |
| 19 | 16 | 7 | 91.542 | 6.965 | 61.440 | 285.95 | 0.961 |
| 19 | 16 | 9 | 92.643 | 6.260 | 164.770 | 180.00 | 0.892 |
| 19 | 16 | 11 | 181.184 | 4.594 | 298.045 | 254.50 | 0.983 |
| 19 | 16 | 13 | 108.585 | 7.233 | 222.884 | 316.18 | 0.869 |
| 19 | 16 | 15 | 53.253 | 11.434 | 50.979 | 231.52 | 0.564 |
| 19 | 16 | 17 | 77.056 | 8.986 | 126.992 | 221.69 | 0.860 |
| 19 | 16 | 19 | 43.321 | 11.664 | 15.109 | 194.44 | 0.772 |
| 19 | 16 | 21 | 84.007 | 7.217 | 110.168 | 109.69 | 0.963 |
| 19 | 16 | 23 | 65.988 | 9.889 | 102.046 | 5.24 | 0.869 |
| 19 | 16 | 25 | 61.521 | 12.225 | 63.916 | 260.79 | 0.919 |
| 19 | 16 | 27 | 31.647 | 10.402 | 13.204 | 270.83 | 0.374 |
| 19 | 17 | 0 | 70.026 | 9.650 | 103.511 | 180.00 | 0.995 |
| 19 | 17 | 2 | 93.766 | 5.966 | 110.476 | 279.17 | 0.951 |
| 19 | 17 | 4 | 44.256 | 11.475 | 15.083 | 129.81 | 0.756 |
| 19 | 17 | 6 | 221.380 | 3.147 | 349.278 | 182.45 | 0.990 |
| 19 | 17 | 8 | 93.851 | 6.816 | 167.487 | 54.77 | 0.770 |
| 19 | 17 | 10 | 56.387 | 11.035 | 49.964 | 186.02 | 0.845 |
| 19 | 17 | 12 | 98.283 | 6.534 | 139.096 | 238.23 | 0.946 |
| 19 | 17 | 14 | 122.254 | 4.958 | 213.914 | 278.97 | 0.963 |
| 19 | 17 | 16 | 60.220 | 9.404 | 55.656 | 267.14 | 0.892 |
| 19 | 17 | 18 | 100.731 | 7.406 | 153.404 | 184.27 | 0.948 |
| 19 | 17 | 20 | 31.904 | 10.325 | 5.736 | 7.89 | 0.718 |
| 19 | 17 | 22 | 65.954 | 11.895 | 89.976 | 199.06 | 0.897 |
| 19 | 17 | 24 | 51.297 | 11.207 | 57.954 | 277.86 | 0.667 |
| 19 | 17 | 26 | 57.725 | 10.643 | 78.387 | 321.19 | 0.744 |
| 19 | 18 | 1 | 61.833 | 9.787 | 84.377 | 4.18 | 0.747 |
| 19 | 18 | 3 | 62.248 | 8.848 | 35.648 | 123.79 | 0.911 |
| 19 | 18 | 5 | 159.455 | 3.911 | 238.438 | 184.02 | 0.981 |
| 19 | 18 | 7 | 108.042 | 5.206 | 151.274 | 98.86 | 0.959 |
| 19 | 18 | 9 | 75.524 | 8.753 | 108.144 | 279.48 | 0.893 |
| 19 | 18 | 11 | 181.442 | 4.399 | 255.400 | 168.20 | 0.988 |
| 19 | 18 | 13 | 73.760 | 10.742 | 108.959 | 104.05 | 0.891 |
| 19 | 18 | 15 | 44.755 | 11.821 | 19.486 | 79.22 | 0.793 |
| 19 | 18 | 17 | 33.043 | 10.071 | 14.240 | 246.88 | 0.511 |
| 19 | 18 | 19 | 50.280 | 11.290 | 50.844 | 203.60 | 0.865 |
| 19 | 18 | 21 | 39.701 | 11.171 | 27.563 | 13.68 | 0.642 |
| 19 | 18 | 23 | 48.464 | 10.692 | 44.856 | 277.61 | 0.869 |
| 19 | 19 | 0 | 76.793 | 17.361 | 108.460 | 180.00 | 0.972 |
| 19 | 19 | 2 | 89.221 | 6.316 | 113.537 | 135.97 | 0.938 |
| 19 | 19 | 4 | 39.441 | 10.967 | 4.899 | 156.26 | 0.727 |
| 19 | 19 | 6 | 125.685 | 4.681 | 118.357 | 143.23 | 0.978 |
| 19 | 19 | 8 | 94.719 | 6.124 | 97.758 | 241.19 | 0.964 |
| 19 | 19 | 10 | 72.777 | 10.813 | 93.899 | 254.14 | 0.912 |
| 19 | 19 | 12 | 103.833 | 6.161 | 152.512 | 138.23 | 0.958 |
| 19 | 19 | 14 | 84.907 | 8.805 | 85.482 | 64.19 | 0.951 |
| 19 | 19 | 16 | 103.267 | 6.468 | 157.759 | 359.95 | 0.972 |
| 19 | 19 | 18 | 39.828 | 10.920 | 27.355 | 328.85 | 0.769 |

| | | | | | | | |
|---|---|---|---|---|---|---|---|
| 19 | 19 | 20 | 37.139 | 11.269 | 10.159 | 296.74 | 0.198 |
| 19 | 19 | 22 | 40.098 | 11.445 | 11.124 | 83.34 | 0.847 |
| 19 | 20 | 1 | 36.648 | 9.987 | 11.024 | 291.09 | 0.509 |
| 19 | 20 | 3 | 88.279 | 8.219 | 95.069 | 285.51 | 0.956 |
| 19 | 20 | 5 | 82.629 | 9.257 | 152.250 | 136.86 | 0.841 |
| 19 | 20 | 7 | 91.137 | 5.954 | 155.894 | 64.80 | 0.929 |
| 19 | 20 | 9 | 82.767 | 9.051 | 120.820 | 339.67 | 0.923 |
| 19 | 20 | 11 | 53.168 | 11.305 | 57.643 | 285.01 | 0.695 |
| 19 | 20 | 13 | 55.734 | 12.163 | 80.583 | 286.56 | 0.801 |
| 19 | 20 | 15 | 56.753 | 12.519 | 28.153 | 343.95 | 0.936 |
| 19 | 20 | 17 | 47.761 | 12.223 | 45.032 | 122.32 | 0.566 |
| 19 | 20 | 19 | 69.569 | 9.191 | 75.156 | 271.21 | 0.950 |
| 19 | 20 | 21 | 33.252 | 9.901 | 13.628 | 108.25 | 0.311 |
| 19 | 21 | 0 | 46.686 | 18.558 | 1.874 | 0.00 | 0.028 |
| 19 | 21 | 2 | 99.080 | 6.479 | 143.842 | 5.32 | 0.954 |
| 19 | 21 | 4 | 74.009 | 10.013 | 103.392 | 302.33 | 0.901 |
| 19 | 21 | 6 | 127.720 | 5.384 | 211.764 | 162.42 | 0.969 |
| 19 | 21 | 8 | 50.689 | 10.215 | 28.985 | 335.20 | 0.842 |
| 19 | 21 | 10 | 37.693 | 10.953 | 11.650 | 350.86 | 0.826 |
| 19 | 21 | 12 | 62.795 | 10.317 | 81.625 | 301.79 | 0.915 |
| 19 | 21 | 14 | 63.051 | 10.856 | 88.520 | 288.75 | 0.903 |
| 19 | 21 | 16 | 110.080 | 6.856 | 203.920 | 210.96 | 0.963 |
| 19 | 21 | 18 | 62.556 | 11.878 | 64.983 | 196.19 | 0.924 |
| 19 | 21 | 20 | 51.328 | 12.308 | 51.653 | 142.17 | 0.854 |
| 19 | 22 | 1 | 55.581 | 11.221 | 60.448 | 188.68 | 0.574 |
| 19 | 22 | 3 | 39.564 | 11.014 | 16.683 | 151.84 | 0.437 |
| 19 | 22 | 5 | 34.880 | 10.595 | 14.237 | 277.91 | 0.312 |
| 19 | 22 | 7 | 32.833 | 9.838 | 13.518 | 185.72 | 0.381 |
| 19 | 22 | 9 | 49.610 | 11.418 | 44.092 | 290.07 | 0.889 |
| 19 | 22 | 11 | 31.715 | 10.320 | 7.990 | 277.91 | 0.700 |
| 19 | 22 | 13 | 41.120 | 10.648 | 32.177 | 57.82 | 0.492 |
| 19 | 22 | 15 | 79.042 | 10.173 | 126.303 | 138.33 | 0.936 |
| 19 | 22 | 17 | 35.520 | 11.168 | 14.615 | 113.34 | 0.749 |
| 19 | 23 | 0 | 37.456 | 17.553 | 13.199 | 0.00 | 0.253 |
| 19 | 23 | 2 | 83.773 | 8.626 | 151.318 | 247.22 | 0.761 |
| 19 | 23 | 4 | 60.113 | 10.648 | 96.393 | 155.57 | 0.853 |
| 19 | 23 | 6 | 75.908 | 8.465 | 96.361 | 288.58 | 0.953 |
| 19 | 23 | 8 | 87.319 | 7.250 | 154.025 | 299.76 | 0.948 |
| 19 | 23 | 10 | 71.283 | 9.231 | 77.704 | 336.30 | 0.496 |
| 19 | 23 | 12 | 66.885 | 10.476 | 84.320 | 140.66 | 0.932 |
| 19 | 23 | 14 | 60.992 | 10.685 | 90.401 | 8.77 | 0.880 |
| 19 | 23 | 16 | 33.921 | 10.818 | 13.368 | 128.61 | 0.754 |
| 19 | 24 | 1 | 34.749 | 10.606 | 17.061 | 156.51 | 0.559 |
| 19 | 24 | 3 | 35.063 | 10.599 | 19.070 | 112.54 | 0.630 |
| 19 | 24 | 5 | 52.220 | 10.604 | 72.458 | 178.33 | 0.780 |
| 19 | 24 | 7 | 40.569 | 11.022 | 36.662 | 91.01 | 0.739 |
| 19 | 24 | 9 | 33.872 | 10.155 | 12.306 | 118.19 | 0.271 |
| 19 | 24 | 11 | 39.683 | 10.878 | 34.986 | 309.26 | 0.688 |
| 19 | 24 | 13 | 78.984 | 11.277 | 137.691 | 53.89 | 0.877 |
| 19 | 25 | 0 | 28.830 | 14.789 | 15.141 | 180.00 | 0.381 |
| 19 | 25 | 2 | 31.012 | 10.089 | 17.020 | 311.91 | 0.559 |
| 19 | 25 | 4 | 38.569 | 10.889 | 28.392 | 192.99 | 0.555 |
| 19 | 25 | 6 | 28.898 | 9.424 | 2.713 | 257.76 | 0.723 |
| 19 | 25 | 8 | 57.649 | 10.668 | 79.030 | 89.57 | 0.884 |
| 19 | 25 | 10 | 27.474 | 8.916 | 3.899 | 101.34 | 0.671 |
| 19 | 26 | 1 | 50.434 | 12.161 | 40.599 | 344.91 | 0.881 |
| 19 | 26 | 3 | 33.060 | 9.145 | 15.597 | 197.28 | 0.686 |
| 19 | 26 | 5 | 45.520 | 12.280 | 39.847 | 214.20 | 0.779 |
| 20 | 0 | 4 | 25.148 | 14.288 | 25.260 | 0.00 | 0.678 |
| 20 | 0 | 6 | 157.419 | 4.450 | 236.631 | 180.00 | 0.999 |
| 20 | 0 | 8 | 98.548 | 11.746 | 120.178 | 0.00 | 0.814 |
| 20 | 0 | 10 | 128.031 | 4.960 | 191.748 | 0.00 | 0.999 |
| 20 | 0 | 12 | 120.333 | 5.228 | 179.722 | 0.00 | 1.000 |
| 20 | 0 | 14 | 134.360 | 5.335 | 200.153 | 0.00 | 1.000 |
| 20 | 0 | 16 | 168.344 | 5.150 | 249.816 | 0.00 | 1.000 |
| 20 | 0 | 18 | 59.320 | 11.989 | 41.348 | 180.00 | 0.477 |
| 20 | 0 | 20 | 94.807 | 11.006 | 138.354 | 180.00 | 1.000 |
| 20 | 0 | 22 | 355.077 | 5.330 | 518.612 | 180.00 | 1.000 |
| 20 | 0 | 24 | 34.504 | 15.225 | 47.393 | 0.00 | 0.976 |
| 20 | 0 | 26 | 60.785 | 17.867 | 82.072 | 180.00 | 0.981 |
| 20 | 0 | 28 | 65.654 | 15.824 | 89.393 | 180.00 | 1.000 |
| 20 | 0 | 30 | 27.624 | 12.894 | 22.573 | 180.00 | 0.606 |
| 20 | 0 | 32 | 31.151 | 14.328 | 11.471 | 0.00 | 0.283 |
| 20 | 1 | 1 | 298.452 | 4.789 | 445.269 | 98.64 | 0.990 |
| 20 | 1 | 3 | 256.785 | 4.621 | 408.787 | 97.50 | 0.985 |
| 20 | 1 | 5 | 235.206 | 4.682 | 403.469 | 228.51 | 0.980 |
| 20 | 1 | 7 | 244.512 | 2.823 | 411.440 | 181.09 | 0.987 |

| | | | | | | | |
|---|---|---|---|---|---|---|---|
| 20 | 1 | 9 | 252.485 | 3.851 | 298.387 | 334.43 | 0.992 |
| 20 | 1 | 11 | 85.204 | 6.099 | 104.987 | 68.13 | 0.905 |
| 20 | 1 | 13 | 95.361 | 4.989 | 171.600 | 117.43 | 0.838 |
| 20 | 1 | 15 | 129.896 | 4.761 | 237.700 | 93.59 | 0.959 |
| 20 | 1 | 17 | 37.437 | 10.047 | 8.580 | 160.10 | 0.523 |
| 20 | 1 | 19 | 49.119 | 10.151 | 37.670 | 6.04 | 0.713 |
| 20 | 1 | 21 | 56.365 | 10.800 | 59.759 | 217.43 | 0.680 |
| 20 | 1 | 23 | 154.159 | 4.645 | 284.659 | 20.91 | 0.969 |
| 20 | 1 | 25 | 96.825 | 6.455 | 151.272 | 222.96 | 0.941 |
| 20 | 1 | 27 | 35.613 | 10.890 | 19.236 | 39.44 | 0.684 |
| 20 | 1 | 29 | 66.660 | 11.161 | 56.256 | 15.39 | 0.379 |
| 20 | 1 | 31 | 73.199 | 10.884 | 83.351 | 347.17 | 0.943 |
| 20 | 2 | 0 | 71.173 | 8.190 | 89.481 | 0.00 | 0.838 |
| 20 | 2 | 2 | 253.109 | 4.118 | 472.048 | 155.69 | 0.976 |
| 20 | 2 | 4 | 181.732 | 3.272 | 254.761 | 108.58 | 0.977 |
| 20 | 2 | 6 | 212.661 | 2.865 | 335.422 | 330.81 | 0.982 |
| 20 | 2 | 8 | 133.528 | 5.225 | 214.521 | 85.09 | 0.958 |
| 20 | 2 | 10 | 49.704 | 8.997 | 32.809 | 48.26 | 0.496 |
| 20 | 2 | 12 | 82.481 | 4.628 | 124.574 | 17.47 | 0.733 |
| 20 | 2 | 14 | 140.412 | 3.720 | 227.272 | 179.43 | 0.962 |
| 20 | 2 | 16 | 97.874 | 6.063 | 188.638 | 132.94 | 0.862 |
| 20 | 2 | 18 | 102.301 | 4.592 | 171.155 | 34.88 | 0.942 |
| 20 | 2 | 20 | 53.017 | 11.248 | 11.690 | 176.87 | 0.877 |
| 20 | 2 | 22 | 214.530 | 3.774 | 259.891 | 334.63 | 0.991 |
| 20 | 2 | 24 | 135.973 | 5.022 | 183.931 | 286.57 | 0.980 |
| 20 | 2 | 26 | 76.845 | 9.338 | 98.935 | 63.98 | 0.912 |
| 20 | 2 | 28 | 39.699 | 11.415 | 24.254 | 253.14 | 0.752 |
| 20 | 2 | 30 | 61.974 | 12.312 | 65.610 | 347.14 | 0.923 |
| 20 | 2 | 32 | 82.870 | 9.433 | 123.580 | 8.88 | 0.943 |
| 20 | 3 | 1 | 249.256 | 3.500 | 356.554 | 102.75 | 0.985 |
| 20 | 3 | 3 | 254.585 | 3.590 | 305.394 | 300.63 | 0.989 |
| 20 | 3 | 5 | 58.322 | 10.839 | 9.557 | 320.20 | 0.767 |
| 20 | 3 | 7 | 26.053 | 7.781 | 21.452 | 105.11 | 0.232 |
| 20 | 3 | 9 | 274.006 | 3.659 | 447.186 | 348.69 | 0.991 |
| 20 | 3 | 11 | 45.589 | 11.058 | 15.052 | 116.63 | 0.491 |
| 20 | 3 | 13 | 86.503 | 5.255 | 118.088 | 166.07 | 0.907 |
| 20 | 3 | 15 | 98.250 | 4.582 | 135.692 | 28.27 | 0.949 |
| 20 | 3 | 17 | 129.835 | 5.828 | 173.188 | 295.88 | 0.973 |
| 20 | 3 | 19 | 104.555 | 4.905 | 112.885 | 182.76 | 0.963 |
| 20 | 3 | 21 | 36.626 | 10.717 | 7.448 | 40.66 | 0.680 |
| 20 | 3 | 23 | 236.395 | 3.863 | 372.686 | 317.85 | 0.990 |
| 20 | 3 | 25 | 109.560 | 7.063 | 172.033 | 327.65 | 0.955 |
| 20 | 3 | 27 | 107.805 | 6.385 | 155.906 | 209.16 | 0.975 |
| 20 | 3 | 29 | 40.356 | 10.491 | 32.218 | 5.01 | 0.550 |
| 20 | 3 | 31 | 54.729 | 10.535 | 57.979 | 271.89 | 0.893 |
| 20 | 4 | 0 | 97.115 | 7.704 | 145.902 | 0.00 | 0.998 |
| 20 | 4 | 2 | 69.966 | 6.742 | 40.210 | 142.60 | 0.414 |
| 20 | 4 | 4 | 175.080 | 3.925 | 250.865 | 338.80 | 0.971 |
| 20 | 4 | 6 | 129.042 | 6.605 | 223.710 | 170.58 | 0.935 |
| 20 | 4 | 8 | 334.842 | 3.758 | 478.634 | 182.77 | 0.995 |
| 20 | 4 | 10 | 160.302 | 3.922 | 270.240 | 202.56 | 0.969 |
| 20 | 4 | 12 | 126.177 | 5.555 | 217.525 | 296.35 | 0.937 |
| 20 | 4 | 14 | 179.156 | 2.991 | 251.820 | 217.71 | 0.986 |
| 20 | 4 | 16 | 182.023 | 3.298 | 246.336 | 293.52 | 0.987 |
| 20 | 4 | 18 | 45.835 | 9.750 | 31.413 | 195.98 | 0.459 |
| 20 | 4 | 20 | 35.296 | 10.414 | 5.113 | 269.68 | 0.268 |
| 20 | 4 | 22 | 148.419 | 4.266 | 197.414 | 27.68 | 0.979 |
| 20 | 4 | 24 | 42.243 | 11.427 | 15.490 | 304.36 | 0.717 |
| 20 | 4 | 26 | 46.838 | 11.004 | 19.723 | 193.86 | 0.365 |
| 20 | 4 | 28 | 53.787 | 11.362 | 67.143 | 117.36 | 0.827 |
| 20 | 4 | 30 | 38.254 | 10.662 | 30.954 | 210.25 | 0.560 |
| 20 | 4 | 32 | 44.725 | 11.604 | 31.287 | 85.75 | 0.456 |
| 20 | 5 | 1 | 72.453 | 8.044 | 81.285 | 260.75 | 0.600 |
| 20 | 5 | 3 | 117.787 | 4.939 | 148.080 | 99.66 | 0.957 |
| 20 | 5 | 5 | 122.881 | 6.762 | 153.641 | 262.83 | 0.961 |
| 20 | 5 | 7 | 239.734 | 3.413 | 327.163 | 201.21 | 0.990 |
| 20 | 5 | 9 | 181.425 | 3.693 | 287.218 | 204.15 | 0.978 |
| 20 | 5 | 11 | 154.172 | 3.990 | 232.117 | 324.77 | 0.972 |
| 20 | 5 | 13 | 54.550 | 9.778 | 43.163 | 310.88 | 0.514 |
| 20 | 5 | 15 | 87.777 | 5.675 | 112.811 | 10.25 | 0.937 |
| 20 | 5 | 17 | 82.379 | 7.102 | 57.530 | 168.48 | 0.951 |
| 20 | 5 | 19 | 97.957 | 5.813 | 139.168 | 53.41 | 0.944 |
| 20 | 5 | 21 | 127.790 | 4.401 | 174.133 | 182.91 | 0.971 |
| 20 | 5 | 23 | 43.298 | 10.763 | 30.468 | 263.43 | 0.594 |
| 20 | 5 | 25 | 118.649 | 6.762 | 150.618 | 133.64 | 0.970 |
| 20 | 5 | 27 | 59.820 | 10.756 | 79.515 | 146.80 | 0.633 |
| 20 | 5 | 29 | 34.165 | 10.153 | 15.698 | 210.68 | 0.669 |

| | | | | | | | |
|---|---|---|---|---|---|---|---|
| 20 | 5 | 31 | 37.598 | 11.168 | 7.919 | 45.75 | 0.220 |
| 20 | 6 | 0 | 253.095 | 5.712 | 381.904 | 180.00 | 1.000 |
| 20 | 6 | 2 | 111.764 | 5.587 | 143.345 | 165.32 | 0.952 |
| 20 | 6 | 4 | 118.539 | 5.763 | 179.998 | 55.54 | 0.948 |
| 20 | 6 | 6 | 138.939 | 2.920 | 207.329 | 295.40 | 0.975 |
| 20 | 6 | 8 | 199.298 | 3.322 | 316.208 | 241.45 | 0.983 |
| 20 | 6 | 10 | 146.842 | 3.649 | 299.180 | 281.62 | 0.940 |
| 20 | 6 | 12 | 91.491 | 6.713 | 101.839 | 137.52 | 0.934 |
| 20 | 6 | 14 | 46.069 | 11.012 | 27.099 | 223.10 | 0.372 |
| 20 | 6 | 16 | 202.771 | 3.425 | 302.323 | 115.44 | 0.988 |
| 20 | 6 | 18 | 131.102 | 4.122 | 175.833 | 353.16 | 0.976 |
| 20 | 6 | 20 | 167.361 | 4.123 | 221.558 | 180.80 | 0.984 |
| 20 | 6 | 22 | 89.735 | 7.395 | 132.485 | 154.09 | 0.926 |
| 20 | 6 | 24 | 70.371 | 9.657 | 94.862 | 259.03 | 0.879 |
| 20 | 6 | 26 | 31.820 | 9.884 | 12.577 | 6.08 | 0.827 |
| 20 | 6 | 28 | 50.279 | 11.330 | 52.042 | 183.00 | 0.844 |
| 20 | 6 | 30 | 76.705 | 9.727 | 132.902 | 340.71 | 0.896 |
| 20 | 7 | 1 | 91.617 | 6.734 | 151.744 | 125.79 | 0.882 |
| 20 | 7 | 3 | 197.346 | 4.332 | 275.763 | 314.77 | 0.985 |
| 20 | 7 | 5 | 204.386 | 4.467 | 292.741 | 350.64 | 0.986 |
| 20 | 7 | 7 | 144.869 | 3.779 | 175.777 | 307.46 | 0.980 |
| 20 | 7 | 9 | 169.913 | 3.558 | 265.131 | 241.81 | 0.976 |
| 20 | 7 | 11 | 311.870 | 4.022 | 489.925 | 180.76 | 0.993 |
| 20 | 7 | 13 | 57.237 | 7.290 | 69.212 | 336.54 | 0.751 |
| 20 | 7 | 15 | 62.603 | 8.543 | 73.031 | 124.86 | 0.854 |
| 20 | 7 | 17 | 45.960 | 9.332 | 36.840 | 38.21 | 0.740 |
| 20 | 7 | 19 | 27.153 | 8.836 | 1.909 | 341.07 | 0.065 |
| 20 | 7 | 21 | 48.162 | 10.014 | 37.345 | 314.93 | 0.686 |
| 20 | 7 | 23 | 92.277 | 6.270 | 141.706 | 247.05 | 0.937 |
| 20 | 7 | 25 | 55.676 | 10.559 | 51.580 | 208.54 | 0.858 |
| 20 | 7 | 27 | 78.824 | 8.855 | 148.267 | 208.96 | 0.832 |
| 20 | 7 | 29 | 92.538 | 8.896 | 155.436 | 12.96 | 0.951 |
| 20 | 7 | 31 | 54.440 | 11.610 | 65.655 | 64.50 | 0.773 |
| 20 | 8 | 0 | 100.230 | 12.636 | 150.486 | 0.00 | 0.999 |
| 20 | 8 | 2 | 101.569 | 7.120 | 147.837 | 173.96 | 0.930 |
| 20 | 8 | 4 | 198.125 | 5.996 | 257.759 | 55.40 | 0.986 |
| 20 | 8 | 6 | 200.055 | 3.582 | 341.046 | 70.36 | 0.980 |
| 20 | 8 | 8 | 32.798 | 13.060 | 22.912 | 163.41 | 0.415 |
| 20 | 8 | 10 | 224.724 | 3.536 | 382.931 | 237.88 | 0.985 |
| 20 | 8 | 12 | 62.602 | 10.183 | 77.795 | 24.37 | 0.831 |
| 20 | 8 | 14 | 88.188 | 6.191 | 125.723 | 15.19 | 0.932 |
| 20 | 8 | 16 | 129.195 | 5.734 | 153.810 | 266.91 | 0.975 |
| 20 | 8 | 18 | 93.127 | 6.758 | 151.690 | 161.97 | 0.926 |
| 20 | 8 | 20 | 135.544 | 4.836 | 235.934 | 268.17 | 0.965 |
| 20 | 8 | 22 | 80.436 | 7.851 | 96.354 | 170.51 | 0.934 |
| 20 | 8 | 24 | 38.007 | 11.096 | 1.467 | 44.68 | 0.707 |
| 20 | 8 | 26 | 102.430 | 8.051 | 148.802 | 149.06 | 0.970 |
| 20 | 8 | 28 | 35.096 | 10.631 | 19.743 | 164.46 | 0.577 |
| 20 | 8 | 30 | 43.580 | 10.912 | 42.019 | 206.47 | 0.682 |
| 20 | 9 | 1 | 104.040 | 7.159 | 157.463 | 295.61 | 0.938 |
| 20 | 9 | 3 | 109.122 | 6.603 | 143.599 | 161.74 | 0.946 |
| 20 | 9 | 5 | 39.114 | 9.887 | 3.061 | 200.07 | 0.507 |
| 20 | 9 | 7 | 120.404 | 4.783 | 107.168 | 117.68 | 0.973 |
| 20 | 9 | 9 | 274.018 | 3.791 | 407.970 | 180.27 | 0.991 |
| 20 | 9 | 11 | 72.245 | 10.629 | 69.272 | 339.43 | 0.921 |
| 20 | 9 | 13 | 70.412 | 6.833 | 107.870 | 77.18 | 0.828 |
| 20 | 9 | 15 | 52.726 | 9.036 | 37.972 | 281.66 | 0.840 |
| 20 | 9 | 17 | 100.401 | 6.859 | 147.364 | 341.26 | 0.946 |
| 20 | 9 | 19 | 128.250 | 5.135 | 171.259 | 99.34 | 0.972 |
| 20 | 9 | 21 | 34.314 | 10.258 | 5.632 | 282.63 | 0.268 |
| 20 | 9 | 23 | 118.384 | 5.284 | 228.452 | 37.16 | 0.945 |
| 20 | 9 | 25 | 40.787 | 11.189 | 16.121 | 78.09 | 0.297 |
| 20 | 9 | 27 | 51.017 | 11.580 | 5.096 | 88.27 | 0.928 |
| 20 | 9 | 29 | 45.352 | 11.765 | 46.520 | 170.52 | 0.753 |
| 20 | 10 | 0 | 98.339 | 12.604 | 147.709 | 0.00 | 0.997 |
| 20 | 10 | 2 | 54.697 | 13.552 | 31.141 | 243.39 | 0.758 |
| 20 | 10 | 4 | 77.729 | 11.135 | 103.708 | 194.49 | 0.852 |
| 20 | 10 | 6 | 53.163 | 9.999 | 27.882 | 171.86 | 0.367 |
| 20 | 10 | 8 | 64.439 | 9.555 | 72.718 | 224.89 | 0.510 |
| 20 | 10 | 10 | 41.874 | 10.681 | 15.164 | 310.96 | 0.366 |
| 20 | 10 | 12 | 41.274 | 10.141 | 21.755 | 203.07 | 0.549 |
| 20 | 10 | 14 | 208.228 | 3.308 | 359.821 | 1.91 | 0.986 |
| 20 | 10 | 16 | 73.611 | 8.871 | 41.929 | 90.93 | 0.939 |
| 20 | 10 | 18 | 49.238 | 10.128 | 41.677 | 346.06 | 0.571 |
| 20 | 10 | 20 | 150.631 | 4.717 | 211.642 | 68.68 | 0.982 |
| 20 | 10 | 22 | 35.199 | 10.066 | 5.886 | 318.17 | 0.544 |
| 20 | 10 | 24 | 38.273 | 10.722 | 27.962 | 10.23 | 0.633 |

| | | | | | | | |
|---|---|---|---|---|---|---|---|
| 20 | 10 | 26 | 61.242 | 11.441 | 29.571 | 53.01 | 0.944 |
| 20 | 10 | 28 | 57.074 | 10.893 | 77.519 | 317.86 | 0.826 |
| 20 | 11 | 1 | 43.476 | 11.940 | 12.997 | 180.01 | 0.514 |
| 20 | 11 | 3 | 135.296 | 7.966 | 188.884 | 31.25 | 0.965 |
| 20 | 11 | 5 | 117.514 | 6.095 | 148.151 | 350.17 | 0.971 |
| 20 | 11 | 7 | 133.234 | 4.554 | 274.317 | 312.31 | 0.929 |
| 20 | 11 | 9 | 36.142 | 9.863 | 3.837 | 115.50 | 0.663 |
| 20 | 11 | 11 | 105.329 | 5.552 | 130.408 | 233.40 | 0.964 |
| 20 | 11 | 13 | 32.871 | 9.599 | 6.614 | 93.58 | 0.660 |
| 20 | 11 | 15 | 142.337 | 4.176 | 288.315 | 245.61 | 0.957 |
| 20 | 11 | 17 | 142.016 | 3.997 | 228.943 | 253.59 | 0.972 |
| 20 | 11 | 19 | 61.940 | 8.743 | 68.889 | 261.79 | 0.912 |
| 20 | 11 | 21 | 67.852 | 8.554 | 91.978 | 127.50 | 0.627 |
| 20 | 11 | 23 | 59.065 | 9.440 | 81.989 | 247.32 | 0.895 |
| 20 | 11 | 25 | 36.615 | 10.566 | 25.962 | 134.88 | 0.662 |
| 20 | 11 | 27 | 31.629 | 9.705 | 12.563 | 164.89 | 0.592 |
| 20 | 11 | 29 | 39.579 | 11.485 | 6.645 | 2.11 | 0.861 |
| 20 | 12 | 0 | 31.837 | 19.975 | 14.160 | 0.00 | 0.305 |
| 20 | 12 | 2 | 66.170 | 8.581 | 45.056 | 223.20 | 0.922 |
| 20 | 12 | 4 | 51.077 | 11.232 | 36.917 | 343.33 | 0.808 |
| 20 | 12 | 6 | 103.194 | 7.326 | 93.940 | 74.14 | 0.967 |
| 20 | 12 | 8 | 123.440 | 5.572 | 213.126 | 296.23 | 0.959 |
| 20 | 12 | 10 | 158.853 | 3.835 | 211.397 | 282.28 | 0.983 |
| 20 | 12 | 12 | 197.258 | 3.771 | 300.401 | 234.77 | 0.988 |
| 20 | 12 | 14 | 47.333 | 9.773 | 6.337 | 281.82 | 0.851 |
| 20 | 12 | 16 | 96.332 | 6.089 | 114.981 | 289.63 | 0.953 |
| 20 | 12 | 18 | 37.103 | 10.209 | 1.842 | 316.56 | 0.719 |
| 20 | 12 | 20 | 65.190 | 10.010 | 44.481 | 118.17 | 0.922 |
| 20 | 12 | 22 | 70.579 | 9.476 | 96.978 | 280.90 | 0.935 |
| 20 | 12 | 24 | 73.517 | 8.818 | 80.193 | 300.47 | 0.952 |
| 20 | 12 | 26 | 38.495 | 11.047 | 11.566 | 272.92 | 0.844 |
| 20 | 12 | 28 | 37.816 | 10.838 | 23.523 | 21.07 | 0.660 |
| 20 | 13 | 1 | 70.119 | 5.433 | 60.004 | 49.91 | 0.922 |
| 20 | 13 | 3 | 165.175 | 4.104 | 273.953 | 161.49 | 0.980 |
| 20 | 13 | 5 | 242.716 | 4.770 | 396.348 | 306.54 | 0.991 |
| 20 | 13 | 7 | 106.183 | 5.140 | 110.077 | 93.83 | 0.970 |
| 20 | 13 | 9 | 272.895 | 3.423 | 442.578 | 107.75 | 0.993 |
| 20 | 13 | 11 | 165.445 | 3.897 | 263.025 | 174.76 | 0.981 |
| 20 | 13 | 13 | 105.955 | 6.404 | 150.470 | 33.83 | 0.955 |
| 20 | 13 | 15 | 62.346 | 9.822 | 55.887 | 290.40 | 0.881 |
| 20 | 13 | 17 | 29.294 | 9.526 | 28.683 | 166.98 | 0.674 |
| 20 | 13 | 19 | 55.958 | 8.750 | 53.727 | 153.09 | 0.853 |
| 20 | 13 | 21 | 39.198 | 11.474 | 17.928 | 252.26 | 0.282 |
| 20 | 13 | 23 | 58.675 | 10.831 | 55.615 | 22.50 | 0.925 |
| 20 | 13 | 25 | 44.986 | 11.852 | 16.644 | 333.31 | 0.226 |
| 20 | 13 | 27 | 29.324 | 9.640 | 4.427 | 76.96 | 0.718 |
| 20 | 14 | 0 | 183.785 | 4.471 | 276.917 | 0.00 | 1.000 |
| 20 | 14 | 2 | 109.169 | 4.766 | 167.316 | 322.51 | 0.957 |
| 20 | 14 | 4 | 173.879 | 3.028 | 288.818 | 231.97 | 0.982 |
| 20 | 14 | 6 | 71.474 | 5.945 | 108.105 | 64.12 | 0.858 |
| 20 | 14 | 8 | 94.714 | 5.957 | 157.850 | 131.37 | 0.927 |
| 20 | 14 | 10 | 132.518 | 5.379 | 242.959 | 132.92 | 0.962 |
| 20 | 14 | 12 | 144.772 | 4.448 | 252.416 | 2.26 | 0.972 |
| 20 | 14 | 14 | 41.922 | 10.810 | 17.864 | 103.54 | 0.633 |
| 20 | 14 | 16 | 45.199 | 10.983 | 22.902 | 118.71 | 0.802 |
| 20 | 14 | 18 | 129.106 | 5.285 | 211.199 | 120.46 | 0.970 |
| 20 | 14 | 20 | 70.942 | 7.648 | 78.860 | 106.62 | 0.952 |
| 20 | 14 | 22 | 30.786 | 9.705 | 8.704 | 114.18 | 0.499 |
| 20 | 14 | 24 | 44.305 | 12.463 | 38.692 | 54.48 | 0.801 |
| 20 | 14 | 26 | 36.825 | 11.211 | 15.406 | 173.65 | 0.365 |
| 20 | 15 | 1 | 31.075 | 9.034 | 2.725 | 82.22 | 0.422 |
| 20 | 15 | 3 | 176.360 | 3.110 | 306.389 | 95.18 | 0.982 |
| 20 | 15 | 5 | 113.729 | 4.489 | 179.805 | 336.37 | 0.962 |
| 20 | 15 | 7 | 169.016 | 3.324 | 231.479 | 31.29 | 0.986 |
| 20 | 15 | 9 | 94.085 | 7.315 | 112.846 | 47.80 | 0.951 |
| 20 | 15 | 11 | 96.610 | 6.687 | 161.477 | 334.74 | 0.926 |
| 20 | 15 | 13 | 61.196 | 11.319 | 35.762 | 337.82 | 0.896 |
| 20 | 15 | 15 | 93.563 | 6.711 | 97.383 | 128.26 | 0.961 |
| 20 | 15 | 17 | 35.581 | 10.155 | 6.059 | 66.95 | 0.446 |
| 20 | 15 | 19 | 69.520 | 10.338 | 82.249 | 59.76 | 0.946 |
| 20 | 15 | 21 | 53.764 | 10.083 | 64.814 | 90.07 | 0.874 |
| 20 | 15 | 23 | 62.363 | 8.879 | 92.340 | 128.92 | 0.904 |
| 20 | 15 | 25 | 36.822 | 11.011 | 16.522 | 144.34 | 0.296 |
| 20 | 16 | 0 | 61.494 | 12.677 | 91.527 | 180.00 | 1.000 |
| 20 | 16 | 2 | 142.896 | 4.653 | 242.619 | 151.89 | 0.973 |
| 20 | 16 | 4 | 87.364 | 5.451 | 109.337 | 39.63 | 0.942 |
| 20 | 16 | 6 | 33.772 | 9.120 | 11.641 | 289.75 | 0.377 |

| | | | | | | | |
|---|---|---|---|---|---|---|---|
| 20 | 16 | 8 | 111.218 | 5.853 | 149.543 | 356.19 | 0.964 |
| 20 | 16 | 10 | 41.599 | 10.144 | 18.681 | 173.94 | 0.554 |
| 20 | 16 | 12 | 88.828 | 8.396 | 104.094 | 184.73 | 0.953 |
| 20 | 16 | 14 | 49.849 | 12.104 | 45.728 | 332.47 | 0.619 |
| 20 | 16 | 16 | 51.818 | 9.900 | 54.874 | 337.10 | 0.767 |
| 20 | 16 | 18 | 38.212 | 10.652 | 13.714 | 288.02 | 0.849 |
| 20 | 16 | 20 | 42.577 | 11.460 | 38.952 | 141.79 | 0.725 |
| 20 | 16 | 22 | 39.826 | 11.582 | 32.520 | 89.25 | 0.713 |
| 20 | 16 | 24 | 68.826 | 9.665 | 96.813 | 127.84 | 0.626 |
| 20 | 17 | 1 | 94.559 | 6.520 | 129.547 | 150.46 | 0.948 |
| 20 | 17 | 3 | 85.693 | 6.483 | 126.388 | 232.20 | 0.926 |
| 20 | 17 | 5 | 104.583 | 5.466 | 154.654 | 314.26 | 0.953 |
| 20 | 17 | 7 | 126.013 | 4.989 | 205.117 | 231.11 | 0.965 |
| 20 | 17 | 9 | 83.993 | 7.515 | 129.179 | 176.66 | 0.928 |
| 20 | 17 | 11 | 61.275 | 10.305 | 73.726 | 260.02 | 0.860 |
| 20 | 17 | 13 | 64.578 | 10.240 | 84.046 | 293.93 | 0.877 |
| 20 | 17 | 15 | 55.248 | 10.896 | 53.944 | 38.89 | 0.537 |
| 20 | 17 | 17 | 57.441 | 10.928 | 45.275 | 183.58 | 0.933 |
| 20 | 17 | 19 | 55.853 | 11.578 | 35.070 | 202.12 | 0.930 |
| 20 | 17 | 21 | 47.875 | 11.830 | 55.114 | 193.13 | 0.716 |
| 20 | 17 | 23 | 47.220 | 12.118 | 42.938 | 15.96 | 0.845 |
| 20 | 18 | 0 | 118.935 | 5.756 | 104.651 | 0.00 | 0.586 |
| 20 | 18 | 2 | 46.629 | 9.912 | 22.708 | 23.93 | 0.800 |
| 20 | 18 | 4 | 35.944 | 10.284 | 9.558 | 38.02 | 0.397 |
| 20 | 18 | 6 | 85.205 | 5.736 | 149.336 | 284.49 | 0.782 |
| 20 | 18 | 8 | 31.886 | 9.397 | 6.791 | 103.74 | 0.434 |
| 20 | 18 | 10 | 43.641 | 11.570 | 20.723 | 11.71 | 0.776 |
| 20 | 18 | 12 | 58.268 | 10.384 | 76.289 | 290.90 | 0.742 |
| 20 | 18 | 14 | 69.054 | 9.483 | 123.093 | 224.92 | 0.798 |
| 20 | 18 | 16 | 36.140 | 10.699 | 13.292 | 250.83 | 0.798 |
| 20 | 18 | 18 | 38.020 | 10.222 | 31.819 | 270.54 | 0.673 |
| 20 | 18 | 20 | 26.373 | 8.973 | 2.410 | 236.00 | 0.475 |
| 20 | 18 | 22 | 33.664 | 10.674 | 1.429 | 141.28 | 0.071 |
| 20 | 19 | 1 | 53.377 | 10.066 | 62.512 | 189.11 | 0.774 |
| 20 | 19 | 3 | 58.889 | 9.391 | 66.397 | 236.62 | 0.865 |
| 20 | 19 | 5 | 39.487 | 10.699 | 6.684 | 346.08 | 0.108 |
| 20 | 19 | 7 | 31.261 | 9.159 | 5.600 | 292.03 | 0.353 |
| 20 | 19 | 9 | 66.182 | 9.610 | 71.512 | 58.15 | 0.901 |
| 20 | 19 | 11 | 36.429 | 10.834 | 16.617 | 205.65 | 0.813 |
| 20 | 19 | 13 | 32.799 | 10.045 | 4.863 | 118.64 | 0.819 |
| 20 | 19 | 15 | 106.182 | 7.593 | 172.241 | 315.57 | 0.971 |
| 20 | 19 | 17 | 36.136 | 10.917 | 22.780 | 67.99 | 0.476 |
| 20 | 19 | 19 | 43.918 | 11.049 | 45.702 | 114.08 | 0.701 |
| 20 | 19 | 21 | 35.499 | 11.653 | 7.529 | 282.21 | 0.176 |
| 20 | 20 | 0 | 75.453 | 13.206 | 110.195 | 180.00 | 0.999 |
| 20 | 20 | 2 | 69.111 | 8.392 | 104.850 | 276.44 | 0.869 |
| 20 | 20 | 4 | 33.586 | 10.039 | 8.741 | 309.93 | 0.363 |
| 20 | 20 | 6 | 24.164 | 8.213 | 6.974 | 154.16 | 0.294 |
| 20 | 20 | 8 | 26.860 | 8.728 | 3.980 | 354.14 | 0.526 |
| 20 | 20 | 10 | 33.223 | 10.394 | 8.794 | 104.21 | 0.774 |
| 20 | 20 | 12 | 60.561 | 10.738 | 71.323 | 171.57 | 0.922 |
| 20 | 20 | 14 | 38.110 | 10.852 | 17.169 | 90.28 | 0.807 |
| 20 | 20 | 16 | 91.418 | 8.764 | 150.093 | 137.46 | 0.957 |
| 20 | 20 | 18 | 39.283 | 11.365 | 28.064 | 306.28 | 0.726 |
| 20 | 21 | 1 | 40.605 | 12.091 | 35.307 | 352.43 | 0.776 |
| 20 | 21 | 3 | 45.842 | 10.864 | 55.386 | 232.61 | 0.694 |
| 20 | 21 | 5 | 52.289 | 11.820 | 65.559 | 185.11 | 0.865 |
| 20 | 21 | 7 | 64.518 | 9.275 | 106.874 | 230.30 | 0.894 |
| 20 | 21 | 9 | 92.272 | 6.526 | 116.482 | 348.72 | 0.972 |
| 20 | 21 | 11 | 73.993 | 11.281 | 128.358 | 221.69 | 0.796 |
| 20 | 21 | 13 | 57.501 | 12.099 | 69.778 | 241.25 | 0.614 |
| 20 | 21 | 15 | 58.531 | 12.104 | 42.230 | 6.45 | 0.338 |
| 20 | 21 | 17 | 42.330 | 11.808 | 37.186 | 284.41 | 0.724 |
| 20 | 22 | 0 | 54.550 | 17.149 | 75.996 | 180.00 | 0.999 |
| 20 | 22 | 2 | 29.307 | 9.377 | 9.230 | 34.32 | 0.590 |
| 20 | 22 | 4 | 29.795 | 9.687 | 8.342 | 152.92 | 0.268 |
| 20 | 22 | 6 | 33.159 | 10.149 | 14.920 | 246.23 | 0.349 |
| 20 | 22 | 8 | 41.521 | 10.959 | 22.846 | 66.88 | 0.348 |
| 20 | 22 | 10 | 59.116 | 10.151 | 88.894 | 64.27 | 0.883 |
| 20 | 22 | 12 | 38.617 | 10.891 | 27.893 | 301.73 | 0.457 |
| 20 | 22 | 14 | 39.964 | 11.541 | 34.650 | 353.88 | 0.674 |
| 20 | 23 | 1 | 46.692 | 13.260 | 40.520 | 280.17 | 0.852 |
| 20 | 23 | 3 | 53.458 | 10.606 | 75.369 | 331.66 | 0.841 |
| 20 | 23 | 5 | 39.021 | 11.002 | 14.855 | 13.17 | 0.217 |
| 20 | 23 | 7 | 26.973 | 8.926 | 1.405 | 352.01 | 0.623 |
| 20 | 23 | 9 | 39.643 | 10.548 | 29.702 | 124.23 | 0.518 |
| 20 | 23 | 11 | 34.812 | 10.428 | 12.862 | 297.18 | 0.769 |

| | | | | | | | |
|---|---|---|---|---|---|---|---|
| 20 | 24 | 0 | 76.146 | 18.399 | 100.822 | 180.00 | 1.000 |
| 20 | 24 | 2 | 28.159 | 9.077 | 8.039 | 212.61 | 0.562 |
| 20 | 24 | 4 | 35.711 | 10.997 | 25.264 | 9.46 | 0.633 |
| 20 | 24 | 6 | 38.079 | 11.043 | 25.528 | 42.59 | 0.425 |
| 20 | 24 | 8 | 37.406 | 11.036 | 27.186 | 337.84 | 0.508 |
| 20 | 25 | 1 | 38.877 | 11.274 | 12.599 | 147.67 | 0.836 |
| 21 | 0 | 3 | 393.447 | 8.505 | 597.651 | 180.00 | 1.000 |
| 21 | 0 | 5 | 22.037 | 14.224 | 16.635 | 0.00 | 0.509 |
| 21 | 0 | 7 | 175.488 | 5.086 | 266.210 | 0.00 | 1.000 |
| 21 | 0 | 9 | 40.937 | 15.204 | 19.200 | 180.00 | 0.312 |
| 21 | 0 | 11 | 44.418 | 13.215 | 66.378 | 0.00 | 0.997 |
| 21 | 0 | 13 | 188.240 | 4.087 | 283.324 | 180.00 | 1.000 |
| 21 | 0 | 15 | 90.314 | 7.550 | 134.908 | 0.00 | 0.999 |
| 21 | 0 | 17 | 27.560 | 12.548 | 6.673 | 0.00 | 0.164 |
| 21 | 0 | 19 | 28.430 | 12.770 | 36.613 | 0.00 | 0.878 |
| 21 | 0 | 21 | 41.824 | 15.131 | 15.339 | 0.00 | 0.254 |
| 21 | 0 | 23 | 126.303 | 8.636 | 183.878 | 0.00 | 1.000 |
| 21 | 0 | 25 | 70.348 | 13.635 | 98.142 | 180.00 | 0.988 |
| 21 | 0 | 27 | 25.555 | 12.183 | 13.334 | 0.00 | 0.374 |
| 21 | 0 | 29 | 35.827 | 15.088 | 33.914 | 0.00 | 0.709 |
| 21 | 1 | 2 | 107.114 | 5.370 | 201.727 | 190.34 | 0.895 |
| 21 | 1 | 4 | 242.055 | 4.552 | 386.698 | 277.20 | 0.989 |
| 21 | 1 | 6 | 91.190 | 4.635 | 135.043 | 156.55 | 0.606 |
| 21 | 1 | 8 | 146.171 | 4.784 | 246.095 | 157.48 | 0.963 |
| 21 | 1 | 10 | 115.317 | 6.467 | 133.083 | 185.58 | 0.959 |
| 21 | 1 | 12 | 81.470 | 5.136 | 115.651 | 266.28 | 0.920 |
| 21 | 1 | 14 | 51.334 | 9.246 | 33.283 | 311.45 | 0.844 |
| 21 | 1 | 16 | 163.996 | 3.680 | 243.969 | 303.64 | 0.983 |
| 21 | 1 | 18 | 61.280 | 9.455 | 65.561 | 300.44 | 0.857 |
| 21 | 1 | 20 | 245.217 | 3.362 | 353.297 | 278.68 | 0.993 |
| 21 | 1 | 22 | 60.069 | 10.744 | 66.590 | 322.21 | 0.578 |
| 21 | 1 | 24 | 100.793 | 7.163 | 141.646 | 74.02 | 0.955 |
| 21 | 1 | 26 | 71.667 | 10.985 | 58.575 | 257.04 | 0.957 |
| 21 | 1 | 28 | 34.911 | 10.884 | 22.874 | 290.65 | 0.572 |
| 21 | 1 | 30 | 113.484 | 6.342 | 188.559 | 318.16 | 0.973 |
| 21 | 2 | 1 | 113.377 | 4.758 | 134.346 | 164.41 | 0.957 |
| 21 | 2 | 3 | 90.831 | 4.649 | 116.549 | 353.77 | 0.929 |
| 21 | 2 | 5 | 236.952 | 3.483 | 405.883 | 354.01 | 0.987 |
| 21 | 2 | 7 | 81.550 | 5.573 | 99.271 | 109.43 | 0.903 |
| 21 | 2 | 9 | 48.120 | 11.751 | 18.504 | 246.48 | 0.322 |
| 21 | 2 | 11 | 134.482 | 4.425 | 190.179 | 197.98 | 0.975 |
| 21 | 2 | 13 | 120.533 | 3.844 | 122.882 | 95.14 | 0.975 |
| 21 | 2 | 15 | 44.852 | 10.180 | 24.826 | 287.75 | 0.743 |
| 21 | 2 | 17 | 212.963 | 3.006 | 310.821 | 74.32 | 0.990 |
| 21 | 2 | 19 | 84.893 | 6.236 | 145.162 | 245.04 | 0.882 |
| 21 | 2 | 21 | 56.479 | 10.864 | 66.343 | 151.47 | 0.793 |
| 21 | 2 | 23 | 153.962 | 4.501 | 236.395 | 309.53 | 0.981 |
| 21 | 2 | 25 | 70.369 | 10.326 | 112.652 | 57.12 | 0.908 |
| 21 | 2 | 27 | 34.016 | 10.236 | 16.564 | 70.57 | 0.855 |
| 21 | 2 | 29 | 90.776 | 6.927 | 138.527 | 86.42 | 0.961 |
| 21 | 3 | 0 | 37.935 | 17.240 | 23.868 | 0.00 | 0.417 |
| 21 | 3 | 2 | 41.082 | 10.741 | 14.652 | 177.81 | 0.766 |
| 21 | 3 | 4 | 320.656 | 4.173 | 524.811 | 98.89 | 0.993 |
| 21 | 3 | 6 | 213.632 | 2.847 | 277.912 | 72.38 | 0.988 |
| 21 | 3 | 8 | 103.549 | 4.338 | 158.749 | 199.24 | 0.936 |
| 21 | 3 | 10 | 124.488 | 4.684 | 128.893 | 263.65 | 0.978 |
| 21 | 3 | 12 | 65.566 | 10.084 | 94.650 | 226.80 | 0.787 |
| 21 | 3 | 14 | 125.239 | 5.482 | 244.178 | 31.75 | 0.938 |
| 21 | 3 | 16 | 95.504 | 5.400 | 151.851 | 22.94 | 0.871 |
| 21 | 3 | 18 | 160.249 | 5.034 | 241.035 | 125.98 | 0.981 |
| 21 | 3 | 20 | 94.354 | 6.554 | 123.608 | 129.18 | 0.948 |
| 21 | 3 | 22 | 38.510 | 11.066 | 16.431 | 229.15 | 0.405 |
| 21 | 3 | 24 | 81.821 | 7.922 | 96.271 | 327.47 | 0.939 |
| 21 | 3 | 26 | 29.031 | 9.489 | 0.730 | 150.96 | 0.592 |
| 21 | 3 | 28 | 72.626 | 10.892 | 125.000 | 85.25 | 0.870 |
| 21 | 3 | 30 | 58.613 | 12.229 | 69.291 | 91.34 | 0.876 |
| 21 | 4 | 1 | 158.644 | 3.803 | 233.457 | 180.88 | 0.974 |
| 21 | 4 | 3 | 121.173 | 5.253 | 176.530 | 8.57 | 0.951 |
| 21 | 4 | 5 | 161.658 | 4.547 | 280.854 | 190.79 | 0.970 |
| 21 | 4 | 7 | 86.699 | 4.288 | 135.498 | 133.86 | 0.882 |
| 21 | 4 | 9 | 166.762 | 3.217 | 213.158 | 313.58 | 0.986 |
| 21 | 4 | 11 | 162.665 | 4.264 | 232.132 | 207.37 | 0.983 |
| 21 | 4 | 13 | 124.029 | 4.965 | 141.211 | 266.74 | 0.975 |
| 21 | 4 | 15 | 70.964 | 7.210 | 83.065 | 4.69 | 0.911 |
| 21 | 4 | 17 | 153.497 | 3.876 | 214.406 | 249.26 | 0.981 |
| 21 | 4 | 19 | 56.310 | 10.319 | 62.426 | 333.12 | 0.767 |
| 21 | 4 | 21 | 152.380 | 4.598 | 295.163 | 174.32 | 0.971 |

| | | | | | | | |
|---|---|---|---|---|---|---|---|
| 21 | 4 | 23 | 113.336 | 8.397 | 218.852 | 240.46 | 0.751 |
| 21 | 4 | 25 | 43.525 | 10.085 | 27.980 | 260.05 | 0.868 |
| 21 | 4 | 27 | 49.440 | 11.442 | 53.560 | 250.66 | 0.798 |
| 21 | 4 | 29 | 63.083 | 10.196 | 59.312 | 7.48 | 0.936 |
| 21 | 5 | 0 | 294.099 | 5.368 | 447.441 | 180.00 | 1.000 |
| 21 | 5 | 2 | 277.419 | 4.003 | 390.046 | 276.06 | 0.993 |
| 21 | 5 | 4 | 271.276 | 4.173 | 417.165 | 290.88 | 0.992 |
| 21 | 5 | 6 | 198.970 | 5.526 | 380.811 | 327.78 | 0.977 |
| 21 | 5 | 8 | 184.781 | 3.886 | 219.193 | 326.55 | 0.990 |
| 21 | 5 | 10 | 115.417 | 4.952 | 228.652 | 220.69 | 0.928 |
| 21 | 5 | 12 | 92.722 | 5.999 | 111.959 | 226.49 | 0.950 |
| 21 | 5 | 14 | 41.031 | 10.158 | 21.324 | 12.94 | 0.709 |
| 21 | 5 | 16 | 95.229 | 6.211 | 134.217 | 235.54 | 0.942 |
| 21 | 5 | 18 | 42.355 | 10.989 | 14.133 | 238.24 | 0.314 |
| 21 | 5 | 20 | 134.282 | 5.711 | 191.313 | 76.38 | 0.978 |
| 21 | 5 | 22 | 41.392 | 10.516 | 25.019 | 357.32 | 0.549 |
| 21 | 5 | 24 | 37.548 | 11.100 | 14.290 | 262.09 | 0.273 |
| 21 | 5 | 26 | 53.459 | 11.040 | 65.942 | 71.82 | 0.702 |
| 21 | 5 | 28 | 44.687 | 11.343 | 47.665 | 263.82 | 0.650 |
| 21 | 5 | 30 | 39.799 | 11.519 | 21.774 | 55.90 | 0.437 |
| 21 | 6 | 1 | 99.866 | 7.848 | 127.105 | 357.34 | 0.938 |
| 21 | 6 | 3 | 134.412 | 4.851 | 246.553 | 9.79 | 0.943 |
| 21 | 6 | 5 | 54.310 | 13.346 | 7.917 | 103.37 | 0.865 |
| 21 | 6 | 7 | 116.335 | 3.509 | 162.048 | 107.94 | 0.968 |
| 21 | 6 | 9 | 85.553 | 6.687 | 148.862 | 104.94 | 0.900 |
| 21 | 6 | 11 | 241.566 | 4.059 | 320.676 | 262.45 | 0.993 |
| 21 | 6 | 13 | 229.279 | 3.649 | 357.543 | 307.60 | 0.991 |
| 21 | 6 | 15 | 90.352 | 9.324 | 130.768 | 219.12 | 0.939 |
| 21 | 6 | 17 | 57.373 | 9.909 | 49.782 | 349.17 | 0.832 |
| 21 | 6 | 19 | 30.217 | 9.921 | 10.301 | 309.35 | 0.452 |
| 21 | 6 | 21 | 98.533 | 5.236 | 131.092 | 256.16 | 0.958 |
| 21 | 6 | 23 | 90.748 | 6.826 | 154.871 | 80.07 | 0.923 |
| 21 | 6 | 25 | 51.681 | 10.780 | 62.107 | 305.54 | 0.851 |
| 21 | 6 | 27 | 75.501 | 8.552 | 129.630 | 234.73 | 0.920 |
| 21 | 6 | 29 | 55.462 | 10.013 | 76.681 | 149.13 | 0.830 |
| 21 | 7 | 0 | 29.836 | 17.949 | 31.002 | 180.00 | 0.697 |
| 21 | 7 | 2 | 209.955 | 4.240 | 284.771 | 19.88 | 0.988 |
| 21 | 7 | 4 | 156.548 | 5.501 | 240.758 | 118.69 | 0.973 |
| 21 | 7 | 6 | 164.036 | 7.819 | 249.416 | 209.32 | 0.982 |
| 21 | 7 | 8 | 213.115 | 3.285 | 337.533 | 263.37 | 0.989 |
| 21 | 7 | 10 | 52.990 | 9.440 | 51.917 | 295.66 | 0.829 |
| 21 | 7 | 12 | 113.820 | 5.659 | 147.040 | 301.50 | 0.967 |
| 21 | 7 | 14 | 157.323 | 3.961 | 300.901 | 25.04 | 0.952 |
| 21 | 7 | 16 | 76.051 | 9.239 | 126.476 | 132.56 | 0.828 |
| 21 | 7 | 18 | 62.139 | 9.685 | 24.682 | 325.23 | 0.915 |
| 21 | 7 | 20 | 112.657 | 5.218 | 145.193 | 247.57 | 0.971 |
| 21 | 7 | 22 | 91.493 | 6.912 | 161.575 | 243.25 | 0.920 |
| 21 | 7 | 24 | 88.649 | 7.984 | 145.692 | 252.69 | 0.954 |
| 21 | 7 | 26 | 84.059 | 8.478 | 147.717 | 248.25 | 0.926 |
| 21 | 7 | 28 | 59.654 | 10.619 | 81.853 | 60.75 | 0.885 |
| 21 | 8 | 1 | 115.404 | 6.146 | 156.802 | 165.42 | 0.966 |
| 21 | 8 | 3 | 197.015 | 4.525 | 340.038 | 93.03 | 0.987 |
| 21 | 8 | 5 | 97.919 | 11.059 | 110.540 | 114.85 | 0.958 |
| 21 | 8 | 7 | 285.144 | 4.274 | 457.477 | 79.66 | 0.994 |
| 21 | 8 | 9 | 112.741 | 4.788 | 161.731 | 211.73 | 0.967 |
| 21 | 8 | 11 | 131.137 | 5.151 | 208.310 | 175.36 | 0.968 |
| 21 | 8 | 13 | 127.167 | 5.708 | 203.206 | 104.25 | 0.968 |
| 21 | 8 | 15 | 82.700 | 7.124 | 133.822 | 275.66 | 0.897 |
| 21 | 8 | 17 | 171.380 | 4.359 | 249.786 | 104.79 | 0.984 |
| 21 | 8 | 19 | 31.938 | 9.696 | 1.198 | 314.24 | 0.241 |
| 21 | 8 | 21 | 38.343 | 10.682 | 8.089 | 160.23 | 0.568 |
| 21 | 8 | 23 | 44.717 | 10.821 | 41.451 | 235.03 | 0.490 |
| 21 | 8 | 25 | 73.251 | 8.626 | 89.021 | 82.32 | 0.949 |
| 21 | 8 | 27 | 50.834 | 11.691 | 51.737 | 82.09 | 0.878 |
| 21 | 9 | 0 | 173.060 | 8.641 | 262.431 | 180.00 | 1.000 |
| 21 | 9 | 2 | 56.818 | 11.993 | 21.972 | 190.68 | 0.897 |
| 21 | 9 | 4 | 143.168 | 6.416 | 179.008 | 123.16 | 0.980 |
| 21 | 9 | 6 | 131.184 | 7.440 | 258.020 | 142.24 | 0.956 |
| 21 | 9 | 8 | 119.046 | 7.304 | 180.574 | 278.35 | 0.965 |
| 21 | 9 | 10 | 141.575 | 4.513 | 216.297 | 108.09 | 0.976 |
| 21 | 9 | 12 | 40.557 | 11.578 | 12.789 | 2.25 | 0.339 |
| 21 | 9 | 14 | 108.483 | 4.378 | 155.324 | 23.16 | 0.960 |
| 21 | 9 | 16 | 96.147 | 6.592 | 176.967 | 162.97 | 0.893 |
| 21 | 9 | 18 | 151.087 | 4.531 | 257.761 | 322.86 | 0.978 |
| 21 | 9 | 20 | 41.042 | 10.760 | 17.049 | 255.00 | 0.690 |
| 21 | 9 | 22 | 97.853 | 7.308 | 155.031 | 140.35 | 0.967 |
| 21 | 9 | 24 | 69.945 | 9.803 | 94.004 | 108.74 | 0.933 |

| | | | | | | | |
|---|---|---|---|---|---|---|---|
| 21 | 9 | 26 | 54.926 | 11.030 | 65.376 | 137.92 | 0.880 |
| 21 | 9 | 28 | 36.316 | 10.400 | 7.153 | 274.74 | 0.130 |
| 21 | 10 | 1 | 78.158 | 9.536 | 122.400 | 282.46 | 0.895 |
| 21 | 10 | 3 | 63.401 | 15.282 | 75.465 | 262.33 | 0.852 |
| 21 | 10 | 5 | 128.097 | 7.574 | 197.413 | 78.35 | 0.969 |
| 21 | 10 | 7 | 241.020 | 3.922 | 426.896 | 331.54 | 0.990 |
| 21 | 10 | 9 | 122.011 | 5.136 | 136.775 | 77.42 | 0.976 |
| 21 | 10 | 11 | 157.902 | 5.998 | 242.182 | 27.98 | 0.981 |
| 21 | 10 | 13 | 83.663 | 12.364 | 71.805 | 279.45 | 0.946 |
| 21 | 10 | 15 | 97.932 | 5.525 | 154.705 | 5.57 | 0.937 |
| 21 | 10 | 17 | 58.214 | 10.837 | 65.429 | 177.81 | 0.565 |
| 21 | 10 | 19 | 53.774 | 11.122 | 54.371 | 14.21 | 0.821 |
| 21 | 10 | 21 | 58.813 | 9.170 | 56.839 | 330.62 | 0.932 |
| 21 | 10 | 23 | 51.121 | 10.796 | 27.165 | 142.38 | 0.919 |
| 21 | 10 | 25 | 77.761 | 8.871 | 114.031 | 167.50 | 0.946 |
| 21 | 10 | 27 | 26.004 | 8.905 | 4.127 | 273.55 | 0.363 |
| 21 | 11 | 0 | 156.632 | 11.586 | 236.410 | 180.00 | 1.000 |
| 21 | 11 | 2 | 97.007 | 9.923 | 128.073 | 272.66 | 0.951 |
| 21 | 11 | 4 | 208.575 | 6.225 | 345.421 | 29.33 | 0.988 |
| 21 | 11 | 6 | 153.237 | 4.036 | 188.436 | 42.54 | 0.983 |
| 21 | 11 | 8 | 230.128 | 3.818 | 394.251 | 135.74 | 0.990 |
| 21 | 11 | 10 | 60.223 | 10.895 | 72.135 | 197.72 | 0.614 |
| 21 | 11 | 12 | 27.264 | 8.698 | 7.558 | 341.17 | 0.233 |
| 21 | 11 | 14 | 75.769 | 7.028 | 108.635 | 242.74 | 0.614 |
| 21 | 11 | 16 | 86.056 | 6.657 | 161.758 | 125.79 | 0.884 |
| 21 | 11 | 18 | 57.488 | 11.850 | 67.517 | 75.19 | 0.792 |
| 21 | 11 | 20 | 67.711 | 9.693 | 29.802 | 76.50 | 0.199 |
| 21 | 11 | 22 | 53.993 | 10.630 | 55.588 | 243.05 | 0.900 |
| 21 | 11 | 24 | 62.717 | 10.566 | 93.430 | 113.34 | 0.889 |
| 21 | 11 | 26 | 30.196 | 9.998 | 8.513 | 89.35 | 0.397 |
| 21 | 12 | 1 | 37.660 | 11.293 | 4.748 | 165.99 | 0.698 |
| 21 | 12 | 3 | 33.236 | 9.801 | 12.980 | 243.88 | 0.718 |
| 21 | 12 | 5 | 195.483 | 3.875 | 234.076 | 292.43 | 0.990 |
| 21 | 12 | 7 | 48.413 | 11.855 | 28.494 | 272.01 | 0.808 |
| 21 | 12 | 9 | 55.983 | 11.454 | 65.388 | 294.37 | 0.747 |
| 21 | 12 | 11 | 97.177 | 6.681 | 171.752 | 178.79 | 0.919 |
| 21 | 12 | 13 | 132.334 | 5.766 | 263.936 | 210.42 | 0.953 |
| 21 | 12 | 15 | 94.009 | 5.088 | 161.587 | 71.37 | 0.942 |
| 21 | 12 | 17 | 24.371 | 8.263 | 10.720 | 64.04 | 0.269 |
| 21 | 12 | 19 | 31.770 | 8.956 | 5.152 | 67.88 | 0.657 |
| 21 | 12 | 21 | 85.104 | 8.578 | 124.854 | 270.83 | 0.959 |
| 21 | 12 | 23 | 54.709 | 11.203 | 56.779 | 115.64 | 0.886 |
| 21 | 12 | 25 | 38.876 | 11.682 | 27.287 | 174.17 | 0.679 |
| 21 | 13 | 0 | 104.412 | 13.297 | 156.804 | 0.00 | 1.000 |
| 21 | 13 | 2 | 37.276 | 11.311 | 7.768 | 270.41 | 0.518 |
| 21 | 13 | 4 | 46.778 | 10.182 | 21.523 | 334.71 | 0.810 |
| 21 | 13 | 6 | 100.265 | 11.380 | 167.593 | 300.64 | 0.935 |
| 21 | 13 | 8 | 173.727 | 4.655 | 277.286 | 24.92 | 0.984 |
| 21 | 13 | 10 | 113.720 | 6.232 | 195.486 | 344.25 | 0.953 |
| 21 | 13 | 12 | 29.205 | 9.187 | 61.259 | 177.46 | 0.764 |
| 21 | 13 | 14 | 60.267 | 11.107 | 30.359 | 336.88 | 0.235 |
| 21 | 13 | 16 | 81.603 | 6.597 | 101.534 | 214.28 | 0.940 |
| 21 | 13 | 18 | 74.444 | 8.282 | 74.814 | 213.34 | 0.961 |
| 21 | 13 | 20 | 32.720 | 10.301 | 4.926 | 96.14 | 0.759 |
| 21 | 13 | 22 | 33.305 | 10.400 | 9.963 | 102.35 | 0.702 |
| 21 | 13 | 24 | 41.849 | 12.748 | 31.965 | 241.31 | 0.571 |
| 21 | 14 | 1 | 105.068 | 5.083 | 148.387 | 173.24 | 0.960 |
| 21 | 14 | 3 | 43.799 | 13.242 | 20.660 | 118.21 | 0.393 |
| 21 | 14 | 5 | 53.670 | 11.830 | 62.569 | 185.91 | 0.722 |
| 21 | 14 | 7 | 188.887 | 3.340 | 309.425 | 182.34 | 0.986 |
| 21 | 14 | 9 | 134.727 | 5.543 | 191.984 | 126.58 | 0.975 |
| 21 | 14 | 11 | 103.880 | 6.853 | 150.814 | 14.92 | 0.962 |
| 21 | 14 | 13 | 59.474 | 9.563 | 74.122 | 356.72 | 0.830 |
| 21 | 14 | 15 | 81.644 | 10.246 | 103.724 | 42.63 | 0.932 |
| 21 | 14 | 17 | 81.441 | 7.241 | 70.048 | 169.65 | 0.971 |
| 21 | 14 | 19 | 100.257 | 7.146 | 218.159 | 236.77 | 0.890 |
| 21 | 14 | 21 | 43.782 | 11.504 | 45.533 | 86.99 | 0.642 |
| 21 | 14 | 23 | 37.317 | 10.505 | 23.751 | 37.92 | 0.792 |
| 21 | 15 | 0 | 25.775 | 12.022 | 10.410 | 0.00 | 0.269 |
| 21 | 15 | 2 | 67.181 | 5.783 | 104.919 | 260.08 | 0.815 |
| 21 | 15 | 4 | 63.181 | 6.704 | 66.655 | 225.12 | 0.889 |
| 21 | 15 | 6 | 104.411 | 4.506 | 138.067 | 205.06 | 0.960 |
| 21 | 15 | 8 | 74.089 | 7.933 | 125.504 | 300.65 | 0.868 |
| 21 | 15 | 10 | 156.280 | 4.743 | 248.811 | 112.04 | 0.982 |
| 21 | 15 | 12 | 55.624 | 11.890 | 64.811 | 254.39 | 0.753 |
| 21 | 15 | 14 | 73.496 | 8.213 | 109.322 | 32.60 | 0.898 |
| 21 | 15 | 16 | 93.568 | 6.656 | 182.173 | 179.30 | 0.948 |

| | | | | | | | |
|---|---|---|---|---|---|---|---|
| 21 | 15 | 18 | 29.951 | 9.907 | 7.727 | 111.15 | 0.494 |
| 21 | 15 | 20 | 42.695 | 12.154 | 39.572 | 345.63 | 0.734 |
| 21 | 15 | 22 | 88.932 | 8.726 | 142.352 | 133.60 | 0.956 |
| 21 | 16 | 1 | 67.728 | 7.298 | 105.072 | 5.05 | 0.790 |
| 21 | 16 | 3 | 30.517 | 9.403 | 9.505 | 144.24 | 0.508 |
| 21 | 16 | 5 | 142.236 | 3.829 | 215.483 | 334.08 | 0.980 |
| 21 | 16 | 7 | 144.769 | 4.657 | 253.506 | 248.28 | 0.977 |
| 21 | 16 | 9 | 169.342 | 4.523 | 297.841 | 258.72 | 0.983 |
| 21 | 16 | 11 | 104.606 | 7.191 | 189.327 | 244.02 | 0.946 |
| 21 | 16 | 13 | 141.415 | 5.031 | 244.319 | 308.15 | 0.975 |
| 21 | 16 | 15 | 41.325 | 9.281 | 25.757 | 333.61 | 0.350 |
| 21 | 16 | 17 | 53.955 | 12.548 | 62.892 | 86.38 | 0.875 |
| 21 | 16 | 19 | 46.646 | 12.650 | 50.356 | 257.38 | 0.793 |
| 21 | 16 | 21 | 38.622 | 11.748 | 14.679 | 268.18 | 0.846 |
| 21 | 17 | 0 | 56.004 | 13.220 | 80.577 | 180.00 | 0.969 |
| 21 | 17 | 2 | 61.909 | 9.263 | 44.970 | 31.39 | 0.925 |
| 21 | 17 | 4 | 97.622 | 4.992 | 173.264 | 155.02 | 0.939 |
| 21 | 17 | 6 | 91.948 | 6.310 | 125.594 | 284.27 | 0.953 |
| 21 | 17 | 8 | 67.218 | 8.082 | 89.779 | 216.43 | 0.891 |
| 21 | 17 | 10 | 54.730 | 9.927 | 64.996 | 211.26 | 0.655 |
| 21 | 17 | 12 | 70.111 | 10.722 | 109.681 | 175.31 | 0.924 |
| 21 | 17 | 14 | 48.104 | 11.598 | 60.326 | 119.00 | 0.709 |
| 21 | 17 | 16 | 39.504 | 10.672 | 37.230 | 117.83 | 0.646 |
| 21 | 17 | 18 | 42.166 | 11.988 | 34.562 | 258.68 | 0.543 |
| 21 | 17 | 20 | 61.221 | 13.113 | 76.970 | 347.81 | 0.886 |
| 21 | 18 | 1 | 89.030 | 6.199 | 148.775 | 121.01 | 0.932 |
| 21 | 18 | 3 | 45.607 | 9.599 | 32.759 | 192.27 | 0.781 |
| 21 | 18 | 5 | 38.487 | 10.190 | 22.229 | 4.01 | 0.546 |
| 21 | 18 | 7 | 58.510 | 9.025 | 37.349 | 253.92 | 0.906 |
| 21 | 18 | 9 | 61.113 | 8.390 | 80.943 | 60.76 | 0.931 |
| 21 | 18 | 11 | 33.187 | 10.609 | 15.825 | 135.62 | 0.343 |
| 21 | 18 | 13 | 40.236 | 9.828 | 35.922 | 300.76 | 0.768 |
| 21 | 18 | 15 | 33.264 | 10.693 | 5.325 | 94.61 | 0.838 |
| 21 | 18 | 17 | 46.187 | 12.566 | 44.548 | 83.54 | 0.784 |
| 21 | 18 | 19 | 46.912 | 13.078 | 32.627 | 100.52 | 0.863 |
| 21 | 19 | 0 | 30.727 | 13.928 | 22.856 | 0.00 | 0.509 |
| 21 | 19 | 2 | 78.091 | 7.302 | 125.891 | 3.09 | 0.639 |
| 21 | 19 | 4 | 63.691 | 7.650 | 84.676 | 293.28 | 0.935 |
| 21 | 19 | 6 | 48.497 | 11.433 | 62.058 | 41.89 | 0.720 |
| 21 | 19 | 8 | 32.397 | 9.443 | 22.057 | 33.19 | 0.559 |
| 21 | 19 | 10 | 39.150 | 10.569 | 20.856 | 48.08 | 0.844 |
| 21 | 19 | 12 | 55.128 | 11.259 | 55.227 | 311.81 | 0.906 |
| 21 | 19 | 14 | 35.318 | 10.869 | 15.842 | 304.05 | 0.799 |
| 21 | 19 | 16 | 33.607 | 10.690 | 17.642 | 261.97 | 0.700 |
| 21 | 19 | 18 | 36.375 | 11.646 | 15.625 | 249.91 | 0.747 |
| 21 | 20 | 1 | 29.500 | 9.243 | 11.419 | 55.36 | 0.475 |
| 21 | 20 | 3 | 83.164 | 7.000 | 122.834 | 81.49 | 0.961 |
| 21 | 20 | 5 | 137.445 | 4.472 | 222.587 | 136.22 | 0.985 |
| 21 | 20 | 7 | 48.144 | 9.837 | 51.238 | 184.05 | 0.865 |
| 21 | 20 | 9 | 46.245 | 12.190 | 32.266 | 85.24 | 0.429 |
| 21 | 20 | 11 | 57.087 | 11.606 | 64.674 | 54.65 | 0.910 |
| 21 | 20 | 13 | 49.048 | 12.169 | 44.201 | 36.62 | 0.476 |
| 21 | 20 | 15 | 56.523 | 10.016 | 72.477 | 307.34 | 0.889 |
| 21 | 21 | 0 | 43.526 | 17.720 | 60.203 | 180.00 | 0.999 |
| 21 | 21 | 2 | 40.459 | 10.370 | 34.584 | 167.10 | 0.760 |
| 21 | 21 | 4 | 36.371 | 10.290 | 26.225 | 149.68 | 0.636 |
| 21 | 21 | 6 | 76.505 | 12.700 | 138.597 | 150.04 | 0.825 |
| 21 | 21 | 8 | 54.217 | 12.492 | 47.035 | 52.84 | 0.468 |
| 21 | 21 | 10 | 70.868 | 9.994 | 87.918 | 202.24 | 0.562 |
| 21 | 21 | 12 | 56.555 | 12.122 | 78.004 | 87.68 | 0.767 |
| 21 | 21 | 14 | 42.742 | 11.840 | 33.675 | 39.82 | 0.809 |
| 21 | 22 | 1 | 62.749 | 12.272 | 78.605 | 286.19 | 0.918 |
| 21 | 22 | 3 | 36.912 | 11.053 | 15.748 | 315.72 | 0.826 |
| 21 | 22 | 5 | 47.416 | 11.394 | 58.163 | 308.10 | 0.714 |
| 21 | 22 | 7 | 30.740 | 10.190 | 10.855 | 166.32 | 0.549 |
| 21 | 22 | 9 | 36.073 | 11.066 | 17.228 | 193.45 | 0.740 |
| 21 | 22 | 11 | 32.307 | 9.976 | 15.670 | 92.48 | 0.494 |
| 21 | 23 | 0 | 24.106 | 16.753 | 10.028 | 0.00 | 0.329 |
| 21 | 23 | 2 | 39.964 | 11.842 | 36.724 | 294.45 | 0.746 |
| 21 | 23 | 4 | 32.315 | 10.801 | 5.680 | 23.94 | 0.709 |
| 21 | 23 | 6 | 39.829 | 12.926 | 18.599 | 179.71 | 0.353 |
| 22 | 0 | 4 | 31.438 | 16.248 | 20.841 | 180.00 | 0.440 |
| 22 | 0 | 6 | 135.535 | 6.613 | 207.055 | 0.00 | 1.000 |
| 22 | 0 | 8 | 69.288 | 12.895 | 62.874 | 180.00 | 0.600 |
| 22 | 0 | 10 | 23.626 | 11.680 | 2.564 | 0.00 | 0.072 |
| 22 | 0 | 12 | 74.217 | 10.758 | 111.738 | 0.00 | 0.999 |
| 22 | 0 | 14 | 33.541 | 14.620 | 37.944 | 0.00 | 0.761 |

| | | | | | | | |
|---|---|---|---|---|---|---|---|
| 22 | 0 | 16 | 76.740 | 14.146 | 113.218 | 0.00 | 0.995 |
| 22 | 0 | 18 | 53.799 | 16.213 | 77.709 | 0.00 | 0.993 |
| 22 | 0 | 20 | 25.269 | 11.939 | 33.063 | 0.00 | 0.897 |
| 22 | 0 | 22 | 30.145 | 13.781 | 39.593 | 0.00 | 0.915 |
| 22 | 0 | 24 | 45.461 | 16.632 | 5.436 | 180.00 | 0.087 |
| 22 | 0 | 26 | 44.774 | 15.930 | 8.905 | 0.00 | 0.147 |
| 22 | 0 | 28 | 29.077 | 13.465 | 31.011 | 0.00 | 0.788 |
| 22 | 1 | 3 | 81.691 | 7.030 | 107.634 | 179.30 | 0.931 |
| 22 | 1 | 5 | 146.996 | 4.280 | 226.901 | 62.48 | 0.979 |
| 22 | 1 | 7 | 65.414 | 6.978 | 96.747 | 140.47 | 0.705 |
| 22 | 1 | 9 | 52.970 | 10.841 | 48.554 | 305.25 | 0.504 |
| 22 | 1 | 11 | 130.274 | 3.603 | 218.702 | 53.78 | 0.968 |
| 22 | 1 | 13 | 86.751 | 7.016 | 161.551 | 301.00 | 0.868 |
| 22 | 1 | 15 | 144.299 | 3.475 | 263.877 | 76.54 | 0.971 |
| 22 | 1 | 17 | 143.567 | 4.396 | 244.384 | 86.49 | 0.973 |
| 22 | 1 | 19 | 84.062 | 7.114 | 96.014 | 73.57 | 0.948 |
| 22 | 1 | 21 | 153.653 | 4.349 | 283.393 | 160.87 | 0.974 |
| 22 | 1 | 23 | 39.664 | 11.019 | 33.940 | 227.86 | 0.567 |
| 22 | 1 | 25 | 110.654 | 6.381 | 144.805 | 33.01 | 0.979 |
| 22 | 1 | 27 | 86.735 | 8.655 | 94.491 | 68.86 | 0.970 |
| 22 | 2 | 0 | 16.791 | 11.301 | 17.309 | 180.00 | 0.741 |
| 22 | 2 | 2 | 72.671 | 8.710 | 64.978 | 282.95 | 0.930 |
| 22 | 2 | 4 | 92.238 | 8.667 | 141.408 | 166.13 | 0.938 |
| 22 | 2 | 6 | 199.040 | 3.378 | 352.440 | 181.27 | 0.985 |
| 22 | 2 | 8 | 109.050 | 4.302 | 123.135 | 89.71 | 0.969 |
| 22 | 2 | 10 | 52.790 | 11.116 | 54.831 | 310.34 | 0.622 |
| 22 | 2 | 12 | 46.755 | 9.532 | 48.588 | 28.66 | 0.672 |
| 22 | 2 | 14 | 76.161 | 6.203 | 93.468 | 261.28 | 0.922 |
| 22 | 2 | 16 | 65.309 | 9.282 | 92.984 | 162.41 | 0.821 |
| 22 | 2 | 18 | 125.281 | 3.883 | 188.102 | 59.38 | 0.974 |
| 22 | 2 | 20 | 65.941 | 8.104 | 18.669 | 124.22 | 0.945 |
| 22 | 2 | 22 | 186.414 | 3.893 | 260.142 | 182.67 | 0.993 |
| 22 | 2 | 24 | 119.761 | 5.913 | 189.968 | 10.76 | 0.980 |
| 22 | 2 | 26 | 46.158 | 11.916 | 22.123 | 106.59 | 0.288 |
| 22 | 2 | 28 | 68.490 | 10.908 | 90.730 | 129.75 | 0.601 |
| 22 | 3 | 1 | 128.550 | 4.949 | 157.399 | 227.93 | 0.977 |
| 22 | 3 | 3 | 41.332 | 9.160 | 6.270 | 39.68 | 0.831 |
| 22 | 3 | 5 | 86.209 | 5.965 | 87.537 | 233.89 | 0.952 |
| 22 | 3 | 7 | 126.001 | 3.272 | 173.303 | 223.09 | 0.972 |
| 22 | 3 | 9 | 133.018 | 3.527 | 250.721 | 190.50 | 0.963 |
| 22 | 3 | 11 | 53.577 | 9.897 | 57.783 | 106.91 | 0.768 |
| 22 | 3 | 13 | 61.193 | 9.789 | 63.749 | 17.25 | 0.870 |
| 22 | 3 | 15 | 104.710 | 4.962 | 185.947 | 133.07 | 0.938 |
| 22 | 3 | 17 | 54.034 | 9.308 | 55.037 | 162.34 | 0.604 |
| 22 | 3 | 19 | 143.079 | 3.782 | 232.997 | 13.05 | 0.978 |
| 22 | 3 | 21 | 80.632 | 8.062 | 94.981 | 176.53 | 0.936 |
| 22 | 3 | 23 | 54.621 | 10.553 | 75.875 | 144.25 | 0.836 |
| 22 | 3 | 25 | 53.909 | 11.528 | 46.909 | 352.20 | 0.906 |
| 22 | 3 | 27 | 124.243 | 6.185 | 215.072 | 205.02 | 0.978 |
| 22 | 4 | 0 | 153.792 | 4.951 | 235.788 | 180.00 | 1.000 |
| 22 | 4 | 2 | 254.742 | 3.952 | 370.681 | 236.69 | 0.994 |
| 22 | 4 | 4 | 70.954 | 10.274 | 113.630 | 67.88 | 0.828 |
| 22 | 4 | 6 | 79.463 | 8.729 | 112.045 | 335.54 | 0.920 |
| 22 | 4 | 8 | 193.161 | 3.294 | 318.059 | 353.89 | 0.987 |
| 22 | 4 | 10 | 48.919 | 8.610 | 22.306 | 72.87 | 0.865 |
| 22 | 4 | 12 | 102.010 | 6.986 | 182.556 | 341.60 | 0.826 |
| 22 | 4 | 14 | 153.895 | 4.898 | 267.219 | 127.43 | 0.976 |
| 22 | 4 | 16 | 82.911 | 6.604 | 110.989 | 198.95 | 0.926 |
| 22 | 4 | 18 | 97.672 | 5.793 | 159.482 | 125.11 | 0.939 |
| 22 | 4 | 20 | 71.268 | 8.988 | 107.769 | 345.97 | 0.873 |
| 22 | 4 | 22 | 54.159 | 10.626 | 77.486 | 255.28 | 0.842 |
| 22 | 4 | 24 | 115.058 | 5.385 | 178.412 | 359.26 | 0.977 |
| 22 | 4 | 26 | 32.766 | 9.971 | 15.850 | 199.45 | 0.371 |
| 22 | 4 | 28 | 51.064 | 10.793 | 33.436 | 108.78 | 0.903 |
| 22 | 5 | 1 | 167.961 | 3.723 | 279.009 | 35.12 | 0.982 |
| 22 | 5 | 3 | 38.373 | 10.403 | 5.806 | 75.75 | 0.669 |
| 22 | 5 | 5 | 151.328 | 5.078 | 179.785 | 322.47 | 0.984 |
| 22 | 5 | 7 | 117.495 | 6.230 | 152.717 | 29.62 | 0.970 |
| 22 | 5 | 9 | 181.041 | 3.491 | 299.448 | 193.57 | 0.985 |
| 22 | 5 | 11 | 153.926 | 3.908 | 264.635 | 250.28 | 0.977 |
| 22 | 5 | 13 | 114.368 | 5.497 | 217.374 | 97.30 | 0.940 |
| 22 | 5 | 15 | 91.702 | 5.426 | 89.118 | 221.79 | 0.960 |
| 22 | 5 | 17 | 152.933 | 3.798 | 248.333 | 336.83 | 0.981 |
| 22 | 5 | 19 | 35.818 | 9.945 | 11.972 | 2.37 | 0.302 |
| 22 | 5 | 21 | 29.967 | 9.567 | 2.735 | 250.26 | 0.120 |
| 22 | 5 | 23 | 52.929 | 10.880 | 53.149 | 304.18 | 0.900 |
| 22 | 5 | 25 | 79.616 | 9.676 | 132.029 | 82.15 | 0.934 |

| | | | | | | | |
|---|---|---|---|---|---|---|---|
| 22 | 5 | 27 | 61.588 | 11.585 | 82.528 | 188.72 | 0.885 |
| 22 | 6 | 0 | 153.901 | 7.428 | 235.210 | 180.00 | 0.999 |
| 22 | 6 | 2 | 189.481 | 3.871 | 311.748 | 308.95 | 0.986 |
| 22 | 6 | 4 | 187.673 | 4.162 | 263.235 | 170.44 | 0.988 |
| 22 | 6 | 6 | 108.917 | 9.959 | 183.921 | 211.67 | 0.946 |
| 22 | 6 | 8 | 155.077 | 7.027 | 257.755 | 246.00 | 0.978 |
| 22 | 6 | 10 | 77.920 | 9.262 | 125.039 | 125.12 | 0.883 |
| 22 | 6 | 12 | 64.409 | 8.845 | 60.585 | 157.36 | 0.896 |
| 22 | 6 | 14 | 67.319 | 9.194 | 102.291 | 71.78 | 0.715 |
| 22 | 6 | 16 | 71.142 | 8.953 | 68.048 | 268.76 | 0.918 |
| 22 | 6 | 18 | 48.294 | 11.039 | 26.479 | 28.78 | 0.838 |
| 22 | 6 | 20 | 33.646 | 9.953 | 3.574 | 216.90 | 0.620 |
| 22 | 6 | 22 | 50.756 | 11.664 | 64.333 | 94.56 | 0.711 |
| 22 | 6 | 24 | 53.556 | 11.300 | 61.442 | 153.35 | 0.853 |
| 22 | 6 | 26 | 32.089 | 10.326 | 8.610 | 223.59 | 0.649 |
| 22 | 7 | 1 | 158.002 | 4.657 | 285.839 | 320.22 | 0.975 |
| 22 | 7 | 3 | 120.716 | 5.581 | 196.824 | 245.36 | 0.965 |
| 22 | 7 | 5 | 205.986 | 7.046 | 316.696 | 214.47 | 0.989 |
| 22 | 7 | 7 | 80.285 | 11.750 | 137.385 | 285.82 | 0.833 |
| 22 | 7 | 9 | 144.279 | 4.235 | 214.641 | 71.84 | 0.979 |
| 22 | 7 | 11 | 137.323 | 4.457 | 164.769 | 19.90 | 0.981 |
| 22 | 7 | 13 | 118.238 | 5.695 | 184.766 | 245.65 | 0.964 |
| 22 | 7 | 15 | 100.275 | 5.676 | 195.227 | 57.08 | 0.889 |
| 22 | 7 | 17 | 48.424 | 10.826 | 38.583 | 79.21 | 0.818 |
| 22 | 7 | 19 | 132.885 | 5.251 | 241.775 | 123.45 | 0.965 |
| 22 | 7 | 21 | 127.965 | 5.457 | 229.881 | 113.18 | 0.979 |
| 22 | 7 | 23 | 79.753 | 10.876 | 110.803 | 65.15 | 0.949 |
| 22 | 7 | 25 | 111.835 | 7.130 | 174.232 | 342.89 | 0.977 |
| 22 | 7 | 27 | 44.957 | 12.329 | 33.464 | 153.02 | 0.811 |
| 22 | 8 | 0 | 134.131 | 7.323 | 205.174 | 180.00 | 1.000 |
| 22 | 8 | 2 | 164.027 | 4.716 | 188.557 | 342.30 | 0.986 |
| 22 | 8 | 4 | 101.153 | 7.370 | 130.359 | 287.75 | 0.959 |
| 22 | 8 | 6 | 65.203 | 16.808 | 76.886 | 137.36 | 0.847 |
| 22 | 8 | 8 | 88.771 | 6.021 | 119.567 | 10.07 | 0.946 |
| 22 | 8 | 10 | 153.244 | 3.949 | 233.568 | 18.78 | 0.981 |
| 22 | 8 | 12 | 83.046 | 8.858 | 134.373 | 184.86 | 0.693 |
| 22 | 8 | 14 | 44.545 | 11.997 | 8.881 | 282.14 | 0.838 |
| 22 | 8 | 16 | 48.197 | 9.663 | 42.379 | 294.63 | 0.798 |
| 22 | 8 | 18 | 124.993 | 4.363 | 217.519 | 286.53 | 0.967 |
| 22 | 8 | 20 | 62.999 | 9.826 | 102.614 | 8.70 | 0.886 |
| 22 | 8 | 22 | 34.004 | 10.606 | 19.096 | 192.53 | 0.509 |
| 22 | 8 | 24 | 76.269 | 11.354 | 112.902 | 347.90 | 0.933 |
| 22 | 8 | 26 | 42.833 | 11.630 | 36.174 | 186.01 | 0.790 |
| 22 | 9 | 1 | 161.164 | 5.732 | 257.592 | 166.55 | 0.982 |
| 22 | 9 | 3 | 110.774 | 7.092 | 163.830 | 98.73 | 0.961 |
| 22 | 9 | 5 | 216.396 | 5.159 | 331.335 | 219.81 | 0.990 |
| 22 | 9 | 7 | 114.084 | 7.442 | 196.383 | 327.81 | 0.957 |
| 22 | 9 | 9 | 123.593 | 4.373 | 162.563 | 339.93 | 0.973 |
| 22 | 9 | 11 | 109.818 | 5.131 | 161.871 | 194.15 | 0.962 |
| 22 | 9 | 13 | 68.881 | 9.903 | 86.799 | 13.84 | 0.874 |
| 22 | 9 | 15 | 48.273 | 8.435 | 40.244 | 285.07 | 0.813 |
| 22 | 9 | 17 | 32.640 | 9.530 | 4.491 | 353.36 | 0.526 |
| 22 | 9 | 19 | 78.219 | 7.736 | 109.509 | 286.12 | 0.955 |
| 22 | 9 | 21 | 33.368 | 10.579 | 9.053 | 304.27 | 0.756 |
| 22 | 9 | 23 | 33.292 | 10.650 | 18.030 | 120.29 | 0.419 |
| 22 | 9 | 25 | 38.600 | 11.931 | 24.380 | 222.63 | 0.758 |
| 22 | 10 | 0 | 48.290 | 21.186 | 24.423 | 0.00 | 0.341 |
| 22 | 10 | 2 | 45.439 | 12.105 | 28.615 | 354.82 | 0.490 |
| 22 | 10 | 4 | 45.038 | 13.327 | 23.757 | 326.73 | 0.716 |
| 22 | 10 | 6 | 65.049 | 13.479 | 66.116 | 142.71 | 0.462 |
| 22 | 10 | 8 | 64.744 | 11.781 | 83.846 | 320.29 | 0.853 |
| 22 | 10 | 10 | 68.351 | 9.102 | 90.345 | 239.03 | 0.892 |
| 22 | 10 | 12 | 98.306 | 6.168 | 97.027 | 199.93 | 0.963 |
| 22 | 10 | 14 | 92.148 | 7.106 | 128.800 | 201.78 | 0.951 |
| 22 | 10 | 16 | 39.788 | 9.342 | 16.330 | 352.28 | 0.759 |
| 22 | 10 | 18 | 80.211 | 8.987 | 118.998 | 317.43 | 0.952 |
| 22 | 10 | 20 | 66.074 | 9.327 | 92.315 | 193.30 | 0.926 |
| 22 | 10 | 22 | 48.316 | 13.049 | 49.770 | 125.84 | 0.739 |
| 22 | 10 | 24 | 39.305 | 12.150 | 28.849 | 287.75 | 0.616 |
| 22 | 11 | 1 | 140.058 | 6.176 | 265.761 | 352.14 | 0.967 |
| 22 | 11 | 3 | 46.644 | 12.311 | 34.427 | 77.84 | 0.667 |
| 22 | 11 | 5 | 169.149 | 7.621 | 216.184 | 161.77 | 0.987 |
| 22 | 11 | 7 | 91.663 | 6.432 | 174.039 | 217.61 | 0.758 |
| 22 | 11 | 9 | 105.325 | 5.845 | 162.223 | 295.36 | 0.954 |
| 22 | 11 | 11 | 31.448 | 14.138 | 35.462 | 92.99 | 0.724 |
| 22 | 11 | 13 | 121.875 | 7.202 | 172.855 | 176.55 | 0.973 |
| 22 | 11 | 15 | 54.591 | 10.176 | 61.185 | 144.52 | 0.801 |

| | | | | | | | |
|---|---|---|---|---|---|---|---|
| 22 | 11 | 17 | 53.328 | 11.661 | 75.750 | 162.59 | 0.847 |
| 22 | 11 | 19 | 29.037 | 9.282 | 0.880 | 239.85 | 0.736 |
| 22 | 11 | 21 | 54.869 | 11.221 | 52.684 | 165.34 | 0.906 |
| 22 | 11 | 23 | 43.952 | 11.592 | 34.595 | 263.60 | 0.844 |
| 22 | 12 | 0 | 55.790 | 26.407 | 79.705 | 180.00 | 0.993 |
| 22 | 12 | 2 | 136.458 | 6.566 | 269.554 | 27.43 | 0.960 |
| 22 | 12 | 4 | 71.233 | 11.470 | 108.910 | 231.48 | 0.691 |
| 22 | 12 | 6 | 86.770 | 7.945 | 90.036 | 203.00 | 0.950 |
| 22 | 12 | 8 | 64.274 | 12.448 | 72.255 | 95.55 | 0.872 |
| 22 | 12 | 10 | 86.315 | 6.367 | 69.321 | 113.58 | 0.964 |
| 22 | 12 | 12 | 51.596 | 11.955 | 31.284 | 4.93 | 0.327 |
| 22 | 12 | 14 | 82.591 | 8.503 | 134.215 | 225.25 | 0.919 |
| 22 | 12 | 16 | 42.185 | 11.067 | 36.339 | 125.87 | 0.529 |
| 22 | 12 | 18 | 75.715 | 11.666 | 79.955 | 201.12 | 0.956 |
| 22 | 12 | 20 | 27.998 | 9.341 | 5.940 | 183.46 | 0.693 |
| 22 | 12 | 22 | 52.294 | 11.945 | 47.248 | 112.25 | 0.899 |
| 22 | 12 | 24 | 56.120 | 11.872 | 72.248 | 74.77 | 0.820 |
| 22 | 13 | 1 | 109.336 | 7.029 | 180.990 | 11.17 | 0.950 |
| 22 | 13 | 3 | 168.158 | 7.323 | 229.859 | 313.56 | 0.985 |
| 22 | 13 | 5 | 62.856 | 10.280 | 79.247 | 138.84 | 0.775 |
| 22 | 13 | 7 | 94.509 | 12.707 | 171.096 | 50.75 | 0.922 |
| 22 | 13 | 9 | 96.877 | 7.185 | 120.218 | 9.90 | 0.962 |
| 22 | 13 | 11 | 51.854 | 12.218 | 50.801 | 355.93 | 0.681 |
| 22 | 13 | 13 | 157.528 | 6.171 | 274.772 | 144.02 | 0.980 |
| 22 | 13 | 15 | 105.567 | 5.980 | 166.877 | 55.31 | 0.975 |
| 22 | 13 | 17 | 38.084 | 11.473 | 9.969 | 301.57 | 0.180 |
| 22 | 13 | 19 | 46.431 | 12.632 | 52.507 | 313.30 | 0.732 |
| 22 | 13 | 21 | 35.179 | 11.003 | 15.357 | 265.29 | 0.751 |
| 22 | 13 | 23 | 42.765 | 12.129 | 22.983 | 190.38 | 0.327 |
| 22 | 14 | 0 | 36.557 | 23.047 | 11.158 | 180.00 | 0.216 |
| 22 | 14 | 2 | 64.976 | 12.077 | 100.293 | 173.85 | 0.781 |
| 22 | 14 | 4 | 68.087 | 12.513 | 93.624 | 21.79 | 0.880 |
| 22 | 14 | 6 | 33.621 | 9.502 | 2.795 | 200.66 | 0.592 |
| 22 | 14 | 8 | 72.800 | 10.504 | 74.638 | 303.05 | 0.933 |
| 22 | 14 | 10 | 142.616 | 5.019 | 277.871 | 356.12 | 0.971 |
| 22 | 14 | 12 | 63.369 | 9.588 | 71.198 | 168.03 | 0.501 |
| 22 | 14 | 14 | 92.890 | 8.753 | 171.066 | 25.38 | 0.951 |
| 22 | 14 | 16 | 54.304 | 11.769 | 59.772 | 32.64 | 0.893 |
| 22 | 14 | 18 | 122.459 | 6.600 | 262.236 | 345.80 | 0.965 |
| 22 | 14 | 20 | 43.810 | 12.501 | 37.257 | 160.62 | 0.789 |
| 22 | 14 | 22 | 34.715 | 10.882 | 0.845 | 151.52 | 0.043 |
| 22 | 15 | 1 | 29.768 | 9.652 | 25.759 | 321.00 | 0.670 |
| 22 | 15 | 3 | 28.496 | 8.917 | 5.884 | 178.37 | 0.427 |
| 22 | 15 | 5 | 56.826 | 10.143 | 72.477 | 216.17 | 0.834 |
| 22 | 15 | 7 | 98.696 | 12.415 | 127.945 | 190.10 | 0.959 |
| 22 | 15 | 9 | 87.332 | 7.616 | 167.468 | 133.13 | 0.885 |
| 22 | 15 | 11 | 114.183 | 6.376 | 185.453 | 353.99 | 0.979 |
| 22 | 15 | 13 | 78.190 | 9.499 | 121.843 | 325.38 | 0.949 |
| 22 | 15 | 15 | 127.753 | 7.282 | 198.983 | 340.27 | 0.983 |
| 22 | 15 | 17 | 48.843 | 12.404 | 47.582 | 298.71 | 0.861 |
| 22 | 15 | 19 | 35.882 | 10.917 | 27.717 | 186.80 | 0.625 |
| 22 | 15 | 21 | 51.041 | 13.066 | 53.518 | 40.30 | 0.689 |
| 22 | 16 | 0 | 54.750 | 15.651 | 41.249 | 180.00 | 0.512 |
| 22 | 16 | 2 | 77.870 | 7.209 | 142.463 | 308.93 | 0.871 |
| 22 | 16 | 4 | 80.016 | 5.961 | 118.328 | 219.25 | 0.931 |
| 22 | 16 | 6 | 55.212 | 8.183 | 67.829 | 185.12 | 0.826 |
| 22 | 16 | 8 | 63.405 | 8.356 | 76.060 | 209.32 | 0.937 |
| 22 | 16 | 10 | 116.853 | 7.362 | 167.387 | 322.85 | 0.982 |
| 22 | 16 | 12 | 86.804 | 9.147 | 134.518 | 44.86 | 0.959 |
| 22 | 16 | 14 | 44.229 | 12.060 | 44.690 | 268.12 | 0.761 |
| 22 | 16 | 16 | 35.440 | 11.226 | 17.091 | 44.95 | 0.744 |
| 22 | 16 | 18 | 39.778 | 11.419 | 34.188 | 177.57 | 0.617 |
| 22 | 17 | 1 | 81.398 | 6.010 | 134.693 | 189.41 | 0.956 |
| 22 | 17 | 3 | 47.590 | 12.089 | 51.674 | 128.13 | 0.851 |
| 22 | 17 | 5 | 71.494 | 11.544 | 77.728 | 101.30 | 0.954 |
| 22 | 17 | 7 | 57.711 | 12.496 | 91.343 | 38.85 | 0.806 |
| 22 | 17 | 9 | 30.886 | 10.439 | 12.230 | 77.61 | 0.482 |
| 22 | 17 | 11 | 33.906 | 10.390 | 16.951 | 62.29 | 0.578 |
| 22 | 17 | 13 | 52.572 | 10.042 | 36.249 | 194.81 | 0.933 |
| 22 | 17 | 15 | 36.288 | 10.900 | 11.253 | 273.45 | 0.191 |
| 22 | 17 | 17 | 59.315 | 13.545 | 81.856 | 17.39 | 0.778 |
| 22 | 18 | 0 | 166.702 | 12.714 | 245.639 | 0.00 | 1.000 |
| 22 | 18 | 2 | 46.549 | 12.996 | 39.730 | 107.92 | 0.867 |
| 22 | 18 | 4 | 55.068 | 10.712 | 63.366 | 3.16 | 0.910 |
| 22 | 18 | 6 | 39.362 | 11.795 | 33.826 | 39.14 | 0.685 |
| 22 | 18 | 8 | 85.025 | 8.474 | 106.589 | 183.33 | 0.966 |
| 22 | 18 | 10 | 38.782 | 11.955 | 6.688 | 109.46 | 0.131 |

| | | | | | | | |
|---|---|---|---|---|---|---|---|
| 22 | 18 | 12 | 47.397 | 11.692 | 56.809 | 249.91 | 0.825 |
| 22 | 18 | 14 | 56.840 | 11.961 | 65.016 | 91.50 | 0.900 |
| 22 | 18 | 16 | 28.236 | 9.309 | 5.574 | 75.20 | 0.185 |
| 22 | 19 | 1 | 46.841 | 14.633 | 38.011 | 319.95 | 0.846 |
| 22 | 19 | 3 | 74.380 | 13.370 | 71.916 | 27.92 | 0.954 |
| 22 | 19 | 5 | 32.211 | 10.557 | 16.568 | 106.46 | 0.567 |
| 22 | 19 | 7 | 55.136 | 15.610 | 47.906 | 224.73 | 0.456 |
| 22 | 19 | 9 | 55.448 | 13.097 | 77.486 | 279.22 | 0.747 |
| 22 | 19 | 11 | 81.057 | 11.533 | 114.226 | 36.92 | 0.950 |
| 22 | 19 | 13 | 40.172 | 12.168 | 26.495 | 120.04 | 0.772 |
| 22 | 20 | 0 | 52.768 | 27.094 | 59.794 | 180.00 | 0.941 |
| 22 | 20 | 2 | 45.517 | 12.498 | 48.450 | 214.39 | 0.776 |
| 22 | 20 | 4 | 35.434 | 11.356 | 16.724 | 200.68 | 0.791 |
| 22 | 20 | 6 | 54.775 | 13.218 | 66.806 | 296.43 | 0.680 |
| 22 | 20 | 8 | 80.243 | 11.587 | 138.534 | 131.48 | 0.926 |
| 22 | 20 | 10 | 43.211 | 12.749 | 33.324 | 152.55 | 0.545 |
| 22 | 20 | 12 | 37.828 | 12.108 | 23.746 | 20.25 | 0.444 |
| 22 | 21 | 1 | 33.061 | 11.577 | 14.039 | 291.99 | 0.554 |
| 22 | 21 | 3 | 44.184 | 12.466 | 18.255 | 259.17 | 0.890 |
| 22 | 21 | 5 | 33.398 | 10.552 | 18.921 | 234.02 | 0.595 |
| 22 | 21 | 7 | 40.898 | 13.491 | 23.281 | 195.12 | 0.497 |
| 22 | 22 | 2 | 57.206 | 13.855 | 67.979 | 7.86 | 0.748 |
| 23 | 0 | 5 | 53.823 | 13.681 | 73.071 | 180.00 | 0.891 |
| 23 | 0 | 7 | 50.299 | 20.165 | 70.696 | 180.00 | 0.940 |
| 23 | 0 | 9 | 54.752 | 15.486 | 36.967 | 180.00 | 0.447 |
| 23 | 0 | 11 | 49.423 | 15.587 | 41.395 | 180.00 | 0.558 |
| 23 | 0 | 13 | 44.227 | 14.304 | 64.927 | 0.00 | 0.981 |
| 23 | 0 | 15 | 126.322 | 6.164 | 191.953 | 0.00 | 1.000 |
| 23 | 0 | 17 | 28.341 | 12.637 | 26.586 | 180.00 | 0.634 |
| 23 | 0 | 19 | 41.312 | 16.258 | 55.836 | 0.00 | 0.941 |
| 23 | 0 | 21 | 41.627 | 15.936 | 40.711 | 180.00 | 0.692 |
| 23 | 0 | 23 | 42.382 | 16.806 | 27.136 | 180.00 | 0.467 |
| 23 | 0 | 25 | 46.993 | 18.792 | 55.715 | 0.00 | 0.912 |
| 23 | 1 | 4 | 90.565 | 7.189 | 106.169 | 111.30 | 0.953 |
| 23 | 1 | 6 | 68.664 | 7.899 | 77.657 | 236.14 | 0.471 |
| 23 | 1 | 8 | 97.813 | 5.014 | 142.295 | 282.70 | 0.953 |
| 23 | 1 | 10 | 126.116 | 5.830 | 160.404 | 230.13 | 0.976 |
| 23 | 1 | 12 | 32.493 | 8.850 | 4.682 | 7.24 | 0.530 |
| 23 | 1 | 14 | 90.258 | 4.123 | 188.813 | 80.59 | 0.854 |
| 23 | 1 | 16 | 31.338 | 8.863 | 42.051 | 173.41 | 0.814 |
| 23 | 1 | 18 | 39.955 | 10.216 | 2.298 | 68.21 | 0.799 |
| 23 | 1 | 20 | 92.451 | 6.891 | 145.747 | 74.99 | 0.965 |
| 23 | 1 | 22 | 95.447 | 7.468 | 193.796 | 33.53 | 0.925 |
| 23 | 1 | 24 | 48.116 | 11.698 | 25.014 | 306.99 | 0.908 |
| 23 | 1 | 26 | 32.380 | 10.710 | 8.675 | 336.96 | 0.378 |
| 23 | 2 | 1 | 70.344 | 8.312 | 80.364 | 279.47 | 0.912 |
| 23 | 2 | 3 | 76.329 | 8.672 | 99.389 | 192.33 | 0.919 |
| 23 | 2 | 5 | 34.715 | 14.532 | 7.755 | 283.62 | 0.581 |
| 23 | 2 | 7 | 69.963 | 7.872 | 115.331 | 304.84 | 0.835 |
| 23 | 2 | 9 | 48.602 | 7.510 | 13.620 | 177.86 | 0.896 |
| 23 | 2 | 11 | 65.794 | 10.405 | 88.817 | 216.44 | 0.873 |
| 23 | 2 | 13 | 83.169 | 7.499 | 127.557 | 312.37 | 0.914 |
| 23 | 2 | 15 | 56.507 | 8.071 | 61.607 | 149.77 | 0.865 |
| 23 | 2 | 17 | 95.536 | 4.923 | 166.672 | 307.41 | 0.942 |
| 23 | 2 | 19 | 86.933 | 7.052 | 160.982 | 43.24 | 0.948 |
| 23 | 2 | 21 | 57.033 | 10.757 | 81.959 | 30.61 | 0.697 |
| 23 | 2 | 23 | 47.570 | 11.805 | 27.175 | 127.82 | 0.906 |
| 23 | 2 | 25 | 120.614 | 7.759 | 184.234 | 115.49 | 0.980 |
| 23 | 3 | 0 | 205.799 | 4.928 | 318.346 | 180.00 | 1.000 |
| 23 | 3 | 2 | 167.026 | 3.595 | 281.698 | 268.84 | 0.983 |
| 23 | 3 | 4 | 84.044 | 6.661 | 150.747 | 245.40 | 0.899 |
| 23 | 3 | 6 | 146.401 | 4.302 | 171.729 | 51.90 | 0.984 |
| 23 | 3 | 8 | 81.226 | 4.777 | 109.009 | 8.57 | 0.930 |
| 23 | 3 | 10 | 92.294 | 4.928 | 144.110 | 18.58 | 0.931 |
| 23 | 3 | 12 | 40.054 | 10.389 | 17.261 | 119.72 | 0.481 |
| 23 | 3 | 14 | 76.646 | 9.806 | 94.503 | 270.98 | 0.935 |
| 23 | 3 | 16 | 35.085 | 9.591 | 12.016 | 212.46 | 0.430 |
| 23 | 3 | 18 | 111.935 | 4.779 | 169.212 | 239.04 | 0.966 |
| 23 | 3 | 20 | 43.473 | 10.990 | 35.339 | 264.09 | 0.841 |
| 23 | 3 | 22 | 54.006 | 11.448 | 75.596 | 87.09 | 0.829 |
| 23 | 3 | 24 | 43.592 | 11.744 | 36.115 | 132.50 | 0.835 |
| 23 | 3 | 26 | 36.514 | 11.530 | 23.334 | 209.85 | 0.497 |
| 23 | 4 | 1 | 60.305 | 8.453 | 82.465 | 189.83 | 0.791 |
| 23 | 4 | 3 | 177.522 | 5.020 | 333.374 | 213.78 | 0.982 |
| 23 | 4 | 5 | 112.787 | 5.776 | 184.470 | 190.79 | 0.961 |
| 23 | 4 | 7 | 137.903 | 5.142 | 181.883 | 68.15 | 0.979 |
| 23 | 4 | 9 | 118.662 | 4.134 | 194.596 | 164.22 | 0.962 |

| | | | | | | | |
|---|---|---|---|---|---|---|---|
| 23 | 4 | 11 | 57.764 | 8.611 | 56.711 | 267.89 | 0.510 |
| 23 | 4 | 13 | 96.204 | 6.574 | 132.534 | 100.12 | 0.960 |
| 23 | 4 | 15 | 59.356 | 10.743 | 62.974 | 305.93 | 0.882 |
| 23 | 4 | 17 | 40.807 | 11.049 | 12.558 | 3.04 | 0.741 |
| 23 | 4 | 19 | 34.220 | 10.003 | 18.456 | 350.38 | 0.498 |
| 23 | 4 | 21 | 52.837 | 11.569 | 53.939 | 105.64 | 0.482 |
| 23 | 4 | 23 | 79.835 | 9.322 | 116.903 | 44.72 | 0.954 |
| 23 | 4 | 25 | 55.092 | 11.860 | 56.780 | 353.75 | 0.901 |
| 23 | 5 | 0 | 259.028 | 7.624 | 399.544 | 0.00 | 1.000 |
| 23 | 5 | 2 | 46.368 | 11.628 | 23.255 | 283.14 | 0.789 |
| 23 | 5 | 4 | 128.601 | 6.206 | 180.359 | 146.69 | 0.976 |
| 23 | 5 | 6 | 222.560 | 6.159 | 373.207 | 171.32 | 0.990 |
| 23 | 5 | 8 | 34.110 | 9.919 | 2.303 | 267.13 | 0.569 |
| 23 | 5 | 10 | 33.279 | 8.819 | 14.083 | 172.98 | 0.360 |
| 23 | 5 | 12 | 92.132 | 6.424 | 139.266 | 215.98 | 0.939 |
| 23 | 5 | 14 | 59.263 | 11.439 | 79.826 | 309.09 | 0.714 |
| 23 | 5 | 16 | 144.699 | 4.837 | 256.480 | 348.14 | 0.976 |
| 23 | 5 | 18 | 128.842 | 5.546 | 236.314 | 135.21 | 0.980 |
| 23 | 5 | 20 | 54.970 | 11.984 | 54.517 | 339.02 | 0.486 |
| 23 | 5 | 22 | 44.441 | 12.296 | 43.362 | 325.60 | 0.627 |
| 23 | 5 | 24 | 53.484 | 12.116 | 71.307 | 350.73 | 0.808 |
| 23 | 6 | 1 | 44.907 | 10.267 | 33.786 | 88.12 | 0.760 |
| 23 | 6 | 3 | 88.331 | 6.305 | 137.739 | 75.22 | 0.935 |
| 23 | 6 | 5 | 93.185 | 9.983 | 27.143 | 234.41 | 0.143 |
| 23 | 6 | 7 | 174.416 | 7.376 | 320.640 | 306.50 | 0.981 |
| 23 | 6 | 9 | 114.951 | 5.135 | 213.487 | 41.36 | 0.950 |
| 23 | 6 | 11 | 61.823 | 8.951 | 86.613 | 118.41 | 0.755 |
| 23 | 6 | 13 | 131.443 | 4.881 | 245.982 | 113.77 | 0.969 |
| 23 | 6 | 15 | 110.781 | 5.701 | 160.881 | 308.07 | 0.968 |
| 23 | 6 | 17 | 66.441 | 9.236 | 98.160 | 186.84 | 0.713 |
| 23 | 6 | 19 | 59.347 | 13.123 | 83.052 | 225.91 | 0.870 |
| 23 | 6 | 21 | 42.123 | 11.746 | 38.664 | 247.92 | 0.610 |
| 23 | 6 | 23 | 38.958 | 12.100 | 9.066 | 223.27 | 0.861 |
| 23 | 6 | 25 | 38.677 | 11.538 | 18.521 | 347.44 | 0.421 |
| 23 | 7 | 0 | 29.518 | 17.774 | 9.814 | 180.00 | 0.223 |
| 23 | 7 | 2 | 167.655 | 5.537 | 267.479 | 226.77 | 0.984 |
| 23 | 7 | 4 | 84.970 | 10.862 | 140.156 | 135.04 | 0.907 |
| 23 | 7 | 6 | 122.973 | 6.825 | 169.885 | 7.01 | 0.973 |
| 23 | 7 | 8 | 159.688 | 7.625 | 206.506 | 283.54 | 0.984 |
| 23 | 7 | 10 | 63.642 | 9.225 | 87.223 | 281.05 | 0.821 |
| 23 | 7 | 12 | 122.556 | 4.637 | 226.917 | 151.43 | 0.965 |
| 23 | 7 | 14 | 38.036 | 10.605 | 10.810 | 169.79 | 0.341 |
| 23 | 7 | 16 | 101.242 | 7.483 | 127.567 | 79.28 | 0.963 |
| 23 | 7 | 18 | 58.874 | 12.297 | 73.497 | 313.46 | 0.907 |
| 23 | 7 | 20 | 58.386 | 13.311 | 79.419 | 67.09 | 0.867 |
| 23 | 7 | 22 | 63.030 | 13.154 | 92.929 | 244.58 | 0.822 |
| 23 | 7 | 24 | 45.544 | 12.090 | 20.156 | 112.08 | 0.253 |
| 23 | 8 | 1 | 164.079 | 4.598 | 312.030 | 342.61 | 0.978 |
| 23 | 8 | 3 | 110.674 | 6.356 | 163.188 | 164.23 | 0.962 |
| 23 | 8 | 5 | 87.709 | 13.249 | 90.854 | 217.09 | 0.949 |
| 23 | 8 | 7 | 118.203 | 8.053 | 196.109 | 331.72 | 0.961 |
| 23 | 8 | 9 | 34.619 | 9.820 | 7.465 | 189.96 | 0.372 |
| 23 | 8 | 11 | 37.488 | 10.032 | 15.117 | 356.93 | 0.679 |
| 23 | 8 | 13 | 76.818 | 8.336 | 84.253 | 249.14 | 0.939 |
| 23 | 8 | 15 | 42.569 | 11.544 | 25.015 | 195.09 | 0.551 |
| 23 | 8 | 17 | 44.686 | 11.661 | 27.268 | 302.00 | 0.881 |
| 23 | 8 | 19 | 81.027 | 9.848 | 107.826 | 131.95 | 0.959 |
| 23 | 8 | 21 | 39.641 | 11.973 | 33.411 | 10.92 | 0.606 |
| 23 | 8 | 23 | 42.739 | 12.649 | 33.731 | 3.17 | 0.789 |
| 23 | 9 | 0 | 62.352 | 17.939 | 83.733 | 0.00 | 0.897 |
| 23 | 9 | 2 | 34.889 | 10.957 | 2.999 | 309.78 | 0.467 |
| 23 | 9 | 4 | 80.276 | 10.413 | 131.168 | 84.80 | 0.678 |
| 23 | 9 | 6 | 39.628 | 11.296 | 14.510 | 139.45 | 0.710 |
| 23 | 9 | 8 | 68.848 | 10.318 | 100.022 | 83.32 | 0.884 |
| 23 | 9 | 10 | 48.932 | 9.735 | 24.313 | 95.43 | 0.867 |
| 23 | 9 | 12 | 56.081 | 9.349 | 43.953 | 206.64 | 0.396 |
| 23 | 9 | 14 | 56.322 | 14.143 | 62.290 | 308.02 | 0.754 |
| 23 | 9 | 16 | 71.820 | 11.172 | 97.843 | 300.23 | 0.941 |
| 23 | 9 | 18 | 38.655 | 11.276 | 30.071 | 132.46 | 0.770 |
| 23 | 9 | 20 | 41.513 | 12.105 | 40.845 | 228.61 | 0.679 |
| 23 | 9 | 22 | 32.880 | 10.640 | 11.375 | 340.20 | 0.269 |
| 23 | 10 | 1 | 73.920 | 11.452 | 118.369 | 108.27 | 0.862 |
| 23 | 10 | 3 | 46.270 | 11.722 | 15.584 | 280.99 | 0.813 |
| 23 | 10 | 5 | 44.260 | 13.367 | 27.732 | 101.93 | 0.740 |
| 23 | 10 | 7 | 118.681 | 7.575 | 209.142 | 253.48 | 0.965 |
| 23 | 10 | 9 | 84.162 | 6.014 | 122.424 | 239.35 | 0.945 |
| 23 | 10 | 11 | 46.266 | 13.654 | 26.108 | 47.01 | 0.781 |

| | | | | | | | |
|---|---|---|---|---|---|---|---|
| 23 | 10 | 13 | 83.350 | 9.259 | 108.919 | 93.32 | 0.942 |
| 23 | 10 | 15 | 32.923 | 10.372 | 14.874 | 235.62 | 0.393 |
| 23 | 10 | 17 | 46.652 | 11.969 | 56.537 | 73.07 | 0.724 |
| 23 | 10 | 19 | 59.065 | 11.880 | 89.047 | 86.55 | 0.843 |
| 23 | 10 | 21 | 34.992 | 10.865 | 20.282 | 197.25 | 0.714 |
| 23 | 11 | 0 | 72.256 | 17.551 | 90.098 | 180.00 | 0.838 |
| 23 | 11 | 2 | 67.958 | 11.985 | 68.824 | 202.32 | 0.923 |
| 23 | 11 | 4 | 101.936 | 8.377 | 207.495 | 82.14 | 0.925 |
| 23 | 11 | 6 | 74.006 | 15.064 | 107.812 | 281.98 | 0.883 |
| 23 | 11 | 8 | 54.586 | 10.051 | 32.497 | 306.89 | 0.897 |
| 23 | 11 | 10 | 50.219 | 11.716 | 37.751 | 319.14 | 0.831 |
| 23 | 11 | 12 | 79.230 | 9.302 | 100.272 | 197.48 | 0.937 |
| 23 | 11 | 14 | 33.765 | 10.168 | 19.865 | 199.07 | 0.713 |
| 23 | 11 | 16 | 47.540 | 11.708 | 54.207 | 90.82 | 0.803 |
| 23 | 11 | 18 | 41.539 | 11.902 | 42.666 | 341.87 | 0.644 |
| 23 | 11 | 20 | 28.534 | 9.533 | 8.131 | 36.62 | 0.338 |
| 23 | 11 | 22 | 37.107 | 11.072 | 21.954 | 27.16 | 0.502 |
| 23 | 12 | 1 | 85.449 | 11.617 | 150.213 | 322.73 | 0.906 |
| 23 | 12 | 3 | 61.820 | 12.763 | 60.782 | 287.80 | 0.901 |
| 23 | 12 | 5 | 109.249 | 12.024 | 193.409 | 347.56 | 0.951 |
| 23 | 12 | 7 | 43.077 | 11.375 | 1.902 | 64.48 | 0.853 |
| 23 | 12 | 9 | 42.902 | 11.214 | 17.851 | 328.86 | 0.794 |
| 23 | 12 | 11 | 113.322 | 6.439 | 187.862 | 171.32 | 0.978 |
| 23 | 12 | 13 | 167.722 | 6.131 | 300.454 | 212.08 | 0.989 |
| 23 | 12 | 15 | 117.054 | 12.045 | 165.770 | 201.82 | 0.978 |
| 23 | 12 | 17 | 39.645 | 11.354 | 36.117 | 348.97 | 0.712 |
| 23 | 12 | 19 | 31.477 | 10.451 | 11.468 | 214.89 | 0.633 |
| 23 | 12 | 21 | 35.707 | 11.553 | 20.178 | 49.40 | 0.670 |
| 23 | 13 | 0 | 47.886 | 22.816 | 19.375 | 0.00 | 0.284 |
| 23 | 13 | 2 | 44.654 | 12.438 | 31.920 | 95.25 | 0.617 |
| 23 | 13 | 4 | 66.566 | 14.503 | 90.272 | 275.90 | 0.854 |
| 23 | 13 | 6 | 54.572 | 10.682 | 64.733 | 58.73 | 0.773 |
| 23 | 13 | 8 | 47.435 | 13.641 | 36.477 | 185.35 | 0.746 |
| 23 | 13 | 10 | 35.741 | 10.781 | 17.191 | 349.33 | 0.801 |
| 23 | 13 | 12 | 54.798 | 12.177 | 74.273 | 285.64 | 0.865 |
| 23 | 13 | 14 | 53.265 | 11.744 | 72.463 | 149.98 | 0.815 |
| 23 | 13 | 16 | 40.173 | 11.536 | 26.232 | 289.73 | 0.404 |
| 23 | 13 | 18 | 48.249 | 11.795 | 48.194 | 78.50 | 0.854 |
| 23 | 13 | 20 | 38.486 | 12.384 | 25.896 | 200.52 | 0.693 |
| 23 | 14 | 1 | 40.337 | 11.480 | 16.294 | 270.40 | 0.699 |
| 23 | 14 | 3 | 40.690 | 12.881 | 13.116 | 294.37 | 0.388 |
| 23 | 14 | 5 | 49.906 | 14.615 | 5.094 | 133.46 | 0.879 |
| 23 | 14 | 7 | 39.675 | 10.069 | 38.604 | 58.99 | 0.634 |
| 23 | 14 | 9 | 55.388 | 11.697 | 84.971 | 274.27 | 0.818 |
| 23 | 14 | 11 | 53.803 | 12.382 | 71.605 | 17.74 | 0.671 |
| 23 | 14 | 13 | 103.145 | 8.076 | 101.525 | 126.86 | 0.982 |
| 23 | 14 | 15 | 45.811 | 13.013 | 28.229 | 58.27 | 0.887 |
| 23 | 14 | 17 | 41.426 | 12.727 | 5.705 | 74.33 | 0.886 |
| 23 | 14 | 19 | 61.771 | 13.878 | 59.129 | 359.99 | 0.911 |
| 23 | 15 | 0 | 53.294 | 17.804 | 24.043 | 0.00 | 0.312 |
| 23 | 15 | 2 | 57.205 | 11.612 | 85.594 | 78.30 | 0.875 |
| 23 | 15 | 4 | 37.569 | 11.377 | 26.692 | 250.59 | 0.745 |
| 23 | 15 | 6 | 45.061 | 12.207 | 37.389 | 306.63 | 0.428 |
| 23 | 15 | 8 | 109.303 | 13.578 | 210.845 | 275.22 | 0.953 |
| 23 | 15 | 10 | 111.501 | 8.988 | 211.006 | 329.85 | 0.967 |
| 23 | 15 | 12 | 77.881 | 11.687 | 139.801 | 53.09 | 0.889 |
| 23 | 15 | 14 | 70.595 | 11.582 | 98.913 | 187.05 | 0.936 |
| 23 | 15 | 16 | 97.392 | 11.543 | 152.689 | 83.80 | 0.962 |
| 23 | 16 | 1 | 40.057 | 12.247 | 34.294 | 148.46 | 0.611 |
| 23 | 16 | 3 | 102.448 | 13.829 | 125.888 | 283.69 | 0.975 |
| 23 | 16 | 5 | 36.730 | 11.843 | 19.144 | 4.31 | 0.382 |
| 23 | 16 | 7 | 55.143 | 13.480 | 74.397 | 241.84 | 0.761 |
| 23 | 16 | 9 | 37.238 | 12.258 | 12.397 | 55.37 | 0.825 |
| 23 | 16 | 11 | 62.435 | 14.347 | 90.999 | 351.63 | 0.783 |
| 23 | 16 | 13 | 86.947 | 11.333 | 169.806 | 210.98 | 0.906 |
| 23 | 16 | 15 | 33.109 | 14.280 | 5.933 | 264.83 | 0.637 |
| 23 | 17 | 0 | 81.915 | 25.565 | 92.185 | 180.00 | 0.876 |
| 23 | 17 | 2 | 47.645 | 13.931 | 17.396 | 79.96 | 0.901 |
| 23 | 17 | 4 | 44.261 | 14.088 | 35.834 | 188.50 | 0.821 |
| 23 | 17 | 6 | 52.663 | 13.087 | 57.721 | 200.25 | 0.876 |
| 23 | 17 | 8 | 80.036 | 15.026 | 118.570 | 119.23 | 0.935 |
| 23 | 17 | 10 | 50.097 | 13.818 | 5.717 | 325.57 | 0.070 |
| 23 | 17 | 12 | 49.036 | 13.800 | 55.712 | 27.95 | 0.778 |
| 23 | 17 | 14 | 33.546 | 10.984 | 14.759 | 58.20 | 0.467 |
| 23 | 18 | 1 | 31.652 | 10.528 | 5.861 | 247.41 | 0.751 |
| 23 | 18 | 3 | 86.591 | 11.998 | 160.077 | 105.30 | 0.932 |
| 23 | 18 | 5 | 57.723 | 14.124 | 22.075 | 115.83 | 0.214 |

| | | | | | | | |
|---|---|---|---|---|---|---|---|
| 23 | 18 | 7 | 47.222 | 13.646 | 29.815 | 92.11 | 0.380 |
| 23 | 18 | 9 | 36.848 | 11.372 | 23.318 | 245.21 | 0.414 |
| 23 | 18 | 11 | 37.965 | 11.841 | 26.207 | 355.83 | 0.739 |
| 23 | 19 | 0 | 25.498 | 18.198 | 6.761 | 180.00 | 0.213 |
| 23 | 19 | 2 | 42.426 | 13.541 | 36.938 | 165.61 | 0.752 |
| 23 | 19 | 4 | 82.625 | 12.947 | 148.170 | 40.87 | 0.905 |
| 23 | 19 | 6 | 38.571 | 11.942 | 24.307 | 334.23 | 0.412 |
| 23 | 19 | 8 | 58.087 | 15.562 | 54.002 | 107.09 | 0.876 |
| 23 | 20 | 1 | 37.964 | 12.179 | 20.185 | 99.80 | 0.765 |
| 23 | 20 | 3 | 32.215 | 10.407 | 16.491 | 210.46 | 0.482 |
| 24 | 0 | 6 | 14.159 | 10.180 | 8.251 | 0.00 | 0.406 |
| 24 | 0 | 8 | 54.986 | 18.422 | 68.295 | 0.00 | 0.832 |
| 24 | 0 | 10 | 29.813 | 18.851 | 15.912 | 180.00 | 0.368 |
| 24 | 0 | 12 | 153.908 | 7.993 | 236.047 | 0.00 | 1.000 |
| 24 | 0 | 14 | 35.344 | 15.482 | 51.835 | 180.00 | 0.993 |
| 24 | 0 | 16 | 32.701 | 15.476 | 25.580 | 180.00 | 0.536 |
| 24 | 0 | 18 | 33.700 | 15.446 | 12.028 | 180.00 | 0.249 |
| 24 | 0 | 20 | 31.206 | 14.858 | 16.188 | 180.00 | 0.367 |
| 24 | 0 | 22 | 29.077 | 13.814 | 28.739 | 180.00 | 0.704 |
| 24 | 1 | 5 | 66.445 | 14.510 | 93.578 | 152.47 | 0.784 |
| 24 | 1 | 7 | 32.254 | 9.741 | 14.549 | 25.44 | 0.630 |
| 24 | 1 | 9 | 41.627 | 9.905 | 9.013 | 126.32 | 0.848 |
| 24 | 1 | 11 | 55.716 | 11.819 | 45.989 | 291.01 | 0.418 |
| 24 | 1 | 13 | 54.759 | 11.642 | 42.609 | 32.79 | 0.884 |
| 24 | 1 | 15 | 67.978 | 11.422 | 117.401 | 200.88 | 0.903 |
| 24 | 1 | 17 | 90.446 | 8.840 | 142.792 | 15.87 | 0.963 |
| 24 | 1 | 19 | 35.816 | 11.338 | 11.962 | 350.52 | 0.788 |
| 24 | 1 | 21 | 29.621 | 10.104 | 6.352 | 311.96 | 0.534 |
| 24 | 1 | 23 | 65.937 | 11.737 | 86.415 | 12.45 | 0.641 |
| 24 | 2 | 2 | 91.019 | 9.675 | 131.304 | 168.29 | 0.943 |
| 24 | 2 | 4 | 35.536 | 13.707 | 2.492 | 340.90 | 0.477 |
| 24 | 2 | 6 | 31.988 | 13.990 | 4.926 | 193.30 | 0.380 |
| 24 | 2 | 8 | 124.415 | 6.504 | 205.763 | 228.21 | 0.972 |
| 24 | 2 | 10 | 31.406 | 8.396 | 17.769 | 306.39 | 0.749 |
| 24 | 2 | 12 | 89.328 | 7.208 | 124.668 | 255.16 | 0.954 |
| 24 | 2 | 14 | 55.779 | 9.745 | 71.106 | 329.93 | 0.662 |
| 24 | 2 | 16 | 68.960 | 11.645 | 121.177 | 103.37 | 0.887 |
| 24 | 2 | 18 | 90.999 | 7.958 | 150.116 | 321.81 | 0.962 |
| 24 | 2 | 20 | 32.428 | 10.405 | 7.481 | 12.14 | 0.787 |
| 24 | 2 | 22 | 42.164 | 12.437 | 36.936 | 17.41 | 0.704 |
| 24 | 3 | 1 | 51.153 | 8.314 | 37.907 | 13.69 | 0.865 |
| 24 | 3 | 3 | 97.209 | 7.683 | 148.062 | 133.63 | 0.950 |
| 24 | 3 | 5 | 55.404 | 15.870 | 52.348 | 112.96 | 0.538 |
| 24 | 3 | 7 | 88.135 | 7.373 | 96.880 | 19.40 | 0.959 |
| 24 | 3 | 9 | 139.010 | 3.481 | 224.444 | 147.73 | 0.979 |
| 24 | 3 | 11 | 49.855 | 9.004 | 50.257 | 127.38 | 0.739 |
| 24 | 3 | 13 | 84.334 | 6.100 | 52.178 | 189.67 | 0.965 |
| 24 | 3 | 15 | 99.751 | 6.132 | 168.262 | 182.36 | 0.969 |
| 24 | 3 | 17 | 27.217 | 9.309 | 6.449 | 70.70 | 0.464 |
| 24 | 3 | 19 | 47.049 | 12.068 | 51.347 | 263.99 | 0.819 |
| 24 | 3 | 21 | 52.990 | 12.299 | 66.360 | 323.53 | 0.684 |
| 24 | 3 | 23 | 36.866 | 11.311 | 10.601 | 264.27 | 0.832 |
| 24 | 4 | 0 | 64.752 | 16.250 | 98.238 | 0.00 | 1.000 |
| 24 | 4 | 2 | 85.836 | 6.145 | 115.282 | 88.89 | 0.945 |
| 24 | 4 | 4 | 116.208 | 5.046 | 166.014 | 170.53 | 0.970 |
| 24 | 4 | 6 | 80.968 | 6.786 | 125.662 | 294.65 | 0.933 |
| 24 | 4 | 8 | 109.295 | 7.154 | 185.339 | 260.74 | 0.962 |
| 24 | 4 | 10 | 115.600 | 4.170 | 166.620 | 114.17 | 0.973 |
| 24 | 4 | 12 | 72.313 | 6.992 | 115.617 | 317.54 | 0.901 |
| 24 | 4 | 14 | 119.964 | 5.624 | 137.981 | 293.31 | 0.978 |
| 24 | 4 | 16 | 35.698 | 10.917 | 24.493 | 84.47 | 0.717 |
| 24 | 4 | 18 | 65.829 | 12.181 | 108.904 | 276.05 | 0.812 |
| 24 | 4 | 20 | 67.241 | 12.109 | 81.918 | 179.74 | 0.936 |
| 24 | 4 | 22 | 58.903 | 12.701 | 80.244 | 132.58 | 0.825 |
| 24 | 5 | 1 | 38.307 | 11.647 | 8.287 | 86.31 | 0.399 |
| 24 | 5 | 3 | 84.628 | 7.817 | 116.499 | 203.53 | 0.938 |
| 24 | 5 | 5 | 94.292 | 6.580 | 185.159 | 276.11 | 0.923 |
| 24 | 5 | 7 | 135.009 | 5.182 | 235.870 | 322.32 | 0.975 |
| 24 | 5 | 9 | 57.552 | 6.792 | 70.791 | 301.31 | 0.869 |
| 24 | 5 | 11 | 90.078 | 10.545 | 161.505 | 271.75 | 0.916 |
| 24 | 5 | 13 | 117.404 | 5.531 | 206.270 | 6.62 | 0.965 |
| 24 | 5 | 15 | 34.736 | 10.401 | 26.351 | 317.29 | 0.600 |
| 24 | 5 | 17 | 50.311 | 11.637 | 60.012 | 97.82 | 0.632 |
| 24 | 5 | 19 | 45.595 | 12.365 | 42.019 | 153.12 | 0.856 |
| 24 | 5 | 21 | 38.059 | 11.907 | 20.034 | 186.08 | 0.376 |
| 24 | 6 | 0 | 67.538 | 12.292 | 99.433 | 0.00 | 0.960 |
| 24 | 6 | 2 | 90.467 | 7.381 | 115.596 | 206.68 | 0.959 |

| | | | | | | | |
|---|---|---|---|---|---|---|---|
| 24 | 6 | 4 | 34.007 | 10.422 | 3.297 | 358.41 | 0.666 |
| 24 | 6 | 6 | 55.834 | 11.824 | 61.646 | 230.45 | 0.549 |
| 24 | 6 | 8 | 56.179 | 13.226 | 69.091 | 343.70 | 0.679 |
| 24 | 6 | 10 | 40.437 | 11.080 | 20.358 | 305.37 | 0.649 |
| 24 | 6 | 12 | 35.840 | 9.733 | 10.591 | 124.48 | 0.661 |
| 24 | 6 | 14 | 80.791 | 8.172 | 107.111 | 22.09 | 0.962 |
| 24 | 6 | 16 | 83.364 | 10.081 | 84.646 | 88.62 | 0.969 |
| 24 | 6 | 18 | 39.447 | 11.046 | 27.714 | 94.09 | 0.433 |
| 24 | 6 | 20 | 31.522 | 10.593 | 12.643 | 88.63 | 0.677 |
| 24 | 6 | 22 | 33.794 | 11.411 | 3.750 | 15.03 | 0.147 |
| 24 | 7 | 1 | 143.800 | 4.943 | 226.353 | 145.91 | 0.982 |
| 24 | 7 | 3 | 79.379 | 7.606 | 107.410 | 131.19 | 0.940 |
| 24 | 7 | 5 | 75.043 | 9.829 | 77.242 | 331.03 | 0.943 |
| 24 | 7 | 7 | 47.272 | 13.430 | 34.646 | 3.36 | 0.799 |
| 24 | 7 | 9 | 37.246 | 14.701 | 8.595 | 202.51 | 0.310 |
| 24 | 7 | 11 | 69.623 | 6.918 | 117.069 | 311.77 | 0.874 |
| 24 | 7 | 13 | 95.262 | 6.120 | 144.028 | 21.76 | 0.972 |
| 24 | 7 | 15 | 41.048 | 10.652 | 36.658 | 305.18 | 0.554 |
| 24 | 7 | 17 | 70.898 | 9.708 | 128.888 | 31.88 | 0.897 |
| 24 | 7 | 19 | 37.572 | 11.896 | 23.632 | 340.59 | 0.784 |
| 24 | 7 | 21 | 41.535 | 13.037 | 32.979 | 238.17 | 0.749 |
| 24 | 8 | 0 | 32.382 | 19.208 | 17.711 | 0.00 | 0.373 |
| 24 | 8 | 2 | 74.454 | 9.663 | 86.198 | 154.85 | 0.935 |
| 24 | 8 | 4 | 54.691 | 12.869 | 34.006 | 84.36 | 0.894 |
| 24 | 8 | 6 | 53.742 | 10.775 | 62.751 | 51.02 | 0.707 |
| 24 | 8 | 8 | 43.029 | 13.324 | 10.642 | 156.57 | 0.859 |
| 24 | 8 | 10 | 105.653 | 6.146 | 150.266 | 164.29 | 0.967 |
| 24 | 8 | 12 | 42.080 | 10.625 | 39.336 | 357.58 | 0.836 |
| 24 | 8 | 14 | 30.688 | 9.707 | 14.770 | 85.02 | 0.392 |
| 24 | 8 | 16 | 44.602 | 10.630 | 43.168 | 324.03 | 0.644 |
| 24 | 8 | 18 | 58.285 | 14.161 | 81.266 | 238.95 | 0.787 |
| 24 | 8 | 20 | 48.030 | 14.622 | 45.957 | 270.14 | 0.604 |
| 24 | 9 | 1 | 34.737 | 10.700 | 3.800 | 200.13 | 0.740 |
| 24 | 9 | 3 | 54.576 | 12.009 | 66.724 | 232.68 | 0.784 |
| 24 | 9 | 5 | 104.229 | 7.242 | 162.741 | 56.91 | 0.961 |
| 24 | 9 | 7 | 88.838 | 9.021 | 121.511 | 132.46 | 0.951 |
| 24 | 9 | 9 | 64.836 | 15.306 | 45.581 | 238.92 | 0.348 |
| 24 | 9 | 11 | 38.400 | 12.029 | 27.185 | 211.72 | 0.768 |
| 24 | 9 | 13 | 57.015 | 14.319 | 73.344 | 100.64 | 0.868 |
| 24 | 9 | 15 | 82.899 | 11.878 | 160.819 | 197.73 | 0.880 |
| 24 | 9 | 17 | 42.301 | 11.544 | 39.246 | 317.92 | 0.802 |
| 24 | 9 | 19 | 32.767 | 11.121 | 8.973 | 44.52 | 0.270 |
| 24 | 10 | 0 | 26.816 | 17.204 | 20.166 | 180.00 | 0.518 |
| 24 | 10 | 2 | 69.127 | 12.594 | 107.942 | 248.42 | 0.725 |
| 24 | 10 | 4 | 55.318 | 12.652 | 42.299 | 288.90 | 0.886 |
| 24 | 10 | 6 | 55.030 | 14.441 | 13.393 | 342.62 | 0.905 |
| 24 | 10 | 8 | 60.426 | 12.175 | 74.877 | 197.71 | 0.925 |
| 24 | 10 | 10 | 35.501 | 11.621 | 12.672 | 191.86 | 0.798 |
| 24 | 10 | 12 | 36.809 | 12.476 | 9.462 | 22.45 | 0.819 |
| 24 | 10 | 14 | 64.506 | 14.990 | 82.268 | 299.38 | 0.907 |
| 24 | 10 | 16 | 37.815 | 13.899 | 27.333 | 251.11 | 0.644 |
| 24 | 10 | 18 | 49.129 | 12.775 | 32.792 | 67.09 | 0.363 |
| 24 | 11 | 1 | 105.877 | 7.982 | 219.313 | 162.63 | 0.932 |
| 24 | 11 | 3 | 77.081 | 10.940 | 133.530 | 143.32 | 0.871 |
| 24 | 11 | 5 | 40.391 | 12.099 | 33.302 | 2.74 | 0.459 |
| 24 | 11 | 7 | 43.339 | 13.293 | 20.560 | 315.82 | 0.885 |
| 24 | 11 | 9 | 39.867 | 13.489 | 15.126 | 179.79 | 0.845 |
| 24 | 11 | 11 | 67.383 | 10.661 | 103.759 | 77.41 | 0.923 |
| 24 | 11 | 13 | 107.059 | 13.785 | 160.295 | 327.03 | 0.968 |
| 24 | 11 | 15 | 43.649 | 12.743 | 44.122 | 43.17 | 0.670 |
| 24 | 11 | 17 | 42.439 | 11.870 | 29.777 | 190.47 | 0.832 |
| 24 | 12 | 0 | 128.129 | 9.343 | 196.377 | 0.00 | 1.000 |
| 24 | 12 | 2 | 109.423 | 7.995 | 185.614 | 119.74 | 0.976 |
| 24 | 12 | 4 | 37.918 | 11.717 | 8.518 | 96.05 | 0.137 |
| 24 | 12 | 6 | 157.794 | 6.366 | 302.850 | 318.25 | 0.987 |
| 24 | 12 | 8 | 46.794 | 12.570 | 51.911 | 276.33 | 0.843 |
| 24 | 12 | 10 | 44.778 | 17.981 | 32.811 | 220.34 | 0.716 |
| 24 | 12 | 12 | 82.792 | 11.342 | 161.127 | 136.16 | 0.818 |
| 24 | 12 | 14 | 56.007 | 13.541 | 78.242 | 102.00 | 0.837 |
| 24 | 12 | 16 | 70.402 | 15.607 | 97.099 | 90.03 | 0.901 |
| 24 | 13 | 1 | 31.007 | 10.072 | 12.963 | 138.07 | 0.526 |
| 24 | 13 | 3 | 64.464 | 12.031 | 51.377 | 99.86 | 0.951 |
| 24 | 13 | 5 | 73.423 | 14.226 | 70.693 | 75.98 | 0.954 |
| 24 | 13 | 7 | 35.998 | 11.877 | 14.274 | 173.31 | 0.807 |
| 24 | 13 | 9 | 43.618 | 12.762 | 44.165 | 227.86 | 0.704 |
| 24 | 13 | 11 | 121.313 | 7.274 | 250.518 | 309.53 | 0.972 |
| 24 | 13 | 13 | 76.739 | 12.221 | 111.856 | 356.61 | 0.944 |

| | | | | | | | |
|---|---|---|---|---|---|---|---|
| 24 | 13 | 15 | 53.956 | 15.035 | 61.217 | 171.46 | 0.722 |
| 24 | 14 | 0 | 29.891 | 18.029 | 40.239 | 0.00 | 0.958 |
| 24 | 14 | 2 | 32.972 | 10.609 | 15.669 | 52.73 | 0.550 |
| 24 | 14 | 4 | 51.367 | 14.014 | 22.452 | 106.27 | 0.919 |
| 24 | 14 | 6 | 50.581 | 15.097 | 40.481 | 296.80 | 0.442 |
| 24 | 14 | 8 | 33.370 | 11.102 | 15.867 | 77.03 | 0.771 |
| 24 | 14 | 10 | 78.679 | 10.583 | 126.472 | 0.50 | 0.946 |
| 24 | 14 | 12 | 48.179 | 16.913 | 39.495 | 267.54 | 0.667 |
| 24 | 14 | 14 | 48.263 | 12.048 | 54.626 | 297.06 | 0.837 |
| 24 | 15 | 1 | 46.695 | 11.871 | 47.558 | 7.59 | 0.585 |
| 24 | 15 | 3 | 40.229 | 11.568 | 28.685 | 251.96 | 0.820 |
| 24 | 15 | 5 | 41.335 | 12.282 | 40.421 | 286.13 | 0.645 |
| 24 | 15 | 7 | 45.386 | 12.460 | 52.751 | 324.54 | 0.687 |
| 24 | 15 | 9 | 42.094 | 13.913 | 31.878 | 359.42 | 0.525 |
| 24 | 15 | 11 | 78.606 | 11.159 | 132.572 | 235.39 | 0.931 |
| 24 | 15 | 13 | 27.940 | 12.916 | 1.522 | 102.73 | 0.398 |
| 24 | 16 | 0 | 28.900 | 18.615 | 11.127 | 180.00 | 0.289 |
| 24 | 16 | 2 | 36.874 | 11.579 | 24.477 | 118.66 | 0.411 |
| 24 | 16 | 4 | 67.567 | 15.180 | 83.782 | 137.64 | 0.922 |
| 24 | 16 | 6 | 35.961 | 10.944 | 20.339 | 197.66 | 0.768 |
| 24 | 16 | 8 | 39.154 | 11.948 | 33.966 | 211.43 | 0.677 |
| 24 | 16 | 10 | 43.279 | 12.625 | 41.068 | 219.76 | 0.788 |
| 24 | 17 | 1 | 42.398 | 12.474 | 40.412 | 25.04 | 0.588 |
| 24 | 17 | 3 | 37.154 | 12.219 | 25.736 | 16.72 | 0.568 |
| 24 | 17 | 5 | 38.253 | 12.809 | 24.222 | 270.13 | 0.638 |
| 24 | 17 | 7 | 44.633 | 13.342 | 41.149 | 231.12 | 0.598 |
| 24 | 18 | 0 | 44.832 | 22.632 | 52.391 | 180.00 | 0.954 |
| 24 | 18 | 2 | 36.243 | 11.334 | 18.231 | 217.96 | 0.358 |
| 25 | 0 | 13 | 33.980 | 20.828 | 33.968 | 180.00 | 0.733 |
| 25 | 0 | 17 | 72.552 | 25.720 | 89.345 | 0.00 | 0.995 |
| 25 | 0 | 19 | 32.253 | 20.799 | 32.541 | 180.00 | 0.818 |
| 25 | 1 | 6 | 41.806 | 14.085 | 20.403 | 79.00 | 0.689 |
| 25 | 1 | 8 | 42.873 | 16.479 | 6.772 | 50.12 | 0.766 |
| 25 | 1 | 10 | 147.776 | 4.874 | 250.303 | 113.88 | 0.988 |
| 25 | 1 | 12 | 39.891 | 12.165 | 35.996 | 152.74 | 0.749 |
| 25 | 1 | 14 | 43.347 | 13.560 | 41.691 | 351.45 | 0.695 |
| 25 | 1 | 16 | 92.797 | 12.575 | 162.740 | 199.42 | 0.951 |
| 25 | 1 | 18 | 34.506 | 16.225 | 3.294 | 79.00 | 0.261 |
| 25 | 1 | 20 | 36.724 | 17.102 | 3.629 | 132.12 | 0.368 |
| 25 | 2 | 5 | 59.605 | 13.228 | 70.268 | 221.44 | 0.870 |
| 25 | 2 | 7 | 97.048 | 8.871 | 168.678 | 42.20 | 0.694 |
| 25 | 2 | 9 | 48.171 | 18.428 | 43.711 | 169.43 | 0.799 |
| 25 | 2 | 11 | 36.522 | 11.602 | 11.912 | 153.12 | 0.892 |
| 25 | 2 | 13 | 42.974 | 12.096 | 40.733 | 36.62 | 0.822 |
| 25 | 2 | 15 | 76.741 | 14.106 | 112.219 | 313.64 | 0.933 |
| 25 | 2 | 17 | 58.419 | 13.049 | 77.100 | 265.75 | 0.895 |
| 25 | 2 | 19 | 98.721 | 12.660 | 155.088 | 214.82 | 0.961 |
| 25 | 3 | 2 | 73.872 | 9.960 | 123.808 | 148.58 | 0.890 |
| 25 | 3 | 4 | 27.904 | 12.921 | 25.832 | 58.37 | 0.555 |
| 25 | 3 | 6 | 102.005 | 13.761 | 138.623 | 208.31 | 0.960 |
| 25 | 3 | 8 | 37.472 | 14.947 | 6.294 | 293.53 | 0.222 |
| 25 | 3 | 10 | 36.090 | 11.279 | 22.792 | 346.76 | 0.776 |
| 25 | 3 | 12 | 36.962 | 11.484 | 23.697 | 300.56 | 0.447 |
| 25 | 3 | 14 | 40.502 | 12.726 | 12.079 | 333.54 | 0.864 |
| 25 | 3 | 16 | 56.160 | 14.929 | 70.282 | 358.21 | 0.849 |
| 25 | 3 | 18 | 57.481 | 15.389 | 66.459 | 7.36 | 0.671 |
| 25 | 3 | 20 | 66.189 | 15.359 | 86.647 | 5.95 | 0.754 |
| 25 | 4 | 1 | 30.669 | 9.636 | 9.760 | 22.25 | 0.682 |
| 25 | 4 | 3 | 35.180 | 9.626 | 5.736 | 295.71 | 0.196 |
| 25 | 4 | 5 | 89.560 | 11.685 | 152.312 | 335.73 | 0.930 |
| 25 | 4 | 7 | 41.322 | 17.304 | 6.396 | 113.24 | 0.246 |
| 25 | 4 | 9 | 75.316 | 19.115 | 125.010 | 271.52 | 0.814 |
| 25 | 4 | 11 | 69.893 | 14.920 | 80.155 | 267.22 | 0.942 |
| 25 | 4 | 13 | 39.312 | 12.538 | 31.987 | 238.48 | 0.537 |
| 25 | 4 | 15 | 40.112 | 18.657 | 15.436 | 359.94 | 0.821 |
| 25 | 4 | 17 | 50.960 | 14.729 | 58.513 | 83.11 | 0.788 |
| 25 | 4 | 19 | 63.350 | 14.478 | 78.700 | 118.07 | 0.886 |
| 25 | 5 | 0 | 97.222 | 9.707 | 150.826 | 180.00 | 1.000 |
| 25 | 5 | 2 | 114.335 | 6.475 | 214.955 | 271.48 | 0.961 |
| 25 | 5 | 4 | 127.744 | 6.274 | 244.145 | 353.23 | 0.969 |
| 25 | 5 | 6 | 77.295 | 15.018 | 129.139 | 76.00 | 0.797 |
| 25 | 5 | 8 | 67.438 | 15.978 | 111.815 | 263.77 | 0.846 |
| 25 | 5 | 10 | 46.594 | 13.065 | 50.032 | 28.57 | 0.834 |
| 25 | 5 | 12 | 52.853 | 13.299 | 49.676 | 0.61 | 0.898 |
| 25 | 5 | 14 | 54.090 | 15.267 | 68.317 | 225.09 | 0.743 |
| 25 | 5 | 16 | 40.272 | 19.292 | 7.963 | 340.52 | 0.765 |
| 25 | 5 | 18 | 63.713 | 17.191 | 71.919 | 237.24 | 0.677 |

| | | | | | | | |
|---|---|---|---|---|---|---|---|
| 25 | 6 | 1 | 60.670 | 12.756 | 46.206 | 212.24 | 0.906 |
| 25 | 6 | 3 | 139.337 | 5.742 | 206.267 | 273.59 | 0.982 |
| 25 | 6 | 5 | 34.492 | 11.285 | 6.240 | 211.05 | 0.627 |
| 25 | 6 | 7 | 85.254 | 13.266 | 135.688 | 126.76 | 0.954 |
| 25 | 6 | 9 | 27.869 | 13.521 | 17.123 | 221.53 | 0.681 |
| 25 | 6 | 11 | 57.870 | 13.533 | 33.731 | 138.66 | 0.290 |
| 25 | 6 | 13 | 55.724 | 14.628 | 63.100 | 25.80 | 0.886 |
| 25 | 6 | 15 | 54.256 | 15.448 | 61.493 | 29.57 | 0.636 |
| 25 | 6 | 17 | 52.545 | 15.553 | 33.655 | 228.63 | 0.899 |
| 25 | 6 | 19 | 36.870 | 12.427 | 17.144 | 89.44 | 0.745 |
| 25 | 7 | 0 | 23.144 | 15.012 | 2.120 | 0.00 | 0.063 |
| 25 | 7 | 2 | 36.673 | 10.602 | 5.884 | 338.25 | 0.731 |
| 25 | 7 | 4 | 51.521 | 12.662 | 73.243 | 72.49 | 0.728 |
| 25 | 7 | 6 | 33.895 | 10.546 | 21.634 | 261.12 | 0.684 |
| 25 | 7 | 8 | 105.447 | 24.688 | 101.667 | 99.98 | 0.966 |
| 25 | 7 | 10 | 40.045 | 12.405 | 8.204 | 65.08 | 0.876 |
| 25 | 7 | 12 | 52.842 | 13.360 | 58.541 | 5.19 | 0.887 |
| 25 | 7 | 14 | 39.809 | 12.063 | 30.496 | 317.71 | 0.818 |
| 25 | 7 | 16 | 42.713 | 13.558 | 36.693 | 285.82 | 0.701 |
| 25 | 7 | 18 | 32.918 | 11.667 | 10.108 | 318.26 | 0.477 |
| 25 | 8 | 1 | 64.741 | 9.157 | 74.139 | 196.43 | 0.948 |
| 25 | 8 | 3 | 50.815 | 16.767 | 55.685 | 341.34 | 0.826 |
| 25 | 8 | 5 | 84.997 | 8.744 | 144.814 | 329.08 | 0.957 |
| 25 | 8 | 7 | 85.850 | 11.333 | 104.324 | 163.06 | 0.968 |
| 25 | 8 | 9 | 40.011 | 18.733 | 13.817 | 231.28 | 0.520 |
| 25 | 8 | 11 | 37.484 | 16.834 | 10.009 | 41.21 | 0.459 |
| 25 | 8 | 13 | 44.434 | 13.439 | 38.567 | 56.29 | 0.821 |
| 25 | 8 | 15 | 38.408 | 11.953 | 25.528 | 120.10 | 0.791 |
| 25 | 8 | 17 | 46.919 | 13.897 | 46.457 | 13.96 | 0.782 |
| 25 | 9 | 0 | 76.981 | 16.759 | 113.265 | 180.00 | 0.999 |
| 25 | 9 | 2 | 62.136 | 11.451 | 39.837 | 130.70 | 0.955 |
| 25 | 9 | 4 | 43.112 | 10.835 | 36.833 | 214.48 | 0.852 |
| 25 | 9 | 6 | 50.846 | 11.306 | 76.704 | 343.64 | 0.770 |
| 25 | 9 | 8 | 34.354 | 11.416 | 19.411 | 108.21 | 0.700 |
| 25 | 9 | 10 | 55.106 | 23.246 | 31.579 | 335.91 | 0.728 |
| 25 | 9 | 12 | 38.672 | 17.242 | 11.248 | 31.50 | 0.469 |
| 25 | 9 | 14 | 49.225 | 14.244 | 47.036 | 141.59 | 0.853 |
| 25 | 9 | 16 | 51.954 | 14.145 | 15.898 | 288.75 | 0.173 |
| 25 | 10 | 1 | 50.285 | 12.363 | 45.839 | 2.77 | 0.901 |
| 25 | 10 | 3 | 59.770 | 11.671 | 69.828 | 5.16 | 0.508 |
| 25 | 10 | 5 | 40.238 | 11.545 | 13.450 | 221.39 | 0.879 |
| 25 | 10 | 7 | 32.458 | 11.000 | 6.794 | 160.52 | 0.771 |
| 25 | 10 | 9 | 57.636 | 14.541 | 74.829 | 68.68 | 0.862 |
| 25 | 10 | 11 | 61.164 | 14.621 | 79.224 | 215.80 | 0.888 |
| 25 | 10 | 13 | 67.145 | 16.285 | 96.296 | 256.83 | 0.803 |
| 25 | 10 | 15 | 45.785 | 18.709 | 19.769 | 50.23 | 0.643 |
| 25 | 11 | 0 | 20.429 | 14.352 | 3.596 | 180.00 | 0.127 |
| 25 | 11 | 2 | 42.399 | 11.663 | 41.979 | 172.21 | 0.754 |
| 25 | 11 | 4 | 118.012 | 7.453 | 209.029 | 233.37 | 0.978 |
| 25 | 11 | 6 | 40.741 | 11.825 | 39.271 | 247.39 | 0.750 |
| 25 | 11 | 8 | 40.871 | 12.660 | 19.667 | 82.03 | 0.866 |
| 25 | 11 | 10 | 40.910 | 12.449 | 35.947 | 169.33 | 0.699 |
| 25 | 11 | 12 | 53.356 | 14.257 | 67.352 | 283.32 | 0.801 |
| 25 | 11 | 14 | 40.774 | 13.521 | 16.769 | 297.83 | 0.286 |
| 25 | 12 | 1 | 43.764 | 11.794 | 40.428 | 55.48 | 0.830 |
| 25 | 12 | 3 | 44.949 | 12.656 | 49.753 | 81.53 | 0.681 |
| 25 | 12 | 5 | 46.219 | 12.845 | 36.390 | 346.89 | 0.410 |
| 25 | 12 | 7 | 37.470 | 11.633 | 26.729 | 39.04 | 0.494 |
| 25 | 12 | 9 | 49.403 | 15.662 | 51.204 | 248.08 | 0.686 |
| 25 | 12 | 11 | 60.873 | 14.059 | 64.858 | 311.66 | 0.914 |
| 25 | 12 | 13 | 46.291 | 14.604 | 39.332 | 351.64 | 0.651 |
| 25 | 13 | 0 | 25.303 | 16.947 | 13.284 | 0.00 | 0.390 |
| 25 | 13 | 2 | 67.331 | 12.240 | 113.027 | 346.19 | 0.878 |
| 25 | 13 | 4 | 42.420 | 12.255 | 43.251 | 317.91 | 0.638 |
| 25 | 13 | 6 | 76.186 | 15.636 | 121.797 | 292.62 | 0.879 |
| 25 | 13 | 8 | 37.153 | 11.731 | 23.514 | 252.51 | 0.520 |
| 25 | 13 | 10 | 43.294 | 14.588 | 27.986 | 180.59 | 0.816 |
| 25 | 14 | 1 | 37.913 | 11.463 | 28.827 | 25.75 | 0.749 |
| 25 | 14 | 3 | 47.494 | 12.880 | 49.241 | 279.23 | 0.560 |
| 25 | 14 | 5 | 60.592 | 12.264 | 87.397 | 313.06 | 0.891 |
| 25 | 14 | 7 | 40.518 | 13.555 | 31.320 | 6.17 | 0.615 |
| 25 | 14 | 9 | 45.000 | 12.792 | 43.118 | 62.00 | 0.794 |
| 25 | 15 | 0 | 43.924 | 22.026 | 55.216 | 0.00 | 0.992 |
| 25 | 15 | 2 | 44.451 | 13.270 | 35.113 | 357.25 | 0.844 |
| 25 | 15 | 4 | 34.857 | 11.244 | 9.395 | 73.79 | 0.795 |
| 25 | 15 | 6 | 50.826 | 13.465 | 23.173 | 219.88 | 0.277 |

Figure 2 (49 pages)

Table 5
Coordinates of the 3A4 structure

Copyright © 2002-2003 Astex Technology Ltd. All rights reserved.

| | | | | | | | | | |
|---|---|---|---|---|---|---|---|---|---|
| ATOM | 1 | CB | TYR | A | 25 | 72.487 | 110.820 | 10.819 | 1.00 97.23 | C |
| ATOM | 2 | CG | TYR | A | 25 | 71.107 | 110.469 | 10.309 | 1.00100.82 | C |
| ATOM | 3 | CD1 | TYR | A | 25 | 70.265 | 111.455 | 9.805 | 1.00102.56 | C |
| ATOM | 4 | CE1 | TYR | A | 25 | 69.008 | 111.139 | 9.305 | 1.00104.13 | C |
| ATOM | 5 | CD2 | TYR | A | 25 | 70.654 | 109.149 | 10.308 | 1.00102.04 | C |
| ATOM | 6 | CE2 | TYR | A | 25 | 69.396 | 108.821 | 9.812 | 1.00102.74 | C |
| ATOM | 7 | CZ | TYR | A | 25 | 68.577 | 109.821 | 9.308 | 1.00103.72 | C |
| ATOM | 8 | OH | TYR | A | 25 | 67.331 | 109.515 | 8.797 | 1.00103.33 | O |
| ATOM | 9 | C | TYR | A | 25 | 73.094 | 110.033 | 13.086 | 1.00 92.29 | C |
| ATOM | 10 | O | TYR | A | 25 | 73.695 | 110.229 | 14.143 | 1.00 93.41 | O |
| ATOM | 11 | N | TYR | A | 25 | 73.342 | 112.448 | 12.482 | 1.00 93.37 | N |
| ATOM | 12 | CA | TYR | A | 25 | 72.528 | 111.207 | 12.291 | 1.00 93.90 | C |
| ATOM | 13 | N | GLY | A | 26 | 72.916 | 108.818 | 12.562 | 1.00 89.43 | N |
| ATOM | 14 | CA | GLY | A | 26 | 73.386 | 107.623 | 13.253 | 1.00 84.98 | C |
| ATOM | 15 | C | GLY | A | 26 | 72.333 | 107.186 | 14.268 | 1.00 82.66 | C |
| ATOM | 16 | O | GLY | A | 26 | 72.176 | 106.005 | 14.572 | 1.00 80.58 | O |
| ATOM | 17 | N | THR | A | 27 | 71.603 | 108.172 | 14.784 | 1.00 80.91 | N |
| ATOM | 18 | CA | THR | A | 27 | 70.540 | 107.975 | 15.762 | 1.00 77.69 | C |
| ATOM | 19 | CB | THR | A | 27 | 70.871 | 108.671 | 17.104 | 1.00 76.20 | C |
| ATOM | 20 | OG1 | THR | A | 27 | 71.149 | 110.057 | 16.879 | 1.00 75.08 | O |
| ATOM | 21 | CG2 | THR | A | 27 | 72.075 | 108.039 | 17.751 | 1.00 75.93 | C |
| ATOM | 22 | C | THR | A | 27 | 69.273 | 108.604 | 15.203 | 1.00 77.49 | C |
| ATOM | 23 | O | THR | A | 27 | 68.879 | 109.690 | 15.623 | 1.00 77.61 | O |
| ATOM | 24 | N | HIS | A | 28 | 68.639 | 107.928 | 14.252 | 1.00 77.19 | N |
| ATOM | 25 | CA | HIS | A | 28 | 67.424 | 108.456 | 13.645 | 1.00 76.85 | C |
| ATOM | 26 | CB | HIS | A | 28 | 67.139 | 107.750 | 12.314 | 1.00 79.62 | C |
| ATOM | 27 | CG | HIS | A | 28 | 65.927 | 108.270 | 11.596 | 1.00 83.48 | C |
| ATOM | 28 | CD2 | HIS | A | 28 | 64.681 | 107.752 | 11.462 | 1.00 84.83 | C |
| ATOM | 29 | ND1 | HIS | A | 28 | 65.914 | 109.474 | 10.922 | 1.00 84.10 | N |
| ATOM | 30 | CE1 | HIS | A | 28 | 64.714 | 109.676 | 10.406 | 1.00 85.01 | C |
| ATOM | 31 | NE2 | HIS | A | 28 | 63.947 | 108.647 | 10.719 | 1.00 85.83 | N |
| ATOM | 32 | C | HIS | A | 28 | 66.208 | 108.328 | 14.558 | 1.00 74.82 | C |
| ATOM | 33 | O | HIS | A | 28 | 65.734 | 109.314 | 15.122 | 1.00 75.03 | O |
| ATOM | 34 | N | SER | A | 29 | 65.711 | 107.112 | 14.715 | 1.00 72.38 | N |
| ATOM | 35 | CA | SER | A | 29 | 64.525 | 106.886 | 15.529 | 1.00 71.57 | C |
| ATOM | 36 | CB | SER | A | 29 | 63.976 | 105.482 | 15.247 | 1.00 71.93 | C |
| ATOM | 37 | OG | SER | A | 29 | 63.499 | 105.371 | 13.920 | 1.00 72.29 | O |
| ATOM | 38 | C | SER | A | 29 | 64.642 | 107.070 | 17.051 | 1.00 70.35 | C |
| ATOM | 39 | O | SER | A | 29 | 63.661 | 106.879 | 17.769 | 1.00 71.64 | O |
| ATOM | 40 | N | HIS | A | 30 | 65.802 | 107.461 | 17.561 | 1.00 67.42 | N |
| ATOM | 41 | CA | HIS | A | 30 | 65.937 | 107.582 | 19.006 | 1.00 64.78 | C |
| ATOM | 42 | CB | HIS | A | 30 | 67.397 | 107.788 | 19.358 | 1.00 63.70 | C |
| ATOM | 43 | CG | HIS | A | 30 | 68.277 | 106.692 | 18.857 | 1.00 63.61 | C |
| ATOM | 44 | CD2 | HIS | A | 30 | 68.009 | 105.643 | 18.044 | 1.00 63.73 | C |
| ATOM | 45 | ND1 | HIS | A | 30 | 69.612 | 106.596 | 19.179 | 1.00 64.49 | N |
| ATOM | 46 | CE1 | HIS | A | 30 | 70.130 | 105.534 | 18.586 | 1.00 63.00 | C |
| ATOM | 47 | NE2 | HIS | A | 30 | 69.179 | 104.939 | 17.890 | 1.00 61.68 | N |
| ATOM | 48 | C | HIS | A | 30 | 65.075 | 108.606 | 19.732 | 1.00 65.09 | C |
| ATOM | 49 | O | HIS | A | 30 | 64.891 | 108.503 | 20.944 | 1.00 64.93 | O |
| ATOM | 50 | N | GLY | A | 31 | 64.538 | 109.588 | 19.016 | 1.00 65.33 | N |
| ATOM | 51 | CA | GLY | A | 31 | 63.703 | 110.564 | 19.690 | 1.00 65.70 | C |
| ATOM | 52 | C | GLY | A | 31 | 62.316 | 110.011 | 19.977 | 1.00 65.77 | C |
| ATOM | 53 | O | GLY | A | 31 | 61.573 | 110.548 | 20.802 | 1.00 64.75 | O |
| ATOM | 54 | N | LEU | A | 32 | 61.989 | 108.903 | 19.316 | 1.00 65.73 | N |
| ATOM | 55 | CA | LEU | A | 32 | 60.679 | 108.284 | 19.433 | 1.00 65.94 | C |
| ATOM | 56 | CB | LEU | A | 32 | 60.594 | 107.071 | 18.523 | 1.00 64.81 | C |
| ATOM | 57 | CG | LEU | A | 32 | 59.135 | 106.706 | 18.258 | 1.00 63.95 | C |
| ATOM | 58 | CD1 | LEU | A | 32 | 58.480 | 107.825 | 17.471 | 1.00 63.50 | C |
| ATOM | 59 | CD2 | LEU | A | 32 | 59.059 | 105.425 | 17.479 | 1.00 64.10 | C |
| ATOM | 60 | C | LEU | A | 32 | 60.147 | 107.878 | 20.798 | 1.00 66.97 | C |
| ATOM | 61 | O | LEU | A | 32 | 59.326 | 108.577 | 21.379 | 1.00 67.82 | O |
| ATOM | 62 | N | PHE | A | 33 | 60.596 | 106.742 | 21.310 | 1.00 67.60 | N |
| ATOM | 63 | CA | PHE | A | 33 | 60.083 | 106.271 | 22.587 | 1.00 68.83 | C |
| ATOM | 64 | CB | PHE | A | 33 | 60.630 | 104.873 | 22.879 | 1.00 67.54 | C |
| ATOM | 65 | CG | PHE | A | 33 | 60.189 | 103.848 | 21.870 | 1.00 66.46 | C |
| ATOM | 66 | CD1 | PHE | A | 33 | 58.931 | 103.947 | 21.283 | 1.00 66.70 | C |
| ATOM | 67 | CD2 | PHE | A | 33 | 61.021 | 102.805 | 21.492 | 1.00 64.99 | C |
| ATOM | 68 | CE1 | PHE | A | 33 | 58.513 | 103.029 | 20.338 | 1.00 64.61 | C |

| | | | | | | | | | |
|---|---|---|---|---|---|---|---|---|---|
| ATOM | 69 | CE2 | PHE | A | 33 | 60.610 | 101.886 | 20.551 | 1.00 63.25 | C |
| ATOM | 70 | CZ | PHE | A | 33 | 59.356 | 101.998 | 19.973 | 1.00 64.37 | C |
| ATOM | 71 | C | PHE | A | 33 | 60.234 | 107.188 | 23.795 | 1.00 70.22 | C |
| ATOM | 72 | O | PHE | A | 33 | 59.866 | 106.812 | 24.910 | 1.00 71.20 | O |
| ATOM | 73 | N | LYS | A | 34 | 60.763 | 108.389 | 23.575 | 1.00 70.55 | N |
| ATOM | 74 | CA | LYS | A | 34 | 60.891 | 109.376 | 24.645 | 1.00 69.93 | C |
| ATOM | 75 | CB | LYS | A | 34 | 62.222 | 110.131 | 24.564 | 1.00 71.90 | C |
| ATOM | 76 | CG | LYS | A | 34 | 63.387 | 109.478 | 25.295 | 1.00 73.81 | C |
| ATOM | 77 | CD | LYS | A | 34 | 64.564 | 110.445 | 25.394 | 1.00 75.47 | C |
| ATOM | 78 | CE | LYS | A | 34 | 65.674 | 109.886 | 26.281 | 1.00 77.21 | C |
| ATOM | 79 | NZ | LYS | A | 34 | 66.765 | 110.887 | 26.537 | 1.00 77.46 | N |
| ATOM | 80 | C | LYS | A | 34 | 59.748 | 110.355 | 24.417 | 1.00 68.46 | C |
| ATOM | 81 | O | LYS | A | 34 | 58.960 | 110.645 | 25.319 | 1.00 68.74 | O |
| ATOM | 82 | N | LYS | A | 35 | 59.664 | 110.842 | 23.186 | 1.00 66.46 | N |
| ATOM | 83 | CA | LYS | A | 35 | 58.634 | 111.784 | 22.805 | 1.00 66.62 | C |
| ATOM | 84 | CB | LYS | A | 35 | 58.909 | 112.325 | 21.402 | 1.00 66.26 | C |
| ATOM | 85 | CG | LYS | A | 35 | 57.795 | 113.205 | 20.830 | 1.00 66.44 | C |
| ATOM | 86 | CD | LYS | A | 35 | 57.041 | 112.502 | 19.689 | 1.00 68.59 | C |
| ATOM | 87 | CE | LYS | A | 35 | 57.939 | 112.236 | 18.455 | 1.00 70.14 | C |
| ATOM | 88 | NZ | LYS | A | 35 | 58.427 | 113.466 | 17.722 | 1.00 68.43 | N |
| ATOM | 89 | C | LYS | A | 35 | 57.246 | 111.161 | 22.856 | 1.00 67.15 | C |
| ATOM | 90 | O | LYS | A | 35 | 56.248 | 111.871 | 22.960 | 1.00 69.70 | O |
| ATOM | 91 | N | LEU | A | 36 | 57.171 | 109.838 | 22.791 | 1.00 66.62 | N |
| ATOM | 92 | CA | LEU | A | 36 | 55.878 | 109.164 | 22.828 | 1.00 65.69 | C |
| ATOM | 93 | CB | LEU | A | 36 | 55.904 | 107.902 | 21.961 | 1.00 66.46 | C |
| ATOM | 94 | CG | LEU | A | 36 | 54.845 | 107.819 | 20.861 | 1.00 67.00 | C |
| ATOM | 95 | CD1 | LEU | A | 36 | 55.221 | 108.732 | 19.694 | 1.00 66.21 | C |
| ATOM | 96 | CD2 | LEU | A | 36 | 54.729 | 106.377 | 20.401 | 1.00 67.42 | C |
| ATOM | 97 | C | LEU | A | 36 | 55.500 | 108.782 | 24.250 | 1.00 64.93 | C |
| ATOM | 98 | O | LEU | A | 36 | 54.343 | 108.473 | 24.528 | 1.00 64.69 | O |
| ATOM | 99 | N | GLY | A | 37 | 56.484 | 108.796 | 25.144 | 1.00 64.48 | N |
| ATOM | 100 | CA | GLY | A | 37 | 56.229 | 108.436 | 26.530 | 1.00 62.51 | C |
| ATOM | 101 | C | GLY | A | 37 | 56.243 | 106.937 | 26.802 | 1.00 60.15 | C |
| ATOM | 102 | O | GLY | A | 37 | 55.563 | 106.467 | 27.718 | 1.00 59.96 | O |
| ATOM | 103 | N | ILE | A | 38 | 57.015 | 106.187 | 26.016 | 1.00 57.42 | N |
| ATOM | 104 | CA | ILE | A | 38 | 57.115 | 104.737 | 26.188 | 1.00 53.23 | C |
| ATOM | 105 | CB | ILE | A | 38 | 56.985 | 104.001 | 24.843 | 1.00 52.64 | C |
| ATOM | 106 | CG2 | ILE | A | 38 | 57.343 | 102.529 | 25.022 | 1.00 50.88 | C |
| ATOM | 107 | CG1 | ILE | A | 38 | 55.566 | 104.180 | 24.291 | 1.00 49.92 | C |
| ATOM | 108 | CD1 | ILE | A | 38 | 55.459 | 103.937 | 22.807 | 1.00 50.27 | C |
| ATOM | 109 | C | ILE | A | 38 | 58.451 | 104.377 | 26.810 | 1.00 50.88 | C |
| ATOM | 110 | O | ILE | A | 38 | 59.499 | 104.806 | 26.347 | 1.00 49.49 | O |
| ATOM | 111 | N | PRO | A | 39 | 58.427 | 103.573 | 27.876 | 1.00 49.68 | N |
| ATOM | 112 | CD | PRO | A | 39 | 57.239 | 102.969 | 28.503 | 1.00 47.60 | C |
| ATOM | 113 | CA | PRO | A | 39 | 59.650 | 103.159 | 28.566 | 1.00 49.00 | C |
| ATOM | 114 | CB | PRO | A | 39 | 59.116 | 102.513 | 29.843 | 1.00 47.02 | C |
| ATOM | 115 | CG | PRO | A | 39 | 57.859 | 101.895 | 29.384 | 1.00 47.09 | C |
| ATOM | 116 | C | PRO | A | 39 | 60.500 | 102.202 | 27.741 | 1.00 50.32 | C |
| ATOM | 117 | O | PRO | A | 39 | 60.033 | 101.668 | 26.734 | 1.00 49.68 | O |
| ATOM | 118 | N | GLY | A | 40 | 61.744 | 101.994 | 28.183 | 1.00 52.47 | N |
| ATOM | 119 | CA | GLY | A | 40 | 62.665 | 101.094 | 27.501 | 1.00 51.82 | C |
| ATOM | 120 | C | GLY | A | 40 | 64.138 | 101.407 | 27.717 | 1.00 51.53 | C |
| ATOM | 121 | O | GLY | A | 40 | 64.498 | 102.457 | 28.241 | 1.00 51.14 | O |
| ATOM | 122 | N | PRO | A | 41 | 65.023 | 100.482 | 27.327 | 1.00 52.79 | N |
| ATOM | 123 | CD | PRO | A | 41 | 64.712 | 99.202 | 26.666 | 1.00 52.82 | C |
| ATOM | 124 | CA | PRO | A | 41 | 66.472 | 100.676 | 27.476 | 1.00 51.87 | C |
| ATOM | 125 | CB | PRO | A | 41 | 67.043 | 99.319 | 27.085 | 1.00 51.42 | C |
| ATOM | 126 | CG | PRO | A | 41 | 66.049 | 98.822 | 26.051 | 1.00 52.48 | C |
| ATOM | 127 | C | PRO | A | 41 | 66.936 | 101.800 | 26.548 | 1.00 52.52 | C |
| ATOM | 128 | O | PRO | A | 41 | 66.505 | 101.908 | 25.395 | 1.00 50.83 | O |
| ATOM | 129 | N | THR | A | 42 | 67.806 | 102.647 | 27.072 | 1.00 54.30 | N |
| ATOM | 130 | CA | THR | A | 42 | 68.325 | 103.778 | 26.330 | 1.00 56.06 | C |
| ATOM | 131 | CB | THR | A | 42 | 68.918 | 104.810 | 27.313 | 1.00 58.36 | C |
| ATOM | 132 | OG1 | THR | A | 42 | 67.937 | 105.110 | 28.319 | 1.00 60.02 | O |
| ATOM | 133 | CG2 | THR | A | 42 | 69.292 | 106.100 | 26.590 | 1.00 58.15 | C |
| ATOM | 134 | C | THR | A | 42 | 69.373 | 103.270 | 25.350 | 1.00 55.42 | C |
| ATOM | 135 | O | THR | A | 42 | 70.319 | 102.585 | 25.738 | 1.00 56.47 | O |
| ATOM | 136 | N | PRO | A | 43 | 69.210 | 103.606 | 24.059 | 1.00 54.46 | N |
| ATOM | 137 | CD | PRO | A | 43 | 68.068 | 104.404 | 23.580 | 1.00 54.38 | C |
| ATOM | 138 | CA | PRO | A | 43 | 70.069 | 103.231 | 22.934 | 1.00 53.73 | C |
| ATOM | 139 | CB | PRO | A | 43 | 69.140 | 103.401 | 21.747 | 1.00 53.99 | C |
| ATOM | 140 | CG | PRO | A | 43 | 68.422 | 104.649 | 22.112 | 1.00 53.95 | C |
| ATOM | 141 | C | PRO | A | 43 | 71.370 | 103.980 | 22.700 | 1.00 53.59 | C |
| ATOM | 142 | O | PRO | A | 43 | 71.499 | 105.168 | 22.991 | 1.00 52.81 | O |
| ATOM | 143 | N | LEU | A | 44 | 72.327 | 103.255 | 22.133 | 1.00 54.44 | N |
| ATOM | 144 | CA | LEU | A | 44 | 73.621 | 103.813 | 21.772 | 1.00 53.63 | C |
| ATOM | 145 | CB | LEU | A | 44 | 74.703 | 102.736 | 21.901 | 1.00 52.03 | C |

```
ATOM    146  CG   LEU A  44      75.283 102.529  23.315  1.00 52.13           C
ATOM    147  CD1  LEU A  44      74.175 102.432  24.333  1.00 51.70           C
ATOM    148  CD2  LEU A  44      76.148 101.288  23.348  1.00 51.28           C
ATOM    149  C    LEU A  44      73.492 104.308  20.317  1.00 54.19           C
ATOM    150  O    LEU A  44      72.565 103.916  19.591  1.00 53.92           O
ATOM    151  N    PRO A  45      74.405 105.197  19.885  1.00 54.09           N
ATOM    152  CD   PRO A  45      75.387 105.835  20.789  1.00 53.59           C
ATOM    153  CA   PRO A  45      74.470 105.803  18.548  1.00 52.41           C
ATOM    154  CB   PRO A  45      75.841 106.457  18.551  1.00 52.53           C
ATOM    155  CG   PRO A  45      75.893 107.013  19.956  1.00 52.88           C
ATOM    156  C    PRO A  45      74.190 104.997  17.263  1.00 51.21           C
ATOM    157  O    PRO A  45      73.367 105.433  16.459  1.00 53.06           O
ATOM    158  N    PHE A  46      74.841 103.867  17.016  1.00 48.25           N
ATOM    159  CA   PHE A  46      74.505 103.153  15.771  1.00 48.54           C
ATOM    160  CB   PHE A  46      75.724 102.975  14.868  1.00 50.34           C
ATOM    161  CG   PHE A  46      76.273 104.252  14.315  1.00 50.91           C
ATOM    162  CD1  PHE A  46      76.895 105.169  15.140  1.00 51.41           C
ATOM    163  CD2  PHE A  46      76.206 104.514  12.955  1.00 52.60           C
ATOM    164  CE1  PHE A  46      77.447 106.323  14.622  1.00 51.58           C
ATOM    165  CE2  PHE A  46      76.754 105.662  12.430  1.00 52.63           C
ATOM    166  CZ   PHE A  46      77.378 106.568  13.266  1.00 52.40           C
ATOM    167  C    PHE A  46      73.916 101.782  16.028  1.00 47.73           C
ATOM    168  O    PHE A  46      73.130 101.254  15.230  1.00 45.89           O
ATOM    169  N    LEU A  47      74.346 101.199  17.140  1.00 47.74           N
ATOM    170  CA   LEU A  47      73.889  99.890  17.569  1.00 47.10           C
ATOM    171  CB   LEU A  47      74.822  99.356  18.643  1.00 43.89           C
ATOM    172  CG   LEU A  47      76.261  99.438  18.182  1.00 44.13           C
ATOM    173  CD1  LEU A  47      77.172  99.371  19.392  1.00 47.38           C
ATOM    174  CD2  LEU A  47      76.553  98.321  17.201  1.00 43.00           C
ATOM    175  C    LEU A  47      72.487 100.008  18.143  1.00 47.05           C
ATOM    176  O    LEU A  47      71.628  99.161  17.892  1.00 48.48           O
ATOM    177  N    GLY A  48      72.250 101.075  18.899  1.00 45.75           N
ATOM    178  CA   GLY A  48      70.949 101.235  19.503  1.00 44.59           C
ATOM    179  C    GLY A  48      70.917 100.292  20.683  1.00 43.31           C
ATOM    180  O    GLY A  48      71.678 100.455  21.622  1.00 43.12           O
ATOM    181  N    ASN A  49      70.077  99.275  20.634  1.00 43.40           N
ATOM    182  CA   ASN A  49      70.008  98.364  21.764  1.00 44.77           C
ATOM    183  CB   ASN A  49      68.568  98.284  22.288  1.00 43.02           C
ATOM    184  CG   ASN A  49      68.137  99.544  22.986  1.00 40.49           C
ATOM    185  OD1  ASN A  49      67.205 100.235  22.551  1.00 39.62           O
ATOM    186  ND2  ASN A  49      68.821  99.863  24.078  1.00 36.15           N
ATOM    187  C    ASN A  49      70.493  96.948  21.529  1.00 46.45           C
ATOM    188  O    ASN A  49      70.174  96.083  22.336  1.00 47.75           O
ATOM    189  N    ILE A  50      71.270  96.684  20.480  1.00 47.68           N
ATOM    190  CA   ILE A  50      71.657  95.299  20.253  1.00 49.56           C
ATOM    191  CB   ILE A  50      72.369  95.059  18.882  1.00 48.68           C
ATOM    192  CG2  ILE A  50      71.356  95.163  17.756  1.00 50.91           C
ATOM    193  CG1  ILE A  50      73.509  96.033  18.641  1.00 48.75           C
ATOM    194  CD1  ILE A  50      74.024  95.948  17.218  1.00 47.43           C
ATOM    195  C    ILE A  50      72.439  94.564  21.324  1.00 52.49           C
ATOM    196  O    ILE A  50      72.034  93.475  21.714  1.00 56.55           O
ATOM    197  N    LEU A  51      73.529  95.123  21.828  1.00 54.24           N
ATOM    198  CA   LEU A  51      74.330  94.414  22.835  1.00 54.59           C
ATOM    199  CB   LEU A  51      75.302  95.382  23.474  1.00 54.93           C
ATOM    200  CG   LEU A  51      76.036  96.210  22.430  1.00 54.23           C
ATOM    201  CD1  LEU A  51      76.679  97.367  23.135  1.00 53.76           C
ATOM    202  CD2  LEU A  51      77.070  95.362  21.681  1.00 53.80           C
ATOM    203  C    LEU A  51      73.524  93.709  23.924  1.00 55.21           C
ATOM    204  O    LEU A  51      74.050  92.886  24.674  1.00 55.99           O
ATOM    205  N    SER A  52      72.249  94.049  24.010  1.00 55.51           N
ATOM    206  CA   SER A  52      71.356  93.445  24.978  1.00 57.50           C
ATOM    207  CB   SER A  52      70.074  94.248  25.026  1.00 59.27           C
ATOM    208  OG   SER A  52      70.366  95.622  25.203  1.00 61.71           O
ATOM    209  C    SER A  52      71.052  92.012  24.546  1.00 58.46           C
ATOM    210  O    SER A  52      70.568  91.192  25.333  1.00 60.24           O
ATOM    211  N    TYR A  53      71.338  91.726  23.281  1.00 58.03           N
ATOM    212  CA   TYR A  53      71.126  90.406  22.702  1.00 56.86           C
ATOM    213  CB   TYR A  53      71.028  90.511  21.184  1.00 54.79           C
ATOM    214  CG   TYR A  53      69.764  91.160  20.688  1.00 54.16           C
ATOM    215  CD1  TYR A  53      69.716  91.756  19.438  1.00 53.52           C
ATOM    216  CE1  TYR A  53      68.543  92.299  18.947  1.00 54.46           C
ATOM    217  CD2  TYR A  53      68.605  91.126  21.439  1.00 53.26           C
ATOM    218  CE2  TYR A  53      67.422  91.662  20.952  1.00 54.53           C
ATOM    219  CZ   TYR A  53      67.394  92.246  19.707  1.00 54.17           C
ATOM    220  OH   TYR A  53      66.213  92.767  19.222  1.00 52.72           O
ATOM    221  C    TYR A  53      72.282  89.484  23.060  1.00 56.85           C
ATOM    222  O    TYR A  53      72.389  88.375  22.525  1.00 56.68           O
```

```
ATOM  223  N    HIS A  54      73.152  89.940  23.957  1.00 57.10           N
ATOM  224  CA   HIS A  54      74.291  89.131  24.351  1.00 58.95           C
ATOM  225  CB   HIS A  54      75.298  89.962  25.151  1.00 62.69           C
ATOM  226  CG   HIS A  54      74.907  90.202  26.578  1.00 67.09           C
ATOM  227  CD2  HIS A  54      75.579  89.977  27.735  1.00 67.57           C
ATOM  228  ND1  HIS A  54      73.707  90.779  26.938  1.00 69.23           N
ATOM  229  CE1  HIS A  54      73.657  90.900  28.254  1.00 69.88           C
ATOM  230  NE2  HIS A  54      74.781  90.422  28.760  1.00 69.56           N
ATOM  231  C    HIS A  54      73.801  87.941  25.156  1.00 58.97           C
ATOM  232  O    HIS A  54      74.506  86.949  25.312  1.00 58.32           O
ATOM  233  N    LYS A  55      72.575  88.036  25.656  1.00 61.19           N
ATOM  234  CA   LYS A  55      71.992  86.935  26.413  1.00 63.10           C
ATOM  235  CB   LYS A  55      71.241  87.464  27.638  1.00 66.40           C
ATOM  236  CG   LYS A  55      71.679  86.790  28.947  1.00 71.48           C
ATOM  237  CD   LYS A  55      73.148  87.099  29.262  1.00 74.69           C
ATOM  238  CE   LYS A  55      73.698  86.249  30.410  1.00 77.96           C
ATOM  239  NZ   LYS A  55      74.000  84.831  30.013  1.00 79.60           N
ATOM  240  C    LYS A  55      71.045  86.128  25.515  1.00 62.07           C
ATOM  241  O    LYS A  55      70.841  84.931  25.722  1.00 63.26           O
ATOM  242  N    GLY A  56      70.488  86.786  24.506  1.00 59.72           N
ATOM  243  CA   GLY A  56      69.586  86.114  23.597  1.00 56.77           C
ATOM  244  C    GLY A  56      68.324  86.926  23.416  1.00 56.82           C
ATOM  245  O    GLY A  56      68.168  87.995  23.999  1.00 57.16           O
ATOM  246  N    PHE A  57      67.418  86.416  22.600  1.00 56.47           N
ATOM  247  CA   PHE A  57      66.160  87.089  22.333  1.00 57.64           C
ATOM  248  CB   PHE A  57      65.519  86.466  21.106  1.00 58.01           C
ATOM  249  CG   PHE A  57      65.831  87.171  19.836  1.00 57.42           C
ATOM  250  CD1  PHE A  57      66.146  86.452  18.701  1.00 56.70           C
ATOM  251  CD2  PHE A  57      65.756  88.545  19.759  1.00 57.59           C
ATOM  252  CE1  PHE A  57      66.374  87.084  17.518  1.00 56.31           C
ATOM  253  CE2  PHE A  57      65.984  89.185  18.577  1.00 58.80           C
ATOM  254  CZ   PHE A  57      66.293  88.451  17.450  1.00 58.79           C
ATOM  255  C    PHE A  57      65.185  86.979  23.500  1.00 59.55           C
ATOM  256  O    PHE A  57      64.586  87.970  23.945  1.00 60.39           O
ATOM  257  N    CYS A  58      65.013  85.754  23.971  1.00 59.64           N
ATOM  258  CA   CYS A  58      64.111  85.475  25.067  1.00 61.60           C
ATOM  259  CB   CYS A  58      63.942  83.970  25.172  1.00 63.68           C
ATOM  260  SG   CYS A  58      63.598  83.232  23.560  1.00 66.01           S
ATOM  261  C    CYS A  58      64.626  86.064  26.378  1.00 62.23           C
ATOM  262  O    CYS A  58      63.858  86.615  27.160  1.00 61.24           O
ATOM  263  N    MET A  59      65.924  85.951  26.616  1.00 63.39           N
ATOM  264  CA   MET A  59      66.502  86.508  27.826  1.00 64.92           C
ATOM  265  CB   MET A  59      67.995  86.200  27.867  1.00 67.80           C
ATOM  266  CG   MET A  59      68.288  84.715  27.999  1.00 73.55           C
ATOM  267  SD   MET A  59      67.440  83.985  29.442  1.00 79.46           S
ATOM  268  CE   MET A  59      66.571  82.572  28.670  1.00 78.72           C
ATOM  269  C    MET A  59      66.264  88.022  27.894  1.00 64.34           C
ATOM  270  O    MET A  59      65.861  88.551  28.931  1.00 64.81           O
ATOM  271  N    PHE A  60      66.503  88.711  26.784  1.00 62.95           N
ATOM  272  CA   PHE A  60      66.313  90.152  26.708  1.00 61.95           C
ATOM  273  CB   PHE A  60      66.774  90.671  25.339  1.00 60.24           C
ATOM  274  CG   PHE A  60      66.471  92.137  25.093  1.00 58.08           C
ATOM  275  CD1  PHE A  60      65.684  92.524  24.018  1.00 56.57           C
ATOM  276  CD2  PHE A  60      67.000  93.125  25.910  1.00 56.97           C
ATOM  277  CE1  PHE A  60      65.434  93.867  23.757  1.00 56.22           C
ATOM  278  CE2  PHE A  60      66.753  94.468  25.651  1.00 56.63           C
ATOM  279  CZ   PHE A  60      65.971  94.837  24.572  1.00 56.40           C
ATOM  280  C    PHE A  60      64.850  90.503  26.916  1.00 63.05           C
ATOM  281  O    PHE A  60      64.534  91.508  27.552  1.00 62.66           O
ATOM  282  N    ASP A  61      63.959  89.674  26.375  1.00 64.97           N
ATOM  283  CA   ASP A  61      62.519  89.915  26.490  1.00 66.89           C
ATOM  284  CB   ASP A  61      61.746  89.056  25.481  1.00 67.63           C
ATOM  285  CG   ASP A  61      61.561  89.756  24.138  1.00 68.17           C
ATOM  286  OD1  ASP A  61      60.881  89.190  23.263  1.00 69.90           O
ATOM  287  OD2  ASP A  61      62.084  90.874  23.952  1.00 67.02           O
ATOM  288  C    ASP A  61      61.947  89.707  27.889  1.00 67.11           C
ATOM  289  O    ASP A  61      61.030  90.421  28.290  1.00 66.49           O
ATOM  290  N    MET A  62      62.472  88.731  28.624  1.00 67.99           N
ATOM  291  CA   MET A  62      61.997  88.502  29.982  1.00 69.17           C
ATOM  292  CB   MET A  62      62.657  87.269  30.597  1.00 69.46           C
ATOM  293  CG   MET A  62      62.281  85.962  29.929  1.00 71.52           C
ATOM  294  SD   MET A  62      60.529  85.538  30.115  1.00 74.87           S
ATOM  295  CE   MET A  62      60.647  83.906  30.843  1.00 72.91           C
ATOM  296  C    MET A  62      62.369  89.733  30.799  1.00 70.35           C
ATOM  297  O    MET A  62      61.518  90.358  31.428  1.00 71.39           O
ATOM  298  N    GLU A  63      63.646  90.087  30.774  1.00 70.85           N
ATOM  299  CA   GLU A  63      64.121  91.241  31.510  1.00 71.90           C
```

| | | | | | | | | | | |
|---|---|---|---|---|---|---|---|---|---|---|
| ATOM | 300 | CB | GLU | A | 63 | 65.580 | 91.518 | 31.162 | 1.00 76.76 | C |
| ATOM | 301 | CG | GLU | A | 63 | 66.541 | 90.383 | 31.534 | 1.00 84.84 | C |
| ATOM | 302 | CD | GLU | A | 63 | 67.998 | 90.701 | 31.185 | 1.00 90.65 | C |
| ATOM | 303 | OE1 | GLU | A | 63 | 68.894 | 89.910 | 31.576 | 1.00 92.78 | O |
| ATOM | 304 | OE2 | GLU | A | 63 | 68.242 | 91.742 | 30.519 | 1.00 93.44 | O |
| ATOM | 305 | C | GLU | A | 63 | 63.277 | 92.474 | 31.221 | 1.00 70.79 | C |
| ATOM | 306 | O | GLU | A | 63 | 62.825 | 93.138 | 32.141 | 1.00 71.84 | O |
| ATOM | 307 | N | CYS | A | 64 | 63.052 | 92.772 | 29.946 | 1.00 69.43 | N |
| ATOM | 308 | CA | CYS | A | 64 | 62.268 | 93.946 | 29.557 | 1.00 68.45 | C |
| ATOM | 309 | CB | CYS | A | 64 | 62.266 | 94.105 | 28.038 | 1.00 69.17 | C |
| ATOM | 310 | SG | CYS | A | 64 | 63.625 | 95.067 | 27.349 | 1.00 67.64 | S |
| ATOM | 311 | C | CYS | A | 64 | 60.825 | 93.961 | 30.040 | 1.00 68.01 | C |
| ATOM | 312 | O | CYS | A | 64 | 60.300 | 95.008 | 30.394 | 1.00 67.27 | O |
| ATOM | 313 | N | HIS | A | 65 | 60.171 | 92.809 | 30.024 | 1.00 68.03 | N |
| ATOM | 314 | CA | HIS | A | 65 | 58.789 | 92.736 | 30.472 | 1.00 68.15 | C |
| ATOM | 315 | CB | HIS | A | 65 | 58.216 | 91.349 | 30.197 | 1.00 67.17 | C |
| ATOM | 316 | CG | HIS | A | 65 | 56.870 | 91.125 | 30.804 | 1.00 65.29 | C |
| ATOM | 317 | CD2 | HIS | A | 65 | 56.425 | 90.177 | 31.662 | 1.00 64.73 | C |
| ATOM | 318 | ND1 | HIS | A | 65 | 55.790 | 91.936 | 30.533 | 1.00 64.29 | N |
| ATOM | 319 | CE1 | HIS | A | 65 | 54.736 | 91.495 | 31.196 | 1.00 65.88 | C |
| ATOM | 320 | NE2 | HIS | A | 65 | 55.095 | 90.429 | 31.889 | 1.00 64.74 | N |
| ATOM | 321 | C | HIS | A | 65 | 58.713 | 93.032 | 31.963 | 1.00 68.83 | C |
| ATOM | 322 | O | HIS | A | 65 | 57.845 | 93.778 | 32.418 | 1.00 68.87 | O |
| ATOM | 323 | N | LYS | A | 66 | 59.626 | 92.439 | 32.724 | 1.00 69.23 | N |
| ATOM | 324 | CA | LYS | A | 66 | 59.655 | 92.662 | 34.156 | 1.00 69.32 | C |
| ATOM | 325 | CB | LYS | A | 66 | 60.772 | 91.841 | 34.812 | 1.00 69.91 | C |
| ATOM | 326 | CG | LYS | A | 66 | 60.825 | 92.009 | 36.323 | 1.00 71.94 | C |
| ATOM | 327 | CD | LYS | A | 66 | 61.658 | 90.935 | 37.014 | 1.00 75.09 | C |
| ATOM | 328 | CE | LYS | A | 66 | 60.823 | 90.191 | 38.077 | 1.00 76.36 | C |
| ATOM | 329 | NZ | LYS | A | 66 | 61.642 | 89.569 | 39.169 | 1.00 76.47 | N |
| ATOM | 330 | C | LYS | A | 66 | 59.883 | 94.144 | 34.434 | 1.00 69.30 | C |
| ATOM | 331 | O | LYS | A | 66 | 59.038 | 94.817 | 35.021 | 1.00 69.76 | O |
| ATOM | 332 | N | LYS | A | 67 | 61.019 | 94.653 | 33.973 | 1.00 68.61 | N |
| ATOM | 333 | CA | LYS | A | 67 | 61.401 | 96.038 | 34.208 | 1.00 67.72 | C |
| ATOM | 334 | CB | LYS | A | 67 | 62.833 | 96.250 | 33.719 | 1.00 68.44 | C |
| ATOM | 335 | CG | LYS | A | 67 | 63.645 | 97.170 | 34.599 | 1.00 69.83 | C |
| ATOM | 336 | CD | LYS | A | 67 | 65.146 | 96.865 | 34.520 | 1.00 71.37 | C |
| ATOM | 337 | CE | LYS | A | 67 | 65.684 | 96.987 | 33.103 | 1.00 72.99 | C |
| ATOM | 338 | NZ | LYS | A | 67 | 67.158 | 97.237 | 33.082 | 1.00 73.99 | N |
| ATOM | 339 | C | LYS | A | 67 | 60.505 | 97.144 | 33.662 | 1.00 66.60 | C |
| ATOM | 340 | O | LYS | A | 67 | 60.024 | 97.968 | 34.421 | 1.00 66.28 | O |
| ATOM | 341 | N | TYR | A | 68 | 60.264 | 97.171 | 32.362 | 1.00 66.78 | N |
| ATOM | 342 | CA | TYR | A | 68 | 59.450 | 98.247 | 31.797 | 1.00 68.17 | C |
| ATOM | 343 | CB | TYR | A | 68 | 59.933 | 98.567 | 30.381 | 1.00 68.57 | C |
| ATOM | 344 | CG | TYR | A | 68 | 61.408 | 98.903 | 30.369 | 1.00 69.78 | C |
| ATOM | 345 | CD1 | TYR | A | 68 | 61.860 | 100.153 | 30.768 | 1.00 67.92 | C |
| ATOM | 346 | CE1 | TYR | A | 68 | 63.208 | 100.427 | 30.841 | 1.00 67.72 | C |
| ATOM | 347 | CD2 | TYR | A | 68 | 62.357 | 97.934 | 30.043 | 1.00 69.75 | C |
| ATOM | 348 | CE2 | TYR | A | 68 | 63.705 | 98.203 | 30.120 | 1.00 68.32 | C |
| ATOM | 349 | CZ | TYR | A | 68 | 64.119 | 99.449 | 30.517 | 1.00 68.04 | C |
| ATOM | 350 | OH | TYR | A | 68 | 65.455 | 99.723 | 30.593 | 1.00 69.83 | O |
| ATOM | 351 | C | TYR | A | 68 | 57.941 | 98.063 | 31.811 | 1.00 68.83 | C |
| ATOM | 352 | O | TYR | A | 68 | 57.199 | 98.916 | 31.313 | 1.00 70.60 | O |
| ATOM | 353 | N | GLY | A | 69 | 57.472 | 96.955 | 32.370 | 1.00 67.97 | N |
| ATOM | 354 | CA | GLY | A | 69 | 56.040 | 96.765 | 32.450 | 1.00 65.17 | C |
| ATOM | 355 | C | GLY | A | 69 | 55.349 | 95.973 | 31.371 | 1.00 63.78 | C |
| ATOM | 356 | O | GLY | A | 69 | 55.818 | 94.921 | 30.952 | 1.00 63.88 | O |
| ATOM | 357 | N | LYS | A | 70 | 54.212 | 96.493 | 30.926 | 1.00 63.19 | N |
| ATOM | 358 | CA | LYS | A | 70 | 53.393 | 95.829 | 29.922 | 1.00 63.76 | C |
| ATOM | 359 | CB | LYS | A | 70 | 51.924 | 96.094 | 30.222 | 1.00 65.75 | C |
| ATOM | 360 | CG | LYS | A | 70 | 51.537 | 97.535 | 29.954 | 1.00 67.53 | C |
| ATOM | 361 | CD | LYS | A | 70 | 50.194 | 97.613 | 29.252 | 1.00 71.23 | C |
| ATOM | 362 | CE | LYS | A | 70 | 50.093 | 98.861 | 28.373 | 1.00 72.87 | C |
| ATOM | 363 | NZ | LYS | A | 70 | 50.254 | 100.138 | 29.132 | 1.00 74.98 | N |
| ATOM | 364 | C | LYS | A | 70 | 53.671 | 96.264 | 28.486 | 1.00 63.14 | C |
| ATOM | 365 | O | LYS | A | 70 | 53.341 | 95.553 | 27.537 | 1.00 63.41 | O |
| ATOM | 366 | N | VAL | A | 71 | 54.247 | 97.450 | 28.336 | 1.00 61.16 | N |
| ATOM | 367 | CA | VAL | A | 71 | 54.559 | 97.999 | 27.030 | 1.00 59.82 | C |
| ATOM | 368 | CB | VAL | A | 71 | 53.464 | 98.966 | 26.558 | 1.00 57.26 | C |
| ATOM | 369 | CG1 | VAL | A | 71 | 54.057 | 100.009 | 25.630 | 1.00 54.84 | C |
| ATOM | 370 | CG2 | VAL | A | 71 | 52.381 | 98.197 | 25.842 | 1.00 55.77 | C |
| ATOM | 371 | C | VAL | A | 71 | 55.864 | 98.761 | 27.113 | 1.00 61.46 | C |
| ATOM | 372 | O | VAL | A | 71 | 56.069 | 99.533 | 28.049 | 1.00 63.60 | O |
| ATOM | 373 | N | TRP | A | 72 | 56.745 | 98.548 | 26.141 | 1.00 60.88 | N |
| ATOM | 374 | CA | TRP | A | 72 | 58.025 | 99.233 | 26.129 | 1.00 60.89 | C |
| ATOM | 375 | CB | TRP | A | 72 | 58.985 | 98.570 | 27.114 | 1.00 62.71 | C |
| ATOM | 376 | CG | TRP | A | 72 | 59.485 | 97.246 | 26.667 | 1.00 63.60 | C |

```
ATOM  377  CD2  TRP A  72      58.809  95.992  26.778  1.00 65.09           C
ATOM  378  CE2  TRP A  72      59.677  95.004  26.277  1.00 64.82           C
ATOM  379  CE3  TRP A  72      57.554  95.607  27.259  1.00 66.31           C
ATOM  380  CD1  TRP A  72      60.695  96.981  26.113  1.00 63.59           C
ATOM  381  NE1  TRP A  72      60.822  95.635  25.877  1.00 64.73           N
ATOM  382  CZ2  TRP A  72      59.337  93.653  26.244  1.00 64.89           C
ATOM  383  CZ3  TRP A  72      57.215  94.260  27.225  1.00 66.69           C
ATOM  384  CH2  TRP A  72      58.107  93.302  26.722  1.00 65.82           C
ATOM  385  C    TRP A  72      58.623  99.213  24.737  1.00 59.96           C
ATOM  386  O    TRP A  72      58.095  98.570  23.838  1.00 60.74           O
ATOM  387  N    GLY A  73      59.733  99.919  24.563  1.00 58.63           N
ATOM  388  CA   GLY A  73      60.363  99.968  23.263  1.00 55.80           C
ATOM  389  C    GLY A  73      61.874  99.938  23.305  1.00 54.31           C
ATOM  390  O    GLY A  73      62.510 100.315  24.296  1.00 53.05           O
ATOM  391  N    PHE A  74      62.446  99.457  22.210  1.00 53.22           N
ATOM  392  CA   PHE A  74      63.889  99.385  22.066  1.00 51.70           C
ATOM  393  CB   PHE A  74      64.407  98.032  22.530  1.00 51.69           C
ATOM  394  CG   PHE A  74      63.808  96.884  21.806  1.00 51.97           C
ATOM  395  CD1  PHE A  74      64.548  96.177  20.880  1.00 51.73           C
ATOM  396  CD2  PHE A  74      62.500  96.509  22.054  1.00 51.87           C
ATOM  397  CE1  PHE A  74      63.998  95.116  20.217  1.00 53.51           C
ATOM  398  CE2  PHE A  74      61.938  95.449  21.396  1.00 53.40           C
ATOM  399  CZ   PHE A  74      62.685  94.745  20.474  1.00 54.47           C
ATOM  400  C    PHE A  74      64.234  99.609  20.609  1.00 49.45           C
ATOM  401  O    PHE A  74      63.355  99.651  19.753  1.00 48.96           O
ATOM  402  N    TYR A  75      65.514  99.766  20.322  1.00 49.16           N
ATOM  403  CA   TYR A  75      65.915  99.987  18.944  1.00 48.77           C
ATOM  404  CB   TYR A  75      66.564 101.357  18.807  1.00 47.24           C
ATOM  405  CG   TYR A  75      65.677 102.473  19.288  1.00 46.80           C
ATOM  406  CD1  TYR A  75      65.781 102.962  20.582  1.00 46.22           C
ATOM  407  CE1  TYR A  75      64.974 103.999  21.018  1.00 44.51           C
ATOM  408  CD2  TYR A  75      64.731 103.046  18.440  1.00 47.39           C
ATOM  409  CE2  TYR A  75      63.923 104.075  18.867  1.00 46.62           C
ATOM  410  CZ   TYR A  75      64.055 104.549  20.157  1.00 44.82           C
ATOM  411  OH   TYR A  75      63.287 105.607  20.561  1.00 46.52           O
ATOM  412  C    TYR A  75      66.852  98.920  18.407  1.00 48.48           C
ATOM  413  O    TYR A  75      67.887  98.618  19.019  1.00 47.33           O
ATOM  414  N    ASP A  76      66.451  98.324  17.285  1.00 48.41           N
ATOM  415  CA   ASP A  76      67.268  97.321  16.607  1.00 48.79           C
ATOM  416  CB   ASP A  76      66.392  96.305  15.882  1.00 48.30           C
ATOM  417  CG   ASP A  76      66.116  95.085  16.729  1.00 50.59           C
ATOM  418  OD1  ASP A  76      66.516  95.092  17.906  1.00 51.75           O
ATOM  419  OD2  ASP A  76      65.507  94.115  16.236  1.00 54.50           O
ATOM  420  C    ASP A  76      68.076  98.157  15.625  1.00 49.04           C
ATOM  421  O    ASP A  76      67.761  98.236  14.432  1.00 49.05           O
ATOM  422  N    GLY A  77      69.108  98.803  16.166  1.00 48.76           N
ATOM  423  CA   GLY A  77      69.936  99.694  15.382  1.00 49.46           C
ATOM  424  C    GLY A  77      69.265 101.059  15.413  1.00 49.59           C
ATOM  425  O    GLY A  77      69.428 101.828  16.354  1.00 48.76           O
ATOM  426  N    GLN A  78      68.494 101.358  14.375  1.00 50.47           N
ATOM  427  CA   GLN A  78      67.788 102.627  14.288  1.00 50.59           C
ATOM  428  CB   GLN A  78      68.442 103.555  13.245  1.00 51.99           C
ATOM  429  CG   GLN A  78      69.784 104.122  13.688  1.00 55.50           C
ATOM  430  CD   GLN A  78      70.448 104.969  12.617  1.00 60.93           C
ATOM  431  OE1  GLN A  78      69.902 105.992  12.185  1.00 63.52           O
ATOM  432  NE2  GLN A  78      71.641 104.547  12.174  1.00 62.77           N
ATOM  433  C    GLN A  78      66.360 102.278  13.907  1.00 48.82           C
ATOM  434  O    GLN A  78      65.580 103.106  13.414  1.00 48.56           O
ATOM  435  N    GLN A  79      66.034 101.015  14.140  1.00 46.49           N
ATOM  436  CA   GLN A  79      64.696 100.520  13.886  1.00 45.40           C
ATOM  437  CB   GLN A  79      64.753  99.176  13.173  1.00 44.29           C
ATOM  438  CG   GLN A  79      63.414  98.490  13.088  1.00 45.35           C
ATOM  439  CD   GLN A  79      62.385  99.288  12.323  1.00 44.23           C
ATOM  440  OE1  GLN A  79      62.433  99.363  11.100  1.00 42.92           O
ATOM  441  NE2  GLN A  79      61.438  99.885  13.047  1.00 44.92           N
ATOM  442  C    GLN A  79      64.013 100.384  15.249  1.00 45.05           C
ATOM  443  O    GLN A  79      64.457  99.621  16.120  1.00 41.90           O
ATOM  444  N    PRO A  80      62.935 101.156  15.457  1.00 46.32           N
ATOM  445  CD   PRO A  80      62.438 102.206  14.548  1.00 47.01           C
ATOM  446  CA   PRO A  80      62.167 101.153  16.703  1.00 46.96           C
ATOM  447  CB   PRO A  80      61.437 102.492  16.647  1.00 48.56           C
ATOM  448  CG   PRO A  80      61.113 102.591  15.189  1.00 47.61           C
ATOM  449  C    PRO A  80      61.206  99.975  16.799  1.00 45.65           C
ATOM  450  O    PRO A  80      60.378  99.759  15.914  1.00 44.17           O
ATOM  451  N    VAL A  81      61.325  99.224  17.888  1.00 45.00           N
ATOM  452  CA   VAL A  81      60.470  98.071  18.116  1.00 46.18           C
ATOM  453  CB   VAL A  81      61.283  96.793  18.208  1.00 46.74           C
```

```
ATOM    454  CG1 VAL A   81      60.343  95.599  18.215  1.00 46.03           C
ATOM    455  CG2 VAL A   81      62.268  96.730  17.054  1.00 48.83           C
ATOM    456  C   VAL A   81      59.679  98.187  19.412  1.00 45.97           C
ATOM    457  O   VAL A   81      60.256  98.136  20.504  1.00 45.49           O
ATOM    458  N   LEU A   82      58.360  98.325  19.280  1.00 45.59           N
ATOM    459  CA  LEU A   82      57.462  98.441  20.427  1.00 45.58           C
ATOM    460  CB  LEU A   82      56.320  99.386  20.078  1.00 45.29           C
ATOM    461  CG  LEU A   82      55.423  99.967  21.171  1.00 45.51           C
ATOM    462  CD1 LEU A   82      54.138 100.478  20.503  1.00 44.30           C
ATOM    463  CD2 LEU A   82      55.081  98.912  22.217  1.00 46.84           C
ATOM    464  C   LEU A   82      56.894  97.062  20.817  1.00 47.14           C
ATOM    465  O   LEU A   82      56.138  96.444  20.060  1.00 47.92           O
ATOM    466  N   ALA A   83      57.260  96.594  22.002  1.00 47.29           N
ATOM    467  CA  ALA A   83      56.796  95.306  22.516  1.00 49.28           C
ATOM    468  CB  ALA A   83      57.866  94.726  23.457  1.00 48.94           C
ATOM    469  C   ALA A   83      55.452  95.419  23.269  1.00 50.10           C
ATOM    470  O   ALA A   83      55.410  95.950  24.368  1.00 50.28           O
ATOM    471  N   ILE A   84      54.355  94.928  22.698  1.00 50.97           N
ATOM    472  CA  ILE A   84      53.083  95.011  23.407  1.00 52.45           C
ATOM    473  CB  ILE A   84      51.891  95.240  22.462  1.00 50.38           C
ATOM    474  CG2 ILE A   84      52.182  96.386  21.544  1.00 50.46           C
ATOM    475  CG1 ILE A   84      51.600  93.983  21.660  1.00 50.66           C
ATOM    476  CD1 ILE A   84      50.461  94.162  20.694  1.00 49.32           C
ATOM    477  C   ILE A   84      52.833  93.746  24.223  1.00 54.89           C
ATOM    478  O   ILE A   84      53.512  92.741  24.038  1.00 54.83           O
ATOM    479  N   THR A   85      51.856  93.801  25.128  1.00 57.94           N
ATOM    480  CA  THR A   85      51.562  92.668  25.997  1.00 60.27           C
ATOM    481  CB  THR A   85      52.419  92.749  27.281  1.00 59.89           C
ATOM    482  OG1 THR A   85      53.724  92.207  27.021  1.00 60.53           O
ATOM    483  CG2 THR A   85      51.763  92.000  28.409  1.00 60.11           C
ATOM    484  C   THR A   85      50.096  92.527  26.388  1.00 61.82           C
ATOM    485  O   THR A   85      49.621  91.427  26.669  1.00 62.96           O
ATOM    486  N   ASP A   86      49.371  93.633  26.417  1.00 63.53           N
ATOM    487  CA  ASP A   86      47.966  93.550  26.782  1.00 63.95           C
ATOM    488  CB  ASP A   86      47.358  94.950  26.963  1.00 66.03           C
ATOM    489  CG  ASP A   86      45.886  94.909  27.374  1.00 66.56           C
ATOM    490  OD1 ASP A   86      45.269  95.991  27.415  1.00 69.35           O
ATOM    491  OD2 ASP A   86      45.342  93.814  27.659  1.00 66.04           O
ATOM    492  C   ASP A   86      47.237  92.809  25.680  1.00 62.81           C
ATOM    493  O   ASP A   86      47.205  93.250  24.534  1.00 62.39           O
ATOM    494  N   PRO A   87      46.653  91.659  26.016  1.00 62.43           N
ATOM    495  CD  PRO A   87      46.776  90.999  27.326  1.00 61.06           C
ATOM    496  CA  PRO A   87      45.908  90.831  25.065  1.00 63.00           C
ATOM    497  CB  PRO A   87      45.277  89.784  25.965  1.00 62.92           C
ATOM    498  CG  PRO A   87      46.357  89.590  27.021  1.00 62.57           C
ATOM    499  C   PRO A   87      44.877  91.622  24.259  1.00 64.56           C
ATOM    500  O   PRO A   87      44.458  91.192  23.190  1.00 65.34           O
ATOM    501  N   ASP A   88      44.471  92.781  24.762  1.00 66.85           N
ATOM    502  CA  ASP A   88      43.497  93.593  24.041  1.00 68.62           C
ATOM    503  CB  ASP A   88      42.951  94.710  24.941  1.00 72.03           C
ATOM    504  CG  ASP A   88      41.426  94.696  25.029  1.00 75.23           C
ATOM    505  OD1 ASP A   88      40.861  93.603  25.271  1.00 76.51           O
ATOM    506  OD2 ASP A   88      40.793  95.768  24.860  1.00 76.57           O
ATOM    507  C   ASP A   88      44.172  94.174  22.804  1.00 68.70           C
ATOM    508  O   ASP A   88      43.604  94.134  21.710  1.00 68.61           O
ATOM    509  N   MET A   89      45.383  94.705  22.984  1.00 67.75           N
ATOM    510  CA  MET A   89      46.159  95.261  21.872  1.00 65.80           C
ATOM    511  CB  MET A   89      47.439  95.928  22.371  1.00 67.29           C
ATOM    512  CG  MET A   89      47.268  97.002  23.411  1.00 72.57           C
ATOM    513  SD  MET A   89      48.878  97.430  24.140  1.00 76.26           S
ATOM    514  CE  MET A   89      49.564  98.485  22.822  1.00 76.13           C
ATOM    515  C   MET A   89      46.575  94.114  20.943  1.00 63.04           C
ATOM    516  O   MET A   89      46.496  94.222  19.720  1.00 62.22           O
ATOM    517  N   ILE A   90      47.024  93.016  21.541  1.00 59.40           N
ATOM    518  CA  ILE A   90      47.477  91.870  20.778  1.00 56.15           C
ATOM    519  CB  ILE A   90      47.883  90.703  21.700  1.00 51.64           C
ATOM    520  CG2 ILE A   90      48.173  89.491  20.887  1.00 50.44           C
ATOM    521  CG1 ILE A   90      49.145  91.063  22.481  1.00 49.56           C
ATOM    522  CD1 ILE A   90      49.759  89.906  23.244  1.00 43.91           C
ATOM    523  C   ILE A   90      46.480  91.371  19.745  1.00 57.56           C
ATOM    524  O   ILE A   90      46.881  90.999  18.645  1.00 58.98           O
ATOM    525  N   LYS A   91      45.189  91.368  20.070  1.00 58.35           N
ATOM    526  CA  LYS A   91      44.183  90.895  19.114  1.00 58.69           C
ATOM    527  CB  LYS A   91      42.854  90.615  19.825  1.00 60.46           C
ATOM    528  CG  LYS A   91      41.715  90.122  18.918  1.00 61.96           C
ATOM    529  CD  LYS A   91      40.412  90.075  19.719  1.00 64.11           C
ATOM    530  CE  LYS A   91      39.421  89.040  19.194  1.00 65.19           C
```

| ATOM | 531 | NZ | LYS A | 91 | 38.521 | 88.540 | 20.298 | 1.00 | 63.54 | N |
|---|---|---|---|---|---|---|---|---|---|---|
| ATOM | 532 | C | LYS A | 91 | 43.955 | 91.921 | 18.010 | 1.00 | 57.66 | C |
| ATOM | 533 | O | LYS A | 91 | 43.694 | 91.577 | 16.860 | 1.00 | 56.47 | O |
| ATOM | 534 | N | THR A | 92 | 44.073 | 93.190 | 18.363 | 1.00 | 58.21 | N |
| ATOM | 535 | CA | THR A | 92 | 43.848 | 94.251 | 17.400 | 1.00 | 60.30 | C |
| ATOM | 536 | CB | THR A | 92 | 43.804 | 95.635 | 18.108 | 1.00 | 60.32 | C |
| ATOM | 537 | OG1 | THR A | 92 | 43.370 | 95.471 | 19.470 | 1.00 | 58.29 | O |
| ATOM | 538 | CG2 | THR A | 92 | 42.818 | 96.559 | 17.389 | 1.00 | 59.88 | C |
| ATOM | 539 | C | THR A | 92 | 44.893 | 94.279 | 16.276 | 1.00 | 61.43 | C |
| ATOM | 540 | O | THR A | 92 | 44.577 | 94.654 | 15.141 | 1.00 | 62.82 | O |
| ATOM | 541 | N | VAL A | 93 | 46.129 | 93.881 | 16.588 | 1.00 | 61.84 | N |
| ATOM | 542 | CA | VAL A | 93 | 47.216 | 93.865 | 15.596 | 1.00 | 61.27 | C |
| ATOM | 543 | CB | VAL A | 93 | 48.602 | 94.162 | 16.245 | 1.00 | 60.23 | C |
| ATOM | 544 | CG1 | VAL A | 93 | 48.499 | 95.329 | 17.215 | 1.00 | 60.12 | C |
| ATOM | 545 | CG2 | VAL A | 93 | 49.116 | 92.946 | 16.942 | 1.00 | 58.65 | C |
| ATOM | 546 | C | VAL A | 93 | 47.301 | 92.508 | 14.887 | 1.00 | 61.69 | C |
| ATOM | 547 | O | VAL A | 93 | 47.642 | 92.421 | 13.701 | 1.00 | 61.56 | O |
| ATOM | 548 | N | LEU A | 94 | 46.988 | 91.447 | 15.618 | 1.00 | 61.46 | N |
| ATOM | 549 | CA | LEU A | 94 | 47.022 | 90.109 | 15.055 | 1.00 | 62.00 | C |
| ATOM | 550 | CB | LEU A | 94 | 47.292 | 89.086 | 16.149 | 1.00 | 61.13 | C |
| ATOM | 551 | CG | LEU A | 94 | 48.733 | 88.621 | 16.348 | 1.00 | 60.81 | C |
| ATOM | 552 | CD1 | LEU A | 94 | 49.672 | 89.481 | 15.526 | 1.00 | 59.77 | C |
| ATOM | 553 | CD2 | LEU A | 94 | 49.082 | 88.670 | 17.827 | 1.00 | 58.81 | C |
| ATOM | 554 | C | LEU A | 94 | 45.726 | 89.741 | 14.357 | 1.00 | 63.35 | C |
| ATOM | 555 | O | LEU A | 94 | 45.670 | 88.731 | 13.661 | 1.00 | 63.99 | O |
| ATOM | 556 | N | VAL A | 95 | 44.683 | 90.546 | 14.546 | 1.00 | 64.52 | N |
| ATOM | 557 | CA | VAL A | 95 | 43.395 | 90.263 | 13.921 | 1.00 | 65.45 | C |
| ATOM | 558 | CB | VAL A | 95 | 42.382 | 89.801 | 14.956 | 1.00 | 63.91 | C |
| ATOM | 559 | CG1 | VAL A | 95 | 41.070 | 89.498 | 14.272 | 1.00 | 64.17 | C |
| ATOM | 560 | CG2 | VAL A | 95 | 42.914 | 88.590 | 15.687 | 1.00 | 62.39 | C |
| ATOM | 561 | C | VAL A | 95 | 42.783 | 91.425 | 13.140 | 1.00 | 67.12 | C |
| ATOM | 562 | O | VAL A | 95 | 42.451 | 91.278 | 11.964 | 1.00 | 67.02 | O |
| ATOM | 563 | N | LYS A | 96 | 42.612 | 92.569 | 13.794 | 1.00 | 69.78 | N |
| ATOM | 564 | CA | LYS A | 96 | 42.046 | 93.738 | 13.130 | 1.00 | 72.87 | C |
| ATOM | 565 | CB | LYS A | 96 | 41.504 | 94.702 | 14.176 | 1.00 | 73.37 | C |
| ATOM | 566 | CG | LYS A | 96 | 40.805 | 93.987 | 15.326 | 1.00 | 74.37 | C |
| ATOM | 567 | CD | LYS A | 96 | 39.780 | 92.963 | 14.817 | 1.00 | 75.90 | C |
| ATOM | 568 | CE | LYS A | 96 | 39.159 | 92.138 | 15.963 | 1.00 | 75.91 | C |
| ATOM | 569 | NZ | LYS A | 96 | 38.281 | 91.016 | 15.493 | 1.00 | 74.20 | N |
| ATOM | 570 | C | LYS A | 96 | 43.217 | 94.350 | 12.377 | 1.00 | 75.61 | C |
| ATOM | 571 | O | LYS A | 96 | 43.769 | 95.384 | 12.782 | 1.00 | 75.69 | O |
| ATOM | 572 | N | GLU A | 97 | 43.587 | 93.700 | 11.272 | 1.00 | 78.30 | N |
| ATOM | 573 | CA | GLU A | 97 | 44.740 | 94.126 | 10.485 | 1.00 | 79.62 | C |
| ATOM | 574 | CB | GLU A | 97 | 45.996 | 93.574 | 11.148 | 1.00 | 77.52 | C |
| ATOM | 575 | CG | GLU A | 97 | 45.991 | 92.039 | 11.272 | 1.00 | 74.56 | C |
| ATOM | 576 | CD | GLU A | 97 | 46.271 | 91.321 | 9.953 | 1.00 | 72.65 | C |
| ATOM | 577 | OE1 | GLU A | 97 | 46.185 | 90.074 | 9.916 | 1.00 | 71.21 | O |
| ATOM | 578 | OE2 | GLU A | 97 | 46.593 | 91.999 | 8.956 | 1.00 | 69.62 | O |
| ATOM | 579 | C | GLU A | 97 | 44.803 | 93.767 | 8.996 | 1.00 | 82.14 | C |
| ATOM | 580 | O | GLU A | 97 | 45.712 | 94.244 | 8.318 | 1.00 | 82.97 | O |
| ATOM | 581 | N | CYS A | 98 | 43.890 | 92.933 | 8.484 | 1.00 | 84.03 | N |
| ATOM | 582 | CA | CYS A | 98 | 43.934 | 92.536 | 7.062 | 1.00 | 84.98 | C |
| ATOM | 583 | CB | CYS A | 98 | 42.690 | 91.725 | 6.682 | 1.00 | 84.46 | C |
| ATOM | 584 | SG | CYS A | 98 | 43.055 | 90.158 | 5.834 | 1.00 | 82.93 | S |
| ATOM | 585 | C | CYS A | 98 | 44.061 | 93.757 | 6.152 | 1.00 | 86.62 | C |
| ATOM | 586 | O | CYS A | 98 | 43.081 | 94.228 | 5.571 | 1.00 | 88.63 | O |
| ATOM | 587 | N | TYR A | 99 | 45.296 | 94.240 | 6.035 | 1.00 | 87.24 | N |
| ATOM | 588 | CA | TYR A | 99 | 45.665 | 95.424 | 5.266 | 1.00 | 87.46 | C |
| ATOM | 589 | CB | TYR A | 99 | 44.919 | 95.508 | 3.928 | 1.00 | 90.32 | C |
| ATOM | 590 | CG | TYR A | 99 | 45.700 | 96.274 | 2.882 | 1.00 | 93.20 | C |
| ATOM | 591 | CD1 | TYR A | 99 | 46.499 | 95.604 | 1.966 | 1.00 | 94.40 | C |
| ATOM | 592 | CE1 | TYR A | 99 | 47.297 | 96.289 | 1.070 | 1.00 | 95.69 | C |
| ATOM | 593 | CD2 | TYR A | 99 | 45.717 | 97.666 | 2.870 | 1.00 | 94.09 | C |
| ATOM | 594 | CE2 | TYR A | 99 | 46.517 | 98.364 | 1.979 | 1.00 | 95.41 | C |
| ATOM | 595 | CZ | TYR A | 99 | 47.310 | 97.670 | 1.081 | 1.00 | 95.63 | C |
| ATOM | 596 | OH | TYR A | 99 | 48.143 | 98.352 | 0.215 | 1.00 | 95.88 | O |
| ATOM | 597 | C | TYR A | 99 | 45.343 | 96.663 | 6.105 | 1.00 | 86.44 | C |
| ATOM | 598 | O | TYR A | 99 | 45.838 | 97.755 | 5.830 | 1.00 | 87.33 | O |
| ATOM | 599 | N | SER A | 100 | 44.522 | 96.467 | 7.134 | 1.00 | 84.74 | N |
| ATOM | 600 | CA | SER A | 100 | 44.096 | 97.527 | 8.040 | 1.00 | 84.28 | C |
| ATOM | 601 | CB | SER A | 100 | 43.540 | 96.911 | 9.324 | 1.00 | 84.57 | C |
| ATOM | 602 | OG | SER A | 100 | 42.995 | 97.900 | 10.177 | 1.00 | 86.04 | O |
| ATOM | 603 | C | SER A | 100 | 45.215 | 98.510 | 8.379 | 1.00 | 83.89 | C |
| ATOM | 604 | O | SER A | 100 | 45.078 | 99.719 | 8.164 | 1.00 | 85.91 | O |
| ATOM | 605 | N | VAL A | 101 | 46.310 | 97.989 | 8.921 | 1.00 | 81.08 | N |
| ATOM | 606 | CA | VAL A | 101 | 47.483 | 98.782 | 9.277 | 1.00 | 77.82 | C |
| ATOM | 607 | CB | VAL A | 101 | 47.345 | 99.476 | 10.684 | 1.00 | 78.44 | C |

```
ATOM    608  CG1 VAL A 101      46.343  98.747  11.541  1.00 79.50           C
ATOM    609  CG2 VAL A 101      48.697  99.547  11.391  1.00 77.82           C
ATOM    610  C   VAL A 101      48.620  97.779   9.274  1.00 75.08           C
ATOM    611  O   VAL A 101      49.489  97.826   8.412  1.00 75.36           O
ATOM    612  N   PHE A 102      48.583  96.851  10.222  1.00 71.08           N
ATOM    613  CA  PHE A 102      49.593  95.808  10.324  1.00 67.16           C
ATOM    614  CB  PHE A 102      49.562  95.194  11.725  1.00 64.40           C
ATOM    615  CG  PHE A 102      49.602  96.207  12.825  1.00 62.40           C
ATOM    616  CD1 PHE A 102      48.446  96.585  13.481  1.00 62.97           C
ATOM    617  CD2 PHE A 102      50.791  96.819  13.174  1.00 61.35           C
ATOM    618  CE1 PHE A 102      48.479  97.563  14.465  1.00 61.08           C
ATOM    619  CE2 PHE A 102      50.827  97.793  14.151  1.00 60.14           C
ATOM    620  CZ  PHE A 102      49.671  98.165  14.796  1.00 59.73           C
ATOM    621  C   PHE A 102      49.292  94.729   9.275  1.00 65.53           C
ATOM    622  O   PHE A 102      48.138  94.521   8.912  1.00 67.36           O
ATOM    623  N   THR A 103      50.320  94.051   8.775  1.00 62.02           N
ATOM    624  CA  THR A 103      50.100  93.009   7.777  1.00 59.01           C
ATOM    625  CB  THR A 103      49.556  93.559   6.433  1.00 58.63           C
ATOM    626  OG1 THR A 103      48.359  94.302   6.657  1.00 57.37           O
ATOM    627  CG2 THR A 103      49.253  92.410   5.473  1.00 55.39           C
ATOM    628  C   THR A 103      51.371  92.272   7.430  1.00 56.88           C
ATOM    629  O   THR A 103      51.351  91.061   7.244  1.00 56.75           O
ATOM    630  N   ASN A 104      52.473  93.003   7.330  1.00 54.33           N
ATOM    631  CA  ASN A 104      53.739  92.391   6.954  1.00 54.20           C
ATOM    632  CB  ASN A 104      54.440  93.270   5.910  1.00 53.80           C
ATOM    633  CG  ASN A 104      53.459  93.920   4.927  1.00 55.06           C
ATOM    634  OD1 ASN A 104      52.771  93.233   4.155  1.00 51.87           O
ATOM    635  ND2 ASN A 104      53.391  95.258   4.956  1.00 53.98           N
ATOM    636  C   ASN A 104      54.662  92.181   8.148  1.00 53.88           C
ATOM    637  O   ASN A 104      54.408  92.697   9.237  1.00 53.31           O
ATOM    638  N   ARG A 105      55.726  91.406   7.947  1.00 53.63           N
ATOM    639  CA  ARG A 105      56.695  91.170   9.016  1.00 53.18           C
ATOM    640  CB  ARG A 105      57.084  89.689   9.111  1.00 53.26           C
ATOM    641  CG  ARG A 105      55.938  88.742   9.468  1.00 53.26           C
ATOM    642  CD  ARG A 105      56.459  87.392   9.983  1.00 50.67           C
ATOM    643  NE  ARG A 105      55.407  86.375  10.108  1.00 49.55           N
ATOM    644  CZ  ARG A 105      54.750  85.831   9.083  1.00 47.99           C
ATOM    645  NH1 ARG A 105      53.816  84.916   9.307  1.00 46.73           N
ATOM    646  NH2 ARG A 105      55.024  86.195   7.837  1.00 46.70           N
ATOM    647  C   ARG A 105      57.935  92.003   8.712  1.00 52.91           C
ATOM    648  O   ARG A 105      58.051  92.581   7.625  1.00 52.69           O
ATOM    649  N   ARG A 106      58.853  92.073   9.672  1.00 52.78           N
ATOM    650  CA  ARG A 106      60.079  92.844   9.495  1.00 52.29           C
ATOM    651  CB  ARG A 106      60.982  92.689  10.722  1.00 51.57           C
ATOM    652  CG  ARG A 106      61.706  93.955  11.124  1.00 52.76           C
ATOM    653  CD  ARG A 106      63.149  93.690  11.506  1.00 55.15           C
ATOM    654  NE  ARG A 106      63.493  94.204  12.831  1.00 57.65           N
ATOM    655  CZ  ARG A 106      63.137  93.612  13.971  1.00 59.56           C
ATOM    656  NH1 ARG A 106      63.482  94.135  15.142  1.00 58.94           N
ATOM    657  NH2 ARG A 106      62.433  92.487  13.937  1.00 59.63           N
ATOM    658  C   ARG A 106      60.800  92.303   8.263  1.00 53.34           C
ATOM    659  O   ARG A 106      60.892  91.089   8.075  1.00 54.18           O
ATOM    660  N   PRO A 107      61.290  93.192   7.388  1.00 53.35           N
ATOM    661  CD  PRO A 107      61.053  94.646   7.342  1.00 52.61           C
ATOM    662  CA  PRO A 107      62.001  92.741   6.188  1.00 53.11           C
ATOM    663  CB  PRO A 107      61.874  93.933   5.256  1.00 52.71           C
ATOM    664  CG  PRO A 107      61.948  95.083   6.213  1.00 52.31           C
ATOM    665  C   PRO A 107      63.445  92.467   6.580  1.00 53.37           C
ATOM    666  O   PRO A 107      64.042  93.258   7.297  1.00 54.97           O
ATOM    667  N   PHE A 108      64.009  91.351   6.139  1.00 54.24           N
ATOM    668  CA  PHE A 108      65.400  91.042   6.488  1.00 55.61           C
ATOM    669  CB  PHE A 108      65.487  89.715   7.261  1.00 52.51           C
ATOM    670  CG  PHE A 108      64.893  88.557   6.530  1.00 50.26           C
ATOM    671  CD1 PHE A 108      65.690  87.528   6.076  1.00 48.21           C
ATOM    672  CD2 PHE A 108      63.534  88.531   6.244  1.00 49.31           C
ATOM    673  CE1 PHE A 108      65.145  86.494   5.343  1.00 47.67           C
ATOM    674  CE2 PHE A 108      62.984  87.510   5.517  1.00 47.48           C
ATOM    675  CZ  PHE A 108      63.788  86.486   5.060  1.00 47.08           C
ATOM    676  C   PHE A 108      66.302  90.997   5.248  1.00 57.28           C
ATOM    677  O   PHE A 108      65.846  91.279   4.130  1.00 57.35           O
ATOM    678  N   GLY A 109      67.578  90.655   5.470  1.00 58.33           N
ATOM    679  CA  GLY A 109      68.581  90.580   4.409  1.00 57.12           C
ATOM    680  C   GLY A 109      68.123  90.277   2.993  1.00 55.65           C
ATOM    681  O   GLY A 109      66.963  89.955   2.755  1.00 56.42           O
ATOM    682  N   PRO A 110      69.036  90.357   2.025  1.00 54.88           N
ATOM    683  CD  PRO A 110      70.478  90.455   2.286  1.00 55.15           C
ATOM    684  CA  PRO A 110      68.768  90.099   0.603  1.00 56.06           C
```

```
ATOM    685  CB  PRO A 110      70.166  90.134  -0.018  1.00 56.37           C
ATOM    686  CG  PRO A 110      71.056  89.697   1.126  1.00 56.42           C
ATOM    687  C   PRO A 110      68.021  88.774   0.353  1.00 56.86           C
ATOM    688  O   PRO A 110      68.562  87.678   0.554  1.00 57.15           O
ATOM    689  N   VAL A 111      66.773  88.895  -0.098  1.00 55.98           N
ATOM    690  CA  VAL A 111      65.904  87.745  -0.340  1.00 55.14           C
ATOM    691  CB  VAL A 111      64.446  88.114   0.026  1.00 54.36           C
ATOM    692  CG1 VAL A 111      63.486  87.063  -0.460  1.00 53.92           C
ATOM    693  CG2 VAL A 111      64.328  88.268   1.521  1.00 54.63           C
ATOM    694  C   VAL A 111      65.933  87.171  -1.756  1.00 55.54           C
ATOM    695  O   VAL A 111      65.697  85.978  -1.958  1.00 54.86           O
ATOM    696  N   GLY A 112      66.203  88.018  -2.742  1.00 57.09           N
ATOM    697  CA  GLY A 112      66.250  87.534  -4.109  1.00 56.31           C
ATOM    698  C   GLY A 112      64.884  87.115  -4.593  1.00 55.19           C
ATOM    699  O   GLY A 112      63.885  87.675  -4.145  1.00 54.30           O
ATOM    700  N   PHE A 113      64.839  86.125  -5.485  1.00 55.17           N
ATOM    701  CA  PHE A 113      63.571  85.667  -6.056  1.00 55.67           C
ATOM    702  CB  PHE A 113      63.809  84.649  -7.178  1.00 55.32           C
ATOM    703  CG  PHE A 113      63.835  83.228  -6.709  1.00 54.61           C
ATOM    704  CD1 PHE A 113      64.946  82.714  -6.077  1.00 55.33           C
ATOM    705  CD2 PHE A 113      62.716  82.425  -6.838  1.00 55.25           C
ATOM    706  CE1 PHE A 113      64.938  81.423  -5.572  1.00 55.69           C
ATOM    707  CE2 PHE A 113      62.703  81.135  -6.334  1.00 55.87           C
ATOM    708  CZ  PHE A 113      63.816  80.637  -5.699  1.00 55.39           C
ATOM    709  C   PHE A 113      62.644  85.057  -5.015  1.00 56.56           C
ATOM    710  O   PHE A 113      61.513  84.643  -5.332  1.00 55.90           O
ATOM    711  N   MET A 114      63.124  84.996  -3.775  1.00 55.95           N
ATOM    712  CA  MET A 114      62.322  84.443  -2.700  1.00 55.70           C
ATOM    713  CB  MET A 114      63.225  83.890  -1.605  1.00 55.58           C
ATOM    714  CG  MET A 114      63.724  82.486  -1.898  1.00 56.08           C
ATOM    715  SD  MET A 114      62.350  81.320  -2.089  1.00 59.37           S
ATOM    716  CE  MET A 114      62.338  80.531  -0.479  1.00 59.29           C
ATOM    717  C   MET A 114      61.365  85.487  -2.144  1.00 56.11           C
ATOM    718  O   MET A 114      60.611  85.224  -1.212  1.00 55.28           O
ATOM    719  N   LYS A 115      61.398  86.676  -2.737  1.00 57.87           N
ATOM    720  CA  LYS A 115      60.520  87.772  -2.335  1.00 59.39           C
ATOM    721  CB  LYS A 115      60.898  89.036  -3.096  1.00 60.03           C
ATOM    722  CG  LYS A 115      60.538  88.942  -4.579  1.00 62.72           C
ATOM    723  CD  LYS A 115      61.187  90.040  -5.429  1.00 63.79           C
ATOM    724  CE  LYS A 115      60.846  89.863  -6.914  1.00 63.19           C
ATOM    725  NZ  LYS A 115      61.645  90.757  -7.795  1.00 64.58           N
ATOM    726  C   LYS A 115      59.097  87.378  -2.720  1.00 59.53           C
ATOM    727  O   LYS A 115      58.155  88.151  -2.565  1.00 60.04           O
ATOM    728  N   SER A 116      58.962  86.165  -3.246  1.00 59.54           N
ATOM    729  CA  SER A 116      57.677  85.648  -3.674  1.00 59.24           C
ATOM    730  CB  SER A 116      57.808  85.038  -5.080  1.00 62.28           C
ATOM    731  OG  SER A 116      58.214  86.018  -6.039  1.00 64.93           O
ATOM    732  C   SER A 116      57.174  84.607  -2.678  1.00 57.16           C
ATOM    733  O   SER A 116      56.073  84.082  -2.815  1.00 57.57           O
ATOM    734  N   ALA A 117      57.991  84.309  -1.674  1.00 54.83           N
ATOM    735  CA  ALA A 117      57.614  83.349  -0.641  1.00 52.47           C
ATOM    736  CB  ALA A 117      58.785  83.104   0.288  1.00 53.21           C
ATOM    737  C   ALA A 117      56.449  83.945   0.138  1.00 51.37           C
ATOM    738  O   ALA A 117      56.425  85.146   0.387  1.00 53.19           O
ATOM    739  N   ILE A 118      55.491  83.118   0.540  1.00 48.66           N
ATOM    740  CA  ILE A 118      54.325  83.624   1.250  1.00 45.84           C
ATOM    741  CB  ILE A 118      53.261  82.533   1.414  1.00 45.19           C
ATOM    742  CG2 ILE A 118      53.721  81.513   2.424  1.00 43.76           C
ATOM    743  CG1 ILE A 118      51.942  83.176   1.840  1.00 46.42           C
ATOM    744  CD1 ILE A 118      50.880  82.191   2.262  1.00 46.17           C
ATOM    745  C   ILE A 118      54.642  84.228   2.615  1.00 45.17           C
ATOM    746  O   ILE A 118      53.986  85.170   3.051  1.00 44.11           O
ATOM    747  N   SER A 119      55.645  83.693   3.296  1.00 45.97           N
ATOM    748  CA  SER A 119      56.020  84.233   4.595  1.00 46.60           C
ATOM    749  CB  SER A 119      56.832  83.205   5.390  1.00 47.40           C
ATOM    750  OG  SER A 119      57.795  82.570   4.570  1.00 50.64           O
ATOM    751  C   SER A 119      56.825  85.519   4.414  1.00 47.22           C
ATOM    752  O   SER A 119      56.923  86.333   5.329  1.00 47.14           O
ATOM    753  N   ILE A 120      57.377  85.709   3.216  1.00 48.57           N
ATOM    754  CA  ILE A 120      58.179  86.893   2.903  1.00 48.73           C
ATOM    755  CB  ILE A 120      59.453  86.511   2.098  1.00 49.35           C
ATOM    756  CG2 ILE A 120      60.417  87.677   2.058  1.00 45.75           C
ATOM    757  CG1 ILE A 120      60.115  85.272   2.710  1.00 49.35           C
ATOM    758  CD1 ILE A 120      60.280  85.330   4.206  1.00 51.11           C
ATOM    759  C   ILE A 120      57.412  87.927   2.079  1.00 48.55           C
ATOM    760  O   ILE A 120      57.828  89.073   1.981  1.00 47.73           O
ATOM    761  N   ALA A 121      56.298  87.524   1.483  1.00 49.56           N
```

```
ATOM    762  CA   ALA A 121      55.511  88.427   0.650  1.00 52.17           C
ATOM    763  CB   ALA A 121      54.506  87.617  -0.172  1.00 48.91           C
ATOM    764  C    ALA A 121      54.791  89.516   1.465  1.00 55.60           C
ATOM    765  O    ALA A 121      54.555  89.361   2.673  1.00 53.72           O
ATOM    766  N    GLU A 122      54.435  90.617   0.800  1.00 59.39           N
ATOM    767  CA   GLU A 122      53.755  91.723   1.479  1.00 62.79           C
ATOM    768  CB   GLU A 122      54.736  92.882   1.673  1.00 62.32           C
ATOM    769  CG   GLU A 122      55.850  92.561   2.645  1.00 64.83           C
ATOM    770  CD   GLU A 122      56.762  93.736   2.896  1.00 66.24           C
ATOM    771  OE1  GLU A 122      57.535  93.684   3.881  1.00 66.70           O
ATOM    772  OE2  GLU A 122      56.707  94.705   2.106  1.00 68.48           O
ATOM    773  C    GLU A 122      52.463  92.259   0.849  1.00 64.33           C
ATOM    774  O    GLU A 122      52.199  92.080  -0.339  1.00 64.10           O
ATOM    775  N    ASP A 123      51.660  92.911   1.686  1.00 67.02           N
ATOM    776  CA   ASP A 123      50.400  93.530   1.281  1.00 69.33           C
ATOM    777  CB   ASP A 123      50.691  94.780   0.537  1.00 71.16           C
ATOM    778  CG   ASP A 123      51.286  95.890   1.439  1.00 73.97           C
ATOM    779  OD1  ASP A 123      51.652  96.969   0.920  1.00 75.44           O
ATOM    780  OD2  ASP A 123      51.381  95.647   2.667  1.00 74.76           O
ATOM    781  C    ASP A 123      49.434  92.699   0.453  1.00 69.89           C
ATOM    782  O    ASP A 123      49.084  91.577   0.818  1.00 69.56           O
ATOM    783  N    GLU A 124      48.991  93.269  -0.661  1.00 70.88           N
ATOM    784  CA   GLU A 124      48.043  92.584  -1.522  1.00 72.59           C
ATOM    785  CB   GLU A 124      47.520  93.531  -2.606  1.00 73.65           C
ATOM    786  CG   GLU A 124      46.181  93.093  -3.189  1.00 75.82           C
ATOM    787  CD   GLU A 124      45.028  93.276  -2.206  1.00 77.38           C
ATOM    788  OE1  GLU A 124      44.594  94.431  -2.000  1.00 78.15           O
ATOM    789  OE2  GLU A 124      44.562  92.268  -1.629  1.00 78.10           O
ATOM    790  C    GLU A 124      48.649  91.341  -2.166  1.00 72.45           C
ATOM    791  O    GLU A 124      47.959  90.335  -2.341  1.00 72.39           O
ATOM    792  N    GLU A 125      49.929  91.402  -2.518  1.00 72.06           N
ATOM    793  CA   GLU A 125      50.572  90.247  -3.134  1.00 72.20           C
ATOM    794  CB   GLU A 125      51.996  90.583  -3.578  1.00 74.53           C
ATOM    795  CG   GLU A 125      52.093  91.080  -5.029  1.00 79.31           C
ATOM    796  CD   GLU A 125      51.628  90.035  -6.055  1.00 81.95           C
ATOM    797  OE1  GLU A 125      50.440  90.075  -6.474  1.00 81.48           O
ATOM    798  OE2  GLU A 125      52.457  89.169  -6.432  1.00 82.16           O
ATOM    799  C    GLU A 125      50.581  89.063  -2.182  1.00 70.58           C
ATOM    800  O    GLU A 125      50.596  87.912  -2.605  1.00 70.65           O
ATOM    801  N    TRP A 126      50.564  89.349  -0.888  1.00 69.67           N
ATOM    802  CA   TRP A 126      50.541  88.291   0.114  1.00 68.01           C
ATOM    803  CB   TRP A 126      50.943  88.835   1.497  1.00 65.76           C
ATOM    804  CG   TRP A 126      50.632  87.868   2.587  1.00 62.83           C
ATOM    805  CD2  TRP A 126      49.530  87.932   3.492  1.00 62.16           C
ATOM    806  CE2  TRP A 126      49.534  86.735   4.242  1.00 62.42           C
ATOM    807  CE3  TRP A 126      48.536  88.878   3.739  1.00 61.98           C
ATOM    808  CD1  TRP A 126      51.251  86.676   2.825  1.00 63.56           C
ATOM    809  NE1  TRP A 126      50.597  85.985   3.814  1.00 61.97           N
ATOM    810  CZ2  TRP A 126      48.580  86.462   5.222  1.00 61.26           C
ATOM    811  CZ3  TRP A 126      47.590  88.604   4.711  1.00 61.72           C
ATOM    812  CH2  TRP A 126      47.619  87.405   5.442  1.00 60.96           C
ATOM    813  C    TRP A 126      49.143  87.660   0.198  1.00 67.54           C
ATOM    814  O    TRP A 126      49.003  86.443   0.129  1.00 66.27           O
ATOM    815  N    LYS A 127      48.113  88.491   0.344  1.00 68.74           N
ATOM    816  CA   LYS A 127      46.742  87.993   0.440  1.00 69.65           C
ATOM    817  CB   LYS A 127      45.743  89.159   0.459  1.00 71.40           C
ATOM    818  CG   LYS A 127      44.354  88.755   0.951  1.00 74.08           C
ATOM    819  CD   LYS A 127      44.418  88.294   2.406  1.00 76.22           C
ATOM    820  CE   LYS A 127      43.218  87.434   2.812  1.00 77.58           C
ATOM    821  NZ   LYS A 127      43.635  86.263   3.666  1.00 75.06           N
ATOM    822  C    LYS A 127      46.435  87.057  -0.732  1.00 68.61           C
ATOM    823  O    LYS A 127      45.669  86.106  -0.600  1.00 67.41           O
ATOM    824  N    ARG A 128      47.045  87.335  -1.876  1.00 68.50           N
ATOM    825  CA   ARG A 128      46.859  86.509  -3.060  1.00 68.51           C
ATOM    826  CB   ARG A 128      47.670  87.074  -4.227  1.00 68.21           C
ATOM    827  CG   ARG A 128      47.724  86.172  -5.436  1.00 69.23           C
ATOM    828  CD   ARG A 128      48.840  86.601  -6.357  1.00 72.44           C
ATOM    829  NE   ARG A 128      49.137  85.587  -7.364  1.00 76.19           N
ATOM    830  CZ   ARG A 128      50.186  85.633  -8.183  1.00 79.26           C
ATOM    831  NH1  ARG A 128      50.386  84.670  -9.076  1.00 80.90           N
ATOM    832  NH2  ARG A 128      51.046  86.641  -8.107  1.00 80.90           N
ATOM    833  C    ARG A 128      47.330  85.091  -2.748  1.00 68.52           C
ATOM    834  O    ARG A 128      46.529  84.155  -2.708  1.00 69.39           O
ATOM    835  N    LEU A 129      48.635  84.950  -2.523  1.00 67.57           N
ATOM    836  CA   LEU A 129      49.250  83.662  -2.209  1.00 65.41           C
ATOM    837  CB   LEU A 129      50.738  83.855  -1.890  1.00 66.55           C
ATOM    838  CG   LEU A 129      51.637  84.490  -2.958  1.00 67.21           C
```

```
ATOM    839  CD1 LEU A 129      52.907  85.024  -2.318  1.00 66.86           C
ATOM    840  CD2 LEU A 129      51.967  83.470  -4.028  1.00 67.37           C
ATOM    841  C   LEU A 129      48.568  82.966  -1.028  1.00 63.82           C
ATOM    842  O   LEU A 129      48.217  81.796  -1.127  1.00 63.64           O
ATOM    843  N   ARG A 130      48.389  83.676   0.086  1.00 61.84           N
ATOM    844  CA  ARG A 130      47.757  83.086   1.266  1.00 60.56           C
ATOM    845  CB  ARG A 130      47.494  84.133   2.351  1.00 59.53           C
ATOM    846  CG  ARG A 130      46.823  83.568   3.616  1.00 57.88           C
ATOM    847  CD  ARG A 130      47.831  82.873   4.541  1.00 57.55           C
ATOM    848  NE  ARG A 130      47.221  82.246   5.714  1.00 55.07           N
ATOM    849  CZ  ARG A 130      47.835  82.121   6.892  1.00 56.25           C
ATOM    850  NH1 ARG A 130      49.068  82.586   7.049  1.00 56.34           N
ATOM    851  NH2 ARG A 130      47.225  81.530   7.916  1.00 55.02           N
ATOM    852  C   ARG A 130      46.440  82.468   0.870  1.00 61.08           C
ATOM    853  O   ARG A 130      46.216  81.281   1.062  1.00 61.16           O
ATOM    854  N   SER A 131      45.558  83.292   0.326  1.00 63.20           N
ATOM    855  CA  SER A 131      44.255  82.817  -0.114  1.00 65.27           C
ATOM    856  CB  SER A 131      43.229  83.960  -0.104  1.00 67.84           C
ATOM    857  OG  SER A 131      41.917  83.483  -0.374  1.00 70.76           O
ATOM    858  C   SER A 131      44.457  82.297  -1.528  1.00 64.09           C
ATOM    859  O   SER A 131      44.125  82.965  -2.505  1.00 64.18           O
ATOM    860  N   LEU A 132      45.031  81.106  -1.611  1.00 62.52           N
ATOM    861  CA  LEU A 132      45.322  80.457  -2.877  1.00 61.88           C
ATOM    862  CB  LEU A 132      46.302  81.308  -3.700  1.00 61.33           C
ATOM    863  CG  LEU A 132      46.485  80.971  -5.191  1.00 62.01           C
ATOM    864  CD1 LEU A 132      45.226  81.349  -5.962  1.00 58.85           C
ATOM    865  CD2 LEU A 132      47.689  81.718  -5.755  1.00 60.29           C
ATOM    866  C   LEU A 132      45.961  79.124  -2.494  1.00 61.14           C
ATOM    867  O   LEU A 132      45.797  78.117  -3.183  1.00 60.72           O
ATOM    868  N   LEU A 133      46.677  79.140  -1.373  1.00 60.59           N
ATOM    869  CA  LEU A 133      47.350  77.962  -0.839  1.00 60.48           C
ATOM    870  CB  LEU A 133      48.734  78.335  -0.316  1.00 59.45           C
ATOM    871  CG  LEU A 133      49.795  78.734  -1.337  1.00 58.53           C
ATOM    872  CD1 LEU A 133      51.011  79.264  -0.604  1.00 58.63           C
ATOM    873  CD2 LEU A 133      50.152  77.546  -2.198  1.00 56.45           C
ATOM    874  C   LEU A 133      46.527  77.366   0.298  1.00 61.68           C
ATOM    875  O   LEU A 133      46.616  76.166   0.577  1.00 61.63           O
ATOM    876  N   SER A 134      45.735  78.212   0.957  1.00 62.97           N
ATOM    877  CA  SER A 134      44.883  77.772   2.059  1.00 64.61           C
ATOM    878  CB  SER A 134      43.832  78.835   2.380  1.00 64.14           C
ATOM    879  OG  SER A 134      44.369  79.829   3.238  1.00 65.13           O
ATOM    880  C   SER A 134      44.201  76.444   1.741  1.00 66.65           C
ATOM    881  O   SER A 134      44.101  75.564   2.600  1.00 67.92           O
ATOM    882  N   PRO A 135      43.703  76.285   0.503  1.00 67.74           N
ATOM    883  CD  PRO A 135      43.514  77.328  -0.526  1.00 68.36           C
ATOM    884  CA  PRO A 135      43.040  75.044   0.097  1.00 67.50           C
ATOM    885  CB  PRO A 135      42.752  75.291  -1.375  1.00 66.75           C
ATOM    886  CG  PRO A 135      42.417  76.738  -1.386  1.00 67.36           C
ATOM    887  C   PRO A 135      43.958  73.838   0.304  1.00 68.08           C
ATOM    888  O   PRO A 135      43.509  72.753   0.683  1.00 67.88           O
ATOM    889  N   THR A 136      45.247  74.053   0.049  1.00 67.66           N
ATOM    890  CA  THR A 136      46.266  73.027   0.184  1.00 66.48           C
ATOM    891  CB  THR A 136      47.602  73.534  -0.341  1.00 65.92           C
ATOM    892  OG1 THR A 136      47.508  73.738  -1.757  1.00 66.80           O
ATOM    893  CG2 THR A 136      48.705  72.539  -0.036  1.00 65.91           C
ATOM    894  C   THR A 136      46.476  72.546   1.609  1.00 67.44           C
ATOM    895  O   THR A 136      47.027  71.466   1.823  1.00 68.10           O
ATOM    896  N   PHE A 137      46.044  73.329   2.592  1.00 68.38           N
ATOM    897  CA  PHE A 137      46.228  72.924   3.987  1.00 69.54           C
ATOM    898  CB  PHE A 137      47.046  73.973   4.744  1.00 67.26           C
ATOM    899  CG  PHE A 137      48.368  74.289   4.107  1.00 64.45           C
ATOM    900  CD1 PHE A 137      48.460  75.231   3.090  1.00 62.54           C
ATOM    901  CD2 PHE A 137      49.516  73.621   4.504  1.00 62.41           C
ATOM    902  CE1 PHE A 137      49.676  75.498   2.483  1.00 61.23           C
ATOM    903  CE2 PHE A 137      50.736  73.885   3.897  1.00 60.74           C
ATOM    904  CZ  PHE A 137      50.818  74.822   2.888  1.00 60.64           C
ATOM    905  C   PHE A 137      44.923  72.678   4.732  1.00 71.69           C
ATOM    906  O   PHE A 137      44.821  72.951   5.929  1.00 72.53           O
ATOM    907  N   THR A 138      43.928  72.149   4.028  1.00 73.86           N
ATOM    908  CA  THR A 138      42.631  71.870   4.632  1.00 75.35           C
ATOM    909  CB  THR A 138      41.488  71.934   3.600  1.00 75.56           C
ATOM    910  OG1 THR A 138      41.627  70.847   2.672  1.00 76.07           O
ATOM    911  CG2 THR A 138      41.509  73.258   2.851  1.00 74.54           C
ATOM    912  C   THR A 138      42.578  70.481   5.236  1.00 76.48           C
ATOM    913  O   THR A 138      43.337  69.587   4.856  1.00 75.98           O
ATOM    914  N   SER A 139      41.677  70.311   6.192  1.00 78.51           N
ATOM    915  CA  SER A 139      41.485  69.010   6.792  1.00 80.91           C
```

```
ATOM    916  CB  SER A 139      40.573  69.111   8.008  1.00 81.09           C
ATOM    917  OG  SER A 139      40.277  67.818   8.504  1.00 82.57           O
ATOM    918  C   SER A 139      40.790  68.261   5.659  1.00 82.54           C
ATOM    919  O   SER A 139      39.859  68.786   5.037  1.00 83.47           O
ATOM    920  N   GLY A 140      41.243  67.046   5.374  1.00 83.61           N
ATOM    921  CA  GLY A 140      40.651  66.294   4.282  1.00 84.54           C
ATOM    922  C   GLY A 140      41.757  66.025   3.283  1.00 84.51           C
ATOM    923  O   GLY A 140      41.838  64.942   2.700  1.00 86.02           O
ATOM    924  N   LYS A 141      42.601  67.033   3.075  1.00 82.84           N
ATOM    925  CA  LYS A 141      43.748  66.899   2.194  1.00 81.18           C
ATOM    926  CB  LYS A 141      44.058  68.215   1.492  1.00 80.46           C
ATOM    927  CG  LYS A 141      42.929  68.708   0.611  1.00 81.06           C
ATOM    928  CD  LYS A 141      43.328  69.951  -0.169  1.00 80.28           C
ATOM    929  CE  LYS A 141      42.144  70.527  -0.928  1.00 79.50           C
ATOM    930  NZ  LYS A 141      42.534  71.690  -1.766  1.00 79.46           N
ATOM    931  C   LYS A 141      44.871  66.536   3.149  1.00 80.80           C
ATOM    932  O   LYS A 141      45.960  66.141   2.738  1.00 81.29           O
ATOM    933  N   LEU A 142      44.586  66.687   4.439  1.00 79.40           N
ATOM    934  CA  LEU A 142      45.545  66.341   5.473  1.00 78.18           C
ATOM    935  CB  LEU A 142      45.371  67.240   6.707  1.00 76.67           C
ATOM    936  CG  LEU A 142      46.196  66.877   7.954  1.00 75.28           C
ATOM    937  CD1 LEU A 142      47.622  66.516   7.579  1.00 75.37           C
ATOM    938  CD2 LEU A 142      46.190  68.043   8.912  1.00 75.05           C
ATOM    939  C   LEU A 142      45.295  64.886   5.841  1.00 77.71           C
ATOM    940  O   LEU A 142      46.230  64.085   5.894  1.00 77.65           O
ATOM    941  N   LYS A 143      44.032  64.543   6.081  1.00 77.14           N
ATOM    942  CA  LYS A 143      43.690  63.175   6.434  1.00 76.99           C
ATOM    943  CB  LYS A 143      42.192  63.040   6.729  1.00 77.92           C
ATOM    944  CG  LYS A 143      41.277  63.257   5.534  1.00 78.60           C
ATOM    945  CD  LYS A 143      39.798  63.124   5.923  1.00 79.67           C
ATOM    946  CE  LYS A 143      39.376  61.673   6.224  1.00 79.75           C
ATOM    947  NZ  LYS A 143      39.995  61.085   7.451  1.00 77.46           N
ATOM    948  C   LYS A 143      44.073  62.303   5.253  1.00 76.67           C
ATOM    949  O   LYS A 143      44.133  61.077   5.359  1.00 76.00           O
ATOM    950  N   GLU A 144      44.349  62.960   4.129  1.00 76.59           N
ATOM    951  CA  GLU A 144      44.730  62.280   2.897  1.00 77.44           C
ATOM    952  CB  GLU A 144      44.249  63.101   1.696  1.00 78.45           C
ATOM    953  CG  GLU A 144      44.636  62.561   0.330  1.00 81.19           C
ATOM    954  CD  GLU A 144      43.791  63.174  -0.782  1.00 83.75           C
ATOM    955  OE1 GLU A 144      42.581  62.865  -0.836  1.00 85.36           O
ATOM    956  OE2 GLU A 144      44.320  63.970  -1.594  1.00 83.55           O
ATOM    957  C   GLU A 144      46.239  62.057   2.820  1.00 77.04           C
ATOM    958  O   GLU A 144      46.707  61.149   2.134  1.00 76.77           O
ATOM    959  N   MET A 145      46.986  62.886   3.543  1.00 76.75           N
ATOM    960  CA  MET A 145      48.447  62.814   3.575  1.00 74.49           C
ATOM    961  CB  MET A 145      49.028  64.209   3.833  1.00 74.88           C
ATOM    962  CG  MET A 145      49.509  64.930   2.586  1.00 75.50           C
ATOM    963  SD  MET A 145      49.835  66.686   2.823  1.00 75.38           S
ATOM    964  CE  MET A 145      49.064  67.370   1.336  1.00 75.15           C
ATOM    965  C   MET A 145      48.947  61.855   4.641  1.00 73.30           C
ATOM    966  O   MET A 145      50.070  61.358   4.558  1.00 73.23           O
ATOM    967  N   VAL A 146      48.107  61.605   5.642  1.00 71.44           N
ATOM    968  CA  VAL A 146      48.447  60.715   6.747  1.00 70.84           C
ATOM    969  CB  VAL A 146      47.190  60.367   7.574  1.00 71.88           C
ATOM    970  CG1 VAL A 146      47.519  59.295   8.610  1.00 70.70           C
ATOM    971  CG2 VAL A 146      46.656  61.624   8.248  1.00 72.08           C
ATOM    972  C   VAL A 146      49.138  59.414   6.332  1.00 69.75           C
ATOM    973  O   VAL A 146      50.229  59.100   6.811  1.00 67.74           O
ATOM    974  N   PRO A 147      48.503  58.632   5.445  1.00 69.25           N
ATOM    975  CD  PRO A 147      47.261  58.925   4.709  1.00 68.53           C
ATOM    976  CA  PRO A 147      49.097  57.374   4.993  1.00 69.16           C
ATOM    977  CB  PRO A 147      48.379  57.126   3.680  1.00 69.38           C
ATOM    978  CG  PRO A 147      47.004  57.633   3.978  1.00 69.54           C
ATOM    979  C   PRO A 147      50.605  57.529   4.803  1.00 70.26           C
ATOM    980  O   PRO A 147      51.402  56.826   5.429  1.00 71.77           O
ATOM    981  N   ILE A 148      50.981  58.478   3.950  1.00 69.51           N
ATOM    982  CA  ILE A 148      52.378  58.759   3.644  1.00 68.19           C
ATOM    983  CB  ILE A 148      52.487  59.948   2.674  1.00 67.98           C
ATOM    984  CG2 ILE A 148      53.936  60.156   2.266  1.00 67.65           C
ATOM    985  CG1 ILE A 148      51.616  59.684   1.442  1.00 68.87           C
ATOM    986  CD1 ILE A 148      51.884  58.332   0.760  1.00 68.16           C
ATOM    987  C   ILE A 148      53.252  59.046   4.864  1.00 67.53           C
ATOM    988  O   ILE A 148      54.348  58.497   4.995  1.00 67.97           O
ATOM    989  N   ILE A 149      52.776  59.909   5.753  1.00 66.33           N
ATOM    990  CA  ILE A 149      53.544  60.250   6.946  1.00 65.31           C
ATOM    991  CB  ILE A 149      52.851  61.377   7.757  1.00 63.09           C
ATOM    992  CG2 ILE A 149      53.649  61.697   9.013  1.00 61.25           C
```

```
ATOM    993  CG1 ILE A 149      52.737  62.636   6.901  1.00 60.98           C
ATOM    994  CD1 ILE A 149      52.052  63.774   7.594  1.00 60.31           C
ATOM    995  C   ILE A 149      53.736  59.023   7.840  1.00 66.45           C
ATOM    996  O   ILE A 149      54.802  58.830   8.440  1.00 66.97           O
ATOM    997  N   ALA A 150      52.701  58.198   7.930  1.00 66.44           N
ATOM    998  CA  ALA A 150      52.771  57.001   8.745  1.00 66.67           C
ATOM    999  CB  ALA A 150      51.478  56.221   8.622  1.00 68.30           C
ATOM   1000  C   ALA A 150      53.939  56.173   8.228  1.00 67.20           C
ATOM   1001  O   ALA A 150      54.704  55.590   9.002  1.00 67.36           O
ATOM   1002  N   GLN A 151      54.071  56.147   6.905  1.00 67.36           N
ATOM   1003  CA  GLN A 151      55.133  55.408   6.237  1.00 67.27           C
ATOM   1004  CB  GLN A 151      55.164  55.783   4.753  1.00 68.28           C
ATOM   1005  CG  GLN A 151      55.837  54.757   3.846  1.00 71.23           C
ATOM   1006  CD  GLN A 151      55.591  55.036   2.365  1.00 72.52           C
ATOM   1007  OE1 GLN A 151      54.473  55.371   1.959  1.00 73.51           O
ATOM   1008  NE2 GLN A 151      56.631  54.885   1.548  1.00 71.63           N
ATOM   1009  C   GLN A 151      56.478  55.713   6.886  1.00 66.46           C
ATOM   1010  O   GLN A 151      57.230  54.804   7.233  1.00 65.73           O
ATOM   1011  N   TYR A 152      56.770  56.999   7.068  1.00 66.22           N
ATOM   1012  CA  TYR A 152      58.034  57.401   7.670  1.00 66.63           C
ATOM   1013  CB  TYR A 152      58.466  58.755   7.092  1.00 66.85           C
ATOM   1014  CG  TYR A 152      58.821  58.591   5.627  1.00 68.52           C
ATOM   1015  CD1 TYR A 152      59.957  57.867   5.248  1.00 68.24           C
ATOM   1016  CE1 TYR A 152      60.204  57.562   3.917  1.00 69.30           C
ATOM   1017  CD2 TYR A 152      57.947  59.018   4.622  1.00 68.68           C
ATOM   1018  CE2 TYR A 152      58.187  58.722   3.285  1.00 68.84           C
ATOM   1019  CZ  TYR A 152      59.312  57.990   2.939  1.00 69.83           C
ATOM   1020  OH  TYR A 152      59.530  57.655   1.620  1.00 70.86           O
ATOM   1021  C   TYR A 152      58.019  57.383   9.194  1.00 66.11           C
ATOM   1022  O   TYR A 152      59.022  57.681   9.849  1.00 65.73           O
ATOM   1023  N   GLY A 153      56.873  57.006   9.750  1.00 65.82           N
ATOM   1024  CA  GLY A 153      56.766  56.888  11.184  1.00 65.16           C
ATOM   1025  C   GLY A 153      57.412  55.550  11.474  1.00 65.85           C
ATOM   1026  O   GLY A 153      58.138  55.382  12.452  1.00 65.76           O
ATOM   1027  N   ASP A 154      57.166  54.589  10.589  1.00 66.88           N
ATOM   1028  CA  ASP A 154      57.727  53.252  10.754  1.00 67.85           C
ATOM   1029  CB  ASP A 154      56.983  52.243   9.875  1.00 70.05           C
ATOM   1030  CG  ASP A 154      55.650  51.823  10.478  1.00 73.44           C
ATOM   1031  OD1 ASP A 154      54.600  52.192   9.906  1.00 76.14           O
ATOM   1032  OD2 ASP A 154      55.653  51.135  11.532  1.00 73.44           O
ATOM   1033  C   ASP A 154      59.217  53.185  10.467  1.00 66.83           C
ATOM   1034  O   ASP A 154      59.937  52.404  11.082  1.00 67.45           O
ATOM   1035  N   VAL A 155      59.687  53.999   9.532  1.00 65.67           N
ATOM   1036  CA  VAL A 155      61.106  53.994   9.219  1.00 64.05           C
ATOM   1037  CB  VAL A 155      61.424  54.907   8.026  1.00 63.54           C
ATOM   1038  CG1 VAL A 155      62.921  54.962   7.815  1.00 62.40           C
ATOM   1039  CG2 VAL A 155      60.725  54.397   6.770  1.00 62.67           C
ATOM   1040  C   VAL A 155      61.850  54.505  10.441  1.00 64.06           C
ATOM   1041  O   VAL A 155      62.949  54.050  10.759  1.00 62.87           O
ATOM   1042  N   LEU A 156      61.229  55.454  11.133  1.00 64.15           N
ATOM   1043  CA  LEU A 156      61.826  56.038  12.325  1.00 64.96           C
ATOM   1044  CB  LEU A 156      60.942  57.174  12.852  1.00 64.24           C
ATOM   1045  CG  LEU A 156      61.353  57.765  14.204  1.00 63.57           C
ATOM   1046  CD1 LEU A 156      62.726  58.392  14.102  1.00 63.36           C
ATOM   1047  CD2 LEU A 156      60.331  58.794  14.636  1.00 64.02           C
ATOM   1048  C   LEU A 156      62.025  54.993  13.420  1.00 65.47           C
ATOM   1049  O   LEU A 156      63.065  54.966  14.095  1.00 64.44           O
ATOM   1050  N   VAL A 157      61.022  54.137  13.596  1.00 65.84           N
ATOM   1051  CA  VAL A 157      61.097  53.108  14.619  1.00 66.95           C
ATOM   1052  CB  VAL A 157      59.752  52.339  14.763  1.00 67.32           C
ATOM   1053  CG1 VAL A 157      58.623  53.329  15.061  1.00 65.73           C
ATOM   1054  CG2 VAL A 157      59.455  51.530  13.506  1.00 67.02           C
ATOM   1055  C   VAL A 157      62.231  52.152  14.288  1.00 67.51           C
ATOM   1056  O   VAL A 157      62.990  51.747  15.176  1.00 66.85           O
ATOM   1057  N   ARG A 158      62.356  51.807  13.011  1.00 68.66           N
ATOM   1058  CA  ARG A 158      63.430  50.923  12.580  1.00 70.30           C
ATOM   1059  CB  ARG A 158      63.402  50.726  11.072  1.00 71.30           C
ATOM   1060  CG  ARG A 158      62.255  49.920  10.496  1.00 73.82           C
ATOM   1061  CD  ARG A 158      62.640  49.643   9.061  1.00 75.08           C
ATOM   1062  NE  ARG A 158      63.585  50.685   8.663  1.00 75.85           N
ATOM   1063  CZ  ARG A 158      64.668  50.488   7.926  1.00 74.73           C
ATOM   1064  NH1 ARG A 158      64.956  49.271   7.484  1.00 75.85           N
ATOM   1065  NH2 ARG A 158      65.477  51.508   7.664  1.00 74.25           N
ATOM   1066  C   ARG A 158      64.779  51.546  12.944  1.00 71.15           C
ATOM   1067  O   ARG A 158      65.591  50.954  13.656  1.00 70.44           O
ATOM   1068  N   ASN A 159      65.011  52.753  12.447  1.00 72.87           N
ATOM   1069  CA  ASN A 159      66.263  53.447  12.708  1.00 75.49           C
```

```
ATOM   1070  CB   ASN A 159      66.314  54.744  11.891  1.00 75.83           C
ATOM   1071  CG   ASN A 159      66.774  54.508  10.463  1.00 76.06           C
ATOM   1072  OD1  ASN A 159      67.962  54.304  10.216  1.00 77.48           O
ATOM   1073  ND2  ASN A 159      65.834  54.511   9.520  1.00 75.54           N
ATOM   1074  C    ASN A 159      66.502  53.734  14.187  1.00 76.80           C
ATOM   1075  O    ASN A 159      67.648  53.929  14.613  1.00 76.94           O
ATOM   1076  N    LEU A 160      65.428  53.750  14.973  1.00 77.63           N
ATOM   1077  CA   LEU A 160      65.565  54.019  16.396  1.00 78.57           C
ATOM   1078  CB   LEU A 160      64.269  54.595  16.967  1.00 77.33           C
ATOM   1079  CG   LEU A 160      64.454  55.714  18.002  1.00 76.73           C
ATOM   1080  CD1  LEU A 160      65.668  55.427  18.877  1.00 75.76           C
ATOM   1081  CD2  LEU A 160      64.638  57.042  17.287  1.00 76.33           C
ATOM   1082  C    LEU A 160      65.900  52.719  17.101  1.00 79.47           C
ATOM   1083  O    LEU A 160      66.516  52.712  18.171  1.00 79.90           O
ATOM   1084  N    ARG A 161      65.503  51.615  16.486  1.00 80.04           N
ATOM   1085  CA   ARG A 161      65.759  50.317  17.067  1.00 81.90           C
ATOM   1086  CB   ARG A 161      64.987  49.242  16.308  1.00 80.68           C
ATOM   1087  CG   ARG A 161      64.908  47.931  17.054  1.00 80.51           C
ATOM   1088  CD   ARG A 161      64.084  46.917  16.304  1.00 79.65           C
ATOM   1089  NE   ARG A 161      62.703  47.345  16.081  1.00 78.82           N
ATOM   1090  CZ   ARG A 161      61.831  47.647  17.041  1.00 78.52           C
ATOM   1091  NH1  ARG A 161      62.184  47.586  18.320  1.00 77.30           N
ATOM   1092  NH2  ARG A 161      60.586  47.982  16.720  1.00 78.38           N
ATOM   1093  C    ARG A 161      67.250  50.002  17.060  1.00 83.83           C
ATOM   1094  O    ARG A 161      67.753  49.291  17.934  1.00 83.95           O
ATOM   1095  N    ARG A 162      67.967  50.544  16.083  1.00 85.85           N
ATOM   1096  CA   ARG A 162      69.396  50.286  16.011  1.00 88.24           C
ATOM   1097  CB   ARG A 162      69.998  50.912  14.748  1.00 88.70           C
ATOM   1098  CG   ARG A 162      70.382  52.384  14.861  1.00 90.27           C
ATOM   1099  CD   ARG A 162      71.901  52.578  14.773  1.00 89.83           C
ATOM   1100  NE   ARG A 162      72.236  53.896  14.248  1.00 89.77           N
ATOM   1101  CZ   ARG A 162      71.825  54.346  13.064  1.00 90.69           C
ATOM   1102  NH1  ARG A 162      71.066  53.576  12.285  1.00 90.16           N
ATOM   1103  NH2  ARG A 162      72.157  55.571  12.666  1.00 90.60           N
ATOM   1104  C    ARG A 162      70.102  50.826  17.246  1.00 89.60           C
ATOM   1105  O    ARG A 162      70.767  50.081  17.962  1.00 89.55           O
ATOM   1106  N    GLU A 163      69.930  52.121  17.505  1.00 91.98           N
ATOM   1107  CA   GLU A 163      70.567  52.783  18.638  1.00 94.30           C
ATOM   1108  CB   GLU A 163      70.306  54.288  18.567  1.00 97.08           C
ATOM   1109  CG   GLU A 163      71.123  54.972  17.481  1.00100.40           C
ATOM   1110  CD   GLU A 163      72.622  54.900  17.755  1.00102.43           C
ATOM   1111  OE1  GLU A 163      73.176  55.893  18.287  1.00102.67           O
ATOM   1112  OE2  GLU A 163      73.237  53.845  17.450  1.00103.02           O
ATOM   1113  C    GLU A 163      70.165  52.248  20.001  1.00 94.05           C
ATOM   1114  O    GLU A 163      70.815  52.537  21.009  1.00 94.28           O
ATOM   1115  N    ALA A 164      69.090  51.474  20.037  1.00 93.27           N
ATOM   1116  CA   ALA A 164      68.656  50.895  21.291  1.00 93.14           C
ATOM   1117  CB   ALA A 164      67.179  50.533  21.218  1.00 93.99           C
ATOM   1118  C    ALA A 164      69.503  49.647  21.496  1.00 92.57           C
ATOM   1119  O    ALA A 164      70.142  49.478  22.537  1.00 91.91           O
ATOM   1120  N    GLU A 165      69.514  48.796  20.469  1.00 92.53           N
ATOM   1121  CA   GLU A 165      70.263  47.540  20.478  1.00 92.10           C
ATOM   1122  CB   GLU A 165      70.077  46.803  19.151  1.00 91.98           C
ATOM   1123  CG   GLU A 165      68.637  46.485  18.786  1.00 93.49           C
ATOM   1124  CD   GLU A 165      68.360  44.989  18.734  1.00 94.32           C
ATOM   1125  OE1  GLU A 165      67.410  44.588  18.023  1.00 95.04           O
ATOM   1126  OE2  GLU A 165      69.084  44.217  19.406  1.00 93.56           O
ATOM   1127  C    GLU A 165      71.753  47.751  20.720  1.00 91.71           C
ATOM   1128  O    GLU A 165      72.387  46.979  21.445  1.00 92.08           O
ATOM   1129  N    THR A 166      72.314  48.789  20.106  1.00 90.28           N
ATOM   1130  CA   THR A 166      73.729  49.085  20.270  1.00 89.47           C
ATOM   1131  CB   THR A 166      74.213  50.083  19.194  1.00 89.36           C
ATOM   1132  OG1  THR A 166      73.524  51.332  19.334  1.00 88.50           O
ATOM   1133  CG2  THR A 166      73.946  49.522  17.808  1.00 88.63           C
ATOM   1134  C    THR A 166      73.999  49.647  21.669  1.00 89.65           C
ATOM   1135  O    THR A 166      75.153  49.732  22.109  1.00 90.23           O
ATOM   1136  N    GLY A 167      72.922  50.025  22.361  1.00 88.78           N
ATOM   1137  CA   GLY A 167      73.030  50.555  23.711  1.00 86.76           C
ATOM   1138  C    GLY A 167      73.630  51.943  23.829  1.00 85.62           C
ATOM   1139  O    GLY A 167      73.787  52.462  24.937  1.00 85.54           O
ATOM   1140  N    ALA A 168      73.965  52.552  22.697  1.00 84.35           N
ATOM   1141  CA   ALA A 168      74.554  53.886  22.696  1.00 83.32           C
ATOM   1142  CB   ALA A 168      75.281  54.129  21.383  1.00 82.55           C
ATOM   1143  C    ALA A 168      73.491  54.960  22.909  1.00 82.62           C
ATOM   1144  O    ALA A 168      72.421  54.903  22.299  1.00 82.14           O
ATOM   1145  N    PRO A 169      73.774  55.948  23.787  1.00 82.18           N
ATOM   1146  CD   PRO A 169      75.041  56.136  24.514  1.00 81.75           C
```

```
ATOM   1147  CA   PRO A 169      72.844  57.050  24.080  1.00 81.25           C
ATOM   1148  CB   PRO A 169      73.597  57.873  25.129  1.00 81.29           C
ATOM   1149  CG   PRO A 169      75.031  57.623  24.784  1.00 81.61           C
ATOM   1150  C    PRO A 169      72.575  57.826  22.793  1.00 80.15           C
ATOM   1151  O    PRO A 169      73.510  58.182  22.074  1.00 80.00           O
ATOM   1152  N    VAL A 170      71.300  58.085  22.511  1.00 78.96           N
ATOM   1153  CA   VAL A 170      70.888  58.763  21.281  1.00 76.42           C
ATOM   1154  CB   VAL A 170      69.485  58.301  20.860  1.00 76.11           C
ATOM   1155  CG1  VAL A 170      69.078  58.983  19.566  1.00 76.25           C
ATOM   1156  CG2  VAL A 170      69.458  56.790  20.714  1.00 77.06           C
ATOM   1157  C    VAL A 170      70.869  60.284  21.266  1.00 74.87           C
ATOM   1158  O    VAL A 170      70.612  60.930  22.286  1.00 74.69           O
ATOM   1159  N    THR A 171      71.159  60.840  20.088  1.00 72.73           N
ATOM   1160  CA   THR A 171      71.123  62.285  19.865  1.00 69.71           C
ATOM   1161  CB   THR A 171      72.314  62.774  19.022  1.00 68.62           C
ATOM   1162  OG1  THR A 171      73.504  62.715  19.816  1.00 67.00           O
ATOM   1163  CG2  THR A 171      72.089  64.210  18.563  1.00 67.44           C
ATOM   1164  C    THR A 171      69.817  62.525  19.116  1.00 67.59           C
ATOM   1165  O    THR A 171      69.658  62.129  17.957  1.00 67.02           O
ATOM   1166  N    LEU A 172      68.888  63.173  19.804  1.00 65.07           N
ATOM   1167  CA   LEU A 172      67.560  63.429  19.283  1.00 63.66           C
ATOM   1168  CB   LEU A 172      66.767  64.250  20.294  1.00 64.11           C
ATOM   1169  CG   LEU A 172      66.682  63.603  21.679  1.00 64.08           C
ATOM   1170  CD1  LEU A 172      65.510  64.219  22.428  1.00 64.53           C
ATOM   1171  CD2  LEU A 172      66.504  62.094  21.553  1.00 61.57           C
ATOM   1172  C    LEU A 172      67.401  64.052  17.915  1.00 62.02           C
ATOM   1173  O    LEU A 172      67.023  63.374  16.962  1.00 61.30           O
ATOM   1174  N    LYS A 173      67.680  65.342  17.816  1.00 61.41           N
ATOM   1175  CA   LYS A 173      67.498  66.036  16.557  1.00 60.73           C
ATOM   1176  CB   LYS A 173      67.991  67.478  16.668  1.00 62.81           C
ATOM   1177  CG   LYS A 173      66.970  68.454  16.073  1.00 63.89           C
ATOM   1178  CD   LYS A 173      67.295  69.915  16.286  1.00 63.48           C
ATOM   1179  CE   LYS A 173      66.393  70.737  15.385  1.00 63.71           C
ATOM   1180  NZ   LYS A 173      66.493  72.202  15.613  1.00 66.17           N
ATOM   1181  C    LYS A 173      68.078  65.372  15.317  1.00 59.95           C
ATOM   1182  O    LYS A 173      67.806  65.800  14.200  1.00 60.56           O
ATOM   1183  N    ASP A 174      68.861  64.318  15.489  1.00 58.51           N
ATOM   1184  CA   ASP A 174      69.404  63.646  14.326  1.00 57.62           C
ATOM   1185  CB   ASP A 174      70.688  62.907  14.697  1.00 61.36           C
ATOM   1186  CG   ASP A 174      71.816  63.860  15.068  1.00 64.45           C
ATOM   1187  OD1  ASP A 174      71.946  64.922  14.415  1.00 65.68           O
ATOM   1188  OD2  ASP A 174      72.579  63.542  16.004  1.00 65.28           O
ATOM   1189  C    ASP A 174      68.383  62.683  13.710  1.00 56.28           C
ATOM   1190  O    ASP A 174      68.230  62.624  12.483  1.00 53.78           O
ATOM   1191  N    VAL A 175      67.684  61.938  14.567  1.00 55.59           N
ATOM   1192  CA   VAL A 175      66.661  60.987  14.121  1.00 53.96           C
ATOM   1193  CB   VAL A 175      66.300  59.963  15.234  1.00 55.13           C
ATOM   1194  CG1  VAL A 175      67.282  58.789  15.220  1.00 53.63           C
ATOM   1195  CG2  VAL A 175      66.300  60.652  16.590  1.00 53.13           C
ATOM   1196  C    VAL A 175      65.396  61.750  13.754  1.00 53.04           C
ATOM   1197  O    VAL A 175      64.661  61.382  12.834  1.00 53.29           O
ATOM   1198  N    PHE A 176      65.143  62.823  14.483  1.00 51.28           N
ATOM   1199  CA   PHE A 176      63.974  63.630  14.223  1.00 50.80           C
ATOM   1200  CB   PHE A 176      63.665  64.423  15.482  1.00 50.12           C
ATOM   1201  CG   PHE A 176      63.106  63.566  16.584  1.00 48.69           C
ATOM   1202  CD1  PHE A 176      63.403  63.819  17.913  1.00 48.66           C
ATOM   1203  CD2  PHE A 176      62.257  62.519  16.278  1.00 45.75           C
ATOM   1204  CE1  PHE A 176      62.857  63.041  18.911  1.00 48.62           C
ATOM   1205  CE2  PHE A 176      61.709  61.745  17.260  1.00 45.15           C
ATOM   1206  CZ   PHE A 176      62.006  62.003  18.583  1.00 48.82           C
ATOM   1207  C    PHE A 176      64.189  64.510  12.989  1.00 51.22           C
ATOM   1208  O    PHE A 176      63.282  64.694  12.162  1.00 50.25           O
ATOM   1209  N    GLY A 177      65.403  65.033  12.851  1.00 51.28           N
ATOM   1210  CA   GLY A 177      65.713  65.829  11.678  1.00 50.91           C
ATOM   1211  C    GLY A 177      65.608  64.946  10.435  1.00 49.77           C
ATOM   1212  O    GLY A 177      65.315  65.419   9.338  1.00 49.55           O
ATOM   1213  N    ALA A 178      65.848  63.650  10.606  1.00 48.89           N
ATOM   1214  CA   ALA A 178      65.772  62.714   9.493  1.00 49.20           C
ATOM   1215  CB   ALA A 178      66.463  61.429   9.854  1.00 47.53           C
ATOM   1216  C    ALA A 178      64.316  62.450   9.186  1.00 50.26           C
ATOM   1217  O    ALA A 178      63.922  62.362   8.023  1.00 48.55           O
ATOM   1218  N    TYR A 179      63.527  62.321  10.253  1.00 51.72           N
ATOM   1219  CA   TYR A 179      62.098  62.073  10.146  1.00 51.18           C
ATOM   1220  CB   TYR A 179      61.488  61.840  11.534  1.00 51.87           C
ATOM   1221  CG   TYR A 179      59.978  61.818  11.507  1.00 50.20           C
ATOM   1222  CD1  TYR A 179      59.228  62.838  12.090  1.00 49.45           C
ATOM   1223  CE1  TYR A 179      57.838  62.834  12.011  1.00 48.73           C
```

```
ATOM   1224  CD2 TYR A 179      59.303  60.799  10.851  1.00 49.50           C
ATOM   1225  CE2 TYR A 179      57.933  60.787  10.769  1.00 48.59           C
ATOM   1226  CZ  TYR A 179      57.204  61.797  11.347  1.00 48.39           C
ATOM   1227  OH  TYR A 179      55.837  61.732  11.260  1.00 50.52           O
ATOM   1228  C   TYR A 179      61.440  63.279   9.507  1.00 51.07           C
ATOM   1229  O   TYR A 179      60.531  63.137   8.681  1.00 49.71           O
ATOM   1230  N   SER A 180      61.906  64.465   9.895  1.00 51.83           N
ATOM   1231  CA  SER A 180      61.366  65.714   9.363  1.00 53.62           C
ATOM   1232  CB  SER A 180      61.984  66.898  10.088  1.00 52.23           C
ATOM   1233  OG  SER A 180      61.094  67.993  10.052  1.00 52.95           O
ATOM   1234  C   SER A 180      61.665  65.795   7.870  1.00 54.92           C
ATOM   1235  O   SER A 180      60.813  66.174   7.064  1.00 54.13           O
ATOM   1236  N   MET A 181      62.887  65.407   7.519  1.00 58.51           N
ATOM   1237  CA  MET A 181      63.344  65.385   6.132  1.00 60.86           C
ATOM   1238  CB  MET A 181      64.799  64.947   6.064  1.00 65.51           C
ATOM   1239  CG  MET A 181      65.433  65.171   4.701  1.00 72.58           C
ATOM   1240  SD  MET A 181      66.119  66.835   4.556  1.00 79.50           S
ATOM   1241  CE  MET A 181      67.701  66.546   5.449  1.00 79.69           C
ATOM   1242  C   MET A 181      62.519  64.398   5.320  1.00 60.02           C
ATOM   1243  O   MET A 181      62.037  64.722   4.236  1.00 61.17           O
ATOM   1244  N   ASP A 182      62.374  63.190   5.855  1.00 58.94           N
ATOM   1245  CA  ASP A 182      61.613  62.131   5.205  1.00 57.82           C
ATOM   1246  CB  ASP A 182      61.537  60.895   6.099  1.00 61.14           C
ATOM   1247  CG  ASP A 182      62.909  60.343   6.471  1.00 64.63           C
ATOM   1248  OD1 ASP A 182      63.108  59.994   7.658  1.00 66.70           O
ATOM   1249  OD2 ASP A 182      63.784  60.246   5.583  1.00 67.38           O
ATOM   1250  C   ASP A 182      60.200  62.583   4.899  1.00 56.44           C
ATOM   1251  O   ASP A 182      59.670  62.286   3.827  1.00 56.06           O
ATOM   1252  N   VAL A 183      59.584  63.298   5.838  1.00 54.67           N
ATOM   1253  CA  VAL A 183      58.214  63.750   5.635  1.00 53.59           C
ATOM   1254  CB  VAL A 183      57.506  64.009   6.978  1.00 51.84           C
ATOM   1255  CG1 VAL A 183      56.096  64.509   6.742  1.00 49.59           C
ATOM   1256  CG2 VAL A 183      57.463  62.732   7.780  1.00 50.62           C
ATOM   1257  C   VAL A 183      58.141  64.993   4.764  1.00 54.19           C
ATOM   1258  O   VAL A 183      57.126  65.252   4.111  1.00 52.78           O
ATOM   1259  N   ILE A 184      59.221  65.765   4.747  1.00 55.01           N
ATOM   1260  CA  ILE A 184      59.227  66.961   3.923  1.00 57.75           C
ATOM   1261  CB  ILE A 184      60.364  67.913   4.321  1.00 57.38           C
ATOM   1262  CG2 ILE A 184      60.652  68.879   3.165  1.00 57.84           C
ATOM   1263  CG1 ILE A 184      59.983  68.673   5.596  1.00 56.20           C
ATOM   1264  CD1 ILE A 184      58.822  69.638   5.411  1.00 56.81           C
ATOM   1265  C   ILE A 184      59.381  66.582   2.453  1.00 59.07           C
ATOM   1266  O   ILE A 184      58.669  67.090   1.583  1.00 58.70           O
ATOM   1267  N   THR A 185      60.311  65.683   2.177  1.00 60.07           N
ATOM   1268  CA  THR A 185      60.526  65.257   0.810  1.00 63.01           C
ATOM   1269  CB  THR A 185      61.619  64.167   0.731  1.00 63.11           C
ATOM   1270  OG1 THR A 185      61.287  63.085   1.610  1.00 64.28           O
ATOM   1271  CG2 THR A 185      62.972  64.737   1.129  1.00 64.45           C
ATOM   1272  C   THR A 185      59.233  64.699   0.219  1.00 64.38           C
ATOM   1273  O   THR A 185      58.669  65.262  -0.717  1.00 64.43           O
ATOM   1274  N   SER A 186      58.764  63.604   0.802  1.00 66.34           N
ATOM   1275  CA  SER A 186      57.572  62.900   0.343  1.00 68.33           C
ATOM   1276  CB  SER A 186      57.340  61.659   1.214  1.00 69.40           C
ATOM   1277  OG  SER A 186      57.251  62.004   2.584  1.00 68.83           O
ATOM   1278  C   SER A 186      56.273  63.677   0.245  1.00 69.08           C
ATOM   1279  O   SER A 186      55.444  63.397  -0.615  1.00 68.91           O
ATOM   1280  N   THR A 187      56.080  64.650   1.117  1.00 71.16           N
ATOM   1281  CA  THR A 187      54.840  65.402   1.082  1.00 72.32           C
ATOM   1282  CB  THR A 187      54.420  65.823   2.493  1.00 73.32           C
ATOM   1283  OG1 THR A 187      54.900  64.865   3.444  1.00 74.13           O
ATOM   1284  CG2 THR A 187      52.910  65.876   2.587  1.00 74.85           C
ATOM   1285  C   THR A 187      54.950  66.647   0.218  1.00 72.62           C
ATOM   1286  O   THR A 187      53.943  67.163  -0.269  1.00 71.99           O
ATOM   1287  N   SER A 188      56.171  67.126   0.024  1.00 73.55           N
ATOM   1288  CA  SER A 188      56.369  68.324  -0.767  1.00 74.75           C
ATOM   1289  CB  SER A 188      57.649  69.042  -0.339  1.00 74.81           C
ATOM   1290  OG  SER A 188      57.478  70.455  -0.380  1.00 75.09           O
ATOM   1291  C   SER A 188      56.405  67.993  -2.251  1.00 75.71           C
ATOM   1292  O   SER A 188      55.885  68.754  -3.067  1.00 76.69           O
ATOM   1293  N   PHE A 189      57.015  66.865  -2.606  1.00 75.95           N
ATOM   1294  CA  PHE A 189      57.076  66.453  -4.013  1.00 76.30           C
ATOM   1295  CB  PHE A 189      58.303  67.029  -4.732  1.00 76.47           C
ATOM   1296  CG  PHE A 189      58.989  68.137  -4.001  1.00 76.48           C
ATOM   1297  CD1 PHE A 189      59.679  67.893  -2.828  1.00 76.79           C
ATOM   1298  CD2 PHE A 189      58.994  69.416  -4.520  1.00 77.23           C
ATOM   1299  CE1 PHE A 189      60.364  68.902  -2.191  1.00 76.43           C
ATOM   1300  CE2 PHE A 189      59.677  70.428  -3.887  1.00 77.11           C
```

| ATOM | 1301 | CZ  | PHE A 189 | 60.363 | 70.170 | -2.722 | 1.00 | 76.83 | C |
| ATOM | 1302 | C   | PHE A 189 | 57.102 | 64.935 | -4.200 | 1.00 | 75.99 | C |
| ATOM | 1303 | O   | PHE A 189 | 57.645 | 64.433 | -5.190 | 1.00 | 76.13 | O |
| ATOM | 1304 | N   | GLY A 190 | 56.518 | 64.208 | -3.253 | 1.00 | 75.36 | N |
| ATOM | 1305 | CA  | GLY A 190 | 56.500 | 62.761 | -3.346 | 1.00 | 74.34 | C |
| ATOM | 1306 | C   | GLY A 190 | 57.844 | 62.123 | -3.670 | 1.00 | 73.69 | C |
| ATOM | 1307 | O   | GLY A 190 | 57.909 | 61.138 | -4.401 | 1.00 | 74.25 | O |
| ATOM | 1308 | N   | VAL A 191 | 58.921 | 62.682 | -3.139 | 1.00 | 73.19 | N |
| ATOM | 1309 | CA  | VAL A 191 | 60.242 | 62.126 | -3.378 | 1.00 | 74.10 | C |
| ATOM | 1310 | CB  | VAL A 191 | 61.314 | 63.234 | -3.388 | 1.00 | 74.46 | C |
| ATOM | 1311 | CG1 | VAL A 191 | 62.682 | 62.635 | -3.684 | 1.00 | 73.78 | C |
| ATOM | 1312 | CG2 | VAL A 191 | 60.947 | 64.305 | -4.410 | 1.00 | 74.21 | C |
| ATOM | 1313 | C   | VAL A 191 | 60.519 | 61.181 | -2.224 | 1.00 | 73.97 | C |
| ATOM | 1314 | O   | VAL A 191 | 61.043 | 61.598 | -1.204 | 1.00 | 74.92 | O |
| ATOM | 1315 | N   | ASN A 192 | 60.169 | 59.913 | -2.378 | 1.00 | 74.37 | N |
| ATOM | 1316 | CA  | ASN A 192 | 60.369 | 58.950 | -1.299 | 1.00 | 76.14 | C |
| ATOM | 1317 | CB  | ASN A 192 | 59.393 | 57.783 | -1.455 | 1.00 | 77.81 | C |
| ATOM | 1318 | CG  | ASN A 192 | 58.011 | 58.104 | -0.905 | 1.00 | 79.36 | C |
| ATOM | 1319 | OD1 | ASN A 192 | 57.455 | 59.170 | -1.168 | 1.00 | 80.10 | O |
| ATOM | 1320 | ND2 | ASN A 192 | 57.448 | 57.174 | -0.141 | 1.00 | 80.24 | N |
| ATOM | 1321 | C   | ASN A 192 | 61.781 | 58.411 | -1.130 | 1.00 | 76.26 | C |
| ATOM | 1322 | O   | ASN A 192 | 62.278 | 57.667 | -1.962 | 1.00 | 76.83 | O |
| ATOM | 1323 | N   | ILE A 193 | 62.417 | 58.781 | -0.028 | 1.00 | 77.55 | N |
| ATOM | 1324 | CA  | ILE A 193 | 63.775 | 58.332 |  0.263 | 1.00 | 78.68 | C |
| ATOM | 1325 | CB  | ILE A 193 | 64.812 | 59.369 | -0.206 | 1.00 | 79.20 | C |
| ATOM | 1326 | CG2 | ILE A 193 | 64.968 | 59.307 | -1.712 | 1.00 | 79.54 | C |
| ATOM | 1327 | CG1 | ILE A 193 | 64.371 | 60.768 |  0.214 | 1.00 | 79.56 | C |
| ATOM | 1328 | CD1 | ILE A 193 | 65.232 | 61.858 | -0.358 | 1.00 | 81.19 | C |
| ATOM | 1329 | C   | ILE A 193 | 63.945 | 58.097 |  1.758 | 1.00 | 78.79 | C |
| ATOM | 1330 | O   | ILE A 193 | 63.119 | 58.530 |  2.560 | 1.00 | 79.14 | O |
| ATOM | 1331 | N   | ASP A 194 | 65.014 | 57.407 |  2.132 | 1.00 | 78.55 | N |
| ATOM | 1332 | CA  | ASP A 194 | 65.264 | 57.118 |  3.537 | 1.00 | 78.35 | C |
| ATOM | 1333 | CB  | ASP A 194 | 65.626 | 55.640 |  3.716 | 1.00 | 77.14 | C |
| ATOM | 1334 | CG  | ASP A 194 | 65.633 | 55.207 |  5.174 | 1.00 | 74.92 | C |
| ATOM | 1335 | OD1 | ASP A 194 | 66.382 | 55.791 |  5.981 | 1.00 | 73.18 | O |
| ATOM | 1336 | OD2 | ASP A 194 | 64.887 | 54.270 |  5.510 | 1.00 | 74.02 | O |
| ATOM | 1337 | C   | ASP A 194 | 66.390 | 57.999 |  4.051 | 1.00 | 79.21 | C |
| ATOM | 1338 | O   | ASP A 194 | 67.427 | 57.509 |  4.504 | 1.00 | 80.60 | O |
| ATOM | 1339 | N   | SER A 195 | 66.176 | 59.306 |  3.967 | 1.00 | 79.30 | N |
| ATOM | 1340 | CA  | SER A 195 | 67.150 | 60.287 |  4.425 | 1.00 | 79.63 | C |
| ATOM | 1341 | CB  | SER A 195 | 66.418 | 61.539 |  4.911 | 1.00 | 78.95 | C |
| ATOM | 1342 | OG  | SER A 195 | 65.481 | 61.978 |  3.940 | 1.00 | 78.47 | O |
| ATOM | 1343 | C   | SER A 195 | 68.022 | 59.736 |  5.550 | 1.00 | 80.24 | C |
| ATOM | 1344 | O   | SER A 195 | 69.227 | 59.544 |  5.378 | 1.00 | 79.18 | O |
| ATOM | 1345 | N   | LEU A 196 | 67.381 | 59.468 |  6.686 | 1.00 | 82.24 | N |
| ATOM | 1346 | CA  | LEU A 196 | 68.026 | 58.952 |  7.898 | 1.00 | 84.37 | C |
| ATOM | 1347 | CB  | LEU A 196 | 67.063 | 58.050 |  8.679 | 1.00 | 84.92 | C |
| ATOM | 1348 | CG  | LEU A 196 | 65.577 | 58.423 |  8.772 | 1.00 | 86.62 | C |
| ATOM | 1349 | CD1 | LEU A 196 | 64.823 | 57.608 |  7.729 | 1.00 | 85.40 | C |
| ATOM | 1350 | CD2 | LEU A 196 | 65.013 | 58.142 | 10.184 | 1.00 | 85.64 | C |
| ATOM | 1351 | C   | LEU A 196 | 69.320 | 58.182 |  7.690 | 1.00 | 85.72 | C |
| ATOM | 1352 | O   | LEU A 196 | 69.302 | 56.966 |  7.551 | 1.00 | 86.77 | O |
| ATOM | 1353 | N   | ASN A 197 | 70.437 | 58.899 |  7.687 | 1.00 | 87.21 | N |
| ATOM | 1354 | CA  | ASN A 197 | 71.768 | 58.321 |  7.525 | 1.00 | 88.52 | C |
| ATOM | 1355 | CB  | ASN A 197 | 72.426 | 58.164 |  8.906 | 1.00 | 88.21 | C |
| ATOM | 1356 | CG  | ASN A 197 | 73.944 | 58.303 |  8.855 | 1.00 | 88.14 | C |
| ATOM | 1357 | OD1 | ASN A 197 | 74.671 | 57.314 |  8.799 | 1.00 | 88.18 | O |
| ATOM | 1358 | ND2 | ASN A 197 | 74.422 | 59.541 |  8.864 | 1.00 | 88.60 | N |
| ATOM | 1359 | C   | ASN A 197 | 71.839 | 56.992 |  6.752 | 1.00 | 89.83 | C |
| ATOM | 1360 | O   | ASN A 197 | 72.696 | 56.139 |  7.032 | 1.00 | 91.17 | O |
| ATOM | 1361 | N   | ASN A 198 | 70.935 | 56.807 |  5.793 | 1.00 | 89.09 | N |
| ATOM | 1362 | CA  | ASN A 198 | 70.958 | 55.606 |  4.973 | 1.00 | 88.55 | C |
| ATOM | 1363 | CB  | ASN A 198 | 69.637 | 54.832 |  5.098 | 1.00 | 88.77 | C |
| ATOM | 1364 | CG  | ASN A 198 | 69.433 | 54.228 |  6.502 | 1.00 | 89.00 | C |
| ATOM | 1365 | OD1 | ASN A 198 | 70.395 | 54.013 |  7.255 | 1.00 | 87.51 | O |
| ATOM | 1366 | ND2 | ASN A 198 | 68.176 | 53.939 |  6.844 | 1.00 | 88.58 | N |
| ATOM | 1367 | C   | ASN A 198 | 71.231 | 56.179 |  3.580 | 1.00 | 88.06 | C |
| ATOM | 1368 | O   | ASN A 198 | 72.375 | 56.533 |  3.306 | 1.00 | 88.81 | O |
| ATOM | 1369 | N   | PRO A 199 | 70.235 | 56.275 |  2.675 | 1.00 | 87.69 | N |
| ATOM | 1370 | CD  | PRO A 199 | 68.855 | 55.785 |  2.507 | 1.00 | 88.08 | C |
| ATOM | 1371 | CA  | PRO A 199 | 70.719 | 56.872 |  1.424 | 1.00 | 86.77 | C |
| ATOM | 1372 | CB  | PRO A 199 | 69.656 | 56.460 |  0.410 | 1.00 | 86.32 | C |
| ATOM | 1373 | CG  | PRO A 199 | 68.419 | 56.470 |  1.217 | 1.00 | 86.67 | C |
| ATOM | 1374 | C   | PRO A 199 | 70.728 | 58.372 |  1.710 | 1.00 | 85.79 | C |
| ATOM | 1375 | O   | PRO A 199 | 70.018 | 59.157 |  1.093 | 1.00 | 85.32 | O |
| ATOM | 1376 | N   | GLN A 200 | 71.556 | 58.729 |  2.682 | 1.00 | 85.79 | N |
| ATOM | 1377 | CA  | GLN A 200 | 71.716 | 60.079 |  3.192 | 1.00 | 86.22 | C |

```
ATOM   1378  CB   GLN A 200      72.684  60.043   4.362  1.00 86.50           C
ATOM   1379  CG   GLN A 200      74.007  59.422   3.989  1.00 87.49           C
ATOM   1380  CD   GLN A 200      75.001  59.497   5.117  1.00 90.09           C
ATOM   1381  OE1  GLN A 200      76.119  58.986   5.014  1.00 92.05           O
ATOM   1382  NE2  GLN A 200      74.600  60.141   6.209  1.00 90.11           N
ATOM   1383  C    GLN A 200      72.157  61.200   2.282  1.00 86.06           C
ATOM   1384  O    GLN A 200      72.197  62.345   2.730  1.00 87.75           O
ATOM   1385  N    ASP A 201      72.496  60.923   1.029  1.00 85.36           N
ATOM   1386  CA   ASP A 201      72.958  62.019   0.189  1.00 83.91           C
ATOM   1387  CB   ASP A 201      74.460  62.225   0.417  1.00 86.25           C
ATOM   1388  CG   ASP A 201      74.786  62.593   1.864  1.00 88.31           C
ATOM   1389  OD1  ASP A 201      74.635  63.781   2.238  1.00 89.57           O
ATOM   1390  OD2  ASP A 201      75.176  61.684   2.631  1.00 88.97           O
ATOM   1391  C    ASP A 201      72.673  61.960  -1.301  1.00 81.69           C
ATOM   1392  O    ASP A 201      73.592  61.888  -2.115  1.00 81.65           O
ATOM   1393  N    PRO A 202      71.387  61.966  -1.674  1.00 79.66           N
ATOM   1394  CD   PRO A 202      70.335  61.413  -0.800  1.00 78.61           C
ATOM   1395  CA   PRO A 202      70.956  61.931  -3.074  1.00 79.08           C
ATOM   1396  CB   PRO A 202      69.828  60.906  -3.051  1.00 78.06           C
ATOM   1397  CG   PRO A 202      69.174  61.186  -1.759  1.00 77.57           C
ATOM   1398  C    PRO A 202      70.471  63.323  -3.515  1.00 78.57           C
ATOM   1399  O    PRO A 202      71.050  63.963  -4.400  1.00 78.27           O
ATOM   1400  N    PHE A 203      69.406  63.768  -2.858  1.00 78.02           N
ATOM   1401  CA   PHE A 203      68.745  65.049  -3.084  1.00 77.01           C
ATOM   1402  CB   PHE A 203      67.441  64.762  -3.856  1.00 77.19           C
ATOM   1403  CG   PHE A 203      66.269  65.633  -3.482  1.00 77.76           C
ATOM   1404  CD1  PHE A 203      65.600  65.455  -2.283  1.00 77.29           C
ATOM   1405  CD2  PHE A 203      65.805  66.601  -4.362  1.00 78.35           C
ATOM   1406  CE1  PHE A 203      64.493  66.224  -1.975  1.00 78.28           C
ATOM   1407  CE2  PHE A 203      64.697  67.374  -4.060  1.00 77.99           C
ATOM   1408  CZ   PHE A 203      64.040  67.186  -2.868  1.00 78.24          .C
ATOM   1409  C    PHE A 203      68.508  65.594  -1.667  1.00 76.64           C
ATOM   1410  O    PHE A 203      67.818  66.587  -1.448  1.00 75.66           O
ATOM   1411  N    VAL A 204      69.136  64.912  -0.712  1.00 75.84           N
ATOM   1412  CA   VAL A 204      69.052  65.214   0.710  1.00 74.05           C
ATOM   1413  CB   VAL A 204      69.254  63.931   1.538  1.00 74.34           C
ATOM   1414  CG1  VAL A 204      69.474  64.269   3.001  1.00 75.26           C
ATOM   1415  CG2  VAL A 204      68.053  63.031   1.379  1.00 74.78           C
ATOM   1416  C    VAL A 204      70.061  66.244   1.195  1.00 73.60           C
ATOM   1417  O    VAL A 204      69.824  66.914   2.198  1.00 73.50           O
ATOM   1418  N    GLU A 205      71.186  66.369   0.503  1.00 72.43           N
ATOM   1419  CA   GLU A 205      72.187  67.338   0.922  1.00 71.43           C
ATOM   1420  CB   GLU A 205      73.489  67.138   0.143  1.00 73.55           C
ATOM   1421  CG   GLU A 205      74.573  68.162   0.477  1.00 74.82           C
ATOM   1422  CD   GLU A 205      74.652  68.474   1.966  1.00 74.77           C
ATOM   1423  OE1  GLU A 205      74.337  67.579   2.781  1.00 73.12           O
ATOM   1424  OE2  GLU A 205      75.044  69.610   2.319  1.00 76.26           O
ATOM   1425  C    GLU A 205      71.678  68.763   0.746  1.00 69.38           C
ATOM   1426  O    GLU A 205      71.957  69.636   1.567  1.00 68.28           O
ATOM   1427  N    ASN A 206      70.934  68.995  -0.330  1.00 67.86           N
ATOM   1428  CA   ASN A 206      70.371  70.318  -0.594  1.00 67.78           C
ATOM   1429  CB   ASN A 206      69.689  70.348  -1.964  1.00 69.41           C
ATOM   1430  CG   ASN A 206      70.676  70.377  -3.105  1.00 71.71           C
ATOM   1431  OD1  ASN A 206      71.299  71.406  -3.381  1.00 72.45           O
ATOM   1432  ND2  ASN A 206      70.835  69.239  -3.772  1.00 73.12           N
ATOM   1433  C    ASN A 206      69.343  70.681   0.475  1.00 65.92           C
ATOM   1434  O    ASN A 206      69.483  71.682   1.182  1.00 65.30           O
ATOM   1435  N    THR A 207      68.303  69.854   0.568  1.00 63.42           N
ATOM   1436  CA   THR A 207      67.224  70.032   1.528  1.00 59.38           C
ATOM   1437  CB   THR A 207      66.294  68.811   1.510  1.00 59.02           C
ATOM   1438  OG1  THR A 207      66.026  68.440   0.153  1.00 58.76           O
ATOM   1439  CG2  THR A 207      64.975  69.127   2.187  1.00 60.91           C
ATOM   1440  C    THR A 207      67.804  70.203   2.929  1.00 57.19           C
ATOM   1441  O    THR A 207      67.494  71.156   3.639  1.00 57.52           O
ATOM   1442  N    LYS A 208      68.671  69.282   3.313  1.00 54.35           N
ATOM   1443  CA   LYS A 208      69.297  69.316   4.622  1.00 53.05           C
ATOM   1444  CB   LYS A 208      70.285  68.155   4.715  1.00 54.16           C
ATOM   1445  CG   LYS A 208      70.956  67.961   6.060  1.00 56.95           C
ATOM   1446  CD   LYS A 208      71.125  66.468   6.382  1.00 58.64           C
ATOM   1447  CE   LYS A 208      71.745  65.689   5.210  1.00 61.22           C
ATOM   1448  NZ   LYS A 208      73.143  66.119   4.852  1.00 61.88           N
ATOM   1449  C    LYS A 208      69.998  70.636   4.943  1.00 52.56           C
ATOM   1450  O    LYS A 208      70.281  70.925   6.099  1.00 52.30           O
ATOM   1451  N    LYS A 209      70.279  71.440   3.925  1.00 52.73           N
ATOM   1452  CA   LYS A 209      70.964  72.718   4.128  1.00 51.59           C
ATOM   1453  CB   LYS A 209      71.863  73.040   2.923  1.00 53.78           C
ATOM   1454  CG   LYS A 209      73.315  72.567   3.032  1.00 54.82           C
```

```
ATOM   1455  CD  LYS A 209      74.116  73.000   1.802  1.00 57.42           C
ATOM   1456  CE  LYS A 209      75.512  73.535   2.178  1.00 60.52           C
ATOM   1457  NZ  LYS A 209      76.326  74.045   1.007  1.00 60.22           N
ATOM   1458  C   LYS A 209      70.023  73.899   4.383  1.00 50.26           C
ATOM   1459  O   LYS A 209      70.478  74.989   4.682  1.00 50.69           O
ATOM   1460  N   LEU A 210      68.720  73.688   4.268  1.00 48.87           N
ATOM   1461  CA  LEU A 210      67.744  74.756   4.504  1.00 47.47           C
ATOM   1462  CB  LEU A 210      66.491  74.481   3.667  1.00 48.12           C
ATOM   1463  CG  LEU A 210      66.481  74.925   2.205  1.00 44.78           C
ATOM   1464  CD1 LEU A 210      65.493  74.090   1.418  1.00 44.67           C
ATOM   1465  CD2 LEU A 210      66.110  76.396   2.148  1.00 44.36           C
ATOM   1466  C   LEU A 210      67.366  74.909   5.999  1.00 46.91           C
ATOM   1467  O   LEU A 210      66.285  74.497   6.440  1.00 44.44           O
ATOM   1468  N   LEU A 211      68.263  75.530   6.761  1.00 46.59           N
ATOM   1469  CA  LEU A 211      68.084  75.731   8.201  1.00 45.91           C
ATOM   1470  CB  LEU A 211      69.429  75.551   8.908  1.00 46.02           C
ATOM   1471  CG  LEU A 211      70.253  74.348   8.440  1.00 44.08           C
ATOM   1472  CD1 LEU A 211      71.713  74.739   8.315  1.00 43.36           C
ATOM   1473  CD2 LEU A 211      70.068  73.197   9.403  1.00 43.80           C
ATOM   1474  C   LEU A 211      67.533  77.108   8.534  1.00 44.79           C
ATOM   1475  O   LEU A 211      67.599  78.018   7.722  1.00 44.41           O
ATOM   1476  N   ARG A 212      66.996  77.258   9.741  1.00 45.17           N
ATOM   1477  CA  ARG A 212      66.440  78.534  10.178  1.00 45.90           C
ATOM   1478  CB  ARG A 212      65.813  78.399  11.570  1.00 49.25           C
ATOM   1479  CG  ARG A 212      64.554  77.550  11.661  1.00 54.48           C
ATOM   1480  CD  ARG A 212      64.241  77.238  13.145  1.00 61.96           C
ATOM   1481  NE  ARG A 212      65.225  76.322  13.749  1.00 66.37           N
ATOM   1482  CZ  ARG A 212      65.367  76.096  15.061  1.00 68.08           C
ATOM   1483  NH1 ARG A 212      64.596  76.719  15.948  1.00 68.53           N
ATOM   1484  NH2 ARG A 212      66.286  75.238  15.490  1.00 68.55           N
ATOM   1485  C   ARG A 212      67.565  79.556  10.251  1.00 43.98           C
ATOM   1486  O   ARG A 212      68.720  79.201  10.450  1.00 46.77           O
ATOM   1487  N   PHE A 213      67.239  80.826  10.098  1.00 39.88           N
ATOM   1488  CA  PHE A 213      68.263  81.847  10.183  1.00 37.53           C
ATOM   1489  CB  PHE A 213      67.834  83.099   9.421  1.00 37.40           C
ATOM   1490  CG  PHE A 213      67.606  82.867   7.967  1.00 38.23           C
ATOM   1491  CD1 PHE A 213      68.604  82.325   7.180  1.00 37.63           C
ATOM   1492  CD2 PHE A 213      66.390  83.198   7.379  1.00 40.12           C
ATOM   1493  CE1 PHE A 213      68.404  82.114   5.837  1.00 40.21           C
ATOM   1494  CE2 PHE A 213      66.174  82.992   6.024  1.00 40.64           C
ATOM   1495  CZ  PHE A 213      67.180  82.449   5.250  1.00 41.08           C
ATOM   1496  C   PHE A 213      68.485  82.234  11.626  1.00 36.63           C
ATOM   1497  O   PHE A 213      67.524  82.332  12.384  1.00 37.85           O
ATOM   1498  N   ASP A 214      69.737  82.445  12.018  1.00 35.91           N
ATOM   1499  CA  ASP A 214      70.023  82.899  13.376  1.00 35.91           C
ATOM   1500  CB  ASP A 214      71.310  82.279  13.938  1.00 35.90           C
ATOM   1501  CG  ASP A 214      71.737  82.907  15.287  1.00 38.67           C
ATOM   1502  OD1 ASP A 214      72.768  82.465  15.853  1.00 40.10           O
ATOM   1503  OD2 ASP A 214      71.058  83.842  15.791  1.00 36.74           O
ATOM   1504  C   ASP A 214      70.198  84.399  13.217  1.00 35.54           C
ATOM   1505  O   ASP A 214      71.259  84.864  12.821  1.00 35.65           O
ATOM   1506  N   PHE A 215      69.158  85.164  13.516  1.00 36.99           N
ATOM   1507  CA  PHE A 215      69.252  86.615  13.355  1.00 37.11           C
ATOM   1508  CB  PHE A 215      67.863  87.250  13.401  1.00 35.84           C
ATOM   1509  CG  PHE A 215      67.073  86.998  12.174  1.00 36.21           C
ATOM   1510  CD1 PHE A 215      66.089  86.024  12.145  1.00 37.52           C
ATOM   1511  CD2 PHE A 215      67.358  87.694  11.018  1.00 36.28           C
ATOM   1512  CE1 PHE A 215      65.402  85.750  10.970  1.00 37.57           C
ATOM   1513  CE2 PHE A 215      66.677  87.431   9.839  1.00 37.13           C
ATOM   1514  CZ  PHE A 215      65.698  86.458   9.815  1.00 38.28           C
ATOM   1515  C   PHE A 215      70.178  87.298  14.337  1.00 36.43           C
ATOM   1516  O   PHE A 215      70.354  88.499  14.287  1.00 35.43           O
ATOM   1517  N   LEU A 216      70.779  86.537  15.228  1.00 38.58           N
ATOM   1518  CA  LEU A 216      71.681  87.148  16.167  1.00 42.10           C
ATOM   1519  CB  LEU A 216      71.339  86.739  17.602  1.00 43.41           C
ATOM   1520  CG  LEU A 216      70.510  87.776  18.380  1.00 44.23           C
ATOM   1521  CD1 LEU A 216      69.446  88.385  17.475  1.00 43.75           C
ATOM   1522  CD2 LEU A 216      69.871  87.123  19.591  1.00 43.00           C
ATOM   1523  C   LEU A 216      73.107  86.794  15.834  1.00 43.36           C
ATOM   1524  O   LEU A 216      74.001  87.054  16.634  1.00 45.90           O
ATOM   1525  N   ASP A 217      73.328  86.202  14.661  1.00 43.63           N
ATOM   1526  CA  ASP A 217      74.688  85.863  14.250  1.00 44.74           C
ATOM   1527  CB  ASP A 217      74.713  84.618  13.342  1.00 48.58           C
ATOM   1528  CG  ASP A 217      74.443  84.932  11.867  1.00 53.05           C
ATOM   1529  OD1 ASP A 217      74.698  84.036  11.033  1.00 53.61           O
ATOM   1530  OD2 ASP A 217      73.973  86.047  11.534  1.00 55.83           O
ATOM   1531  C   ASP A 217      75.306  87.071  13.542  1.00 43.17           C
```

```
ATOM   1532  O    ASP A 217      74.598  87.983  13.114  1.00 43.59           O
ATOM   1533  N    PRO A 218      76.637  87.096  13.413  1.00 42.05           N
ATOM   1534  CD   PRO A 218      77.608  86.074  13.851  1.00 40.99           C
ATOM   1535  CA   PRO A 218      77.322  88.213  12.756  1.00 40.34           C
ATOM   1536  CB   PRO A 218      78.702  87.633  12.475  1.00 40.39           C
ATOM   1537  CG   PRO A 218      78.935  86.789  13.698  1.00 40.03           C
ATOM   1538  C    PRO A 218      76.671  88.823  11.509  1.00 38.33           C
ATOM   1539  O    PRO A 218      76.356  90.009  11.480  1.00 37.70           O
ATOM   1540  N    PHE A 219      76.457  88.017  10.483  1.00 37.64           N
ATOM   1541  CA   PHE A 219      75.890  88.540   9.247  1.00 37.63           C
ATOM   1542  CB   PHE A 219      75.670  87.394   8.261  1.00 35.91           C
ATOM   1543  CG   PHE A 219      75.029  87.812   6.974  1.00 34.29           C
ATOM   1544  CD1  PHE A 219      73.655  87.768   6.821  1.00 36.12           C
ATOM   1545  CD2  PHE A 219      75.802  88.199   5.902  1.00 35.64           C
ATOM   1546  CE1  PHE A 219      73.064  88.097   5.606  1.00 37.73           C
ATOM   1547  CE2  PHE A 219      75.225  88.531   4.687  1.00 36.48           C
ATOM   1548  CZ   PHE A 219      73.855  88.478   4.535  1.00 36.24           C
ATOM   1549  C    PHE A 219      74.614  89.361   9.402  1.00 37.89           C
ATOM   1550  O    PHE A 219      74.590  90.535   9.045  1.00 37.99           O
ATOM   1551  N    PHE A 220      73.554  88.745   9.928  1.00 38.42           N
ATOM   1552  CA   PHE A 220      72.273  89.423  10.114  1.00 36.44           C
ATOM   1553  CB   PHE A 220      71.234  88.416  10.558  1.00 32.24           C
ATOM   1554  CG   PHE A 220      70.825  87.459   9.475  1.00 28.58           C
ATOM   1555  CD1  PHE A 220      69.859  87.814   8.542  1.00 27.17           C
ATOM   1556  CD2  PHE A 220      71.345  86.184   9.438  1.00 26.61           C
ATOM   1557  CE1  PHE A 220      69.415  86.914   7.614  1.00 23.05           C
ATOM   1558  CE2  PHE A 220      70.905  85.276   8.506  1.00 24.36           C
ATOM   1559  CZ   PHE A 220      69.939  85.640   7.600  1.00 25.11           C
ATOM   1560  C    PHE A 220      72.354  90.570  11.112  1.00 36.52           C
ATOM   1561  O    PHE A 220      71.719  91.615  10.937  1.00 36.91           O
ATOM   1562  N    LEU A 221      73.148  90.384  12.154  1.00 36.64           N
ATOM   1563  CA   LEU A 221      73.311  91.436  13.140  1.00 37.97           C
ATOM   1564  CB   LEU A 221      74.291  90.997  14.220  1.00 37.06           C
ATOM   1565  CG   LEU A 221      73.939  91.465  15.634  1.00 37.25           C
ATOM   1566  CD1  LEU A 221      72.433  91.721  15.776  1.00 31.98           C
ATOM   1567  CD2  LEU A 221      74.416  90.383  16.612  1.00 38.18           C
ATOM   1568  C    LEU A 221      73.808  92.707  12.452  1.00 38.85           C
ATOM   1569  O    LEU A 221      73.339  93.796  12.773  1.00 41.89           O
ATOM   1570  N    SER A 222      74.741  92.569  11.507  1.00 38.11           N
ATOM   1571  CA   SER A 222      75.273  93.715  10.754  1.00 38.23           C
ATOM   1572  CB   SER A 222      76.376  93.271   9.778  1.00 36.48           C
ATOM   1573  OG   SER A 222      77.540  92.833  10.451  1.00 34.78           O
ATOM   1574  C    SER A 222      74.185  94.424   9.941  1.00 39.48           C
ATOM   1575  O    SER A 222      74.017  95.640  10.030  1.00 39.01           O
ATOM   1576  N    ILE A 223      73.457  93.653   9.137  1.00 41.70           N
ATOM   1577  CA   ILE A 223      72.399  94.184   8.287  1.00 43.85           C
ATOM   1578  CB   ILE A 223      71.777  93.073   7.440  1.00 43.32           C
ATOM   1579  CG2  ILE A 223      70.602  93.601   6.638  1.00 44.09           C
ATOM   1580  CG1  ILE A 223      72.815  92.535   6.475  1.00 42.66           C
ATOM   1581  CD1  ILE A 223      72.264  91.441   5.626  1.00 45.57           C
ATOM   1582  C    ILE A 223      71.300  94.868   9.081  1.00 45.78           C
ATOM   1583  O    ILE A 223      70.643  95.792   8.593  1.00 45.66           O
ATOM   1584  N    THR A 224      71.087  94.413  10.306  1.00 48.53           N
ATOM   1585  CA   THR A 224      70.068  95.040  11.121  1.00 52.10           C
ATOM   1586  CB   THR A 224      69.781  94.219  12.365  1.00 53.14           C
ATOM   1587  OG1  THR A 224      69.362  92.907  11.967  1.00 54.87           O
ATOM   1588  CG2  THR A 224      68.670  94.882  13.183  1.00 54.37           C
ATOM   1589  C    THR A 224      70.561  96.426  11.509  1.00 52.48           C
ATOM   1590  O    THR A 224      69.782  97.378  11.599  1.00 53.01           O
ATOM   1591  N    VAL A 225      71.866  96.530  11.715  1.00 52.21           N
ATOM   1592  CA   VAL A 225      72.468  97.795  12.070  1.00 54.58           C
ATOM   1593  CB   VAL A 225      73.864  97.603  12.719  1.00 57.17           C
ATOM   1594  CG1  VAL A 225      74.244  98.839  13.529  1.00 58.66           C
ATOM   1595  CG2  VAL A 225      73.861  96.374  13.622  1.00 59.58           C
ATOM   1596  C    VAL A 225      72.635  98.647  10.819  1.00 54.40           C
ATOM   1597  O    VAL A 225      72.444  99.853  10.853  1.00 56.64           O
ATOM   1598  N    PHE A 226      72.985  98.024   9.706  1.00 54.19           N
ATOM   1599  CA   PHE A 226      73.195  98.768   8.471  1.00 53.87           C
ATOM   1600  CB   PHE A 226      74.673  98.704   8.102  1.00 58.60           C
ATOM   1601  CG   PHE A 226      75.588  98.901   9.281  1.00 63.39           C
ATOM   1602  CD1  PHE A 226      76.790  98.203   9.372  1.00 64.29           C
ATOM   1603  CD2  PHE A 226      75.233  99.762  10.320  1.00 63.52           C
ATOM   1604  CE1  PHE A 226      77.622  98.356  10.485  1.00 65.48           C
ATOM   1605  CE2  PHE A 226      76.051  99.920  11.429  1.00 64.86           C
ATOM   1606  CZ   PHE A 226      77.247  99.216  11.517  1.00 65.17           C
ATOM   1607  C    PHE A 226      72.352  98.208   7.339  1.00 50.64           C
ATOM   1608  O    PHE A 226      72.848  97.503   6.470  1.00 50.28           O
```

```
ATOM   1609  N    PRO A 227      71.061  98.532   7.342  1.00 48.16           N
ATOM   1610  CD   PRO A 227      70.407  99.258   8.437  1.00 45.67           C
ATOM   1611  CA   PRO A 227      70.071  98.101   6.360  1.00 47.74           C
ATOM   1612  CB   PRO A 227      68.770  98.685   6.915  1.00 46.52           C
ATOM   1613  CG   PRO A 227      69.019  98.723   8.366  1.00 44.56           C
ATOM   1614  C    PRO A 227      70.335  98.540   4.928  1.00 47.91           C
ATOM   1615  O    PRO A 227      69.708  98.013   3.998  1.00 46.37           O
ATOM   1616  N    PHE A 228      71.247  99.499   4.748  1.00 49.70           N
ATOM   1617  CA   PHE A 228      71.578 100.008   3.406  1.00 51.77           C
ATOM   1618  CB   PHE A 228      72.321 101.349   3.500  1.00 51.00           C
ATOM   1619  CG   PHE A 228      73.610 101.291   4.275  1.00 50.10           C
ATOM   1620  CD1  PHE A 228      74.780 100.880   3.671  1.00 49.44           C
ATOM   1621  CD2  PHE A 228      73.644 101.662   5.610  1.00 51.28           C
ATOM   1622  CE1  PHE A 228      75.966 100.842   4.383  1.00 51.87           C
ATOM   1623  CE2  PHE A 228      74.826 101.624   6.336  1.00 51.75           C
ATOM   1624  CZ   PHE A 228      75.988 101.214   5.723  1.00 52.41           C
ATOM   1625  C    PHE A 228      72.401  99.002   2.610  1.00 52.96           C
ATOM   1626  O    PHE A 228      72.622  99.173   1.411  1.00 54.94           O
ATOM   1627  N    LEU A 229      72.833  97.950   3.299  1.00 52.02           N
ATOM   1628  CA   LEU A 229      73.607  96.867   2.720  1.00 51.08           C
ATOM   1629  CB   LEU A 229      74.201  96.024   3.846  1.00 53.14           C
ATOM   1630  CG   LEU A 229      75.517  96.406   4.520  1.00 55.74           C
ATOM   1631  CD1  LEU A 229      75.874  97.813   4.138  1.00 57.65           C
ATOM   1632  CD2  LEU A 229      75.408  96.234   6.035  1.00 53.58           C
ATOM   1633  C    LEU A 229      72.725  95.961   1.853  1.00 50.95           C
ATOM   1634  O    LEU A 229      73.166  95.386   0.852  1.00 51.80           O
ATOM   1635  N    ILE A 230      71.476  95.809   2.253  1.00 49.19           N
ATOM   1636  CA   ILE A 230      70.581  94.940   1.522  1.00 49.23           C
ATOM   1637  CB   ILE A 230      69.155  95.015   2.138  1.00 49.37           C
ATOM   1638  CG2  ILE A 230      68.160  94.171   1.343  1.00 46.72           C
ATOM   1639  CG1  ILE A 230      69.223  94.523   3.585  1.00 49.41           C
ATOM   1640  CD1  ILE A 230      67.879  94.176   4.188  1.00 51.39           C
ATOM   1641  C    ILE A 230      70.557  95.222   0.016  1.00 49.83           C
ATOM   1642  O    ILE A 230      70.722  94.315  -0.797  1.00 47.91           O
ATOM   1643  N    PRO A 231      70.388  96.493  -0.376  1.00 51.49           N
ATOM   1644  CD   PRO A 231      70.422  97.718   0.437  1.00 50.40           C
ATOM   1645  CA   PRO A 231      70.349  96.827  -1.804  1.00 51.42           C
ATOM   1646  CB   PRO A 231      69.990  98.315  -1.810  1.00 52.61           C
ATOM   1647  CG   PRO A 231      69.579  98.621  -0.379  1.00 51.92           C
ATOM   1648  C    PRO A 231      71.706  96.585  -2.452  1.00 50.43           C
ATOM   1649  O    PRO A 231      71.800  96.297  -3.633  1.00 51.85           O
ATOM   1650  N    ILE A 232      72.760  96.736  -1.667  1.00 48.87           N
ATOM   1651  CA   ILE A 232      74.106  96.529  -2.152  1.00 48.50           C
ATOM   1652  CB   ILE A 232      75.084  96.993  -1.110  1.00 47.54           C
ATOM   1653  CG2  ILE A 232      76.435  96.435  -1.392  1.00 50.35           C
ATOM   1654  CG1  ILE A 232      75.087  98.506  -1.054  1.00 47.81           C
ATOM   1655  CD1  ILE A 232      76.159  99.056  -0.153  1.00 49.20           C
ATOM   1656  C    ILE A 232      74.368  95.045  -2.448  1.00 50.69           C
ATOM   1657  O    ILE A 232      74.869  94.680  -3.516  1.00 51.11           O
ATOM   1658  N    LEU A 233      74.022  94.186  -1.497  1.00 50.84           N
ATOM   1659  CA   LEU A 233      74.227  92.759  -1.660  1.00 51.68           C
ATOM   1660  CB   LEU A 233      73.879  92.037  -0.367  1.00 51.19           C
ATOM   1661  CG   LEU A 233      74.634  92.470   0.884  1.00 50.97           C
ATOM   1662  CD1  LEU A 233      73.803  92.077   2.069  1.00 50.98           C
ATOM   1663  CD2  LEU A 233      76.032  91.839   0.950  1.00 50.51           C
ATOM   1664  C    LEU A 233      73.390  92.171  -2.778  1.00 53.15           C
ATOM   1665  O    LEU A 233      73.827  91.288  -3.504  1.00 55.12           O
ATOM   1666  N    GLU A 234      72.168  92.650  -2.911  1.00 55.77           N
ATOM   1667  CA   GLU A 234      71.291  92.112  -3.930  1.00 59.27           C
ATOM   1668  CB   GLU A 234      69.874  92.637  -3.745  1.00 61.38           C
ATOM   1669  CG   GLU A 234      69.207  92.012  -2.541  1.00 65.76           C
ATOM   1670  CD   GLU A 234      67.862  92.606  -2.258  1.00 67.31           C
ATOM   1671  OE1  GLU A 234      67.768  93.858  -2.339  1.00 67.85           O
ATOM   1672  OE2  GLU A 234      66.923  91.824  -1.949  1.00 66.55           O
ATOM   1673  C    GLU A 234      71.749  92.374  -5.331  1.00 60.27           C
ATOM   1674  O    GLU A 234      71.355  91.660  -6.251  1.00 61.41           O
ATOM   1675  N    VAL A 235      72.577  93.392  -5.517  1.00 60.09           N
ATOM   1676  CA   VAL A 235      73.032  93.653  -6.861  1.00 60.73           C
ATOM   1677  CB   VAL A 235      73.541  95.110  -7.037  1.00 61.44           C
ATOM   1678  CG1  VAL A 235      75.045  95.188  -6.744  1.00 60.47           C
ATOM   1679  CG2  VAL A 235      73.203  95.609  -8.455  1.00 58.65           C
ATOM   1680  C    VAL A 235      74.135  92.656  -7.179  1.00 61.08           C
ATOM   1681  O    VAL A 235      74.403  92.385  -8.345  1.00 62.61           O
ATOM   1682  N    LEU A 236      74.760  92.096  -6.141  1.00 61.00           N
ATOM   1683  CA   LEU A 236      75.835  91.110  -6.321  1.00 60.23           C
ATOM   1684  CB   LEU A 236      76.872  91.226  -5.209  1.00 59.25           C
ATOM   1685  CG   LEU A 236      77.471  92.609  -5.020  1.00 60.06           C
```

```
ATOM   1686  CD1 LEU A 236      78.711  92.519  -4.129  1.00 59.14           C
ATOM   1687  CD2 LEU A 236      77.833  93.166  -6.383  1.00 62.27           C
ATOM   1688  C   LEU A 236      75.242  89.717  -6.278  1.00 59.84           C
ATOM   1689  O   LEU A 236      75.940  88.725  -6.051  1.00 59.88           O
ATOM   1690  N   ASN A 237      73.936  89.665  -6.496  1.00 59.59           N
ATOM   1691  CA  ASN A 237      73.181  88.424  -6.469  1.00 61.32           C
ATOM   1692  CB  ASN A 237      73.407  87.624  -7.752  1.00 63.16           C
ATOM   1693  CG  ASN A 237      72.267  86.652  -8.030  1.00 66.13           C
ATOM   1694  OD1 ASN A 237      71.342  86.518  -7.224  1.00 66.08           O
ATOM   1695  ND2 ASN A 237      72.328  85.969  -9.173  1.00 68.22           N
ATOM   1696  C   ASN A 237      73.448  87.536  -5.232  1.00 60.25           C
ATOM   1697  O   ASN A 237      73.335  86.304  -5.296  1.00 59.71           O
ATOM   1698  N   ILE A 238      73.795  88.165  -4.111  1.00 56.84           N
ATOM   1699  CA  ILE A 238      74.015  87.426  -2.882  1.00 55.18           C
ATOM   1700  CB  ILE A 238      74.886  88.198  -1.905  1.00 54.86           C
ATOM   1701  CG2 ILE A 238      74.928  87.474  -0.567  1.00 51.70           C
ATOM   1702  CG1 ILE A 238      76.276  88.407  -2.496  1.00 54.32           C
ATOM   1703  CD1 ILE A 238      77.131  89.337  -1.661  1.00 54.26           C
ATOM   1704  C   ILE A 238      72.644  87.319  -2.249  1.00 55.84           C
ATOM   1705  O   ILE A 238      72.034  88.340  -1.948  1.00 56.71           O
ATOM   1706  N   CYS A 239      72.141  86.105  -2.062  1.00 55.46           N
ATOM   1707  CA  CYS A 239      70.829  85.930  -1.443  1.00 54.27           C
ATOM   1708  CB  CYS A 239      69.910  85.110  -2.349  1.00 54.81           C
ATOM   1709  SG  CYS A 239      68.324  84.635  -1.589  1.00 55.18           S
ATOM   1710  C   CYS A 239      70.975  85.237  -0.092  1.00 53.74           C
ATOM   1711  O   CYS A 239      71.940  84.516   0.150  1.00 53.48           O
ATOM   1712  N   VAL A 240      70.011  85.457   0.792  1.00 53.20           N
ATOM   1713  CA  VAL A 240      70.065  84.841   2.104  1.00 50.95           C
ATOM   1714  CB  VAL A 240      69.228  85.643   3.116  1.00 50.00           C
ATOM   1715  CG1 VAL A 240      67.840  85.059   3.245  1.00 49.47           C
ATOM   1716  CG2 VAL A 240      69.958  85.688   4.437  1.00 48.60           C
ATOM   1717  C   VAL A 240      69.628  83.378   2.039  1.00 50.83           C
ATOM   1718  O   VAL A 240      69.802  82.634   2.989  1.00 51.19           O
ATOM   1719  N   PHE A 241      69.039  82.973   0.920  1.00 52.90           N
ATOM   1720  CA  PHE A 241      68.684  81.566   0.701  1.00 55.74           C
ATOM   1721  CB  PHE A 241      67.274  81.400   0.112  1.00 53.91           C
ATOM   1722  CG  PHE A 241      66.159  81.651   1.094  1.00 51.86           C
ATOM   1723  CD1 PHE A 241      65.576  82.902   1.204  1.00 51.38           C
ATOM   1724  CD2 PHE A 241      65.691  80.636   1.907  1.00 50.54           C
ATOM   1725  CE1 PHE A 241      64.550  83.127   2.103  1.00 48.30           C
ATOM   1726  CE2 PHE A 241      64.666  80.866   2.806  1.00 48.38           C
ATOM   1727  CZ  PHE A 241      64.100  82.110   2.898  1.00 46.73           C
ATOM   1728  C   PHE A 241      69.739  81.179  -0.346  1.00 58.71           C
ATOM   1729  O   PHE A 241      69.593  81.490  -1.532  1.00 58.31           O
ATOM   1730  N   PRO A 242      70.815  80.495   0.085  1.00 61.95           N
ATOM   1731  CD  PRO A 242      70.784  79.657   1.299  1.00 62.53           C
ATOM   1732  CA  PRO A 242      71.915  80.072  -0.789  1.00 64.19           C
ATOM   1733  CB  PRO A 242      72.622  78.998   0.037  1.00 63.77           C
ATOM   1734  CG  PRO A 242      71.518  78.412   0.843  1.00 63.33           C
ATOM   1735  C   PRO A 242      71.534  79.590  -2.185  1.00 66.51           C
ATOM   1736  O   PRO A 242      70.829  78.583  -2.347  1.00 66.42           O
ATOM   1737  N   ARG A 243      72.028  80.326  -3.181  1.00 68.28           N
ATOM   1738  CA  ARG A 243      71.794  80.054  -4.602  1.00 68.97           C
ATOM   1739  CB  ARG A 243      72.721  80.925  -5.451  1.00 71.51           C
ATOM   1740  CG  ARG A 243      72.020  81.880  -6.381  1.00 74.58           C
ATOM   1741  CD  ARG A 243      73.040  82.645  -7.215  1.00 77.18           C
ATOM   1742  NE  ARG A 243      73.954  83.432  -6.392  1.00 78.51           N
ATOM   1743  CZ  ARG A 243      74.894  84.231  -6.886  1.00 80.38           C
ATOM   1744  NH1 ARG A 243      75.688  84.916  -6.069  1.00 81.23           N
ATOM   1745  NH2 ARG A 243      75.041  84.345  -8.203  1.00 80.43           N
ATOM   1746  C   ARG A 243      72.036  78.597  -4.973  1.00 67.76           C
ATOM   1747  O   ARG A 243      71.359  78.045  -5.840  1.00 66.74           O
ATOM   1748  N   GLU A 244      73.017  77.987  -4.320  1.00 66.91           N
ATOM   1749  CA  GLU A 244      73.361  76.602  -4.596  1.00 67.43           C
ATOM   1750  CB  GLU A 244      74.449  76.126  -3.624  1.00 68.91           C
ATOM   1751  CG  GLU A 244      75.356  75.024  -4.182  1.00 70.60           C
ATOM   1752  CD  GLU A 244      76.416  75.559  -5.139  1.00 72.16           C
ATOM   1753  OE1 GLU A 244      77.619  75.434  -4.806  1.00 72.42           O
ATOM   1754  OE2 GLU A 244      76.049  76.105  -6.212  1.00 71.74           O
ATOM   1755  C   GLU A 244      72.134  75.701  -4.473  1.00 66.42           C
ATOM   1756  O   GLU A 244      71.749  75.010  -5.430  1.00 65.77           O
ATOM   1757  N   VAL A 245      71.520  75.732  -3.290  1.00 64.63           N
ATOM   1758  CA  VAL A 245      70.346  74.916  -2.983  1.00 61.48           C
ATOM   1759  CB  VAL A 245      70.087  74.919  -1.480  1.00 59.59           C
ATOM   1760  CG1 VAL A 245      69.195  73.775  -1.117  1.00 59.44           C
ATOM   1761  CG2 VAL A 245      71.392  74.835  -0.738  1.00 59.34           C
ATOM   1762  C   VAL A 245      69.060  75.337  -3.705  1.00 59.70           C
```

```
ATOM   1763  O    VAL A 245      68.302  74.490  -4.178  1.00 57.38           O
ATOM   1764  N    THR A 246      68.815  76.639  -3.782  1.00 59.17           N
ATOM   1765  CA   THR A 246      67.620  77.131  -4.454  1.00 61.05           C
ATOM   1766  CB   THR A 246      67.495  78.666  -4.340  1.00 61.06           C
ATOM   1767  OG1  THR A 246      68.675  79.286  -4.860  1.00 62.22           O
ATOM   1768  CG2  THR A 246      67.318  79.074  -2.896  1.00 61.61           C
ATOM   1769  C    THR A 246      67.632  76.742  -5.930  1.00 61.15           C
ATOM   1770  O    THR A 246      66.596  76.396  -6.495  1.00 60.71           O
ATOM   1771  N    ASN A 247      68.805  76.801  -6.551  1.00 61.25           N
ATOM   1772  CA   ASN A 247      68.924  76.438  -7.953  1.00 61.91           C
ATOM   1773  CB   ASN A 247      70.322  76.751  -8.475  1.00 61.38           C
ATOM   1774  CG   ASN A 247      70.430  78.152  -9.015  1.00 61.73           C
ATOM   1775  OD1  ASN A 247      69.894  79.099  -8.436  1.00 62.58           O
ATOM   1776  ND2  ASN A 247      71.131  78.296 -10.127  1.00 61.96           N
ATOM   1777  C    ASN A 247      68.632  74.963  -8.133  1.00 62.55           C
ATOM   1778  O    ASN A 247      67.822  74.578  -8.987  1.00 63.23           O
ATOM   1779  N    PHE A 248      69.285  74.131  -7.333  1.00 62.19           N
ATOM   1780  CA   PHE A 248      69.052  72.710  -7.457  1.00 63.55           C
ATOM   1781  CB   PHE A 248      69.727  71.940  -6.330  1.00 62.76           C
ATOM   1782  CG   PHE A 248      69.344  70.492  -6.293  1.00 63.70           C
ATOM   1783  CD1  PHE A 248      68.265  70.064  -5.538  1.00 62.96           C
ATOM   1784  CD2  PHE A 248      70.021  69.560  -7.069  1.00 64.68           C
ATOM   1785  CE1  PHE A 248      67.865  68.738  -5.559  1.00 61.69           C
ATOM   1786  CE2  PHE A 248      69.619  68.223  -7.092  1.00 64.07           C
ATOM   1787  CZ   PHE A 248      68.541  67.818  -6.336  1.00 61.72           C
ATOM   1788  C    PHE A 248      67.557  72.437  -7.431  1.00 65.10           C
ATOM   1789  O    PHE A 248      66.993  71.912  -8.391  1.00 66.46           O
ATOM   1790  N    LEU A 249      66.921  72.822  -6.333  1.00 66.16           N
ATOM   1791  CA   LEU A 249      65.493  72.616  -6.151  1.00 67.41           C
ATOM   1792  CB   LEU A 249      65.076  73.117  -4.769  1.00 68.40           C
ATOM   1793  CG   LEU A 249      64.643  72.058  -3.756  1.00 68.67           C
ATOM   1794  CD1  LEU A 249      65.776  71.074  -3.487  1.00 68.83           C
ATOM   1795  CD2  LEU A 249      64.219  72.757  -2.481  1.00 70.40           C
ATOM   1796  C    LEU A 249      64.583  73.249  -7.203  1.00 68.35           C
ATOM   1797  O    LEU A 249      63.509  72.721  -7.500  1.00 68.64           O
ATOM   1798  N    ARG A 250      64.989  74.381  -7.766  1.00 69.07           N
ATOM   1799  CA   ARG A 250      64.145  75.026  -8.761  1.00 69.84           C
ATOM   1800  CB   ARG A 250      64.632  76.447  -9.036  1.00 71.44           C
ATOM   1801  CG   ARG A 250      63.589  77.314  -9.722  1.00 74.12           C
ATOM   1802  CD   ARG A 250      63.844  78.777  -9.428  1.00 75.81           C
ATOM   1803  NE   ARG A 250      64.308  79.523 -10.592  1.00 76.95           N
ATOM   1804  CZ   ARG A 250      64.986  80.663 -10.512  1.00 76.94           C
ATOM   1805  NH1  ARG A 250      65.277  81.172  -9.323  1.00 77.20           N
ATOM   1806  NH2  ARG A 250      65.373  81.289 -11.613  1.00 77.10           N
ATOM   1807  C    ARG A 250      64.143  74.207 -10.041  1.00 69.26           C
ATOM   1808  O    ARG A 250      63.155  74.179 -10.782  1.00 68.83           O
ATOM   1809  N    LYS A 251      65.255  73.529 -10.294  1.00 68.87           N
ATOM   1810  CA   LYS A 251      65.360  72.698 -11.476  1.00 68.67           C
ATOM   1811  CB   LYS A 251      66.835  72.537 -11.868  1.00 69.35           C
ATOM   1812  CG   LYS A 251      67.279  73.589 -12.921  1.00 71.13           C
ATOM   1813  CD   LYS A 251      66.786  75.027 -12.581  1.00 71.39           C
ATOM   1814  CE   LYS A 251      66.431  75.854 -13.851  1.00 71.16           C
ATOM   1815  NZ   LYS A 251      65.779  77.185 -13.584  1.00 67.56           N
ATOM   1816  C    LYS A 251      64.669  71.358 -11.237  1.00 67.41           C
ATOM   1817  O    LYS A 251      64.072  70.785 -12.152  1.00 67.67           O
ATOM   1818  N    SER A 252      64.720  70.882  -9.996  1.00 65.95           N
ATOM   1819  CA   SER A 252      64.075  69.627  -9.627  1.00 64.46           C
ATOM   1820  CB   SER A 252      64.358  69.290  -8.167  1.00 62.92           C
ATOM   1821  OG   SER A 252      65.707  68.906  -7.976  1.00 62.07           O
ATOM   1822  C    SER A 252      62.575  69.733  -9.824  1.00 64.66           C
ATOM   1823  O    SER A 252      61.956  68.882 -10.450  1.00 63.12           O
ATOM   1824  N    VAL A 253      61.993  70.789  -9.276  1.00 67.42           N
ATOM   1825  CA   VAL A 253      60.561  71.004  -9.394  1.00 71.19           C
ATOM   1826  CB   VAL A 253      60.145  72.356  -8.776  1.00 71.68           C
ATOM   1827  CG1  VAL A 253      58.640  72.536  -8.873  1.00 71.64           C
ATOM   1828  CG2  VAL A 253      60.589  72.419  -7.330  1.00 72.20           C
ATOM   1829  C    VAL A 253      60.160  70.991 -10.860  1.00 73.42           C
ATOM   1830  O    VAL A 253      59.164  70.380 -11.232  1.00 73.33           O
ATOM   1831  N    LYS A 254      60.943  71.667 -11.692  1.00 77.09           N
ATOM   1832  CA   LYS A 254      60.653  71.723 -13.118  1.00 80.12           C
ATOM   1833  CB   LYS A 254      61.675  72.619 -13.834  1.00 80.17           C
ATOM   1834  CG   LYS A 254      61.271  72.974 -15.261  1.00 81.18           C
ATOM   1835  CD   LYS A 254      59.906  73.665 -15.280  1.00 82.37           C
ATOM   1836  CE   LYS A 254      59.350  73.812 -16.694  1.00 83.26           C
ATOM   1837  NZ   LYS A 254      60.203  74.653 -17.585  1.00 82.75           N
ATOM   1838  C    LYS A 254      60.666  70.313 -13.724  1.00 81.69           C
ATOM   1839  O    LYS A 254      59.806  69.967 -14.544  1.00 81.01           O
```

| | | | | | | | | |
|---|---|---|---|---|---|---|---|---|
| ATOM | 1840 | N | ARG A 255 | 61.639 | 69.503 | -13.301 | 1.00 84.03 | N |
| ATOM | 1841 | CA | ARG A 255 | 61.780 | 68.138 | -13.801 | 1.00 85.48 | C |
| ATOM | 1842 | CB | ARG A 255 | 62.938 | 67.416 | -13.090 | 1.00 87.11 | C |
| ATOM | 1843 | CG | ARG A 255 | 63.298 | 66.072 | -13.716 | 1.00 91.67 | C |
| ATOM | 1844 | CD | ARG A 255 | 64.819 | 65.884 | -13.863 | 1.00 96.29 | C |
| ATOM | 1845 | NE | ARG A 255 | 65.166 | 64.847 | -14.848 | 1.00100.11 | N |
| ATOM | 1846 | CZ | ARG A 255 | 66.409 | 64.555 | -15.242 | 1.00101.34 | C |
| ATOM | 1847 | NH1 | ARG A 255 | 67.447 | 65.215 | -14.737 | 1.00101.99 | N |
| ATOM | 1848 | NH2 | ARG A 255 | 66.618 | 63.606 | -16.151 | 1.00100.47 | N |
| ATOM | 1849 | C | ARG A 255 | 60.486 | 67.361 | -13.618 | 1.00 85.04 | C |
| ATOM | 1850 | O | ARG A 255 | 59.864 | 66.936 | -14.592 | 1.00 85.13 | O |
| ATOM | 1851 | N | MET A 256 | 60.066 | 67.201 | -12.372 | 1.00 84.88 | N |
| ATOM | 1852 | CA | MET A 256 | 58.847 | 66.464 | -12.090 | 1.00 85.50 | C |
| ATOM | 1853 | CB | MET A 256 | 58.817 | 66.060 | -10.618 | 1.00 86.75 | C |
| ATOM | 1854 | CG | MET A 256 | 58.904 | 67.219 | -9.637 | 1.00 88.47 | C |
| ATOM | 1855 | SD | MET A 256 | 59.887 | 66.792 | -8.172 | 1.00 88.96 | S |
| ATOM | 1856 | CE | MET A 256 | 59.600 | 64.999 | -8.077 | 1.00 89.97 | C |
| ATOM | 1857 | C | MET A 256 | 57.576 | 67.215 | -12.461 | 1.00 85.60 | C |
| ATOM | 1858 | O | MET A 256 | 56.491 | 66.641 | -12.447 | 1.00 85.12 | O |
| ATOM | 1859 | N | LYS A 257 | 57.701 | 68.499 | -12.784 | 1.00 86.71 | N |
| ATOM | 1860 | CA | LYS A 257 | 56.537 | 69.283 | -13.187 | 1.00 87.28 | C |
| ATOM | 1861 | CB | LYS A 257 | 56.893 | 70.770 | -13.309 | 1.00 87.64 | C |
| ATOM | 1862 | CG | LYS A 257 | 56.076 | 71.700 | -12.414 | 1.00 88.78 | C |
| ATOM | 1863 | CD | LYS A 257 | 56.122 | 73.143 | -12.936 | 1.00 90.89 | C |
| ATOM | 1864 | CE | LYS A 257 | 56.869 | 74.091 | -11.992 | 1.00 91.75 | C |
| ATOM | 1865 | NZ | LYS A 257 | 57.690 | 75.112 | -12.723 | 1.00 91.61 | N |
| ATOM | 1866 | C | LYS A 257 | 56.164 | 68.738 | -14.561 | 1.00 87.65 | C |
| ATOM | 1867 | O | LYS A 257 | 55.006 | 68.796 | -14.988 | 1.00 87.21 | O |
| ATOM | 1868 | N | GLU A 258 | 57.175 | 68.191 | -15.235 | 1.00 87.44 | N |
| ATOM | 1869 | CA | GLU A 258 | 57.023 | 67.625 | -16.564 | 1.00 86.49 | C |
| ATOM | 1870 | CB | GLU A 258 | 58.320 | 67.814 | -17.327 | 1.00 85.59 | C |
| ATOM | 1871 | CG | GLU A 258 | 58.214 | 67.561 | -18.801 | 1.00 86.38 | C |
| ATOM | 1872 | CD | GLU A 258 | 59.503 | 67.898 | -19.500 | 1.00 86.74 | C |
| ATOM | 1873 | OE1 | GLU A 258 | 60.570 | 67.660 | -18.891 | 1.00 88.12 | O |
| ATOM | 1874 | OE2 | GLU A 258 | 59.454 | 68.390 | -20.646 | 1.00 86.22 | O |
| ATOM | 1875 | C | GLU A 258 | 56.662 | 66.147 | -16.489 | 1.00 86.42 | C |
| ATOM | 1876 | O | GLU A 258 | 55.809 | 65.669 | -17.239 | 1.00 86.28 | O |
| ATOM | 1877 | N | SER A 259 | 57.311 | 65.430 | -15.576 | 1.00 86.82 | N |
| ATOM | 1878 | CA | SER A 259 | 57.059 | 64.003 | -15.377 | 1.00 86.93 | C |
| ATOM | 1879 | CB | SER A 259 | 57.989 | 63.445 | -14.304 | 1.00 85.96 | C |
| ATOM | 1880 | OG | SER A 259 | 59.346 | 63.703 | -14.612 | 1.00 86.12 | O |
| ATOM | 1881 | C | SER A 259 | 55.613 | 63.757 | -14.950 | 1.00 88.16 | C |
| ATOM | 1882 | O | SER A 259 | 55.025 | 62.732 | -15.282 | 1.00 89.52 | O |
| ATOM | 1883 | N | ARG A 260 | 55.053 | 64.696 | -14.197 | 1.00 89.15 | N |
| ATOM | 1884 | CA | ARG A 260 | 53.675 | 64.591 | -13.722 | 1.00 88.66 | C |
| ATOM | 1885 | CB | ARG A 260 | 53.325 | 65.814 | -12.866 | 1.00 89.39 | C |
| ATOM | 1886 | CG | ARG A 260 | 53.017 | 65.534 | -11.393 | 1.00 90.26 | C |
| ATOM | 1887 | CD | ARG A 260 | 54.252 | 65.178 | -10.566 | 1.00 91.20 | C |
| ATOM | 1888 | NE | ARG A 260 | 54.030 | 65.467 | -9.146 | 1.00 91.98 | N |
| ATOM | 1889 | CZ | ARG A 260 | 54.915 | 65.253 | -8.173 | 1.00 92.26 | C |
| ATOM | 1890 | NH1 | ARG A 260 | 56.109 | 64.734 | -8.445 | 1.00 91.50 | N |
| ATOM | 1891 | NH2 | ARG A 260 | 54.608 | 65.565 | -6.920 | 1.00 91.55 | N |
| ATOM | 1892 | C | ARG A 260 | 52.690 | 64.484 | -14.890 | 1.00 87.72 | C |
| ATOM | 1893 | O | ARG A 260 | 51.841 | 63.577 | -14.837 | 1.00 87.49 | O |
| ATOM | 1894 | OXT | ARG A 260 | 52.773 | 65.311 | -15.832 | 1.00 87.12 | O |
| TER | 1895 | | ARG A 260 | | | | | |
| ATOM | 1896 | CB | PHE A 271 | 52.933 | 70.571 | -1.015 | 1.00 84.01 | C |
| ATOM | 1897 | CG | PHE A 271 | 52.577 | 70.439 | 0.446 | 1.00 83.52 | C |
| ATOM | 1898 | CD1 | PHE A 271 | 51.275 | 70.646 | 0.877 | 1.00 83.34 | C |
| ATOM | 1899 | CD2 | PHE A 271 | 53.542 | 70.127 | 1.393 | 1.00 83.27 | C |
| ATOM | 1900 | CE1 | PHE A 271 | 50.939 | 70.545 | 2.223 | 1.00 81.78 | C |
| ATOM | 1901 | CE2 | PHE A 271 | 53.208 | 70.026 | 2.742 | 1.00 82.77 | C |
| ATOM | 1902 | CZ | PHE A 271 | 51.905 | 70.236 | 3.153 | 1.00 81.02 | C |
| ATOM | 1903 | C | PHE A 271 | 52.218 | 70.358 | -3.394 | 1.00 85.67 | C |
| ATOM | 1904 | O | PHE A 271 | 51.600 | 71.308 | -3.879 | 1.00 85.70 | O |
| ATOM | 1905 | N | PHE A 271 | 52.055 | 68.396 | -1.895 | 1.00 84.31 | N |
| ATOM | 1906 | CA | PHE A 271 | 51.947 | 69.879 | -1.974 | 1.00 85.08 | C |
| ATOM | 1907 | N | LEU A 272 | 53.155 | 69.701 | -4.061 | 1.00 86.76 | N |
| ATOM | 1908 | CA | LEU A 272 | 53.505 | 70.062 | -5.431 | 1.00 87.88 | C |
| ATOM | 1909 | CB | LEU A 272 | 54.774 | 69.311 | -5.873 | 1.00 88.58 | C |
| ATOM | 1910 | CG | LEU A 272 | 55.445 | 69.613 | -7.222 | 1.00 88.85 | C |
| ATOM | 1911 | CD1 | LEU A 272 | 54.856 | 68.745 | -8.316 | 1.00 89.82 | C |
| ATOM | 1912 | CD2 | LEU A 272 | 55.297 | 71.091 | -7.549 | 1.00 88.91 | C |
| ATOM | 1913 | C | LEU A 272 | 52.334 | 69.701 | -6.327 | 1.00 88.04 | C |
| ATOM | 1914 | O | LEU A 272 | 51.936 | 70.469 | -7.203 | 1.00 87.07 | O |
| ATOM | 1915 | N | GLN A 273 | 51.765 | 68.527 | -6.083 | 1.00 88.92 | N |
| ATOM | 1916 | CA | GLN A 273 | 50.640 | 68.071 | -6.874 | 1.00 89.93 | C |

| | | | | | | | | |
|---|---|---|---|---|---|---|---|---|
| ATOM | 1917 | CB | GLN A 273 | 50.335 | 66.609 | -6.550 | 1.00 | 90.28 | C |
| ATOM | 1918 | CG | GLN A 273 | 50.915 | 65.633 | -7.566 | 1.00 | 90.56 | C |
| ATOM | 1919 | CD | GLN A 273 | 50.049 | 65.509 | -8.805 | 1.00 | 90.80 | C |
| ATOM | 1920 | OE1 | GLN A 273 | 50.465 | 64.939 | -9.811 | 1.00 | 91.09 | O |
| ATOM | 1921 | NE2 | GLN A 273 | 48.830 | 66.033 | -8.731 | 1.00 | 90.80 | N |
| ATOM | 1922 | C | GLN A 273 | 49.394 | 68.934 | -6.695 | 1.00 | 90.08 | C |
| ATOM | 1923 | O | GLN A 273 | 48.567 | 69.030 | -7.604 | 1.00 | 90.81 | O |
| ATOM | 1924 | N | LEU A 274 | 49.255 | 69.576 | -5.540 | 1.00 | 89.50 | N |
| ATOM | 1925 | CA | LEU A 274 | 48.087 | 70.423 | -5.321 | 1.00 | 88.77 | C |
| ATOM | 1926 | CB | LEU A 274 | 47.719 | 70.447 | -3.836 | 1.00 | 89.43 | C |
| ATOM | 1927 | CG | LEU A 274 | 47.155 | 69.100 | -3.371 | 1.00 | 89.82 | C |
| ATOM | 1928 | CD1 | LEU A 274 | 46.907 | 69.117 | -1.877 | 1.00 | 89.39 | C |
| ATOM | 1929 | CD2 | LEU A 274 | 45.860 | 68.806 | -4.127 | 1.00 | 90.92 | C |
| ATOM | 1930 | C | LEU A 274 | 48.243 | 71.846 | -5.864 | 1.00 | 87.80 | C |
| ATOM | 1931 | O | LEU A 274 | 47.281 | 72.424 | -6.374 | 1.00 | 87.76 | O |
| ATOM | 1932 | N | MET A 275 | 49.444 | 72.408 | -5.764 | 1.00 | 86.98 | N |
| ATOM | 1933 | CA | MET A 275 | 49.679 | 73.751 | -6.271 | 1.00 | 85.99 | C |
| ATOM | 1934 | CB | MET A 275 | 51.088 | 74.250 | -5.902 | 1.00 | 84.89 | C |
| ATOM | 1935 | CG | MET A 275 | 51.283 | 74.466 | -4.404 | 1.00 | 83.55 | C |
| ATOM | 1936 | SD | MET A 275 | 52.918 | 75.097 | -3.982 | 1.00 | 79.59 | S |
| ATOM | 1937 | CE | MET A 275 | 53.834 | 73.579 | -3.846 | 1.00 | 80.56 | C |
| ATOM | 1938 | C | MET A 275 | 49.603 | 73.618 | -7.745 | 1.00 | 85.79 | C |
| ATOM | 1939 | O | MET A 275 | 48.985 | 74.451 | -8.448 | 1.00 | 85.44 | O |
| ATOM | 1940 | N | ILE A 276 | 50.185 | 72.526 | -8.226 | 1.00 | 86.83 | N |
| ATOM | 1941 | CA | ILE A 276 | 50.231 | 72.308 | -9.660 | 1.00 | 87.57 | C |
| ATOM | 1942 | CB | ILE A 276 | 50.946 | 70.979 | -10.069 | 1.00 | 86.86 | C |
| ATOM | 1943 | CG2 | ILE A 276 | 50.084 | 69.821 | -9.779 | 1.00 | 86.84 | C |
| ATOM | 1944 | CG1 | ILE A 276 | 51.276 | 71.039 | -11.555 | 1.00 | 86.68 | C |
| ATOM | 1945 | CD1 | ILE A 276 | 52.556 | 71.809 | -11.888 | 1.00 | 88.48 | C |
| ATOM | 1946 | C | ILE A 276 | 48.784 | 72.320 | -10.243 | 1.00 | 87.91 | C |
| ATOM | 1947 | O | ILE A 276 | 47.669 | 72.737 | -10.750 | 1.00 | 88.59 | O |
| ATOM | 1948 | OXT | ILE A 276 | 49.491 | 73.307 | -10.761 | 1.00 | 89.97 | O |
| TER | 1949 | | ILE A 276 | | | | | | |
| ATOM | 1950 | CB | SER A 291 | 53.803 | 82.862 | -11.128 | 1.00 | 79.93 | C |
| ATOM | 1951 | OG | SER A 291 | 54.923 | 82.734 | -11.997 | 1.00 | 78.70 | O |
| ATOM | 1952 | C | SER A 291 | 53.541 | 80.406 | -11.324 | 1.00 | 82.96 | C |
| ATOM | 1953 | O | SER A 291 | 53.602 | 79.749 | -10.285 | 1.00 | 82.74 | O |
| ATOM | 1954 | N | SER A 291 | 51.612 | 81.841 | -10.474 | 1.00 | 80.41 | N |
| ATOM | 1955 | CA | SER A 291 | 52.792 | 81.739 | -11.387 | 1.00 | 81.80 | C |
| ATOM | 1956 | N | ASP A 292 | 54.129 | 80.038 | -12.462 | 1.00 | 84.46 | N |
| ATOM | 1957 | CA | ASP A 292 | 54.875 | 78.803 | -12.627 | 1.00 | 85.52 | C |
| ATOM | 1958 | CB | ASP A 292 | 55.234 | 78.648 | -14.109 | 1.00 | 86.87 | C |
| ATOM | 1959 | CG | ASP A 292 | 55.546 | 77.220 | -14.493 | 1.00 | 88.91 | C |
| ATOM | 1960 | OD1 | ASP A 292 | 54.626 | 76.373 | -14.424 | 1.00 | 89.18 | O |
| ATOM | 1961 | OD2 | ASP A 292 | 56.710 | 76.944 | -14.863 | 1.00 | 90.57 | O |
| ATOM | 1962 | C | ASP A 292 | 56.144 | 78.786 | -11.765 | 1.00 | 85.35 | C |
| ATOM | 1963 | O | ASP A 292 | 56.578 | 77.729 | -11.297 | 1.00 | 86.10 | O |
| ATOM | 1964 | N | LEU A 293 | 56.737 | 79.954 | -11.553 | 1.00 | 84.34 | N |
| ATOM | 1965 | CA | LEU A 293 | 57.955 | 80.029 | -10.759 | 1.00 | 83.49 | C |
| ATOM | 1966 | CB | LEU A 293 | 59.045 | 80.811 | -11.510 | 1.00 | 84.86 | C |
| ATOM | 1967 | CG | LEU A 293 | 59.775 | 80.110 | -12.683 | 1.00 | 86.18 | C |
| ATOM | 1968 | CD1 | LEU A 293 | 60.465 | 78.833 | -12.177 | 1.00 | 86.14 | C |
| ATOM | 1969 | CD2 | LEU A 293 | 58.800 | 79.781 | -13.817 | 1.00 | 85.00 | C |
| ATOM | 1970 | C | LEU A 293 | 57.731 | 80.613 | -9.368 | 1.00 | 81.93 | C |
| ATOM | 1971 | O | LEU A 293 | 58.682 | 80.842 | -8.617 | 1.00 | 81.80 | O |
| ATOM | 1972 | N | GLU A 294 | 56.477 | 80.875 | -9.027 | 1.00 | 79.39 | N |
| ATOM | 1973 | CA | GLU A 294 | 56.186 | 81.365 | -7.689 | 1.00 | 77.23 | C |
| ATOM | 1974 | CB | GLU A 294 | 54.888 | 82.171 | -7.638 | 1.00 | 78.17 | C |
| ATOM | 1975 | CG | GLU A 294 | 54.999 | 83.609 | -8.102 | 1.00 | 79.28 | C |
| ATOM | 1976 | CD | GLU A 294 | 53.756 | 84.420 | -7.765 | 1.00 | 79.99 | C |
| ATOM | 1977 | OE1 | GLU A 294 | 52.633 | 83.898 | -7.931 | 1.00 | 79.62 | O |
| ATOM | 1978 | OE2 | GLU A 294 | 53.902 | 85.584 | -7.344 | 1.00 | 80.88 | O |
| ATOM | 1979 | C | GLU A 294 | 56.001 | 80.076 | -6.917 | 1.00 | 75.48 | C |
| ATOM | 1980 | O | GLU A 294 | 56.252 | 80.005 | -5.714 | 1.00 | 76.05 | O |
| ATOM | 1981 | N | LEU A 295 | 55.560 | 79.051 | -7.642 | 1.00 | 72.72 | N |
| ATOM | 1982 | CA | LEU A 295 | 55.333 | 77.731 | -7.076 | 1.00 | 69.55 | C |
| ATOM | 1983 | CB | LEU A 295 | 54.815 | 76.784 | -8.165 | 1.00 | 69.21 | C |
| ATOM | 1984 | CG | LEU A 295 | 54.459 | 75.333 | -7.807 | 1.00 | 69.19 | C |
| ATOM | 1985 | CD1 | LEU A 295 | 53.582 | 74.747 | -8.904 | 1.00 | 67.85 | C |
| ATOM | 1986 | CD2 | LEU A 295 | 55.725 | 74.495 | -7.615 | 1.00 | 67.61 | C |
| ATOM | 1987 | C | LEU A 295 | 56.633 | 77.195 | -6.477 | 1.00 | 67.89 | C |
| ATOM | 1988 | O | LEU A 295 | 56.618 | 76.525 | -5.443 | 1.00 | 67.09 | O |
| ATOM | 1989 | N | VAL A 296 | 57.756 | 77.495 | -7.125 | 1.00 | 65.95 | N |
| ATOM | 1990 | CA | VAL A 296 | 59.059 | 77.044 | -6.636 | 1.00 | 64.35 | C |
| ATOM | 1991 | CB | VAL A 296 | 60.185 | 77.319 | -7.665 | 1.00 | 65.14 | C |
| ATOM | 1992 | CG1 | VAL A 296 | 61.515 | 76.768 | -7.146 | 1.00 | 64.90 | C |
| ATOM | 1993 | CG2 | VAL A 296 | 59.836 | 76.700 | -9.006 | 1.00 | 65.15 | C |

```
ATOM   1994  C    VAL A 296      59.417  77.772  -5.341  1.00 62.97           C
ATOM   1995  O    VAL A 296      60.153  77.247  -4.508  1.00 61.25           O
ATOM   1996  N    ALA A 297      58.891  78.985  -5.187  1.00 62.12           N
ATOM   1997  CA   ALA A 297      59.151  79.795  -4.005  1.00 60.86           C
ATOM   1998  CB   ALA A 297      58.693  81.211  -4.232  1.00 61.28           C
ATOM   1999  C    ALA A 297      58.446  79.223  -2.800  1.00 60.33           C
ATOM   2000  O    ALA A 297      59.037  79.113  -1.729  1.00 61.18           O
ATOM   2001  N    GLN A 298      57.178  78.869  -2.968  1.00 59.16           N
ATOM   2002  CA   GLN A 298      56.408  78.306  -1.865  1.00 58.27           C
ATOM   2003  CB   GLN A 298      54.961  78.062  -2.287  1.00 58.12           C
ATOM   2004  CG   GLN A 298      54.266  79.276  -2.841  1.00 58.03           C
ATOM   2005  CD   GLN A 298      54.679  80.531  -2.123  1.00 58.19           C
ATOM   2006  OE1  GLN A 298      54.743  80.564  -0.895  1.00 57.09           O
ATOM   2007  NE2  GLN A 298      54.962  81.581  -2.884  1.00 59.28           N
ATOM   2008  C    GLN A 298      57.014  76.984  -1.421  1.00 57.88           C
ATOM   2009  O    GLN A 298      57.331  76.785  -0.243  1.00 58.41           O
ATOM   2010  N    SER A 299      57.175  76.078  -2.378  1.00 56.54           N
ATOM   2011  CA   SER A 299      57.723  74.767  -2.086  1.00 55.28           C
ATOM   2012  CB   SER A 299      58.042  74.015  -3.386  1.00 56.28           C
ATOM   2013  OG   SER A 299      59.018  74.696  -4.155  1.00 60.37           O
ATOM   2014  C    SER A 299      58.958  74.868  -1.201  1.00 52.92           C
ATOM   2015  O    SER A 299      59.040  74.189  -0.189  1.00 55.06           O
ATOM   2016  N    ILE A 300      59.910  75.719  -1.564  1.00 50.24           N
ATOM   2017  CA   ILE A 300      61.121  75.878  -0.761  1.00 48.49           C
ATOM   2018  CB   ILE A 300      62.101  76.856  -1.437  1.00 47.48           C
ATOM   2019  CG2  ILE A 300      63.365  76.977  -0.621  1.00 46.03           C
ATOM   2020  CG1  ILE A 300      62.441  76.360  -2.837  1.00 48.64           C
ATOM   2021  CD1  ILE A 300      63.396  77.262  -3.594  1.00 49.55           C
ATOM   2022  C    ILE A 300      60.804  76.397   0.656  1.00 48.27           C
ATOM   2023  O    ILE A 300      61.384  75.947   1.653  1.00 46.44           O
ATOM   2024  N    ILE A 301      59.876  77.343   0.743  1.00 46.96           N
ATOM   2025  CA   ILE A 301      59.504  77.897   2.024  1.00 45.69           C
ATOM   2026  CB   ILE A 301      58.481  79.030   1.851  1.00 44.94           C
ATOM   2027  CG2  ILE A 301      57.267  78.797   2.730  1.00 44.43           C
ATOM   2028  CG1  ILE A 301      59.157  80.373   2.169  1.00 45.89           C
ATOM   2029  CD1  ILE A 301      59.887  80.412   3.507  1.00 41.75           C
ATOM   2030  C    ILE A 301      58.950  76.835   2.962  1.00 45.81           C
ATOM   2031  O    ILE A 301      59.429  76.684   4.081  1.00 46.78           O
ATOM   2032  N    PHE A 302      57.959  76.077   2.517  1.00 45.21           N
ATOM   2033  CA   PHE A 302      57.393  75.064   3.393  1.00 44.89           C
ATOM   2034  CB   PHE A 302      56.429  74.161   2.625  1.00 45.70           C
ATOM   2035  CG   PHE A 302      55.304  74.901   1.966  1.00 46.47           C
ATOM   2036  CD1  PHE A 302      54.868  76.119   2.467  1.00 45.06           C
ATOM   2037  CD2  PHE A 302      54.668  74.369   0.851  1.00 46.48           C
ATOM   2038  CE1  PHE A 302      53.826  76.791   1.870  1.00 44.88           C
ATOM   2039  CE2  PHE A 302      53.622  75.040   0.250  1.00 44.47           C
ATOM   2040  CZ   PHE A 302      53.203  76.248   0.757  1.00 45.56           C
ATOM   2041  C    PHE A 302      58.487  74.220   4.033  1.00 43.87           C
ATOM   2042  O    PHE A 302      58.402  73.853   5.205  1.00 46.21           O
ATOM   2043  N    ILE A 303      59.519  73.914   3.264  1.00 42.11           N
ATOM   2044  CA   ILE A 303      60.612  73.115   3.778  1.00 40.82           C
ATOM   2045  CB   ILE A 303      61.552  72.711   2.660  1.00 41.11           C
ATOM   2046  CG2  ILE A 303      62.754  71.981   3.236  1.00 39.44           C
ATOM   2047  CG1  ILE A 303      60.779  71.869   1.641  1.00 40.98           C
ATOM   2048  CD1  ILE A 303      61.604  71.424   0.462  1.00 42.18           C
ATOM   2049  C    ILE A 303      61.381  73.932   4.792  1.00 41.03           C
ATOM   2050  O    ILE A 303      61.807  73.424   5.829  1.00 39.60           O
ATOM   2051  N    PHE A 304      61.548  75.212   4.486  1.00 41.41           N
ATOM   2052  CA   PHE A 304      62.261  76.123   5.374  1.00 41.06           C
ATOM   2053  CB   PHE A 304      62.367  77.500   4.715  1.00 41.56           C
ATOM   2054  CG   PHE A 304      63.162  78.491   5.499  1.00 41.44           C
ATOM   2055  CD1  PHE A 304      64.504  78.274   5.764  1.00 42.60           C
ATOM   2056  CD2  PHE A 304      62.557  79.639   5.982  1.00 42.71           C
ATOM   2057  CE1  PHE A 304      65.236  79.194   6.513  1.00 46.19           C
ATOM   2058  CE2  PHE A 304      63.270  80.567   6.727  1.00 45.91           C
ATOM   2059  CZ   PHE A 304      64.616  80.346   6.999  1.00 47.40           C
ATOM   2060  C    PHE A 304      61.537  76.224   6.720  1.00 40.37           C
ATOM   2061  O    PHE A 304      62.156  76.086   7.778  1.00 40.57           O
ATOM   2062  N    ALA A 305      60.225  76.435   6.673  1.00 39.93           N
ATOM   2063  CA   ALA A 305      59.416  76.562   7.879  1.00 40.31           C
ATOM   2064  CB   ALA A 305      58.136  77.273   7.548  1.00 40.25           C
ATOM   2065  C    ALA A 305      59.100  75.250   8.609  1.00 41.49           C
ATOM   2066  O    ALA A 305      58.877  75.250   9.817  1.00 41.75           O
ATOM   2067  N    GLY A 306      59.106  74.128   7.902  1.00 42.25           N
ATOM   2068  CA   GLY A 306      58.781  72.881   8.568  1.00 44.33           C
ATOM   2069  C    GLY A 306      59.866  71.908   8.999  1.00 45.88           C
ATOM   2070  O    GLY A 306      59.645  71.105   9.898  1.00 44.90           O
```

```
ATOM   2071  N    TYR A 307      61.031  71.968   8.374  1.00 47.86           N
ATOM   2072  CA   TYR A 307      62.112  71.054   8.688  1.00 49.83           C
ATOM   2073  CB   TYR A 307      63.248  71.270   7.706  1.00 51.28           C
ATOM   2074  CG   TYR A 307      64.454  70.382   7.917  1.00 53.27           C
ATOM   2075  CD1  TYR A 307      65.723  70.829   7.588  1.00 53.44           C
ATOM   2076  CE1  TYR A 307      66.820  70.010   7.705  1.00 55.21           C
ATOM   2077  CD2  TYR A 307      64.320  69.081   8.379  1.00 54.97           C
ATOM   2078  CE2  TYR A 307      65.415  68.251   8.497  1.00 55.96           C
ATOM   2079  CZ   TYR A 307      66.662  68.721   8.157  1.00 56.58           C
ATOM   2080  OH   TYR A 307      67.751  67.888   8.262  1.00 57.93           O
ATOM   2081  C    TYR A 307      62.663  71.149  10.099  1.00 52.25           C
ATOM   2082  O    TYR A 307      62.139  70.545  11.026  1.00 54.31           O
ATOM   2083  N    GLU A 308      63.745  71.899  10.256  1.00 55.10           N
ATOM   2084  CA   GLU A 308      64.400  72.045  11.551  1.00 56.71           C
ATOM   2085  CB   GLU A 308      65.617  72.968  11.412  1.00 59.62           C
ATOM   2086  CG   GLU A 308      66.610  72.867  12.562  1.00 66.07           C
ATOM   2087  CD   GLU A 308      67.843  73.748  12.367  1.00 69.94           C
ATOM   2088  OE1  GLU A 308      67.683  74.988  12.265  1.00 71.24           O
ATOM   2089  OE2  GLU A 308      68.972  73.197  12.320  1.00 71.71           O
ATOM   2090  C    GLU A 308      63.439  72.589  12.599  1.00 55.70           C
ATOM   2091  O    GLU A 308      63.731  72.615  13.794  1.00 56.24           O
ATOM   2092  N    THR A 309      62.276  73.023  12.141  1.00 55.41           N
ATOM   2093  CA   THR A 309      61.280  73.573  13.045  1.00 54.57           C
ATOM   2094  CB   THR A 309      60.243  74.395  12.248  1.00 52.99           C
ATOM   2095  OG1  THR A 309      59.911  75.580  12.976  1.00 54.68           O
ATOM   2096  CG2  THR A 309      58.994  73.595  12.021  1.00 51.97           C
ATOM   2097  C    THR A 309      60.588  72.449  13.827  1.00 53.85           C
ATOM   2098  O    THR A 309      60.376  72.559  15.036  1.00 53.57           O
ATOM   2099  N    THR A 310      60.278  71.359  13.123  1.00 52.78           N
ATOM   2100  CA   THR A 310      59.603  70.198  13.685  1.00 50.84           C
ATOM   2101  CB   THR A 310      59.035  69.317  12.591  1.00 48.98           C
ATOM   2102  OG1  THR A 310      58.023  70.026  11.881  1.00 50.30           O
ATOM   2103  CG2  THR A 310      58.436  68.099  13.174  1.00 47.37           C
ATOM   2104  C    THR A 310      60.500  69.317  14.519  1.00 52.31           C
ATOM   2105  O    THR A 310      60.133  68.912  15.618  1.00 53.63           O
ATOM   2106  N    SER A 311      61.672  68.996  13.994  1.00 52.55           N
ATOM   2107  CA   SER A 311      62.581  68.130  14.728  1.00 53.33           C
ATOM   2108  CB   SER A 311      63.786  67.776  13.862  1.00 55.53           C
ATOM   2109  OG   SER A 311      64.608  68.911  13.661  1.00 58.23           O
ATOM   2110  C    SER A 311      63.054  68.821  15.997  1.00 52.93           C
ATOM   2111  O    SER A 311      63.392  68.165  16.987  1.00 53.23           O
ATOM   2112  N    SER A 312      63.068  70.149  15.959  1.00 51.05           N
ATOM   2113  CA   SER A 312      63.511  70.944  17.088  1.00 48.76           C
ATOM   2114  CB   SER A 312      63.662  72.397  16.662  1.00 48.33           C
ATOM   2115  OG   SER A 312      64.213  73.160  17.709  1.00 51.69           O
ATOM   2116  C    SER A 312      62.515  70.839  18.227  1.00 48.70           C
ATOM   2117  O    SER A 312      62.896  70.685  19.388  1.00 50.33           O
ATOM   2118  N    VAL A 313      61.232  70.929  17.888  1.00 47.71           N
ATOM   2119  CA   VAL A 313      60.153  70.846  18.874  1.00 43.91           C
ATOM   2120  CB   VAL A 313      58.810  71.178  18.233  1.00 40.84           C
ATOM   2121  CG1  VAL A 313      57.693  70.748  19.139  1.00 39.06           C
ATOM   2122  CG2  VAL A 313      58.739  72.644  17.948  1.00 37.87           C
ATOM   2123  C    VAL A 313      60.068  69.444  19.454  1.00 43.89           C
ATOM   2124  O    VAL A 313      59.978  69.277  20.667  1.00 41.56           O
ATOM   2125  N    LEU A 314      60.104  68.453  18.557  1.00 44.11           N
ATOM   2126  CA   LEU A 314      60.044  67.030  18.898  1.00 44.47           C
ATOM   2127  CB   LEU A 314      60.170  66.172  17.632  1.00 42.64           C
ATOM   2128  CG   LEU A 314      58.914  65.708  16.903  1.00 41.01           C
ATOM   2129  CD1  LEU A 314      59.302  64.959  15.661  1.00 38.79           C
ATOM   2130  CD2  LEU A 314      58.093  64.815  17.823  1.00 41.33           C
ATOM   2131  C    LEU A 314      61.139  66.609  19.862  1.00 44.80           C
ATOM   2132  O    LEU A 314      60.918  65.813  20.760  1.00 45.52           O
ATOM   2133  N    SER A 315      62.336  67.128  19.666  1.00 46.33           N
ATOM   2134  CA   SER A 315      63.422  66.755  20.545  1.00 47.90           C
ATOM   2135  CB   SER A 315      64.758  67.245  19.978  1.00 48.57           C
ATOM   2136  OG   SER A 315      64.944  68.627  20.238  1.00 50.05           O
ATOM   2137  C    SER A 315      63.193  67.341  21.933  1.00 48.37           C
ATOM   2138  O    SER A 315      63.625  66.759  22.921  1.00 49.78           O
ATOM   2139  N    PHE A 316      62.521  68.489  22.002  1.00 48.92           N
ATOM   2140  CA   PHE A 316      62.234  69.150  23.277  1.00 50.54           C
ATOM   2141  CB   PHE A 316      61.616  70.528  23.035  1.00 52.62           C
ATOM   2142  CG   PHE A 316      62.614  71.632  22.854  1.00 54.97           C
ATOM   2143  CD1  PHE A 316      62.508  72.512  21.784  1.00 55.99           C
ATOM   2144  CD2  PHE A 316      63.632  71.826  23.774  1.00 55.81           C
ATOM   2145  CE1  PHE A 316      63.404  73.571  21.638  1.00 57.37           C
ATOM   2146  CE2  PHE A 316      64.534  72.885  23.636  1.00 57.14           C
ATOM   2147  CZ   PHE A 316      64.419  73.757  22.569  1.00 57.18           C
```

| | | | | | | | | | |
|---|---|---|---|---|---|---|---|---|---|
| ATOM | 2148 | C | PHE | A | 316 | 61.238 | 68.303 | 24.059 | 1.00 51.65 | C |
| ATOM | 2149 | O | PHE | A | 316 | 61.357 | 68.113 | 25.271 | 1.00 52.31 | O |
| ATOM | 2150 | N | ILE | A | 317 | 60.243 | 67.800 | 23.343 | 1.00 51.76 | N |
| ATOM | 2151 | CA | ILE | A | 317 | 59.212 | 66.977 | 23.930 | 1.00 51.52 | C |
| ATOM | 2152 | CB | ILE | A | 317 | 58.156 | 66.638 | 22.878 | 1.00 50.09 | C |
| ATOM | 2153 | CG2 | ILE | A | 317 | 57.365 | 65.426 | 23.294 | 1.00 49.27 | C |
| ATOM | 2154 | CG1 | ILE | A | 317 | 57.283 | 67.868 | 22.641 | 1.00 47.42 | C |
| ATOM | 2155 | CD1 | ILE | A | 317 | 56.291 | 67.716 | 21.513 | 1.00 46.85 | C |
| ATOM | 2156 | C | ILE | A | 317 | 59.797 | 65.707 | 24.529 | 1.00 53.41 | C |
| ATOM | 2157 | O | ILE | A | 317 | 59.498 | 65.367 | 25.671 | 1.00 55.16 | O |
| ATOM | 2158 | N | MET | A | 318 | 60.638 | 65.003 | 23.787 | 1.00 54.62 | N |
| ATOM | 2159 | CA | MET | A | 318 | 61.217 | 63.791 | 24.341 | 1.00 56.74 | C |
| ATOM | 2160 | CB | MET | A | 318 | 62.050 | 63.050 | 23.310 | 1.00 58.37 | C |
| ATOM | 2161 | CG | MET | A | 318 | 61.628 | 61.616 | 23.180 | 1.00 61.07 | C |
| ATOM | 2162 | SD | MET | A | 318 | 59.886 | 61.592 | 22.720 | 1.00 66.46 | S |
| ATOM | 2163 | CE | MET | A | 318 | 59.351 | 60.027 | 23.419 | 1.00 62.85 | C |
| ATOM | 2164 | C | MET | A | 318 | 62.091 | 64.120 | 25.537 | 1.00 57.67 | C |
| ATOM | 2165 | O | MET | A | 318 | 62.405 | 63.246 | 26.354 | 1.00 58.89 | O |
| ATOM | 2166 | N | TYR | A | 319 | 62.499 | 65.379 | 25.648 | 1.00 56.25 | N |
| ATOM | 2167 | CA | TYR | A | 319 | 63.324 | 65.756 | 26.776 | 1.00 56.55 | C |
| ATOM | 2168 | CB | TYR | A | 319 | 64.028 | 67.086 | 26.525 | 1.00 53.69 | C |
| ATOM | 2169 | CG | TYR | A | 319 | 64.508 | 67.737 | 27.802 | 1.00 52.15 | C |
| ATOM | 2170 | CD1 | TYR | A | 319 | 65.689 | 67.326 | 28.427 | 1.00 50.67 | C |
| ATOM | 2171 | CE1 | TYR | A | 319 | 66.099 | 67.895 | 29.635 | 1.00 50.07 | C |
| ATOM | 2172 | CD2 | TYR | A | 319 | 63.747 | 68.734 | 28.417 | 1.00 51.81 | C |
| ATOM | 2173 | CE2 | TYR | A | 319 | 64.141 | 69.306 | 29.616 | 1.00 52.15 | C |
| ATOM | 2174 | CZ | TYR | A | 319 | 65.316 | 68.884 | 30.222 | 1.00 52.41 | C |
| ATOM | 2175 | OH | TYR | A | 319 | 65.692 | 69.469 | 31.417 | 1.00 53.91 | O |
| ATOM | 2176 | C | TYR | A | 319 | 62.438 | 65.872 | 28.011 | 1.00 58.79 | C |
| ATOM | 2177 | O | TYR | A | 319 | 62.755 | 65.326 | 29.077 | 1.00 57.62 | O |
| ATOM | 2178 | N | GLU | A | 320 | 61.318 | 66.579 | 27.874 | 1.00 60.90 | N |
| ATOM | 2179 | CA | GLU | A | 320 | 60.437 | 66.738 | 29.017 | 1.00 63.67 | C |
| ATOM | 2180 | CB | GLU | A | 320 | 59.245 | 67.639 | 28.680 | 1.00 63.16 | C |
| ATOM | 2181 | CG | GLU | A | 320 | 59.600 | 69.114 | 28.420 | 1.00 66.69 | C |
| ATOM | 2182 | CD | GLU | A | 320 | 60.375 | 69.793 | 29.562 | 1.00 69.68 | C |
| ATOM | 2183 | OE1 | GLU | A | 320 | 60.266 | 71.029 | 29.695 | 1.00 70.39 | O |
| ATOM | 2184 | OE2 | GLU | A | 320 | 61.105 | 69.116 | 30.319 | 1.00 73.22 | O |
| ATOM | 2185 | C | GLU | A | 320 | 59.975 | 65.384 | 29.551 | 1.00 65.25 | C |
| ATOM | 2186 | O | GLU | A | 320 | 59.692 | 65.255 | 30.736 | 1.00 66.40 | O |
| ATOM | 2187 | N | LEU | A | 321 | 59.930 | 64.369 | 28.693 | 1.00 65.99 | N |
| ATOM | 2188 | CA | LEU | A | 321 | 59.534 | 63.037 | 29.134 | 1.00 67.73 | C |
| ATOM | 2189 | CB | LEU | A | 321 | 59.061 | 62.227 | 27.935 | 1.00 66.31 | C |
| ATOM | 2190 | CG | LEU | A | 321 | 57.898 | 62.883 | 27.186 | 1.00 65.93 | C |
| ATOM | 2191 | CD1 | LEU | A | 321 | 57.359 | 61.926 | 26.141 | 1.00 63.44 | C |
| ATOM | 2192 | CD2 | LEU | A | 321 | 56.794 | 63.259 | 28.164 | 1.00 65.41 | C |
| ATOM | 2193 | C | LEU | A | 321 | 60.694 | 62.313 | 29.863 | 1.00 71.45 | C |
| ATOM | 2194 | O | LEU | A | 321 | 60.740 | 61.074 | 29.935 | 1.00 70.46 | O |
| ATOM | 2195 | N | ALA | A | 322 | 61.613 | 63.121 | 30.402 | 1.00 74.86 | N |
| ATOM | 2196 | CA | ALA | A | 322 | 62.794 | 62.682 | 31.155 | 1.00 75.39 | C |
| ATOM | 2197 | CB | ALA | A | 322 | 64.043 | 62.801 | 30.294 | 1.00 75.36 | C |
| ATOM | 2198 | C | ALA | A | 322 | 62.879 | 63.622 | 32.365 | 1.00 76.85 | C |
| ATOM | 2199 | O | ALA | A | 322 | 63.454 | 64.713 | 32.305 | 1.00 76.79 | O |
| ATOM | 2200 | N | THR | A | 323 | 62.273 | 63.144 | 33.447 | 1.00 78.45 | N |
| ATOM | 2201 | CA | THR | A | 323 | 62.106 | 63.774 | 34.760 | 1.00 79.70 | C |
| ATOM | 2202 | CB | THR | A | 323 | 63.039 | 64.957 | 35.081 | 1.00 82.15 | C |
| ATOM | 2203 | OG1 | THR | A | 323 | 63.076 | 65.117 | 36.513 | 1.00 83.63 | O |
| ATOM | 2204 | CG2 | THR | A | 323 | 62.537 | 66.262 | 34.456 | 1.00 83.58 | C |
| ATOM | 2205 | C | THR | A | 323 | 60.667 | 64.225 | 34.698 | 1.00 78.97 | C |
| ATOM | 2206 | O | THR | A | 323 | 60.258 | 65.302 | 35.149 | 1.00 78.99 | O |
| ATOM | 2207 | N | HIS | A | 324 | 59.935 | 63.324 | 34.063 | 1.00 76.73 | N |
| ATOM | 2208 | CA | HIS | A | 324 | 58.516 | 63.343 | 33.850 | 1.00 74.57 | C |
| ATOM | 2209 | CB | HIS | A | 324 | 58.111 | 64.429 | 32.872 | 1.00 75.23 | C |
| ATOM | 2210 | CG | HIS | A | 324 | 58.342 | 65.812 | 33.389 | 1.00 76.24 | C |
| ATOM | 2211 | CD2 | HIS | A | 324 | 57.576 | 66.608 | 34.171 | 1.00 76.91 | C |
| ATOM | 2212 | ND1 | HIS | A | 324 | 59.498 | 66.521 | 33.134 | 1.00 76.19 | N |
| ATOM | 2213 | CE1 | HIS | A | 324 | 59.431 | 67.695 | 33.735 | 1.00 77.46 | C |
| ATOM | 2214 | NE2 | HIS | A | 324 | 58.276 | 67.772 | 34.371 | 1.00 78.23 | N |
| ATOM | 2215 | C | HIS | A | 324 | 58.306 | 61.956 | 33.251 | 1.00 73.15 | C |
| ATOM | 2216 | O | HIS | A | 324 | 57.445 | 61.754 | 32.383 | 1.00 74.10 | O |
| ATOM | 2217 | N | PRO | A | 325 | 59.118 | 60.971 | 33.700 | 1.00 70.09 | N |
| ATOM | 2218 | CD | PRO | A | 325 | 60.108 | 60.914 | 34.796 | 1.00 68.30 | C |
| ATOM | 2219 | CA | PRO | A | 325 | 58.909 | 59.644 | 33.129 | 1.00 67.81 | C |
| ATOM | 2220 | CB | PRO | A | 325 | 60.003 | 58.801 | 33.794 | 1.00 67.18 | C |
| ATOM | 2221 | CG | PRO | A | 325 | 60.175 | 59.443 | 35.110 | 1.00 67.05 | C |
| ATOM | 2222 | C | PRO | A | 325 | 57.499 | 59.213 | 33.500 | 1.00 65.95 | C |
| ATOM | 2223 | O | PRO | A | 325 | 56.942 | 58.298 | 32.899 | 1.00 66.69 | O |
| ATOM | 2224 | N | ASP | A | 326 | 56.925 | 59.897 | 34.490 | 1.00 63.82 | N |

| | | | | | | | | | |
|---|---|---|---|---|---|---|---|---|---|
| ATOM | 2225 | CA | ASP | A | 326 | 55.573 | 59.607 | 34.936 | 1.00 62.94 | C |
| ATOM | 2226 | CB | ASP | A | 326 | 55.287 | 60.310 | 36.279 | 1.00 64.69 | C |
| ATOM | 2227 | CG | ASP | A | 326 | 55.534 | 61.820 | 36.239 | 1.00 66.83 | C |
| ATOM | 2228 | OD1 | ASP | A | 326 | 54.651 | 62.560 | 35.745 | 1.00 66.44 | O |
| ATOM | 2229 | OD2 | ASP | A | 326 | 56.611 | 62.265 | 36.712 | 1.00 66.26 | O |
| ATOM | 2230 | C | ASP | A | 326 | 54.604 | 60.049 | 33.845 | 1.00 61.69 | C |
| ATOM | 2231 | O | ASP | A | 326 | 53.644 | 59.347 | 33.521 | 1.00 61.11 | O |
| ATOM | 2232 | N | VAL | A | 327 | 54.884 | 61.200 | 33.245 | 1.00 60.12 | N |
| ATOM | 2233 | CA | VAL | A | 327 | 54.036 | 61.714 | 32.181 | 1.00 59.92 | C |
| ATOM | 2234 | CB | VAL | A | 327 | 54.492 | 63.116 | 31.737 | 1.00 58.72 | C |
| ATOM | 2235 | CG1 | VAL | A | 327 | 53.554 | 63.645 | 30.681 | 1.00 59.00 | C |
| ATOM | 2236 | CG2 | VAL | A | 327 | 54.522 | 64.055 | 32.918 | 1.00 59.80 | C |
| ATOM | 2237 | C | VAL | A | 327 | 54.076 | 60.777 | 30.970 | 1.00 60.33 | C |
| ATOM | 2238 | O | VAL | A | 327 | 53.051 | 60.539 | 30.315 | 1.00 58.95 | O |
| ATOM | 2239 | N | GLN | A | 328 | 55.273 | 60.262 | 30.681 | 1.00 60.36 | N |
| ATOM | 2240 | CA | GLN | A | 328 | 55.493 | 59.356 | 29.558 | 1.00 59.91 | C |
| ATOM | 2241 | CB | GLN | A | 328 | 56.990 | 59.020 | 29.436 | 1.00 59.42 | C |
| ATOM | 2242 | CG | GLN | A | 328 | 57.344 | 58.047 | 28.288 | 1.00 59.45 | C |
| ATOM | 2243 | CD | GLN | A | 328 | 58.861 | 57.789 | 28.127 | 1.00 60.80 | C |
| ATOM | 2244 | OE1 | GLN | A | 328 | 59.280 | 56.953 | 27.313 | 1.00 59.37 | O |
| ATOM | 2245 | NE2 | GLN | A | 328 | 59.679 | 58.507 | 28.899 | 1.00 61.40 | N |
| ATOM | 2246 | C | GLN | A | 328 | 54.684 | 58.078 | 29.751 | 1.00 60.97 | C |
| ATOM | 2247 | O | GLN | A | 328 | 54.156 | 57.504 | 28.788 | 1.00 59.56 | O |
| ATOM | 2248 | N | GLN | A | 329 | 54.581 | 57.642 | 31.006 | 1.00 61.85 | N |
| ATOM | 2249 | CA | GLN | A | 329 | 53.838 | 56.431 | 31.329 | 1.00 62.09 | C |
| ATOM | 2250 | CB | GLN | A | 329 | 54.020 | 56.066 | 32.808 | 1.00 63.71 | C |
| ATOM | 2251 | CG | GLN | A | 329 | 53.841 | 54.572 | 33.084 | 1.00 67.41 | C |
| ATOM | 2252 | CD | GLN | A | 329 | 53.767 | 54.227 | 34.568 | 1.00 69.87 | C |
| ATOM | 2253 | OE1 | GLN | A | 329 | 54.619 | 54.643 | 35.369 | 1.00 69.63 | O |
| ATOM | 2254 | NE2 | GLN | A | 329 | 52.745 | 53.452 | 34.938 | 1.00 70.33 | N |
| ATOM | 2255 | C | GLN | A | 329 | 52.359 | 56.657 | 31.018 | 1.00 61.14 | C |
| ATOM | 2256 | O | GLN | A | 329 | 51.715 | 55.846 | 30.350 | 1.00 60.70 | O |
| ATOM | 2257 | N | LYS | A | 330 | 51.828 | 57.777 | 31.492 | 1.00 59.11 | N |
| ATOM | 2258 | CA | LYS | A | 330 | 50.438 | 58.095 | 31.246 | 1.00 58.72 | C |
| ATOM | 2259 | CB | LYS | A | 330 | 50.106 | 59.447 | 31.879 | 1.00 58.82 | C |
| ATOM | 2260 | CG | LYS | A | 330 | 48.620 | 59.781 | 31.955 | 1.00 58.97 | C |
| ATOM | 2261 | CD | LYS | A | 330 | 48.395 | 60.917 | 32.937 | 1.00 59.75 | C |
| ATOM | 2262 | CE | LYS | A | 330 | 46.915 | 61.224 | 33.135 | 1.00 62.13 | C |
| ATOM | 2263 | NZ | LYS | A | 330 | 46.205 | 61.573 | 31.868 | 1.00 60.52 | N |
| ATOM | 2264 | C | LYS | A | 330 | 50.208 | 58.136 | 29.738 | 1.00 60.13 | C |
| ATOM | 2265 | O | LYS | A | 330 | 49.271 | 57.517 | 29.217 | 1.00 59.75 | O |
| ATOM | 2266 | N | LEU | A | 331 | 51.085 | 58.857 | 29.038 | 1.00 61.59 | N |
| ATOM | 2267 | CA | LEU | A | 331 | 50.984 | 59.002 | 27.591 | 1.00 61.45 | C |
| ATOM | 2268 | CB | LEU | A | 331 | 52.142 | 59.859 | 27.055 | 1.00 60.33 | C |
| ATOM | 2269 | CG | LEU | A | 331 | 51.970 | 60.731 | 25.791 | 1.00 58.12 | C |
| ATOM | 2270 | CD1 | LEU | A | 331 | 53.081 | 60.408 | 24.838 | 1.00 56.63 | C |
| ATOM | 2271 | CD2 | LEU | A | 331 | 50.635 | 60.502 | 25.109 | 1.00 58.89 | C |
| ATOM | 2272 | C | LEU | A | 331 | 51.017 | 57.626 | 26.943 | 1.00 62.59 | C |
| ATOM | 2273 | O | LEU | A | 331 | 50.189 | 57.076 | 26.078 | 1.00 61.45 | O |
| ATOM | 2274 | N | GLN | A | 332 | 51.971 | 56.806 | 27.371 | 1.00 64.43 | N |
| ATOM | 2275 | CA | GLN | A | 332 | 52.102 | 55.473 | 26.809 | 1.00 65.50 | C |
| ATOM | 2276 | CB | GLN | A | 332 | 53.297 | 54.751 | 27.438 | 1.00 66.15 | C |
| ATOM | 2277 | CG | GLN | A | 332 | 54.631 | 55.344 | 26.971 | 1.00 68.59 | C |
| ATOM | 2278 | CD | GLN | A | 332 | 55.868 | 54.643 | 27.533 | 1.00 71.13 | C |
| ATOM | 2279 | OE1 | GLN | A | 332 | 56.173 | 54.725 | 28.733 | 1.00 71.66 | O |
| ATOM | 2280 | NE2 | GLN | A | 332 | 56.595 | 53.956 | 26.657 | 1.00 72.13 | N |
| ATOM | 2281 | C | GLN | A | 332 | 50.809 | 54.687 | 26.967 | 1.00 65.86 | C |
| ATOM | 2282 | O | GLN | A | 332 | 50.322 | 54.097 | 26.003 | 1.00 66.77 | O |
| ATOM | 2283 | N | GLU | A | 333 | 50.227 | 54.709 | 28.161 | 1.00 66.01 | N |
| ATOM | 2284 | CA | GLU | A | 333 | 48.974 | 53.997 | 28.392 | 1.00 66.70 | C |
| ATOM | 2285 | CB | GLU | A | 333 | 48.565 | 54.120 | 29.851 | 1.00 65.69 | C |
| ATOM | 2286 | CG | GLU | A | 333 | 49.481 | 53.385 | 30.807 | 1.00 65.29 | C |
| ATOM | 2287 | CD | GLU | A | 333 | 49.513 | 54.031 | 32.171 | 1.00 65.18 | C |
| ATOM | 2288 | OE1 | GLU | A | 333 | 48.616 | 54.854 | 32.461 | 1.00 66.24 | O |
| ATOM | 2289 | OE2 | GLU | A | 333 | 50.430 | 53.718 | 32.956 | 1.00 65.39 | O |
| ATOM | 2290 | C | GLU | A | 333 | 47.853 | 54.534 | 27.507 | 1.00 68.11 | C |
| ATOM | 2291 | O | GLU | A | 333 | 47.081 | 53.758 | 26.933 | 1.00 69.22 | O |
| ATOM | 2292 | N | GLU | A | 334 | 47.769 | 55.860 | 27.399 | 1.00 68.27 | N |
| ATOM | 2293 | CA | GLU | A | 334 | 46.742 | 56.498 | 26.584 | 1.00 68.30 | C |
| ATOM | 2294 | CB | GLU | A | 334 | 46.870 | 58.018 | 26.666 | 1.00 69.97 | C |
| ATOM | 2295 | CG | GLU | A | 334 | 46.132 | 58.757 | 25.546 | 1.00 74.51 | C |
| ATOM | 2296 | CD | GLU | A | 334 | 45.305 | 59.938 | 26.049 | 1.00 77.84 | C |
| ATOM | 2297 | OE1 | GLU | A | 334 | 45.500 | 60.352 | 27.216 | 1.00 80.29 | O |
| ATOM | 2298 | OE2 | GLU | A | 334 | 44.463 | 60.456 | 25.279 | 1.00 77.48 | O |
| ATOM | 2299 | C | GLU | A | 334 | 46.815 | 56.062 | 25.129 | 1.00 67.90 | C |
| ATOM | 2300 | O | GLU | A | 334 | 45.797 | 55.979 | 24.436 | 1.00 67.11 | O |
| ATOM | 2301 | N | ILE | A | 335 | 48.029 | 55.783 | 24.669 | 1.00 68.08 | N |

```
ATOM   2302  CA   ILE A 335      48.233  55.368  23.291  1.00 68.99           C
ATOM   2303  CB   ILE A 335      49.709  55.516  22.877  1.00 68.85           C
ATOM   2304  CG2  ILE A 335      49.953  54.785  21.570  1.00 67.50           C
ATOM   2305  CG1  ILE A 335      50.062  57.005  22.760  1.00 69.71           C
ATOM   2306  CD1  ILE A 335      51.492  57.283  22.327  1.00 69.54           C
ATOM   2307  C    ILE A 335      47.817  53.928  23.116  1.00 69.26           C
ATOM   2308  O    ILE A 335      47.332  53.526  22.053  1.00 69.62           O
ATOM   2309  N    ASP A 336      48.005  53.151  24.172  1.00 69.11           N
ATOM   2310  CA   ASP A 336      47.653  51.750  24.121  1.00 69.31           C
ATOM   2311  CB   ASP A 336      48.437  50.975  25.181  1.00 69.54           C
ATOM   2312  CG   ASP A 336      49.945  51.028  24.946  1.00 70.25           C
ATOM   2313  OD1  ASP A 336      50.371  51.195  23.777  1.00 69.10           O
ATOM   2314  OD2  ASP A 336      50.705  50.889  25.926  1.00 70.25           O
ATOM   2315  C    ASP A 336      46.150  51.569  24.293  1.00 69.32           C
ATOM   2316  O    ASP A 336      45.560  50.650  23.729  1.00 69.75           O
ATOM   2317  N    ALA A 337      45.520  52.454  25.053  1.00 68.88           N
ATOM   2318  CA   ALA A 337      44.088  52.343  25.243  1.00 69.67           C
ATOM   2319  CB   ALA A 337      43.613  53.382  26.239  1.00 68.16           C
ATOM   2320  C    ALA A 337      43.389  52.542  23.899  1.00 71.32           C
ATOM   2321  O    ALA A 337      42.511  51.769  23.513  1.00 72.15           O
ATOM   2322  N    VAL A 338      43.796  53.580  23.180  1.00 72.06           N
ATOM   2323  CA   VAL A 338      43.193  53.893  21.896  1.00 71.74           C
ATOM   2324  CB   VAL A 338      43.621  55.285  21.430  1.00 70.62           C
ATOM   2325  CG1  VAL A 338      42.806  55.705  20.228  1.00 70.24           C
ATOM   2326  CG2  VAL A 338      43.460  56.274  22.561  1.00 69.14           C
ATOM   2327  C    VAL A 338      43.584  52.882  20.837  1.00 72.98           C
ATOM   2328  O    VAL A 338      42.731  52.289  20.182  1.00 73.47           O
ATOM   2329  N    LEU A 339      44.886  52.698  20.672  1.00 74.51           N
ATOM   2330  CA   LEU A 339      45.420  51.767  19.688  1.00 75.75           C
ATOM   2331  CB   LEU A 339      46.557  52.431  18.920  1.00 73.75           C
ATOM   2332  CG   LEU A 339      46.254  53.684  18.108  1.00 71.72           C
ATOM   2333  CD1  LEU A 339      47.497  54.542  18.027  1.00 70.79           C
ATOM   2334  CD2  LEU A 339      45.771  53.294  16.730  1.00 71.36           C
ATOM   2335  C    LEU A 339      45.969  50.554  20.422  1.00 78.10           C
ATOM   2336  O    LEU A 339      46.905  50.691  21.211  1.00 78.46           O
ATOM   2337  N    PRO A 340      45.393  49.358  20.176  1.00 79.80           N
ATOM   2338  CD   PRO A 340      44.255  49.172  19.259  1.00 80.06           C
ATOM   2339  CA   PRO A 340      45.783  48.076  20.779  1.00 80.90           C
ATOM   2340  CB   PRO A 340      45.062  47.063  19.903  1.00 80.52           C
ATOM   2341  CG   PRO A 340      43.795  47.769  19.593  1.00 80.40           C
ATOM   2342  C    PRO A 340      47.300  47.876  20.756  1.00 83.04           C
ATOM   2343  O    PRO A 340      48.059  48.843  20.746  1.00 84.90           O
ATOM   2344  N    ASN A 341      47.760  46.633  20.730  1.00 83.79           N
ATOM   2345  CA   ASN A 341      49.201  46.425  20.722  1.00 84.25           C
ATOM   2346  CB   ASN A 341      49.547  44.963  21.010  1.00 87.01           C
ATOM   2347  CG   ASN A 341      50.827  44.824  21.828  1.00 89.31           C
ATOM   2348  OD1  ASN A 341      50.939  45.389  22.920  1.00 90.03           O
ATOM   2349  ND2  ASN A 341      51.797  44.077  21.305  1.00 90.41           N
ATOM   2350  C    ASN A 341      49.823  46.869  19.397  1.00 83.41           C
ATOM   2351  O    ASN A 341      49.597  46.249  18.350  1.00 84.49           O
ATOM   2352  N    LYS A 342      50.600  47.952  19.470  1.00 80.58           N
ATOM   2353  CA   LYS A 342      51.286  48.549  18.322  1.00 77.06           C
ATOM   2354  CB   LYS A 342      52.391  47.616  17.809  1.00 73.64           C
ATOM   2355  CG   LYS A 342      53.269  46.965  18.873  1.00 70.43           C
ATOM   2356  CD   LYS A 342      54.333  47.888  19.461  1.00 67.27           C
ATOM   2357  CE   LYS A 342      55.412  47.065  20.183  1.00 63.73           C
ATOM   2358  NZ   LYS A 342      56.291  47.845  21.093  1.00 59.47           N
ATOM   2359  C    LYS A 342      50.324  48.865  17.167  1.00 76.77           C
ATOM   2360  O    LYS A 342      50.691  48.752  16.002  1.00 77.24           O
ATOM   2361  N    ALA A 343      49.098  49.262  17.475  1.00 76.05           N
ATOM   2362  CA   ALA A 343      48.149  49.567  16.411  1.00 76.49           C
ATOM   2363  CB   ALA A 343      46.751  49.776  16.997  1.00 77.16           C
ATOM   2364  C    ALA A 343      48.582  50.797  15.611  1.00 76.41           C
ATOM   2365  O    ALA A 343      49.073  51.779  16.174  1.00 76.02           O
ATOM   2366  N    PRO A 344      48.393  50.757  14.279  1.00 76.34           N
ATOM   2367  CD   PRO A 344      47.759  49.643  13.560  1.00 76.38           C
ATOM   2368  CA   PRO A 344      48.743  51.832  13.342  1.00 75.94           C
ATOM   2369  CB   PRO A 344      48.503  51.197  11.970  1.00 75.98           C
ATOM   2370  CG   PRO A 344      48.453  49.712  12.245  1.00 76.39           C
ATOM   2371  C    PRO A 344      47.848  53.051  13.552  1.00 75.21           C
ATOM   2372  O    PRO A 344      46.624  52.937  13.553  1.00 75.16           O
ATOM   2373  N    PRO A 345      48.447  54.236  13.721  1.00 74.01           N
ATOM   2374  CD   PRO A 345      49.887  54.492  13.852  1.00 73.21           C
ATOM   2375  CA   PRO A 345      47.689  55.470  13.931  1.00 73.60           C
ATOM   2376  CB   PRO A 345      48.778  56.504  14.220  1.00 71.87           C
ATOM   2377  CG   PRO A 345      49.898  55.702  14.745  1.00 72.03           C
ATOM   2378  C    PRO A 345      46.864  55.858  12.712  1.00 73.77           C
```

```
ATOM   2379  O   PRO A 345      47.271  55.615  11.580  1.00 73.80           O
ATOM   2380  N   THR A 346      45.700  56.451  12.951  1.00 74.49           N
ATOM   2381  CA  THR A 346      44.844  56.913  11.868  1.00 75.71           C
ATOM   2382  CB  THR A 346      43.435  56.275  11.900  1.00 76.42           C
ATOM   2383  OG1 THR A 346      43.554  54.857  12.043  1.00 77.11           O
ATOM   2384  CG2 THR A 346      42.679  56.580  10.600  1.00 76.28           C
ATOM   2385  C   THR A 346      44.683  58.407  12.088  1.00 75.98           C
ATOM   2386  O   THR A 346      44.967  58.919  13.180  1.00 74.62           O
ATOM   2387  N   TYR A 347      44.240  59.107  11.049  1.00 76.36           N
ATOM   2388  CA  TYR A 347      44.037  60.536  11.164  1.00 75.88           C
ATOM   2389  CB  TYR A 347      43.359  61.089   9.911  1.00 76.62           C
ATOM   2390  CG  TYR A 347      42.736  62.441  10.140  1.00 77.96           C
ATOM   2391  CD1 TYR A 347      41.461  62.557  10.673  1.00 78.51           C
ATOM   2392  CE1 TYR A 347      40.917  63.792  10.957  1.00 80.67           C
ATOM   2393  CD2 TYR A 347      43.448  63.604   9.887  1.00 79.53           C
ATOM   2394  CE2 TYR A 347      42.913  64.848  10.165  1.00 80.20           C
ATOM   2395  CZ  TYR A 347      41.646  64.938  10.705  1.00 80.88           C
ATOM   2396  OH  TYR A 347      41.109  66.168  11.027  1.00 80.64           O
ATOM   2397  C   TYR A 347      43.176  60.830  12.383  1.00 75.59           C
ATOM   2398  O   TYR A 347      43.433  61.783  13.114  1.00 76.81           O
ATOM   2399  N   ASP A 348      42.160  60.005  12.618  1.00 74.64           N
ATOM   2400  CA  ASP A 348      41.276  60.253  13.746  1.00 72.66           C
ATOM   2401  CB  ASP A 348      39.843  59.854  13.402  1.00 73.57           C
ATOM   2402  CG  ASP A 348      38.845  60.410  14.392  1.00 76.24           C
ATOM   2403  OD1 ASP A 348      38.478  59.689  15.352  1.00 76.99           O
ATOM   2404  OD2 ASP A 348      38.447  61.586  14.217  1.00 77.98           O
ATOM   2405  C   ASP A 348      41.693  59.598  15.046  1.00 70.14           C
ATOM   2406  O   ASP A 348      41.200  59.958  16.107  1.00 69.67           O
ATOM   2407  N   THR A 349      42.601  58.640  14.982  1.00 68.76           N
ATOM   2408  CA  THR A 349      43.035  58.000  16.211  1.00 68.13           C
ATOM   2409  CB  THR A 349      43.954  56.808  15.935  1.00 67.18           C
ATOM   2410  OG1 THR A 349      43.492  56.102  14.780  1.00 66.85           O
ATOM   2411  CG2 THR A 349      43.949  55.871  17.119  1.00 65.71           C
ATOM   2412  C   THR A 349      43.828  59.032  17.005  1.00 68.43           C
ATOM   2413  O   THR A 349      43.935  58.966  18.235  1.00 68.06           O
ATOM   2414  N   VAL A 350      44.371  60.002  16.283  1.00 68.40           N
ATOM   2415  CA  VAL A 350      45.178  61.042  16.893  1.00 68.67           C
ATOM   2416  CB  VAL A 350      46.109  61.656  15.847  1.00 68.70           C
ATOM   2417  CG1 VAL A 350      47.039  62.669  16.500  1.00 68.84           C
ATOM   2418  CG2 VAL A 350      46.896  60.555  15.166  1.00 68.23           C
ATOM   2419  C   VAL A 350      44.393  62.158  17.590  1.00 69.08           C
ATOM   2420  O   VAL A 350      44.760  62.574  18.693  1.00 68.89           O
ATOM   2421  N   LEU A 351      43.333  62.651  16.951  1.00 68.54           N
ATOM   2422  CA  LEU A 351      42.518  63.707  17.544  1.00 68.43           C
ATOM   2423  CB  LEU A 351      41.369  64.067  16.603  1.00 69.02           C
ATOM   2424  CG  LEU A 351      41.908  64.526  15.250  1.00 69.80           C
ATOM   2425  CD1 LEU A 351      40.898  65.424  14.528  1.00 69.43           C
ATOM   2426  CD2 LEU A 351      43.203  65.278  15.505  1.00 69.09           C
ATOM   2427  C   LEU A 351      41.972  63.264  18.906  1.00 68.48           C
ATOM   2428  O   LEU A 351      41.852  64.064  19.843  1.00 66.82           O
ATOM   2429  N   GLN A 352      41.652  61.980  19.009  1.00 68.75           N
ATOM   2430  CA  GLN A 352      41.144  61.417  20.251  1.00 69.37           C
ATOM   2431  CB  GLN A 352      40.309  60.172  19.950  1.00 69.79           C
ATOM   2432  CG  GLN A 352      39.427  59.748  21.111  1.00 74.42           C
ATOM   2433  CD  GLN A 352      39.711  58.339  21.605  1.00 76.38           C
ATOM   2434  OE1 GLN A 352      39.795  57.397  20.813  1.00 76.80           O
ATOM   2435  NE2 GLN A 352      39.841  58.185  22.926  1.00 77.71           N
ATOM   2436  C   GLN A 352      42.322  61.042  21.162  1.00 68.50           C
ATOM   2437  O   GLN A 352      42.624  59.859  21.327  1.00 69.74           O
ATOM   2438  N   MET A 353      42.985  62.038  21.744  1.00 65.41           N
ATOM   2439  CA  MET A 353      44.130  61.786  22.617  1.00 64.35           C
ATOM   2440  CB  MET A 353      45.373  61.458  21.784  1.00 63.82           C
ATOM   2441  CG  MET A 353      45.918  60.059  22.006  1.00 63.67           C
ATOM   2442  SD  MET A 353      46.071  59.086  20.475  1.00 65.42           S
ATOM   2443  CE  MET A 353      47.578  58.166  20.790  1.00 62.05           C
ATOM   2444  C   MET A 353      44.400  63.011  23.476  1.00 64.30           C
ATOM   2445  O   MET A 353      45.347  63.763  23.229  1.00 65.29           O
ATOM   2446  N   GLU A 354      43.563  63.197  24.493  1.00 63.21           N
ATOM   2447  CA  GLU A 354      43.660  64.340  25.396  1.00 60.99           C
ATOM   2448  CB  GLU A 354      42.700  64.162  26.582  1.00 64.02           C
ATOM   2449  CG  GLU A 354      42.122  65.474  27.141  1.00 66.98           C
ATOM   2450  CD  GLU A 354      41.738  65.374  28.616  1.00 68.25           C
ATOM   2451  OE1 GLU A 354      41.562  64.234  29.102  1.00 68.69           O
ATOM   2452  OE2 GLU A 354      41.609  66.431  29.283  1.00 67.15           O
ATOM   2453  C   GLU A 354      45.072  64.566  25.916  1.00 57.57           C
ATOM   2454  O   GLU A 354      45.615  65.663  25.770  1.00 56.02           O
ATOM   2455  N   TYR A 355      45.660  63.529  26.518  1.00 54.20           N
```

```
ATOM   2456  CA   TYR A 355      47.008  63.638  27.072  1.00 51.79           C
ATOM   2457  CB   TYR A 355      47.443  62.348  27.766  1.00 46.63           C
ATOM   2458  CG   TYR A 355      48.366  62.636  28.924  1.00 41.89           C
ATOM   2459  CD1  TYR A 355      49.534  61.919  29.123  1.00 41.23           C
ATOM   2460  CE1  TYR A 355      50.376  62.215  30.197  1.00 41.74           C
ATOM   2461  CD2  TYR A 355      48.060  63.648  29.816  1.00 39.80           C
ATOM   2462  CE2  TYR A 355      48.878  63.951  30.877  1.00 39.15           C
ATOM   2463  CZ   TYR A 355      50.034  63.245  31.074  1.00 39.81           C
ATOM   2464  OH   TYR A 355      50.844  63.615  32.131  1.00 36.62           O
ATOM   2465  C    TYR A 355      48.071  64.015  26.045  1.00 52.45           C
ATOM   2466  O    TYR A 355      48.880  64.911  26.293  1.00 53.72           O
ATOM   2467  N    LEU A 356      48.088  63.327  24.907  1.00 51.88           N
ATOM   2468  CA   LEU A 356      49.059  63.639  23.870  1.00 52.62           C
ATOM   2469  CB   LEU A 356      48.793  62.801  22.626  1.00 51.42           C
ATOM   2470  CG   LEU A 356      49.758  63.092  21.484  1.00 48.92           C
ATOM   2471  CD1  LEU A 356      51.186  62.920  21.983  1.00 49.44           C
ATOM   2472  CD2  LEU A 356      49.474  62.158  20.326  1.00 48.85           C
ATOM   2473  C    LEU A 356      48.981  65.120  23.500  1.00 54.05           C
ATOM   2474  O    LEU A 356      49.994  65.782  23.292  1.00 54.83           O
ATOM   2475  N    ASP A 357      47.768  65.642  23.427  1.00 54.59           N
ATOM   2476  CA   ASP A 357      47.597  67.027  23.078  1.00 55.54           C
ATOM   2477  CB   ASP A 357      46.129  67.286  22.757  1.00 57.57           C
ATOM   2478  CG   ASP A 357      45.916  68.594  22.028  1.00 59.66           C
ATOM   2479  OD1  ASP A 357      45.840  69.646  22.699  1.00 62.81           O
ATOM   2480  OD2  ASP A 357      45.838  68.574  20.781  1.00 59.59           O
ATOM   2481  C    ASP A 357      48.078  67.919  24.217  1.00 56.46           C
ATOM   2482  O    ASP A 357      48.537  69.038  23.993  1.00 58.29           O
ATOM   2483  N    MET A 358      47.989  67.422  25.445  1.00 56.75           N
ATOM   2484  CA   MET A 358      48.413  68.206  26.606  1.00 56.27           C
ATOM   2485  CB   MET A 358      47.878  67.580  27.902  1.00 58.45           C
ATOM   2486  CG   MET A 358      46.389  67.820  28.177  1.00 59.93           C
ATOM   2487  SD   MET A 358      45.820  66.961  29.662  1.00 60.48           S
ATOM   2488  CE   MET A 358      45.067  65.520  28.946  1.00 57.43           C
ATOM   2489  C    MET A 358      49.926  68.320  26.700  1.00 54.63           C
ATOM   2490  O    MET A 358      50.462  69.386  27.023  1.00 53.23           O
ATOM   2491  N    VAL A 359      50.599  67.207  26.425  1.00 52.98           N
ATOM   2492  CA   VAL A 359      52.055  67.137  26.472  1.00 51.71           C
ATOM   2493  CB   VAL A 359      52.538  65.702  26.289  1.00 51.16           C
ATOM   2494  CG1  VAL A 359      54.017  65.697  26.023  1.00 50.79           C
ATOM   2495  CG2  VAL A 359      52.215  64.880  27.540  1.00 51.03           C
ATOM   2496  C    VAL A 359      52.667  67.993  25.383  1.00 51.24           C
ATOM   2497  O    VAL A 359      53.632  68.719  25.608  1.00 51.39           O
ATOM   2498  N    VAL A 360      52.095  67.904  24.193  1.00 50.43           N
ATOM   2499  CA   VAL A 360      52.579  68.689  23.078  1.00 48.44           C
ATOM   2500  CB   VAL A 360      51.796  68.383  21.790  1.00 46.47           C
ATOM   2501  CG1  VAL A 360      52.005  69.507  20.798  1.00 46.34           C
ATOM   2502  CG2  VAL A 360      52.247  67.059  21.203  1.00 43.56           C
ATOM   2503  C    VAL A 360      52.452  70.180  23.366  1.00 48.48           C
ATOM   2504  O    VAL A 360      53.429  70.920  23.242  1.00 49.95           O
ATOM   2505  N    ASN A 361      51.259  70.608  23.772  1.00 47.19           N
ATOM   2506  CA   ASN A 361      50.996  72.019  24.030  1.00 47.97           C
ATOM   2507  CB   ASN A 361      49.513  72.233  24.293  1.00 49.32           C
ATOM   2508  CG   ASN A 361      48.674  72.020  23.049  1.00 53.93           C
ATOM   2509  OD1  ASN A 361      49.172  72.134  21.920  1.00 57.55           O
ATOM   2510  ND2  ASN A 361      47.392  71.724  23.239  1.00 55.11           N
ATOM   2511  C    ASN A 361      51.800  72.655  25.136  1.00 47.35           C
ATOM   2512  O    ASN A 361      52.247  73.800  25.022  1.00 44.50           O
ATOM   2513  N    GLU A 362      51.971  71.908  26.215  1.00 49.85           N
ATOM   2514  CA   GLU A 362      52.724  72.382  27.369  1.00 50.16           C
ATOM   2515  CB   GLU A 362      52.499  71.418  28.550  1.00 51.02           C
ATOM   2516  CG   GLU A 362      53.414  71.596  29.767  1.00 53.76           C
ATOM   2517  CD   GLU A 362      53.209  72.918  30.504  1.00 55.83           C
ATOM   2518  OE1  GLU A 362      53.923  73.158  31.514  1.00 55.23           O
ATOM   2519  OE2  GLU A 362      52.339  73.714  30.070  1.00 55.33           O
ATOM   2520  C    GLU A 362      54.199  72.470  26.974  1.00 49.24           C
ATOM   2521  O    GLU A 362      54.942  73.277  27.520  1.00 49.02           O
ATOM   2522  N    THR A 363      54.622  71.643  26.020  1.00 49.04           N
ATOM   2523  CA   THR A 363      56.001  71.697  25.572  1.00 48.86           C
ATOM   2524  CB   THR A 363      56.371  70.502  24.706  1.00 48.47           C
ATOM   2525  OG1  THR A 363      56.527  69.347  25.537  1.00 50.26           O
ATOM   2526  CG2  THR A 363      57.677  70.762  23.988  1.00 48.33           C
ATOM   2527  C    THR A 363      56.150  72.967  24.759  1.00 49.77           C
ATOM   2528  O    THR A 363      57.095  73.733  24.943  1.00 51.19           O
ATOM   2529  N    LEU A 364      55.199  73.207  23.865  1.00 49.15           N
ATOM   2530  CA   LEU A 364      55.232  74.408  23.050  1.00 48.83           C
ATOM   2531  CB   LEU A 364      54.104  74.396  22.027  1.00 49.50           C
ATOM   2532  CG   LEU A 364      54.123  73.295  20.971  1.00 51.97           C
```

```
ATOM   2533  CD1 LEU A 364      52.997  73.553  19.976  1.00 51.90           C
ATOM   2534  CD2 LEU A 364      55.489  73.278  20.262  1.00 52.41           C
ATOM   2535  C   LEU A 364      55.077  75.651  23.907  1.00 49.56           C
ATOM   2536  O   LEU A 364      55.378  76.748  23.455  1.00 51.59           O
ATOM   2537  N   ARG A 365      54.576  75.504  25.130  1.00 49.12           N
ATOM   2538  CA  ARG A 365      54.411  76.680  25.980  1.00 47.66           C
ATOM   2539  CB  ARG A 365      53.590  76.364  27.233  1.00 45.87           C
ATOM   2540  CG  ARG A 365      53.299  77.601  28.106  1.00 41.58           C
ATOM   2541  CD  ARG A 365      52.686  77.202  29.424  1.00 37.11           C
ATOM   2542  NE  ARG A 365      53.590  76.363  30.202  1.00 38.13           N
ATOM   2543  CZ  ARG A 365      54.404  76.811  31.160  1.00 40.81           C
ATOM   2544  NH1 ARG A 365      54.431  78.107  31.477  1.00 38.20           N
ATOM   2545  NH2 ARG A 365      55.208  75.962  31.799  1.00 39.79           N
ATOM   2546  C   ARG A 365      55.788  77.140  26.401  1.00 47.96           C
ATOM   2547  O   ARG A 365      56.191  78.272  26.136  1.00 49.46           O
ATOM   2548  N   LEU A 366      56.502  76.251  27.068  1.00 47.15           N
ATOM   2549  CA  LEU A 366      57.838  76.552  27.526  1.00 48.63           C
ATOM   2550  CB  LEU A 366      58.440  75.335  28.243  1.00 49.78           C
ATOM   2551  CG  LEU A 366      57.734  74.755  29.476  1.00 48.57           C
ATOM   2552  CD1 LEU A 366      58.359  73.423  29.848  1.00 46.25           C
ATOM   2553  CD2 LEU A 366      57.840  75.727  30.624  1.00 48.66           C
ATOM   2554  C   LEU A 366      58.741  76.936  26.353  1.00 48.65           C
ATOM   2555  O   LEU A 366      59.475  77.908  26.433  1.00 49.74           O
ATOM   2556  N   PHE A 367      58.667  76.180  25.262  1.00 48.31           N
ATOM   2557  CA  PHE A 367      59.523  76.411  24.094  1.00 46.38           C
ATOM   2558  CB  PHE A 367      60.322  75.146  23.791  1.00 48.17           C
ATOM   2559  CG  PHE A 367      61.117  74.651  24.948  1.00 52.20           C
ATOM   2560  CD1 PHE A 367      61.189  73.296  25.224  1.00 53.73           C
ATOM   2561  CD2 PHE A 367      61.800  75.535  25.759  1.00 52.17           C
ATOM   2562  CE1 PHE A 367      61.928  72.834  26.286  1.00 53.81           C
ATOM   2563  CE2 PHE A 367      62.540  75.078  26.818  1.00 53.56           C
ATOM   2564  CZ  PHE A 367      62.605  73.725  27.082  1.00 53.85           C
ATOM   2565  C   PHE A 367      58.856  76.864  22.798  1.00 43.90           C
ATOM   2566  O   PHE A 367      58.714  76.097  21.852  1.00 42.06           O
ATOM   2567  N   PRO A 368      58.436  78.116  22.738  1.00 42.12           N
ATOM   2568  CD  PRO A 368      58.229  79.082  23.827  1.00 41.26           C
ATOM   2569  CA  PRO A 368      57.809  78.557  21.494  1.00 42.32           C
ATOM   2570  CB  PRO A 368      56.973  79.744  21.944  1.00 42.71           C
ATOM   2571  CG  PRO A 368      57.784  80.312  23.080  1.00 42.45           C
ATOM   2572  C   PRO A 368      58.911  78.937  20.494  1.00 43.68           C
ATOM   2573  O   PRO A 368      59.444  80.052  20.535  1.00 44.00           O
ATOM   2574  N   ILE A 369      59.249  77.997  19.613  1.00 43.48           N
ATOM   2575  CA  ILE A 369      60.291  78.159  18.589  1.00 42.49           C
ATOM   2576  CB  ILE A 369      60.051  77.189  17.415  1.00 43.36           C
ATOM   2577  CG2 ILE A 369      61.034  77.462  16.285  1.00 45.63           C
ATOM   2578  CG1 ILE A 369      60.238  75.769  17.918  1.00 43.35           C
ATOM   2579  CD1 ILE A 369      61.263  75.708  19.034  1.00 45.04           C
ATOM   2580  C   ILE A 369      60.534  79.556  18.011  1.00 41.09           C
ATOM   2581  O   ILE A 369      61.682  80.001  17.933  1.00 38.97           O
ATOM   2582  N   ALA A 370      59.462  80.223  17.584  1.00 39.82           N
ATOM   2583  CA  ALA A 370      59.550  81.575  17.030  1.00 40.59           C
ATOM   2584  CB  ALA A 370      58.394  81.820  16.065  1.00 37.17           C
ATOM   2585  C   ALA A 370      59.504  82.598  18.169  1.00 41.91           C
ATOM   2586  O   ALA A 370      58.652  83.472  18.182  1.00 44.16           O
ATOM   2587  N   MET A 371      60.415  82.471  19.121  1.00 42.45           N
ATOM   2588  CA  MET A 371      60.495  83.352  20.279  1.00 43.26           C
ATOM   2589  CB  MET A 371      61.946  83.740  20.484  1.00 44.84           C
ATOM   2590  CG  MET A 371      62.848  82.527  20.469  1.00 49.55           C
ATOM   2591  SD  MET A 371      64.356  82.763  19.496  1.00 56.48           S
ATOM   2592  CE  MET A 371      63.667  83.426  17.970  1.00 54.40           C
ATOM   2593  C   MET A 371      59.615  84.603  20.276  1.00 42.90           C
ATOM   2594  O   MET A 371      58.937  84.894  21.259  1.00 44.24           O
ATOM   2595  N   ARG A 372      59.628  85.349  19.182  1.00 42.43           N
ATOM   2596  CA  ARG A 372      58.827  86.560  19.081  1.00 41.07           C
ATOM   2597  CB  ARG A 372      59.721  87.774  18.818  1.00 41.15           C
ATOM   2598  CG  ARG A 372      60.859  87.972  19.801  1.00 42.45           C
ATOM   2599  CD  ARG A 372      61.718  89.147  19.380  1.00 45.61           C
ATOM   2600  NE  ARG A 372      62.722  89.511  20.380  1.00 49.29           N
ATOM   2601  CZ  ARG A 372      63.500  90.589  20.287  1.00 51.35           C
ATOM   2602  NH1 ARG A 372      64.393  90.867  21.228  1.00 49.71           N
ATOM   2603  NH2 ARG A 372      63.383  91.392  19.237  1.00 53.81           N
ATOM   2604  C   ARG A 372      57.822  86.454  17.944  1.00 41.37           C
ATOM   2605  O   ARG A 372      57.863  85.547  17.129  1.00 41.92           O
ATOM   2606  N   LEU A 373      56.932  87.422  17.876  1.00 42.25           N
ATOM   2607  CA  LEU A 373      55.917  87.462  16.851  1.00 41.63           C
ATOM   2608  CB  LEU A 373      54.599  87.027  17.458  1.00 42.99           C
ATOM   2609  CG  LEU A 373      53.651  86.109  16.699  1.00 46.09           C
```

```
ATOM   2610  CD1 LEU A 373      54.300  84.715  16.500  1.00 46.74           C
ATOM   2611  CD2 LEU A 373      52.348  86.007  17.504  1.00 44.80           C
ATOM   2612  C   LEU A 373      55.868  88.937  16.528  1.00 42.90           C
ATOM   2613  O   LEU A 373      55.596  89.745  17.409  1.00 44.38           O
ATOM   2614  N   GLU A 374      56.143  89.324  15.296  1.00 44.47           N
ATOM   2615  CA  GLU A 374      56.097  90.743  15.019  1.00 47.56           C
ATOM   2616  CB  GLU A 374      57.498  91.332  15.046  1.00 51.61           C
ATOM   2617  CG  GLU A 374      58.200  91.275  13.721  1.00 60.48           C
ATOM   2618  CD  GLU A 374      59.430  90.423  13.787  1.00 65.98           C
ATOM   2619  OE1 GLU A 374      60.180  90.584  14.782  1.00 68.28           O
ATOM   2620  OE2 GLU A 374      59.639  89.605  12.851  1.00 68.36           O
ATOM   2621  C   GLU A 374      55.423  91.093  13.714  1.00 47.14           C
ATOM   2622  O   GLU A 374      55.369  90.293  12.794  1.00 46.71           O
ATOM   2623  N   ARG A 375      54.909  92.313  13.654  1.00 48.66           N
ATOM   2624  CA  ARG A 375      54.212  92.808  12.481  1.00 50.61           C
ATOM   2625  CB  ARG A 375      52.702  92.762  12.742  1.00 49.51           C
ATOM   2626  CG  ARG A 375      51.827  92.399  11.530  1.00 54.07           C
ATOM   2627  CD  ARG A 375      51.246  90.981  11.630  1.00 53.39           C
ATOM   2628  NE  ARG A 375      52.311  89.986  11.682  1.00 55.71           N
ATOM   2629  CZ  ARG A 375      52.166  88.751  12.145  1.00 56.03           C
ATOM   2630  NH1 ARG A 375      53.196  87.923  12.150  1.00 55.92           N
ATOM   2631  NH2 ARG A 375      50.998  88.347  12.613  1.00 55.79           N
ATOM   2632  C   ARG A 375      54.687  94.247  12.272  1.00 52.03           C
ATOM   2633  O   ARG A 375      55.147  94.903  13.213  1.00 52.66           O
ATOM   2634  N   VAL A 376      54.600  94.739  11.046  1.00 53.73           N
ATOM   2635  CA  VAL A 376      55.033  96.103  10.781  1.00 55.90           C
ATOM   2636  CB  VAL A 376      55.876  96.192   9.501  1.00 53.71           C
ATOM   2637  CG1 VAL A 376      55.499  97.426   8.725  1.00 50.59           C
ATOM   2638  CG2 VAL A 376      57.344  96.232   9.863  1.00 51.01           C
ATOM   2639  C   VAL A 376      53.858  97.057  10.653  1.00 58.89           C
ATOM   2640  O   VAL A 376      52.858  96.745   9.992  1.00 59.07           O
ATOM   2641  N   CYS A 377      53.996  98.221  11.293  1.00 61.49           N
ATOM   2642  CA  CYS A 377      52.973  99.264  11.283  1.00 63.65           C
ATOM   2643  CB  CYS A 377      53.181 100.198  12.466  1.00 62.78           C
ATOM   2644  SG  CYS A 377      51.882 101.397  12.612  1.00 63.56           S
ATOM   2645  C   CYS A 377      53.007 100.060   9.975  1.00 65.73           C
ATOM   2646  O   CYS A 377      53.804 100.985   9.800  1.00 65.87           O
ATOM   2647  N   LYS A 378      52.118  99.684   9.066  1.00 68.03           N
ATOM   2648  CA  LYS A 378      52.021 100.283   7.744  1.00 71.12           C
ATOM   2649  CB  LYS A 378      50.936  99.546   6.968  1.00 72.02           C
ATOM   2650  CG  LYS A 378      51.075  99.602   5.479  1.00 75.25           C
ATOM   2651  CD  LYS A 378      50.761  98.235   4.877  1.00 77.55           C
ATOM   2652  CE  LYS A 378      49.441  97.679   5.400  1.00 77.79           C
ATOM   2653  NZ  LYS A 378      48.945  96.567   4.535  1.00 78.60           N
ATOM   2654  C   LYS A 378      51.742 101.783   7.710  1.00 73.11           C
ATOM   2655  O   LYS A 378      52.267 102.497   6.848  1.00 72.98           O
ATOM   2656  N   LYS A 379      50.916 102.249   8.649  1.00 75.56           N
ATOM   2657  CA  LYS A 379      50.512 103.657   8.736  1.00 76.26           C
ATOM   2658  CB  LYS A 379      49.158 103.842   8.054  1.00 78.12           C
ATOM   2659  CG  LYS A 379      48.118 102.831   8.533  1.00 79.98           C
ATOM   2660  CD  LYS A 379      46.691 103.272   8.237  1.00 83.06           C
ATOM   2661  CE  LYS A 379      46.446 103.493   6.746  1.00 85.07           C
ATOM   2662  NZ  LYS A 379      45.035 103.925   6.472  1.00 85.07           N
ATOM   2663  C   LYS A 379      50.377 104.102  10.179  1.00 75.73           C
ATOM   2664  O   LYS A 379      50.415 103.280  11.090  1.00 74.94           O
ATOM   2665  N   ASP A 380      50.204 105.407  10.381  1.00 76.27           N
ATOM   2666  CA  ASP A 380      50.039 105.953  11.727  1.00 76.99           C
ATOM   2667  CB  ASP A 380      50.192 107.483  11.717  1.00 76.01           C
ATOM   2668  CG  ASP A 380      51.512 107.953  12.338  1.00 75.67           C
ATOM   2669  OD1 ASP A 380      52.441 108.349  11.598  1.00 72.60           O
ATOM   2670  OD2 ASP A 380      51.618 107.921  13.580  1.00 75.78           O
ATOM   2671  C   ASP A 380      48.654 105.552  12.231  1.00 76.92           C
ATOM   2672  O   ASP A 380      47.657 105.752  11.542  1.00 75.53           O
ATOM   2673  N   VAL A 381      48.603 104.974  13.428  1.00 78.62           N
ATOM   2674  CA  VAL A 381      47.345 104.513  14.014  1.00 81.82           C
ATOM   2675  CB  VAL A 381      46.952 103.156  13.400  1.00 81.74           C
ATOM   2676  CG1 VAL A 381      46.400 102.237  14.465  1.00 81.48           C
ATOM   2677  CG2 VAL A 381      45.925 103.373  12.291  1.00 82.58           C
ATOM   2678  C   VAL A 381      47.425 104.392  15.543  1.00 84.15           C
ATOM   2679  O   VAL A 381      48.498 104.135  16.088  1.00 85.59           O
ATOM   2680  N   GLU A 382      46.300 104.570  16.239  1.00 86.19           N
ATOM   2681  CA  GLU A 382      46.315 104.509  17.703  1.00 88.95           C
ATOM   2682  CB  GLU A 382      45.383 105.571  18.298  1.00 91.37           C
ATOM   2683  CG  GLU A 382      45.588 105.797  19.798  1.00 93.71           C
ATOM   2684  CD  GLU A 382      44.799 106.981  20.328  1.00 95.20           C
ATOM   2685  OE1 GLU A 382      44.933 107.290  21.535  1.00 95.57           O
ATOM   2686  OE2 GLU A 382      44.047 107.600  19.539  1.00 95.01           O
```

```
ATOM   2687  C    GLU A 382      46.004 103.147  18.321  1.00 89.52           C
ATOM   2688  O    GLU A 382      46.865 102.569  18.980  1.00 90.79           O
ATOM   2689  N    ILE A 383      44.784 102.643  18.152  1.00 89.18           N
ATOM   2690  CA   ILE A 383      44.447 101.326  18.696  1.00 90.01           C
ATOM   2691  CB   ILE A 383      45.416 100.270  18.126  1.00 89.76           C
ATOM   2692  CG2  ILE A 383      45.524  99.081  19.048  1.00 91.30           C
ATOM   2693  CG1  ILE A 383      44.941  99.837  16.750  1.00 90.40           C
ATOM   2694  CD1  ILE A 383      45.903  98.926  16.056  1.00 91.62           C
ATOM   2695  C    ILE A 383      44.432 101.208  20.231  1.00 90.87           C
ATOM   2696  O    ILE A 383      45.482 101.275  20.888  1.00 91.45           O
ATOM   2697  N    ASN A 384      43.236 101.008  20.791  1.00 90.57           N
ATOM   2698  CA   ASN A 384      43.046 100.871  22.240  1.00 89.24           C
ATOM   2699  CB   ASN A 384      43.577  99.524  22.730  1.00 89.28           C
ATOM   2700  CG   ASN A 384      42.792  98.358  22.189  1.00 90.60           C
ATOM   2701  OD1  ASN A 384      43.051  97.206  22.536  1.00 90.92           O
ATOM   2702  ND2  ASN A 384      41.824  98.648  21.329  1.00 91.49           N
ATOM   2703  C    ASN A 384      43.746 101.965  23.024  1.00 88.32           C
ATOM   2704  O    ASN A 384      44.198 101.726  24.141  1.00 88.50           O
ATOM   2705  N    GLY A 385      43.827 103.162  22.457  1.00 87.09           N
ATOM   2706  CA   GLY A 385      44.519 104.232  23.144  1.00 86.63           C
ATOM   2707  C    GLY A 385      45.968 103.806  23.315  1.00 86.77           C
ATOM   2708  O    GLY A 385      46.292 103.026  24.217  1.00 86.88           O
ATOM   2709  N    MET A 386      46.842 104.307  22.444  1.00 85.72           N
ATOM   2710  CA   MET A 386      48.261 103.956  22.490  1.00 83.55           C
ATOM   2711  CB   MET A 386      48.433 102.462  22.172  1.00 83.19           C
ATOM   2712  CG   MET A 386      49.869 102.009  21.888  1.00 84.53           C
ATOM   2713  SD   MET A 386      50.978 101.841  23.323  1.00 84.48           S
ATOM   2714  CE   MET A 386      51.653 103.490  23.407  1.00 85.10           C
ATOM   2715  C    MET A 386      49.043 104.793  21.481  1.00 82.03           C
ATOM   2716  O    MET A 386      50.039 105.445  21.823  1.00 83.08           O
ATOM   2717  N    PHE A 387      48.564 104.775  20.240  1.00 79.43           N
ATOM   2718  CA   PHE A 387      49.183 105.486  19.122  1.00 75.72           C
ATOM   2719  CB   PHE A 387      49.223 106.999  19.342  1.00 73.93           C
ATOM   2720  CG   PHE A 387      50.037 107.726  18.302  1.00 71.75           C
ATOM   2721  CD1  PHE A 387      51.350 108.117  18.562  1.00 71.07           C
ATOM   2722  CD2  PHE A 387      49.515 107.948  17.038  1.00 69.86           C
ATOM   2723  CE1  PHE A 387      52.125 108.713  17.573  1.00 70.13           C
ATOM   2724  CE2  PHE A 387      50.276 108.536  16.054  1.00 69.08           C
ATOM   2725  CZ   PHE A 387      51.586 108.921  16.318  1.00 69.97           C
ATOM   2726  C    PHE A 387      50.597 105.024  18.808  1.00 74.33           C
ATOM   2727  O    PHE A 387      51.555 105.312  19.549  1.00 75.09           O
ATOM   2728  N    ILE A 388      50.713 104.305  17.698  1.00 70.36           N
ATOM   2729  CA   ILE A 388      51.987 103.816  17.221  1.00 67.06           C
ATOM   2730  CB   ILE A 388      51.960 102.291  17.045  1.00 67.89           C
ATOM   2731  CG2  ILE A 388      53.324 101.795  16.599  1.00 70.80           C
ATOM   2732  CG1  ILE A 388      51.570 101.617  18.361  1.00 67.84           C
ATOM   2733  CD1  ILE A 388      50.091 101.369  18.504  1.00 67.15           C
ATOM   2734  C    ILE A 388      52.175 104.499  15.867  1.00 64.54           C
ATOM   2735  O    ILE A 388      51.227 104.625  15.092  1.00 63.26           O
ATOM   2736  N    PRO A 389      53.393 104.971  15.571  1.00 62.70           N
ATOM   2737  CD   PRO A 389      54.554 105.204  16.448  1.00 61.40           C
ATOM   2738  CA   PRO A 389      53.577 105.630  14.277  1.00 62.56           C
ATOM   2739  CB   PRO A 389      54.637 106.680  14.589  1.00 60.66           C
ATOM   2740  CG   PRO A 389      55.521 105.950  15.535  1.00 60.84           C
ATOM   2741  C    PRO A 389      53.998 104.699  13.137  1.00 62.71           C
ATOM   2742  O    PRO A 389      54.394 103.556  13.358  1.00 62.39           O
ATOM   2743  N    LYS A 390      53.903 105.212  11.918  1.00 62.60           N
ATOM   2744  CA   LYS A 390      54.282 104.473  10.730  1.00 62.08           C
ATOM   2745  CB   LYS A 390      54.154 105.369   9.505  1.00 62.82           C
ATOM   2746  CG   LYS A 390      54.545 104.714   8.206  1.00 63.61           C
ATOM   2747  CD   LYS A 390      53.944 105.488   7.058  1.00 65.62           C
ATOM   2748  CE   LYS A 390      54.194 104.805   5.724  1.00 69.00           C
ATOM   2749  NZ   LYS A 390      55.225 105.538   4.923  1.00 69.85           N
ATOM   2750  C    LYS A 390      55.714 103.977  10.831  1.00 62.17           C
ATOM   2751  O    LYS A 390      56.575 104.639  11.414  1.00 61.58           O
ATOM   2752  N    GLY A 391      55.953 102.796  10.265  1.00 61.91           N
ATOM   2753  CA   GLY A 391      57.284 102.221  10.260  1.00 60.72           C
ATOM   2754  C    GLY A 391      57.785 101.589  11.538  1.00 59.73           C
ATOM   2755  O    GLY A 391      58.921 101.131  11.584  1.00 61.11           O
ATOM   2756  N    VAL A 392      56.967 101.552  12.578  1.00 58.18           N
ATOM   2757  CA   VAL A 392      57.410 100.948  13.823  1.00 57.34           C
ATOM   2758  CB   VAL A 392      56.720 101.607  15.034  1.00 57.76           C
ATOM   2759  CG1  VAL A 392      57.136 100.914  16.326  1.00 57.84           C
ATOM   2760  CG2  VAL A 392      57.090 103.070  15.091  1.00 56.99           C
ATOM   2761  C    VAL A 392      57.108  99.454  13.808  1.00 56.97           C
ATOM   2762  O    VAL A 392      56.036  99.034  13.374  1.00 58.58           O
ATOM   2763  N    VAL A 393      58.062  98.651  14.262  1.00 55.91           N
```

```
ATOM   2764  CA   VAL A 393      57.881  97.204  14.300  1.00 55.56           C
ATOM   2765  CB   VAL A 393      59.241  96.461  14.143  1.00 55.56           C
ATOM   2766  CG1  VAL A 393      59.126  95.026  14.628  1.00 54.31           C
ATOM   2767  CG2  VAL A 393      59.665  96.475  12.687  1.00 54.58           C
ATOM   2768  C    VAL A 393      57.226  96.808  15.617  1.00 55.73           C
ATOM   2769  O    VAL A 393      57.784  97.034  16.701  1.00 55.41           O
ATOM   2770  N    VAL A 394      56.037  96.218  15.519  1.00 54.55           N
ATOM   2771  CA   VAL A 394      55.295  95.808  16.706  1.00 53.66           C
ATOM   2772  CB   VAL A 394      53.763  95.949  16.458  1.00 53.53           C
ATOM   2773  CG1  VAL A 394      52.977  95.630  17.730  1.00 54.16           C
ATOM   2774  CG2  VAL A 394      53.452  97.364  16.009  1.00 52.87           C
ATOM   2775  C    VAL A 394      55.649  94.373  17.101  1.00 52.26           C
ATOM   2776  O    VAL A 394      55.309  93.426  16.394  1.00 52.78           O
ATOM   2777  N    MET A 395      56.328  94.222  18.235  1.00 49.93           N
ATOM   2778  CA   MET A 395      56.747  92.905  18.713  1.00 48.51           C
ATOM   2779  CB   MET A 395      58.199  92.986  19.172  1.00 47.79           C
ATOM   2780  CG   MET A 395      58.871  91.652  19.387  1.00 46.71           C
ATOM   2781  SD   MET A 395      58.992  91.211  21.110  1.00 46.77           S
ATOM   2782  CE   MET A 395      60.452  92.110  21.644  1.00 44.60           C
ATOM   2783  C    MET A 395      55.872  92.336  19.843  1.00 48.14           C
ATOM   2784  O    MET A 395      55.356  93.080  20.677  1.00 49.73           O
ATOM   2785  N    ILE A 396      55.727  91.014  19.875  1.00 45.02           N
ATOM   2786  CA   ILE A 396      54.906  90.335  20.874  1.00 41.08           C
ATOM   2787  CB   ILE A 396      53.706  89.732  20.199  1.00 38.68           C
ATOM   2788  CG2  ILE A 396      52.839  89.061  21.194  1.00 39.67           C
ATOM   2789  CG1  ILE A 396      52.957  90.816  19.447  1.00 39.53           C
ATOM   2790  CD1  ILE A 396      51.826  90.280  18.606  1.00 40.69           C
ATOM   2791  C    ILE A 396      55.737  89.215  21.489  1.00 41.44           C
ATOM   2792  O    ILE A 396      55.891  88.155  20.892  1.00 42.73           O
ATOM   2793  N    PRO A 397      56.272  89.431  22.701  1.00 40.86           N
ATOM   2794  CD   PRO A 397      56.026  90.639  23.503  1.00 39.62           C
ATOM   2795  CA   PRO A 397      57.116  88.482  23.444  1.00 41.03           C
ATOM   2796  CB   PRO A 397      57.365  89.196  24.766  1.00 39.62           C
ATOM   2797  CG   PRO A 397      57.208  90.652  24.414  1.00 38.44           C
ATOM   2798  C    PRO A 397      56.502  87.126  23.677  1.00 42.19           C
ATOM   2799  O    PRO A 397      56.116  86.826  24.795  1.00 44.15           O
ATOM   2800  N    SER A 398      56.431  86.287  22.654  1.00 42.01           N
ATOM   2801  CA   SER A 398      55.814  84.994  22.862  1.00 41.94           C
ATOM   2802  CB   SER A 398      55.787  84.181  21.561  1.00 42.84           C
ATOM   2803  OG   SER A 398      54.735  84.617  20.704  1.00 43.01           O
ATOM   2804  C    SER A 398      56.455  84.194  23.983  1.00 41.79           C
ATOM   2805  O    SER A 398      55.755  83.692  24.849  1.00 42.44           O
ATOM   2806  N    TYR A 399      57.774  84.087  24.003  1.00 41.56           N
ATOM   2807  CA   TYR A 399      58.408  83.299  25.057  1.00 42.36           C
ATOM   2808  CB   TYR A 399      59.903  83.138  24.766  1.00 38.72           C
ATOM   2809  CG   TYR A 399      60.714  82.456  25.845  1.00 35.18           C
ATOM   2810  CD1  TYR A 399      61.119  83.149  26.983  1.00 34.04           C
ATOM   2811  CE1  TYR A 399      61.955  82.549  27.931  1.00 34.52           C
ATOM   2812  CD2  TYR A 399      61.152  81.139  25.686  1.00 32.78           C
ATOM   2813  CE2  TYR A 399      61.982  80.526  26.630  1.00 31.00           C
ATOM   2814  CZ   TYR A 399      62.386  81.235  27.748  1.00 34.56           C
ATOM   2815  OH   TYR A 399      63.243  80.659  28.682  1.00 35.74           O
ATOM   2816  C    TYR A 399      58.184  83.879  26.449  1.00 43.31           C
ATOM   2817  O    TYR A 399      57.785  83.158  27.357  1.00 45.03           O
ATOM   2818  N    ALA A 400      58.428  85.174  26.614  1.00 44.85           N
ATOM   2819  CA   ALA A 400      58.241  85.835  27.909  1.00 46.47           C
ATOM   2820  CB   ALA A 400      58.650  87.308  27.809  1.00 46.04           C
ATOM   2821  C    ALA A 400      56.801  85.722  28.446  1.00 47.76           C
ATOM   2822  O    ALA A 400      56.593  85.479  29.639  1.00 46.91           O
ATOM   2823  N    LEU A 401      55.813  85.917  27.571  1.00 48.47           N
ATOM   2824  CA   LEU A 401      54.414  85.811  27.967  1.00 48.18           C
ATOM   2825  CB   LEU A 401      53.488  86.153  26.788  1.00 46.45           C
ATOM   2826  CG   LEU A 401      53.416  87.622  26.331  1.00 46.86           C
ATOM   2827  CD1  LEU A 401      52.738  87.747  24.970  1.00 45.06           C
ATOM   2828  CD2  LEU A 401      52.651  88.435  27.359  1.00 47.84           C
ATOM   2829  C    LEU A 401      54.160  84.382  28.452  1.00 49.32           C
ATOM   2830  O    LEU A 401      53.598  84.183  29.523  1.00 51.40           O
ATOM   2831  N    HIS A 402      54.604  83.395  27.684  1.00 49.24           N
ATOM   2832  CA   HIS A 402      54.429  81.988  28.047  1.00 50.18           C
ATOM   2833  CB   HIS A 402      54.989  81.059  26.951  1.00 49.15           C
ATOM   2834  CG   HIS A 402      54.244  81.105  25.649  1.00 45.71           C
ATOM   2835  CD2  HIS A 402      53.392  82.023  25.134  1.00 43.38           C
ATOM   2836  ND1  HIS A 402      54.350  80.107  24.703  1.00 43.87           N
ATOM   2837  CE1  HIS A 402      53.591  80.408  23.663  1.00 42.23           C
ATOM   2838  NE2  HIS A 402      53.000  81.565  23.899  1.00 40.12           N
ATOM   2839  C    HIS A 402      55.110  81.598  29.366  1.00 51.95           C
ATOM   2840  O    HIS A 402      55.044  80.440  29.777  1.00 51.77           O
```

```
ATOM   2841  N    ARG A 403      55.773  82.538  30.025  1.00 54.94           N
ATOM   2842  CA   ARG A 403      56.467  82.217  31.274  1.00 58.55           C
ATOM   2843  CB   ARG A 403      57.935  81.919  30.976  1.00 58.35           C
ATOM   2844  CG   ARG A 403      58.163  80.612  30.229  1.00 58.47           C
ATOM   2845  CD   ARG A 403      59.443  80.664  29.426  1.00 57.00           C
ATOM   2846  NE   ARG A 403      59.888  79.336  29.029  1.00 56.41           N
ATOM   2847  CZ   ARG A 403      60.467  78.475  29.859  1.00 58.89           C
ATOM   2848  NH1  ARG A 403      60.670  78.809  31.130  1.00 59.02           N
ATOM   2849  NH2  ARG A 403      60.846  77.282  29.422  1.00 59.80           N
ATOM   2850  C    ARG A 403      56.370  83.326  32.312  1.00 61.10           C
ATOM   2851  O    ARG A 403      57.267  83.508  33.132  1.00 60.77           O
ATOM   2852  N    ASP A 404      55.261  84.050  32.269  1.00 64.40           N
ATOM   2853  CA   ASP A 404      55.008  85.158  33.172  1.00 67.53           C
ATOM   2854  CB   ASP A 404      54.475  86.330  32.347  1.00 67.40           C
ATOM   2855  CG   ASP A 404      53.752  87.363  33.184  1.00 68.83           C
ATOM   2856  OD1  ASP A 404      54.196  87.630  34.323  1.00 69.32           O
ATOM   2857  OD2  ASP A 404      52.743  87.920  32.687  1.00 68.89           O
ATOM   2858  C    ASP A 404      54.026  84.779  34.280  1.00 70.96           C
ATOM   2859  O    ASP A 404      52.901  84.355  34.014  1.00 72.09           O
ATOM   2860  N    PRO A 405      54.445  84.926  35.544  1.00 73.28           N
ATOM   2861  CD   PRO A 405      55.798  85.338  35.956  1.00 74.50           C
ATOM   2862  CA   PRO A 405      53.617  84.608  36.711  1.00 75.11           C
ATOM   2863  CB   PRO A 405      54.361  85.294  37.844  1.00 74.74           C
ATOM   2864  CG   PRO A 405      55.795  85.037  37.454  1.00 75.75           C
ATOM   2865  C    PRO A 405      52.163  85.059  36.609  1.00 76.63           C
ATOM   2866  O    PRO A 405      51.267  84.386  37.121  1.00 77.54           O
ATOM   2867  N    LYS A 406      51.926  86.183  35.942  1.00 78.16           N
ATOM   2868  CA   LYS A 406      50.572  86.712  35.798  1.00 80.94           C
ATOM   2869  CB   LYS A 406      50.584  87.943  34.881  1.00 82.28           C
ATOM   2870  CG   LYS A 406      49.280  88.744  34.856  1.00 83.95           C
ATOM   2871  CD   LYS A 406      49.529  90.218  35.186  1.00 86.00           C
ATOM   2872  CE   LYS A 406      48.263  91.075  35.035  1.00 86.68           C
ATOM   2873  NZ   LYS A 406      47.809  91.204  33.615  1.00 86.25           N
ATOM   2874  C    LYS A 406      49.548  85.680  35.295  1.00 82.05           C
ATOM   2875  O    LYS A 406      48.458  85.563  35.871  1.00 82.81           O
ATOM   2876  N    TYR A 407      49.877  84.935  34.239  1.00 81.95           N
ATOM   2877  CA   TYR A 407      48.936  83.936  33.724  1.00 82.45           C
ATOM   2878  CB   TYR A 407      48.751  84.070  32.216  1.00 84.32           C
ATOM   2879  CG   TYR A 407      48.215  85.395  31.750  1.00 88.52           C
ATOM   2880  CD1  TYR A 407      49.079  86.424  31.386  1.00 90.44           C
ATOM   2881  CE1  TYR A 407      48.597  87.636  30.908  1.00 90.96           C
ATOM   2882  CD2  TYR A 407      46.845  85.613  31.632  1.00 89.28           C
ATOM   2883  CE2  TYR A 407      46.352  86.823  31.157  1.00 90.90           C
ATOM   2884  CZ   TYR A 407      47.234  87.828  30.794  1.00 91.43           C
ATOM   2885  OH   TYR A 407      46.757  89.020  30.299  1.00 92.69           O
ATOM   2886  C    TYR A 407      49.322  82.489  34.003  1.00 81.77           C
ATOM   2887  O    TYR A 407      48.538  81.572  33.737  1.00 80.90           O
ATOM   2888  N    TRP A 408      50.523  82.274  34.526  1.00 81.35           N
ATOM   2889  CA   TRP A 408      50.984  80.917  34.787  1.00 81.25           C
ATOM   2890  CB   TRP A 408      52.015  80.509  33.727  1.00 78.47           C
ATOM   2891  CG   TRP A 408      51.618  80.927  32.331  1.00 75.22           C
ATOM   2892  CD2  TRP A 408      50.882  80.152  31.381  1.00 73.82           C
ATOM   2893  CE2  TRP A 408      50.697  80.956  30.236  1.00 73.48           C
ATOM   2894  CE3  TRP A 408      50.361  78.854  31.387  1.00 73.22           C
ATOM   2895  CD1  TRP A 408      51.843  82.141  31.737  1.00 74.20           C
ATOM   2896  NE1  TRP A 408      51.292  82.165  30.480  1.00 72.34           N
ATOM   2897  CZ2  TRP A 408      50.016  80.502  29.109  1.00 73.72           C
ATOM   2898  CZ3  TRP A 408      49.686  78.407  30.271  1.00 73.12           C
ATOM   2899  CH2  TRP A 408      49.520  79.227  29.146  1.00 73.88           C
ATOM   2900  C    TRP A 408      51.581  80.766  36.176  1.00 82.93           C
ATOM   2901  O    TRP A 408      52.413  81.567  36.605  1.00 82.90           O
ATOM   2902  N    THR A 409      51.145  79.729  36.878  1.00 84.47           N
ATOM   2903  CA   THR A 409      51.632  79.475  38.225  1.00 86.09           C
ATOM   2904  CB   THR A 409      50.511  78.888  39.104  1.00 87.06           C
ATOM   2905  OG1  THR A 409      50.271  77.527  38.724  1.00 87.79           O
ATOM   2906  CG2  THR A 409      49.208  79.703  38.924  1.00 87.16           C
ATOM   2907  C    THR A 409      52.782  78.486  38.111  1.00 86.26           C
ATOM   2908  O    THR A 409      52.648  77.457  37.455  1.00 86.44           O
ATOM   2909  N    GLU A 410      53.909  78.791  38.742  1.00 86.98           N
ATOM   2910  CA   GLU A 410      55.061  77.904  38.638  1.00 87.40           C
ATOM   2911  CB   GLU A 410      54.817  76.627  39.431  1.00 89.36           C
ATOM   2912  CG   GLU A 410      55.058  76.786  40.917  1.00 92.64           C
ATOM   2913  CD   GLU A 410      56.047  75.765  41.438  1.00 94.42           C
ATOM   2914  OE1  GLU A 410      55.661  74.581  41.571  1.00 95.45           O
ATOM   2915  OE2  GLU A 410      57.212  76.146  41.694  1.00 94.78           O
ATOM   2916  C    GLU A 410      55.228  77.575  37.161  1.00 86.21           C
ATOM   2917  O    GLU A 410      55.168  76.411  36.761  1.00 85.25           O
```

```
ATOM   2918  N   PRO A 411      55.443  78.614  36.333  1.00 85.53           N
ATOM   2919  CD  PRO A 411      55.613  79.983  36.845  1.00 85.19           C
ATOM   2920  CA  PRO A 411      55.626  78.596  34.877  1.00 84.18           C
ATOM   2921  CB  PRO A 411      55.684  80.081  34.513  1.00 84.63           C
ATOM   2922  CG  PRO A 411      55.084  80.785  35.707  1.00 85.11           C
ATOM   2923  C   PRO A 411      56.852  77.845  34.365  1.00 82.74           C
ATOM   2924  O   PRO A 411      56.901  77.465  33.200  1.00 82.74           O
ATOM   2925  N   GLU A 412      57.839  77.642  35.227  1.00 80.81           N
ATOM   2926  CA  GLU A 412      59.049  76.943  34.828  1.00 79.52           C
ATOM   2927  CB  GLU A 412      60.188  77.282  35.797  1.00 82.25           C
ATOM   2928  CG  GLU A 412      59.913  78.489  36.703  1.00 85.77           C
ATOM   2929  CD  GLU A 412      59.294  78.107  38.050  1.00 87.49           C
ATOM   2930  OE1 GLU A 412      58.348  78.801  38.496  1.00 87.57           O
ATOM   2931  OE2 GLU A 412      59.762  77.122  38.668  1.00 89.23           O
ATOM   2932  C   GLU A 412      58.812  75.439  34.821  1.00 77.63           C
ATOM   2933  O   GLU A 412      59.597  74.673  34.253  1.00 76.61           O
ATOM   2934  N   LYS A 413      57.713  75.031  35.449  1.00 76.27           N
ATOM   2935  CA  LYS A 413      57.339  73.619  35.579  1.00 75.22           C
ATOM   2936  CB  LYS A 413      56.425  73.443  36.797  1.00 76.98           C
ATOM   2937  CG  LYS A 413      57.025  73.871  38.134  1.00 79.14           C
ATOM   2938  CD  LYS A 413      57.888  72.768  38.732  1.00 80.04           C
ATOM   2939  CE  LYS A 413      57.636  72.624  40.235  1.00 80.03           C
ATOM   2940  NZ  LYS A 413      58.352  71.448  40.818  1.00 78.99           N
ATOM   2941  C   LYS A 413      56.641  72.992  34.369  1.00 73.00           C
ATOM   2942  O   LYS A 413      55.739  73.587  33.769  1.00 72.26           O
ATOM   2943  N   PHE A 414      57.057  71.781  34.017  1.00 69.88           N
ATOM   2944  CA  PHE A 414      56.416  71.089  32.915  1.00 66.96           C
ATOM   2945  CB  PHE A 414      57.390  70.157  32.188  1.00 65.33           C
ATOM   2946  CG  PHE A 414      56.726  69.296  31.143  1.00 64.44           C
ATOM   2947  CD1 PHE A 414      56.205  69.859  29.988  1.00 64.63           C
ATOM   2948  CD2 PHE A 414      56.562  67.936  31.346  1.00 63.37           C
ATOM   2949  CE1 PHE A 414      55.527  69.076  29.059  1.00 64.39           C
ATOM   2950  CE2 PHE A 414      55.887  67.147  30.422  1.00 62.30           C
ATOM   2951  CZ  PHE A 414      55.368  67.717  29.280  1.00 63.31           C
ATOM   2952  C   PHE A 414      55.270  70.265  33.494  1.00 65.58           C
ATOM   2953  O   PHE A 414      55.481  69.165  34.003  1.00 64.94           O
ATOM   2954  N   LEU A 415      54.060  70.808  33.440  1.00 63.82           N
ATOM   2955  CA  LEU A 415      52.899  70.094  33.944  1.00 62.06           C
ATOM   2956  CB  LEU A 415      52.560  70.542  35.376  1.00 63.36           C
ATOM   2957  CG  LEU A 415      52.624  72.003  35.820  1.00 65.03           C
ATOM   2958  CD1 LEU A 415      51.207  72.554  35.996  1.00 66.26           C
ATOM   2959  CD2 LEU A 415      53.394  72.087  37.141  1.00 63.11           C
ATOM   2960  C   LEU A 415      51.702  70.235  33.010  1.00 59.31           C
ATOM   2961  O   LEU A 415      50.958  71.213  33.055  1.00 57.99           O
ATOM   2962  N   PRO A 416      51.523  69.231  32.142  1.00 56.80           N
ATOM   2963  CD  PRO A 416      52.381  68.043  32.235  1.00 55.03           C
ATOM   2964  CA  PRO A 416      50.505  69.027  31.114  1.00 57.76           C
ATOM   2965  CB  PRO A 416      50.641  67.549  30.801  1.00 55.93           C
ATOM   2966  CG  PRO A 416      52.066  67.328  30.969  1.00 54.71           C
ATOM   2967  C   PRO A 416      49.085  69.387  31.523  1.00 59.50           C
ATOM   2968  O   PRO A 416      48.345  70.001  30.743  1.00 60.52           O
ATOM   2969  N   GLU A 417      48.705  68.993  32.738  1.00 60.71           N
ATOM   2970  CA  GLU A 417      47.362  69.265  33.247  1.00 60.33           C
ATOM   2971  CB  GLU A 417      47.294  69.038  34.764  1.00 60.86           C
ATOM   2972  CG  GLU A 417      47.261  67.570  35.178  1.00 62.60           C
ATOM   2973  CD  GLU A 417      46.198  66.746  34.427  1.00 64.30           C
ATOM   2974  OE1 GLU A 417      45.072  67.248  34.178  1.00 62.85           O
ATOM   2975  OE2 GLU A 417      46.494  65.573  34.099  1.00 66.95           O
ATOM   2976  C   GLU A 417      46.836  70.658  32.910  1.00 59.16           C
ATOM   2977  O   GLU A 417      45.622  70.855  32.862  1.00 60.54           O
ATOM   2978  N   ARG A 418      47.731  71.618  32.667  1.00 56.79           N
ATOM   2979  CA  ARG A 418      47.298  72.965  32.323  1.00 55.21           C
ATOM   2980  CB  ARG A 418      48.466  73.837  31.868  1.00 52.28           C
ATOM   2981  CG  ARG A 418      49.490  74.195  32.910  1.00 50.43           C
ATOM   2982  CD  ARG A 418      50.547  75.142  32.313  1.00 46.70           C
ATOM   2983  NE  ARG A 418      51.854  74.903  32.918  1.00 45.52           N
ATOM   2984  CZ  ARG A 418      52.318  75.526  33.996  1.00 45.12           C
ATOM   2985  NH1 ARG A 418      53.518  75.205  34.466  1.00 43.80           N
ATOM   2986  NH2 ARG A 418      51.609  76.492  34.579  1.00 43.75           N
ATOM   2987  C   ARG A 418      46.297  72.944  31.180  1.00 56.94           C
ATOM   2988  O   ARG A 418      45.353  73.725  31.175  1.00 57.38           O
ATOM   2989  N   PHE A 419      46.508  72.051  30.215  1.00 59.06           N
ATOM   2990  CA  PHE A 419      45.650  71.986  29.039  1.00 61.40           C
ATOM   2991  CB  PHE A 419      46.530  71.797  27.800  1.00 57.81           C
ATOM   2992  CG  PHE A 419      47.517  72.929  27.580  1.00 54.63           C
ATOM   2993  CD1 PHE A 419      47.141  74.086  26.894  1.00 52.52           C
ATOM   2994  CD2 PHE A 419      48.805  72.856  28.100  1.00 52.13           C
```

```
ATOM   2995  CE1 PHE A 419      48.023  75.145  26.733  1.00 49.54           C
ATOM   2996  CE2 PHE A 419      49.694  73.914  27.943  1.00 50.55           C
ATOM   2997  CZ  PHE A 419      49.298  75.060  27.259  1.00 50.28           C
ATOM   2998  C   PHE A 419      44.503  70.976  29.043  1.00 65.83           C
ATOM   2999  O   PHE A 419      43.871  70.746  28.009  1.00 67.98           O
ATOM   3000  N   SER A 420      44.223  70.372  30.194  1.00 69.41           N
ATOM   3001  CA  SER A 420      43.105  69.429  30.295  1.00 71.83           C
ATOM   3002  CB  SER A 420      43.246  68.565  31.551  1.00 71.89           C
ATOM   3003  OG  SER A 420      43.212  69.365  32.725  1.00 69.71           O
ATOM   3004  C   SER A 420      41.891  70.330  30.449  1.00 73.51           C
ATOM   3005  O   SER A 420      41.958  71.298  31.204  1.00 74.73           O
ATOM   3006  N   LYS A 421      40.788  70.051  29.763  1.00 75.00           N
ATOM   3007  CA  LYS A 421      39.643  70.940  29.926  1.00 77.65           C
ATOM   3008  CB  LYS A 421      38.482  70.546  29.029  1.00 79.14           C
ATOM   3009  CG  LYS A 421      37.309  71.505  29.185  1.00 81.13           C
ATOM   3010  CD  LYS A 421      37.731  72.948  28.909  1.00 82.55           C
ATOM   3011  CE  LYS A 421      37.330  73.885  30.048  1.00 83.90           C
ATOM   3012  NZ  LYS A 421      35.878  73.784  30.400  1.00 85.13           N
ATOM   3013  C   LYS A 421      39.157  70.993  31.366  1.00 78.39           C
ATOM   3014  O   LYS A 421      38.476  70.088  31.834  1.00 78.36           O
ATOM   3015  N   LYS A 422      39.517  72.078  32.043  1.00 80.10           N
ATOM   3016  CA  LYS A 422      39.188  72.351  33.442  1.00 81.99           C
ATOM   3017  CB  LYS A 422      39.348  71.093  34.305  1.00 82.16           C
ATOM   3018  CG  LYS A 422      40.729  70.476  34.301  1.00 83.20           C
ATOM   3019  CD  LYS A 422      40.697  69.033  34.814  1.00 84.03           C
ATOM   3020  CE  LYS A 422      40.042  68.086  33.802  1.00 82.53           C
ATOM   3021  NZ  LYS A 422      40.881  66.881  33.543  1.00 81.12           N
ATOM   3022  C   LYS A 422      40.204  73.424  33.824  1.00 83.47           C
ATOM   3023  O   LYS A 422      39.910  74.356  34.578  1.00 83.82           O
ATOM   3024  N   ASN A 423      41.409  73.272  33.285  1.00 84.47           N
ATOM   3025  CA  ASN A 423      42.473  74.251  33.460  1.00 85.03           C
ATOM   3026  CB  ASN A 423      43.821  73.581  33.702  1.00 85.50           C
ATOM   3027  CG  ASN A 423      43.871  72.820  35.002  1.00 86.12           C
ATOM   3028  OD1 ASN A 423      43.185  71.811  35.167  1.00 87.33           O
ATOM   3029  ND2 ASN A 423      44.692  73.298  35.938  1.00 85.27           N
ATOM   3030  C   ASN A 423      42.482  74.887  32.077  1.00 85.44           C
ATOM   3031  O   ASN A 423      42.756  76.073  31.902  1.00 84.97           O
ATOM   3032  N   LYS A 424      42.158  74.053  31.094  1.00 86.36           N
ATOM   3033  CA  LYS A 424      42.097  74.455  29.702  1.00 87.70           C
ATOM   3034  CB  LYS A 424      41.852  73.227  28.824  1.00 87.18           C
ATOM   3035  CG  LYS A 424      41.294  73.548  27.453  1.00 87.36           C
ATOM   3036  CD  LYS A 424      41.127  72.297  26.609  1.00 87.06           C
ATOM   3037  CE  LYS A 424      40.391  72.617  25.317  1.00 87.49           C
ATOM   3038  NZ  LYS A 424      40.393  71.480  24.355  1.00 86.37           N
ATOM   3039  C   LYS A 424      40.985  75.470  29.494  1.00 89.08           C
ATOM   3040  O   LYS A 424      39.963  75.443  30.184  1.00 91.55           O
ATOM   3041  N   ASP A 425      41.189  76.364  28.536  1.00 88.83           N
ATOM   3042  CA  ASP A 425      40.211  77.390  28.222  1.00 89.26           C
ATOM   3043  CB  ASP A 425      38.912  76.759  27.727  1.00 91.28           C
ATOM   3044  CG  ASP A 425      39.103  75.993  26.437  1.00 93.01           C
ATOM   3045  OD1 ASP A 425      40.045  76.329  25.680  1.00 93.46           O
ATOM   3046  OD2 ASP A 425      38.307  75.065  26.179  1.00 94.08           O
ATOM   3047  C   ASP A 425      39.935  78.330  29.377  1.00 88.58           C
ATOM   3048  O   ASP A 425      38.823  78.816  29.561  1.00 89.41           O
ATOM   3049  N   ASN A 426      40.964  78.552  30.174  1.00 87.61           N
ATOM   3050  CA  ASN A 426      40.903  79.492  31.274  1.00 87.62           C
ATOM   3051  CB  ASN A 426      41.075  78.785  32.619  1.00 87.78           C
ATOM   3052  CG  ASN A 426      42.352  79.189  33.322  1.00 89.31           C
ATOM   3053  OD1 ASN A 426      43.389  78.540  33.179  1.00 89.52           O
ATOM   3054  ND2 ASN A 426      42.293  80.287  34.072  1.00 90.69           N
ATOM   3055  C   ASN A 426      42.148  80.312  30.922  1.00 87.24           C
ATOM   3056  O   ASN A 426      42.519  81.288  31.587  1.00 87.47           O
ATOM   3057  N   ILE A 427      42.773  79.878  29.827  1.00 85.46           N
ATOM   3058  CA  ILE A 427      43.979  80.490  29.295  1.00 82.27           C
ATOM   3059  CB  ILE A 427      45.022  79.448  28.941  1.00 83.02           C
ATOM   3060  CG2 ILE A 427      46.383  80.105  28.910  1.00 84.64           C
ATOM   3061  CG1 ILE A 427      45.019  78.326  29.979  1.00 84.02           C
ATOM   3062  CD1 ILE A 427      45.814  77.102  29.546  1.00 83.31           C
ATOM   3063  C   ILE A 427      43.666  81.264  28.032  1.00 79.52           C
ATOM   3064  O   ILE A 427      43.032  80.754  27.103  1.00 77.44           O
ATOM   3065  N   ASP A 428      44.163  82.490  28.000  1.00 77.26           N
ATOM   3066  CA  ASP A 428      43.923  83.397  26.897  1.00 75.56           C
ATOM   3067  CB  ASP A 428      44.189  84.834  27.367  1.00 76.12           C
ATOM   3068  CG  ASP A 428      43.310  85.856  26.666  1.00 77.95           C
ATOM   3069  OD1 ASP A 428      43.632  87.060  26.725  1.00 78.23           O
ATOM   3070  OD2 ASP A 428      42.285  85.466  26.071  1.00 79.89           O
ATOM   3071  C   ASP A 428      44.721  83.170  25.623  1.00 73.68           C
```

```
ATOM   3072  O    ASP A 428      45.945  82.962  25.661  1.00 72.74           O
ATOM   3073  N    PRO A 429      44.030  83.144  24.468  1.00 70.95           N
ATOM   3074  CD   PRO A 429      42.598  83.181  24.134  1.00 68.72           C
ATOM   3075  CA   PRO A 429      44.847  82.968  23.272  1.00 69.32           C
ATOM   3076  CB   PRO A 429      43.806  82.746  22.175  1.00 68.32           C
ATOM   3077  CG   PRO A 429      42.626  83.512  22.661  1.00 67.95           C
ATOM   3078  C    PRO A 429      45.452  84.385  23.273  1.00 68.69           C
ATOM   3079  O    PRO A 429      45.107  85.190  24.144  1.00 70.00           O
ATOM   3080  N    TYR A 430      46.326  84.728  22.346  1.00 66.25           N
ATOM   3081  CA   TYR A 430      46.910  86.066  22.390  1.00 63.22           C
ATOM   3082  CB   TYR A 430      45.845  87.135  22.649  1.00 64.44           C
ATOM   3083  CG   TYR A 430      44.685  87.065  21.681  1.00 67.09           C
ATOM   3084  CD1  TYR A 430      43.390  86.799  22.128  1.00 66.80           C
ATOM   3085  CE1  TYR A 430      42.335  86.677  21.239  1.00 66.92           C
ATOM   3086  CD2  TYR A 430      44.889  87.213  20.311  1.00 67.97           C
ATOM   3087  CE2  TYR A 430      43.837  87.094  19.411  1.00 68.43           C
ATOM   3088  CZ   TYR A 430      42.565  86.824  19.881  1.00 67.89           C
ATOM   3089  OH   TYR A 430      41.529  86.694  18.985  1.00 67.03           O
ATOM   3090  C    TYR A 430      47.937  86.066  23.504  1.00 60.64           C
ATOM   3091  O    TYR A 430      48.764  86.957  23.585  1.00 62.09           O
ATOM   3092  N    ILE A 431      47.869  85.068  24.375  1.00 58.64           N
ATOM   3093  CA   ILE A 431      48.858  84.918  25.441  1.00 57.22           C
ATOM   3094  CB   ILE A 431      48.217  84.714  26.841  1.00 57.21           C
ATOM   3095  CG2  ILE A 431      49.259  84.190  27.837  1.00 56.12           C
ATOM   3096  CG1  ILE A 431      47.709  86.050  27.372  1.00 56.15           C
ATOM   3097  CD1  ILE A 431      48.810  87.023  27.682  1.00 55.11           C
ATOM   3098  C    ILE A 431      49.666  83.681  25.056  1.00 55.93           C
ATOM   3099  O    ILE A 431      50.883  83.759  24.915  1.00 57.99           O
ATOM   3100  N    TYR A 432      48.990  82.546  24.879  1.00 52.58           N
ATOM   3101  CA   TYR A 432      49.666  81.320  24.452  1.00 49.30           C
ATOM   3102  CB   TYR A 432      48.968  80.080  25.000  1.00 43.39           C
ATOM   3103  CG   TYR A 432      49.501  78.769  24.457  1.00 38.44           C
ATOM   3104  CD1  TYR A 432      48.849  78.108  23.419  1.00 35.88           C
ATOM   3105  CE1  TYR A 432      49.271  76.842  22.996  1.00 34.27           C
ATOM   3106  CD2  TYR A 432      50.608  78.142  25.050  1.00 34.89           C
ATOM   3107  CE2  TYR A 432      51.039  76.891  24.635  1.00 30.57           C
ATOM   3108  CZ   TYR A 432      50.365  76.242  23.616  1.00 34.10           C
ATOM   3109  OH   TYR A 432      50.753  74.971  23.235  1.00 36.03           O
ATOM   3110  C    TYR A 432      49.575  81.331  22.943  1.00 49.27           C
ATOM   3111  O    TYR A 432      48.528  81.035  22.377  1.00 49.87           O
ATOM   3112  N    THR A 433      50.680  81.671  22.290  1.00 50.82           N
ATOM   3113  CA   THR A 433      50.690  81.767  20.832  1.00 51.72           C
ATOM   3114  CB   THR A 433      50.562  83.249  20.430  1.00 52.66           C
ATOM   3115  OG1  THR A 433      51.387  84.050  21.297  1.00 53.38           O
ATOM   3116  CG2  THR A 433      49.107  83.697  20.545  1.00 51.36           C
ATOM   3117  C    THR A 433      51.901  81.151  20.122  1.00 49.85           C
ATOM   3118  O    THR A 433      52.727  81.868  19.565  1.00 51.57           O
ATOM   3119  N    PRO A 434      51.993  79.811  20.096  1.00 47.58           N
ATOM   3120  CD   PRO A 434      50.973  78.855  20.532  1.00 46.77           C
ATOM   3121  CA   PRO A 434      53.099  79.099  19.458  1.00 46.02           C
ATOM   3122  CB   PRO A 434      52.969  77.669  20.003  1.00 45.58           C
ATOM   3123  CG   PRO A 434      51.826  77.712  20.967  1.00 46.02           C
ATOM   3124  C    PRO A 434      53.047  79.114  17.934  1.00 44.61           C
ATOM   3125  O    PRO A 434      54.073  78.941  17.288  1.00 45.49           O
ATOM   3126  N    PHE A 435      51.858  79.296  17.371  1.00 42.59           N
ATOM   3127  CA   PHE A 435      51.685  79.313  15.924  1.00 41.94           C
ATOM   3128  CB   PHE A 435      50.701  78.223  15.476  1.00 41.81           C
ATOM   3129  CG   PHE A 435      51.198  76.814  15.684  1.00 43.99           C
ATOM   3130  CD1  PHE A 435      52.000  76.193  14.728  1.00 45.35           C
ATOM   3131  CD2  PHE A 435      50.872  76.107  16.838  1.00 43.81           C
ATOM   3132  CE1  PHE A 435      52.470  74.890  14.915  1.00 44.79           C
ATOM   3133  CE2  PHE A 435      51.335  74.810  17.037  1.00 44.53           C
ATOM   3134  CZ   PHE A 435      52.138  74.201  16.067  1.00 47.00           C
ATOM   3135  C    PHE A 435      51.117  80.667  15.569  1.00 43.42           C
ATOM   3136  O    PHE A 435      50.595  80.868  14.459  1.00 42.21           O
ATOM   3137  N    GLY A 436      51.212  81.595  16.524  1.00 44.41           N
ATOM   3138  CA   GLY A 436      50.683  82.930  16.312  1.00 46.37           C
ATOM   3139  C    GLY A 436      49.158  82.943  16.311  1.00 48.21           C
ATOM   3140  O    GLY A 436      48.522  82.010  16.803  1.00 46.65           O
ATOM   3141  N    SER A 437      48.570  84.002  15.760  1.00 49.76           N
ATOM   3142  CA   SER A 437      47.120  84.133  15.696  1.00 51.99           C
ATOM   3143  CB   SER A 437      46.559  84.643  17.033  1.00 53.88           C
ATOM   3144  OG   SER A 437      46.130  83.585  17.885  1.00 56.32           O
ATOM   3145  C    SER A 437      46.682  85.073  14.579  1.00 52.96           C
ATOM   3146  O    SER A 437      47.470  85.872  14.069  1.00 54.55           O
ATOM   3147  N    GLY A 438      45.415  84.963  14.199  1.00 53.57           N
ATOM   3148  CA   GLY A 438      44.882  85.814  13.152  1.00 52.86           C
```

```
ATOM   3149  C   GLY A 438      45.185  85.335  11.747  1.00 51.96           C
ATOM   3150  O   GLY A 438      45.753  84.262  11.553  1.00 50.86           O
ATOM   3151  N   PRO A 439      44.809  86.130  10.737  1.00 51.87           N
ATOM   3152  CD  PRO A 439      44.160  87.447  10.891  1.00 51.23           C
ATOM   3153  CA  PRO A 439      45.024  85.814   9.325  1.00 51.47           C
ATOM   3154  CB  PRO A 439      44.728  87.138   8.626  1.00 52.80           C
ATOM   3155  CG  PRO A 439      43.659  87.732   9.492  1.00 52.15           C
ATOM   3156  C   PRO A 439      46.422  85.308   8.997  1.00 50.60           C
ATOM   3157  O   PRO A 439      46.574  84.243   8.412  1.00 50.88           O
ATOM   3158  N   ARG A 440      47.442  86.055   9.399  1.00 49.74           N
ATOM   3159  CA  ARG A 440      48.811  85.672   9.074  1.00 48.06           C
ATOM   3160  CB  ARG A 440      49.619  86.941   8.786  1.00 47.69           C
ATOM   3161  CG  ARG A 440      50.813  86.684   7.931  1.00 47.48           C
ATOM   3162  CD  ARG A 440      51.236  87.865   7.095  1.00 48.52           C
ATOM   3163  NE  ARG A 440      52.322  87.429   6.219  1.00 50.53           N
ATOM   3164  CZ  ARG A 440      52.974  88.199   5.361  1.00 52.22           C
ATOM   3165  NH1 ARG A 440      53.938  87.666   4.625  1.00 54.08           N
ATOM   3166  NH2 ARG A 440      52.675  89.488   5.236  1.00 53.19           N
ATOM   3167  C   ARG A 440      49.568  84.772  10.061  1.00 46.88           C
ATOM   3168  O   ARG A 440      50.743  85.009  10.354  1.00 46.99           O
ATOM   3169  N   ASN A 441      48.909  83.728  10.555  1.00 45.30           N
ATOM   3170  CA  ASN A 441      49.546  82.810  11.492  1.00 43.38           C
ATOM   3171  CB  ASN A 441      48.525  82.322  12.518  1.00 43.95           C
ATOM   3172  CG  ASN A 441      47.619  81.230  11.961  1.00 46.26           C
ATOM   3173  OD1 ASN A 441      47.037  81.371  10.879  1.00 46.77           O
ATOM   3174  ND2 ASN A 441      47.499  80.134  12.699  1.00 46.24           N
ATOM   3175  C   ASN A 441      50.099  81.625  10.698  1.00 42.25           C
ATOM   3176  O   ASN A 441      50.002  81.589   9.475  1.00 41.24           O
ATOM   3177  N   CYS A 442      50.671  80.652  11.394  1.00 41.89           N
ATOM   3178  CA  CYS A 442      51.228  79.477  10.741  1.00 42.37           C
ATOM   3179  CB  CYS A 442      51.693  78.446  11.774  1.00 42.58           C
ATOM   3180  SG  CYS A 442      52.602  77.050  11.028  1.00 43.40           S
ATOM   3181  C   CYS A 442      50.224  78.815   9.827  1.00 42.63           C
ATOM   3182  O   CYS A 442      49.262  78.217  10.306  1.00 42.82           O
ATOM   3183  N   ILE A 443      50.454  78.901   8.519  1.00 43.64           N
ATOM   3184  CA  ILE A 443      49.554  78.290   7.539  1.00 43.12           C
ATOM   3185  CB  ILE A 443      49.923  78.655   6.101  1.00 42.28           C
ATOM   3186  CG2 ILE A 443      51.117  77.825   5.660  1.00 44.50           C
ATOM   3187  CG1 ILE A 443      48.757  78.319   5.161  1.00 42.95           C
ATOM   3188  CD1 ILE A 443      48.882  78.901   3.735  1.00 40.73           C
ATOM   3189  C   ILE A 443      49.587  76.771   7.624  1.00 43.48           C
ATOM   3190  O   ILE A 443      48.661  76.104   7.179  1.00 45.01           O
ATOM   3191  N   GLY A 444      50.653  76.224   8.192  1.00 43.65           N
ATOM   3192  CA  GLY A 444      50.756  74.785   8.300  1.00 43.63           C
ATOM   3193  C   GLY A 444      50.823  74.314   9.732  1.00 44.52           C
ATOM   3194  O   GLY A 444      51.610  73.436  10.062  1.00 44.80           O
ATOM   3195  N   MET A 445      49.982  74.880  10.582  1.00 46.39           N
ATOM   3196  CA  MET A 445      49.965  74.512  11.995  1.00 48.75           C
ATOM   3197  CB  MET A 445      49.085  75.488  12.771  1.00 49.32           C
ATOM   3198  CG  MET A 445      48.605  74.970  14.112  1.00 49.96           C
ATOM   3199  SD  MET A 445      47.702  76.230  15.037  1.00 51.66           S
ATOM   3200  CE  MET A 445      46.526  76.856  13.786  1.00 50.54           C
ATOM   3201  C   MET A 445      49.500  73.089  12.260  1.00 50.07           C
ATOM   3202  O   MET A 445      50.172  72.309  12.940  1.00 50.62           O
ATOM   3203  N   ARG A 446      48.335  72.755  11.728  1.00 52.44           N
ATOM   3204  CA  ARG A 446      47.771  71.430  11.923  1.00 53.55           C
ATOM   3205  CB  ARG A 446      46.404  71.348  11.238  1.00 55.83           C
ATOM   3206  CG  ARG A 446      45.441  72.344  11.827  1.00 61.50           C
ATOM   3207  CD  ARG A 446      44.061  72.195  11.259  1.00 68.74           C
ATOM   3208  NE  ARG A 446      44.017  72.506   9.838  1.00 73.45           N
ATOM   3209  CZ  ARG A 446      42.893  72.579   9.133  1.00 75.98           C
ATOM   3210  NH1 ARG A 446      41.719  72.362   9.725  1.00 76.91           N
ATOM   3211  NH2 ARG A 446      42.946  72.874   7.841  1.00 76.60           N
ATOM   3212  C   ARG A 446      48.713  70.369  11.386  1.00 51.59           C
ATOM   3213  O   ARG A 446      49.020  69.390  12.077  1.00 51.80           O
ATOM   3214  N   PHE A 447      49.178  70.575  10.159  1.00 48.83           N
ATOM   3215  CA  PHE A 447      50.091  69.628   9.545  1.00 45.66           C
ATOM   3216  CB  PHE A 447      50.606  70.176   8.209  1.00 46.38           C
ATOM   3217  CG  PHE A 447      51.593  69.273   7.514  1.00 47.64           C
ATOM   3218  CD1 PHE A 447      52.903  69.184   7.953  1.00 46.46           C
ATOM   3219  CD2 PHE A 447      51.219  68.540   6.392  1.00 49.10           C
ATOM   3220  CE1 PHE A 447      53.817  68.391   7.289  1.00 46.84           C
ATOM   3221  CE2 PHE A 447      52.142  67.741   5.719  1.00 47.89           C
ATOM   3222  CZ  PHE A 447      53.439  67.671   6.170  1.00 46.13           C
ATOM   3223  C   PHE A 447      51.232  69.430  10.521  1.00 42.58           C
ATOM   3224  O   PHE A 447      51.590  68.290  10.862  1.00 40.08           O
ATOM   3225  N   ALA A 448      51.776  70.543  11.001  1.00 38.95           N
```

```
ATOM   3226  CA   ALA A 448      52.883  70.468  11.940  1.00 37.31           C
ATOM   3227  CB   ALA A 448      53.243  71.862  12.425  1.00 35.61           C
ATOM   3228  C    ALA A 448      52.533  69.552  13.118  1.00 37.05           C
ATOM   3229  O    ALA A 448      53.297  68.646  13.470  1.00 34.69           O
ATOM   3230  N    LEU A 449      51.357  69.776  13.705  1.00 39.95           N
ATOM   3231  CA   LEU A 449      50.888  68.996  14.854  1.00 41.35           C
ATOM   3232  CB   LEU A 449      49.606  69.610  15.416  1.00 40.31           C
ATOM   3233  CG   LEU A 449      49.779  70.956  16.126  1.00 40.13           C
ATOM   3234  CD1  LEU A 449      48.427  71.598  16.309  1.00 39.37           C
ATOM   3235  CD2  LEU A 449      50.486  70.766  17.465  1.00 37.04           C
ATOM   3236  C    LEU A 449      50.666  67.519  14.548  1.00 43.80           C
ATOM   3237  O    LEU A 449      51.156  66.658  15.287  1.00 43.67           O
ATOM   3238  N    MET A 450      49.922  67.227  13.479  1.00 45.61           N
ATOM   3239  CA   MET A 450      49.679  65.844  13.078  1.00 49.02           C
ATOM   3240  CB   MET A 450      49.120  65.786  11.657  1.00 52.44           C
ATOM   3241  CG   MET A 450      47.685  65.271  11.511  1.00 55.90           C
ATOM   3242  SD   MET A 450      47.453  63.488  11.685  1.00 61.87           S
ATOM   3243  CE   MET A 450      46.837  63.379  13.349  1.00 55.95           C
ATOM   3244  C    MET A 450      51.038  65.179  13.081  1.00 50.93           C
ATOM   3245  O    MET A 450      51.323  64.321  13.917  1.00 51.61           O
ATOM   3246  N    ASN A 451      51.873  65.614  12.141  1.00 51.85           N
ATOM   3247  CA   ASN A 451      53.232  65.112  11.961  1.00 53.46           C
ATOM   3248  CB   ASN A 451      54.042  66.154  11.198  1.00 55.60           C
ATOM   3249  CG   ASN A 451      55.332  65.597  10.637  1.00 56.70           C
ATOM   3250  OD1  ASN A 451      56.327  66.315  10.521  1.00 57.54           O
ATOM   3251  ND2  ASN A 451      55.317  64.319  10.269  1.00 57.20           N
ATOM   3252  C    ASN A 451      53.955  64.788  13.273  1.00 54.29           C
ATOM   3253  O    ASN A 451      54.467  63.671  13.484  1.00 53.02           O
ATOM   3254  N    MET A 452      54.008  65.785  14.149  1.00 54.40           N
ATOM   3255  CA   MET A 452      54.673  65.637  15.438  1.00 54.56           C
ATOM   3256  CB   MET A 452      54.672  66.968  16.168  1.00 56.21           C
ATOM   3257  CG   MET A 452      56.046  67.528  16.399  1.00 58.72           C
ATOM   3258  SD   MET A 452      55.914  69.240  16.887  1.00 63.46           S
ATOM   3259  CE   MET A 452      55.290  69.943  15.353  1.00 61.34           C
ATOM   3260  C    MET A 452      54.059  64.582  16.341  1.00 52.58           C
ATOM   3261  O    MET A 452      54.758  63.950  17.127  1.00 54.00           O
ATOM   3262  N    LYS A 453      52.747  64.413  16.252  1.00 50.78           N
ATOM   3263  CA   LYS A 453      52.054  63.430  17.077  1.00 47.77           C
ATOM   3264  CB   LYS A 453      50.557  63.750  17.131  1.00 45.88           C
ATOM   3265  CG   LYS A 453      50.238  65.043  17.865  1.00 43.68           C
ATOM   3266  CD   LYS A 453      48.742  65.273  17.913  1.00 45.57           C
ATOM   3267  CE   LYS A 453      48.370  66.485  18.759  1.00 46.51           C
ATOM   3268  NZ   LYS A 453      48.832  66.386  20.178  1.00 48.65           N
ATOM   3269  C    LYS A 453      52.289  62.044  16.497  1.00 46.67           C
ATOM   3270  O    LYS A 453      52.712  61.130  17.202  1.00 44.59           O
ATOM   3271  N    LEU A 454      52.003  61.891  15.208  1.00 46.39           N
ATOM   3272  CA   LEU A 454      52.228  60.622  14.552  1.00 45.66           C
ATOM   3273  CB   LEU A 454      52.187  60.773  13.036  1.00 43.99           C
ATOM   3274  CG   LEU A 454      50.920  60.521  12.217  1.00 43.83           C
ATOM   3275  CD1  LEU A 454      49.978  59.638  13.005  1.00 43.49           C
ATOM   3276  CD2  LEU A 454      50.270  61.833  11.832  1.00 42.33           C
ATOM   3277  C    LEU A 454      53.618  60.159  14.968  1.00 47.16           C
ATOM   3278  O    LEU A 454      53.822  59.006  15.305  1.00 48.83           O
ATOM   3279  N    ALA A 455      54.585  61.064  14.955  1.00 48.86           N
ATOM   3280  CA   ALA A 455      55.936  60.676  15.332  1.00 51.92           C
ATOM   3281  CB   ALA A 455      56.892  61.828  15.115  1.00 53.88           C
ATOM   3282  C    ALA A 455      55.997  60.212  16.779  1.00 52.24           C
ATOM   3283  O    ALA A 455      56.726  59.293  17.113  1.00 53.09           O
ATOM   3284  N    LEU A 456      55.237  60.854  17.647  1.00 54.03           N
ATOM   3285  CA   LEU A 456      55.228  60.453  19.037  1.00 54.61           C
ATOM   3286  CB   LEU A 456      54.515  61.508  19.879  1.00 54.59           C
ATOM   3287  CG   LEU A 456      55.395  62.558  20.564  1.00 54.47           C
ATOM   3288  CD1  LEU A 456      56.834  62.400  20.125  1.00 55.80           C
ATOM   3289  CD2  LEU A 456      54.860  63.947  20.254  1.00 52.69           C
ATOM   3290  C    LEU A 456      54.554  59.094  19.201  1.00 54.97           C
ATOM   3291  O    LEU A 456      55.064  58.231  19.896  1.00 56.23           O
ATOM   3292  N    ILE A 457      53.423  58.889  18.546  1.00 55.88           N
ATOM   3293  CA   ILE A 457      52.728  57.612  18.675  1.00 58.86           C
ATOM   3294  CB   ILE A 457      51.564  57.495  17.673  1.00 59.31           C
ATOM   3295  CG2  ILE A 457      50.873  56.151  17.839  1.00 58.30           C
ATOM   3296  CG1  ILE A 457      50.599  58.669  17.871  1.00 60.28           C
ATOM   3297  CD1  ILE A 457      50.433  59.085  19.324  1.00 59.98           C
ATOM   3298  C    ILE A 457      53.639  56.401  18.489  1.00 59.59           C
ATOM   3299  O    ILE A 457      54.018  55.744  19.462  1.00 60.07           O
ATOM   3300  N    ARG A 458      53.970  56.104  17.233  1.00 60.82           N
ATOM   3301  CA   ARG A 458      54.834  54.976  16.899  1.00 61.26           C
ATOM   3302  CB   ARG A 458      55.270  55.045  15.427  1.00 61.56           C
```

```
ATOM   3303  CG   ARG A 458      54.202  54.566  14.442  1.00 65.27           C
ATOM   3304  CD   ARG A 458      54.772  53.532  13.466  1.00 68.28           C
ATOM   3305  NE   ARG A 458      53.755  52.643  12.906  1.00 69.00           N
ATOM   3306  CZ   ARG A 458      53.029  51.790  13.629  1.00 71.69           C
ATOM   3307  NH1  ARG A 458      52.122  51.013  13.040  1.00 71.55           N
ATOM   3308  NH2  ARG A 458      53.202  51.716  14.948  1.00 70.68           N
ATOM   3309  C    ARG A 458      56.063  54.922  17.797  1.00 60.85           C
ATOM   3310  O    ARG A 458      56.466  53.847  18.252  1.00 62.10           O
ATOM   3311  N    VAL A 459      56.658  56.076  18.071  1.00 58.84           N
ATOM   3312  CA   VAL A 459      57.839  56.095  18.916  1.00 56.32           C
ATOM   3313  CB   VAL A 459      58.477  57.473  18.944  1.00 55.05           C
ATOM   3314  CG1  VAL A 459      59.556  57.506  19.979  1.00 57.52           C
ATOM   3315  CG2  VAL A 459      59.077  57.777  17.603  1.00 56.09           C
ATOM   3316  C    VAL A 459      57.555  55.652  20.341  1.00 55.21           C
ATOM   3317  O    VAL A 459      58.166  54.707  20.827  1.00 55.40           O
ATOM   3318  N    LEU A 460      56.633  56.331  21.014  1.00 55.14           N
ATOM   3319  CA   LEU A 460      56.295  55.976  22.388  1.00 54.59           C
ATOM   3320  CB   LEU A 460      55.209  56.902  22.949  1.00 54.39           C
ATOM   3321  CG   LEU A 460      55.540  58.268  23.584  1.00 54.12           C
ATOM   3322  CD1  LEU A 460      56.757  58.131  24.517  1.00 51.69           C
ATOM   3323  CD2  LEU A 460      55.783  59.315  22.503  1.00 52.28           C
ATOM   3324  C    LEU A 460      55.811  54.539  22.496  1.00 54.75           C
ATOM   3325  O    LEU A 460      56.117  53.852  23.466  1.00 54.60           O
ATOM   3326  N    GLN A 461      55.061  54.080  21.501  1.00 54.62           N
ATOM   3327  CA   GLN A 461      54.541  52.724  21.537  1.00 55.27           C
ATOM   3328  CB   GLN A 461      53.236  52.642  20.728  1.00 54.29           C
ATOM   3329  CG   GLN A 461      53.369  52.485  19.244  1.00 54.74           C
ATOM   3330  CD   GLN A 461      52.039  52.667  18.538  1.00 57.16           C
ATOM   3331  OE1  GLN A 461      50.999  52.810  19.178  1.00 54.77           O
ATOM   3332  NE2  GLN A 461      52.066  52.663  17.207  1.00 59.85           N
ATOM   3333  C    GLN A 461      55.540  51.667  21.071  1.00 56.56           C
ATOM   3334  O    GLN A 461      55.165  50.642  20.508  1.00 57.32           O
ATOM   3335  N    ASN A 462      56.818  51.908  21.339  1.00 58.25           N
ATOM   3336  CA   ASN A 462      57.869  50.979  20.935  1.00 59.97           C
ATOM   3337  CB   ASN A 462      58.269  51.226  19.474  1.00 57.75           C
ATOM   3338  CG   ASN A 462      57.361  50.527  18.485  1.00 58.70           C
ATOM   3339  OD1  ASN A 462      57.443  49.313  18.311  1.00 60.10           O
ATOM   3340  ND2  ASN A 462      56.488  51.289  17.825  1.00 57.51           N
ATOM   3341  C    ASN A 462      59.104  51.141  21.810  1.00 62.17           C
ATOM   3342  O    ASN A 462      59.903  50.217  21.943  1.00 62.60           O
ATOM   3343  N    PHE A 463      59.258  52.318  22.408  1.00 64.68           N
ATOM   3344  CA   PHE A 463      60.433  52.593  23.224  1.00 68.16           C
ATOM   3345  CB   PHE A 463      61.481  53.376  22.419  1.00 69.16           C
ATOM   3346  CG   PHE A 463      61.839  52.753  21.107  1.00 69.63           C
ATOM   3347  CD1  PHE A 463      62.930  51.915  21.000  1.00 69.81           C
ATOM   3348  CD2  PHE A 463      61.054  52.976  19.988  1.00 69.91           C
ATOM   3349  CE1  PHE A 463      63.229  51.309  19.805  1.00 70.99           C
ATOM   3350  CE2  PHE A 463      61.346  52.373  18.791  1.00 70.47           C
ATOM   3351  CZ   PHE A 463      62.437  51.537  18.697  1.00 71.80           C
ATOM   3352  C    PHE A 463      60.117  53.422  24.441  1.00 70.05           C
ATOM   3353  O    PHE A 463      59.017  53.951  24.602  1.00 70.63           O
ATOM   3354  N    SER A 464      61.128  53.551  25.283  1.00 71.30           N
ATOM   3355  CA   SER A 464      61.031  54.352  26.476  1.00 73.72           C
ATOM   3356  CB   SER A 464      60.946  53.461  27.717  1.00 74.94           C
ATOM   3357  OG   SER A 464      60.562  54.210  28.862  1.00 77.33           O
ATOM   3358  C    SER A 464      62.327  55.156  26.458  1.00 75.11           C
ATOM   3359  O    SER A 464      63.407  54.624  26.180  1.00 76.01           O
ATOM   3360  N    PHE A 465      62.215  56.449  26.726  1.00 75.85           N
ATOM   3361  CA   PHE A 465      63.369  57.326  26.719  1.00 75.09           C
ATOM   3362  CB   PHE A 465      63.064  58.563  25.871  1.00 72.43           C
ATOM   3363  CG   PHE A 465      62.760  58.255  24.435  1.00 68.60           C
ATOM   3364  CD1  PHE A 465      63.701  58.478  23.451  1.00 67.58           C
ATOM   3365  CD2  PHE A 465      61.551  57.704  24.075  1.00 67.77           C
ATOM   3366  CE1  PHE A 465      63.443  58.153  22.135  1.00 66.09           C
ATOM   3367  CE2  PHE A 465      61.287  57.377  22.757  1.00 67.13           C
ATOM   3368  CZ   PHE A 465      62.236  57.601  21.787  1.00 65.73           C
ATOM   3369  C    PHE A 465      63.679  57.745  28.138  1.00 77.00           C
ATOM   3370  O    PHE A 465      62.823  58.290  28.828  1.00 77.98           O
ATOM   3371  N    LYS A 466      64.902  57.482  28.578  1.00 80.01           N
ATOM   3372  CA   LYS A 466      65.322  57.861  29.923  1.00 82.34           C
ATOM   3373  CB   LYS A 466      65.341  56.613  30.817  1.00 83.20           C
ATOM   3374  CG   LYS A 466      64.178  55.641  30.490  1.00 85.33           C
ATOM   3375  CD   LYS A 466      63.613  54.887  31.709  1.00 85.17           C
ATOM   3376  CE   LYS A 466      62.197  55.361  32.071  1.00 85.07           C
ATOM   3377  NZ   LYS A 466      62.138  56.764  32.605  1.00 84.14           N
ATOM   3378  C    LYS A 466      66.707  58.510  29.797  1.00 83.63           C
ATOM   3379  O    LYS A 466      67.493  58.142  28.921  1.00 83.98           O
```

```
ATOM   3380  N   PRO A 467      67.013  59.498  30.652  1.00 84.42           N
ATOM   3381  CD  PRO A 467      66.225  59.918  31.822  1.00 84.42           C
ATOM   3382  CA  PRO A 467      68.306  60.197  30.617  1.00 86.03           C
ATOM   3383  CB  PRO A 467      68.195  61.189  31.776  1.00 85.50           C
ATOM   3384  CG  PRO A 467      67.294  60.482  32.733  1.00 85.62           C
ATOM   3385  C   PRO A 467      69.551  59.320  30.734  1.00 87.89           C
ATOM   3386  O   PRO A 467      69.461  58.104  30.934  1.00 88.65           O
ATOM   3387  N   CYS A 468      70.717  59.945  30.583  1.00 89.28           N
ATOM   3388  CA  CYS A 468      71.978  59.225  30.709  1.00 90.86           C
ATOM   3389  CB  CYS A 468      72.287  58.417  29.433  1.00 90.91           C
ATOM   3390  SG  CYS A 468      72.790  59.339  27.970  1.00 91.24           S
ATOM   3391  C   CYS A 468      73.148  60.145  31.081  1.00 91.68           C
ATOM   3392  O   CYS A 468      72.968  61.135  31.799  1.00 91.57           O
ATOM   3393  N   LYS A 469      74.341  59.821  30.597  1.00 92.47           N
ATOM   3394  CA  LYS A 469      75.525  60.600  30.933  1.00 93.36           C
ATOM   3395  CB  LYS A 469      76.765  59.963  30.293  1.00 94.51           C
ATOM   3396  CG  LYS A 469      78.089  60.510  30.832  1.00 96.03           C
ATOM   3397  CD  LYS A 469      78.205  60.290  32.339  1.00 96.70           C
ATOM   3398  CE  LYS A 469      78.604  61.571  33.060  1.00 96.88           C
ATOM   3399  NZ  LYS A 469      78.699  61.370  34.533  1.00 96.95           N
ATOM   3400  C   LYS A 469      75.484  62.093  30.593  1.00 93.30           C
ATOM   3401  O   LYS A 469      75.142  62.923  31.443  1.00 92.84           O
ATOM   3402  N   GLU A 470      75.835  62.421  29.352  1.00 92.95           N
ATOM   3403  CA  GLU A 470      75.898  63.806  28.879  1.00 92.65           C
ATOM   3404  CB  GLU A 470      76.531  63.823  27.477  1.00 93.95           C
ATOM   3405  CG  GLU A 470      76.857  65.208  26.920  1.00 95.51           C
ATOM   3406  CD  GLU A 470      77.833  65.143  25.753  1.00 96.76           C
ATOM   3407  OE1 GLU A 470      79.033  64.878  25.994  1.00 96.48           O
ATOM   3408  OE2 GLU A 470      77.400  65.347  24.597  1.00 96.79           O
ATOM   3409  C   GLU A 470      74.577  64.593  28.880  1.00 91.27           C
ATOM   3410  O   GLU A 470      74.569  65.804  28.624  1.00 90.63           O
ATOM   3411  N   THR A 471      73.471  63.914  29.182  1.00 89.59           N
ATOM   3412  CA  THR A 471      72.155  64.556  29.218  1.00 87.70           C
ATOM   3413  CB  THR A 471      71.052  63.557  29.587  1.00 86.52           C
ATOM   3414  OG1 THR A 471      71.117  62.420  28.723  1.00 85.58           O
ATOM   3415  CG2 THR A 471      69.701  64.203  29.445  1.00 85.35           C
ATOM   3416  C   THR A 471      72.094  65.685  30.242  1.00 87.13           C
ATOM   3417  O   THR A 471      72.024  65.433  31.443  1.00 86.67           O
ATOM   3418  N   GLN A 472      72.112  66.928  29.767  1.00 86.65           N
ATOM   3419  CA  GLN A 472      72.054  68.071  30.670  1.00 85.66           C
ATOM   3420  CB  GLN A 472      71.982  69.403  29.923  1.00 85.77           C
ATOM   3421  CG  GLN A 472      73.122  69.761  29.002  1.00 85.77           C
ATOM   3422  CD  GLN A 472      72.894  71.127  28.373  1.00 86.24           C
ATOM   3423  OE1 GLN A 472      73.205  72.161  28.968  1.00 87.48           O
ATOM   3424  NE2 GLN A 472      72.315  71.136  27.177  1.00 85.35           N
ATOM   3425  C   GLN A 472      70.805  67.999  31.512  1.00 84.85           C
ATOM   3426  O   GLN A 472      69.760  67.542  31.058  1.00 84.90           O
ATOM   3427  N   ILE A 473      70.926  68.481  32.738  1.00 84.59           N
ATOM   3428  CA  ILE A 473      69.819  68.539  33.678  1.00 83.90           C
ATOM   3429  CB  ILE A 473      69.639  67.188  34.429  1.00 83.38           C
ATOM   3430  CG2 ILE A 473      69.016  67.423  35.803  1.00 83.85           C
ATOM   3431  CG1 ILE A 473      68.774  66.250  33.577  1.00 80.35           C
ATOM   3432  CD1 ILE A 473      68.958  64.788  33.863  1.00 78.59           C
ATOM   3433  C   ILE A 473      70.169  69.676  34.625  1.00 83.31           C
ATOM   3434  O   ILE A 473      71.206  69.654  35.283  1.00 83.04           O
ATOM   3435  N   PRO A 474      69.315  70.705  34.681  1.00 83.47           N
ATOM   3436  CD  PRO A 474      69.473  71.811  35.637  1.00 83.57           C
ATOM   3437  CA  PRO A 474      68.065  70.853  33.923  1.00 83.84           C
ATOM   3438  CB  PRO A 474      67.458  72.135  34.503  1.00 83.27           C
ATOM   3439  CG  PRO A 474      68.042  72.203  35.883  1.00 83.61           C
ATOM   3440  C   PRO A 474      68.153  70.913  32.386  1.00 83.91           C
ATOM   3441  O   PRO A 474      68.295  69.888  31.712  1.00 84.75           O
ATOM   3442  N   LEU A 475      68.067  72.120  31.837  1.00 82.65           N
ATOM   3443  CA  LEU A 475      68.073  72.299  30.394  1.00 80.69           C
ATOM   3444  CB  LEU A 475      66.721  72.868  29.957  1.00 82.28           C
ATOM   3445  CG  LEU A 475      66.254  74.099  30.757  1.00 84.03           C
ATOM   3446  CD1 LEU A 475      66.185  75.307  29.849  1.00 85.08           C
ATOM   3447  CD2 LEU A 475      64.886  73.848  31.383  1.00 85.66           C
ATOM   3448  C   LEU A 475      69.172  73.186  29.850  1.00 79.56           C
ATOM   3449  O   LEU A 475      70.096  72.710  29.191  1.00 80.64           O
ATOM   3450  N   LYS A 476      69.054  74.482  30.122  1.00 77.44           N
ATOM   3451  CA  LYS A 476      69.995  75.489  29.639  1.00 74.67           C
ATOM   3452  CB  LYS A 476      71.456  75.039  29.830  1.00 75.70           C
ATOM   3453  CG  LYS A 476      72.081  75.605  31.093  1.00 77.06           C
ATOM   3454  CD  LYS A 476      72.834  74.563  31.887  1.00 79.95           C
ATOM   3455  CE  LYS A 476      73.134  75.088  33.292  1.00 82.33           C
ATOM   3456  NZ  LYS A 476      74.584  75.039  33.654  1.00 83.55           N
```

```
ATOM   3457  C    LYS A 476      69.709  75.771  28.171  1.00 71.26           C
ATOM   3458  O    LYS A 476      69.823  74.891  27.323  1.00 69.34           O
ATOM   3459  N    LEU A 477      69.309  77.006  27.900  1.00 68.72           N
ATOM   3460  CA   LEU A 477      68.988  77.469  26.552  1.00 65.46           C
ATOM   3461  CB   LEU A 477      67.748  78.374  26.604  1.00 63.17           C
ATOM   3462  CG   LEU A 477      66.467  77.848  25.957  1.00 60.25           C
ATOM   3463  CD1  LEU A 477      66.424  76.340  26.019  1.00 59.16           C
ATOM   3464  CD2  LEU A 477      65.280  78.458  26.654  1.00 58.03           C
ATOM   3465  C    LEU A 477      70.176  78.233  25.956  1.00 63.26           C
ATOM   3466  O    LEU A 477      70.924  78.902  26.676  1.00 61.98           O
ATOM   3467  N    SER A 478      70.347  78.130  24.641  1.00 61.51           N
ATOM   3468  CA   SER A 478      71.453  78.811  23.974  1.00 59.41           C
ATOM   3469  CB   SER A 478      71.602  78.336  22.527  1.00 58.52           C
ATOM   3470  OG   SER A 478      70.695  79.018  21.687  1.00 57.26           O
ATOM   3471  C    SER A 478      71.214  80.306  23.972  1.00 58.23           C
ATOM   3472  O    SER A 478      70.067  80.752  23.941  1.00 58.32           O
ATOM   3473  N    LEU A 479      72.302  81.071  23.993  1.00 57.27           N
ATOM   3474  CA   LEU A 479      72.221  82.523  23.991  1.00 55.67           C
ATOM   3475  CB   LEU A 479      73.306  83.119  24.890  1.00 56.38           C
ATOM   3476  CG   LEU A 479      74.666  82.434  25.030  1.00 56.11           C
ATOM   3477  CD1  LEU A 479      75.547  83.348  25.885  1.00 54.87           C
ATOM   3478  CD2  LEU A 479      74.529  81.039  25.669  1.00 53.49           C
ATOM   3479  C    LEU A 479      72.300  83.116  22.590  1.00 54.59           C
ATOM   3480  O    LEU A 479      72.600  84.299  22.415  1.00 54.59           O
ATOM   3481  N    GLY A 480      72.006  82.279  21.595  1.00 53.30           N
ATOM   3482  CA   GLY A 480      72.004  82.718  20.213  1.00 50.79           C
ATOM   3483  C    GLY A 480      70.621  83.224  19.872  1.00 49.78           C
ATOM   3484  O    GLY A 480      69.845  83.528  20.771  1.00 49.26           O
ATOM   3485  N    GLY A 481      70.302  83.309  18.584  1.00 50.21           N
ATOM   3486  CA   GLY A 481      68.994  83.803  18.174  1.00 50.39           C
ATOM   3487  C    GLY A 481      68.034  82.709  17.743  1.00 51.45           C
ATOM   3488  O    GLY A 481      67.054  82.956  17.031  1.00 49.14           O
ATOM   3489  N    LEU A 482      68.338  81.487  18.172  1.00 52.62           N
ATOM   3490  CA   LEU A 482      67.527  80.319  17.867  1.00 52.96           C
ATOM   3491  CB   LEU A 482      68.321  79.323  17.018  1.00 53.24           C
ATOM   3492  CG   LEU A 482      68.615  79.829  15.606  1.00 53.31           C
ATOM   3493  CD1  LEU A 482      69.379  78.783  14.818  1.00 53.84           C
ATOM   3494  CD2  LEU A 482      67.297  80.164  14.920  1.00 52.71           C
ATOM   3495  C    LEU A 482      67.231  79.699  19.204  1.00 52.86           C
ATOM   3496  O    LEU A 482      68.099  79.695  20.070  1.00 53.57           O
ATOM   3497  N    LEU A 483      66.017  79.197  19.396  1.00 53.72           N
ATOM   3498  CA   LEU A 483      65.692  78.569  20.667  1.00 54.10           C
ATOM   3499  CB   LEU A 483      64.201  78.689  20.987  1.00 53.70           C
ATOM   3500  CG   LEU A 483      63.881  78.685  22.489  1.00 53.64           C
ATOM   3501  CD1  LEU A 483      62.397  78.820  22.752  1.00 52.95           C
ATOM   3502  CD2  LEU A 483      64.376  77.404  23.081  1.00 57.21           C
ATOM   3503  C    LEU A 483      66.081  77.108  20.557  1.00 55.15           C
ATOM   3504  O    LEU A 483      65.320  76.292  20.053  1.00 56.30           O
ATOM   3505  N    GLN A 484      67.286  76.789  21.004  1.00 55.77           N
ATOM   3506  CA   GLN A 484      67.757  75.424  20.968  1.00 57.24           C
ATOM   3507  CB   GLN A 484      68.807  75.215  19.884  1.00 58.02           C
ATOM   3508  CG   GLN A 484      68.891  76.290  18.849  1.00 60.22           C
ATOM   3509  CD   GLN A 484      70.316  76.478  18.390  1.00 61.72           C
ATOM   3510  OE1  GLN A 484      70.884  75.623  17.712  1.00 61.80           O
ATOM   3511  NE2  GLN A 484      70.913  77.598  18.779  1.00 63.48           N
ATOM   3512  C    GLN A 484      68.400  75.166  22.307  1.00 59.69           C
ATOM   3513  O    GLN A 484      68.710  76.100  23.057  1.00 59.01           O
ATOM   3514  N    PRO A 485      68.630  73.887  22.616  1.00 61.46           N
ATOM   3515  CD   PRO A 485      68.272  72.729  21.776  1.00 61.47           C
ATOM   3516  CA   PRO A 485      69.238  73.450  23.867  1.00 63.70           C
ATOM   3517  CB   PRO A 485      69.381  71.943  23.664  1.00 63.23           C
ATOM   3518  CG   PRO A 485      68.217  71.610  22.774  1.00 61.81           C
ATOM   3519  C    PRO A 485      70.571  74.099  24.221  1.00 66.52           C
ATOM   3520  O    PRO A 485      70.717  74.672  25.302  1.00 66.17           O
ATOM   3521  N    GLU A 486      71.522  74.031  23.285  1.00 69.94           N
ATOM   3522  CA   GLU A 486      72.894  74.502  23.508  1.00 72.21           C
ATOM   3523  CB   GLU A 486      72.941  75.600  24.570  1.00 72.66           C
ATOM   3524  CG   GLU A 486      74.327  75.913  25.093  1.00 75.01           C
ATOM   3525  CD   GLU A 486      74.452  75.669  26.592  1.00 76.42           C
ATOM   3526  OE1  GLU A 486      74.754  74.518  26.990  1.00 76.67           O
ATOM   3527  OE2  GLU A 486      74.238  76.630  27.372  1.00 77.13           O
ATOM   3528  C    GLU A 486      73.443  73.202  24.080  1.00 73.35           C
ATOM   3529  O    GLU A 486      73.214  72.900  25.251  1.00 74.97           O
ATOM   3530  N    LYS A 487      74.137  72.424  23.256  1.00 73.88           N
ATOM   3531  CA   LYS A 487      74.624  71.112  23.680  1.00 74.67           C
ATOM   3532  CB   LYS A 487      75.037  71.132  25.166  1.00 75.31           C
ATOM   3533  CG   LYS A 487      75.991  70.025  25.610  1.00 77.20           C
```

| | | | | | | | | | |
|---|---|---|---|---|---|---|---|---|---|
| ATOM | 3534 | CD | LYS A 487 | 76.638 | 70.332 | 26.982 | 1.00 | 79.60 | C |
| ATOM | 3535 | CE | LYS A 487 | 77.940 | 71.164 | 26.856 | 1.00 | 81.77 | C |
| ATOM | 3536 | NZ | LYS A 487 | 78.602 | 71.516 | 28.168 | 1.00 | 80.54 | N |
| ATOM | 3537 | C | LYS A 487 | 73.330 | 70.323 | 23.460 | 1.00 | 74.65 | C |
| ATOM | 3538 | O | LYS A 487 | 72.410 | 70.358 | 24.289 | 1.00 | 74.18 | O |
| ATOM | 3539 | N | PRO A 488 | 73.223 | 69.639 | 22.306 | 1.00 | 74.84 | N |
| ATOM | 3540 | CD | PRO A 488 | 74.303 | 69.421 | 21.327 | 1.00 | 74.46 | C |
| ATOM | 3541 | CA | PRO A 488 | 72.043 | 68.847 | 21.947 | 1.00 | 74.56 | C |
| ATOM | 3542 | CB | PRO A 488 | 72.434 | 68.231 | 20.602 | 1.00 | 73.75 | C |
| ATOM | 3543 | CG | PRO A 488 | 73.909 | 68.098 | 20.718 | 1.00 | 74.04 | C |
| ATOM | 3544 | C | PRO A 488 | 71.609 | 67.806 | 22.973 | 1.00 | 74.61 | C |
| ATOM | 3545 | O | PRO A 488 | 72.415 | 67.296 | 23.760 | 1.00 | 76.12 | O |
| ATOM | 3546 | N | VAL A 489 | 70.314 | 67.509 | 22.952 | 1.00 | 73.20 | N |
| ATOM | 3547 | CA | VAL A 489 | 69.714 | 66.545 | 23.854 | 1.00 | 70.20 | C |
| ATOM | 3548 | CB | VAL A 489 | 68.188 | 66.603 | 23.778 | 1.00 | 69.77 | C |
| ATOM | 3549 | CG1 | VAL A 489 | 67.586 | 65.544 | 24.667 | 1.00 | 68.04 | C |
| ATOM | 3550 | CG2 | VAL A 489 | 67.711 | 67.990 | 24.169 | 1.00 | 69.38 | C |
| ATOM | 3551 | C | VAL A 489 | 70.143 | 65.142 | 23.499 | 1.00 | 69.74 | C |
| ATOM | 3552 | O | VAL A 489 | 70.076 | 64.733 | 22.334 | 1.00 | 68.15 | O |
| ATOM | 3553 | N | VAL A 490 | 70.595 | 64.418 | 24.516 | 1.00 | 69.94 | N |
| ATOM | 3554 | CA | VAL A 490 | 71.016 | 63.035 | 24.355 | 1.00 | 69.59 | C |
| ATOM | 3555 | CB | VAL A 490 | 72.498 | 62.857 | 24.691 | 1.00 | 68.81 | C |
| ATOM | 3556 | CG1 | VAL A 490 | 73.144 | 61.930 | 23.682 | 1.00 | 68.21 | C |
| ATOM | 3557 | CG2 | VAL A 490 | 73.184 | 64.200 | 24.709 | 1.00 | 68.31 | C |
| ATOM | 3558 | C | VAL A 490 | 70.182 | 62.211 | 25.331 | 1.00 | 69.92 | C |
| ATOM | 3559 | O | VAL A 490 | 70.042 | 62.573 | 26.505 | 1.00 | 71.01 | O |
| ATOM | 3560 | N | LEU A 491 | 69.602 | 61.123 | 24.838 | 1.00 | 69.54 | N |
| ATOM | 3561 | CA | LEU A 491 | 68.786 | 60.260 | 25.678 | 1.00 | 69.63 | C |
| ATOM | 3562 | CB | LEU A 491 | 67.295 | 60.523 | 25.443 | 1.00 | 66.55 | C |
| ATOM | 3563 | CG | LEU A 491 | 66.730 | 61.870 | 25.892 | 1.00 | 64.07 | C |
| ATOM | 3564 | CD1 | LEU A 491 | 65.231 | 61.909 | 25.615 | 1.00 | 62.62 | C |
| ATOM | 3565 | CD2 | LEU A 491 | 67.010 | 62.084 | 27.362 | 1.00 | 62.00 | C |
| ATOM | 3566 | C | LEU A 491 | 69.093 | 58.808 | 25.363 | 1.00 | 71.54 | C |
| ATOM | 3567 | O | LEU A 491 | 69.394 | 58.469 | 24.218 | 1.00 | 70.37 | O |
| ATOM | 3568 | N | LYS A 492 | 69.043 | 57.955 | 26.384 | 1.00 | 74.23 | N |
| ATOM | 3569 | CA | LYS A 492 | 69.280 | 56.541 | 26.166 | 1.00 | 76.73 | C |
| ATOM | 3570 | CB | LYS A 492 | 69.866 | 55.850 | 27.404 | 1.00 | 78.57 | C |
| ATOM | 3571 | CG | LYS A 492 | 70.236 | 54.373 | 27.140 | 1.00 | 79.58 | C |
| ATOM | 3572 | CD | LYS A 492 | 70.720 | 53.621 | 28.385 | 1.00 | 80.62 | C |
| ATOM | 3573 | CE | LYS A 492 | 69.623 | 53.486 | 29.447 | 1.00 | 80.48 | C |
| ATOM | 3574 | NZ | LYS A 492 | 69.297 | 54.790 | 30.113 | 1.00 | 78.82 | N |
| ATOM | 3575 | C | LYS A 492 | 67.911 | 55.975 | 25.854 | 1.00 | 77.75 | C |
| ATOM | 3576 | O | LYS A 492 | 66.939 | 56.235 | 26.570 | 1.00 | 76.87 | O |
| ATOM | 3577 | N | VAL A 493 | 67.837 | 55.222 | 24.767 | 1.00 | 79.64 | N |
| ATOM | 3578 | CA | VAL A 493 | 66.584 | 54.635 | 24.339 | 1.00 | 82.03 | C |
| ATOM | 3579 | CB | VAL A 493 | 66.309 | 54.957 | 22.879 | 1.00 | 80.82 | C |
| ATOM | 3580 | CG1 | VAL A 493 | 64.966 | 54.375 | 22.465 | 1.00 | 80.12 | C |
| ATOM | 3581 | CG2 | VAL A 493 | 66.361 | 56.454 | 22.676 | 1.00 | 81.29 | C |
| ATOM | 3582 | C | VAL A 493 | 66.609 | 53.133 | 24.489 | 1.00 | 84.94 | C |
| ATOM | 3583 | O | VAL A 493 | 67.564 | 52.472 | 24.076 | 1.00 | 85.32 | O |
| ATOM | 3584 | N | GLU A 494 | 65.549 | 52.596 | 25.085 | 1.00 | 87.47 | N |
| ATOM | 3585 | CA | GLU A 494 | 65.438 | 51.163 | 25.280 | 1.00 | 89.43 | C |
| ATOM | 3586 | CB | GLU A 494 | 65.511 | 50.828 | 26.776 | 1.00 | 91.70 | C |
| ATOM | 3587 | CG | GLU A 494 | 66.801 | 51.340 | 27.434 | 1.00 | 95.85 | C |
| ATOM | 3588 | CD | GLU A 494 | 67.101 | 50.687 | 28.778 | 1.00 | 98.41 | C |
| ATOM | 3589 | OE1 | GLU A 494 | 67.142 | 49.435 | 28.834 | 1.00 | 99.54 | O |
| ATOM | 3590 | OE2 | GLU A 494 | 67.310 | 51.423 | 29.772 | 1.00 | 99.76 | O |
| ATOM | 3591 | C | GLU A 494 | 64.131 | 50.679 | 24.670 | 1.00 | 89.37 | C |
| ATOM | 3592 | O | GLU A 494 | 63.114 | 51.379 | 24.708 | 1.00 | 88.51 | O |
| ATOM | 3593 | N | SER A 495 | 64.173 | 49.493 | 24.079 | 1.00 | 89.75 | N |
| ATOM | 3594 | CA | SER A 495 | 62.992 | 48.913 | 23.463 | 1.00 | 90.89 | C |
| ATOM | 3595 | CB | SER A 495 | 63.386 | 47.660 | 22.673 | 1.00 | 90.57 | C |
| ATOM | 3596 | OG | SER A 495 | 62.277 | 47.100 | 21.990 | 1.00 | 91.28 | O |
| ATOM | 3597 | C | SER A 495 | 61.987 | 48.554 | 24.557 | 1.00 | 92.03 | C |
| ATOM | 3598 | O | SER A 495 | 62.368 | 48.325 | 25.704 | 1.00 | 92.76 | O |
| ATOM | 3599 | N | ARG A 496 | 60.703 | 48.527 | 24.218 | 1.00 | 92.96 | N |
| ATOM | 3600 | CA | ARG A 496 | 59.684 | 48.168 | 25.196 | 1.00 | 93.24 | C |
| ATOM | 3601 | CB | ARG A 496 | 58.456 | 49.064 | 25.058 | 1.00 | 92.29 | C |
| ATOM | 3602 | CG | ARG A 496 | 58.510 | 50.290 | 25.959 | 1.00 | 91.17 | C |
| ATOM | 3603 | CD | ARG A 496 | 57.230 | 51.090 | 25.867 | 1.00 | 90.04 | C |
| ATOM | 3604 | NE | ARG A 496 | 56.051 | 50.261 | 26.099 | 1.00 | 89.62 | N |
| ATOM | 3605 | CZ | ARG A 496 | 54.800 | 50.671 | 25.912 | 1.00 | 89.38 | C |
| ATOM | 3606 | NH1 | ARG A 496 | 53.791 | 49.848 | 26.148 | 1.00 | 89.44 | N |
| ATOM | 3607 | NH2 | ARG A 496 | 54.555 | 51.901 | 25.483 | 1.00 | 88.60 | N |
| ATOM | 3608 | C | ARG A 496 | 59.309 | 46.713 | 24.991 | 1.00 | 94.25 | C |
| ATOM | 3609 | O | ARG A 496 | 58.267 | 46.402 | 24.409 | 1.00 | 93.61 | O |
| ATOM | 3610 | N | ALA A 497 | 60.182 | 45.836 | 25.479 | 1.00 | 95.76 | N |

| | | | | | | | | | | |
|---|---|---|---|---|---|---|---|---|---|---|
| ATOM | 3611 | CA | ALA | A | 497 | 60.010 | 44.396 | 25.355 | 1.00 97.32 | C |
| ATOM | 3612 | CB | ALA | A | 497 | 58.646 | 43.979 | 25.915 | 1.00 97.48 | C |
| ATOM | 3613 | C | ALA | A | 497 | 60.132 | 44.014 | 23.873 | 1.00 98.09 | C |
| ATOM | 3614 | O | ALA | A | 497 | 59.136 | 43.701 | 23.213 | 1.00 97.67 | O |
| ATOM | 3615 | N | GLY | A | 498 | 61.359 | 44.052 | 23.352 | 1.00 98.57 | N |
| ATOM | 3616 | CA | GLY | A | 498 | 61.579 | 43.716 | 21.954 | 1.00 99.46 | C |
| ATOM | 3617 | C | GLY | A | 498 | 62.823 | 42.887 | 21.682 | 1.00 99.73 | C |
| ATOM | 3618 | O | GLY | A | 498 | 63.694 | 43.353 | 20.908 | 1.00 99.36 | O |
| ATOM | 3619 | OXT | GLY | A | 498 | 62.925 | 41.766 | 22.236 | 1.00 99.99 | O |
| TER | 3620 | | GLY | A | 498 | | | | | |
| ATOM | 3621 | O | HOH | A | 1001 | 54.898 | 91.487 | -1.627 | 1.00 32.11 | A O |
| ATOM | 3622 | O | HOH | A | 1002 | 68.987 | 66.032 | 9.986 | 1.00 40.88 | A O |
| ATOM | 3623 | O | HOH | A | 1003 | 52.505 | 62.145 | -3.799 | 1.00 55.48 | A O |
| ATOM | 3624 | O | HOH | A | 1004 | 67.908 | 84.509 | -5.902 | 1.00 46.98 | A O |
| ATOM | 3625 | O | HOH | A | 1005 | 58.132 | 82.846 | 9.612 | 1.00 26.93 | A O |
| ATOM | 3626 | O | HOH | A | 1006 | 60.044 | 70.172 | 35.137 | 1.00 51.30 | A O |
| ATOM | 3627 | O | HOH | A | 1007 | 48.838 | 77.448 | 34.981 | 1.00 27.10 | A O |
| ATOM | 3628 | O | HOH | A | 1008 | 67.304 | 80.127 | -7.945 | 1.00 45.85 | A O |
| ATOM | 3629 | O | HOH | A | 1009 | 67.037 | 83.117 | 22.321 | 1.00 44.27 | A O |
| ATOM | 3630 | O | HOH | A | 1010 | 62.800 | 112.945 | 21.553 | 1.00 54.32 | A O |
| ATOM | 3631 | O | HOH | A | 1011 | 57.537 | 87.489 | 31.602 | 1.00 43.32 | A O |
| ATOM | 3632 | O | HOH | A | 1012 | 66.885 | 91.489 | 15.525 | 1.00 53.66 | A O |
| ATOM | 3633 | O | HOH | A | 1013 | 52.634 | 99.006 | -1.080 | 1.00 49.49 | A O |
| ATOM | 3634 | O | HOH | A | 1014 | 56.271 | 86.649 | 13.241 | 1.00 29.96 | A O |
| ATOM | 3635 | O | HOH | A | 1015 | 63.341 | 90.324 | 3.637 | 1.00 49.09 | A O |
| ATOM | 3636 | O | HOH | A | 1016 | 59.096 | 87.134 | 7.295 | 1.00 40.36 | A O |
| ATOM | 3637 | O | HOH | A | 1017 | 50.679 | 79.172 | -6.240 | 1.00 43.11 | A O |
| ATOM | 3638 | O | HOH | A | 1018 | 74.015 | 83.586 | 17.906 | 1.00 37.86 | A O |
| ATOM | 3639 | O | HOH | A | 1019 | 74.310 | 83.376 | -3.328 | 1.00 40.41 | A O |
| ATOM | 3640 | O | HOH | A | 1020 | 75.160 | 78.606 | -2.004 | 1.00 51.22 | A O |
| ATOM | 3641 | O | HOH | A | 1021 | 67.693 | 79.340 | -11.637 | 1.00 69.29 | A O |
| ATOM | 3642 | O | HOH | A | 1022 | 58.062 | 80.427 | 8.316 | 1.00 54.86 | A O |
| ATOM | 3643 | O | HOH | A | 1023 | 67.045 | 72.222 | 18.507 | 1.00 34.54 | A O |
| ATOM | 3644 | O | HOH | A | 1024 | 74.786 | 72.412 | 18.708 | 1.00 54.16 | A O |
| ATOM | 3645 | O | HOH | A | 1025 | 58.261 | 90.911 | 4.025 | 1.00 33.47 | A O |
| ATOM | 3646 | O | HOH | A | 1026 | 73.328 | 77.303 | -8.463 | 1.00 44.61 | A O |
| ATOM | 3647 | O | HOH | A | 1027 | 64.928 | 111.589 | 13.285 | 1.00 45.12 | A O |
| ATOM | 3648 | O | HOH | A | 1028 | 75.741 | 49.803 | 26.627 | 1.00 51.53 | A O |
| ATOM | 3649 | O | HOH | A | 1029 | 74.567 | 89.038 | 20.275 | 1.00 46.83 | A O |
| TER | 3650 | | HOH | A | 1029 | | | | | A |
| ATOM | 3651 | FE | HEM | A | 501 | 54.952 | 77.691 | 10.637 | 1.00 27.43 | FE |
| ATOM | 3652 | CHA | HEM | A | 501 | 54.428 | 81.031 | 10.081 | 1.00 32.49 | C |
| ATOM | 3653 | CHB | HEM | A | 501 | 55.287 | 78.365 | 13.992 | 1.00 33.03 | C |
| ATOM | 3654 | CHC | HEM | A | 501 | 55.528 | 74.394 | 11.262 | 1.00 31.60 | C |
| ATOM | 3655 | CHD | HEM | A | 501 | 54.602 | 77.054 | 7.353 | 1.00 32.68 | C |
| ATOM | 3656 | NA | HEM | A | 501 | 54.843 | 79.361 | 11.807 | 1.00 32.28 | N |
| ATOM | 3657 | C1A | HEM | A | 501 | 54.615 | 80.651 | 11.406 | 1.00 34.41 | C |
| ATOM | 3658 | C2A | HEM | A | 501 | 54.582 | 81.524 | 12.584 | 1.00 36.00 | C |
| ATOM | 3659 | C3A | HEM | A | 501 | 54.824 | 80.765 | 13.643 | 1.00 32.35 | C |
| ATOM | 3660 | C4A | HEM | A | 501 | 54.998 | 79.429 | 13.160 | 1.00 32.21 | C |
| ATOM | 3661 | CMA | HEM | A | 501 | 54.884 | 81.195 | 15.077 | 1.00 32.95 | C |
| ATOM | 3662 | CAA | HEM | A | 501 | 54.323 | 82.989 | 12.628 | 1.00 40.53 | C |
| ATOM | 3663 | CBA | HEM | A | 501 | 52.883 | 83.293 | 12.993 | 1.00 47.08 | C |
| ATOM | 3664 | CGA | HEM | A | 501 | 52.579 | 84.758 | 13.147 | 1.00 50.37 | C |
| ATOM | 3665 | O1A | HEM | A | 501 | 53.509 | 85.576 | 12.992 | 1.00 52.71 | O |
| ATOM | 3666 | O2A | HEM | A | 501 | 51.416 | 85.093 | 13.470 | 1.00 52.41 | O |
| ATOM | 3667 | NB | HEM | A | 501 | 55.352 | 76.588 | 12.311 | 1.00 33.15 | N |
| ATOM | 3668 | C1B | HEM | A | 501 | 55.460 | 77.050 | 13.601 | 1.00 34.74 | C |
| ATOM | 3669 | C2B | HEM | A | 501 | 55.784 | 75.964 | 14.518 | 1.00 35.37 | C |
| ATOM | 3670 | C3B | HEM | A | 501 | 55.866 | 74.852 | 13.742 | 1.00 34.85 | C |
| ATOM | 3671 | C4B | HEM | A | 501 | 55.569 | 75.257 | 12.371 | 1.00 33.67 | C |
| ATOM | 3672 | CMB | HEM | A | 501 | 55.979 | 76.121 | 16.001 | 1.00 34.31 | C |
| ATOM | 3673 | CAB | HEM | A | 501 | 56.176 | 73.445 | 14.085 | 1.00 34.32 | C |
| ATOM | 3674 | CBB | HEM | A | 501 | 56.843 | 72.941 | 15.104 | 1.00 37.81 | C |
| ATOM | 3675 | NC | HEM | A | 501 | 55.046 | 75.965 | 9.497 | 1.00 33.61 | N |
| ATOM | 3676 | C1C | HEM | A | 501 | 55.272 | 74.709 | 9.955 | 1.00 32.38 | C |
| ATOM | 3677 | C2C | HEM | A | 501 | 55.162 | 73.764 | 8.878 | 1.00 31.12 | C |
| ATOM | 3678 | C3C | HEM | A | 501 | 54.884 | 74.489 | 7.764 | 1.00 32.72 | C |
| ATOM | 3679 | C4C | HEM | A | 501 | 54.834 | 75.904 | 8.181 | 1.00 33.62 | C |
| ATOM | 3680 | CMC | HEM | A | 501 | 55.338 | 72.269 | 9.051 | 1.00 29.89 | C |
| ATOM | 3681 | CAC | HEM | A | 501 | 54.676 | 74.008 | 6.393 | 1.00 35.84 | C |
| ATOM | 3682 | CBC | HEM | A | 501 | 53.566 | 74.148 | 5.652 | 1.00 39.50 | C |
| ATOM | 3683 | ND | HEM | A | 501 | 54.610 | 78.872 | 9.017 | 1.00 33.81 | N |
| ATOM | 3684 | C1D | HEM | A | 501 | 54.524 | 78.417 | 7.731 | 1.00 33.95 | C |
| ATOM | 3685 | C2D | HEM | A | 501 | 54.282 | 79.506 | 6.834 | 1.00 33.11 | C |
| ATOM | 3686 | C3D | HEM | A | 501 | 54.233 | 80.628 | 7.597 | 1.00 34.25 | C |
| ATOM | 3687 | C4D | HEM | A | 501 | 54.440 | 80.220 | 8.973 | 1.00 33.58 | C |

```
ATOM   3688  CMD HEM A 501      54.115  79.423   5.369  1.00 30.36           C
ATOM   3689  CAD HEM A 501      54.004  81.989   7.057  1.00 36.17           C
ATOM   3690  CBD HEM A 501      52.516  82.292   6.884  1.00 38.78           C
ATOM   3691  CGD HEM A 501      52.256  83.662   6.286  1.00 41.58           C
ATOM   3692  O1D HEM A 501      52.957  84.721   6.608  1.00 43.17           O
ATOM   3693  O2D HEM A 501      51.281  83.668   5.503  1.00 42.40           O
TER    3694      HEM A 501
END
```

Figure 3 (2 pages)

Table 6

Coordinates of the 3A4 261-270 loop structure

Copyright © 2002-2003 Astex Technology Ltd. All rights reserved.

| ATOM | 1894 | N   | LEU A 261 | 52.809 | 65.356 | -15.866 | 1.00 | 102.07 | N |
|------|------|-----|-----------|--------|--------|---------|------|--------|---|
| ATOM | 1895 | CA  | LEU A 261 | 51.938 | 65.312 | -17.035 | 1.00 | 104.54 | C |
| ATOM | 1896 | CB  | LEU A 261 | 51.546 | 66.732 | -17.473 | 1.00 | 102.70 | C |
| ATOM | 1897 | CG  | LEU A 261 | 52.518 | 67.892 | -17.241 | 1.00 | 102.30 | C |
| ATOM | 1898 | CD1 | LEU A 261 | 53.418 | 68.082 | -18.454 | 1.00 | 102.69 | C |
| ATOM | 1899 | CD2 | LEU A 261 | 51.718 | 69.161 | -16.978 | 1.00 | 101.43 | C |
| ATOM | 1900 | C   | LEU A 261 | 52.646 | 64.544 | -18.155 | 1.00 | 106.98 | C |
| ATOM | 1901 | O   | LEU A 261 | 53.247 | 65.115 | -19.070 | 1.00 | 107.60 | O |
| ATOM | 1902 | N   | GLU A 262 | 52.569 | 63.223 | -18.043 | 1.00 | 108.81 | N |
| ATOM | 1903 | CA  | GLU A 262 | 53.182 | 62.311 | -18.988 | 1.00 | 110.47 | C |
| ATOM | 1904 | CB  | GLU A 262 | 54.693 | 62.311 | -18.780 | 1.00 | 109.84 | C |
| ATOM | 1905 | CG  | GLU A 262 | 55.473 | 61.587 | -19.846 | 1.00 | 110.14 | C |
| ATOM | 1906 | CD  | GLU A 262 | 56.955 | 61.627 | -19.573 | 1.00 | 109.89 | C |
| ATOM | 1907 | OE1 | GLU A 262 | 57.377 | 61.055 | -18.546 | 1.00 | 109.50 | O |
| ATOM | 1908 | OE2 | GLU A 262 | 57.694 | 62.237 | -20.379 | 1.00 | 110.06 | O |
| ATOM | 1909 | C   | GLU A 262 | 52.595 | 60.942 | -18.664 | 1.00 | 111.82 | C |
| ATOM | 1910 | O   | GLU A 262 | 52.036 | 60.261 | -19.528 | 1.00 | 112.37 | O |
| ATOM | 1911 | N   | ASP A 263 | 52.717 | 60.550 | -17.401 | 1.00 | 112.85 | N |
| ATOM | 1912 | CA  | ASP A 263 | 52.177 | 59.278 | -16.954 | 1.00 | 113.85 | C |
| ATOM | 1913 | CB  | ASP A 263 | 53.117 | 58.605 | -15.950 | 1.00 | 114.14 | C |
| ATOM | 1914 | CG  | ASP A 263 | 54.316 | 59.461 | -15.607 | 1.00 | 113.74 | C |
| ATOM | 1915 | OD1 | ASP A 263 | 55.093 | 59.791 | -16.530 | 1.00 | 113.10 | O |
| ATOM | 1916 | OD2 | ASP A 263 | 54.480 | 59.797 | -14.414 | 1.00 | 113.67 | O |
| ATOM | 1917 | C   | ASP A 263 | 50.839 | 59.537 | -16.293 | 1.00 | 114.22 | C |
| ATOM | 1918 | O   | ASP A 263 | 49.819 | 58.988 | -16.705 | 1.00 | 114.75 | O |
| ATOM | 1919 | N   | THR A 264 | 50.853 | 60.391 | -15.274 | 1.00 | 114.49 | N |
| ATOM | 1920 | CA  | THR A 264 | 49.641 | 60.714 | -14.537 | 1.00 | 114.90 | C |
| ATOM | 1921 | CB  | THR A 264 | 48.516 | 61.153 | -15.490 | 1.00 | 115.03 | C |
| ATOM | 1922 | OG1 | THR A 264 | 49.081 | 61.908 | -16.570 | 1.00 | 114.99 | O |
| ATOM | 1923 | CG2 | THR A 264 | 47.497 | 62.019 | -14.755 | 1.00 | 115.23 | C |
| ATOM | 1924 | C   | THR A 264 | 49.239 | 59.423 | -13.831 | 1.00 | 114.81 | C |
| ATOM | 1925 | O   | THR A 264 | 50.049 | 58.820 | -13.124 | 1.00 | 115.42 | O |
| ATOM | 1926 | N   | GLN A 265 | 47.999 | 58.991 | -14.025 | 1.00 | 114.27 | N |
| ATOM | 1927 | CA  | GLN A 265 | 47.540 | 57.751 | -13.413 | 1.00 | 113.80 | C |
| ATOM | 1928 | CB  | GLN A 265 | 48.352 | 56.581 | -13.981 | 1.00 | 113.85 | C |
| ATOM | 1929 | CG  | GLN A 265 | 47.763 | 55.192 | -13.768 | 1.00 | 113.36 | C |
| ATOM | 1930 | CD  | GLN A 265 | 47.026 | 54.669 | -14.993 | 1.00 | 113.79 | C |
| ATOM | 1931 | OE1 | GLN A 265 | 47.575 | 54.631 | -16.099 | 1.00 | 113.51 | O |
| ATOM | 1932 | NE2 | GLN A 265 | 45.779 | 54.255 | -14.798 | 1.00 | 113.94 | N |
| ATOM | 1933 | C   | GLN A 265 | 47.710 | 57.816 | -11.892 | 1.00 | 113.66 | C |
| ATOM | 1934 | O   | GLN A 265 | 48.716 | 57.348 | -11.350 | 1.00 | 113.22 | O |
| ATOM | 1935 | N   | LYS A 266 | 46.713 | 58.395 | -11.219 | 1.00 | 113.47 | N |
| ATOM | 1936 | CA  | LYS A 266 | 46.706 | 58.551 | -9.758  | 1.00 | 112.97 | C |
| ATOM | 1937 | CB  | LYS A 266 | 46.427 | 57.198 | -9.090  | 1.00 | 111.85 | C |
| ATOM | 1938 | CG  | LYS A 266 | 44.941 | 56.813 | -9.108  | 1.00 | 110.12 | C |
| ATOM | 1939 | CD  | LYS A 266 | 44.371 | 56.739 | -10.522 | 1.00 | 108.98 | C |
| ATOM | 1940 | CE  | LYS A 266 | 42.896 | 56.359 | -10.503 | 1.00 | 108.31 | C |
| ATOM | 1941 | NZ  | LYS A 266 | 42.304 | 56.315 | -11.870 | 1.00 | 107.62 | N |
| ATOM | 1942 | C   | LYS A 266 | 48.028 | 59.164 | -9.287  | 1.00 | 112.84 | C |
| ATOM | 1943 | O   | LYS A 266 | 49.065 | 58.502 | -9.294  | 1.00 | 112.56 | O |
| ATOM | 1944 | N   | HIS A 267 | 47.965 | 60.414 | -8.833  | 1.00 | 112.66 | N |
| ATOM | 1945 | CA  | HIS A 267 | 49.172 | 61.133 | -8.476  | 1.00 | 112.74 | C |
| ATOM | 1946 | CB  | HIS A 267 | 49.669 | 61.837 | -9.729  | 1.00 | 112.79 | C |
| ATOM | 1947 | CG  | HIS A 267 | 51.022 | 61.408 | -10.175 | 1.00 | 112.83 | C |
| ATOM | 1948 | CD2 | HIS A 267 | 51.455 | 60.891 | -11.349 | 1.00 | 112.43 | C |
| ATOM | 1949 | ND1 | HIS A 267 | 52.133 | 61.538 | -9.375  | 1.00 | 112.77 | N |
| ATOM | 1950 | CE1 | HIS A 267 | 53.196 | 61.132 | -10.041 | 1.00 | 111.86 | C |
| ATOM | 1951 | NE2 | HIS A 267 | 52.812 | 60.729 | -11.239 | 1.00 | 111.68 | N |

| ATOM | 1952 | C   | HIS | A | 267 | 49.153 | 62.160 | -7.368 | 1.00 | 112.48 | C |
|------|------|-----|-----|---|-----|--------|--------|--------|------|--------|---|
| ATOM | 1953 | O   | HIS | A | 267 | 50.210 | 62.530 | -6.851 | 1.00 | 113.12 | O |
| ATOM | 1954 | N   | ARG | A | 268 | 47.961 | 62.644 | -7.013 | 1.00 | 111.61 | N |
| ATOM | 1955 | CA  | ARG | A | 268 | 47.821 | 63.677 | -5.988 | 1.00 | 110.42 | C |
| ATOM | 1956 | CB  | ARG | A | 268 | 46.334 | 63.929 | -5.718 | 1.00 | 111.44 | C |
| ATOM | 1957 | CG  | ARG | A | 268 | 45.614 | 62.678 | -5.249 | 1.00 | 112.41 | C |
| ATOM | 1958 | CD  | ARG | A | 268 | 44.793 | 62.016 | -6.348 | 1.00 | 113.12 | C |
| ATOM | 1959 | NE  | ARG | A | 268 | 43.639 | 61.344 | -5.762 | 1.00 | 113.24 | N |
| ATOM | 1960 | CZ  | ARG | A | 268 | 42.700 | 60.699 | -6.446 | 1.00 | 113.64 | C |
| ATOM | 1961 | NH1 | ARG | A | 268 | 42.761 | 60.620 | -7.771 | 1.00 | 114.01 | N |
| ATOM | 1962 | NH2 | ARG | A | 268 | 41.687 | 60.141 | -5.796 | 1.00 | 113.31 | N |
| ATOM | 1963 | C   | ARG | A | 268 | 48.518 | 63.380 | -4.656 | 1.00 | 109.06 | C |
| ATOM | 1964 | O   | ARG | A | 268 | 49.530 | 62.668 | -4.590 | 1.00 | 108.79 | O |
| ATOM | 1965 | N   | VAL | A | 269 | 47.961 | 63.957 | -3.593 | 1.00 | 107.37 | N |
| ATOM | 1966 | CA  | VAL | A | 269 | 48.490 | 63.779 | -2.248 | 1.00 | 105.27 | C |
| ATOM | 1967 | CB  | VAL | A | 269 | 48.444 | 62.289 | -1.853 | 1.00 | 105.02 | C |
| ATOM | 1968 | CG1 | VAL | A | 269 | 48.637 | 62.138 | -0.361 | 1.00 | 105.40 | C |
| ATOM | 1969 | CG2 | VAL | A | 269 | 47.118 | 61.678 | -2.289 | 1.00 | 104.28 | C |
| ATOM | 1970 | C   | VAL | A | 269 | 49.932 | 64.282 | -2.201 | 1.00 | 104.06 | C |
| ATOM | 1971 | O   | VAL | A | 269 | 50.851 | 63.533 | -1.874 | 1.00 | 104.02 | O |
| ATOM | 1972 | N   | ASP | A | 270 | 50.117 | 65.562 | -2.522 | 1.00 | 102.29 | N |
| ATOM | 1973 | CA  | ASP | A | 270 | 51.445 | 66.166 | -2.559 | 1.00 | 99.69  | C |
| ATOM | 1974 | CB  | ASP | A | 270 | 52.208 | 65.596 | -3.749 | 1.00 | 101.09 | C |
| ATOM | 1975 | CG  | ASP | A | 270 | 53.653 | 65.321 | -3.436 | 1.00 | 103.19 | C |
| ATOM | 1976 | OD1 | ASP | A | 270 | 54.132 | 64.239 | -3.833 | 1.00 | 103.99 | O |
| ATOM | 1977 | OD2 | ASP | A | 270 | 54.307 | 66.178 | -2.802 | 1.00 | 104.67 | O |
| ATOM | 1978 | C   | ASP | A | 270 | 51.325 | 67.682 | -2.712 | 1.00 | 97.55  | C |
| ATOM | 1979 | O   | ASP | A | 270 | 50.597 | 68.161 | -3.583 | 1.00 | 96.89  | O |

SEQUENCE LISTING

<160> NUMBER OF SEQ ID NOS: 6

<210> SEQ ID NO 1
<211> LENGTH: 1458
<212> TYPE: DNA
<213> ORGANISM: Artificial sequence
<220> FEATURE:
<223> OTHER INFORMATION: Codes for SEQ ID NO: 2, a human 3A4 P450 protein truncated in its N-terminal region to delete the hydrophobic trans-membrane domain, and the region replaced by a short N-terminal sequence.

<400> SEQUENCE: 1

```
atggcatacg gtactcattc acatggtctg tttaaaaaac tgggaattcc agggcccaca      60
cctctgcctt ttttgggaaa tattttgtcc taccataagg gcttttgtat gtttgacatg     120
gaatgtcata aaaagtatgg aaaagtgtgg ggcttttatg atggtcaaca gcctgtgctg     180
gctatcacag atcctgacat gatcaaaaca gtgctagtga agaatgttta ttctgtcttc     240
acaaaccgga ggccttttgg tccagtggga tttatgaaaa gtgccatctc tatagctgag     300
gatgaagaat ggaagagatt acgatcattg ctgtctccaa ccttcaccag tggaaaactc     360
aaggagatgg tccctatcat tgcccagtat ggagatgtgt tggtgagaaa tctgaggcgg     420
gaagcagaga caggcaagcc tgtcaccttg aaagacgtct ttggggccta cagcatggat     480
gtgatcacta gcacatcatt ggagtgaac atcgactctc tcaacaatcc acaagacccc     540
tttgtggaaa acaccaagaa gcttttaaga tttgattttt tggatccatt ctttctctca     600
ataacagtct ttccattcct catcccaatt cttgaagtat aaatatctg tgtgtttcca     660
agagaagtta caaattttt aagaaaatct gtaaaaagga tgaaagaaag tcgcctcgaa     720
gatacacaaa agcaccgagt ggatttcctt cagctgatga ttgactctca gaattcaaaa     780
gaaactgagt cccacaaagc tctgtccgat ctggagctcg tggcccaatc aattatcttt     840
atttttgctg gctatgaaac cacgagcagt gttctctcct tcattatgta tgaactggcc     900
actcaccctg atgtccagca gaaactgcag gaggaaattg atgcagtttt acccaataag     960
gcaccaccca cctatgatac tgtgctacag atggagtatc ttgacatggt ggtgaatgaa    1020
acgctcagat tattcccaat tgctatgaga cttgagaggg tctgcaaaaa agatgttgag    1080
atcaatggga tgttcattcc aaaggggtg gtggtgatga ttccaagcta tgctcttcac    1140
cgtgacccaa agtactggac agagcctgag aagttcctcc ctgaaagatt cagcaagaag    1200
aacaaggaca acatagatcc ttacatatac acacccttg gaagtggacc cagaaactgc    1260
attggcatga ggtttgctct catgaacatg aaacttgctc taatcagagt ccttcagaac    1320
ttctccttca aaccttgtaa agaaacacag atcccctga aattaagctt aggaggactt    1380
cttcaaccag aaaaacccgt tgttctaaag gttgagtcaa gggatggcac cgtaagtgga    1440
gcccaccatc accattga                                                  1458
```

<210> SEQ ID NO 2
<211> LENGTH: 485
<212> TYPE: PRT
<213> ORGANISM: Artificial sequence
<220> FEATURE:
<223> OTHER INFORMATION: Human 3A4 P450 protein truncated in its N-terminal region to delete the hydrophobic trans-membrane domain, and the region replaced by a short N-terminal sequence.

<400> SEQUENCE: 2

```
Met Ala Tyr Gly Thr His Ser His Gly Leu Phe Lys Lys Leu Gly Ile
1               5                   10                  15

Pro Gly Pro Thr Pro Leu Pro Phe Leu Gly Asn Ile Leu Ser Tyr His
            20                  25                  30

Lys Gly Phe Cys Met Phe Asp Met Glu Cys His Lys Lys Tyr Gly Lys
            35                  40                  45

Val Trp Gly Phe Tyr Asp Gly Gln Gln Pro Val Leu Ala Ile Thr Asp
    50                  55                  60

Pro Asp Met Ile Lys Thr Val Leu Val Lys Glu Cys Tyr Ser Val Phe
65                  70                  75                  80

Thr Asn Arg Arg Pro Phe Gly Pro Val Gly Phe Met Lys Ser Ala Ile
                85                  90                  95

Ser Ile Ala Glu Asp Glu Glu Trp Lys Arg Leu Arg Ser Leu Leu Ser
            100                 105                 110

Pro Thr Phe Thr Ser Gly Lys Leu Lys Glu Met Val Pro Ile Ile Ala
            115                 120                 125

Gln Tyr Gly Asp Val Leu Val Arg Asn Leu Arg Arg Glu Ala Glu Thr
130                 135                 140

Gly Lys Pro Val Thr Leu Lys Asp Val Phe Gly Ala Tyr Ser Met Asp
145                 150                 155                 160

Val Ile Thr Ser Thr Ser Phe Gly Val Asn Ile Asp Ser Leu Asn Asn
                165                 170                 175

Pro Gln Asp Pro Phe Val Glu Asn Thr Lys Lys Leu Leu Arg Phe Asp
            180                 185                 190

Phe Leu Asp Pro Phe Phe Leu Ser Ile Thr Val Phe Pro Phe Leu Ile
        195                 200                 205

Pro Ile Leu Glu Val Leu Asn Ile Cys Val Phe Pro Arg Glu Val Thr
        210                 215                 220

Asn Phe Leu Arg Lys Ser Val Lys Arg Met Lys Glu Ser Arg Leu Glu
225                 230                 235                 240

Asp Thr Gln Lys His Arg Val Asp Phe Leu Gln Leu Met Ile Asp Ser
                245                 250                 255

Gln Asn Ser Lys Glu Thr Glu Ser His Lys Ala Leu Ser Asp Leu Glu
            260                 265                 270

Leu Val Ala Gln Ser Ile Ile Phe Ile Phe Ala Gly Tyr Glu Thr Thr
            275                 280                 285

Ser Ser Val Leu Ser Phe Ile Met Tyr Glu Leu Ala Thr His Pro Asp
    290                 295                 300

Val Gln Gln Lys Leu Gln Glu Glu Ile Asp Ala Val Leu Pro Asn Lys
305                 310                 315                 320

Ala Pro Pro Thr Tyr Asp Thr Val Leu Gln Met Glu Tyr Leu Asp Met
                325                 330                 335

Val Val Asn Glu Thr Leu Arg Leu Phe Pro Ile Ala Met Arg Leu Glu
            340                 345                 350

Arg Val Cys Lys Lys Asp Val Glu Ile Asn Gly Met Phe Ile Pro Lys
            355                 360                 365

Gly Val Val Met Ile Pro Ser Tyr Ala Leu His Arg Asp Pro Lys
    370                 375                 380

Tyr Trp Thr Glu Pro Glu Lys Phe Leu Pro Glu Arg Phe Ser Lys Lys
385                 390                 395                 400

Asn Lys Asp Asn Ile Asp Pro Tyr Ile Tyr Thr Pro Phe Gly Ser Gly
                405                 410                 415

Pro Arg Asn Cys Ile Gly Met Arg Phe Ala Leu Met Asn Met Lys Leu
```

```
                420              425             430
Ala Leu Ile Arg Val Leu Gln Asn Phe Ser Phe Lys Pro Cys Lys Glu
        435             440             445

Thr Gln Ile Pro Leu Lys Leu Ser Leu Gly Gly Leu Leu Gln Pro Glu
    450             455             460

Lys Pro Val Val Leu Lys Val Glu Ser Arg Asp Gly Thr Val Ser Gly
465             470             475             480

Ala His His His His
            485

<210> SEQ ID NO 3
<211> LENGTH: 16
<212> TYPE: PRT
<213> ORGANISM: Artificial sequence
<220> FEATURE:
<223> OTHER INFORMATION: N-terminal sequence for expression of human
      3A4 P450

<400> SEQUENCE: 3

Met Ala Tyr Gly Thr His Ser His Gly Leu Phe Lys Lys Leu Gly Ile
1               5                   10                  15

<210> SEQ ID NO 4
<211> LENGTH: 33
<212> TYPE: DNA
<213> ORGANISM: Artificial sequence
<220> FEATURE:
<223> OTHER INFORMATION: Primer

<400> SEQUENCE: 4
ggaattcata tggctctcat cccagacttg gcc                                   33

<210> SEQ ID NO 5
<211> LENGTH: 47
<212> TYPE: DNA
<213> ORGANISM: Artificial sequence
<220> FEATURE:
<223> OTHER INFORMATION: Primer

<400> SEQUENCE: 5
tgcggtcgac tcaatggtga tggtgggctc cacttacggt gccatcc                    47

<210> SEQ ID NO 6
<211> LENGTH: 69
<212> TYPE: DNA
<213> ORGANISM: Artificial sequence
<220> FEATURE:
<223> OTHER INFORMATION: Primer

<400> SEQUENCE: 6
ttaacatatg gcatatggta ctcattcaca tggtctgttt aaaaaactgg gaattccagg      60
gcccacacc                                                              69
```

CRYSTAL STRUCTURE OF CYTOCHROME P450

The present application is a continuation-in-part of applications PCT/GB02/02668 filed May 30, 2002 and designating the US, and Ser. No. 10/221,036, filed Apr. 2, 2002, and claims benefit of the following U.S. Provisional Application Ser. Nos. 60/479,448, filed Jun. 19, 2003; 60/421,063, filed Oct. 25, 2002. U.S. Ser. No. 10/221,036 claims the benefit of priority of Ser. No. 60/306,873, filed Jul. 23, 2001, Ser. No. 60/306,874, filed Jul. 23, 2001, and UK applications GB 0108214.8 filed Apr. 2, 2001 and GB 0108212.2 filed Apr. 2, 2001. The contents of all these applications are incorporated herein by reference.

FIELD OF THE INVENTION

The present invention relates to the human cytochrome P450 protein 3A4, methods for its crystallization, crystals of 3A4 and their 3-dimensional structures, and uses thereof.

BACKGROUND TO THE INVENTION

Introduction to Cytochrome P450

Cytochrome P450s (CYP450) form a very large and complex gene superfamily of hemeproteins that metabolise physiologically important compounds in many species of microorganisms, plants and animals. Cytochrome P450s are important in the oxidative, peroxidative and reductive metabolism of numerous and diverse endogenous compounds such as steroids, bile, fatty acids, prostaglandins, leukotrienes, retinoids and lipids. Many of these enzymes also metabolise a wide range of xenobiotics including drugs, environmental compounds and pollutants. Their involvement in drug metabolism is extensive, it is estimated that 50% of all known drugs are affected in some way by the action of CYP450 enzymes. Significant resource is employed by the pharmaceutical industry to optimise drug candidates in order to avoid their detrimental interactions with the CYP450 enzymes. Another level of complication results from the fact that these enzymes exhibit different tissue distributions and polymorphisms between individuals and ethnic populations Most mammalian P450s are located in the liver, but other organs and tissues have high concentrations of certain cytochrome P450s, including the intestinal wall, lung, kidney, adrenal cortex and nasal epithelium. Mammals have about 50 unique CYP450 genes and each family member is 45–55 KDa in size and contains a heme moiety that catalyses a two-electron activation of oxygen. The source of electrons may be used to classify CYP450s. Those that receive electrons in a three protein chain in which electrons flow from a flavin adenine dinucleotide (FAD) containing reductase, to an iron-sulphur protein, and then to P450 belong to the group of class I P450s, and include most of the bacterial enzymes. Class II P450s receive electrons from a reductase containing both FAD and flavin mononucleotide (FMN), and comprise the microsomal P450s that are the main culprits of drug metabolism. The mammalian microsomal cytochrome P450s are integral membrane proteins anchored by an N-terminal transmembrane spanning α-helix. They are inserted in the membrane of the endoplasmic reticulum by a short, highly hydrophobic N-terminal segment that acts as a non-cleavable signal sequence for insertion into the membrane. The remainder of the mammalian cytochrome P450 protein is a globular structure that protrudes into the cytoplasmic space. Hence, the bulk of the enzyme faces the cytoplasmic surface of the lipid bilayer. P450s require other membranous enzymatic components for activity including the flavoprotein NADPH-cytochrome P450 oxidoreductase and, in some cases, cytochrome b5. A single cytochrome P450 oxidoreductase supports the activity of all the mammalian microsomal enzymes by interacting directly with the P450s and transferring the required two electrons from NADPH. Cytochrome P450s are able to incorporate one of the two oxygen atoms of an $O_2$ molecule into a broad variety of substrates with concomitant reduction of the other oxygen atom by two electrons to $H_2O$. Cytochrome P450 are known to catalyse hydroxylations, epoxidation, N—, S—, and O-dealkylations, N-oxidations, sulfoxidations, dehalogenations, and other reactions.

The genes of the P450 superfamily have been categorized by Nelson et al (Pharmacogenetics, 6; 1–42, 1996) who proposed a systematic nomenclature for the family members. This nomenclature is used widely in the art, and is adopted herein. Nelson et al provide cross-references to sequence database entries for P450 sequences.

*Homo sapiens* has 17 cytochrome P450 gene families and 42 subfamilies that total more than 50 sequenced isoforms. Cytochrome P450s from families 1, 2 and 3 constitute the major pathways for drug metabolism. Many drugs rely on hepatic metabolism by cytochrome P450s for clearance from the circulation and for pharmacological inactivation. Conversely, some drugs have to be converted in the body to their pharmacologically active metabolites by P450s. Many promising lead compounds are terminated in the development phase due to their interaction with one or more P450s. One of the greatest problems in drug discovery is the prediction of the role of cytochrome P450s on the metabolism or modification of drug leads. Early detection of metabolic problems associated with a chemical lead series is of paramount importance for the pharmaceutical industry. Obtaining crystal structures of the main human drug metabolising cytochrome P450s would be highly valuable for drug design, as this would provide detailed information on how P450 enzymes recognize drug molecules and the mode of drug binding. This in turn would allow drug companies to develop strategies to modify metabolic clearance and decrease the attrition rates of compounds in development.

The major human CYP450 isoforms involved in drug metabolism are CYP1A2, CYP2C9, CYP2C19, CYP2D6 and CYP3A4. The level of sequence identity between these family members ranges from about 20–80%, with much of the variability within the residues involved in substrate recognition. CYP450 enzymes are also present in bacteria and much of the understanding of substrate recognition is derived from crystal structures obtained of bacterial CYP450 enzymes.

CYP3A is both the most abundant and most clinically significant subfamily of cytochrome P450 enzymes. The CYP3A subfamily has four human isoforms, 3A4, 3A5, 3A7 and 3A43, CYP3A4 being the most commonly associated with drug interactions. The CYP3A isoforms make up approximately 50% of the liver's total cytochrome P450 and are widely expressed throughout the gastrointestinal tract, kidneys and lungs and therefore are ultimately responsible for the majority of first-pass metabolism. This is important as increases or decreases in first-pass metabolism can have the effect of administering a much smaller or larger dose of drug than usual. More than 150 drugs are known substrates of CYP3A4, including many of the opiate analgesics, steroids, antiarrhythmic agents, tricyclic antidepressants, calcium-channel blockers and macrolide antibiotics. Although several substrates show age-dependent reductions in elimination, the enzyme itself does not appear to be altered. CYP3A4 is important in the metabolism of many drugs including cyclosporine, codeine, tamoxifen, lovastatin, and many more, and endogenous compounds such as testosterone, estradiol and cortisol. Ketoconazole, itraconazole, erythromycin, clarithromycin, diltiazem, fluvoxamine, nefazodone, and dihydroxybergamottin and various substances found in grapefruit juice, green tea and other foods are potent inhibitors of CYP3A4 and are known to be responsible for many drug interactions. These interactions can have serious clinical consequences.

Background to Crystallisation

It is well-known in the art of protein chemistry, that crystallising a protein is a chancy and difficult process without any clear expectation of success. It is now evident that protein crystallization is the main hurdle in protein structure determination. For this reason, protein crystallization has become a research subject in and of itself, and is not simply an extension of the protein crystallographer's laboratory. There are many references which describe the difficulties associated with growing protein crystals. For example, Kierzek, A. M. and Zielenkiewicz, P., (2001), Biophysical Chemistry, 91, 1–20, *Models of protein crystal growth*, and Wiencek, J. M. (1999) Annu. Rev. Biomed. Eng., 1, 505–534, *New Strategies for crystal growth*.

It is commonly held that crystallization of protein molecules from solution is the major obstacle in the process of determining protein structures. The reasons for this are many; proteins are complex molecules, and the delicate balance involving specific and non-specific interactions with other protein molecules and small molecules in solution, is difficult to predict.

Each protein crystallizes under a unique set of conditions, which cannot be predicted in advance. Simply supersaturating the protein to bring it out of solution may not work, the result would, in most cases, be an amorphous precipitate. Many precipitating agents are used, common ones are different salts, and polyethylene glycols, but others are known. In addition, additives such as metals and detergents can be added to modulate the behaviour of the protein in solution. Many kits are available (e.g. from Hampton Research), which attempt to cover as many parameters in crystallization space as possible, but in many cases these are just a starting point to optimise crystalline precipitates and crystals which are unsuitable for diffraction analysis. Successful crystallization is aided by a knowledge of the proteins behaviour in terms of solubility, dependence on metal ions for correct folding or activity, interactions with other molecules and any other information that is available. Even so, crystallization of proteins is often regarded as a time-consuming process, whereby subsequent experiments build on observations of past trials.

In cases where protein crystals are obtained, these are not necessarily always suitable for diffraction analysis; they may be limited in resolution, and it may subsequently be difficult to improve them to the point at which they will diffract to the resolution required for analysis. Limited resolution in a crystal can be due to several things. It may be due to intrinsic mobility of the protein within the crystal, which can be difficult to overcome, even with other crystal forms. It may be due to high solvent content within the crystal, which consequently results in weak scattering. Alternatively, it could be due to defects within the crystal lattice which mean that the diffracted x-rays will not be completely in phase from unit to unit within the lattice. Any one of these or a combination of these could mean that the crystals are not suitable for structure determination.

Some proteins never crystallize, and after a reasonable attempt it is necessary to examine the protein itself and consider whether it is possible to make individual domains, different N or C-terminal truncations, or point mutations. It is often hard to predict how a protein could be re-engineered in such a manner as to improve crystallisability. Our understanding of crystallisation mechanisms are still incomplete and the factors of protein structure which are involved in crystallisation are poorly understood.

Determination of Protein Structure

A mathematical operation termed a Fourier transform relates the diffraction pattern observed from a crystal and the molecular structure of the protein comprising the crystal. A Fourier transform may be considered to be a summation of sine and cosine waves each with a defined amplitude and phase. Thus, in theory, it is possible to calculate the electron density associated with a protein structure by carrying out an inverse Fourier transform on the diffraction data. This, however, requires amplitude and phase information to be extracted from the diffraction data. Amplitude information may be obtained by analysing the intensities of the spots within a diffraction pattern. The conventional methods for recording diffraction data do, however, mean that any phase information is lost. This "phase information" must be in some way recovered and the loss of this information represents the "crystallographic phase problem". The phase information necessary for carrying out the inverse Fourier transform can be obtained via a variety of methods. If a protein structure exists a set of theoretical amplitudes and phases may be calculated using the protein model and then the theoretical phases combined with the experimentally derived amplitudes. An electron density map may then be calculated and the protein structure observed.

If there is no known structure of the protein then alternative methods for obtaining phases must be explored. One method is multiple isomorphous replacement (MIR). This relies on soaking "heavy atom" (i.e. platinum, uranium, mercury, etc) compounds into the crystals and observing how their incorporation into the crystals modifies the spot intensities observed in the diffraction pattern. This method relies on the heavy atoms being incorporated into the protein at a finite number of defined sites. It is a pre-requisite of an isomorphous replacement experiment that the heavy atom soaked crystals remain isomorphous. That is, there should be no appreciable alterations in the physical characteristics of the protein crystal (i.e. perturbations to crystallographic cell dimensions, or significant loss of resolution). Perturbations to the physical properties of the crystal are termed non-isomorphisms and prevent this type of experiment being successfully completed. Successful isomorphous incorporation of heavy atoms into a protein crystal results in the intensities of the spots within the diffraction pattern obtained from the crystal being modified, as compared to the data collected from an identical, unsoaked, (native) crystal. The diffraction data obtained from a successful isomorphous replacement experiment are termed a "derivative" dataset. By mathematically analysing the "native" and "derivative" datasets it is possible to extract preliminary phase information from the datasets. This phase information, when combined with the experimentally obtained amplitudes from the native dataset, enables an electron density map of the unknown protein molecule to be calculated using the Fourier transform method.

An alternative method for obtaining phase information for a protein of unknown structure is to perform a multi-wavelength anomalous dispersion (MAD) experiment. This relies on the absorption of X-rays by electrons at certain characteristic X-ray wavelengths. Different elements have different characteristic absorption edges. Anomalous scattering by atoms within a protein will modify the diffraction pattern obtained from the protein crystal. Thus if a protein contains atoms which are capable of anomalous scattering a diffraction dataset (anomalous dataset) may be collected at an X-ray wavelength at which this anomalous scattering is maximal. By altering the X-ray wavelength to a value at which there is no anomalous scattering a native dataset may then be collected. Similarly to the MIR case, by mathematically processing the anomalous and native datasets the phase information necessary for the calculation of an electron density map may be determined. The most usual way to introduce anomalous scatterers into a protein is to replace the sulphur containing methionine amino acid residues with selenium containing seleno-methionine residues. This is done by generating recombinant protein that is isolated from cells grown on growth media that contain seleno-methionine. Selenium is capable of anomalously scattering X-rays and may thus be used for a MAD experiment. Further methods for phase determination such as single isomorphous replacement (SIR), single isomorphous replacement anomalous scattering (SIRAS) and direct methods exist, but the principles behind them are similar to MIR and MAD.

The final method generally available for the calculation of the phases necessary for the determination of an unknown protein structure is molecular replacement. This method relies upon the assumption that proteins with similar amino acid sequences (primary sequences) will have a similar fold and three-dimensional structure (tertiary structure). Proteins related by amino acid sequence are termed homologous proteins. If an X-ray diffraction dataset has been collected from a crystal whose protein structure is not known, but a structure has been determined for a homologous protein, then molecular replacement can be attempted. Molecular replacement is a mathematical process that attempts to correlate the dataset obtained from a new protein crystal with the theoretical diffraction pattern calculated for a protein of known structure. If the correlation is sufficiently high some phase information can be extracted from the known protein structure and combined with the amplitudes obtained from the new protein dataset. This enables calculation of a preliminary electron density map for the protein of unknown structure.

If an electron density map has been calculated for a protein of unknown structure then the amino acids comprising the protein must be fitted into the electron density for the protein. This is normally done manually, although high resolution data may enable automatic model building. The process of model building and fitting the amino acids to the electron density can be both a time consuming and laborious process. Once the amino acids have been fitted to the electron density it is necessary to refine the structure. Refinement attempts to maximise the correlation between the experimentally calculated electron density and the electron density calculated from the protein model built. Refinement also attempts to optimise the geometry and disposition of the atoms and amino acids within the user-constructed model of the protein structure. Sometimes manual re-building of the structure will be required to release the structure from local energetic minima. There are now several software packages available that enable an experimentalist to carry out refinement of a protein structure. There are certain geometry and correlation diagnostics that are used to monitor the progress of a refinement. These diagnostic parameters are monitored and rebuilding/refinement continued until the experimenter is satisfied that the structure has been adequately refined.

Description of Anomalous Scattering Theory

If the energy of incident X-rays is close to the minimum energy that is required to eject a bound electron from an innermost shell of an atom, the scattering of the X-rays is described as "anomalous". In the process of "normal" scattering, the electrons are forced to undergo vibrations at the same frequency as that of the incident X-ray photon, emitting elastically scattered photons (i.e. no change in frequency) in the process. However, because this frequency is far from the natural frequency of vibration of the electron there is no effect on the scattered photon from this natural vibration. In the process of "anomalous" scattering, the frequency of the incident photon is close to the natural frequency of the electron, resulting in a resonance effect, which is manifested as a dispersion (decrease in velocity, though still no change in frequency) of the photon, as well as a vibration damping effect, which is manifested as absorption (decrease in intensity) of a fraction of the incident photons.

The anomalously scattered photon will thus have a phase angle associated with it that is retarded when compared with one being scattered normally, all other conditions being equal. If the structure consists of a mixture normal and anomalous scatterers this phase lag results in the breakdown of Friedel's law, as pairs of reflections with indices (h,k,l) and (−h,−k,−l) that are diffracted from opposite sides of the same crystal plane no longer have the same amplitudes.

By careful measurement of the two reflection intensities, and by consideration of their relative amplitudes, it is possible to make an initial estimate of the phases of all reflections that have been observed.

In theory all atoms could give rise to an anomalous scattering effect if irradiated with X-ray radiation of the appropriate wavelength. However as the scattering is directly proportional to the weight of the scatterer, heavier elements are normally chosen, e.g. sulphur or larger. The choice of element is also dependent on the ability to tune the energy of the X-rays to the required transition energy. As access to tuneable synchrotron X-radiation has become routine, the MAD technique has come of age. Incorporation of an anomalous scatterer may be via a number of routes e.g. by soaking crystals in solutions containing heavy atoms which then bind to the protein, by expressing recombinant proteins in media in which an element has been replaced by a suitable heavier element (e.g. the replacement of methionine with selenomethionine) leading to the incorporation of the element in certain amino acids themselves, or making use of naturally occurring co-factors which contain heavy elements.

As the contribution from the anomalous scatterer may be small, it is often important to obtain well-recorded, redundant data, and to facilitate detection of what may be a small signal, it is helpful to have a reference dataset to which the anomalous dataset can be compared. The routine collection of X-ray data at cryo-temperatures has prolonged crystal lifetime and has made collection of multiple datasets (at different wavelengths) from a single crystal now feasible for many crystal systems. Collection and analysis of multiple datasets from a single crystal has the advantage of eliminating all effects related to non-isomorphism (variations in structure between different crystals due to random variations in soaking and/or freezing conditions).

In the case of cytochrome P450, the haem group that forms the site of enzymatic activity naturally contains a single iron atom. Iron has transition energies at the high energies (long wavelengths) obtainable at tunable synchrotron beamlines.

P450 Crystal Stuctures

As of 2002, eight cytochrome P450 structures had been solved by X-ray crystallography and were available in the public domain. All of the cytochrome P450s, whose structures had been solved, were expressed in *E. coli*. Six structures correspond to bacterial cytochrome P450s: P450cam (CYP101 Poulos et al., 1985, *J. Biol. Chem.*, 260, 16122), the hemeprotein domain of P450BM3 (CYP102, Ravichandran et al., 1993, *Science*, 261, 731), P450terp (CYP108, Hasemann et al., 1994, *J Mol. Biol.* 236, 1169), P450eryF (CYP107A1, Cupp-Vickery and Poulos, 1995, *Nature Struct. Biol.* 2, 144), P450 14α-sterol demethylase (CYP51, Podust et al., 2001, *Proc. Natl. Acad. Sci. USA*, 98, 3068) and the crystal structure of a thermophilic cytochrome P450 (CYP119) from Archaeon sulfolobus solfataricus was solved (Yano et al., 2000, *J. Biol. Chem.* 275, 31086). The structure of cytochrome P450nor was obtained from the denitrifying fungus *Fusarium oxysporum* (Shimizu et al. 2000, *J. Inorg. Biochem.* 81, 191). The eighth structure is that of the rabbit 2C5 isoform, the first structure of a mammalian cytochrome P450 (Williams et al. 2000, *Mol. Cell.* 5, 121).

WO 03/035693 describes the crystallisation of a human 2C9 P450 protein molecule and provides an analysis of the protein crystal structure.

The reason why the mammalian cytochrome P450s have been particularly difficult to crystallize, compared to their bacterial counterparts, resides in the nature of these proteins. The bacterial cytochrome P450s are soluble whereas the mammalian P450s are membrane-associated proteins. Thus, structural studies on mammalian cytochrome P450s may use the combination of heterologous expression systems that allow expression of single cytochrome P450s at high concentration with modification of their sequences to improve the solubility and the behaviour of these proteins in solution.

Due to significant sequence differences from both the bacterial proteins and rabbit proteins, to fully understand the role of the human CYP450 enzymes in drug metabolism, the crystal structures of other human isoforms are still required.

DISCLOSURE OF THE INVENTION

The present invention relates to the crystal structure of human 3A4, which allows the binding location of the substrates in the enzyme to be investigated and determined.

More particularly, the present inventors have obtained an electron density map for 3A4 which is useful for the provision of atomic coordinate models of this protein, and also for other applications which are discussed in Section H below. In addition, the data of Table 3 herein provides structure factor phase data, permitting others of skill in the art to solve X-ray diffraction data of 3A4 and homologous protein crystals more readily in order to provide electron density maps.

In a further aspect, the invention provides a three dimensional structure of 3A4 set out in Table 5, and uses thereof.

In general aspects, the present invention is concerned with the provision of a 3A4 structure and its use in modelling the interaction of molecular structures, e.g. potential and existing pharmaceutical compounds, prodrugs, P450 inhibitors or substrates, or fragments of such compounds, prodrugs, inhibitors or substrates with this 3A4 structure.

These and other aspects and embodiments of the present invention are discussed below.

The above aspects of the invention, both singly and in combination, all contribute to features of the invention, which are advantageous.

BRIEF DESCRIPTION OF THE TABLES

Table 1 provides the data statistics
Table 2 provides the phasing statistics.
Table 3 (FIG. 1) provides the structure factors and phases which can be used to generate an electron density map of the 3A4 crystal structure.
Table 4 provides refinement statistics.
Table 5 (FIG. 2) sets out the coordinate data of the structure of 3A4.
Table 6 (FIG. 3) sets out one possible set of coordinate data of a loop region of 3A4.
Table 7 details binding site residues of 3A4.
Table 8 sets out newly identified binding site residues of 3A4.

BRIEF DESCRIPTION OF THE DRAWINGS

FIG. 1 sets out Table 3.
FIG. 2 sets out Table 5.
FIG. 3 sets out Table 6.

DETAILED DESCRIPTION OF THE INVENTION

A. Protein Crystals.

The present invention provides a crystal of 3A4 having an orthorhomobic space group I222, and unit cell dimensions 78 Å, 100 Å, 132 Å, 90°, 90°, 90°. Unit cell variability of 5% may be observed in all dimensions.

Such a crystal may be obtained using the methods described in the accompanying examples.

The crystal may be of a 3A4 protein which is desirably truncated in its N-terminal region to delete the hydrophobic trans-membrane domain, and the region is replaced by a short (e.g. 8 to 20) amino acid sequence. For expression of the human 3A4 P450, we have used an N-terminal sequence MAYGTHSHGLFKKLGI (SEQ ID NO:3) in place of the native N-terminal residues, which increases expression of the proteins in *E. coli* and increases solubility.

The 3A4 P450 may optionally comprise a tag, such as a C-terminal polyhistidine tag to allow for recovery and purification of the protein.

Our experiments have been based on the use of the particular N-terminal truncation mentioned above, and this protein also comprises a polyhistidine tag at the C-terminus. The N-terminal truncation and tag are both features which can be varied by those of skill in the art using routine skill. For example, alternative N-terminal sequence might be utilised, for example for production in host cells other than *E. coli*. Likewise, other tags may be used for purification of the protein as described below. These N- and C-terminal modification may be made to a 3A4 protein which retains the core sequence of the wild type protein from the residue 17 onwards of SEQ ID NO:2 shown herein, up to the residue immediately preceding the polyhistidine tag.

Where present, the N-terminal sequence is preferably not the full length wild-type sequence, and preferably smaller than 30, e.g. 20 residues in size. Preferably, it is shorter that the wild type sequence. Preferably, the N-terminal region is the truncation illustrated in the accompanying examples. This type of N-terminal sequence reduces the tendency of 3A4 to anchor to membranes and to aggregate compared to the wild type sequence. The truncation utilised here has wild-type residues 3–24 deleted.

Where present, the C-terminal sequence is preferably no larger than 30, and preferably no larger than 10 amino acids in size.

The 3A4 sequence may be that of the core sequence illustrated herein, or an allele thereof, or a variant which retains the ability to form crystals under the conditions illustrated herein. Such variants include those with a number of amino acid substitutions, for example 1, 2, 3, 4, 5, 6, 7, 8, 9 or 10 amino acids by an equivalent or fewer number of amino acids. Further examples of variants, including mutants, are discussed further herein below.

The methodology used to provide a P450 crystal illustrated herein may be used generally to provide a human 3A4 crystal resolvable at a resolution of at least 3.0 Å, and preferably at least 2.8 Å.

The invention thus further provides a 3A4 crystal having a resolution of at least 3.0 Å, preferably at least 2.8 Å.

The proteins may be wild-type proteins or variants thereof, which are modified to promote crystal formation, for example by N-terminal truncations and/or deletion of loop regions, which prevent crystal formation.

In a further aspect, the invention provides a method for making a P450 protein crystal, particularly of a 3A4 protein comprising the core sequence of 3A4 (as defined above) or a variant thereof, which method comprises growing a crystal by vapor diffusion using a reservoir buffer that contains 0.05–0.2 M HEPES pH 7.0–7.8, 2.5–10% IPA, 0–20% PEG 4000, 0–0.3 M sodium chloride, 0–10% PEG 400, 0–10% glycerol, preferably 0.1 M HEPES pH 7.2, 5% IPA, 10% PEG 4000. The crystal is grown by vapor diffusion and is performed by placing an aliquot of the solution on a cover slip as a hanging drop above a well containing the reservoir buffer. The concentration of the protein solution used was 0.3–0.7 mM.

Crystals of the invention also include crystals of 3A4 mutants, chimeras, homologues in the 3A family (e.g. 3A1, 3A5, 3A7, 3A12 and 3A43) and alleles.

(i) Mutants

A mutant is a 3A4 protein characterized by the replacement or deletion of at least one amino acid from the wild type 3A4. Such a mutant may be prepared for example by site-specific mutagenesis, or incorporation of natural or unnatural amino acids.

The present invention contemplates "mutants" wherein a "mutant" refers to a polypeptide which is obtained by replacing at least one amino acid residue in a native or synthetic 3A4 with a different amino acid residue and/or by adding and/or deleting amino acid residues within the native polypeptide or at the N— and/or C-terminus of a polypeptide corresponding to 3A4, and which has substantially the same three-dimensional structure as 3A4 from which it is derived. By having substantially the same three-dimensional structure is meant having a set of atomic structure co-ordinates that have a root mean square deviation (r.m.s.d.) of less than or equal to about 2.0 Å (preferably less than 1.55 or 1.5 Å, more preferably less than 1.0 Å, and most preferably less than 0.5 Å) when superimposed with the atomic structure co-ordinates of the 3A4 from which the mutant is derived when at least about 50% to 100% of the $C_\alpha$ atoms of the 3A4 are included in the superposition. A mutant may have, but need not have, enzymatic or catalytic activity.

To produce homologues or mutants, amino acids present in the said protein can be replaced by other amino acids having similar properties, for example hydrophobicity, hydrophobic moment, antigenicity, propensity to form or break α-helical or β-sheet structures, and so on. Substitutional variants of a protein are those in which at least one amino acid in the protein sequence has been removed and a different residue inserted in its place. Amino acid substitutions are typically of single residues but may be clustered depending on functional constraints e.g. at a crystal contact. Preferably amino acid substitutions will comprise conservative amino acid substitutions. Insertional amino acid variants are those in which one or more amino acids are introduced. This can be amino-terminal and/or carboxy-terminal fusion as well as intrasequence. Examples of amino-terminal and/or carboxy-terminal fusions are affinity tags, MBP tag, and epitope tags.

Amino acid substitutions, deletions and additions which do not significantly interfere with the three-dimensional structure of the 3A4 will depend, in part, on the region of the 3A4 where the substitution, addition or deletion occurs. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well-known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

In some instances, it may be particularly advantageous or convenient to substitute, delete and/or add amino acid residues in order to provide convenient cloning sites in the cDNA encoding the polypeptide, to aid in purification of the polypeptide, etc. Such substitutions, deletions and/or additions which do not substantially alter the three dimensional structure of 3A4 will be apparent to those having skills in the art.

It should be noted that the mutants contemplated herein need not exhibit enzymatic activity. Indeed, amino acid substitutions, additions or deletions that interfere with the catalytic activity of the 3A4 but which do not significantly alter the three-dimensional structure of the catalytic region are specifically contemplated by the invention. Such crystalline polypeptides, or the atomic structure co-ordinates obtained there from, can be used to identify compounds that bind to the protein.

The residues for mutation could easily be identified by those skilled in the art and these mutations can be introduced by site-directed mutagenesis e.g. using a Stratagene QuikChange™ Site-Directed Mutagenesis Kit or cassette mutagenesis methods (see e.g. Ausubel et al., eds., *Current Protocols in Molecular Biology*, John Wiley & Sons, Inc., New York, and Sambrook et al., *Molecular Cloning: a Laboratory Manual,* 2nd ed., Cold Spring Harbor Laboratory Press, Cold Spring Harbor, N.Y., (1989)).

(ii) Alleles

The present invention contemplates "alleles" wherein allele is a term coined by Bateson and Saunders (1902) for characters which are alternative to one another in Mendelian inheritance (Gk. Allelon, one another; morphe, form). Now the term allele is used for two or more alternative forms of a gene resulting in different gene products and thus different phenotypes. An allele contains nucleotide changes that have been shown to affect transcription, splicing, translation, post-transcriptional or post-translational modifications or result in at least one amino acid change. These different alleles are particularly important in P450s as some confer different metabolic clearance rates of specific drugs onto the phenotype. Alleles of P450s are often only different by one or two amino acids. As of 2002, 25 alleles of 3A4 have been identified, where wild type is CYP3A4*1A (NCBI ACCESSION M18907, Gonzalez F J, Schmid B J, Umeno M, Mcbride O W, Hardwick J P, Meyer U A, Gelboin H V, Idle J R, DNA 1988 Mar,7(2):79–86).

To the extent that the present invention relates to 3A4-ligand complexes and mutant, homologue, analogue, allelic form, species variant proteins of 3A4, crystals of such proteins may be formed. The skilled person would recognize that the conditions provided herein for crystallising 3A4 may be used to form such crystals. Alternatively, the skilled person would use the conditions as a basis for identifying modified conditions for forming the crystals.

Thus the aspects of the invention relating to crystals of 3A4, may be extended to crystals of mutant and mutants of 3A4 which result in homologue, allelic form, and species variant.

(iii) Crystallization of 3A4

To produce crystals of 3A4 protein the final protein is, conveniently, concentrated to 10–60, e.g. 20–40 mg/ml in 10–100 mM potassium phosphate with high salt (e.g. 500 mM NaCl or KCl) by using concentration devices which are commercially available. Crystallisation of the protein is set up by the 0.5–2 µl hanging drop method and the protein is crystallised by vapour diffusion at 5–25° C. against a range of vapour diffusion buffer compositions.

Typically the vapour diffusion buffer comprises 0–27.5%, preferably 2.5–27.5% PEG 1K–20 K, preferably 1–8K or PEG 2000MME–5000MME, preferably PEG 2000 MME, or 0–10% Jeffamine M-600 and/or 5–20%, e.g. 10–20% propanol or 15–20% ethanol or about 15%–30%, e.g. about 15% 2-methyl-2,4-pentanediol (MPD), optionally with 0.01 M –1.6 M salt or salts and/or 0–0.15, e.g. 0–0.1, M of a solution buffer and/or 0–35%, such as 0–15%, glycerol and/or 0–35% PEG300–400; but preferably:

10–25% PEG 1K–8K or PEG 2000MME or 0–10% Jeffamine M-600 and/or 5–15%, e.g. 10–15% propanol or ethanol, optionally with 0.1 M –0.2 M salt or salts and/or 0–0.15, e.g. 0–0.1 M solution buffer and/or PEG400, but more preferably:

15–20% PEG 3350 or PEG 4000 or PEG 2000MME or 0–10% Jeffamine M-600 or 5–15%, e.g. 10–15% propanol or ethanol, optionally with 0.1 M –0.2 M salt or salts and/or 0–0.15 M solution buffer.

The salt may be an alkali metal (particularly lithium, sodium and potassium), alkaline earth metal (e.g. magnesium or calcium), ammonium, ferric, ferrous or transition metal salt (e.g. zinc) of a halide (e.g. bromide, chloride or fluoride), acetate, formate, nitrate, sulfate, tartrate, citrate or phosphate. This includes sodium fluoride, potassium fluoride, ammonium fluoride, ammonium acetate, lithium acetate, magnesium acetate, sodium acetate, potassium acetate, calcium acetate, zinc acetate, ammonium chloride, lithium chloride, magnesium chloride, potassium chloride, sodium chloride, potassium bromide, magnesium formate, sodium formate, potassium formate, ammonium formate, ammonium nitrate, lithium nitrate, potassium nitrate, sodium nitrate, ammonium sulfate, potassium sulfate, lithium sulfate, sodium sulfate, di-sodium tartrate, potassium sodium tartrate, di-ammonium tartrate, potassium dihydrogen phosphate, tri-sodium citrate, tri-potassium citrate, zinc acetate, ferric chloride, calcium chloride, magnesium nitrate, magnesium sulfate, sodium dihydrogen phosphate, di-sodium hydrogen phosphate, di-potassium hydrogen phosphate, ammonium dihydrogen phosphate, di-ammonium hydrogen phosphate, tri-lithium citrate, nickel chloride, ammonium iodide, di-ammonium hydrogen citrate.

Solution buffers if present include, for example, Hepes, Tris, imidazole, cacodylate, tri-sodium citrate/citric acid, tri-sodium citrate/HCl, acetic acid/sodium acetate, phosphate-citrate, sodium potassium phosphate, 2-(N-morpholino)-ethane sulphonic acid/NaOH (MES), CHES or bis-trispropane.

The pH range is desirably maintained at pH 4.2–8.5, preferably 4.7–8.5.

Solution buffers if present can also include, for example, bicine, bis-tris, CAPS, MOPS, ADA which allow the pH to be maintained in the range 5.8–11.

Crystals may be prepared using a Hampton Research Screening kits, Poly-ethylene glycol (PEG)/ion screens, PEG grid, Ammonium sulphate grid, PEG/ammonium sulphate grid or the like.

Crystallisation may also be performed in the presence of an inhibitor of P450, e.g. fluoroxamine or 2-phenyl imidazole. 3A4 crystallisation may also be performed in the presence of one or more inhibitors e.g. ketoconazole and/or in the presence of one or more substrate(s) e.g. testosterone.

Additives can be added to a crystallisation condition identified to influence crystallisation. Additive Screens are to be used during the optimisation of preliminary crystallisation conditions where the presence of additives may assist in the crystallisation of the sample and the additives may improve the quality of the crystal e.g. Hampton Research additive screens which use glycerol, polyols and other protein stabilizing agents in protein crystallisation (R. Sousa. Acta. Cryst. (1995) D51, 271–277) or divalent cations (Trakhanov, S. and Quiocho, F. A. Protein Science (1995) 4,9, 1914–1919).

In addition, detergents may be added to a crystallisation condition to improve the crystallisation behaviour e.g. the ionic, non-ionic and zwitterionic detergents found in the Hampton Research detergent screens (McPherson, A., et al., The effects of neutral detergents on the crystallization of soluble proteins, J. Crystal Growth (1986) 76, 547–553).

Alternatively, the vapour diffusion buffer typically comprises 0–27.5% PEG 1K–20 K, preferably 1–8K or PEG 2000MME–5000MME, preferably PEG 2000 MME, or 0–10% Jeffamine M-600 and/or 1–20%, e.g. 1–20% propanol or 15–20% ethanol or about 1%–30%, e.g. about 2–25% 2-methyl-2,4-pentanediol (MPD), optionally with 0.01 M –1.6 M salt or salts and/or 0–0.15 M, e.g. 0–0.1 M, of a solution buffer and/or 0–35%, such as 0–15%, glycerol and/or 0–35% PEG300–400; but preferably:

0–27.5%, preferably 2.5–27.5% PEG 1K–20 K, most preferably 5–20% PEG 4K or PEG 2000MME–5000MME, preferably PEG 2000 MME, and 1–20% alcohol, e.g. 1–20% propanol e.g. iso-propanol or 2–25% 2-methyl-2,4-pentanediol (MPD), optionally with 0.01 M –1.6 M salt or salts and/or 0–0.15 M, e.g. 0–0.1 M, of a solution buffer and/or 0–35%, such as 0–15%, glycerol and/or 0–35% PEG300–400.

B. Electron Density Map

In one aspect, the invention provides a crystal of 3A4 having the structure factors and phases of Table 3.

In a further aspect, the invention also provides a crystal of P450 having the electron density map generated from the data of Table 3.

An advantageous feature of the electron density map is that it has a resolution of about 2.8 Å.

Table 3 has eight columns. The first three columns are the indices h, k and l of each individual reflection. Columns four and five are the experimentally measured structure factors and the associated standard deviations of the peak wavelength, respectively. Column six is the solvent flattened structure factor amplitude. Column seven is the solvent flattened structure factor phase. Column eight is the solvent flattened figure of merit associated with the reflection. The data of columns six to eight were generated from the experimentally measured structure factors and by using the phasing procedure in SHARP (see equation (2) in de la Fortelle & Bricogne, 1997) that are then used in density modification.

The best electron density map for structural interpretation is then calculated via a Fourier transform, using the following formula $$\rho(x, y, z) = \frac{1}{V} \sum_h \sum_k \sum_l |F(h, k, l)| \exp[-2\pi i(hx + ky + lz) + i\varphi(h, k, l)]$$

Thus the electron density map can be generated from Table 3 using columns six and seven using, for example, the FFT program which is part of the CCP4 suite of programs (Collaborative Computational Project 4. The CCP4 Suite: Programs for Protein Crystallography, *Acta Crystallographica*, D50, (1994), 760–763.). The resulting electron density map can then be viewed, interpreted or models built into it using a crystallographic graphical viewing program such as "O" (Jones et al., *Acta Crystallographica*, A47, (1991), 110–119) or "QUANTA" (1994, San Diego, Calif.: Molecular Simulations, Jones et al., Acta Crystallography A47 (1991), 110–119).

Errors in electron density maps derive principally from errors in the phase angles (ϕ) of the structure factors used in their calculation; errors in the corresponding amplitudes (|F|) are normally insignificant in comparison. The expected error in the phase of a structure factor is normally expressed as a "figure of merit" (m), which can be defined as the expected value of the cosine of the error in the "best" phase (that value of the phase which minimises the root-mean-square error $\sigma(\rho)$ in the electron density).

$$m = <\cos(\Delta\phi_{best})>$$

The actual (but unknown) phase error will vary significantly from one structure factor to the next, partly because of the random nature of experimental error and partly because structure factors with small amplitudes on average tend to have larger errors than those with large amplitudes (small amplitudes clearly do not contribute to the electron density summation as much as large ones; a structure factor with zero amplitude contributes nothing and so has a phase angle which is completely indeterminate). In addition, the phase error will tend to be greater at high resolution, because, for example, the small errors in locating the atoms used in the phase calculation have a greater effect at high resolution. For these reasons the figures of merit and phase errors are normally binned together and averaged either according to amplitude or to resolution (we have chosen to present the averaged figures of merit by resolution).

Blow & Crick (Blow, D. M. and Crick, F. H. C. Acta Cryst. (1959) 12, 794–802) derived an estimate of the RMS error in the electron density:

$$\sigma(\rho) = V^{-1}(\Sigma_h \Sigma_k \Sigma_l |F_{hkl}|^2 (l - m_{hkl}^2))^{1/2}$$

where the summation must be performed over the entire sphere of reciprocal space, not just the asymmetric unit.

Taking this formula, the above definition of the figure of merit and the above argument concerning the dependence of the phase error on the amplitude, it is suggested that for future purposes of comparing any set of phases with those in Table 3 the following weighted average of the cosine of the phase difference should be calculated:

$$\cos(\Delta\phi_{mean}) = (\Sigma_h \Sigma_k \Sigma_l |F_{hkl}|^2 \cos^2(\Delta\phi) / \Sigma_h \Sigma_k \Sigma_l |F_{hkl}|^2)^{1/2}$$

where the summations are performed in resolution shells, as well as over the entire sphere. From this the average phase difference $\Delta\phi_{mean}$ for the shell can be obtained: this is a measure of the average similarity of the two sets of phases, which may then be directly compared with the expected values of the phase error in column 10 of Table 2. Thus a value of the average phase difference less than the expected phase error for most of the resolution shells would imply that the two phase sets are providing similar information.

From Table 2 it can be seen that the average phase error for the phases in Table 3 is 45°, and hence if the difference between a second set of phases and the set of phases in Table 3 is less than 45° (over the same resolution) for the purposes of this invention the two set of phases and there resulting maps will be considered to be equivalent. The skilled person would understand that the values of the phases would change for a different origin of the coordinates and would make the appropriate adjustments.

This electron density map will allow the placement of a large percentage of all the atoms of 3A4, and reveals for the first time the spatial arrangement of the atoms of 3A4. Knowledge of the spatial arrangement of these atoms has clear implications in various fields. For example, knowledge of those atoms that form the enzymatic active site of the molecule will determine the physico-chemical properties of compounds that are ligands for the enzyme. The ability to modify these properties and hence to ultimately modify the enzyme's ability to metabolise a particular compound has clear value to the pharmacological industry. An indicator of the quality of the phases used to generate the map is as follows: inspection of anomalous log-likelihood gradient maps within SHARP (La Fortelle, E. de and Bricogne, G. (1997) *Methods in Enzymology* 276, 472–494) using the current heavy atom model reveals several peaks that correlate with the position of the sulphur atoms from cysteine and methionine residues (there is an expected contribution to the anomalous scattering from sulphur atoms of cysteine and methionine residues within the protein at the long wavelengths used to collect the data). The identification of the location of sulphur containing residues will facilitate assignment of the protein sequence to the model that will be built into the electron density map.

The data of Table 3 will in practice be used by those of skill in the art in electronic form to allow for processing of the data by computer programs such as those discussed herein. Thus in practice the programs will use all the data points of the Table. However, as indicated by the values in column 8 of the Table, the figure of merit values for some data points are relatively low. Whereas this may be taken into account in the processing of the data for the production of an electron density map, an alternative would be to ignore one or more of the data points associated with low merit values. Thus it will be understood by those of skill in the art that reference to the data of Table 3 includes the situation where a small fraction (less than 5% and preferably less than 1%, such as less than 0.5%) of the data point rows are not utilised.

Once interpretation of the current map has been completed to provide an electron density map it is possible to combine the experimental phase with phases derived from the model and thus generate a new electron density map that will allow most of the crystal structure to be defined.

From the electron density map provided herein one can obtain the co-ordinate data of the 3A4 crystal structure. An electron density map is interpreted by placing an atomic structure in the model such that the model fits the map. An assessment of how the model agrees with the map can be derived by calculating a correlation coefficient between the map and the transformed model, calculation of a 2Fo-Fc map or generation of R factor and Free R factors by a refinement protocol. Partial interpretation of the electron density map at high resolutions (e.g. 2.5–1.0 Å) can be automated in the case of high quality maps. For a lower resolution map (e.g. less than 2.5Å), or maps generated from phases with less than ideal phasing statistics, interpretation is more subjective and may require manual input. The coordinates then obtained from this provide a measure of atomic location in Ångstroms. The coordinates are a relative set of positions that define a shape in three dimensions, but the skilled person would understand that an entirely different set of coordinates having a different origin and/or axes could define a similar or identical shape. Furthermore, the skilled person would understand that varying the relative atomic positions of the atoms of the structure so that the root mean square deviation of the residue backbone atoms (i.e. the nitrogen-carbon-carbon backbone atoms) of the protein amino acid residues) is less than 2.0 Å, preferably less than 1.55 or 1.5 Å, more preferably less than 1.0 Å and most preferably less than 0.5 Å when superimposed on the coordinates derived from the data in Table 3 for the residue backbone atoms, will generally result in a structure which is substantially the same as the structure derived from of Table 3 in terms of both its structural characteristics and usefulness for structure-based analysis of P450-interactivity molecular structures.

Likewise the skilled person would understand that changing the number and/or positions of the water molecules and/or substrate molecules available from the electron density map from Table 3 will not generally affect the usefulness of the structure for structure-based analysis of P450-interacting structure. Thus for the purposes described herein as being aspects of the present invention, it is within the scope of the invention if: the coordinates available from Table 3 are transposed to a different origin and/or axes; the relative atomic positions of the atoms of the structure are varied so that the root mean square deviation of residue backbone atoms is less than 2.0 Å, preferably less than 1.55 or 1.5 Å, more preferably less than 1.0 Å, and most preferably less than 0.5 Å when superimposed on the coordinates for the residue backbone atoms; and/or the number and/or positions of water molecules and/or substrate molecules is varied.

Reference herein to the coordinate data derived from Table 3 and the like thus includes the coordinate data in which one or more individual values of the Table are varied in this way. By "root mean square deviation" we mean the square root of the arithmetic mean of the squares of the deviations from the mean.

Those of skill in the art will appreciate that in many applications of the invention, it is not necessary to utilise all the coordinates of a structure derived using the data in Table 3, but merely a portion of them. Such a portion of coordinates is also referred to herein as "selected coordinates". For example, as described below, in methods of modelling candidate compounds with 3A4, selected coordinates of 3A4 may be used, for example at least 5, preferably at least 10, more preferably at least 50 and even more preferably at least 100 atoms such as at least 500 or at least 1,000 of the 3A4 structure. Likewise, the other applications of the invention described herein, including homology modelling and structure solution, and data storage and computer assisted manipulation of the coordinates, may also utilise all or a portion of the coordinates from the electron density map in Table 3 may be used.

Also, modifications in the 3A4 crystal structure due to e.g. mutations, additions, substitutions, and/or deletions of amino acid residues (including the deletion of one or more 3A4 protomers) could account for variations in the 3A4 atomic coordinates. However, atomic coordinate data of 3A4 modified so that a ligand that bound to one or more binding sites of 3A4 would be expected to bind to the corresponding binding sites of the modified 3A4 are, for the purposes described herein as being aspects of the present invention, also within the scope of the invention. Reference herein to the coordinates from the electron density map from Table 3 thus includes the coordinates modified in this way. Preferably, the modified data define at least one 3A4 binding cavity.

By providing structure factor phase data, the present invention allows electron density models of other 3A4 crystals or crystals of homologous proteins to be obtained without the need to perform multiple anomalous diffraction (MAD) structure determination or MIR. Thus the invention provides a method of determining an electron density map of a target protein which is, or is homologous to, 3A4, which method comprises providing a crystal of the target protein, obtaining an X-ray diffraction of said protein, and generating an electron density map of said target protein by reference to the structure factor phase data of Table 3.

Analysis of phase differences is applicable when the crystal forms are the same. A more general method of comparing structures is based on an analysis of electron density maps. Therefore preferably, for the purposes of this invention two maps are considered to be equivalent if the linear correlation coefficient calculated for the maps is greater than 0, and more preferably greater than 0.25 or 0.5. If the electron densities of two maps are respectively defined by the variates $\rho_1$ and $\rho_2$, the linear correlation coefficient, CC, is defined as:

$$CC(\rho_1, \rho_2) = \frac{\sum (\rho_1 - \bar{\rho}_1)(\rho_2 - \bar{\rho}_2)}{\sqrt{\sum (\rho_1 - \bar{\rho}_1)^2 \sum (\rho_2 - \bar{\rho}_2)^2}}$$

where $\bar{\rho}_1$ and $\bar{\rho}_2$ are the respective average densities of the two maps. Clearly, if two maps are identical, the CC takes a value of 1. More detail regarding the use of the CC as a quantifier of the similarity of electron density maps is provided in Section K below.

To compute the CC for two maps, the following procedure may be used. Firstly, for each map a molecular (i.e. P450 3A4) mask is determined. This can be done, for example, using the CCP4 DM program to distinguish the P450 3A4 molecule from the solvent region. Each grid point within a molecular boundary is labelled '1' and each grid point outside a boundary is labelled '0'. One map is then transformed into maximum coincidence with the other map. This is accomplished, for example, using the CCP4 FFFEAR program to search for a best fit between two maps. During the transformation, rigid-body translations and rotations are allowed. One of the maps and the corresponding mask are then interpolated onto the grid points of the other map and mask. The interpolation can be performed using the Astex-ROTMAP program provided in Annex 1. Finally, the CC is computed for the masked maps, e.g. using the Astex-DENCOR program provided in Annex 2.

Furthermore, for the purposes of this invention an electron density map generated from the data of Table 3 and a set of atomic coordinates are considered to be equivalent if the CC calculated for the map generated from the data of Table 3 and a further electron density map generated from the atomic coordinate data is greater than 0, and more preferably greater than 0.25 or 0.5.

The computation of the CC in this case can follow the procedure discussed above with the additional prior step of generating the further electron density map from the atomic coordinate data. The generation can be conveniently performed using the standard CCP4 programs REFMAC and FFT to respectively calculate structure factors and then electron densities.

C. Crystal Coordinates.

In a further aspect, the invention also provides a crystal of P450 having the three dimensional atomic coordinates of Table 5. The atomic coordinates of Table 5 exclude residues from a loop region (261–270), which are not as clear and amenable for unambiguous interpretation as other regions of the protein. It is not unconceivable that this loop may adopt a different conformation under different conditions e.g. data from a different crystal, upon additional of compound, and the like. Crystals of the invention will thus comprise the coordinates of Table 5, with the coordinates of the loop region optionally being as further described herein, though other atomic coordinates for this loop region are not excluded.

An advantageous feature of the structure defined by the atomic coordinates of Table 5 is that it has a resolution of about 2.8 Å. More particularly, the residues in the binding pocket are well resolved.

A further advantage of the 3A4 structure described herein is that it is an unliganded, apo structure. This makes it particularly suitable for soaking in ligands and hence determining co-complex structures and is also ideal for homology modelling purposes as there is no conformational bias from a ligand.

Tables 5 and 6 gives atomic coordinate data for P450 3A4. In Tables 5 and 6 the third column denotes the atom, the fourth the residue type, the fifth the chain identification (in this case, chain A), the sixth the residue number (the atom numbering is with respect to the full length wild type protein), the seventh, eighth and ninth columns are the X, Y, Z coordinates respectively of the atom in question, the tenth column the occupancy of the atom, the eleventh the temperature factor of the atom, the twelfth the atom type.

Tables 5 and 6 are set out in an internally consistent format. For example (except in the case of Tyr 25), the coordinates of the atoms of each amino acid residue are listed such that the backbone nitrogen atom is first, followed by the C-alpha backbone carbon atom, designated CA, followed by side chain residues (designated according to one standard convention) and finally the carbon and oxygen of the protein backbone. Alternative file formats (e.g. such as a format consistent with that of the EBI Macromolecular Structure Database (Hinxton, UK)) which may include a different ordering of these atoms, or a different designation of the side-chain residues or haem molecule atoms, may be used or preferred by others of skill in the art. However it will be apparent that the use of a different file format to present or manipulate the coordinates of the Table is within the scope of the present invention.

The coordinates of Tables 5 and 6 provide a measure of atomic location in Angstroms, to 3 decimal places. The coordinates are a relative set of positions that define a shape in three dimensions, but the skilled person would understand that an entirely different set of coordinates having a different origin and/or axes could define a similar or identical shape. Furthermore, the skilled person would understand that varying the relative atomic positions of the atoms of the structure so that the root mean square deviation of the residue backbone atoms (i.e. the nitrogen-carbon-carbon backbone atoms of the protein amino acid residues) is less than 2.0 Å, preferably less than 1.55 or 1.5 Å, more preferably less than 1.0 Å, and most preferably less than 0.5 Å when superimposed on the coordinates provided in Table 5 or 6 for the residue backbone atoms, will generally result in a structure which is substantially the same as the structure of Tables 5 or 6 in terms of both its structural characteristics and usefulness for structure-based analysis of P450-interactivity molecular structures.

Likewise the skilled person would understand that changing the number and/or positions of the water molecules molecules of Table 5 will not generally affect the usefulness of the structure for structure-based analysis of P450-interacting structure. Thus for the purposes described herein as being aspects of the present invention, it is within the scope of the invention if: the Tables 5 or 6 coordinates are transposed to a different origin and/or axes; the relative atomic positions of the atoms of the structure are varied so that the root mean square deviation of residue backbone atoms is less than 2.0 Å, preferably less than 1.55 or 1.5 Å, more preferably less than 1.0 Å, and most preferably less than 0.5 Å when superimposed on the coordinates provided in Tables 5 or 6 for the residue backbone atoms; and/or the number and/or positions of water molecules is varied.

Reference herein to the coordinate data of Tables 5 or 6 and the like thus includes the coordinate data in which one or more individual values of the Table are varied in this way. By "root mean square deviation" we mean the square root of the arithmetic mean of the squares of the deviations from the mean.

With regard to the loop region referred to above, comparision of the different P450 structures determined to date indicates that various loops within the proteins can adopt very different conformations, often in response to compound binding. In the apo form of 3A4 which has been crystallized herein, a possible form of the loop region 261–270 is set out in Table 6. Thus in one aspect, the invention provides a crystal of P450 comprising amino acids having the atomic coordinates of Table 5, wherein the crystal additionally comprises amino acids having the atomic coordinates of Table 6.

Unless explicitly set out to the contrary, or otherwise clear from the context, reference throughout the present specification to the use of all or selected coordinates of or from Table 5 does not exclude the use of additional coordinates, particularly some or all of the coordinates of Table 6.

Protein structure similarity is routinely expressed and measured by the root mean square deviation (r.m.s.d.), which measures the difference in positioning in space between two sets of atoms. The r.m.s.d. measures distance between equivalent atoms after their optimal superposition. The r.m.s.d. can be calculated over all atoms, over residue backbone atoms (i.e. the nitrogen-carbon-carbon backbone atoms of the protein amino acid residues), main chain atoms only (i.e. the nitrogen-carbon-oxygen-carbon backbone atoms of the protein amino acid residues), side chain atoms only or more usually over C-alpha atoms only. For the purposes of this invention, the r.m.s.d. can be calculated over any of these, using any of the methods outlined below.

Methods of comparing protein structures are discussed in Methods of Enzymology, vol 115, pg 397–420. The necessary least-squares algebra to calculate r.m.s.d. has been given by Rossman and Argos (J. Biol. Chem., vol 250, pp7525 (1975)) although faster methods have been described by Kabsch (Acta Crystallogr., Section A, A92, 922 (1976)); Acta Cryst. A34, 827–828 (1978)), Hendrickson (Acta Crystallogr., Section A, A35, 158 (1979)); McLachan (J. Mol. Biol., vol 128, pp49 (1979)) and Kearsley (Acta Crystallogr., Section A, A45, 208 (1989)). Some algorithms use an iterative procedure in which the one molecule is moved relative to the other, such as that described by Ferro and Hermans (Ferro and Hermans, Acta Crystallographic, A33, 345–347 (1977)). Other methods e.g. Kabsch's algorithm locate the best fit directly.

Programs for determining r.m.s.d include MNYFIT (part of a collection of programs called COMPOSER, Sutcliffe, M. J., Haneef, I., Carney, D. and Blundell, T. L. (1987) Protein Engineering, 1, 377–384), MAPS (Lu, G. An Approach for Multiple Alignment of Protein Structures (1998, in manuscript and on http://bioinfo1.mbfys.lu.se/TOP/maps.html)).

It is usual to consider C-alpha atoms and the rmsd can then be calculated using programs such as LSQKAB (Collaborative Computational Project 4. The CCP4 Suite: Programs for Protein Crystallography, *Acta Crystallographica*, D50, (1994), 760–763), QUANTA (Jones et al., Acta Crystallography A47 (1991), 110–119 and commercially available from Accelerys, San Diego, Calif.), Insight (commercially available from Accelerys, San Diego, Calif.), Sybyl® (commercially available from Tripos, Inc., St Louis), O (Jones et al., *Acta Crystallographica*, A47, (1991), 110–119), and other coordinate fitting programs.

In, for example the programs LSQKAB and O, the user can define the residues in the two proteins that are to be paired for the purpose of the calculation. Alternatively, the pairing of residues can be determined by generating a sequence alignment of the two proteins, programs for sequence alignment are discussed in more detail in Section G. The atomic coordinates can then be superimposed according to this alignment and an r.m.s.d. value calculated. The program Sequoia (C. M. Bruns, I. Hubatsch, M. Ridderström, B. Mannervik, and J. A. Tainer (1999) Human Glutathione Transferase A4-4 Crystal Structures and Mutagenesis Reveal the Basis of High Catalytic Efficiency with Toxic Lipid Peroxidation Products, *Journal of Molecular Biology* 288(3): 427–439) performs the alignment of homologous protein sequences, and the superposition of homologous protein atomic coordinates. Alternatively, the program Astex-KFIT (see Annex 4) can be used. Once aligned, the r.m.s.d. can be calculated using programs detailed above. For sequence identical, or highly identical, the structural alignment of proteins can be done manually or automatically as outlined above. Another approach would be to generate a superposition of protein atomic coordinates without considering the sequence.

It is more normal when comparing significantly different sets of coordinates to calculate the r.m.s.d. value over C-alpha atoms only. It is particularly useful when analysing side chain movement to calculate the r.m.s.d. over all atoms and this can be done using LSQKAB and other programs.

Thus, for example, varying the atomic positions of the atoms of the structure by up to about 0.5 Å, preferably up to about 0.3 Å in any direction will result in a structure which is substantially the same as the structure of Table 5 in terms of both its structural characteristics and utility e.g. for molecular structure-based analysis.

Those of skill in the art will appreciate that in many applications of the invention, it is not necessary to utilise all the coordinates of Table 5, but merely a portion of them. For example, as described below, in methods of modelling candidate compounds with P450, selected coordinates of 3A4 may be used.

By "selected coordinates" it is meant for example at least 5, preferably at least 10, more preferably at least 50 and even more preferably at least 100, for example at least 500 or at least 1000 atoms of the 3A4 structure. Likewise, the other applications of the invention described herein, including homology modelling and structure solution, and data storage and computer assisted manipulation of the coordinates, may also utilise all or a portion of the coordinates (i.e. selected coordinates) of Table 5. The selected coordinates may include or may consist of atoms found in the 3A4 P450 binding pocket, as described herein below, and particularly those of Tables 7 and more particularly those of Table 8.

D. Description of Structure.

In the structure of 3A4 set out herein, the first resolvable residue is Tyr25 and the last residue Gly498 (the protein as purified comprises residues residues 1, 2, and 25–503 of the wild type sequence (using wild type numbering from M18907) and a four histidine tag as shown in SEQ ID 2). The overall fold of the protein is typical of all P450 structures solved to date and the secondary structure elements are named according to the convention adopted for P450s Ravichandran, K. G., Boddupalli, S. S., Hasermann, C. A., Peterson, J. A., and Deisenhofer, J. (1993) *Science* 261, 731–736. The haem sits centrally within the molecule with the single cysteine 442 coordinating and hydrogen bonds between the haem propionates and Arg 05, Trp126, Arg375 and Arg440.

There are a number of distinguishing differences between previously solved P450 structures and the structure of 3A4. There is a short helix towards the N terminus (here denoted helix A"), not observed previously the mammalian P450 structures, before helix A'. The B–C loop has less helical nature in 3A4 than in the previously solved human P450 2C9 structure (as contained in WO 03/035693 A2). This region along with the F–G loop region, has been implicated in forming an access channel (Podust, L. M., Stojan, J., Poulos, T. L., and Waterman, M. R. (2001) *J Inorg Biochem* 87, 227–235).

There are also some differences in the F helix (which is shorter than in the 2C9 structure), the F' helix and G' helix (which is shorter). The FG loop comprised 34 residues (210–243) and includes helix F' and helix G', compared to the 23 residues in the FG loop of 2C9. When compared to other P450s, the long FG loop of 3A4 is more due to the shortness of helix F than to the length of the FG loop itself. The B–C and F–G loops are in close proximity, forming two sides of the active site. It is widely accepted that 3A4 may bind several compound simultaneously, and can bind large compounds in excess of 1000 Da (e.g. erythromycin). Movement of these regions may be required to allow the compound entry and egress, and they may become more structured if in alternative conformations. The loops between helices G and H, and helices H and I are not clearly resolved in the electron density maps (residues 261–270, 277–290) and have been excluded from the model.

The dominating feature of the active site of substrate-free 3A4 is the cluster of phenylalanine residues (Phe57, Phe108, Phe213, Phe215, Phe219, Phe220, Phe241, Phe304) above the haem. Of these, some have been implicated by site directed mutagenesis to play a role in cooperativity and stereoselectivity. The majority of these residues lie within substrate region sites (SRS) (Gotoh, O. (1992) *J Biol Chem* 267, 83–90) first identified for the CYP 2C family of proteins.

Another cluster of four phenylalanine residues is found just below and to the side of the haem itself, in a position less clearly important for compound binding.

The kinetics exhibited by 3A4 can be complicated, with many literature examples citing one or more compound being accommodated simultaneously within the active site of 3A4 (Domanski et al, Biochemistry 2001, 40, 10150–10160). Site directed mutagenesis suggests that different substrates may bind at different regions of the active site. There is also evidence for homotropic cooperativity (interactions between a substrate and one or more effector molecules of the same chemical structure) and hetertropic cooperativity (where the substrate and effector molecules have different chemical structures).

Identification and Use of P450 Binding Pocket Residues.

The crystal structure for 3A4 has for the first time allowed the precise identification of all the residues that line the binding site of the enzyme (Table 7). Some residues proposed to be in the catalytic site by a variety of sources can now be shown not to be binding pocket residues but residues that hold the catalytic residues in place.

TABLE 7 below details all the residues that line the binding site of 3A4.

| Phe 57 | Asp 76 | Val 81 | Asn 104 | Arg 105 | Arg 106 |
|---|---|---|---|---|---|
| Pro 107 | Phe 108 | Gly 109 | Pro 110 | Val 111 | Met 114 |
| Ser 116 | Ala 117 | Ile 118 | Ser 119 | Ile 120 | Glu 122 |
| Thr 207 | Leu 210 | Leu 211 | Phe 215 | Phe 220 | Leu 221 |
| Ile 223 | Thr 224 | Ile 230 | Glu 234 | Val 235 | Leu 236 |
| Ile 238 | Cys 239 | Phe 241 | Pro 242 | Ala 297 | Ile 301 |
| Phe 302 | Ile 303 | Phe 304 | Ala 305 | Gly 306 | Glu 308 |
| Thr 309 | Ser 312 | Val 313 | Pro 368 | Ile 369 | Ala 370 |
| Met 371 | Arg 372 | Leu 373 | Glu 374 | Arg 375 | Ser 398 |
| Gly 481 | Leu 482 | Leu 483 | Glu 484 | | |

Some of these residues have previously been inferred to be in the binding site of 3A4 from modelling (e.g. homology modelling, SRS proposals, 3D/4D-QSAR, sequence alignments, or mutagenesis studies) which with the aid of the crystal structure can now be known to line the 3A4 binding pocket. Some residues found in the binding pocket have never before been identified as binding site residues. These are listed in Table 8. The identification of these will greatly facilitate the modelling of compound binding.

TABLE 8

Residues newly identified as lining the 3A4 binding pocket

| Phe 57 | Asp 76 | Val 81 | Arg 106 | Gly 109 | Pro 110 |
|---|---|---|---|---|---|
| Val 111 | Ser 116 | Ala 117 | Ile 118 | Glu 122 | Thr 207 |
| Phe 220 | Leu 221 | Ile 223 | Thr 224 | Ile 230 | Glu 234 |
| Val 235 | Leu 236 | Cys 239 | Phe 241 | Pro 242 | Ala 297 |
| Phe 302 | Ile 303 | Gly 306 | Ser 312 | Val 313 | Pro 368 |
| Arg 372 | Ser 398 | Gly 481 | Leu 482 | Leu 483 | Glu 484 |

Accordingly, in a preferred aspect of the invention, where the invention contemplates the use of selected coordinates in a method of the invention, such selected coordinates will comprise at least one coordinate, preferably at least one side-chain coordinate of an amino acid residue selected from either Table 7 or 8.

Preferably, the selected coordinates include the coordinates of all the atoms of Table 5 or Table 6 relating to at least one amino acid from Table 7 or 8.

Also preferred, whether all or just some atoms of a particular amino acid are selected, is that at least 2, more preferably at least 5, and most preferably at least 10 of the selected coordinates are of side chain residues from the corresponding number of different amino acid residues. These may be selected exclusively from either of Table 7 or 8, or a combination thereof. Preferably at least one side chain residue coordinate of Table 8 is included.

E. Chimeras.

The use of chimeric proteins to achieve desired properties is now common in the scientific literature. For example, Sieber et al (Nature Biotechnology (2001) 19, 456–460) produced hybrids between human cytochrome P450 isoform 1A2 and the bacterial P450 BM3, in order to make proteins with the specificity of 1A2, but which had desirable expression and solubility properties of BM3. Active site chimeras are also described: for example, Swairjo et al (Biochemistry (1998) 37, 10928–10936) made loop chimeras of HIV-1 and HIV-2 protease to try to understand determinants of inhibitor-binding specificity.

Of particular relevance are cases where the active site is modified so as to provide a surrogate system to obtain structural information. Thus Ikuta et al (J Biol Chem (2001) 276, 27548–27554) modified the active site of cdk2, for which they could obtain structural data, to resemble that of cdk4, for which no X-ray structure is currently available. In this way they were able to obtain protein/ligand structures from the chimaeric protein which were useful in cdk4 inhibitor design. In a similar way, based on comparison of primary sequences of highly related isoforms (such as 3A1, 3A5, 3A7, 3A12 or 3A43) the active site of the 3A4 protein could be modified to resemble those isoforms. Protein structures or protein/ligand structures of the chimaeric proteins could be used in structure-based alteration of the metabolism of compounds which are substrates of that related P450 isoform.

Even if the percentage of the amino acid sequence identity between mammalian P450 ranks from 20 to 80%, the overall folding of mammalian P450s is expected to be very similar, with the same spatial distribution of the structural elements. Furthermore, this class of enzymes exhibits distinct substrate specificities that rely on only a limited number of residues located in non-contiguous parts of the polypeptide chain. The substrate-binding pocket of P450 is generally constituted by residues that fall in the SRS regions (substrate recognition sites) defined by Gotoh (Gotoh, O, J. Biol. Chem, 267; 83–90 (1992)) and in loops of the molecule.

(i) Converting other P450 Proteins to 3A4-like Chimeras

Aspects of the present invention therefore relate to modification of P450 proteins such that the active sites mimic those of related isoforms. For example, from a knowledge of the structure and residues of the active site of the human 3A4 structure contained herein, a person skilled in the art could modify a P450 protein such that the active site mimicked that of human 3A4. This protein could then be used to obtain information on compound binding through the determination of protein/ligand complex structures using the chimaeric P450 protein.

For example, in one aspect the present invention provides a chimaeric protein having a binding cavity which provides a substrate specificity substantially identical to that of P450 3A4 protein, wherein the chimaeric protein binding cavity is lined by a plurality of atoms which correspond to selected P450 3A4 atoms lining the P450 3A4 binding cavity, and the relative positions of the plurality of atoms corresponding to the relative positions, as defined by Table 5, of the selected P450 3A4 atoms.

It is possible to postulate that only few changes would be required to inter-convert the substrate specificities of P450 isoforms that exhibit more than 70% of amino acid identity. 3A4 is 89% identical to 3A7, and 3A43 shares 76, 76, and 71% sequence identity on the amino acid level with CYP3A4, 3A5, and 3A7, respectively (Westlind et al, Biochemical and Biophysical Research Communications (2001), 281(5), 1349–1355; Gellner et al, Pharmacogenetics (2001), 11(2), 111–121). For example, although 3A4 and 3A5 are 84% identical they exhibit clear substrate specificity differences (Aoyama T; Yamano S; Waxman D J; Lapenson D P; Meyer U A; Fischer V; Tyndale R; Inaba T; Kalow W; Gelboin H V; Journal Of Biological Chemistry (Jun. 25, 1989), 264(18), 10388–95). CYP3A4 is inhibited by mifepristone and yet CYP3A5 is not. Using a panel of 3A4/3A5 chimaeric proteins, Khan et al (Khan, Kishore K.; He, You Qun; Correia, Maria Almira; Halpert, James R; Drug Metabolism and Disposition (2002), 30(9), 985–990) have identified the sequence differences that explain the lack of inhibition of CYP3A5. These studies have demonstrated the feasibility of the transfer of substrate specificities between 3A4 and 3A5 by mutating residues within the SRS regions. CYP3A4 and CYP3A5 also show different regioselectivity towards aflatoxin B1 (AFB1) biotransformation, and a site-directed mutagenesis program to understand the structural features responsible for these differences, concluded that residues within the SRS region 2 alone were responsible for these differences (Huifen Wang, Ryan Dick, Hequn Yin, Estefania Licad-Coles, Deanna L. Kroetz, Grazyna Szklarz, Greg Harlow, James R. Halpert, and Maria Almira Correia, Biochemistry, 37 (36), 12536–12545, 1998).

The substrate specificity of an enzyme generally relies on only a limited number of residues located in non-contiguous parts of the polypeptide chain. The substrate specificities of these isoforms could be analysed by substituting these residues by site-directed mutagenesis. The minimal changes that would be required to convert another P450 protein into a 3A4-like chimera could be at least two amino acids selected from binding pocket, particularly the amino acid binding pocket residues of Table 7 or 8, more preferably Table 8. These mutations can be introduced by site-directed mutagenesis e.g. using a Stratagene QuikChange™ Site-Directed Mutagenesis Kit or cassette mutagenesis methods (Ausubel, F. M., Brent, R., Kingston, R. E. et al. editors. Current Protocols in Molecular Biology. John Wiley & Sons, Inc., New York, Sambrook, J., Fritsch, E. F., and Maniatis, T. (1989). Molecular Cloning: a Laboratory Manual. 2nd ed. Cold Spring Harbor Laboratory Press, Cold Spring Harbor, N.Y.). Thus the invention provides a chimaeric protein having one or more binding pockets defined by the residues of Table 5 and preferably including some or all of the binding pocket residues of Tables 7 or 8.

(ii) Converting 3A4 to Other 3A Isoforms

This strategy could clearly be applied for proteins that exhibit high sequence homology with or without overlapping substrate specificities and from different species. The use of the crystal structure solved for 3A4 would allow the characterization of the binding mode of a variety of molecules in the substrate pocket of these proteins. This in turn would allow the identification of residues to be modified in the human isoforms to convert them into metabolising enzymes with different substrate or regioselective preferences.

In one embodiment, a chimaeric 3A4 enzyme is produced which is isoformal with another enzyme of the 3A subfamily. For example, 3A4 could be turned into a 3A1-like, 3A5-like, 3A7-like, 3A12-like or 3A43-like isoform with a few amino acid changes. Based on the information available from the literature on the structure/activity studies performed on the human 3A4, 3A5, 3A7 and 3A43 isoforms, and the analysis of the structure of the human 3A4, we postulate that the 3A4 protein could be converted to a 3A5-like, 3A7-like or 3A43-like isoform with the substrate specificities attributed to 3A5, 3A7 or 3A43, 3A5 in particular based on the references above. The mutations can be introduced by site-directed mutagenesis or cassette mutagenesis methods, as described herein.

The crystallization of such chimeras and the determination of the three-dimensional structures relies on the ability of our 3A4 protein to yield crystals that diffract at high resolution. The aim is to modify the inside part of 3A4 to produce a new substrate binding site of 3A5, 3A7 or 3A43 without modifying the outside shell of the proteins that allow the protein to crystallize.

F. Homology Modelling.

The invention also provides a means for homology modelling of other proteins (referred to below as target P450 proteins). By "homology modelling", it is meant the prediction of related P450 structures based either on X-ray crystallographic data or computer-assisted de novo prediction of structure, based upon manipulation of the coordinate data derivable from the electron density map calculated from Table 3.

"Homology modelling" extends to target P450 proteins which are analogues or homologues of the 3A4 protein whose structure has been determined in the accompanying examples. It also extends to P450 protein mutants of 3A4 protein itself.

The term "homologous regions" describes amino acid residues in two sequences that are identical or have similar (e.g. aliphatic, aromatic, polar, negatively charged, or positively charged) side-chain chemical groups. Identical and similar residues in homologous regions are sometimes described as being respectively "invariant" and "conserved" by those skilled in the art.

In general, the method involves comparing the amino acid sequences of the 3A4 protein of SEQ ID 2 with a target P450 protein by aligning the amino acid sequences. Amino acids in the sequences are then compared and groups of amino acids that are homologous (conveniently referred to as "corresponding regions") are grouped together. This method detects conserved regions of the polypeptides and accounts for amino acid insertions or deletions.

Homology between amino acid sequences can be determined using commercially available algorithms. The programs BLAST, gapped BLAST, BLASTN, PSI-BLAST and BLAST2 (provided by the National Center for Biotechnology Information) are widely used in the art for this purpose, and can align homologous regions of two amino acid sequences. These may be used with default parameters to determine the degree of homology between the amino acid sequence of the SEQ ID 2 protein and other target P450 proteins which are to be modelled.

Analogues are defined as proteins with similar three-dimensional structures and/or functions with little evidence of a common ancestor at a sequence level.

Homologues are defined as proteins with evidence of a common ancestor, i.e. likely to be the result of evolutionary divergence and are divided into remote, medium and close sub-divisions based on the degree (usually expressed as a percentage) of sequence identity.

A homologue is defined here as a protein with at least 15% sequence identity or which has at least one functional domain, which is characteristic of 3A4. This includes polymorphic forms of 3A4.

There are two types of homologue: orthologues and paralogues. Orthologues are defined as homologous genes in different organisms, i.e. the genes share a common ancestor coincident with the speciation event that generated them. Paralogues are defined as homologous genes in the same organism derived from a gene/chromosome/genome duplication, i.e. the common ancestor of the genes occurred since the last speciation event.

The homlogues could also be polymorphic forms of 3A4 such as alleles or mutants as described in section (A).

Once the amino acid sequences of the polypeptides with known and unknown structures are aligned, the structures of the conserved amino acids in a computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions may be assigned manually by using standard peptide geometries or by molecular simulation techniques, such as molecular dynamics. The final step in the process is accomplished by refining the entire structure using molecular dynamics and/or energy minimization.

Homology modelling as such is a technique that is well known to those skilled in the art (see e.g. Greer, *Science*, Vol. 228, (1985), 1055, and Blundell et al., *Eur. J. Biochem*, Vol. 172, (1988), 513). The techniques described in these references, as well as other homology modelling techniques, generally available in the art, may be used in performing the present invention.

Homology modelling may be performed on a three dimensional atomic coordinate model of 3A4 obtained using the present invention. A preferred model is that of Table 5. Thus a person of skill in the art will be able to obtain a representation of the three dimensional structure of a crystal of cytochrome P450 3A4 by a method which comprises providing the data of at least columns 1, 2, 3, 6 and 7 of Table 3 and constructing an electron density map of said data. This method is optionally performed by reference to the data of column 8 of said Table. Having obtained an electron density map, the person of skill in the art will be able to generate an initial model of 3A4 fitted to said map, which may then be refined by reference to the data of columns 4 and 5 of said Table. Refinement may also take place of other models generated from other 3A4 crystal structures.

The refined data may then be used in a method which comprises calculating the three-dimensional coordinates of one or more atoms of 3A4 in said crystal to provide a first three dimensional structure of 3A4. The positions of one or more atoms in said first structure may be varied to provide a second structure with three-dimensional coordinates having a r.m.s.d of less than 2.0 Å from said first structure, preferably less than 1.55 or 1.5 Å, more preferably less than 1.0 Å, and most preferably less than 0.5 Å. This may be performed for a variety of reasons, for example in the light of other P450 models, or to manually fit regions of 3A4 structures which may need to be further optimised.

Thus the invention provides a method of homology modelling comprising the steps of:
  (a) aligning a representation of an amino acid sequence of a target P450 protein of unknown three-dimensional structure with the amino acid sequence of the P450 of SEQ ID 2 to match homologous regions of the amino acid sequences;
  (b) modelling the structure of the matched homologous regions of said target P450 of unknown structure on the corresponding regions of the P450 structure as obtained as described above and/or that of Table 5 or selected coordinates thereof; and
  (c) determining a conformation (e.g. so that favourable interactions are formed within the target P450 of unknown structure and/or so that a low energy conformation is formed) for said target P450 of unknown structure which substantially preserves the structure of said matched homologous regions.

Preferably one or all of steps (a) to (c) are performed by computer modelling.

The co-ordinate data obtained from the Table 3, e.g. that of Table 5 or selected coordinates thereof, will be particularly advantageous for homology modelling of other human P450 proteins, in particular human P450s such as 2C9, 2C19, 2D6, 3A5, 3A7, 1A1, 1A2, 2E1 preferably 3A5, 3A7 and 3A43. These proteins may be the target P450 protein in the method of the invention described above.

The aspects of the invention described herein which utilise the P450 structure in silico may be equally applied to homologue models of P450 obtained by the above aspect of the invention, and this application forms a further aspect of the present invention. Thus having determined a conformation of a P450 by the method described above, such a conformation may be used in a computer-based method of rational drug design as described herein.

G. Structure Solution

The electron density map of the human 3A4 P450 or the atomic coordinate data of 3A4 can also be used to solve the crystal structure of other target P450 proteins including other crystal forms of 3A4, mutants, co-complexes of 3A4, where X-ray diffraction data or NMR spectroscopic data of these target P450 proteins has been generated and requires interpretation in order to provide a structure.

In the case of 3A4, this protein may crystallize in more than one crystal form. The data of Tables 3 or 5, or portions thereof, as provided by this invention, are particularly useful to solve the structure of those other crystal forms of 3A4. It may also be used to solve the structure of 3A4 mutants, 3A4 co-complexes, or of the crystalline form of any other protein with significant amino acid sequence homology to any functional domain of 3A4.

In the case of other target P450 proteins, particularly the human P450 proteins referred to in Section F above, the present invention allows the structures of such targets to be obtained more readily where raw X-ray diffraction data is generated.

Thus, where X-ray crystallographic or NMR spectroscopic data is provided for a target P450 of unknown three-dimensional structure, the electron density map of P450, derived from Table 3, or the atomic coordinate data derived from Table 5, may be used to interpret that data to provide a likely structure for the other P450 by techniques which are well known in the art, e.g. phasing in the case of X-ray crystallography and assisting peak assignments in NMR spectra.

One method that may be employed for these purposes is molecular replacement. In this method, the unknown crystal structure, whether it is another crystal form of 3A4, a 3A4 mutant, a 3A4 chimera or an 3A4 co-complex, or the crystal of a target P450 protein with amino acid sequence homology to any functional domain of 3A4, may be determined using the 3A4 structure coordinates derivable from Table 3 or the coordinates of Table 5 of this invention. Furthermore, the electron density map as defined in Table 3 can be used directly for this purpose. This method will provide an accurate structural form for the unknown crystal more quickly and efficiently than attempting to determine such information ab initio.

Examples of computer programs known in the art for performing molecular replacement are CNX (Brunger A. T.; Adams P. D.; Rice L. M., Current Opinion in Structural Biology, Volume 8, Issue 5, October 1998, Pages 606–611 (also commercially available from Accelrys San Diego, Calif.), MOLREP (A. Vagin, A. Teplyakov, MOLREP: an automated program for molecular replacement, J. Appl. Cryst. (1997) 30, 1022–1025, part of the CCP4 suite) or AMoRe (Navaza, J. (1994). AMoRe: an automated package for molecular replacement. Acta Cryst. A50, 157–163).

Thus, in a further aspect of the invention provides a method for determining the structure of a protein, which method comprises;
  providing the coordinates obtained from the electron density map of Table 3,
  positioning the coordinates in the crystal unit cell of said protein so as to provide a structure for said protein.

Preferably the coordinates are those of Table 5 or selected coordinates thereof, which may include coordinates of atoms of the amino acid residues set out in Table 7 and more preferably in Table 8.

In a further aspect of the invention provides a method for determining the structure of a protein, which method comprises;
  providing the structure factor and phases of Table 3,
  positioning of a search model in the crystal unit cell of said protein so as to provide a structure for said protein.

The invention may also be used to assign peaks of NMR spectra of such proteins, by manipulation of the data of Tables 3 or 5.

In a preferred aspect of this invention the co-ordinates are used to solve the structure of target 3A4 particularly homologues of 3A4 for example P450s such as 3A5, 3A7 and 3A43.

H. Further Uses of Structure Factor and Phase Data

The data contained within Table 3 allows for the calculation of an electron density map using the solvent flattened phases (column 7) and the weighted structure factors (column 6). In addition, the data allows for the calculation of an electron density map using the solvent flattened phases (column 7), the Figure of Merit (column 8) and the observed structure factor amplitudes (column 4).

The phases provided in Table 3 can also be used to calculate a map with the Figure of Merit and a different structure factor amplitude from a same or related crystal form of 3A4, or a same or related crystal form of a homologous protein.

All of these maps can be used for the phased molecular replacement of other homologous proteins, as discussed above in Section G, specifically 3A4 homologues.

Aspects of the present invention therefore are, methods of using the phases of Table 3 (reciprocal space) for:
  a) calculating a map together with the solvent flattened structure factor amplitude (Table 3), or
  b) calculating a map together with the figure-of-merit and the measured structure factor amplitude (Table 3), or
  c) calculating a map together with the figure-of-merit (Table 3) and structure factor amplitudes from the same or related crystal form of 3A4 or a same or related crystal form of a 3A4 homologue, and
  d) use of any of these resulting electron densities (real space) from step a), b) or c) for molecular replacement.

In addition the map calculated from these structure factors and phases could be used in cross crystal form averaging between different crystals forms of CYP 3A4. If a different crystal form of 3A4 or a crystal form of a 3A4 homologue was obtained, the data of Table 3 can be used in cross crystal averaging, in reciprocal space, to improve the phases of either crystal form.

Complexes can be crystallized and analysed, and difference Fourier electron density maps can be calculated based on X-ray diffraction patterns of soaked or co-crystallized 3A4 and the structure factor and phases of Table 3. The difference Fourier electron density maps can then be analysed to determine whether and where a particular compound binds to 3A4 and/or changes the conformation of 3A4.

Thus it is possible to screen for ligand binding by the use of the differences between the structure factors of Table 3 and the structure factors derived from crystals into which a ligand has been introduced by soaking or co-crystallisation. The phases of Table 3 can then be used to generate a difference map.

A further aspect of the invention is therefore the use of the phases of Table 3 for calculating the difference Fourier map to identify whether a ligand has bound and its mode of binding:
  a) calculating a difference Fourier map (together with the figure-of-merit) between the measured amplitudes (as presented in Table 3) and structure factor amplitudes from a ligand co-complex, or
  b) calculating a difference Fourier map (together with the figure-of-merit) between any two sets of structure factor amplitudes for detecting ligands and/or heavy atoms, or
  c) calculating an anomalous Fourier map (together with the figure-of-merit) for any structure factor amplitudes for detecting ligands and/or heavy atoms which have an anomalous scattering contribution.

I. Computer Systems.

In another aspect, the present invention provides systems, particularly a computer system, the systems containing either (a) electron density map derivable from Table 3 or co-ordinate data therefrom, said data defining the three-dimensional structure of P450 or at least selected coordinates thereof; (b) structure factor data (where a structure factor comprises the amplitude and phase of the diffracted wave) for 3A4, said structure factor data being the data of Table 3; (c) atomic coordinate data of a target P450 protein generated by homology modelling of the target based on the coordinate data derivable from Table 3; (d) atomic coordinate data of a target P450 protein generated by interpreting X-ray crystallographic data or NMR data by reference to the electron density map according to Table 3 or co-ordinate data therefrom; or (e) structure factor data derivable from the atomic coordinate data of (c) or (d).

In a preferred aspect, the atomic coordinate data are the data of Table 5, or selected coordinates thereof.

For example the computer system may comprise: (i) a computer-readable data storage medium comprising data storage material encoded with the computer-readable data; (ii) a working memory for storing instructions for processing said computer-readable data; and (iii) a central-processing unit coupled to said working memory and to said computer-readable data storage medium for processing said computer-readable data and thereby generating structures and/or performing rational drug design. The computer system may further comprise a display coupled to said central-processing unit for displaying said structures.

The invention also provides such systems containing atomic coordinate data of target P450 proteins wherein such data has been generated according to the methods of the invention described herein based on the starting data provided by Table 3. In one aspect, such data are those of Table 5 or selected coordinates thereof.

Such data is useful for a number of purposes, including the generation of structures to analyse the mechanisms of action of P450 proteins and/or to perform rational drug design of compounds, which interact with P450, such as compounds, which are metabolised by P450s.

In a further aspect, the present invention provides computer readable media with at least one of (a) electron density map derivable from Table 3 or co-ordinate data therefrom, recorded thereon, said data defining the three-dimensional structure of P450, or at least selected coordinates thereof; (b) structure factor data for P450 recorded thereon, the structure factor data of Table 3; (c) atomic coordinate data of a target P450 protein generated by homology modelling of the target based on the coordinate data derivable from Table 3; (d) atomic coordinate data of a target P450 protein generated by interpreting X-ray crystallographic data or NMR data by reference to the data of Table 3; or (e) structure factor data derivable from the atomic coordinate data of (c) or (d). The atomic coordinate data may be that of Table 5, or selected coordinates thereof.

In another aspect, the invention provides a computer-readable storage medium, comprising a data storage material encoded with computer readable data, wherein the data are defined by all or a portion (e.g. selected coordinates as defined herein) of the structure coordinates of P450 of Table 5, or a homologue of said P450, wherein said homologue comprises backbone atoms that have a root mean square deviation from the Cα or backbone atoms (nitrogen-carbon$_\alpha$-carbon) of Table 5 of less than 2 Å, preferably less than 1.55 or 1.5 Å, more preferably less than 1.0 Å, and most preferably less than 0.5 Å.

As used herein, "computer readable media" refers to any medium or media, which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

By providing such computer readable media, the atomic coordinate data derived from Table 3 can be routinely accessed to model P450s or selected coordinates thereof. For example, RASMOL (Sayle et al., *TIBS*, Vol. 20, (1995), 374) is a publicly available computer software package, which allows access and analysis of atomic coordinate data for structure determination and/or rational drug design.

As used herein, "a computer system" refers to the hardware means, software means and data storage means used to analyse the atomic coordinate data derived from Table 3 (e.g. that of Table 5 or selected coordinates thereof), as well as the electron density map of Table 3 of the present invention. The minimum hardware means of the computer-based systems of the present invention comprises a central processing unit (CPU), input means, output means and data storage means. Desirably a monitor is provided to visualize structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

In another aspect, the invention provides a computer-readable storage medium, comprising a data storage material encoded with computer readable data, wherein the data are defined by all or a portion (e.g. selected coordinates as defined herein) of the structure coordinates of 3A4 obtainable from the data of Table 3 (such as that of Table 5 or selected coordinates thereof), or the electron density map of Table 3, or a homologue of 3A4, wherein said homologue comprises backbone atoms that have a root mean square deviation from the backbone atoms (nitrogen-carbon$_\alpha$-carbon) of co-ordinate data generated from Table 3 of not more than 2.0 Å, preferably less than 1.55 or 1.5 Å, more preferably less than 1.0 Å, and most preferably less than 0.5 Å.

The invention also provides a computer-readable data storage medium comprising a data storage material encoded with a first set of computer-readable data comprising Table 3, Table 5 or selected coordinates thereof; which, when combined with a second set of machine readable data comprising an X-ray diffraction pattern of a molecule or molecular complex of unknown structure, using a machine programmed with the instructions for using said first set of data and said second set of data, can determine at least a portion of the electron density corresponding to the second set of machine readable data.

A further aspect of the invention provides a method of providing data for generating structures and/or performing rational drug redesign with 3A4, 3A4 homologues or analogues, complexes of 3A4 with a compound, or complexes of 3A4 homologues or analogues with compounds, the method comprising:

(i) establishing communication with a remote device containing computer-readable data comprising at least one of:
   (a) ) electron density map derivable from Table 3 or co-ordinate data therefrom, said data defining the three-dimensional structure of 3A4, at least one sub-domain of the three-dimensional structure of 3A4, or the coordinates of a plurality of atoms of 3A4; (b) structure factor data for 3A4, said structure factor data of Table 3; (c) atomic coordinate data of a target 3A4 homologue or analogue generated by homology modelling of the target based on the coordinate data derivable from Table 3; (d) atomic coordinate data of a protein generated by interpreting X-ray crystallographic data or NMR data by reference to the data of Table 3; and (e) structure factor data derivable from the atomic coordinate data of (c) or (d); and (ii) receiving said computer-readable data from said remote device. The atomic coordinate data may be that of Table 5 or selected coordinates thereof.

Thus the remote device may comprise e.g. a computer system or computer readable media of one of the previous aspects of the invention. The device may be in a different country or jurisdiction from where the computer-readable data is received.

The communication may be via the internet, intranet, e-mail etc, transmitted through wires or by wireless means such as by terrestrial radio or by satellite. Typically the communication will be electronic in nature, but some or all of the communication pathway may be optical, for example, over optical fibers.

J. Uses of the Structures of the Invention.

The crystal structures obtained according to the present invention (including the structure derivable from Table 3 (e.g. that of Table 5 or selected coordinates thereof) as well as the structures of target P450 proteins obtained in accordance with the methods described herein), may be used in several ways for drug design. For example, many drugs or drug candidates fail to be of clinical use due to the detrimental interactions with P450 proteins, resulting in a rapid clearance of the drugs from the body. The present invention will allow those of skill in the art to attempt to rescue such compounds from development, by following the structure-based chemical strategies detailed below.

In the case where a drug molecule is being metabolised by a P450, information on the binding orientation by either co-crystallization, soaking or computationally docking the binding orientation of the drug in the binding pocket can be determined. This will guide specific modifications to the chemical structure designed to mediate or control the interaction of the drug with the protein. Such modifications can be designed with an aim to reduce the metabolism of the drug by P450 and so improve its therapeutic action.

The crystal structure could also be useful to understand drug-drug interactions. Many examples exist where adverse reactions to drugs are recorded if administered while the patient is already taking other medicines. The mechanism behind this detrimental and often dangerous drug-drug interaction scenario may be when one drug behaves as an inhibitor of a P450 resulting in toxic levels of the other drug building-up due to less or no metabolism occurring. The crystal structure of the present invention complexed to such an inhibitor (either in vitro or in silico) may also allow rational modifications either to modify the inhibitor such that it no longer inhibits or inhibits less, or to modify the second drug such that it could bind better to the P450 (so becoming metabolised) and so displace the inhibitor.

P450s display significant polymorphic variations dependent on the age, gender, or ethnic origin of the patient. This can manifest itself in adverse reactions from some segments of patient populations to some drugs. By using the crystal structures of the present invention to map the relevant mutation with respect to the binding mode of the drug, chemical modifications could also be made to the drug to avoid interactions with the variable region of the protein. This could ensure more consistent therapeutic value from the drug for such segments of the population and avoid dangerous side effects.

Some pharmaceutical compounds are converted by P450s into active metabolites. In the case of such compounds, a greater understanding of how such compounds are converted by a P450 will allow modification of the compound so that it can be converted at a different rate. For example, increasing the rate of conversion may allow a more rapid delivery of a desired therapeutic effect, whereas decreasing the rate of conversion may allow for higher doses to be administered or the development of sustained release pharmaceutical preparations, for example comprising a mixture of compounds which are metabolized at different rates to form the same active metabolite.

Thus, the determination of the three-dimensional structure of P450 provides a basis for the design of new compounds, which interact with P450 in novel ways. For example, knowing the three-dimensional structure of P450, computer modelling programs may be used to design different molecules expected to interact with possible or confirmed active sites, such as binding sites or other structural or functional features of P450.

(i) Obtaining and Analysing Crystal Complexes.

In one approach, the structure of a compound bound to a P450 may be determined by experiment. This will provide a starting point in the analysis of the compound bound to P450, thus providing those of skill in the art with a detailed insight as to how that particular compound interacts with P450 and the mechanism by which it is metabolised.

Many of the techniques and approaches to structure-based drug design described above rely at some stage on X-ray analysis to identify the binding position of a ligand in a ligand-protein complex. A common way of doing this is to perform X-ray crystallography on the complex, produce a difference Fourier electron density map, and associate a particular pattern of electron density with the ligand. However, in order to produce the map (as explained e.g. by Blundell et al., in *Protein Crystallography*, Academic Press, New York, London and San Francisco, (1976)), it is necessary to know beforehand the protein 3D structure (or at least the protein structure factors). Therefore, determination of the P450 structure also allows difference Fourier electron density maps of P450-compound complexes to be produced, determination of the binding position of the drug and hence may greatly assist the process of rational drug design.

Accordingly, the invention provides a method for determining the structure of a compound bound to P450, said method comprising:

providing a crystal of P450 according to the invention;

soaking the crystal with said compounds; and determining the structure of said P450 compound complex by employing the coordinate data derivable from Table 3 (e.g. that of Table 5 or selected coordinates thereof), or by employing the phases of Table 3, or by employing the electron density derivable from Table 3.

Alternatively, the P450 and compound may be co-crystallized. Thus the invention provides a method for determining the structure of a compound bound to P450, said method comprising; mixing the protein with the compound(s), crystallizing the protein-compound(s) complex; and determining the structure of said P450-compound(s) complex by reference to the coordinate data derivable from Table 3 (e.g. that of Table 5 or selected coordinates thereof), or by reference to the phases of Table 3, or by reference to the electron density derivable from Table 3.

The analysis of such structures may employ (i) X-ray crystallographic diffraction data from the complex and (ii) a three-dimensional structure of P450, or at least selected coordinates thereof, to generate a difference Fourier electron density map of the complex, the three-dimensional structure being defined by atomic coordinate data derivable from Table 3 (e.g. that of Table 5 or selected coordinates thereof), or by employing the phases of Table 3, or by employing the electron density derivable from Table 3. The difference Fourier electron density map may then be analysed.

Therefore, such complexes can be crystallized and analysed using X-ray diffraction methods, e.g. according to the approach described by Greer et al., *J. of Medicinal Chemistry*, Vol. 37, (1994), 1035–1054, and difference Fourier electron density maps can be calculated based on X-ray diffraction patterns of soaked or co-crystallized P450 and the solved structure of uncomplexed P450. These maps can then be analysed e.g. to determine whether and where a particular compound binds to P450 and/or changes the conformation of P450.

Electron density maps can be calculated using programs such as those from the CCP4 computing package (Collaborative Computational Project 4. The CCP4 Suite: Programs for Protein Crystallography, *Acta Crystallographica*, D50, (1994), 760–763.). For map visualization and model building programs such as "O" (Jones et al., *Acta Crystallographica*, A47, (1991), 110–119) can be used.

In addition, in accordance with this invention, 3A4 mutants may be crystallized in co-complex with known 3A4 substrates or inhibitors or novel compounds. The crystal structures of a series of such complexes may then be solved by molecular replacement and compared with that of the 3A4 structure from Table 3 or Table 5 or selected coordinates thereof. Potential sites for modification within the various binding sites of the enzyme may thus be identified. This information provides an additional tool for determining the most efficient binding interactions, for example, increased hydrophobic interactions, between 3A4 and a chemical entity or compound.

For example there are alleles of 3A4, which differ from the native 3A4 by only 1–2 amino acid substitutions, and yet individuals who express these allelic variants may exhibit very different drug metabolism profiles. Polymorphisms in the human CYP3A4 genes can influence the outcome of a treatment for a range of diseases including cancer. The metabolism of chemotherapeutic agents used in the treatment of cancer can be investigated using the structure provided here and the agents then altered using the methods described herein.

By generating such allelic proteins and determining the co-complex with compounds a greater understanding of allelic interactions with compounds may be developed.

All of the complexes referred to above may be studied using well-known X-ray diffraction techniques and may be refined against 1.5 to 3.5 Å resolution X-ray data to an R value of about 0.30 or less using computer software, such as CNX (Brunger et al., *Current Opinion in Structural Biology*, Vol. 8, Issue 5, October 1998, 606–611, and commercially available from Accelrys, San Diego, Calif.), and as described by Blundell et al, (1976) and Methods in Enzymology, vol. 114 & 115, H. W. Wyckoff et al., eds., Academic Press (1985).

This information may thus be used to optimise known classes of 3A4 substrates or inhibitors, and more importantly, to design and synthesize novel classes of 3A4 inhibitors and design drug with modified P450 metabolism.

(ii) In Silico Analysis and Design

Although the invention will facilitate the determination of actual crystal structures comprising a P450 and a compound, which interacts with the P450, current computational techniques provide a powerful alternative to the need to generate such crystals and generate and analyse diffraction date. Accordingly, a particularly preferred aspect of the invention relates to in silico methods directed to the analysis and development of compounds which interact with P450 structures of the present invention.

Determination of the three-dimensional structure of 3A4 provides important information about the binding sites of 3A4, particularly when comparisons are made with similar enzymes. This information may then be used for rational design and modification of 3A4 substrates and inhibitors, e.g. by computational techniques which identify possible binding ligands for the binding sites, by enabling linked-fragment approaches to drug design, and by enabling the identification and location of bound ligands using X-ray crystallographic analysis. These techniques are discussed in more detail below.

Thus as a result of the determination of the P450 three-dimensional structure, more purely computational techniques for rational drug design may also be used to design structures whose interaction with P450 is better understood (for an overview of these techniques see e.g. Walters et al (*Drug Discovery Today*, Vol.3, No.4, (1998), 160–178; Abagyan, R.; Totrov, M. *Curr. Opin. Chem. Biol.* 2001, 5, 375–382). For example, automated ligand-receptor docking programs (discussed e.g. by Jones et al. in *Current Opinion in Biotechnology*, Vol.6, (1995), 652–656 and Halperin, I.; Ma, B.; Wolfson, H.; Nussinov, R. *Proteins* 2002, 47, 409–443), which require accurate information on the atomic coordinates of target receptors may be used.

The aspects of the invention described herein which utilize the P450 structure in silico may be equally applied to both the 3A4 structure from the data of Table 3 (e.g. that of Table 5 or selected coordinates thereof) and the models of target P450 proteins obtained by other aspects of the invention. Thus having determined a conformation of a P450 by the method described above, such a conformation may be used in a computer-based method of rational drug design as described herein. In addition the availability of the structure of the P450 3A4 will allow the generation of highly predictive pharmacophore models for virtual library screening or compound design.

Accordingly, the invention provides a computer-based method for the analysis of the interaction of a molecular structure with a P450 structure of the invention, which comprises:

providing the structure of a P450 of the invention;

providing a molecular structure to be fitted to said P450 structure; and fitting the molecular structure to the P450 structure.

The P450 structure of the invention may be that of Table 5, or selected coordinates thereof.

In an alternative aspect, the method of the invention may utilize the coordinates of atoms of interest of the P450 binding region, which are in the vicinity of a putative molecular structure, for example within 10–25 Å of the catalytic regions or within 5–10 Å of a compound bound, in order to model the pocket in which the structure binds. These coordinates may be used to define a space, which is then analysed "in silico". Thus the invention provides a computer-based method for the analysis of molecular structures which comprises:

provifing the coordinates of at least two atoms of a P450 structure of the invention ("selected coordinates");

providing the structure of a molecular structure to be fitted to said coordinates; and fitting the structure to the selected coordinates of the P450.

In practice, it will be desirable to model a sufficient number of atoms of the P450 as defined by the coordinates derivable from Table 3 (e.g. those of Table 5 or selected coordinates thereof), which represent a binding pocket, e.g. the atoms of the residues identified in Tables 7 and 8, preferably Table 8. Binding pockets and other features of the interaction of P450 with co-factor are described in the accompanying example. Thus, in this embodiment of the invention, there will preferably be provided the coordinates of at least 5, preferably at least 10, more preferably at least 50 and even more preferably at least 100, e.g. at least 500 such as at least 1000, selected atoms of the P450 structure.

Although every different compound metabolised by P450 may interact with different parts of the binding pocket of the protein, the structure of this P450 allows the identification of a number of particular sites which are likely to be involved in many of the interactions of P450 with a drug candidate. The residues are set out in Tables 7 and 8. Thus in this aspect of the invention, the selected coordinates may comprise coordinates of some or all of these residues.

In order to provide a three-dimensional structure of compounds to be fitted to a P450 structure of the invention, the compound structure may be modelled in three dimensions using commercially available software for this purpose or, if its crystal structure is available, the coordinates of the structure may be used to provide a representation of the compound for fitting to a P450 structure of the invention.

The binding pockets of cytochrome P450 molecules are of a size which can accommodate more than one ligand. Indeed, some drug-drug interactions may occur as a result of interaction of the compounds within the binding pocket of the same P450. In any event, the findings of the present invention may be used to examine or predict the interaction of two or more separate molecular structures within the P450 3A4 binding pocket of the invention.

Thus the invention provides a computer-based method for the analysis of the interaction of two molecular structures within a P450 binding pocket structure, which comprises:

providing the P450 structure of Table 5 or selected coordinates thereof;

providing a first molecular structure;

fitting the first molecular structure to said P450 structure;

providing a second molecular structure; and fitting the second molecular structure to a different part said P450 structure.

Optionally the method of analysis further comprises providing a third molecular structure and also fitting that structure to the P450 structure. Indeed, further molecular structures may be provided and fitted in the same way.

In one aspect, one or more of the molecular structures may be fitted to one or more of the phenylalanine residues of the 3A4 binding pocket mentioned above, and one or more of the other molecular structures may be fitted to coordinates of amino acids from another part of the P450 binding pocket, such as another part of the ligand-binding region, to the haem-binding region, or to atoms of the amino acid residues of Tables 7 or 8. In one embodiment, the one or more other molecular structures may be fitted, in addition to or instead of, to the haem structure in the P450 binding pocket.

Following the fitting of the molecular structures, a person of skill in the art may seek to use molecular modelling to determine to what extent the structures interact with each other (e.g. by hydrogen bonding, other non-covalent interactions, or by reaction to provide a covalent bond between parts of the structures) or the interaction of one structure with 3A4 is altered by the presence of another structure.

The person of skill in the art may use in silico modelling methods to alter one or more of the structures in order to design new structures which interact in different ways with 3A4, so as to speed up or slow down their metabolism, as the case may be.

Newly designed structures may be synthesised and their interaction with 3A4 may be determined or predicted as to how the newly designed structure is metabolised by said P450 structure. This process may be iterated so as to further alter the interaction between it and the 3A4.

By "fitting", it is meant determining by automatic, or semi-automatic means, interactions between at least one atom of a molecular structure and at least one atom of a P450 structure of the invention, and calculating the extent to which such an interaction is stable. Interactions include attraction and repulsion, brought about by charge, steric considerations and the like. Various computer-based methods for fitting are described further herein.

More specifically, the interaction of a compound or compounds with P450 can be examined through the use of computer modelling using a docking program such as GOLD (Jones et al., *J. Mol. Biol.*, 245, 43–53 (1995), Jones et al., *J. Mol. Biol.*, 267, 727–748 (1997)), GRAMM (Vakser, I. A., *Proteins*, Suppl., 1:226–230 (1997)), DOCK (Kuntz et al, *J. Mol. Biol.* 1982, 161, 269–288, Makino et al, *J. Comput. Chem.* 1997, 18, 1812–1825), AUTODOCK (Goodsell et al, *Proteins* 1990, 8, 195–202, Morris et al, *J. Comput. Chem.* 1998, 19, 1639–1662.), FlexX, (Rarey et al, *J. Mol. Biol.* 1996, 261, 470–489) or ICM (Abagyan et al, *J. Comput. Chem.* 1994, 15, 488–506). This procedure can include computer fitting of compounds to P450 to ascertain how well the shape and the chemical structure of the compound will bind to the P450.

Also computer-assisted, manual examination of the active site structure of P450 may be performed. The use of programs such as GRID (Goodford, *J. Med. Chem.*, 28, (1985), 849–857)—a program that determines probable interaction sites between molecules with various functional groups and an enzyme surface—may also be used to analyse the active site to predict, for example, the types of modifications which will alter the rate of metabolism of a compound.

Computer programs can be employed to estimate the attraction, repulsion, and steric hindrance of the two binding partners (i.e. the P450 and a compound).

If more than one P450 active site is characterized and a plurality of respective smaller compounds are designed or selected, a compound may be formed by linking the respective small compounds into a larger compound, which maintains the relative positions and orientations of the respective compounds at the active sites. The larger compound may be formed as a real molecule or by computer modelling.

Detailed structural information can then be obtained about the binding of the compound to P450, and in the light of this information adjustments can be made to the structure or functionality of the compound, e.g. to alter its interaction with P450. The above steps may be repeated and re-repeated as necessary.

As indicated above, molecular structures, which may be fitted to the P450 structure of the invention, include compounds under development as potential pharmaceutical agents. The agents may be fitted in order to determine how the action of P450 modifies the agent and to provide a basis for modelling candidate agents, which are metabolised at a different rate by a P450.

Molecular structures, which may be used in the present invention, will usually be compounds under development for pharmaceutical use. Generally such compounds will be organic molecules, which are typically from about 100 to 2000 Da, more preferably from about 100 to 1000 Da in molecular weight. Such compounds include peptides and derivatives thereof, steroids, anti-inflammatory drugs, anti-cancer agents, anti-bacterial or antiviral agents, neurological agents and the like. In principle, any compound under development in the field of pharmacy can be used in the present invention in order to facilitate its development or to allow further rational drug design to improve its properties.

(iii) Analysis and Modification of Compounds and Metabolites

Where the primary metabolite of a potential or actual pharmaceutical compound is known, and this metabolite is generated by the action of P450, the structure of the agent and its metabolite may both be modelled and compared to each other in order to better determine residues of P450 which interact with the agent. In any event, the present invention provides a process for predicting potential pharmaceutical compounds with a desired activity which are metabolised by P450 at a rate different from a starting compound having the same desired activity, which method comprises:

fitting a starting compound to a P450 structure of the invention or selected coordinates thereof;

determining or predicting how said compound is metabolized by said P450 structure; and modifying the compound structure so as to alter the interaction between it and the P450.

It would be understood by those of skill in the art that modification of the structure will usually occur in silico, allowing predictions to be made as to how the modified structure interacts with the P450.

Modification will be those conventional in the art known to the skilled medicinal chemist, and will include, for example, substitutions or removal of groups containing residues which interact with the amino acid side chain groups of a P450 structure of the invention. For example, the replacements may include the addition or removal of groups in order to decrease or increase the charge of a group in a test compound, the replacement of a charge group with a group of the opposite charge, or the replacement of a hydrophobic group with a hydrophilic group or vice versa. It will be understood that these are only examples of the type of substitutions considered by medicinal chemists in the development of new pharmaceutical compounds and other modifications may be made, depending upon the nature of the starting compound and its activity.

Although it is usually desired to alter a compound to prevent its metabolism by P450, or at least to reduce the rate at which P450 metabolises the compound, the present invention also includes developing compounds which are metabolised more rapidly than a starting compound, for example where such a compound blocks metabolism of another drug.

Where a potential modified compound has been developed by fitting a starting compound to the P450 structure of the invention and predicting from this a modified compound with an altered rate of metabolism, the invention further includes the step of synthesizing the modified compound and testing it in a in vivo or in vitro biological system in order to determine its activity and/or the rate at which it is metabolised.

The above-described processes of the invention may be iterated in that the modified compound may itself be the basis for further compound design. The above-described processes may also be used to modify a compound which interacts with a second compound within the 3A4 binding pocket.

(iv) Analysis of Compounds in Binding Pocket Regions

Our finding of a cluster of phenylalanine residues in the vicinity of the haem of 3A4 allows the analysis and design methods described in the preceding subsections to be focused on compounds which interact with one or more of these residues.

For example, compounds which dock in the 3A4 substrate binding pocket in a manner which includes pi:pi stacking interactions with a phenylalanine side chain, may be modified in order to alter their metabolism. For example, such interactions may be influential in determining the rate at which the compounds undergo metabolism via movement towards, and reaction with, the haem moiety, located in the haem binding region of the 3A4 binding pocket. By altering (i.e. increasing or decreasing) their affinity of the compound to these phenylalanine residues, or other features of the ligand binding region compared to the haem binding region it may alter (i.e. increase or decrease) their ability to move towards, or be retained by, the haem-binding region.

For example by increasing their affinity to the ligand-binding region over the haem binding region may decrease their ability to move towards the haem-binding region. Alternatively, decreasing their affinity to the ligand-binding region may be desired to decrease their affinity to this region compared to the haem binding region and hence increase their ability to move towards the haem binding region. If compound binding to the ligand-binding pocket is a necessary prerequisite of compound binding in the haem-binding region and its subsequent metabolism by or inhibition of 3A4, elimination of binding to the ligand-binding region may eliminate all compound metabolism by 3A4 or inhibition of 3A4. An alternative or additional approach is to modify such substrates to increase or decrease their affinity for residues of the haem-binding region. Changes of this type may be introduced in order to increase or decrease the turnover of the substrates.

Some molecules are known to be effectors or activators of 3A4 metabolism. Modification of the binding between 3A4 and such a compound would mediate metabolism of the substrate.

Thus in one embodiment, the present invention provides a method for modifying the structure of a compound in order to alter its metabolism by a P450, which method comprises:

fitting a starting compound to one or more coordinates of at least one amino acid residue of the ligand-binding region of the P450;

modifying the starting compound structure so as to increase or decrease its interaction with the ligand-binding region;

wherein said ligand-binding region is defined as including at least one of the P450 residues numbered as Phe57, Phe108, Phe213, Phe215, Phe219, Phe220, Phe241 and Phe304.

In another embodiment, the present invention provides a method for modifying the structure of a compound in order to alter its metabolism by a P450, which method comprises:
fitting a starting compound to one or more coordinates of at least one amino acid residue of the ligand-binding region of the P450;
modifying the starting compound structure so as to increase or decrease its interaction with the ligand-binding region;
wherein said ligand-binding region is defined as including at least one of the P450 residues of Table 7 and preferably of Table 8.

In another embodiment, the invention provides a method for modifying the structure of a compound in order to alter its metabolism by a P450 3A4, which method comprises:
fitting a starting compound to one or more coordinates of at least one amino acid residue of the haem-binding region of the P450;
modifying the starting compound structure so as to increase or decrease its interaction with the haem-binding region.

The haem binding region also optionally includes the iron ion bound to the haem molecule, and if desired, one or more of the other atoms of the haem molecule itself. In a preferred aspect of the invention, the iron ion is also included in the haem-binding region.

Desirably, in the above aspects of the invention, coordinates from at least two, preferably at least five, and more preferably at least ten amino acid residues of the P450 (including where desired the iron ion) will be used.

For the avoidance of doubt, the term "modifying" is used as defined in the preceding subsection, and once such a compound has been developed it may be synthesised and tested also as described above.

(v) Fragment Linking and Growing.

The provision of the crystal structures of the invention will also allow the development of compounds which interact with the binding pocket regions of P450s (for example to act as inhibitors of a P450) based on a fragment linking or fragment growing approach.

For example, the binding of one or more molecular fragments can be determined in the protein binding pocket by X-ray crystallography. Molecular fragments are typically compounds with a molecular weight between 100 and 200 Da (Carr et al, 2002). This can then provide a starting point for medicinal chemistry to optimise the interactions using a structure-based approach. The fragments can be combined onto a template or used as the starting point for 'growing out' an inhibitor into other pockets of the protein (Blundell et al, 2002). The fragments can be positioned in the binding pocket of the P450 and then 'grown' to fill the space available, exploring the electrostatic, van der Waals or hydrogen-bonding interactions that are involved in molecular recognition. The potency of the original weakly binding fragment thus can be rapidly improved using iterative structure-based chemical synthesis.

At one or more stages in the fragment growing approach, the compound may be synthesized and tested in a biological system for its activity. This can be used to guide the further growing out of the fragment.

Where two fragment-binding regions are identified, a linked fragment approach may be based upon attempting to link the two fragments directly, or growing one or both fragments in the manner described above in order to obtain a larger, linked structure, which may have the desired properties.

Where the binding site of two or more ligands are determined they may be connected to form a potential lead compound that can be further refined using e.g. the iterative technique of Greer et al. For a virtual linked-fragment approach see Verlinde et al., *J. of Computer-Aided Molecular Design*, 6, (1992), 131–147, and for NMR and X-ray approaches see Shuker et al., *Science*, 274, (1996), 1531–1534 and Stout et al., *Structure*, 6, (1998), 839–848. The use of these approaches to design P450 inhibitors is made possible by the determination of the P450 structure.

(vi) Compounds of the Invention.

Where a potential modified compound has been developed by fitting a starting compound to the P450 structure of the invention and predicting from this a modified compound with an altered rate of metabolism (including a slower, faster or zero rate), the invention further includes the step of synthesizing the modified compound and testing it in an in vivo or in vitro biological system in order to determine its activity and/or the rate at which it is metabolised.

The method comprises: (a) providing 3A4 under conditions where, in the absence of modulator, the 3A4 is able to metabolise known substrates; (b) providing the compound; and (c) determining the extent to which the compound is metabolised in the presence of 3A4 or (d) determining the extent to which the compound inhibits metabolism of a known substrate of 3A4.

More preferably, in the latter steps the compound is contacted with P450 under conditions to determine its function.

For example, in the contacting step above the compound is contacted with P450 in the presence of the compound, and typically a buffer and substrate, to determine the ability of said compound to inhibit P450 or to be metabolised by P450. The substrate may be e.g. dibenzylfluorescein. So, for example, an assay mixture for P450 may be produced which comprises the compound, substrate and buffer.

In another aspect, the invention includes a compound, which is identified by the methods of the invention described above.

Following identification of such a compound, it may be manufactured and/or used in the preparation, i.e. manufacture or formulation, of a composition such as a medicament, pharmaceutical composition or drug. These may be administered to individuals.

Thus, the present invention extends in various aspects not only to a compound as provided by the invention, but also a pharmaceutical composition, medicament, drug or other composition comprising such a compound. The compositions may be used for treatment (which may include preventative treatment) of disease such as cancer. Such a treatment may comprise administration of such a composition to a patient, e.g. for treatment of disease; the use of such an inhibitor in the manufacture of a composition for administration, e.g. for treatment of disease; and a method of making a pharmaceutical composition comprising admixing such an inhibitor with a pharmaceutically acceptable excipient, vehicle or carrier, and optionally other ingredients.

Thus a further aspect of the present invention provides a method for preparing a medicament, pharmaceutical composition or drug, the method comprising:
(a) identifying or modifying a compound by a method of any one of the other aspects of the invention disclosed herein;
(b) optimising the structure of the molecule; and (c) preparing a medicament, pharmaceutical composition or drug containing the optimised compound.

The above-described processes of the invention may be iterated in that the modified compound may itself be the basis for further compound design.

By "optimising the structure" we mean e.g. adding molecular scaffolding, adding or varying functional groups, or connecting the molecule with other molecules (e.g. using a fragment linking approach) such that the chemical structure of the modulator molecule is changed while its original modulating functionality is maintained or enhanced. Such optimisation is regularly undertaken during drug development programmes to e.g. enhance potency, promote pharmacological acceptability, increase chemical stability etc. of lead compounds.

Modification will be those conventional in the art known to the skilled medicinal chemist, and will include, for example, substitutions or removal of groups containing residues which interact with the amino acid side chain groups of a P450 structure of the invention. For example, the replacements may include the addition or removal of groups in order to decrease or increase the charge of a group in a test compound, the replacement of a charge group with a group of the opposite charge, or the replacement of a hydrophobic group with a hydrophilic group or vice versa. It will be understood that these are only examples of the type of substitutions considered by medicinal chemists in the development of new pharmaceutical compounds and other modifications may be made, depending upon the nature of the starting compound and its activity.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975.

K. Quantifier of Similarity for Electron Density Maps

As discussed in Section B above, the linear correlation coefficient, CC, can be used to quantify the degree of similarity between two electron density maps.

In general terms, therefore, we provide a method for comparing two molecular structures comprising the steps of:
providing respective first and second electron density maps for the molecular structures,
transforming one or both of the maps so that the two maps are in maximum coincidence with each other, and
quantifying the degree of correlation between the coinciding maps.

Preferably, the degree of correlation is quantified by calculating the CC for the coinciding maps. A mask may be applied to the maps before the quantification step to prevent e.g. solvent molecules from contributing to the degree of correlation. Either or both of the electron density maps may be determined experimentally, e.g. by X-ray crystallographic analysis. Alternatively or additionally, either or both may be calculated e.g. from atomic coordinate data.

The use of the CC has been tested for three structural families (i.e. three different molecular types). Within each family a number of different sets of atomic coordinates were provided. Each set varied from the other sets by an r.m.s.d. of up to about 1.8 Å. Electron density maps were computed for each atomic coordinate set. The aim was to confirm that the CC determined for each pair of maps correlated with the r.m.s.d. value for the corresponding pair of atomic coordinate sets (both within and across families). A number of CCP4 (Collaborative Computational Project 4. The CCP4 Suite: Programs for Protein Crystallography, *Acta Crystallographica*, D50, (1994), 760–763.), Unix and specially developed programs were used to perform the test. The specially developed programs are provided in Annexes 1 to 4. Annexes 5 and 6 provided respective subroutines used by the programs of Annexes 1 to 4.

In order to perform the test, the first step was to compute, for each set of atomic coordinates, the asymmetric unit of the electron density map on a relatively fine grid (e.g. $\frac{1}{6}^{th}$ of the minimum d-spacing). This was accomplished with weighted $2F_o - F_c$ coefficients using the CCP4 FFT program.

Next, for each molecule in the asymmetric unit, the atomic coordinates of the molecule were extracted from the complete coordinate set using Unix GREP. Using Astex-EXTENDC (see Annex 3), the electron density map was then extended to cover the molecule thus extracted, including a minimum 3 Å border to ensure that no parts of electron density for any atom of the molecule were unintentionally excluded.

The extracted atomic coordinates were also used to generate a molecular mask with the CCP4 NCSMASK program. Such a mask is a 3D array of grid points wherein each grid point covered by the molecule is labelled '1' and each grid point outside the molecule is labelled '0'. The coverage of the molecule was determined by 2 Å radius spheres centred on each atomic position.

Using the Astex-KFIT program (see Annex 4), each set of atomic coordinates was superposed onto a common reference and the rigid-body transformation was determined for r.m.s.d. minimisation between each pair of molecules. Each transformation was then applied, using Astex-ROTMAP (Annex 1), to the corresponding pair of electron density maps and associated masks, interpolating maps and masks onto a common unit cell and grid (e.g. at ¼ of the minimum d-spacing). The masks were interpolated linearly, whereas the electron densities were interpolated using quadratic functions.

Finally, the CCs for the pairs of transformed and interpolated electron density maps were calculated using Astex-DENCOR (Annex 2). The transformed and interpolated masks were used to ensure that only electron densities covered by the molecules contributed to the CCs.

A graph of calculated CC against calculated r.m.s.d. was plotted and the graph points fitted to the straight line y=1−x/2. This line is constrained to pass through the point (x,y)=(0,1) because for zero r.m.s.d. perfect correlation is expected. The graph demonstrated that CC was strongly anticorrelated with r.m.s.d., and a linear relationship y=1−x/2 where x=r.m.s.d. and y=CC was observed. Thus an r.m.s.d. of 1.5 Å corresponds approximately to a CC of 0.25. The equation implies that for an r.m.s.d. of 2 Å or greater, no correlation of the electron densities is expected. As expected, the r.m.s.d. distances were significantly lower for pairs of molecules within the same structural family then for those taken from different families, and consequently CCs for pairs of molecules within a structural family were consistently higher than those taken from different families.

The invention is illustrated by the following example:

EXAMPLE

Cloning of 3A4

3A4 corresponding to M18907 (GI__181373) was cloned from human liver library (Origene Technologies, Inc.).

PCR carried out as recommended by the manufacturer:

| | |
|---|---|
| Liver library | 2.0 µl |
| 10X PCR buffer (−Mg$^{2+}$) | 2.5 µl |
| 10 mM dNTPs | 0.5 µl |
| 10 mM MgSO$_4$ | 2.5 µl |
| Water | 11.0 µl |
| Primer 1 (@10 pmol/µl) | 3.0 µl |
| Primer 2 (@10 pmol/µl) | 3.0 µl |

Primer 1 is complementary to the 5' end of the full length 3A4 cDNA. Primer 2 is complementary to the 3' end of the cDNA and adds a four histidine tag onto the C-terminus of the 3A4 protein.

Heat to 94° C., add 0.51 µl (1 Unit) Vent polymerase 35 cycles as follows:

| | |
|---|---|
| 94° C. | 30 seconds |
| 65° C. | 60 seconds |
| 72° C. | 60 seconds |

1 cycle of 72° C. for 5 minutes.

Following the addition of 1 µl (2.5 Units) Taq polymerase and incubation at 72° C. for 10 minutes, 1 µl of product was used in a TOPO cloning reaction (vector pCR4TOPO, Invitrogen). The cloning reaction was used to transform *E. coli* XL1-blue and positive clones identified by NdeI/SalI restriction digestion of purified plasmids. Positive clones were sequenced fully on both strands and the NdeI/SalI insert subcloned into pET20b to yield the template clone. This clone was used as the template in subsequent PCR reactions.

N-Terminal Truncation of 3A4

The expression vector pCWOri+, provided by Prof. F. W. Dahlquist, University of Oregon, Eugene, Oreg., USA, was used to express the truncated human cytochrome P450 in the *E. coli* strain XL1 Blue (Stratagene). Full-length cDNA encoding cytochrome P450 3A4 isolated above was used as a template for PCR amplification, engineering the 5' terminus and insertion of a four Histidine tag at the C-terminus.

N-terminal truncation of 3A4 was carried out by PCR as outlined below, to generate the published NF10 N-terminal truncation described by Gillam (Gillam et al, Arch. Biochem. Biophys. Vol. 305, 123–131, 1993).

| | |
|---|---|
| Template | ~5 ng |
| 10X PCR buffer (+Mg$^{2+}$) | 5.0 µl |
| 10 mM dNTPs | 1.0 µl |
| Water | 42.0 µl |
| Primer 2 (@100 pmol/µl) | 0.5 µl |
| Primer 3 (@100 pmol/µl) | 0.5 µl |
| Vent polymerase (2 U/µl) | 0.5 µl |

25 cycles of:

| | |
|---|---|
| 94° C. | 30 seconds |
| 65° C. | 60 seconds |
| 72° C. | 60 seconds |

1 cycle of 72° C. for 5 minutes.

Following the addition of 1 µl (2.5 units) Taq polymerase and incubation at 72° C. for 10 minutes, 1 µl of product was used in a TOPO cloning reaction (vector pCR4TOPO, Invitrogen). The cloning reaction was used to transform *E. coli* XL1-blue and positive clones identified by NdeI/SalI restriction digestion of purified plasmids. Positive clones were sequenced fully and the NdeI/SalI insert subcloned into pCWori+ to yield clone p3A4. This clone was used for protein expression.

Primers 1, 2 and 3 are represented by SEQ ID NOs: 4, 5 and 6, respectively.

Primer 1
5'-GGAATTCATATGGCTCTCATCCCAGACTTGGCC-3'

Primer 2
5'-TGCGGTCGACTCAATGGTGATGGTGGGCTCCACTTACGGTGCCATCC-3'

Primer 3
5'-TTAACATATGGCATATGGTACTCATTCACATGGTCTGTTTAAAAAACTGGGAATTCCAGGGCCCACACC-3'

Bacterial Expression

A single ampicillin resistant colony of XL1 blue cells was grown overnight at 37° C. in Terrific Broth (TB) with shaking to near saturation and used to inoculate fresh TB media. Bacteria were grown to an OD600 nm=0.5 in 1 liter of TB broth containing 100 µg/ml of ampicillin at 37° C. at 185 rpm in 2 liter flask. The haem precursor delta aminolevulinic acid (80 mg/l) was added 30 min prior to induction with 1 mM isopropyl-β-D-thiogalactopyranoside (IPTG) and the temperature lowered to 25° C. The bacterial culture was continued under agitation at 25° C. for 48 hours.

Protein Purification 1A

Cells expressing 3A4 grown as described above were pelleted at 10000 g for 10 min and resuspended in a buffer containing 500 mM KPi, pH 7.4, 20% glycerol, 10 mM mercaptoethanol, 0.1% (v/v) of protease inhibitor cocktail (Calbiochem), 10 mM imidazole, 40 U/ml DNase 1 and 5 mM MgSO$_4$.

The cells were lysed by passing twice through a Constant Systems Cell Homogeniser at 10000 psi. The cell debris was then removed by centrifugation at 22000×g at 4° C. for 30 min.

Detergent IGEPAL CA630 (Sigma) was added dropwise from a 10% stock solution to the lysate at a final concentration of 0.3% (v/v) and the lysate was incubated with previously washed NiNTA resin (Qiagen) overnight at 4° C., using agitation. The protein bound-NiNTA resin was pelleted by centrifugation at 2000 g for 2 min at 4° C. The resin was washed with 20 resin volumes of 500 mM KPi, pH 7.4, 20% glycerol, 10 mM mercaptoethanol, 10 mM imidazole, 1:1000 dilution of protease inhibitor cocktail, 0.3%(v/v) IGEPAL CA630 and the resin pelleted by centrifugation at 2000×g for 2 min at 4° C. The resin was then washed with 10 resin volumes of 500 mM KPi, pH 7.4, 20% glycerol, 10 mM mercaptoethanol, 20 mM imidazole, 0.1% (v/v) protease inhibitors, 0.3% IGEPAL CA630 and the resin recovered by centrifugation as described above.

The resin was packed into a column at 4° C. and the cytochrome P450 eluted with 500 mM KPi, pH 7.4, 20% glycerol, 10 mM mercaptoethanol, 300 mM imidazole, 0.1% (v/v) of protease inhibitor cocktail, 0.3%(v/v) IGEPAL CA630.

The cytochrome P450 obtained from the NiNTA column was quickly desalted into 10 mM KPi, pH 7.4, 20% glycerol, 2.0 mM DTT, 1 mM EDTA using a HiPrep 26/10 desalting column (Pharmacia), at a flow rate of 5 ml/min.

The desalted cytochrome P450 was directly applied to a CM Sepharose column (Pharmacia), previously equilibrated with 10 mM KPi, pH 7.4, 20% glycerol, 2.0 mM DTT, 1 mM EDTA. The following step elution was applied: wash with 20 column volumes of 10 mM KPi, pH 7.4, 20% glycerol, 2.0 mM DTT, 1 mM EDTA, wash with the above buffer with 75 mM KCl in order to remove any trace of detergent, then eluted with the above buffer with KCl concentration increased to 500 mM.

The protein was concentrated up to 40 mg/ml using a microconcentrator for crystallization assays.

Protein Characterization

The quality of the final preparation was evaluated by:

(a) SDS polyacrylamide gel electrophoresis: This was performed using commercial gels (Nugen) followed by CBB staining according to the manufacturer's instructions. The purity as estimated by scanning a digital image of a gel was estimated to be at least 95%.

(b) Mass Spectroscopy: This was performed using a Bruker "BioTOF" electrospray time of flight instrument. Samples were either diluted by a factor of 1000 straight from storage buffer into methanol/water/formic acid (50:48:2 v/v/v), or subjected to reverse phase HPLC separation using a C4 column.

Calibration was achieved using Bombesin and angiotensin I using the 2+ and 1+ charged states. Data were acquired between 200 and 2000 m/z range and were subsequently processed using Bruker's X-mass program. Mass accuracy was typically below 1 in 10 000.

| | |
|---|---|
| Mass spec of 3A4: | 55281 Da(observed) |
| | 55278 Da (predicted minus N-terminal methionine) |

Crystallization 1A

Crystals of the 3A4 were grown using the hanging drop vapor diffusion method. Protein at 40 mg/ml in 10 mM Kpi pH 7.4, 0.5 M KCl, 2 mM DTT, 1 mM EDTA. 20% glycerol, was mixed in a 1:1 ratio, using 0.5 ul drops, with a reservoir solution. The crystals of 3A4 grew over a reservoir solution containing 0.1 M HEPES pH 7.5, 0.2 M sodium chloride, 30% PEG 400.

Alterative conditions are listed below:

0.1 M HEPES pH 7.5, 0.2 M sodium chloride, 30% PEG 400
0.05 M HEPES pH 7.5, 0.2 M sodium chloride, 35% PEG 400
0.05 M HEPES pH 7.5, 0.2 M sodium chloride, 30% PEG 400
0.15 M Imidazole-HCl pH 8, 10% 2-propanol
0.1 M 2-(N-cyclohexylamino)ethanesulfonic acid (CHES) pH 9.5, 30% PEG 400
0.15 M Hepes—Na pH 7.5, 5% IPA, 10% Peg 4000
0.1 M phosphate-citrate pH 4.2, 1.6 M NaH2PO4/0.4M K2HPO4
0.1 M citrate pH 5.5, 0.2 sodium chloride, 1.0 M Ammonium phosphate
0.2 M Lithium chloride, 20% PEG 3350
0.2 M Potassium chloride, 20% PEG 3350
0.2 M Sodium formate, 20% PEG 3350
0.2 M Potassium formate, 20% PEG 3350
0.2 M Ammonium formate, 20% PEG 3350
0.2 M Lithium acetate, 20% PEG 3350
0.2 M Potassium chloride, 20% PEG 3350
0.2 M Sodium formate, 20% PEG 3350
0.2 M Lithium acetate, 20% PEG 3350
0.2 M Sodium acetate, 20% PEG 3350
0.2 M Potassium acetate, 20% PEG 3350
0.2 M Ammonium acetate, 20% PEG 3350
0.1 M HEPES pH 7.5, 0.2 M sodium chloride, 30% PEG 400
0.1 M HEPES pH 7.5, 5% Iso-Propanol, 10% PEG 4000
200 mM K Acetate, 25% peg 3350
200 mM K Acetate, 25% peg 3350
300 mM Na acetate, 25% peg 3350
200 mM Sodium formate, 25% PEG 3350
0.300 M Lithium acetate, 25.0% PEG 3350
0.100 M Imidazole-HCl pH 8, 10% 2-propanol
0.150 M Imidazole-HCl pH 8, 10% 2-propanol Crystals formed within 1–7 days at 25° C., and were rod shaped in morphology.

The approximate cell dimensions of the crystals were a=77 Å, b=99 Å, c=129 Å, β=90°. The space group is I222.

The crystals were flash frozen in liquid nitrogen, using 80% reservoir solution, 20% ethylene glycol as a cryoprotectant.

Crystals of 3A4 were also grown over a reservoir solution containing:

0. 15M HEPES pH7.5, 5% IPA, 10% PEG 4000.

Crystals were obtained with unit cell C2: a=152 Å, b=101 Å, c=78 Å, α=90°, β=120°, γ=90°. The invention thus provides crystal of 3A4 having this space group and unit cell dimensions, the dimensions a, b and c and β varying independently by +/−5%.

In summary the invention includes a crystal of 3A4 having a space group I222 and unit cell size a=77 Å, b=99 Å, c=129 Å, β=90°; or having a space group C2 and unit cell size a=152 Å, b=101 Å, c=78 Å, α=90°, β=120°, γ=90°. Those of skill in the art will recognise that the cell dimensions of the crystal may vary by 5%, though preferably by 1–2 Å, upon repeat crystallization, and such variation resides within the spirit and scope of the invention.

Protein Purification (1B)

The cells were pelleted at 10000 g for 10 min and resuspended in a buffer containing 500 mM KPi, pH 7.4, 20% glycerol (v/v), 10 mM mercaptoethanol, 0.1% (v/v) of protease inhibitor cocktail 3 (Calbiochem), 10 mM imidazole, 40 U/ml DNase 1 and 5 mM MgSO$_4$.

Passing twice through a Constant Systems Cell Homogeniser at 10000 psi lysed the cells. The cell debris was then removed by centrifugation at 22000×g at 4° C. for 30 min.

Detergent IGEPAL CA630 (Sigma) was added dropwise from a 10% stock solution to the lysate at a final concentration of 0.3% (v/v) and the lysate was incubated with previously washed NiNTA resin (Qiagen) overnight at 4° C., using agitation. The protein bound-NiNTA resin was pelleted by centrifugation at 2000 g for 5 min at 4° C. The resin was washed with 20 resin volumes of 500 mM KPi, pH 7.4, 20% glycerol, 10 mM mercaptoethanol, 10 mM imidazole, 0.1% (v/v) of protease inhibitor cocktail, 0.3%(v/v) IGEPAL CA630 and the resin pelleted by centrifugation at 2000 g for 5 min at 4° C. The resin was then washed with 10 resin volumes of 500 mM KPi, pH 7.4, 20% glycerol, 10 mM mercaptoethanol, 20 mM imidazole, 0.1% (v/v) protease inhibitors, 0.3% IGEPAL CA630 and the resin recovered by centrifugation as described above.

The resin was packed into a column at room temperature and the cytochrome P450 eluted with cold 500 mM KPi, pH 7.4, 20% glycerol, 10 mM mercaptoethanol, 300 mM imidazole, 0.1% (v/v) of protease inhibitor cocktail, 0.3%(v/v) IGEPAL CA630.

The cytochrome P450 obtained from the NiNTA column was quickly desalted into 20 mM KPi, pH 7.2, 20% glycerol, 2.0 mM DTT, 1 mM EDTA using a HiPrep 26/10 desalting column (Pharmacia), at a flow rate of 5 ml/min on a Akta FPLC system (Pharmacia). A watch UV command (280 nm) of greater than 750 mAu was then used to divert the desalted P450 from the HiPrep 26/10 desalting column onto a CM Sepharose column (Pharmacia), previously equilibrated with 20 mM KPi, pH 7.2, 20% glycerol, 2.0 mM DTT, 1 mM EDTA for final purification. The peak divert was ended when the mAu fell below 750 mAu. The following step elution was then applied to the CM Sepharose column: wash with 10 column volumes of 20 mM KPi, pH 7.2, 20% glycerol, 2.0 mM DTT, 1 mM EDTA, followed by a wash with 6 column volumes with the above buffer with 75 mM KCl added in order to remove any trace of detergent, then eluted with the above buffer with KCl concentration increased to 500 mM.

The protein was concentrated up to 40 mg/ml using a microconcentrator for crystallization trials.

Crystallization (1B)

Crystals of the 3A4 were grown using the hanging drop vapour diffusion method. Protein at 37.4 mg/ml in 20 mM Kpi pH 7.2, 0.5 M KCl, 2mM DTT, 1 mM EDTA, 20% glycerol, was mixed in a 1:1 ratio, using 0.5 ul drops, with a reservoir solution. The crystals of 3A4 grew over a reservoir solution containing 0.15 M HEPES pH 7.5, 2.5% IPA, 10% PEG 4000.

Crystals formed within 1–7 days at 25° C., and were rod shaped in morphology.

The crystals were flash frozen in liquid nitrogen, using crystallisation solution supplemented with 15% glycerol as a cryoprotectant.

Dataset Collection (1)

A native dataset was collected at the ESRF beamline 14.2 to a resolution of 2.7 Å, from a crystal produced using the protocol above in Protein purification (1B) and Crystallisation (1B).

The cell dimensions of the crystals were a=77.85 Å, b=99.71 Å, c=132.74 Å, $\alpha=\beta=\gamma=90°$. The space group was I222.

A total of 100 one degree oscillation images were collected, processed with MOSFLM (Leslie, A. G. W. (1992). In *Joint CCP4 and EESF-EACMB Newsletter on Protein Crystallography*, vol. 26, Warrington, Daresbury Laboratory), scaled using SCALA (CCP4—Collaborative Computational Project 4. (1994) The CCP4 Suite: Programs for Protein Crystallography. *Acta Crystallographica* D50, 760–763) and reduced using the CCP4 suite of programs.

Protein Purification (2)

The cells were pelleted at 10000 g for 10 min and resuspended in a buffer containing 500 mM KPi, pH 7.4, 20% glycerol, 10 mM mercaptoethanol, 0.1% (v/v) of protease inhibitor cocktail 3 (Calbiochem), 10 mM imidazole, 40 U/ml DNase 1 and 5 mM MgSO$_4$.

Passing twice through a Constant Systems Cell Homogeniser at 10000 psi lysed the cells. The cell debris was then removed by centrifugation at 22000 g at 4° C. for 30 min.

Detergent IGEPAL CA630 (Sigma) was added dropwise from a 10% stock solution to the lysate at a final concentration of 0.3% (v/v) and the lysate was incubated with previously washed NiNTA resin (Qiagen) overnight at 4° C., using agitation. The protein bound-NiNTA resin was pelleted by centrifugation at 2000 g for 5 min at 4° C. The resin was washed with 20 resin volumes of 500 mM KPi, pH 7.4, 20% glycerol, 10 mM mercaptoethanol, 10 mM imidazole, 0.1% (v/v) of protease inhibitor cocktail, 0.3%(v/v) IGEPAL CA630 and the resin pelleted by centrifugation at 2000 g for 5 min at 4° C. The resin was then washed with 10 resin volumes of 500 mM KPi, pH 7.4, 20% glycerol, 10 mM mercaptoethanol, 20 mM imidazole, 0.1% (v/v) protease inhibitors, 0.3% IGEPAL CA630 and the resin recovered by centrifugation as described above.

The resin was packed into a column at room temperature and the cytochrome P450 eluted with cold 500 mM KPi, pH 7.4, 20% glycerol, 10 mM mercaptoethanol, 300 mM imidazole, 0.1% (v/v) of protease inhibitor cocktail, 0.3%(v/v) IGEPAL CA630.

The cytochrome P450 obtained from the NiNTA column was quickly desalted into 10 mM KPi, pH 7.2, 20% glycerol, 2.0 mM DTT, 1 mM EDTA, 10 mM K$_2$SO$_4$ using a HiPrep 26/10 desalting column (Pharmacia), at a flow rate of 5 ml/min.

The desalted cytochrome P450 was directly applied to a CM Sepharose column (Pharmacia) previously equilibrated with 10 mM KPi, pH 7.2, 20% glycerol, 2.0 mM DTT, 1 mM EDTA, 10 mM K$_2$SO$_4$. The following step elution was applied: wash with 20 column volumes of 10 mM KPi, pH 7.2, 20% glycerol, 2.0 mM DTT, 1 mM EDTA, 10 mM K$_2$SO$_4$ followed by a wash with 20 column volumes of the above buffer with 75 mM KCl in order to remove any trace of detergent, then eluted with the above buffer with KCl concentration increased to 500 mM.

The protein was concentrated up to 20 mg/ml using a microconcentrator for crystallization assays.

Crystallization (2)

Crystals of the 3A4 were grown using the hanging drop vapour diffusion method. Protein at 18.5 mg/ml in 10 mM Kpi pH 7.2, 0.5 M KCl, 2 mM DTT, 1 mM EDTA, 20% glycerol, 10 mM K2SO4 was mixed in a 1:1 ratio, using 0.5 ul drops, with a reservoir solution. The crystals of 3A4 grew over a reservoir solution containing 0.1 M HEPES pH 7.2, 5% IPA, 10% PEG 4000. The crystal was frozen using the crystallization solution supplemented by glycerol to 33%.

Crystals formed within 1–7 days at 25° C., and were rod shaped in morphology.

Dataset Collection (2)

A native dataset was collected at the ESRF beamline 14.2 to a resolution of 2.8 Å, from a crystal produced using the protocol above in Protein purification (2) and Crystallisation (2).

The approximate cell dimensions of the crystals were a=77.32 Å, b=100.37 Å, c=132.72 Å, $\alpha=\beta=\gamma=90°$. The space group was I222.

A total of eighty one degree oscillation images were collected, processed with MOSFLM (Leslie, A. G. W. (1992). In *Joint CCP4 and EESF-EACMB Newsletter on Protein Crystallography*, vol. 26, Warrington, Daresbury Laboratory), scaled using SCALA (CCP4-Collaborative Computational Project 4. (1994) The CCP4 Suite: Programs for Protein Crystallography, *Acta Crystallographica* D50, 760–763) and reduced using the CCP4 suite of programs.

Protein Purification (3)

The cells were pelleted at 10000 g for 10 min and resuspended in a buffer containing 500 mM KPi, pH 7.4, 20% glycerol, 10 mM mercaptoethanol, 0.1% (v/v) of protease inhibitor cocktail 3 (Calbiochem), 10 mM imidazole, 40 U/ml DNase 1 and 5 mM $MgSO_4$.

Passing twice through a Constant Systems Cell Homogeniser at 10000 psi lysed the cells. The cell debris was then removed by centrifugation at 22000×g at 4° C. for 30 min.

Detergent IGEPAL CA630 (Sigma) was added dropwise from a 10% stock solution to the lysate at a final concentration of 0.3% (v/v) and the lysate was incubated with previously washed NiNTA resin (Qiagen) overnight at 4° C., using agitation. The protein bound-NiNTA resin was pelleted by centrifugation, 2000 g for 5 min at 4° C. The resin was washed with 20 resin volumes of 500 mM KPi, pH 7.4, 20% glycerol, 10 mM mercaptoethanol, 10 mM imidazole, 0.1% (v/v) of protease inhibitor cocktail, 0.3%(v/v) IGEPAL CA630 and the resin pelleted by centrifugation at 2000 g for 5 min at 4° C. The resin was then washed with 10 resin volumes of 500 mM KPi, pH 7.4, 20% glycerol, 10 mM mercaptoethanol, 20 mM imidazole, 0.1% (v/v) protease inhibitors, 0.3% IGEPAL CA630 and the resin recovered by centrifugation as described above.

The resin was packed into a column at room temperature and the cytochrome P450 eluted with cold 500 mM KPi, pH 7.4, 20% glycerol, 10 mM mercaptoethanol, 300 mM imidazole, 0.1% (v/v) of protease inhibitor cocktail, 0.3%(v/v) IGEPAL CA630.

The cytochrome P450 obtained from the NiNTA column was quickly desalted into 10 mM KPi, pH 7.2, 20% glycerol, 2.0 mM DTT, 1 mM EDTA using a HiPrep 26/10 desalting column (Pharmacia), at a flow rate of 5 m/min.

The desalted cytochrome P450 was directly applied to a CM Sepharose column (Pharmacia) previously equilibrated with 10 mM KPi, pH 7.2, 20% glycerol, 2.0 mM DTT, 1 mM EDTA. The following step elution was applied: wash with 20 column volumes of 10 mM KPi, pH 7.2, 20% glycerol, 2.0 mM DTT, 1 mM EDTA, followed by a wash with 20 column volumes of the above buffer with 75 mM KCl in order to remove any trace of detergent, then eluted with the above buffer with KCl concentration increased to 500 mM.

The concentrated sample (200 μL, 7.9 mg protein) was then gel filtered using a Superdex 200 HR10/30 column (Pharmacia) in 10 mM KPi, pH7.2, 20% glycerol, 1 mM EDTA, 2 mM DTT, 500 mM KCl at a flow rate of 0.4 m/min. Fractions of 0.5 ml were collected. Three peaks of protein were collected, of these the first (elution volume, Ve=8.64 ml) represented aggregated protein that had been excluded by the void volume, Vo (Vo=8.66 ml) of the column, the second peak (Ve=12.4 ml) was the largest and represented the P450, and the third and smallest peak (Ve=15.49 ml) was low molecular weight protein contaminants.

The P450 peak was then pooled and concentrated up to 40 mg/ml using a microconcentrator for crystallization trials. 3A4 can alternatively be purified by gel filtration chromatography, by passage down a 26/60 Superdex 200 column equilibrated in 10 mM K Pi pH 7.2, 20% glycerol, 0.5M KCl, 2 mM DTT run at 1.5 mg/ml, to improve homogeneity for crystallisation.

Crystallization (3)

Crystals of the 3A4 were grown using the hanging drop vapour diffusion method. Protein at 36 mg/ml in 10 mM Kpi pH 7.2, 0.5 M KCl, 2 mM DTT, 1 mM EDTA, 20% glycerol, was mixed in a 1:1 ratio, using 0.5 μl drops, with a reservoir solution. The crystals of 3A4 grew over a reservoir solution containing 0.1 M HEPES pH 7.5, 0.025 M sodium chloride, 7.5% IPA, 10% PEG 4000.

The crystals formed over a number of days at 25° C., and were rod shaped in morphology.

The crystals were transferred to a cryo-solution consisting of 0.1 M HEPES pH 7.5, 0.25 M KCl, 15% PEG 4000 and 20% glycerol and then frozen in liquid nitrogen prior to data collection.

Dataset Collection (3)

Data was collected from a single crystal, produced using the protocol above in Protein purification (3) and Crystallisation (3), at beamline ID29 at the European Synchrotron Radiation Facility to a resolution of 2.8 Å. An energy scan was taken from the crystal prior to data collection to determine the precise energy at which the haem iron provided a detectable signal. The energy scan indicated the peak energy to be 7.126 KeV (corresponding to a wavelength of 1.7398 Å), and a suitable point of inflection wavelength to be 7.123 KeV (corresponding to a wavelength of 1.7406 Å).

The approximate cell dimensions of the crystals were a=77.94 Å, b=100.91 Å, c=131.00 Å, $\alpha=\beta=\gamma=90°$. The space group was I222.

Two datasets were collected from a single crystal, one at a wavelength of 1.7398 Å (peak dataset) to a resolution of 2.8 Å and the second at a wavelength of 1.7406 Å (inflection dataset) to a resolution of 3.1 Å. A total of 180° of data were collected at each wavelength to ensure that the data were redundant. The data were processed using MOSFLM (Leslie, A. G. W. (1992). In *Joint CCP4 and EESF-EACMB Newsletter on Protein Crystallography*, vol. 26, Warrington, Daresbury Laboratory), scaled using SCALA (CCP4 computing package (Collaborative Computational Project 4. The CCP4 Suite: Programs for Protein Crystallography, *Acta Crystallographica*, D50, (1994), 760–763) and further reduced using the CCP4 suite of programs.

Table 1 below contains the data statistics for the peak wavelength data.

TABLE 1

Data statistics

| Dmax (Å) | Dmin (Å) | Rmerge | Rfull | Rcum | Ranom | I/sigma | Mn (I)/sd |
|---|---|---|---|---|---|---|---|
| 50.00 | 8.85 | 0.052 | 0.043 | 0.052 | 0.034 | 9.2 | 41.5 |
| 8.85 | 6.26 | 0.044 | 0.037 | 0.048 | 0.031 | 9.4 | 37.9 |
| 6.26 | 5.11 | 0.045 | 0.039 | 0.048 | 0.029 | 14.7 | 34.9 |
| 5.11 | 4.43 | 0.047 | 0.038 | 0.047 | 0.023 | 13.7 | 34.2 |
| 4.43 | 3.96 | 0.054 | 0.044 | 0.049 | 0.027 | 12.3 | 29.4 |
| 3.96 | 3.61 | 0.082 | 0.069 | 0.053 | 0.035 | 8.0 | 21.3 |

TABLE 1-continued

Data statistics

| Dmax (Å) | Dmin (Å) | Rmerge | Rfull | Rcum | Ranom | I/sigma | Mn (I)/sd |
|---|---|---|---|---|---|---|---|
| 3.61 | 3.35 | 0.135 | 0.112 | 0.058 | 0.060 | 5.1 | 12.4 |
| 3.35 | 3.13 | 0.221 | 0.180 | 0.064 | 0.095 | 3.3 | 7.6 |
| 3.13 | 2.95 | 0.380 | 0.280 | 0.069 | 0.193 | 1.9 | 3.9 |
| 2.95 | 2.80 | 0.626 | 0.430 | 0.073 | 0.352 | 1.2 | 2.0 |
| Overall: | | 0.073 | 0.059 | 0.073 | 0.049 | 6.6 | 18.8 |

Where:
Dmax=minimum resolution
Dmin=maximum resolution $$Rmerge = \frac{sum \sim i \sim (sum \sim j \sim |I \sim j \sim -\langle I \rangle|)}{sum \sim i \sim (sum \sim j \sim \langle I \rangle)}$$

I~j~=the intensity of the jth observation of reflection i
<I>=the mean of the intensities of all observations of reflection I
sum~i~is taken over all reflections
sum~j~is taken over all observations of each reflection.
Rfull=Rmerge for fully recorded reflections only
Rcum=cumulative Rmerge for all reflection
Ranom=Sum |Mn(I+)−Mn(I−)|/Sum(Mn(I+)+Mn(I−)), where MN(I) is the mean I of that shell.
I/sigma=I/Sigma
Mn(D/Sd=Mn(I)/standard deviation of I/Sigma(I)

MAD Structure Determination

The location of the iron atom within the unit cell was determined by visual inspection of the three Harker sections of the anomalous difference Patterson map calculated using the peak anomalous data by the program FFT (part of the CCP4 suite).

The refined parameters of the iron atom used to generated phases are as follows: x=23.255, y=23.237, z=10.742, occupancy=0.92, temperature factor=69.45. These refined parameters were obtained using the program SHARP, by refinement against the experimental data obtained from the crystal (columns 4 and 5 of Table 3). These atom parameters were then used within SHARP to generate phases for 3A4. These phases can then be modified by density modification procedures. The phases from SHARP were solvent flattened using SOLOMON/DM as available through the SHARP program. The resulting solvent flattened structure factor amplitudes and phases are given in columns 6 and 7 of Table 3.

We choose to refine the iron atom parameters within SHARP, generate phases within SHARP and then perform density modification using SOLOMON and DM as implemented through SHARP. It however would be possible to generate phases using the heavy atom parameters given above and to solvent flatten the resulting phases using alternative programs (for example using the CCP4 program MLPHARE ((Z. Otwinowski: Daresbury Study Weekend proceedings, 1991) to generate the phases and the CCP4 program DM (K. Cowtan (1994), Joint CCP4 and ESF-EACBM Newsletter on Protein Crystallography, 31, p34–38).

The generation of such phases (unflattened or solvent flattened) is reliant on determining accurate parameters that describe the heavy or anomalous atom (in this case the iron of the haem), as are given above.

Thus in a further aspect the invention provides a method of generating phases of crystals of 3A4 using the iron parameters x=23.255, y=23.237, z=10.742, occupancy=0.92, temperature factor=69.45 and the experimental structure factor data obtained from the crystal (columns 4 and 5 of Table 3) or structure factor data obtained from another crystal of 3A4 in the same crystal form.

This assignment of the iron position was consistent with the given space group I222 and not with the alternative choice I2$_1$2$_1$2$_1$. Both datasets together with the spacegroup I222 were giving to the program autoSHARP (Vonrhein, C. & Bricogne, G., (2002), Global Phasing) that automatically determined the position and handedness of the heavy atom substructure solution, resulting in a set of phases after density modification. The resulting density modified phases were used as phase restraints during further refinement of the heavy atom model in SHARP (La Fortelle, E. de and Bricogne, G. (1997). Maximum-likelihood heavy-atom parameter refinement for multiple isomorphous replacement and multiwavelength anomalous diffraction methods. *Methods in Enzymology* 276, 472–494) to give a set of phases (phase set I). In a similar heavy atom refinement and phasing experiment, using the peak wavelength alone, a set of phases (phase set II) was obtained.

The resulting phases (phase set I) were used in phased molecular replacement as implemented in MOLREP (A. Vagin, A. Teplyakov, J. Appl. Cryst. (1997) 30, 1022–1025, part of the CCP4 suite) and using 2C5 with the haem excluded (pdbent 1DT6) as a search model together with the sequence of SEQ ID 2. This gave an unambiguous solution where the haem moiety was consistent with the iron position obtained through inspection of the Harker sections.

The oriented and positioned model (based on 1DT6 and the sequence of SEQ ID 2), model-A, was used together with the phase set II phases in density modification as implement in SOLOMON (Abrahams J. P. and Leslie A. G. W., *Acta Crystallographica* D52, (1996), 30–42) through the SHARP program package.

Table 2 contains the phasing statistics in resolution bins. The columns are:
Minimum resolution
Maximum resolution
Number of acentric reflections for peak and inflection dataset used in phasing power calculation
Anomalous phasing power for peak and inflection dataset (phase set I)
Number of acentric reflections used in SHARP figure-of-merit calculation
SHARP figure-of-merit for acentric reflections (phase set I)
Number of centric reflections used in SHARP figure-of-merit calculation
SHARP figure-of-merit for centric reflections (phase set I)
Figure-of-merit after density modification of phase set II with SOLOMON including model-A at the very first cycle—final cycle of solvent flipping.
10. Average phase error derived from the FOM given in column 9 using the relationship
FOM=cos(average phase error)

Structure factors and phases from which the electron density map can be calculated are contained in Table 3. The resulting electron density map showed clear structural features. When comparing the electron density with the molecular replacement solution, the secondary structure of P450 was apparent, although structural elements were clearly slightly displaced from their location in the 2C5 search model. The haem group, missing from the molecular replacement model, has clearly defined planar electron density.

Protein Characterization

The final quality of each of the protein preparations was evaluated by:

(a) SDS Polyacrylamide Gel Electrophoresis

This was performed using commercial gels (Nugen) followed by coomassie brilliant blue (CBB) staining according to the manufacturer's instructions. The purity as estimated by scanning a digital image of a gel was estimated to be at least 95%.

(b) Mass Spectroscopy

Mass spectrometry was performed using a Bruker BioTOF II electrospray time of flight instrument. Samples were either diluted by a factor of 1000 straight from storage buffer into methanol/water/formic acid (50:48:2 v/v/v), or subjected to a reverse phase separation using a C4 Millipore 'zip-tip' or a C4 HPLC column, before being diluted into methanol/water/formic acid.

Calibration was achieved by measurement of the 2+ and 1+ charge states of a peptide mixture containing Bombesin and angiotensin I or by using the multiple charge states of Horse Myoglobin. Data were acquired in the m/z range 200 to 2000 and were subsequently processed using Bruker's X-mass program. Mass accuracy was expected to be better than 1 in 10 000 (100 ppm).

| Mass spec of 3A4: | 55279.43 Da (observed) |
| --- | --- |
| | 55277.81 Da (predicted for protein minus the N-terminus Methionine) |

(c) Functionality Assays

Activity assays on 3A4 were performed using dibenzylfluorescein (Gentest), which is dealkylated to the fluorescein ester, as a fluorescent substrate.

Assays were carried out in 96-well half-area black, Costar plates in a final assay volume of 50 µl. The reaction rates were monitored for 1 hour at room temperature on a Fluoroscan Ascent FL Instruments (Labsystem) platereader with excitation and emission wavelengths of 485 nm and 538 nm respectively. Reaction rates were measured using Prizm (GraphPad) software Reaction mixtures were composed of 300 nM of 3A4 enzyme incubated with 2 units/ml purified human oxidoreductase, 2.8 µM dibenzylfluorescein and a regeneration system composed of 140 µM $NADP^+$, 400 µM glucose-6-phosphate and 2.8 units/ml glucose-6-phosphate dehydrogenase in 100 mM potassium phosphate pH 7.8, 1 mM $MgCl_2$.

TABLE 2

Phasing statistics in resolution bins

| Dmin | Dmax | Nacen peak/infl | PP_acen peak/infl | Nacen | FOMacen | Ncen | FOMcen | FOM denmod | Average phase error |
| --- | --- | --- | --- | --- | --- | --- | --- | --- | --- |
| 66.98 | 12.32 | 107/104 | 2.593/1.151 | 108 | 0.57611 | 75 | 0.14648 | 0.75897 | 40.6° |
| 12.32 | 8.78 | 206/195 | 1.813/1.459 | 207 | 0.52620 | 72 | 0.07944 | 0.89841 | 26.1° |
| 8.78 | 7.19 | 287/275 | 2.437/1.473 | 288 | 0.56634 | 74 | 0.08138 | 0.90077 | 25.7° |
| 7.19 | 6.24 | 348/333 | 2.606/1.648 | 349 | 0.53477 | 75 | 0.07990 | 0.83914 | 33.0° |
| 6.24 | 5.58 | 396/386 | 2.420/1.434 | 396 | 0.53154 | 62 | 0.10538 | 0.85947 | 30.7° |
| 5.58 | 5.10 | 440/436 | 2.000/1.087 | 440 | 0.48298 | 77 | 0.07540 | 0.84261 | 32.6° |
| 5.10 | 4.72 | 491/489 | 1.658/0.863 | 492 | 0.45701 | 77 | 0.05287 | 0.86452 | 30.2° |
| 4.72 | 4.42 | 532/530 | 1.477/0.666 | 532 | 0.41346 | 65 | 0.04342 | 0.86050 | 30.6° |
| 4.42 | 4.17 | 557/555 | 1.180/0.488 | 557 | 0.38258 | 79 | 0.04054 | 0.85383 | 31.4° |
| 4.17 | 3.95 | 594/593 | 0.994/0.429 | 595 | 0.36431 | 60 | 0.03930 | 0.84404 | 32.4° |
| 3.95 | 3.77 | 615/614 | 0.763/0.290 | 618 | 0.30101 | 77 | 0.04647 | 0.81426 | 35.5° |
| 3.77 | 3.61 | 656/653 | 0.611/0.219 | 659 | 0.24232 | 77 | 0.03926 | 0.83271 | 33.6° |
| 3.61 | 3.47 | 679/676 | 0.474/0.189 | 682 | 0.19202 | 75 | 0.04716 | 0.77315 | 39.4° |
| 3.47 | 3.34 | 709/707 | 0.420/0.156 | 715 | 0.16313 | 72 | 0.05622 | 0.73713 | 42.5° |
| 3.34 | 3.23 | 738/734 | 0.340/0.141 | 740 | 0.13450 | 73 | 0.04334 | 0.70163 | 45.4° |
| 3.23 | 3.13 | 757/305 | 0.299/0.132 | 763 | 0.11239 | 78 | 0.04350 | 0.64421 | 49.9° |
| 3.13 | 3.04 | 772/0 | 0.241/0.000 | 785 | 0.09334 | 69 | 0.05388 | 0.59097 | 53.8° |
| 3.04 | 2.95 | 716/0 | 0.205/0.000 | 781 | 0.08119 | 40 | 0.06355 | 0.52079 | 58.6° |
| 2.95 | 2.87 | 626/0 | 0.189/0.000 | 689 | 0.08130 | 34 | 0.05063 | 0.38949 | 67.1° |
| 2.87 | 2.80 | 563/0 | 0.167/0.000 | 617 | 0.07522 | 22 | 0.05246 | 0.30668 | 72.1° |
| Total | | 10789/7585 | 0.779/0.446 | 11013 | 0.25754 | 1333 | 0.06256 | 0.70319 | 45.3° |

3A4 Structure Determination.

The electron density map, described by Table 3 allowed a model of 3A4 to be built using the graphical program O (Jones, T. A., Zou, J. Y., Cowan, S. W., and Kjeldgaard (1991) *Acta Cryst.* A47, 110–119). This model was then refined to 2.8 Å resolution against the peak wavelength dataset from the iron MAD experiment (statistics of the data given in Table 1) using the programs CNX (Brünger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998) *Acta Cryst.* D54, 905–921) and Refmac (Murshudov, G. N., Vagin, A. A., and Dodson, E. J. (1997) *Acta Cryst.* D50, 760–763). The refinement statistics in Table 4 are of the model given in Table 5. The model includes 29 ordered water molecules.

TABLE 4

Refinement statistics of the 3A4 crystal structure:

| Resolution | 2.8 Å |
| --- | --- |
| R factor | 24.36% |
| Free R factor (5% of data) | 27.38% |
| r.m.s.d. bonds | 0.0083 Å |
| r.m.s.d. angles | 1.904° |
| Average B factor (all atoms) | 64 Å$^2$ |

We claim:

1. A crystal of a P450 3A4 of SEQ ID NO:2 having an orthorhomobic space group I222, and unit cell dimensions a=78 Å, b=100 Å, c=132 Å, α=β=γ=90°, with a unit cell variability of 5% in all dimensions.

2. A crystal of P450 3A4 having an orthorhomobic space group I222, and unit cell dimensions a=78 Å, b=100 Å, c=132 Å, α=β=γ=90°, with a unit cell variability of 5% in all dimensions, wherein said P450 3A4 is of SEQ ID NO:2 or comprises 1 or 2 amino acid substitutions or deletions thereof.

* * * * *